(12) United States Patent
Aso et al.

(10) Patent No.: US 8,901,141 B2
(45) Date of Patent: Dec. 2, 2014

(54) TRICYCLIC COMPOUNDS HAVING CORTICOTROPIN-RELEASING FACTOR ANTAGONISTIC ACTIVITY AND PHARMACEUTICAL COMPOSITIONS CONTAINING THEM

(75) Inventors: Kazuyoshi Aso, Osaka (JP); Katsumi Kobayashi, Osaka (JP); Takafumi Takai, Osaka (JP); Takuto Kojima, Osaka (JP); Kazuyuki Tokumaru, Aichi (JP); Michiyo Mochizuki, Osaka (JP)

(73) Assignee: Takeda Pharmaceutical Company, Limited, Osaka (JP)

( * ) Notice: Subject to any disclaimer, the term of this patent is extended or adjusted under 35 U.S.C. 154(b) by 661 days.

(21) Appl. No.: 12/863,851

(22) PCT Filed: Jan. 21, 2009

(86) PCT No.: PCT/JP2009/051299
§ 371 (c)(1),
(2), (4) Date: Jul. 21, 2010

(87) PCT Pub. No.: WO2009/093747
PCT Pub. Date: Jul. 30, 2009

(65) Prior Publication Data
US 2010/0298287 A1 Nov. 25, 2010

Related U.S. Application Data

(60) Provisional application No. 61/006,554, filed on Jan. 22, 2008.

(51) Int. Cl.
*A61K 31/505* (2006.01)
*C07D 239/70* (2006.01)
*C07D 498/04* (2006.01)
*C07D 487/04* (2006.01)

(52) U.S. Cl.
CPC ............ *C07D 487/04* (2013.01); *C07D 498/04* (2013.01)
USPC .......................................... 514/267; 544/250

(58) Field of Classification Search
CPC .................................................... C07D 487/04
USPC ......... 514/338, 267, 395, 252.02, 220, 233.2, 514/252.16, 211.1, 250, 292, 230.2; 544/346, 101, 115, 250; 548/302.1; 546/273.1; 540/548, 562
See application file for complete search history.

(56) References Cited

U.S. PATENT DOCUMENTS

| 7,034,153 | B2 | 4/2006 | Nakai et al. |
| 7,427,630 | B2 | 9/2008 | Di Fabio et al. |
| 7,459,459 | B2 | 12/2008 | Nakai et al. |
| 7,709,522 | B2 | 5/2010 | Buezo et al. |
| 7,807,688 | B2 | 10/2010 | Nakai et al. |
| 8,173,695 | B2 | 5/2012 | Diaz Buezo et al. |
| 2004/0072833 | A1 | 4/2004 | Nakai et al. |
| 2006/0122392 | A1 | 6/2006 | Nakai et al. |
| 2006/0154944 | A1 | 7/2006 | Ohmoto et al. |
| 2007/0004708 | A1 | 1/2007 | Andreotti et al. |
| 2009/0137604 | A1 | 5/2009 | Nakai et al. |
| 2009/0186873 | A1 | 7/2009 | Buezo et al. |
| 2010/0197669 | A1 | 8/2010 | Diaz Buezo et al. |
| 2011/0009364 | A1 | 1/2011 | Dubois et al. |
| 2011/0009444 | A1 | 1/2011 | Dubois et al. |
| 2011/0172255 | A1 | 7/2011 | Andreotti et al. |
| 2011/0288139 | A1 | 11/2011 | Fuchs et al. |

FOREIGN PATENT DOCUMENTS

| JP | 51-6993 | 1/1976 |
| RU | 2 382 785 | 5/2006 |
| WO | 2005/099688 | 10/2005 |
| WO | 2006/116412 | 11/2006 |
| WO | 2008/051533 | 5/2008 |
| WO | 2008/082003 | 7/2008 |

OTHER PUBLICATIONS

Caroon, JM, Fisher, LE. "Preparation of Substituted, Annulated Benzimidazoles Via Benzyne Mediated Cyclization." Heterocycles, vol. 32, No. 3, 1991. pp. 459-467.*
Zorrilla, E.P., et al. "Progress in corticotropin-releasing factor-1 antagonist development." Drug Discovery Today. NIH. (2010), 15(9-10), pp. 371-383.*
Nemeroff, C.B., et al. "Treatment of mood disorders." Nature Neuroscience Supplement. (Nov. 2002), vol. 5, pp. 1068-1070.*
Mayo Clinic. "Depression (major depression)." © Aug. 2011.*
Caroon, J.M., et al. "Preparation of Substituted, Annulated Benzimidazoles via Benzene Mediated Cyclization." Heterocycles. vol. 32, No. 3 (1991), pp. 459-467.*
Romanenko, N.I., et al. "Reactions of Tetrahydropyrimido [2,1-f] Xanthines with Some Electrophilic and Nucleophilic Reagents." © 1986.*

(Continued)

*Primary Examiner* — Andrew D Kosar
*Assistant Examiner* — John S Kenyon
(74) *Attorney, Agent, or Firm* — Wenderoth, Lind & Ponack, LLP

(57) ABSTRACT

There is provided a compound of the formula (I'): wherein X is a nitrogen or CRx, Rx is a hydrogen, etc., $R^1$ is an optionally substituted hydrocarbon group, etc., $R^2$ is an optionally substituted hydrocarbon group, etc., ring A is 5- to -8-membered heterocyclic ring, etc., and each of $Y^1$, $Y^2$ and $Y^3$ is an optionally substituted carbon or a nitrogen, etc.; or 'a salt thereof or a prodrug thereof, which have CRF receptor antagonistic activity and use thereof.

(I')

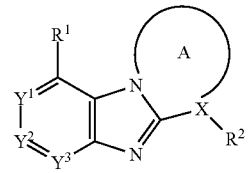

5 Claims, No Drawings

(56) References Cited

OTHER PUBLICATIONS

Ahn, C.M., et al. "Synthesis and in vitro Antitumor Activity of Isoazamitosene and Isoiminoazamitosene Derivatives." Arch. Pharm. Res. (1996), vol. 19, No. 6, pp. 535-542.*

Ettmayer, P., et al. "Lessons Learned from Marketed and Investigational Prodrugs." J. Med. Chem. (2004), vol. 47, No. 10, pp. 2393-2404.*

Han, H.K. "Targeted Prodrug Design to Optimize Drug Delivery." AAPS Pharmsci. (2000), vol. 2, (1), pp. 1-11.*

Testa, B. "Prodrug research: futile or fertile?" Biochemical Pharmacology. (2004), vol. 68, pp. 2097-2106.*

American Chemical Society (ACS). STN Chemical Abstract Service (CAS) RN 143097-30-7. © 2013.*

G. S. Banker et al., "Modem Pharmaceutics", Marcel Dekker, New York, 1996, pp. 596 and 451.

M. E. Wolff, "Burger's Medicinal Chemistry and Drug Discovery", Fifth Ed., vol. 1, Principles and Practice, John Wiley & Sons, 1995, pp. 975-977.

First Report issued in the corresponding Chilean patent application dated Mar. 15, 2012.

International Search Report issued Jun. 3, 2009 in International (PCT) Application No. PCT/JP2009/051299 along with the Written Opinion.

N. I. Romanenko et al., "Reactions of Tetrahydropyrimido[2,1-f]Xanthines with Some Electrophilic and Nucleophilic Reagents", vol. 29, vol. 6, pp. 20-23, 1986 with English translation.

K. Hino et al., "Syntheses of 4-Aminodihydrothiazolopurines, 4-Aminodihydroimidazopurines and 4-Aminotetrahydropyrimidopurines", Chem. Pharm. Bull., vol. 23, No. 8, pp. 1696-1701, 1975.

A. Bortolato et al., "In Silico Binding Free Energy Predictability by Using the Linear Interaction Energy (LIE) Method: Bromobenzimidazole CK2 Inhibitors as a Case Study", Journal of Chemical Information and Modeling, vol. 47, No. 2, pp. 572-582, 2007.

F. Esser et al., "Cyclic Guanidines; IV. Intramolecular Nucleophilic Aromatic Substitution of Hydrogen in (3-Nitrophenyl)guanidines", Synthesis, vol. 6, pp. 596-601, 1992.

Search Report and English translation issued in corresponding Georgian Patent Application No. 121925 dated Sep. 28, 2011.

Documentary Conclusion on Defining of the State of Art and English translation issued in corresponding Georgian Patent Application No. 121925 dated Sep. 28, 2011.

C. Ferrarese et al.; "Benzodiazepine Receptors and Diazepam Binding Inhibitor: A Possible Link Between Stress, Anxiety and the Immune System"; Psychoneuroendocrinology; vol. 18, No. 1; 1993; pp. 3-22.

* cited by examiner

TRICYCLIC COMPOUNDS HAVING CORTICOTROPIN-RELEASING FACTOR ANTAGONISTIC ACTIVITY AND PHARMACEUTICAL COMPOSITIONS CONTAINING THEM

This application is a U.S. national stage of International Application No. PCT/JP2009/051299 filed Jan. 21, 2009, which claims the benefit of U.S. provisional application Serial No. 61/006,554 filed Jan. 22, 2008.

TECHNICAL FIELD

The present invention relates to novel Tricyclic compounds having corticotropin releasing factor antagonistic activity and pharmaceutical compositions containing them.

BACKGROUND OF INVENTION

Corticotropin-releasing factor (hereinafter, abbreviated as "CRF") is a neuropeptide composed of 41 amino acids, and was isolated and purified as a peptide promoting release of adrenocorticotropic hormone (ACTH) from pituitary gland. First, the structure thereof was determined from sheep hypothalamus and, thereafter, the presence thereof was confirmed also in a rat or a human, and the structure thereof was determined [Science, 213, 1394 (1981); Proc. Natl. Acad. Sci. USA, 80, 4851 (1983); EMBO J. 5, 775 (1983)]. An amino acid sequence is the same in a human and a rat, but differed in 7 amino acids in bovine. CRF is synthesized as a carboxy-terminal of prepro CRF, cleaved and secreted. The CRF peptide and an mRNA thereof are present at the largest amount in hypothalamus and pituitary gland, and are widely distributed in a brain such as cerebral cortex, cerebellum, hippocampus and corpus amygdaloideum. In addition, in peripheral tissues, the existence has been confirmed in placenta, adrenal gland, lung, liver, pancreas, skin and digestive tract [J. Olin. Endocrinol. Metab., 65, 176 (1987); J. Clin. Endocrinol. Metab., 67, 768 (1988); Regul. Pept., 18, 173 (1987), Peptides, 5 (Suppl. 1), 71 (1984)]. A CRF receptor is a 7-transmembrane G protein-coupled receptor, and two subtypes of CRF1 and CRF2 are present. It is reported that CRF1 is present mainly in cerebral cortex, cerebellum, olfactory bulb, pituitary gland and tonsil nucleus. On the other hand, the CRF2 receptor has two subtypes of CRF2α and CRF2β. It was made clear that the CRF2α receptor is distributed much in hypothalamus, septal area and choroids plexus, and the CRF2β receptor is present mainly in peripheral tissues such as skeletal muscle and is distributed in a blood vessel in a brain [J. Neurosci. 15, 6340 (1995); Endocrinology, 137, 72 (1996); Biochim. Biophys. Acta., 1352, 129 (1997)]. Since each receptor differs in distribution in a living body, it is suggested that a role thereof is also different [Trends. Pharmacol. Sci. 23, 71 (2002)].

As a physiological action of CRF, the action on the endocrine system is known in which CRF is produced and secreted in response to stress in hypothalamus and acts on pituitary gland to promote the release of ACTH [Recent Prog. Horm. Res., 39, 245 (1983)]. In addition to the action on the endocrine system, CRF acts as a neurotransmitter or a neuroregulating factor in a brain, and integrates electrophysiology, autonomic nerve and conducts to stress [Brain Res. Rev., 15, 71 (1990); Pharmacol. Rev., 43, 425 (1991)]. When CRF is administered in a cerebral ventricle of experimental animal such as a rat, anxiety conduct is observed, and much more anxiety conduct is observed in a CRF-overexpressing mouse as compared with a normal animal [Brain Res., 574, 70 (1992); J. Neurosci., 10, 176 (1992); J. Neurosci., 14, 2579 (1994)]. In addition, α-helical CRF(9-41) of a peptidergic CRF receptor antagonist exerts an anti-anxiety action in an animal model [Brain Res., 509, 80 (1990); J. Neurosci., 14, 2579(1994)]. A blood pressure, a heart rate and a body temperature of a rat are increased by stress or CRF administration, but the α-helical CRF(9-41) of a peptidergic CRF antagonist inhibits the increase in a blood pressure, a heart rate and a body temperature due to stress [J. Physiol., 460, 221 (1993)]. The α-helical CRF(9-41) of a peptidergic CRF receptor antagonist inhibits abnormal conducts due to withdrawal of a dependent drug such as an alcohol and a cocaine [Psychopharmacology, 103, 227 (1991); Pharmacol. Rev. 53, 209 (2001)]. In addition, it has been reported that learning and memory are promoted by CRF administration in a rat [Nature, 375, 284 (1995); Neuroendocrinology, 57, 1071 (1993); Eur. J. Pharmacol., 405, 225 (2000)].

Since CRF is associated with stress response in a living body, there are clinical reports regarding stress-associated depression or anxiety. The CRF concentration in a cerebrospinal fluid of a depression patient is higher as compared with that of a normal person [Am. J. Psychiatry, 144, 873 (1987)], and the mRNA level of CRF in hypothalamus of a depression patient is increased as compared with that of a normal person [Am. J. Psychiatry, 152, 1372 (1995)]. The CRF binding site of the cerebral cortex from a patient who committed suicide was found to have decreased [Arch. Gen. Psychiatry, 45, 577 (1988)]. The increase in the plasma ACTH concentration due to CRF administration is small in a depression patient [N. Engl. J. Med., 314, 1329 (1986)]. In a patient with panic disorder, the increase of plasma ACTH concentration due to CRF administration is small [Am. J. Psychiatry, 143, 896 (1986)]. The CRF concentration in a cerebrospinal fluid of a patient with anxiety induced by stress such as obsessive-compulsive neurosis, post-psychic trauma stress disorder, Tourette's syndrome and the like is higher as compared with that of a normal person [Arch. Gen. Psychiatry, 51, 794(1994); Am. J. Psychiatry, 154, 624 (1997); Biol. Psychiatry, 39, 776 (1996)]. The CRF concentration in a cerebrospinal fluid of schizophrenics is higher as compared with that of a normal person [Brain Res., 437, 355 (1987); Neurology, 37, 905 (1987)]. Thus, it has been reported that there is abnormality in the living body response system via CRF in stress-associated mental disease.

The action of CRF on the endocrine system can be presumed by the characteristics of CRF gene-introduced animal and actions in an experimental animal. In a CRF-overexpressing mouse, excessive secretions of ACTH and adrenal cortex steroid occur, and abnormalities analogous to Cushing's syndrome such as atrophy of muscle, alopecia, infertility and the like are observed [Endorcrinology, 130, 3378 (1992)]. CRF inhibits ingestion in an experimental animal such as a rat [Life Sci., 31, 363 (1982); Neurophamacology, 22, 337 (1983)]. In addition, α-helical CRF(9-41) of a peptidergic CRF antagonist inhibited decrease of ingestion due to stress loading in an experimental model [Brain Res. Bull., 17, 285 (1986)]. CRF inhibited weight gain in a hereditary obesity animal [Physiol. Behav., 45, 565 (1989)]. In a nervous orexia inactivity patient, the increase of ACTH in plasma upon CRF administration is small [J. Clin. Endocrinol. Metab., 62, 319 (1986)]. It has been suggested that a low CRF value is associated with obesity syndrome [Endocrinology, 130, 1931 (1992)]. There has been suggested a possibility that ingestion inhibition and weight loss action of a serotonin reuptake inhibiting agent are exerted via release of CRF [Pharmacol. Rev., 43, 425 (1991)].

CRF is centrally or peripherally associated with the digestive tract movement involved in stress or inflammation [Am. J. Physiol. Gastrointest. Liver Physiol. 280, G315 (2001)].

CRF acts centrally or peripherally, weakens the shrinkablity of stomach, and decreases the gastric excreting ability [Regulatory Peptides, 21, 173 (1988); Am. J. Physiol., 253, G241 (1987)]. In addition, α-helical CRF (9-41) of a peptidergic CRF antagonist has a restoring action for hypofunction of stomach by abdominal operation [Am. J. Physiol., 258, G152 (1990)]. CRF inhibits secretion of a bicarbonate ion in stomach, decreases gastric acid secretion and inhibits ulcer due to cold restriction stress [Am. J. Physiol., 258, G152 (1990)]. Furthermore, α-helical CRF (9-41) of a peptidergic CRF antagonist shows the inhibitory action on gastric acid secretion decrease, gastric excretion decrease, small intestinal transport decrease and large intestinal transport enhancement due to restriction stress [Gastroenterology, 95, 1510 (1988)]. In a healthy person, mental stress increases a gas and abdominal pain due to anxiety and intestine dilation, and CRF decreases a threshold of discomfort [Gastroenterology, 109, 1772 (1995); Neurogastroenterol. Mot., 8, 9 [1996]. In an irritable bowel syndrome patient, large intestinal movement is excessively enhanced by CRF administration as compared with a healthy person [Gut, 42, 845 (1998)].

It has been reported from studies on experimental animals and clinical studies that CRF is induced by inflammation and is involved in an inflammatory reaction. In an inflammatory site of an experimental animal and in a joint fluid of a rheumatoid arthritis patient, production of CRF is topically increased [Science, 254, 421 (1991); J. Clin. Invest., 90, 2555 (1992); J. Immunol., 151, 1587 (1993)]. CRF induces degranulation of a mast cell and enhances the blood vessel permeability [Endocrinology, 139, 403 (1998); J. Pharmacol. Exp. Ther., 288, 1349 (1999)]. CRF can be detected also in a thyroid gland of autoimmune thyroiditis patient [Am. J. Pathol. 145, 1159(1994)]. When CRF is administered to an experimental autoimmune cerebrospinal meningitis rat, the progression of symptom such as paralysis was remarkably inhibited [J. Immunol., 158, 5751 (1997)]. In a rat, the immune response activities such as T-lymphocyte proliferation and the natural killer cell activity are reduced by CRF administration or stress loading [Endocrinology, 128, 1329 (1991)].

From the above-mentioned reports, it is expected that the CRF receptor antagonistic compound would exert an excellent effect for treating or preventing various diseases in which CRF is associated.

As a CRF antagonist, for example, peptide CRF receptor antagonists are reported in which a part of an amino acid sequence of CRF or associated peptides of a human or other mammals is altered or deleted, and they are reported to show a pharmacological action such as ACTH release-inhibiting action and anti-anxiety action [Science, 224, 889(1984); J. Pharmacol. Exp. Ther., 269, 564(1994); Brain Res. Rev., 15, 71 (1990)]. However, from a pharmacokinetic point of view such as chemical stability and absorbability for oral administration in a living body, bioavailability and intracerebral transferability, peptide derivatives have a low utility value as a medicine.

As a CRF antagonistic compound, for example, nitrogen-containing fused heterocyclic compounds are reported in WO 2005/44793, WO 2005/099688 and WO 2006/116412.

As tricyclic compounds, for example, compounds disclosed in JP-A-51-006993, Izvestiya Vysshikh Uchebnykh Zavedenii, Khimiya i Khimicheskaya Tekhnologiya (1986), 29(6), 20-3; Chemical & Pharmaceutical Bulletin (1975), 23(8), 1696-701; Journal of Chemical Information and Modeling (2007), 47(2), 572-582; Synthesis (1992), (6), 596-601; and so forth are reported.

DISCLOSURE OF INVENTION

According to the present invention, there is provided:
[1] A compound represented by the formula (I'):

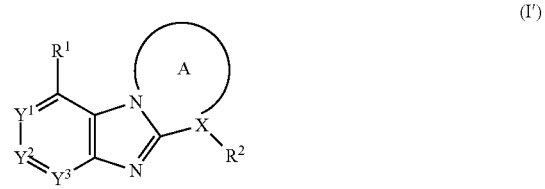

wherein X is a nitrogen or CRx (wherein Rx is a hydrogen or a $C_{1-9}$ alkyl, provided that when X forms a double bond, Rx is absent);
$R^1$ is
(1) an optionally substituted hydrocarbon group,
(2) an acyl,
(3) an optionally substituted heterocyclic group,
(4) an optionally substituted amino,
(5) nitro,
(6) an optionally substituted hydroxy,
(7) an optionally substituted mercapto,
(8) cyano, or
(9) halogen;
$R^2$ is
(1) an optionally substituted hydrocarbon group,
(2) an acyl,
(3) an optionally substituted heterocyclic group, or
(4) an optionally substituted amino,
provided that methyl, ethyl, propyl and methoxymethyl are excluded;
ring A is an optionally substituted 5- to 8-membered heterocyclic ring; and
$Y^1$, $Y^2$, and $Y^3$ are each an optionally substituted carbon or a nitrogen; excluding
(i) a compound wherein $Y^1$ and $Y^3$ are each a nitrogen, $R^1$ is amino and $R^2$ is an optionally substituted alkyl,
(ii) 2,4,7-trichloro-9-(4-methylphenyl)-6,7,8,9-tetrahydropyrimido[2,1-f]purine,
(iii) N-acetyl-N-(8-acetyl-7,8-dihydro-6H-imidazo[2,1-f]purin-4-yl) acetamide, and
(iv) a compound wherein $R^1$ and $R^2$ are each simultaneously

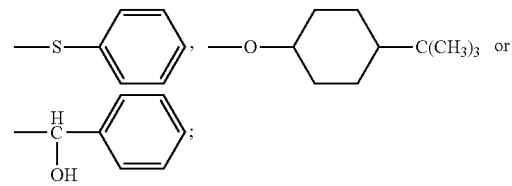

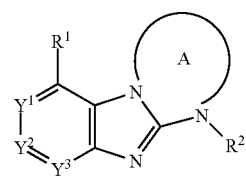

or a salt thereof;
[2] A compound represented by the formula (I):

wherein R¹ is
(1) an optionally substituted hydrocarbon group,
(2) an acyl,
(3) an optionally substituted heterocyclic group,
(4) an optionally substituted amino,
(5) nitro,
(6) an optionally substituted hydroxy,
(7) an optionally substituted mercapto,
(8) cyano, or
(9) halogen;
R² is
(1) an optionally substituted hydrocarbon group,
(2) an acyl,
(3) an optionally substituted heterocyclic group, or
(4) an optionally substituted amino,
provided that methyl is excluded;
ring A is an optionally substituted 5- to 8-membered heterocyclic ring; and
Y¹, Y², and Y³ are each an optionally substituted carbon or a nitrogen; excluding
(i) a compound wherein Y¹ and Y³ are each a nitrogen, R¹ is amino and R² is an optionally substituted alkyl,
(ii) 2,4,7-trichloro-9-(4-methylphenyl)-6,7,8,9-tetrahydropyrimido[2,1-f]purine, and
(iii) N-acetyl-N-(8-acetyl-7,8-dihydro-6H-imidazo[2,1-f]purin-4-yl)acetamide; or a salt thereof;
[3] The compound according to the above-mentioned [1] wherein ring A is an optionally substituted 5- to 7-membered heterocyclic ring;
[4] The compound according to the above-mentioned [1] wherein Y¹, Y² and Y³ are each an optionally substituted carbon;
[5] The compound according to the above-mentioned [1] wherein Y¹, Y² and Y³ are each independently a carbon optionally substituted by substituent(s) selected from halogen, cyano, an optionally substituted $C_{1-9}$ alkyl, optionally substituted $C_{1-6}$ alkoxy and a $C_{3-6}$ cycloalkyl;
[6] The compound according to the above-mentioned [1] wherein Y³ is a carbon optionally substituted by halogen;
[7] The compound according to the above-mentioned [1] wherein R¹ is nitro, halogen, cyano, carboxy, an optionally substituted carbamoyl, an acyl, an optionally substituted $C_{1-9}$ alkyl, an optionally substituted $C_{2-6}$ alkenyl, an optionally substituted amino or an optionally substituted N-linked 5- or 6-membered heterocyclic group;
[8] The compound according to the above-mentioned [1] wherein R¹ is
(1) mono- or di-$C_{1-6}$ alkylamino, or
(2) a $C_{1-9}$ alkyl optionally substituted by substituent(s) selected from halogen, hydroxy, $C_{3-6}$ cycloalkyl, an optionally substituted $C_{1-6}$ alkoxy, $C_{1-6}$ alkyl-carbonyloxy, $C_{3-6}$ cycloalkyl-carbonyloxy and an optionally substituted $C_{3-6}$ cycloalkyloxy;
[9] The compound according to the above-mentioned [1] wherein R² is an optionally substituted $C_{6-10}$ aryl or an optionally substituted 5- to 10-membered heterocyclic group;
[10] The compound according to the above-mentioned [1] wherein R² is an optionally substituted phenyl, an optionally substituted pyridyl or an optionally substituted pyrimidinyl;
[11] The compound according to the above-mentioned [1] wherein R² is phenyl, pyridyl or pyrimidinyl, each of which is optionally substituted by substituent(s) selected from an optionally substituted amino, cyano, halogen, an optionally substituted. $C_{1-9}$ alkyl and an optionally substituted $C_{1-6}$ alkoxy;

[12] The compound according to the above-mentioned [1] wherein the formula (I') is selected from the following formulas:

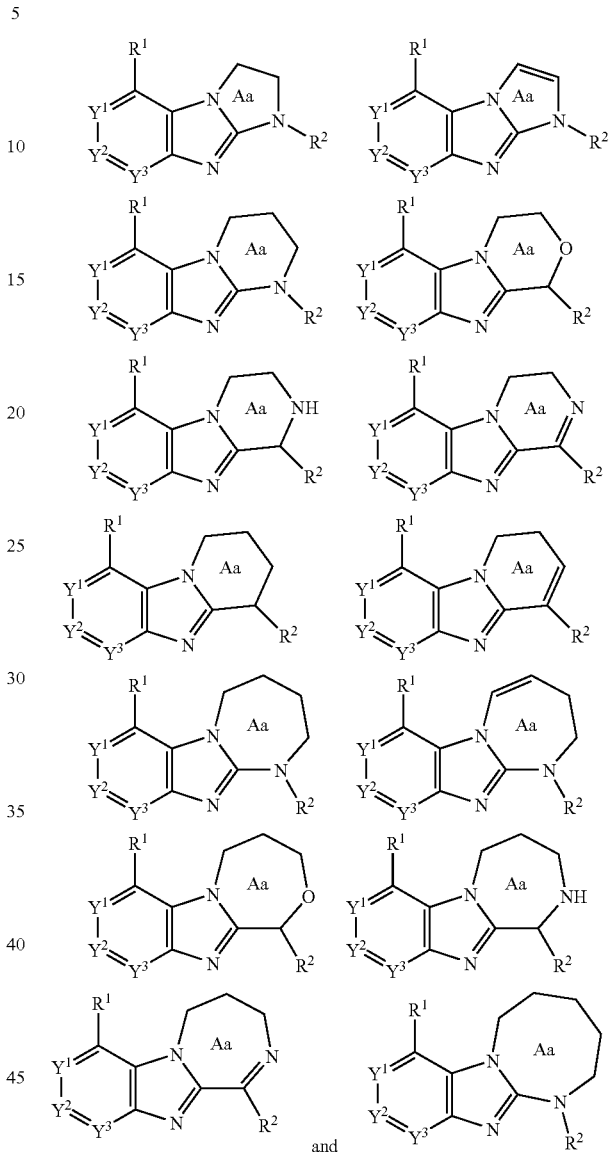

(wherein R¹, R², Y¹, Y² and Y³ are as defined in the above-mentioned [1], and ring Aa is optionally further substituted);

[13] The compound according to the above-mentioned [1] wherein the formula (I') is the following formula:

(I'')

(wherein $R^1$ and $R^2$ are as defined in the above-mentioned [1], and Rb is hydrogen, halogen, cyano, an optionally substituted $C_{1-9}$ alkyl, an optionally substituted $C_{1-6}$ alkoxy, or $C_{3-6}$ cycloalkyl);

[14] The compound according to the above-mentioned [13] wherein $R^1$ is
(1) mono- or di-$C_{1-6}$ alkylamino, or
(2) a $C_{1-9}$ alkyl optionally substituted by substituent(s) selected from halogen, hydroxy, $C_{3-6}$ cycloalkyl, an optionally substituted $C_{1-6}$ alkoxy, $C_{1-6}$ alkyl-carbonyloxy, $C_{3-6}$ cycloalkyl-carbonyloxy and an optionally substituted $C_{3-6}$ cycloalkyloxy; and $R^2$ is an optionally substituted phenyl, an optionally substituted pyridyl or an optionally substituted pyrimidinyl;

[15] The compound according to the above-mentioned [1] wherein the formula (I') is the following formula:

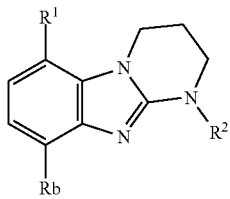

(I''')

(wherein $R^1$ and $R^2$ are as defined in the above-mentioned [1], and Rb is as defined in the above-mentioned [13]);

[16] The compound according to the above-mentioned [15] wherein $R^1$ is
(1) mono- or di-$C_{1-6}$ alkylamino, or
(2) a $C_{1-9}$ alkyl optionally substituted by substituent selected from halogen, hydroxy, $C_{3-6}$ cycloalkyl, an optionally substituted $C_{1-6}$ alkoxy, $C_{1-6}$ alkyl-carbonyloxy, $C_{3-6}$ cycloalkyl-carbonyloxy and an optionally substituted $C_{3-6}$ cycloalkyloxy; and $R^2$ is an optionally substituted phenyl, an optionally substituted pyridyl or an optionally substituted pyrimidinyl;

[17] The compound according to the above-mentioned [15] wherein $R^1$ is a $C_{1-9}$ alkyl optionally substituted by substituent selected from halogen, hydroxy, $C_{3-6}$ cycloalkyl, an optionally substituted $C_{1-6}$ alkoxy, $C_{1-6}$ alkyl-carbonyloxy, $C_{3-6}$ cycloalkyl-carbonyloxy and an optionally substituted $C_{3-6}$ cycloalkyloxy; $R^2$ is
(1) phenyl optionally substituted by substituent(s) selected from halogen, an optionally halogenated $C_{1-6}$ alkoxy and an optionally halogenated $C_{1-9}$ alkyl,
(2) pyridyl optionally substituted by substituent(s) selected from halogen, an optionally halogenated $C_{1-9}$ alkyl, $C_{3-6}$ cycloalkyl and an optionally halogenated $C_{1-6}$ alkoxy, or
(3) pyrimidinyl optionally substituted by substituent selected from $C_{1-9}$ alkyl, an optionally halogenated $C_{1-6}$ alkoxy and $C_{3-6}$ cycloalkyl; and
Rb is hydrogen, halogen or $C_{1-6}$ alkoxy;

[18] The compound according to the above-mentioned [1] wherein the formula (I') is the following formula:

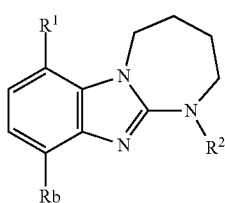

(I'''')

(wherein $R^1$ and $R^2$ are as defined in the above-mentioned [1], and Rb is as defined in the above-mentioned [14]);

[19] The compound according to the above-mentioned [18] wherein $R^1$ is
(1) mono- or di-$C_{1-6}$ alkylamino, or
(2) a $C_{1-9}$ alkyl optionally substituted by substituent selected from halogen, hydroxy, $C_{3-6}$ cycloalkyl, an optionally substituted $C_{1-6}$ alkoxy, $C_{1-6}$ alkyl-carbonyloxy, $C_{3-6}$ cycloalkyl-carbonyloxy and an optionally substituted $C_{3-6}$ cycloalkyloxy; and $R^2$ is an optionally substituted phenyl, an optionally substituted pyridyl or an optionally substituted pyrimidinyl;

[20] A compound represented by the formula (Ix):

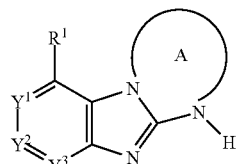

(Ix)

(wherein $Y^1$, $Y^2$, $Y^3$, $R^1$ and ring A are as defined in the above-mentioned [1]),
excluding, a compound wherein $R^1$ is nitro, methyl, halogen or a group of the formula:

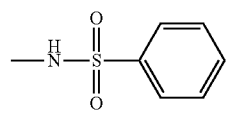

wherein benzene ring is optionally substituted;
or a salt thereof;

[21] 9-Chloro-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole or salt thereof;

[22] The compound according to the above-mentioned [21] wherein 9-chloro-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole is (+)-9-chloro-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole;

[23] The compound according to the above-mentioned [21] wherein 9-chloro-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole is (−)-9-chloro-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole;

[24] 9-Chloro-6-[1-(difluoromethoxy)-2,2,2-trifluoroethyl]-1-(6-methoxy-2-methylpyridin-3-yl)-1,2,3,4-tetrahydropyrimido[1,2-a]benzimidazole or a salt thereof;

[25] The compound according to the above-mentioned [24] wherein 9-chloro-6-[1-(difluoromethoxy)-2,2,2-trifluoroethyl]-1-(6-methoxy-2-methylpyridin-3-yl)-1,2,3,4-tetrahydropyrimido[1,2-a]benzimidazole is (+)-9-chloro-6-[1-(difluoromethoxy)-2,2,2-trifluoroethyl]-1-(6-methoxy-2-methylpyridin-3-yl)-1,2,3,4-tetrahydropyrimido[1,2-a]benzimidazole;

[26] The compound according to the above-mentioned [24] wherein 9-chloro-6-[1-(difluoromethoxy)-2,2,2-trifluoroethyl]-1-(6-methoxy-2-methylpyridin-3-yl)-1,2,3,4-tetrahydropyrimido[1,2-a]benzimidazole is (−)-9-chloro-6-[1-(difluoromethoxy)-2,2,2-trifluoroethyl]-1-(6-methoxy-2-methylpyridin-3-yl)-1,2,3,4-tetrahydropyrimido[1,2-a]benzimidazole;

[27] 1-[9-Chloro-1-(2,4-dichlorophenyl)-1,2,3,4-tetrahydropyrimido[1,2-a]benzimidazol-6-yl]propyl acetate or a salt thereof;

[28] The compound according to the above-mentioned [27] wherein 1-[9-chloro-1-(2,4-dichlorophenyl)-1,2,3,4-tetrahydropyrimido[1,2-a]benzimidazol-6-yl]propyl acetate is (+)-1-[9-chloro-1-(2,4-dichlorophenyl)-1,2,3,4-tetrahydropyrimido[1,2-a]benzimidazol-6-yl]propyl acetate;

[29] The compound according to the above-mentioned [27] wherein 1-[9-chloro-1-(2,4-dichlorophenyl)-1,2,3,4-tetrahydropyrimido[1,2-a]benzimidazol-6-yl]propyl acetate is (−)-1-[9-chloro-1-(2,4-dichlorophenyl)-1,2,3,4-tetrahydropyrimido[1,2-a]benzimidazol-6-yl]propyl acetate;

[30] 9-Chloro-1-(2,4-dichlorophenyl)-6-[1-(difluoromethoxy)-2,2,2-trifluoroethyl]-1,2,3,4-tetrahydropyrimido[1,2-a]benzimidazole or a salt thereof;

[31] The compound according to the above-mentioned [30] wherein 9-chloro-1-(2,4-dichlorophenyl)-6-[1-(difluoromethoxy)-2,2,2-trifluoroethyl]-1,2,3,4-tetrahydropyrimido[1,2-a]benzimidazole is (+)-9-chloro-1-(2,4-dichlorophenyl)-6-[1-(difluoromethoxy)-2,2,2-trifluoroethyl]-1,2,3,4-tetrahydropyrimido[1,2-a]benzimidazole;

[32] The compound according to the above-mentioned [30] wherein 9-chloro-1-(2,4-dichlorophenyl)-6-[1-(difluoromethoxy)-2,2,2-trifluoroethyl]-1,2,3,4-tetrahydropyrimido[1,2-a]benzimidazole is (−)-9-chloro-1-(2,4-dichlorophenyl)-6-[1-(difluoromethoxy)-2,2,2-trifluoroethyl]-1,2,3,4-tetrahydropyrimido[1,2-a]benzimidazole;

[33] 1-[9-Chloro-1-(6-methoxy-2-methylpyridin-3-yl)-1,2,3,4-tetrahydropyrimido[1,2-a]benzimidazol-6-yl]propyl acetate or a salt thereof;

[34] The compound according to the above-mentioned [33] wherein 1-[9-chloro-1-(6-methoxy-2-methylpyridin-3-yl)-1,2,3,4-tetrahydropyrimido[1,2-a]benzimidazol-6-yl]propyl acetate is (+)-1-[9-chloro-1-(6-methoxy-2-methylpyridin-3-yl)-1,2,3,4-tetrahydropyrimido[1,2-a]benzimidazol-6-yl]propyl acetate;

[35] The compound according to the above-mentioned [33] wherein 1-[9-chloro-1-(6-methoxy-2-methylpyridin-3-yl)-1,2,3,4-tetrahydropyrimido[1,2-a]benzimidazol-6-yl]propyl acetate is (−)-1-[9-chloro-1-(6-methoxy-2-methylpyridin-3-yl)-1,2,3,4-tetrahydropyrimido[1,2-a]benzimidazol-6-yl]propyl acetate;

[36] 1-[9-Chloro-1-(2,4-dichlorophenyl)-1,2,3,4-tetrahydropyrimido[1,2-a]benzimidazol-6-yl]propan-1-ol or a salt thereof;

[37] The compound according to the above-mentioned [36] wherein 1-[9-chloro-1-(2,4-dichlorophenyl)-1,2,3,4-tetrahydropyrimido[1,2-a]benzimidazol-6-yl]propan-1-ol is (+)-1-[9-chloro-1-(2,4-dichlorophenyl)-1,2,3,4-tetrahydropyrimido[1,2-a]benzimidazol-6-yl]propan-1-ol;

[38] The compound according to the above-mentioned [36] wherein 1-[9-chloro-1-(2,4-dichlorophenyl)-1,2,3,4-tetrahydropyrimido[1,2-a]benzimidazol-6-yl]propan-1-ol is (−)-1-[9-chloro-1-(2,4-dichlorophenyl)-1,2,3,4-tetrahydropyrimido[1,2-a]benzimidazol-6-yl]propan-1-ol;

[39] 5-[10-Chloro-7-(1-ethylpropyl)-2,3,4,5-tetrahydro-1H-[1,3]diazepino[1,2-a]benzimidazol-1-yl]-N,N,4-trimethylpyridin-2-amine or a salt thereof;

[40] 3-[9-Chloro-1-(2,4-dichlorophenyl)-1,2,3,4-tetrahydropyrimido[1,2-a]benzimidazol-6-yl]pentan-3-ol or a salt thereof;

[41] 1-(2,4-Dichlorophenyl)-N,N-diethyl-9-fluoro-1,2,3,4-tetrahydropyrimido[1,2-a]benzimidazol-6-amine or a salt thereof;

[42] [8-Chloro-1-(2,4-dichloro-6-methylphenyl)-2,3-dihydro-1H-imidazo[1,2-a]benzimidazol-5-yl](dicyclopropyl)methanol or a salt thereof;

[43] Dicyclopropyl[1-(2,4-dichlorophenyl)-9-methoxy-1,2,3,4-tetrahydropyrimido[1,2-a]benzimidazol-6-yl]methanol or a salt thereof;

[44] [9-Chloro-1-(6-methoxy-2-methylpyridin-3-yl)-1,2,3,4-tetrahydropyrimido[1,2-a]benzimidazol-6-yl](dicyclopropyl)methanol or a salt thereof;

[45] A prodrug of the compound according to the above-mentioned [1];

[46] A pharmaceutical which comprises the compound according to the above-mentioned [1] or a prodrug thereof;

[47] The pharmaceutical according to the above-mentioned [46] which is for treating or preventing a disease associated with the functions of a CRF receptor;

[48] The pharmaceutical according to the above-mentioned [47] wherein the disease is affective disorder, depression or anxiety;

[49] A method for treating or preventing a disease associated with the functions of a CRF receptor, which comprises administering to a subject in need thereof an effective amount of the compound according to the above-mentioned [1] or a prodrug thereof;

[50] A use of the compound according to the above-mentioned [1] or a prodrug thereof for manufacturing an agent for treating or preventing a disease associated with the functions of a CRF receptor; and the like.

Each symbol in the above formula is hereinafter described in more detail.

As the "halogen atom" or "halogen" used in the present specification, fluorine, chlorine, bromine or iodine can be mentioned.

The term "optionally halogenated" used in the present specification means being optionally substituted by 1 to 5, preferably 1 to 3, halogen atoms.

As the "hydrocarbon group" of the term "optionally substituted hydrocarbon group" used in the present specification, for example, aliphatic hydrocarbon group, monocyclic saturated hydrocarbon group and aromatic hydrocarbon group and the like can be mentioned, with preference given to those having 1 to 16 carbon atoms. Specifically, for example, alkyl, alkenyl, alkynyl, cycloalkyl, aryl and the like are used.

The "alkyl" is preferably, for example, lower alkyl or the like, and, for example, $C_{1-6}$ alkyl such as methyl, ethyl, propyl, isopropyl, butyl, isobutyl, sec-butyl, tert-butyl, pentyl, hexyl etc., and the like are widely used.

The "alkenyl" is preferably, for example, lower alkenyl or the like, and, for example, $C_{2-6}$ alkenyl such as vinyl, 1-propenyl, allyl, isopropenyl, butenyl, isobutenyl etc., and the like are widely used.

The "alkynyl" is preferably, for example, lower alkynyl or the like, and, for example, $C_{2-6}$ alkynyl such as ethynyl, propargyl, 1-propynyl etc., and the like are widely used.

The "cycloalkyl" is preferably, for example, lower cycloalkyl or the like, and, for example, $C_{3-6}$ cycloalkyl such as cyclopropyl, cyclobutyl, cyclopentyl and cyclohexyl and the like are widely used.

The "aryl" is preferably, for example, $C_{6-14}$ aryl such as phenyl, 1-naphthyl, 2-naphthyl, biphenylyl, 2-anthryl etc., or the like, more preferably $C_{6-10}$ aryl, and, for example, phenyl and the like are widely used.

As the "$C_{1-9}$ alkyl" used in the present specification, for example, methyl, ethyl, propyl, isopropyl, butyl, isobutyl, sec-butyl, tert-butyl, pentyl, isopentyl, neopentyl, hexyl, isohexyl, heptyl, octyl, nonyl etc., and the like can be mentioned.

As the substituent which the "hydrocarbon group" of the "optionally substituted hydrocarbon group" may have, for example, (1) halogen atom (e.g., fluorine, chlorine; bromine, iodine),
(2) nitro,
(3) cyano, (4) optionally substituted alkyl (e.g., $C_{1-9}$ alkyl (preferably alkyl) optionally having 1 to 5 substituent(s) selected from a halogen atom, nitro, cyano, hydroxy, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, optionally halogenated $C_{1-6}$ alkyl such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl etc., and the like), (5) optionally substituted aryl (e.g., $C_{6-10}$ aryl optionally having 1 to 5 substituent(s) selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryl such as phenyl, naphthyl etc., and the like), (6) hydroxy, (7) optionally halogenated alkylenedioxy (e.g., optionally halogenated $C_{1-3}$ alkylenedioxy such as methylenedioxy, difluoromethylenedioxy etc., and the like), (8) optionally substituted lower alkoxy (e.g., $C_{1-6}$ alkoxy optionally having 1 to 5 substituent(s) selected from a halogen atom, nitro, cyano, hydroxy, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{3-6}$ cycloalkyl, $C_{6-10}$ aryloxy, optionally halogenated $C_{1-6}$ alkyl-carbonylamino and the like; for example, optionally halogenated $C_{1-6}$ alkoxy such as methoxy, ethoxy, propoxy, isopropoxy, butoxy, isobutoxy, pentyloxy, hexyloxy, trifluoromethoxy etc., and the like), (9) optionally substituted aryloxy (e.g., $C_{6-10}$ aryloxy optionally having 1 to 5 substituent(s) selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ carbamoyl, alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryloxy such as phenyloxy, naphthyloxy etc., and the like),

(10) optionally substituted lower alkanoyloxy (e.g., formyloxy; $C_{3-6}$ cycloalkyl-carbonyloxy; $C_{1-6}$ alkyl-carbonyloxy optionally having 1 to 5 substituent(s) selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, alkylamino, $C_{1-6}$ alkylsulfonyl, carboxy, $C_{1-6}$ alkyl-carbonyl, $C_{1-6}$ alkoxy-carbonyl, carbamoyl, mono-$C_{1-6}$ alkyl-carbamoyl, alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino, tert-butyl(dimethyl)silyloxy; and the like; for example, $C_{1-6}$ alkyl-carbonyloxy such as acetyloxy, propionyloxy, butyryloxy, isobutyryloxy etc., and the like),

(11) optionally substituted arylcarbonyloxy (e.g., $C_{6-10}$ arylcarbonyloxy optionally having 1 to 5 substituent(s) selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryl-carbonyloxy such as benzoyloxy, naphthoyloxy etc., and the like),

(12) optionally halogenated lower alkylsulfonyloxy (e.g., optionally halogenated $C_{1-6}$ alkylsulfonyloxy such as methylsulfonyloxy etc.),

(13) carboxy,

(14) optionally substituted lower alkanoyl (e.g., $C_{1-6}$ alkyl-carbonyl optionally having 1 to 5 substituent(s) selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like or formyl; for example, $C_{1-6}$ alkyl-carbonyl such as acetyl, propionyl etc., or formyl and the like),

(15) optionally substituted arylcarbonyl (e.g., $C_{6-10}$ aryl-carbonyl optionally having 1 to 5 substituent(s) selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryl-carbonyl such as benzoyl, naphthoyl etc., and the like),

(16) optionally substituted lower alkoxycarbonyl (e.g., $C_{1-6}$ alkoxy-carbonyl optionally having 1 to 5 substituent(s) selected from a halogen atom, nitro, cyano, hydroxy, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{1-6}$ alkoxy-carbonyl such as methoxycarbonyl, ethoxycarbonyl, propoxycarbonyl, butoxycarbonyl etc., and the like),

(17) optionally substituted aralkyloxycarbonyl (e.g., $C_{7-12}$ aralkyloxy-carbonyl optionally having 1 to 5 substituent(s) selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{7-12}$ aralkyloxy-carbonyl such as benzyloxycarbonyl etc., and the like),

(18) carbamoyl,

(19) carbamoyl substituted by one optionally-substituted lower alkyl (e.g., mono-$C_{1-6}$ alkyl-carbamoyl optionally having 1 to 5 substituent(s) selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, mono-$C_{1-6}$ alkyl-carbamoyl such as methylcarbamoyl, ethylcarbamoyl etc., and the like),

(20) carbamoyl substituted by two optionally substituted lower alkyl (e.g., di-$C_{1-6}$ alkyl-carbamoyl optionally having 1 to 5 substituent(s) selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, di-$C_{1-6}$ alkyl-carbamoyl such as dimethylcarbamoyl, diethylcarbamoyl etc., and the like),

(21) optionally substituted arylcarbamoyl (e.g., $C_{6-10}$ arylcarbamoyl optionally having 1 to 5 substituent(s) selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryl-carbamoyl such as phenylcarbamoyl, naphthylcarbamoyl etc., and the like),

(22) amino,

(23) amino substituted by one optionally substituted lower alkyl (e.g., mono-$C_{1-6}$ alkylamino optionally having 1 to 5 substituent(s) selected from halogen atom, nitro, cyano, hydroxy, optionally halogenated $C_{1-6}$ alkoxy, amino, mono-$C_{1-6}$ alkylamino, di-$C_{1-6}$ alkylamino, carboxy, optionally halogenated $C_{1-6}$ alkyl-carbonyl, optionally halogenated $C_{1-6}$ alkylsulfonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino, and the like; for example, mono-$C_{1-6}$ alkylamino such as methylamino, ethylamino etc., and the like),

(24) amino substituted by two optionally substituted lower alkyls (e.g., di-$C_{1-6}$ alkylamino optionally having 1 to 5 substituent(s) selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, di-$C_{1-6}$ alkylamino such as dimethylamino, diethylamino etc., and the like),

(25) 3- to 6-membered cyclic amino optionally containing, besides a carbon atom and one nitrogen atom, 1 to 3 hetero atoms selected from a nitrogen atom, an oxygen atom and a sulfur atom, which optionally has substituent(s) (e.g., 3- to 6-membered cyclic amino optionally containing, besides a carbon atom and one nitrogen atom, 1 to 3 hetero atoms selected from a nitrogen atom, an oxygen atom and a sulfur atom, which optionally has 1 to 5 substituent(s) selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino, oxo and the like; for example, aziridinyl, azetidinyl, pyrrolidinyl, pyrrolinyl, pyrrolyl, imidazolyl, pyrazolyl, imidazolidinyl, piperidyl, morpholinyl, dihydropyridyl, tetrahydropyridyl, piperazinyl, N-methylpiperazinyl, N-ethylpiperazinyl and the like),

(26) amino substituted by optionally substituted lower alkylcarbonyl (e.g., $C_{1-6}$ alkyl-carbonylamino optionally having 1 to 5 substituent(s) selected from a halogen atom, nitro, cyano, hydroxy, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ arylcarbamoyl, $C_{6-10}$ aryl, $C_{6-10}$ aryloxy, optionally halogenated $C_{1-6}$ alkyl-carbonylamino and the like; for example, optionally halogenated $C_{1-6}$ alkyl-carbonylamino such as acetylamino, trifluoroacetylamino etc., and the like),

(27) oxo,

(28) optionally substituted heterocyclic group (e.g., 5- or 6-membered heterocyclic group optionally containing, besides a carbon atom and one nitrogen atom, 1 to 3 hetero atoms selected from a nitrogen atom, an oxygen atom and a sulfur atom, which optionally has 1 to 5 substituent(s) selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino, oxo and the like; for example, thienyl, furyl, pyrrolyl, pyrrolidinyl, oxazolyl, isoxazolyl, thiazolyl, isothiazolyl, pyrazolyl, pyrazolidinyl, imidazolyl, imidazolinyl, triazolyl, tetrazolyl, pyridyl, pyrimidinyl, thiomorpholinyl, morpholinyl, piperidino, piperidyl, thiopyranyl, oxazinyl, thiazinyl, piperazinyl, triazinyl, pyridazinyl, pyrazinyl and the like; preferably pyridyl and the like),

(29) mercapto,

(30) lower alkylthio (e.g., $C_{1-6}$ alkylthio such as methylthio, ethylthio, propylthio, isopropylthio, butylthio, sec-butylthio, tert-butylthio etc., and the like),

(31) arylthio (e.g., $C_{6-10}$ arylthio such as phenylthio, naphthylthio etc., and the like),

(32) lower alkylsulfinyl (e.g., $C_{1-6}$ alkylsulfinyl such as methylsulfinyl, ethylsulfinyl, propylsulfinyl, butylsulfinyl etc., and the like),

(33) arylsulfinyl (e.g., $C_{6-10}$ arylsulfinyl such as phenylsulfinyl, naphthylsulfinyl etc., and the like),

(34) lower alkylsulfonyl (e.g., $C_{1-6}$ alkylsulfonyl such as methylsulfonyl, ethylsulfonyl, propylsulfonyl, butylsulfonyl etc., and the like),

(35) arylsulfonyl (e.g., $C_{6-10}$ arylsulfonyl such as phenylsulfonyl, naphthylsulfonyl etc., and the like)

(36) sulfamoyl,

(37) sulfamoyl substituted by one lower alkyl (e.g., mono-$C_{1-6}$ alkylsulfamoyl such as N-methylsulfamoyl, ethylsulfamoyl, N-propylsulfamoyl, N-isopropylsulfamoyl, N-butylsulfamoyl etc., and the like),

(38) sulfamoyl substituted by two lower alkyls (e.g., di-$C_{1-6}$ alkylsulfamoyl such as N,N-dimethylsulfamoyl, N,N-diethylsulfamoyl, N,N-dipropylsulfamoyl, N,N-dibutylsulfamoyl etc., and the like),

(39) $C_{3-6}$ cycloalkyl,

(40) imino substituted by optionally halogenated $C_{1-6}$ alkoxy (e.g., methoxyimino, difluoromethoxyimino etc.),

(41) formyl,

(42) $C_{2-6}$ alkenyloxy (e.g., ethenyloxy etc.),

(43) an optionally substituted lower cycloalkyloxy (e.g., $C_{3-6}$ cycloalkyl optionally having 1 to 5 substituent(s) selected from halogen atom, nitro, cyano, hydroxy, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, alkylcarbamoyl, $C_{6-10}$ aryl-carbamoyl, $C_{6-10}$ aryl, $C_{6-10}$ aryloxy, optionally halogenated $C_{1-6}$ alkyl-carbonylamino and the like),

(44) amino optionally having 1 to 5 substituent(s) selected from halogenated $C_{1-6}$ alkylsulfonyl, $C_{1-6}$ alkylcarbamoyl, $C_{1-6}$ alkoxy-carbonyl and $C_{3-6}$ cycloalkyl-carbonyl (e.g., methylsulfonylamino, trifluoroethylamino, ethylcarbamoylamino, difluoromethylcarbonylamino, methoxycarbonylamino, cyclopropylcarbonylamino etc.),

(45) azido, and the like are used.

The "hydrocarbon group" of the "optionally substituted hydrocarbon group" may have 1 to 5, preferably 1 to 3, substituent(s) selected from the aforementioned substituents (1)-(45) [hereinafter the group consisting of these (1)-(45) is sometimes to be abbreviated as "substituent group A"] at substitutable position(s) of the hydrocarbon group. When the number of substituents is two or more, each substituent may be the same or different.

As the substituent which the "hydrocarbon group" optionally has, preferably, 1 to 5 (preferably 1 to 3) substituent(s) selected from (1) halogen atom, (2) nitro, (3) cyano, (4) hydroxy, (5) optionally substituted $C_{1-6}$ alkyl (e.g., $C_{1-6}$ alkyl optionally having substituent(s) selected from halogen atom, hydroxy and di-$C_{1-6}$ alkylamino, etc.), (6) optionally halogenated $C_{1-6}$ alkoxy, (7) $C_{7-13}$ aralkyloxy, (8) amino, (9) mono-$C_{1-6}$ alkylamino, (10) di-$C_{1-6}$ alkylamino, (11) carboxy, (12) $C_{1-6}$ alkyl-carbonyl, (13) $C_{1-6}$ alkoxy-carbonyl, (14) carbamoyl, (15) mono-$C_{1-6}$ alkyl-carbamoyl, (16) di-$C_{1-6}$ alkyl-carbamoyl, (17) $C_{6-10}$ aryl-carbamoyl, (18) $C_{6-10}$ aryl (e.g., phenyl), (19) $C_{6-10}$ aryloxy, (20) $C_{1-6}$ alkyl-carbonylamino, (21) $C_{1-6}$ alkyl-carbonyloxy, (22) heterocyclic group (e.g., pyridyl and the like) and the like can be mentioned.

As the "heterocyclic group" of the term "optionally substituted heterocyclic group" used in the present specification, for example, a 5- to 14-membered (preferably 5- to 10-membered) (monocyclic, bicyclic or tricyclic, preferably monocyclic or bicyclic) heterocyclic group optionally containing, besides a carbon atom, 1 to 4 (preferably 1 to 3) hetero atoms of one or two kinds selected from a nitrogen atom, an oxygen atom and a sulfur atom, can be mentioned. For example, a 5-membered ring group containing, besides a carbon atom, 1 to 4 hetero atoms selected from a nitrogen atom, an oxygen atom and a sulfur atom, such as 2- or 3-thienyl, 2- or 3-furyl, 1-, 2-or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 2- or 4-imidazolinyl, 1,2,3-triazolyl, 1,2,4-triazolyl, 1H- or 2H-tetrazolyl and the like; for example, a 6-membered ring group containing, besides a carbon atom, 1 to 4 hetero atoms selected from a nitrogen atom, an oxygen atom and a sulfur atom, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidino, 2-, 3- or 4-piperidyl, thiopyranyl, 1,4-oxazinyl, 1,4-thiazinyl, 1,3-thiazinyl, 1- or 2-piperazinyl, triazinyl, 3- or 4-pyridazinyl, pyrazinyl, N-oxido-3- or 4-pyridazinyl and the like; for example, a bicyclic or tricyclic fused ring group containing, besides a carbon atom, 1 to 4 hetero atoms selected from a nitrogen atom, an oxygen atom and a sulfur atom (preferably, a group formed by condensation of the aforementioned 5- or 6-membered ring with one or two 5- or 6-membered ring group(s) optionally containing, besides a carbon atom, 1 to 4 hetero atoms selected from a nitrogen atom, an oxygen atom and a sulfur atom), such as indolyl, benzofuryl, benzothiazolyl, benzoxazolyl, benzimidazolyl, quinolyl, isoquinolyl, phthalazinyl, quinazolinyl, quinoxalinyl, indolizinyl, quinolizinyl, 1,8-naphthyridinyl, dibenzofuranyl, carbazolyl, acridinyl, phenanthridinyl, chromanyl, phenothiazinyl, phenoxazinyl and the like; and the like are used. Of these, a 5- to 7-membered (preferably 5- or 6-membered) heterocyclic group containing, besides a carbon atom, 1 to 3 heteroatoms selected from a nitrogen atom, an oxygen atom and a sulfur atom is preferable.

As the substituent that the "heterocyclic group" of the "optionally substituted heterocyclic group" may have, (i) the aforementioned "optionally substituted hydrocarbon group", (ii) the groups recited as example's of the substituent(s) that the "optionally substituted hydrocarbon group" may have, and the like can be mentioned. Particularly preferably, for example, (1) halogen atom (e.g., fluorine, chlorine, bromine, iodine), (2) optionally halogenated alkyl (e.g., optionally halogenated $C_{1-9}$ alkyl (preferably $C_{1-6}$ alkyl) such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl etc., and the like), (3) cycloalkyl (e.g., $C_{3-6}$ cycloalkyl such as cyclopropyl, cyclobutyl, cyclopentyl, cyclohexyl and the like), (4) lower alkynyl (e.g., $C_{2-6}$ alkynyl such as ethynyl, 1-propynyl, propargyl etc., and the like), (5) lower alkenyl (e.g., $C_{2-6}$ alkenyl such as vinyl, allyl, isopropenyl, butenyl, isobutenyl etc., and the like), (6) aralkyl (e.g., $C_{7-12}$ aralkyl such as benzyl, α-methylbenzyl, phenethyl etc., and the like), (7) aryl (e.g., $C_{6-10}$ aryl such as phenyl, naphthyl etc., and the like, preferably phenyl), (8) optionally halogenated lower alkoxy (e.g., optionally halogenated $C_{1-6}$ alkoxy such as methoxy, ethoxy, propoxy, isopropoxy, butoxy, isobutoxy, sec-butoxy, tert-butoxy, difluoromethoxy etc., and the like), (9) aryloxy (e.g.; $C_{6-10}$ aryloxy such as phenoxy etc., and the like),

(10) lower alkanoyl (e.g., formyl; $C_{1-6}$ alkyl-carbonyl such as acetyl, propionyl, butyryl, isobutyryl etc., and the like),

(11) arylcarbonyl (e.g., $C_{6-10}$ aryl-carbonyl such as benzoyl, naphthoyl etc., and the like),

(12) lower alkanoyloxy (e.g., formyloxy; $C_{1-6}$ alkyl-carbonyloxy such as acetyloxy, propionyloxy, butyryloxy, isobutyryloxy etc., and the like),

(13) arylcarbonyloxy (e.g., $C_{6-10}$ aryl-carbonyloxy such as benzoyloxy, naphthoyloxy etc., and the like),

(14) optionally halogenated lower alkylsulfonyloxy (e.g., optionally halogenated $C_{1-6}$ alkylsulfonyloxy such as methylsulfonyloxy etc.),

(15) carboxy,

(16) lower alkoxycarbonyl (e.g., $C_{1-6}$ alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl etc., and the like),

(17) aralkyloxycarbonyl (e.g., $C_{7-12}$ aralkyloxy-carbonyl such as benzyloxycarbonyl etc., and the like),

(18) carbamoyl,

(19) oxo,

(20) amidino,

(21) imino,

(22) amino,

(23) amino substituted by one lower alkyl (e.g., mono-$C_{1-6}$ alkylamino such as methylamino, ethylamino, propylamino, isopropylamino, butylamino etc., and the like),

(24) amino substituted by two lower alkyls (e.g., di-$C_{1-6}$ alkylamino such as dimethylamino, diethylamino, dipropylamino, diisopropylamino, dibutylamino, N-ethyl-N-methylamino etc., and the like),

(25) 3- to 6-membered cyclic amino optionally containing, besides a carbon atom and one nitrogen atom, 1 to 3 hetero atoms selected from a nitrogen atom, an oxygen atom and a sulfur atom, which optionally has substituent(s) (e.g., 3- to 6-membered cyclic amino optionally containing, besides a carbon atom and one nitrogen atom, 1 to 3 hetero atoms selected from a nitrogen atom, an oxygen atom and a sulfur atom, which optionally has 1 to 5 substituent(s) selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino, oxo and the like; for example, aziridinyl, azetidinyl, pyrrolidinyl, pyrrolinyl, pyrrolyl, imidazolyl, pyrazolyl, imidazolidinyl, piperidyl, morpholinyl, dihydropyridyl, tetrahydropyridyl, piperazinyl, N-methylpiperazinyl, N-ethylpiperazinyl and the like),

(26) optionally halogenated alkylenedioxy (e.g., optionally halogenated $C_{1-3}$ alkylenedioxy such as methylenedioxy, difluoromethylenedioxy etc., and the like),

(27) hydroxy,

(28) nitro,

(29) cyano,

(30) mercapto,

(31) sulfo,

(32) sulfino,

(33) phosphono,

(34) sulfamoyl,

(35) sulfamoyl substituted by one lower alkyl (e.g., mono-$C_{1-6}$ alkylsulfamoyl such as N-methylsulfamoyl, N-ethylsulfamoyl, N-propylsulfamoyl, N-isopropylsulfamoyl, N-butylsulfamoyl etc., and the like),

(36) sulfamoyl substituted by two lower alkyls (e.g., di-$C_{1-6}$ alkylsulfamoyl such as N,N-dimethylsulfamoyl, diethylsulfamoyl, N,N-dipropylsulfamoyl, N,N-dibutylsulfamoyl etc., and the like),

(37) lower alkylthio (e.g., $C_{1-6}$ alkylthio such as methylthio, ethylthio, propylthio, isopropylthio, butylthio, sec-butylthio, tert-butylthio etc., and the like),

(38) arylthio (e.g., $C_{6-10}$ arylthio such as phenylthio, naphthylthio etc., and the like),

(39) lower alkylsulfinyl (e.g., $C_{1-6}$ alkylsulfinyl such as methylsulfinyl, ethylsulfinyl, propylsulfinyl, butylsulfinyl etc., and the like),

(40) arylsulfinyl (e.g., $C_{6-10}$ arylsulfinyl such as phenylsulfinyl, naphthylsulfinyl etc., and the like),

(41) lower alkylsulfonyl (e.g., $C_{1-6}$ alkylsulfonyl such as methylsulfonyl, ethylsulfonyl, propylsulfonyl, butylsulfonyl etc., and the like),

(42) arylsulfonyl (e.g., $C_{6-10}$ arylsulfonyl such as phenylsulfonyl, naphthylsulfonyl etc., and the like)

(43) amino substituted by one lower cycloalkyl (e.g., mono-$C_{3-6}$ cycloalkylamino such as cyclopropylamino) and the like are used.

The "heterocyclic group" of the "optionally substituted heterocyclic group" may have 1 to 5, preferably 1 to 3, substituent(s) selected from the aforementioned substituents (1)-(43) [hereinafter the group consisting of these (1)-(43) is sometimes to be abbreviated as "substituent group B"], at substitutable position(s) of the heterocyclic group. When the number of the substituents is two or more, each substituent may be the same or different.

As the "acyl" used in the present specification, for example, a group of the formula: —$COR^A$, —CO—$OR^A$, —$SO_2R^A$, $SOR^A$, —CO—$NR^{A'}R^{B'}$ or —CS—$NR^{A'}R^{B'}$ wherein $R^A$ is a hydrogen, an optionally substituted hydrocarbon group or an optionally substituted heterocyclic group; $R^{A'}$ and $R^{B'}$ are each independently a hydrogen, an optionally substituted hydrocarbon group or an optionally substituted heterocyclic group or $R^{A'}$ and $R^{B'}$ may form, taken together with the adjacent nitrogen atom, an optionally substituted nitrogen-containing heterocyclic ring.

The "nitrogen-containing heterocyclic ring" of the term "optionally substituted nitrogen-containing heterocyclic ring" formed by $R^{A'}$ and $R^{B'}$ taken together with the adjacent nitrogen atom is, for example, a 5- to 7-membered nitrogen-containing heterocyclic ring having at least one nitrogen atom besides a carbon atom, optionally further containing 1 or 2 hetero atoms selected from a nitrogen atom, an oxygen atom and a sulfur atom. As the "nitrogen-containing heterocyclic ring", may have, for example, pyrrolidine, imidazolidine, pyrazolidine, piperidine, piperazine, morpholine, thiomorpholine and the like.

The "nitrogen-containing heterocyclic ring" may have 1 to 3, preferably 1 or 2, substituent(s) at substitutable position(s) of the nitrogen-containing heterocyclic ring. As the substituent, those similar to the substituent(s) that the aforementioned "hydrocarbon group" may have are used. When the number of substituents is two or more, each substituent may be the same or different.

Examples of the "acyl" include formyl, $C_{1-6}$ alkyl-carbonyl (e.g., acetyl, propionyl, etc.), $C_{3-6}$ cycloalkyl-carbonyl (e.g., cyclopropyl carbonyl, cyclobutyl carbonyl, cyclopentyl carbonyl, cyclohexyl carbonyl, etc.), $C_{1-6}$ alkoxy-carbonyl (e.g., methoxycarbonyl, ethoxycarbonyl, etc.), $C_{6-14}$ aryl-carbonyl (e.g., benzoyl, etc.), $C_{7-16}$ aralkyl-carbonyl (e.g., phenylacetyl, 3-phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, etc.), 5- or 6-membered heterocyclic-carbonyl (e.g., nicotinoyl, isonicotinoyl, thenyl, furoyl, morpholinocarbonyl, thiomorpholinocarbonyl, piperazin-1-ylcarbonyl, pyrrolidin-1-ylcarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-14}$ arylcarbamoyl (e.g., phenylcarbamoyl, 1-naphthylcarbamoyl, etc.), $C_{1-6}$ alkoxy-carbamoyl (e.g., methoxycarbamoyl, ethoxycarbamoyl, etc.), 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), $C_{1-6}$ alkylsulfinyl (e.g., methylsulfinyl, ethylsulfinyl, propylsulfinyl, butylsulfinyl etc.), $C_{6-14}$ arylsulfinyl (e.g., phenylsulfinyl, etc.), $C_{1-6}$ alkylsulfonyl (e.g., methylsulfonyl, ethylsulfonyl, propylsulfonyl, butylsulfonyl, etc.), $C_{6-14}$ arylsulfinyl (e.g., phenylsulfinyl, etc.) and the like.

The term used in the present specification "optionally substituted amino" means amino optionally having, as substituent, 1 or 2, the same or different groups selected from, for example, (i) the aforementioned "optionally substituted hydrocarbon group", (ii) the groups recited as examples of the substituent that the "optionally substituted hydrocarbon group" may have and the like. Preferable examples of the substituent that the "amino" may have include an optionally substituted $C_{1-6}$ alkyl, an optionally substituted $C_{6-10}$ aryl, $C_{3-6}$ cycloalkyl and the like. As the substituent that the "$C_{1-6}$ alkyl", "$C_{6-10}$ aryl" and "$C_{3-6}$ cycloalkyl" may have, those similar to the substituent(s) that the aforementioned "hydrocarbon group" may have are used.

The term used in the present specification "optionally substituted carbamoyl" means (1) carbamoyl or (2) carbamoyl having, instead of the hydrogen atom of carbamoyl, one group selected from, for example, (i) the aforementioned "optionally substituted hydrocarbon group", (ii) the groups recited as examples of the substituent that the "optionally substituted hydrocarbon group" may have and the like. Preferable examples of the substituent that the "carbamoyl" may have include an optionally substituted $C_{1-6}$ alkyl, an optionally substituted $C_{6-10}$ aryl, $C_{3-6}$ cycloalkyl and the like. As the substituent that the "$C_{1-6}$ alkyl", "$C_{6-10}$ aryl" and "$C_{3-6}$ cycloalkyl" may have, those similar to the substituent(s) that the aforementioned "hydrocarbon group" may have are used.

The term used in the present specification "optionally substituted hydroxy" means (1) hydroxy or (2) hydroxy having, instead of the hydrogen atom of hydroxy, one group selected from, for example, (i) the aforementioned "optionally substituted hydrocarbon group", (ii) the groups recited as examples of the substituent that the "optionally substituted hydrocarbon group" may have and the like. As the "optionally substituted hydroxy", for example, hydroxy, an optionally substituted $C_{1-6}$ alkoxy, an optionally substituted $C_{2-6}$ alkenyloxy, an optionally substituted $C_{2-6}$ alkynyloxy, an optionally substituted $C_{3-6}$ cycloalkyloxy, an optionally substituted $C_{6-14}$ aryloxy and the like can be mentioned. Preferred are a hydroxy, an optionally substituted $C_{1-6}$ alkoxy, an optionally substituted $C_{6-14}$ aryloxy and the like. As the substituent that the "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" may have, those similar to the substituent(s) that the aforementioned "hydrocarbon group" may have are used.

The term used in the present specification "optionally substituted mercapto" means (1) mercapto or (2) mercapto having, instead of the hydrogen atom of mercapto, one group selected from, for example, (i) the aforementioned "optionally substituted hydrocarbon group", (ii) the groups recited as examples of the substituent that the "optionally substituted hydrocarbon group" may have and the like. As the "optionally substituted mercapto", for example, mercapto, an optionally substituted $C_{1-6}$ alkylthio, an optionally substituted $C_{2-6}$ alkenylthio, an optionally substituted $C_{2-6}$ alkynylthio, an optionally substituted $C_{3-6}$ cycloalkylthio, an optionally substituted $C_{6-14}$ arylthio and the like can be mentioned. Preferred are a mercapto, an optionally substituted $C_{1-6}$ alkylthio, an optionally substituted $C_{6-14}$ arylthio and the like. As the substituent that the "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, those similar to the substituent(s) that the aforementioned "hydrocarbon group" may have are used.

As the "alkyl" of the term "optionally substituted alkyl" used in the present specification, for example, $C_{1-6}$ alkyl such as methyl, ethyl, propyl, isopropyl, butyl, isobutyl, sec-butyl, tert-butyl etc., and the like can be mentioned. The "alkyl" may have, as the substituent, for example, 1 to 3 substituent(s) that the aforementioned "hydrocarbon group" may have, and the like.

As the "lower alkyl" of the term "optionally substituted lower alkyl" used in the present specification, for example, $C_{1-6}$ alkyl such as methyl, ethyl, propyl, isopropyl, butyl, isobutyl, sec-butyl, test-butyl etc., and the like can be mentioned. The "lower alkyl" may have, as the substituent, for example, 1 to 3 substituent(s) that the aforementioned "hydrocarbon group" may have, and the like.

As the "$C_{1-9}$ alkyl" of the term "optionally substituted $C_{1-9}$ alkyl" used in the present specification, for example, $C_{1-9}$ alkyl such as methyl, ethyl, propyl, isopropyl, butyl, isobutyl, sec-butyl, tert-butyl, pentyl, isopentyl, neopentyl, hexyl, isohexyl, heptyl, octyl, nonyl etc., and the like can be mentioned. The "$C_{1-9}$ alkyl" may have, as the substituent, for example, 1 to 3 substituent(s) that the aforementioned "hydrocarbon group" may have, and the like.

As the "$C_{1-6}$ alkyl" of the term "optionally substituted $C_{1-6}$ alkyl" used in the present specification, for example, $C_{1-6}$ alkyl such as methyl, ethyl, propyl, isopropyl, butyl, isobutyl, sec-butyl, tert-butyl, pentyl, isopentyl, neopentyl, hexyl, isohexyl etc., and the like can be mentioned. The "$C_{1-6}$ alkyl" may have, as the substituent, for example, 1 to 3 substituent(s) that the aforementioned "hydrocarbon group" may have, and the like.

As the "$C_{2-6}$ alkenyl" of the term "optionally substituted $C_{2-6}$ alkenyl" used in the present specification, for example, $C_{2-6}$ alkenyl such as vinyl, allyl, isopropenyl, butenyl, isobutenyl etc., and the like can be mentioned. The "alkenyl" may have, as the substituent, for example, 1 to 3 substituent(s) that the aforementioned "hydrocarbon group" may have, and the like.

As the "optionally halogenated $C_{1-9}$ alkyl" used in the present specification, for example, $C_{1-9}$ alkyl optionally having 1 to 5 (preferably 1 to 3) halogen atoms such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl and the like can be mentioned.

As the "optionally halogenated $C_{1-6}$ alkyl" used in the present specification, for example, $C_{1-6}$ alkyl optionally having 1 to 5 (preferably 1 to 3) halogen atoms such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl and the like can be mentioned.

As the "optionally halogenated $C_{1-6}$ alkoxy" used in the present specification, for example, $C_{1-6}$ alkoxy optionally having 1 to 5 (preferably 1 to 3) halogen atoms such as methoxy, ethoxy, propoxy, isopropoxy, butoxy, isobutoxy, pentyloxy, hexyloxy, trifluoromethoxy and the like can be mentioned.

As the "optionally halogenated $C_{1-6}$ alkyl-carbonylamino" used in the present specification, for example, $C_{1-6}$ alkyl-carbonylamino optionally having 1 to 5 (preferably 1 to 3) halogen atoms such as acetylamino, trifluoroacetylamino and the like can be mentioned.

As the "$C_{7-13}$ aralkyloxy" used in the present specification, for example, benzyloxy, phenethyloxy and the like can be mentioned.

X in the formula (I') is a nitrogen or CRx (wherein Rx is a hydrogen or a $C_{1-9}$ alkyl, provided that when X forms a double bond, Rx is absent).

Preferable examples of the "$C_{1-9}$ alkyl" for Rx include methyl, ethyl, propyl, isopropyl, butyl, isobutyl, sec-butyl, tert-butyl, pentyl, isopentyl, neopentyl, hexyl, isohexyl, heptyl, octyl, nonyl and the like.

X is preferably a nitrogen.

$R^1$ in the formula (I') or (I) is (1) an optionally substituted hydrocarbon group, (2) an acyl, (3) an optionally substituted heterocyclic group, (4) an optionally substituted amino, (5)

nitro, (6) an optionally substituted hydroxy, (7) an optionally substituted mercapto, (8) cyano, or (9) halogen.

$R^1$ in the formula (I') or (I) is, more preferably, (1) nitro, (2) halogen, (3) cyano, (4) carboxy, (5) an optionally substituted carbamoyl, (6) an acyl, (7) an optionally substituted $C_{1-9}$ alkyl, (8) an optionally substituted $C_{2-6}$ alkenyl, (9) an optionally substituted amino, or (10) an optionally substituted N-linked 5- or 6-membered heterocyclic group.

The term "N-linked" of the "optionally substituted N-linked 5- or 6-membered heterocyclic group" means that $R^1$ is linked via a nitrogen atom of the 5- or 6-membered heterocyclic group of $R^1$ to the fused tricyclic ring moiety in the compound represented by the formula (I) or (I'). Examples of the "5- or 6-membered heterocyclic group" in the "optionally substituted N-linked 5- or 6-membered heterocyclic group" for $R^1$ include 5- or 6-membered cyclic groups (e.g., thienyl, pyridyl, thiazolyl, imidazolyl, pyrazolyl, pyrrolidinyl) of the aforementioned "heterocyclic group" of the "optionally substituted heterocyclic group".

As the substituent that the "N-linked 5- or 6-membered heterocyclic group" of the "optionally substituted N-linked 5- or 6-membered heterocyclic group" may have, (i) the aforementioned "optionally substituted hydrocarbon group", (ii) the groups recited as examples of the substituent(s) that the "optionally substituted hydrocarbon group" may have, and the like can be mentioned.

Preferable examples of the "hydrocarbon group" of the "optionally substituted hydrocarbon group" for $R^1$ include alkyl (e.g., $C_{1-9}$ alkyl such as methyl, ethyl, propyl, isopropyl, butyl, isobutyl, sec-butyl, tert-butyl, pentyl, isopentyl, neopentyl, hexyl, isohexyl, heptyl, octyl, nonyl etc.) and the like. The "alkyl" may have, for example, 1 to 5, preferably 1 to 3, substituent(s) that the aforementioned "hydrocarbon group" may have, and the like.

Preferable examples of the substituent of the "optionally substituted hydrocarbon group" for $R^1$ include (i) halogen, (ii) nitro, (iii) cyano, (iv) an optionally substituted lower alkyl, (v) hydroxy, (vi) an optionally substituted lower alkoxy, (vii) an optionally substituted lower alkanoyloxy, (viii) an optionally substituted lower alkanoyl, (ix) an optionally substituted lower alkoxycarbonyl, (x) carbamoyl, (xi) an alkylcarbamoyl substituted by one optionally substituted lower alkyl, (xii) amino, (xiii) amino substituted by one optionally substituted lower alkyl, (xiv) amino substituted by two optionally substituted lower alkyls, (xv) a 3- to 6-membered cyclic amino optionally containing, besides a carbon atom and one nitrogen atom, 1 to 3 hetero atoms selected from a nitrogen atom, an oxygen atom and a sulfur atom, which optionally has substituent(s), (xvi) an optionally substituted amino, (xvii) oxo, (xxvii) an optionally substituted heterocyclic group, (xix) a lower alkylthio, (xx) a lower alkylsulfonyl, (xxi) $C_{3-6}$ cycloalkyl, (xxii) imino optionally substituted by optionally halogenated $C_{1-6}$ alkoxy, (xxvii) formyl, (xxiv) $C_{2-6}$ alkenyloxy, (xxv) an optionally substituted $C_{3-6}$ cycloalkyloxy, (xxvi) amino optionally having 1 to 5 substituent(s) selected from halogenated $C_{1-6}$ alkylsulfonyl, $C_{1-6}$ alkylcarbamoyl, $C_{1-6}$ alkoxy-carbonyl and $C_{3-6}$ cycloalkyl-carbonyl, (xxvii) azido, and the like.

More preferable examples of the substituent of the "optionally substituted hydrocarbon group" for $R^1$ include halogen, hydroxy, $C_{3-6}$ cycloalkyl, an optionally substituted $C_{1-6}$ alkoxy, $C_{1-6}$ alkyl-carbonyloxy, $C_{3-6}$ cycloalkyl-carbonyloxy and an optionally substituted $C_{3-6}$ cycloalkyloxy.

Preferable examples of the "optionally substituted amino" for $R^1$ include amino substituted by two optionally substituted lower alkyls (e.g., di-$C_{1-6}$ alkylamino such as dimethylamino, diethylamino, dipropylamino etc.) and the like. The "alkyl" may have, for example, 1 to 5, preferably 1 to 3, substituent(s) that the aforementioned "hydrocarbon group" may have, and the like.

$R^1$ is preferably an optionally substituted hydrocarbon group, a substituted amino, and the like.

$R^2$ in the formula (I') or (I) is (1) an optionally substituted hydrocarbon group, (2) an acyl, (3) an optionally substituted heterocyclic group, or (4) an optionally substituted amino, provided that methyl, ethyl, propyl and methoxymethyl are excluded.

Preferable examples of the "hydrocarbon group" of the "optionally substituted hydrocarbon group" for $R^2$ include aryl (e.g., $C_{6-14}$ aryl such as phenyl, 1-naphthyl, 2-naphthyl, biphenylyl, 2-anthryl etc.), more preferably $C_{6-10}$ aryl (e.g., phenyl etc.) and the like. The "aryl" may have, for example, 1 to 5, preferably 1 to 3, substituent(s) that the aforementioned "hydrocarbon group" may have, and the like.

Preferable examples of the "heterocyclic group" of the "optionally substituted heterocyclic group" for $R^2$ include a 5- to 10-membered (preferably 5- to 7-membered, more preferably 5- or 6-membered) heterocyclic group (e.g., pyrimidinyl, pyridyl, pyrazolyl, etc.) and the like. The "5- to 10-membered heterocyclic group" may have, for example, 1 to 5, preferably 1 to 3, substituent(s) that the aforementioned "heterocyclic, group" may have, and the like.

$R^2$ is preferably an optionally substituted $C_{6-10}$ aryl, an optionally substituted 5- to 10-membered heterocyclic group, and the like.

Preferable examples of the substituent of the "optionally substituted $C_{6-10}$ aryl" for $R^2$ include, (i) halogen, (ii) cyano, (iii) an optionally substituted alkyl, (iv) an optionally substituted-lower alkoxy, (v) carboxy, (vi) carbamoyl, (vii) an alkylcarbamoyl substituted by one optionally substituted lower alkyl, (viii) an alkylcarbamoyl substituted by two optionally substituted lower alkyl (ix) amino, (x) amino substituted by one optionally substituted lower alkyl, (xi) amino substituted by two optionally substituted lower alkyls, (xii) amino substituted by optionally substituted lower alkylcarbonyl, (xiii) a lower alkylthio, (xiv) a lower alkylsulfinyl, (xv) a lower alkylsulfonyl, (xvi) formyl, and the like.

Preferable examples of the substituent of the "optionally substituted 5- to 10-membered heterocyclic group" for $R^2$ include, (i) halogen, (ii) an optionally halogenated alkyl, (iii) a cycloalkyl, (iv) an optionally halogenated lower alkoxy, (v) a lower alkanoyl, (vi) an optionally halogenated lower alkylsulfonyloxy, (vii) carbamoyl, (viii) oxo, (ix) amino, (x) amino substituted by one lower alkyl, (xi) amino substituted by two lower alkyls, (xii) a 3- to 6-membered cyclic amino optionally containing, besides a carbon atom and one nitrogen atom, 1 to 3 hetero atoms selected from a nitrogen atom, an oxygen atom and a sulfur atom, which optionally has substituent(s), (xiii) hydroxy, (xiv) nitro, (xv) cyano, (xvi) a lower alkylsulfonyl, (xvii) amino substituted by one lower cycloalkyl, and the like.

As the substituent which the hydrocarbon group (e.g., phenyl) or the heterocyclic group (e.g., 5- to 10-membered heterocyclic group such as pyrimidinyl pyridyl, pyrazolyl) optionally has, preferably, 1 to 5 (preferably 1 to 3) substituent(s) selected from an optionally substituted amino, cyano, halogen, an optionally substituted $C_{1-9}$ alkyl and an optionally substituted $C_{1-6}$ alkoxy.

Ring A in the formula (I') or (I) is an optionally substituted 5- to 8-membered heterocyclic ring.

The "5- to 8-membered heterocyclic ring" of the term "optionally substituted 5- to 8-membered heterocyclic ring" is, for example, a 5- to 8-membered ring group containing, besides two nitrogen atoms, 1 to 3 hetero atoms selected from a nitrogen atom, an oxygen atom and a sulfur atom.

The "5- to 8-membered heterocyclic ring" may have, for example, 1 to 3, substituent(s) at substitutable position(s) of the 5- to 8-membered heterocyclic ring. As the substituent, those similar to the substituent(s) that the aforementioned "heterocyclic group" may have are used. When the number of substituents is two or more, each substituent may be the same or different.

Examples of the "5- to 8-membered heterocyclic ring" include the ring of the formula as follows:

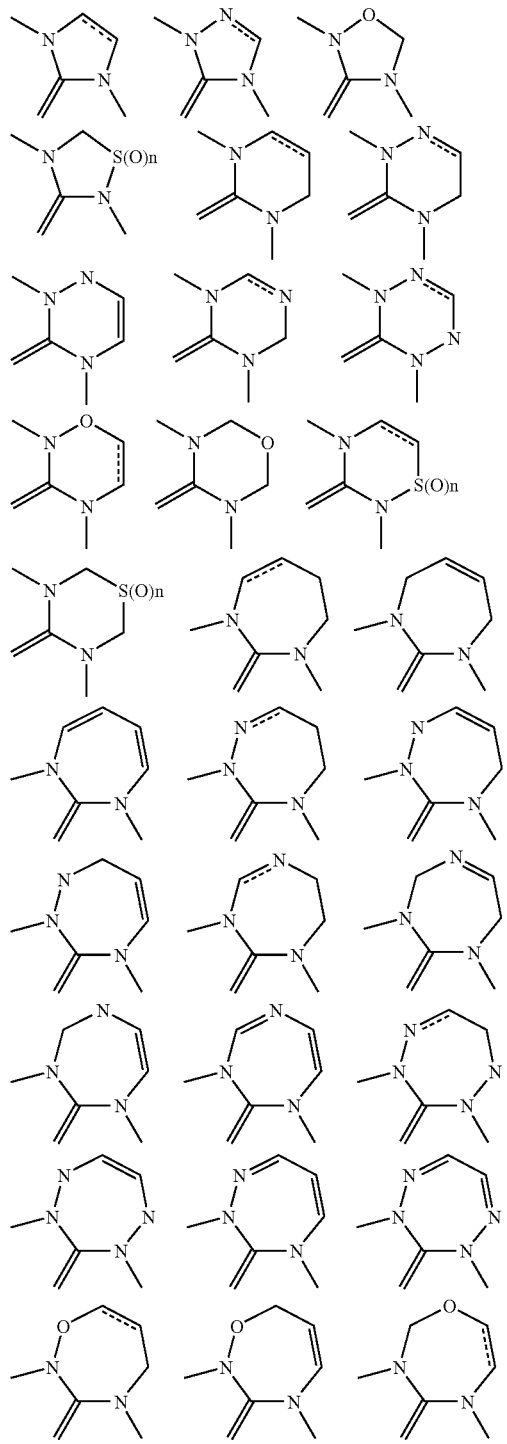

-continued

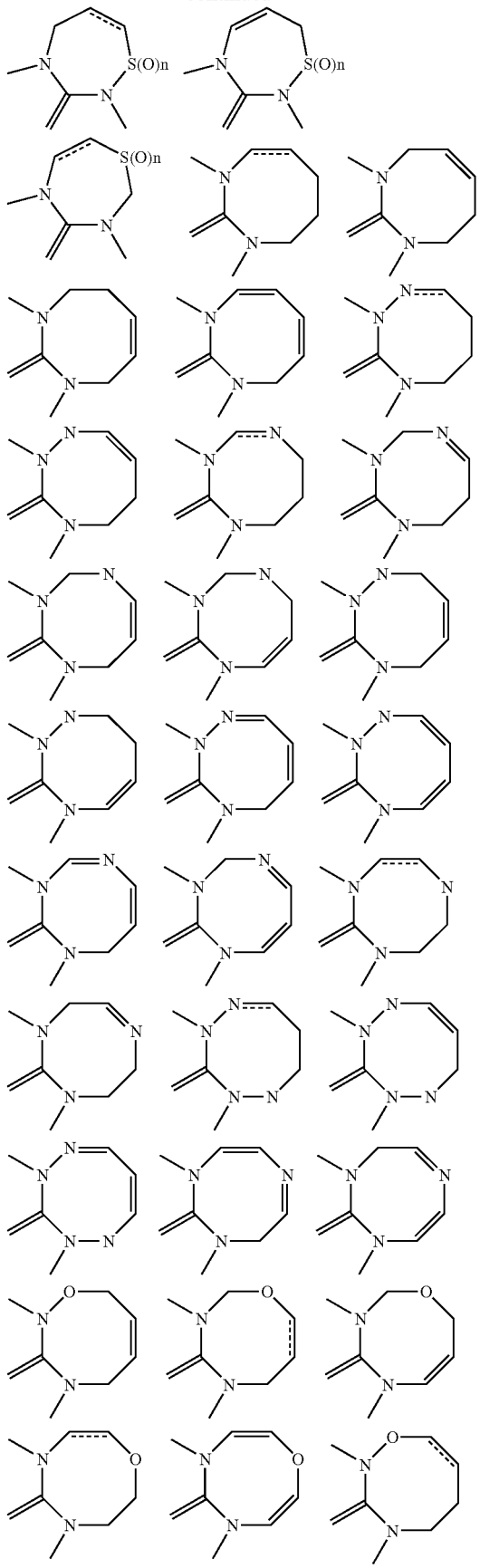

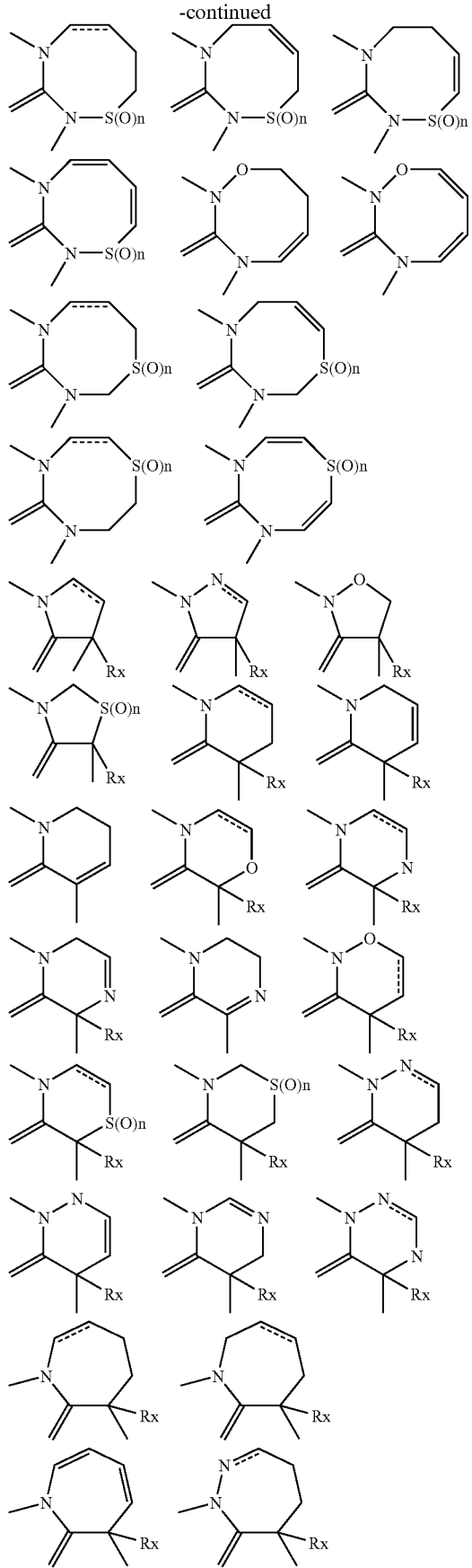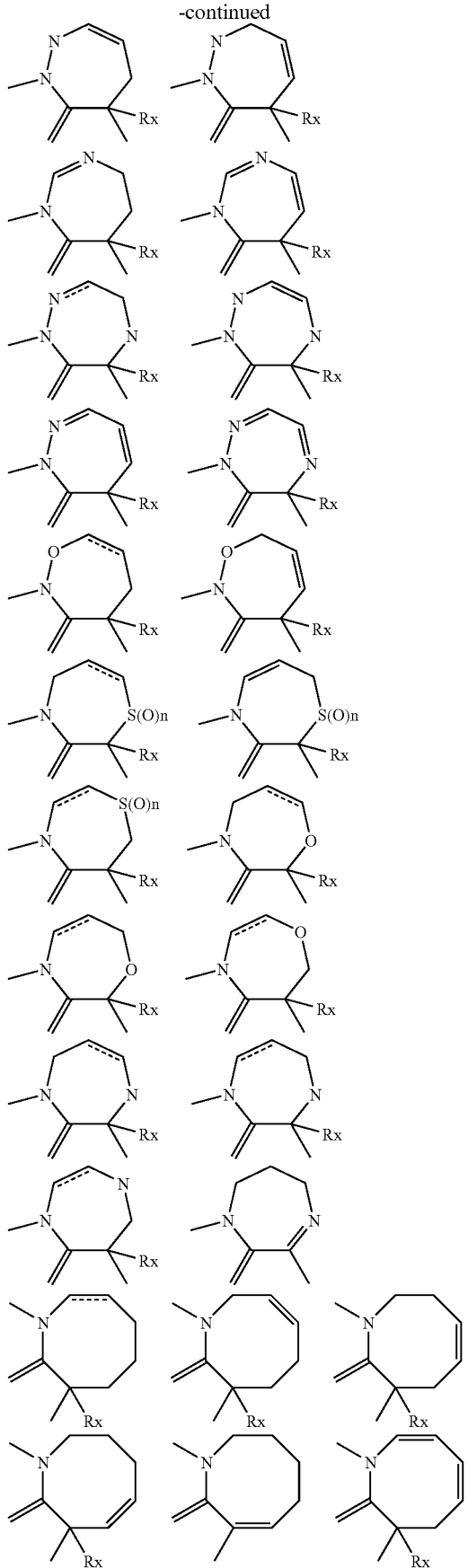

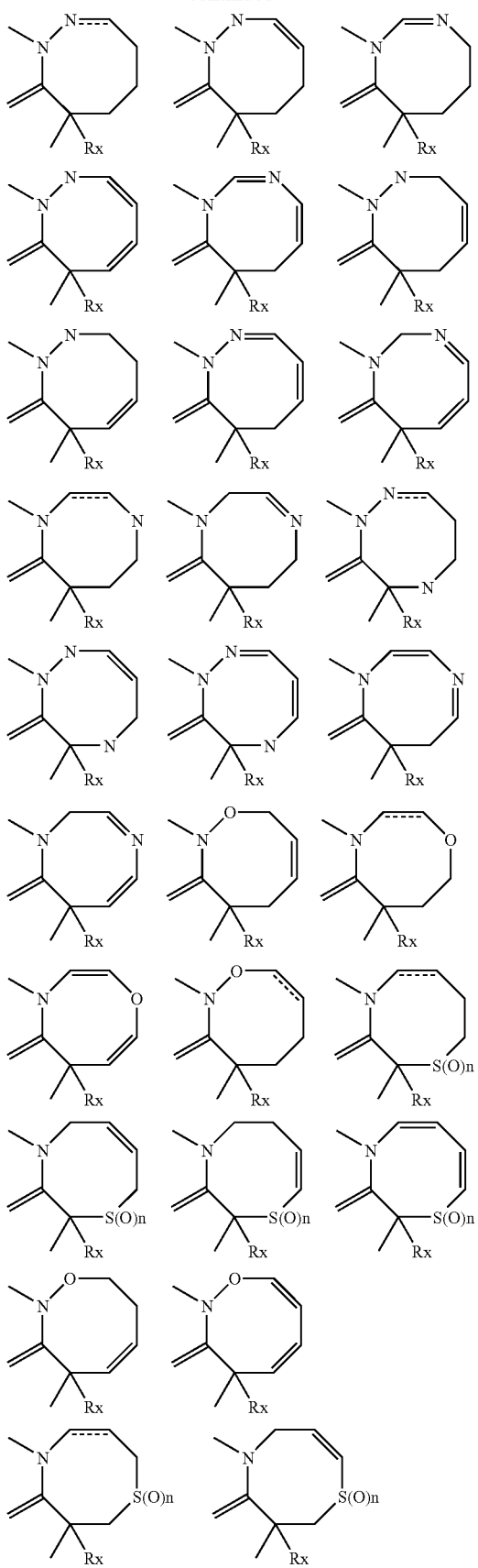

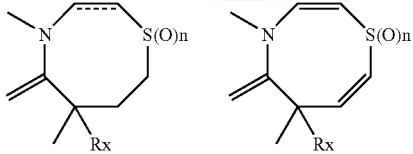

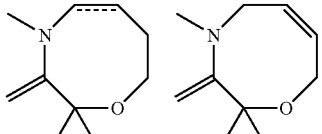

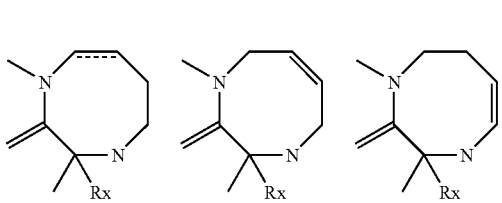

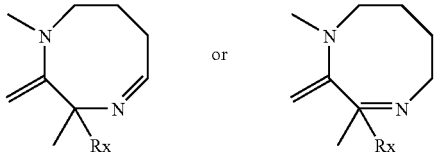

wherein n is 0 to 2, the dashed line is a single or double bond, Rx is hydrogen or $C_{1-9}$ alkyl; and the like. The above "5- to 8-membered heterocyclic ring" may have, for example, 1 to 3, substituent(s) that the aforementioned "heterocyclic ring" may have, and the like.

The preferred substituents of the "5- to 8-membered heterocyclic ring" for Ring A include, for example, halogen atom, lower alkoxy, lower alkoxycarbonyl, oxo and the like.

Ring A is preferably an optionally substituted 5- to 7-membered heterocyclic ring.

$Y^1$, $Y^2$, and $Y^3$ in the formula (I') or (I) are each an optionally substituted carbon or a nitrogen.

The substituents of the "optionally substituted carbon" for $Y^1$, $Y^2$ and $Y^3$ include, for example, (1) an optionally substituted hydrocarbon group, (2) an acyl, (3) an optionally substituted heterocyclic group, (4) an optionally substituted amino, (5) nitro, (6) an optionally substituted hydroxy, (7) an optionally substituted mercapto, (8) cyano, (9) halogen and the like.

The preferred substituents of the "optionally substituted carbon" for $Y^1$, $Y^2$ and $Y^3$ are halogen, an optionally substituted $C_{1-6}$ alkoxy, an optionally substituted $C_{1-9}$ alkyl, cyano, $C_{3-6}$ cycloalkyl and the like.

The more preferred substituents of the "optionally substituted carbon" for $Y^1$, $Y^2$ and $Y^3$ are halogen, $C_{1-4}$ alkoxy, $C_{1-4}$ alkyl, cyano and the like.

The more preferred substituent of the "optionally substituted carbon" for $Y^3$ is halogen.

X in the formula (I') is a nitrogen or CRx, preferably a nitrogen. Rx is a hydrogen or a $C_{1-9}$ alkyl, preferably a hydrogen.

Preferred examples of the tricycle of the formula:

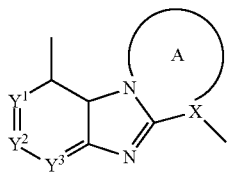

in the formula (I') include the tricycle of the formula:

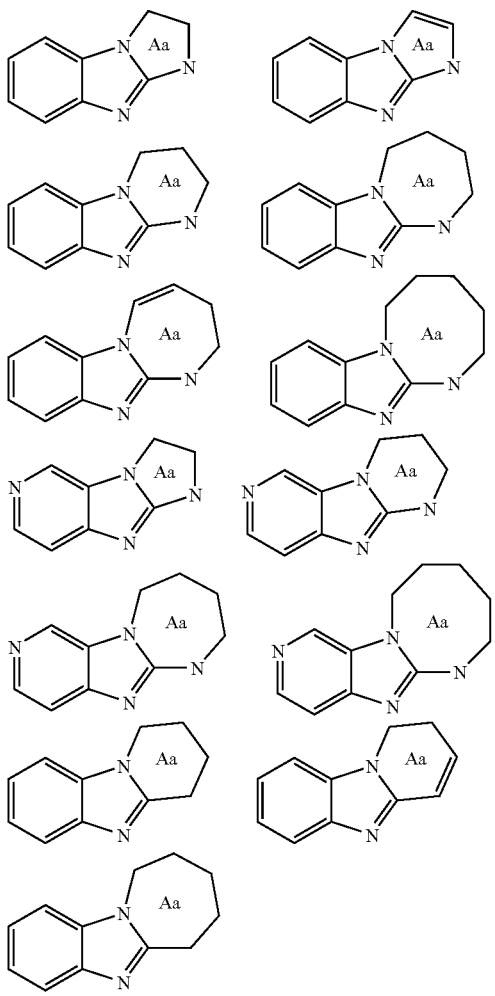

wherein ring Aa is as defined for ring A. The above tricycles may have substituent(s) that the aforementioned "optionally substituted carbon" for $Y^1$, $Y^2$ and $Y^3$, may have.

Of the compound represented by the formula (I') (hereinafter sometimes to be abbreviated as the compound (I')), the compound wherein X is a nitrogen is the compound represented by the formula (I) (hereinafter sometimes to be abbreviated as the compound (I)).

Preferable examples of compound (I) include a compound wherein $R^1$ is (1) a $C_{1-9}$ alkyl which may be substituted with one or two substituents selected from the group consisting of (i) halogen, (ii) nitro, (iii) cyano, (iv) an optionally substituted lower alkyl, (v) hydroxy, (vi) an optionally substituted lower alkoxy, (vii) an optionally substituted lower alkanoyloxy, (viii) an optionally substituted lower alkanoyl, (ix) an optionally substituted lower alkoxycarbonyl, (x) carbamoyl, (xi) an alkylcarbamoyl substituted by one optionally substituted lower alkyl, (xii) amino, (xiii) amino substituted by one optionally substituted lower alkyl, (xiv) amino substituted by two optionally substituted lower alkyls, (xv) a 3- to 6-membered cyclic amino (e.g., azetidinyl) optionally containing, besides a carbon atom and one nitrogen atom, 1 to 3 hetero atoms selected from a nitrogen atom, an oxygen atom and a sulfur atom, which optionally has substituent(s), (xvi) an optionally substituted amino, (xvii) oxo, (xviii) an optionally substituted heterocyclic group, (xix) a lower alkylthio, (xx) a lower alkylsulfonyl, (xxi) $C_{3-6}$ cycloalkyl, (xxii) imino optionally substituted by optionally halogenated $C_{1-6}$ alkoxy, (xxiii) formyl, (xxiv) $C_{2-6}$ alkenyloxy, (xxv) an optionally substituted $C_{3-6}$ cycloalkyloxy, (xxvi) amino optionally having 1 to 5 substituent(s) selected from halogenated $C_{1-6}$ alkylsulfonyl, $C_{1-6}$ alkylcarbamoyl, $C_{1-6}$ alkoxy-carbonyl and $C_{3-6}$ cycloalkyl-carbonyl, (xxvii) azido, (2) an acyl selected from the group consisting of (i) carboxy, (ii) $C_{1-6}$ alkyl-carbonyl, (iii) $C_{1-6}$ alkoxy-carbonyl, (iv) formyl, (v) $C_{3-6}$ cycloalkyl-carbonyl,(vi) carbamoyl which may be substituted by one or two $C_{1-6}$ alkyl, and (vi) 3- to 6-membered cyclic aminocarbonyl (e.g., azetidinylcarbonyl) which may be substituted by a hydroxy, (3) amino which may be substituted by $C_{1-6}$ alkyl, (4) nitro, (5) cyano, (6) a 5- or 6-membered heterocyclic group which may be substituted by oxo or $C_{1-6}$ alkyl, (7) a $C_{2-6}$ alkenyl which may be substituted by hydroxy, halogen or optionally halogenated $C_{1-6}$ alkoxy-carbonyl, or (8) halogen atom;

$R^2$ is (i) phenyl substituted with 1-3 substituent(s) selected from the group consisting of (1) halogen, (2) cyano, (3) an optionally substituted alkyl, (4) an optionally substituted lower alkoxy, (5) carboxy, (6) carbamoyl, (7) an alkylcarbamoyl substituted by one optionally substituted lower alkyl, (8) an alkylcarbamoyl substituted by two optionally substituted lower alkyl (9) amino, (10) amino substituted by one optionally substituted lower alkyl, (11) amino substituted by two optionally substituted lower alkyls, (12) amino substituted by optionally substituted lower alkylcarbonyl, (13) a lower alkylthio, (14) a lower alkylsulfinyl, (15) a lower alkylsulfonyl, (16) formyl, or (ii) pyrazolyl, pyrimidinyl, pyridazinyl, pyrazinyl, benzimidazolyl, isoxazolyl or pyridyl, which are substituted with 1-3 substituent(s) selected from the group consisting of (1) halogen, (2) an optionally halogenated alkyl, (3) a cycloalkyl, (4) an optionally halogenated lower alkoxy, (5) a lower alkanoyl, (6) an optionally halogenated lower alkylsulfonyloxy, (7) carbamoyl, (8) oxo, (9) amino, (10) amino substituted by one lower alkyl, (11) amino substituted by two lower alkyls, (12) 3- to 6-membered cyclic amino optionally containing, besides a carbon atom and one nitrogen atom, 1 to 3 hetero atoms selected from a nitrogen atom, an oxygen atom and a sulfur atom, which optionally has substituent(s), (13) hydroxy, (14) nitro, (15) cyano, (16) a lower alkylsulfonyl, (17) amino substituted by one lower cycloalkyl; ring A is a ring of the formula as follows:

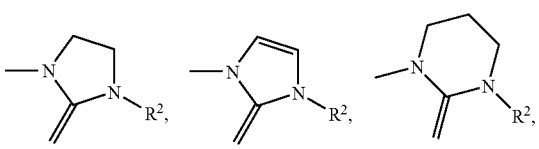

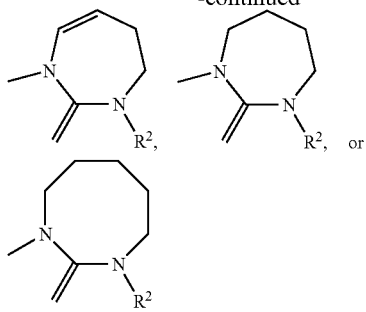

wherein R² is as defined in the aforementioned, and which ring further may be substituted with 1 or 2 substituent(s) selected from the group consisting of (1) oxo, (2) halogen atom, (3) hydroxy, (4) $C_{1-6}$ alkylsulfonyloxy, (5) $C_{1-6}$ alkoxy, (6) $C_{1-6}$ alkylsulfonyloxy, (7) azido, (8) amino, (9) $C_{1-6}$ alkyl-carbonylamino and (10) $C_{1-6}$ alkyl which may be substituted with 1-3 substituent(s) selected from the group consisting of carboxy, hydroxy, $C_{1-6}$ alkoxy-carbonyl, $C_{1-6}$ alkyl-carbonyloxy;

$Y^1$ and $Y^2$ are carbons; and $Y^3$ is an optionally halogenated carbon.

Preferable examples of compound (I') other than the compound (I) include a compound wherein R¹ is (1) a $C_{1-9}$ alkyl which may be substituted with one or two substituent(s) selected from the group consisting of (i) hydroxy and (ii) $C_{3-6}$ cycloalkyl, (2) an acyl selected from the group consisting of (i) formyl, (ii) $C_{1-6}$ alkoxy-carbonyl, and (iii) $C_{3-6}$ cycloalkyl-carbonyl, or (3) di-$C_{1-6}$ alkylamino;

R² is an optionally halogenated phenyl; ring A is a ring of the formula as follows:

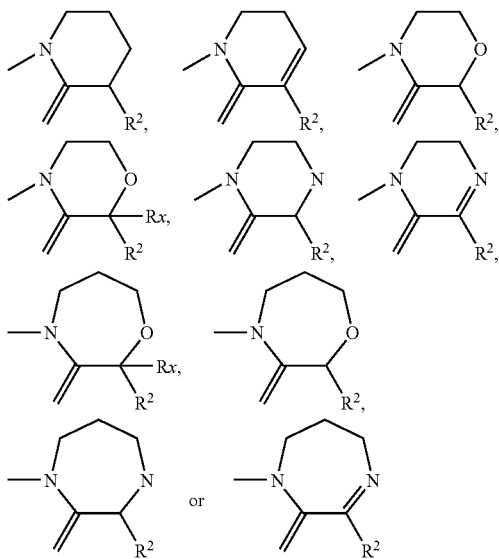

wherein R² and Rx is as defined in the aforementioned, and which ring further may be substituted with 1 or 2 substituent(s) selected from the group consisting of (1) $C_{1-6}$ alkyl, (2) $C_{1-6}$ alkoxy-carbonyl and (3) oxo;

$Y^1$ and $Y^2$ are carbons; and $Y^3$ is an optionally halogenated carbon.

More preferable examples of compound (I') include a compound represented the formula selected from the following formula:

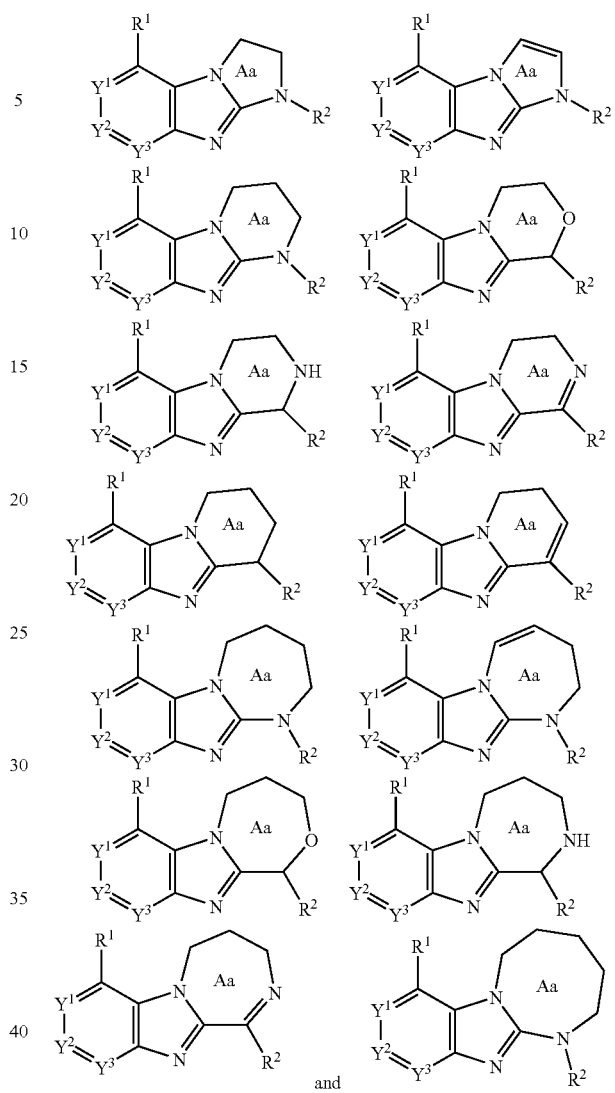

(wherein $R^1$, $R^2$, $Y^1$, $Y^2$ and $Y^3$ are as in the aforementioned, and ring Aa is optionally further substituted).

Of the compound (I'), the compound represented by the following formula (I"):

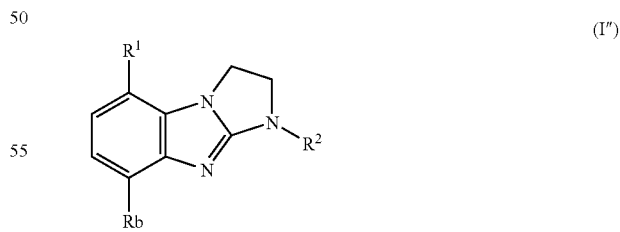

(I")

(wherein R¹ and R² are as defined in the aforementioned, and Rb is hydrogen, halogen, cyano, an optionally substituted $C_{1-9}$ alkyl, an optionally substituted $C_{1-6}$ alkoxy, or $C_{3-6}$ cycloalkyl) is preferable.

Among these, the compound wherein R¹ is (1) mono- or di-$C_{1-6}$ alkylamino, or (2) a $C_{1-9}$ alkyl optionally substituted by substituent(s) selected from halogen, hydroxy, $C_{3-6}$ cycloalkyl, an optionally substituted $C_{1-6}$ alkoxy, $C_{1-6}$ alkyl-carbonyloxy, $C_{3-6}$ cycloalkyl-carbonyloxy and an optionally substituted $C_{3-6}$ cycloalkyloxy; and $R^2$ is an optionally substituted phenyl, an optionally substituted pyridyl or an optionally substituted pyrimidinyl, is preferable.

Of the compound (I'), the compound represented by the following formula (I'''):

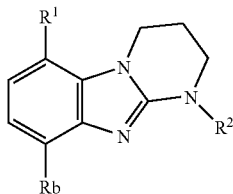

(I''')

(wherein $R^1$ and $R^2$ are as defined in the aforementioned, and Rb is as defined in the aforementioned) is preferable.

Among these, the compound wherein $R^1$ is
(1) mono- or di-$C_{1-6}$ alkylamino, or
(2) a $C_{1-9}$ alkyl optionally substituted by substituent selected from halogen, hydroxy, $C_{3-6}$ cycloalkyl, an optionally substituted $C_{1-6}$ alkoxy, $C_{1-6}$ alkyl-carbonyloxy, $C_{3-6}$ cycloalkyl-carbonyloxy and an optionally substituted $C_{3-6}$ cycloalkyloxy; and $R^2$ is an optionally substituted phenyl, an optionally substituted pyridyl or an optionally substituted pyrimidinyl, or the compound wherein $R^1$ is a $C_{1-9}$ alkyl optionally substituted by substituent selected from halogen, hydroxy, $C_{3-6}$ cycloalkyl, an optionally substituted $C_{1-6}$ alkoxy, $C_{1-6}$ alkyl-carbonyloxy, $C_{3-6}$ cycloalkyl-carbonyloxy and an optionally substituted $C_{3-6}$ cycloalkyloxy; $R^2$ is
(1) phenyl optionally substituted by substituent(s) selected from halogen, an optionally halogenated $C_{1-6}$ alkoxy and an optionally halogenated $C_{1-9}$ alkyl,
(2) pyridyl optionally substituted by substituent(s) selected from halogen, an optionally halogenated $C_{1-9}$ alkyl, $C_{3-6}$ cycloalkyl and an optionally halogenated $C_{1-6}$ alkoxy, or
(3) pyrimidinyl optionally substituted by substituent selected from $C_{1-9}$ alkyl, an optionally halogenated $C_{1-6}$ alkoxy and $C_{3-6}$ cycloalkyl; and
Rb is hydrogen, halogen or $C_{1-6}$ alkoxy, is preferable.

Of the compound (I'), the compound represented by the following formula (I''''):

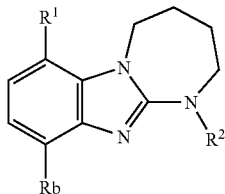

(I'''')

(wherein $R^1$ and $R^2$ are as defined in the aforementioned, and Rb is as defined in the aforementioned) is preferable.

Among these, the compound wherein $R^1$ is
(1) mono- or di-$C_{1-6}$ alkylamino, or
(2) a $C_{1-9}$ alkyl optionally substituted by substituent selected from halogen, hydroxy, $C_{3-6}$ cycloalkyl, an optionally substituted $C_{1-6}$ alkoxy, $C_{1-6}$ alkyl-carbonyloxy, $C_{3-6}$ cycloalkyl-carbonyloxy and an optionally substituted $C_{3-6}$ cycloalkyloxy; and $R^2$ is an optionally substituted phenyl, an optionally substituted pyridyl or an optionally substituted pyrimidinyl, is preferable In the present invention, the compound represented by the following formula (IX):

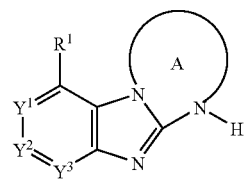

(IX)

(wherein $Y^1$, $Y^2$, $Y^3$, $R^1$ and ring A are as defined in the aforementioned),
excluding, a compound wherein $R^1$ is nitro, methyl, halogen or a group of the formula:

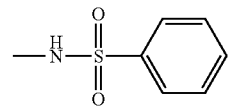

wherein benzene ring is optionally substituted;
or a salt thereof, is also preferable.

As a salt of compound (I') or (I), for example, a pharmacologically acceptable salt and the like are used. For example, a salt with inorganic base, a salt with organic base, a salt with inorganic acid, a salt with organic acid, a salt with basic or acidic amino acid and the like can be mentioned. Preferable examples of salts with inorganic base include alkali metal salt such as sodium salt, potassium salt and the like, alkaline earth metal salt such as calcium salt, magnesium salt and the like, and aluminum salt, ammonium salt and the like. Preferable examples of salts with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acid include salts with hydrochloric acid, hydrobromic acid, nitric acid, sulfuric acid, phosphoric acid and the like. Preferable examples of salts with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acid include salts with arginine, lysine, ornithine and the like, and preferable examples of salts with acidic amino acid include salts with aspartic acid, glutamic acid and the like. Of these, a pharmaceutically acceptable salt is preferable. Examples thereof when compound (I') or (I) has a basic functional group include salts with inorganic acid such as hydrochloric acid, hydrobromic acid, nitric acid, sulfuric acid, phosphoric acid and the like, and salts with organic acid such as acetic acid, phthalic acid, fumaric acid, tartaric acid, maleic acid, citric acid, succinic acid, methanesulfonic acid, p-toluenesulfonic acid and the like.

Examples thereof when compound (I') or (I) has an acidic functional group include alkali metal salts such as sodium salt, potassium salt and the like, alkaline earth metal salts such as calcium salt, magnesium salt and the like, ammonium salt and the like.

When compound (I') or (I) has isomers such as optical isomer, stereoisomer, positional isomer, rotational isomer and the like, and any isomers and mixtures are encompassed in the compound (I') or (I). For example, when compound (I') or (I) has an optical isomer, an optical isomer separated from a racemate is also encompassed in the compound (I') or (I). These isomers can be obtained as independent products by a synthesis means or a separation means (e.g., concentration, solvent extraction, column chromatography, recrystallization and the like), optical resolution methods (e.g., fractional recrystallization, chiral column method, diastereomer method and the like) and the like known per se.

The compound (I') or (I) may be a crystal, and both a single crystal and crystal mixtures are encompassed in the compound (I') or (I) of the present invention. Crystals can be produced by crystallization according to crystallization methods known per se.

The compound (I') or (I) may be a solvate (e.g., hydrate etc.) or a non-solvate (e.g., non-hydrate etc.), both of which are encompassed in the compound (I') or (I).

A compound (I') or (I) labeled with an isotope (e.g., $^3$H, $^{14}$C, $^{35}$S, $^{125}$I and the like) is also encompassed in the compound (I') or (I). A deuterated compound (I') or (I) is also encompassed in the compound (I') or (I).

The production methods of compound (I') or (I) are described in the following. The following examples are given to illustrate the invention and are not intended to be inclusive in any manner. Alternative methods may be employed by one skilled in the art, and substituent(s) of compound (I') or (I) may be converted to other substituent(s) by known arts.

Compound (I') or (I) can be obtained, for example, by the method shown by the following reaction scheme or a method analogous thereto and the like.

Compounds in the schemes include salts thereof. As the salt, for example, one similar to the salt of compound (I') or (I) and the like are used.

The compound obtained in each step can be directly used as a reaction mixture or a crude product for the next reaction. It can be isolated from a reaction mixture according to a conventional method, and can be easily purified by a separation means such as recrystallization, distillation, chromatography and the like.

In the following, reaction schemes are shown, wherein each symbol of the compound in the schemes is as defined above.

Each of the materials in the schemes can be used as it is when it can be commercially available, and it can be produced in accordance with the known methods per se or analogous methods thereof.

(Scheme 1)

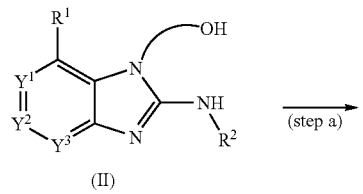

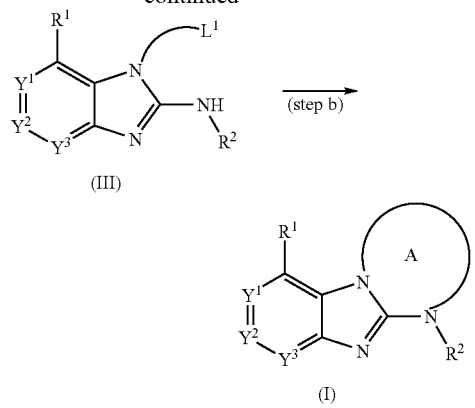

The above $L^1$ is a leaving group including halogen atom such as chlorine, bromine, iodine, etc., sulfonyloxy such as p-toluenesulfonyloxy, methanesulfonyloxy, trifluoromethanesulfonyloxy, etc., and acyloxy such as acetyloxy, benzoyloxy, phosphoniumoxy, etc.

In the step a, compound (III) can be prepared by halogenation, sulfonylation or acylation of compound (II) with a halogenation reagent, sulfonylation reagent or acylation reagent, respectively. Compound (II) can be prepared in the scheme 2 or 10. Compound (II) and compound (III) can be also prepared from the methods according to WO 2005/044793, WO 2006/116412, etc.

Examples of the halogenation reagent include phosphorous oxychloride, phosphorous oxybromide, phosphorous trichloride, phosphorous tribromide, phosphorous pentachloride, chlorine, bromine, thionyl chloride, etc. The halogenation reagent may be employed in an amount of 1 mole to excess per 1 mole of compound (II) or as a solvent.

Examples of the solvent having no adverse effect on the reaction include aromatic hydrocarbons such as benzene, toluene, xylene, etc., ethers such as diethyl ether, dioxane, tetrahydrofuran, etc., esters such as ethyl acetate, etc., nitriles such as acetonitrile, etc., halogenated hydrocarbon such as chloroform, dichloromethane, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio, or may not be used.

While the reaction temperature may vary depending on compound (II) employed as well as other conditions, it is 0 to 200° C., preferably 20 to 150° C. The reaction time is 10 minutes to 24 hours, preferably 30 minutes to 12 hours.

When $L^1$ is a sulfonyloxy, an acyloxy or phosphoniumoxy in compound (III), compound (III) can be prepared by reacting compound (II) with a sulfonylation reagent, an acylation reagent, or a phosphine reagent. In this step, a base may be used.

Examples of the base include an alkaline metal hydroxide such as sodium hydroxide, potassium hydroxide, etc., an alkaline metal hydrogen carbonate such as sodium hydrogen carbonate, potassium hydrogen carbonate, etc., an alkaline metal carbonate such as sodium carbonate, potassium carbonate, etc., a cesium salt such as cesium carbonate, etc., an alkaline metal hydride such as sodium hydride, potassium hydride, sodium amide, etc., an alkaline metal alkoxide such as sodium methoxide, sodium ethoxide, etc., an amine such as trimethylamine, triethylamine, diisopropylethylamine, etc., a cyclic amine such as pyridine, 4-dimethylaminopyridine, DBU, etc. The base may be employed in an amount of 1 mole to excess per 1 mole of compound (II) or as a solvent.

Examples of the sulfonylation reagent include p-toluenesulfonyl chloride, methanesulfonyl chloride, trifluoromethanesulfonyl chloride, etc. The sulfonylation reagent may be employed in an amount of 1 to 10 moles, preferably 1 to 5 moles per 1 mole of compound (II).

Examples of the acylation reagent include acetyl chloride, benzoyl chloride, etc. The acylation reagent may be employed in an amount of 1 to 10 moles, preferably 1 to 5 moles per 1 mole of compound (II).

Examples of the phosphine reagent include triphenyl phosphine, tri-n-butyl phosphine, etc. The phosphine reagent may be employed in an amount of 1 to 10 moles, preferably 1 to 5 moles per 1 mole of compound (II).

Examples of the solvent having no adverse effect on the reaction include water, alcohols such as methanol, ethanol, etc., ethers such as diethyl ether, dioxane, tetrahydrofuran, etc., aromatic hydrocarbons such as benzene, toluene, xylene, etc., esters such as ethyl acetate, etc., halogenated hydrocarbons such as chloroform dichloromethane, etc., nitriles such as acetonitrile, etc., amides such as N,N-dimethylformamide, N,N-dimethylacetamide, etc., and sulfoxides such as dimethylsulfoxide, etc. These solvents may be used by mixing at an appropriate ratio, or may not be used.

While the reaction temperature may vary depending on compound (II) employed as well as other conditions, it is 0 to 200° C., preferably 0 to 150° C. The reaction time is 10 minutes to 24 hours, preferably 30 minutes to 12 hours.

Thus obtained compound (III) can be isolated and purified by the known isolating and purifying methods, for example, concentration under reduced pressure, extraction with solvent, crystallization, recrystallization, transfer dissolution and chromatography.

In the step b, compound (I) can be prepared by cyclization of compound (III). In this step, a base may be used.

Examples of the base are described above in the step a. The base may be employed in an amount of 1 mole to excess per 1 mole of compound (III) or as a solvent.

Examples of the solvent having no adverse effect on the reaction include alcohols such as methanol, ethanol, etc., ethers such as dioxane, tetrahydrofuran, etc., aromatic hydrocarbons such as benzene, toluene, xylene, etc., esters such as ethyl acetate, etc., halogenated hydrocarbons such as chloroform dichloromethane, etc., nitriles such as acetonitrile, etc., amides such as N,N-dimethylformamide, N,N-dimethylacetamide, etc., and sulfoxides such as dimethylsulfoxide, etc. These solvents may be used by mixing at an appropriate ratio, or may not be used.

While the reaction temperature may vary depending on compound (III) employed as well as other reaction conditions, it is −20 to 200° C., preferably 0 to 150° C. The reaction time is 5 minutes to 48 hours, preferably 5 minutes to 24 hours.

Thus obtained compound (I) can be isolated and purified by the known isolating and purifying methods, for example, concentration, concentration under reduced pressure, extraction with solvent, crystallization, recrystallization, transfer dissolution and chromatography.

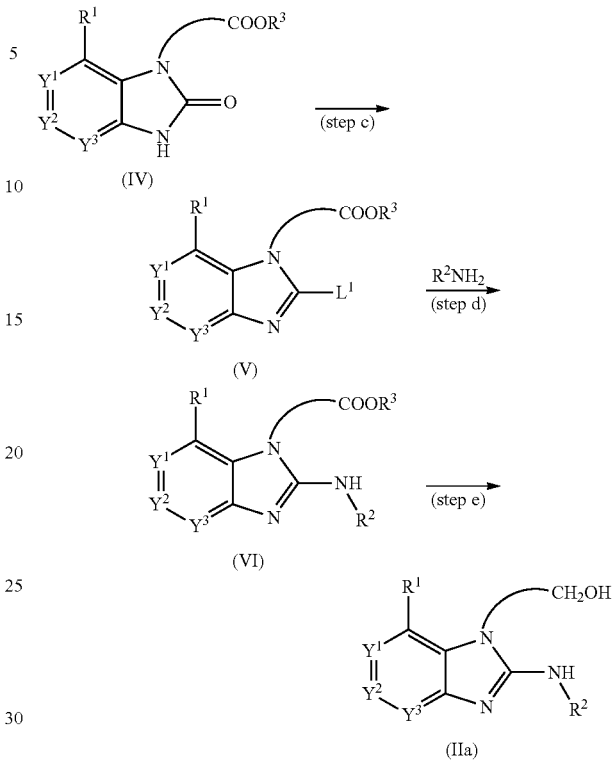

(Scheme 2)

The above $R^3$ is an optionally substituted hydrocarbon.

In the step c, compound (V) can be prepared by halogenation, sulfonylation or acylation of compound (IV) with a halogenation reagent, sulfonylation reagent or acylation reagent, respectively. Compound (IV) can be prepared in the schemes 3 and 19. Compound (IV) can be also prepared from the methods according to WO 2005/044793, WO 2006/116412, etc.

Examples of the halogenation reagent are described above in the step a. The halogenation reagent is employed in an amount of 1 mole to excess per 1 mole of compound (IV) or as a solvent.

Examples of the solvent having no adverse effect on the reaction include aromatic hydrocarbons such as benzene, toluene, xylene, etc., ethers such as diethyl ether, dioxane, tetrahydrofuran, etc., esters such as ethyl acetate, etc., nitriles such as acetonitrile, etc., halogenated hydrocarbon such as chloroform, dichloromethane, etc., amides such as N,N-dimethylformamide, N,N-dimethylacetamide, 1-methyl-2-pyrrolidinone, etc., ketones such as acetone 2-butanone, etc., and sulfoxides such as dimethylsulfoxide, etc. These solvents may be used by mixing at an appropriate ratio, or may not be used.

While the reaction temperature may vary depending on compound (IV) employed as well as other conditions, it is 0 to 200° C., preferably 20 to 150° C. The reaction time is 10 minutes to 24 hours, preferably 30 minutes to 12 hours.

When $L^1$ is a sulfonyloxy or an acyloxy in compound (V), compound (V) can be prepared by reacting compound (IV) with a sulfonylation reagent or an acylation reagent under basic conditions.

Examples of the base are described above in the step a. The base may be employed in an amount of 1 mole to excess per 1 mole of compound (IV) or as a solvent.

Examples of the sulfonylation reagent are described above in the step a. The sulfonylation reagent may be employed in an amount of 1 to 10 moles, preferably 1 to 5 moles per 1 mole of compound (IV).

Examples of an acylation reagent are described above in the step a. The acylation reagent may be employed in an amount of 1 to 10 moles, preferably 1 to 5 moles per 1 mole of compound (IV).

Examples of the solvent having no adverse effect on the reaction include water, alcohols such as methanol, ethanol, etc., ethers such as diethyl ether, dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, etc., and sulfoxides such as dimethylsulfoxide, etc. These solvents may be used by mixing at an appropriate ratio, or may not be used.

While the reaction temperature may vary depending on compound (IV) employed as well as other conditions, it is 0 to 200° C., preferably 0 to 150° C. The reaction time is 10 minutes to 24 hours, preferably 30 minutes to 12 hours.

Thus obtained compound (V) can be isolated and purified by the known isolating and purifying methods, for example, concentration under reduced pressure, extraction with solvent, crystallization, recrystallization, transfer dissolution and chromatography.

In the step d, compound (VI) can be prepared by reacting compound (V) with $R^2NH_2$. In this step, an acid, a base, a palladium catalyst or a copper reagent may be used. A catalytic amount of a phosphine ligand may be employed. Compound (VI) can be also prepared from the methods according to WO 2005/044793, WO 2006/116412, etc.

In this step, 1 to 20 moles, preferably 1 to 10 moles of a compound represented by $R^2NH_2$ or a salt thereof are employed per 1 mole of compound (V).

Examples of an acid include an inorganic acid such as hydrochloric acid, sulfuric acid, nitric acid, thionyl chloride, etc., and an ordinary organic acid such as formic acid, acetic acid, trifluoroacetic acid, methanesulfonic acid, p-toluenesulfonic acid, etc., as well as a Lewis acid such as aluminum trichloride, iron trichloride, zirconium tetrachloride, etc. The acid may be employed in an amount of 1 to 10 moles, preferably 1 to 5 moles per 1 mole of compound (V).

Examples of the base are described above in the step a. The base may be employed in an amount of 1 mole to excess per 1 mole of compound (V) or as a solvent.

Examples of the palladium catalyst include tetrakis(triphenylphosphine)palladium(0), bis(triphenylphosphine)palladium(II) dichloride, tris(dibenzylidineacetone)dipalladium (0), trans-dichlorobis(tri-o-tolylphosphine)palladium(II), palladium(II) trifluoroacetate and palladium(II) acetate, etc. The palladium catalyst may be employed in an amount of 0.001 mole to 0.5 mole per 1 mole of compound (V).

Examples of the phosphine ligand include triphenylphosphine, 2,2'-bis(diphenylphosphino)-1,1'-binaphtyl, 2-(di-tert-butylphosphino)biphenyl, 2-(dicyclohexylphosphino)biphenyl, 2-(dicyclohexylphosphino)-2',6'-dimethoxy-1,1'-biphenyl, 2-(dicyclohexylphosphino)-2'-(N,N-dimethylamino)biphenyl, 1,1'-bis(diphenylphosphino) ferrocene, tri-tert-butylphosphine and tricyclohexylphosphine, etc. The phosphine ligand may be employed in an amount of 1 mole to 5.0 moles per 1 mole of the palladium catalyst.

Examples of the copper reagent include copper iodide, copper bromide, copper chloride, copper acetate, etc. The copper reagent may be employed in an amount of 0.01 mole to 10 moles per 1 mole of compound (V).

Examples of the solvent having no adverse effect on the reaction include water, alcohols such as methanol, ethanol, etc., ethers such as diethyl ether, dioxane tetrahydrofuran, etc., aromatic hydrocarbons such as benzene, toluene xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio, or may not be used.

While the reaction temperature may vary depending on compound (V) employed as well as other reaction conditions, it is 0 to 200° C., preferably 20 to 150° C., or the reaction may be heated by microwave irradiation. The reaction time is 5 minutes to 48 hours, preferably 5 minutes to 24 hours.

Thus obtained compound (VI) can be isolated and purified by the known isolating and purifying methods, for example, concentration, concentration under reduced pressure, extraction with solvent, crystallization, recrystallization, transfer dissolution and chromatography.

In the step e, compound (IIa), which is encompassed within compound (II), can be prepared by reduction or hydrogenation of compound (VI).

Examples of the reduction reagent include aluminum hydride, lithium aluminum hydride, sodium aluminum hydride, sodium borohydride, lithium borohydride, calcium borohydride, borane tetrahydrofuran complex, etc. The reduction reagent may be employed in an amount of 0.25 mole to 10 moles per 1 mole of compound (VI).

Examples of the hydrogenation reagent include rhenium oxide, copper chromite, etc. The hydrogenation reagent may be employed in an amount of 0.01 mole to 5 moles per 1 mole of compound (VI).

Examples of the hydrogen source include hydrogen, formic acid, ammonium formate, triethylammonium formate, sodium phosphinate, hydrazine, etc. The hydrogen source may be employed in an amount of 1 mole to excess per 1 mole of compound (VI).

Examples of the solvent having no adverse effect on the reaction include alcohols such as methanol, ethanol, etc., aromatic hydrocarbons such as benzene, toluene, xylene, etc., ethers such as diethyl ether, dioxane, tetrahydrofuran, etc., esters such as ethyl acetate, etc., nitriles such as acetonitrile, etc., halogenated hydrocarbon such as chloroform dichloromethane, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio.

While the reaction temperature may vary depending on compound (VI) employed as well as other conditions, it is 0 to 300° C., preferably 0 to 250° C. The reaction time is 10 minutes to 24 hours, preferably 30 minutes to 12 hours.

Thus obtained compound (IIa) can be isolated and purified by the known isolating and purifying methods, for example, concentration under reduced pressure, extraction with solvent, crystallization, recrystallization, transfer dissolution and chromatography.

(Scheme 3)

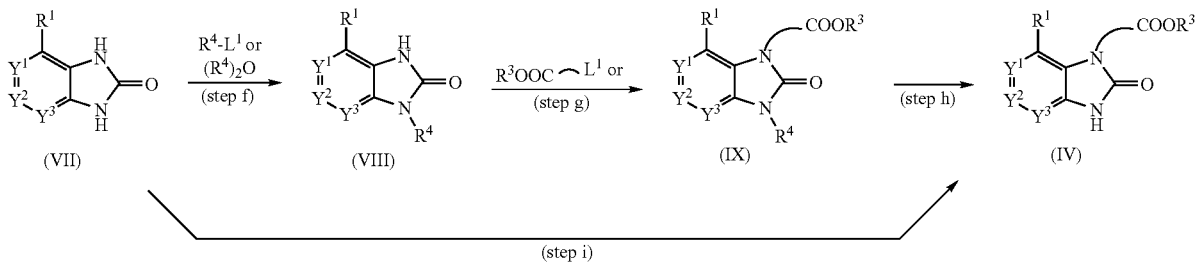

(step i)

The above R⁴ is an optionally substituted $C_{1-6}$ alkyl-carbonyl such as formyl, methylcarbonyl and ethylcarbonyl, etc., phenylcarbonyl, $C_{1-6}$ alkyloxycarbonyl such as methoxycarbonyl, ethoxycarbonyl, t-butoxycarbonyl, etc., phenyloxycarbonyl such as benzoxycarbonyl, etc., $C_{7-10}$ aralkyl-carbonyl such as benzyloxycarbonyl, etc., $C_{7-10}$ aralkyl such as benzyl, 4-methoxybenzyl, etc., trityl, and phthaloyl, etc. As the substituents on each of the groups listed above a halogen atom such as fluorine, chlorine, bromine, iodine, etc., $C_{1-6}$ alkyl-carbonyl such as methylcarbonyl, ethylcarbonyl, butylcarbonyl, etc., and a nitro may be employed.

In the step f, compound (VIII) can be prepared by reacting compound (VII) with $R^4$-$L^1$ or anhydride $(R^4)_2O$. In this step, a base may be used. Compound (VII) can be prepared in the scheme, 20. Compound (VII) can be also prepared from the methods according to WO 2005/044793, WO 2006/116412, etc.

In this step, 1 to 10 moles, preferably 1 to 5 moles of a compound represented by $R^4$-$L^1$ or anhydride $(R^4)_2O$ or a salt thereof are employed per 1 mole of compound (VII).

Examples of the base are described above in the step a. The base may be employed in an amount of 1 mole to excess per 1 mole of compound (VII) or as a solvent.

Examples of the solvent having no adverse effect on the reaction include water, alcohols such as methanol, ethanol, etc., ethers such as diethyl ether, dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio, or may not be used.

While the reaction temperature may vary depending on compound (VII) employed as well as other reaction conditions, it is 0 to 200° C., preferably 20 to 150° C., or the reaction may be heated by microwave irradiation. The reaction time is 5 minutes to 48 hours, preferably 5 minutes to 24 hours.

Thus obtained compound (VIII) can be isolated and purified by the known isolating and purifying methods, for example, concentration, concentration under reduced pressure, extraction with solvent, crystallization, recrystallization, transfer dissolution and chromatography.

In the step g, compound (IX) can be prepared from compound (VIII) by similar methods in the step f.

In the step h, compound (IV) can be prepared by deprotection of compound (IX) with an acid, a base, or catalytic hydrogenation.

Examples of an acid are described above in the step d. The acid may be employed in an amount of 1 mole to excess per 1 mole of compound (IX) or as a solvent.

Examples of the base are described above in the step a. The base may be employed in an amount of 1 mole to excess per 1 mole of compound (IX) or as a solvent.

Examples of the hydrogenation catalyst include a palladium catalyst such as palladium black, palladium oxide, palladium barium sulfate, palladium on carbon, palladium hydroxide, etc., a platinum catalyst such as platinum black, platinum oxide, platinum on carbon, etc., or nickel catalyst such as reduced nickel, oxidized nickel, etc., and Raney nickel, etc. The hydrogenation catalyst may be employed in an amount of 0.01 mole to 0.5 mole per 1 mole of compound (IX). In this step, 1 mole to excess of an acid or a base may be employed per 1 mole of compound (IX), or an acid may be employed as a solvent.

Examples of the hydrogen source are described above in the step e. The hydrogen source may be employed in an amount of 1 mole to excess per 1 mole of compound (IX).

Examples of the solvent having no adverse effect on the reaction include water, alcohols such as methanol, ethanol, etc., ethers such as diethyl ether, dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio, or may not be used.

While the reaction temperature may vary depending on compound (IX) employed as well as other reaction conditions, it is 0 to 200° C., preferably 20 to 150° C. The reaction time is 5 minutes to 48 hours, preferably 5 minutes to 24 hours. While a reaction is usually performed at atmospheric pressure, it can be performed under pressure (3 to 10 atm) if necessary.

While the amount of a catalyst employed may vary depending on the type of the catalyst employed, it is usually 0.1 to 20% by weight based on an active intermediate or a salt thereof.

Thus obtained compound (IV) can be isolated and purified by the known isolating and purifying methods, for example, concentration, concentration under reduced pressure, extraction with solvent, crystallization, recrystallization, transfer dissolution and chromatography.

In the step i, compound (IV) may be prepared from compound (VII) by similar methods in the step g.

(Scheme 4)

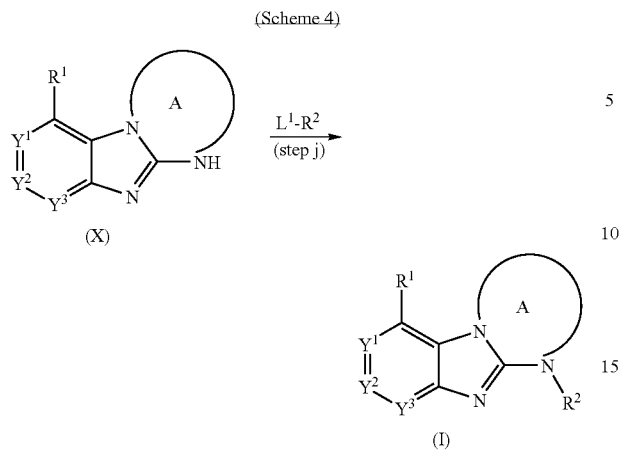

In the step j, compound (I) may be prepared by reacting compound (X) with $L^1$-$R^2$. In this step, an acid, a base, a palladium catalyst or a copper reagent may be used. A catalytic amount of a phosphine ligand may be employed. Compound (X) can be prepared in the schemes 5 and 8.

In this step, 1 to 20 moles, preferably 1 to 10 moles of a compound represented by $L^1$-$R^2$ or a salt thereof are employed per 1 mole of compound (X).

Examples of an acid are described above in the step d. The acid may be employed in an amount of 1 to 10 moles, preferably 1 to 5 moles per 1 mole of compound (X).

Examples of the base are described above in the step a. The base may be employed in an amount of 1 mole to excess per 1 mole of compound (X) or as a solvent.

Examples of the palladium catalyst are described above in the step d. The palladium catalyst may be employed in an amount of 0.001 mole to 0.5 mole per 1 mole of compound (X).

Examples of the phosphine ligand are described above in the step d. The phosphine ligand may be employed in an amount of 1 mole to 5.0 moles per 1 mole of the palladium catalyst.

Examples of the copper reagent are described above in the step d. The copper reagent may be employed in an amount of 0.01 mole to 10 moles per 1 mole of compound (X).

Examples of the solvent having no adverse effect on the reaction include water, alcohols such as methanol, ethanol, etc., ethers such as diethyl ether, dioxane tetrahydrofuran, etc., aromatic hydrocarbons such as benzene, toluene xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio, or may not be used.

While the reaction temperature may vary depending on compound (X) employed as well as other reaction conditions, it is 0 to 200° C., preferably 20 to 150° C., or the reaction may be heated by microwave irradiation. The reaction time is 5 minutes to 48 hours, preferably 5 minutes to 24 hours.

Thus obtained compound (I) can be isolated and purified by the known isolating and purifying methods, for example, concentration, concentration under reduced pressure, extraction with solvent, crystallization, recrystallization, transfer dissolution and chromatography.

(Scheme 5)

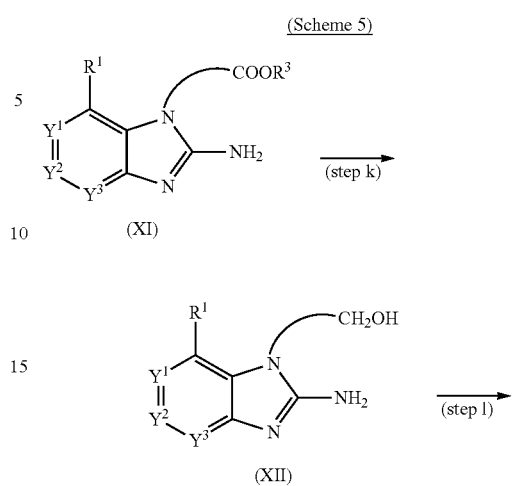

In the step k, compound (XII) can be prepared from compound (XI) by similar methods in the step e. Compound (XI) can be prepared in the scheme 6.

In the step l, compound (XIII) can be prepared from compound (XII) by similar methods in the step a.

In the step m, compound (X) can be prepared from compound (XIII) by similar methods in the step b.

(Scheme 6)

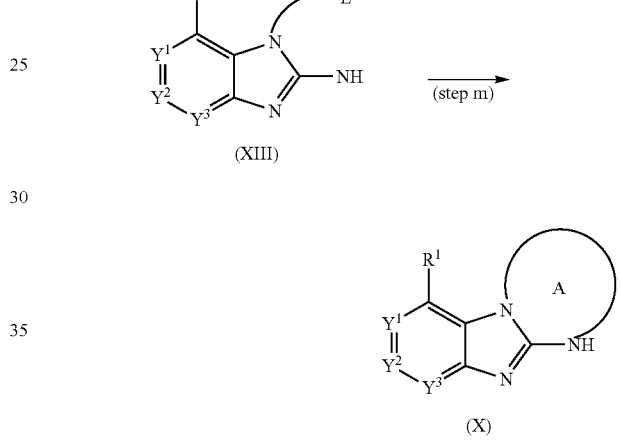

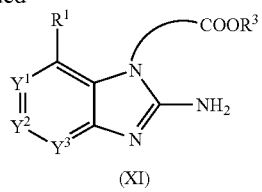

In the step o, compound (XIV) can be prepared by reacting compound (V) with an azide source. Compound (V) can be prepared in the scheme 2.

Examples of an azide source may be diphenylphosphoryl azide, alkaline metal azide such as sodium azide, lithium azide, etc., silyl azide such as trimethylsilyl azide, triethylsilyl azide, triphenylsilyl azide, etc. The azide source is employed in an amount of 1 mole to 10 moles, preferably 1 mole to 5 moles per 1 mole of compound (V).

Examples of the solvents having no adverse effect on the reaction include water, alcohols such as methanol, ethanol, etc., ethers such as diethyl ether, dioxane, tetrahydrofuran, etc., aromatic hydrocarbons such as benzene, chlorobenzene, toluene, xylene, etc., esters such as ethyl acetate, etc., halogenated hydrocarbons such as 1,2-dichloroethane, carbon tetrachloride, chloroform, dichloromethane, etc., nitriles such as acetonitrile, etc., amides such as N,N-dimethylformamide, N,N-dimethylacetamide, 1-methyl-2-pyrrolidinone, etc., ketones such as acetone, 2-butanone, etc., sulfoxides such as dimethylsulfoxide, etc., and acids such as acetic acid, etc. These solvents may be used by mixing at an appropriate ratio.

While the reaction temperature may vary depending on compound (V) employed as well as other conditions, it is 0 to 200° C., preferably 0 to 150° C. The reaction time is 10 minutes to 24 hours, preferably 30 minutes to 12 hours.

Thus obtained compound (XIV) can be isolated and purified by the known isolating and purifying methods, for example, concentration under reduced pressure, extraction with solvent, crystallization, recrystallization, transfer dissolution and chromatography.

In the step p, compound (XI) can be prepared by reacting compound (XIV) by reduction with a reducing reagent, or hydrogenation.

Examples of the reducing reagent include a hydride source such as sodium borohydride, lithium borohydride, lithium aluminum hydride, sodium cyanoborohydride, sodium triacetoxyborohydride, etc., trialkyl or triaryl phosphines such as trimethyl phosphine, triphenyl phosphine, etc. The reducing reagent is employed in an amount of 1 mole to excess per 1 mole of compound (XIV).

Examples of the hydrogenation catalyst are described above in the step h. The hydrogenation catalyst may be employed in an amount of 0.01 mole to 0.5 per 1 mole of compound (XIV). In this step, 1 mole to excess of an acid or a base may be employed per 1 mole of compound (XIV), or an acid may be employed as a solvent.

Examples of the hydrogen source are described above in the step e. The hydrogen source may be employed in an amount of 1 mole to excess per 1 mole of compound (XIV).

Examples of the solvent having no adverse effect on the reaction include water, alcohols such as methanol, ethanol, etc., ethers such as diethyl ether, dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio, or may not be used.

While the reaction temperature may vary depending on compound (XIV) employed as well as other reaction conditions, it is 0 to 200° C., preferably 20 to 150° C. The reaction time is 5 minutes to 48 hours, preferably 5 minutes to 24 hours. While a reaction is usually performed at atmospheric pressure, it can be performed under pressure (3 to 10 atm) if necessary. While the amount of a catalyst employed may vary depending on the type of the catalyst employed, it is usually 0.1 to 20% by weight based on an active intermediate or a salt thereof.

Thus obtained compound (XI) can be isolated and purified by the known isolating and purifying methods, for example, concentration, concentration under reduced pressure, extraction with solvent, crystallization, recrystallization, transfer dissolution and chromatography.

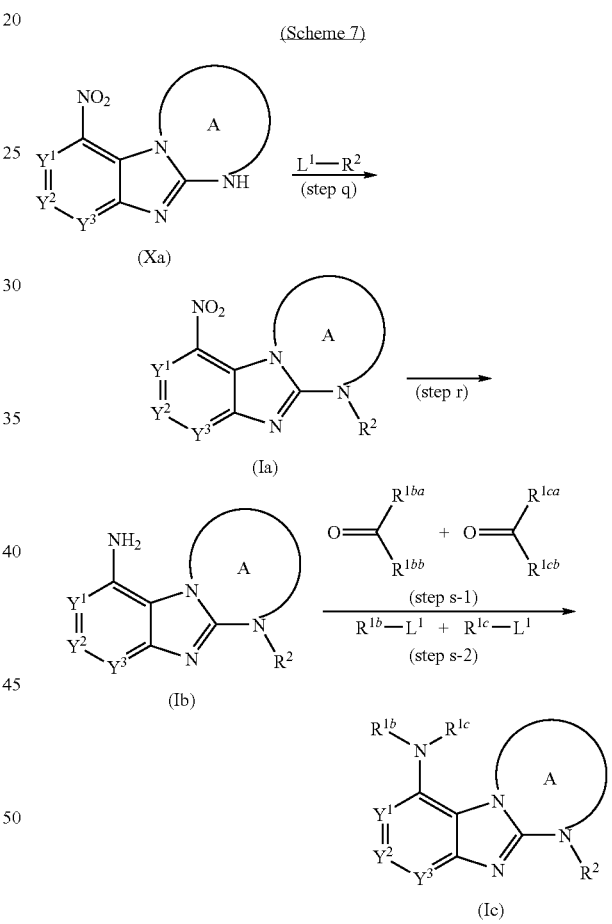

The above $R^{1b}$, $R^{1c}$ are independently an optionally substituted hydrocarbon group, or $R^{1b}$ and $R^{1c}$ may be optionally substituted cyclic form, $R^{1ba}$, $R^{1bb}$, $R^{1ca}$ and $R^{1cb}$ are independently hydrogen or an optionally substituted hydrocarbon group, or $R^{1ba}$ and $R^{1bb}$ or $R^{1ca}$ and $R^{1cb}$ may be optionally substituted cyclic form.

In the step q, compound (Ia), which is encompassed within compound (I), can be prepared from compound (Xa), which is encompassed within compound (X), by similar methods in the step j. Compound (Xa) can be prepared in the scheme 8.

In the step r, compound (Ib), which is encompassed within compound (I), can be prepared by hydrogenation of compound (Ia) in the presence of a hydrogenation catalyst, or prepared by a reduction reaction for compound (Ia).

Examples of the hydrogenation catalyst are described above in the step h. The hydrogenation catalyst may be employed in an amount of 0.01 mole to 0.5 per 1 mole of compound (Ia). In this step, 1 mole to excess of an acid or a base may be employed per 1 mole of compound (Ia), or an acid may be employed as a solvent.

Examples of the hydrogen source are described above in the step e. The hydrogen source may be employed in an amount of 1 mole to excess per 1 mole of compound (Ia).

Examples of the solvent having no adverse effect on the reaction include water, alcohols such as methanol, ethanol, etc., ethers such as diethyl ether, dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio, or may not be used.

The reaction temperature is 0° C. to 200° C., preferably 20° C. to 100° C. The reaction time is usually 0.5 to 48 hours, preferably 1 to 16 hours. While a reaction is usually performed at atmospheric pressure, it can be performed under pressure (3 to 10 atm) if necessary. While the amount of a catalyst employed may vary depending on the type of the catalyst employed, it is usually 0.1 to 20% by weight based on an active intermediate or a salt thereof.

In the step r, compound (Ib), which is encompassed within compound (I), can be also prepared by reduction of compound (Ia). A reducing reagent is preferably Fe, Zn, Sn or $SnCl_2$. In this step, acidic conditions may be used.

Examples of an acid are described above in the step d. The acid may be employed in an amount of 1 mole to excess per 1 mole of compound (Ia) or as a solvent.

A reaction solvent may for example be alcohols such as methanol, ethanol, etc., ethers such as dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, etc. and sulfoxides such as dimethylsulfoxide, etc. These solvents may be used by mixing at an appropriate ratio, or may not be used.

While the reaction temperature may vary depending on the substrate employed as well as other conditions, it is −20 to 200° C., preferably 0 to 100° C. The reaction time is usually 5 minutes to 24 hours, preferably 5 minutes to 10 hours.

Thus obtained compound (Ib) can be isolated and purified by the known isolating and purifying methods, for example, concentration, concentration under reduced pressure, extraction with solvent, crystallization, recrystallization, transfer dissolution and chromatography.

In step s-1, compound (Ic), which is encompassed within compound (I), can be prepared from compound (Ib) and a carbonyl compound $R^{1ba}R^{1bc}C=O$ or $R^{1ca}R^{1cb}C=O$ by in situ production of an imine which is then reduced by an appropriate reducing reagent or hydrogenation in the presence of a hydrogenation catalyst. When $R^{1b}$ is equal to $R^{1c}$ in compound (Ic), $R^{1ba}R^{1bc}C=O$ may be used in step s-1. When $R^{1b}$ is not equal to $R^{1c}$ in compound (Ic), the alkylation reactions may be performed stepwise by $R^{1ba}R^{1bc}C=O$ and $R^{1ca}R^{1cb}C=O$ in step s-1.

Examples of the reducing reagent are preferably sodium borohydride, lithium borohydride, sodium cyanoborohydride and sodium triacetoxyborohydride, etc. The reducing reagent may be employed in an amount of 1 mole to 10 moles per 1 mole of compound (Ib).

Examples of the hydrogenation catalyst are described above in the step h. The hydrogenation catalyst may be employed in an amount of 0.01 mole to 0.5 per 1 mole of compound (Ib). In this step, 1 mole to excess of an acid or a base may be employed per 1 mole of compound (Ib), or an acid may be employed as a solvent.

Examples of the hydrogen source are described above in the step e. The hydrogen source may be employed in an amount of 1 mole to excess per 1 mole of compound (Ib).

Examples of the solvent having no adverse effect on the reaction include water, alcohols such as methanol, ethanol, etc., ethers such as diethyl ether, dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio, or may not be used.

While the reaction temperature may vary depending on compound (Ib) employed as well as other reaction conditions, it is 0 to 200° C., preferably 20 to 150° C. The reaction time is 5 minutes to 48 hours, preferably 5 minutes to 24 hours. While a reaction is usually performed at atmospheric pressure, it can be performed under pressure (3 to 10 atm) if necessary.

While the amount of a catalyst employed may vary depending on the type of the catalyst employed, it is usually 0.1 to 20% by weight based on an active intermediate or a salt thereof.

When producing an imine, use of molecular sieves or addition of an acid serves to promote the reaction. An acid employed here is preferably acetic acid and trifluoroacetic acid, etc.

While the reaction temperature in this imine production may vary depending on compound (Ib) as well as other conditions, it is 0 to 200° C., preferably 0 to 150° C. The reaction time is 30 minutes to 48 hours, preferably 1 hour to 24 hours.

The reaction temperature in the reducing reaction is −20 to 200° C., preferably 0 to 100° C. The reaction time is 30 minutes to 24 hours, preferably 30 minutes to 12 hours.

Compound (Ic) can be also prepared by reacting compound (Ib) with $R^{1b}L^1$ or $R^{1c}L^1$. When $R^{1b}$ is equal to $R^{1c}$ in compound (Ic), $R^{1b}L^1$ may be used in step s-2. When $R^{1b}$ is not equal to $R^{1c}$ in compound (Ic), the alkylation reactions may be performed stepwise by $R^{1b}L^1$ and $R^{1c}L^1$ in step s-2.

In step s-2, 1 to 10 moles, preferably 1 to 5 moles of a compound represented by $R^{1b}L^1$ and $R^{1c}L^1$ or a salt thereof and 1 to 10 moles, preferably 1 to 3 moles of a base are employed per 1 mole of compound (Ib).

Examples of the base are described above in the step a. The base may be employed in an amount of 1 mole to excess per 1 mole of compound (Ib) or as a solvent.

Examples of the solvent having no adverse effect on the reaction include alcohols such as methanol, ethanol, etc., ethers such as dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, etc., and sulfoxides such as dimethylsulfoxide, etc. These solvents may be used by mixing at an appropriate ratio, or may not be used.

While the reaction temperature may vary depending on compound (Ib) employed as well as other reaction conditions, it is −20 to 200° C., preferably 0 to 150° C. The reaction time is 5 minutes to 48 hours, preferably 5 minutes to 24 hours.

Alkylation of compound (Ib) to prepare compound (Ic) may be performed by combined reactions of steps s-1 and s-2.

Thus obtained compound (Ic) can be isolated and purified by the known isolating and purifying methods, for example, concentration, concentration under reduced pressure, extraction with solvent, crystallization, recrystallization, transfer dissolution and chromatography.

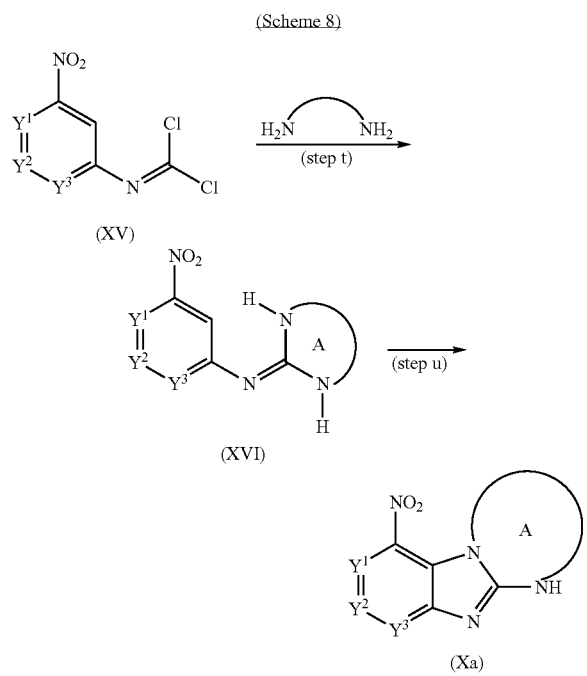

In the step t, compound (XVI) can be prepared by reacting compound (XV) with

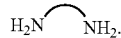

In the step, a base may be used.

In this step, 1 to 20 moles, preferably 1 to 10 moles of

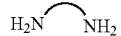

or a salt thereof are employed per 1 mole of compound (XV). Compound (XV) can be prepared in the scheme 9.

Examples of the base are described above in the step a. The base may be employed in an amount of 1 mole to excess per 1 mole of compound (XV) or as a solvent.

Examples of the solvent having no adverse effect on the reaction include alcohols such as methanol, ethanol, etc., ethers such as dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as dimethylformamide, N,N-dimethylacetamide, etc., and sulfoxides such as dimethylsulfoxide, etc. These solvents may be used by mixing at an appropriate ratio, or may not be used.

While the reaction temperature may vary depending on compound (XV) employed as well as other reaction conditions, it is −20 to 200° C., preferably 0 to 150° C. The reaction time is 5 minutes to 48 hours, preferably 5 minutes to 24 hours.

Thus obtained compound (XVI) can be isolated and purified by the known isolating and purifying methods, for example, concentration, concentration under reduced pressure, extraction with solvent, crystallization, recrystallization, transfer dissolution and chromatography.

In the step u, compound (Xa), which is encompassed within compound (X), can be prepared by cyclization of compound (XVI) under basic conditions.

Examples of the base are described above in the step a. The base may be employed in an amount of 0.001 mole to 5.0 per 1 mole of compound (XVI).

Examples of solvent having no adverse effect on the reaction include alcohols such as methanol, ethanol, etc., ethers such as dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, etc., and sulfoxides such as dimethylsulfoxide, etc. These solvents may be used by mixing at an appropriate ratio.

While the reaction temperature may vary depending on compound (XVI) employed as well as other reaction conditions, it is −20 to 200° C., preferably 0 to 150° C. The reaction time is 5 minutes to 72 hours, preferably 5 minutes to 48 hours.

Thus obtained compound (Xa) can be isolated and purified by the known isolating and purifying methods, for example, concentration, concentration under reduced pressure, extraction with solvent, crystallization, recrystallization, transfer dissolution and chromatography.

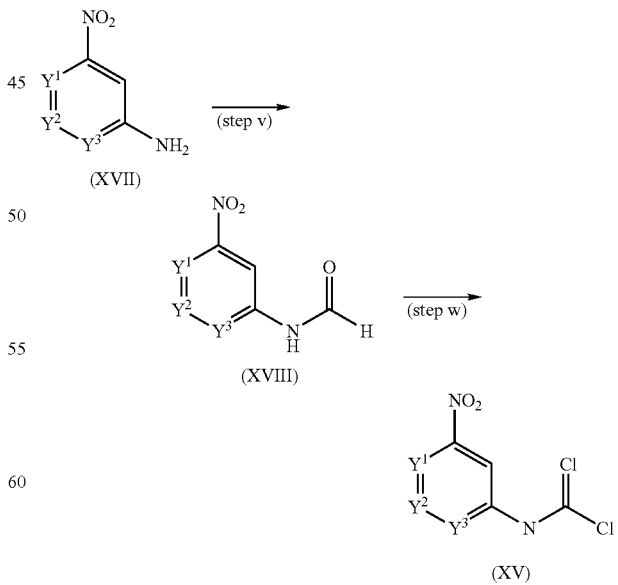

In the step v, compound (XVIII) can be prepared by reacting compound (XVII) with a formylating source.

Examples of the formylating source include formic acetic anhydride, formic acid, N,N-dimethylformamide, N,N-formylpiperidine, etc. The formylating source may be employed in an amount of 1 mole to excess per 1 mole of compound (XVII) as a solvent.

Examples of the solvent having no adverse effect on the reaction include alcohols such as methanol, ethanol, etc., ethers such as dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, etc., and sulfoxides such as dimethylsulfoxide, etc. These solvents may be used by mixing at an appropriate ratio, or may not be used.

While the reaction temperature may vary depending on compound (XVII) employed as well as other reaction conditions, it is −20 to 200° C., preferably 0 to 150° C. The reaction time is 5 minutes to 48 hours, preferably 5 minutes to 24 hours.

Thus obtained compound (XVIII) can be isolated and purified by the known isolating and purifying methods, for example, concentration, concentration under reduced pressure, extraction with solvent, crystallization, recrystallization, transfer dissolution and chromatography.

In the step w, compound (XV) can be prepared by reacting compound (XVIII) by halogenation. This reaction can be carried out according to the procedure of Ferchland et al. (DE 3134134) and Kuhle et al. (Angew. Chem., 1967, 79, 663) and its modified methods.

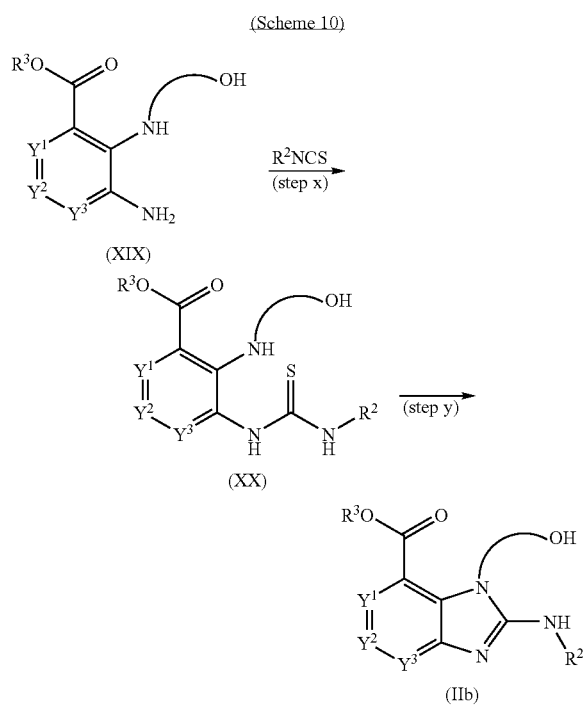

In the step x, compound (XX) can be prepared by reacting (XIX) with $R^2NCS$ or a salt thereof. Compound (XIX) can be prepared in the scheme 11.

In this step, 1 to 20 moles, preferably 1 to 10 moles of $R^2NCS$ or a salt thereof are employed per 1 mole of compound (XIX).

Examples of the solvent having no adverse effect on the reaction include alcohols such as methanol, ethanol, etc., ethers such as dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, etc., and sulfoxides such as dimethylsulfoxide, etc. These solvents may be used by mixing at an appropriate ratio.

While the reaction temperature may vary depending on compound (XIX) employed as well as other conditions, it is 0 to 200° C., preferably 20 to 150° C. The reaction time is 30 minutes to 120 hours, preferably 1 to 72 hours.

Thus obtained compound (XX) can be isolated and purified by the known isolating and purifying methods, for example, concentration, concentration under reduced pressure, extraction with solvent, crystallization, recrystallization, transfer dissolution and chromatography.

In the step y, Compound (IIb), which is encompassed within compound (II), can be prepared by treatment of compound (XX) with a dehydrothiolation reagent. In this step, a base may be used.

Examples of the dehydrothiolation reagent include N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, methyl iodide mercury (II) chloride, mercury(II) oxide, copper(II) bromide, copper (II) chloride, silver oxide, silver(I) oxide, silver carbonate, etc. The dehydrothiolation reagent may be employed in an amount of 1 to 10 moles, preferably 1 to 3 moles per 1 mole of compound (XX).

Examples of the base are described above in the step a. The base may be employed in an amount of 1 mole to excess per 1 mole of compound (XX) or as a solvent.

Examples of the solvent having no adverse effect on the reaction include alcohols such as methanol, ethanol, etc., ethers such as dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, etc., and sulfoxides such as dimethylsulfoxide, etc. These solvents may be used by mixing at an appropriate ratio, or may not be used.

While the reaction temperature may vary depending on the reagent employed as well as other conditions; it is −20 to 150° C., preferably 20 to 100° C. The reaction time is 5 minutes to 10 hours, preferably 5 minutes to 2 hours.

Thus obtained compound (IIb) can be isolated and purified by the known isolating and purifying methods, for example, concentration, concentration under reduced pressure, extraction with solvent, crystallization, recrystallization, transfer dissolution and chromatography.

(Scheme 11)

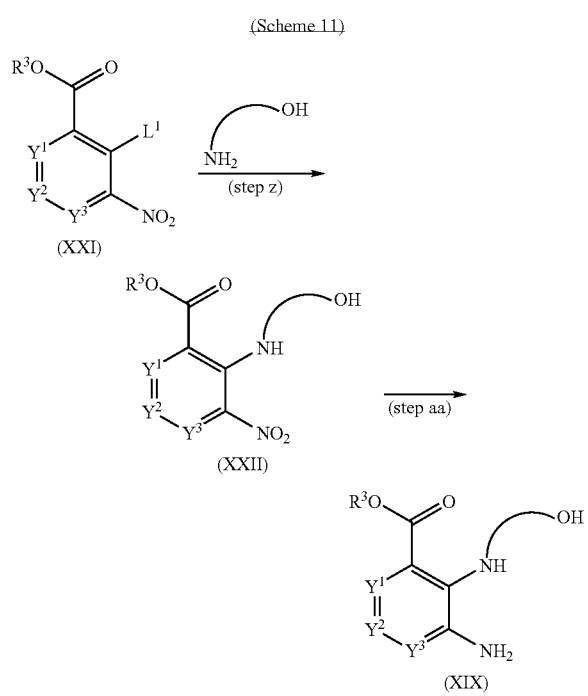

Examples of the base are described above in the step a. The base may be employed in an amount of 1 mole to excess per 1 mole of compound (XXI) or as a solvent.

Examples of the solvent having no adverse effect on the reaction include alcohols such as methanol, ethanol, etc., ethers such as dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, etc., and sulfoxides such as dimethylsulfoxide, etc. These solvents may be used by mixing at an appropriate ratio, or may not be used.

While the reaction temperature may vary, depending on Compound (XXI) employed as well as other reaction conditions, it is −20 to 200° C., preferably 0 to 150° C. The reaction time is 5 minutes to 48 hours, preferably 5 minutes to 24 hours.

Thus obtained compound (XXII) can be isolated and purified by the known isolating and purifying methods, for example, concentration, concentration under reduced pressure, extraction with solvent, crystallization, recrystallization, transfer dissolution and chromatography.

In the step aa, compound (XIX) can be prepared from compound (XXII) by similar method in the step r.

(Scheme 12)

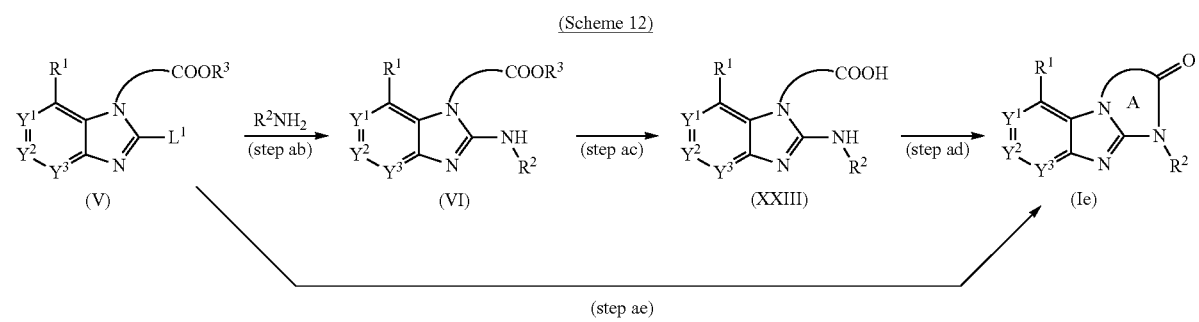

In the step z, compound (XXII) can be prepared by reacting compound (XXI) with

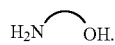

In this step, a base may be used.

In this step, 1 to 5 moles, preferably 1 to 3 moles of a compound represented by

or a salt thereof and 1 to 5 moles, preferably 1 to 3 moles of a base are employed per 1 mole of compound (XXI).

In the step ab, compound (VI) can be prepared from compound (V) by same methods in the step d. Compound (V) can be prepared in the scheme 2.

In the step ac, compound (XXIII) is prepared by removing a carboxyl-protecting group of compound (VI).

Examples of conventional methods used in a reaction for removal of a carboxyl-protecting group include hydrolysis, reduction and elimination using a Lewis acid. It is preferable that hydrolysis is carried out in the presence of a base or an acid.

Examples of the base are described above in the step a. Hydrolysis using a base is carried out in water or a hydrophilic organic solvent or a mixed solvent in many cases. The base may be employed in an amount of 1 mole to excess per 1 mole of compound (VI) or as a solvent.

Examples of an acid are described above in the step d. The acid may be employed in an amount of 1 mole to excess per 1 mole of compound (VI) or as a solvent.

The present hydrolysis reaction is usually carried out in an organic solvent, water or a mixed solvent thereof.

A reaction temperature is not particularly limited, but is appropriately selected depending on a kind of a carboxyl-protecting group and an elimination method.

Elimination using a Lewis acid is carried out by reacting compound (VI) with a Lewis acid.

Examples of the Lewis acid include trihalogenated boron such as boron trichloride, boron trifluoride, etc., tetrahalogenated titanium such as titanium tetrachloride, titanium tetrabromide, etc., and halogenated aluminum such as aluminum chloride, aluminum bromide, etc., or an organic acid such as trichloroacetic acid, trifluoroacetic acid, etc.

This elimination reaction is preferably carried out in the presence of a cation scavenger such as anisole, phenol, etc.

Examples of the solvent include nitroalkane such as nitromethane, nitroethane, etc., alkylene halide such as methylene chloride, ethylene chloride, etc., diethyl ether, carbon disulfide, and a solvent having no adverse effect on the reaction. These solvents may be used by mixing at an appropriate ratio, or may not be used.

It is preferable that elimination by reduction is applied to elimination of a protecting group including halogenated alkyl such as 2-iodoethyl, 2,2,2-trichloroethyl, etc., ester, and aralkyl such as benzyl, etc., ester, etc.

Examples of the reduction method using in the present elimination reaction include the conventional catalytic reduction in the presence of a combination of a metal such as zinc, zinc amalgam, etc., or a salt of a chromium compound such as chromate chloride, chromate acetate, etc., and an organic or inorganic acid such as acetic acid, propionic acid, hydrochloric acid, etc.; or the conventional metal catalyst such as palladium carbon and Raney nickel, etc.

A reaction temperature is not particularly limited, but a reaction is carried out under cooling, at room temperature or under heating.

Thus obtained compound (XXIII) can be isolated and purified by the known isolating and purifying methods, for example, concentration, concentration under reduced pressure, extraction with solvent, crystallization, recrystallization, transfer dissolution and chromatography.

In the step ad, compound (Ie), which is encompassed within compound (I), is prepared by reacting a carboxylic acid (XXIII) or a reactive derivative at a carboxy thereof and a salt thereof.

Specific examples of the suitable reactive derivative at a carboxy of compound (XXIII) include acid halide, acid anhydride, activated amide, activated ester and the like. Examples of the suitable reactive derivative include: acid chloride; acid azide; mixed acid anhydride with an acid such as substituted phosphoric acid such as dialkylphosphoric acid, phenylphosphoric acid, diphenylphosphoric acid, dibenzylphosphoric acid, halogenated phosphoric acid and the like, dialkylphosphorous acid, sulfurous acid, thiosulfuric acid, sulfuric acid, sulfonic acid such as methanesulfonic acid and the like, aliphatic carboxylic acid such as acetic acid, propionic acid, butyric acid, isobutyric acid, pivalic acid, pentanoic acid, isopentanoic acid, trichloroacetic acid and the like or aromatic carboxylic acid such as benzoic acid and the like; symmetric acid anhydride; activated amide with imidazole; 4-substituted imidazole, dimethylpyrazole, triazole or tetrazole; activated ester such as cyanomethyl ester, methoxymethyl ester, dimethyliminomethyl ester, vinyl ester, propargyl ester, p-nitrophenyl ester, trichlorophenyl ester, pentachlorophenyl ester, mesityl ester, phenylazophenyl ester, phenyl thioester, p-nitrophenyl ester, p-cresyl thioester, carboxylmethyl thioester, pyranyl ester, pyridyl ester, piperidyl ester, 8-quinolyl thioester and the like, or esters with N-hydroxy compound such as N,N-dimethylhydroxyamine, 1-hydroxy-2-(1H)-pyridone, N-hydroxysuccinimide, N-hydroxyphthalimide, 1-hydroxy-1H-benzotriazole and the like.

Examples of the suitable reactive derivative of compound (XXIII) include alkali metal salts such as sodium salt, potassium salt and the like, alkaline earth metal salts such as calcium salt, magnesium salt and the like, and basic salts such as organic base salts such as ammonium salt, trimethylamine salt, triethylamine salt, pyridine salt, picoline salt, dicyclohexylamine salt, N,N-dibenzylethylenediamine salt and the like.

Although the reaction is usually carried out in the conventional solvent such as water, alcohols such as methanol, ethanol and the like, acetone, dioxane, acetonitrile, chloroform, dichloromethane, tetrahydrofuran, ethyl acetate, N,N-dimethylformamide and pyridine, the reaction may be carried out in any other organic solvents as long as they have no adverse effect on the reaction. These solvents may be used as a mixture with water.

When compound (XXIII) is used as the form of a free acid or a salt thereof in this reaction, it is desirable that the reaction is carried out in the presence of the normally used condensing reagent such as so-called Vilsmeier regent and the like prepared by a reaction of N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide, N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; polyethyl phosphate; polyisopropyl phosphate; phosphorus oxychloride; diphenylphosphorylazide; thionyl chloride; oxalyl chloride; lower alkyl haloformate such as ethyl chloroformate, isopropyl chloroformate and the like; triphenylphosphine; 2-ethyl-7-hydroxybenzisooxazolium salt; 2-ethyl-5-(m-sulfophenyl)isooxazolium hydroxide internal salt; N-hydroxybenzotriazole; 1-(p-chlorobenzenesulfonyloxy)-6-chloro-1H-benzotriazole; N,N-dimethylformamide with thionyl chloride, phosgene, trichloromethyl chloroformate, phosphorus oxychloride or the like. Alternatively, the reaction may be carried out in the presence of an inorganic base or an organic base such as alkali metal bicarbonate salt, tri(lower)alkylamine, pyridine, N-(lower)alkylmorpholine, N,N-di(lower)alkylbenzylamine and the like. A reaction temperature is not particularly limited, but the reaction is carried out under cooling or under warming.

While the reaction temperature may vary depending on compound (XXIII) employed as well as other reaction conditions, it is −78 to 200° C., preferably 30 to 100° C.

The reaction time is 5 minutes to 48 hours, preferably 5 minutes to 20 hours.

Thus obtained compound (Ie) can be isolated and purified by the known isolating and purifying methods, for example, concentration, concentration under reduced pressure, extraction with solvent, crystallization, recrystallization, transfer dissolution and chromatography.

In the step ae, compound (Ie) may be also prepared from compound (V) by an intramolecular cyclization with $R^2NH_2$. In this step, an acid, a base, a palladium catalyst or a copper reagent may be used. A catalytic amount of a phosphine ligand may be employed.

In this step, 1 to 20 moles, preferably 1 to 10 moles of a compound represented by $R^2NH_2$ or a salt thereof are employed per 1 mole of compound (V).

Examples of an acid are described above in the step d. The acid may be employed in an amount of 1 to 10 moles, preferably 1 to 5 moles per 1 mole of compound (V).

Examples of the base are described above in the step a. The base may be employed in an amount of 1 mole to excess per 1 mole of compound (V) or as a solvent.

Examples of the palladium catalyst are described above in the step d. The palladium catalyst may be employed in an amount of 0.001 mole to 0.5 mole per 1 mole of compound (V).

Examples of the phosphine ligand are described above in the step d. The phosphine ligand may be employed in an amount of 1 mole to 5.0 moles per 1 mole of the palladium catalyst.

Examples of the copper reagent are described above in the step d. The copper reagent may be employed in an amount of 0.01 mole to 10 moles per 1 mole of compound (V).

Examples of the solvent having no adverse effect on the reaction include water, alcohols such as methanol, ethanol, etc., ethers such as diethyl ether, dioxane tetrahydrofuran, etc., aromatic hydrocarbons such as benzene, toluene xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio, or may not be used.

While the reaction temperature may vary depending on compound (V) employed as well as other reaction conditions, it is 0 to 200° C., preferably 20 to 150° C., or the reaction may be heated by microwave irradiation. The reaction time is 5 minutes to 48 hours, preferably 5 minutes to 24 hours.

Thus obtained compound (Ie) can be isolated and purified by the known isolating and purifying methods, for example, concentration, concentration under reduced pressure, extraction with solvent, crystallization, recrystallization, transfer dissolution and chromatography.

cyclic form, $R^{1d}$ is an optionally substituted hydrocarbon group, an optionally substituted heterocyclic group, an optionally substituted amino, an optionally substituted alkoxy, —$SR^{3b}$ (an optionally substituted sulfanyl), —$SOR^{3b}$ (an optionally substituted sulfinyl), or —$SO_2R^{3b}$ (an optionally substituted sulfonyl).

In the step af, compound (Ig), which is encompassed within compound (I), can be prepared by alkylation of compound (If), which is encompassed within compound (I), with an aldehyde represented by $R^{3a}CHO$ or a salt thereof after treating by an organometallic reagent. Compound (If) can be prepared in the scheme 1.

Examples of an organic metal reagent include n-butyl lithium, sec-butyl lithium, tert-butyl lithium, methyl magnesium bromide, lithium diisopropylamide and lithium bis(trimethylsilyl)amide, etc. The organic metal reagent may be employed in amount of 1 to 10 moles; preferably 1 to 5 per 1 mole of compound (If).

$R^{3a}CHO$ may be employed in amount of 1 to 10 moles, preferably 1 to 5 per 1 mole of compound (If).

Examples of the solvent having no adverse effect on the reaction include hydrocarbons such as pentane, hexane, heptane, etc., aromatic hydrocarbons such as benzene, toluene, xylene, etc., ethers such as diethyl ether, dioxane, tetrahydrofuran, etc., and halogenated hydrocarbon such as chloroform, dichloromethane, etc. These solvents may be used by mixing at an appropriate ratio.

While the reaction temperature may vary depending on compound (If) as well as other conditions, it is –80 to 100° C., preferably –80 to 50° C. The reaction time is 10 min to 24 hr, preferably 30 min to 12 hr.

Thus obtained compound (Ig) can be isolated and purified by the known isolating and purifying methods, for example, concentration under reduced pressure, extraction with solvents, crystallization, recrystallization, transfer dissolution and chromatography.

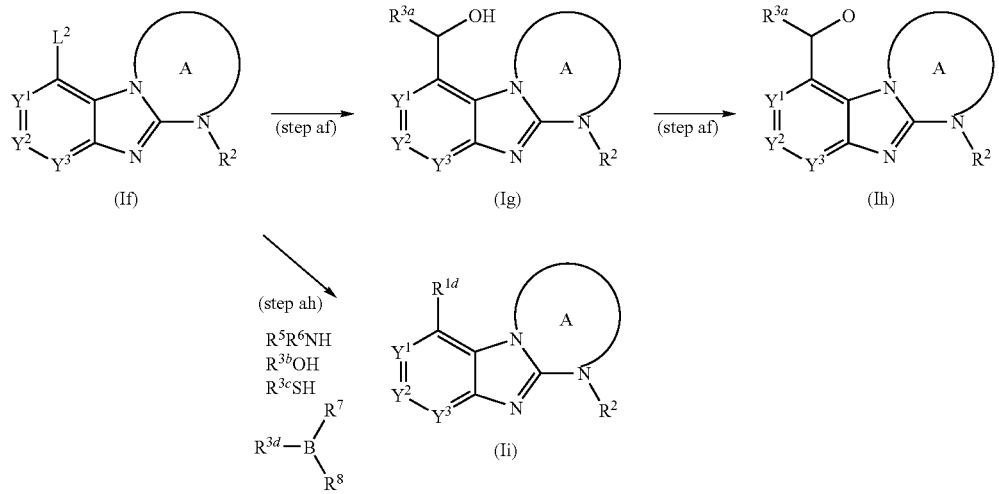

(Scheme 13)

The above $L^2$ is a halogen atom such as chlorine, bromine and iodine, $R^{3a}$, $R^{3b}$, $R^{3b}$ and $R^{3d}$ are independently optionally substituted hydrocarbon group, $R^5$ and $R^6$ are independently hydrogen or an optionally substituted hydrocarbon group, or $R^5$ and $R^6$ may be an optionally substituted cyclic form, $R^7$ and $R^8$ are independently hydrogen or an optionally substituted hydrocarbon group, hydroxy or an optionally substituted alkoxy, or $R^7$ and $R^8$ may be optionally substituted In the step ag, compound (Ih), which is encompassed within compound (I), can be prepared by conventional oxidation of compound (Ig) or a salt according to Organic Synthesis, Organic Reactions, etc. In this step, an oxidation reagent may be used.

Examples of an oxidation reagent include perbenzoic acid, m-chloroperbenzoic acid, peracetic acid, Dess Martin periodinane, o-iodoxybenzoic acid, pyridinium chlorochromate, pyridinium dichromate, manganese(IV) oxide, lead(IV) acetate, potassium permanganate, a combination of tetrapropylammonium perruthenate and N-methylmorpholine N-oxide, and a combination of dimethylsulfoxide and oxalyl dichloride, etc. The oxidation reagent may be employed in an amount of 0.8 to 20 moles, preferably 1 to 5 moles per 1 mole of compound (Ig).

Examples of the solvent having no adverse effect on the reaction include water, amines such as triethylamine, pyridine, etc., acids such as formic acid, acetic acid, trifluoro acetic acid, methanesulfonic acid, sulfuric acid, etc., alcohols such as methanol, ethanol, etc., hydrocarbons such as pentane, hexane, heptane, etc., aromatic hydrocarbons such as benzene, toluene, xylene, etc., ethers such as diethyl ether, dioxane, tetrahydrofuran, etc., esters such as ethyl acetate, etc., nitriles such as acetonitrile, etc., halogenated hydrocarbon such as chloroform, dichloromethane, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio.

While the reaction temperature may vary depending on compound (Ig) as well as other conditions, it is 0 to 200° C., preferably 0 to 100° C. The reaction time is 10 min to 24 hr, preferably 30 min to 12 hr.

Thus obtained compound (Ih) can be isolated and purified by the known isolating and purifying methods, for example, concentration under reduced pressure, extraction with solvents, crystallization, recrystallization, transfer dissolution and chromatography.

In the step ah, when $R^{1d}$ is an optionally substituted amino, an optionally substituted alkoxy, —$SR^{3c}$ in compound (Ii), which is encompassed within compound (I), compound (Ii) can be prepared by reacting compound (If) with an amine represented by $R^5R^6NH$, an alcohol represented by $R^{3b}OH$ or a mercaptan by $R^{3c}SH$, or a salt thereof in the presence of a copper reagent and a base.

$R^5R^6NH$, $R^{3b}OH$ or $R^{3c}SH$ may be employed in an amount of 1 to 20 moles, preferably 1 to 10 moles per 1 mole of compound (If).

Examples of the copper reagent are described above in the step d. The copper reagent may be employed in an amount of 0.01 mole to 10 mole per 1 mole of compound (If).

Examples of the base are described above in the step a. The base may be employed in an amount of 1 mole to excess per 1 mole of compound (If) or as a solvent.

Examples of the solvent having no adverse effect on the reaction include water, amines such as triethylamine, pyridine, etc., alcohols such as methanol, ethanol, etc., hydrocarbons such as pentane, hexane, heptane, etc., aromatic hydrocarbons such as benzene, toluene, xylene, etc., ethers such as diethyl ether, dioxane, tetrahydrofuran, etc., nitriles such as acetonitrile, etc., halogenated hydrocarbon such as chloroform, dichloromethane, etc., amides such as N,N-dimethylformamide, N,N-dimethylacetamide, 1-methyl-2-pyrrolidinone, etc., and sulfoxides such as dimethylsulfoxide, etc. These solvents may be used by mixing at an appropriate ratio, or may not be used.

While the reaction temperature may vary depending on compound (If) as well as other conditions, it is 0 to 200° C., preferably 20 to 150° C. The reaction time is 10 min to 24 hr, preferably 30 min to 12 hr.

When $R^{1d}$ is —$SOR^{3c}$ or —$SO_2R^{3c}$ in compound (Ii), compound (Ii) can be prepared from compound (Ii) wherein $R^{1d}$ is —$SR^{3b}$ by oxidation.

Examples of conventional methods used in a reaction for oxidation are described above in the step ag. The oxidation reagent may be employed in an amount of 0.8 to 20 moles, preferably 1 to 5 moles per 1 mole of compound (Ii).

When $R^{1d}$ is an optionally substituted hydrocarbon or an optionally substituted heterocyclic in compound (Ii), compound (Ii) can be prepared by reacting compound (If) with $R^{3d}BR^7R^8$ or a salt thereof in the presence of a palladium catalyst, phosphine ligand and a base.

$R^{3d}BR^7R^8$ may be employed in an amount of 1 to 10 moles, preferably 1 to 5 moles per 1 mole of compound (If).

Examples of the palladium catalyst are described above in the step d. The palladium catalyst may be employed in an amount of 0.001 mole to 0.5 mole per 1 mole of compound (If).

Examples of the phosphine ligand are described above in the step d. The phosphine ligand may be employed in an amount of 1 mole to 5.0 mole per 1 mole of the palladium catalyst.

Examples of the base are described above in the step a. The base may be employed in an amount of 1 mole to excess per 1 mole of compound (If) or as a solvent.

Examples of the solvent having no adverse effect on the reaction include water, alcohols such as methanol, ethanol, etc., hydrocarbons such as pentane, hexane, heptane, etc., aromatic hydrocarbons such as benzene, toluene, xylene, etc., ethers such as diethyl ether, dioxane, tetrahydrofuran, etc., esters such as ethyl acetate, etc., nitriles such as acetonitrile, etc., halogenated hydrocarbon such as chloroform, dichloromethane, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio, or may not be used.

While the reaction temperature may vary depending on compound (If) as well as other conditions, it is 0 to 200° C., preferably 20 to 100° C. The reaction time is 10 min to 24 hr, preferably 30 min to 12 hr.

Thus obtained compound (Ii) can be isolated and purified by the known isolating and purifying methods, for example, concentration under reduced pressure, extraction with solvents, crystallization, recrystallization, transfer dissolution and chromatography.

(Scheme 14)

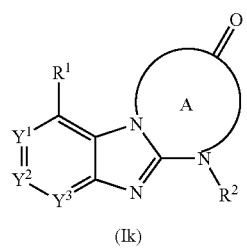

(Ik)

-continued

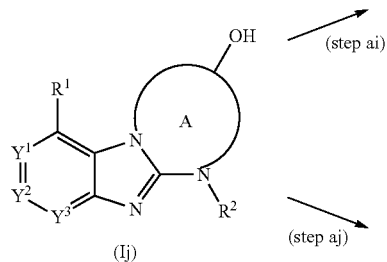

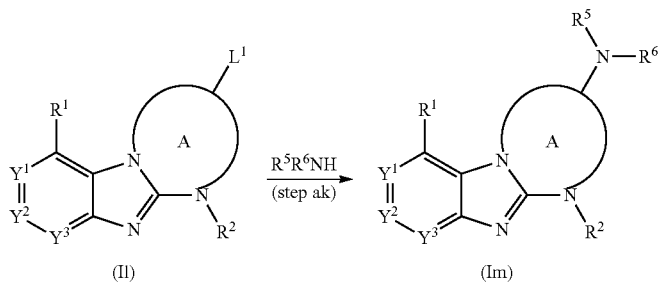

In the step ai, compound (Ik), which is encompassed within compound (I), may be prepared from compound (Ij), which is encompassed within compound (I), by oxidation. Compound (Ij) can be prepared in the scheme 1.

Examples of conventional methods used in a reaction for oxidation are described above in the step ag. The oxidation reagent may be employed in an amount of 0.8 to 20 moles, preferably 1 to 5 moles per 1 mole of compound (Ij).

In the step aj, compound (Il), which is encompassed within compound (I), may be prepared from compound (Ij) by halogenation, sulfonylation or acylation.

Examples of conventional methods used in a reaction for halogenation, sulfonylation or acylation are described above in the step a.

In the step ak, compound (Im), which is encompassed within compound (I), can be prepared by amination of compound (Il) with $R^5R^6NH$ or a salt thereof. In this step, a base may be used.

$R^5R^6NH$ or a salt thereof may be employed in amount of 1 mole to excess per 1 mole of compound (Il) or as a solvent.

Examples of the base are described above in the step a. A base may be employed in amount of 1 mole to excess per 1 mole of compound (Il) or as a solvent.

Examples of the solvent having no adverse effect on the reaction include water, amines such as triethylamine, pyridine, etc., alcohols such as methanol, ethanol, etc., hydrocarbons such as pentane, hexane, heptane, etc., aromatic hydrocarbons such as benzene, toluene, xylene, etc., ethers such as diethyl ether, dioxane, tetrahydrofuran, etc., halogenated hydrocarbon such as chloroform, dichloromethane, etc., amides such as N,N-dimethylformamide, N,N-dimethylacetamide, 1-methyl-2-pyrrolidinone, etc., and sulfoxides such as dimethylsulfoxide, etc. These solvents may be used by mixing at an appropriate ratio, or may not be used.

While the reaction temperature may vary depending on compound (Il) as well as other conditions, it is −80 to 100° C., preferably −80 to 50° C. The reaction time is 10 min to 24 hr, preferably 30 min to 12 hr.

Thus obtained compound (Im) can be isolated and purified by the known isolating and purifying methods, for example, concentration under reduced pressure, extraction with solvents, crystallization, recrystallization, transfer dissolution and chromatography.

(Scheme 15)

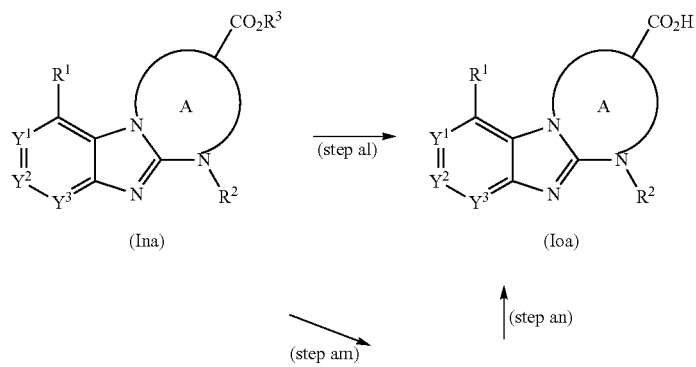

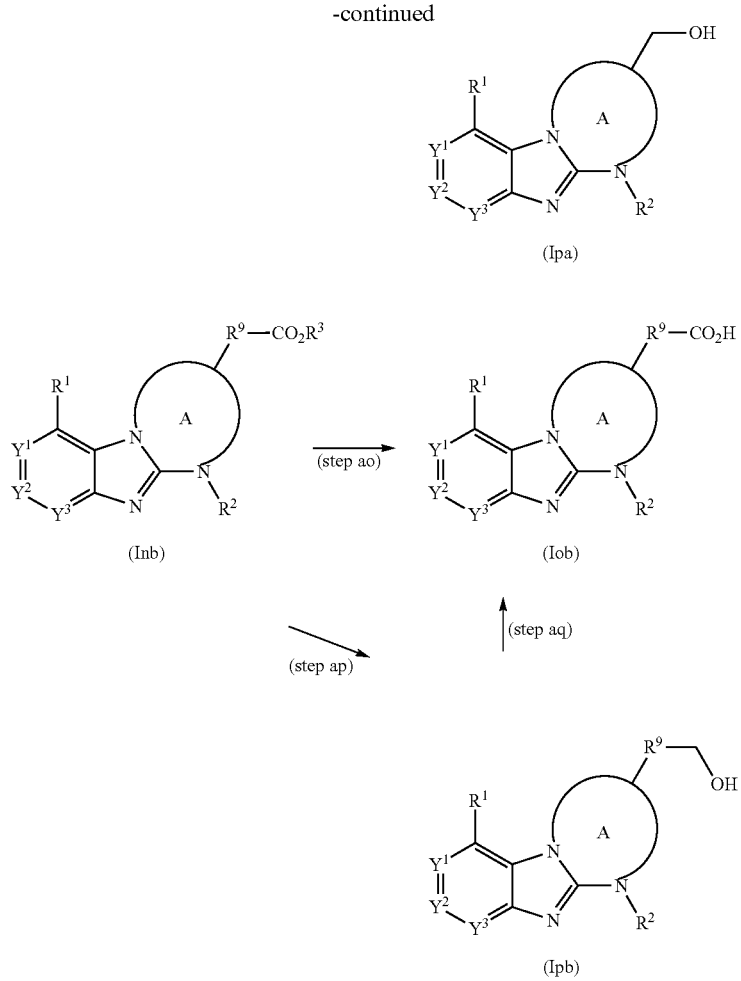

The above R⁹ is an optionally substituted hydrocarbon group.

In the step al, compound (Ioa), which is encompassed within compound (I), may be prepared from compound (Ina), which is encompassed within compound (I), by removing a carboxyl-protecting group of compound (Ina). Compound (Ina) can be prepared in the scheme 1.

Examples of conventional methods used for removal of a carboxyl-protecting group are described above in the step ac.

In the step am, compound (Ipa), which is encompassed within compound (I), may be prepared from compound (Ina) by reduction or hydrogenation.

Examples of conventional methods used for reduction or hydrogenation are described above in the step e.

In the step an, compound (Ioa) may be prepared from compound (Ipa) by conventional oxidation.

Examples of conventional methods used in a reaction for oxidation are described above in the step ag.

In the step ao, compound (Iob), which is encompassed within compound (I), may be prepared from compound (Inb), which is encompassed within compound (I), by similar methods in the step al. Compound (Inb) can be prepared in the scheme 1.

In the step ap, compound (Ipb), which is encompassed within compound (I), may be prepared from compound (Inb) by similar methods in the step am.

In the step aq, compound (Iob) may be prepared from compound (Ipb) by similar methods in the step an.

(Scheme 16)

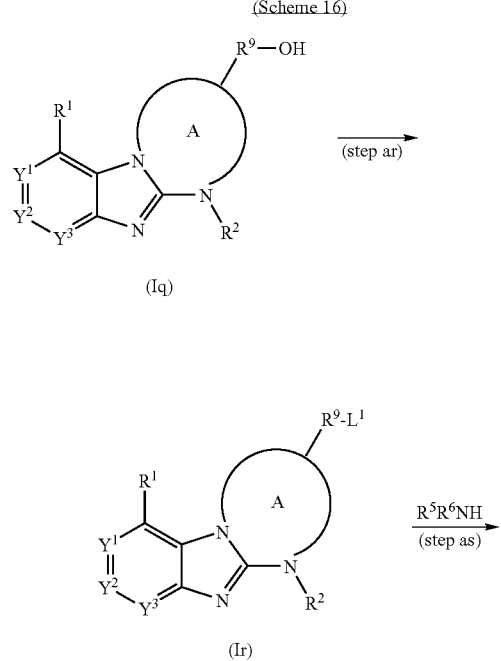

-continued

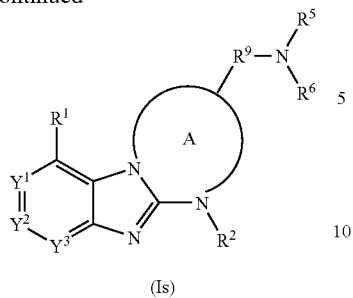

(Is)

In the step ar, compound (Ir), which is encompassed within compound (I), may be prepared from compound (Iq), which is encompassed within compound (I), by halogenation, sulfonylation or acylation. Compound (Iq) can be prepared in the scheme 1 or the scheme 15.

Examples of conventional methods used for halogenation, sulfonylation or acylation are described above in the step a.

In the step as, compound (Is), which is encompassed within compound (I), may be prepared from compound (Ir) by amination with $R^5R^6NH$ or a salt thereof.

Examples of conventional methods used for amination are described above in the step ak.

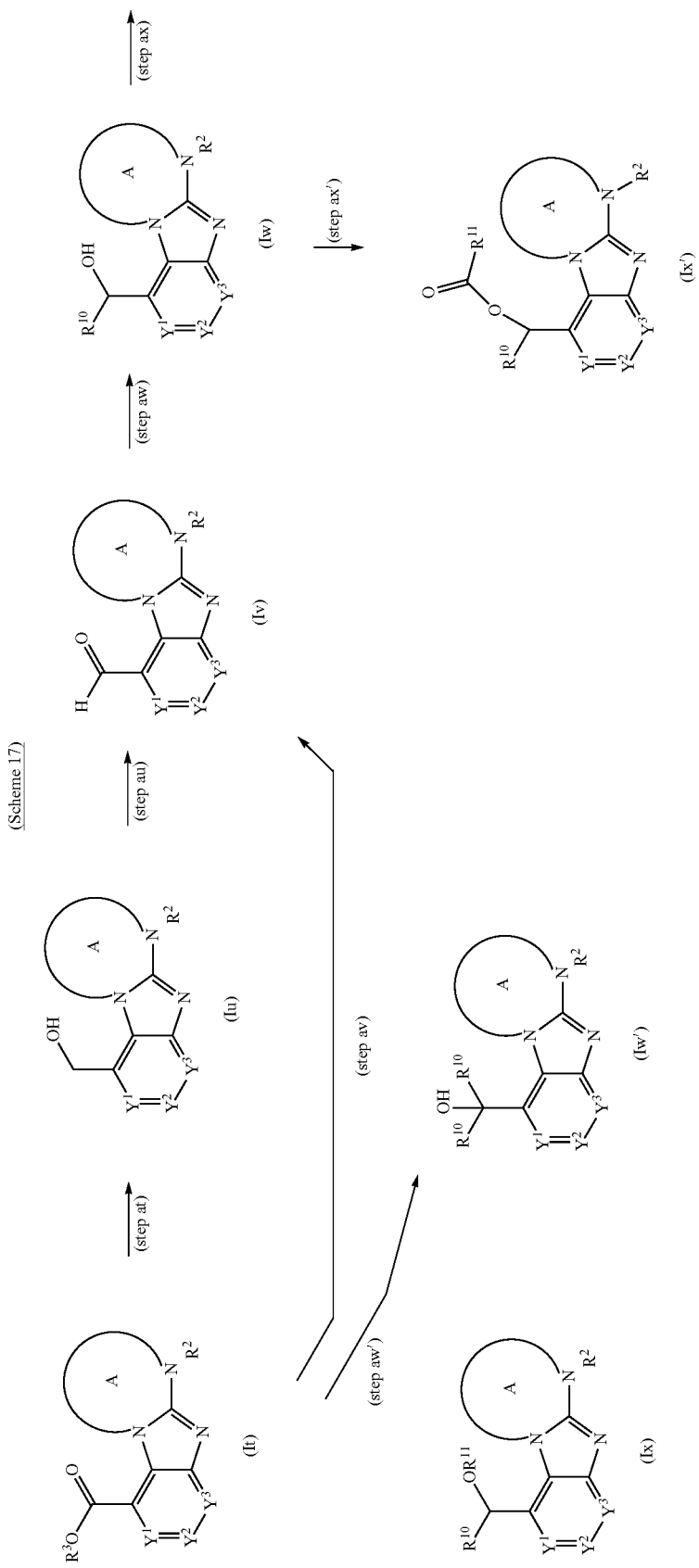
(Scheme 17)

The above $R^{10}$ and $R^{11}$ are independently an optionally substituted hydrocarbon group, or an optionally substituted heterocyclic group.

In the step at, compound (Iu), which is encompassed within compound (I), may be prepared from compound (It), which is encompassed within compound (I), by reduction or hydrogenation. Compound (It) can be prepared in the scheme 1.

Examples of conventional methods used for reduction or hydrogenation are described above in the step e.

In the step au, compound (Iv), which is encompassed within compound (I), may be prepared from compound (Iu) by conventional oxidation.

Examples of conventional methods used for oxidation are described above in the step ag.

In the step av, compound (Iv) may be prepared from compound (It) by reduction or hydrogenation.

Examples of conventional methods used for reduction or hydrogenation are described above in the step e.

In the step aw, compound (Iw), which is encompassed within compound (I), can be prepared by reacting with compound (Iv) with an organometallic reagent.

Examples of the organometallic reagent include Grignard reagent, an alkyl lithium, trifluoromethyl trialkylsilane, etc. The organometal reagent may be employed in amount of 1 to 20 moles, preferably 1 to 10 moles per 1 mole of compound (Iv). When trifluoromethyl trialkylsilane is used as a organometal reagent, catalytic amount of weak bases such as tri(n-butyl)ammonium fluoride, tetra(n-butyl)ammonium acetate, lithium acetate, etc may be used. The base may be employed in amount of 0.001 to 0.2 moles, preferably 0.1 to 0.15 moles per 1 mole of compound (Iv).

Examples of the solvent having no adverse effect on the reaction include hydrocarbons such as pentane, hexane, heptane, etc., aromatic hydrocarbons such as benzene, toluene, xylene, etc., ethers such as diethyl ether, dioxane, tetrahydrofuran, etc., and halogenated hydrocarbon such as chloroform, dichloromethane, etc. In addition, amides such as N,N-dimethylformamide, N,N-dimethylacetamide, etc and sulfoxides such as dimethylsulfoxide, etc may be used as a solvent, when trifluoromethyl trialkylsilane is used as a organometal reagent. These solvents may be used by mixing at an appropriate ratio.

While the reaction temperature may vary depending on compound (Iv) as well as other conditions, it is −80 to 110° C., preferably −80 to 20° C. The reaction time is 10 min to 24 hr, preferably 30 min to 12 hr.

Thus obtained compound (Iw) can be isolated and purified by the known isolating and purifying methods, for example, concentration under reduced pressure, extraction with solvents, crystallization, recrystallization, transfer dissolution and chromatography.

In the step ax, compound (Ix), which is encompassed within compound (I), can be prepared by reacting with compound (Iw) with $R^{11}L^1$ or $(R^{11}O)_2SO_2$. In this step, a base may be used.

$R^{11}L^1$ or $(R^{11}O)_2SO_2$ may be employed in amount of 1 to excess moles, preferably 1 to 5 moles per 1 mole of compound (Iw).

Examples of the base are described above in the step a. The base may be employed in amount of 1 to 5 moles, preferably 1 to 3 moles per 1 mole of compound (Iw).

This reaction may be carried out in the presence of additives. Examples of additives include phase transfer catalysts such as triethylbenzylammonium chloride, tetrabutylammonium bromide and benzyltriethylammonium chloride, etc. The additive may be employed in amount of 0.01 to 1 moles, preferably 0.1 to 0.5 moles per 1 mole of compound (Iw).

Examples of the solvent having no adverse effect on the reaction include amines such as triethylamine, pyridine, etc., hydrocarbons such as pentane, hexane, heptane, etc., aromatic hydrocarbons such as benzene, toluene, xylene, etc., ethers such as diethyl ether, dioxane, tetrahydrofuran, etc., esters such as ethyl acetate, etc., nitriles such as acetonitrile, etc., halogenated hydrocarbon such as chloroform, dichloromethane, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio. In addition, a mixture of these solvents and water at an appropriate ratio may be used.

While the reaction temperature may vary depending on compound (Iw) as well as other conditions, it is −80 to 110° C., preferably −80 to 20° C. The reaction time is 10 min to 24 hr, preferably 30 min to 12 hr.

Thus obtained compound (Ix) can be isolated and purified by the known isolating and purifying methods, for example, concentration under reduced pressure, extraction with solvents, crystallization, recrystallization, transfer dissolution and chromatography.

In the step ax', compound (Ix'), which is encompassed within compound (I), can be prepared by reaction of compound (Iw) with $R^{11}COL_1$, $(R^{11}CO)O$ or condensation with $R^{11}CO_2H$. In this step, base may be used.

Examples of the reaction of compound (Iw) with $R^{11}COL_1$ are described above in the step f.

In the step aw', compound (Iw), which is encompassed within compound (I), can be prepared from compound (It) by reaction with an organometal reagent.

Examples of conventional methods used for reaction with an organometal reagent are described above in the step aw.

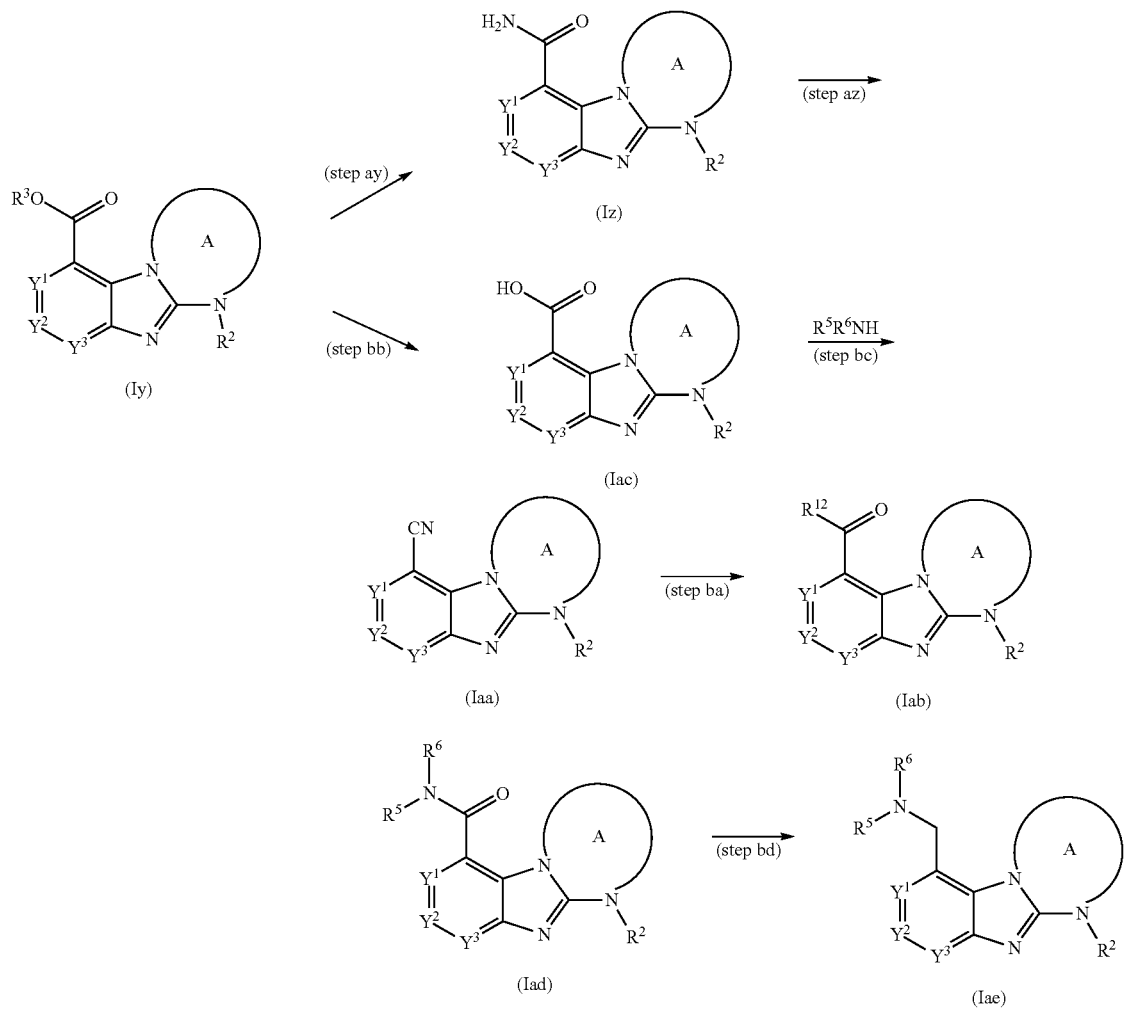

The above $R^{12}$ is an optionally substituted hydrocarbon group.

In the step ay, compound (Iz), which is encompassed within compound (I), can be prepared by amidation of compound (Iy) with an amidation reagent in the presence of a base. Compound (Iy) can be prepared in the scheme 1.

Examples of an amidation reagent include ammonia, formamide, acetamide etc. The amidation reagent may be employed in an amount of 1 to 10 moles, preferably 1 to 5 moles per 1 mole of compound (Iy).

Examples of the base are described above in the step a. The base may be employed in an amount of 1 mole to 10, preferably 1 to 5 moles per 1 mole of compound (Iy).

Examples of the solvent having no adverse effect on the reaction include amines such as triethylamine, pyridine, etc., hydrocarbons such as pentane, hexane, heptane, etc., aromatic hydrocarbons such as benzene, toluene, xylene, etc., ethers such as diethyl ether, dioxane, tetrahydrofuran, etc., halogenated hydrocarbon such as chloroform, dichloromethane, etc., amides such as N,N-dimethylformamide, N,N-dimethylacetamide, 1-methyl-2-pyrrolidinone, etc., and sulfoxides such as dimethylsulfoxide, etc. These solvents may be, used by mixing at an appropriate ratio.

While the reaction temperature may vary depending on compound (Iy) as well as other conditions, it is 0 to 200° C., preferably 20 to 100° C. The reaction time is 10 min to 24 hr, preferably 30 min to 12 hr.

Thus obtained compound (Iz) can be isolated and purified by the known isolating and purifying methods, for example, concentration under reduced pressure, extraction with solvents, crystallization, recrystallization, transfer dissolution and chromatography.

In the step az, compound (Iaa), which is encompassed within compound (I), can be prepared by dehydration of compound (Iz) with a dehydration reagent.

Examples of the dehydration reagent include thionyl chloride, phosphorous oxychloride, trifluoroacetic anhydride, trifluoromethanesulfonic anhydride, sulfuric acid etc. The dehydration reagent may be employed in an amount of 0.01 to 10 moles, preferably 1 to 5 moles per 1 mole of compound (Iz).

Examples of the solvent having no adverse effect on the reaction include hydrocarbons such as pentane, hexane, heptane, etc., aromatic hydrocarbons such as benzene, toluene, xylene, etc., ethers such as diethyl ether, dioxane, tetrahydrofuran, etc., nitriles such as acetonitrile, etc., halogenated hydrocarbon such as chloroform, dichloromethane, etc., amides such as N,N-dimethylformamide, N,N-dimethylacetamide, 1-methyl-2-pyrrolidinone, etc., and sulfoxides such as dimethylsulfoxide, etc. These solvents may be used by mixing at an appropriate ratio.

While the reaction temperature may vary depending on compound (Iz) as well as other conditions, it is 0 to 200° C., preferably 0 to 100° C. The reaction time is 10 min to 24 hr, preferably 30 min to 12 hr.

Thus obtained compound (Iaa) can be isolated and purified by the known isolating and purifying methods, for example, concentration under reduced pressure, extraction with solvents, crystallization, recrystallization, transfer dissolution and chromatography.

In the step ba, compound (Iab), which is encompassed within compound (I), can be prepared by alkylation of compound (Iaa) with an organometal reagent before hydrolysis.

Examples of the organometal reagent are described above in the step au. The organometal reagent may be employed in amount of 1 to 20 moles, preferably 1 to 10 moles per 1 mole of compound (Iaa).

Examples of conventional methods used in a reaction for hydrolysis are described above in the step ac.

Examples of the solvent having no adverse effect on the reaction include hydrocarbons such as pentane, hexane, heptane, etc., aromatic hydrocarbons such as benzene, toluene, xylene, etc., ethers such as diethyl ether, dioxane, tetrahydrofuran, etc., and halogenated hydrocarbon such as chloroform, dichloromethane, etc. These solvents may be used by mixing at an appropriate ratio.

While the reaction temperature may vary depending on compound (Iaa) as well as other conditions, it is –100 to 110° C., preferably –80 to 20° C. The reaction time is 10 min to 24 hr, preferably 30 min to 12 hr.

Thus obtained compound (Iab) can be isolated and purified by the known isolating and purifying methods, for example, concentration under reduced pressure, extraction with solvents, crystallization, recrystallization, transfer dissolution and chromatography.

In the step bb, compound (Iac), which is encompassed within compound (I), may be prepared from compound (Iy) by removing a carboxyl-protecting group of compound (Iy).

Examples of conventional methods used in a reaction for removal of a carboxyl-protecting group are described above in the step ac.

In the step bc, compound (Iad), which is encompassed within compound (I), may be prepared from compound (Iac) by condensation with $R^5R^6NH$.

Examples of conventional methods used for condensation are described above in the step ad.

In the step bd, compound (Iae), which is encompassed within compound (I), may be prepared from compound (Iad) by reduction or hydrogenation.

Examples of conventional methods used for reduction or hydrogenation are described above in the step e.

(Scheme 19)

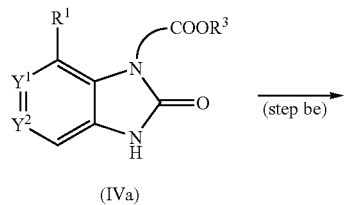

(IVa)

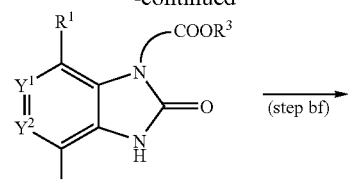

(IVb)

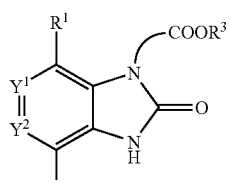

(IVc)

The above $R^{13}$ is a cyano, a $C_{1-6}$ alkyl, or a $C_{1-6}$ alkoxy.

In the step be, compound (IVb), which is encompassed within compound (IV), can be prepared by reaction of compound (IVa), which is encompassed within compound (IV), with a halogenation reagent. In this step, an acid, a base and an additive may also be employed. Compound (IVa) can be prepared in the scheme 3.

Examples of the halogenation reagent include chlorine, bromine, iodine, thionyl chloride, sulfuryl chloride, N-chlorosuccinimide, N-bromosuccinimide, N-iodosuccinimide, phosphorous oxychloride, phosphorous oxybromide, phosphorous trichloride, phosphorous tribromide, phosphorous pentachloride, potassium bromide, potassium bromate, hydrochloric acid, hydrobromic acid, hydroiodic acid, sodium chloride, sodium bromide, sodium iodide, aluminum chloride, aluminum bromide, etc. The halogenation reagent may be employed in an amount of 1 mole to 5 moles, preferably 1 mole to 3 moles per 1 mole of compound (IVa).

In this step, catalytic amount to 2 moles, preferably catalytic amount to 1 mole of a radical initiator such as 2,2'-azobis (isobutyronitrile), 2,2'-azobis(4-methoxy-2,4-dimethylvaleronitrile), benzoylperoxide and m-chloroperbenzoic acid may be employed per 1 mole of compound (IVa).

Examples of an acid are described above in the step d. The acid may be employed in an amount of 1 mole to excess per 1 mole of compound (IVa) or as a solvent.

Examples of the base are described above in the step a. The base may be employed in an amount of 1 mole to excess per 1 mole of compound (IVa) or as a solvent.

An additive such as iron, reductive iron and a Lewis acid may be employed in an appropriate amount.

Examples of the solvents having no adverse effect on the reaction include water, alcohols such as methanol, ethanol, etc., ethers such as diethyl ether, dioxane, tetrahydrofuran, etc., aromatic hydrocarbons such as benzene, chlorobenzene, toluene xylene, etc., esters such as ethyl acetate, etc., halogenated hydrocarbons such as 1,2-dichloroethane, carbon tetrachloride, chloroform, dichloromethane, etc., nitriles such as acetonitrile, etc., amides such as N,N-dimethylformamide, N,N-dimethylacetamide, 1-methyl-2-pyrrolidinone, etc., ketones such as acetone, 2-butanone, etc., sulfoxides such as dimethylsulfoxide, etc., and acids such as acetic acid, etc. These solvents may be used by mixing at an appropriate ratio, or may not be used.

While the reaction temperature may vary depending on compound (IVa) as well as other reaction conditions, it is –20 to 150° C., preferably 0 to 100° C. The reaction time is 5 minutes to 48 hours, preferably 5 minutes to 24 hours.

Thus obtained compound (IVb) can be isolated and purified by the known isolating and purifying methods, for example, concentration, concentration under reduced pressure, extraction with solvents, crystallization, recrystallization, transfer dissolution and chromatography.

In the step bf, compound (IVc), which is encompassed within compound (IV), can be prepared by reaction of compound (IVb) with a cyanation reagent or an alkylation reagent. In this step, an acid, a base and an additive may also be employed.

Examples of the cyanation reagent include, sodium cyanide, potassium cyanide, copper(I) cyanide, zinc(II) cyanide, palladium(II) cyanide, etc. The cyanation reagent is employed in an amount of 1 mole to 10 moles, preferably 1 mole to 5 moles per 1 mole of compound (IVb).

Examples of the alkylation agent include a $C_{1-6}$ alkyl boronic acid such as methylboronic acid, ethylboronic acid, isopropylboronic acid, etc., a $C_{1-6}$ alkyl borane such as triethylborane, trimethylboroxine, etc., a $C_{1-6}$ alkyl stannane such as tetramethyltin, tetraethyltin, etc., a $C_{1-6}$ alkyl halide such as methyliodide, ethylbromide, ethyliodide, etc., and $C_{1-6}$ alkylmagnesium halide such as methylmagnesium chloride, methylmagnesium bromide, methylmagnesium iodide, ethylmagnesium iodide, etc. The alkylation reagent is employed in an amount of 1 mole to 20 moles, preferably 1 mole to 10 moles per 1 mole of compound (IVb).

In this step, a palladium catalyst and a catalytic phosphine ligand may be employed. In this step, a base may be used.

Examples of the palladium catalyst are described above in the step d. The palladium catalyst may be employed in an amount of 0.001 mole to 0.5 mole per 1 mole of compound (IVb).

Examples of the phosphine ligand are described above in the step d. The phosphine ligand may be employed in an amount of 1 mole to 5.0 moles per 1 mole of the palladium catalyst.

Examples of the base are described above in the step a. The base may be employed in an amount of 1 mole to excess per 1 mole of compound (IVb).

This reaction may be carried out in the presence of additives. Examples of additives include copper(I) iodide, copper(II) sulfate, sodium iodide, potassium iodide, zinc(II) bromide, 18-crown-6 and phase transfer catalyst such as tetrabutylammonium bromide and benzyltriethylammonium chloride, etc.

Another metal catalyst may be employed.

Examples of other metal catalysts include a copper ate complex, which may be produced from compound (IVb) or the lithium salt of compound (IVb) and $C_{1-6}$ alkyl lithium with copper bromide in situ. The copper ate complex may be employed in an amount of 1.0 to 5.0 moles, preferably 1.0 to 3 moles per 1 mole of compound (IVb).

Examples of solvents having no adverse effect on the reaction include water, alcohols such as methanol, ethanol, ethylene glycol and 2-methoxyethanol, ethers such as diethyl ether, dioxane, tetrahydrofuran and 1,2-dimethoxyethane, aromatic hydrocarbons such as benzene, toluene and xylene, halogenated hydrocarbons such as 1,2-dichloroethane, chloroform and dichloromethane, nitriles such as acetonitrile, amides such as N,N-dimethylformamide, N,N-dimethylacetamide, 1-methyl-2-pyrrolidone and hexamethylphosphoramide, ketones such as acetone and 2-butanone, sulfoxides such as dimethylsulfoxide and pyridine. These solvents may be used by mixing at an appropriate ratio, or may not be used.

While the reaction temperature may vary depending on compound (IVb) as well as other reaction conditions, it is 0 to 250° C., preferably 50 to 200° C., or the reaction may be heated by microwave irradiation. The reaction time is 5 minutes to 120 hours, preferably 5 minutes to 48 hours.

When $R^{13}$ is a $C_{1-6}$ alkoxy, compound (IVc) can be prepared from compound (IVb) with a $C_{1-6}$ alkoxide, which may be commercially available or produced in situ from a corresponding alcohol and a base.

The alkoxide is employed in an amount of 1 mole to excess per 1 mole of compound (IVb) or may be employed as a solvent. In this step, a base may be employed.

Examples of the base are described above in the step a. The base may be employed in an amount of 1 mole to excess, preferably 1 mole to 20 moles per 1 mole of compound (IVb).

An additive may also be employed in an amount of catalytic amount to 1 mole per 1 mole of compound (IVb). Examples of additives include copper(I) iodide, copper(I) cyanide, copper(II) chloride, copper(I) bromide, manganese (II) oxide, manganese(IV) oxide, tetrabutylammonium bromide and collidine.

Examples of the solvent having no adverse effect on the reaction include water, alcohols such as the corresponding alcohol and ethylene glycol, ethers such as dioxane, tetrahydrofuran and 1,2-dimethoxyethane, aromatic hydrocarbons such as benzene, toluene and xylene, halogenated hydrocarbons such as 1,2-dichloroethane, chloroform and dichloromethane, nitriles such as acetonitrile, amides such as N,N-dimethylformamide, N,N-dimethylacetamide, 1-methyl-2-pyrrolidone and hexamethylphosphoramide, sulfoxides such as dimethylsulfoxide and pyridine. These solvents may be used by mixing at an appropriate ratio.

While the reaction temperature may vary depending on compound (IVb) as well as other reaction conditions, it is 0 to 250° C., preferably 50 to 200° C., or the reaction may be heated by microwave irradiation. The reaction time is 5 minutes to 12.0 hours, preferably 5 minutes to 48 hours.

Thus obtained compound (IVc) can be isolated and purified by the known isolating and purifying methods, for example, concentration, concentration under reduced pressure, extraction with solvents, crystallization, recrystallization, transfer dissolution and chromatography.

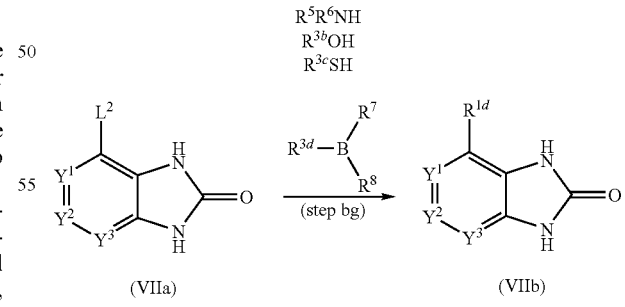

(Scheme 20)

In the step bg, compound (VIIb), which is encompassed within compound (VII), can be prepared from compound (VIIa), which is encompassed within compound (VII), by similar methods in the step ah. Compound (VIIa) can be prepared from the methods according to WO 2006/116412, etc.

(Scheme 21)

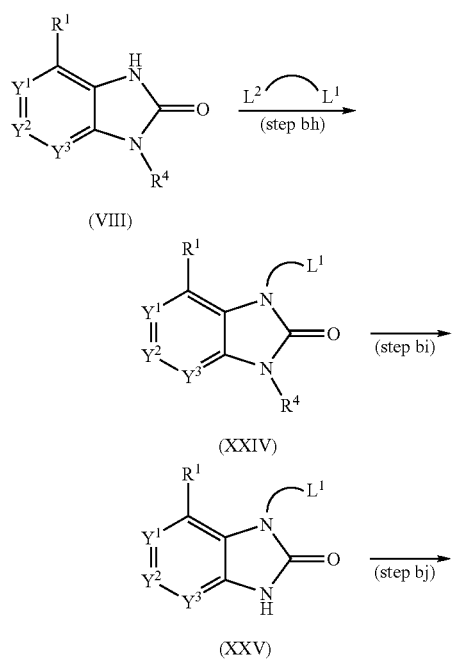

In the step bh, compound (XXIV) can be prepared from compound (VIII) by similar method in step f. Compound (VIII) can be prepared in the scheme 3.

In the step bi, compound (XXV) can be prepared from compound (XXIV) by similar method in step h.

In the step bj, compound (XXVI) can be prepared from compound (XXV) by similar method in step c.

In the step bk, compound (I) can be prepared from compound (XXVI) by similar method in the step d.

(Scheme 22)

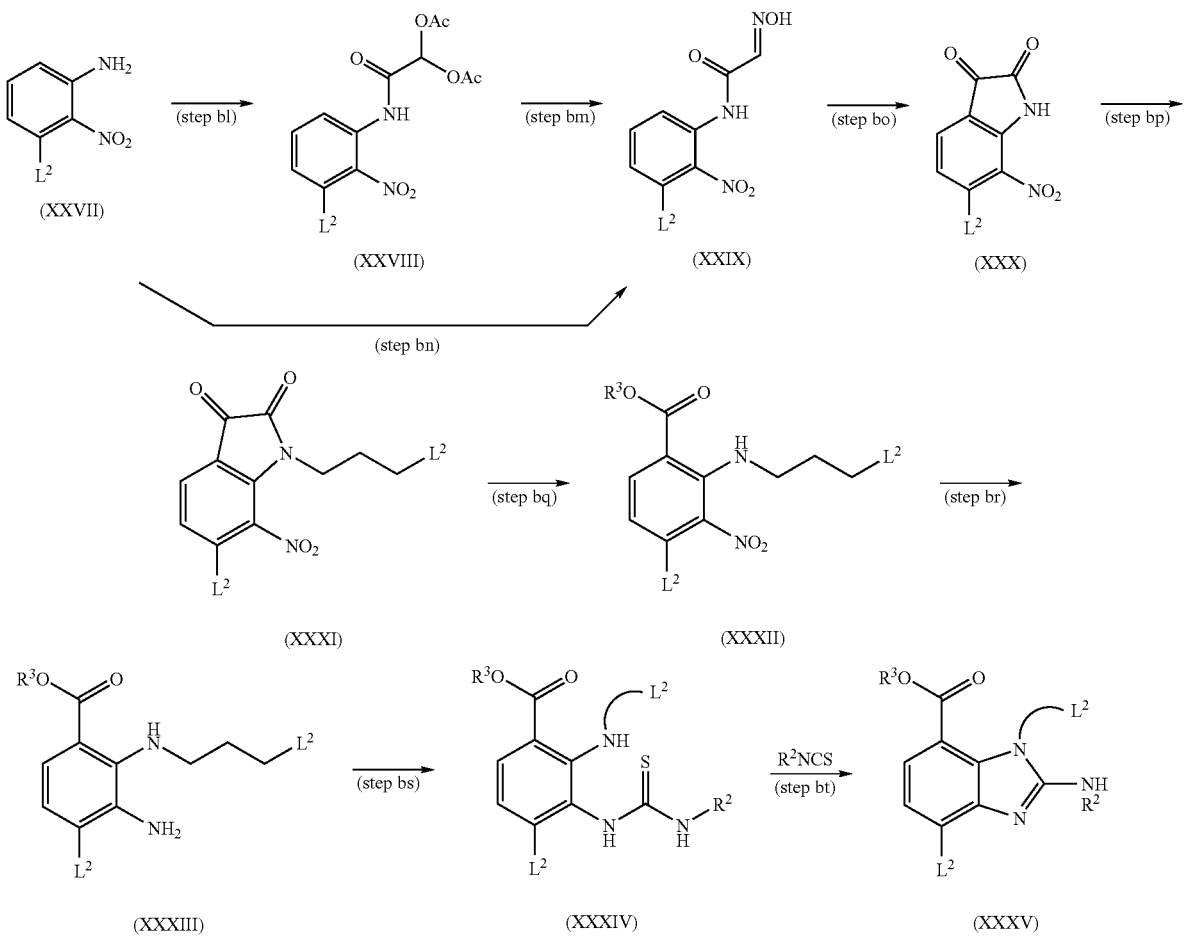

In the step bl, compound (XXVIII) can be prepared by reacting compound (XXVII) with 2,2-diacetoxyacetyl chloride. In this step, a base may be used. 2,2-Diacetoxyacetyl chloride may be employed in an amount of 1 to 5 moles per 1 mole of compound (XXVII).

Examples of the base are described above in the step a. The base may be employed in an amount of 1 mole to excess per 1 mole of compound (XXVIII).

Examples of the solvent having no adverse effect on the reaction include ethers such as diethyl ether, dioxane, tetrahydrofuran, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, 1-methyl-2-pyrrolidinone, etc., ketones such as acetone, 2-butanone, etc., and sulfoxides such as dimethylsulfoxide, etc. These solvents may be used by mixing at an appropriate ratio, or may not be used.

While the reaction temperature may vary depending on compound (XXVII) employed as well as other reaction conditions, it is −50 to 100° C., preferably −20 to 50° C., or the reaction may be heated by microwave irradiation. The reaction time is 5 minutes to 12 hours, preferably 5 minutes to 1 hour.

Thus obtained compound (XXVIII) can be isolated and purified by the known isolating and purifying methods, for example, concentration, concentration under reduced pressure, extraction with solvent, crystallization, recrystallization, transfer dissolution and chromatography.

In the step bm, compound (XXIX) can be prepared from compound (XXVIII) by reaction with hydroxylamine hydrochloride. Hydroxylamine hydrochloride may be employed in an amount of 1 to 20 moles per 1 mole of compound (XXVIII).

Examples of the solvent having no adverse effect on the reaction include water, alcohols such as methanol, ethanol, etc., ethers such as diethyl ether, dioxane, tetrahydrofuran, etc., aromatic hydrocarbons such as benzene, toluene, xylene, etc., esters such as ethyl acetate, etc., halogenated hydrocarbons such as chloroform dichloromethane, etc., nitriles such as acetonitrile, etc., amides such as N,N-dimethylformamide N,N-dimethylacetamide, etc., and sulfoxides such as dimethylsulfoxide, etc. These solvents may be used by mixing at an appropriate ratio, or may not be used.

While the reaction temperature may vary depending on compound (XXVIII) employed as well as other conditions, it is 0 to 200° C., preferably 20 to 100° C. The reaction time is 10 minutes to 24 hours, preferably 30 minutes to 12 hours.

Thus obtained compound (XXIX) can be isolated and purified by the known isolating and purifying methods, for example, concentration, concentration under reduced pressure, extraction with solvent, crystallization, recrystallization, transfer dissolution and chromatography.

In the step bn, compound (XXIX) can be prepared directly from compound (XXVII) by the known method (for example, Hel. Chem. Acta 1919, 2, 234-232.), such as a reaction of compound (XXX) with chloral hydrate and hydroxylamine hydrochloride in an aqueous sodium sulfate.

In the step bo, compound (XXX) can be prepared from compound (XXIX) by the known method (for example, Hel. Chem. Acta. 1919, 2, 234-232.) under acidic conditions.

Examples of an acid are include an inorganic acid such as sulfuric acid, hydrochloric acid, nitric acid, etc.

Solvent may be used. Examples of a solvent include an alcohol such as methanol, ethanol, etc.

While the reaction temperature may vary depending on compound (XXIX) employed as well as other conditions, it is 0 to 150° C., preferably 20 to 100° C. The reaction time is 10 minutes to 12 hours, preferably 30 minutes to 6 hours.

Thus obtained compound (XXX) can be isolated and purified by the known isolating and purifying methods, for example, concentration, concentration under reduced pressure, extraction with solvent, crystallization, recrystallization, transfer dissolution and chromatography.

In the step bp, compound (XXXI) can be prepared from compound (XXX) by similar method in the step g.

In the step bq, compound (XXXII) can be prepared by Baeyer-Villiger oxidation of compound (XXXI) and subsequent usual esterification of the resulting acid, such as reaction of the acid with $R^3L^1$ or condensation of the acid with $R^3OH$ under acidic condition. In the step of esterification, base may be used.

Examples of an oxidant, peroxide such as hydrogen peroxide, peracetic acid, m-chloroperbenzoic acid, etc. The oxidant may be employed in an amount of 1 to 20 moles, preferably 1 to 10 moles per 1 mole of compound (XXXI).

Examples of a solvent having no adverse effect on the reaction include water, alcohols such as methanol, ethanol, etc., aromatic hydrocarbons such as benzene, toluene, xylene, etc., esters such as ethyl acetate, etc., halogenated hydrocarbons such as chloroform, dichloromethane, etc., nitriles such as acetonitrile, etc., amides such as N,N-dimethylformamide, N,N-dimethylacetamide, etc. acids such as acetic acid, etc. These solvents may be used by mixing at an appropriate ratio, or may not be used.

While the reaction temperature may vary depending on compound (XXXI) employed as well as other conditions, it is −10 to 150° C., preferably 0 to 100° C. The reaction time is 10 minutes to 24 hours, preferably 30 minutes to 12 hours.

Examples of the base in the step of the esterification include alkaline metal carbonate such as sodium carbonate, potassium carbonate, etc.

Examples of the solvent having no adverse effect in the step of esterification include amide such as N,N-dimethylformamide, N,N-dimethylacetamide, etc., While the reaction temperature may vary depending on the acid employed as well as other conditions, it is 0 to 150° C., preferably 10 to 100° C. The reaction time is 10 minutes to 24 hours, preferably 30 minutes to 12 hours.

Examples of the acid in the step of the esterification include an inorganic acid such as hydrochloric acid, sulfuric acid, nitric acid, thionyl chloride, etc. In this step, $R^3OH$ is used as a solvent.

While the reaction temperature may vary depending on the acid employed as well as other conditions, it is 0 to 150° C., preferably 10 to 100° C. The reaction time is 30 minutes to 168 hours, preferably 1 hour to 120 hours.

Thus obtained compound (XXXI) can be isolated and purified by the known isolating and purifying methods, for example, concentration, concentration under reduced pressure, extraction with solvent, crystallization, recrystallization, transfer dissolution and chromatography.

In the step br, compound (XXXIII) can be prepared from compound (XXXII) by similar methods in the step aa.

In the step bs, compound (XXXIV) can be prepared from compound (XXXIII) by similar methods in step x.

In the step bt, compound (XXXV) can be prepared from compound (XXXIV) by similar methods in the step y.

(Scheme 23)

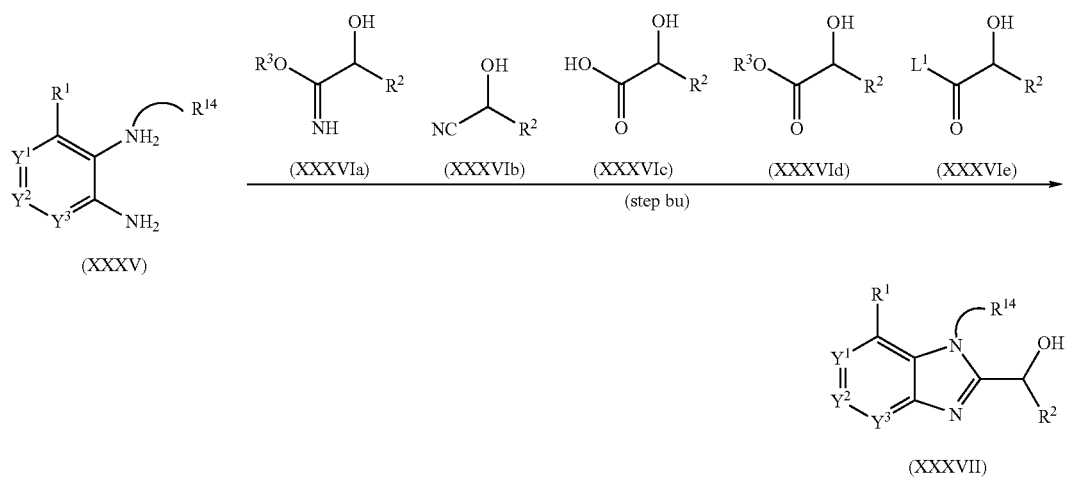

The above R$^{14}$ is an optionally substituted hydrocarbon, an acyl, an optionally substituted amino, nitro, an optionally substituted hydroxy, an optionally substituted mercapto, cyano or halogen.

In step bu, compound (XXXVII) can be prepared by reacting compound (XXXV) with compound (XXXVIa), (XXXVIb), (XXXVIc), (XXXVId) or (XXXVIe). In this step, an acid or a condensing reagent may be used. Compound (XXXV) can be prepared from the methods according to WO 2005/044793, WO 2006/116412, etc. Compound (XXXV) can be also prepared in the scheme 11. Compounds (XXXVIa), (XXXVIb), (XXXVIc), (XXXVId) and (XXXVIe) are commercially available or can be produced in accordance with the known methods per se or analogues method thereof.

Examples of the acid are described above in the step d. The acid may be employed in an amount of 0.01 mole to excess per 1 mole of compound (XXXV) or as a, solvent.

Examples of the condensing reagent are described above in the step ad. The condensing reagent may be employed in an amount of 1 mole to excess per 1 mole of compound (XXXV).

Examples of a solvent having no adverse effect on the reaction include acids such as formic acid, acetic acid, trifluoro acetic acid, methanesulfonic acid and sulfuric acid, alcohols such as methanol and ethanol, hydrocarbons such as pentane, hexane and heptane, aromatic hydrocarbons such as benzene, toluene and xylene, ethers such as diethyl ether, dioxane and tetrahydrofuran, esters such as ethyl acetate, nitriles such as acetonitrile, halogenated hydrocarbon such as chloroform and dichloromethane, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio.

While the reaction temperature may vary depending on compound (XXXV) as well as other conditions, it is 0 to 200° C., preferably 0 to 100° C. The reaction time is 10 min to 24 hr, preferably 30 min to 12 hr.

Thus obtained compound (XXXVII) can be isolated and purified by the known isolating and purifying methods, for example, concentration under reduced pressure, extraction with solvents, crystallization, recrystallization, transfer dissolution and, chromatography.

(Scheme 24)

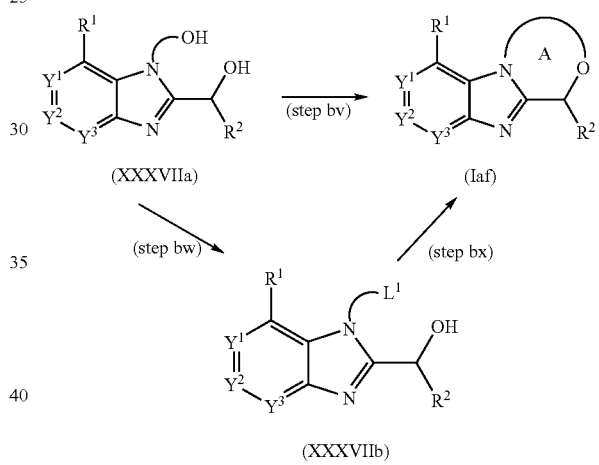

In the step bv, compound (Iaf), which is encompassed within compound (I'), can be prepared by reacting compound (XXXVIIa), which is encompassed within compound (XXXVII), with a cyclization reagent or dehydration of compound (XXXVIIa). Compound (XXXVIIa) can be prepared in the scheme 23.

Examples of the cyclization reagent include a combination of diethyl azodicarboxylate and triphenylphosphine, a combination of 1,1'-(azodicarbonyl)dipiperidine and tributylphosphine, cyanomethylenetributylphosphorane, etc. The cyclization reagent may be employed in an amount of 1 to 10 moles, preferably 1 to 5 moles per 1 mole of compound (XXXVIIa).

Examples of the solvent having no adverse effect on the reaction include hydrocarbons such as pentane, hexane, heptane, etc., aromatic hydrocarbons such as benzene, toluene, xylene, etc., ethers such as diethyl ether, dioxane, tetrahydrofuran, etc., nitriles such as acetonitrile, etc., halogenated hydrocarbon such as chloroform, dichloromethane, etc., amides such as dimethylformamide, N,N-dimethylacetamide, 1-methyl-2-pyrrolidinone, etc., and sulfoxides such as dimethylsulfoxide, etc. These solvents may be used by mixing at an appropriate ratio.

While the reaction temperature may vary depending on compound (XXXVIIa) as well as other conditions, it is 0 to 200° C., preferably 0 to 100° C. The reaction time is 10 min to 24 hr, preferably 30 min to 12 hr.

Examples on conventional methods used for dehydration are described above in the step az.

Thus obtained compound (Iaf) can be isolated and purified by the known isolating and purifying methods, for example, concentration under reduced pressure, extraction with solvents, crystallization, recrystallization, transfer dissolution and chromatography.

In the step bw, compound (XXXVIIb) may be prepared from compound (XXXVIIa) by same methods in the step a.

In the step bx, compound (Iaf) may be prepared from compound (XXXVIIb) by same methods in the step b.

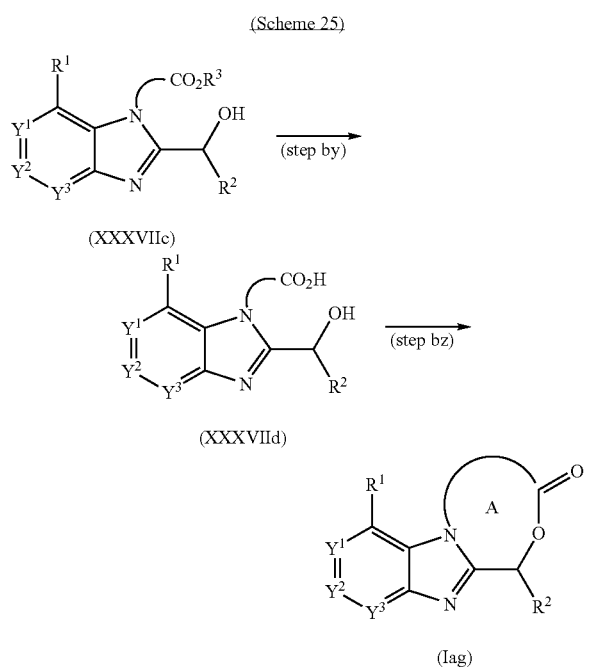

(Scheme 25)

In the step by, compound (XXXVIId), which is encompassed within compound (XXXVII), may be prepared from compound (XXXVIIc), which is encompassed within compound (XXXVII), by same methods in the step ac. Compound (XXXVIIc) can be prepared in the scheme 23. Compound (XXXVIId) can be also prepared in the scheme 23.

In the step bz, compound (Iag), which is encompassed within compound (I'), may be prepared from compound (XXXVIId) by same methods in the step ad.

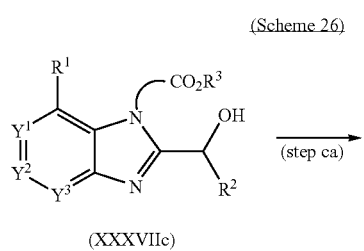

(Scheme 26)

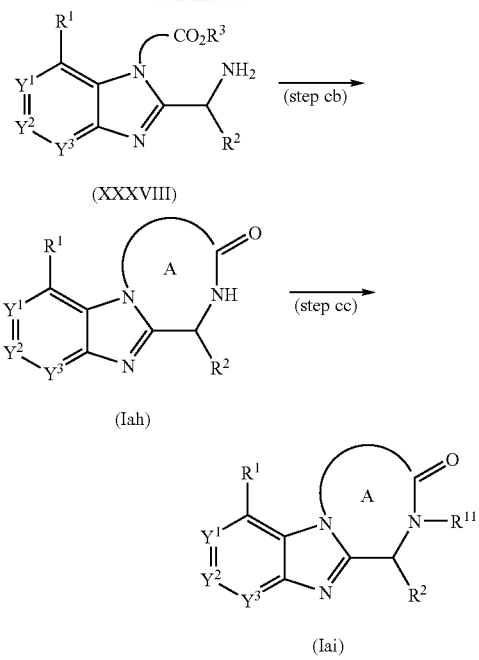

In the step ca, compound (XXXVIII) may be, prepared by reacting compound (XXXVIIc) with an azide source and following reduction.

Examples of an azide source are described above in the step o. The azide source is employed in an amount of 1 to 10 moles, preferably 1 to 5 moles per 1 mole of compound (XXXVIIc).

Examples of the solvent having no adverse effect on the reaction include hydrocarbons such as pentane, hexane, heptane, etc., aromatic hydrocarbons such as benzene, toluene, xylene, etc., ethers such as diethyl ether, dioxane, tetrahydrofuran, etc., nitriles such as acetonitrile, etc., halogenated hydrocarbon such as chloroform, dichloromethane, etc., amides such as N,N-dimethylformamide, N,N-dimethylacetamide, 1-methyl-2-pyrrolidinone, etc., and sulfoxides such as dimethylsulfoxide, etc. These solvents may be used by mixing at an appropriate ratio.

While the reaction temperature may vary depending on compound (XXXVIIc) as well as other conditions, it is 0 to 200° C., preferably 0 to 100° C. The reaction time is 10 min to 24 hr, preferably 30 min to 12 hr.

Examples of following reduction condition are described in the step p.

Thus obtained compound (XXXVIII) can be isolated and purified by the known isolating and purifying methods, for example, concentration under reduced pressure, extraction with solvents, crystallization, recrystallization, transfer dissolution and chromatography.

In the step cb, compound (Iah), which is encompassed within compound (I'), may be prepared from compound (XXXVIII) by same methods in the step ac and ad.

In the step cc, compound (Iai), which is encompassed within compound (I'), may be prepared from compound (Iah) by same methods in the step ax.

(Scheme 27)

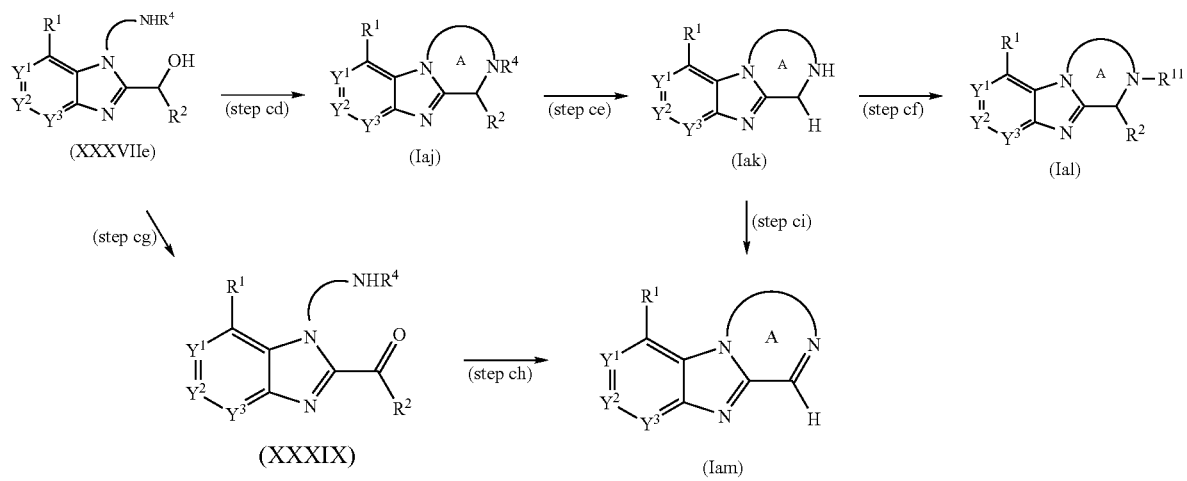

In the step cd, compound (Iaj), which is encompassed within compound (I'), can be prepared by reacting compound (XXXVIIe), which is encompassed within compound (XXX-VII), with a cyclization reagent. Compound (XXXVIIe) can be prepared in the scheme 23.

Example of the cyclization reagent and the condition are described above in step ay.

In the step ce, compound (Iak), which is encompassed within compound (I'), may be prepared from compound (Iaj) by same methods in the step h.

In the step cf, compound (Ial), which is encompassed within compound (I'), may be prepared from compound (Iak) by same methods in the step ax.

In the step cg, compound (XXXIX) may be prepared from compound (XXXVIIe) by same methods in the step ag.

In the step ch, compound (Iam), which is encompassed within compound (I'), may be prepared by deprotection of compound (XXXIX) and following acid treatment as needed.

Examples of deprotection condition are described in the step h.

Examples of the acid are described above in the step d. The acid may be employed in an amount of 0.01 mole to excess per 1 mole of compound (XXXIX) or as a solvent.

Examples of a solvent having no adverse effect on the reaction include acids such as formic acid, acetic acid, trifluoro acetic acid, methanesulfonic acid and sulfuric acid, alcohols such as methanol and ethanol, hydrocarbons such as pentane, hexane and heptane, aromatic hydrocarbons such as benzene, toluene and xylene, ethers such as diethyl ether, dioxane and tetrahydrofuran, esters such as ethyl acetate, nitriles such as acetonitrile, halogenated hydrocarbon such as chloroform and dichloromethane, amides such as N,N-dimethylformamide, N,N-dimethylacetamide and 1-methyl-2-pirrolidinone, ketones such as acetone and 2-butanone and sulfoxides such as dimethylsulfoxide. These solvents may be used by mixing at an appropriate ratio.

While the reaction temperature may vary depending on compound (XXXIX) as well as other conditions, it is 0 to 200° C., preferably 0 to 100° C. The reaction time is 10 min to 24 hr, preferably 30 min to 12 hr.

Thus obtained compound (Iam) can be isolated and purified by the known isolating and purifying methods, for example, concentration under reduced pressure, extraction with solvents, crystallization, recrystallization, transfer dissolution and chromatography.

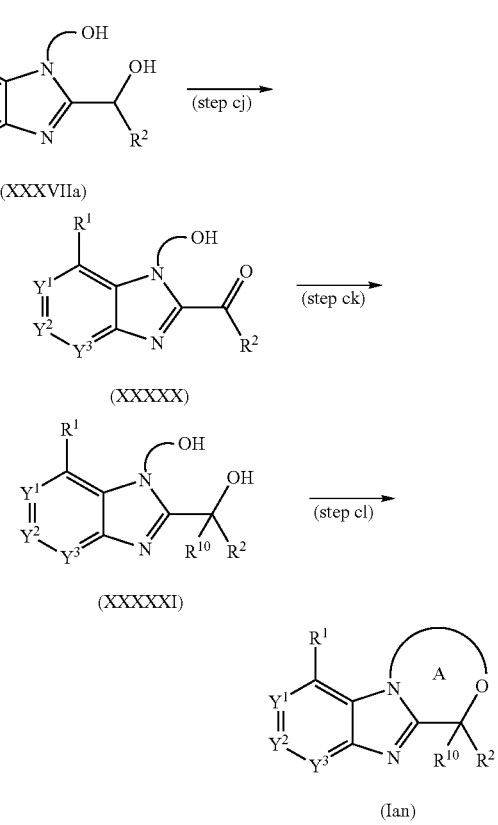

(Scheme 28)

In the step cj, compound (XXXXX) may be prepared from compound (XXXVIIa) by same methods in the step ag. Compound (XXXVIIa) can be prepared in the scheme 23.

In the step ck, compound (XXXXXI) may be prepared from compound (XXXXX) by same methods in the step aw.

In the step ch, compound (Ian), which is encompassed within compound (I'), may be prepared from compound (XXXXXI) by same methods in the scheme 24.

(Scheme 29)

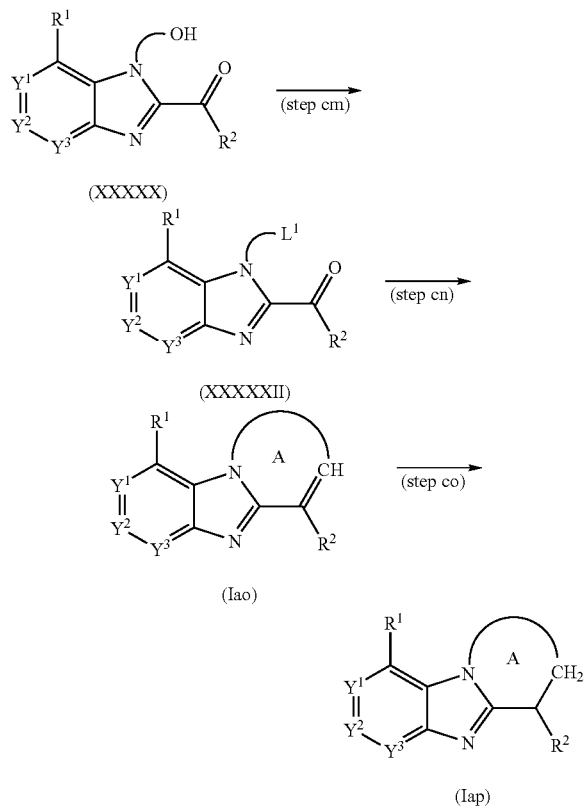

In the step cm, compound (XXXXXII) may be, prepared from compound (XXXXX) by same methods in the step a. Compound (XXXXX) can be prepared in the scheme 23.

In the stem cn, compound (Iao), which is encompassed within compound (I'), may be prepared by reacting compound (XXXXXII) with a phosphine or phosphite and following base treatment.

Examples of the phosphine include triethylphosphine, tributylphosphine, triphenylphosphine, etc. The phosphine may be employed in an amount of 1 to 10 moles, preferably 1 to 5 moles per 1 mole of compound (XXXXXII).

Examples of the phosphite include trimethylphosphite, triethylphosphite, etc. The phosphite may be employed in an amount of 1 to 10 moles, preferably 1 to 5 moles per 1 mole of compound (XXXXXII).

Examples of a solvent having no adverse effect on the reaction include hydrocarbons such as pentane, hexane and heptane, aromatic hydrocarbons such as benzene, toluene and xylene, ethers such as diethyl ether, dioxane and tetrahydrofuran, esters such as ethyl acetate, nitriles such as acetonitrile, halogenated hydrocarbon such as chloroform and dichloromethane, amides such as N,N-dimethylformamide, N,N-dimethylacetamide and 1-methyl-2-pirrolidinone and sulfoxides such as dimethylsulfoxide. These solvents may be used by mixing at an appropriate ratio.

While the reaction temperature may vary depending on compound (XXXXXII) as well as other conditions, it is 0 to 200° C., preferably 0 to 100° C. The reaction time is 10 min to 80 hr, preferably 30 min to 60 hr.

Examples of a base are described above in the step a. The base may be employed in an amount of 1 mole to excess per 1 mole of compound (XXXXXII) or as a solvent.

Examples of a solvent having no adverse effect on the reaction include alcohols such as methanol, ethanol, etc., ethers such as dioxane, tetrahydrofuran, etc., aromatic hydrocarbons such as benzene, toluene, xylene, etc., esters such as ethyl acetate, etc., halogenated hydrocarbons such as chloroform dichloromethane, etc., nitriles such as acetonitrile, etc., amides such as N,N-dimethylformamide, N,N-dimethylacetamide, etc., and sulfoxides such as dimethylsulfoxide, etc. These solvents may be used by mixing at an appropriate ratio, or may not be used.

While the reaction temperature may vary depending on compound (XXXXXII) or a salt thereof employed as well as other reaction conditions, it is −20 to 200° C., preferably 0 to 150° C. The reaction time is 5 minutes to 48 hours, preferably 5 minutes to 24 hours.

Thus obtained compound (Iao) can be isolated and purified by the known isolating and purifying methods, for example, concentration under reduced pressure, extraction with solvents, crystallization, recrystallization, transfer dissolution and chromatography.

In the stem co, compound (Iap), which is encompassed within compound (I'), may be prepared from compound (Iao) by catalytic hydrogenation.

Examples on conventional methods used for catalytic hydrogenation are described above in the step h.

In each of the reactions described above, when a starting compound carries as a substituent an amino, an amide, a hydrazine, a urea, a carboxy or a hydroxy, then such group may be derivatized with a protective group employed ordinarily in peptide chemistry, which is cleaved after a reaction if desired to yield an intended compound.

A protective group for an amino, an amide and a urea may for example be an optionally substituted $C_{1-6}$ alkyl-carbonyl (for example, methylcarbonyl and ethylcarbonyl, etc.), phenylcarbonyl, a $C_{1-6}$ alkyloxycarbonyl (for example, methoxycarbonyl, ethoxycarbonyl and tert-butoxycarbonyl, etc.), phenyloxycarbonyl, benzoxycarbonyl, $C_{7-10}$ aralkyl-carbonyl (for example, benzyloxycarbonyl), $C_{7-10}$ aralkyl (for example, benzyl and 4-methoxybenzyl, etc.), trityl, phthaloyl, etc. A substituent on each of the groups listed above may be a halogen atom (for example, fluorine, chlorine, bromine and iodine, etc.), a $C_{1-6}$ alkyl-carbonyl (for example, methylcarbonyl, ethylcarbonyl and butylcarbonyl, etc.) and a nitro group, which may occur 1 to about 3 times.

A protective group for a carboxy may, for example, be an optionally substituted $C_{1-6}$ alkyl (for example, methyl, ethyl, n-propyl, isopropyl, n-butyl and tert-butyl, etc.), phenyl, trityl and silyl, etc. A substituent on each of the groups listed above may be a halogen atom (for example, fluorine, chlorine, bromine and iodine, etc.), a $C_{1-6}$ alkyl-carbonyl (for example, methylcarbonyl, ethylcarbonyl and butylcarbonyl, etc.) and a nitro group, which may occur 1 to about 3 times.

A protective group for a hydroxy may for example be an optionally substituted $C_{1-6}$ alkyl (for example, methyl, ethyl, n-propyl, isopropyl, n-butyl and tert-butyl, etc.), phenyl, a $C_{7-10}$ aralkyl (for example, benzyl, etc.), a $C_{1-6}$ alkyl-carbonyl (for example, formyl, methylcarbonyl and ethylcarbonyl, etc.), phenyloxycarbonyl, $C_{7-10}$ aralkyloxy-carbonyl (for example, benzyloxycarbonyl, etc.), pyranyl, furanyl, silyl, etc. A substituent on each of the group listed above may be a halogen atom (for example, fluorine, chlorine, bromine and iodine, etc.), a $C_{1-6}$ alkyl, a $C_{1-6}$ alkoxy (for example, methoxy, etc.), phenyl, a $C_{7-10}$ aralkyl, nitro, etc., which may occur 1 to about 4 times.

A method for cleaving a protective group is a method known per se or an analogous method, such as a treatment for example with an acid, a base, a reduction, UV light, hydrazine, phenylhydrazine, sodium N-methyldithiocarbamate, tetrabutylammonium fluoride, palladium acetate, etc.

The configuration isomers of the aforementioned compounds can be isolated and purified by, for example, a conventional separation means such as extraction, recrystallization, distillation, chromatography and the like, when isomerization occurs, whereby a pure compound can be produced. In addition, isomerization of double bond may be promoted by heating, acid catalyst, transition metal complex, metal catalyst, radical species catalyst, photoirradiation or strong basic catalyst and the like according to the method described in Shin Jikken Kagaku Koza (New Experimental Chemistry Course), vol. 14, pp. 251-253 (edited by the Chemical Society of Japan), Jikken Kagaku Koza (Courses in Experimental Chemistry), 4th Ed., vol. 19, pp. 273-274 (edited by the Chemical Society of Japan) and the like or a method analogous thereto, whereby a corresponding pure isomer can be obtained. While compound (I') or (I) has a stereoisomer depending on the kind of the substituent, not only the isomer itself but also a mixture thereof are encompassed in the present invention.

In the above-mentioned reaction steps, where desired, compound (I') or (I) can be produced by a known hydrolysis, deprotection, acylation reaction, alkylation reaction, hydrogenation reaction, oxidation reaction, reduction reaction, carbon chain extension reaction or substituent exchange reaction, conducted individually or by a combination of two or more thereof. These reactions can be carried out, for example, according to the method described in Shin Jikken Kagaku Koza (New Experimental Chemistry Course), vols. 14 and 15 (edited by the Chemical Society of Japan) and the like.

Compound (I') or (I) can be isolated and purified by a known means, for example, phase transfer, concentration, solvent extraction, fractional distillation, liquid conversion, crystallization, recrystallization, chromatography and the like.

If compound (I') or (I) is obtained as a free compound, it can be converted into a desired salt by a method known per se or a modification thereof; conversely, if compound (I') or (I) is obtained as a salt, it can be converted into a free form or another desired salt by a method known per se or a modification thereof.

The compound (I') or (I) may be used as 4 prodrug. A prodrug of the compound (I) means a compound which is converted to the compound (I') or (I) with a reaction due to an enzyme, an gastric acid, etc. under the physiological condition in the living body, that is, a compound which is converted to the compound (I') or (I) with oxidation, reduction, hydrolysis, etc. according to an enzyme; a compound which is converted to the compound (I') or (I) by hydrolysis etc. due to gastric acid, etc.

A prodrug of compound (I') or (I) may be a compound obtained by subjecting an amino group in compound (I') or (I) to an acylation, alkylation or phosphorylation (e.g., a compound obtained by subjecting an amino group in compound (I') or (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I') or (I) to an acylation, alkylation, phosphorylation or boration (e.g., a compound obtained by subjecting a hydroxy group in compound (I') or (I) to an acetylation, palmitoylation, propanoylation, pivaloylation, succinylation, fumarylation, alanylation, dimethylaminomethylcarbonylation, etc.); a compound obtained by subjecting a carboxyl group in compound (I') or (I) to an esterification or amidation (e.g., a compound obtained by subjecting a carboxy group in compound (I') or (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I') or (I) by a method known per se.

A prodrug for compound (I') or (I) may also be one which is converted into compound (I') or (I) under a physiological condition, such as those described in IYAKUHIN no KAIHATSU (Development of Pharmaceuticals), Vol. 7, Design of Molecules, p. 163-198, Published by HIROKAWA SHOTEN.

Compound (I') or (I) and its prodrug (hereinafter, abbreviated as "Compound (I') or (I)") shows high affinity for CRF receptors. Compound (I') or (I) has physiological activities such as CRF receptor affinity, acts as an antagonist of CRF1, especially a selective antagonist of CRF1 receptor, shows low toxicity (e.g., acute toxicity, chronic toxicity, genetic toxicity, reproductive toxicity, cardiotoxicity, drug interaction, carcinogenicity etc.), good pharmacokinetic profiles (absorption, distribution, metabolism, etc.), and good physicochemical properties (solubility, etc.), and exhibits anxiolytic and antidepressive effects to an animal, especially to a mammal (e.g., human, monkey, bovine, sheep, dog, cat, rabbit, guinea pig, rat, mouse, etc.).

On the basis of that, Compound (I') or (I) is useful as a safe pharmaceutical and can be used as a pharmaceutical for preventing and/or treating diseases associated with the functions of a CRF receptor or a CRF.

As the "diseases associated with the functions of a CRF receptor or a CRF", for example, psychiatric disorders (e.g., depression, major depression, bipolar depression, psychotic major depression, dysthymia, seasonal affective disorder, affective disorder, recurrent depression, postpartum depression, suppression symptom, mania, anxiety disorders (generalized anxiety disorder, anxiety syndrome, panic disorder, phobia, social phobia, social anxiety disorder, obsessive-compulsive disorder, posttraumatic stress disorder, etc.), stress-induced insomnia, post psychic trauma stress disorder, Tourette's syndrome, autism, passion disorder, adjustment disorder, sleep disorder (extrinsic sleep disorder, intrinsic sleep disorder, circadian rhythm disorder, etc.), insomnia, bipolar disorder, circulatory disease, neurosis, schizophrenia, attention deficit/hyperactivity disorder (ADHD), nicotine addiction, etc.); neurodegenerative disorders (e.g., Alzheimer's disease (familial Alzheimer's disease, sporadic Alzheimer's disease, juvenile Alzheimer's disease, etc.), Alzheimer's type senile dementia, mild cognitive impairment, Parkinson's disease, Alzheimer's dementia, alcohol-induced dementia, HIV dementia, multi-infarct dementia, senile dementia, primary dementia, Frontotemporal dementia (FTD), frontotemporal dementia Parkinson's Type, progressive supranuclear palsy, Pick's Disease, Niemann-Pick's Disease, corticobasal degeneration, traumatic brain injury (TBI) or deMentia pugilistica, Huntington's disease, Down's syndrome, vascular dementia, postencephalitic parkinsonism, Lewy body dementia, amyotrophic lateral sclerosis (ALS), multiple sclerosis, motor neuron diseases (MND), Creurtfeld-Jacob's disease or Prion diseases), HIV encephalopathy, spinocerebellar degeneration, etc.); stress-related disorders (e.g., digestive ulcer, irritable bowel syndrome, inflammatory bowel disease, ulcerative colitis, Crohn's disease, stress-induced gastrointestinal disorder, nervous emesis, peptic ulcer, diarrhea, constipation, postoperative ileus, gastrointestinal dysfunction and nervous vomiting associated with stress; nervous orexia inactivity, eating disorder, anorexia nervosa, hyperphagia and other ingestion disorder, obesity, diabetes, alcohol dependency, alcoholics, alcohol abuse, alcohol addiction, alcohol amnesic syndrome, alcohol paranoia, alcohol preference, alcohol withdrawal, alcoholic insanity, alcoholic intoxication, alcoholic jealousy, alcoholic mania, alcoholic mental disorder, alcoholic psychosis, pharmacophilia, pharmacophobia, pharmacomania, drug withdrawal, migraine, stress headache, tension headache, ischemic nervous disorder, nervous disorder, cerebral paralysis, muscular convulsion, chronic fatigue syndrome, glaucoma, fibromyalgia syndrome, epilepsy, narcolepsy, sleep apnea syndrome, restless legs syndrome, meniere syndrome, autonomic imbalance, alopecia, hypertension, cardiovascular disorder, tachycardia, congestive heart attack, hyperpnea, bronchial asthma, apnea, sudden infant death syndrome, inflammatory disorder, pain, allergic disorder, impotence, menopausal disorder, fertilization disorder, infertility, cancer, immune function abnormality at HIV infection, immune functional abnormality due to stress, cerebrospinal meningitis, acromegaly, incontinence, metabolic syndrome, osteoporosis, diabetic neuropathy, etc.) and the like.

Preferably, Compound (I') or (I) can be used as a pharmaceutical for preventing and/or treating affective disorder, depression or anxiety.

When Compound (I') or (I) is used as a pharmaceutical for preventing and/or treating diseases described above, the administration route may be oral or parenteral in accordance with the known method per se.

Compound (I') or (I) can be formulated with a pharmaceutically acceptable carrier and can be orally or parenterally administered as solid formulations such as tablets, capsules, granules, powders, or the like; or liquid formulations such as syrups, injections, or the like. Also, there can be prepared formulations for transdermal administration such as patchings, cataplasms, ointments (including creams), plasters, tapes, lotions, liquids and solutions, suspensions, emulsions, sprays, and the like.

As for a pharmaceutically acceptable carrier, a variety of organic or inorganic carrier substances, which have been conventionally employed as formulation materials, is used and compounded as a bulking agent, a lubricant, a binding agent, and a disintegrator in solid formulations; a vehicle, a solubilizing agent, a suspending agent, an isotonicity agent, a buffering agent, and an analgesic in liquid formulations. If necessary, formulation excipients such as a preservative, an antioxidant, a stabilizer, a coloring agent, a sweetening agent, and the like can be used.

Preferred examples of the bulking agent include lactose, sucrose, D-mannitol, starch, crystalline cellulose, light anhydrous silicic acid, and the like. Preferred examples of the lubricant include magnesium stearate, potassium stearate, talc, colloidal silica, and the like. Preferred examples of the binding agent include crystalline cellulose, α-starch, sucrose, D-mannitol, dextrin, hydroxypropyl cellulose, hydroxypropylmethyl cellulose, polyvinyl pyrrolidone, and the like. Preferred examples of the disintegrator include starch, carboxymethyl cellulose, calcium carboxymethyl cellulose, croscarmellose sodium, sodium carboxymethyl starch, low-substituted hydroxypropyl cellulose, and the like. Preferred examples of the vehicle include water for injection, alcohol, propylene glycol, macrogol, sesame oil, corn oil, and the like.

If necessary, for the purpose of taste masking, enteric coating, or prolonged action, oral formulations can be prepared by coating by a per se known method. Examples of this coating agent include hydroxypropylmethyl ethyl cellulose, hydroxymethyl cellulose, hydroxypropyl cellulose, polyoxyethylene glycol, Tween 80, Pluronic F68 [polyoxyethylene (160) polyoxypropylene (30) glycol], cellulose acetate phthalate, hydroxypropylmethyl cellulose phthalate, hydroxymethyl cellulose acetate phthalate, Eudragit (manufactured by Rohm Company, methacrylic acid-acrylic acid copolymer), and the like.

Preferred examples of the solubilizing agent include polyethylene glycol, propylene glycol, benzyl benzoate, ethanol, trisamiomethane, cholesterol, triethanolamine, sodium carbonate, sodium citrate, and the like. Preferred examples of the suspending agent include surface active agents such as stearyltriethanolamine, sodium lauryl sulfate, laurylaminopropionic acid, lecithin, benzalkonium chloride, benzethonium chloride, glycerin monostearate, and the like; hydrophilic, high molecular substances such as polyvinyl alcohol, polyvinyl pyrrolidone, sodium carboxymethyl cellulose, methyl cellulose, hydroxymethyl cellulose, hydroxyethyl cellulose, hydroxypropyl cellulose, and the like; and so on. Preferred examples of the isotonicity agent include sodium chloride, glycerin, D-mannitol, and the like. Preferred examples of the buffering agent include buffer solutions of a phosphate, an acetate, a carbonate, a citrate, or the like. Preferable examples of the analgesic include benzyl alcohol and the like. Preferred examples of the preservative include paraoxybenzoic acid esters, chlorobutanol, benzyl alcohol, phenethyl alcohol, dehydroacetic acid, sorbic acid, and the like. Preferred examples of the antioxidant include sulfites, ascorbic acid, and the like.

The content of Compound (I') or (I) in the formulation of the present invention is, for example, about 0.01 to about 100% by weight of the whole preparation.

The dose varies depending on an administration subject, an administration route, disease and the like. For example, when Compound (I') or (I) is orally administered to an adult as an antidepressant, Compound (I') or (I) as an active ingredient may be administered in an amount of about 0.1 to about 20 mg/kg body weight, preferably about 0.2 to about 10 mg/kg body weight, further preferably about 0.5 to about 10 mg/kg body weight, preferably about 0.5 to about 5 mg/kg body weight. The dose may be administered in one or several divided portions per day.

When Compound (I') or (I) is applied to each of the above-mentioned diseases, it can be used in appropriate combination with a pharmaceutical agent or a treatment method generally employed for the disease.

In the following, a combined use of Compound (I') or (I) with a concomitant drug is referred to as "the combination agent of the present invention".

As such concomitant drug, for example, benzodiazepines (chlordiazepoxide, diazepam, clorazepate dipotassium, lorazepam, clonazepam, alprazolam, etc.), L-type calcium channel blockers (pregabalin, etc.), tricyclic or tetracyclic antidepressants (imipramine hydrochloride, amitriptyline hydrochloride, desipramine hydrochloride, clomipramine hydrochloride, carpipramine, etc.), selective serotonin reuptake inhibitors (fluvoxamine maleate, fluoxetine hydrochloride, citalopram hydrobromide, sertraline hydrochloride, paroxetine hydrochloride, escitalopram oxalate, etc.), serotonin and norepinephrine reuptake inhibitors (venlafaxine hydrochloride, duloxetine hydrochloride, desvenlafaxine hydrochloride, etc.), norepinephrine reuptake inhibitors (reboxetine mesilate, etc.), mirtazapine, trazodone hydrochloride, nefazodone hydrochloride, bupropion hydrochloride, setiptiline maleate, 5-$HT_{1A}$ agonists (buspirone hydrochloride, tandospirone citrate, osemozotan hydrochloride, etc.), 5-$HT_3$ antagonists (cyamemazine, etc.), noncardioselective beta-blockers (propranolol hydrochloride, oxprenolol hydrochloride, etc.), histamine $H_1$ antagonists (hydroxyzine hydrochloride, etc.), antipsychotic agents (chlorpromazine, haloperidol, sulpiride, clozapine, trifluoperazine hydrochloride, fluphenazine hydrochloride, olanzapine, quetiapine fumarate, risperidone, aripiprazole, etc.), other anxiolytics (meprobamate, etc.), tachykinin antagonist (MK-869, saredutant, etc.), drugs acting on metabotropic glutamate receptors, CCK antagonists, beta3-adrenoceptor agonists (amibegron hydrochloride, etc.), GAT-1 inhibitors (tiagabine hydrochloride, etc.), N-type calcium channel blockers, carbonic anhydrase type II inhibitors, NMDA glycine site agonists, NMDA antagonist (memantine, etc.), peripheral benzodiazepine receptor ligands; vasopressin antagonist, vasopressin V1b antagonist, phosphodiesterase inhibitors, opioid antagonists, opioid agonists, uridine, nicotinic receptor agonist, thyroid hormone (T3, T4), TSH, TRH, MAO inhibitors (phenelzine sulfate, tranylcypromine sulfate, moclobemide, etc.), $5\text{-}HT_{2A}$ Antagonists, $5\text{-}HT_{2A}$ inverse agonists, COMT inhibitor (entacapone, etc.), agents for bipolar disorder (lithium carbonate, valproate semisodium, lamotrigine, riluzole, felbamate, etc.), cannabinoid CB1 antagonist (rimonabant, etc.), FAAH inhibitors, sodium channel blockers, anti ADHD drugs (methylphenidate hydrochloride, methamphetamine hydrochloride, etc.), agents for alcoholism, agents for autism, agents for chronic fatigue syndrome, agents for epilepsy, agents for fibromyalgia syndrome, agents for headache, agents for insomnia (etizolam, zopiclone, triazolam, zolpidem, ramelteon, indiplon, etc.), agents for smoking cessation therapy, agents for myasthenia gravis, agents for stroke, agents for mania, agents for narcolepsy, agents for pain, agents for dysthymia, agents for autonomic imbalance, agents for male and female sexual dysfunction, agents for migraine, agents for pathological gambling, agents for restless legs syndrome, agents for substance dependence, agents for alcohol related disorders, agents for irritable bowel syndrome, agents for Alzheimer's disease (donepezil, galantamine, memantine, etc.), agents for Parkinson's Disease, agents for an amyotrophic lateral sclerosis (e.g. riluzole etc., neurotrophic factor etc.), agents for a hyperlipidemia such as a cholesterol lowering drug [statin series (e.g. sodium pravastatin, atorvastatin, simvastatin, rosuvastatin, etc.), fibrate (e.g. clofibrate, etc.), a squalene synthase inhibitor], agents for treating abnormal behavior or dromomania accompanied with progression of dementia (e.g. sedative, anti-anxiety drug, etc.), agents for an apoptosis inhibitor, agents for anti-obesity, agents for diabetes, agents for hypertension, agents for rheumatoid (DMARD), agents for cancer, agents for parathyroid hormone (PTH), calcium receptor antagonist, sex hormone or a derivative thereof (e.g. progesterone, estradiol, estradiol benzoate etc.), a nerve differentiation/regeneration promoting agent, a non-steroidal anti-inflammatory drug (e.g. meloxicam, tenoxicam, indomethacin, ibuprofen, celecoxib, rofecoxib, aspirin, indomethacin etc.), steroids (e.g. dexamethasone, hexestrol, cortisone acetate etc.), an anti-cytokine drug (e.g. TNF inhibitor, MAP kinase inhibitor etc.), antibody drugs for various disorders, nucleic acids or its derivative types drugs for various disorders, aptamer drugs for various disorders and the like can be employed.

By combining Compound (I') or (I) and a concomitant drug, a superior effect such as
(1) the dose can be reduced as compared to single administration of the compound of the present invention or a concomitant drug,
(2) the concomitant drug can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

A combination agent of the present invention has low toxicity, and for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules, solutions, emulsions, suspensions, injections, suppositories, sustained release preparations (e.g., sublingual tablet, microcapsule, etc.), plasters, orally disintegrating tablets, orally disintegrating films and the like, which can be safely administered orally or parenterally (e.g., subcutaneous, topical, rectal, intravenous administrations, etc.).

As pharmacologically acceptable carriers usable for the production of the combination agent of the present invention, various organic or inorganic carrier substances conventionally used as preparation materials can be mentioned. For example, suitable amounts of additives such as excipient, lubricant, binder and disintegrant for solid preparations, or solvent, solubilizing agent, suspending agent, isotonicity agent, buffer and soothing agent for liquid preparations, and where necessary, conventional preservative, antioxidant, coloring agent, sweetening agent, adsorbent, wetting agent and the like can be used appropriately.

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the administration amount clinically used, and can be appropriately selected depending on an administration subject, administration route, disease, combination and the like.

Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The compounding ratio of the compound of the present invention to the concomitant drug in the combination agent of the present invention can be appropriately selected depending on an administration subject, administration route, diseases and the like.

For example, the content of compound (I') or (I) in the combination agent of the present invention varies depending on the form of a preparation, and usually from about 0.01 to 100 wt %, preferably from about 0.1 to 50 wt %, further preferably from about 0.5 to 20 wt %, based on the whole preparation.

While the content of the concomitant drug in the combination agent of the present invention varies depending on the form of a preparation, it is usually from about 0.01 to 100 wt %, preferably from about 0.1 to 50 wt %, further preferably from about 0.5 to 20 wt %, based on the whole preparation.

While the content of the additives such as carrier and the like in the combination agent of the present invention varies depending on the form of a preparation, it is generally about 1 to 99.99 wt %, preferably about 10 to 90 wt %, based on the whole preparation.

Similar contents can be employed for individual preparations of Compound (I') or (I) and the concomitant drug.

EXAMPLES

The present invention is explained in detail in the following by referring to Reference Examples, Examples, Formulation Examples and Experimental Examples. However, the examples are mere exemplifications and do not limit the present invention. The present invention may be modified without departing from the scope of the invention.

In the following examples, the room temperature is ranged between 0 to 30° C., melting points were determined on a Yanaco micro melting point apparatus and were uncorrected. Proton nuclear magnetic resonance ($^1$H-NMR) spectra were recorded on Varian Mercury-300 (300 MHz). Chemical shifts are given in parts per million (ppm) with tetramethylsilane as an internal standard. Abbreviations are used as follows: s=singlet, d=doublet, t=triplet, q=quartet, m=multiplet, dd=doublets of doublet, dt=doublets of triplet, td=triplets of doublet, tt=triplets of triplet, ddd=doublets of doublets of doublet, brs=broad singlet. Coupling constants (J values) are given in hertz (Hz). LC-MS (ESI$^+$) was performed on a Micromass ZMD, using a CAPCELL PAK UG-120 ODS (Shiseido Co., Ltd.) column (2.0 mm i.d. x 50 mm) with aqueous MeCN (10-95%) containing 0.05% trifluoroacetic acid, and a HP-1100 (Agilent Technologies) apparatus for monitoring at 220 nm. Preparative HPLC purification was performed using a Gilson pumping system in conjunction with a photodiode array detector (Hewlett Packard 1100 series) and a Gilson 215 auto sampler. Separations were achieved using an YMC packed column (CombiPrep ODS-A, 5 μm, 50×20 mm) and a linear gradient (90% H$_2$O for 1.0 min, a linear gradient from 10 - 100% for 3.70 min, then 100% acetonitrile for 2.7 min. 25 mL/min.). Preparative HPLC purification was also performed using a Waters Preparative HPLC system. Separations were achieved using an Develosil ODS-UG-10 column (50×100 mm) with a 10-100% acetonitrile/water containing 0.1% trifluoroacetic acid gradient (flow rate: 150 mL/min) or an YMC packed column (CombiPrep ODS-A, 5 μm, 50×20 mm) with a 5-100% acetonitrile/water containing 0.1% trifluoroacetic acid gradient (flow rate: 25 mL/min). Chromatographic purification was carried out on silica gel columns (Kieselgel 60, 0.063-0.22 mm, Merck) or on Purif-Pack (SI 60 μm or NH 60 μm, Fuji Silysia, Ltd.). Preparative TLC purification was conducted using TLC plate (silica gel 60, Merck). Reagents and solvents were obtained from commercial sources and used without further purification.

Reference Example 1

Methyl 3-amino-2-[(tert-butoxycarbonyl)amino]benzoate

To a suspension of methyl 2-[(tert-butoxycarbonyl)amino]-3-nitrobenzoate (103 g, 0.348 mmol) in methanol (800 mL) was added 10% palladium on carbon (50% wet; 10 g), and the mixture was purged with hydrogen and stirred under balloon pressure hydrogen at room temperature for 5 hr. The catalyst was removed by filtration, and the filtrate was concentrated in vacuo. The residual solid was suspended in diisopropyl ether (300 mL), and the suspension was stirred at room temperature for 3 hr. The resulting solid was collected by filtration and washed with diisopropyl ether to give the title compound (42.0 g, 158 mmol, 45%). The mixture of the removed catalyst described above and a colorless solid (the title compound) was suspended in tetrahydrofuran (200 mL), and the suspension was stirred at room temperature for 30 minutes. The insoluble material (the catalyst) was removed by filtration, and the filtrate was concentrated in vacuo. The residual solid was suspended in diisopropyl ether (300 mL), and the suspension was refluxed for 30 min. The resulting solid was collected by filtration and washed with diisopropyl ether to give the title compound (33.9 g, 127 mmol, 36%) as a colorless solid. Total amount: 75.9 g, 285 mmol, 82%.

$^1$H NMR (CDCl$_3$) δ: 1.52 (9H, s), 3.90 (3H, s), 4.28 (2H, s), 6.95 (1H, dd, J=7.8, 1.8 Hz), 7.04 (1H, t, J=7.8 Hz), 7.41 (1H, dd, J=7.8, 1.8 Hz).

MS Calcd.: 266; MS Found: 267 (M+H).

Reference Example 2

Methyl 2,3-diaminobenzoate (Method 1)

Methyl 3-amino-2-[(tert-butoxycarbonyl)amino]benzoate (61.8 g, 232 mmol) was added to trifluoroacetic acid (250 mL), and the mixture was stirred at room temperature for 3 hr. Trifluoroacetic acid was evaporated in vacuo, and the resulting solid was suspended in ethyl acetate (200 mL), collected by filtration and washed with ethyl acetate (50 mL). The solid was partitioned between ethyl acetate (300 mL) and saturated aqueous sodium hydrogen carbonate (400 mL), and the aqueous layer was separated and extracted with ethyl acetate (300 mL). The combined organic layer was washed with water (300 mL×2) and concentrated in vacuo to give the title compound (24.6 g, 148 mmol, 64%) as a brown solid. The filtrate described above was concentrated in vacuo, and the resulting solid was collected by filtration and washed with ethyl acetate. The filtrate was concentrated in vacuo, and the resulting solid was collected by filtration and washed with diethyl ether. The combined solid was partitioned between ethyl acetate (100 mL) and saturated aqueous sodium hydrogen carbonate (100 mL), and the aqueous layer was separated and extracted with ethyl, acetate). The combined organic layer was washed with water and brine, dried over anhydrous sodium sulfate and concentrated in vacuo to give the title compound (8.29 g, 49.9 mmol, 22%) as a brown solid. Total amount: 32.9 g, 198 mmol, 85%.

$^1$H NMR (CDCl$_3$) δ: 3.33 (2H, brs), 3.07 (3H, s), 5.56 (2H, brs), 6.60 (1H, dd, J=8.1, 7.5 Hz), 6.85 (1H, dd, J=7.5, 1.5 Hz), 7.47 (1H, dd, J=8.1, 1.5 Hz).

MS Calcd.: 166; MS Found: 167 (M+H).

Reference Example 3

Methyl 2,3-diaminobenzoate (Method 2)

To a solution of methyl 2-amino-3-nitrobenzoate (29.6 g, 151 mmol) in tetrahydrofuran (containing stabilizer; 500 mL) was added palladium on carbon (3.0 g), and the mixture was purged with hydrogen and stirred under balloon pressure hydrogen at room temperature for 4 hr. The catalyst was removed by filtration, and the filtrate was concentrated in vacuo. The residual solid was washed with diethyl ether-n-hexane to give the title compound (25.0 g, 150 mmol, >99%) as a pale yellow solid.

$^1$H NMR (CDCl$_3$) δ: 3.33 (2H, brs), 3.07 (3H, s), 5.56 (2H, brs), 6.60 (1H, dd, J=8.1, 7.5 Hz), 6.85 (1H, dd, J=7.5, 1.5 Hz), 7.47 (1H, dd, J=8.1, 1.5 Hz).

MS Calcd.: 166; MS Found: 167 (M+H).

Reference Example 4

Methyl 2-oxo-2,3-dihydro-1H-benzimidazole-4-carboxylate

To a suspension of methyl 2,3-diaminobenzoate (32.9 g, 198 mmol) in tetrahydrofuran (300 mL) was added N,N'-carbonyldiimidazole (33.7 g, 208 mmol), and the mixture was stirred at room temperature for 15 hr. The solvent was evaporated in vacuo, and the residual solid was suspended in ethyl acetate (110 mL) and stirred at 80° C. After 30 min, the mixture was stirred at room temperature for 1 hr, and the resulting solid was collected by filtration and washed with ethyl acetate to give the title compound (35.6 g, 185 mmol, 94%) as a colorless solid.

$^1$H NMR (DMSO-d$_6$) δ: 3.87 (3H, s), 7.03 (1H, dd, J=8.1, 7.5 Hz), 6.85 (1H, dd, J=7.5, 1.2 Hz), 7.48 (1H, dd, J=8.1, 1.2 Hz), 10.82 (2H, brs).

MS Calcd.: 192; MS Found: 193 (M+H).

Reference Example 5

4-(1-Ethyl-1-hydroxypropyl)-1,3-dihydro-2H-benzimidazol-2-one

To a suspension of methyl 2-oxo-2,3-dihydro-1H-benzimidazole-4-carboxylate (35.9 g, 189 mmol) in tetrahydrofuran (700 mL) was added dropwise 3M solution of ethylmagnesium bromide in diethyl ether (374 mL, 1.12 mol), and the mixture was refluxed for 3 hr. After cooling, methanol (70 mL) was added dropwise at 0° C., and 1 N hydrochloric acid (1300 mL) was added at 0° C. The mixture was stirred at room temperature for 40 min, and the organic layer was separated and concentrated in vacuo. The aqueous layer was extracted with ethyl acetate (400 mL×2). The combined organic layer was concentrated in vacuo. The resulting solid was suspended in diisopropyl ether (70 mL)-water (10 mL)-ethyl acetate (40 mL), and the mixture was refluxed for 30 min. After cooling to room temperature, the resulting solid was collected by filtration and washed with diisopropyl ether to give the title compound (33.0 g, 150 mmol, 79%) cas a pale yellow solid.

$^1$H NMR (CDCl$_3$) δ: 0.83 (6H, t, J=7.5 Hz), 1.7.6-1.98 (4H, m), 2.19 (1H, brs), 6.72 (1H, d, J=7.8 Hz), 6.92-7.02 (2H, m), 9.16 (1H, brs), 9.44 (1H, brs).

MS Calcd.: 220; Found: 203 (M−H$_2$O+H).

Reference Example 6

4-(1-Ethylpropyl)-1,3-dihydro-2H-benzimidazol-2-one

A mixture of 4-(1-ethyl-1-hydroxypropyl)-1,3-dihydro-2H-benzimidazol-2-one (32.9 g, 149 mmol), 10% palladium on carbon (50% wet; 3.3 g), concentrated hydrochloric acid (3 mL) and acetic acid (300 mL) was purged with hydrogen and stirred under balloon pressure hydrogen at 80° C. for 6 hr. The catalyst was removed by filtration, and the filter cake was washed with tetrahydrofuran. The filtrate was concentrated in vacuo. The residue was suspended in diisopropyl ether (25 ml), and the suspension was stirred at 70° C. for 30 min. n-Hexane (25 mL) was added to the suspension, cooled to room temperature and stirred for 30 min. The resulting solid was collected by filtration and washed with n-hexane to give the title compound (24.6 g, 120 mmol, 81%) as a colorless solid.

$^1$H NMR (CDCl$_3$) δ: 0.80 (6H, t, J=7.2 Hz), 1.57-1.82 (4H, m), 2.50-2.62 (1H, m), 6.88 (1H, d, J=7.8 Hz), 6.92 (1H, d, J=7.8 Hz), 7.03 (1H, t, J=7.8 Hz), 9.44 (1H, s), 9.54 (1H, s).

MS Calcd.: 204; Found: 205 (M+H).

Reference Example 7 tert-Butyl 4-(1-ethylpropyl)-2-oxo-2,3-dihydro-1H-benzimidazole-1-carboxylate To a suspension of 4-(1-ethylpropyl)-1,3-dihydro-2H-benzimidazol-2-one (22.2 g, 109 mmol) in tetrahydrofuran (210 mL) was added potassium carbonate (15.1 g, 109 mmol) and di-tert-butyl dicarbonate (25.0 mL, 109 mmol), and the mixture was stirred at 55° C. for 3 hr. After cooling, the reaction mixture was diluted with water (200 mL). The organic layer was separated and concentrated in vacuo. The aqueous layer was extracted with ethyl acetate, (200 mL). The organic layer was combined with the residue described above, washed with water (150 mL×2) and concentrated in vacuo. The residual solid was suspended in n-hexane (150 mL), and the suspension was stirred at 60° C. for 30 min and at room temperature for 1 hr. The resulting solid was collected by filtration and washed with n-hexane to give the title compound (23.5 g, 77.2 mmol, 71%) as a colorless solid.

$^1$H NMR (CDCl$_3$) δ: 0.79 (6H, t, J=7.4 Hz), 1.55-1.83 (4H, m), 1.68 (9H, s), 2.40-2.60 (1H, m), 6.97 (1H, d, J=8.0 Hz), 7.09 (1H, t, J=8.0 Hz), 7.65 (1H, d, J=8.0 Hz), 8.93 (1H, s).

Reference Example 8

Isopropyl [7-(1-ethylpropyl)-2-oxo-2,3-dihydro-1H-benzimidazol-1-yl]acetate

To a suspension of tert-butyl 4-(1-ethylpropyl)-2-oxo-2,3-dihydro-1H-benzimidazole-1-carboxylate (23.2 g, 76.2 mmol) in N,N-dimethylformamide (120 mL) was added potassium carbonate (11.6 g, 83.9 mmol) and isopropyl bromoacetate (10.9 mL, 83.9 mmol), and the mixture was stirred at room temperature for 3 hours. The reaction mixture was diluted with water (200 ml) and extracted with ethyl acetate (200 mL). The organic layer was washed with water (100 mL×2) and brine (100 mL), dried over anhydrous sodium sulfate and concentrated in vacuo to give a crude tert-butyl 4-(1-ethylpropyl)-3-(2-isopropoxy-2-oxoethyl)-2-oxo-2,3-dihydro-1H-benzimidazole-1-carboxylate.

$^1$H NMR (CDCl$_3$) δ: 0.82 (6H, t, J=7.5 Hz), 1.26 (6H, d, J=6.3 Hz), 1.53-1.76 (4H, m), 1.67 (9H, s), 2.57-2.68 (1H, m), 4.80 (2H, s), 5.02-5.14 (1H, m), 7.03 (1H, dd, J=8.1, 1.5 Hz), 7.11 (1H, t, J=8.1 Hz), 7.79 (1H, dd, J=8.1, 1.5 Hz).

To a solution of tert-butyl 4-(1-ethylpropyl)-3-(2-isopropoxy-2-oxoethyl)-2-oxo-2,3-dihydro-1H-benzimidazole-1-carboxylate (obtained above) in ethyl acetate (20 mL) was added a 4N solution of hydrogen chloride in ethyl acetate (40 mL) at 0° C., and the mixture was stirred at room temperature for 2.5 hr. The reaction mixture was diluted with saturated aqueous sodium hydrogen carbonate (100 ml) and ethyl acetate (40 mL). The organic layer was separated, washed with water (70 mL) and brine (50 mL), dried over anhydrous sodium sulfate and concentrated in vacuo. The residual solid was suspended in n-hexane (40 mL), and the suspension was stirred at 60° C. for 30 min and then at room temperature for 1 hr. The resulting solid was collected by filtration and washed with n-hexane to give the title compound (17.9 g, 58.8 mmol, 77%) as a colorless solid.

$^1$H NMR (CDCl$_3$) δ: 0.81 (6H, t, J=7.5 Hz), 1.26 (6H, d, J=6.3 Hz), 1.55-1.79 (4H, m), 2.62-2.73 (1H, m), 4.82 (2H, s), 5.05-5.15 (1H, m), 6.90-6.94 (2H, m), 7.04 (1H, d, J=7.8 Hz), 9.12 (1H, s).

MS Calcd.: 304; Found: 305 (M+H).

Reference Example 9

Isopropyl [4-chloro-7-(1-ethylpropyl)-2-oxo-2,3-dihydro-1H-benzimidazol-1-yl]acetate To a solution of isopropyl [7-(1-ethylpropyl)-2-oxo-2,3-dihydro-1H-benzimidazol-1-yl]acetate (17.9 g, 58.8 mmol) and 2,2'-azobisisobutyronitrile (966 mg, 5.88 mmol) in chlorobenzene (170 mL) was added portionwise N-chlorosuccinimide (7.85 g, 58.8 mmol) at 65° C., and the mixture was stirred at 70° C. for 3.5 days. After cooling, the reaction mixture was neutralized with saturated aqueous sodium hydrogen carbonate (200 mL), and the aqueous layer was separated and extracted with ethyl acetate (200 mL). The combined organic layer was washed with aqueous sodium chloride (200 mL) and brine (150 mL), dried over anhydrous sodium sulfate and concentrated in vacuo. The residue was purified by silica gel column chromatography eluting with a 15-25% ethyl acetate/n-hexane gradient mixture to give the title compound (15.0 g, 44.3 mmol, 75.3%) as a solid.

$^1$H NMR (CDCl$_3$) δ: 0.83 (6H, t, J=7.5 Hz), 1.27 (6H, d, J=6.3 Hz), 1.57-1.78 (4H, m), 2.59-2.68 (1H, m), 4.80 (2H, s), 5.02-5.14 (1H, m), 6.86 (1H, d, J=8.7 Hz), 7.04 (1H, d, J=8.7 Hz), 8.67 (1H, s).

MS Calcd.: 338; Found: 339 (M+H).

Reference Example 10

Isopropyl [2,4-dichloro-7-(1-ethylpropyl)-1H-benzimidazol-1-yl]acetate

A mixture of isopropyl [4-chloro-7-(1-ethylpropyl)-2-oxo-2,3-dihydro-1H-benzimidazol-1-yl]acetate (14.5 g, 42.8 mmol) and phosphorus oxychloride (60 mL) was stirred at 100° C. for 3 days. After cooling, phosphorus oxychloride was evaporated in vacuo. The residue was poured into ice-cold saturated aqueous sodium hydrogen carbonate and extracted with ethyl acetate (×2). The combined organic layer was washed with water and brine, dried over anhydrous sodium sulfate and concentrated in vacuo. The residue was purified by silica gel column chromatography eluting with a 5-15% ethyl acetate/n-hexane gradient mixture to give the title compound (14.1 g, 39.5 mmol, 92%) as an oil.

$^1$H NMR (CDCl$_3$) δ: 0.81 (6H, t, J=7.5 Hz), 1.28 (6H, d, J=6.3 Hz), 1.62-1.83 (4H, m), 2.72-2.82 (1H, m), 5.06-5.21 (1H, m), 5.08 (2H, s), 7.05 (1H, d, J=8.0 Hz), 7.28 (1H, d, J=8.0 Hz).

MS Calcd.: 356; Found: 357 (M+H).

Reference Example 11

Isopropyl [4-chloro-2-[(4-chloro-2-methoxy-6-methylphenyl)amino]-7-(1-ethylpropyl)-1H-benzimidazol-1-yl]acetate A mixture of isopropyl [2,4-dichloro-7-(1-ethylpropyl)-1H-benzimidazol-1-yl]acetate (1.60 g, 4.48 mmol), (4-chloro-2-methoxy-6-methyl)aniline (3.18 g, 18.6 mmol) and N-methyl-2-pyrrolidinone (1 mL) was stirred at 110° C. for 4.5 days. After cooling, the reaction mixture was diluted with saturated aqueous sodium hydrogen carbonate and extracted with ethyl acetate. The organic layer was washed with brine, dried over anhydrous sodium sulfate and concentrated in vacuo. The residue was purified by silica gel column chromatography eluting with a 5-20% ethyl acetate/n-hexane gradient mixture. The residual solid was washed with ethyl acetate/diisopropyl ether and n-hexane to give the title compound (1.18 g, 2.40 mmol, 53.5%) as a colorless solid. The filtrate was purified by preparative HPLC to give 204 mg (0.414 mmol, 9.2%) of the title compound as a solid. Total amount: 1.38 g, 2.80 mmol, 63%.

$^1$H NMR (CDCl$_3$) δ: 0.82 (6H, t, J=7.4 Hz), 1.30 (6H, d, J=6.3 Hz), 1.58-1.81 (4H, m), 2.11 (3H, s), 2.80-2.92 (1H, m), 3.83 (3H, s), 4.89 (2H, s), 5.09-5.20 (1H, m), 6.56 (1H, s), 6.78 (1H, s), 6.87 (1H, d, J=7.6 Hz), 6.87 (1H, s), 7.14 (1H, d, J=7.6 Hz).

MS Calcd.: 491; Found: 492 (M+H).

Reference Example 12

2-[4-Chloro-2-[(4-chloro-2-methoxy-6-methylphenyl)amino]-7-(1-ethylpropyl)-1H-benzimidazol-1-yl]ethanol To a solution of isopropyl [4-chloro-2-[(4-chloro-2-methoxy-6-methylphenyl)amino]-7-(1-ethylpropyl)-1H-benzimidazol-1-yl]acetate (453 mg, 0.920 mmol) in tetrahydrofuran (5 mL) was added lithium tetrahydroborate (60 mg, 2.76 mmol), and the mixture was refluxed for 2 hr. After cooling, the reaction mixture was quenched with water and extracted with ethyl acetate (×2). The combined organic layer was washed with brine, dried over anhydrous sodium sulfate and concentrated in vacuo. The residual solid was recrystallized from ethyl acetate-n-hexane to give the title compound (250 mg, 0.573 mmol, 62.3%) as a colorless crystal. The filtrate was concentrated in vacuo, and the residual solid was recrystallized from ethyl acetate-n-hexane to give the title compound (91 mg, 0.209 mmol, 22.7%) as a colorless crystal. Total amount: 341 mg, 0.781 mmol, 85%.

$^1$H NMR (CDCl$_3$) δ: 0.85 (6H, t, J=7.2 Hz), 1.65-1.83 (4H, m), 2.16 (3H, s), 2.53 (1H, brs), 2.79-2.87 (1H, m), 3.76 (3H, s), 4.14 (2H, t, J=4.5 Hz), 4.43 (2H, t, J=4.5 Hz), 6.76 (1H, d, J=1.8 Hz), 6.83 (1H, d, J=7.8 Hz), 6.87 (1H, d, J=1.8 Hz), 6.99 (1H, d, J=7.8 Hz), 7.60 (1H, brs).

MS Calcd.: 435; Found: 436 (M+H).

Reference Example 13

[4-Chloro-2-[(4-chloro-2-methoxy-6-methylphenyl)amino]-7-(1-ethylpropyl)-1H-benzimidazol-1-yl]acetic acid To a solution of isopropyl [4-chloro-2-[(4-chloro-2-methoxy-6-methylphenyl)amino]-7-(1-ethylpropyl)-1H-benzimidazol-1-yl]acetate (Reference Example 11; 861 mg, 1.75 mmol) in methanol (5 mL) was added 8N aqueous sodium hydroxide (1.5 mL), and the mixture was stirred at room temperature for 15 hr. Water was added to the reaction mixture, followed by neutralization with 6N hydrochloric acid. The mixture was concentrated in vacuo, and the residue was dissolved in methanol. The precipitate was removed by filtration, and the filtrate was concentrated in vacuo to give the title compound (781 mg, 1.73 mmol, 99.1%) as an amorphous.

$^1$H NMR (CDCl$_3$) δ: 0.76 (6H, t, J=7.2 Hz), 1.52-1.73 (4H, m), 2.07 (3H, s), 3.06-3.15 (1H, m), 3.76 (3H, s), 4.77 (2H, s), 6.77 (1H, d, J=8.4 Hz), 6.93-6.99 (3H, m), 8.64 (1H, s).

MS Calcd.: 449; Found: 450 (M+H).

Reference Example 14 tert-Butyl 3-(2-ethoxy-2-oxoethyl)-4-(1-ethylpropyl)-2-oxo-2,3-dihydro-1H-benzimidazole-1-carboxylate To a solution of tert-butyl 4-(1-ethylpropyl)-2-oxo-2,3-dihydro-1H-benzimidazole-1-carboxylate (Reference Example 7; 4.94 g, 16.2 mmol) in N,N-dimethylformamide (40 mL) were added potassium carbonate (2.47 g, 17.9 mmol) and ethyl bromoacetate (1.98 mL, 17.9 mmol), and the mixture was stirred at room temperature for 3 hr. The reaction mixture was diluted with water and extracted with ethyl acetate. The organic layer was washed with brine, dried over anhydrous sodium sulfate and concentrated in vacuo. The residue was purified by silica gel column chromatography eluting with a 5-20% ethyl acetate/n-hexane gradient mixture to give the title compound (6.17 g, 15.8 mmol, 98%) as a colorless oil.

$^1$H NMR (CDCl$_3$) δ: 0.78 (6H, t, J=7.2 Hz), 1.27 (3H, t, J=7.2 Hz), 1.43-1.76 (4H, m), 1.67 (9H, s), 2.58-2.70 (1H, m), 4.22 (2H, q, J=7.2 Hz), 4.85 (2H, s), 7.03 (1H, dd, J=8.1, 1.2 Hz), 7.14 (1H, t, J=8.1 Hz), 7.80 (1H, dd, J=8.1, 1.2 Hz).

Reference Example 15

Ethyl [7-(1-ethylpropyl)-2-oxo-2,3-dihydro-1H-benzimidazol-1-yl]acetate

To a solution of tert-butyl 3-(2-ethoxy-2-oxoethyl)-4-(1-ethylpropyl)-2-oxo-2,3-dihydro-1H-benzimidazole-1-carboxylate (6.16 g, 15.8 mmol) in ethyl acetate (15 mL) was added a 4N solution of hydrogen chloride in ethyl acetate (15 mL) at 0° C., and the mixture was stirred at the same temperature for 2 hr. An additional 4N solution of hydrogen chloride in ethyl acetate (15 mL) was added to the mixture at 0° C., followed by stirring at the same temperature for 1 hr. The reaction mixture was diluted with saturated aqueous sodium hydrogen carbonate and ethyl acetate. The organic layer was separated, washed with brine, dried over sodium sulfate and concentrated in vacuo. The resulting solid was washed with n-hexane to give the title compound (4.28 g, 14.7 mmol, 93%) as a colorless crystal.

$^1$H NMR (CDCl$_3$) δ: 0.78-0.83 (6H, m), 1.24-1.30 (3H, m), 1.54-1.80 (4H, m), 2.63-2.73 (1H, m), 4.20-4.27 (2H, m), 4.88 (2H, s), 6.91-6.97 (2H, m), 7.03-7.26 (1H, m), 9.53 (1H, s).

MS Calcd.: 290; Found: 291 (M+H).

Reference Example 16

Ethyl [4-chloro-7-(1-ethylpropyl)-2-oxo-2,3-dihydro-1H-benzimidazol-1-yl]acetate To a solution of ethyl [7-(1-ethylpropyl)-2-oxo-2,3-dihydro-1H-benzimidazol-1-yl]acetate (3.91 g, 13.5 mmol) and 2,2'-azobisisobutyronitrile (222 mg, 1.35 mmol) in chlorobenzene (40 mL) was added portionwise N-chlorosuccinimide (1.80 g, 13.5 mmol) at 65° C., and the mixture was stirred at 70° C. for 2 days. After cooling, the reaction mixture was washed with saturated aqueous sodium hydrogen carbonate. The aqueous layer was separated and extracted with ethyl acetate. The organic layer was washed with brine, dried over anhydrous sodium sulfate and concentrated in vacuo. The residue was purified by silica gel column chromatography eluting with a 15-50% ethyl acetate/n-hexane gradient mixture, and the fractions containing the title compound were concentrated in vacuo. The mixture was suspended in diisopropyl ether, and the suspension was stirred at 60° C. for 2 hr. After cooling, the resulting solid was collected by filtration and washed with n-hexane to give the title compound (2.77 g, 8.53 mmol, 63%) as a colorless solid.

$^1$H NMR (CDCl$_3$) δ: 0.79 (6H, t, J=7.5 Hz), 1.28 (3H, t, J=7.2 Hz), 1.51-1.78 (4H, m), 2.58-2.68 (1H, m), 4.23 (2H, q, J=7.2 Hz), 4.85 (2H, s), 6.86 (1H, d, J=8.7 Hz), 7.04 (1H, d, J=8.7 Hz), 8.84 (1H, s).

MS Calcd.: 324; Found: 325 (M+H).

Reference Example 17

Ethyl [2,4-dichloro-7-(1-ethylpropyl)-1H-benzimidazol-1-yl]acetate

A mixture of ethyl [4-chloro-7-(1-ethylpropyl)-2-oxo-2,3-dihydro-1H-benzimidazol-1-yl]acetate (2.57 g, 7.91 mmol) and phosphorus oxychloride (15 mL) was stirred at 90° C. for 3 days. After cooling, phosphorus oxychloride was evaporated in vacuo. The residue was poured into ice-cold 2N aqueous sodium hydroxide and extracted with ethyl acetate. The organic layer was washed with brine, dried over anhydrous sodium sulfate and concentrated in vacuo. The residue was purified by silica gel column chromatography eluting with a 10-20% ethyl acetate/n-hexane gradient mixture to give the title compound (2.49 g, 7.25 mmol, 92%) as an oil.

$^1$H NMR (CDCl$_3$) δ: 0.80 (6H, t, J=7.5 Hz), 1.29 (3H, t, J=7.2 Hz), 1.59-1.83 (4H, m), 2.75-2.84 (1H, m), 4.25 (2H, q, J=7.2 Hz), 5.12 (2H, m), 7.05 (1H, d, J=8.1 Hz), 7.28 (1H, d, J=8.1 Hz).

MS Calcd.: 342; Found: 343 (M+H).

Reference Example 18

Ethyl {4-chloro-2-[(2,4-dichlorophenyl)amino]-7-(1-ethylpropyl)-1H-benzimidazol-1-yl}acetate A mixture of ethyl [2,4-dichloro-7-(1-ethylpropyl)-1H-benzimidazol-1-yl]acetate (708 mg, 2.06 mmol), 2,4-dichloroaniline (1.00 g, 6.19 mmol) and N-methyl-2-pyrrolidinone (0.5 mL) was stirred at 100° C. for 3.5 days. After cooling, the reaction mixture was neutralized with saturated aqueous sodium hydrogen carbonate and extracted with ethyl acetate. The organic layer was washed with brine, dried over anhydrous sodium sulfate and concentrated in vacuo. The residue was purified by basic silica gel column chromatography eluting with a 3-15% ethyl acetate/n-hexane gradient mixture. The resulting solid was washed with n-hexane to give the title compound (115 mg, 0.245 mmol, 12%) as a colorless solid.

$^1$H NMR (CDCl$_3$) δ: 0.82 (6H, t, J=7.5 Hz), 1.34 (3H, t, J=7.2 Hz), 1.63-1.86 (4H, m), 2.90-3.05 (1H, m), 4.35 (2H, q, J=7.2 Hz), 4.93 (2H, s), 6.96 (1H, d, J=8.4 Hz), 7.21-7.44 (4H, m), 8.28 (1H, d, J=8.4 Hz).

MS Calcd.: 467; Found: 468 (M+H).

Reference Example 19

2-{4-Chloro-2-[(2,4-dichlorophenyl)amino]-7-(1-ethylpropyl)-1H-benzimidazol-1-yl}ethanol To a solution of ethyl {4-chloro-2-[(2,4-dichlorophenyl)amino]-7-(1-ethylpropyl)-1H-benzimidazol-1-yl}acetate (99 mg, 0.211 mmol) in tetrahydrofuran (1.5 mL) was added lithium tetrahydroborate (14 mg, 0.634 mmol), and the mixture was stirred at 65° C. for 1.5 hr. After cooling, the reaction mixture was quenched with water and extracted with ethyl acetate. The organic layer was washed with brine, dried over anhydrous sodium sulfate and concentrated in vacuo. The resulting solid was washed with n-hexane to give the title compound (86 mg, 0.202 mmol, 96%) as a colorless solid.

$^1$H NMR (CDCl$_3$) δ: 0.77 (6H, t, J=7.5 Hz), 1.47-1.78 (4H, m), 2.65-2.75 (1H, m), 4.15 (2H, t, J=4.2 Hz), 4.29 (2H, t, J=4.2 Hz), 5.03 (1H, brs), 6.79 (1H, d, J=8.4 Hz), 7.07 (1H, d, J=8.4 Hz), 7.20-7.30 (2H, m), 8.43 (1H, d, J=9.0 Hz), 8.82 (1H, brs).

MS Calcd.: 425; Found: 426 (M+H).

Reference Example 20

Isopropyl {4-chloro-2-[(2,4-dichlorophenyl)amino]-7-(1-ethylpropyl)-1H-benzimidazol-1-yl}acetate A mixture of isopropyl [2,4-dichloro-7-(1-ethylpropyl)-1H-benzimidazol-1-yl]acetate (Reference Example 10; 1.96 g, 5.49 mmol), 2,4-dichloroaniline (2.67 g, 16.5 mmol) and N-methyl-2-pyrrolidinone (1.5 mL) was stirred at 100° C. for 15 hr. After cooling, the reaction mixture was neutralized with saturated aqueous sodium hydrogen carbonate and extracted with ethyl acetate. The organic layer was washed with water and brine, dried over anhydrous sodium sulfate and concentrated in vacuo. The residue was purified by silica gel column chromatography eluting with a 3-15% ethyl acetate/n-hexane gradient mixture to give the title compound (546 mg, 1.13 mmol, 21%) as an oil.

$^1$H NMR (CDCl$_3$) δ: 0.82 (6H, t, J=7.2 Hz), 1.32 (6H, d, J=6.3 Hz), 1.63-1.84 (4H, m), 2.90-3.05 (1H, m), 4.88 (2H, s), 5.16-5.25 (1H, m), 6.95 (1H, d, J=8.1 Hz), 7.22 (1H, d, J=8.1 Hz), 7.29 (1H, dd, J=8.7, 2.4 Hz), 7.3.9 (1H, d, J=2.4 Hz), 7.46 (1H, s), 8.31 (1H, d, J=8.7 Hz).

MS Calcd.: 481; Found: 482 (M+H).

Reference Example 21

{4-Chloro-2-[(2,4-dichlorophenyl)amino]-7-(1-ethylpropyl)-1H-benzimidazol-1-yl}acetic acid To a solution of isopropyl {4-chloro-2-[(2,4-dichlorophenyl)amino]-7-(1-ethylpropyl)-1H-benzimidazol-1-yl}acetate (521 mg, 1.08 mmol) in methanol (4 mL) was added 8N aqueous sodium hydroxide (1 mL) at 0° C., and the mixture was stirred at the same temperature for 4 hours. Methanol was evaporated in vacuo; and the aqueous residue was adjusted to pH 4. Ethyl acetate was added to the mixture, followed by stirring at 0° C. for 1 hour. The resulting solid was collected by filtration and washed with water to give the title compound (330 mg, 0.749 mmol, 69%) as a colorless solid.

$^1$H NMR (DMSO-d$_6$) δ: 0.75 (6H, t, J=7.2 Hz), 1.55-1.80 (4H, m), 2.80-2.95 (1H, m), 5.08 (2H, s), 6.89 (1H, d, J=8.1 Hz), 7.11 (1H, d, J=8.1 Hz), 7.43 (1H, d, J=8.7 Hz), 7.64 (1H, s), 7.74 (1H, d, J=8.7 Hz), 8.65 (1H, s), 13.40 (1H, brs).

MS Calcd.: 439; Found: 440 (M+H).

Reference Example 22

2-{2-[(2-Bromo-4-chlorophenyl)amino-4-chloro]-7-(1ethylpropyl)-1H-benzimidazol-1-Yl}ethanol A mixture of isopropyl [2,4-dichloro-7-(1-ethylpropyl)-1H-benzimidazol-1-yl]acetate (Reference Example 10; 1.00 g, 2.80 mmol), 2-bromo-4-chloroaniline (1.73 g, 8.40 mmol) and p-toluenesulfonic acid monohydrate (586 mg, 3.08 mmol) in xylene (5 mL) was refluxed for 18 hr. After cooling, the reaction mixture was diluted with water and extracted with ethyl acetate. The extracts were washed with saturated aqueous sodium hydrogen carbonate, 1N hydrochloric acid and brine, dried over anhydrous magnesium sulfate and concentrated in vacuo. The residue was purified by silica gel column chromatography eluting with a 1-10% ethyl acetate/n-hexane gradient mixture to give a mixture of isopropyl {2-[(2-bromo-4-chlorophenyl)amino-4-chloro]-7-(1-ethylpropyl)-1H-benzimidazol-1-yl}acetate and 2-bromo-4-chloroaniline. The mixture was used for the next step without further purification.

To a solution of the above mixture (1.30 g) in tetrahydrofuran (5 mL) was added lithium tetrahydroborate (161 mg, 7.38 mmol), and the mixture was stirred at room temperature for 60 hr. The mixture was diluted with water and extracted with ethyl acetate. The extracts were washed with brine, dried over anhydrous magnesium sulfate and concentrated in vacuo. The residue was purified by silica gel column chromatography eluting with a 1-20% ethyl acetate/n-hexane gradient mixture to give the title compound (262 mg, 0.556 mmol, 20%) as a colorless solid.

$^1$H NMR (CDCl$_3$) δ: 0.77 (6H, t, J=7.5 Hz), 1.50-1.80 (4H, m), 2.65-2.80 (1H, m), 4.16-4.20 (2H, m), 4.25-4.35 (2H, m), 4.45-4.65 (1H, m), 6.79 (1H, d, J=8.7 Hz), 7.07 (1H, d, J=8.7 Hz), 7.30 (1H, dd, J=2.4, 8.7 Hz), 7.46 (1H, d, J=2.4 Hz), 8.46 (1H, d, J=8.7 Hz), 8.59 (1H, s).

MS Calcd.: 469; Found: 470 (M+H).

Reference Example 23

2-[2-[(4-Bromo-2-chlorophenyl)amino]-4-chloro-7-(1-ethylpropyl)-1H-benzimidazol-1-yl]ethanol A mixture of isopropyl [2,4-dichloro-7-(1-ethylpropyl)-1H-benzimidazol-1-yl]acetate (Reference Example 10; 1.33 g, 3.72 mmol), 4-bromo-2-choloroaniline (1.92 g, 9.31 mmol), p-toluenesulfonic acid monohydrate (707.6 mg, 3.98 mmol) and xylene (10.0 mL) was stirred at 150° C. for 2 hr. After cooling, the reaction mixture was diluted with water and extracted with ethyl acetate (×3). The combined organic layer was washed with brine, dried over anhydrous magnesium sulfate, filtered and concentrated in vacuo. The residue was purified by silica gel column chromatography eluting with a 0-15% ethyl acetate/n-hexane gradient mixture to give isopropyl {2-[(4-bromo-2-chlorophenyl)amino-4-chloro]-7-(1-ethylpropyl)-1H-benzimidazol-1-yl}acetate and 4-bromo-4-chloroaniline. The mixture was used for the next step without further purification.

To a solution of the above in tetrahydrofuran (5.0 mL) was added lithium borohydride (243.1 mg, 11.16 mmol) at 0° C. The reaction mixture was stirred at 50° C. for 3 hr. After cooling, the reaction mixture was quenched with water at 0° C. and extracted with ethyl acetate (×3). The combined organic layer was washed with brine, dried over anhydrous magnesium sulfate, filtered and concentrated in vacuo. The residue was purified by silica gel column chromatography eluting with a 0-20% ethyl acetate/n-hexane gradient mixture to give the title compound as a colorless powder (624.6 mg, 1.33 mmol, 36%).

$^1$H NMR (CDCl$_3$) δ: 0.77 (t, J=7.2 Hz, 6H), 1.50-1.74 (m, 4H), 2.69-2.73 (m, 1H), 4.16 (d, J=3.9 Hz, 2H), 4.31 (d, J=3.9 Hz, 2H), 6.80 (d, J=8.1 Hz, 1H), 7.09 (d, J=8.1 Hz, 1H), 7.38-7.43 (m, 2H), 8.44 (d, J=8.7 Hz, 1H), 8.72 (s, 1H).

MS Calcd.: 469, MS Found: 470 (M+H).

Reference Example 24

Ethyl N-(2,6-dinitrophenyl)-beta-alaninate

A mixture of beta-alanine ethyl ester hydrochloride (911 mg, 5.39 mmol), 2-chloro-1,3-dinitrobenzene (1.00 g, 4.94 mmol), triethylamine (2.07 mL, 14.9 mmol) and tetrahydrofuran (50 mL) was stirred at room temperature for 2 hr. To the reaction mixture were added beta-alanine ethyl ester hydrochloride (455 mg, 2.96 mmol) and triethylamine (1.03 mL, 7.39 mmol) at room temperature and the resultant mixture was stirred at room temperature for 2 hr. The reaction mixture was diluted with ethyl acetate, washed with water and brine, dried over anhydrous sodium sulfate, filtered and concentrated in vacuo. The residue was purified by flash column chromatography on, silica gel eluting with a 0-20% ethyl acetate/n-hexane gradient mixture to give the title compound as an oil (1.39 g, 4.92 mmol, 99.6%).

$^1$H NMR (CDCl$_3$) δ 1.26 (t, J=7.1 Hz, 3H), 2.66 (t, J=5.8 Hz, 2H), 3.23-3.31 (m, 2H), 4.17 (q, J=7.1 Hz, 2H), 6.78 (t, J=8.2 Hz, 1H), 8.17 (d, J=8.2 Hz, 2H), 8.53 (brs, 1H).

MS Calcd.: 283; MS Found: 284 (M+H).

Reference Example 25

Ethyl N-(2,6-diaminophenyl)-beta-alaninate

Under hydrogen gas atmosphere, a mixture of ethyl N-(2,6-dinitrophenyl)-beta-alaninate (Reference Example 24; 1.39 g, 4.92 mmol), 10% palladium on carbon (50% wet, 280 mg) and tetrahydrofuran (50 mL) was stirred at room temperature for 6 hr. The reaction mixture was filtered and concentrated in vacuo to give the title compound as an oil (1.00 g, 4.50 mmol, 91%)

$^1$H NMR (CDCl$_3$) δ 1.30 (t, J=7.2 Hz, 3H), 2.56-2.62 (m, 2H), 3.12-3.17 (m, 2H), 3.95 (brs, 4H), 4.21 (q, J=7.2 Hz, 2H), 6.19 (d, J=7.8 Hz, 2H), 6.75 (t, J=7.8 Hz, 1H), hidden (1H).

MS Calcd.: 223; MS Found: 224 (M+H).

Reference Example 26

Ethyl N-[2-amino-6-({[(2,4-dichlorophenyl)amino] carbonothioyl}amino)phenyl]-beta-alaninate To a solution of ethyl N-(2,6-diaminophenyl)-beta-alaninate (Reference Example 25; 500 mg, 2.24 mmol) in tetrahydrofuran (22 mL) was added 2,4-dichlorophenyl isothiocyanate (503 mg, 2.46 mmol) at room temperature. The resultant mixture was stirred at room temperature for 1 hr and concentrated in vacuo. The residue was purified by flash column chromatography on silica gel eluting with a 10-40% ethyl acetate/n-hexane gradient mixture and NH-silica gel eluting with a 10-90% ethyl acetate/n-hexane gradient mixture to give the title compound as a solid (533 mg, 1.25 mmol, 56%).

$^1$H NMR (CDCl$_3$) δ 1.27 (t, J=7.1 Hz, 3H), 2.49-2.56 (m, 2H), 3.27 (t, J=5.6 Hz, 2H), 3.51 (brs, 1H), 4.01-4.25 (m, 4H), 6.69 (dd, J=8.0, 1.4 Hz, 1H), 6.83 (d, J=8.0 Hz, 1H), 6.93 (t, J=8.0 Hz, 1H), 7.24 (dd, J=8.8, 2.2 Hz, 1H), 7.36 (d, J=2.2 Hz, 1H), 8.09-8.17 (m, 2H), 8.27 (brs, 1H).

MS Calcd.: 426; MS Found: 427 (M+H).

Reference Example 27

Ethyl 3-{7-amino-2-[(2,4-dichlorophenyl)amino]-1H-benzimidazol-1-yl}propanoate

To a solution of ethyl N-[2-amino-6-({[(2,4-dichlorophenyl)amino]carbonothioyl}amino)phenyl]-beta-alaninate (Reference Example 26; 174 mg, 0.407 mmol) in tetrahydrofuran (4 mL) was added 1-ethyl-3-(3-dimethylaminopropyl)carbodiimide hydrochloride (234 mg, 1.22 mmol) at room temperature. The resultant mixture was stirred at 50° C. for 2 hr. The reaction mixture was diluted with ethyl acetate, washed with water and brine, dried over anhydrous sodium sulfate, filtered and concentrated in vacuo. The residue was purified by column chromatography on silica gel eluting with ethyl acetate to give the title compound as an oil (122 mg, 0.309 mmol, 76%).

$^1$H NMR (CDCl$_3$) δ 1.21 (t, J=7.2 Hz, 3H), 3.06-3.14 (m, 2H), 3.70 (brs, 2H), 4.14 (q, J=7.2 Hz, 2H), 4.48-4.53 (m, 2H), 6.53 (d, J=7.8 Hz, 1H), 6.98 (t, J=7.8 Hz, 1H), 7.12-7.23 (m, 2H), 7.36 (d, J=2.2 Hz, 1H), 8.08 (brs, 1H), 8.16-8.27 (m, 1H).

MS Calcd.: 392; MS Found: 393 (M+H).

Reference Example 28

Ethyl 3-[2-[(2,4-dichlorophenyl)amino]-7-(diethylamino)-1H-benzimidazol-1-yl]propanoate To a solution of ethyl 3-{7-amino-2-[(2,4-dichlorophenyl)amino]-1H-benzimidazol-1-yl}propanoate (Reference Example 27; 214 mg, 0.544 mmol) in methanol (5.5 mL) and acetic acid (0.110 mL) was added acetaldehyde (0.204 mL, 3.27 mmol) at 0° C. The resultant mixture was stirred at 0° C. for 30 min. To the reaction mixture was added sodium acetoxyborohydride (692 mg, 3.27 mmol) at 0° C. After the resultant mixture was stirred at room temperature for 12 hr, the mixture was diluted with aqueous saturated sodium hydrogen carbonate and, extracted with ethyl acetate. The combined organic layer was washed with brine, dried over anhydrous sodium sulfate, filtered and concentrated in vacuo. The residue was purified by column chromatography on NH-silica gel eluting with ethyl acetate to give the title compound as a solid (255 mg, 0.567 mmol, quant).

$^1$H NMR (CDCl$_3$) δ 1.06 (t, J=7.1 Hz, 6H), 1.21 (t, J=7.2 Hz, 3H), 3.00 (t, J=5.9 Hz, 2H), 3.07 (q, J=7.1 Hz, 4H), 4.14 (q, J=7.2 Hz, 2H), 4.62 (t, J=5.9 Hz, 2H), 7.01 (dd, J=1.1, 7.8 Hz, 1H), 7.14 (t, J=7.8 Hz, 1H), 7.20-7.25 (m, 1H), 7.37-7.42 (m, 2H), 8.16 (s, 1H), 8.30 (d, J=9.1 Hz, 1H).

MS Calcd.: 448; MS Found: 449 (M+H).

Reference Example 29

3-[2-[(2,4-Dichlorophenyl)amino]-7-(diethylamino)-1H-benzimidazol-1-yl]propan-1-ol To a suspension of lithium borohydride (22.5 mg, 1.03 mmol) in tetrahydrofuran (3.5 mL) was added ethyl 3-[2-[(2,4-dichlorophenyl)amino]-7-(diethylamino)-1H-benzimidazol-1-yl]propanoate (Reference Example 28; 155 mg, 0.345 mmol) at 0° C. After the resultant mixture was stirred at room temperature for 20 hr, the mixture was diluted with aqueous ammonium chloride at 0° C. and stirred at 0° C. for 30 min. The resultant mixture was diluted with aqueous sodium hydrogen carbonate and extracted with ethyl acetate. The combined organic layer was washed with brine, dried over anhydrous sodium sulfate, filtered and concentrated in vacuo. The residue was purified by flash column chromatography on silica gel eluting with a 25% ethyl acetate/n-hexane mixture to give the title compound as a solid (35.7 mg, 0.0876 mmol, 25%).

$^1$H NMR (CDCl$_3$) δ 1.06 (t, J=7.2 Hz, 6H), 1.25 (s, 1H), 2.03-2.14 (m, 2H), 3.09 (q, J=7.2 Hz, 4H), 3.56 (t, J=5.5 Hz, 2H), 4.56 (t, J=6.2 Hz, 2H), 6.98 (d, J=8.0 Hz, 1H), 7.11 (t, J=8.0 Hz, 1H), 7.22-7.28 (m, 2H), 7.32-7.40 (m, 2H), 8.40 (brs, 1H).

MS Calcd.: 406; MS Found: 407 (M+H).

Reference Example 30

3-[2-[(2,4-Dichlorophenyl)amino]-7-(diethylamino)-1H-benzimidazol-1-yl]propanoic acid To a solution of ethyl 3-[2-[2,4-dichlorophenyl)amino]-7-(diethylamino)-1H-benzimidazol-1-yl]propanoate (Reference Example 28; 100 mg, 0.223 mmol) in a mixture of tetrahydrofuran (2 mL) and methanol (1 mL) was added 1N sodium hydroxide solution (0.446 mL, 0.446 mmol) at 0° C. After the resultant mixture was stirred at room temperature for 1 hr, the mixture was neutralized with 1N hydrochloric acid and extracted with ethyl acetate. The combined organic layer was washed with brine, dried over anhydrous sodium sulfate, filtered and concentrated in vacuo. The residue was purified by column chromatography on silica gel eluting with ethyl acetate to give the title compound as a solid (73.3 mg, 0.174 mmol, 78%).

$^1$H NMR (DMSO-d$_6$) δ 0.98 (t, J=7.0 Hz, 6 H), 2.70-2.84 (m, 2 H), 3.01 (q, J=7.0 Hz, 4 H), 4.51-4.67 (m, 2 H), 6.89-7.29 (m, 3 H), 7.31-7.47 (m, 1 H), 7.60 (brs, 1 H), 8.07 (brs, 1 H), 8.74 (brs, 1 H), 12.57 (brs, 1 H).

MS Calcd.: 420; MS Found: 421 (M+H).

Reference Example 31

Ethyl 4-[7-(1-ethylpropyl)-2-oxo-2,3-dihydro-1H-benzimidazol-1-yl]butanoate

To a solution of tert-butyl 4-(1-ethylpropyl)-2-oxo-2,3-dihydro-1H-benzimidazole-1-carboxylate (Reference Example 7; 10.37 g, 34.11 mmol) in N,N-dimethylformamide (100 mL) was added potassium carbonate (5.18 g, 37.52 mmol) and ethyl 4-bromobutyrate (8.55 g, 37.52 mmol), and the mixture was stirred at 80-90° C. overnight. The reaction solution was concentrated to dryness and diluted with water (150 mL). The resulting mixture was extracted with ethyl acetate (100 mL×2). The combined extracts were washed with water (80 mL×2), brine (100 mL), dried over anhydrous sodium sulfate and concentrated in vacuo to give 19.3 g of crude tert-butyl 3-(4-ethoxy-4-oxobutyl)-4-(1-ethylpropyl)-2-oxo-2,3-dihydro-1H-benzimidazole-1-carboxylate, which was used for the next step without further purification.

To a solution of the above crude compound (19.3 g, 34.11 mmol) in ethyl acetate (50 mL) was added a 4N solution of hydrogen chloride in ethyl acetate (50 mL) at 0° C., and the mixture was stirred at 25° C. overnight. An additional of 4N hydrogen chloride solution in ethyl acetate (50 mL) was added and the solution was continued stirring at the same temperature for 2 hr. The mixture was concentrated to dryness and the residue was neutralized with saturated aqueous sodium bicarbonate (50 mL). The resulting aqueous layer was extracted with ethyl acetate (150 mL×3), washed with saturated aqueous sodium bicarbonate (50 mL×2) and water (50 mL), dried over anhydrous sodium sulfate and concentrated to dryness. The residue was purified by silica gel column eluting with a 5-100 ethyl acetate/petroleum ether gradient mixture to afford the title compound (9.7 g, 86%) as light yellow oil.

$^1$H NMR (CDCl$_3$) δ 0.79 (6H, t, J=7.4 Hz), 1.26 (3H, t, J=7.2 Hz), 1.63-1.71 (2H, m), 1.73-1.82 (2H, m), 2.03-2.11 (2H, m), 2.45 (2H, t, J=7.4 Hz), 2.96-3.05 (1H, m), 4.10-4.16 (4H, m), 6.91 (1H, d, J=7.6 Hz), 6.94 (1H, d, J=7.6 Hz), 7.04 (1H, t, J=7.8 Hz), 8.88 (1H, brs).

MS Calcd.: 318; MS Found: 319 (M+H).

Reference Example 32

Ethyl 4-[4-chloro-7-(1-ethylpropyl)-2-oxo-2,3-dihydro-1H-benzimidazol-1-yl]butanoate To a solution of ethyl 4-[7-(1-ethylpropyl)-2-oxo-2,3-dihydro-1H-benzimidazol-1-yl]butanoate (9.7 g, 30.5 mmol) and 2,2'-azobisisobutyronitrile (AIBN; 0.5 g, 3.05 mmol) in chlorobenzene (100 mL) was added N-chlorosuccinimide (NCS; 4.35 g, 32.6 mmol) in portions at 65° C., and the mixture was stirred at 80-90° C. for 2 days. After cooled to room temperature, the reaction mixture was partitioned between ethyl acetate (50 mL) and water (50 mL). The aqueous phase was extracted with ethyl acetate (100 ml×3), washed with brine (100 mL), dried over anhydrous sodium sulfate and purified by silica gel column (petroleum ether/ethyl acetate, 50/1) to afford the title compound (6.8 g, 61%) as yellow oil.

$^1$H NMR (CDCl$_3$) δ 0.78 (6H, t, J=7.4 Hz), 1.27 (3H, t, J=7.2 Hz), 1.61-1.70 (2H, m), 1.74-1.84 (2H, m), 2.04-2.10 (2H, m), 2.47 (2H, t, J=7.2 Hz), 2.87-3.04 (1H, m), 4.11-4.22 (4H, m), 6.89 (1H, d, J=8.8 Hz), 7.05 (1H, d, J=8.4 Hz), 8.97 (1H, brs).

MS Calcd.: 352.2; MS Found: 353.0 (M+H).

Reference Example 33

Ethyl 4-[2,4-dichloro-7-(1-ethylpropyl)-1H-benzimidazol-1-yl]butanoate

The solution of ethyl 4-[4-chloro-7-(1-ethylpropyl)-2-oxo-2,3-dihydro-1H-benzimidazol-1-yl]butanoate (6.8 g, 19.32 mmol) in phosphorus oxychloride (70 mL) was stirred at 100-110° C. for 2 days. After cooled to room temperature, the excess phosphorus oxychloride was removed by distillation and the residue was poured into water. The aqueous phase was extracted with ethyl acetate (100 mL×3) and the combined extracts were washed with saturated aqueous sodium bicarbonate (100 mL×2) and water (100 mL), dried over sodium sulfate and concentrated in vacuo. The residue was purified by silica gel column (petroleum ether/ethyl acetate, 50/1) to afford the title compound (2.4 g, 34%) as light yellow oil.

$^1$H NMR (CDCl$_3$) δ 0.86 (6H, t, J=7.6 Hz), 1.27 (3H, t, J=7.0 Hz), 1.64-1.86 (4H, m), 2.08-2.15 (2H, m), 2.45 (2H, t, J=6.8 Hz), 3.05-3.12 (1H, m), 4.16 (2H, q, J=7.2 Hz), 4.43 (2H, t, J=7.6 Hz), 7.06 (1H, d, J=8.4 Hz), 7.27 (1H, d, J=8.4 Hz).

MS Calcd.: 370.1; MS Found: 371.0 (M+H).

Reference Example 34

Ethyl 4-{4-chloro-2-[(2,4-dichlorophenyl)amino]-7-(1-ethylpropyl)-1H-benzimidazol-1-yl}butanoate The solution of ethyl 4-[2,4-dichloro-7-(1-ethylpropyl)-1H-benzimidazol-1-yl]butanoate (500 mg, 1.20 mmol), (4-chloro-2-methoxy-6-methyl)aniline (780 mg, 4.80 mmol) in N-methyl-2-pyrrolidinone (2 mL) was stirred at 110-120° C. for 3 days. After cooled to room temperature, the reaction mixture was partitioned between ethyl acetate (10 mL) and water (10 mL). The aqueous layer was extracted with ethyl acetate (20 mL×3) and the combined extracts were washed with brine (20 mL), dried over anhydrous sodium sulfate and concentrated in vacuo. The resulting residue was purified by silica gel column chromatography (petroleum ether/ethyl acetate, 50/1) to afford the title compound (260 mg, 44%) as colorless oil.

$^1$H NMR (CDCl$_3$, Bruker Avance 400 MHz): δ 0.78 (6H, t, J=7.4 Hz), 1.23 (3H, t, J=7.2 Hz), 1.70-1.87 (4H, m), 2.11-2.18 (2H, m), 2.45 (2H, t, J=6.4 Hz), 2.98-3.12 (1H, m), 4.15 (2H, q, J=7.2 Hz), 4.31 (2H, t, J=7.8 Hz), 6.94 (1H, d, J=8.4 Hz), 7.12 (1H, s), 7.20 (1H, d, J=8.8 Hz), 7.31 (1H, dd, J=9.0, 2.2 Hz), 7.41 (1H, d, J=2.4 Hz), 8.44 (1H, d, J=8.8 Hz).

MS Calcd.: 495.1; MS Found: 496.2 (M+H).

Reference Example 35

Ethyl 4-[4-chloro-2-[(4-chlorophenyl)amino]-7-(1-ethylpropyl)-1H-benzimidazol-1-yl]butanoate A mixture of ethyl 4-[2,4-dichloro-7-(1-ethylpropyl)-1H-benzimidazo-1-yl]butanoate (Reference Example 33; 1.00 g, 2.70 mmol) and 4-chloroaniline (1.04 g, 8.0.9 mmol) in 1-methyl-2-pyrrolidinone (10 mL) was stirred at 150° C. for 12 hr. After cooling, the mixture was diluted with ethyl acetate and washed with 1N hydrochloric acid, water and brine. Organic layer was dried over anhydrous sodium sulfate and concentrated in vacuo. The residue was purified by flash chromatography on silica gel eluting with a 10-25% ethyl acetate/n-hexane gradient mixture. The filtrate was concentrated in vacuo to give the solid, which was recrystallized from ethyl acetate/n-hexane to give the title compound (600 mg, 1.30 mmol, 48%) as a colorless solid.

mp 149-150° C.

$^1$H NMR (CDCl$_3$) δ 0.84 (t, J=7.3 Hz, 6 H), 1.35 (t, J=7.2 Hz, 3 H), 1.62-1.88 (m, 4 H), 2.12 (dd, J=8.1, 4.0 Hz, 2 H), 2.48-2.58 (m, 2 H), 2.87-2.99 (m, 1 H), 4.15-4.25 (m, 2 H), 4.31 (q, J=6.9 Hz, 2 H), 6.86 (d, J=8.3 Hz, 1 H), 7.15 (d, J=8.3 Hz, 1 H), 7.31 (d, J=8.7 Hz, 2 H), 7.95 (d, J=8.7 Hz, 2 H), 8.30 (s, 1 H).

MS Calcd.: 461; Found: 462 (M+H).

Reference Example 36

4-[4-Chloro-2-[(4-chlorophenyl)amino]-7-(1-ethylpropyl)-1H-benzimidazol-1-yl]butan-1-ol To a solution of ethyl 4-[4-chloro-2-[(4-chlorophenyl)amino]-7-(1-ethylpropyl)-1H-benzimidazol-1-yl]butanoate (400 mg, 0.86 mmol) in tetrahydrofuran (5 mL) was added lithium borohydride (57 mg, 2.59 mmol) portionwise at 0° C. The mixture was warmed to room temperature and stirred for 12 hr. Water was added and the mixture was extracted with ethyl acetate. Organic layer was washed with brine, dried over anhydrous sodium sulfate and concentrated in vacuo to give a solid, which was recrystallized from ethyl acetate to give the title compound (250 mg, 0.60 mmol, 69%) as a colorless solid.

mp 213-214° C.

$^1$H NMR (CDCl$_3$) δ 0.86 (t, J=7.3 Hz, 6 H), 1.49-1.89 (m, 8 H), 2.85-3.04 (m, 1 H), 3.79 (brs, 1 H), 3.88 (t, J=5.3 Hz, 2 H), 4.12 (t, J=7.0 Hz, 2 H), 6.91 (d, J=8.3 Hz, 1 H), 7.03 (d, J=7.9 Hz, 2 H), 7.19 (d, J=8.3 Hz, 1H), 7.40 (d, J=7.9 Hz, 2 H), 8.29 (brs, 1 H).

MS Calcd.: 419; Found: 420 (M+H).

Reference Example 37

Ethyl 4-{4-chloro-7-(1-ethylpropyl)-2-[(1,3,5-trimethyl-1H-pyrazol-4-yl)amino]-1H-benzimidazol-1-yl}butanoate A mixture of ethyl 4-[2,4-dichloro-7-(1-ethylpropyl)-1H-benzimidazol-1-yl]butanoate (Reference Example 33; 371 mg, 1.00 mmol), 4-amino-1,3,5-trimethylpyrazole (375 mg, 3.00 mmol) and p-toluenesulfonic acid monohydrate (190 mg, 1.00 mmol) in 1-methyl-2-pyrrolidinone (3 mL) was stirred at 150° C. for 16 hr. After cooling, aqueous sodium bicarbonate was added and the mixture was extracted with ethyl acetate. Organic layer was washed with water and brine, dried over anhydrous sodium sulfate and concentrated in vacuo. The residue was purified by flash chromatography on silica gel eluting with a 0-5% methanol/ethyl acetate gradient mixture. The filtrate was concentrated in vacuo to give the solid, which was recrystallized from ethyl acetate/n-hexane to give the title compound (340 mg, 0.74 mmol, 74%) as a colorless solid.

mp 177-178° C.

$^1$H NMR (CDCl$_3$) δ 0.86 (t, J=7.3 Hz, 6 H), 1.28 (t, J=7.0 Hz, 3 H), 1.64-1.85 (m, 4 H), 2.03-2.16 (m, 2 H), 2.20 (s, 3 H), 2.22 (s, 3 H), 2.44-2.51 (m, 2 H), 2.87-2.99 (m, 1 H), 3.74 (s, 3 H), 4.10-4.24 (m, 4 H), 6.79 (d, J=8.3 Hz, 1 H), 6.90 (s, 1 H), 7.08 (d, J=8.3 Hz, 1 H).

MS Calcd.: 459; Found: 460 (M+H).

Reference Example 38

4-{4-Chloro-7-(1-ethylpropyl)-2-[(1,3,5-trimethyl-1H-pyrazol-4-yl)amino]-1H-benzimidazol-1-yl}butan-1-ol To a solution of ethyl 4-{4-chloro-7-(1-ethylpropyl)-2-[(1, 3,5-trimethyl-1H-pyrazol-4-yl)amino]-1H-benzimidazol-1-yl}butanoate (240 mg, 0.52 mmol) in tetrahydrofuran (3 mL) was added lithium borohydride (34 mg, 1.57 mmol) portionwise at 0° C. The mixture was warmed to room temperature and stirred for 16 hr. Water was added and the mixture was extracted with ethyl acetate. Organic layer was washed with brine, dried over anhydrous sodium sulfate and concentrated in vacuo. The residue was purified by flash chromatography on silica gel eluting with a 0-10% methanol/ethyl acetate gradient mixture. The filtrate was concentrated in vacuo to give the title compound (74 mg, 0.17 mmol, 34%) as a colorless amorphous.

$^1$H NMR (CDCl$_3$) δ 0.87 (t, J=7.3 Hz, 6 H), 1.59-2.15 (m, 8 H), 2.21 (s, 3 H), 2.22 (s, 3 H), 2.90-3.03 (m, 1 H), 3.74-3.82 (m, 2 H), 3.84 (s, 3 H), 4.28 (t, J=7.5 Hz, 2H), 6.82 (d, J=8.3 Hz, 1 H), 7.06 (d, J=8.3 Hz, 1 H).

MS Calcd.: 417; Found: 418 (M+H).

Reference Example 39

Ethyl 4-[4-chloro-2-{[6-(dimethylamino)-4-methylpyridin-3-yl]amino}-7-(1-ethylpropyl)-1H-benzimidazol-1-yl]butanoate A mixture of ethyl 4-[2,4-dichloro-7-(1-ethylpropyl)-1H-benzimidazol-1-yl]butanoate (Reference Example 33; 472 mg, 1.27 mmol), N$^2$,N$^2$,4-trimethylpyridine-2,5-diamine (580 mg, 3.81 mmol) and p-toluenesulfonic acid monohydrate (241 mg, 1.27 mmol) in 1-methyl-2-pyrrolidinone (4 mL) was irradiated by microwave at 180° C. for 135 min. After cooling, aqueous sodium bicarbonate was added and the mixture was extracted with ethyl acetate. Organic layer was washed with water and brine, dried over anhydrous sodium sulfate and concentrated in vacuo. The residue was purified by flash chromatography on silica gel eluting with a 20-80% ethyl acetate/n-hexane gradient mixture. The filtrate was concentrated in vacuo to give a solid, which was recrystallized from ethyl acetate/n-hexane to give the title compound (266 mg, 0.547 mmol, 43%) as a colorless solid.

mp 158-159° C.

$^1$H NMR (CDCl$_3$) δ 0.86 (t, J=7.3 Hz, 6 H), 1.26 (t, J=7.2 Hz, 3 H), 1.66-1.85 (m, 4 H), 2.03-2.16 (m, 2 H), 2.29 (s, 3 H), 2.41-2.50 (m, 2 H), 2.87-3.01 (m, 1 H), 3.08 (s, 6 H), 4.09-4.26 (m, 4 H), 6.42 (s, 1 H), 6.81 (d, J=8.3 Hz, 1 H), 6.91 (s, 1 H), 7.09 (d, J=8.3 Hz, 1 H), 8.29 (s, 1 H).

MS Calcd.: 485; Found: 486 (M+H).

Reference Example 40

4-[4-Chloro-2-{[6-(dimethylamino)-4-methylpyridin-3-yl]amino}-7-(1-ethylpropyl)-1H-benzimidazol-1-yl]butan-1-ol To a Solution of ethyl 4-[4-chloro-2-{[6-(dimethylamino)-4-methylpyridin-3-yl]amino}-7-(1-ethylpropyl)-1H-benzimidazol-1-yl]butanoate (200 mg, 0.41 mmol) in tetrahydrofuran (4 mL) was added lithium borohydride (27 mg, 1.23 mmol) portionwise at 0° C. The mixture was warmed to room temperature and stirred for 24 hr. Water was added and the mixture was extracted with ethyl acetate. Organic layer was washed with brine, dried over anhydrous sodium sulfate and concentrated in vacuo to give a solid, which was recrystallized from ethyl acetate to give the title compound (95 mg, 0.214 mmol, 52%) as a colorless solid.

mp 195-197° C.

$^1$H NMR (CDCl$_3$) δ 0.86 (t, J=7.3 Hz, 6 H), 1.57-1.98 (m, 8 H), 2.21 (s, 3 H), 2.89-3.05 (m, 1 H), 3.01 (s, 6 H), 3.72 (t, J=5.8 Hz, 2 H), 4.23 (t, J=7.4 Hz, 2 H), 6.35 (s, 1 H), 6.80 (d, J=8.2 Hz, 1 H), 7.04 (d, J=8.2 Hz, 1H), 8.03 (brs, 1 H).

MS Calcd.: 443; Found: 444 (M+H).

Reference Example 41

Ethyl 4-[4-chloro-2-[(3,5-dichlorophenyl)amino]-7-(1-ethylpropyl)-1H-benzimidazol-1-yl]butanoate A mixture of ethyl 4-[2,4-dichloro-7-(1-ethylpropyl)-1H-benzimidazol-1-yl]butanoate (Reference Example 33; 500 mg, 1.35 mmol), 3,5-dichloroaniline (655 mg, 4.04 mmol) and p-toluenesulfonic acid monohydrate (257 mg, 1.35 mmol) in 1-methyl-2-pyrrolidinone (4 mL) was irradiated by microwave at 180° C. for 15 min. After cooling, aqueous sodium bicarbonate was added and the mixture was extracted with ethyl acetate. Organic layer was washed with water and brine, dried over anhydrous sodium sulfate and concentrated in vacuo. The residue was purified by flash chromatography on silica gel eluting with a 5-20% ethyl acetate/n-hexane gradient mixture. The filtrate was concentrated in vacuo to give a residue, which was purified by preparative HPLC to give the title compound (270 mg, 0.542 mmol, 40%) as a colorless amorphous.

$^1$H NMR (CDCl$_3$) δ 0.81 (t, J=7.3 Hz, 6 H), 1.35 (t, J=7.2 Hz, 3 H), 1.57-1.87 (m, 4 H), 2.01-2.16 (m, 2 H), 2.53 (dd, J=7.3, 4.3 Hz, 2 H), 2.84-2.98 (m, 1 H), 4.11-4.23 (m, 2 H), 4.31 (q, J=7.2 Hz, 2 H), 6.86 (d, J=8.3 Hz, 1 H), 6.96 (t, J=1.7 Hz, 1 H), 7.14 (d, J=8.3 Hz, 1 H), 7.96 (d, J=1.9 Hz, 2 H), 8.62 (brs, 1 H).

MS Calcd.: 495; Found: 496 (M+H).

Reference Example 42

4-[4-Chloro-2-[(3,5-dichlorophenyl)amino]-7-(1-ethylpropyl)-1H-benzimidazol-1-yl]butan-1-ol To a solution of ethyl 4-[4-chloro-2-[(3,5-dichlorophenyl)amino]-7-(1-ethylpropyl)-1H-benzimidazol-1-yl]butanoate (250 mg, 0.50 mmol) in tetrahydrofuran (5 mL) was added lithium borohydride (33 mg, 1.51 mmol) portionwise at 0° C. The mixture was warmed to room temperature and stirred for 36 hr. Water was added and the resulting precipitate was collected by filtration to afford the title compound (213 mg, 0.469 mmol, 94%) as a colorless solid.

mp 208-210° C.

$^1$H NMR (DMSO-d$_6$) δ 0.82 (t, J=7.3 Hz, 6 H), 1.40-1.55 (m, 2 H), 1.55-1.88 (m, 6 H), 3.01-3.15 (m, 1 H), 3.43 (t, J=6.2 Hz, 2 H), 4.33 (t, J=7.5 Hz, 2 H), 4.59 (brs, 1 H), 6.95 (d, J=8.3 Hz, 1 H), 7.13-7.19 (m, 2 H), 8.04 (d, J=1.9 Hz, 2 H), 9.28 (brs, 1 H)

MS Calcd.: 453; Found: 454 (M+H).

Reference Example 43

Ethyl 4-[4-chloro-2-[(2,6-dimethoxypyridin-3-yl)amino]-7-(1-ethylpropyl)-1H-benzimidazol-1-yl]butanoate A mixture of ethyl 4-[2,4-dichloro-7-(1-ethylpropyl)-1H-benzimidazol-1-yl]butanoate (Reference Example 33; 500 mg, 1.35 mmol) and 2,6-dimethoxypyridin-3-amine monohydrochloride (768 mg, 4.04 mmol) in 1-methyl-2-pyrrolidinone (4 mL) was irradiated by microwave at 180° C. for 15 min. After cooling, aqueous sodium bicarbonate was added and the mixture was extracted with ethyl acetate. Organic layer was washed with water and brine, dried over anhydrous sodium sulfate and concentrated in vacuo. The residue was purified by flash chromatography on silica gel eluting with a 5-20% ethyl acetate/n-hexane gradient mixture. The filtrate was concentrated in vacuo to give the title compound (133 mg, 0.272 mmol, 20%) as a colorless amorphous.

$^1$H NMR (CDCl$_3$) δ 0.85 (t, J=7.3 Hz, 6 H), 1.26 (t, J=7.2 Hz, 3 H), 1.60-1.89 (m, 4 H), 2.03-2.22 (m, 2 H), 2.45 (t, J=6.6 Hz, 2 H), 2.89-3.04 (m, 1 H), 3.90 (s, 3 H), 4.06 (s, 3 H), 4.11-4.34 (m, 4 H), 6.42 (d, J=8.3 Hz, 1H), 6.86 (d, J=8.3 Hz, 1 H), 6.93 (s, 1 H), 7.14 (d, J=8.3 Hz, 1 H), 8.77 (d, J=8.3 Hz, 1 H).

MS Calcd.: 488; Found: 489 (M+H).

Reference Example 44

4-[4-Chloro-2-[(2,6-dimethoxypyridin-3-yl)amino]-7-(1-ethylpropyl)-1H-benzimidazol-1-yl]butan-1-ol To a solution of ethyl 4-[4-chloro-2-[(2,6-dimethoxypyridin-3-yl)amino]-7-(1-ethylpropyl)-1H-benzimidazol-1-yl]butanoate (120 mg, 0.245 mmol) in tetrahydrofuran (3 mL) was added lithium borohydride (16 mg, 0.736 mmol) portionwise at 0° C. The mixture was warmed to room temperature and stirred for 36 hr. Water was added and the mixture was extracted with ethyl acetate. Organic layer was washed with brine, dried over anhydrous sodium sulfate and concentrated in vacuo to give a solid, which was recrystallized from ethyl acetate/n-hexane to give the title compound (70 mg, 0.157 mmol, 64%) as a pale blue solid.

mp 116-118° C.

$^1$H NMR (CDCl$_3$) δ 0.86 (t, J=7.3 Hz, 6 H), 1.46-2.08 (m, 8 H), 2.90-3.08 (m, 1 H), 3.74-3.82 (m, 2 H), 3.90 (s, 3 H), 4.05 (s, 3 H), 4.22 (t, J=7.7 Hz, 2 H), 6.43 (d, J=8.3 Hz, 1 H), 6.79 (s, 1 H), 6.86 (d, J=8.3 Hz, 1 H), 7.14 (d, J=8.3 Hz, 1 H), 8.78 (d, J=8.7 Hz, 1 H).

MS Calcd.: 446; Found: 447 (M+H).

Reference Example 45

4-Methyl-5-nitro-2-pyrrolidin-1-ylpyridine

A solution of 2-chloro-4-methyl-5-nitropyridine (3.0 g, 17.3 mmol) in pyrrolidine (50 mL) was stirred at 80° C. for 12 hr. The mixture was concentrated in vacuo to give a residue which was poured into water and extracted with ethyl acetate. Organic layer was washed with brine, dried over anhydrous sodium sulfate and concentrated in vacuo to give the title compound (3.6 g, 17.3 mmol, 100%) as a yellow solid.

$^1$H NMR (CDCl$_3$) δ 2.05 (br, 4 H), 2.60 (s, 3 H), 3.54 (br, 4H), 6.09 (s, 1 H), 9.00 (s, 1 H).

MS Calcd.: 207; Found: 208 (M+H).

Reference Example 46

4-Methyl-6-pyrrolidin-1-ylpyridin-3-amine

A mixture of 4-methyl-5-nitro-2-pyrrolidin-1-ylpyridine (2.08 g, 10.0 mmol) and 10% palladium on carbon (208 mg) in tetrahydrofuran (10 mL) was stirred under hydrogen atmosphere at room temperature for 16 hr. Catalyst was removed by filtration and the filtrate was concentrated in vacuo to give the title compound (1.76 g, 9.89 mmol, 99%), as a purple solid.

$^1$H NMR (CDCl$_3$) δ 1.93-2.01 (m, 4 H), 2.16 (s, 3 H), 3.07 (brs, 2 H), 3.34-3.42 (m, 4 H), 6.17 (s, 1 H), 7.69 (s, 1 H).

MS Calcd.: 177; Found: 178 (M+H).

Reference Example 47

Ethyl 4-{4-chloro-7-(1-ethylpropyl)-2-[(4-methyl-6-pyrrolidin-1-ylpyridin-3-yl)amino]-1H-benzimidazol-1-yl}butanoate A mixture of ethyl 4-[2,4-dichloro-7-(1-ethylpropyl)-1H-benzimidazol-1-yl]butanoate (Reference Example 33; 1.50 g, 4.04 mmol), 4-methyl-6-pyrrolidin-1-ylpyridin-3-amine (1.44 g, 8.09 mmol) and p-toluenesulfonic acid monohydrate (695 mg, 4.04 mmol) in 1-methyl-2-pyrrolidinone (8 mL) was irradiated by microwave at 180° C. for 110 min. After cooling, the mixture was diluted with ethyl acetate, washed with water and brine, dried over anhydrous magnesium sulfate and concentrated in vacuo. The residue was purified by flash chromatography on silica gel eluting with a 20-100% ethyl acetate/n-hexane gradient mixture. The filtrate was concentrated in vacuo to give a solid, which was recrystallized from ethyl acetate/isopropyl ether to give the title compound (745 mg, 1.46 mmol, 36%) as a colorless solid.

mp 195-196° C.

$^1$H NMR (CDCl$_3$) δ 0.85 (t, J=7.3 Hz, 6 H), 1.26 (t, J=7.2 Hz, 3 H), 1.65-1.86 (m, 4 H), 1.94-2.17 (m, 6 H), 2.28 (s, 3 H), 2.40-2.50 (m, 2 H), 2.86-3.01 (m, 1 H), 3.39-3.51 (m, 4 H), 4.10-4.23 (m, 4 H), 6.26 (s, 1 H), 6.80 (d, J=8.3 Hz, 1 H), 6.89 (s, 1 H), 7.08 (d, J=8.3 Hz, 1 H), 8.24 (s, 1 H).

MS Calcd.: 511; Found: 512 (M+H).

Reference Example 48

4-{4-Chloro-7-(1-ethylpropyl)-2-[(4-methyl-6-pyrrolidin-1-ylpyridin-3-yl)amino]-1H-benzimidazol-1-yl}butan-1-ol To a solution of ethyl 4-{4-chloro-7-(1-ethylpropyl)-2-[(4-methyl-6-pyrrolidin-1-ylpyridin-3-yl)amino]-1H-benzimidazol-1-yl}butanoate (650 mg, 1.27 mmol) in tetrahydrofuran (5 mL) was added lithium borohydride (84 mg, 3.82 mmol) portionwise at 0° C. The mixture was warmed to room temperature and stirred for 24 hr. Aqueous ammonium chloride was added and the mixture was stirred for 30 minutes followed by addition of aqueous sodium bicarbonate. The mixture was extracted with ethyl acetate. Organic layer was washed with brine, dried over anhydrous magnesium sulfate and concentrated in vacuo to give a light brown solid, which was recrystallized from ethyl acetate/isopropyl ether to give the title compound (375 mg, 0.798 mmol, 63%) as a colorless solid.

mp 197-199° C.

$^1$H NMR (CDCl$_3$) δ 0.84 (t, J=7.3 Hz, 6 H), 1.47-2.10 (m, 12 H), 2.16 (s, 3 H), 2.80-3.06 (m, 1 H), 3.39 (t, J=6.2 Hz, 4 H), 3.71 (t, J=5.7 Hz, 2 H), 4.21 (t, J=7.5 Hz, 2 H), 6.18 (s, 1 H), 6.78 (d, J=8.3 Hz, 1 H), 7.05 (d, J=8.3 Hz, 1 H), 7.50 (brs, 1 H), 8.03 (s, 1 H).

MS Calcd.: 469; Found: 470 (M+H).

Reference Example 49

2-Methoxy-4-methyl-5-nitropyridine

A solution of 2-chloro-4-methyl-5-nitropyridine (3.0 g, 17.3 mmol) in methanol (20 mL) was added a solution of sodium methoxide (28% in methanol, 10 mL) dropwise at 0° C. The mixture was warmed to room temperature and stirred for 16 hr. The mixture was neutralized by addition of aqueous ammonium chloride and concentrated in vacuo. The residue was dissolved in water and extracted with ethyl acetate. Organic layer was washed with brine, dried over anhydrous magnesium sulfate and concentrated in vacuo to give the title compound (2.84 g, 16.8 mmol, 98%) as a yellow solid.

$^1$H NMR (CDCl$_3$) δ 2.62 (s, 3 H), 4.01 (s, 3 H), 6.64 (s, 1 H), 8.94 (s, 1 H).

MS Calcd.: 168; Found: 169 (M+H).

Reference Example 50

6-Methoxy-4-methylpyridin-3-amine

A mixture of 2-methoxy-4-methyl-5-nitropyridine 4-Methyl-5-nitro-2-pyrrolidin-1-ylpyridine (1.68 g, 10.0 mmol) and 10% palladium on carbon (168 mg) in tetrahydrofuran (10 mL) was stirred under hydrogen atmosphere at room temperature for 6 hr. Catalyst was removed by filtration and the filtrate was concentrated in vacuo to give the title compound (1.31 g, 9.49 mmol, 95%) as a pale brown solid.

$^1$H NMR (CDCl$_3$) δ 2.16 (s, 3 H), 3.28 (brs, 2 H), 3.85 (s, 3 H), 6.50 (s, 1 H), 7.59 (s, 1 H).

MS Calcd.: 138; Found: 139 (M+H).

Reference Example 51

Ethyl 4-{4-chloro-7-(1-ethylpropyl)-2-[(6-methoxy-4-methylpyridin-3-yl)amino]-1H-benzimidazol-1-yl}butanoate A mixture of ethyl 4-[2,4-dichloro-7-(1-ethylpropyl)-1H-benzimidazol-1-yl]butanoate (Reference Example 33; 1.50 g, 4.04 mmol), 6-methoxy-4-methylpyridin-3-amine (1.10 g, 8.09 mmol) and p-toluenesulfonic acid monohydrate (487 mg, 2.83 mmol) in 1-methyl-2-pyrrolidinone (8 mL) was irradiated by microwave at 180° C. for 10 min. After cooling, the mixture was diluted with ethyl acetate, washed with aqueous sodium bicarbonate, water and brine, dried over anhydrous magnesium sulfate and concentrated in vacuo. The residue was purified by flash chromatography on silica gel eluting with a 20-50% ethyl acetate/n-hexane gradient mixture. The filtrate was concentrated in vacuo to give an amorphous which was recrystallized from ethyl acetate/n-hexane to give the title compound (190 mg, 0.402 mmol, 10%) as a colorless solid.

mp 140-142° C.

$^1$H NMR (CDCl$_3$) δ 0.86 (t, J=7.3 Hz, 6 H), 1.27 (t, J=7.2 Hz, 3 H), 1.65-1.89 (m, 4 H), 2.02-2.23 (m, 2 H), 2.32 (s, 3 H), 2.41-2.56 (m, 2 H), 2.87-3.02 (m, 1 H), 3.92 (s, 3 H), 4.10-4.29 (m, 4 H), 6.63 (s, 1 H), 6.83 (d, J=8.3 Hz, 1 H), 7.11 (d, J=8.7 Hz, 1 H), 7.13 (s, 1 H), 8.43 (s, 1 H).

MS Calcd.: 472; Found: 473 (M+H).

Reference Example 52

4-{4-Chloro-7-(1-ethylpropyl)-2-[(6-methoxy-4-methylpyridin-3-yl)amino]-1H-benzimidazol-1-yl}butan-1-ol To a solution of ethyl 4-{4-chloro-7-(1-ethylpropyl)-2-[(6-methoxy-4-methylpyridin-3-yl)amino]-1H-benzimidazol-1-yl}butanoate (170 mg, 0.359 mmol) in tetrahydrofuran (3 mL) was added lithium borohydride (24 mg, 1.08 mmol) portionwise at 0° C. The mixture was warmed, to room temperature and stirred for 12 hr. Water was added and the mixture was extracted with ethyl acetate. Organic layer was washed with brine, dried over magnesium sulfate and concentrated in vacuo. The residue was purified by flash chromatography on silica gel eluting with a 50-80% ethyl acetate/n-hexane gradient mixture. The filtrate was concentrated in vacuo to give a solid, which was recrystallized from ethyl acetate/n-hexane to give the title compound (109 mg, 0.252 mmol, 70%) as a colorless solid.

mp 146-147° C.

$^1$H NMR (CDCl$_3$) δ 0.87 (t, J=7.4 Hz, 6 H), 1.58-2.02 (m, 8 H), 2.13 (brs, 1 H), 2.26 (s, 3 H), 2.91-3.03 (m, 1 H), 3.79 (t, J=5.9 Hz, 2 H), 3.90 (s, 3 H), 4.23 (t, J=7.3 Hz, 2 H), 6.62 (s, 1 H), 6.78 (brs, 1 H), 6.85 (d, J=8.5 Hz, 1 H), 7.11 (d, J=7.7 Hz, 1 H), 8.21 (brs, 1 H).

MS Calcd.: 430; Found: 431 (M+H).

Reference Example 53

Ethyl 4-[2-[(2-bromo-4-methylphenyl)amino]-4-chloro-7-(1-ethylpropyl)-1H-benzimidazol-1-yl]butanoate A mixture of ethyl 4-[2,4-dichloro-7-(1-ethylpropyl)-1H-benzimidazol-1-yl]butanoate (Reference Example 33; 1.50 g, 4.04 mmol), 2-bromo-4-methylaniline (1.0 mL, 8.08 mmol), p-toluenesulfonic acid monohydrate (822.2 mg, 4.32 mmol) and xylene (5.0 mL) was stirred at 130° C. for 12 hr. After cooling, the reaction mixture was neutralized with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified by silica gel column chromatography eluting with a 0-30% ethyl acetate/n-hexane gradient mixture to give the title compound as an oil (1.42 g, 2.73 mmol, 68%).

$^1$H NMR (CDCl$_3$) δ: 0.87 (t, J=7.5 Hz, 6H), 1.23 (t, J=7.2 Hz, 3H), 1.66-1.85 (m, 4H), 2.11-2.18 (m, 2H), 2.31 (s, 3H), 2.43 (t, J=6.6 Hz, 2H), 3.00-3.04 (m, 1H), 4.12 (q, J=7.2 Hz, 2H), 4.26 (t, J=7.8 Hz, 2H), 6.91 (d, J=8.4 Hz, 2H), 7.14-7.19 (m, 2H), 7.36 (s, 1H), 8.18 (d, J=8.4 Hz, 1H).

MS Calcd.: 519, MS Found: 520 (M+H).

Reference Example 54

4-[2-[(2-Bromo-4-methylphenyl)amino]-4-chloro-7-(1-ethylpropyl)-1H-benzimidazol-1-yl]butan-1-ol To a solution of ethyl 4-[2-[(2-bromo-4-methylphenyl)amino]-4-chloro-7-(1-ethylpropyl)-1H-benzimidazol-1-yl]butanoate (1.42 g, 2.74 mmol) in tetrahydrofuran (15.0 mL) was added lithium borohydride (178.7 mg, 8.20 mmol) at 0° C. The reaction mixture was stirred at room temperature for 24 hr. The reaction mixture was quenched with water at 0° C. and extracted with ethyl acetate (×3). The combined organic layer was washed with brine (×1), dried over anhydrous magnesium sulfate, filtered and concentrated in vacuo. The resulting solid was suspended n-hexane and stirred at 70° C. for 30 min. After cooling, the solid was collected by filtration to give the title compound as a colorless powder (1.03 g, 2.16 mmol, 79%).

mp 115-118° C.

$^1$H NMR (CDCl$_3$) δ: 0.87 (t, J=7.5 Hz, 6H), 1.37 (brs, 1H), 1.65-1.87 (m, 6H), 1.91-2.01 (m, 2H), 2.31 (s, 3H), 2.95-3.05 (m, 1H), 3.70-3.75 (m, 2H), 4.24 (t, J=8.4 Hz, 2H), 6.90 (d, J=8.1 Hz, 2H), 7.17 (d, J=8.1 Hz, 2H), 7.36 (s, 1H), 8.26 (d, J=8.1 Hz, 1H).

MS Calcd.: 477, MS Found: 478 (M+H).

Reference Example 55

Ethyl 4-[2-chloro-7-(1-ethylpropyl)-1H-benzimidazol-1-yl]butanoate

The mixture of ethyl 4-[7-(1-ethylpropyl)-2-oxo-2,3-dihydro-1H-benzimidazol-1-yl]butanoate (Reference Example 31; 1.94 g, 6.09 mmol) and phosphorus oxychloride (4.33 mL) was stirred at 100° C. for 2.5 hr. After cooling, the mixture was poured into ice water and neutralized with sodium hydrogen carbonate. The precipitate was removed by filtration and the filtrate was extracted with ethyl acetate (×3). The combined organic layer was washed with brine, dried over anhydrous magnesium sulfate, filtered and concentrated in vacuo. The residue was purified by silica gel column chromatography eluting with a 0-15% ethyl acetate/n-hexane gradient mixture to give the title compound as a colorless oil (942.6 mg, 2.80 mmol, 46%).

$^1$H NMR (CDCl$_3$) δ: 0.86 (t, J=7.5 Hz, 6H), 1.24-1.29 (m, 3H), 1.63-1.89 (m, 4H), 2.08-2.18 (m, 2H), 2.44 (t, J=7.2 Hz, 2H), 3.04-3.14 (m, 1H), 4.16 (q, J=7.2 Hz, 2H), 4.40-4.45 (m, 2H), 7.13 (d, J=7.8 Hz, 1H), 7.22 (d, J=7.8 Hz, 1H), 7.52 (d, J=7.8 Hz, 1H).

MS Calcd.: 336, MS Found: 337 (M+H).

Reference Example 56

Ethyl 4-[2-[(2,4-dimethoxyphenyl)amino]-7-(1-ethylpropyl)-1H-benzimidazol-1-yl]butanoate A mixture of ethyl 4-[2-chloro-7-(1-ethylpropyl)-1H-benzimidazol-1-yl]butanoate (475.2 mg, 1.41 mmol), 2,4-dimethoxyaniline (0.60 mL, 4.23 mmol) and 1-methyl-2-pyrrolidone (0.5 mL) was stirred at 110° C. for 14 hr. After cooling, the reaction mixture was neutralized with aqueous saturated sodium hydrogen carbonate and extracted with ethyl acetate (×3). The combined organic, layer was washed with brine, dried over anhydrous magnesium sulfate, filtered and concentrated in vacuo. The residue was purified by silica gel column chromatography eluting with a 0-30% ethyl acetate/n-hexane gradient mixture to give the title compound as a brown solid (570.0 mg, 1.26 mmol, 89%).

$^1$H NMR (CDCl$_3$) δ: 0.87 (t, J=7.5 Hz, 6H), 1.27 (t, J=7.2 Hz, 3H), 1.67-1.86 (m, 4H), 1.97-2.07 (m, 1H), 2.11-2.18 (m, 1H), 2.37 (t, J=7.8 Hz, 1H), 2.45 (t, J=6.9 Hz, 1H), 2.96-3.02 (m, 1H), 3.38 (t, J=6.9 Hz, 1H), 3.81 (s, 3H), 3.91 (s, 3H), 4.14 (q, J=7.2 Hz, 2H), 4.25 (t, J=7.8 Hz, 1H), 6.52-6.58 (m, 2H), 6.83 (brs, 1H), 6.94 (d, J=7.5 Hz, 1H), 7.11 (t, J=7.8 Hz, 1H), 7.40 (d, J=7.8 Hz, 1H), 8.15 (d, J=8.4 Hz, 1H).

MS Calcd.: 453, MS Found: 454 (M+H).

Reference Example 57

4-[2-{[2-Bromo-4-(trifluoromethyl)phenyl]amino}-4-chloro-7-(1-ethylpropyl)-1H-benzimidazol-1-yl]butan-1-ol A mixture of ethyl 4-[2,4-dichloro-7-(1-ethylpropyl)-1H-benzimidazol-1-yl]butanoate (Reference Example 33; 2.24 g, 6.63 mmol), 2-bromo-4-trifluoromethylaniline (3.18 g, 13.25 mmol), p-toluenesulfonic acid monohydrate (1.35 g, 7.09 mmol) and xylene (5.0 mL) was stirred at 130° C. for 15 hr. After cooling, the reaction mixture was neutralized with aqueous saturated sodium hydrogen carbonate and extracted with ethyl acetate (×3). The combined organic layer was washed with brine, dried over anhydrous magnesium sulfate, filtered and concentrated in vacuo. The residue was purified by silica gel column chromatography eluting with a 0-15% ethyl acetate/n-hexane gradient mixture to give crude ethyl 4-[2-{[2-bromo-4-(trifluoromethyl)phenyl]amino}-4-chloro-7-(1-ethylpropyl)-1H-benzimidazol-1-yl]butanoate.

The crude material (MS Calcd.: 573; Found: 574 (M+H)) was subjected for the next step without further purification. To a solution of the crude material in tetrahydrofuran (15.0 mL) was added lithium borohydride (193.0 mg, 8.86 mmol) at 0° C. The reaction mixture was stirred at room temperature for 2 hr and warmed to 60° C. and stirred for 19 hr. The reaction mixture was quenched with water at 0° C. and extracted with ethyl acetate (×3). The combined organic layer was washed with brine (×1), dried over magnesium sulfate, filtered and concentrated in vacuo. The residue was purified by silica gel column chromatography eluting with a 0-20% ethyl acetate/n-hexane gradient mixture to give a mixture contained the title compound. The residue was purified by preparative HPLC to give the title compound as the trifluoroacetic acid salt. The salt was washed with aqueous sodium hydrogen carbonate and extracted with ethyl acetate. The extract was washed with brine, dried over anhydrous magnesium sulfate, filtered and concentrated in vacuo to give the title compound as a colorless powder (110.4 mg, 0.207 mmol, 3.1% (2 steps)).

$^1$H NMR (CDCl$_3$) δ: 0.87 (t, J=7.5 Hz, 6H), 1.70-1.87 (m, 6H), 1.94-2.04 (m, 2H), 2.99-3.04 (m, 1H), 3.75 (t, J=6.3 Hz, 2H), 4.30 (t, J=7.8 Hz, 2H), 6.96 (d, J=8.1 Hz, 1H), 7.21 (d, J=7.5 Hz, 1H), 7.63 (d, J=7.5 Hz, 1H), 7.81 (s, 1H), 8.60 (brs, 1H).

MS Calcd.: 531, MS Found: 532 (M+H).

Reference Example 58

Ethyl 4-[2-{[2-bromo-4-(trifluoromethoxy)phenyl]amino}-4-chloro-7-(1-ethylpropyl)-1H-benzimidazol-1-yl]butanoate A mixture of ethyl 4-[2,4-dichloro-7-(1-ethylpropyl)-1H-benzimidazol-1-yl]butanoate (Reference Example 33; 3.00 g, 8.08 mmol), 2-bromo-4-(trifluoromethoxy)aniline (2.44 mL, 16.16 mmol), p-toluenesulfonic acid monohydrate (1.64 g, 8.65 mmol) and xylene (7.0 mL) was stirred at 130° C. for 12 hr. After cooling, the reaction mixture was neutralized with aqueous saturated sodium hydrogen carbonate and extracted with ethyl acetate (×3). The combined organic layer was washed with brine, dried over anhydrous magnesium sulfate, filtered and concentrated in vacuo. The residue was purified by silica gel column chromatography eluting with a 0-15% ethyl acetate/n-hexane gradient mixture to give the title compound as a pale red oil (1.38 g, 2.34 mmol, 29%).

$^1$H NMR (CDCl$_3$) δ: 0.87 (t, J=7.5 Hz, 6H), 1.23 (t, J=7.2 Hz, 3H), 1.66-1.86 (m, 4H), 2.10-2.18 (m, 2H), 2.46 (t, J=6.3 Hz, 2H), 3.00-3.04 (m, 1H), 4.13 (q, J=7.2 Hz, 2H), 4.30 (t, J=8.1 Hz, 2H), 6.93 (d, J=8.1 Hz, 1H), 7.06 (s, 1H), 7.14-7.31 (m, 1H), 7.45 (s, 1H), 7.61-7.70 (m, 1H), 8.47-8.50 (m, 1H).

MS Calcd.: 589, MS Found: 590 (M+H).

Reference Example 59

4-[2-{[2-Bromo-4-(trifluoromethoxy)phenyl]amino}-4-chloro-7-(1-ethylpropyl)-1H-benzimidazol-1-yl]butan-1-ol To a solution of ethyl 4-[2-{[2-bromo-4-(trifluoromethoxy)phenyl]amino}-4-chloro-7-(1-ethylpropyl)-1H-benzimidazol-1-yl]butanoate (1.37 g, 2.32 mmol) in tetrahydrofuran (15.0 mL) was added lithium borohydride (151.5 mg, 6.96 mmol) at 0° C. The reaction mixture was stirred at room temperature for 12 hr. The reaction mixture was warmed to 60° C. and stirred for 24 hr. After cooling, the reaction mixture was quenched with water at 0° C. and extracted with ethyl acetate (×3). The combined organic layer was washed with brine, dried over anhydrous magnesium sulfate, filtered and concentrated in vacuo. The residue was purified by silica gel column chromatography eluting with a 0-20% ethyl acetate/n-hexane gradient mixture to give the title compound as a colorless powder (558.0 mg, 1.02 mmol, 44%).

$^1$H NMR (CDCl$_3$) δ: 0.87 (t, J=7.5 Hz, 6H), 1.40 (brs, 1H), 1.66-1.86 (m, 6H), 1.94-2.04 (m, 2H), 2.99-3.03 (m, 1H), 3.75-3.76 (m, 2H), 4.26-4.31 (m, 2H), 6.91 (d, J=8.1 Hz, 1H), 7.02 (s, 1H), 7.19 (d, J=8.1 Hz, 1H), 7.25-7.29 (m, 1H), 7.45 (s, 1H), 8.58 (d, J=9.0 Hz, 1H).

MS Calcd.: 547, MS Found: 548 (M+H).

Reference Example 60

Ethyl 4-[2-[(4-bromo-2-methylphenyl)amino]-4-chloro-7-(1-ethylpropyl)-1H-benzimidazol-1-yl]butanoate A mixture of ethyl 4-[2,4-dichloro-7-(1-ethylpropyl)-1H-benzimidazol-1-yl]butanoate (Reference Example 33; 2.00 g, 5.39 mmol), 4-bromo-2-methylaniline (3.01 g, 16.2 mmol), p-toluenesulfonic acid monohydrate (1.10 g, 5.78 mmol) and xylene (15 mL) was stirred at 150° C. for 20 hr. The mixture was neutralized with aqueous sodium hydrogen carbonate and extracted with ethyl acetate. The combined organic layer was washed with brine, dried over anhydrous magnesium sulfate, filtered and concentrated, in vacuo. The residue was purified by flash column chromatography on silica gel eluting with a 0-15% ethyl acetate/n-hexane gradient mixture. The filtrate was concentrated in vacuo to give the solid, which was recrystallized from ethyl acetate/n-hexane to give the title compound as a colorless crystal (2.11 g, 4.05 mmol, 75%).

mp 114-116° C.

$^1$H NMR (CDCl$_3$) δ 0.86 (t, J=7.2 Hz, 6H), 1.25 (t, J=6.9 Hz, 3H), 1.68-1.83 (m, 4H), 2.00-2.13 (m, 2H), 2.37 (s, 3H), 2.42 (t, J=6.3 Hz, 2H), 2.89-2.99 (m, 1H), 4.14 (q, J=6.9 Hz, 2H), 4.20 (t, J=6.3 Hz, 2H), 6.83 (s, 1H), 6.88 (d, J=8.7 Hz, 1H), 7.15 (d, J=8.7 Hz, 1H), 7.28-7.34 (m, 2H), 7.72 (d, J=9.0 Hz, 1H).

MS Calcd.: 519; MS Found: 520 (M+H).

Reference Example 61

4-[2-[(4-Bromo-2-methylphenyl)amino]-4-chloro-7-(1-ethylpropyl)-1H-benzimidazol-1-yl]butan-1-ol To a solution of ethyl 4-[2-[(4-bromo-2-methylphenyl)amino]-4-chloro-7-(1-ethylpropyl)-1H-benzimidazol-1-yl]butanoate (2.07 g, 3.97 mmol) in tetrahydrofuran (40 mL) was added lithium tetrahydroborate (260 mg, 11.9 mmol) at 0° C. The mixture was stirred at room temperature for 19 hr, and the reaction was quenched by methanol. The mixture was concentrated in vacuo, neutralized with aqueous saturated ammonium chloride, and extracted with ethyl acetate. The combined organic layer was washed with brine, dried over anhydrous magnesium sulfate, filtered, and concentrated in vacuo. The residue was recrystallized from ethyl acetate to give the title compound as a colorless crystal (1.10 g, 2.30 mmol, 58%).

mp 151-152° C.

$^1$H NMR (CDCl$_3$) δ 0.87 (t, J=7.2 Hz, 6H), 1.46-1.88 (m, 9H), 2.31 (s, 3H), 2.94-3.03 (m, 1H), 3.67-3.72 (m, 2H), 4.16 (t, J=7.5 Hz, 2H), 6.33 (s, 1H), 6.91 (d, J=8.1 Hz, 1H), 7.17 (d, J=8.1 Hz, 1H), 7.25-7.32 (m, 2H), 7.44-7.52 (m, 1H).

MS Calcd.: 477; MS Found: 478 (M+H).

Reference Example 62

4-[2-{[4-Bromo-2-(trifluoromethoxy)phenyl]amino}-4-chloro-7-(1-ethylpropyl)-1H-benzimidazol-1-yl]butan-1-ol A mixture of ethyl 4-[2,4-dichloro-7-(1-ethylpropyl)-1H-benzimidazol-1-yl]butanoate (Reference Example 33; 2.90 g, 7.81 mmol), 4-methyl-2-trifluoromethoxyaniline (3.01 g, 16.2 mmol), p-toluenesulfonic acid monohydrate (1.49 g, 7.83 mmol) and xylene (20 mL) was stirred at 150° C. for 4 hr. The mixture was neutralized with aqueous sodium hydrogen carbonate and extracted with ethyl acetate. The combined organic layer was washed with brine, dried over anhydrous magnesium sulfate, filtered and concentrated in vacuo. The residue was purified by flash column chromatography on silica gel eluting with a 0-15% ethyl acetate/n-hexane gradient mixture. The filtrate was concentrated in vacuo to give the solid, which was recrystallized from ethyl acetate/n-hexane to give a mixture (4.31 g) of ethyl 4-[2-{[4-bromo-2-(trifluoromethoxy)phenyl]amino}-4-chloro-7-(1-ethylpropyl)-1H-benzimidazol-1-yl]butanoate (MS Calcd.: 589; MS Found: 590 (M+H)) and 4-methyl-2-trifluoromethoxyaniline.

To a solution of the crude product (4.31 g) in tetrahydrofuran, (100 ml) was added lithium tetrahydroborate (790 mg, 36.5 mmol) at 0° C. The mixture was stirred at room temperature for 4 days, and the reaction was quenched by methanol. The mixture was neutralized with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 5-30% ethyl acetate/n-hexane gradient mixture. The filtrate was concentrated in vacuo to give the solid, which was washed with n-hexane to give the title compound as a colorless crystal (1.63 g, 2.97 mmol, 38%).

$^1$H NMR (CDCl$_3$) δ 0.87 (t, J=7.5 Hz, 6H), 1.65-1.81 (m, 7H), 1.97 (t, J=4.8 Hz, 2H), 2.94-3.03 (m, 1H), 3.75-3.82 (m, 2H), 4.28 (t, J=4.8 Hz, 2H), 6.92 (d, J=8.1 Hz, 1H), 7.11 (s, 1H), 7.18 (d, J=8.1 Hz, 1H), 7.40 (d, J=1.2 Hz, 1H), 7.46 (d, J=1.2 Hz, 9.0 Hz, 1H), 8.54 (d, J=9.0 Hz, 1H)

MS Calcd.: 547; MS Found: 548 (M+H).

Reference Example 63

Ethyl 4-[4-chloro-2-[(2,2-difluoro-1,3-benzodioxol-4-yl)amino]-7-(1-ethylpropyl)-1H-benzimidazol-1-yl]butanoate A mixture of ethyl 4-[2,4-dichloro-7-(1-ethylpropyl)-1H-benzimidazol-1-yl]butanoate (Reference Example 33; 815 mg, 2.19 mmol), 4-amino-2,2-difluoro-1,3-benzodioxole (950 mg, 5.49 mmol), p-toluenesulfonic acid monohydrate (416 mg, 2.19 mmol) and xylene (3.0 mL) was stirred at 150° C. for 2 hr. The mixture was neutralized with aqueous sodium hydrogen carbonate and extracted with ethyl acetate. The combined organic layer was washed with brine, dried over anhydrous magnesium sulfate, filtered and concentrated in vacuo. The residue was purified by flash column chromatography on silica gel eluting with a 0-20% ethyl acetate/n-hexane gradient mixture. The filtrate was concentrated in vacuo to give the solid, which was washed with n-hexane to give the title compound as a colorless powder (900 mg, 1.77 mmol, 81%).

$^1$H NMR (CDCl$_3$) δ 0.86 (t, J=7.2 Hz, 6H), 1.29 (t, J=7.2 Hz, 3H), 1.65-1.85 (m, 4H), 2.08-2.18 (m, 2H), 2.48 (t, J=6.0 Hz, 2H), 2.93-3.02 (m, 1H), 4.21-4.31 (m, 4H), 6.75 (d, J=7.8 Hz, 1H), 6.82 (d, J=7.8 Hz, 1H), 7.00-7.22 (m, 2H), 7.81 (s, 1H), 8.12 (s, 1H).

MS Calcd.: 507; MS Found: 508 (M+H).

Reference Example 64

4-[4-Chloro-2-[(2,2-difluoro-1,3-benzodioxol-4-yl)amino]-7-(1-ethylpropyl)-1H-benzimidazol-1-yl]butan-1-ol To a solution of ethyl 4-[4-chloro-2-[(2,2-difluoro-1,3-benzodioxol-4-yl)amino]-7-(1-ethylpropyl)-1H-benzimidazol-1-yl]butanoate (900 mg, 1.77 mmol) in tetrahydrofuran (8.0 mL) was added lithium tetrahydroborate (193 mg, 8.86 mmol) at 0° C. The mixture was stirred at room temperature for 19 hr, and the reaction was quenched by methanol. The mixture was neutralized with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 15-50% ethyl acetate/n-hexane gradient mixture. The filtrate was concentrated in vacuo to give the solid, which was washed with n-hexane to give the title compound as a colorless powder (630 mg, 1.35 mmol, 76%).

$^1$H NMR (CDCl$_3$) δ 0.87 (t, J=7.5 Hz, 6H), 1.65-1.87 (m, 7H), 2.02 (t, J=6.0 Hz, 2H), 2.94-3.03 (m, 1H), 3.91 (s, 2H), 4.40 (t, J=6.0 Hz, 2H), 6.73 (d, J=7.8 Hz, 1H), 6.90 (d, J=7.8 Hz, 1H), 7.02-7.12 (m, 2H), 7.88 (s, 1H), 8.21 (s, 1H).

MS Calcd.: 465; MS Found: 466 (M+H).

Reference Example 65

Ethyl 4-{4-chloro-7-(1-ethylpropyl)-2-[(2-methoxypyridin-3-yl)amino]-1H-benzimidazol-1-yl}butanoate Reference Example 66

Ethyl 4-{4-chloro-7-(1-ethylpropyl)-2-[(2-hydroxypyridin-3-yl)amino]-1H-benzimidazol-1-yl}butanoate A mixture of ethyl 4-[2,4-dichloro-7-(1-ethylpropyl)-1H-benzimidazol-1-yl]butanoate (Reference Example 33; 1.50 g, 4.04 mmol), 2-methoxypyridin-3-amine (1.50 g, 12.1 mmol), p-toluenesulfonic acid (822 mg, 4.32 mmol) and xylene (5.0 mL) was irradiated by microwave at 125° C. for 2 hr. After cooling, the reaction mixture, was extracted with ethyl acetate (×3). The organics were dried over anhydrous magnesium sulfate, filtered, and concentrated in vacuo. The residue was purified by silica gel column chromatography eluting with a 10-50% ethyl acetate/n-hexane gradient mixture to give reference example 65 (350 mg, 0.763 mmol, 18.9%) as a brown amorphous and reference example 66 (75 mg, 0.169 mmol, 4.2%) as a brown amorphous.

Reference Example 65

$^1$H-NMR (CDCl$_3$, 300 MHz) δ: 0.86 (6H, t, J=7.2 Hz), 1.26 (3H, t, J=7.2 Hz), 1.64-1.85 (4H, m), 2.10-2.17 (2H, m), 2.45 (2H, t, J=6.3 Hz), 2.92-3.03 (1H, m), 4.10 (3H, s), 4.17 (2H, q, J=7.2 Hz), 4.28 (2H, t, J=6.3 Hz), 6.90 (1H, d, J=8.4 Hz), 6.99 (1H, dd, J=5.4, 7.8 Hz), 7.16 (1H, d, J=8.4 Hz), 7.78 (1H, dd, J=1.8, 5.4 Hz), 8.86 (1H, dd, J=1.8, 7.8 Hz).

MS Calcd.: 458, MS Found: 459 (M+H).

Reference Example 66

$^1$H-NMR (DMSO-d$_6$, 300 MHz) δ: 0.80 (6H, t, J=7.2 Hz), 1.13 (3H, t, J=7.2 Hz), 1.60-1.80 (4H, m), 1.94-1.99 (2H, m), 2.42 (2H, t, J=6.3 Hz), 3.05-3.15 (1H, m), 4.01 (2H, q, J=7.2 Hz), 4.29 (2H, t, J=6.3 Hz), 6.35 (1H, t, J=7.2 Hz), 6.93 (1H, d, J=8.4 Hz), 6.04 (1H, dd, J=1.8, 7.2 Hz), 7.14 (1H, d, J=8.4 Hz), 8.17 (1H, brs), 8.41 (1H, dd, J=1.8, 7.2 Hz), 12.0 (1H, brs).

MS Calcd.: 444, MS Found: 445 (M+H).

Reference Example 67

4-{4-Chloro-7-(1-ethylpropyl)-2-[(2-methoxypyridin-3-yl)amino]-1H-benzimidazol-1-yl}butan-1-ol To a suspension of lithium borohydride (45.6 mg, 2.09 mmol) in tetrahydrofuran (5 mL) was added ethyl 4-{4-chloro-7-(1-ethylpropyl)-2-[(2-methoxypyridin-3-yl)amino]-1H-benzimidazol-1-yl}butanoate (320 mg, 0.697 mmol) at 0° C. The mixture was stirred at room temperature for 6 hr. The reaction mixture was quenched with water and extracted with ethyl acetate (×3). The organics were dried over anhydrous magnesium sulfate, filtered, and concentrated in vacuo. The residue was purified by silica gel column chromatography eluting with 10-50% ethyl acetate/n-hexane gradient mixture to give the title compound (250 mg, 0.60 mmol, 86%) as a white amorphous.

$^1$H-NMR (CDCl$_3$, 300 MHz) δ: 0.86 (6H, t, J=7.2 Hz), 1.65-1.87 (8H, m), 1.92-2.02 (2H, m), 2.95-3.03 (1H, m), 3.78 (1H, brs), 4.08 (3H, s), 4.26 (2H, t, J=7.5 Hz), 6.90 (1H, d, J=8.4 Hz), 6.99 (1H, dd, J=5.1, 7.8 Hz), 7.11 (1H, brs), 7.16 (1H, d, J=8.4 Hz), 7.78 (1H, dd, J=1.8, 5.1 Hz), 8.84 (1H, dd, J=1.8, 7.8 Hz).

MS Calcd.: 416, MS Found: 417 (M+H).

Reference Example 68

Ethyl 4-[4-chloro-2-[(4-chloro-2-methoxy-6-methylphenyl)amino]-7-(1-ethylpropyl)-1H-benzimidazol-1-yl]butanoate A mixture of ethyl 4-[2,4-dichloro-7-(1-ethylpropyl)-1H-benzimidazol-1-yl]butanoate (Reference Example 33; 470 mg, 1.27 mmol), 4-chloro-2-methoxy-6-methylaniline (650 mg, 3.81 mmol) and p-toluenesulfonic acid (241 mg, 1.27 mmol) and xylene (5.0 mL) was irradiated by microwave at 150° C. for 4 hr. After cooling, the reaction mixture was extracted with ethyl acetate (×3). The organics were dried over anhydrous magnesium sulfate, filtered, and concentrated in vacuo. The residue was purified by silica gel column chromatography eluting with a 10-50% ethyl acetate/n-hexane gradient mixture to give the title compound (120 mg, 0.289 mmol, 18.7%) as a brown amorphous $^1$H-NMR (CDCl$_3$, 300 MHz) δ: 0.87 (6H, t, J=7.2 Hz), 1.25 (3H, t, J=7.2 Hz), 1.62-1.86 (4H, m), 2.10-2.19 (2H, m), 2.24 (3H, s), 2.49 (2H, t, J=6.3 Hz), 2.93-3.02 (1H, m), 3.78 (3H, s), 4.14 (2H, q, J=7.2. Hz), 4.25 (2H, t, J=6.3 Hz), 6.63 (1H, brs), 6.77 (1H, d, J=2.4 Hz), 6.82 (1H, d, J=8.4 Hz), 6.88 (1H, d, J=2.4 Hz), 7.07 (1H, d, J=8.4 Hz), MS Calcd.: 505; Found: 506 (M+H)

Reference Example 69

2-{4-Chloro-2-[(4-chloro-2-methoxy-6-methylphenyl)amino]-7-(1-ethylpropyl)-1H-benzimidazol-1-yl}butan-1-ol To a solution of ethyl {4-chloro-2-[(4-chloro-2-methoxy-6-methylphenyl)amino]-7-(1-ethylpropyl)-1H-benzimidazol-1-yl}butanoate (100 mg, 0.197 mmol) in tetrahydrofuran (1.5 mL) was added lithium tetrahydroborate (13 mg, 0.597 mmol), and the mixture was stirred at room temperature for 84 hr. An additional lithium tetrahydroborate (26 mg, 1.19 mmol) was added, followed by stirring at 50° C. for 24 hr. The mixture was diluted with water and extracted with ethyl acetate. The extracts were washed with brine, dried over anhydrous magnesium sulfate and concentrated in vacuo. The residue was purified by silica gel column chromatography eluting with a 20-50% ethyl acetate/n-hexane gradient mixture to give the title compound (61 mg, 0.132 mmol, 20%) as a colorless solid.

$^1$H NMR (CDCl$_3$) δ: 0.87 (6H, t, J=7.5 Hz), 1.60-1.85 (7H, m), 1.85-2.00 (2H, m), 2.19 (3H, s), 2.90-3.00 (1H, m), 3.70-3.75 (2H, m), 3.78 (3H, s), 4.23 (2H, t, J=7.5 Hz), 6.30-6.50 (1H, m), 6.75 (1H, s), 6.82 (1H, d, J=8.1 Hz), 6.87 (1H, s), 7.05 (1H, d, J=8.1 Hz).

MS Calcd.: 463; Found: 464 (M+H).

Reference Example 70

Ethyl 4-[2-azido-4-chloro-7-(1-ethylpropyl)-1H-benzimidazol-1-yl]butanoate

A mixture of ethyl 4-[2,4-dichloro-7-(1-ethylpropyl)-1H-benzimidazol-1-yl]butanoate (Reference Example 33; 7.40 g, 20.0 mmol) and sodium azide (2.60 g, 40.0 mmol) in 1-methyl-2-pyrrolidinone (20 mL) was stirred at 110° C. for 12 hr. After cooling, water was added to the mixture, which was extracted with ethyl acetate. Organic layer was washed with water and brine, dried over anhydrous sodium sulfate and concentrated in vacuo. The residue was purified by flash chromatography on silica gel eluting with a 10-30% ethyl acetate/n-hexane gradient mixture. The filtrate was concentrated in vacuo to give the title compound (4.90 g, 12.9 mmol, 64%) as a pale yellow solid.

$^1$H NMR (CDCl$_3$) δ 0.84 (t, J=7.4 Hz, 6 H), 1.26 (t, J=7.2 Hz, 3 H), 1.58-1.88 (m, 4 H), 1.99-2.13 (m, 2 H), 2.38 (d, J=7.0 Hz, 2 H), 2.95-3.06 (m, 1 H), 4.10-4.24 (m, 4 H), 6.97 (d, J=8.3 Hz, 1 H), 7.23 (d, J=8.3 Hz, 1 H).

MS Calcd.: 377; Found: 378 (M+H).

Reference Example 71

4-[2-Amino-4-chloro-7-(1-ethylpropyl)-1H-benzimidazol-1-yl]butan-1-ol

To a solution of ethyl 4-[2-azido-4-chloro-7-(1-ethylpropyl)-1H-benzimidazol-1-yl]butanoate (190 mg, 0.500 mmol) in tetrahydrofuran (3.0 mL) was added lithium aluminum hydride (57 mg, 1.5 mmol) portionwise at 0° C. After stirring for 1 hr, sodium sulfate decahydrate (300 mg) was added to the mixture, which was stirred for 1 hr. Insoluble materials were filtered off and the filtrate was concentrated in vacuo to give the title compound (135 mg, 0.435 mmol, 87%) as a colorless solid.

$^1$H NMR (CDCl$_3$) δ 0.83 (t, J=7.3 Hz, 6 H), 1.57-2.06 (m, 8 H), 2.86-3.01 (m, 1 H), 3.83 (t, J=5.8 Hz, 2 H), 4.12-4.20 (m, 2 H), 5.59 (brs, 2 H), 6.80 (d, J=8.3 Hz, 1 H), 7.09 (d, J=8.3 Hz, 1 H).

MS Calcd.: 309; Found: 310 (M+H).

Reference Example 72

10-Chloro-7-(1-ethylpropyl)-2,3,4,5-tetrahydro-1H-[1,3]diazepino[1,2-a]benzimidazole To a solution of 4-[2-amino-4-chloro-7-(1-ethylpropyl)-1H-benzimidazol-1-yl]butan-1-ol (3.40 g, 10.8 mmol) in pyridine (50 mL) was added methanesulfonyl chloride (2.60 mL, 32.9 mmol) dropwise at 0° C. After stirring for 1 hr, aqueous sodium bicarbonate was added to the mixture, which was extracted with ethyl acetate. Organic layer was washed with 2N hydrochloric acid, water and brine, dried over sodium sulfate and concentrated in vacuo. The residue was dissolved in N,N-dimethylformamide (100 mL) and potassium carbonate (4.50 g, 32.9 mmol) was added. The mixture was stirred at 110° C. for 15 hr. After cooling, the mixture was diluted with ethyl acetate, washed with water and brine, dried over sodium sulfate and concentrated in vacuo. The residue was purified by flash chromatography on silica gel eluting with a 30-100% ethyl acetate/n-hexane gradient mixture. The filtrate was concentrated in vacuo to give the title compound (1.51 g, 5.17 mmol, 47%) as a pale yellow solid.

$^1$H NMR (CDCl$_3$) δ 0.82 (t, J=7.4 Hz, 6 H), 1.59-2.08 (m, 8 H), 2.93-3.09 (m, 1 H), 3.24-3.37 (m, 2 H), 4.12-4.26 (m, 2 H), 5.60 (brs, 1 H), 6.8.2 (d, J=8.5 Hz, 1 H), 7.11 (d, J=8.2 Hz, 1 H).

MS Calcd.: 291; Found: 292 (M+H).

Reference Example 73

Ethyl 4-[(2,6-dinitrophenyl)amino]butanoate

A mixture of 2-chloro-1,3-dinitrobenzene (30.0 g, 0.148 mol), ethyl 4-aminobutyrate hydrochloride (74.5 g, 0.444 mol), triethylamine (165 mL) in methanol (600 mL) was stirred at room temperature for 5 days. The mixture was diluted with aqueous sodium hydrogen carbonate and extracted with ethyl acetate. The combined organic layer was washed with brine, washed with 1N hydrochloric acid, dried over magnesium sulfate, filtered and concentrated in vacuo to give the title compound as a brown oil (44.0 g, 0.148 mol, 100%).

$^1$H NMR (CDCl$_3$) δ 1.24 (t, J=7.2 Hz, 3H), 1.95-2.05 (m, 2H), 2.35-2.43 (m, 2H), 3.01-3.08 (m, 2H), 4.12 (q, J=7.2 Hz, 2H), 6.77 (t, J=8.1 Hz, 1H), 8.17 (d, J=8.1 Hz, 2H), 8.29 (s, 1H).

Reference Example 74

Ethyl 4-[(2,6-diaminophenyl)amino]butanoate

To a solution of ethyl 4-[(2,6-dinitrophenyl)amino]butanoate (44.0 g, 0.148 mol) in tetrahydrofuran (800 mL) was added 10% palladium on carbon (50% wet; 4.63 g), and the mixture was purged with hydrogen and stirred under balloon pressure hydrogen at room temperature for 20 hr. The catalyst was removed by filtration, and the filtrate was concentrated in vacuo to give the title compound as a brown oil (35.1 g, 0.148 mmol, 100%).

¹H NMR (CDCl₃) δ 1.26 (t, J=7.2 Hz, 3H), 1.88-1.98 (m, 2H), 2.42-2.48 (m, 2H), 2.94 (t, J=6.9 Hz, 2H), 3.77 (s, 5H), 4.13 (q, J=7.2 Hz, 2H), 6.19 (d, J=8.1 Hz, 2H), 6.73 (t, J=8.1 Hz, 1H).
MS Calcd.: 237; MS Found: 238 (M+H).

Reference Example 75

Ethyl 4-(7-amino-2-oxo-2,3-dihydro-1H-benzimidazol-1-yl)butanoate

A mixture of ethyl 4-[(2,6-diaminophenyl)amino]butanoate (35.1 g, 0.148 mol), N,N'-carbonyldiimidazole (74.5 g, 0.444 mol) in tetrahydrofuran (600 mL) was stirred at room temperature for 16 hr. The mixture was concentrated, and the residue was washed with ethyl acetate/diisopropyl ether to give the title compound as a colorless powder (26.5 g, 0.101 mol, 68%).
¹H NMR (CDCl₃) δ 1.27 (t, J=7.2 Hz, 3H), 2.07-2.11 (m, 2H), 2.49 (t, J=6.0 Hz, 2H), 4.07-4.19 (m, 6H), 6.42 (d, J=8.4 Hz, 1H), 6.56 (d, J=8.4 Hz, 1H), 6.85 (t, J=8.4 Hz, 1H), 9.14 (s, 1H).
MS Calcd.: 263; MS Found: 264 (M+H).

Reference Example 76

Ethyl 4-(7-bromo-2-oxo-2,3-dihydro-1H-benzimidazol-1-yl)butanoate

To a solution of ethyl 4-(7-amino-2-oxo-2,3-dihydro-1H-benzimidazol-1-yl)butanoate (23.0 g, 87.3 mmol) in acetic acid (250 mL) was added dropwise sodium nitrite (6.32 g, 91.7 mmol) in conc. sulfuric acid (80 mL) at 0° C., and the mixture was stirred at 0° C. for 20 min. The mixture was added dropwise to a solution of copper(I) bromide (50.1 g, 350 mmol) in conc. hydrobromic acid (150 mL) at 0° C., and the mixture was stirred at room temperature for 2 hr. The mixture was poured into aqueous sodium hydrogen carbonate, neutralized with potassium carbonate, and extracted with ethyl acetate. The combined organic layer was washed with brine, dried over anhydrous magnesium sulfate, filtered and concentrated in vacuo. The residue was washed with diisopropyl ether, recrystallized from ethyl acetate to give the title compound as a pale yellow crystal (5.79 g, 17.7 mmol, 20%).
¹H NMR (CDCl₃) δ 1.24 (t, J=6.9 Hz, 3H), 2.12-2.19 (m, 2H), 2.44 (t, J=6.3 Hz, 2H), 4.10 (q, J=6.9 Hz, 2H), 4.30 (t, J=6.3 Hz, 2H), 6.91 (d, J=7.8 Hz, 1H), 7.03 (d, J=7.8 Hz, 1H), 7.20 (t, J=7.8 Hz, 1H), 9.65 (s, 1H).
MS Calcd.: 326; MS Found: 327 (M+H).

Reference Example 77

Ethyl 4-(7-bromo-2-chloro-1H-benzimidazol-1-yl)butanoate

A mixture of ethyl 4-(7-bromo-2-oxo-2,3-dihydro-1H-benzimidazol-1-yl)butanoate (4.11 g, 12.6 mmol) and phosphoryl chloride (49 g, 320 mmol) was stirred at 100° C. for 4 hr. After cooling, phosphoryl chloride was evaporated in vacuo. The residue was neutralized with saturated aqueous sodium hydrogen carbonate, and the mixture was extracted with ethyl acetate. The extract was washed with brine, dried over anhydrous magnesium sulfate, filtered and concentrated in vacuo. The residue was purified by flash column chromatography on silica gel eluting with a 5-30% ethyl acetate/n-hexane gradient mixture. The filtrate was concentrated in vacuo to give the title compound as a colorless powder (1.57 g, 4.54 mmol, 36%).
¹H NMR (CDCl₃) δ 1.26 (t, J=6.9 Hz, 3H), 2.16-2.20 (m, 2H), 2.41-2.46 (m, 2H), 4.09-4.16 (m, 2H), 4.60-4.65 (m, 2H), 7.12 (t, J=8.1 Hz, 1H), 7.42 (d, J=8.1 Hz, 1H), 7.62 (d, J=8.1 Hz, 1H).
MS Calcd.: 344; MS Found: 345 (M+H).

Reference Example 78

Ethyl 4-{7-bromo-2-[(2,4-dichlorophenyl)amino]-1H-benzimidazol-1-yl}butanoate

A mixture of ethyl 4-(7-bromo-2-chloro-1H-benzimidazol-1-yl)butanoate (1.57 g, 4.54 Mmol), 2,4-di-chloroaniline (2.21 g, 13.6 mmol), p-toluenesulfonic acid monohydrate (930 mg, 4.89 mmol) and xylene (8.0 mL) was stirred at 150° C. for 3 hr. The mixture was neutralized with aqueous sodium hydrogen carbonate and extracted with ethyl acetate. The combined organic layer was washed with brine, dried over magnesium sulfate, filtered and concentrated in vacuo. The residue was purified by flash column chromatography on silica gel eluting with a 5-30% ethyl acetate/n-hexane gradient mixture. The filtrate was concentrated in vacuo to give the title compound as a colorless solid (1.61 g, 3.42 mmol, 75%).
¹H NMR (CDCl₃) δ 1.21-1.28 (m, 3H), 2.18-2.25 (m, 2H), 2.48 (t, J=6.3 Hz, 2H), 4.08-4.17 (m, 2H), 4.54 (t, J=6.3 Hz, 2H), 6.90 (s, 1H), 6.99-7.04 (m, 1H), 7.18-7.31 (m, 2H), 7.48-7.51 (m, 1H), 7.58-7.63 (m, 1H), 8.36 (d, J=8.7 Hz, 1H).
MS Calcd.: 469; MS Found: 470 (M+H).

Reference Example 79

Methyl 4-[(2,6-dinitrophenyl)amino]-3-hydroxybutanoate

To a solution of rac-4-amino-3-hydroxybutyric acid (2.00 g, 16.8 mmol) in methanol (40 mL) was added thionyl chloride (1.72 mL, 23.6 mmol) at 0° C. The resultant mixture was stirred at room temperature for 1 hr and concentrated in vacuo. To a mixture of the residue, triethylamine (5.85 mL, 42.0 mmol) and tetrahydrofuran (34 mL) was added 2-chloro-1,3-dinitrobenzene (1.70 g, 8.39 mmol) at room temperature. After the resultant mixture was stirred at 50° C. for 2 hr, the mixture was diluted with ethyl acetate, washed with water and brine, dried over anhydrous sodium sulfate, filtered and concentrated in vacuo to give the title compound as a yellow, solid (2.53 g, 8.45 mmol, quant).
¹H NMR (CDCl₃) δ 2.48-2.56 (m, 2H), 2.99-3.10 (m, 2H), 3.73 (s, 3H), 4.18-4.32 (m, 1H), 6.78 (t, J=8.1 Hz, 1H), 8.18 (d, J=8.1 Hz, 2H), 8.78 (brs, 1H), hidden (1H).
MS Calcd.: 299; MS Found: 300 (M+H).

Reference Example 80

Methyl 4-[(2,6-diaminophenyl)amino]-3-hydroxybutanoate

Under hydrogen gas atmosphere, a mixture of methyl 4-[(2,6-dinitrophenyl)amino]-3-hydroxybutanoate (Reference Example 79; 2.53 g, 8.45 mmol), 10% palladium on carbon (50% wet, 500 mg) and tetrahydrofuran (85 mL) was stirred at room temperature for 6 hr. The reaction mixture was filtered and concentrated in vacuo to give the title compound as a solid (2.00 g, 8.36 mmol, 99%).

¹H NMR (CDCl₃) δ 2.42 (d, J=2.5 Hz, 1H), 2.44 (s, 1H), 2.88 (dd, J=13.4, 9.3 Hz, 1H), 3.08 (dd, J=13.4, 2.5 Hz, 1H), 3.70 (s, 3H), 3.86 (brs, 4H), 3.95-4.06 (m, 1H), 6.20 (d, J=7.8 Hz, 2H), 6.73 (t, J=7.8 Hz, 1H), hidden (2H).
MS Calcd.: 239; MS Found: 240 (M+H).

Reference Example 81

Methyl 4-{[2-amino-6-({[(2,4-dichlorophenyl) amino]carbonothioyl}amino)phenyl]amino}-3-hydroxybutanoate To a solution of methyl 4-[(2,6-diaminophenyl)amino]-3-hydroxybutanoate (Reference Example 80; 100 mg, 0.418 mmol) in tetrahydrofuran (2 mL) was added a solution of 2,4-dichlorophenyl isothiocyanate (93.8 mg, 0.460 mmol) in tetrahydrofuran (2 mL) at 0° C. The resultant mixture was stirred at 0° C. for 1 hr and concentrated in vacuo. The residue was purified by flash column chromatography on silica gel eluting with a 50-70% ethyl acetate/n-hexane gradient to give the title compound as an oil (62.5 mg, 0.141 mmol, 34%).
¹H NMR (CDCl₃) δ 2.31-2.50 (m, 2H), 2.95 (dd, J=13.7, 9.6 Hz, 1H), 3.22 (dd, J=13.7, 2.7 Hz, 1H), 3.68 (s, 3H), 3.80-3.96 (m, 2H), 4.03 (brs, 2H), 6.66 (dd, J=8.0, 1.4 Hz, 1H), 6.82 (dd, J=8.0, 1.4 Hz, 1H), 6.93 (t, J=8.0 Hz, 1H), 7.25 (dd, J=8.8, 2.5 Hz, 1H), 7.36 (d, J=2.5 Hz, 1H), 8.18 (d, J=8.8 Hz, 1H), 8.29 (s, 1H), 8.66 (s, 1H), hidden (1H).
MS Calcd.: 442; MS Found: 443 (M+H).

Reference Example 82

Methyl 4-{7-amino-2-[(2,4-dichlorophenyl)amino]-1H-benzimidazol-1-yl}-3-hydroxybutanoate Under nitrogen atmosphere, a mixture of methyl 4-{[2-amino-6-({[(2,4-dichlorophenyl)amino] carbonothioyl}amino)phenyl]amino}-3-hydroxybutanoate (Reference Example 81; 1.42 g, 3.20 mmol), 1-ethyl-3-(3-dimethylaminopropyl)carbodiimide hydrochloride (1.84 g, 9.60 mmol) and tetrahydrofuran (30 mL) was stirred at 50° C. for 2 hr. The reaction mixture was diluted with ethyl acetate, washed with water and brine, dried over anhydrous sodium sulfate, filtered and concentrated in vacuo. The residue was purified by flash column chromatography on silica gel eluting with a 20-50% ethyl acetate/n-hexane gradient to give the title compound as an oil (790 mg, 1.93 mmol, 60%).
¹H NMR (CDCl₃) δ 2.73 (d, J=6.3 Hz, 2H), 3.66 (brs, 2H), 3.75 (s, 3H), 3.89-4.01 (m, 1H), 4.50-4.62 (m, 2H), 5.46 (brs, 1H), 6.35 (dd, J=7.7, 0.5 Hz, 1H), 6.89 (t, J=7.7 Hz, 1H), 7.05 (d, J=7.7 Hz, 1H), 7.19 (dd, J=8.8, 2.5 Hz, 1H), 7.29 (d, J=2.5 Hz, 1H), 8.21-8.26 (m, 2H).
MS Calcd.: 408; MS Found: 409 (M+H).

Reference Example 83

Methyl 4-[2-[(2,4-dichlorophenyl)amino]-7-(diethylamino)-1H-benzimidazol-1-yl]-3-hydroxybutanoate To a suspension of methyl 4-{7-amino-2-[(2,4-dichlorophenyl)amino]-1H-benzimidazol-1-yl}-3-hydroxybutanoate (Reference Example 82; 760 mg, 1.85 mmol) in methanol (19 mL) and acetic acid (0.380 mL) was added acetaldehyde (0.692 mL, 11.1 mmol) at 0° C. The resultant mixture was stirred at 0° C. for 30 min. To the reaction mixture was added sodium acetoxyborohydride (2.35 g, 11.1 mmol) at 0° C. After the resultant mixture was stirred at room temperature for 15 hr, the mixture was diluted with aqueous sodium hydrogen carbonate and extracted with ethyl acetate. The combined organic layer was washed with brine, dried over anhydrous sodium sulfate, filtered and concentrated in vacuo. The residue was purified by column chromatography on silica gel eluting with ethyl acetate to give the title compound as a solid (838 mg, 1.80 mmol, 97%).
¹H NMR (CDCl₃) δ 0.96-1.08 (m, 6H), 2.58 (dd, J=16.5, 9.9 Hz, 1H), 2.70 (dd, J=16.5, 2.7 Hz, 1H), 2.92-3.09 (m, 4H), 3.75 (s, 3H), 4.15 (dd, J=14.6, 8.5 Hz, 1H), 4.45-4.57 (m, 2H), 5.07 (dd, J=14.6, 1.2 Hz, 1H), 6.97 (dd, J=8.0, 1.1 Hz, 1H), 7.10 (t, J=8.0 Hz, 1H), 7.22 (dd, J=8.8, 2.5 Hz, 1H), 7.33 (d, J=2.5 Hz, 1H), 7.40 (d, J=8.0 Hz, 1H), 8.32 (d, J=8.8 Hz, 1H), 8.67 (brs, 1H).
MS Calcd.: 464; MS Found: 465 (M+H).

Reference Example 84

4-[2-[(2,4-Dichlorophenyl)amino]-7-(diethylamino)-1H-benzimidazol-1-yl]butane-1,3-diol To a suspension of lithium aluminum hydride (15.9 mg, 0.429 mmol) in tetrahydrofuran (1 mL) was added a solution of methyl 4-[2-[(2,4-dichlorophenyl)amino]-7-(diethylamino)-1H-benzimidazol-1-yl]-3-hydroxybutanoate (Reference Example 83; 50.0 mg, 0.107 mmol) in tetrahydrofuran (1 mL) at 0° C. and the resultant mixture was stirred at 0° C. for 10 min. After sodium sulfate decahydrate (500 mg) was added at 0° C., the resultant mixture was filtered and concentrated in vacuo to give the title compound as an oil (45.0 mg, 0.103 mmol, 96%).
¹H NMR (CDCl₃) δ 0.96 (t, J=7.1 Hz, 6 H), 1.71-1.89 (m, 2 H), 2.81-3.06 (m, 4 H), 3.14 (brs, 1 H), 3.87-3.95 (m, 2 H), 4.01-4.09 (m, 1 H), 4.22-4.32 (m, 1 H), 5.04 (dd, J=14.3, 1.6 Hz, 1 H), 5.70 (brs, 1 H), 6.90 (d, J=8.0 Hz, 1 H), 7.02 (t, J=8.0 Hz, 1 H), 7.17 (dd, J=8.8, 2.5 Hz, 1 H), 7.23-7.29 (m, 2 H), 8.20 (d, J=8.8 Hz, 1 H), 8.84 (s, 1 H).
MS Calcd.: 436; MS Found: 437 (M+H).

Reference Example 85

3-[(2,6-Dinitrophenyl)amino]propane-1,2-diol

To a stirred solution of 2-chloro-1,3-dinitrobenzene (4.05 g, 20.0 mmol) and triethylamine (3.35 mL, 24.0 mmol) in tetrahydrofuran (70 mL) was added a solution of 3-amino-1,2-propandiol (3.64 g, 40.0 mmol) in tetrahydrofuran (10 mL) at room temperature. After 40 hr, the reaction mixture was diluted with water, extracted with ethyl acetate. The extracts were washed with brine, dried over anhydrous sodium sulfate, filtered and concentrated in vacuo. The residue was purified by flash column chromatography on silica gel eluting with a 30-70% ethyl acetate/n-hexane gradient mixture to give the title compound (5.02 g, 19.6 mmol, 98%) as a yellow solid.
¹H NMR (CDCl₃) δ 1.83 (brs, 1H), 2.46-2.58 (m, 1H), 3.00-3.19 (m, 2H), 3.54-3.67 (m, 1H), 3.69-3.80 (m, 1H), 3.91-4.03 (m, 1H), 6.78 (t, J=8.2 Hz, 1H), 8.19 (d, J=8.2 Hz, 2H), 8.75 (brs, 1H).
MS Calcd.: 257; MS Found: 258 (M+H).

Reference Example 86

N-{3-Amino-2-[(2,3-dihydroxypropyl)amino]phenyl}-N'-(2,4-dichlorophenyl)thiourea Under hydrogen gas atmosphere, a mixture of 3-[(2,6-dinitrophenyl)amino]propane-1,2-diol (Reference Example 85; 4.92 g, 19.1 mmol), 10% palladium on carbon (50% wet, 1.00 g) and tetrahydrofuran (19 mL) was stirred at room temperature for 24 hr. The reaction mixture was filtered and concentrated in vacuo to give a pale red oil. The mixture was used for the next step without further purification.

To a solution of the above mixture in tetrahydrofuran (170 mL) was added a solution of 2,4-dichlorophenyl isothiocyanate (3.90 g, 19.1 mmol) in tetrahydrofuran (20 mL) at 0° C. After 30 min, the reaction mixture was concentrated in vacuo. The residue was purified by flash column chromatography on silica gel eluting with a 50-100% ethyl acetate/n-hexane gradient mixture to give the title compound (1.69 g, 4.20 mmol, 22%) as a colorless amorphous.

$^1$H NMR (CDCl$_3$) δ 2.85 (brs, 1H), 3.03 (dd, J=13.8, 8.8 Hz, 1H), 3.15-3.26 (m, 1H), 3.47-3.58 (m, 1H), 3.64-3.77 (m, 2H), 3.81 (brs, 1H), 4.09 (brs, 2H), 6.69 (dd, J=7.8, 1.4 Hz, 1H), 6.75-6.82 (m, 1H), 6.94 (t, J=7.8 Hz, 1H), 7.21-7.28 (m, 1H), 7.37 (d, J=2.5 Hz, 1H), 8.04-8.17 (m, 2H), 9.03 (brs, 1H).

MS Calcd.: 400; MS Found: 401 (M+H).

Reference Example 87

3-{7-Amino-2-[(2,4-dichlorophenyl)amino]-1H-benzimidazol-1-yl}propane-1,2-diol

A mixture of N-{3-amino-2-[(2,3-dihydroxypropyl)amino]phenyl}-N'-(2,4-dichlorophenyl)thiourea (Reference Example 86; 1.71 g, 4.25 mmol) and 1-ethyl-3-(3-dimethylaminopropyl)carbodiimide hydrochloride (2.44 g, 12.8 mmol) in tetrahydrofuran (43 mL) was stirred at 50° C. for 30 min. The reaction mixture was diluted with ethyl acetate, washed with water and brine, dried over anhydrous sodium sulfate, filtered and concentrated in vacuo. The residue was purified by column chromatography on silica gel eluting with ethyl acetate to give the title compound (687 mg, 1.87 mmol, 44%) as a colorless amorphous.

$^1$H NMR (CDCl$_3$) δ 3.55-3.69 (m, 2H), 4.08-4.17 (m, 1H), 4.17-4.29 (m, 1H), 4.49 (d, J=15.4 Hz, 1H), 6.44 (d, J=7.7 Hz, 1H), 6.92 (t, J=7.7 Hz, 1H), 7.06 (brs, 1H), 7.20 (dd, J=8.9, 2.3 Hz, 1H), 7.31 (d, J=2.3 Hz, 1H), 8.21 (brs, 1H).

MS Calcd.: 366; MS Found: 367 (M+H).

Reference Example 88

3-[2-[(2,4-Dichlorophenyl)amino]-7-(diethylamino)-1H-benzimidazol-1-yl]propane-1,2-diol To a solution of 3-{7-amino-2-[(2,4-dichlorophenyl)amino]-1H-benzimidazol-1-yl}propane-1,2-diol (Reference Example 87; 630 mg, 1.72 mmol) in methanol (17 mL) and acetic acid (0.34 mL) was added acetaldehyde (0.642 mL, 10.3 mmol) at 0° C. The resultant mixture was stirred at 0° C. for 30 min. To the reaction mixture was added sodium acetoxyborohydride (2.18 g, 10.3 mmol) at 0° C. After 1 hr, the mixture was diluted with ethyl acetate, washed with water and brine, dried over anhydrous sodium sulfate, filtered and concentrated in vacuo to give the title compound (714 mg, 1.69 mmol, 98%) as a colorless solid.

$^1$H NMR (CDCl$_3$) δ 0.93-1.08 (m, 6H), 2.83-3.08 (m, 4H), 3.53-3.72 (m, 2H), 4.03-4.24 (m, 2H), 4.89 (d, J=14.6 Hz, 1H), 6.93 (d, J=8.0 Hz, 1H), 7.07 (t, J=8.0 Hz, 1H), 7.19 (dd, J=8.7, 2.1 Hz, 1H), 7.26-7.35 (m, 2H), 8.18 (brs, 1H), 8.64 (brs, 1H).

MS Calcd.: 422; MS Found: 423 (M+H).

Reference Example 89

3-[2-[(2,4-Dichlorophenyl)amino]-7-(diethylamino)-1H-benzimidazol-1-yl]-2-hydroxypropyl acetate To a solution of 3-[2-[(2,4-dichlorophenyl)amino]-7-(diethylamino)-1H-benzimidazol-1-yl]propane-1,2-diol (Reference Example 88; 46.2 mg, 0.109 mmol) in pyridine (0.5 mL) was added acetyl chloride (0.0155 mL, 0.218 mmol) at 0° C. After 5 hr, the mixture was quenched with aqueous sodium hydrogen carbonate, diluted with ethyl acetate, washed with water and brine, dried over anhydrous sodium sulfate, filtered, and concentrated in vacuo. The residue was purified by NH flash column chromatography on silica gel eluting with a 10-50% ethyl acetate/n-hexane gradient mixture to give the title compound as a colorless solid (32.5 mg, 0.0698 mmol, 64%).

$^1$H NMR (CDCl$_3$) δ 0.90-1.08 (m, 6H), 2.15 (s, 3H), 2.84-3.09 (m, 4H), 4.00-4.22 (m, 2H), 4.23-4.39 (m, 2H), 4.53 (brs, 1H), 5.18 (d, J=13.5 Hz, 1H), 6.96 (d, J=7.7 Hz, 1H), 7.09 (t, J=7.7 Hz, 1H), 7.22 (dd, J=8.9, 2.3 Hz, 1H), 7.28-7.42 (m, 2H), 8.33 (d, J=8.9 Hz, 1H), 8.52 (brs, 1H).

MS Calcd.: 464; MS Found: 465 (M+H).

Reference Example 90

1-Allyl-7-(1-ethylpropyl)-1,3-dihydro-2H-benzimidazol-2-one

To a solution of tert-butyl 4-(1-ethylpropyl)-2-oxo-2,3-dihydro-1H-benzimidazole-1-carboxylate (Reference Example 7; 30.4 g, 100 mmol) in N,N-dimethylformamide (300 mL) was added sodium hydride (60% dispersion in mineral oil, 4.80 g, 120 mmol) portionwise at 0° C. After stirring for 30 min, allyl bromide (10.4 mL, 120 mmol) was added dropwise. The mixture was warmed to room temperature and stirred for 16 hours. Water was added to the mixture, which was extracted with ethyl acetate. Organic layer was washed with water and brine, dried over anhydrous magnesium sulfate and concentrated in vacuo. The residue was dissolved in ethyl acetate (300 mL) and 4N hydrogen chloride solution in ethyl acetate (300 mL) was added. After stirring for 70 hr, the mixture was concentrated in vacuo to give a solid which was washed with n-hexane to afford the title compound (22.2 g, 90.6 mmol, 91%) as a colorless solid.

$^1$H NMR (CDCl$_3$) δ 0.82 (t, J=7.3 Hz, 6 H), 1.51-1.83 (m, 4 H), 2.88-3.04 (m, 1 H), 4.73-4.79 (m, 2 H), 5.03 (d, J=17.3 Hz, 1 H), 5.22 (d, J=10.4 Hz, 1 H), 5.92-6.07 (m, 1 H), 6.89-7.08 (m, 3 H), 10.76 (brs, 1 H).

MS Calcd.: 244; Found: 245 (M+H).

Reference Example 91

1-Allyl-4-chloro-7-(1-ethylpropyl)-1,3-dihydro-2H-benzimidazol-2-one

To a mixture of 1-allyl-7-(1-ethylpropyl)-1,3-dihydro-2H-benzimidazol-2-one (22.0 g, 89.8 mmol) and zirconium chloride (1.05 g, 4.49 mmol) in toluene (300 mL) was added N-chlorosuccinimide (12.4 g, 92.5 g) portionwise at 0° C. After stirring for 15 hr, the mixture was concentrated in vacuo to give a residue which was partitioned in aqueous sodium bicarbonate and ethyl acetate. The aqueous layer was extracted with ethyl acetate. Combined organic layer was washed with aqueous sodium bicarbonate and brine, dried over anhydrous sodium sulfate and concentrated in vacuo. The residue was dissolved in hot ethyl acetate. n-Hexane was then added and the solution was cooled down. Resulting precipitate was collected by filtration to afford the title compound (9.60 g, 34.4 mmol, 38%) as a colorless solid.

$^1$H NMR (CDCl$_3$) δ 0.81 (t, J=7.4 Hz, 6 H), 1.45-1.84 (m, 4 H), 2.86-2.98 (m, 1 H), 4.65-4.76 (m, 2 H), 4.97-5.06 (m, 1 H), 5.19-5.25 (m, 1 H), 5.89-6.02 (m, 1 H), 6.86 (d, J=8.5 Hz, 1 H), 7.03 (d, J=8.8 Hz, 1 H), 8.88 (brs, 1 H).

MS Calcd.: 278; Found: 279 (M+H).

Reference Example 92

1-Allyl-2,4-dichloro-7-(1-ethylpropyl)-1H-benzimidazole

A solution of 1-allyl-4-chloro-7-(1-ethylpropyl)-1,3-dihydro-2H-benzimidazol-2-one (9.80 g, 35.1 mmol) in phosphoryl chloride (35 mL) was stirred at 100° C. for 2 hr. The mixture was concentrated in vacuo to give a residue which was dissolved in ethyl acetate, washed with aqueous sodium bicarbonate and brine, dried over sodium sulfate and concentrated in vacuo. The residue was purified by flash chromatography on silica gel eluting with a 5-20% ethyl acetate/n-hexane gradient mixture. The filtrate was concentrated in vacuo to give the title compound (9.90 g, 33.3 mmol, 95%) as a colorless solid.

$^1$H NMR (CDCl$_3$) δ 0.80 (t, J=7.4 Hz, 6 H), 1.56-1.83 (m, 4 H), 2.91-3.06 (m, 1 H), 4.80 (dt, J=17.2, 2.0 Hz, 1H), 4.99 (dt, J=4.0, 2.0 Hz, 2 H), 5.26 (dt, J=10.7, 1.9 Hz, 1 H), 5.91-6.04 (m, 1 H), 7.03 (d, J=8.2 Hz, 1H), 7.26 (d, J=8.5 Hz, 1 H).

MS Calcd.: 296; Found: 297 (M+H).

Reference Example 93

N$^5$-[4-Chloro-7-(1-ethylpropyl)-1-prop-2-en-1-yl-1H-benzimidazol-2-yl]-N$^2$,N$^2$,4-trimethylpyridine-2,5-diamine A mixture of 1-allyl-2,4-dichloro-7-(1-ethylpropyl)-1H-benzimidazole (1.19 g, 4.00 mmol), N$^2$,N$^2$,4-trimethylpyridine-2,5-diamine (1.21 g, 8.00 mmol) and p-toluenesulfonic acid monohydrate (760 mg, 4.00 mmol) in 1-methyl-2-pyrrolidinone (12 mL) was irradiated by microwave at 180° C. for 1 hr. After cooling, the mixture was diluted with ethyl acetate, washed with aqueous sodium bicarbonate, water and brine, dried over anhydrous sodium sulfate and concentrated in vacuo. The residue was purified by flash chromatography on silica gel eluting with a 30-80% ethyl acetate/n-hexane gradient mixture. The filtrate was concentrated in vacuo to give the solid, which was recrystallized from ethyl acetate/n-hexane to give the title compound (430 mg, 1.04 mmol, 26%) as a colorless solid.

$^1$H NMR (CDCl$_3$) δ 0.81 (t, J=7.4 Hz, 6 H), 1.53-1.86 (m, 4 H), 2.20 (s, 3 H), 2.81-2.97 (m, 1 H), 3.07 (s, 6 H), 4.74-4.82 (m, 2 H), 5.06 (d, J=17.0 Hz, 1 H), 5.32 (d, J=10.4 Hz, 1 H), 5.67-5.75 (m, 1 H), 5.93-6.07 (m, 1 H), 6.38 (s, 1 H), 6.83 (d, J=8.2 Hz, 1 H), 7.11 (d, J=8.5 Hz, 1 H), 8.25 (s, 1 H).

MS Calcd.: 411; Found: 412 (M+H).

Reference Example 94

1-[4-Chloro-2-{[6-(dimethylamino)-4-methylpyridin-3-yl]amino}-7-(1-ethylpropyl)-1H-benzimidazol-1-yl]propan-2-ol To a solution of N$^5$-[4-chloro-7-(1-ethylpropyl)-1-prop-2-en-1-yl-1H-benzimidazol-2-yl]-N$^2$,N$^2$,4-trimethylpyridine-2,5-diamine (41 mg, 0.100 mmol) in tetrahydrofuran (1.0 mL) was added borane-tetrahydrofuran complex (1.18 M solution in tetrahydrofuran, 0.17 mL, 0.200 mmol) at 0° C. After 2 hr, additional borane-tetrahydrofuran complex (1.18 M solution in tetrahydrofuran, 0.17 mL, 0.200 mmol) was added to the mixture. After 1 hr, additional borane-tetrahydrofuran complex (1.18 M solution in tetrahydrofuran, 0.17 mL, 0.200 mmol) was added to the mixture. After 1 hr, sodium peroxyborate tetrahydrate (154 mg, 1.00 mmol) and water (0.50 mL) was added to the mixture, which was stirred at room temperature for 60 hr. Water was added and the mixture was extracted with ethyl acetate. Organic layer was washed with brine, dried over sodium sulfate and concentrated in vacuo. The residue was purified by flash chromatography on silica gel eluting with a 50-100% ethyl acetate/n-hexane gradient mixture. The filtrate was concentrated in vacuo to give the title compound (23 mg, 0.0535 mmol, 53%) as a colorless solid.

$^1$H NMR (CDCl$_3$) δ 0.71 (t, J=7.3 Hz, 3 H), 0.89 (t, J=7.4 Hz, 3 H), 1.32 (d, J=6.3 Hz, 3 H), 1.39-1.81 (m, 4H), 2.05 (s, 3 H), 2.65-2.79 (m, 1 H), 3.02 (s, 6 H), 3.85 (dd, J=15.7, 9.6 Hz, 1 H), 4.18-4.33 (m, 2 H), 6.28 (s, 1 H), 6.73 (d, J=8.5 Hz, 1 H), 7.00 (d, J=8.2 Hz, 1 H), 8.25 (brs, 1 H), 8.37 (s, 1 H).

MS Calcd.: 429; Found: 430 (M+H).

Reference Example 95

5-Isothiocyanato-2,4-dimethoxypyrimidine

To a solution of 2,4-dimethoxypyrimidin-5-amine (prepared by the method described in U.S. Pat. No. 6,342,503B1) (4.68 g, 30.0 mmol) in tetrahydrofuran (60 mL) was added 1,1'-thiocarbonyldiimidazole (6.41 g, 36.0 mmol) portionwise at 0° C. The mixture was warmed to room temperature and stirred for 20 hr. The mixture was concentrated in vacuo to give a residue which was passed through a pad of silica gel eluting with n-hexane/ethyl acetate. The filtrate was concentrated in vacuo to give the title compound (5.0 g, 84%) as a colorless solid.

$^1$H NMR (CDCl$_3$) δ 3.99 (s, 3 H), 4.09 (s, 3 H), 8.06 (s, 1 H).

MS Calcd.: 197; Found: 198 (M+H).

Reference Example 96

3-{7-Amino-2-[(2,4-dimethoxypyrimidin-5-yl)amino]-1H-benzimidazol-1-yl}propan-1-ol To a solution of 3-[(2,6-diaminophenyl)amino]propan-1-ol (Reference Example 115; 363 mg, 2.00 mmol) in tetrahydrofuran (5.0 mL) was added 5-isothiocyanato-2,4-dimethoxypyrimidine (440 mg, 2.20 mmol) portionwise at room temperature. After stirring for 2 hr, N-(3-dimethylaminopropyl)-N'-ethylcarbodiimide hydrochloride (422 mg, 2.20 mmol) and trimethylamine (0.331 mL, 2.40 mmol) was added. The mixture was warmed to 50° C. and stirred for additional 3 hr. Water and ethyl acetate were added to the mixture and the insoluble materials were filtered off. The filtrate was extracted with ethyl acetate. Organic layer was washed with brine, dried over anhydrous sodium sulfate and concentrated in vacuo. The residue was purified by flash chromatography on silica gel eluting with a 0-15% methanol/ethyl acetate gradient mixture. The filtrate was concentrated in vacuo to give the title compound (99 mg, 0.287 mmol, 14%) as a pale yellow amorphous.

$^1$H NMR (CDCl$_3$) δ 2.03-2.15 (m, 2 H), 3.60 (t, 2 H), 3.92 (d, J=1.1 Hz, 3 H), 3.97 (d, J=1.9 Hz, 3 H), 4.36 (t, J=4.9 Hz, 2 H), 6.46 (d, J=7.4 Hz, 1 H), 6.91 (t, J=7.7 Hz, 1 H), 6.99 (brs, 1 H), 8.98 (brs, 1 H).

MS Calcd.: 344; Found: 345 (M+H).

Reference Example 97

3-{7-(Diethylamino)-2-[(2,4-dimethoxypyrimidin-5-yl)amino]-1H-benzimidazol-1-yl}propan-1-ol To a mixture of 3-{7-amino-2-[(2,4-dimethoxypyrimidin-5-yl)amino]-1H-benzimidazol-1-yl}propan-1-ol (99 mg, 0.287 mmol), acetaldehyde (90%, 0.178 mL, 2.87 mmol) and acetic acid (0.066 mL, 1.15 mmol) in tetrahydrofuran (2.0 mL) was added sodium triacetoxyborohydride (384 mg, 1.72 mmol) portionwise at 0° C. The mixture was warmed to room temperature and stirred for 14 hr. Aqueous sodium bicarbonate was added and the mixture was extracted with ethyl acetate. Organic layer was washed with brine, dried over sodium sulfate and concentrated in vacuo. The residue was purified by flash chromatography on silica gel eluting with a 50-100% ethyl acetate/n-hexane gradient mixture. The filtrate was concentrated in vacuo to give the title compound (90 mg, 0.224 mmol, 78%) as a colorless amorphous.
$^1$H NMR (CDCl$_3$) δ 1.04 (t, J=7.0 Hz, 6 H), 2.01-2.13 (m, 2 H), 3.06 (q, J=7.1 Hz, 4 H), 3.58 (t, J=5.4 Hz, 2 H), 3.94 (s, 3 H), 3.99 (s, 3 H), 4.52 (t, J=6.0 Hz, 2 H), 6.93 (d, J=8.0 Hz, 1 H), 7.05 (t, J=7.7 Hz, 1 H), 7.55 (brs, 1 H), 9.08 (brs, 1 H).
MS Calcd.: 400; Found: 401 (M+H).

Reference Example 98

6-Chloro-3-isothiocyanato-4-methylpyridazine

To a solution of 6-chloro-4-methylpyridazin-3-amine (2.86 g, 20.0 mmol) in aqueous sodium bicarbonate (10 mL) and tetrahydrofuran (40 mL) was added thiophosgene (1.69 mL, 22.0 mmol) dropwise at 0° C. After stirring for 1 hr, water and ethyl acetate were added to the mixture and the insoluble materials were filtered off. The filtrate was washed with brine, dried over anhydrous sodium sulfate and concentrated in vacuo. The residue was purified by flash chromatography on silica gel eluting with a 10-50% ethyl acetate/n-hexane gradient mixture. The filtrate was concentrated in vacuo to give the title compound (304 mg, 1.64 mmol, 8%) as a pale yellow solid.
$^1$H NMR (CDCl$_3$) δ 2.38 (d, J=1.1 Hz, 3 H), 7.37 (q, J=0.8 Hz, 1 H).
MS Calcd.: 185; Found: 186 (M+H).

Reference Example 99

Methyl 2-chloro-3-nitrobenzoate

To a solution of 2-chloro-3-nitrobenzoic acid (100 g, 0.496 mol) in tetrahydrofuran (1000 mL) was added dropwise oxalyl chloride (46.8 mL, 0.546 mol) at 0° C., and the mixture was stirred at room temperature for 3 hr. To the mixture was added dropwise methanol (300 mL) at 0° C., and the mixture was stirred at room temperature for 14 hr. The mixture was concentrated and the residue was neutralized with saturated aqueous sodium hydrogen carbonate, and extracted with ethyl acetate. The combined organic layer was washed with brine, dried over anhydrous magnesium sulfate, filtered and concentrated in vacuo to give the solid, which was washed with n-hexane to give the title compound as a yellow powder (103 g, 0.478 mol, 96%).
$^1$H NMR (CDCl$_3$) δ 3.98 (s, 3H), 7.47 (t, J=8.7 Hz, 1H), 7.83 (dd, J=1.8 Hz, 8.7 Hz, 1H), 7.94 (dd, J=1.8 Hz, 8.7 Hz, 1H).

Reference Example 100

Methyl 2-[(3-hydroxypropyl)amino]-3-nitrobenzoate

To a solution of methyl 2-chloro-3-nitrobenzoate (100 g, 0.463 mol) in methanol (800 mL) and triethylamine (129 mL) was added 3-amino-1-propanol (52.2 g, 0.696 mol), and the mixture was stirred at 50° C. for 6 hr. The mixture was concentrated and the residue was diluted with aqueous saturated ammonium chloride, and extracted with ethyl acetate. The combined organic layer was washed with brine, dried over anhydrous magnesium sulfate, filtered and concentrated in vacuo. The residue was purified by flash column chromatography on silica gel eluting with a 50% ethyl acetate/n-hexane mixture (short column). The filtrate was concentrated in vacuo to give the title compound as a brown oil (86.6 g, 0.341 mol, 74%).
$^1$H NMR (CDCl$_3$) δ 1.61 (s, 1H), 1.86-1.95 (m, 2H), 3.04-3.12 (m, 2H), 3.77 (q, J=6.0 Hz, 2H), 3.91 (s, 3H), 6.66 (t, J=7.8 Hz, 1H), 7.95 (dd, J=2.4 Hz, 8.7 Hz, 1H), 8.04 (dd, J=2.4 Hz, 8.7 Hz, 1H), 8.52 (s, 1H).

Reference Example 101

Methyl 3-amino-2-[(3-hydroxypropyl)amino]benzoate

To a solution of methyl 2-[(3-hydroxypropyl)amino]-3-nitrobenzoate (86.6 g, 0.341 mol) in tetrahydrofuran (1000 mL) was added 10% palladium on carbon (50% wet; 8.70 g), and the mixture was purged with hydrogen and stirred under balloon pressure hydrogen at room temperature for 23 hr. The catalyst was removed by filtration, and the filtrate was concentrated in vacuo to give the title compound as a brown oil (59.8 g, 0.267 mol, 78%).
$^1$H NMR (CDCl$_3$) δ 1.75 (s, 1H), 1.81-1.86 (m, 2H), 3.15 (t, J=6.3 Hz, 2H), 3.86 (t, J=6.3 Hz, 2H), 3.87 (s, 3H), 3.99 (s, 2H), 6.10 (s, 1H), 6.84-6.86 (m, 2H), 7.35-7.39 (m, 1H).
MS Calcd.: 224; MS Found: 225 (M+H).

Reference Example 102

Methyl 3-({[(2,4-dichlorophenyl)amino]carbonothioyl}amino)-2-[(3-hydroxypropyl)amino]benzoate To a solution of methyl 3-amino-2-[(3-hydroxypropyl)amino]benzoate (1.00 g, 4.46 mmol) in tetrahydrofuran (12 mL) was added 2,4-dichlorophenyl isothiocyanate (910 mg, 4.46 mmol), and the mixture was stirred at room temperature for 3 hr. The mixture was concentrated and the residue was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 10-50% ethyl acetate/n-hexane gradient mixture. The filtrate was concentrated in vacuo to give the title compound as a brown solid (1.87 g, 4.37 mmol, 98%).
$^1$H NMR (CDCl$_3$) δ 1.81-1.90 (m, 2H), 2.24 (s, 1H), 3.43-3.48 (m, 2H), 3.79 (t, J=4.8 Hz, 2H), 3.89 (s, 3H), 6.84 (t, J=8.1 Hz, 1H), 7.23-7.27 (m, 1H), 7.37 (d, J=2.1 Hz, 1H), 7.52-7.55 (m, 2H), 7.96 (dd, J=2.1 Hz, 7.8 Hz, 1H), 8.00-8.02 (m, 1H), 8.13 (d, J=8.1 Hz, 1H), 8.34 (s, 1H).
MS Calcd.: 427; MS Found: 428 (M+H).

Reference Example 103

Methyl 2-[(2,4-dichlorophenyl)amino]-1-(3-hydroxypropyl)-1H-benzimidazole-7-carboxylate A mixture of methyl 3-({[(2,4-dichlorophenyl)amino]carbonothioyl}amino)-2-[(3-hydroxypropyl)amino]benzoate (1.87 g, 4.37 mmol), triethylamine (0.67 mL), and 1-ethyl-3-(3-dimethylaminopropyl)-carbodiimide hydrochloride (838 mg, 4.37 mmol) in tetrahydrofuran (15 mL) was stirred at 50° C. for 2 hr. The mixture was diluted with water, concentrated in vacuo, and extracted with ethyl acetate. The combined organic layer was washed with brine, dried over anhydrous magnesium sulfate, filtered and concentrated in vacuo. The residue was washed with diisopropyl ether to give the title compound as a pale yellow powder (1.67 g, 4.24 mmol, 97%).

$^1$H NMR (CDCl$_3$) δ 1.72 (s, 1H), 2.00-2.06 (m, 2H), 3.57 (t, J=5.1 Hz, 2H), 3.96 (s, 3H), 4.63 (t, J=5.1 Hz, 2H), 7.15-7.26 (m, 2H), 7.35 (d, J=2.1 Hz, 1H), 7.64 (d, J=7.8 Hz, 1H), 7.74 (d, J=7.5 Hz, 1H), 7.91 (s, 1H), 8.32 (d, J=7.5 Hz, 1H).

MS Calcd.: 393; MS Found: 394 (M+H).

Reference Example 104

(2-Chloro-5-nitrophenyl)carbonimidic dichloride

2-Chloro-5-nitroaniline (43.1 g, 250 mmol), formic acid (250 mL) was stirred at room temperature for 5 h. The reaction mixture was concentrated in vacuo. The solid residue was taken up in water (350 mL), filtered, washed with water (×2). The solid residue was dried at 50° C. under vacuum to give a crude formanilide as a light brown amorphous. The crude formanilide, thionyl chloride (164 mL) and sulfuryl chloride (58 mL) was combined, and heated at 55° C. for 48 hr. The mixture was concentrated in vacuo. The residue was dissolved in petroleum ether, decanted from a precipitate and the clear solution was evaporated in vacuo to give the title compound (42.2 g, 166 mmol, 67%) as a light brown amorphous.

$^1$H-NMR (CDCl$_3$, 300 MHz) δ: 7.62 (1H, d, J=8.7 Hz), 7.83 (1H, d, J=2.7 Hz), 8.04 (1H, dd, J=2.7, 8.7 Hz).

MS Calcd.: 252; Found: 253 (M+H).

Reference Example 105

2-Chloro-N-1,3-diazepan-2-ylidene-5-nitroaniline (2-Chloro-5-nitrophenyl)carbonimidic dichloride (17.8 g, 70.0 mmol) was dissolved in tetrahydrofuran (68 mL).

The solution was added dropwise within 30 min to a solution of 1,4-butanediamine (30.9 g, 350 mmol) in tetrahydrofuran (168 mL) which was kept at 5-10° C. The reaction mixture was stirred for 1 h at 5-10° C. another 2 hr at room temperature. The suspension was filtered, and washed with tetrahydrofuran. The filtrate was concentrated in vacuo. The residue was taken up in water, filtered, and washed with water and diisopropyl ether. After drying at 50° C. under vacuum, the title compound (8.9 g, 33.4 mmol, 48%) was obtained as a yellow amorphous.

$^1$H-NMR (DMSO-d$_6$, 300 MHz) δ: 1.50 (4H, brs), 2.99 (4H, brs), 6.15 (2H, brs), 7.51 (1H, d, J=3.0 Hz), 7.55 (1H, d, J=8.7 Hz), 7.61 (1H, dd, J=3.0, 8.7 Hz).

MS Calcd.: 268; Found: 269 (M+H).

Reference Example 106

10-Chloro-7-nitro-2,3,4,5-tetrahydro-1H-[1,3]diazepino[1,2-a]benzimidazole

2-Chloro-N-1,3-diazepan-2-ylidene-5-nitroaniline (5.0 g, 18.6 mmol) and potassium t-butoxide (417 mg, 3.7 mmol) were dissolved in N,N-dimethylsulfoxide (100 mL), and heated at 60° C. for 24 hr. After cooling to room temperature, the reaction mixture was directly purified by silica gel column chromatography eluting with a 50-100% ethyl acetate/n-hexane gradient mixture to give the title compound (3.38 g, 12.7 mmol, 68%) as a yellow amorphous.

$^1$H-NMR (CDCl$_3$, 300 MHz) δ: 1.93-2.01 (2H, m), 2.09-2.17 (2H, m), 3.37-3.42 (2H, m), 3.94-3.97 (2H, m), 5.73 (1H, brs), 7.20 (1H, d, J=9.0 Hz), 7.68 (1H, d, J=9.0 Hz).

MS Calcd.: 266; Found: 267 (M+H).

Reference Example 107

2-Chloro-5-nitro-N-(tetrahydropyrimidin-2(1H)-ylidene)aniline (2-Chloro-5-nitrophenyl)carbonimidic dichloride (35.5 g, 140 mmol) was dissolved in tetrahydrofuran (135 mL). The solution was added dropwise within 30 min to a solution of 1,3-propanediamine (58 mL, 700 mmol) in tetrahydrofuran (335 mL) which was kept at 5-10° C. The reaction mixture was stirred for 1 h at 5-10° C. another 2 hr at room temperature. The suspension was filtered, and washed with tetrahydrofuran. The filtrate was concentrated in vacuo. The residue was taken up in water, filtered, and washed with water and diisopropyl ether. After drying at 50° C. under vacuum, the title compound (35.0 g, 137.4 mmol, 98%) was obtained as yellow crystals.

mp 189-191° C.

$^1$H-NMR (CDCl$_3$, 300 MHz) δ: 1.95-2.03 (2H, m), 3.35 (4H, t, J=6.0 Hz), 4.67 (2H, brs), 7.47 (1H, d, J=8.7 Hz), 7.68 (1H, dd, J=2.7, 8.7 Hz), 7.85 (1H, d, J=8.7 Hz).

MS Calcd.: 254; Found: 255 (M+H).

Reference Example 108

9-Chloro-6-nitro-1,2,3,4-tetrahydropyrimido[1,2-a]benzimidazole

2-Chloro-N-1,3-diazepan-2-ylidene-5-nitroaniline (5.0 g, 19.6 mmol) and potassium t-butoxide (440 mg, 3.93 mmol) were dissolved in N,N-dimethylsulfoxide (100 mL), and heated at 60° C. for 24 hr. After cooling to room temperature, to the reaction mixture was directly purified by silica gel column chromatography eluting with a 50-100% ethyl acetate/n-hexane gradient mixture to give the title compound (3.63 g, 14.3 mmol, 73%) as a yellow amorphous.

$^1$H-NMR (DMSO-d$_6$, 300 MHz) δ: 1.91-2.01 (2H, m), 3.03-3.40 (2H, m), 4.12 (2H, t, J=6.0 Hz), 7.16 (1H, d, J=9.0 Hz), 7.47 (1H, d, J=9.0 Hz), 8.13 (1H, brs).

MS Calcd.: 252; Found: 253 (M+H).

Reference Example 109

5-[(2,6-Dinitrophenyl)amino]pentan-1-ol

A mixture of 5-amino-1-pentanol (619 mg, 6.00 mmol), 2-chloro-1,3-dinitrobenzene (1.01 g, 4.99 mmol), triethylamine (0.837 mL, 6.01 mmol) and tetrahydrofuran (20 mL) was stirred at room temperature for 1 hr. To the reaction mixture was added 5-amino-1-pentanol (520 mg, 5.04 mmol) at room temperature and the resultant mixture was stirred at room temperature for 0.5 hr. The reaction mixture was diluted with ethyl acetate, washed with water and brine, dried over anhydrous sodium sulfate, filtered and concentrated in vacuo. The residue was purified by flash column chromatography on silica gel eluting with a 10-40% ethyl acetate/n-hexane gradient mixture to give the title compound as a yellow oil (1.30 g, 4.82 mmol, 97%).

$^1$H NMR (CDCl$_3$) δ 1.40 (m, 2H), 1.54-1.65 (m, 2H), 1.66-1.80 (m, 2H), 3.01 (td, J=6.9, 4.8 Hz, 2H), 3.59-3.71 (m, 2H), 6.75 (t, J=8.3 Hz, 1H), 8.17 (d, J=8.3 Hz, 2H), 8.34 (brs, 1H).

MS Calcd.: 269; MS Found: 270 (M+H).

Reference Example 110

5-[(2,6-Diaminophenyl)amino]pentan-1-ol

Under hydrogen gas atmosphere, a mixture of 5-[(2,6-dinitrophenyl)amino]pentan-1-ol (Reference Example 109; 1.30 g, 4.82 mmol), 10% palladium on carbon (50% wet, 260 mg) and tetrahydrofuran (48 mL) was stirred at room temperature for 2 hr. The reaction mixture was filtered and concentrated in vacuo to give the title compound as an oil (873 mg, 4.17 mmol, 86%).

$^1$H NMR (CDCl$_3$) δ 1.45-1.55 (m, 2H), 1.56-1.70 (m, 4H), 2.93 (t, J=7.1 Hz, 2H), 3.58-3.93 (m, 6H), 6.21 (d, J=8.0 Hz, 2H), 6.74 (t, J=8.0 Hz, 1H), hidden (2H).

MS Calcd.: 209; MS Found: 210 (M+H).

Reference Example 111

N-{3-Amino-2-[(5-hydroxypentyl)amino]phenyl}-N'-(2,4-dichlorophenyl)thiourea

To a solution of 5-[(2,6-diaminophenyl)amino]pentan-1-ol (Reference Example 110; 873 mg, 4.17 mmol) in tetrahydrofuran (30 mL) was added a solution of 2,4-dichlorophenyl isothiocyanate (936 mg, 4.59 mmol) in tetrahydrofuran (10 mL) at 0° C. The resultant mixture was stirred at 0° C. for 2 hr and concentrated in vacuo. The residue was purified by flash column chromatography on silica gel eluting with a 50-90% ethyl acetate/n-hexane gradient mixture to give the title compound as an oil (554 mg, 1.34 mmol, 32%).

$^1$H NMR (CDCl$_3$) δ 1.46-1.71 (m, 6H), 3.02 (t, J=6.1 Hz, 2H), 3.67 (t, J=5.8 Hz, 2H), 3.90 (brs, 2 H), 6.73-6.79 (m, 2H), 6.93 (t, J=7.8 Hz, 1H), 7.26 (dd, J=8.8, 2.5 Hz, 1H), 7.36 (d, J=2.5 Hz, 1H), 7.82 (s, 1 H), 8.14 (s, 1 H), 8.20 (d, J=8.8 Hz, 1H), hidden (2H).

MS Calcd.: 412; MS Found: 413 (M+H).

Reference Example 112

5-{7-Amino-2-[(2,4-dichlorophenyl)amino]-1H-benzimidazol-1-yl}pentan-1-ol

To a solution of N-{3-amino-2-[(5-hydroxypentyl)amino]phenyl}-N'-(2,4-dichlorophenyl)thiourea (Reference Example 111; 554 mg, 1.34 mmol) in tetrahydrofuran (15 mL) was added 1-ethyl-3-(3-dimethylaminopropyl)carbodiimide hydrochloride (771 mg, 4.02 mmol) at room temperature. The resultant mixture was stirred at 40° C. for 2.5 hr. The reaction mixture was diluted with ethyl acetate, washed with water and brine, dried over anhydrous sodium sulfate, filtered and concentrated in vacuo. The residue was purified by flash column chromatography on silica gel eluting with a 30-90% ethyl acetate/n-hexane gradient mixture to give the title compound as an oil (308 mg, 0.813 mmol, 61%).

$^1$H NMR (CDCl$_3$) δ 1.42-1.68 (m, 4 H), 1.85-1.97 (m, 2 H), 3.59 (brs, 2 H), 3.62 (t, J=6.0 Hz, 2 H), 4.24 (t, J=7.4 Hz, 2 H), 6.51 (dd, J=7.8, 0.8 Hz, 1 H), 6.74 (brs, 1H), 6.98 (t, J=7.8 Hz, 1 H), 7.14 (d, J=7.8 Hz, 1 H), 7.25 (dd, J=8.9, 2.3 Hz, 1 H), 7.37 (d, J=2.3 Hz, 1 H), 8.31 (d, J=8.9 Hz, 1 H), hidden (1H).

MS Calcd.: 378; MS Found: 379 (M+H).

Reference Example 113

5-[2-[(2,4-Dichlorophenyl)amino]-7-(diethylamino)-1H-benzimidazol-1-yl]pentan-1-ol To a solution of methyl 5-{7-amino-2-[(2,4-dichlorophenyl)amino]-1H-benzimidazol-1-yl}pentan-1-ol (Reference Example 112; 308 mg, 1.85 mmol) in methanol (8 mL) and acetic acid (0.160 mL) was added acetaldehyde (0.304 mL, 4.88 mmol) at 0° C. The resultant mixture was stirred at 0° C. for 30 min. To the reaction mixture was added sodium acetoxyborohydride (1.03 g, 4.86 mmol) at 0° C. After the resultant mixture was stirred at room temperature for 14 hr, the mixture was diluted with aqueous sodium hydrogen carbonate and extracted with ethyl acetate. The combined organic layer was washed with brine, dried over anhydrous sodium sulfate, filtered and concentrated in vacuo. The residue was purified by column chromatography on silica gel eluting with ethyl acetate to give the title compound as a solid (317 mg, 0.729 mmol, 90%).

$^1$H NMR (CDCl$_3$) 1.02 (t, J=7.1 Hz, 6 H), 1.40-1.52 (m, 2 H), 1.54-1.64 (m, 2 H), 1.71-1.86 (m, 2 H), 3.01-3.12 (m, 4 H), 3.61 (t, J=6.3 Hz, 2 H), 4.47-4.56 (m, 2 H), 6.96 (dd, J=7.8, 1.0 Hz, 1 H), 7.10 (t, J=7.8 Hz, 1 H), 7.27 (dd, J=8.9, 2.5 Hz, 1 H), 7.33-7.39 (m, 2 H), 8.50 (d, J=8.9 Hz, 1 H), hidden (2H).

MS Calcd.: 434; MS Found: 435 (M+H).

Reference Example 114

3-[(2,6-Dinitrophenyl)amino]propan-1-ol

A mixture of 3-amino-1-propanol (6.77 mL, 89.0 mmol), 2-chloro-1,3-dinitrobenzene (15.0 g, 74.1 mmol), triethylamine (12.4 mL, 89.0 mmol) and tetrahydrofuran (370 mL) was stirred at room temperature for 12 hr. The reaction mixture was diluted with ethyl acetate, washed with water and brine, dried over anhydrous sodium sulfate, filtered and concentrated in vacuo to give the title compound as a solid (17.7 g, 73.3 mmol, 99%).

$^1$H NMR (CDCl$_3$) δ 1.87-1.97 (m, 2 H), 3.10-3.19 (m, 2 H), 3.83 (t, J=5.8 Hz, 2 H), 6.73 (t, J=8.1 Hz, 1 H), 8.16 (d, J=8.1 Hz, 2 H), 8.64 (brs, 1 H), hidden (1H).

MS Calcd.: 241; MS Found: 242 (M+H).

Reference Example 115

3-[(2,6-Diaminophenyl)amino]propan-1-ol

Under hydrogen gas atmosphere, a mixture of 3-[(2,6-dinitrophenyl)amino]propan-1-ol (Reference Example 114; 17.7 g, 73.3 mmol), 10% palladium on carbon (50% wet, 3.5 g) and tetrahydrofuran (360 mL) was stirred at room temperature for 6 hr. The reaction mixture was filtered and concentrated in vacuo to give the title compound as an oil (12.1 g, 66.7 mmol, 91%).

¹H NMR (CDCl₃) δ 1.79-1.90 (m, 2 H), 3.07-3.13 (m, 2 H), 3.90 (t, J=5.8 Hz, 2 H), 6.21 (d, J=7.8 Hz, 2 H), 6.74 (t, J=7.8 Hz, 1 H), hidden (6H).

MS Calcd.: 181; MS Found: 182 (M+H).

Reference Example 116

Methyl 3-amino-4-chloro-2-[(3-hydroxypropyl) amino]benzoate

N-Chlorosuccinimide (74.1 g, 555 mmol) was added to a stirred solution of methyl 3-amino-2-[(3-hydroxypropyl) amino]benzoate (81.9 g, 370 mmol) in acetonitrile (1480 mL) at room temperature, and the mixture was stirred at room temperature for 16 hr. Additional N-chlorosuccinimide (9.88 g, 74.0 mmol) was added to the mixture, and the mixture was stirred at room temperature for 90 min. The mixture was diluted with saturated aqueous sodium hydrogen carbonate, concentrated in vacuo, and extracted with ethyl acetate. The combined organic layer was washed with brine, dried over anhydrous magnesium sulfate, filtered and concentrated in vacuo. The residue was purified by flash column chromatography on silica gel eluting with a 20-45% ethyl acetate/n-hexane gradient mixture. The filtrate was concentrated in vacuo to give the title compound as a brown oil (15.7 g, 60.8 mmol, 16%).

¹H NMR (CDCl₃) δ 1.79-1.87 (m, 2H), 2.33 (s, 1H), 3.15 (t, J=6.3 Hz, 2H), 3.81-3.93 (m, 2H), 3.86 (s, 3H), 4.41 (s, 2H), 6.22 (s, 1H), 6.95 (d, J=9.0 Hz, 1H), 7.29 (d, J=9.0 Hz, 1H).

MS Calcd.: 258; MS Found: 259 (M+H).

Reference Example 117

Methyl 4-chloro-2-[(2,4-dichlorophenyl)amino]-1-(3-hydroxypropyl)-1H-benzimidazole-7-carboxylate A mixture of methyl 3-amino-4-chloro-2-[(3-hydroxypropyl)amino]benzoate (13.1 g, 50.6 mmol) and 2,4-dichloro-1-isothiocyanatobenzene (13.4 g, 65.8 mmol) in tetrahydrofuran (150 mL) was stirred at room temperature for 3 days. The mixture was diluted with saturated aqueous sodium hydrogen carbonate, concentrated in vacuo, and extracted with ethyl acetate. The combined organic layer was washed with brine, dried over anhydrous magnesium sulfate, filtered and concentrated in vacuo. The residue was washed with diisopropyl ether to give methyl 4-chloro-3-{[(2,4-dichlorophenyl)carbamothioyl]amino}-2-[(3-hydroxypropyl)amino] benzoate as a colorless powder (19.6 g)

MS Calcd.: 461; MS Found: 462 (M+H).

A mixture of the resulting thiourea (19.6 g), 1-ethyl-3-(3-dimethylaminopropyl)carbodiimide hydrochloride (8.12 g, 42.3 mmol), and triethylamine (6.5 mL) in tetrahydrofuran (200 mL) was stirred at 50° C. for 3 hr. The mixture was concentrated in vacuo, diluted with saturated aqueous sodium hydrogen carbonate, and extracted with ethyl acetate. The combined organic layer was washed with brine, dried over anhydrous magnesium sulfate, filtered and concentrated in vacuo. The residue was washed with diisopropyl ether to give the title compound as a colorless powder (15.4 g, 35.9 mmol, 71% in 2 steps).

¹H NMR (CDCl₃) δ 2.00-2.11 (m, 3H), 3.54-3.61 (m, 2H), 3.95 (s, 3H), 4.64 (t, J=6.3 Hz, 2H), 7.22 (d, J=8.7 Hz, 1H), 7.28 (dd, J=2.4 Hz, 9.0 Hz, 1H), 7.35 (d, J=2.4 Hz, 1H), 7.59 (d, J=8.7 Hz, 1H), 8.00 (s, 1H), 8.52 (d, J=9.0 Hz, 1H).

MS Calcd.: 427; MS Found: 428 (M+H).

Reference Example 118

Methyl 4-chloro-3-{[(2,4-dichloro-6-methylphenyl) carbamothioyl]amino}-2-[(3-hydroxypropyl)amino] benzoate A mixture of methyl 3-amino-4-chloro-2-[(3-hydroxypropyl)amino]benzoate (1.50 g, 5.80 mmol) and 1,5-dichloro-2-isothiocyanato-3-methylbenzene (1.64 g, 7.52 mmol) in tetrahydrofuran (15 mL) was stirred at 60° C. for 17 hr. The mixture was diluted with saturated aqueous sodium hydrogen carbonate and extracted with ethyl acetate. The combined organic layer was washed with brine, dried over anhydrous magnesium sulfate, filtered and concentrated in vacuo. The residue was washed with diisopropyl ether to give the title compound as a brown powder (2.18 g, 4.57 mmol, 79%).

¹H NMR (CDCl₃) δ 1.89-1.91 (m, 2H), 2.25-2.43 (s, 1H), 2.30 (s, 3H), 3.68-3.80 (m, 4H), 3.88 (s, 3H), 6.85 (d, J=8.4 Hz, 1H), 6.97 (s, 1H), 7.10-7.13 (m, 1H), 7.25-7.27 (m, 1H), 7.92 (d, J=8.4 Hz, 1H), 8.14 (s, 1H), 8.34 (s, 1H).

MS Calcd.: 475; MS Found: 476 (M+H).

Reference Example 119

Methyl 4-chloro-2-{[6-(dimethylamino)-4-methylpyridin-3-yl]amino}-1-(3-hydroxypropyl)-1H-benzimidazole-7-carboxylate A mixture of methyl 3-amino-4-chloro-2-[(3-hydroxypropyl)amino]benzoate (4.00 g, 15.5 mmol) and 5-isothiocyanato-N,N,4-trimethylpyridin-2-amine (8.96 g, 46.4 mmol) in tetrahydrofuran (30 mL) was stirred at 70° C. for 7 hr. The mixture was concentrated in vacuo, and the residue was purified by flash column chromatography on silica gel eluting with a 50-100% ethyl acetate/n-hexane gradient mixture. The filtrate was concentrated in vacuo to give methyl 4-chloro-3-({[6-(dimethylamino)-4-methylpyridin-3-yl] carbamothioyl}amino)-2-[(3-hydroxypropyl)amino]benzoate as a brown amorphous (3.01 g).

MS Calcd.: 451; MS Found: 452 (M+H).

A mixture of the resulting thiourea (3.01 g), 1-ethyl-3-(3-dimethylaminopropyl)carbodiimide hydrochloride (1.28 g, 6.66 mmol), and triethylamine (0.93 mL) in tetrahydrofuran (30 mL) was stirred at 50° C. for 90 min. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with diisopropyl ether to give the title compound as a colorless powder (2.20 g, 5.26 mmol, 34% in 2 steps).

¹H NMR (DMSO-d₆) δ 1.71-1.79 (m, 2H), 2.15 (s, 3H), 3.03 (s, 6H), 3.30-3.40 (m, 2H), 3.90 (s, 3H), 4.41 (t, J=6.9 Hz, 2H), 4.73 (t, J=4.8 Hz, 1H), 6.59 (s, 1H), 7.11 (d, J=8.4 Hz, 1H), 7.29 (d, J=8.4 Hz, 1H), 8.01 (s, 1H), 8.51 (s, 1H).

MS Calcd.: 417; MS Found: 418 (M+H).

Reference Example 120

Methyl 4-chloro-1-(3-hydroxypropyl)-2-[(6-methoxy-4-methylpyridin-3-yl)amino]-1H-benzimidazole-7-carboxylate A mixture of methyl 3-amino-4-chloro-2-[(3-hydroxypropyl)amino]benzoate (4.00 g, 15.5 mmol) and 5-isothiocyanato-2-methoxy-4-methylpyridine (8.36 g, 46.4 mmol) in tetrahydrofuran (30 mL) was stirred at 70° C. for 8 hr. The mixture was concentrated in vacuo, and the residue was purified by flash column chromatography on silica gel eluting with a 50-100% ethyl acetate/n-hexane gradient mixture. The filtrate was concentrated in vacuo to give methyl 4-chloro-2-[(3-hydroxypropyl)amino]-3-{[(6-methoxy-4-methylpyridin-3-yl)carbamothioyl]amino}benzoate as a brown amorphous (3.90 g).

MS Calcd.: 438; MS Found: 439 (M+H).

A mixture of the resulting thiourea (3.90 g), 1-ethyl-3-(3-dimethylaminopropyl)carbodiimide hydrochloride (1.70 g, 8.89 mmol), and triethylamine (1.2 mL) in tetrahydrofuran (40 mL) was stirred at 50° C. for 2 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with diisopropyl ether to give the title compound as a colorless powder (2.20 g, 8.89 mmol, 57% in 2 steps).

$^1$H NMR (DMSO-$d_6$) δ 1.72-1.80 (m, 2H), 2.20 (s, 3H), 3.32-3.40 (m, 2H), 3.86 (s, 3H), 3.91 (s, 3H), 4.44 (t, J=6.9 Hz, 2H), 4.78 (t, J=4.8 Hz, 1H), 6.79 (s, 1H), 7.15 (d, J=8.7 Hz, 1H), 7.33 (d, J=8.7 Hz, 1H), 8.18 (s, 1H), 8.69 (s, 1H).

MS Calcd.: 404; MS Found: 405 (M+H).

Reference Example 121

Methyl 4-chloro-2-{[6-(dimethylamino)-2-methylpyridin-3-yl]amino}-1-(3-hydroxypropyl)-1H-benzimidazole-7-carboxylate A mixture of methyl 3-amino-4-chloro-2-[(3-hydroxypropyl)amino]benzoate (1.13 g, 4.38 mmol) and 5-isothiocyanato-N,N,6-trimethylpyridin-2-amine (1.27 g, 6.57 mmol) in tetrahydrofuran (15 mL) was stirred at 65° C. for 3 days. The mixture was concentrated in vacuo, and the residue was washed with ethyl acetate/diisopropyl ether to give methyl 4-chloro-3-({[6-(dimethylamino)-2-methylpyridin-3-yl]carbamothioyl}amino)-2-[(3-hydroxypropyl)amino]benzoate as a brown amorphous (1.09 g).

MS Calcd.: 451; MS Found: 452 (M+H).

A mixture of the resulting thiourea (1.09 g), 1-ethyl-3-(3-dimethylaminopropyl)carbodiimide hydrochloride (509 mg, 2.65 mmol), and triethylamine (0.37 mL) in tetrahydrofuran (10 mL) was stirred at 50° C. for 3 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 30-80% ethyl acetate/n-hexane gradient mixture. The filtrate was concentrated in vacuo to give the title compound as a colorless solid (510 mg, 1.22 mmol, 28% in 2 steps).

$^1$H NMR (CDCl$_3$) δ 2.04-2.12 (m, 2H), 2.35 (s, 1H), 2.39 (s, 3H), 3.05 (s, 6H), 3.63-3.69 (m, 2H), 3.93 (s, 3H), 4.49 (t, J=6.0 Hz, 2H), 6.41 (d, J=9.0 Hz, 1H), 7.12 (d, J=8.4 Hz, 1H), 7.26 (s, 1H), 7.48 (d, J=8.4 Hz, 1H), 7.87 (d, J=9.0 Hz, 1H).

MS Calcd.: 417; MS Found: 418 (M+H).

Reference Example 122

Methyl 4-chloro-3-{[(3,5-dichloropyridin-2-yl)carbamothioyl]amino}-2-[(3-hydroxypropyl)amino] benzoate A mixture of methyl 3-amino-4-chloro-2-[(3-hydroxypropyl)amino]benzoate (3.13 g, 12.1 mmol) and 3,5-dichloro-2-isothiocyanatopyridine (3.23 g, 15.7 mmol) in tetrahydrofuran (40 mL) was stirred at room temperature for 3 days. The mixture was concentrated in vacuo, and the residue was washed with ethyl acetate/diisopropyl ether to give the title compound as a colorless crystal (3.43 g, 7.4.0 mmol, 61%).

$^1$H NMR (CDCl$_3$) δ 1.65 (t, J=5.4 Hz, 1H), 1.79-1.87 (m, 2H), 3.44-3.62 (m, 2H), 3.67-3.76 (m, 2H), 3.85 (s, 3H), 6.79 (d, J=8.7 Hz, 1H), 7.81 (d, J=2.1 Hz, 1H), 7.88 (d, J=8.7 Hz, 1H), 7.94 (s, 1H), 8.14 (d, J=2.1 Hz, 1H), 8.79 (s, 1H), 12.29 (s, 1H).

MS Calcd.: 462; MS Found: 463 (M+H).

Reference Example 123

Methyl 4-chloro-2-[(3,5-dichloropyridin-2-yl) amino]-1-(3-hydroxypropyl)-1H-benzimidazole-7-carboxylate A mixture of methyl 4-chloro-3-{[(3,5-dichloropyridin-2-yl)carbamothioyl]amino}-2-[(3-hydroxypropyl)amino]benzoate (3.58 g, 7.73 mmol), 1-ethyl-3-(3-dimethylaminopropyl)carbodiimide hydrochloride (1.63 g, 8.50 mmol), and triethylamine (1.2 mL) in tetrahydrofuran (30 mL) was stirred at 50° C. for 3 hr. The mixture was diluted with saturated aqueous sodium hydrogen carbonate, and extracted with tetrahydrofuran/ethyl acetate. The combined organic layer was washed with brine, dried over anhydrous magnesium sulfate, filtered and concentrated in vacuo. The residue was washed with diisopropyl ether to give the title compound as a colorless powder (3.32 g, 7.73 mmol, 100%).

$^1$H NMR (CDCl$_3$) δ 1.85-1.95 (m, 2H), 3.38-3.49 (m, 2H), 3.97 (s, 3H), 4.66 (t, J=7.2 Hz, 1H), 4.75 (t, J=6.0 Hz, 2H), 7.18 (d, J=8.4 Hz, 1H), 7.56 (d, J=8.4 Hz, 1H), 7.70 (d, J=2.4 Hz, 1H), 8.19 (d, J=2.4 Hz, 1H), 12.80 (s, 1H).

MS Calcd.: 428; MS Found: 429 (M+H).

Reference Example 124

Methyl 4-chloro-2-[(4,6-dimethoxy-2-methylpyrimidin-5-yl)amino]-1-(3-hydroxypropyl)-1H-benzimidazole-7-carboxylate A mixture of methyl 3-amino-4-chloro-2-[(3-hydroxypropyl)amino]benzoate (2.00 g, 7.73 mmol) and 5-isothiocyanato-4,6-dimethoxy-2-methylpyrimidine (4.89 g, 23.2 mmol) in tetrahydrofuran (25 mL) was stirred at 70° C. for 3 days. The mixture was concentrated in vacuo, and the residue was purified by flash column chromatography on silica gel eluting with a 40-100% ethyl acetate/n-hexane gradient mixture. The filtrate was concentrated in vacuo to give methyl 4-chloro-3-{[(4,6-dimethoxy-2-methylpyrimidin-5-yl)carbamothioyl]amino}-2-[(3-hydroxypropyl)amino]benzoate (435 mg).

MS Calcd.: 469; MS Found: 470 (M+H).

A mixture of the resulting thiourea (435 mg), 1-ethyl-3-(3-dimethylaminopropyl)carbodiimide hydrochloride (195 mg, 1.02 mmol), and triethylamine (0.15 mL) in tetrahydrofuran (5.0 mL) was stirred at 50° C. for 13 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with diisopropyl ether to give the title compound as a colorless powder (210 mg, 0.482 mmol, 6% in 2 steps).

$^1$H NMR (CDCl$_3$) δ 1.99-2.08 (m, 2H), 2.19-2.24 (m, 1H), 2.54 (s, 3H), 3.57-3.64 (m, 2H), 3.94 (s, 6H), 3.95 (s, 3H), 4.59 (t, J=6.0 Hz, 2H), 7.01 (s, 1H), 7.12 (d, J=8.4 Hz, 1H), 7.50 (d, J=8.4 Hz, 1H).

MS Calcd.: 435; MS Found: 436 (M+H).

Reference Example 125

Methyl 4-chloro-2-[(4,6-diethyl-2-methylpyrimidin-5-yl)amino]-1-(3-hydroxypropyl)-1H-benzimidazole-7-carboxylate A mixture of methyl 3-amino-4-chloro-2-[(3-hydroxypropyl)amino]benzoate (3.30 g, 12.8 mmol) and 4,6-diethyl-5-isothiocyanato-2-methylpyrimidine (5.28 g, 25.5 mmol) in tetrahydrofuran (25 mL) was stirred at 65° C. for 3 days. The mixture was concentrated in vacuo, and the residue was purified by flash column chromatography on silica gel eluting with a 50-100% ethyl acetate/n-hexane gradient mixture. The filtrate was concentrated in vacuo to give methyl 4-chloro-3-{[(4,6-diethyl-2-methylpyrimidin-5-yl)carbamothioyl]amino}-2-[(3-hydroxypropyl)amino]benzoate as a yellow solid (3.22 g).

MS Calcd.: 465; MS Found: 466 (M+H).

A mixture of the resulting thiourea (3.22 g), 1-ethyl-3-(3-dimethylaminopropyl)carbodiimide hydrochloride (1.46 g, 7.59 mmol), and triethylamine (1.1 mL) in tetrahydrofuran (35 mL) was stirred at 60° C. for 2 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with ethyl acetate/diisopropyl ether to give the title compound as a colorless powder (2.90 g, 6.71 mmol, 52% in 2 steps).

$^1$H NMR (CDCl$_3$) δ 1.24 (t, J=7.5 Hz, 6H), 2.15-2.25 (m, 2H), 2.31-2.37 (m, 1H), 2.68 (q, J=7.5 Hz, 4H), 2.71 (s, 3H), 3.76-3.85 (m, 2H), 3.95 (m, 3H), 4.59 (t, J=6.0 Hz, 2H), 7.12 (d, J=8.7 Hz, 1H), 7.50 (s, 1H), 7.52 (d, J=8.7 Hz, 1H).

MS Calcd.: 431; MS Found: 432 (M+H).

Reference Example 126

Methyl 4-chloro-2-[(3-hydroxypropyl)amino]-3-{[(2-methoxy-4,6-dimethylpyrimidin-5-yl)carbamothioyl]amino}benzoate A mixture of methyl 3-amino-4-chloro-2-[(3-hydroxypropyl)amino]benzoate (11.4 g, 44.2 mmol) and 5-isothiocyanato-2-methoxy-4,6-dimethylpyrimidine (17.3 g, 88.4 mmol) in tetrahydrofuran (170 mL) was stirred at 65° C. for 3 days. The mixture was concentrated in vacuo, and the residue was purified by flash column chromatography on silica gel eluting with a 50-100% ethyl acetate/n-hexane gradient mixture. The filtrate was concentrated in vacuo to give the title compound as a yellow amorphous (13.1 g, 28.9 mmol, 65%).

$^1$H NMR (CDCl$_3$) δ 1.81-1.94 (m, 2H), 2.36 (s, 6H), 2.51-2.57 (brs, 1H), 3.60-3.80 (m, 4H), 3.89 (s, 3H), 3.95 (s, 3H), 6.75 (s, 1H), 6.88 (d, J=9.0 Hz, 1H), 7.94 (d, J=9.0 Hz, 1H), 8.15 (s, 1H), 8.26 (s, 1H).

MS Calcd.: 453; MS Found: 454 (M+H).

Reference Example 127

Methyl 4-chloro-1-(3-hydroxypropyl)-2-[(2-methoxy-4,6-dimethylpyrimidin-5-yl)amino]-1H-benzimidazole-7-carboxylate A mixture of methyl 4-chloro-2-[(3-hydroxypropyl)amino]-3-{[(2-methoxy-4,6-dimethylpyrimidin-5-yl)carbamothioyl]amino}benzoate (13.1 g, 28.9 mmol), 1-ethyl-3-(3-dimethylaminopropyl)carbodiimide hydrochloride (6.10 g, 31.8 mmol), and triethylamine (4.4 mL) in tetrahydrofuran (96 mL) was stirred at 60° C. for 2 hr. The mixture was diluted with saturated aqueous sodium hydrogen carbonate, and extracted with tetrahydrofuran/ethyl acetate. The combined organic layer was washed with brine, dried over anhydrous magnesium sulfate, filtered and concentrated in vacuo. The residue was washed with ethyl acetate/diisopropyl ether to give the title compound as a pale yellow powder (11.9 g, 28.3 mmol, 98%).

$^1$H NMR (DMSO-d$_6$) δ 1.73-1.81 (m, 2H), 2.31 (s, 6H), 3.31-3.42 (m, 2H), 3.91 (s, 3H), 3.92 (s, 3H), 4.46 (t, J=Hz, 2H), 4.70-4.76 (m, 1H), 7.13 (d, J=8.4 Hz, 1H), 7.32 (d, J=8.4 Hz, 1H), 8.69 (s, 1H).

MS Calcd.: 419; MS Found: 420 (M+H).

Reference Example 128

Methyl 2-[(4-carbamoyl-2-methylphenyl)amino]-4-chloro-1-(3-hydroxypropyl)-1H-benzimidazole-7-carboxylate A mixture of methyl 3-amino-4-chloro-2-[(3-hydroxypropyl)amino]benzoate (2.09 g, 8.08 mmol) and 4-isothiocyanato-3-methylbenzamide (2.33 g, 12.1 mmol) in tetrahydrofuran (20 mL) was stirred at 60° C. for 2 days. The mixture was concentrated in vacuo, and the residue was washed with ethyl acetate to give methyl 3-{[(4-carbamoyl-2-methylphenyl)carbamothioyl]amino}-4-chloro-2-[(3-hydroxypropyl)amino]benzoate as a colorless powder (2.10 g).

MS Calcd.: 450; MS Found: 451 (M+H).

A mixture of the resulting thiourea (2.10 g), 1-ethyl-3-(3-dimethylaminopropyl)carbodiimide hydrochloride (981 mg, 5.12 mmol), and triethylamine (0.72 mL) in tetrahydrofuran (60 mL) was stirred at 50° C. for 2 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with ethyl acetate to give the title compound as a colorless powder (1.30 g, 3.12 mmol, 39% in 2 steps).

$^1$H NMR (DMSO-d$_6$) δ 1.74 (t, J=6.0 Hz, 3H), 2.30 (s, 3H), 3.25-3.40 (m, 2H), 3.91 (s, 3H), 4.47 (t, J=6.6 Hz, 2H), 4.94 (t, J=6.6 Hz, 1H), 7.23 (d, J=8.1 Hz, 1H), 7.41 (d, J=8.1 Hz, 1H), 7.71-7.95 (m, 4H), 8.70 (s, 1H).

MS Calcd.: 416; MS Found: 417 (M+H).

Reference Example 129

1,5-Dichloro-2-isothiocyanato-3-methylbenzene

Thiophosgene (17.0 g, 148 mmol) was added dropwise to a stirred mixture of 2,4-dichloro-6-methylaniline (20.0 g, 114 mmol) in tetrahydrofuran (100 mL) and saturated aqueous sodium hydrogen carbonate (100 mL) at 0° C., and the mixture was stirred at room temperature for 90 minutes. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with n-hexane to give the title compound as a colorless powder (14.4 g, 66.0 mmol, 58%).

$^1$H NMR (CDCl$_3$) δ 2.38 (s, 3H), 7.08-7.10 (m, 1H), 7.25-7.26 (m, 1H).

Reference Example 130

5-Isothiocyanato-2-methoxy-4-methylpyridine

Thiophosgene (8.9 mL, 120 mmol) was added dropwise to a stirred mixture of 6-methoxy-4-methylpyridin-3-amine (13.8 g, 99.8 mmol) in tetrahydrofuran (100 mL) and saturated aqueous sodium hydrogen carbonate (150 mL) at 0° C., and the mixture was stirred at 0° C. for 2 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with n-hexane to give the title compound as a colorless powder (10.6 g, 58.8 mmol, 59%).
$^1$H NMR (CDCl$_3$) δ 2.34 (s, 3H), 3.90 (s, 3H), 6.58 (s, 1H).
MS Calcd.: 180; MS Found: 181 (M+H).

Reference Example 131

N,N,4-Trimethyl-5-nitropyridin-2-amine

Dimethylamine (50% solution in water, 20 mL) was added to a stirred solution of 2-chloro-4-methyl-5-nitropyridine (15.0 g, 86.9 mmol) in tetrahydrofuran (150 mL), and the mixture was stirred at 0° C. for 2 hr. The mixture was concentrated in vacuo, diluted with saturated aqueous sodium hydrogen carbonate and extracted with ethyl acetate. The combined organic layer was washed with brine, dried over anhydrous magnesium sulfate, filtered and concentrated in vacuo to give the title compound as a yellow solid (15.7 g, 86.6 mmol, 99%).
$^1$H NMR (CDCl$_3$) δ 2.61 (s, 3H), 3.20 (s, 6H), 6.24 (s, 1H), 8.99 (s, 1H).
MS Calcd.: 181; MS Found: 182 (M+H).

Reference Example 132

N$^2$,N$^2$,4-Trimethylpyridine-2,5-diamine

To a solution of N,N,4-trimethyl-5-nitropyridin-2-amine (15.7 g, 86.6 mmol) in ethanol (200 ml) was added 10% palladium on carbon (50% wet, 1.57 g), and the mixture was purged with hydrogen and stirred under balloon pressure hydrogen at room temperature for 2 days. The catalyst was removed by filtration, and the filtrate was concentrated in vacuo to give the title compound as a brown solid (15.7 g), which was used next reaction without purification.
$^1$H NMR (CDCl$_3$) δ 2.16 (s, 3H), 2.98 (s, 6H), 3.13 (s, 2H), 6.35 (s, 1H), 7.69 (s, 1H).
MS Calcd.: 151; MS Found: 152 (M+H).

Reference Example 133

5-Isothiocyanato-N,N,4-trimethylpyridin-2-amine

Thiophosgene (9.3 mL, 125 mmol) was added dropwise to a stirred mixture of N$^2$,N$^2$,4-trimethylpyridine-2,5-diamine (15.7 g) in tetrahydrofuran (100 mL) and saturated aqueous sodium hydrogen carbonate (150 mL) at 0° C., and the mixture was stirred at 0° C. for 2 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with n-hexane to give the title compound as a colorless powder (14.1 g, 73.0 mmol, 70% in 2 steps).
$^1$H NMR (CDCl$_3$) δ 2.30 (s, 3H), 3.08 (s, 6H), 6.29 (s, 1H), 8.01 (s, 1H).
MS Calcd.: 193; MS Found: 194 (M+H).

Reference Example 134

N,N,6-Trimethyl-5-nitropyridin-2-amine

Potassium t-butoxide (18.3 g, 163 mmol) was added to a stirred solution of 6-methyl-5-nitropyridin-2-amine (9.98 g, 65.2 mmol) and methyl iodide (10.1 mL, 163 mmol) in tetrahydrofuran (200 mL) at 0° C., and the mixture was stirred at room temperature for 15 hr. The mixture was diluted with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 5-50% ethyl acetate/n-hexane gradient mixture. The filtrate was concentrated in vacuo to give the title compound as a yellow solid (2.73 g, 15.1 mmol, 23%).
$^1$H NMR (CDCl$_3$) δ 2.79 (s, 3H), 3.20 (s, 6H), 6.35 (d, J=9.3 Hz, 1H), 8.21 (d, J=9.3 Hz, 1H).

Reference Example 135

N$^2$,N$^2$,6-Trimethylpyridine-2,5-diamine

To a solution of N,N,6-trimethyl-5-nitropyridin-2-amine (2.73 g, 15.1 mmol) in tetrahydrofuran (50 mL) was added 10% palladium on carbon (50% wet, 273 mg), and the mixture was purged with hydrogen and stirred under balloon pressure hydrogen at room temperature for 14 hr. The catalyst was removed by filtration, and the filtrate was concentrated in vacuo to give the title compound as a brown solid (2.30 g, 15.1 mmol).
$^1$H NMR (CDCl$_3$) 2.33 (s, 3H), 2.98 (s, 6H), 3.11 (s, 2H), 6.31 (d, J=8.7 Hz, 1H), 6.88 (d, J=8.7 Hz, 1H).
MS Calcd.: 151; MS Found: 152 (M+H).

Reference Example 136

5-Isothiocyanato-N,N,6-trimethylpyridin-2-amine

Thiophosgene (1.3 mL, 16.7 mmol) was added dropwise to a stirred mixture of N$^2$,N$^2$,6-trimethylpyridine-2,5-diamine (2.30 g, 15.2 mmol) in tetrahydrofuran (20 mL) and saturated aqueous sodium hydrogen carbonate (20 mL) at 0° C., and the mixture was stirred at 0° C. for 2 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with diisopropyl ether to give the title compound as a pale yellow powder (1.27 g, 6.57 mmol, 43%).
$^1$H NMR (CDCl$_3$) δ 2.53 (s, 3H), 3.13 (s, 6H), 6.33 (d, J=9.0 Hz, 1H), 7.28 (d, J=9.0 Hz, 1H).
MS Calcd.: 193; MS Found: 194 (M+H).

Reference Example 137

3,5-Dichloro-2-isothiocyanatopyridine

Thiophosgene (21.9 ml, 288 mmol) was added dropwise to a stirred mixture of 3,5-dichloropyridin-2-amine (23.5 g, 144 mmol) in tetrahydrofuran (150 mL) and saturated aqueous sodium hydrogen carbonate (150 mL) at 0° C., and the mixture was stirred at room temperature for 4 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 5-30% ethyl acetate/n-hexane gradient mixture. The filtrate was concentrated in vacuo to give the title compound as a yellow solid (11.4 g, 55.6 mmol, 39%).

$^1$H NMR (CDCl$_3$) δ 7.76 (d, J=2.1 Hz, 1H), 8.26 (d, J=2.1 Hz, 1H).

Reference Example 138

4,6-Dimethoxy-2-methylpyrimidin-5-amine

Sodium methoxide (28% solution in methanol, 150 mL) was added dropwise to a stirred solution of 4,6-dichloro-2-methylpyrimidin-5-amine (15.0 g, 84.3 mmol) in methanol (150 mL) at 0° C., and the mixture was stirred at room temperature for 1 hr, at 70° C. for 6 hr. The mixture was concentrated, diluted with aqueous saturated ammonium chloride and extracted with ethyl acetate. The combined organic layer was washed with brine, dried over anhydrous magnesium sulfate, filtered and concentrated in vacuo to give the title compound as a yellow solid (14.2 g, 84.3 mmol, 100%).

$^1$H NMR (CDCl$_3$) δ 2.45 (s, 3H), 3.36 (s, 2H), 3.97 (s, 6H). MS Calcd.: 169; MS Found: 170 (M+H).

Reference Example 139

5-Isothiocyanato-4,6-dimethoxy-2-methylpyrimidine

Thiophosgene (7.7 mL, 101 mmol) was added dropwise to a stirred mixture of 4,6-dimethoxy-2-methylpyrimidin-5-amine (14.2 g, 84.3 mmol) in tetrahydrofuran, (110 mL) and saturated aqueous sodium hydrogen carbonate (110 mL) at 0° C., and the mixture was stirred at 0° C. for 1 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with n-hexane to give the title compound as a brown powder (12.5 g, 59.0 mmol, 70%).

$^1$H NMR (CDCl$_3$) δ 2.50 (s, 3H), 4.02 (s, 6H).

Reference Example 140

2-Isothiocyanato-3,5-dimethylpyrazine

Thiophosgene (1.59 mL, 20.9 mmol) was added dropwise to a stirred mixture of 3,5-dimethylpyrazin-2-amine (1.98 g, 16.1 mmol) in tetrahydrofuran (20 mL) and saturated aqueous sodium hydrogen carbonate (20 mL) at 0° C., and the mixture was stirred at 0° C. for 1 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 10-50% ethyl acetate/n-hexane gradient mixture. The filtrate was concentrated in vacuo to give the title compound as a brown solid (866 mg, 5.24 mmol, 33%).

$^1$H NMR (CDCl$_3$) δ 2.53 (s, 3H), 2.59 (s, 3H), 8.08 (s, 1H). MS Calcd.: 165; MS Found: 166 (M+H).

Reference Example 141

4-Chloro-2-methoxy-6-methyl-5-nitropyrimidine

Sodium methoxide (28% solution in methanol, 47.0 g, 244 mmol) was added dropwise to a stirred solution of 2,4-dichloro-6-methyl-5-nitropyrimidine (48.3 g, 232 mmol) in methanol (600 mL) at 0° C., and the mixture was stirred at 0° C. for 30 min. The mixture was diluted with water, concentrated, and extracted with ethyl acetate. The combined organic layer was washed with brine, dried over anhydrous magnesium sulfate, filtered and concentrated in vacuo. The residue was purified by flash column chromatography on silica gel eluting with a 0-15% ethyl acetate/n-hexane gradient mixture. The filtrate was concentrated in vacuo to give the title compound as a yellow solid (11.9 g, 58.5 mmol, 25%).

$^1$H NMR (CDCl$_3$) δ 2.56 (s, 3H), 4.09 (s, 3H).

Reference Example 142

2-Methoxy-4,6-dimethyl-5-nitropyrimidine

Methylzinc chloride (2.0 M solution in tetrahydrofuran, 14.8 mL, 29.6 mmol) was added dropwise to a solution of 4-chloro-2-methoxy-6-methyl-5-nitropyrimidine (4.01 g, 19.7 mmol) and tetrakis(triphenyl phosphine)palladium (2.20 g, 1.90 mmol) in tetrahydrofuran (60 mL) at 0° C., and the mixture was stirred at 50° C. for 50 minutes. The mixture was diluted with water, and extracted with ethyl acetate. The combined organic layer was washed with brine, dried over anhydrous magnesium sulfate, filtered and concentrated in vacuo. The residue was purified by flash column chromatography on silica gel eluting with a 5-20% ethyl acetate/n-hexane gradient mixture. The filtrate was concentrated in vacuo to give the title compound as a pale yellow solid (3-0.37 g, 18.4 mmol, 93%).

$^1$H NMR (CDCl$_3$) δ 2.54 (s, 6H), 4.05 (s, 3H).

Reference Example 143

2-Methoxy-4,6-dimethylpyrimidin-5-amine

To a solution of 2-methoxy-4,6-dimethyl-5-nitropyrimidine (3.37 g, 18.4 mmol) in tetrahydrofuran (80 mL) was added 10% palladium on carbon (50% wet, 330 mg), and the mixture was purged with hydrogen and stirred under balloon pressure hydrogen at room temperature for 4 hours. The catalyst was removed by filtration, and the filtrate was concentrated in vacuo to give the title compound as a pale yellow solid (2.82 g, 18.4 mmol, 100%).

$^1$H NMR (CDCl$_3$) δ 2.35 (s, 6H), 3.21 (s, 2H), 3.91 (s, 3H). MS Calcd.: 153; MS Found: 154 (M+H).

Reference Example 144

5-Isothiocyanato-2-methoxy-4,6-dimethylpyrimidine

Thiophosgene (1.8 mL, 23.6 mmol) was added dropwise to a stirred mixture of 2-methoxy-4,6-dimethylpyrimidin-5-amine (2.82 g, 18.4 mmol) in tetrahydrofuran (25 mL) and saturated aqueous sodium hydrogen carbonate (25 mL) at 0° C., and the mixture was stirred at 0° C. for 40 minutes. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with diisopropyl ether/n-hexane to give the title compound as a pale yellow powder (3.16 g, 16.2 mmol, 88%).

$^1$H NMR (CDCl$_3$) δ 2.52 (s, 6H), 3.98 (s, 3H).
MS Calcd.: 195; MS Found: 196 (M+H).

Reference Example 145

4,6-Diethyl-2-methylpyrimidin-5-amine

Ethylmagnesium bromide (3.0 M solution in diethyl ether, 100 mL, 300 mmol) was added to a stirred suspension of 4,6-dichloro-2-methylpyrimidin-5-amine (10.7 g, 60.1 mmol) and [1,3-bis(diphenylphosphino)propane]dichloronickel(II) (3.26 g, 6.01 mmol) in tetrahydrofuran (400 mL) at 0° C., and the mixture was stirred at room temperature for 4 hr. The reaction was quenched by water, acidified by 1N hydrochloric acid and extracted with ethyl acetate. The aqueous layer was neutralized by 1N sodium hydroxide, extracted with ethyl acetate, and the combined organic layer was washed with brine, dried over anhydrous magnesium sulfate, filtered and concentrated in vacuo. The residue was purified by flash column chromatography on silica gel eluting with a 10-100% ethyl acetate/n-hexane gradient mixture. The filtrate was concentrated in vacuo to give the title compound as a yellow wax (4.22 g, 25.5 mmol, 42%).

$^1$H NMR (CDCl$_3$) δ 1.28 (t, J=7.5 Hz, 6H), 2.58 (s, 3H), 2.64 (q, J=7.5 Hz, 4H), 3.60 (s, 2H).
MS Calcd.: 165; MS Found: 166 (M+H).

Reference Example 146

4,6-Diethyl-5-isothiocyanato-2-methylpyrimidine

Thiophosgene (2.53 mL, 33.2 mmol) was added dropwise to a stirred mixture of 4,6-diethyl-2-methylpyrimidin-5-amine (4.22 g, 25.5 mmol) in tetrahydrofuran (40 mL) and saturated aqueous sodium hydrogen carbonate (40 mL) at 0° C., and the mixture was stirred at 0° C. for 20 minutes. The mixture was diluted with saturated aqueous sodium hydrogen carbonate, and extracted with ethyl acetate. The combined organic layer was washed with brine, dried over anhydrous magnesium sulfate, filtered and concentrated in vacuo to give the title compound as a pale yellow solid (5.28 g, 25.5 mmol, 100%).

$^1$H NMR (CDCl$_3$) δ 1.31 (t, J=7.5 Hz, 6H), 2.70 (s, 3H), 2.86 (q, J=7.5 Hz, 4H).

Reference Example 147

2-[2,4-Dichloro-7-(1-ethylpropyl)-1H-benzimidazol-1-yl]ethanol

To a solution of isopropyl [2,4-dichloro-7-(1-ethylpropyl)-1H-benzimidazol-1-yl]acetate (2.06 g, 5.773 mmol) in tetrahydrofuran (15.0 mL) was added lithium tetrahydroborate (377.2 mg, 17.318 mmol) at 0° C. The reaction mixture was stirred at 60° C. for 1 hr. After cooling, the reaction mixture was quenched with water at 0° C. and extracted with ethyl acetate (×3). The combined organic layer was washed with brine (×1), dried over anhydrous magnesium sulfate, filtered and concentrated in vacuo. The residue was purified by silica gel column chromatography eluting with a 0-35% ethyl acetate/n-hexane gradient mixture to give the title compound as a colorless solid (883.0 mg, 2.932 mmol, 51%).

$^1$H NMR (CDCl$_3$) δ: 0.85 (t, J=7.29 Hz, 6H), 1.63-1.87 (m, 4H), 2.12 (brs, 1H), 3.07-3.23 (m, 1H), 4.01 (t, J=6.05 Hz, 2H), 4.57 (t, J=6.05 Hz, 2H), 7.04 (d, J=8.25 Hz, 1H), 7.24 (d, J=8.25 Hz, 1H).
MS Calcd.: 300, MS Found: 301 (M+H).

Reference Example 148

3-[(2,6-Dinitrophenyl)amino]-2,2-difluoropropanoic acid

To a solution of 2-chloro-1,3-dinitrobenzene (2.94 g, 14.54 mmol) in methanol (30.0 mL) were added 3-amino-2,2-difluoropropanoic acid (2.0 g, 15.99 mmol), sodium hydrogen carbonate (2.69 g, 31.98 mmol) and water (15 mL). The reaction mixture was stirred at 80° C. for 1 day. The starting material wasn't consumed completely. To the mixture was added sodium hydrogen carbonate (5.88 g, 63.96 mmol) and the mixture was stirred at 80° C. for 0.5 day. After cooling, the solvent was removed. The residue was neutralized with 1N hydrochloric acid (100 mL) and extracted with ethyl acetate (×3). The combined organic layer was washed with brine (×1), dried over anhydrous magnesium sulfate, filtered and concentrated in vacuo to give the title compound as a yellow solid (3.52 g, 12.09 mmol, 83%).

$^1$H NMR (DMSO-d$_6$) δ: 3.58-3.79 (m, 2H), 7.11 (t, J=8.1 Hz, 1H), 7.90 (t, J=6.4 Hz, 1H), 8.30 (d, J=8.1 Hz, 2H).
MS Calcd.: 291, MS Found: 292 (M+H).

Reference Example 149

Ethyl 3-[(2,6-dinitrophenyl)amino]-2,2-difluoropropanoate

To a solution of 3-[(2,6-dinitrophenyl)amino]-2,2-difluoropropanoic acid (3.52 g, 12.09 mmol) in ethanol (30.0 mL) was added sulfuric acid (4 mL) at 0° C. The reaction mixture was stirred at 100° C. for 1 hr. After cooling, the reaction mixture was neutralized with aqueous saturated sodium hydrogen carbonate and the solvent was removed. The residue was extracted with ethyl acetate (×3). The combined organic layer was washed with brine (×1), dried over anhydrous magnesium sulfate, filtered and concentrated in vacuo. The residue was purified by silica gel column chromatography eluting with a 0-20% ethyl acetate/n-hexane gradient mixture to give the title compound as a yellow oil (2.94 g, 9.210 mmol, 76%).

$^1$H NMR (CDCl$_3$) δ: 1.32 (t, J=7.19 Hz, 3H), 3.61 (td, J=5.87, 12.97 Hz, 2H), 4.31 (q, J=7.19 Hz, 2H), 6.96 (t, J=8.33 Hz, 1H), 8.25 (t, J=8.33 Hz, 2H), 8.33 (brs, 1H).
MS Calcd.: 319, MS Found: 320 (M+H).

Reference Example 150

Ethyl 3-[(2,6-diaminophenyl)amino]-2,2-difluoropropanoate

To a solution of ethyl 3-[(2,6-dinitrophenyl)amino]-2,2-difluoropropanoate (2.44 g, 7.644 mmol) in tetrahydrofuran (50 mL) was added 10% palladium on carbon (50% wet; 588.0 mg), and the mixture was purged with hydrogen and stirred under balloon pressure hydrogen at room temperature for 16 hrs. The catalyst was removed by filtration, and the filtrate was concentrated in vacuo to give the title compound as a pale yellow oil (2.00 g, 7.715 mmol, quant.).

¹H NMR (CDCl₃) δ: 1.31 (t, J=7.19 Hz, 3H), 2.70 (brs, 1H), 3.51-3.83 (m, 6H), 4.26 (q, J=7.19 Hz, 2H), 6.19 (d, J=7.95 Hz, 2H), 6.75 (d, J=7.95 Hz, 1H).
MS Calcd.: 259, MS Found: 260 (M+H).

Reference Example 151

Ethyl 3-[(2-amino-6-{[(2,4-dichlorophenyl)carbamothioyl]amino}phenyl)amino]-2,2-difluoropropanoate To a solution of ethyl 3-[(2,6-diaminophenyl)amino]-2,2-difluoropropanoate (998.3 mg, 3.851 mmol) in tetrahydrofuran (20 mL) was added a solution of 2,4-dichlorophenyl isothiocyanate (785.9 mg, 3.851 mmol) at 0° C. The resultant mixture was stirred at 0° C. for 1 hr and warmed to room temperature and stirred for 2 hrs. After removal of solvent, the residue was purified by silica gel column chromatography eluting with a 0-60% ethyl acetate/n-hexane gradient mixture to give the title compound as an amorphous (1.61 g, 3.486 mmol, 91%).
¹H NMR (CDCl₃) δ 1.27 (t, J=7.2 Hz, 3H), 3.62-3.78 (m, 3H), 3.96 (s, 2H), 4.19 (q, J=7.2 Hz, 2H), 6.68-6.81 (m, 2H), 6.96 (t, J=7.9 Hz, 1H), 7.27-7.31 (m, 1H), 7.40 (d, J=2.3 Hz, 1H), 7.76 (s, 1H), 7.83 (s, 1H), 8.10 (d, J=8.7 Hz, 1H).
MS Calcd.: 462; MS Found: 463 (M+H).

Reference Example 152

1-{3-Amino-2-[(2,2-difluoro-3-hydroxypropyl)amino]phenyl}-3-(2,4-dichlorophenyl)thiourea To a solution of ethyl 3-[(2-amino-6-{[(2,4-dichlorophenyl)carbamothioyl]amino}phenyl)amino]-2,2-difluoropropanoate (694.5 mg, 1.50 mmol) in tetrahydrofuran (10 mL) was added lithium tetrahydroborate (65.3 mg, 3.00 mmol) at 0° C. The mixture was stirred at 0° C. for 30 min. The reaction mixture was quenched with H₂O. The mixture was extracted with ethyl acetate (×3). The combined organic layer was washed with brine (×1), dried over anhydrous magnesium sulfate, filtered and concentrated in vacuo. The residue was purified by silica gel column chromatography eluting with a 0-50% ethyl acetate/n-hexane gradient mixture to give a title compound (70.0 mg) and a mixture contained the title compound. The mixture was purified by preparative HPLC to give the title compound as the trifluoroacetic acid salt. The salt was neutralized with aqueous saturated sodium hydrogen carbonate and extracted with ethyl acetate. The extract was washed with brine, dried over anhydrous magnesium sulfate, filtered and concentrated in vacuo to give the title compound as a colorless amorphous (273.3 mg). Total amount was 343.3 mg (0.815 mmol, 54%).
¹H NMR (DMSO-d₆) δ 3.16-3.39 (m, 2H), 3.64-3.89 (m, 2H), 4.95 (s, 2H), 5.65 (t, J=5.9 Hz, 1H), 6.52 (t, J=7.6 Hz, 1H), 6.60 (d, J=7.6 Hz, 1H), 6.79 (t, J=8.0 Hz, 1H), 7.41 (dd, J=2.5, 8.5 Hz, 1H), 7.59 (d, J=8.7 Hz, 1H), 7.66 (d, J=2.7 Hz, 1H), 9.31 (brs, 1H), 9.52 (s, 1H).
MS Calcd.: 420; MS Found: 421 (M+H).

Reference Example 153

3-{7-Amino-2-[(2,4-dichlorophenyl)amino]-1H-benzimidazol-1-yl}-2,2-difluoropropan-1-ol To a mixture of 1-{3-amino-2-[(2,2-difluoro-3-hydroxypropyl)amino]phenyl}-3-(2,4-dichlorophenyl)thiourea (65.0 mg, 0.154 mmol) in tetrahydrofuran (1.5 mL) were added triethylamine (23.4 μL, 0.169 mmol) and 1-ethyl-3-(3-dimethylaminopropyl)-carbodiimide hydrochloride (29.6 mg, 0.154 mmol). The mixture was stirred at 50° C. for 3 hrs. After cooling, the mixture was diluted with water, extracted with ethyl acetate. The combined organic layer was washed with brine, dried over anhydrous magnesium sulfate, filtered and concentrated in vacuo. The residue was purified by silica gel column chromatography eluting with a 0-40% ethyl acetate/n-hexane gradient mixture to give the title compound as an amorphous (53.0 mg, 0.137 mmol, 89%).
¹H NMR (CDCl₃) δ 3.74-4.00 (m, 3H), 4.80 (brs, 2H), 6.49 (brs, 2H), 6.88 (brs, 1H), 7.02 (brs, 1H), 7.22 (d, J=1.9 Hz, 1H), 7.40-7.48 (m, 1H), 8.30 (brs, 1H). (2H hidden)
MS Calcd.: 386; MS Found: 387 (M+H).

Reference Example 154

3-{2-[(2,4-Dichlorophenyl)amino]-7-(diethylamino)-1H-benzimidazol-1-yl}-2,2-difluoropropan-1-ol To a solution of 3-{7-amino-2-[(2,4-dichlorophenyl)amino]-1H-benzimidazol-1-yl}-2,2-difluoropropan-1-ol (51.0 mg, 0.132 mmol) in methanol (1.3 mL) and acetic acid (26 μL) was added acetaldehyde (49 μL, 0.790 mmol) at 0° C. The mixture was stirred at 0° C. for 30 min. To the reaction mixture was added sodium triacetoxyborohydride (176.2 mg, 0.790 mmol) at 0° C. After 1 hr, the mixture was diluted with water and extracted with ethyl acetate (×3). The combined organic layer was washed with brine (×1), dried over anhydrous magnesium sulfate, filtered and concentrated in vacuo. The residue was purified by silica gel column chromatography eluting with a 0-30% ethyl acetate/n-hexane gradient mixture to give the title compound as an amorphous (49.8 mg, 0.112 mmol, 85%).
¹H NMR (CDCl₃) δ 1.10 (t, J=7.0 Hz, 6H), 3.00-3.19 (m, 4H), 3.63-3.88 (m, 2H), 4.94 (brs, 2H), 7.03 (d, J=7.9 Hz, 1H), 7.42 (brs, 2H), 8.38 (brs, 1H). (4H hidden)
MS Calcd.: 442; MS Found: 443 (M+H).

Reference Example 155

Methyl 2-[(4-bromo-2-chlorophenyl)amino]-4-chloro-1-(3-hydroxypropyl)-1H-benzimidazole-7-carboxylate To a solution of methyl 3-amino-4-chloro-2-[(3-hydroxypropyl)amino]benzoate (7.67 g, 29.72 mmol) in tetrahydrofuran (200 mL) was added 4-bromo-2-chloro-1-isothiocyanatobenzene (8.86 g, 35.66 mmol). The reaction mixture was stirred at room temperature for 2.5 d. The starting material wasn't consumed completely. To the mixture was added 4-bromo-2-chloro-1-isothiocyanatobenzene (1.47 g, 5.91 mmol). The reaction mixture was stirred at room temperature for 5 hrs. The solvent was removed by concentration. The residue was washed with diisopropyl ether to give a mixture contained the thiourea. The mixture was subject to next step without further purification. The mixture was dissolved into tetrahydrofuran (200 mL) were added 1-ethyl-3-(3-dimethylaminopropyl)-carbodiimide hydrochloride (4.41 g, 22.97 mmol) and triethylamine (3.50 mL, 25.27 mmol). The reaction mixture was stirred at 50° C. for 13 hrs. After cooling, the mixture was diluted with aqueous sodium hydrogen carbonate and extracted with ethyl acetate (×3). The combined organic layer was washed with brine (×1), dried over anhydrous magnesium sulfate, filtered and concentrated in vacuo.

The residue was washed with diisopropyl ether/ethyl acetate to give the title compound as a colorless solid (9.08 g, 19.19 mmol, 65% (2 steps)).

$^1$H NMR (CDCl$_3$) δ 1.97 (t, J=4.0 Hz, 1H), 2.00-2.11 (m, 2H), 3.56-3.63 (m, 2H), 3.96 (s, 3H), 4.65 (t, J=6.4 Hz, 2H), 7.23 (d, J=8.3 Hz, 1H), 7.44 (dd, J=2.3, 9.1 Hz, 1H), 7.51 (d, J=2.3 Hz, 1H), 7.60 (d, J=8.7 Hz, 1H), 8.00 (s, 1H), 8.51 (d, J=8.7 Hz, 1H).

MS Calcd.: 471; MS Found: 472 (M+H).

Reference Example 156

Methyl 4-chloro-1-(3-hydroxypropyl)-2-[(6-methoxy-2-methylpyridin-3-yl)amino]-1H-benzimidazole-7-carboxylate To a solution of methyl 3-amino-4-chloro-2-[(3-hydroxypropyl)amino]benzoate (2.00 g) in tetrahydrofuran (40.0 mL) was added 3-isothiocyanato-6-methoxy-2-methylpyridine (1.67 g, 9.277 mmol). The reaction mixture was stirred at 70° C. for 14 hrs. The starting material wasn't consumed completely. To the mixture was added 3-isothiocyanato-6-methoxy-2-methylpyridine (1.67 g, 9.277 mmol). The reaction mixture was stirred at 70° C. for 36 hrs. After cooling, the solvent was removed by concentration. The residue was purified by silica gel column chromatography eluting with a 30-80% ethyl acetate/n-hexane gradient mixture to give the mixture contained thiourea and title compound. The mixture was subject to next step without further purification. The mixture was dissolved into tetrahydrofuran (30 mL) were added 1-ethyl-3-(3-dimethylaminopropyl)-carbodiimide hydrochloride (885.7 mg, 4.62 mmol) and triethylamine (0.71 mL, 5.08 mmol). The reaction mixture was stirred at 50° C. for 2 hrs. After cooling, the mixture was diluted with water, extracted with ethyl acetate (×3). The combined organic layer was washed with brine (×1), dried over anhydrous magnesium sulfate, filtered and concentrated in vacuo. The residue was washed with diisopropyl ether to give the title compound as a colorless solid, (1.50 g, 3.72 mmol, 48% (2 steps)).

$^1$H NMR (CDCl$_3$) δ 1.96-2.24 (m, 3H), 2.46 (s, 3H), 3.65-3.78 (m, 2H), 3.91 (s, 3H), 3.95 (s, 3H), 4.56 (t, J=6.2 Hz, 2H), 6.64 (d, J=9.0 Hz, 1H), 7.16 (d, J=8.7 Hz, 1H), 7.44 (brs, 1 H), 7.53 (d, J=8.7 Hz, 1H), 8.17 (d, J=9.0 Hz, 1H).

MS Calcd.: 404; MS Found: 405 (M+H).

Reference Example 157

4-Bromo-2-chloro-1-isothiocyanatobenzene

A mixture of 4-bromo-2-chloroaniline (30.0 g, 0.145 mol) in tetrahydrofuran (150 mL) and aqueous saturated sodium hydrogen carbonate (150 mL) was added thiophosgene (13.3 mL, 0.174 mol) at 0° C. The reaction mixture was stirred at room temperature for 1 hr. The mixture was extracted with ethyl acetate (×3). The combined organic layer was washed with brine (×1), dried over anhydrous magnesium sulfate, filtered and concentrated in vacuo. The residue was washed with cold-n-hexane to give the title compound as a colorless solid (25.51 g, 0.103 mol, 71%).

$^1$H NMR (CDCl$_3$) δ 7.10 (d, J=8.7 Hz, 1H), 7.37 (dd, J=2.3, 8.7 Hz, 1H), 7.59 (d, J=2.3 Hz, 1H).

Reference Example 158

6-Methoxy-2-methyl-3-nitropyridine

A mixture of 2-methoxy-6-methylpyridine (49.15 g, 0.292 mol) and nitric acid (76.0 mL, 0.292 mol) was added dropwise sulfuric acid (177.0 mL, 0.876 mol) at 0° C. The reaction mixture was stirred at room temperature for 1 hr. The mixture was poured into ice-water. The precipitate was collected by filtration and washed with water to give the title compound as a pale yellow solid (53.37 g, 0.317 mol, quant.).

$^1$H NMR (CDCl$_3$) δ 2.82 (s, 3H), 4.02 (s, 3H), 6.67 (d, J=9.1 Hz, 1H), 8.27 (d, J=9.1 Hz, 1H).

MS Calcd.: 168; MS Found: 169 (M+H).

Reference Example 159

6-Methoxy-2-methylpyridin-3-amine

To a solution of 6-methoxy-2-methyl-3-nitropyridine (62.4 g, 0.371 mol) in methanol (1700 mL) was added 10% palladium on carbon (50% wet; 6.24 g), and the mixture was purged with hydrogen and stirred under balloon pressure hydrogen at room temperature for 4.5 hrs. The catalyst was removed by filtration, and the filtrate was concentrated in vacuo to give the title compound as a brown oil (47.0 g, 0.340 mol, 92%).

$^1$H NMR (CDCl$_3$) δ 2.34 (s, 3H), 3.86 (s, 3H), 6.46 (d, J=8.3 Hz, 1H), 6.95 (d, J=8.3 Hz, 1H). 2H hidden MS Calcd.: 138; MS Found: 139 (M+H).

Reference Example 160

3-Isothiocyanato-6-methoxy-2-methylpyridine

A mixture of 6-methoxy-2-methylpyridin-3-amine (10.0 g, 0.0724 mol) in tetrahydrofuran (50 mL) and aqueous saturated sodium hydrogen carbonate (50 mL) was added thiophosgene (6.62 mL, 0.0868 mol) at 0° C. The reaction mixture was stirred at room temperature for 1 hr. The mixture was extracted with ethyl acetate (×3). The combined organic layer was washed with brine (×1), dried over anhydrous magnesium sulfate, filtered and concentrated in vacuo. To the residue was added n-hexane and the precipitate was removed by filtration and the filtrate was concentrated in vacuo. The residue was washed with cold-n-hexane to give the title compound as a pale yellow solid (5.35 g, 0.0297 mol, 41%).

$^1$H NMR (CDCl$_3$) δ 2.52 (s, 3H), 3.91 (s, 3H), 6.55 (d, J=8.7 Hz, 1H), 7.36 (d, J=8.7 Hz, 1H).

MS Calcd.: 180; MS Found: 181 (M+H).

Reference Example 161

Methyl 2-[(4-hydroxybutyl)amino]-3-nitrobenzoate

A solution of methyl 2-chloro-3-nitrobenzoate (53.5 g, 248 mmol), triethylamine (41.5 mL, 298 mmol), and 4-amino-1-butanol (45.7 mL, 496 mmol) in tetrahydrofuran (400 mL) was stirred for 60 h at 50° C. The mixture was diluted with water, concentrated in vacuo, extracted with ethyl acetate, washed with brine, dried over sodium sulfate, filtered and concentrated in vacuo. The residue was purified by flash column chromatography on silica gel eluting with ethyl acetate (short column) to give the title compound as a yellow oil (66.5 g, 248 mmol, 100%).

$^1$H NMR (CDCl$_3$) δ 1.36 (t, J=4.9 Hz, 1H), 1.62-1.83 (m, 4H), 2.93-3.03 (m, 2H), 3.60-3.71 (m, 2H), 3.91 (s, 3H), 6.66 (t, J=7.9 Hz, 1H), 7.95 (dd, J=7.9, 1.8 Hz, 1H), 8.06 (dd, J=7.9, 1.8 Hz, 1H), 8.46 (brs, 1H).

Reference Example 162

Methyl 3-amino-2-[(4-hydroxybutyl)amino]benzoate

A solution of methyl 2-[(4-hydroxybutyl)amino]-3-nitrobenzoate (66.5 g, 248 mmol) in tetrahydrofuran (1600 mL)

was stirred in the presence of 10% palladium on carbon (50% wet; 6.80 g) under hydrogen atmosphere at room temperature for 5 h. The catalyst was removed by filtration, and the filtrate was concentrated in vacuo to give the title compound as a yellow oil (58.4 g, 245 mmol, 99%).

$^1$H NMR (CDCl$_3$) δ 1.56-1.77 (m, 4H), 2.98-3.08 (m, 2H), 3.60-3.71 (m, 2H), 3.88 (s, 3H), 3.91 (brs, 2H), 6.78-6.89 (m, 2H), 7.32-7.43 (m, 1H).

MS Calcd.: 238; MS Found: 239 (M+H).

Reference Example 163

Methyl 3-amino-4-chloro-2-[(4-hydroxybutyl)amino]benzoate

To a stirred solution of methyl 3-amino-2-[(4-hydroxybutyl)amino]benzoate (29.8 g, 125 mmol) in dichloromethane (500 mL) was added N-chlorosuccinimide (33.3 g, 250 mmol) at room temperature. After 4 h, the reaction mixture was quenched with aqueous sodium hydrogen carbonate and purified by flash column chromatography on silica gel eluting with a 30% ethyl acetate/n-hexane mixture to give the title compound as a pale red solid (5.81 g, 21.3 mmol, 17%).

$^1$H NMR (CDCl$_3$) δ 1.57-1.76 (m, 4H), 2.98-3.09 (m, 2H), 3.61-3.70 (m, 2H), 3.87 (s, 3H), 4.30 (brs, 2H), 6.95 (d, J=8.5 Hz, 1H), 7.30 (d, J=8.5 Hz, 1H).

MS Calcd.: 273; MS Found: 273 (M+H).

Reference Example 164

Methyl 4-chloro-3-{[(3,5-dichloropyridin-2-yl)carbamothioyl]amino}-2-[(4-hydroxybutyl)amino]benzoate A solution of methyl 3-amino-4-chloro-2-[(4-hydroxybutyl)amino]benzoate (2.00 g, 7.33 mmol) and 3,5-dichloro-2-isothiocyanatopyridine (1.80 g, 8.80 mmol) in tetrahydrofuran (20 mL) was stirred for 12 h at room temperature. The reaction mixture was concentrated in vacuo and purified by flash column chromatography on NH-silica gel eluting with a 10-80% ethyl acetate/n-hexane gradient mixture to give the title compound as a colorless solid (2.76 g, 5.78 mmol, 79%).

$^1$H NMR (CDCl$_3$) δ 1.35 (brs, 1H), 1.55-1.76 (m, 4H), 3.32-3.56 (m, 2H), 3.62 (t, J=6.0 Hz, 2H), 3.87 (s, 3H), 6.77 (d, J=8.8 Hz, 1H), 7.82 (d, J=2.2 Hz, 1H), 7.89 (d, J=8.8 Hz, 1H), 7.99 (brs, 1H), 8.14 (d, J=2.2 Hz, 1H), 8.78 (brs, 1H), 12.24 (brs, 1H).

MS Calcd.: 476; MS Found: 477 (M+H).

Reference Example 165

Methyl 4-chloro-2-[(3,5-dichloropyridin-2-yl)amino]-1-(4-hydroxybutyl)-1H-benzimidazole-7-carboxylate A suspension of methyl 4-chloro-3-{[(3,5-dichloropyridin-2-yl)carbamothioyl]amino}-2-[(4-hydroxybutyl)amino]benzoate (2.76 g, 5.78 mmol), triethylamine (886 μL, 6.36 mmol), and 1-ethyl-3-(3-dimethylaminopropyl)-carbodiimide hydrochloride (1.22 g, 6.36 mmol) in tetrahydrofuran (25 mL) was stirred at 50° C. for 1 h. The reaction mixture was diluted with ethyl acetate, washed with water and brine, dried over sodium sulfate, filtered and concentrated in vacuo. The resulting solid was washed with diisopropyl ether to give the title compound as a pale yellow solid (2.45 g, 5.52 mmol, 96%).

$^1$H NMR (CDCl$_3$) δ 1.58-1.69 (m, 2H), 1.75-1.92 (m, 2H), 3.73 (t, J=6.1 Hz, 2H), 3.98 (s, 3H), 4.49-4.61 (m, 2H), 7.13 (d, J=8.5 Hz, 1H), 7.55 (d, J=8.5 Hz, 1H), 7.68 (d, J=2.2 Hz, 1H), 8.17 (d, J=2.2 Hz, 1H).

MS Calcd.: 442; MS Found: 443 (M+H).

Reference Example 166

2-Chloro-4-methoxyaniline

A mixture of 4-bromo-2-chloro-aniline (25.0 g, 121 mmol), copper iodide (23.1 g, 121 mmol), and a solution of sodium methoxide in methanol (28%, 125 mL) was stirred for 1 h at 100° C. The reaction mixture was poured into a mixture of hydrochloric acid (6 M, 100 mL) and ice, and washed with ethyl acetate. The aqueous phase was basified with aqueous sodium hydroxide (8 M) and extracted with ethyl acetate. The extracts was washed with brine, dried over sodium sulfate, filtrated, and concentrated in vacuo. The residue was purified by column chromatography on silica gel eluting with a 30% ethyl acetate/n-hexane gradient mixture to give the title compound as a pale yellow oil (7.90 g, 50.1 mmol, 41%).

$^1$H NMR (CDCl$_3$) δ 3.74 (brs, 2H), 3.73 (s, 3H), 6.65-6.75 (m, 2H), 6.85 (dd, J=2.5, 0.5 Hz, 1H).

MS Calcd.: 157; MS Found: 158 (M+H).

Reference Example 167

2-Chloro-1-isothiocyanato-4-methoxybenzene

To a stirred solution of 2-chloro-4-methoxyaniline (7.90 g, 50.1 mmol) in saturated aqueous sodium hydrogen carbonate (40 mL) and tetrahydrofuran (40 mL) was added thiophosgene (4.99 mL, 65.1 mmol) at room temperature. After 30 min, the reaction mixture was extracted with ethyl acetate, washed with aqueous sodium hydrogen carbonate and brine, dried over sodium sulfate, filtrated, and concentrated in vacuo. The resulting solid was washed with n-hexane to give the title compound as a pale red solid (6.85 g, 34.3 mmol, 68%).

$^1$H NMR (CDCl$_3$) δ 3.81 (s, 3H), 6.76 (dd, J=8.9, 2.8 Hz, 1H), 6.95 (d, J=2.8 Hz, 1H), 7.16 (d, J=8.8 Hz, 1H).

Reference Example 168

Methyl 4-chloro-3-{[(2-chloro-4-methoxyphenyl)carbamothioyl]amino}-2-[(4-hydroxybutyl)amino]benzoate A solution of methyl 3-amino-4-chloro-2-[(4-hydroxybutyl)amino]benzoate (2.00 g, 7.33 mmol) and 2-chloro-1-isothiocyanato-4-methoxybenzene (2.94 g, 14.7 mmol) in tetrahydrofuran (20 mL) was stirred for 36 h at 70° C. The reaction mixture was concentrated in vacuo and purified by flash column chromatography on silica gel eluting with a 50% ethyl acetate/n-hexane mixture to give the title compound as a pale yellow oil (1.57 g, 3.32 mmol, 45%).

MS Calcd.: 471; MS Found: 472 (M+H).

Reference Example 169

Methyl 4-chloro-2-[(2-chloro-4-methoxyphenyl)amino]-1-(4-hydroxybutyl)-1H-benzimidazole-7-carboxylate A suspension of methyl 4-chloro-3-{[(2-chloro-4-methoxyphenyl)carbamothioyl]amino}-2-[(4-hydroxybutyl)amino]

benzoate (1.57 g, 3.32 mmol), triethylamine (509 µL, 3.65 mmol), and 1-ethyl-3-(3-dimethylaminopropyl)-carbodiimide hydrochloride (700 mg, 3.65 mmol) in tetrahydrofuran (15 mL) was stirred at 50° C. for 1 h. The reaction mixture was diluted with ethyl acetate, washed with water and brine, dried over sodium sulfate, filtered and concentrated in vacuo. The resulting solid was washed with diisopropyl ether to give the title compound as a pale brown solid (1.31 g, 2.98 mmol, 90%).
$^1$H NMR (CDCl$_3$) δ 1.61-1.71 (m, 2H), 1.82 (brs, 1H), 1.88-2.04 (m, 2H), 3.73 (t, J=6.0 Hz, 2H), 3.81 (s, 3H), 3.96 (s, 3H), 4.43 (t, J=8.0 Hz, 2H), 6.87-7.06 (m, 3H), 7.19 (d, J=8.5 Hz, 1H), 7.59 (d, J=8.5 Hz, 1H), 8.49 (d, J=8.8 Hz, 1H).
MS Calcd.: 437; MS Found: 438 (M+H).

Reference Example 170

2-Chloro-5-fluoro-1,3-dinitrobenzene

To a stirred solution of N,N-dimethylformamide (2.02, 26.1 mmol) in toluene (20 mL) was added thionyl chloride (2.86 mL, 39.2 mmol) at room temperature. After 10 min, 4-fluoro-2,6-dinitrophenol (5.27 g, 26.1 mmol) was added and the mixture was stirred for 7 h at 80° C. The reaction mixture was concentrated in vacuo, and the resulting solid was washed with ethanol to give the title compound as a pale yellow solid (3.24 g, 14.7 mmol, 56%).
$^1$H NMR (CDCl$_3$) δ 7.79 (d, J=6.6 Hz, 2H).

Reference Example 171

3-[(4-Fluoro-2,6-dinitrophenyl)amino]propan-1-ol

To a stirred solution of 2-chloro-5-fluoro-1,3-dinitrobenzene (3.24 g, 14.7 mmol) in tetrahydrofuran (50 mL) was added 3-amino-1-propanol (2.80 mL, 36.8 mmol) at 0° C. After being stirred for 3 h at room temperature, the mixture was diluted with ethyl acetate, washed with aqueous sodium hydrogen carbonate and brine, dried over sodium sulfate, filtrated, and concentrated in vacuo to give the title compound as a yellow solid (3.59 g, 13.8 mmol, 94%).
$^1$H NMR (CDCl$_3$) δ 1.55 (t, J=4.4 Hz, 1H), 1.83-2.00 (m, 2H), 3.04-3.19 (m, 2H), 3.76-3.89 (m, 2H), 7.98 (d, J=7.4 Hz, 2H), 8.47 (brs, 1 H).

Reference Example 172

3-[(2,6-Diamino-4-fluorophenyl)amino]propan-1-ol

A solution of 3-[(4-fluoro-2,6-dinitrophenyl)amino]propan-1-ol (3.59 g, 13.8 mmol) in tetrahydrofuran (140 mL) was stirred in the presence of 10% palladium on carbon (50% wet; 720 mg) under hydrogen atmosphere at room temperature for 1.5 h. The catalyst was removed by filtration, and the filtrate was concentrated in vacuo to give the title compound as a pale brown oil (2.75 g, 13.8 mmol, 100%).
$^1$H NMR (CDCl$_3$) δ 1.78-1.88 (m, 2H), 3.04 (t, J=6.0 Hz, 2H), 3.90 (t, J=5.8 Hz, 2H), 5.90 (d, J=10.4 Hz, 2H).

Reference Example 173 tert-Butyl (2-amino-6-{[(2,4-dichlorophenyl)carbamothioyl]amino}-4-fluorophenyl)(3-hydroxypropyl)carbamate To a stirred solution of 3-[(2,6-diamino-4-fluorophenyl)amino]propan-1-ol (2.13 g, 10.7 mmol) in tetrahydrofuran (50 mL) added di-tert-butyl dicarbonate (2.58 mL, 11.2 mmol) at 0° C. After 24 h, the reaction mixture was warmed up to room temperature. After 12 h, the reaction mixture was concentrated in vacuo, purified by column chromatography on silica gel eluting with a 40-80% ethyl acetate/n-hexane gradient mixture, and dissolved in tetrahydrofuran (20 mL). 2,4-Dichloro-1-isothiocyanatobenzene (1.72 g, 8.45 mmol) was added and the mixture was stirred for 20 h at room temperature. The reaction mixture was concentrated in vacuo, purified by column chromatography on NH-silica gel eluting with ethyl acetate to give the title compound as a colorless amorphous (2.80 g, 5.56 mmol, 52%).
MS Calcd.: 502; MS Found: 503 (M+H).

Reference Example 174

1-{3-Amino-5-fluoro-2-[(3-hydroxypropyl)amino]phenyl}-3-(2,4-dichlorophenyl)thiourea A mixture of tert-butyl (2-amino-6-{[(2,4-dichlorophenyl)carbamothioyl]amino}-4-fluorophenyl) (3-hydroxypropyl)carbamate (2.65 µg, 5.26 mmol) and a solution of hydrogen chloride in ethyl acetate (4 M, 26 mL) was stirred for 20 min at 0° C. The reaction mixture was diluted with ethyl acetate, washed with aqueous sodium hydrogen carbonate and brine, dried over sodium sulfate, filtrated, and concentrated in vacuo. The residue was purified by column chromatography on silica gel eluting with a 50-100% ethyl acetate/n-hexane gradient mixture to give the title compound as a colorless amorphous (1.96 g, 4.86 mmol, 92%).
$^1$H NMR (CDCl$_3$) δ 1.72-1.83 (m, 2H), 3.06 (d, J=5.8 Hz, 2H), 3.92 (t, J=5.5 Hz, 2H), 4.24 (brs, 2H), 6.41 (dd, J=9.9, 2.7 Hz, 1H), 6.67 (dd, J=8.9, 2.7 Hz, 1H), 7.27 (dd, J=8.8, 2.5 Hz, 1H), 7.40 (d, J=2.5 Hz, 1H), 8.08 (d, J=8.8 Hz, 1H), 8.11 (brs, 1H), 8.60 (brs, 1H).
MS Calcd.: 402; MS Found: 403 (M+H).

Reference Example 175

3-{7-Amino-2-[(2,4-dichlorophenyl)amino]-5-fluoro-1H-benzimidazol-1-yl}propan-1-ol A suspension of 1-{3-amino-5-fluoro-2-[(3-hydroxypropyl)amino]phenyl}-3-(2,4-dichlorophenyl)thiourea (1.95 g, 4.84 mmol), triethylamine (743 µL, 5.32 mmol), and 1-ethyl-3-(3-dimethylaminopropyl)-carbodiimide hydrochloride (974 mg, 5.08 mmol) in tetrahydrofuran (25 mL) was stirred at 50° C. for 2 h. The reaction mixture was concentrated in vacuo. The residue was purified by column chromatography on silica gel eluting with a 50-100% ethyl acetate/n-hexane gradient mixture to give the title compound as a colorless amorphous (1.64 g, 4.43 mmol, 92%).
$^1$H NMR (CDCl$_3$) δ 2.09-2.26 (m, 2H), 3.65 (t, J=5.3 Hz, 2H), 3.90 (brs, 2H), 4.41 (t, J=6.2 Hz, 2H), 6.27 (dd, J=10.7, 2.2 Hz, 1H), 6.80 (d, J=9.6 Hz, 1H), 7.24 (dd, J=9.1, 2.5 Hz, 1H), 7.35 (d, J=2.5 Hz, 1H), 7.52 (brs, 1H), 8.29 (brs, 1H).
MS Calcd.: 368; MS Found: 369 (M+H).

Reference Example 176

3-{2-[(2,4-Dichlorophenyl)amino]-7-(diethylamino)-5-fluoro-1H-benzimidazol-1-yl}propan-1-ol To a suspension of 3-{7-amino-2-[(2,4-dichlorophenyl)amino]-5-fluoro-1H-benzimidazol-1-yl}propan-1-ol (369 mg, 1.00 mmol) and acetic acid (0.5 mL) in methanol (10 mL) was added acetaldehyde (374 µL, 6.00 mmol) at room temperature. After 30 min, sodium acetoxyborohydride (1.27 g, 6.00 mmol) was added. After 4 h, the mixture was cooled down to 0° C. Then acetic acid (0.5 mL) and acetoaldehyde (374 μL, 6.00 mmol) was added. After 30 min, sodium acetoxyborohydride (1.27 g, 6.00 mmol) was added. After 1 h, the reaction mixture was quenched with water, concentrated in vacuo, diluted with ethyl acetate, washed with aqueous sodium hydroxide (1 M) and brine, dried over sodium sulfate, filtered and concentrated in vacuo to give the title compound as a solid (408 mg, 0.983 mmol, 98%).

$^1$H NMR (CDCl$_3$) δ 1.07 (t, J=7.1 Hz, 6H), 2.03-2.14 (m, 2H), 2.31 (brs, 1H), 3.07 (q, J=7.1 Hz, 4H), 3.51-3.63 (m, 2H), 4.52 (t, J=6.3 Hz, 2H), 6.73 (dd, J=11.4, 2.3 Hz, 1H), 7.07 (d, J=8.8 Hz, 1H), 7.26 (dd, J=8.9, 2.3 Hz, 1H), 7.37 (d, J=2.3 Hz, 1H), 7.68 (brs, 1 H), 8.42 (d, J=8.9 Hz, 1H).

MS Calcd.: 424; MS Found: 425 (M+H).

Reference Example 177 tert-Butyl [4-chloro-7-(1-ethylpropyl)-1-prop-2-en-1-yl-1H-benzimidazol-2-yl][6-(dimethylamino)-4-methylpyridin-3-yl]carbamate To a solution of N$^5$-[4-chloro-7-(1-ethylpropyl)-1-prop-2-en-1-yl-1H-benzimidazol-2-yl]-N$^2$,N$^2$,4-trimethylpyridine-2,5-diamine (Reference example 93, 82 mg, 0.20 mmol) and triethylamine (0.083 mL, 0.60 mmol) in tetrahydrofuran (1.0 mL) was added di-tert-butyl pyrocarbonate (87 mg, 0.40 mmol) and 4-dimethylaminopyridine (2.4 mg, 0.020 mmol) at room temperature. After stirring for 0.5 hr, solvent was removed in vacuo. The residue was purified by flash chromatography on silica gel eluting with a 3-30% ethyl acetate/n-hexane gradient mixture to give the title compound (105 mg, 0.20 mmol, 103%) as a colorless amorphous.

$^1$H NMR (CDCl$_3$) δ 0.79 (t, J=7.4 Hz, 6 H), 1.42 (s, 9 H), 1.53-1.80 (m, 4 H), 2.56 (s, 3 H), 2.96-3.07 (m, 1 H), 3.04 (s, 6 H), 4.74 (d, J=17.3 Hz, 1 H), 4.92-4.99 (m, 2 H), 5.19-5.26 (m, 1 H), 5.91-6.06 (m, 1 H), 6.39 (s, 1 H), 6.98 (d, J=8.2 Hz, 1 H), 7.21 (d, J=8.2 Hz, 1 H), 8.07 (brs, 1 H).

MS Calcd.: 511; Found: 512 (M+H).

Reference Example 178

3-[4-Chloro-2-{[6-(dimethylamino)-4-methylpyridin-3-yl]amino}-7-(1-ethylpropyl)-1H-benzimidazol-1-yl]propan-1-ol To a solution of tert-butyl [4-chloro-7-(1-ethylpropyl)-1-prop-2-en-1-yl-1H-benzimidazol-2-yl][6-(dimethylamino)-4-methylpyridin-3-yl]carbamate (450 mg, 0.88 mmol) in tetrahydrofuran (8.8 mL) was added borane-tetrahydrofuran complex (1.18 M in tetrahydrofuran, 7.46 mL, 8.8 mmol) at room temperature. After stirring for 2 hr, the mixture was poured into a suspension of sodium peroxyborate tetrahydrate (2.03 g, 13.2 mmol) in water (10 mL). The mixture was stirred for 14 hr at room temperature. The mixture was extracted with ethyl acetate. Organic layer was washed with brine, dried over anhydrous sodium sulfate and concentrated in vacuo. The residue was dissolved in methanol (5 mL) followed by addition of 6 N hydrochloric acid (5 mL). After stirring for 14 hr at room temperature, aqueous sodium bicarbonate was added and the mixture was extracted with ethyl acetate. Organic layer was washed with brine, dried over anhydrous sodium sulfate and concentrated in vacuo. The residue was purified by flash chromatography on silica gel eluting with a 50-100% ethyl acetate/n-hexane gradient mixture to give the title compound (110 mg, 0.26 mmol, 29%) as a colorless solid.

$^1$H NMR (CDCl$_3$) δ 0.82 (t, J=7.3 Hz, 6 H), 1.56-1.97 (m, 6 H), 2.15 (s, 3 H), 3.03 (s, 6 H), 3.10-3.23 (m, 1 H), 3.53-3.62 (m, 2 H), 4.26-4.37 (m, 2 H), 4.97 (br. s., 1 H), 6.59 (s, 1 H), 6.79 (d, J=8.3 Hz, 1 H), 6.99 (d, J=8.3 Hz, 1 H), 8.04 (s, 1 H), 8.23 (brs, 1 H).

MS Calcd.: 429; Found: 430 (M+H).

Reference Example 179

Ethyl 4-{4-chloro-2-[(3,5-dimethylisoxazol-4-yl)amino]-7-(1-ethylpropyl)-1H-benzimidazol-1-yl}butanoate A mixture of ethyl 4-[2,4-dichloro-7-(1-ethylpropyl)-1H-benzimidazol-1-yl]butanoate (Reference Example 33; 740 mg, 2.0 mmol), 3,5-dimethylisoxazol-4-amine (672 mg, 6.0 mmol) and p-toluenesulfonic acid monohydrate (380 mg, 2.0 mmol) in 1-methyl-2-pyrrolidinone (3 mL) was stirred at 130° C. for 16 hr. After cooling, the mixture was diluted with ethyl acetate, washed with aqueous sodium bicarbonate and brine, dried over anhydrous sodium sulfate and concentrated in vacuo. The residue was purified by flash chromatography on silica gel eluting with a 20-60% ethyl acetate/n-hexane gradient mixture followed by recrystallization from ethyl acetate/n-hexane to give the title compound (450 mg, 1.0 mmol, 50%) as a colorless solid.

mp 135-138° C.

$^1$H NMR (CDCl$_3$) δ 0.86 (t, J=7.3 Hz, 6 H), 1.31 (t, J=7.0 Hz, 3 H), 1.61-1.88 (m, 4 H), 2.07-2.21 (m, 2 H), 2.30 (s, 3 H), 2.43 (s, 3 H), 2.50-2.58 (m, 2 H), 2.87-2.99 (m, 1 H), 4.14-4.28 (m, 4 H), 6.82 (d, J=8.3 Hz, 1 H), 7.10 (d, J=8.3 Hz, 1 H), 7.36 (s, 1 H).

MS Calcd.: 446; Found: 447 (M+H).

Reference Example 180

4-{4-Chloro-2-[(3,5-dimethylisoxazol-4-yl)amino]-7-(1-ethylpropyl)-1H-benzimidazol-1-yl}butan-1-ol To a solution of ethyl 4-{4-chloro-2-[(3,5-dimethylisoxazol-4-yl)amino]-7-(1-ethylpropyl)-1H-benzimidazol-1-yl}butanoate (400 mg, 0.90 mmol) in tetrahydrofuran (5 mL) was added lithium borohydride (62 mg, 2.68 mmol) portionwise at 0° C. The mixture was warmed to room temperature and stirred for 16 hr. Additional lithium borohydride (62 mg, 2.68 mmol) was added and the mixture was warmed to 50° C. for 4 hr. Water was added and the mixture was extracted with ethyl acetate. Organic layer was washed with brine, dried over anhydrous sodium sulfate and concentrated in vacuo. The residue was purified by flash chromatography on silica gel eluting with a 50-100% ethyl acetate/n-hexane gradient mixture followed by recrystallization from ethyl acetate/n-hexane to give the title compound (193 mg, 0.47 mmol, 53%) as a colorless solid.

mp 150-155° C.

$^1$H NMR (CDCl$_3$) δ 0.87 (t, J=7.3 Hz, 6 H), 1.63-1.86 (m, 6 H), 1.96-2.07 (m, 2 H), 2.20 (s, 3 H), 2.33 (s, 3 H), 2.90-3.03 (m, 1 H), 3.82-3.92 (m, 2 H), 4.29 (t, J=7.2 Hz, 2 H), 6.83 (d, J=8.3 Hz, 1 H), 7.08 (d, J=8.3 Hz, 1 H).

MS Calcd.: 404; Found: 405 (M+H).

Reference Example 181

4-Bromo-2-methylphenylisothiocyanate

To a solution of 4-bromo-2-methylaniline (11.0 g, 59.0 mmol) and saturated aqueous sodium hydrogen carbonate (150 mL) in tetrahydrofuran (150 mL) was added thiophosgene (4.50 mL, 59.0 mmol), and the mixture was stirred at 0° C. for 30 min. The reaction mixture was extracted with ethyl acetate. The combined organic layer was washed with brine, dried over anhydrous magnesium sulfate, filtered, and concentrated in vacuo. The residual solid was collected by filtration and was washed with n-hexane to give the title compound as a brown powder (8.16 g, 35.8 mmol, 61%).

$^1$H NMR (CDCl$_3$) δ: 2.35 (s, 3H), 7.04 (d, J=8.4 Hz, 1H), 7.27 (m, 1H), 7.35 (s, 1H).

Reference Example 182

4-Methoxy-2-methylphenylisothiocyanate

To a solution of 4-methoxy-2-methylaniline (2.51 mL, 19.7 mmol) and saturated aqueous sodium hydrogen carbonate (13.5 ml) in tetrahydrofuran (13.5 mL) was added thiophosgene (1.50 mL, 19.7 mmol), and the mixture was stirred at 0° C. for 30 min. The reaction mixture was extracted with ethyl acetate. The combined organic layer was washed with brine, dried over anhydrous magnesium sulfate, filtered and concentrated in vacuo. The residue was purified by flash column chromatography on silica gel eluting with a 0-10% ethyl acetate/n-hexane gradient mixture. The desired fractions were concentrated in vacuo to give the title compound as a colorless oil (2.80 g, 15.6 mmol, 79%).

$^1$H NMR (CDCl$_3$) δ: 2.35 (s, 3H), 3.78 (s, 3H), 6.67 (d, J=8.4 Hz, 1H), 6.70 (s, 1H), 7.10 (d, J=8.4 Hz, 1H).

Reference Example 183

$N^1,N^1$-Diethyl-4-fluoro-3-nitrobenzene-1,2-diamine

To a mixture of 4-fluoro-3-nitrobenzene-1,2-diamine (800 mg, 4.67 mmol), sodium acetoxyborohydride (5.94 g, 28.0 mmol), methanol (9 mL) and acetic acid (2.3 mL) was added acetoaldehyde (90%, 1.75 mL, 28.1 mmol) at 0° C. After the resultant mixture was stirred at 0° C. for 30 min, the mixture was diluted with aqueous sodium hydrogen carbonate and aqueous sodium hydroxide and extracted with ethyl acetate. The combined organic layer was washed with brine, dried over anhydrous sodium sulfate, filtered and concentrated in vacuo. The residue was purified by flash column chromatography on silica gel eluting with a 10 ethyl acetate/n-hexane mixture to give the title compound as a red oil (942 mg, 4.15 mmol, 89%).

$^1$H NMR (CDCl$_3$) δ: 0.99 (t, J=7.2 Hz, 6H), 2.92 (q, J=7.2 Hz, 4H), 6.39 (dd, J=11.5, 8.5 Hz, 1H), 6.46 (brs, 2H), 7.10 (dd, J=8.5, 4.9 Hz, 1H).

MS Calcd.: 227 MS Found: 228 (M+H).

Reference Example 184

1-[2-Amino-6-(diethylamine)-3-fluorophenyl]-3-(2,4-dichlorophenyl)thiourea

Under hydrogen gas atmosphere, a mixture of $N^1,N^1$-diethyl-4-fluoro-3-nitrobenzene-1,2-diamine (380 mg, 1.67 mmol), 10% palladium on carbon (50% wet, 80 mg) and tetrahydrofuran (8 mL) was stirred at room temperature for 20 hr. The reaction mixture was filtered and concentrated in vacuo to give $N^1,N^1$-diethyl-4-fluorobenzene-1,2,3-triamine as a brown oil, which was used for the next step without further purification. To a solution of above crude compound in tetrahydrofuran (16 mL) was added 2,4-dichlorophenyl isothiocyanate (320 mg, 1.57 mmol) at room temperature. The resultant mixture was stirred at room temperature for 2 h and concentrated in vacuo. The residue was purified by flash column chromatography on silica gel eluting with a 10-30% ethyl acetate/n-hexane gradient mixture to give a solid, which was washed with diisopropyl ether to afford the title compound as a colorless solid (306 mg, 0.762 mmol, 49%).

$^1$H NMR (CDCl$_3$) δ: 0.98 (t, J=7.0 Hz, 6H), 3.02 (q, J=7.0 Hz, 4H), 4.12 (brs, 2H), 6.50 (dd, J=8.8, 4.9 Hz, 1H), 6.96 (dd, J=10.0, 8.8 Hz, 1H), 7.25-7.30 (m, 1H), 7.43 (d, J=2.2 Hz, 1H), 7.68 (brs, 1H), 7.86-8.00 (m, 1H), 8.91 (brs, 1H).

MS Calcd.: 400 MS Found: 401 (M+H).

Reference Example 185

$N^2$-(2,4-Dichlorophenyl)-$N^7,N^7$-diethyl-4-fluoro-1H-benzimidazole-2,7-diamine A mixture of 1-[2-amino-6-(diethylamino)-3-fluorophenyl]-3-(2,4-dichlorophenyl)thiourea (300 mg, 0.748 mmol), 1-ethyl-3-(3-dimethylaminopropyl)carbodiimide hydrochloride (151 mg, 0.788 mmol) and triethylamine (0.115 mL, 0.825 mmol) in tetrahydrofuran (3 mL) was stirred at 50° C. for 2 hr. The reaction mixture was diluted with ethyl acetate, washed with water and brine, dried over anhydrous sodium sulfate, filtered and concentrated in vacuo. The residue was purified by flash column chromatography on silica gel eluting with a 25% ethyl acetate/n-hexane mixture to give the title compound as a colorless solid (191 mg, 0.521 mmol, 70%).

mp 204-205° C. (ethyl acetate/hexane).

$^1$H NMR (DMSO-d$_6$) δ: 0.97 (brs, 6H), 2.99-3.58 (m, 4H), 6.59-6.86 (m, 2H), 7.44-7.50 (m, 1H), 7.63 (d, J=2.5 Hz, 1H), 8.60 (brs, 1H), 8.79-8.91 (m, 1H), 11.30 (brs, 1H).

MS Calcd.: 366, MS Found: 367 (M+H).

Reference Example 186

Methyl 3-amino-4-bromo-2-[(3-chloropropyl)amino]benzoate

To a mixture of methyl 2-[(tert-butoxycarbonyl)amino]-3-nitrobenzoate (10.0 g, 33.8 mmol), 3-chloro-1-propanol (8.50 mL, 102 mmol), triphenylphosphine (26.6 g, 101 mmol) in tetrahydrofuran (170 mL) was added diethyl azodicarboxylate (46.2 mL, 101 mmol) at 0° C. The resultant mixture was stirred at room temperature for 3 days, diluted with ethyl acetate, washed with water and brine, dried over anhydrous sodium sulfate, filtered and concentrated in vacuo. The residue was purified by column chromatography on silica gel eluting with a 5-20% ethyl acetate/n-hexane gradient mixture to give a yellow oil, which was used for the next step without further purification.

Under hydrogen gas atmosphere, a mixture of above crude compound, 10% palladium on carbon (50% wet, 3 g) and tetrahydrofuran (170 mL) was stirred at room temperature for 3 hr. The reaction mixture was filtered and concentrated in vacuo. The residue was purified by flash column chromatography on silica gel eluting with a 10-40% ethyl acetate/n-hexane gradient mixture to give a colorless oil (14.5 g), which was used for the next step without further purification.

A mixture of above crude compound (10.0 g) and 2,2'-azobis(isobutyronitrile) (3.06 g, 18.6 mmol) in ethyl acetate (115 mL) was stirred at 80° C. for 1 hr. N-Bromosuccinimide (3.32 g, 18.7 mmol) was added portionwise to the reaction mixture and the resultant mixture was stirred 80° C. for 10 min. The reaction mixture was diluted with ethyl acetate, washed with aqueous saturated sodium hydrogen carbonate and brine, dried over anhydrous sodium sulfate, filtered, and concentrated in vacuo. The residue was purified by flash column chromatography on silica gel eluting with a 10-20% ethyl acetate/n-hexane gradient mixture to give a yellow solid, which was used for the next step without further purification. A mixture of above crude compound and 4N hydrogen chloride in ethyl acetate (22 mL) was stirred at room temperature for 1 hr and concentrated in vacuo. The residue was diluted with water and aqueous saturated sodium hydrogen carbonate. The resultant mixture was extracted with ethyl acetate. The combined organic layer was washed with brine, dried over anhydrous sodium sulfate, filtered, and concentrated in vacuo. The residue was purified by flash column chromatography on silica gel eluting with a 10-20% ethyl acetate/n-hexane gradient mixture to give the title compound as a yellow oil (521 mg, 1.62 mmol).

$^1$H NMR (CDCl$_3$) δ: 1.97-2.07 (m, 2 H), 3.17 (t, J=6.7 Hz, 2 H), 3.70 (t, J=6.3 Hz, 2 H), 3.87 (s, 3 H), 4.35 (s, 2 H), 6.16 (brs, 1 H), 7.12 (d, J=8.8 Hz, 1 H), 7.23 (d, J=8.8 Hz, 1 H).

MS Calcd.: 320, MS Found: 321 (M+H).

Reference Example 187

Methyl 4-bromo-2-[(3-chloropropyl)amino]-3-{[(2,4-dichlorophenyl)carbamothioyl]amino}benzoate To a solution of methyl 3-amino-4-bromo-2-[(3-chloropropyl)amino]benzoate (520 mg, 1.59 mmol) in tetrahydrofuran (16 mL) was added 2,4-dichlorophenyl isothiocyanate (324 mg, 1.59 mmol) at room temperature. The resultant mixture was stirred at 50° C. for 1 day and at 70° C. for 5 hr and concentrated in vacuo. The residue was purified by flash column chromatography on silica gel eluting with a 10-20% ethyl acetate/n-hexane gradient mixture to give the title compound as a colorless solid (520 mg, 0.989 mmol, 62%).

$^1$H NMR (CDCl$_3$) δ: 2.03-2.15 (m, 2 H), 3.61-3.68 (m, 4 H), 3.91 (s, 3 H), 7.09 (d, J=8.5 Hz, 1 H), 7.23-7.30 (m, 1 H), 7.37 (brs, 1 H), 7.65 (brs, 1 H), 7.82-7.90 (m, 2 H), 8.03 (brs, 1 H), 8.20-8.33 (m, 1 H).

MS Calcd.: 523, MS Found: 524 (M+H).

Reference Example 188

Methyl 4-bromo-1-(3-chloropropyl)-2-[(2,4-dichlorophenyl)amino]-1H-benzimidazole-7-carboxylate A mixture of methyl 4-bromo-2-[(3-chloropropyl)amino]-3-{[(2,4-dichlorophenyl)carbamothioyl]amino}benzoate (520 mg, 0.989 mmol), 1-ethyl-3-(3-dimethylaminopropyl)carbodiimide hydrochloride (209 mg, 1.09 mmol) and triethylamine (0.152 mL, 1.09 mmol) in tetrahydrofuran (10 mL) was stirred at 50° C. for 1 hr. The reaction mixture was diluted with ethyl acetate, washed with water and brine, dried over anhydrous sodium sulfate, filtered and concentrated in vacuo to give the title compound as a colorless solid, which was used for the next step without further purification.

MS Calcd.: 489, MS Found: 490 (M+H).

Reference Example 189

Methyl 4-chloro-2-[(3-hydroxypropyl)amino]-3-{[(2,4,6-trichlorophenyl)carbamothioyl]amino}benzoate A mixture of methyl 3-amino-4-chloro-2-[(3-hydroxypropyl)amino]benzoate (200 mg, 0.773 mmol) and 2,4,6-trichlorophenyl isothiocyanate (406 mg, 1.70 mmol) was stirred at room temperature for 2 days and concentrated in vacuo. The residue was purified by flash column chromatography on silica gel eluting with a 30-70% ethyl acetate/n-hexane gradient mixture to give the title compound as a red oil (285 mg, 0.574 mmol, 74%).

$^1$H NMR (CDCl$_3$) δ: 1.82-2.02 (m, 3 H), 3.64-3.73 (m, 2 H), 3.74-3.82 (m, 2 H), 3.88 (s, 3 H), 6.88 (d, J=8.8 Hz, 1 H), 7.27-7.32 (m, 1 H), 7.38 (s, 2 H), 7.93 (d, J=8.8 Hz, 1 H), 8.04 (brs, 1 H), 8.13 (brs, 1 H).

MS Calcd.: 495, MS Found: 496 (M+H).

Reference Example 190

Methyl 4-chloro-1-(3-hydroxypropyl)-2-[(2,4,6-trichlorophenyl)amino]-1H-benzimidazole-7-carboxylate A mixture of methyl 4-chloro-2-[(3-hydroxypropyl)amino]-3-{[(2,4,6-trichlorophenyl)carbamothioyl]amino}benzoate (285 mg, 0.574 mmol), 1-ethyl-3-(3-dimethylaminopropyl)carbodiimide hydrochloride (121 mg, 0.631 mmol) and triethylamine (0.0880 mL, 0.631 mmol) in tetrahydrofuran (6 mL) was stirred at 50° C. for 14 hr. The reaction mixture was diluted with ethyl acetate, washed with water and brine, dried over anhydrous sodium sulfate, filtered and concentrated in vacuo. The residue was purified by flash column chromatography on silica gel eluting with a 20-50% ethyl acetate/n-hexane gradient mixture to give the title compound as a colorless solid (256 mg, 0.553 mmol, 96%).

$^1$H NMR (CDCl$_3$) δ: 1.89-2.26 (m, 2 H), 3.72 (brs, 2 H), 3.96 (s, 3 H), 4.47-4.77 (m, 2 H), 6.99-7.20 (m, 1 H), 7.38 (s, 2 H), 7.45-7.66 (m, 1 H), 7.89 (brs, 1 H).

MS Calcd.: 461, MS Found: 462 (M+H).

Reference Example 191

Methyl 4-chloro-3-{[(2,6-dichloro-4-methoxyphenyl)carbamothioyl]amino}-2-[(3-hydroxypropyl)amino]benzoate A mixture of methyl 3-amino-4-chloro-2-[(3-hydroxypropyl)amino]benzoate (500 mg, 1.93 mmol) and 1,3-dichloro-2-isothiocyanato-5-methoxybenzene (678 mg, 2.90 mmol) was stirred at room temperature for 1 day and concentrated in vacuo. The residue was purified by flash column chromatography on silica gel eluting with a 30-70% ethyl acetate/n-hexane gradient mixture to give the title compound as a brown oil (255 mg, 0.517 mmol, 27%).

$^1$H NMR (CDCl$_3$) δ: 1.80-1.95 (m, 2 H), 3.59-3.94 (m, 10 H), 6.82 (d, J=8.8 Hz, 1 H), 6.89 (s, 2 H), 7.05 (brs, 1H), 7.90 (d, J=8.8 Hz, 1 H), 8.12 (brs, 1 H), 8.43 (brs, 1 H).

Reference Example 192

Methyl 4-chloro-2-[(2,6-dichloro-4-methoxyphenyl)amino]-1-(3-hydroxypropyl)-1H-benzimidazole-7-carboxylate A mixture of methyl 4-chloro-3-{[(2,6-dichloro-4-methoxyphenyl)carbamothioyl]amino}-2-[(3-hydroxypropyl)amino]benzoate (255 mg, 0.517 mmol), 1-ethyl-3-(3-dimethylaminopropyl)carbodiimide hydrochloride (109 mg, 0.569 mmol) and triethylamine (0.0793 mL, 0.569 mmol) in tetrahydrofuran (5 mL) was stirred at 50° C. for 2 hr. The reaction mixture was diluted with ethyl acetate, washed with water and brine, dried over anhydrous sodium sulfate, filtered and concentrated in vacuo. The residue was purified by flash column chromatography on silica gel eluting with a 30-70% ethyl acetate/n-hexane gradient mixture to give the title compound as a colorless solid (215 mg, 0.469 mmol, 91%).

$^1$H NMR (CDCl$_3$) δ: 1.91-2.25 (m, 3 H), 3.67-3.84 (m, 5 H), 3.94 (s, 3 H), 4.41-4.68 (m, 2 H), 6.95 (s, 2 H), 7.08-7.15 (m, 1 H), 7.47-7.62 (m, 2 H).

MS Calcd.: 457, MS Found: 458 (M+H).

Reference Example 193

Methyl 4-chloro-3-{[(2,6-dibromo-4-methoxyphenyl)carbamothioyl]amino}-2-[(3-hydroxypropyl)amino]benzoate A mixture of methyl 3-amino-4-chloro-2-[(3-hydroxypropyl)amino]benzoate (1.00 g, 3.87 mmol), 1,3-dibromo-2-isothiocyanato-5-methoxybenzene (1.50 g, 4.64 mmol) and catalytic amount of 4-dimethylaminopyridine was stirred at 80° C. for 16 h and concentrated in vacuo. The residue was purified by flash column chromatography on silica gel eluting with a 30-70% ethyl acetate/n-hexane gradient mixture to give the title compound as a brown oil (560 mg, 0.963 mmol, 25%).

$^1$H NMR (CDCl$_3$) δ: 1.80-1.94 (m, 2 H), 3.67-3.81 (m, 7 H), 3.87 (s, 3 H), 6.85 (d, J=8.8 Hz, 1 H), 7.08-7.18 (m, 3 H), 7.88-8.00 (m, 2 H), 8.13 (brs, 1 H).

MS Calcd.: 579, MS Found: 580 (M+H).

Reference Example 194

Methyl 7-bromo-3-(3-chloropropyl)-2-oxo-2,3-dihydro-1H-benzimidazole-4-carboxylate A mixture of methyl 3-(3-chloropropyl)-2-oxo-2,3-dihydro-1H-benzimidazole-4-carboxylate (5.00 g, 18.6 mmol) and 2,2'-azobis(isobutyronitrile) (3.06 g, 18.6 mmol) in ethyl acetate (90 mL) was stirred at 70° C. for 40 min. N-Bromosuccinimide (3.31 g, 18.6 mmol) was added portionwise to the reaction mixture and the resultant mixture was stirred 70° C. for 5 h. The reaction mixture was washed with aqueous saturated sodium hydrogen carbonate and brine, dried over anhydrous sodium sulfate, filtered, and concentrated in vacuo. The residue was purified by flash column chromatography on silica gel eluting with a 10-50% ethyl acetate/n-hexane gradient mixture to give the title compound as a colorless solid (490 mg, 1.41 mmol, 7.6%).

$^1$H NMR (CDCl$_3$) δ: 2.08-2.19 (2 H, m), 3.57 (2 H, t, J=6.6 Hz), 3.95 (3 H, s), 4.32-4.39 (2 H, m), 7.22 (1 H, d, J=8.5 Hz), 7.44 (1 H, d, J=8.5 Hz), 8.81 (1 H, brs).

MS Calcd.: 346, MS Found: 347 (M+H).

Reference Example 195

Methyl 4-bromo-2-chloro-1-(3-chloropropyl)-1H-benzimidazole-7-carboxylate

A mixture of methyl 7-bromo-3-(3-chloropropyl)-2-oxo-2,3-dihydro-1H-benzimidazole-4-carboxylate (490 mg, 1.41 mmol) and phosphoryl chloride (14 mL) was stirred at 100° C. for 2 h. Phosphoryl chloride (9 mL) was added to the reaction mixture and the resultant mixture was stirred at 100° C. for 3 h. Phosphoryl chloride (15 mL) was added to the reaction mixture, and the resultant mixture was stirred at 100° C. for 3 h, concentrated in vacuo, and diluted with ethyl acetate and aqueous sodium bicarbonate. The resultant mixture was extracted with ethyl acetate. The extract was washed with brine, dried over anhydrous sodium sulfate, filtered and concentrated in vacuo. The residue was purified by flash column chromatography on silica gel eluting with a 10-50% ethyl acetate/n-hexane gradient mixture to give the title compound as a colorless solid (429 mg, 1.17 mmol, 83%).

$^1$H NMR (CDCl$_3$) δ: 2.16-2.28 (2 H, m), 3.56 (2 H, t, J=6.2 Hz), 3.97 (3 H, s), 4.74-4.80 (2 H, m), 7.50 (1 H, d, J=8.5 Hz), 7.72 (1 H, d, J=8.5 Hz).

MS Calcd.: 364, MS Found: 365 (M+H).

Reference Example 196

1,3-Dichloro-2-isothiocyanate-5-methoxybenzene

Thiophosgene (1.62 mL, 21.8 mmol) was added dropwise to a stirred mixture of 2,6-dichloro-4-methoxyaniline (2.00 g, 10.4 mmol) in tetrahydrofuran (25 mL) and saturated aqueous sodium hydrogen carbonate (25 mL) at 0° C. The mixture was stirred at room temperature for 1 h, and extracted with ethyl acetate. The combined organic layer was washed with brine, dried over anhydrous sodium sulfate, filtered and concentrated in vacuo. The residue was washed with n-hexane to give the title compound as a brown solid (2.21 g, 9.44 mmol, 91%).

$^1$H NMR (CDCl$_3$) δ 3.80 (s, 3H), 6.86 (s, 2H).

Reference Example 197

1,3-Dibromo-2-isothiocyanato-5-methoxybenzene

Thiophosgene (1.52 mL, 20.5 mmol) was added dropwise to a stirred mixture of 2,6-dibromo-4-methoxyaniline (2.86 g, 10.2 mmol) in tetrahydrofuran (25 mL) and saturated aqueous sodium hydrogen carbonate (25 mL) at 0° C. The mixture was stirred at room temperature for 1 h, and extracted with ethyl acetate. The combined organic layer was washed with brine, dried over anhydrous sodium sulfate, filtered and concentrated in vacuo to give the title compound as a yellow solid (3.22 g, 9.97 mmol, 98%).

$^1$H NMR (CDCl$_3$) δ 3.79 (s, 3H), 7.06 (s, 2H).

Reference Example 198

4-Isothiocyanato-3-methylbenzamide

Thiophosgene (2.57 mL, 34.6 mmol) was added dropwise to a stirred mixture of 4-amino-3-methylbenzamide (2.60 g, 17.3 mmol) in tetrahydrofuran (43 mL) and saturated aqueous sodium hydrogen carbonate (43 mL) at 0° C. The mixture was stirred at room temperature for 10 min, and extracted with ethyl acetate. The combined organic layer was washed with brine, dried over anhydrous sodium sulfate, filtered and concentrated in vacuo. The residue was washed with diisopropylether to give the title compound as a brown solid (3.02 g, 15.7 mmol, 91%).

$^1$H NMR (CDCl$_3$) δ 2.43 (s, 3H), 5.62-6.17 (m, 2H), 7.24 (d, J=8.3 Hz, 1H), 7.58 (dd, J=8.3, 2.2 Hz, 1H), 7.68 (d, J=2.2 Hz).

Reference Example 199

Methyl 3-amino-2-[(2-hydroxyethyl)amino]benzoate

A mixture of methyl 2-[(2-hydroxyethyl)amino]-3-nitrobenzoate (10.0 g, 41.6 mmol) and 10% palladium on carbon (0.10 g) in tetrahydrofuran (200 mL) was stirred under hydrogen atmosphere at room temperature for 24 hr. Catalyst was removed by filtration and the filtrate was concentrated in vacuo to give the title compound (36 mg, 0.090 mmol, 90%) as a pale yellow oil. This product was used next steps without purification.

$^1$H NMR (CDCl$_3$) δ 3.23-3.26 (m, 2H), 3.64-3.66 (m, 2H), 3.88 (s, 3H), 6.84-6.86 (m, 2H), 7.36-7.40 (m, 1H).

Reference Example 200

Methyl 3-amino-4-chloro-2-[(2-hydroxyethyl)amino]benzoate

To a solution of methyl 3-amino-2-[(2-hydroxyethyl)amino]benzoate (114.1 mg, 0.543 mmol) in dichloromethane (2.7 mL) was added N-chlorosuccinimide (14.5 mg, 1.09 mmol) at room temperature. The mixture was stirred at room temperature for 1.5 hr and at 30° C. for 0.5 hr. Aqueous sodium sulfite was added to the reaction mixture at room temperature and the mixture was extracted with ethyl acetate. The organic layer was washed with water and brine, dried over anhydrous magnesium sulfate and concentrated in vacuo. The residue was purified by flash chromatography on silica gel eluting with a 25-70% ethyl acetate/n-hexane gradient mixture to give the title compound (29.0 mg, 0.12 mmol, 22%) as an orange amorphous.

$^1$H NMR (CDCl$_3$) δ 2.36-2.77 (m, 1 H), 3.25 (t, J=5.0 Hz, 2 H), 3.67 (t, J=5.0 Hz, 2 H), 3.88 (s, 3 H), 4.24-4.56 (m, 2 H), 6.03 (m, 1 H), 6.95 (d, J=8.6 Hz, 1 H), 7.30 (d, J=8.6 Hz, 1 H).

MS Calcd.: 244; Found: 245 (M+H).

Reference Example 201

Methyl 4-chloro-2-[(2,4-dichloro-6-methylphenyl)amino]-1-(2-hydroxyethyl)-1H-benzimidazole-7-carboxylate A solution of methyl 3-amino-4-chloro-2-[(2-hydroxyethyl)amino]benzoate (290 mg, 1.19 mmol) and 2,4-dichloro-6-methylphenylisothiocyanate (284.4 mg, 1.3 mmol) in tetrahydrofuran (12 mL) was stirred at 45° C. for 62 hr. The mixture was warmed to 60° C. and stirred at, 60° C. for 24 hr. 2,4-Dichloro-6-methylphenylisothiocyanate (104 mg, 0.48 mmol) was added to the reaction mixture and the mixture was stirred at 60° C. for 26 hr. Water was added to the reaction mixture at room temperature and the mixture was extracted with ethyl acetate. The organic layer was washed with brine, dried over anhydrous magnesium sulfate and concentrated in vacuo. The residue was purified by flash chromatography on NH-silica gel eluting with a 50-100% ethyl acetate/n-hexane gradient mixture give a red amorphous (261.4 mg). To a mixture of the amorphous (261.4 mg) and 1-ethyl-3-(3-dimethylaminopropyl)carbodiimide hydrochloride (119 mg, 0.62 mmol) in tetrahydrofuran (11.2 mL) was added triethylamine (0.0866 mL, 0.62 mmol) at room temperature. The mixture was stirred at 50° C. for 16 hr. Water was added to the reaction mixture at room temperature and the mixture was extracted with ethyl acetate. The organic layer was washed with water and brine, dried over anhydrous magnesium sulfate and concentrated in vacuo to give the title compound (156.3 mg, 0.36 mmol, 30%) as a pale yellow solid.

$^1$H NMR (CDCl$_3$) δ 2.20 (s, 3 H), 3.74-3.83 (m, 2 H), 3.88 (s, 3 H), 4.41-4.50 (m, 2 H), 5.25-5.51 (m, 1 H), 7.15 (d, J=8.6 Hz, 1 H), 7.37 (d, J=8.6 Hz, 1 H), 7.43 (d, J=2.6 Hz, 1 H), 7.57 (d, J=2.6 Hz, 1 H), 8.70-8.99 (m, 1 H).

MS Calcd.: 427; Found: 428 (M+H).

Reference Example 202

Methyl 3-{[(2,4-dichloro-6-methylphenyl)carbamothioyl]amino}-2-[(2-hydroxyethyl)amino]benzoate A solution of 3-amino-2-[(2-hydroxyethyl)amino]benzoate (521 mg, 2.48 mmol) and 2,4-dichloro-6-methylphenylisothiocyanate (595 mg, 2.73 mmol) in tetrahydrofuran (25 mL) was stirred at room temperature for 18 hr. The mixture was warmed to 50° C. and it was stirred at 50° C. for 24 hr. The reaction mixture was concentrated in vacuo. The residue was purified by flash chromatography on silica gel eluting with a 20-80% ethyl acetate/n-hexane gradient mixture to give the title compound (959.9 mg) as a colorless amorphous.

$^1$H NMR (CDCl$_3$) δ 2.22-2.44 (m, 4 H), 3.43-3.64 (m, 2 H), 3.74-3.90 (m, 2 H), 3.90 (s, 3 H), 6.84-6.90 (m, 1 H), 7.15-7.20 (m, 1 H), 7.30-7.34 (m, 1 H), 7.43-7.60 (m, 2 H), 7.91-7.94 (m, 1 H), 8.12-8.41 (m, 1 H).

MS Calcd.: 427; Found: 428 (M+H).

Reference Example 203

Methyl 4-chloro-3-{[(2,4-dichlorophenyl)carbamothioyl]amino}-2-[(2-hydroxyethyl)amino]benzoate A solution of methyl 3-amino-4-chloro-2-[(2-hydroxyethyl)amino]benzoate (1.068 g, 3.16 mmol) and 2,4-dichlorophenylisothiocyanate (0.86 g, 4.21 mmol) in tetrahydrofuran (40 mL) was stirred at 50° C. for 14 hr. The reaction mixture was concentrated in vacuo. The residue was purified by flash chromatography on silica gel eluting with a 25-70% ethyl acetate/n-hexane gradient mixture and flash chromatography on NH-silica gel eluting with a 50-100% ethyl acetate/n-hexane gradient mixture to give the title compound (686.9 mg, 1.53 mmol, 48%) as a pale orange amorphous.

$^1$H NMR (CDCl$_3$) δ 1.95 (t, J=5.3 Hz, 1 H), 3.57-3.68 (m, 2 H), 3.83-3.86 (m, 2 H), 3.90 (s, 3 H), 6.88 (d, J=8.7 Hz, 1 H), 7.24-7.28 (m, 2 H), 7.35-7.42 (m, 1 H), 7.79 (br s, 1 H), 7.92-7.95 (m, 2 H), 8.11-8.33 (m, 2 H).

MS Calcd.: 447; Found: 448 (M+H).

Reference Example 204

Methyl 2-(2,4-dichlorophenyl)-2-hydroxyethanimidoate hydrochloride

To a stirred solution of 2,4-dichlorobenzaldehyde (18.3 g, 105 mmol) and 4-dimethylaminopyridine (128 mg, 1.05 mmol) in acetonitrile (200 mL) was added, trimethylsilyl cyanide (13.7 mL, 110 mmol) at room temperature. After 2 h, the reaction mixture was evaporated. To a stirred solution of methanol (150 mL) was added acetyl chloride (100 mL) at 0° C., and the mixture was warmed up to room temperature. After 30 min, the residue was added. After 2 h, the reaction mixture was evaporated. The resulting solid was washed with diethyl ether to afford the desired product as colorless solid (25.5 g, 94.3 mmol, 90%).

Reference Example 205

Methyl 3-{7-amino-2-[(2,4-dichlorophenyl)(hydroxy)methyl]-1H-benzimidazol-1-yl}propanoate To a stirred solution of ethyl N-(2,6-diaminophenyl)-beta-alaninate (4.11 g, 18.4 mmol) in ethanol (36.8 mL) was added methyl 2-(2,4-dichlorophenyl)-2-hydroxyethanimidoate hydrochloride (5.59 g, 20.7 mmol) at room temperature. After 12 h, the reaction mixture was poured into water (120 mL). The resulting solid was collected by filtration and washed with ethyl acetate to afford the desired product as colorless solid (6.77 g, 16.6 mmol, 90%).

$^1$H NMR (CDCl$_3$) δ 1.20 (t, J=7.2 Hz, 3H), 2.55-2.70 (m, 1H), 2.76-2.90 (m, 1H), 3.94 (brs, 2H), 4.09 (q, J=7.1 Hz, 2H), 4.36-4.61 (m, 2H), 4.93 (brs, 1H), 6.36 (s, 1H), 6.59 (d, J=7.8 Hz, 1H), 7.05 (t, J=7.8 Hz, 1H), 7.19-7.30 (m, 2H), 7.34-7.46 (m, 2H).

MS Calcd.: 407; MS Found: 408 (M+H).

Reference Example 206

Methyl 3-{2-[(2,4-dichlorophenyl)(hydroxy)methyl]-7-(diethylamino)-1H-benzimidazol-1-yl}propanoate To a suspension of methyl 3-{7-amino-2-[(2,4-dichlorophenyl)(hydroxy)methyl]-1H-benzimidazol-1-yl}propanoate (6.00 g, 14.7 mmol) and acetic acid (7.4 mL) in methanol (147 mL) was added acetaldehyde (4.95 mL, 88.2 mmol) at 0° C. After 30 min, sodium acetoxyborohydride (18.7 g, 88.2 mmol) was added. After 2 h, the reaction mixture was quenched with water, concentrated in vacuo, diluted with ethyl acetate, washed with aqueous sodium hydroxide (1 M) and brine, dried over sodium sulfate, filtered and concentrated in vacuo. The residue was purified by column chromatography on silica gel eluting with a 10-30% ethyl acetate/n-hexane gradient mixture to give the title compound as a colorless amorphous (6.30 g, 13.6 mmol, 92%).

$^1$H NMR (CDCl$_3$) δ 0.92-1.11 (m, 6H), 1.23 (t, J=7.1 Hz, 3H), 2.24-2.41 (m, 1H), 2.65-2.84 (m, 1H), 2.87-3.17 (m, 4H), 4.11 (q, J=7.1 Hz, 2H), 4.44-4.68 (m, 2H), 5.13 (brs, 1H), 6.42 (s, 1H), 7.05 (d, J=7.7 Hz, 1H), 7.13-7.30 (m, 2H), 7.33-7.54 (m, 3H).

MS Calcd.: 463; MS Found: 464 (M+H).

Reference Example 207

3-{2-[(2,4-Dichlorophenyl)(hydroxy)methyl]-7-(diethylamino)-1H-benzimidazol-1-yl}propan-1-ol To a suspension of lithium aluminum hydride (327 mg, 8.61 mmol) in tetrahydrofuran (38 mL) was added a solution of methyl 3-{2-[(2,4-dichlorophenyl)(hydroxy)methyl]-7-(diethylamino)-1H-benzimidazol-1-yl}propanoate (2.00 g, 4.31 mmol) in tetrahydrofuran (5 mL) at −5° C. After the addition, sodium sulfate decahydrate (3.3 g) was added. After 1 h, the resultant mixture was filtrated and concentrated in vacuo. The residue was purified by column chromatography on silica gel eluting with a 30-70% ethyl acetate/n-hexane gradient mixture to give the title compound as a colorless solid (1.42 g, 3.36 mmol, 78%).

$^1$H NMR (CDCl$_3$) δ 0.88-1.15 (m, 6H), 1.71-1.85 (m, 1H), 1.87-2.01 (m, 1H), 2.98-3.19 (m, 4H), 3.31-3.56 (m, 2H), 4.23-4.39 (m, 1H), 4.49-4.65 (m, 1H), 4.92 (brs, 1H), 6.41 (s, 1H), 7.04 (d, J=7.4 Hz, 1H), 7.15-7.25 (m, 2H), 7.38-7.47 (m, 2H), 7.51 (d, J=8.0 Hz, 1H).

MS Calcd.: 421; MS Found: 422 (M+H).

Reference Example 208

(2,4-Dichlorophenyl)[7-(diethylamino)-1-(3-hydroxypropyl)-1H-benzimidazol-2-yl]methanone A suspension of 3-{2-[(2,4-dichlorophenyl)(hydroxy)methyl]-7-(diethylamino)-1H-benzimidazol-1-yl}propan-1-ol (1.18 g, 2.7.9 mmol) and manganese dioxide (2.43 g, 27.9 mmol) in tetrahydrofuran (14 mL) was stirred for 1.5 h at room temperature. The reaction mixture was filtrated and the filtrate was concentrated in vacuo to afford the desired product as a yellow solid (1.16 g, 2.76 mmol, 99%).

$^1$H NMR (CDCl$_3$) δ 1.10 (t, J=7.0 Hz, 6H), 2.02-2.14 (m, 2H), 2.55 (t, J=5.9 Hz, 1H), 3.07-3.28 (m, 4H), 3.57 (q, J=5.9 Hz, 2H), 5.21 (t, J=6.9 Hz, 2H), 7.18 (dd, J=7.7, 1.1 Hz, 1H), 7.23-7.31 (m, 1H), 7.38 (dd, J=8.2, 1.9 Hz, 1H), 7.49 (d, J=1.9 Hz, 1H), 7.56-7.65 (m, 2H).

MS Calcd.: 419; MS Found: 420 (M+H).

Reference Example 209

3-{2-[1-(2,4-Dichlorophenyl)-1-hydroxyethyl]-7-(diethylamino)-1H-benzimidazol-1-yl}propan-1-ol To a stirred solution of (2,4-dichlorophenyl)[7-(diethylamino)-1-(3-hydroxypropyl)-1H-benzimidazol-2-yl]methanone (300 mg, 0.714 mmol) in tetrahydrofuran (7 mL) was added a solution of methyl magnesium bromide in diethyl ether (3.0 M, 714 µL, 2.14 mmol) at 0° C. After being stirred for 6.5 h at room temperature, the reaction mixture was quenched with aqueous ammonium chloride at 0° C., diluted with ethyl acetate, washed with water and brine, dried over sodium sulfate, filtrated, and concentrated in vacuo. The resulting solid was washed with diethyl ether to afford the desired product as a yellow solid (210 mg, 0.481 mmol, 67%).

MS Calcd.: 435; MS Found: 436 (M+H).

Reference Example 210

1-(2,4-Dichlorophenyl)-1-[7-(diethylamino)-1-(2-hydroxyethyl)-1H-benzimidazol-2-yl]ethanol A suspension of 3-{2-[(2,4-dichlorophenyl)(hydroxy)methyl]-7-(diethylamino)-1H-benzimidazol-1-yl}ethanol (102 mg, 0.250 mmol) and manganese dioxide (217 mg, 2.50 mmol) in tetrahydrofuran (1 mL) was stirred for 4.5 h at room temperature. The reaction mixture was filtrated and the filtrate was concentrated in vacuo. To a stirred solution of the residue in tetrahydrofuran (2.5 mL) was added a solution of methyl magnesium bromide in diethyl ether (3.0 M, 204 µL, 0.613 mmol) at 0° C. After 1 h, the reaction mixture was warmed up to room temperature and stirred for 2 h. After the addition of a solution of methyl magnesium bromide in diethyl ether (3.0 M, 98 µL, 0.294 mmol), the reaction mixture was stirred for 3.5 h. The reaction mixture was quenched with aqueous ammonium chloride at 0° C., diluted with ethyl acetate, washed with water and brine, dried over sodium sulfate, filtrated, and concentrated in vacuo. The residue was purified by column chromatography on silica gel eluting with a 0-60% ethyl acetate/n-hexane gradient mixture to afford the desired product as a colorless solid (63.8 mg, 0.151 mmol, 62%).

$^1$H NMR (CDCl$_3$) δ 0.84 (t, J=7.0 Hz, 3H), 1.06 (t, J=7.0 Hz, 3H), 2.05 (s, 3H), 2.74-2.97 (m, 2H), 3.06 (d, J=7.0 Hz, 2H), 3.56-3.86 (m, 3H), 4.43-4.56 (m, 1H), 4.72 (brs, 1H), 6.00 (brs, 1H), 6.97 (d, J=7.6 Hz, 1H), 7.08 (t, J=7.8 Hz, 1H), 7.27 (d, J=2.2 Hz, 1H), 7.32-7.39 (m, 2H), 8.07 (d, J=8.5 Hz, 1H).

MS Calcd.: 421; MS Found: 422 (M+H).

Reference Example 211

[1-(3-Bromopropyl)-7-(diethylamino)-1H-benzimidazol-2-yl](2,4-dichlorophenyl)methanone To a stirred suspension of (2,4-dichlorophenyl)[7-(diethylamino)-1-(3-hydroxypropyl)-1H-benzimidazol-2-yl]methanone (404 mg, 0.961 mmol) and tetrabromomethane (637 mg, 1.92 mmol) in acetonitrile was added triphenylphosphine (504 mg, 1.92 mmol). After 15 min, the reaction mixture was diluted with ethyl acetate, washed with aqueous sodium hydrogen carbonate and brine, dried over sodium sulfate, filtrated, and concentrated in vacuo. The residue was purified by column chromatography on silica gel eluting with a 0-30% ethyl acetate/n-hexane gradient mixture to afford the desired product as yellow solid (407 mg, 0.842 mmol, 88%).

$^1$H NMR (CDCl$_3$) δ 1.09 (t, J=7.1 Hz, 6 H), 2.33-2.46 (m, 2H), 3.02-3.26 (m, 4H), 3.47 (t, J=6.6 Hz, 2H), 5.19-5.28 (m, 2H), 7.20 (d, J=7.8 Hz, 1H), 7.28 (t, J=7.8 Hz, 1H), 7.38 (dd, J=8.2, 1.9 Hz, 1H), 7.49 (d, J=1.9 Hz, 1H), 7.56-7.64 (m, 2H).

MS Calcd.: 481; MS Found: 482 (M+H).

Reference Example 212

3-{2-[(2,4-Dichlorophenyl)(hydroxy)methyl]-7-(diethylamino)-5-fluoro-1H-benzimidazol-1-yl}propan-1-ol A solution of 3-[(2,6-diamino-4-fluorophenyl)amino]propan-1-ol (498 mg, 2.50 mmol) and methyl 2-(2,4-dichlorophenyl)-2-hydroxyethanimidoate hydrochloride (812 mg, 3.00 mmol) in ethanol (5 mL) was stirred for 12 h at room temperature. The reaction mixture was diluted with aqueous sodium hydrogen carbonate, extracted with ethyl acetate, washed with brine, dried over sodium sulfate, filtrated, and concentrated in vacuo. The residue was dissolved in acetic acid (1.2 mL) and methanol (25 mL), and acetaldehyde (935 µL, 15.0 mmol) was added at 0° C. After 30 min, sodium triacetoxyborohydride (3.18 g, 15.0 mmol) was added. After 6 h, the reaction mixture was quenched with water, concentrated in vacuo, diluted with ethyl acetate, washed with aqueous sodium hydroxide (1 M) and brine, dried over sodium sulfate, filtered and concentrated in vacuo. The residue was purified by column chromatography on silica gel eluting with a 10-50% ethyl acetate/n-hexane gradient mixture to give the title compound as a colorless solid (192 mg, 0.436 mmol, 17%).

$^1$H NMR (CDCl$_3$) δ 0.89-1.20 (m, 6H), 1.67-1.85 (m, 1H), 1.87-2.02 (m, 1H), 2.25 (brs, 1H), 2.89-3.20 (m, 4H), 3.31-3.46 (m, 1H), 3.46-3.60 (m, 1H), 4.26-4.40 (m, 1H), 4.47-4.61 (m, 1H), 4.80 (brs, 1H), 6.39 (s, 1H), 6.80 (dd, J=11.4, 2.1 Hz, 1H), 7.17 (dd, J=8.7, 2.1 Hz, 1H), 7.23-7.28 (m, 1H), 7.41 (d, J=1.9 Hz, 1H), 7.48 (d, J=8.2 Hz, 1H).

MS Calcd.: 439; MS Found: 440 (M+H).

Reference Example 213

(2,4-Dichlorophenyl)(hydroxy)acetic acid

To a stirred solution of 2,4-dichlorobenzaldehyde (5.00 g, 28.6 mmol) and 4-dimethylaminopyridine (34.9 mg, 0.286 mmol) in acetonitrile (60 mL) was added trimethylsilyl cyanide (3.75 mL, 30.0 mmol) at room temperature. After 1 h, the reaction mixture was evaporated. The residue was dissolved in hydrochloric acid (6 M, 15 mL) and stirred for 2 h at reflux. Ice (50 g) was added and the mixture was stirred for 0.5 h. The resulting solid was collected, dissolved in ethyl acetate, dried over sodium sulfate, filtered and concentrated in vacuo to give the title compound as a colorless solid (4.73 g, 21.4 mmol, 75%).

Reference Example 214

2-Chloro-1-(2,4-dichlorophenyl)-2-oxoethyl acetate

A mixture of (2,4-dichlorophenyl)(hydroxy)acetic acid (884 mg, 4.00 mmol) and acetyl chloride (853 µL, 12.0 mmol) was stirred for 30 min at room temperature. The mixture was concentrated in vacuo, and the residue was dissolved in thionyl chloride (1.7 mL). The mixture was stirred for 5 h at reflux and concentrated in vacuo to afford the desired product as pale yellow oil (1.12 g, 100%).

$^1$H NMR (CDCl$_3$) δ 2.22 (s, 3H), 6.60 (s, 1H), 7.30-7.44 (m, 2H), 7.51 (d, J=1.9 Hz, 1H).

Reference Example 215

Methyl 4-chloro-2-[(2,4-dichlorophenyl)(hydroxy)methyl]-1-(3-hydroxypropyl)-1H-benzimidazole-7-carboxylate To a stirred solution of methyl 3-amino-4-chloro-2-[(3-hydroxypropyl)amino]benzoate (1.01 g, 3.90 mmol) and triethylamine (1.20 mL, 8.58 mmol) in tetrahydrofuran (20 mL) was added a solution of 2-chloro-1-(2,4-dichlorophenyl)-2-oxoethyl acetate (2.20 g, 7.80 mmol) in tetrahydrofuran (10 mL) at 0° C. After 30 min, the reaction mixture was diluted with ethyl acetate, washed with brine, dried over sodium sulfate, filtrated, and concentrated in vacuo. The residue was dissolved in acetic acid (20 mL), and the mixture was stirred for 1 h at 80° C. The reaction mixture was concentrated in vacuo, diluted with ethyl acetate, washed with aqueous sodium hydrogen carbonate and brine, dried over sodium sulfate, filtrated, and concentrated in vacuo. The residue was dissolved in methanol (20 mL) and potassium carbonate (539 mg, 3.90 mmol) was added at room temperature. After 30 min, the reaction mixture was diluted with ethyl acetate, washed with brine, dried over sodium sulfate, filtrated, and concentrated in vacuo. The residue was purified by column chromatography on NH-silica gel eluting with a 0-10% methanol/ethyl acetate gradient mixture to afford the desired product as pale yellow solid (745 mg, 1.61 mmol, 41%).

$^1$H NMR (CDCl$_3$) δ 1.66-1.86 (m, 2H), 3.35-3.49 (m, 1H), 3.49-3.61 (m, 1H), 3.94 (s, 3H), 4.27-4.42 (m, 1H), 4.56-4.69 (m, 1H), 4.75 (brs, 1H), 6.50 (s, 1H), 7.20-7.25 (m, 1H), 7.29-7.37 (m, 2H), 7.44 (d, J=1.9 Hz, 1H), 7.74 (d, J=8.2 Hz, 1H).

MS Calcd.: 442; MS Found: 443 (M+H).

Reference Example 216

2-[(2,6-Dinitrophenyl)amino]ethanol

A mixture of ethanol amine (5.96 mL, 49.4 mmol) and 2-chloro-1,3-dinitrobenzene (5.00 g, 24.7 mmol) in tetrahydrofuran (50 mL) was stirred at room temperature for 2 h. The reaction mixture was diluted with ethyl acetate, washed with aqueous sodium hydrogen carbonate and brine, dried over sodium sulfate, filtered and concentrated in vacuo to give the title compound as a brown solid (5.54 g, 24.4 mmol, 99%).

$^1$H NMR (CDCl$_3$) δ 3.12-3.19 (m, 2 H), 3.85-3.90 (m, 2 H), 6.77 (t, J=8.2 Hz, 1 H), 8.19 (d, J=8.2 Hz, 2 H), 8.71 (br. s., 1 H). hidden (1H)

MS Calcd.: 227; MS Found: 228 (M+H).

Reference Example 217

2-[(2,6-Diaminophenyl)amino]ethanol

Under hydrogen gas atmosphere, a mixture of 2-[(2,6-dinitrophenyl)amino]ethanol (5.54 g, 24.4 mmol) and 10% palladium on carbon (50% wet, 1.1 g) in tetrahydrofuran (240 mL) was stirred at room temperature for 2 h. The reaction mixture was filtered and concentrated in vacuo to give the title compound as a brown oil (3.63 g, 21.7 mmol, 89%).

$^1$H NMR (CDCl$_3$) δ 3.09-3.15 (m, 2 H), 3.55-3.60 (m, 2 H), 3.83 (br. s., 4 H), 6.24 (d, J=7.8 Hz, 2 H), 6.75 (t, J=7.8 Hz, 1 H). hidden (2H)

MS Calcd.: 167; MS Found: 168 (M+H).

Reference Example 218

2-{7-Amino-2-[(2,4-dichlorophenyl)(hydroxy)methyl]-1H-benzimidazol-1-yl}ethanol

To a stirred solution of 2-[(2,6-diaminophenyl)amino]ethanol (3.63 g, 21.7 mmol) in ethanol (43 mL) was added methyl 2-(2,4-dichlorophenyl)-2-hydroxyethanimidoate hydrochloride (7.04 g, 26.0 mmol) at room temperature. After 12 h, the reaction mixture was diluted with aqueous sodium hydrogen carbonate. The resultant mixture was extracted with ethyl acetate. The combined organic layer was washed with brine, dried over anhydrous sodium sulfate, filtered, and concentrated in vacuo. The residue was purified by flash column chromatography on silica gel eluting with ethyl acetate to give the title compound as an orange amorphous solid (7.58 g, 21.5 mmol, 99%).

$^1$H NMR (CDCl$_3$) δ: 3.55-3.71 (m, 2 H), 4.10-4.21 (m, 1 H), 4.23 (br. s., 2 H), 4.43-4.54 (m, 1 H), 6.01 (s, 1 H), 6.48 (dd, J=6.5, 2.2 Hz, 1 H), 6.89-6.98 (m, 2 H), 7.00 (dd, J=8.5, 2.2 Hz, 1 H), 7.25-7.32 (m, 2 H). hidden (2H)

MS Calcd.: 351, MS Found: 352 (M+H).

Reference Example 219

2-{2-[(2,4-Dichlorophenyl)(hydroxy)methyl]-7-(diethylamino)-1H-benzimidazol-1-yl}ethanol To a solution of 2-{7-amino-2-[(2,4-dichlorophenyl)(hydroxy)methyl]-1H-benzimidazol-1-yl}ethanol (7.58 g, 21.5 mmol) in methanol (220 mL) and acetic acid (11 mL) was added acetoaldehyde (8.04 mL, 129 mmol) at 0° C. The resultant mixture was stirred at 0° C. for 30 min. To the reaction mixture was added sodium triacetoxyborohydride (27.3 g, 129 mmol) at 0° C. After the resultant mixture was stirred at room temperature for 2 h, the mixture was diluted with aqueous sodium hydrogen carbonate and water, and extracted with ethyl acetate. The combined organic layer was washed with 1N aqueous sodium hydroxide and brine, dried over sodium sulfate, filtered and concentrated in vacuo. The residue was purified by column chromatography on silica gel eluting with ethyl acetate to afford a crude solid, which was washed with diisopropylether to give the title compound as a colorless solid (8.70 g, 21.3 mmol, 99%).

mp 177-179° C. (ethyl acetate/n-hexane).

$^1$H NMR (CDCl$_3$) δ 0.94-1.09 (6 H, m), 2.91-3.13 (4 H, m), 3.62-3.82 (2 H, m), 4.38-4.56 (2 H, m), 4.71-4.81 (1H, m), 5.61 (1 H, br. s.), 6.31 (1 H, s), 6.98 (1 H, dd, J=7.8, 0.8 Hz), 7.08 (1 H, t, J=7.8 Hz), 7.25 (1 H, dd, J=8.3, 2.1 Hz), 7.32-7.37 (2 H, m), 7.63 (1 H, d, J=8.3 Hz).

MS Calcd.: 407; MS Found: 408 (M+H).

Reference Example 220 tert-Butyl {2-[(2,6-dinitrophenyl)amino]ethyl}carbamate

A mixture of tert-butyl (2-aminoethyl)carbamate (5.00 g, 31.2 mmol), 2-chloro-1,3-dinitrobenzene (5.27 g, 26.0 mmol) and triethylamine (7.25 mL, 52.0 mmol) in tetrahydrofuran (260 mL) was stirred at room temperature for 1 h. The reaction mixture was diluted with ethyl acetate, washed with water and brine, dried over sodium sulfate, filtered and concentrated in vacuo to give the title compound as a yellow solid (8.44 g, 25.9 mmol, 99.6%).

$^1$H NMR (CDCl$_3$) δ 1.43 (s, 9 H), 3.07-3.14 (m, 2 H), 3.37-3.45 (m, 2 H), 4.74 (br. s., 1 H), 6.78 (t, J=8.1 Hz, 1H), 8.16 (d, J=8.1 Hz, 2 H), 8.42 (br. s., 1 H).

Reference Example 221 tert-Butyl {2-[(2,6-diaminophenyl)amino]ethyl}carbamate

Under hydrogen gas atmosphere, a mixture of tert-butyl {2-[(2,6-dinitrophenyl)amino]ethyl}carbamate (8.44 g, 25.9 mmol) and 10% palladium on carbon (50% wet, 1.67 g) in tetrahydrofuran (260 mL) was stirred at room temperature for 4 h. The reaction mixture was filtered and concentrated in vacuo to give the title compound as a brown oil (6.82 g, 25.6 mmol, 99%)

$^1$H NMR (CDCl$_3$) δ 1.45 (s, 9 H), 3.04-3.12 (m, 2 H), 3.21-3.30 (m, 2 H), 3.65 (br. s., 4 H), 5.13 (br. s., 1 H), 6.21 (d, J=8.0 Hz, 2 H), 6.73 (d, J=8.0 Hz, 1 H). hidden (1H)

MS Calcd.: 266; MS Found: 267 (M+H).

Reference Example 222 tert-Butyl (2-{7-amino-2-[(2,4-dichlorophenyl)(hydroxy)methyl]-1H-benzimidazol-1-yl}ethyl)carbamate To a stirred solution of tert-butyl {2-[(2,6-diaminophenyl)amino]ethyl}carbamate (5.00 g, 18.8 mmol) in ethanol (38 mL) was added methyl 2-(2,4-dichlorophenyl)-2-hydroxyethanimidoate hydrochloride (5.59 g, 20.7 mmol) at room temperature. After 12 h, the reaction mixture was diluted with aqueous sodium hydrogen carbonate and water. The resultant mixture was extracted with ethyl acetate. The combined organic layer was washed with brine, dried over anhydrous sodium sulfate, filtered, and concentrated in vacuo. The residue was purified by flash column chromatography on silica gel eluting with ethyl acetate to give the title compound as a brown amorphous solid (8.46 g, 18.7 mmol, 99%).

$^1$H NMR (CDCl$_3$) δ: 1.38 (s, 9 H), 3.09-3.34 (m, 2 H), 4.16-4.50 (m, 4 H), 4.97-5.05 (m, 1 H), 6.23 (s, 1 H), 6.51 (d, J=8.0 Hz, 1 H), 6.98 (t, J=8.0 Hz, 1 H), 7.09 (d, J=8.0 Hz, 1 H), 7.16 (dd, J=8.4, 2.1 Hz, 1 H), 7.35 (d, J=2.1 Hz, 1 H), 7.47 (d, J=8.4 Hz, 1 H). hidden (1H)

MS Calcd.: 450, MS Found: 451 (M+H).

Reference Example 223 tert-Butyl (2-{2-[(2,4-dichlorophenyl)(hydroxy)methyl]-7-(diethylamino)-1H-benzimidazol-1-yl}ethyl)carbamate To a solution of tert-butyl (2-{7-amino-2-[(2,4-dichlorophenyl)(hydroxy)methyl]-1H-benzimidazol-1-yl}ethyl)carbamate (5.00 g, 11.1 mmol) in methanol (110 mL) and acetic acid (5.5 mL) was added acetoaldehyde (4.15 mL, 66.6 mmol) at 0° C. The resultant mixture was stirred at 0° C. for 30 min. To the reaction mixture was added sodium triacetoxyborohydride (14.1 g, 66.5 mmol) at 0° C. After the resultant mixture was stirred at room temperature for 3 h, the mixture was diluted with aqueous sodium hydrogen carbonate and 8N aqueous sodium hydroxide, and extracted with ethyl acetate.

The combined organic layer was washed with water and brine, dried over sodium sulfate, filtered and concentrated in vacuo. The residue was purified by column chromatography on silica gel eluting with a 20-50% ethyl acetate/n-hexane gradient mixture to give a colorless solid (4.15 mg, 8.18 mmol, 74%).

$^1$H NMR (CDCl$_3$) δ 0.97 (t, J=7.0 Hz, 3 H), 1.11 (t, J=7.0 Hz, 3 H), 1.28 (s, 9 H), 2.90-3.19 (m, 4 H), 3.28-3.42 (m, 1 H), 3.55-3.75 (m, 1 H), 4.31-4.42 (m, 1 H), 4.77-4.91 (m, 2 H), 5.12-5.20 (m, 1 H), 6.34 (d, J=5.2 Hz, 1 H), 7.03 (dd, J=7.7, 1.1 Hz, 1 H), 7.15 (t, J=7.7 Hz, 1 H), 7.28 (dd, J=8.2, 2.2 Hz, 1 H), 7.36 (d, J=2.2 Hz, 1 H), 7.48 (dd, J=7.7, 1.1 Hz, 1 H), 7.66 (d, J=8.2 Hz, 1 H).

MS Calcd.: 506; MS Found: 507 (M+H).

Reference Example 224 tert-Butyl (2-{2-[(2,4-dichlorophenyl)carbonyl]-7-(diethylamino)-1H-benzimidazol-1-yl}ethyl)carbamate A mixture of tert-butyl (2-{2-[(2,4-dichlorophenyl)(hydroxy)methyl]-7-(diethylamino)-1H-benzimidazol-1-yl}ethyl)carbamate (500 mg, 0.985 mmol) and manganese (IV) oxide (856 mg, 9.85 mmol) in tetrahydrofuran (5 mL) was stirred at room temperature for 4 h, filtered and concentrated in vacuo. The residue was purified by column chromatography on silica gel eluting with a 0-20% ethyl acetate/n-hexane gradient mixture to give a yellow amorphous solid (404 mg, 0.800 mmol, 81%).

$^1$H NMR (CDCl$_3$) δ 1.09 (t, J=7.1 Hz, 6 H), 1.23 (s, 9 H), 3.06-3.24 (m, 4 H), 3.47-3.58 (m, 2 H), 4.82 (br. s., 1 H), 5.25 (t, J=5.2 Hz, 2 H), 7.18 (dd, J=7.8, 1.1 Hz, 1 H), 7.26 (t, J=7.8 Hz, 1 H), 7.36 (dd, J=8.2, 1.9 Hz, 1 H), 7.49 (d, J=1.9 Hz, 1 H), 7.60 (d, J=7.8 Hz, 1 H), 7.67 (d, J=8.2 Hz, 1 H).

MS Calcd.: 504; MS Found: 505 (M+H).

Reference Example 225 tert-Butyl {3-[(2,6-dinitrophenyl)amino]propyl}carbamate

A mixture of tert-butyl (3-aminopropyl)carbamate (4.20 g, 24.1 mmol), 2-chloro-1,3-dinitrobenzene (4.07 g, 20.1 mmol) and triethylamine (5.60 mL, 40.2 mmol) in tetrahydrofuran (200 mL) was stirred at room temperature for 3 h. The reaction mixture was diluted with ethyl acetate, washed with water and brine, dried over sodium sulfate, filtered and concentrated in vacuo. The residue was purified by column chromatography on silica gel eluting with a 30% ethyl acetate/n-hexane mixture to give a yellow solid (6.79 g, 20.0 mmol, 99.5%).

$^1$H NMR (CDCl$_3$) δ 1.40 (s, 9 H), 1.79-1.92 (m, 2 H), 3.00-3.07 (m, 2 H), 3.21 (q, J=6.4 Hz, 2 H), 4.54 (br. s., 1H), 6.75 (t, J=8.2 Hz, 1 H), 8.16 (d, J=8.2 Hz, 2 H), 8.32 (br. s., 1 H).

Reference Example 226 tert-Butyl {3-[(2,6-diaminophenyl)amino]propyl}carbamate

Under hydrogen gas atmosphere, a mixture of tert-butyl {3-[(2,6-dinitrophenyl)amino]propyl}carbamate (6.79 g, 20.0 mmol) and 10% palladium on carbon (50% wet, 1.4 g) in tetrahydrofuran (200 mL) was stirred at room temperature for 2 h. The reaction mixture was filtered and concentrated in vacuo to give the title compound as an orange oil (5.47 g, 19.5 mmol, 98%).

$^1$H NMR (CDCl$_3$) δ 1.44 (s, 9 H), 1.69-1.79 (m, 2 H), 2.93 (t, J=6.2 Hz, 2 H), 3.32 (q, J=6.1 Hz, 2 H), 3.80 (br. s., 4 H), 4.71 (br. s., 1 H), 6.17 (d, J=8.0 Hz, 2 H), 6.71 (t, J=8.0 Hz, 1 H). hidden (1 H)

MS Calcd.: 280; MS Found: 281 (M+H).

Reference Example 227 tert-Butyl (3-{7-amino-2-[(2,4-dichlorophenyl)(hydroxy)methyl]-1H-benzimidazol-1-yl}propyl)carbamate To a stirred solution of tert-butyl {3-[(2,6-diaminophenyl)amino]propyl}carbamate (5.47 g, 19.5 mmol) in ethanol (39 mL) was added methyl 2-(2,4-dichlorophenyl)-2-hydroxyethanimidoate hydrochloride (5.80 g, 19.5 mmol) at room temperature. After 14 h, the reaction mixture was diluted with water. The resultant precipitate was collected by filtration and washed with water and ethyl acetate to give the title compound as a colorless solid (7.67 g, 16.5 mmol, 85%).

$^1$H NMR (DMSO-d$_6$) δ: 1.38 (s, 9 H), 1.91-2.06 (m, 2 H), 3.02-3.12 (m, 2 H), 4.47-4.56 (m, 2 H), 4.99 (s, 2 H), 6.13 (d, J=7.1 Hz, 1 H), 6.49-6.54 (m, 2 H), 6.75-6.86 (m, 2 H), 6.92-6.99 (m, 1 H), 7.49-7.57 (m, 2 H), 7.80 (d, J=8.8 Hz, 1 H).

MS Calcd.: 464, MS Found: 465 (M+H).

Reference Example 228 tert-Butyl (3-{2-[(2,4-dichlorophenyl)(hydroxy)methyl]-7-(diethylamino)-1H-benzimidazol-1-yl}propyl)carbamate To a solution of tert-butyl (3-{7-amino-2-[(2,4-dichlorophenyl)(hydroxy)methyl]-1H-benzimidazol-1-yl}propyl)carbamate (3.00 g, 6.45 mmol) in methanol (65 mL) and acetic acid (3.3 mL) was added acetaldehyde (2.41 mL, 38.7 mmol) at 0° C. The resultant mixture was stirred at 0° C. for 30 min. To the reaction mixture was added sodium triacetoxyborohydride (8.20 g, 38.7 mmol) at 0° C. After the resultant mixture was stirred at 0° C. for 3 h, the mixture was diluted with aqueous sodium hydrogen carbonate and 1N aqueous sodium hydroxide, and extracted with ethyl acetate. The combined organic layer was washed with brine, dried over sodium sulfate, filtered and concentrated in vacuo. The residue was purified by column chromatography on silica gel eluting with a ethyl acetate to give a crude solid, which was washed with diisopropyl ether to give the title compound as a colorless solid (3.04 g, 5.83 mmol, 90%).

$^1$H NMR (CDCl$_3$) δ 0.93-1.09 (m, 6 H), 1.45 (s, 9 H), 1.46-1.58 (m, 1 H), 1.76-1.89 (m, 1 H), 2.90-3.17 (m, 6 H), 4.13-4.25 (m, 1 H), 4.39-4.51 (m, 1 H), 4.67 (br. s., 1 H), 5.16-5.24 (m, 1 H), 6.34 (d, J=4.1 Hz, 1 H), 7.04 (dd, J=8.0, 1.1 Hz, 1 H), 7.15-7.22 (m, 2 H), 7.38-7.44 (m, 2 H), 7.49 (dd, J=8.0, 1.1 Hz, 1 H).

MS Calcd.: 520; MS Found: 521 (M+H).

Reference Example 229

2-Chloro-2-oxoethane-1,1-diyl diacetate

A mixture of glyoxylic acid monohydrate (53.2 g, 578 mmol), acetic anhydride (530 mL, 5.61 mol) and acetic acid (120 mL) was refluxed for 2 h, concentrated in vacuo and azeotroped with toluene. The residue was diluted with toluene (270 mL), and thionyl chloride (84 mL, 1.15 mol) was added to the mixture. The resultant mixture was stirred at 60° C. for 16 h and concentrated in vacuo. The residue was purified by distillation (6-8 hpa, 70-80° C.) to afford compound the title compound as a colorless oil (70.7 g, 363 mmol, 63%).

$^1$H NMR (CDCl$_3$) δ2.22 (6 H, s), 6.92 (1 H, s).

Reference Example 230

6-Chloro-7-nitro-1H-indole-2,3-dione

A solution of 2-chloro-2-oxoethane-1,1-diyl diacetate (70.7 g, 363 mmol) in THF (225 mL) was added dropwise to a mixture of 3-chloro-2-nitroaniline (44.7 g, 259 mmol) and potassium hydrogen carbonate (130 g, 1.30 mmol) in THF (450 mL) at 0° C. The resultant mixture was stirred at room temperature for 4 h, filtered and concentrated in vacuo. The residue was diluted with ethanol (450 mL) and a solution of hydroxylammonium chloride (90.0 g, 1.30 mmol) in water (225 mL) was added to the mixture at room temperature. The resultant mixture was refluxed for 2 h and concentrated in vacuo. Water (225 mL) was added to the residue and the resultant mixture was extracted with ethyl acetate. The extract was washed with brine, dried over sodium sulfate, filtered and concentrated in vacuo. The residue was purified by column chromatography on silica gel eluting with ethyl acetate to afford a crude orange solid. The crude solid was added portionwise to conc. sulfuric acid (260 mL) at 50° C., and the resultant mixture was stirred at 70° C. for 2 h, cooled to room temperature and poured into iced water (780 mL). The resultant mixture was extracted with ethyl acetate. The extract was washed with brine, dried over sodium sulfate, filtered through silica gel and concentrated in vacuo. Diisopropyl ether (800 mL) was added to the residue, and the resultant suspension was refluxed for 30 min and cooled to room temperature with stirring. The precipitate was collected by filtration and washed with diisopropyl ether to afford the title compound as a brown solid (33.5 g, 152 mmol 59%).

$^1$H NMR (DMSO-d$_6$) δ 7.38 (1H, d, J=8.0 Hz), 7.75 (1H, d, J=8.0 Hz), 11.77 (1H, s).

MS Calcd.: 226; MS Found: 225 (M−H).

Reference Example 231

4-Chloro-2-[(3-chloropropyl)amino]-3-nitrobenzoic acid

A mixture of 6-chloro-7-nitro-1H-indole-2,3-dione (1.50 g, 6.80 mmol), 1-chloro-3-iodopropane (2.92 mL, 27.2 mmol) and cesium carbonate (8.86 g, 27.2 mmol) in N,N-dimethylacetamide (30 mL) was stirred at room temperature for 6 h. 1N Aqueous sodium hydroxide (30 mL) was added dropwise to the reaction mixture at 0° C., and the resultant mixture was stirred at room temperature for 15 min. 30% Aqueous hydrogen peroxide (1.16 mL) was added dropwise to the reaction mixture at 0° C., and the resultant mixture was stirred at room temperature for 15 min and acidified with 1N aqueous hydrochloric acid at 0° C. The resultant mixture was extracted with ethyl acetate. The extract was washed with water and brine, dried over sodium sulfate, filtered and concentrated in vacuo. The residue was purified by column chromatography on silica gel eluting with a 3% methanol/ethyl acetate mixture to give a crude solid, which was washed with diisopropyl ether/hexane to afford the title compound as an orange solid (1.39 g, 4.74 mmol, 70%).

$^1$H NMR (CDCl$_3$) δ 2.04-2.15 (2H, m), 3.28 (2H, t, J=6.7 Hz), 3.61 (2H, t, J=6.3 Hz), 6.76 (1H, d, J=8.8 Hz), 8.03 (1H, d, J=8.8 Hz), 8.17 (1H, brs), hidden (1H).

Reference Example 232

Methyl 4-chloro-2-[(3-chloropropyl)amino]-3-nitrobenzoate

A mixture of 4-chloro-2-[(3-chloropropyl)amino]-3-nitrobenzoic acid (150 mg, 0.512 mmol), methyl iodide (0.0319 mL, 0.512 mmol) and potassium carbonate (70.8 mg, 0.512 mmol) in N,N-dimethylformamide (1.5 mL) was stirred at room temperature for 12 h. After addition of ethyl acetate, the resultant mixture was washed with water and brine, dried over sodium sulfate, filtered and concentrated in vacuo. The residue was purified by flash column chromatography on NH silica gel eluting with a 5% ethyl acetate/n-hexane mixture to afford a yellow oil (141 mg, 0.459 mmol, 90%).

$^1$H NMR (CDCl$_3$) δ 2.04-2.16 (2H, m), 3.21-3.30 (2H, m), 3.62 (2H, t, J=6.3 Hz), 3.89 (3H, s), 6.72 (1H, d, J=8.8 Hz), 7.95 (1H, d, J=8.8 Hz), 8.34 (1H, brs).

MS Calcd.: 306; MS Found: 305 (M−H).

Reference Example 233

Methyl 3-amino-4-chloro-2-[(3-chloropropyl)amino]benzoate

A mixture of methyl 4-chloro-2-[(3-chloropropyl)amino]-3-nitrobenzoate (275 mg, 0.895) and Fe (150 mg, 2.69 mmol) in AcOH (2.8 mL) was stirred at 80° C. for 1 h. AcOH (2.8 mL) and Fe (350 mg, 6.27) were added to the reaction mixture at room temperature, and the resultant mixture was stirred at 80° C. for 30 min, filtered through Celite and concentrated in vacuo. After water was added to the residue, the resultant mixture was extracted with ethyl acetate. The extract was washed with aqueous sodium hydrogen carbonate and brine, dried over sodium sulfate, filtered and concentrated in vacuo. The residue was purified by flash column chromatography on NH silica gel eluting with a 3% ethyl acetate/n-hexane mixture to afford a yellow oil (201 mg, 0.725 mmol, 81%).

$^1$H NMR (CDCl$_3$) δ 1.97-2.08 (2 H, m), 3.13-3.24 (2 H, m), 3.70 (2 H, t, J=6.3 Hz), 3.87 (3 H, s), 4.29 (2 H, brs), 6.16 (1 H, brs), 6.96 (1 H, d, J=8.5 Hz), 7.31 (1 H, d, J=8.5 Hz).

MS Calcd.: 276; MS Found: 277 (M+H).

Reference Example 234

4,6-Dimethyl-5-nitropyrimidin-2-ol 4,6-Dimethylpyrimidin-2-ol (10.0 g, 80.6 mmol) was added to sulfuric acid (80 mL) at 0° C. Then potassium nitrate (16.29 g, 161.1 mmol), was added to the reaction mixture at 0° C. The mixture was stirred at room temperature for 24 hr. The reaction mixture was poured slowly into diethyl ether (1000 mL) at 0° C. The precipitated solid was collected by filtration and washed with diethyl ether. A suspension of the solid in ethanol (50.0 mL) was neutralized with sodium hydrogen carbonate at room temperature. The solid was removed by filtration and the filter cake was washed with ethanol (ca. 3000 mL). The filtrate was concentrated in vacuo to give the title compound (13.15 g) as a pale yellow solid.

$^1$H NMR (DMSO-d$_6$) δ 2.37 (s, 6H).

Reference Example 235

2-Methoxy-4,6-dimethyl-5-nitropyrimidine 4,6-Dimethyl-5-nitropyrimidin-2-ol (18.4 g, 108 mmol) wad added portionwise to a stirred phosphoryl chloride (3.0 mL) at 0° C., and the mixture was stirred at 100° C. for 80 min. The mixture was concentrated in vacuo, and methanol (180 mL) was added to the residue carefully at 0° C. Sodium methoxide (28% solution in methanol, 68.8 g, 357 mmol) was added dropwise to a stirred mixture at 0° C., and the mixture was stirred at 0° C. for 10 min. The mixture was diluted with aqueous saturated ammonium chloride and concentrated in vacuo. The residue was diluted with water and extracted with ethyl acetate. The combined organic layer was washed with brine, dried over anhydrous magnesium sulfate, filtered and concentrated in vacuo. The residue was purified by flash column chromatography on silica gel eluting with a 5-20% ethyl acetate/n-hexane gradient mixture. The filtrate was concentrated in vacuo to give the title compound as a yellow wax (13.0 g, 71.0 mmol, 66%).

$^1$H NMR (CDCl$_3$) δ 2.54 (s, 6H), 4.05 (s, 3H).

Reference Example 236

3-Isothiocyanato-6-methoxy-2-(trifluoromethyl)pyridine

To a solution of 6-methoxy-2-(trifluoromethyl)pyridin-3-amine (6.99 g, 36.4 mmol) in tetrahydrofuran (60 mL) and saturated aqueous sodium hydrogen carbonate (60 mL) was added dropwise thiophosgene (2.8 mL, 36.5 mmol) at 0° C. The mixture was stirred at 0° C. for 0.5 hr. Water was added to the reaction mixture and the mixture was extracted with ethyl acetate. The organic layer was washed with brine, dried over anhydrous magnesium sulfate, and concentrated in vacuo to give the title compound (8.49 g, 36.3 mmol, quant.) as a pale orange oil.

$^1$H NMR (CDCl$_3$) δ 3.98 (s, 3 H), 6.92 (dd, J=8.9, 0.6 Hz, 1 H), 7.57 (dd, J=8.9, 0.6 Hz, 1 H).

Reference Example 237

Methyl 4-chloro-2-[(3-hydroxypropyl)amino]-3-({[6-methoxy-2-(trifluoromethyl)pyridin-3-yl]carbamothioyl}amino)benzoate A solution of methyl 3-amino-4-chloro-2-[(3-hydroxypropyl)amino]benzoate (1.00 g, 3.87 mmol) and 3-isothiocyanato-6-methoxy-2-(trifluoromethyl)pyridine (1.81 g, 7.73 mmol) in tetrahydrofuran (10 mL) was stirred at room temperature for 3 days. The reaction mixture was concentrated in vacuo. The residue was purified by flash chromatography on silica gel eluting with a 30-100% ethyl acetate/n-hexane gradient mixture to give the title compound (1.85 g, 3.75 mmol, 97%) as a pale red amorphous.

$^1$H NMR (CDCl$_3$) δ 1.82-1.92 (m, 2 H), 1.98-2.06 (m, 1 H), 3.55-3.66 (m, 2 H), 3.73-3.82 (m, 2 H), 3.89 (s, 3 H), 3.94 (s, 3 H), 6.86 (d, J=8.4 Hz, 1 H), 6.92 (d, J=8.4 Hz, 1 H), 7.39-7.39 (m, 1 H), 7.86-8.13 (m, 3 H).

MS Calcd.: 492; Found: 493 (M+H).

Reference Example 238

Methyl 4-chloro-1-(3-hydroxypropyl)-2-{[6-methoxy-2-(trifluoromethyl)pyridin-3-yl]amino}-1H-benzimidazole-7-carboxylate A mixture of methyl 4-chloro-2-[(3-hydroxypropyl)amino]-3-({[6-methoxy-2-(trifluoromethyl)pyridin-3-yl]carbamothioyl}amino)benzoate (1.85 g, 3.75 mmol), 1-ethyl-3-(3-dimethylaminopropyl)carbodiimide hydrochloride (0.79 g, 4.12 mmol) and triethylamine (0.57 mL, 4.16 mmol) in tetrahydrofuran (20 mL) was stirred at 50° C. for 3 hr. Water was added to the reaction mixture at room temperature and the mixture was extracted with ethyl acetate. The organic layer was washed with water and brine, dried over anhydrous magnesium sulfate and concentrated in vacuo. The residue was purified by flash chromatography on silica gel eluting with a 25-80% ethyl acetate/n-hexane gradient mixture to give the title compound (1.50 g, 3.27 mmol, 87%) as a pale yellow solid.

$^1$H NMR (CDCl$_3$) δ 1.89 (t, J=4.1 Hz, 1 H), 2.04-2.12 (m, 2 H), 3.63-3.68 (m, 2 H), 3.95 (s, 6 H), 4.57 (t, J=6.3 Hz, 2 H), 6.99 (d, J=9.0 Hz, 1 H), 7.19 (d, J=8.4 Hz, 1H), 7.56 (d, J=8.4 Hz, 1 H), 7.79 (br s, 1 H), 8.61 (d, J=9.0 Hz, 1 H).

MS Calcd.: 458; Found: 459 (M+H).

Reference Example 239

6-Methoxy-7-nitro-1H-indole-2,3-dione

To a solution of 6-chloro-7-nitro-1H-indole-2,3-dione (2.0 g, 8.83 mmol) in methanol (20 mL) was added a solution of sodium methoxide in methanol (28%, 3.8 mL) at room temperature. The mixture was stirred at 60° C. for 14 hr. 1N Hydrogen chloride (10 mL) was added to the reaction mixture at 0° C. and the mixture was extracted with ethyl acetate. The organic layer was washed with brine (×3), dried over anhydrous magnesium sulfate, and concentrated in vacuo. The residue was purified by flash column chromatography on silica gel eluting with a 30-100% ethyl acetate/n-hexane gradient mixture to give the title compound (1.349 g, 6.07 mmol, 69%) as a yellow solid.

$^1$H NMR (CDCl$_3$) δ 4.10 (s, 3 H), 6.76 (d, J=8.6 Hz, 1 H), 7.83 (d, J=8.6 Hz, 1 H), 8.98 (br s, 1 H).

MS Calcd.: 221; MS Found: 221 (M–H).

Reference Example 240

2-[(3-Chloropropyl)amino]-4-methoxy-3-nitrobenzoic acid

A mixture of 6-methoxy-7-nitro-1H-indole-2,3-dione (1.44 g, 6.37 mmol), cesium carbonate (6.22 g, 19.09 mmol) and 1-chloro-3-iodopropane (2.05 mL, 19.09 mmol) in N,N-dimethylacetamide (30 mL) was stirred at room temperature for 3 hr. 1N Aqueous sodium hydroxide (30 mL) was added to the reaction mixture at 0° C. and the mixture was stirred at room temperature for 0.5 hr. To the reaction mixture was added 30% aqueous hydrogen peroxide (1.08 mL) at 0° C. and the mixture was stirred at 50° C. for 0.5 hr. The mixture was acidified with 6N hydrogen chloride at 0° C., and the mixture was extracted with ethyl acetate. The organic layer was washed with aqueous sodium thiosulfate, water (×3) and brine, dried over anhydrous magnesium sulfate, and concentrated in vacuo. The residue was purified by flash column chromatography on silica gel eluting with a 0-20% methanol/ethyl acetate gradient mixture to give the title compound (1.776 g, 6.15 mmol, 97%) as a yellow solid.

$^1$H NMR (CDCl$_3$) δ 1.96-2.11 (m, 2 H), 3.27 (t, J=6.8 Hz, 2 H), 3.60 (t, J=6.5 Hz, 2 H), 3.92 (s, 3 H), 6.32 (d, J=9.0 Hz, 1 H), 7.94-8.19 (m, 2 H).

MS Calcd.: 288; MS Found: 289 (M+H).

Reference Example 241

Methyl 2-[(3-chloropropyl)amino]-4-methoxy-3-nitrobenzoate

To a mixture of 2-[(3-chloropropyl)amino]-4-methoxy-3-nitrobenzoic acid (1.77 g, 6.13 mmol) and potassium carbonate (847 mg, 6.13 mmol) in N,N-dimethylformamide (18 mL) was added iodomethane (0.38 mL, 6.10 mmol) at room temperature. After stirring at room temperature for 14 hr, water was added to the reaction mixture and the mixture was extracted with ethyl acetate. The organic layer was washed with water (×5) and brine, dried over anhydrous magnesium sulfate, and concentrated in vacuo. The residue was purified by flash column chromatography on silica gel eluting with a 10-50% ethyl acetate/n-hexane gradient mixture to give the title compound (1.60 g, 5.29 mmol, 86%) as a yellow amorphous.

$^1$H NMR (CDCl$_3$) δ 2.03-2.12 (m, 2 H), 3.21-3.28 (m, 2 H), 3.61 (t, J=6.6 Hz, 2 H), 3.85 (s, 3 H), 3.90 (s, 3 H), 6.26 (d, J=9.2 Hz, 1 H), 7.99 (d, J=9.2 Hz, 1 H), 8.20-8.30 (m, 1 H).
MS Calcd.: 302; MS Found: 303 (M+H).

Reference Example 242

Methyl 3-amino-2-[(3-chloropropyl)amino]-4-methoxybenzoate

A mixture of methyl 2-[(3-chloropropyl)amino]-4-methoxy-3-nitrobenzoate (1.61 g, 5.23 mmol) and iron (1.46 g, 26.1 mmol) in acetic acid (32 mL) was stirred at 80° C. for 3 hr. Iron (0.58 g, 10.4 mmol) was added to the reaction mixture at room temperature and the mixture was stirred at 80° C. for 1 hr. To the reaction mixture was added iron (0.88 g, 15.8 mmol) at room temperature and the mixture was stirred at 80° C. for 1 hr. The solid was removed by filtration and the filter cake was washed with tetrahydrofuran. The filtrate was concentrated in vacuo. Water was added to the residue and the mixture was extracted with ethyl acetate. The organic layer was washed with aqueous sodium hydrogen carbonate and brine, dried over anhydrous magnesium sulfate, and concentrated in vacuo. The residue was purified by flash column chromatography on silica gel eluting with a 10-50% ethyl acetate/n-hexane gradient mixture to give the title compound (967.5 mg, 3.55 mmol, 68%) as a yellow amorphous.

$^1$H NMR (CDCl$_3$) δ 1.96-2.05 (m, 2 H), 3.21 (t, J=6.8 Hz, 2 H), 3.69 (t, J=6.8 Hz, 2 H), 3.85 (s, 3 H), 3.90 (s, 3 H), 6.53 (d, J=9.0 Hz, 1 H), 7.44 (d, J=9.0 Hz, 1 H).
MS Calcd.: 272; MS Found: 273 (M+H).

Reference Example 243

Methyl 1-(3-chloropropyl)-4-methoxy-2-[(2-methoxy-4,6-dimethylpyrimidin-5-yl)amino]-1H-benzimidazole-7-carboxylate A mixture of methyl 3-amino-2-[(3-chloropropyl)amino]-4-methoxybenzoate (965 mg, 3.55 mmol) and 5-isothiocyanato-2-methoxy-4,6-dimethylpyrimidine (1.04 g, 5.32 mmol) in tetrahydrofuran (15 mL) was stirred at 40° C. for 3 days. The solvent was removed in vacuo and the solid was collected by filtration, washed with diisopropyl ether. A mixture of the solid (1.589 g), 1-ethyl-3-(3-dimethylaminopropyl)carbodiimide hydrochloride (0.72 g, 3.76 mmol) and triethylamine (0.52 mL, 3.73 mmol) in tetrahydrofuran (16 mL) was stirred at 50° C. for 3 hr. 1-Ethyl-3-(3-dimethylaminopropyl)carbodiimide hydrochloride (130 mg, 0.678 mmol) and triethylamine (0.095 mL, 0.682 mmol) were added to the reaction mixture at room temperature and the mixture was stirred at 50° C. for 1 hr. Water was added to the reaction mixture at room temperature and the mixture was extracted with a mixture of ethyl acetate, THF and N,N-dimethylformamide. The organic layer was washed with water and brine, dried over anhydrous magnesium sulfate and concentrated in vacuo to give the title compound (878.9 mg, 2.03 mmol, 66%) as a pale red solid.

$^1$H NMR (DMSO-d$_6$) δ 2.02-2.12 (m, 2 H), 2.29 (s, 6 H), 3.59 (t, J=6.3 Hz, 2 H), 3.81 (s, 3 H), 3.87 (s, 3 H), 3.91 (s, 3 H), 4.52-4.61 (m, 2 H), 6.70 (d, J=8.6 Hz, 1 H), 7.46 (d, J=8.6 Hz, 1 H), 8.38 (s, 1 H).
MS Calcd.: 433; Found: 434 (M+H).

Reference Example 244

Methyl 4-chloro-1-(3-chloropropyl)-2-[(2-methoxy-4,6-dimethylpyrimidin-5-yl)amino]-1H-benzimidazole-7-carboxylate A mixture of methyl 3-amino-4-chloro-2-[(3-chloropropyl)amino]benzoate (500 mg, 1.80 mmol), 5-isothiocyanato-2-methoxy-4,6-dimethylpyrimidine (527 mg, 2.70 mmol) and sodium hydrogen carbonate (454 mg, 5.40 mmol) in tetrahydrofuran (1 mL) was stirred at 60° C. for 36 h. After tetrahydrofuran (4 mL), 1-ethyl-3-(3-dimethylaminopropyl)carbodiimide hydrochloride (345 mg, 1.80 mmol) and triethylamine (0.251 mL, 1.80 mmol) were added to the mixture at room temperature, the resultant mixture was stirred at 50° C. for 40 min and poured into water (50 mL). The precipitate was collected by filtration and washed with water and diethyl ether to afford the title compound as a colorless solid (589 mg, 1.34 mmol, 74%).

$^1$H NMR (DMSO-d$_6$) δ 2.03-2.19 (m, 2 H), 2.31 (s, 6 H), 3.62 (t, J=6.3 Hz, 2 H), 3.88-3.94 (m, 6 H), 4.52 (t, J=7.1 Hz, 2 H), 7.14 (d, J=8.5 Hz, 1 H), 7.34 (d, J=8.5 Hz, 1 H), 8.71 (s, 1 H).
MS Calcd.: 437; MS Found: 438 (M+H).

Example 1

8-Chloro-1-(4-chloro-2-methoxy-6-methylphenyl)-5-(1-ethylpropyl)-2,3-dihydro-1H-imidazo[1,2-a]benzimidazole

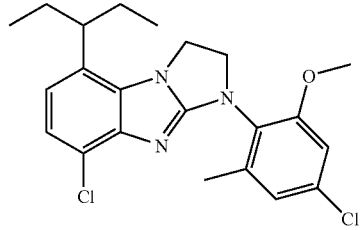 [SMILES: CCC(CC)c1ccc(Cl)c2nc3n(c12)CCN3c1c(C)cc(Cl)cc1OC]

To a solution of 2-[4-chloro-2-[(4-chloro-2-methoxy-6-methylphenyl)amino]-7-(1-ethylpropyl)-1H-benzimidazol-1-yl]ethanol (Reference Example 12; 183 mg, 0.419 mmol) in tetrahydrofuran (2 mL) was added diisopropylethylamine (0.11 ml, 0.629 mmol) and methanesulfonyl chloride (0.049 mL, 0.629 mmol), and the mixture was stirred at room temperature for 72 hr. The reaction mixture was diluted with saturated aqueous sodium hydrogen carbonate and extracted with ethyl acetate. The organic layer was washed with brine, dried over sodium sulfate and concentrated in vacuo. The residue was purified by silica gel column chromatography eluting with a 4-25% ethyl acetate/n-hexane gradient mixture to give the title compound (141 mg, 0.337 mmol, 80%) as an oil. The oil was crystallized from ethyl acetate-diisopropyl ether to give the title compound (73 mg, 0.174 mmol, 42%) as a colorless crystal.

$^1$H NMR (CDCl$_3$) δ: 0.82-0.88 (6H, m), 1.61-1.84 (4H, m), 2.33 (3H, s), 2.70-2.79 (1H, m), 3.76 (3H, s), 4.04-4.16 (1H, m), 4.36-4.49 (3H, m), 6.75 (1H, d, J=8.4 Hz), 6.78 (1H, d, J=1.5 Hz), 6.88 (1H, d, J=1.5 Hz), 7.03 (1H, d, J=8.4 Hz).

MS Calcd.: 417; Found: 418 (M+H).

Example 2

8-Chloro-1-(4-chloro-2-methoxy-6-methylphenyl)-5-(1-ethylpropyl)-1H-imidazo[1,2-a]benzimidazol-2(3H)-one

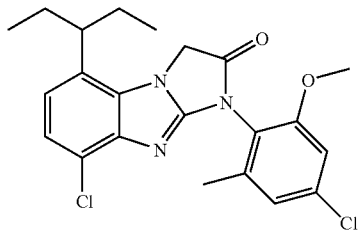 [SMILES: CCC(CC)c1ccc(Cl)c2nc3n(c12)CC(=O)N3c1c(C)cc(Cl)cc1OC]

To a solution of [4-chloro-2-[(4-chloro-2-methoxy-6-methylphenyl)amino]-7-(1-ethylpropyl)-1H-benzimidazol-1-yl]acetic acid (Reference Example 13; 770 mg, 1.71 mmol) in N,N-dimethylformamide (6 mL) was added HOBt (288 mg, 1.88 mmol), triethylamine (0.595 mL, 4.28 mmol) and WSC (426 mg, 2.22 mmol), and the mixture was stirred at room temperature for 15 hr. The reaction mixture was diluted with saturated aqueous sodium hydrogen carbonate and extracted with ethyl acetate (×2). The combined organic layer was washed with saturated aqueous sodium hydrogen carbonate and brine (×2), dried over sodium sulfate and concentrated in vacuo. The residue was purified by basic silica gel column chromatography eluting with a 10-25% ethyl acetate/n-hexane gradient mixture to give the crude title compound as an oil. The oil was crystallized from diisopropyl ether-n-hexane to give the title compound (519 mg, 1.20 mmol, 70%) as a colorless crystal.

$^1$H NMR (CDCl$_3$) δ: 0.83-0.89 (6H, m), 1.64-1.89 (4H, m), 2.26 (3H, s), 2.64-2.76 (1H, m), 3.78 (3H, s), 4.85 (1H, d, J=16.8 Hz), 4.92 (1H, d, J=16.8 Hz), 6.88 (1H, d, J=2.0 Hz), 6.95 (1H, d, J=8.2 Hz), 6.97 (1H, d, J=2.0 Hz), 7.19 (1H, d, J=8.2 Hz).

MS Calcd.: 431; Found: 432 (M+H).

Example 3

8-Chloro-1-(2,4-dichlorophenyl)-5-(1-ethylpropyl)-2,3-dihydro-1H-imidazo[1,2-a]benzimidazole

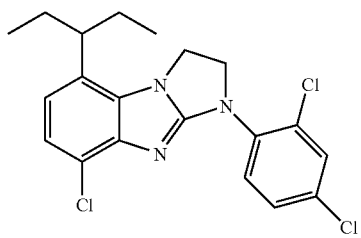 [SMILES: CCC(CC)c1ccc(Cl)c2nc3n(c12)CCN3c1ccc(Cl)cc1Cl]

To a solution of 2-{4-chloro-2-[(2,4-dichlorophenyl)amino]-7-(1-ethylpropyl)-1H-benzimidazol-1-yl}ethanol (Reference Example 19; 66 mg, 0.155 mmol) in tetrahydrofuran (0.8 mL) were added diisopropylethylamine (0.053 ml, 0.310 mmol) and methanesulfonyl chloride (0.013 ml, 0.170 mmol) at 0° C., and the mixture was stirred at room temperature for 2 hr. Additional diisopropylethylamine (0.053 ml, 0.310 mmol) and methanesulfonyl chloride (0.013 mL, 0.170 mmol) were added at 0° C., followed by stirring at room temperature for 15 hr. The reaction mixture was diluted with ethyl acetate. The organic layer was washed with brine, dried over anhydrous sodium sulfate and concentrated in vacuo. The residue was purified by silica gel column chromatography eluting with a 10-25% ethyl acetate/n-hexane gradient mixture. The desired fractions were concentrated in vacuo, and the resulting solid was washed with n-hexane to give the title compound (15 mg, 0.0360 mmol, 23%) as a colorless solid.

mp: 171-173° C.

$^1$H NMR (CDCl$_3$) δ: 0.83 (6H, t, J=7.5 Hz), 1.63-1.85 (4H, m), 2.69-2.78 (1H, m), 4.41-4.53 (4H, m), 6.81 (1H, d, J=8.1 Hz), 7.10 (1H, d, J=8.1 Hz), 7.29-7.32 (1H, m), 7.43-7.45 (1H, m), 7.80 (1H, d, J=8.7 Hz).

MS Calcd.: 407; Found: 408 (M+H).

Example 4

8-Chloro-1-(2,4-dichlorophenyl)-5-(1-ethylpropyl)-1H-imidazo[1,2-a]benzimidazol-2(3H)-one

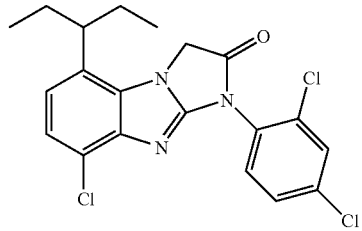 [SMILES: CCC(CC)c1ccc(Cl)c2nc3n(c12)CC(=O)N3c1ccc(Cl)cc1Cl]

To a suspension of {4-chloro-2-[(2,4-dichlorophenyl)amino]-7-(1-ethylpropyl)-1H-benzimidazol-1-yl}acetic acid (Reference Example 21; 294 mg, 0.667 mmol) in N,N-dimethylformamide (3 mL) were added triethylamine (0.11 mL, 0.800 mmol) and 1-ethyl-3-(3-dimethylaminopropyl)carbodiimide hydrochloride (153 mg, 0.800 mmol), and the mixture was stirred at room temperature for 15 hr. The reaction mixture was diluted with water, and the suspension was stirred at room temperature for 1.5 hr. The resulting solid was collected by filtration and washed with water. The crystal was recrystallized from diisopropyl ether-n-hexane to give 160 mg (0.378 mmol, 57%) as a colorless crystal.

mp: 200-202° C.

$^1$H NMR (CDCl$_3$) δ: 0.84 (3H, t, J=7.8 Hz), 0.87 (3H, t, J=7.8 Hz), 1.64-1.90 (4H, m), 2.65-2.80 (1H, m), 4.88 (1H, d, J=16.8 Hz), 4.96 (1H, d, J=16.8 Hz), 6.98 (1H, d, J=8.1 Hz), 7.22 (1H, d, J=8.1 Hz), 7.42-7.51 (2H, m), 7.61 (1H, d, J=2.1 Hz).

MS Calcd.: 421; Found: 422 (M+H).

Example 5

1-(2-Bromo-4-chlorophenyl)-8-chloro-5-(1-ethylpropyl)-2,3-dihydro-1H-imidazo[1,2-a]benzimidazole

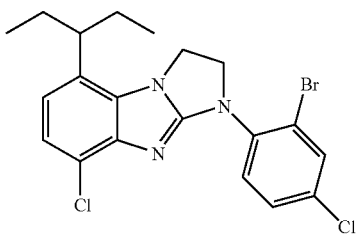 [SMILES: CCC(CC)c1ccc(Cl)c2nc3n(c12)CCN3c1ccc(Cl)cc1Br]

To a solution of 2-{2-[(2-bromo-4-chlorophenyl)amino-4-chloro]-7-(1-ethylpropyl)-1H-benzimidazol-1-yl}ethanol (Reference Example 22; 260 mg, 0.552 mmol) in pyridine (2 mL) was added methanesulfonyl chloride (0.214 ml, 2.76 mmol) at 0° C., and the mixture was stirred at room temperature for 1 hr. The mixture was diluted with saturated aqueous sodium hydrogen carbonate at 0° C. and extracted with ethyl acetate. The extracts were washed with brine, dried over magnesium sulfate and concentrated in vacuo. The residue was dissolved in N,N-dimethylformamide (4 mL) and potassium carbonate (153 mg, 1.10 mmol) was added. The mixture was stirred at 80° C. for 3 hr. After cooling, the mixture was diluted with water and extracted with ethyl acetate. The extracts were washed with saturated aqueous sodium hydrogen carbonate and brine, dried over anhydrous magnesium sulfate and concentrated in vacuo. The residue was purified by silica gel column chromatography eluting with a 1-20% ethyl acetate/n-hexane gradient mixture. The desired fractions were concentrated in vacuo, and the resulting solid was recrystallized from methanol to give the title compound (184 mg, 0.406 mmol, 74%) as a colorless crystal.

mp: 169-171° C.
$^1$H NMR (CDCl$_3$) δ: 0.83 (6H, t, J=7.5 Hz), 1.60-1.85 (4H, m), 2.70-2.80 (1H, m), 4.47 (4H, bs), 6.81 (1H, d, J=8.1 Hz), 7.10 (1H, d, J=8.1 Hz), 7.36 (1H, dd, J=2.4, 8.7 Hz), 7.63 (1H, d, J=2.4 Hz), 7.72 (1H, d, J=8.7 Hz).
MS Calcd.: 451; Found: 452 (M+H).

Example 6

5-Chloro-2-[8-chloro-5-(1-ethylpropyl)-2,3-dihydro-1H-imidazo[1,2-a]benzimidazol-1-yl]benzaldehyde and

Example 7

8-Chloro-1-(4-chlorophenyl)-5-(1-ethylpropyl)-2,3-dihydro-1H-imidazo[1,2-a]benzimidazole

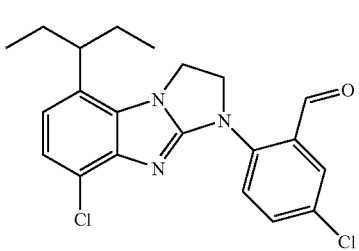
Example 6

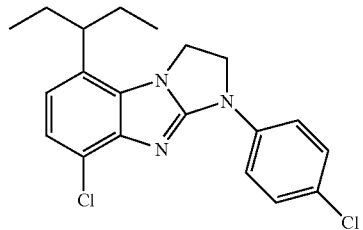
Example 7

A solution of 1-(2-bromo-4-chlorophenyl)-8-Chloro-5-(1-ethylpropyl)-2,3-dihydro-1H-imidazo[1,2-a]benzimidazole (140 mg, 0.309 mmol) in tetrahydrofuran was cooled to −78° C. under nitrogen atmosphere and n-butyllithium (1.6 M solution in n-hexane, 0.213 mL, 0.340 mmol) was added dropwise. After the mixture was stirred at −78° C. for 1 hr, N,N-dimethylformamide (0.120 mL, 1.545 mmol) was added. The mixture was allowed to warm to room temperature for 1 hr. The reaction was quenched by an addition of saturated aqueous ammonium chloride. The mixture was extracted with ethyl acetate. The extracts were washed with brine, dried over anhydrous magnesium sulfate and concentrated in vacuo. The residue was purified by silica gel column chromatography eluting with a 5-40% ethyl acetate/n-hexane gradient mixture. The desired fractions for 5-chloro-2-[8-chloro-5-(1-ethylpropyl)-2,3-dihydro-1H-imidazo[1,2-a]benzimidazol-1-yl]benzaldehyde were concentrated in vacuo, and the resulting solid was recrystallized from methanol to give the title compound of example 6 (41 mg, 0.102 mmol, 33%) as a colorless crystal. The desired fractions for 8-chloro-1-(4-chlorophenyl)-5-(1-ethylpropyl)-2,3-dihydro-1H-imidazo[1,2-a]benzimidazole were concentrated in vacuo, and the resulting solid was recrystallized from methanol to give the title compound of example 7 (17 mg, 0.04542 mmol, 15%) as a colorless crystal.

Example 6 mp: 207-209° C.
$^1$H NMR (CDCl$_3$) δ: 0.83 (6H, t, J=7.5 Hz), 1.60-1.85 (4H, m), 2.70-2.80 (1H, m), 4.40-4.60 (4H, m), 6.83 (1H, d, J=8.4 Hz), 7.10 (1H, d, J=8.4 Hz), 7.56 (1H, dd, J=2.7, 8.7 Hz), 7.67 (1H, d, J=8.7 Hz), 7.88 (1H, d, J=2.7 Hz), 10.16 (1H, s).
MS Calcd.: 401; Found: 402 (M+H).

Example 7 mp: 220-222° C.
$^1$H NMR (CDCl$_3$) δ: 0.81 (6H, t, J=7.4 Hz), 1.60-1.85 (4H, m), 2.65-2.80 (1H, m), 4.49 (4H, s), 6.83 (1H, d, J=8.7 Hz), 7.13 (1H, d, J=8.7 Hz), 7.36 (2H, d, J=8.7 Hz), 7.73 (2H, d, J=8.7 Hz).
MS Calcd.: 373; Found: 374 (M+H).

Example 8

1-{5-Chloro-2-[8-chloro-5-(1-ethylpropyl)-2,3-dihydro-1H-imidazo[1,2-a]benzimidazol-1-yl]phenyl}-N,N-dimethylmethanamine

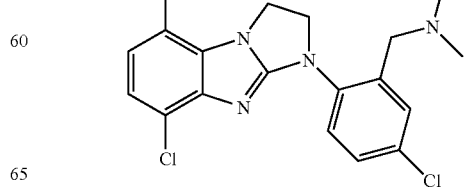

Dimethylamine (2.0 M solution in tetrahydrofuran, 0.096 mL, 0.194 mmol) was added to a solution of 5-chloro-2-[8-chloro-5-(1-ethylpropyl)-2,3-dihydro-1H-imidazo[1,2-a]benzimidazol-1-yl]benzaldehyde (26 mg, 0.0646 mmol) in a mixture of methanol (0.5 mL) and tetrahydrofuran (0.5 mL). After the mixture was stirred for 30 min at room temperature, acetic acid (0.037 mL, 0.0646 mmol) and sodium cyanoborohydride (12 mg, 0.194 mmol) were added. The mixture was stirred at room temperature for 18 hr. The mixture was diluted with water and extracted with ethyl acetate. The extracts were washed with saturated aqueous sodium hydrogen carbonate and brine, dried over anhydrous magnesium sulfate and concentrated in vacuo. The residue was purified by NH-silica gel column chromatography eluting with a 3-30% ethyl acetate/n-hexane gradient mixture. The desired fractions were concentrated in vacuo, and the resulting solid was triturated with n-hexane to give the title compound (10.3 mg, 0.0239 mmol, 37%) as an amorphous.

$^1$H NMR (CDCl$_3$) δ: 0.83 (6H, t, J=7.5 Hz), 1.60-1.85 (4H, m), 2.16 (6H, s), 2.70-2.80 (1H, m), 3.49 (2H, s), 4.35-4.45 (4H, m), 6.78 (1H, d, J=8.1 Hz), 7.07 (1H, d, J=8.1 Hz), 7.27 (1H, dd, J=2.7, 8.1 Hz), 7.42 (1H, d, J=8.1 Hz), 7.44 (1H, d, J=2.7 Hz).

MS Calcd.: 430; Found: 431 (M+H).

Example 9

8-Chloro-1-[6-(dimethylamino)-4-methylpyridin-3-yl]-5-(1-ethylpropyl)-1H-imidazo[1,2-a]benzimidazol-2(3H)-one

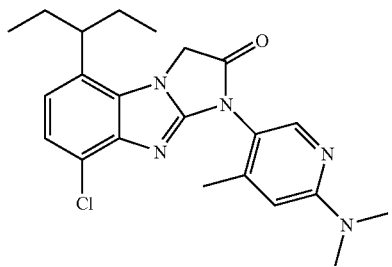 [SMILES: CCC(CC)c1ccc(Cl)c2nc3n(c12)CC(=O)N3c1cnc(N(C)C)cc1C]

A mixture of isopropyl [2,4-dichloro-7-(1-ethylpropyl)-1H-benzimidazol-1-yl]acetate (Reference Example 10; 1.62 g, 4.53 mmol), N$^2$,N$^2$,4-trimethylpyridine-2,5-diamine (2.06 g, 4.85 mmol), p-toluenesulfonic acid monohydrate (922.9 mg, 4.85 mmol) and xylene (8.0 mL) was stirred at 150° C. for 3 days. After cooling, the reaction mixture was diluted with water and the resulting precipitate was removed by filtration. The filtrate was extracted with ethyl acetate (×3). The combined organic layer was washed with 1N hydrochloric acid (×2) and brine, dried over anhydrous magnesium sulfate, filtered and concentrated in vacuo. The residue was purified by silica gel column chromatography eluting with a 0-15% ethyl acetate/n-hexane gradient mixture to give a mixture containing the title compound. The residue was purified by preparative HPLC to give the title compound as the trifluoroacetic acid salt. The salt was washed with aqueous saturated sodium hydrogen carbonate and extracted with ethyl acetate. The extract was washed with brine, dried over magnesium sulfate, filtered and concentrated in vacuo. The resulting solid was recrystallized from n-hexane to give the title compound as a colorless powder (49.7 mg, 0.121 mmol, 2.7%).

mp 222-224° C.

$^1$H NMR (CDCl$_3$) δ: 0.86 (brs, 6H), 1.73-1.84 (m, 4H), 2.22 (s, 3H), 2.66-2.74 (m, 1H), 3.12 (m, 6H), 4.89 (s, 2H), 6.44 (s, 1H), 6.95 (d, J=8.1 Hz, 1H), 7.19 (d, J=8.1 Hz, 1H), 8.11 (s, 1H).

Example 10

2,8-Dichloro-1-(4-chloro-2-methoxy-6-methylphenyl)-5-(1-ethylpropyl)-1H-imidazo[1,2-a]benzimidazole

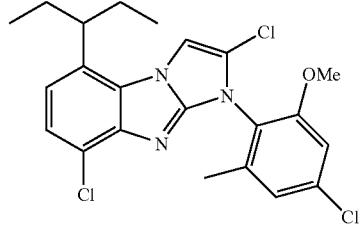 [SMILES: CCC(CC)c1ccc(Cl)c2nc3n(-c4c(C)cc(Cl)cc4OC)c(Cl)cn3c12]

The mixture of 8-chloro-1-(4-chloro-2-methoxy-6-methylphenyl)-5-(1-ethylpropyl)-1H-imidazo[1,2-a]benzimidazol-2(3H)-one (31.8 mg, 0.0736 mmol) and phosphorus oxychloride (0.76 mL) and pyridine (11.9 μL, 0.147 mmol) was stirred at 150° C. for 5 days. After cooling, the mixture was concentrated in vacuo. The residue was neutralized with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified by silica gel column chromatography eluting with a 0-15% ethyl acetate/n-hexane gradient mixture to give the title compound as an amorphous (8.7 mg, 0.0193 mmol, 26%).

$^1$H NMR (CDCl$_3$) δ: 0.88 (dt, J=2.1, 7.5 Hz, 6H), 1.72-1.90 (m, 4H), 2.17 (s, 3H), 2.93-3.02 (m, 1H), 3.74 (s, 3H), 6.87 (d, J=1.8 Hz, 1H), 6.90 (s, 1H), 6.98 (d, J=1.8 Hz, 1H), 7.30 (s, 1H), 7.50 (s, 1H).

MS Calcd.: 449, MS Found: 450 (M+H).

Example 11

3,3,8-Trichloro-1-(4-chloro-2-methoxy-6-methylphenyl)-5-(1-ethylpropyl)-1H-imidazo[1,2-a]benzimidazol-2(3H)-one

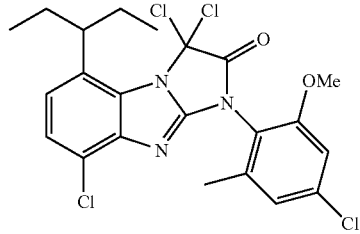 [SMILES: CCC(CC)c1ccc(Cl)c2nc3n(c12)C(Cl)(Cl)C(=O)N3c1c(C)cc(Cl)cc1OC]

The mixture of 8-chloro-1-(4-chloro-2-methoxy-6-methylphenyl)-5-(1-ethylpropyl)-1H-imidazo[1,2-a]benzimidazol-2(3H)-one (54.9 mg, 0.127 mmol) and phosphorus oxychloride (0.58 mL) and diisopropylethylamine (0.2 mL) was stirred at 100° C. for 12 hr. After cooling, the mixture was concentrated in vacuo. The residue was purified by silica gel column chromatography eluting with a 0-10% ethyl acetate/n-hexane gradient mixture. The resulting solid was recrystallized from methanol to give the title compound as a solid (27.4 mg, 0.0547 mmol, 43%).

mp 190-192° C.

$^1$H NMR (CDCl$_3$) δ: 0.94-1.00 (m, 6H), 1.71-1.93 (m, 4H), 2.28 (s, 3H), 3.49-3.54 (m, 1H), 3.80 (s, 3H), 6.89 (d, J=2.1 Hz, 1H), 6.98 (d, J=2.1 Hz, 1H), 7.10 (d, J=8.1 Hz, 1H), 7.29 (d, J=8.1 Hz, 1H).

MS Calcd.: 499, MS Found: 500 (M+H).

Example 12

1-(4-Bromo-2-chlorophenyl)-8-chloro-5-(1-ethylpropyl)-2,3-dihydro-1H-imidazo[1,2-a]benzimidazole

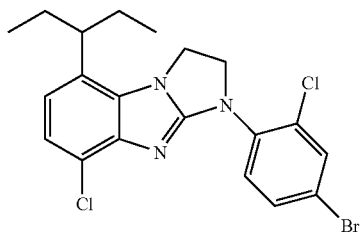 [SMILES: CCC(CC)c1ccc(Cl)c2nc3n(c12)CCN3c1ccc(Br)cc1Cl]

To a solution of 2-[2-[(4-bromo-2-chlorophenyl)amino]-4-chloro-7-(1-ethylpropyl)-1H-benzimidazol-1-yl]ethanol (Reference Example 23; 1.19 g, 2.53 mmol) in pyridine (6.0 mL) was added methanesulfonyl chloride (979 μL, 12.65 mmol) at 0° C. The reaction mixture was stirred at room temperature for 1.5 hr. The reaction mixture was quenched with saturated aqueous sodium hydrogen carbonate at 0° C. and extracted with ethyl acetate (×3). The combined organic layer was washed with brine, dried over anhydrous magnesium sulfate, filtered and concentrated in vacuo. The residue was purified by silica gel column chromatography eluting with a 0-15% ethyl acetate/n-hexane gradient mixture to give a solid. The resulting solid was recrystallized from n-hexane to give the title compound as a colorless powder (975.2 mg, 2.15 mmol, 85%).

mp 165-168° C.

$^1$H NMR (CDCl$_3$) δ: 0.83 (t, J=7.5 Hz, 6H), 1.63-1.85 (m, 4H), 2.69-2.78 (m, 1H), 4.42-4.53 (m, 4H), 6.82 (d, J=8.1 Hz, 1H), 7.11 (d, J=8.1 Hz, 1H), 7.46 (dd, J=2.1, 8.7 Hz, 1H), 7.60 (d, J=2.1 Hz, 1H), 7.76 (d, J=8.7 Hz, 1H).

MS Calcd.: 451, MS Found: 452 (M+H).

Example 13

8-Chloro-1-(2-chlorophenyl)-5-(1-ethylpropyl)-2,3-dihydro-1H-imidazo[1,2-a]benzimidazole Example 14

3-Chloro-4-[8-chloro-5-(1-ethylpropyl)-2,3-dihydro-1H-imidazo[1,2-a]benzimidazol-1-yl]benzoic acid

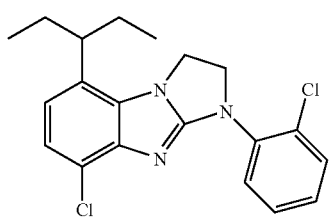

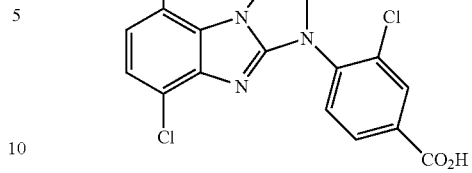

To a solution of 1-(4-bromo-2-chlorophenyl)-8-chloro-5-(1-ethylpropyl)-2,3-dihydro-1H-imidazo[1,2-a]benzimidazole (209.9 mg, 0.463 mmol) in tetrahydrofuran (4.0 mL) was added n-butyllithium (1.60 M solution in n-hexane, 0.35 mL, 0.556 mmol) at −78° C., and the mixture was stirred for 45 min. Carbon dioxide gas was bubbled through the mixture for 3 hr. The mixture was quenched with aqueous saturated ammonium chloride and added 1N sodium hydroxide solution and extracted with ethyl acetate. The organic layer was washed with brine, dried over anhydrous magnesium sulfate, filtered and concentrated in vacuo. The residue was purified by silica gel column chromatography eluting with a 0-15% ethyl acetate/n-hexane gradient mixture. The resulting solid was recrystallized with ethyl acetate/n-hexane to give example 13 as a colorless powder (38.4 mg, 0.103 mmol, 22%). The aqueous layer was neutralized with 1N hydrochloric acid and extracted with ethyl acetate (×3). The organic layer was washed with brine, dried over anhydrous magnesium sulfate, filtered and concentrated in vacuo. The resulting solid was recrystallized with n-hexane to give example 14 as a colorless powder (52.0 mg, 0.124 mmol, 27%).

Example 13 mp 144-146° C.

$^1$H NMR (CDCl$_3$) δ: 0.84 (t, J=7.2 Hz, 6H), 1.66-1.83 (m, 4H), 2.70-2.76 (m, 1H), 4.42-4.55 (m, 4H), 6.81 (d, J=8.1 Hz, 1H), 7.10 (d, J=8.1 Hz, 1H), 7.21 (dt, J=1.5, 7.8 Hz, 1H), 7.34 (dt, J=1.5, 7.8 Hz, 1H), 7.44 (dd, J=1.5, 7.8 Hz, 1H), 7.83 (dd, J=1.5, 7.8 Hz, 1H).

MS Calcd.: 373, MS Found: 374 (M+H).

Example 14 mp >300° C.

$^1$H NMR (DMSO-d$_6$) δ 0.79 (t, J=7.5 Hz, 6H), 1.63-1.74 (m, 4H), 2.83 (brs, 1H), 4.58 (s, 4H), 6.87 (d, J=8.1 Hz, 1H), 7.08 (d, J=8.1 Hz, 1H), 7.98-8.03 (m, 3H), 13.28 (brs, 1H).

MS Calcd.: 417; MS Found: 418 (M+H).

Example 15

3-Chloro-4-[8-chloro-5-(1-ethylpropyl)-2,3-dihydro-1H-imidazo[1,2-a]benzimidazol-1-yl]benzamide

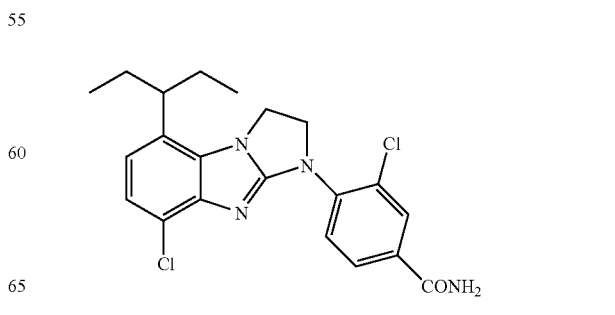

To a solution of 3-chloro-4-[8-chloro-5-(1-ethylpropyl)-2,3-dihydro-1H-imidazo[1,2-a]benzimidazol-1-yl]benzoic acid (45.4 mg, 0.109 mmol) in N,N-dimethylformamide (1.0 mL) were added 1-hydroxy-1H-benzotriazole ammonium salt (21.4 mg, 0.141 mmol) and 1-ethyl-3-(3-dimethylaminopropyl)carbodiimide hydrochloride (22.9 mg, 0.119 mmol). The reaction mixture was stirred at room temperature for 8 hr. The reaction mixture was quenched with aqueous saturated sodium hydrogen carbonate and extracted with ethyl acetate (×3). The combined organic layer was washed with water (×2), aqueous saturated sodium hydrogen carbonate (×1) and brine (×1), dried over magnesium sulfate, filtered and concentrated in vacuo. The residue was recrystallized from ethyl acetate/n-hexane to give the title compound as a colorless solid (36.4 mg, 0.0872 mmol, 80%).

mp 225-229° C.

$^1$H NMR (CDCl$_3$) δ: 0.84 (t, J=7.5 Hz, 6H), 1.61-1.83 (m, 4H), 2.70-2.80 (m, 1H), 4.46-4.62 (m, 4H), 5.59 (brs, 2H), 6.84 (d, J=8.4 Hz, 1H), 7.13 (d, J=8.4 Hz, 1H), 7.73 (dd, J=1.8, 8.4 Hz, 1H), 7.92 (d, J=8.4 Hz, 1H), 8.01 (d, J=1.8 Hz, 1H).

MS Calcd.: 416, MS Found: 417 (M+H).

Example 16

3-Chloro-4-[8-chloro-5-(1-ethylpropyl)-2,3-dihydro-1H-imidazo[1,2-a]benzimidazol-1-yl]benzaldehyde

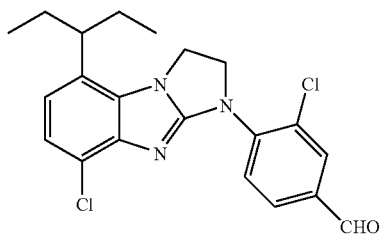 [SMILES: CCC(CC)c1ccc(Cl)c2nc3n(c12)CCN3c1ccc(C=O)cc1Cl]

To a solution of 1-(4-bromo-2-chlorophenyl)-8-chloro-5-(1-ethylpropyl)-2,3-dihydro-1H-imidazo[1,2-a]benzimidazole (204.6 mg, 0.451 mmol) in tetrahydrofuran (3.0 mL) was added n-butyllithium (1.60 M solution in n-hexane, 0.34 mL, 0.542 mmol) at −78° C. The reaction mixture was stirred at same temperature for 1 hr, to the mixture was added N,N-dimethylformamide (0.17 mL, 2.255 mmol). The reaction mixture was allowed to warm to 0° C. and stirred for 1 hr. The reaction mixture was quenched with aqueous saturated ammonium chloride at 0° C. and extracted with ethyl acetate (×3). The combined organic layer was washed with water (×2) and brine, dried over magnesium sulfate, filtered and concentrated in vacuo. The residue was purified by silica gel column chromatography eluting with a 0-15% ethyl acetate/n-hexane gradient mixture to give the title compound as a yellow amorphous (89.5 mg, 0.156 mmol, 49%).

$^1$H NMR (CDCl$_3$) δ: 0.84 (t, J=7.2 Hz, 6H), 1.64-1.83 (m, 4H), 2.70-2.80 (m, 1H), 4.48-4.53 (m, 2H), 4.67-4.72 (m, 2H), 6.86 (d, J=8.1 Hz, 1H), 7.15 (d, J=8.1 Hz, 1H), 7.84 (dd, J=1.8, 8.1 Hz, 1H), 7.96 (d, J=1.8 Hz, 1H), 8.25 (d, J=8.1 Hz, 1H), 9.94 (s, 1H).

MS Calcd.: 401, MS Found: 402 (M+H).

Example 17

1-{3-Chloro-4-[8-chloro-5-(1-ethylpropyl)-2,3-dihydro-1H-imidazo[1,2-a]benzimidazol-1-yl]phenyl}-N,N-dimethylmethanamine

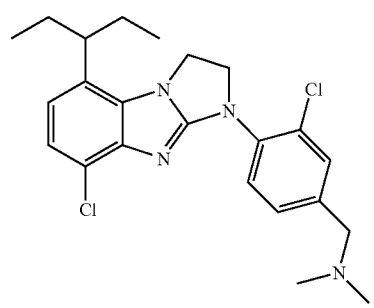 [SMILES: CCC(CC)c1ccc(Cl)c2nc3n(c12)CCN3c1ccc(CN(C)C)cc1Cl]

To a solution of 3-chloro-4-[8-chloro-5-(1-ethylpropyl)-2,3-dihydro-1H-imidazo[1,2-a]benzimidazol-1-yl]benzaldehyde (68.3 mg, 0.170 mmol) in tetrahydrofuran (0.5 mL) and ethanol (0.5 mL) were added dimethylamine (2.0 M solution in tetrahydrofuran, 850 μL, 1.70 mmol) and titanium tetraisopropoxide (100.0 μL, 0.340 mmol). The reaction mixture was stirred at room temperature for 16 hr. To the mixture was added sodium triacetoxyborohydride (72.1 mg, 0.340 mmol) and the reaction mixture was stirred at room temperature for 5 hr. The reaction mixture was warmed to 40° C. and stirred for 3 hr. To the mixture were added sodium triacetoxyborohydride (360.0 mg, 1.70 mmol) and dimethylamine (2.0 M solution in tetrahydrofuran, 425 μL, 0.85 mmol). The reaction mixture was stirred at 40° C. for 0.5 hr. The reaction mixture was quenched with water and extracted with ethyl acetate (×3). The combined organic layer was washed with brine, dried over anhydrous magnesium sulfate, filtered and concentrated in vacuo. The residue was purified by silica gel column chromatography eluting with a 0-100% ethyl acetate/n-hexane gradient mixture to give the title compound as an amorphous (32.5 mg, 0.0753 mmol, 44%).

$^1$H NMR (CDCl$_3$) δ: 0.83 (t, J=7.5 Hz, 6H), 1.60-1.80 (m, 4H), 2.30 (s, 6H), 2.70-2.79 (m, 1H), 3.45 (s, 2H), 4.41-4.53 (m, 4H), 6.80 (d, J=8.4 Hz, 1H), 7.09 (d, J=8.4 Hz, 1H), 7.26-7.29 (m, 1H), 7.44 (d, J=1.8 Hz, 1H), 7.78 (d, J=8.1 Hz, 1H).

MS Calcd.: 430, MS Found: 431 (M+H).

Example 18

5-Chloro-2-[8-chloro-5-(1-ethylpropyl)-2,3-dihydro-1H-imidazo[1,2-a]benzimidazol-1-yl]benzonitrile

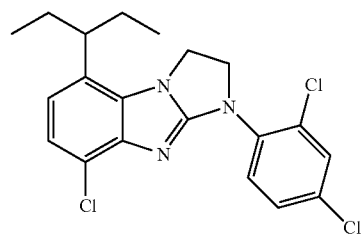 [SMILES: CCC(CC)c1ccc(Cl)c2nc3n(c12)CCN3c1ccc(Cl)cc1Cl]

To a solution of 1-(2-bromo-4-chlorophenyl)-8-chloro-5-(1-ethylpropyl)-2,3-dihydro-1H-imidazo[1,2-a]benzimidazole (30.7 mg, 0.0677 mmol) in 1-methyl-2-pyrrolidone (0.5 mL) was added copper(I) cyanide (18.2 mg, 0.203 mmol). The reaction mixture was stirred at 150° C. for 6 hr. After cooling, the reaction mixture was diluted with water and ethyl acetate and the precipitate was removed by filtration. The filtrate was extracted with ethyl acetate (×3). The combined organic layer was washed with water, brine, dried over anhydrous magnesium sulfate, filtered and concentrated in vacuo. The residue was purified by silica gel column chromatography eluting with a 0-15% ethyl acetate/n-hexane gradient mixture to give the title compound as an amorphous (18.7 mg, 0.468 mmol, 69%).

$^1$H NMR (CDCl$_3$) δ: 0.82 (t, J=7.2 Hz, 6H), 1.60-1.86 (m, 4H), 2.68-2.78 (m, 1H), 4.49-4.54 (m, 2H), 4.85-4.90 (m, 2H), 6.87 (d, J=8.4 Hz, 1H), 7.16 (d, J=8.4 Hz, 1H), 7.59 (dd, J=2.1, 7.8 Hz, 1H), 7.60 (d, J=2.1 Hz, 1H), 8.52 (dd, J=2.1, 7.8 Hz, 1H).

MS Calcd.: 398, MS Found: 399 (M+H).

Example 19

1-(2,4-Dichlorophenyl)-6-(diethylamino)-3,4-dihydropyrimido[1,2-a]benzimidazol-2(1H)-one

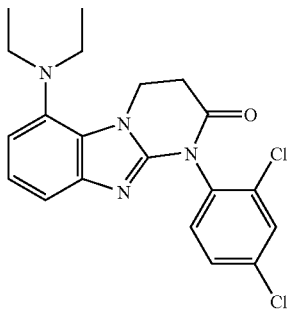 [SMILES: CCN(CC)c1cccc2nc3n(c12)CCC(=O)N3c1ccc(Cl)cc1Cl]

A mixture of 3-[2-[(2,4-dichlorophenyl)amino]-7-(diethylamino)-1H-benzimidazol-1-yl]propanoic acid (Reference Example 30; 57.0 mg, 0.135 mmol), 1-ethyl-3-(3-dimethylaminopropyl)carbodiimide hydrochloride (31.1 mg, 0.162 mmol), triethylamine (0.0226 mL, 0.162 mmol) and N,N-dimethylformamide (3 mL) was stirred at room temperature for 1 day. The reaction mixture was diluted with ethyl acetate, washed with water and brine, dried over anhydrous sodium sulfate, filtered and concentrated in vacuo. The residue was purified by flash column chromatography on silica gel eluting with a 20-50% ethyl acetate/n-hexane gradient mixture to give the title compound as a solid (44.8 mg, 0.111 mmol, 82%). Analytically pure material was obtained by recrystallization from ethyl acetate/n-hexane.

mp 113-114° C.

$^1$H NMR (CDCl$_3$) δ 1.02 (t, J=7.1 Hz, 6H), 3.05-3.22 (m, 6H), 4.73-5.01 (m, 2H), 7.03 (dd, J=7.9, 0.9 Hz, 1H), 7.13 (t, J=7.9 Hz, 1H), 7.36 (dd, J=7.9, 0.9 Hz, 1H), 7.39-7.46 (m, 2H), 7.59 (d, J=1.9 Hz, 1H).

MS Calcd.: 402; MS Found: 403 (M+H).

Example 20

1-(2,4-Dichlorophenyl)-N,N-diethyl-1,2,3,4-tetrahydropyrimido[1,2-a]benzimidazol-6-amine

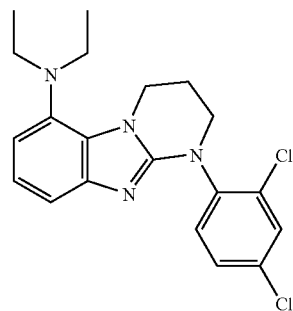 [SMILES: CCN(CC)c1cccc2nc3n(c12)CCCN3c1ccc(Cl)cc1Cl]

To a solution of 3-[2-[(2,4-dichlorophenyl)amino]-7-(diethylamino)-1H-benzimidazol-1-yl]propan-1-ol (Reference Example 29; 35.7 mg, 0.0876 mmol) in pyridine (1 mL) was added methanesulfonyl chloride (0.0339 mL, 0.438 mmol) at 0° C. After the resultant mixture was stirred at room temperature for 2 hr, the mixture was diluted with aqueous sodium hydrogen carbonate and extracted with ethyl acetate. The combined organic layer was washed with brine, dried over anhydrous sodium sulfate, filtered and concentrated in vacuo. The residue was purified by flash column chromatography on silica gel eluting with a 10-40% ethyl acetate/n-hexane gradient mixture to give the title compound as a solid (29.2 mg, 0.0750 mmol, 86%). Analytically pure material was obtained by recrystallization from ethyl acetate/n-hexane.

mp 131-133° C.

$^1$H NMR (CDCl$_3$) δ 1.01 (t, J=7.0 Hz, 6H), 2.27-2.38 (m, 2H), 3.01-3.12 (m, 4H), 3.63-3.75 (m, 2H), 4.59-4.67 (m, 2H), 6.86 (dd, J=7.9, 1.1 Hz, 1H), 7.01 (t, J=7.9 Hz, 1H), 7.21 (dd, J=7.9, 1.1 Hz, 1H), 7.31 (dd, J=8.5, 2.5 Hz, 1H), 7.48 (d, J=8.5 Hz, 1H), 7.51 (d, J=2.5 Hz, 1H).

MS Calcd.: 388; MS Found: 389 (M+H).

Example 21

10-Chloro-1-(2,4-dichlorophenyl)-7-(1-ethylpropyl)-2,3,4,5-tetrahydro-1H-[1,3]diazepino[1,2-a]benzimidazole

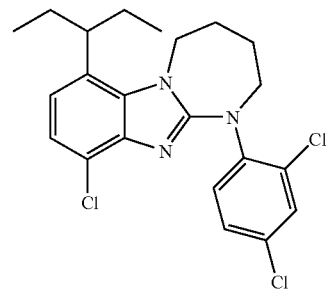 [SMILES: CCC(CC)c1ccc(Cl)c2nc3n(c12)CCCCN3c1ccc(Cl)cc1Cl]

To a solution of ethyl 4-{4-chloro-2-[(2,4-dichlorophenyl)amino]-7-(1-ethylpropyl)-1H-benzimidazol-1-yl}butanoate (Reference Example 34; 453 mg, 0.920 mmol) in tetrahydrofuran (5 mL) was added lithium borohydride (60 mg, 2.76 mmol), and the mixture was refluxed for 2 hr. After cooled to room temperature, the reaction mixture was quenched with methanol (0.5 mL) and concentrated to dryness. The residue was partitioned between ethyl acetate (10 mL) and water (5 mL). The aqueous layer was extracted with ethyl acetate (10 mL×3), washed with brine (15 mL), dried over anhydrous sodium sulfate and concentrated in vacuo to give 4-{4-chloro-2-[(2,4-dichlorophenyl)amino]-7-(1-ethylpropyl)-1H-benzimidazol-1-yl}butan-1-ol, which was subjected for example without further purification.

$^1$H NMR (CDCl$_3$) δ 0.86 (6H, t, J=7.4 Hz), 1.52-1.90 (6H, m), 1.94-2.12 (2H, m), 2.96-3.07 (1H, m), 3.77 (2H, t, J=7.2 Hz), 4.28-4.41 (2H, m), 6.97 (1H, t, J=8.2 Hz), 7.19 (2H, d, J=8.2 Hz), 7.32 (1H, s), 8.06-8.24 (1H, m).

MS Calcd.: 453.1; MS Found: 454.0 (M+H).

To a solution of the above obtained butanol (202 mg, 0.446 mmol) and triphenylphosphine (175 mg, 0.669 mmol) in anhydrous tetrahydrofuran (5 mL) at 0° C., was added dropwise diisopropyl azodicarboxylate (135° mg, 0.669 mmol). The solution was allowed to warm to room temperature and stirred at this temperature overnight. The reaction was quenched with water. The aqueous layer was extracted with ethyl acetate (20 mL×3), washed with water (20 mL), dried over anhydrous magnesium sulfate, concentrated and purified by silica gel column eluting with a 3.3-10% ethyl acetate/petroleum ether gradient mixture to afford the title compound (101 mg, 52%) as a white solid.

mp 160-162° C.

$^1$H NMR (CDCl$_3$) δ 0.86 (6H, t, J=7.2 Hz), 1.67-1.88 (4H, m), 1.93-2.19 (4H, m), 2.98-3.08 (1H, m), 3.77-3.82 (2H, m), 4.42-4.48 (2H, m), 6.89 (1H, d, J=8.4 Hz), 7.14 (1H, d, J=8.4 Hz), 7.34 (1H, d, J=8.4 Hz), 7.43 (1H, s), 7.49 (1H, d, J=8.8 Hz).

MS Calcd.: 435.1; MS Found: 436.1 (M+H).

Example 22

10-Chloro-1-(2,4-dichlorophenyl)-7-(1-ethylpropyl)-4,5-dihydro-1H-[1,3]diazepino[1,2-a]benzimidazol-2(3H)-one

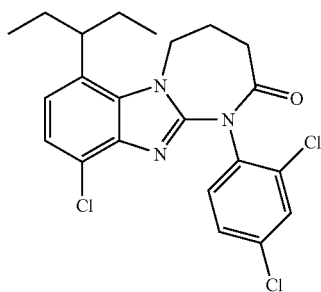 [SMILES: CCC(CC)c1ccc(Cl)c2nc3n(c12)CCCC(=O)N3c1ccc(Cl)cc1Cl]

To a solution of ethyl 4-{4-chloro-2-[(2,4-dichlorophenyl)amino]-7-(1-ethylpropyl)-1H-benzimidazol-1-yl}butanoate (Reference Example 34; 230 mg, 0.46 mmol) in ethanol (5 mL) was added 4N aqueous sodium hydroxide (0.58 mL), and the mixture was stirred at 25° C. overnight. The solution was concentrated to dryness. The residue was suspended with tetrahydrofuran (5 mL) and the suspension was neutralized with 1 mL of 4N hydrogen chloride in ethyl acetate solution. After concentrated to dryness, the resulting crude 4-{4-chloro-2-[(2,4-dichlorophenyl)amino]-7-(1-ethylpropyl)-1H-benzimidazol-1-yl}butanoic acid (210 mg) was subjected for the next step without further purification.

To a solution of the above obtained crude acid (210 mg, 0.46 mmol) in N,N-dimethylformamide (5 mL) were added 1-hydroxybenzotriazole hydrate (HOBt; 211 mg, 1.88 mmol), 1-(3-dimethylaminopropyl)-3-ethylcarbodiimide hydrochloride (EDCI; 265 mg, 1.88 mmol) and triethylamine (230 mg, 2.30 mmol), and the mixture was stirred at 25° C. overnight. The reaction mixture was diluted with saturated aqueous sodium bicarbonate (5 mL) and the aqueous phase was extracted with ethyl acetate (15 mL×2), washed with brine (10 mL), dried over anhydrous sodium sulfate and concentrated in vacuo. The residue was purified by preparative TLC (petroleum ether/ethyl acetate, ⅛, with 0.5% TEA) to afford the title compound (130 mg, 81%) as an off-white solid.

mp 135-137° C.

$^1$H NMR (CDCl$_3$, Varian 400 MHz) δ: 0.65-0.94 (6H, m), 1.62-1.83 (4H, m), 2.36-2.50 (2H, m), 2.53-2.77 (2H, m), 2.95-3.02 (1H, s), 4.50-4.65 (1H, m), 4.70-4.80 (1H, m), 6.97 (1H, d, J=8.8 Hz), 7.15-7.25 (1H, m), 7.35 (1H, d, J=8.8 Hz), 7.41 (1H, s), 7.56 (1H, d, J=8.8 Hz).

MS Calcd.: 449.1; MS Found: 450.0 (M+H).

Example 23

10-Chloro-1-(4-chlorophenyl)-7-(1-ethylpropyl)-2,3,4,5-tetrahydro-1H-[1,3]diazepino[1,2-a]benzimidazole

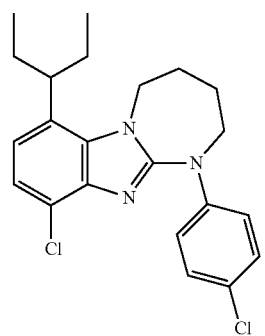 [SMILES: CCC(CC)c1ccc(Cl)c2nc3n(c12)CCCCN3c1ccc(Cl)cc1]

To a solution of 4-[4-chloro-2-[(4-chlorophenyl)amino]-7-(1-ethylpropyl)-1H-benzimidazol-1-yl]butan-1-ol (Reference Example 36; 200 mg, 0.48 mmol) and triphenylphosphine (186 mg, 0.71 mmol) in tetrahydrofuran (10 mL) was added diisopropyl azodicarboxylate (0.140 mL, 0.71 mmol) dropwise at 0° C. The mixture was warmed to room temperature and stirred for 24 hours followed by concentration in vacuo. The residue was purified by flash chromatography on silica gel eluting with a 10-25% ethyl acetate/n-hexane gradient mixture. The filtrate was concentrated in vacuo to give the solid, which was recrystallized from ethyl acetate/isopropyl ether to give the title compound (105 mg, 0.26 mmol, 54%) as a colorless solid.

mp 133-135° C.

$^1$H NMR (CDCl$_3$) δ 0.85 (t, J=7.5 Hz, 6 H), 1.65-1.87 (m, 4 H), 1.89-2.06 (m, 4 H), 2.99-3.11 (m, 1 H), 3.74-3.84 (m, 2 H), 4.30-4.40 (m, 2 H), 6.97 (d, J=8.3 Hz, 1H), 7.10-7.16 (m, 2 H), 7.19-7.27 (m, 3 H).

MS Calcd.: 401; Found: 402 (M+H).

Example 24

10-Chloro-7-(1-ethylpropyl)-1-(1,3,5-trimethyl-1H-pyrazol-4-yl)-2,3,4,5-tetrahydro-1H-[1,3]diazepino[1,2-a]benzimidazole

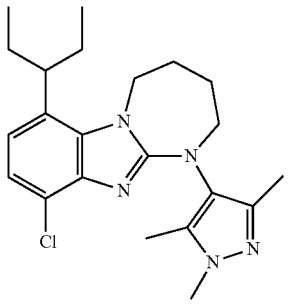 [SMILES: CCC(CC)c1ccc(Cl)c2nc3n(c12)CCCCN3c1c(C)nn(C)c1C]

To a solution of 4-{4-chloro-7-(1-ethylpropyl)-2-[(1,3,5-trimethyl-1H-pyrazol-4-yl)amino]-1H-benzimidazol-1-yl}butan-1-ol (Reference Example 38; 10 mg, 0.024 mmol) in pyridine (0.5 mL) was added a solution of methanesulfonyl chloride in tetrahydrofuran (1.0 M, 0.029 mL, 0.029 mmol) at 0° C. The mixture was warmed to room temperature and stirred for 24 hr. Aqueous sodium bicarbonate was added and the mixture was extracted with ethyl acetate. Organic layer was washed with brine, dried over sodium sulfate and concentrated in vacuo. The resulting crude mesylate was dissolved in N,N-dimethylformamide (1 mL) and potassium carbonate (17 mg, 0.12 mmol) was added. The mixture was stirred at 80° C. for 60 hr. The mixture was diluted with ethyl acetate, washed with water and brine, dried over anhydrous sodium sulfate and concentrated in vacuo. The residue was purified by flash chromatography on silica gel eluting with a 50-100% ethyl acetate/n-hexane gradient mixture. The filtrate was concentrated in vacuo to give the title compound (4.0 mg, 0.010 mmol, 42%) as a colorless amorphous.

$^1$H NMR (CDCl$_3$) δ 0.84 (t, J=7.3 Hz, 6 H), 1.58-2.14 (m, 8 H), 2.23 (s, 3 H), 2.24 (s, 3 H), 2.91-3.04 (m, 1 H), 3.56-3.65 (m, 2 H), 3.74 (s, 3 H), 4.21-4.30 (m, 2 H), 6.81 (d, J=8.3 Hz, 1 H), 7.08 (d, J=8.3 Hz, 1 H).

MS Calcd.: 399; Found: 400 (M+H).

Example 25

5-[10-Chloro-7-(1-ethylpropyl)-2,3,4,5-tetrahydro-1H-[1,3]diazepino[1,2-a]benzimidazol-1-yl]-N,N,4-trimethylpyridin-2-amine

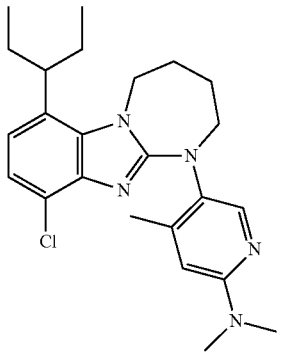 [SMILES: CCC(CC)c1ccc(Cl)c2nc3n(c12)CCCCN3c1cnc(N(C)C)cc1C]

To a solution of 4-[4-chloro-2-{[6-(dimethylamino)-4-methylpyridin-3-yl]amino}-7-(1-ethylpropyl)-1H-benzimidazol-1-yl]butan-1-ol (Reference Example 40; 100 mg, 0.23 mmol) in pyridine (2.3 mL) was added methanesulfonyl chloride (0.088 mL, 1.13 mmol) dropwise at 0° C. The mixture was warmed to room temperature and stirred for 4 hr. Aqueous sodium bicarbonate was added and the mixture was extracted with ethyl acetate. Organic layer was washed with brine, dried over anhydrous sodium sulfate and concentrated in vacuo. The resulting crude mesylate was dissolved in N,N-dimethylformamide (4.6 mL) and potassium carbonate (96 mg, 0.69 mmol) was added. The mixture was stirred at 80° C. for 16 hours. Water was added and the mixture was extracted with ethyl acetate. Organic layer was washed with water and brine, dried over anhydrous sodium sulfate and concentrated in vacuo. The residue was purified by flash chromatography on silica gel eluting with a 20-50% ethyl acetate/n-hexane gradient mixture. The filtrate was concentrated in vacuo to give a solid, which was recrystallized from ethyl acetate/n-hexane to give the title compound (44 mg, 0.103 mmol, 45%) as a colorless solid.

mp 156-157° C.

$^1$H NMR (CDCl$_3$) δ 0.84 (t, J=7.4 Hz, 6 H), 1.60-1.89 (m, 4 H), 1.91-2.14 (m, 4 H), 2.18 (s, 3 H), 2.92-3.03 (m, 1 H), 3.10 (s, 6 H), 3.68-3.78 (m, 2 H), 4.21-4.30 (m, 2 H), 6.41 (s, 1 H), 6.80 (d, J=8.2 Hz, 1 H), 7.07 (d, J=8.5 Hz, 1 H), 8.13 (s, 1 H).

MS Calcd.: 425; Found: 426 (M+H).

Example 26

5-[10-Chloro-7-(1-ethylpropyl)-2,3,4,5-tetrahydro-1H-[1,3]diazepino[1,2-a]benzimidazol-1-yl]-N,N,4-trimethylpyridin-2-amine 1-oxide

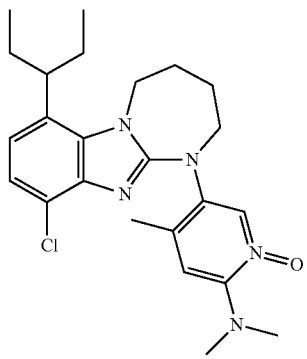 [SMILES: CCC(CC)c1ccc(Cl)c2nc3n(c12)CCCCN3c1c[n+]([O-])c(N(C)C)cc1C]

To a solution of 5-[10-chloro-7-(1-ethylpropyl)-2,3,4,5-tetrahydro-1H-[1,3]diazepino[1,2-a]benzimidazol-1-yl]-N,N,4-trimethylpyridin-2-amine (43 mg, 0.10 mmol) in dichloromethane (2 mL) was added m-chloroperbenzoic acid (27 mg, 0.11 mmol) at 0° C. The mixture was warmed to room temperature and stirred for 2 hr. The reaction mixture was purified by flash chromatography on NH-silica gel eluting with a 0-20% methanol/ethyl acetate gradient mixture. The filtrate was concentrated in vacuo to give a solid, which was recrystallized from ethyl acetate/n-hexane to give the title compound (30 mg, 0.0678 mmol, 68%) as a colorless solid.

mp 142-143° C.

$^1$H NMR (CDCl$_3$) δ 0.84 (t, J=7.3 Hz, 6 H), 1.61-1.88 (m, 4 H), 1.94-2.12 (m, 4 H), 2.14 (s, 3 H), 2.93-3.09 (m, 1 H), 3.58 (s, 6 H), 3.80-3.90 (m, 2 H), 4.30-4.41 (m, 2 H), 6.87 (d, J=8.5 Hz, 1 H), 7.11 (d, J=8.2 Hz, 1 H), 8.37 (s, 1 H), 8.39 (s, 1 H).

MS Calcd.: 441; Found: 442 (M+H).

Example 27

10-Chloro-1-(3,5-dichlorophenyl)-7-(1-ethylpropyl)-2,3,4,5-tetrahydro-1H-[1,3]diazepino[1,2-a]benzimidazole

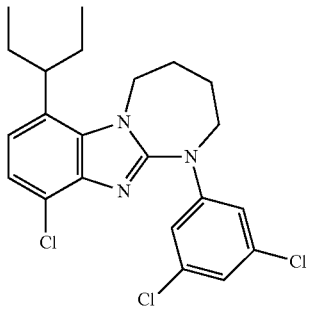 [SMILES: CCC(CC)c1ccc(Cl)c2nc3n(c12)CCCCN3c1cc(Cl)cc(Cl)c1]

To a solution of 4-[4-chloro-2-[(3,5-dichlorophenyl)amino]-7-(1-ethylpropyl)-1H-benzimidazol-1-yl]butan-1-ol (Reference Example 42; 7.0 mg, 0.015 mmol) in pyridine (1.0 mL) was added methanesulfonyl chloride (0.050 mL, 0.064 mmol) dropwise at 0° C. The mixture was warmed to room temperature and stirred for 26 hr. Aqueous sodium bicarbonate was added and the mixture was extracted with ethyl acetate. Organic layer was washed with brine, dried over sodium sulfate and concentrated in vacuo. The resulting crude mesylate was dissolved in N,N-dimethylformamide (1.0 mL) and potassium carbonate (11 mg, 0.077 mmol) was added. The mixture was stirred at 80° C. for 16 hr. Water was added and the mixture was extracted with ethyl acetate. Organic layer was washed with water and brine, dried over anhydrous sodium sulfate and concentrated in vacuo. The residue was purified by flash chromatography on silica gel eluting with a 5-20% ethyl acetate/n-hexane gradient mixture. The filtrate was concentrated in vacuo to give the title compound (6.1 mg, 0.014 mmol, 93%) as a colorless amorphous.

$^1$H NMR (CDCl$_3$) δ 0.86 (t, J=7.3 Hz, 6 H), 1.66-2.11 (m, 8 H), 2.96-3.17 (m, 1 H), 3.69-3.80 (m, 2 H), 4.27-4.42 (m, 2 H), 6.90 (t, J=1.7 Hz, 1 H), 7.00-7.05 (m, 3 H), 7.23-7.29 (m, 1 H).

MS Calcd.: 435; Found: 436 (M+H).

Example 28

10-Chloro-1-(2,6-dimethoxypyridin-3-yl)-7-(1-ethylpropyl)-2,3,4,5-tetrahydro-1H-[1,3]diazepino[1,2-a]benzimidazole

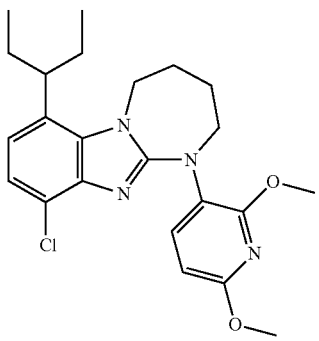 [SMILES: CCC(CC)c1ccc(Cl)c2nc3n(c12)CCCCN3c1ccc(OC)nc1OC]

To a solution of 4-[4-chloro-2-[(2,6-dimethoxypyridin-3-yl)amino]-7-(1-ethylpropyl)-1H-benzimidazol-1-yl]butan-1-ol (Reference Example 44; 80 mg, 0.18 mmol) in pyridine (1.8 mL) was added methanesulfonyl chloride (0.070 mL, 0.89 mmol) dropwise at 0° C. The mixture was warmed to room temperature and stirred for 16 hr. Aqueous sodium bicarbonate was added and the mixture was extracted with ethyl acetate. Organic layer was washed with brine, dried over sodium sulfate and concentrated in vacuo. The resulting crude mesylate was dissolved in N,N-dimethylformamide (3.6 mL) and potassium carbonate (123 mg, 0.89 mmol) was added. The mixture was stirred at 80° C. for 16 hr. Water was added and the mixture was extracted with ethyl acetate. Organic layer was washed with water and brine, dried over anhydrous sodium sulfate and concentrated in vacuo. The residue was purified by flash chromatography on silica gel eluting with a 5-20% ethyl acetate/n-hexane gradient mixture. The filtrate was concentrated in vacuo to give a solid, which was recrystallized from ethyl acetate/n-hexane to give the title compound (15 mg, 0.035 mmol, 19%) as a colorless solid.

mp 85-88° C.

$^1$H NMR (CDCl$_3$) δ 0.83 (t, J=7.4 Hz, 6 H), 1.58-2.14 (m, 8 H), 2.90-3.06 (m, 1 H), 3.63-3.74 (m, 2 H), 3.87 (s, 3 H), 3.92 (s, 3 H), 4.25-4.34 (m, 2 H), 6.35 (d, J=8.2 Hz, 1 H), 6.81 (d, J=8.5 Hz, 1 H), 7.08 (d, J=8.2 Hz, 1 H), 7.69 (d, J=8.2 Hz, 1 H).

MS Calcd.: 428; Found: 429 (M+H).

Example 29

10-Chloro-7-(1-ethylpropyl)-1-(4-methyl-6-pyrrolidin-1-ylpyridin-3-yl)-2,3,4,5-tetrahydro-1H-[1,3]diazepino[1,2-a]benzimidazole

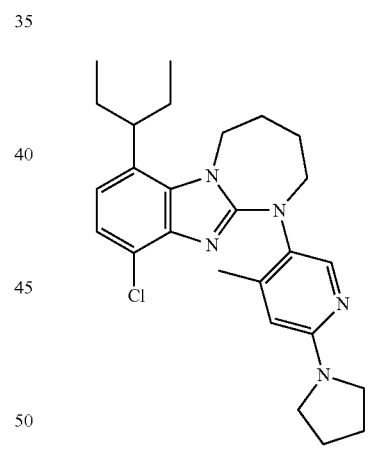

To a solution of 4-{4-chloro-7-(1-ethylpropyl)-2-[(4-methyl-6-pyrrolidin-1-ylpyridin-3-yl)amino]-1H-benzimidazol-1-yl}butan-1-ol (Reference Example 48; 400 mg, 0.85 mmol) in pyridine (5 mL) was added methanesulfonyl chloride (0.330 mL, 4.25 mmol) dropwise at 0° C. The mixture was warmed to room temperature and stirred for 8 hr. Aqueous sodium bicarbonate was added and the mixture was extracted with ethyl acetate. Organic layer was washed with brine, dried over sodium sulfate and concentrated in vacuo. The resulting crude mesylate was dissolved in N,N-dimethylformamide (10 mL) and potassium carbonate (586 mg, 4.25 mmol) was added. The mixture was stirred at 80° C. for 16 hr. Water was added and the mixture was extracted with ethyl acetate. Organic layer was washed with water and brine, dried over anhydrous magnesium sulfate and concentrated in vacuo. The residue was purified by flash chromatography on silica gel eluting with a 50-80% ethyl acetate/n-hexane gradient mixture. The filtrate was concentrated in vacuo to give a solid, which was recrystallized from ethyl acetate/n-hexane to give the title compound (150 mg, 0.331 mmol, 39%) as a colorless solid.

mp 160-161° C.

$^1$H NMR (CDCl$_3$) δ 0.84 (t, J=7.4 Hz, 6 H), 1.60-2.14 (m, 12 H), 2.18 (s, 3 H), 2.91-3.04 (m, 1 H), 3.40-3.55 (m, 4 H), 3.69-3.78 (m, 2 H), 4.21-4.31 (m, 2 H), 6.26 (s, 1 H), 6.80 (d, J=8.2 Hz, 1 H), 7.07 (d, J=8.2 Hz, 1 H), 8.12 (s, 1 H).

MS Calcd.: 451; Found: 452 (M+H).

Example 30

10-Chloro-7-(1-ethylpropyl)-1-(6-methoxy-4-methylpyridin-3-yl)-2,3,4,5-tetrahydro-1H-[1,3]diazepino[1,2-a]benzimidazole

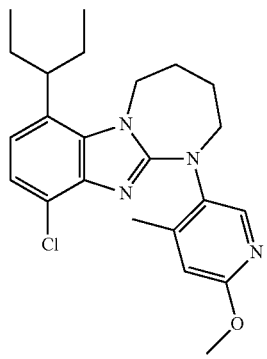 [SMILES: CCC(CC)c1ccc(Cl)c2nc3n(c12)CCCCN3c1cnc(OC)cc1C]

To a solution of 4-{4-chloro-7-(1-ethylpropyl)-2-[(6-methoxy-4-methylpyridin-3-yl)amino]-1H-benzimidazol-1-yl}butan-1-ol (100 mg, 0.23 mmol) in pyridine (2 mL) was added methanesulfonyl chloride (0.090 mL, 1.16 mmol) dropwise at 0° C. The mixture was warmed to room temperature and stirred for 40 hr. Aqueous sodium bicarbonate was added and the mixture was extracted with ethyl acetate. Organic layer was washed with brine, dried over magnesium sulfate and concentrated in vacuo. The resulting crude mesylate was dissolved in N,N-dimethylformamide (4 mL) and potassium carbonate (160 mg, 1.16 mmol) was added. The mixture was stirred at 80° C. for 3 hr. Water was added and the mixture was extracted with ethyl acetate. Organic layer was washed with water and brine, dried over magnesium sulfate and concentrated in vacuo. The residue was purified by flash chromatography on silica gel eluting with a 20-40% ethyl acetate/n-hexane gradient mixture. The filtrate was concentrated in vacuo to give the solid, which was recrystallized from ethyl acetate/n-hexane to give the title compound (45 mg, 0.109 mmol, 47%) as a colorless solid.

mp 112-114° C.

$^1$H NMR (CDCl$_3$) δ 0.85 (t, J=7.4 Hz, 6 H), 1.63-1.89 (m, 4 H), 1.95-2.13 (m, 4 H), 2.16 (d, J=0.8 Hz, 3 H), 2.92-3.05 (m, 1 H), 3.73-3.81 (m, 2 H), 3.94 (s, 3 H), 4.25-4.34 (m, 2 H), 6.64 (s, 1 H), 6.83 (d, J=8.2 Hz, 1 H), 7.09 (d, J=8.2 Hz, 1 H), 8.14 (s, 1 H).

MS Calcd.: 412; Found: 413 (M+H).

Example 31

1-(2-Bromo-4-methylphenyl)-10-chloro-7-(1-ethylpropyl)-2,3,4,5-tetrahydro-1H-[1,3]diazepino[1,2-a]benzimidazole

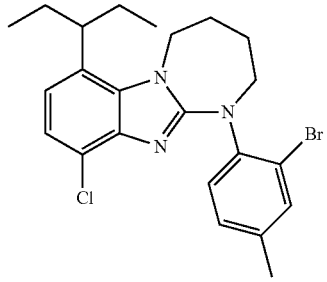 [SMILES: CCC(CC)c1ccc(Cl)c2nc3n(c12)CCCCN3c1ccc(C)cc1Br]

To a solution of 4-[2-[(2-bromo-4-methylphenyl)amino]-4-chloro-7-(1-ethylpropyl)-1H-benzimidazol-1-yl]butan-1-ol) (Reference Example 54; 1.02 g, 2.13 mmol) in pyridine (2.5 mL) was added methanesulfonyl chloride (824 μL, 10.65 mmol) at 0° C. The reaction mixture was stirred at room temperature for 0.5 hr. The reaction mixture was quenched with aqueous sodium hydrogen carbonate and extracted with ethyl acetate (×3). The combined organic layer was washed with brine, dried over magnesium sulfate, filtered and concentrated in vacuo. The resulting crude mesylate (MS Calcd.: 555; Found: 556 (M+H)) was subjected for the next step without further purification. To the crude material in N,N-dimethylformamide (2.0 mL) was added potassium carbonate (588.8 mg, 4.26 mmol). The reaction mixture was stirred at 80° C. for 12 hr. After cooling, the reaction mixture was diluted with water and extracted with ethyl acetate (×3). The combined organic layer was washed with water (×2) and brine, dried over anhydrous magnesium sulfate, filtered and concentrated in vacuo. The residue was purified by silica gel column chromatography eluting with a 0-20% ethyl acetate/n-hexane gradient mixture. The resulting solid was washed with n-hexane to give the title compound as a colorless powder (810.1 mg, 1.77 mmol, 83% (2 steps)).

mp 152-155° C.

$^1$H NMR (CDCl$_3$) δ 0.84 (t, J=7.5 Hz, 6H), 1.65-1.84 (m, 4H), 2.00-2.04 (m, 4H), 2.34 (s, 3H), 2.99-3.03 (m, 1H), 3.75-3.78 (m, 2H), 4.43-4.46 (m, 2H), 6.83 (d, J=8.7 Hz, 1H), 7.08 (d, J=8.7 Hz, 1H), 7.18-7.21 (m, 1H), 7.43 (d, J=7.8 Hz, 2H).

MS Calcd.: 459, MS Found: 460 (M+H).

Example 32

10-Chloro-7-(1-ethylpropyl)-1-(4-methylphenyl)-2,3,4,5-tetrahydro-1H-[1,3]diazepino[1,2-a]benzimidazole Example 33

{2-[10-Chloro-7-(1-ethylpropyl)-2,3,4,5-tetrahydro-1H-[1,3]diazepino[1,2-a]benzimidazol-1-yl]-5-methylphenyl}methanol Example 34

2-[10-Chloro-7-(1-ethylpropyl)-2,3,4,5-tetrahydro-1H-[1,3]diazepino[1,2-a]benzimidazol-1-yl]-5-methylbenzaldehyde Example 32

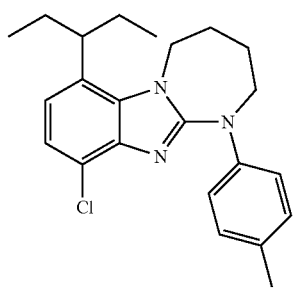

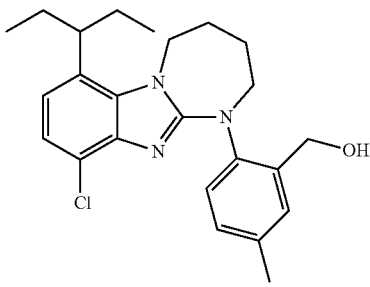

Example 33

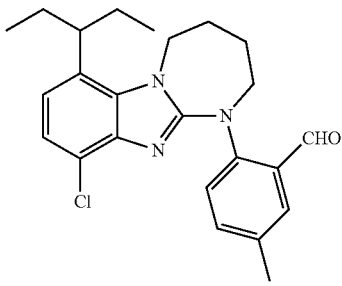

Example 34

To a solution of 1-(2-bromo-4-methylphenyl)-10-chloro-7-(1-ethylpropyl)-2,3,4,5-tetrahydro-1H-[1,3]diazepino[1,2-a]benzimidazole (207.0 mg, 0.449 mmol) in tetrahydrofuran (2.0 mL) was added n-butyllithium (1.60 M solution in n-hexane, 0.33 mL, 0.539 mmol) at −78° C. The reaction mixture was stirred at same temperature for 1 hr, to the mixture was added N,N-dimethylformamide (0.17 mL, 2.245 mmol). The reaction mixture was allowed to warm to room temperature and stirred for 15 hr. The reaction mixture was quenched with aqueous ammonium chloride at 0° C. and extracted with ethyl acetate (×3). The combined organic layer was washed with water (×2) and brine, dried over anhydrous magnesium sulfate, filtered and concentrated in vacuo. The residue was purified by silica gel, column chromatography eluting with a 3-100% ethyl acetate/n-hexane gradient mixture to give example 32 as an oil (53.0 mg, 0.139 mmol, 31%), example 33 as an amorphous (26.9 mg, 0.0653 mmol, 15%) and example 34 as a powder (63.8 mg, 0.156 mmol, 35%), respectively.

Example 32

$^1$H NMR (CDCl$_3$) δ: 0.84 (t, J=7.2 Hz, 6H), 1.69-1.84 (m, 4H), 1.87-1.99 (m, 4H), 2.29 (s, 3H), 2.99-3.08 (m, 1H), 3.79 (t, J=4.8 Hz, 2H), 4.31 (t, J=4.8 Hz, 2H), 6.92 (d, J=8.4 Hz, 1H), 7.08 (s, 4H), 7.24 (d, J=8.4 Hz, 1H).
MS Calcd.: 381, MS Found: 382 (M+H).

Example 33

$^1$H NMR (CDCl$_3$) δ: 0.83 (t, J=7.5 Hz, 6H), 1.61-1.81 (m, 4H), 1.99-2.07 (m, 2H), 2.09-2.16 (m, 2H), 2.39 (s, 3H), 2.92-3.02 (m, 1H), 3.67 (t, J=5.1 Hz, 2H), 4.32 (t, J=5.1 Hz, 2H), 4.51 (s, 2H), 6.67 (brs, D$_2$O exchangeable, 1H), 6.81 (d, J=8.4 Hz, 1H), 7.06 (d, J=8.4 Hz, 1H), 7.11-7.12 (m, 2H), 7.42 (s, 1H).
MS Calcd.: 411, MS Found: 412 (M+H).

Example 34 mp 168-171° C.
$^1$H NMR (CDCl$_3$) δ: 0.85 (t, J=7.5 Hz, 6H), 1.66-1.85 (m, 4H), 2.01-2.04 (m, 4H), 2.42 (s, 3H), 3.00-3.04 (m, 1H), 3.83-3.86 (m, 2H), 4.42-4.44 (m, 2H), 6.84 (d, J=8.1 Hz, 1H), 7.07 (d, J=8.1 Hz, 1H), 7.38 (d, J=8.1 Hz, 1H), 7.46 (d, J=9.9 Hz, 1H), 7.65 (s, 1H), 10.00 (s, 1H).
MS Calcd.: 409, MS Found: 410 (M+H).

Example 35

1-{2-[10-Chloro-7-(1-ethylpropyl)-2,3,4,5-tetrahydro-1H-[1,3]diazepino[1,2-a]benzimidazol-1-yl]-5-methylphenyl}-N,N-dimethylmethanamine hydrochloride

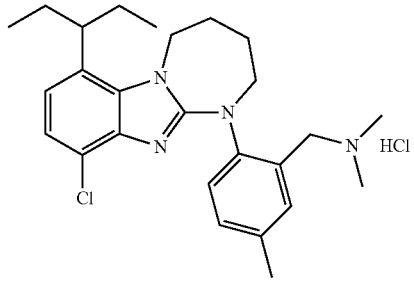 [SMILES: CCC(CC)c1ccc(Cl)c2nc3n(c12)CCCCN3c1ccc(C)cc1CN(C)C ; Cl]

To a solution of 2-[10-chloro-7-(1-ethylpropyl)-2,3,4,5-tetrahydro-1H-[1,3]diazepino[1,2-a]benzimidazol-1-yl]-5-methylbenzaldehyde (50.0 mg, 0.122 mmol) in tetrahydrofuran (0.5 mL) and ethanol (0.5 mL) was added dimethylamine (2.0 M solution in tetrahydrofuran, 305 μL, 0.610 mmol). The reaction mixture was stirred at room temperature for 12 hr. To the mixture were added sodium borohydride (9.23 mg, 0.244 mmol) and titanium tetraisopropoxide (72.0 μL, 0.244 mmol). The reaction mixture was stirred at room temperature for 9 hr. The reaction mixture was quenched with aqueous ammonia at 0° C. and extracted with ethyl acetate (×3). The combined organic layer was washed with brine, dried over anhydrous magnesium sulfate, filtered and concentrated in vacuo. The residue was purified by basic silica gel column chromatography eluting with a 0-20% ethyl acetate/n-hexane gradient mixture. The residue was dissolved into ethyl acetate and 4.0 M hydrochloric acid in ethyl acetate was added (0.20 mL) to the solution. The mixture was stirred for 5 min, and concentrated in vacuo to give the title compounds as an amorphous (30.0 mg, 0.0631 mmol, 52%).

$^1$H NMR (DMSO-d$_6$) δ: 0.81 (t, J=7.5 Hz, 6H), 1.70-1.77 (m, 4H), 2.02 (brs, 2H), 2.12 (brs, 2H), 2.40 (s, 6H), 2.82-2.83 (m, 5H), 3.12 (brs, 1H), 4.25 (brs, 2H), 4.49 (brs, 2H), 6.54 (s, 1H), 6.96 (d, J=8.4 Hz, 1H), 7.16 (d, J=8.4 Hz, 1H), 7.40 (d, J=8.4 Hz, 1H), 7.51 (d, J=8.4 Hz, 1H), 12.13 (brs, 1H).
MS Calcd.: 438, MS Found: 439 (M+H).

Example 36

2-[10-Chloro-7-(1-ethylpropyl)-2,3,4,5-tetrahydro-1H-[1,3]diazepino[1,2-a]benzimidazol-1-yl]-5-methylbenzonitrile

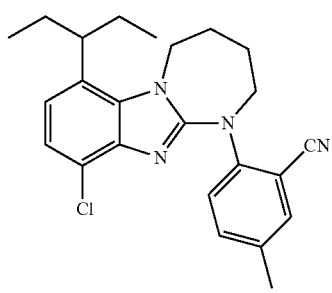 [SMILES: CCC(CC)c1ccc(Cl)c2nc3n(c12)CCCCN3c1ccc(C)cc1C#N]

To a solution of 1-(2-bromo-4-methylphenyl)-10-chloro-7-(1-ethylpropyl)-2,3,4,5-tetrahydro-1H-[1,3]diazepino[1,2-a]benzimidazole (146.3 mg, 0.317 mmol) in 1-methyl-2-pyrrolidone (2.0 mL) was added copper(I) cyanide (85.3 mg, 0.952 mmol). The reaction mixture was stirred at 150° C. for 36 hr. After cooling, the reaction mixture was diluted with water and ethyl acetate and the precipitate was removed by filtration. The filtrate was extracted with ethyl acetate (×3). The combined organic layer was washed with brine, dried over anhydrous magnesium sulfate, filtered and concentrated in vacuo. The residue was purified by preparative HPLC to give the title compound as the trifluoroacetic acid salt. The salt was washed with aqueous sodium hydrogen carbonate and extracted with ethyl acetate. The extract was washed with brine, dried over anhydrous magnesium sulfate, filtered and concentrated in vacuo. The resulting solid was washed with n-hexane to give the title compound as a pale brown powder (28.0 mg, 0.0688 mmol, 22%).

mp 176-180° C.

$^1$H NMR (CDCl$_3$) δ: 0.84 (t, J=7.5 Hz, 6H), 1.66-1.85 (m, 4H), 2.02 (brs, 4H), 2.37 (s, 3H), 3.01-3.05 (m, 1H), 3.78-3.82 (m, 2H), 4.47-4.49 (m, 2H), 6.88 (d, J=8.1 Hz, 1H), 7.12 (d, J=8.1 Hz, 1H), 7.39-7.43 (m, 3H).

MS Calcd.: 406, MS Found: 407 (M+H).

Example 37

1-(2,4-Dimethoxyphenyl)-7-(1-ethylpropyl)-2,3,4,5-tetrahydro-1H-[1,3]diazepino[1,2-a]benzimidazole

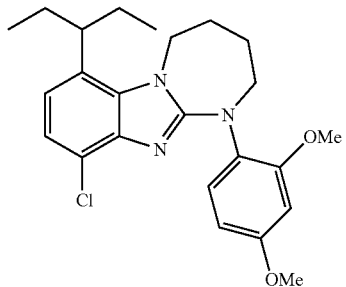 [SMILES: CCC(CC)c1ccc(Cl)c2nc3n(c12)CCCCN3c1ccc(OC)cc1OC]

To a solution of ethyl 4-[2-[(2,4-dimethoxyphenyl)amino]-7-(1-ethylpropyl)-1H-benzimidazol-1-yl]butanoate (Reference Example 56; 569.3 mg, 1.26 mmol) in tetrahydrofuran (5.0 mL) was added lithium borohydride (82.0 mg, 3.77 mmol) at 0° C. The reaction mixture was stirred at 60° C. for 1.5 hr. After cooling, the reaction mixture was quenched with water at 0° C. and extracted with ethyl acetate (×3). The combined organic layer was washed with brine, dried over anhydrous magnesium sulfate, filtered and concentrated in vacuo. The resulting crude butanol (MS Calcd.: 411; Found: 412 (M+H)) was subjected for the next step without further purification. To a solution of the crude material in pyridine (1.0 mL) was added methanesulfonyl chloride (490 μL, 6.28 mmol) at 0° C. The reaction mixture was stirred at room temperature for 2 hr. The reaction mixture was quenched with aqueous sodium hydrogen carbonate and extracted with ethyl acetate (×3). The combined organic layer was washed with brine, dried over anhydrous magnesium sulfate, filtered and concentrated in vacuo. The crude mesylate was subjected for the next step without further purification. To the crude material (MS Calcd.: 489; Found: 490 (M+H)) in N,N-dimethylformamide (1.0 mL) was added potassium carbonate (346.9 mg, 2.51 mmol). The reaction mixture was stirred at 60° C. for 19 hr. After cooling, the reaction mixture was diluted with water and extracted with ethyl acetate (×3). The combined organic layer was washed with water (×2) and brine, dried over anhydrous magnesium sulfate, filtered and concentrated in vacuo. The residue was purified by silica gel column chromatography eluting with a 10-40% ethyl acetate/n-hexane gradient mixture. The resulting solid was washed with n-hexane to give the title compound as a colorless powder (144.5 mg, 0.367 mmol, 29%).

mp 145-148° C.

$^1$H NMR (CDCl$_3$) δ: 0.85 (t, J=7.5 Hz, 6H), 1.65-1.83 (m, 4H), 1.92 (brs, 2H), 2.07 (brs, 2H), 2.99-3.03 (m, 1H), 3.71 (s, 3H), 3.75 (brs, 2H), 3.81 (s, 3H), 4.29 (brs, 2H), 6.50-6.52 (m, 2H), 6.87 (d, J=7.8 Hz, 1H), 7.04 (d, J=7.8 Hz, 1H), 7.22-7.29 (m, 2H).

MS Calcd.: 393, MS Found: 394 (M+H).

Example 38

1-[2-Bromo-4-(trifluoromethyl)phenyl]-10-chloro-7-(1-ethylpropyl)-2,3,4,5-tetrahydro-1H-[1,3]diazepino[1,2-a]benzimidazole

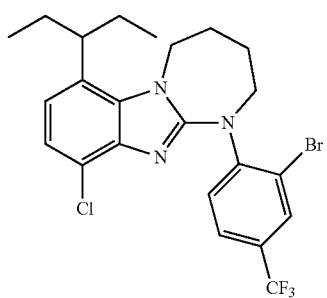 [SMILES: CCC(CC)c1ccc(Cl)c2nc3n(c12)CCCCN3c1ccc(C(F)(F)F)cc1Br]

To a solution of 4-[2-{[2-bromo-4-(trifluoromethyl)phenyl]amino}-4-chloro-7-(1-ethylpropyl)-1H-benzimidazol-1-yl]butan-1-ol (Reference Example 57; 109.2 mg, 0.205 mmol) in pyridine (0.5 mL) was added methanesulfonyl chloride (79.3 μL, 1.03 mmol) at 0° C. The reaction mixture was stirred at room temperature for 4 hr.

The reaction mixture was quenched with aqueous sodium hydrogen carbonate and extracted with ethyl acetate (×3). The combined organic layer was washed with brine, dried over anhydrous magnesium sulfate, filtered and concentrated in vacuo. The resulting crude mesylate (MS Calcd.: 609; Found: 610 (M+H)) was subjected for the next step without further purification. To the crude material in N,N-dimethylformamide (1.0 mL) was added potassium carbonate (56.7 mg, 0.410 mmol). The reaction mixture was stirred at 80° C. for 4 hr. After cooling, the reaction mixture was diluted with water and extracted with ethyl acetate (×3). The combined organic layer was washed with water (×2) and brine, dried over anhydrous magnesium sulfate, filtered and concentrated in vacuo. The residue was purified by silica gel column chromatography eluting with a 0-20% ethyl acetate/n-hexane gradient mixture. The resulting solid was washed with n-hexane to give the title compound as a colorless powder (810.1 mg, 1.77 mmol, 71% (2 steps)).

mp 158-160° C.

$^1$H NMR (CDCl$_3$) δ: 0.85 (t, J=7.5 Hz, 6H), 1.67-1.86 (m, 4H), 1.99-2.05 (m, 4H), 3.02-3.06 (m, 1H), 3.83 (t, J=4.8 Hz, 2H), 4.51 (t, J=4.8 Hz, 2H), 6.90 (d, J=8.4 Hz, 1H), 7.13 (d, J=8.4 Hz, 1H), 7.58 (d, J=8.7 Hz, 1H), 7.65 (d, J=8.7 Hz, 1H), 7.83 (s, 1H).

MS Calcd.: 513, MS Found: 514 (M+H).

Example 39

1-[2-Bromo-4-(trifluoromethoxy)phenyl]-10-chloro-7-(1-ethylpropyl)-2,3,4,5-tetrahydro-1H-[1,3]diazepino[1,2-a]benzimidazole

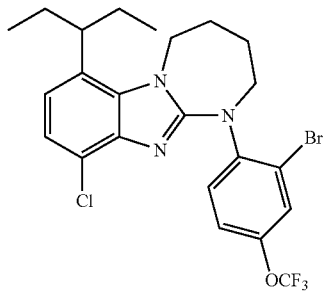 [SMILES: CCC(CC)c1ccc(Cl)c2nc3n(c12)CCCCN3c1ccc(OC(F)(F)F)cc1Br]

To a solution of 4-[2-{[2-bromo-4-(trifluoromethoxy)phenyl]amino}-4-chloro-7-(1-ethylpropyl)-1H-benzimidazol-1-yl]butan-1-ol (Reference Example 59; 558.0 mg, 1.02 mmol) in pyridine (1.2 mL) was added methanesulfonyl chloride (394 μL, 5.09 mmol) at 0° C. The reaction mixture was stirred at room temperature for 3 hr. The reaction mixture was quenched with aqueous sodium hydrogen carbonate and extracted with ethyl acetate (×3). The combined organic layer was washed with brine, dried over anhydrous magnesium sulfate, filtered and concentrated in vacuo. The resulting crude mesylate (MS Calcd.: 625; Found: 626 (M+H)) was subjected for the next step without further purification. To the crude material in N,N-dimethylformamide (3.0 mL) was added potassium carbonate (281.1 mg, 2.03 mmol). The reaction mixture was stirred at 80° C. for 2.5 days. After cooling, the reaction mixture was diluted with water and extracted with ethyl acetate (×3). The combined organic layer was washed with water (×2) and brine, dried over magnesium sulfate, filtered and concentrated in vacuo. The residue was purified by preparative HPLC to give the title compound as the trifluoroacetic acid salt. The salt was washed with aqueous sodium hydrogen carbonate and extracted with ethyl acetate. The extract was washed with brine, dried over anhydrous magnesium sulfate, filtered and concentrated in vacuo. The resulting solid was washed with n-hexane to give the title compound as a colorless powder (264.0 mg, 0.497 mmol, 49%).

mp 114-117° C.

$^1$H NMR (CDCl$_3$) δ: 0.85 (t, J=7.5 Hz, 6H), 1.66-1.79 (m, 4H), 2.03 (brs, 4H), 3.00-3.04 (m, 1H), 3.77-3.79 (m, 2H), 4.45-4.47 (m, 2H), 6.87 (d, J=8.1 Hz, 1H), 7.11 (d, J=8.1 Hz, 1H), 7.29 (s, 1H), 7.47 (s, 1H), 7.57 (d, J=8.1 Hz, 1H).

MS Calcd.: 529, MS Found: 530 (M+H).

Example 40

10-Chloro-7-(1-ethylpropyl)-1-[4-(trifluoromethoxy)phenyl]-2,3,4,5-tetrahydro-1H-[1,3]diazepino[1,2-a]benzimidazole

Example 41

2-[10-Chloro-7-(1-ethylpropyl)-2,3,4,5-tetrahydro-1H-[1,3]diazepino[1,2-a]benzimidazol-1-yl]-5-(trifluoromethoxy)benzaldehyde Example 40

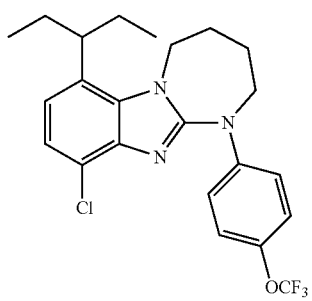

Example 41

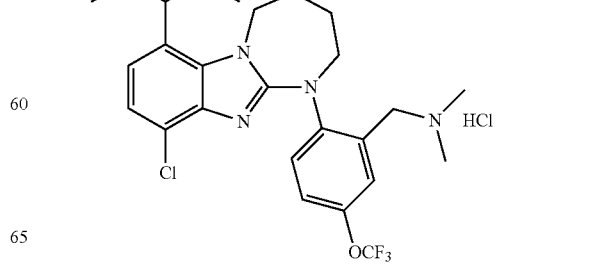

To a solution of 1-[2-bromo-4-(trifluoromethoxy)phenyl]-10-chloro-7-(1-ethylpropyl)-2,3,4,5-tetrahydro-1H-[1,3]diazepino[1,2-a]benzimidazole (144.7 mg, 0.273 mmol) in tetrahydrofuran (2.0 mL) was added n-butyllithium (1.60 M solution in n-hexane, 0.20 mL, 0.327 mmol) at −78° C. The reaction mixture was stirred at same temperature for 1 hr, to the mixture was added N,N-dimethylformamide (0.11 mL, 1.37 mmol). The reaction mixture was allowed to warm to room temperature and stirred for 15 hr. The reaction mixture was quenched with aqueous ammonium chloride at 0° C. and extracted with ethyl acetate (×3). The combined organic layer was washed with water (×2) and brine, dried over anhydrous magnesium sulfate, filtered and concentrated in vacuo. The residue was purified by silica gel column chromatography, eluting with a 30-50% ethyl acetate/n-hexane gradient mixture to give example 40 as a colorless powder (32.8 mg, 0.0726 mmol, 27%) and example 41 as a yellow amorphous (61.7 mg, 0129 mmol, 47%), respectively.

Example 40 mp 151-153° C.

$^1$H NMR (CDCl$_3$) δ: 0.85 (t, J=7.5 Hz, 6H), 1.71-1.83 (m, 4H), 1.93-2.03 (m, 4H), 3.00-3.10 (m, 1H), 3.79 (t, J=4.8 Hz, 2H), 4.35 (t, J=4.8 Hz, 2H), 6.98 (d, J=8.4 Hz, 1H), 7.11-7.24 (m, 5H).

MS Calcd.: 451, MS Found: 452 (M+H).

Example 41

$^1$H NMR (CDCl$_3$) δ: 0.86 (t, J=7.5 Hz, 6H), 1.67-1.86 (m, 4H), 2.03-2.09 (m, 4H), 2.98-3.08 (m, 1H), 3.84-3.88 (m, 2H), 4.44-4.48 (m, 2H), 6.88 (d, J=8.1 Hz, 1H), 7.10 (d, J=8.1 Hz, 1H), 7.49 (d, J=8.7 Hz, 1H), 7.53 (d, J=8.7 Hz, 1H), 7.69 (s, 1H), 9.94 (s, 1H).

MS Calcd.: 479, MS Found: 480 (M+H).

Example 42

1-[2-[10-Chloro-7-(1-ethylpropyl)-2,3,4,5-tetrahydro-1H-[1,3]diazepino[1,2-a]benzimidazol-1-yl]-5-(trifluoromethoxy)phenyl]-N,N-dimethylmethanamine hydrochloride

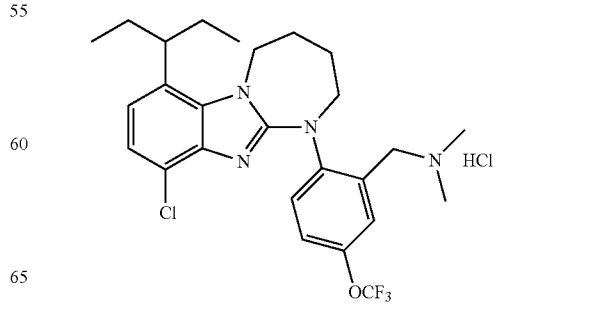

209

To a solution of 2-[10-chloro-7-(1-ethylpropyl)-2,3,4,5-tetrahydro-1H-[1,3]diazepino[1,2-a]benzimidazol-1-yl]-5-(trifluoromethoxy)benzaldehyde (48.9 mg, 0.102 mmol) in tetrahydrofuran (0.5 mL) and ethanol (0.2 mL) was added dimethylamine (2.0 M solution in tetrahydrofuran, 250 µL, 0.509 mmol). The reaction mixture was stirred at room temperature for 14 hr. To the mixture were added anhydrous sodium borohydride (46.2 mg, 1.22 mmol) and titanium tetraisopropoxide (60.3 µL, 0.204 mmol). The reaction mixture was stirred at room temperature for 9 hr and warmed to 40° C. and stirred for 14 hr. The reaction mixture was quenched with aqueous ammonia at 0° C. The precipitate was filtered and the filtrate was extracted with ethyl acetate (×3). The combined organic layer was washed with brine, dried over magnesium sulfate, filtered and concentrated in vacuo. The residue was purified by basic silica gel column chromatography eluting with a 0-15% ethyl acetate/n-hexane gradient mixture. The residue was dissolved into ethyl acetate and to the solution was added 4.0 M hydrochloric acid in ethyl acetate (0.20 mL), and the mixture was stirred for 5 min, and concentrated in vacuo to give the title compounds as a colorless amorphous (38.1 mg, 0.0698 mol, 69%).

$^1$H NMR (DMSO-d$_6$) δ: 0.82 (t, J=7.5 Hz, 6H), 1.68-1.77 (m, 4H), 2.02 (brs, 2H), 2.11 (brs, 2H), 2.84 (s, 6H), 3.14 (brs, 1H), 3.75 (brs, 2H), 4.31 (brs, 2H), 4.49 (brs, 2H), 6.96 (d, J=8.4 Hz, 1H), 7.16 (d, J=8.4 Hz, 1H), 7.63 (brs, 1H), 7.78 (d, J=9.6 Hz, 1H), 7.84 (s, 1H), 11.83 (brs, 1H).

MS Calcd.: 508, MS Found: 509 (M+H).

Example 43

1-(4-Bromo-2-methylphenyl)-10-chloro-7-(1-ethylpropyl)-2,3,4,5-tetrahydro-1H-[1,3]diazepino[1,2-a]benzimidazole

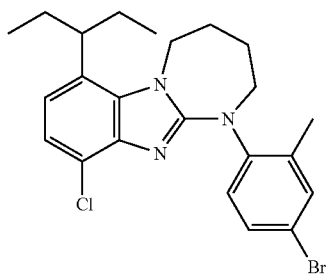 [SMILES: CCC(CC)c1ccc(Cl)c2nc3n(c12)CCCCN3c1ccc(Br)cc1C]

To a solution of 4-[2-[(4-bromo-2-methylphenyl)amino]-4-chloro-7-(1-ethylpropyl)-1H-benzimidazol-1-yl]butan-1-ol (Reference Example 61; 1.10 g, 2.30 mmol) in tetrahydrofuran (20 mL) and triethylamine (1.6 mL) was added methanesulfonyl chloride (0.72 mL, 9.24 mmol) at 0° C. The mixture was stirred at 0° C. for 14 hr, and diluted with aqueous sodium hydrogen carbonate and extracted with ethyl acetate. The combined organic layer was washed with brine, dried over anhydrous magnesium sulfate, filtered, and concentrated in vacuo. A mixture of the resulting mesylate, potassium carbonate (150 mg, 1.09 mmol) in N,N-dimethylformamide (15 mL) was stirred at 70° C. for 3 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 0-30 % ethyl acetate/n-hexane gradi-

210 ent mixture. The filtrate was concentrated in vacuo to give the solid, which was purified by preparative HPLC to give a mixture contained the title compound as the trifluoroacetic acid salt. The trifluoroacetic acid salt was washed with aqueous sodium hydrogen carbonate and extracted with ethyl acetate. The extract was washed with brine, dried over anhydrous magnesium sulfate, filtered and concentrated in vacuo to give the title compound as a colorless amorphous (680 mg, 1.48 mmol, 64% in 2 steps).

$^1$H NMR (CDCl$_3$) δ 0.84 (t, J=7.2 Hz, 6H), 1.64-1.84 (m, 4H), 1.94-1.99 (m, 4H), 2.05 (s, 3H), 2.94-3.05 (m, 1H), 3.76 (t, J=5.7 Hz, 2H), 4.31 (t, J=5.7 Hz, 2H), 6.83 (d, J=8.4 Hz, 1H), 7.08 (d, J=8.4 Hz, 1H), 7.22-7.24 (m, 1H), 7.36-7.39 (m, 2H).

MS Calcd.: 459; MS Found: 460 (M+H).

Example 44

10-Chloro-7-(1-ethylpropyl)-1-[2-methyl-4-(methylthio)phenyl]-2,3,4,5-tetrahydro-1H-[1,3]diazepino[1,2-a]benzimidazole

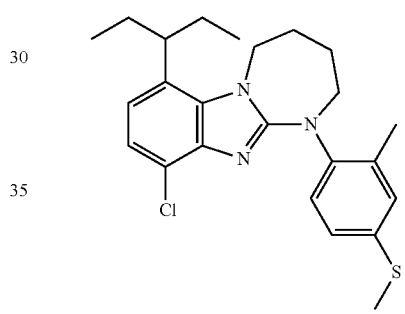

To a solution of 1-(4-bromo-2-methylphenyl)-10-chloro-7-(1-ethylpropyl)-2,3,4,5-tetrahydro-1H-[1,3]diazepino[1,2-a]benzimidazole (572 mg, 1.24 mmol) in tetrahydrofuran (10 mL) was added n-butyllithium (1.60 M solution in n-hexane, 0.85 mL, 1.36 mmol) at −78° C., and the mixture was stirred for 20 min. To the mixture was added dimethyl disulfide (0.34 mL, 3.72 mmol), and the mixture was stirred at −78° C. for 30 min, at 0° C. for 1 hr. The mixture was diluted with saturated aqueous ammonium chloride and extracted with ethyl acetate. The combined organic layer was washed with brine, dried over anhydrous magnesium sulfate, filtered, and concentrated in vacuo. The residue was purified by flash column chromatography on silica gel eluting with a 5-25% ethyl acetate/n-hexane gradient mixture. The filtrate was concentrated in vacuo to give the solid, which was washed with n-hexane to give the title compound as a colorless powder (285 mg, 0.666 mmol, 54%).

mp 113-115° C.

$^1$H NMR (CDCl$_3$) δ 0.84 (t, J=6.9 Hz, 6H), 1.64-1.82 (m, 4H), 1.96-2.01 (m, 4H), 2.06 (s, 3H), 2.49 (s, 3H), 2.94-3.03 (m, 1H), 1.77 (t, J=5.4 Hz, 2H), 4.30 (t, J=5.4 Hz, 2H), 6.82 (d, J=8.4 Hz, 1H), 7.08 (d, J=8.4 Hz, 1H), 7.12-7.25 (m, 2H), 7.25-7.30 (m, 1H).

MS Calcd.: 427; MS Found: 428 (M+H).

Example 45

10-Chloro-7-(1-ethylpropyl)-1-[2-methyl-4-(methylsulfinyl)phenyl]-2,3,4,5-tetrahydro-1H-[1,3]diazepino[1,2-a]benzimidazole

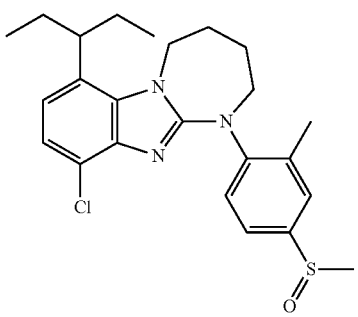 [SMILES: CCC(CC)c1ccc(Cl)c2nc3n(c12)CCCCN3c1ccc(S(C)=O)cc1C]

To a solution of 10-chloro-7-(1-ethylpropyl)-1-[2-methyl-4-(methylthio)phenyl]-2,3,4,5-tetrahydro-1H-[1,3]diazepino[1,2-a]benzimidazole (106 mg, 0.248 mmol) in dichloromethane (2.5 mL) was added m-chloroperbenzoic acid (47.0 mg, 0.272 mmol), and the mixture was stirred at 0° C. for 2 hr. The mixture was neutralized with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 50-100% ethyl acetate/n-hexane gradient mixture. The filtrate was concentrated in vacuo to give the solid, which was recrystallized from ethyl acetate/n-hexane to give the title compound as a colorless crystal (32.1 mg, 0.0723 mmol, 29%).

mp 189-190° C.

$^1$H NMR (CDCl$_3$) δ 0.85 (t, J=7.5 Hz, 6H), 1.66-1.84 (m, 4H), 1.96-2.03 (m, 4H), 2.08 (s, 3H), 2.78 (s, 3H), 2.97-3.04 (m, 1H), 3.83 (t, J=5.1 Hz, 2H), 4.36 (t, J=5.1 Hz, 2H), 6.87 (d, J=8.4 Hz, 1H), 7.11 (d, J=8.4 Hz, 1H), 7.48-7.56 (m, 3H).

MS Calcd.: 443; MS Found: 444 (M+H).

Example 46

10-Chloro-7-(1-ethylpropyl)-1-[2-methyl-4-(methylsulfonyl)phenyl]-2,3,4,5-tetrahydro-1H-[1,3]diazepino[1,2-a]benzimidazole

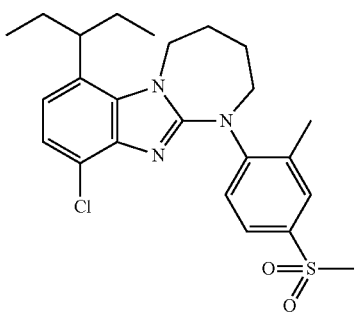 [SMILES: CCC(CC)c1ccc(Cl)c2nc3n(c12)CCCCN3c1ccc(S(C)(=O)=O)cc1C]

To a solution of 10-chloro-7-(1-ethylpropyl)-1-[2-methyl-4-(methylthio)phenyl]-2,3,4,5-tetrahydro-1H-[1,3]diazepino[1,2-a]benzimidazole (156 mg, 0.364 mmol) in dichloromethane (3.6 mL) was added m-chloroperbenzoic acid (138 mg, 0.802 mmol), and the mixture was stirred at 0° C. for 2 hr. The mixture was neutralized with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 5-50% ethyl acetate/n-hexane gradient mixture. The filtrate was concentrated in vacuo to give the solid, which was recrystallized from ethyl acetate/n-hexane to give the title compound as a colorless crystal (144 mg, 0.313 mmol, 86%).

mp 170-171° C.

$^1$H NMR (CDCl$_3$) δ 0.85 (t, J=7.2 Hz, 6H), 1.69-1.84 (m, 4H), 2.01 (s, 3H), 2.02-2.08 (m, 4H), 3.00-3.09 (m, 1H), 3.10 (s, 3H), 3.86 (t, J=5.1 Hz, 2H), 4.40 (t, J=5.1 Hz, 2H), 6.90 (d, J=8.1 Hz, 1H), 7.13 (d, J=8.1 Hz, 1H), 7.50 (d, J=8.4 Hz, 1H), 7.75 (d, J=1.8 Hz, 1H), 7.13 (dd, J=1.8 Hz, 8.4 Hz, 1H).

MS Calcd.: 459; MS Found: 460 (M+H).

Example 47

4-[10-Chloro-7-(1-ethylpropyl)-2,3,4,5-tetrahydro-1H-[1,3]diazepino[1,2-a]benzimidazol-1-yl]-3-methylbenzoic acid

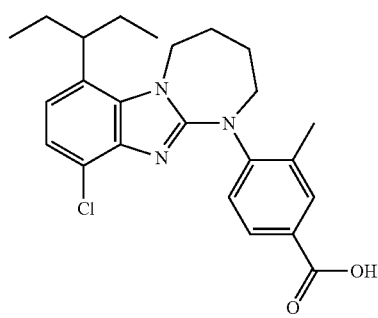 [SMILES: CCC(CC)c1ccc(Cl)c2nc3n(c12)CCCCN3c1ccc(C(=O)O)cc1C]

To a solution of 1-(4-bromo-2-methylphenyl)-10-chloro-7-(1-ethylpropyl)-2,3,4,5-tetrahydro-1H-[1,3]diazepino[1,2-a]benzimidazole (2.00 g, 4.34 mmol) in tetrahydrofuran (20 mL) was added n-butyllithium (1.60 M solution in n-hexane, 2.99 mL, 4.78 mmol) at −78° C., and the mixture was stirred for 15 min. Carbon dioxide gas was bubbled through the mixture for 20 min. The mixture was diluted with water, and extracted with ethyl acetate. The combined organic layer was washed with brine, dried over anhydrous magnesium sulfate, filtered and concentrated in vacuo. The residue was washed with ethyl acetate to give the title compound as a colorless powder (1.08 g, 2.54 mmol, 59%).

$^1$H NMR (DMSO-d$_6$) δ 0.80 (t, J=7.2 Hz, 6H), 1.64-1.76 (m, 4H), 1.80-2.03 (m, 4H), 1.93 (s, 3H), 3.08-3.15 (m, 1H), 3.76-3.85 (m, 2H), 4.31-4.41 (m, 2H), 6.90 (d, J=8.4 Hz, 1H), 7.08 (d, J=8.4 Hz, 1H), 7.48 (d, J=8.4 Hz, 1H), 7.80-7.87 (m, 2H), 12.80 (s, 1H).

MS Calcd.: 425; MS Found: 426 (M+H).

Example 48

4-[10-Chloro-7-(1-ethylpropyl)-2,3,4,5-tetrahydro-1H-[1,3]diazepino[1,2-a]benzimidazol-1-yl]-3-methylbenzamide

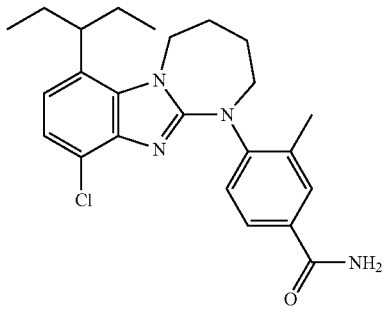 [SMILES: CCC(CC)c1ccc(Cl)c2nc3n(c12)CCCCN3c1ccc(C(N)=O)cc1C]

To a solution of 4-[10-chloro-7-(1-ethylpropyl)-2,3,4,5-tetrahydro-1H-[1,3]diazepino[1,2-a]benzimidazol-1H-yl]-3-methylbenzoic acid (330 mg, 0.775 mmol) in N,N-dimethylformamide (4.0 mL) were added 1-hydroxy-1H-benzotriazole ammonium salt (172 mg, 1.01 mmol) and 1-ethyl-3-(3-dimethylaminopropyl)carbodiimide hydrochloride (163 mg, 0.853 mmol). The mixture was stirred at room temperature for 11 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 80-100% ethyl acetate/n-hexane gradient mixture. The filtrate was concentrated in vacuo to give the solid, which was purified by preparative HPLC to give a mixture contained an intermediate of the title compound as the trifluoroacetic acid salt. The mixture was washed with aqueous sodium hydrogen carbonate and extracted with ethyl acetate. The extract was washed with brine, dried over magnesium sulfate, filtered and concentrated in vacuo to give the solid, which was recrystallized from ethanol/diisopropyl ether to give the title compound as a colorless crystal (58.5 mg, 0.138 mmol, 18%).

mp 185-186° C.

$^1$H NMR (CDCl$_3$) δ 0.85 (t, J=7.5 Hz, 6H), 1.66-1.86 (m, 4H), 1.90-2.07 (m, 4H), 1.98 (s, 3H), 2.96-3.05 (m, 1H), 3.82-3.86 (m, 2H), 4.32-4.36 (m, 2H), 5.39 (s, 1H), 6.88 (d, J=8.4 Hz, 1H), 7.12 (d, J=8.4 Hz, 1H), 7.26-7.29 (m, 2H), 7.72-7.78 (m, 2H).

MS Calcd.: 424; MS Found: 425 (M+H).

Example 49

4-[10-Chloro-7-(1-ethylpropyl)-2,3,4,5-tetrahydro-1H-[1,3]diazepino[1,2-a]benzimidazol-1-yl]-N,3-dimethylbenzamide

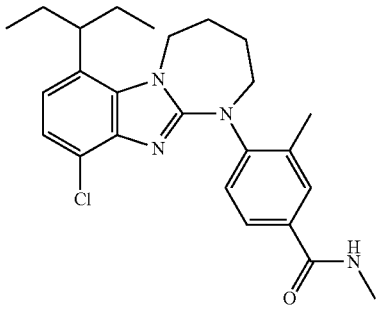 [SMILES: CCC(CC)c1ccc(Cl)c2nc3n(c12)CCCCN3c1ccc(C(=O)NC)cc1C]

To a solution of 4-[10-chloro-7-(1-ethylpropyl)-2,3,4,5-tetrahydro-1H-[1,3]diazepino[1,2-a]benzimidazol-1-yl]-3-methylbenzoic acid (330 mg, 0.775 mmol) in N,N-dimethylformamide (4.0 mL) were added 1-hydroxy-1H-benzotriazole (155 mg, 1.01 mmol), 1-ethyl-3-(3-dimethylaminopropyl)carbodiimide hydrochloride (163 mg, 0.853 mmol), and methylamine (2.0 M solution in tetrahydrofuran, 0.78 mL, 1.56 mmol). The mixture was stirred at room temperature for 11 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by preparative HPLC to give a mixture contained an intermediate of the title compound as the trifluoroacetic acid salt. The mixture was washed with aqueous sodium hydrogen carbonate and extracted with ethyl acetate. The extract was washed with brine, dried over magnesium sulfate, filtered and concentrated in vacuo to give the solid, which was recrystallized from ethanol/diisopropyl ether to give the title compound as a colorless crystal (129 mg, 0.294 mmol, 38%).

mp 127-128° C.

$^1$H NMR (CDCl$_3$) δ 0.86 (t, J=7.5 Hz, 6H), 1.66-1.86 (m, 4H), 1.95-2.09 (m, 4H), 1.97 (s, 3H), 2.79 (d, J=4.8 Hz, 3H); 2.98-3.06 (m, 1H), 3.82 (t, J=5.1 Hz, 2H), 4.31-4.34 (m, 2H), 6.88 (d, J=8.7 Hz, 1H), 7.11 (d, J=8.7 Hz, 1H), 7.21 (d, J=8.1 Hz, 1H), 7.40 (s, 1H), 7.61 (d, J=1.5 Hz, 1H), 7.69 (dd, J=1.5 Hz, 8.1 Hz, 1H).

MS Calcd.: 438; MS Found: 439 (M+H).

Example 50

4-[10-Chloro-7-(1-ethylpropyl)-2,3,4,5-tetrahydro-1H-[1,3]diazepino[1,2-a]benzimidazol-1-yl]-N,N,3-trimethylbenzamide

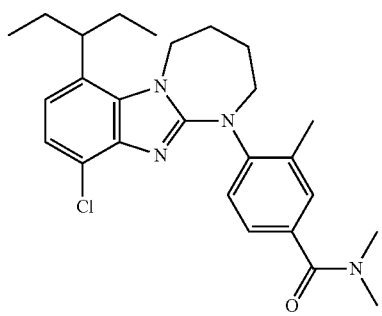 [SMILES: CCC(CC)c1ccc(Cl)c2nc3n(c12)CCCCN3c1ccc(C(=O)N(C)C)cc1C]

To a solution of 4-[10-chloro-7-(1-ethylpropyl)-2,3,4,5-tetrahydro-1H-[1,3]diazepino[1,2-a]benzimidazol-1-yl]-3-methylbenzoic acid (330 mg, 0.775 mmol) in N,N-dimethylformamide (4.0 mL) were added 1-hydroxy-1H-benzotriazole (155 mg, 1.01 mmol), 1-ethyl-3-(3-dimethylaminopropyl)carbodiimide hydrochloride (163 mg, 0.853 mmol), and dimethylamine (2.0 M solution in tetrahydrofuran, 0.78 mL, 1.56 mmol). The mixture was stirred at room temperature for 11 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by preparative HPLC to give a mixture contained an intermediate of the title compound as the trifluoroacetic acid salt. The trifluoroacetic acid salt was washed with aqueous sodium hydrogen carbonate and extracted with ethyl acetate. The extract was washed with brine, dried over magnesium sulfate, filtered and concentrated in vacuo to give the solid, which was recrystallized from ethanol/diisopropyl ether to give the title compound as a colorless crystal (88.8 mg, 0.196 mmol, 25%).

mp 113-114° C.

¹H NMR (CDCl₃) δ 0.84 (t, J=6.9 Hz, 6H), 1.69-1.83 (m, 4H), 1.80-2.06 (m, 4H), 2.05 (s, 3H), 2.95-3.04 (m, 1H), 3.10 (s, 6H), 3.81 (t, J=5.1 Hz, 2H), 4.30-4.34 (m, 2H), 6.85 (d, J=8.4 Hz, 1H), 7.09 (d, J=8.4 Hz, 1H), 7.29-7.40 (m, 3H).
MS Calcd.: 452; MS Found: 453 (M+H).

Example 51

4-[10-Chloro-7-(1-ethylpropyl)-2,3,4,5-tetrahydro-1H-[1,3]diazepino[1,2-a]benzimidazol-1-yl]-N,N,3-trimethylaniline

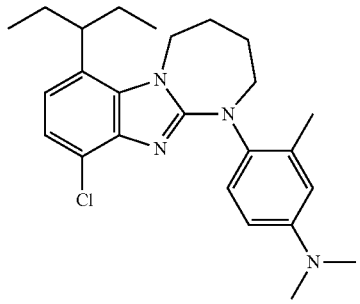 [SMILES: CCC(CC)c1ccc(Cl)c2nc3n(c12)CCCCN3c1ccc(N(C)C)cc1C]

A mixture of 1-(4-bromo-2-methylphenyl)-10-chloro-7-(1-ethylpropyl)-2,3,4,5-tetrahydro-1H-[1,3]diazepino[1,2-a]benzimidazole (700 mg, 1.65 mmol), sodium tert-butoxide (396 mg, 4.13 mmol), 2-(di-tert-butylphosphino)biphenyl (39.4 mg, 0.132 mmol), tris(dibenzylideneacetone)dipalladium (151 mg, 0.165 mmol), and dimethylamine (2.0 M solution of tetrahydrofuran, 2.5 mL, 5.0 mmol) in toluene (2.5 ml) was stirred at 70° C. under nitrogen for 3 hr. The mixture was diluted with water, and extracted with ethyl acetate. The combined organic layer was washed with brine, dried over anhydrous magnesium sulfate, filtered and concentrated in vacuo. The residue was purified by flash column chromatography on silica gel eluting with a 0-30% ethyl acetate/n-hexane gradient mixture. The filtrate was concentrated in vacuo to give the solid, which was recrystallized from ethyl acetate/n-hexane to give the title compound as a colorless crystal (341 mg, 0.802 mmol, 49%).
mp 174-175° C.
¹H NMR (CDCl₃) δ 0.83 (t, J=7.5 Hz, 6H), 1.63-1.83 (m, 4H), 1.94-2.00 (m, 2H), 2.02-2.09 (m, 2H), 2.15 (s, 3H), 2.93-2.98 (m, 1H), 2.95 (s, 6H), 3.74 (t, J=5.1 Hz, 2H), 4.26 (t, J=5.1 Hz, 2H), 6.58-6.67 (m, 2H), 6.78 (d, J=8.7 Hz, 1H), 7.05 (d, J=8.7 Hz, 1H), 7.23 (d, J=9.0 Hz, 1H).
MS Calcd.: 424; MS Found: 425 (M+H).

Example 52

1-[4-Bromo-2-(trifluoromethoxy)phenyl]-10-chloro-7-(1-ethylpropyl)-2,3,4,5-tetrahydro-1H-[1,3]diazepino[1,2-a]benzimidazole

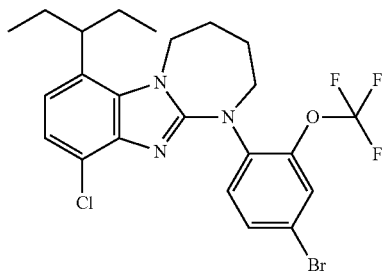 [SMILES: CCC(CC)c1ccc(Cl)c2nc3n(c12)CCCCN3c1ccc(Br)cc1OC(F)(F)F]

To a solution of 4-[2-{[4-bromo-2-(trifluoromethoxy)phenyl]amino}-4-chloro-7-(1-ethylpropyl)-1H-benzimidazol-1-yl]butan-1-ol (Reference Example 62; 1.63 g, 2.97 mmol) in tetrahydrofuran (40 mL) and triethylamine (2.0 mL) was added methanesulfonyl chloride (0.69 mL, 11.9 mmol) at 0° C. The mixture was stirred at 0° C. for 4 hr, diluted with aqueous sodium hydrogen carbonate and extracted with ethyl acetate. The combined organic layer was washed with brine, dried over anhydrous magnesium sulfate, filtered, and concentrated in vacuo. A mixture of the resulting mesylate, potassium carbonate (2.04 g, 14.8 mmol) in N,N-dimethylformamide (15 mL) was stirred at 70° C. for 3 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 0-30% ethyl acetate/n-hexane gradient mixture. The filtrate was concentrated in vacuo to give the solid, which was washed with n-hexane to give the title compound as a colorless powder (770 mg, 1.45 mmol, 49%).
¹H NMR (CDCl₃) δ 0.83 (t, J=7.5 Hz, 6H), 1.69-1.83 (m, 4H), 1.94-2.04 (m, 4H), 2.98-3.07 (m, 1H), 3.74 (t, J=5.1 Hz, 2H), 4.36 (t, J=5.1 Hz, 2H), 6.88 (d, J=8.1 Hz, 1H), 7.12 (d, J=8.1 Hz, 1H), 7.39-7.40 (m, 1H), 7.44-7.47 (m, 2H).
MS Calcd.: 529; MS Found: 530 (M+H).

Example 53

4-[10-Chloro-7-(1-ethylpropyl)-2,3,4,5-tetrahydro-1H-[1,3]diazepino[1,2-a]benzimidazol-1-yl]-N,N-dimethyl-3-(trifluoromethoxy)aniline

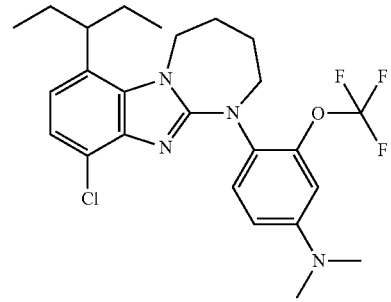 [SMILES: CCC(CC)c1ccc(Cl)c2nc3n(c12)CCCCN3c1ccc(N(C)C)cc1OC(F)(F)F]

A mixture of 1-[4-bromo-2-(trifluoromethoxy)phenyl]-10-chloro-7-(1-ethylpropyl)-2,3,4,5-tetrahydro-1H-[1,3]diazepino[1,2-a]benzimidazole (500 mg, 0.942 mmol), sodium tert-butoxide (226 mg, 2.35 mmol), 2-(di-tert-butylphosphino)biphenyl (22.4 mg, 0.0754 mmol), tris(dibenzylideneacetone)dipalladium (86.2 mg, 0.0942 mmol), and dimethylamine (2.0 M solution of tetrahydrofuran, 1.4 mL, 2.8 mmol) in toluene (1.4 ml) was stirred at 70° C. under nitrogen for 3 hr. The mixture was diluted with water, and extracted with ethyl acetate. The combined organic layer was washed with brine, dried over anhydrous magnesium sulfate, filtered and concentrated in vacuo. The residue was purified by flash column chromatography on silica gel eluting with a 0-20% ethyl acetate/n-hexane gradient mixture. The filtrate was concentrated in vacuo to give the solid, which was recrystallized from ethyl acetate/n-hexane to give the title compound as a colorless crystal (221 mg, 0.446 mmol, 47%).
mp 158-159° C.
¹H NMR (CDCl₃) δ 0.83 (t, J=7.2 Hz, 6H), 1.62-1.85 (m, 4H), 1.92-2.05 (m, 4H), 2.95-3.03 (m, 1H), 2.97 (s, 6H), 3.69 (t, J=5.1 Hz, 2H), 4.29 (t, J=5.1 Hz, 2H), 6.55-6.58 (m, 1H), 6.68 (dd, J=2.7 Hz, 9.0 Hz, 1H), 6.81 (d, J=8.4 Hz, 1H), 7.07 (d, J=8.4 Hz, 1H), 7.50 (d, J=9.0 Hz, 1H).
MS Calcd.: 494; MS Found: 495 (M+H).

Example 54

10-Chloro-1-(2,2-difluoro-1,3-benzodioxol-4-yl)-7-(1-ethylpropyl)-2,3,4,5-tetrahydro-1H-[1,3]diazepino[1,2-a]benzimidazole

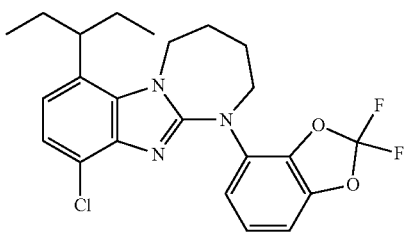 [SMILES: CCC(CC)c1ccc(Cl)c2nc3n(c12)CCCCN3c1cccc2c1OC(F)(F)O2]

To a solution of 4-[4-chloro-2-[(2,2-difluoro-1,3-benzodioxol-4-yl)amino]-7-(1-ethylpropyl)-1H-benzimidazol-1-yl]butan-1-ol (Reference Example 64; 630 mg, 1.35 mmol) in tetrahydrofuran (10 mL) and triethylamine (0.94 mL) was added methanesulfonyl chloride (0.31 mL, 5.41 mmol) at 0° C. The mixture was stirred at 0° C. for 4 hr, diluted with aqueous sodium hydrogen carbonate and extracted with ethyl acetate. The combined organic layer was washed with brine, dried over anhydrous magnesium sulfate, filtered, and concentrated in vacuo. A mixture of the resulting mesylate, potassium carbonate (746 mg, 5.40 mmol) in N,N-dimethylformamide (10 mL) was stirred at 80° C. for 4 hr. The mixture was diluted with water, and extracted with ethyl acetate. The combined organic layer was washed with brine, dried over anhydrous magnesium sulfate, filtered, and concentrated in vacuo. The residue was purified by preparative HPLC to give the title compound as, the trifluoroacetic acid salt. The trifluoroacetic acid salt was washed with aqueous sodium hydrogen carbonate and extracted with ethyl acetate. The extract was washed with brine, dried over magnesium sulfate, filtered and concentrated in vacuo to give the solid, which was recrystallized from ethyl acetate/n-hexane to give the title compound as a colorless crystal (161 mg, 0.359 mmol, 27% in 2 steps).

mp 156-158° C.

$^1$H NMR (CDCl$_3$) δ 0.85 (t, J=7.5 Hz, 6H), 1.70-1.84 (m, 4H), 1.97-2.06 (m, 4H), 3.00-3.09 (m, 1H), 3.90 (t, J=5.1 Hz, 2H), 4.37 (t, J=5.1 Hz, 2H), 6.74 (d, J=7.8 Hz, 1H), 6.93-7.01 (m, 2H), 7.08 (d, J=7.8 Hz, 1H), 7.18 (d, J=8.1 Hz, 1H).

MS Calcd.: 447; MS Found: 448 (M+H).

Example 55

10-Chloro-7-(1-ethylpropyl)-1-(2-methoxypyridin-3-yl)-2,3,4,5-tetrahydro-1H-[1,3]diazepino[1,2-a]benzimidazole

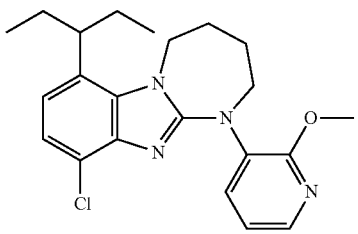 [SMILES: CCC(CC)c1ccc(Cl)c2nc3n(c12)CCCCN3c1cccnc1OC]

To a solution of 4-{4-chloro-7-(1-ethylpropyl)-2-[(2-methoxypyridin-3-yl)amino]-1H-benzimidazol-1-yl}butan-1-ol (200 mg, 0.480 mmol) in pyridine (5 mL) was added methanesulfonyl chloride (275 mg, 2.40 mmol) at 0° C. The mixture was stirred at room temperature for 1 hr. The reaction mixture was concentrated in vacuo. The residue was dissolved in water and ethyl acetate. The mixture was extracted with ethyl acetate (×2). The organics were dried over magnesium sulfate, filtered, and concentrated in vacuo. The resulting crude mesylate (MS Calcd.: 398; Found: 399 (M+H)) was subjected for the next step without further purification. The crude material in N,N-dimethylformamide (3.0 mL) was added potassium carbonate (663 mg, 4.80 mmol). The reaction mixture was stirred at 80° C. for 12 hr. After cooling, the reaction mixture was diluted with water and extracted with ethyl acetate (×3). The combined organic layer was dried over anhydrous magnesium sulfate, filtered and concentrated in vacuo. The residue was purified by silica gel column chromatography eluting with a 0-20% ethyl acetate/n-hexane gradient mixture to give the title compound (137 mg, 0.343 mmol, 71.6% yield) as a white amorphous.

$^1$H-NMR (CDCl$_3$, 300 MHz) δ: 0.84 (6H, t, J=7.2 Hz), 1.63-1.85 (4H, m), 1.92-2.04 (4H, m), 3.00-3.04 (1H, m), 3.74-3.77 (2H, m), 3.80 (3H, s), 4.34-4.38 (2H, m), 6.86 (1H, d, J=8.1 Hz), 6.94 (1H, dd, J=4.8, 7.8 Hz), 7.11 (1H, d, J=8.1 Hz), 7.71 (1H, dd, J=1.8, 8.1 Hz), 7.98 (1H, dd, J=1.8, 4.8 Hz).

MS Calcd.: 398; Found: 399 (M+H).

Example 56

10-Chloro-7-(1-ethylpropyl)-1-(2-methoxy-4,6-dimethylphenyl)-2,3,4,5-tetrahydro-1H-[1,3]diazepino[1,2-a]benzimidazole

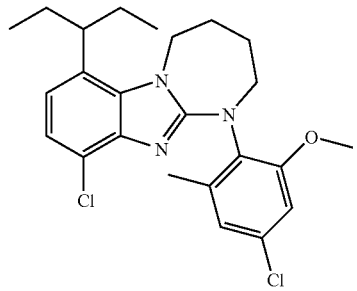 [SMILES: CCC(CC)c1ccc(Cl)c2nc3n(c12)CCCCN3c1c(C)cc(Cl)cc1OC]

To a solution of 2-{4-chloro-2-[(4-chloro-2-methoxy-6-methylphenyl)amino]-7-(1-ethylpropyl)-1H-benzimidazol-1-yl}butan-1-ol (60 mg, 0.129 mmol) in pyridine (0.5 mL) was added methanesulfonyl chloride (0.050 ml, 0.645 mmol) at 0° C., and the mixture was stirred at room temperature for 1 hr. The mixture was diluted with saturated aqueous sodium hydrogen carbonate at 0° C. and extracted with ethyl acetate. The extracts were washed with brine, dried over anhydrous magnesium sulfate and concentrated in vacuo. The resulting mesylate was dissolved in N,N-dimethylformamide (1 mL) and potassium carbonate (36 mg, 258 mmol) was added. The mixture was stirred at 80° C. for 15 hr. After cooling, the mixture was diluted with water and extracted with ethyl acetate. The extracts were washed with saturated aqueous sodium hydrogen carbonate and brine, dried over magnesium sulfate and concentrated in vacuo. The residue was purified by silica gel column chromatography eluting with a 1-15% ethyl acetate/n-hexane gradient mixture. The desired fractions were concentrated in vacuo, and the resulting solid was recrystallized from methanol to give the title compound (23 mg, 0.0515 mmol, 40%) as a colorless crystal.

mp: 196-198° C.

¹H NMR (CDCl₃) δ: 0.79-0.90 (6H, m), 1.65-1.82 (4H, m), 1.82-1.95 (2H, m), 2.00-2.15 (2H, m), 2.25 (3H, s), 2.90-3.00 (1H, m), 3.40-3.70 (2H, m), 3.78 (3H, s), 4.05-4.20 (1H, m), 4.35-4.45 (1H, m), 6.77 (1H, d, J=8.4 Hz), 6.82 (1H, d, J=2.1 Hz), 6.88 (1H, d, J=2.41 Hz), 7.04 (1H, d, J=8.4 Hz).

MS Calcd.: 445; Found: 446 (M+H).

Example 57

5-[10-Chloro-7-(1-ethylpropyl)-2,3,4,5-tetrahydro-1H-[1,3]diazepino[1,2-a]benzimidazol-1-yl]-4-methylpyridin-2(1H)-one

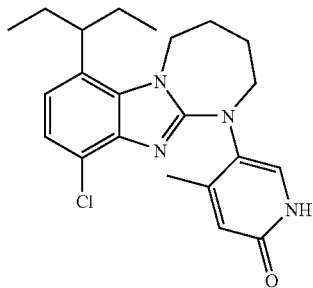 [SMILES: CCC(CC)c1ccc(Cl)c2nc3n(c12)CCCCN3c1c[nH]c(=O)cc1C]

To a Mixture of 10-chloro-7-(1-ethylpropyl)-1-(6-methoxy-4-methylpyridin-3-yl)-2,3,4,5-tetrahydro-1H-[1,3]diazepino[1,2-a]benzimidazole (Example 30; 410 mg, 0.993 mmol), sodium iodide (447 mg, 2.98 mmol) and acetonitrile (10 mL) was added chlorotrimethylsilane (0.381 mL, 2.99 mmol) at 0° C. After the resultant mixture was stirred at room temperature for 24 hr, the mixture was diluted with aqueous saturated sodium hydrogen carbonate and extracted with ethyl acetate. The combined organic layer was washed with brine, dried over anhydrous sodium sulfate, filtered and concentrated in vacuo. The residue was purified by column chromatography on silica gel eluting with ethyl acetate to give the title compound as a solid (285 mg, 0.714 mmol, 72%).

¹H NMR (DMSO-d₆) δ 0.78 (t, J=7.3 Hz, 6H), 1.57-1.83 (m, 4H), 1.85-1.95 (m, 2H), 1.97-2.08 (m, 5H), 2.99-3.11 (m, 1H), 3.58-3.66 (m, 2H), 4.22-4.32 (m, 2H), 6.26 (s, 1H), 6.84 (d, J=8.3 Hz, 1H), 7.05 (d, J=8.3 Hz, 1H), 7.48 (s, 1H), 11.49 (brs, 1H).

MS Calcd.: 398; MS Found: 399 (M+H).

Example 58

5-[10-Chloro-7-(1-ethylpropyl)-2,3,4,5-tetrahydro-1H-[1,3]diazepino[1,2-a]benzimidazol-1-yl]-4-methylpyridin-2-yl trifluoromethanesulfonate

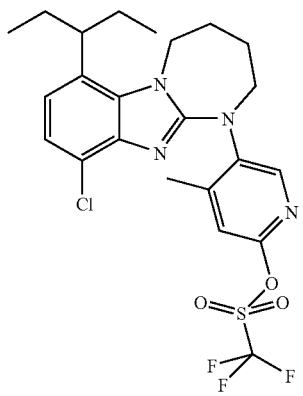 [SMILES: CCC(CC)c1ccc(Cl)c2nc3n(c12)CCCCN3c1cnc(OS(=O)(=O)C(F)(F)F)cc1C]

To a solution of 5-[10-chloro-7-(1-ethylpropyl)-2,3,4,5-tetrahydro-1H-[1,3]diazepino[1,2-a]benzimidazol-1-yl]-4-methylpyridin-2(1H)-one (Example 57; 270 mg, 0.677 mmol) in pyridine (7 mL) was added trifluoromethanesulfonic anhydride (0.342 mL, 2.03 mmol) at 0° C. After the resultant mixture was stirred at room temperature for 12 hr, the mixture was diluted with aqueous saturated sodium hydrogen carbonate and extracted with ethyl acetate. The combined organic layer was washed with brine, dried over anhydrous sodium sulfate, filtered and concentrated in vacuo. The residue was purified by flash column chromatography on silica gel eluting with a 10-40% ethyl acetate/n-hexane gradient mixture to give the title compound as a solid (305 mg, 0.574 mmol, 85%).

¹H NMR (CDCl₃) δ 0.85 (t, J=7.3 Hz, 6H), 1.64-1.91 (m, 4H), 1.95-2.16 (m, 7H), 2.96-3.08 (m, 1H), 3.82-3.89 (m, 2H), 4.32-4.39 (m, 2H), 6.89 (d, J=8.2 Hz, 1H), 7.04 (s, 1H), 7.13 (d, J=8.2 Hz, 1H), 8.34, (s, 1H).

MS Calcd.: 530; MS Found: 531 (M+H).

Example 59

5-[10-Chloro-7-(1-ethylpropyl)-2,3,4,5-tetrahydro-1H-[1,3]diazepino[1,2-a]benzimidazol-1-yl]-4-methylpyridine-2-carbonitrile

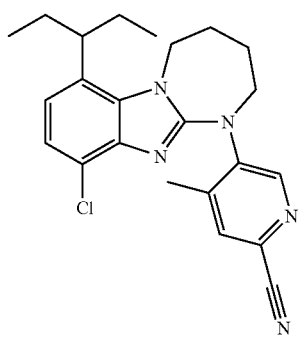 [SMILES: CCC(CC)c1ccc(Cl)c2nc3n(c12)CCCCN3c1cnc(C#N)cc1C]

Under argon atmosphere a mixture of 5-[10-chloro-7-(1-ethylpropyl)-2,3,4,5-tetrahydro-1H-[1,3]diazepino[1,2-a]benzimidazol-1-yl]-4-methylpyridin-2-yl trifluoromethanesulfonate (Example 58; 285 mg, 0.537 mmol), zinc cyanide (94.5 mg, 0.805 mmol), tetrakis(triphenylphosphine)palladium(0) (62.1 mg, 0.0537 mmol) and N,N-dimethylformamide (2.7 mL) was stirred at 120° C. for 3 hr. The reaction mixture was diluted with ethyl acetate, washed with water and brine, dried over anhydrous sodium sulfate, filtered and concentrated in vacuo. The residue was purified by flash column chromatography on silica gel eluting with a 10-40% ethyl acetate/n-hexane gradient mixture to give the title compound as a solid (166 mg, 0.407 mmol, 76%). Analytically pure material was obtained by recrystallization from ethyl acetate/n-hexane.

mp 177-178° C.

¹H NMR (CDCl₃) δ 0.85 (t, J=7.3 Hz, 6 H), 1.64-1.90 (m, 4 H), 1.96-2.15 (m, 7 H), 2.96-3.08 (m, 1 H), 3.87-3.95 (m, 2 H), 4.36-4.44 (m, 2 H), 6.92 (d, J=8.2 Hz, 1 H), 7.15 (d, J=8.2 Hz, 1 H), 7.52 (s, 1 H), 8.65 (s, 1 H).

MS Calcd.: 407; MS Found: 408 (M+H).

Example 60

1-{5-[10-Chloro-7-(1-ethylpropyl)-2,3,4,5-tetrahydro-1H-[1,3]diazepino[1,2-a]benzimidazol-1-yl]-4-methylpyridin-2-yl}ethanone

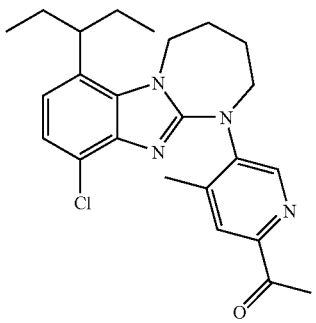 [SMILES: CCC(CC)c1ccc(Cl)c2nc3n(c12)CCCCN3c1cnc(C(C)=O)cc1C]

Under nitrogen atmosphere to a solution of 5-[10-chloro-7-(1-ethylpropyl)-2,3,4,5-tetrahydro-1H-[1,3]diazepino[1,2-a]benzimidazol-1-yl]-4-methylpyridine-2-carbonitrile (Example 59; 70.0 mg, 0.172 mmol) in tetrahydrofuran (2 mL) was added 3M methylmagnesium bromide solution in diethyl ether (0.115 mL, 0.345 mmol) at 0° C. After the resultant mixture was stirred at room temperature for 30 min, the mixture was diluted with 0.1N hydrochloric acid (5 mL) at 0° C. After the resultant mixture was stirred at room temperature for 30 min, the mixture was neutralized with aqueous sodium hydrogen carbonate and extracted with ethyl acetate. The combined organic layer was washed with brine, dried over anhydrous sodium sulfate, filtered and concentrated in vacuo. The residue was purified by flash column chromatography on silica gel eluting with a 20-50% ethyl acetate/n-hexane gradient mixture to give, the title compound as a solid (59.6 mg, 0.140 mmol, 81%). Analytically pure material was obtained by recrystallization from ethyl acetate/n-hexane.

mp 144-145° C.

$^1$H NMR (CDCl$_3$) δ 0.85 (t, J=7.4 Hz, 6H), 1.66-1.88 (m, 4H), 1.95-2.15 (m, 7H), 2.72 (s, 3H), 2.97-3.07 (m, 1H), 3.89-3.97 (m, 2H), 4.35-4.42 (m, 2H), 6.90 (d, J=8.2 Hz, 1H), 7.13 (d, J=8.2 Hz, 1H), 7.90 (s, 1H), 8.63 (s, 1H).

MS Calcd.: 424; MS Found: 425 (M+H).

Example 61

5-[10-Chloro-7-(1-ethylpropyl)-2,3,4,5-tetrahydro-1H-[1,3]diazepino[1,2-a]benzimidazol-1-yl]-4-methylpyridine-2-carboxamide

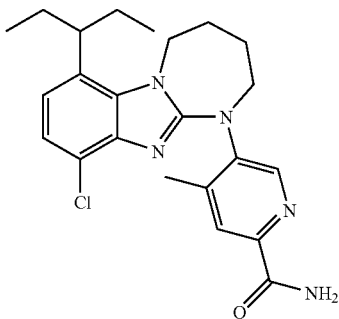 [SMILES: CCC(CC)c1ccc(Cl)c2nc3n(c12)CCCCN3c1cnc(C(N)=O)cc1C]

A mixture of 5-[10-chloro-7-(1-ethylpropyl)-2,3,4,5-tetrahydro-1H-[1,3]diazepino[1,2-a]benzimidazol-1-yl]-4-methylpyridine-2-carbonitrile (Example 59; 70.0 mg, 0.172 mmol), potassium hydroxide (38.5 mg, 0.687 mmol) and t-butyl alcohol (2 mL) was stirred at 80° C. for 15 min. After the reaction mixture was diluted with water at 0° C., the precipitate was collected by filtration and washed with water and diisopropyl ether to give the title compound as a solid (64.8 mg, 0.152 mmol, 88%). Analytically pure material was obtained by recrystallization from ethyl acetate/n-hexane.

mp 267-269° C.

$^1$H NMR (CDCl$_3$) δ 0.85 (t, J=7.4 Hz, 6H), 1.65-1.89 (m, 4H), 1.96-2.17 (m, 7H), 2.96-3.09 (m, 1H), 3.85-3.94 (m, 2H), 4.34-4.41 (m, 2H), 5.61 (brs, 1H), 6.89 (d, J=8.2 Hz, 1H), 7.13 (d, J=8.2 Hz, 1H), 7.74 (brs, 1H), 8.06 (s, 1H), 8.54 (s, 1H).

MS Calcd.: 425; MS Found: 426 (M+H).

Example 62

10-Chloro-1-(3,5-dichloropyridin-2-yl)-7-(1-ethylpropyl)-2,3,4,5-tetrahydro-1H-[1,3]diazepino[1,2-a]benzimidazole

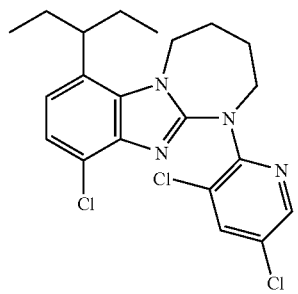 [SMILES: CCC(CC)c1ccc(Cl)c2nc3n(c12)CCCCN3c1ncc(Cl)cc1Cl]

A mixture of 10-chloro-7-(1-ethylpropyl)-2,3,4,5-tetrahydro-1H-[1,3]diazepino[1,2-a]benzimidazole (Reference Example 72; 100 mg, 0.34 mmol), 2-bromo-3,5-dichloropyridine (239 mg, 1.03 mmol), copper(I) iodide (65 mg, 0.34 mmol), 2,2'-bipyridyl (106 mg, 0.68 mmol) and cesium carbonate (222 mg, 0.68 mmol) in 1-methyl-2-pyrrolidinone (1.5 mL) was stirred at 150° C. for 12 hr. The mixture was diluted with ethyl acetate, filtered through a pad of celite, washed with water and brine, dried over anhydrous sodium sulfate and concentrated in vacuo. The residue was purified by flash chromatography on silica gel eluting with a 5-30% ethyl acetate/n-hexane gradient mixture. The filtrate was concentrated in vacuo to give a solid, which was recrystallized from n-hexane/ethyl acetate to give the title compound (50 mg, 0.114 mmol, 34%) as a colorless solid.

mp 175-176° C.

$^1$H NMR (CDCl$_3$) δ 0.86 (t, J=7.3 Hz, 6 H), 1.64-2.12 (m, 8 H), 2.96-3.18 (m, 1 H), 4.07-4.19 (m, 2 H), 4.44-4.53 (m, 2 H), 6.95 (d, J=8.3 Hz, 1 H), 7.17 (d, J=8.3 Hz, 1 H), 7.62 (d, J=2.3 Hz, 1 H), 8.23 (d, J=2.6 Hz, 1 H).

MS Calcd.: 436; Found: 437 (M+H).

Example 63

10-Chloro-1-[3-chloro-5-(trifluoromethyl)pyridin-2-yl]-7-(1-ethylpropyl)-2,3,4,5-tetrahydro-1H-[1,3]diazepino[1,2-a]benzimidazole

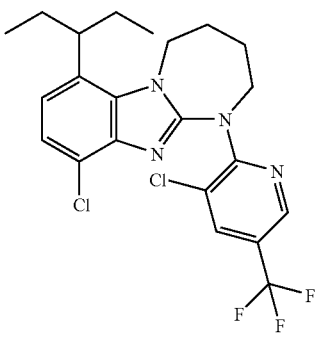 [SMILES: CCC(CC)c1ccc(Cl)c2nc3n(c12)CCCCN3c1ncc(C(F)(F)F)cc1Cl]

A mixture of 10-chloro-7-(1-ethylpropyl)-2,3,4,5-tetrahydro-1H-[1,3]diazepino[1,2-a]benzimidazole (Reference Example 72; 150 mg, 0.51 mmol), 2-bromo-3-chloro-5-(trifluoromethyl)pyridine (401 mg, 1.54 mmol), copper(I) iodide (97 mg, 0.51 mmol), 2,2'-bipyridyl (159 mg, 1.02 mmol) and cesium carbonate (333 mg, 1.02 mmol) in 1-methyl-2-pyrrolidinone (2.0 mL) was stirred at 150° C. for 16 hr. The mixture was diluted with ethyl acetate, filtered through a pad of celite, washed with 2N hydrochloric acid, water and brine, dried over anhydrous sodium sulfate and concentrated in vacuo. The residue was purified by flash chromatography on silica gel eluting with a 5-20% ethyl acetate/n-hexane gradient mixture. The filtrate was concentrated in vacuo to give a residue, which was purified by preparative HPLC to give a solid, which was recrystallized from n-hexane/ethyl acetate to give the title compound (104 mg, 0.221 mmol, 43%) as a colorless solid.

mp 108-110° C.

$^1$H NMR (CDCl$_3$) δ 0.87 (t, J=7.3 Hz, 6 H), 1.67-2.13 (m, 8 H), 3.02-3.19 (m, 1 H), 4.18-4.28 (m, 2 H), 4.48-4.56 (m, 2 H), 6.99 (d, J=8.3 Hz, 1 H), 7.21 (d, J=8.3 Hz, 1 H), 7.73-7.85 (m, 1 H), 8.43-8.57 (m, 1 H).

MS Calcd.: 470; Found: 471 (M+H).

Example 64

10-Chloro-7-(1-ethylpropyl)-1-(3-methyl-5-nitropyridin-2-yl)-2,3,4,5-tetrahydro-1H-[1,3]diazepino[1,2-a]benzimidazole

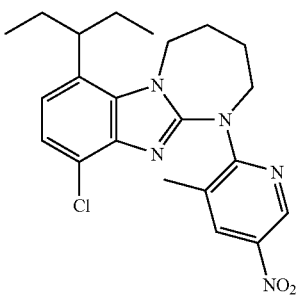 [SMILES: CCC(CC)c1ccc(Cl)c2nc3n(c12)CCCCN3c1ncc([N+](=O)[O-])cc1C]

A mixture of 10-chloro-7-(1-ethylpropyl)-2,3,4,5-tetrahydro-1H-[1,3]diazepino[1,2-a]benzimidazole (Reference Example 72; 292 mg, 1.00 mmol), 2-bromo-3-methyl-5-nitropyridine (651 mg, 3.00 mmol), copper(I) iodide (190 mg, 1.00 mmol), 2,2'-bipyridyl (312 mg, 2.00 mmol) and cesium carbonate (652 mg, 2.00 mmol) in 1-methyl-2-pyrrolidinone (3.0 mL) was stirred at 150° C. for 16 hr. The mixture was diluted with ethyl acetate, filtered through a pad of celite, washed with 1N hydrochloric acid and brine, dried over anhydrous sodium sulfate and concentrated in vacuo. The residue was purified by flash chromatography on silica gel eluting with a 5-30% ethyl acetate/n-hexane gradient mixture. The filtrate was concentrated in vacuo to give a solid, which was recrystallized from n-hexane/ethyl acetate to give the title compound (170 mg, 0.397 mmol, 40%) as a yellow solid.

mp 204-205° C.

$^1$H NMR (CDCl$_3$) δ 0.88 (t, J=7.3 Hz, 6 H), 1.69-2.11 (m, 8 H), 1.73 (s, 3 H), 3.02-3.22 (m, 1 H), 4.18-4.41 (m, 2 H), 4.43-4.64 (m, 2 H), 7.01 (d, J=8.2 Hz, 1 H), 7.22 (d, J=8.2 Hz, 1 H), 8.16 (dd, J=2.6, 0.7 Hz, 1 H), 9.07 (d, J=2.5 Hz, 1 H).

MS Calcd.: 427; Found: 428 (M+H).

Example 65

6-[10-Chloro-7-(1-ethylpropyl)-2,3,4,5-tetrahydro-1H-[1,3]diazepino[1,2-a]benzimidazol-1-yl]-5-methylpyridin-3-amine

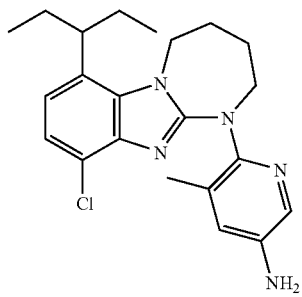

A mixture of 10-chloro-7-(1-ethylpropyl)-1-(3-methyl-5-nitropyridin-2-yl)-2,3,4,5-tetrahydro-1H-[1,3]diazepino[1,2-a]benzimidazole (43 mg, 0.100 mmol) and 10% palladium on carbon (4.3 mg) in tetrahydrofuran (1.0 mL) was stirred under hydrogen atmosphere at room temperature for 4 hr. Catalyst was removed by filtration and the filtrate was concentrated in vacuo. The residue was purified by flash chromatography on silica gel eluting with a 50-100% ethyl acetate/n-hexane gradient mixture. The filtrate was concentrated in vacuo to give the title compound (36 mg, 0.090 mmol, 90%) as a pale yellow amorphous.

$^1$H NMR (CDCl$_3$) δ 0.86 (t, J=7.4 Hz, 6 H), 1.64-2.10 (m, 8 H), 1.82 (s, 3 H), 2.95-3.13 (m, 1 H), 3.99-4.07 (m, 2 H), 4.29-4.38 (m, 2 H), 6.83-6.89 (m, 2 H), 7.12 (d, J=8.2 Hz, 1 H), 7.69 (d, J=2.5 Hz, 1 H).

MS Calcd.: 397; Found: 398 (M+H).

Example 66

6-[10-Chloro-7-(1-ethylpropyl)-2,3,4,5-tetrahydro-1H-[1,3]diazepino[1,2-a]benzimidazol-1-yl]-N,N,5-trimethylpyridin-3-amine

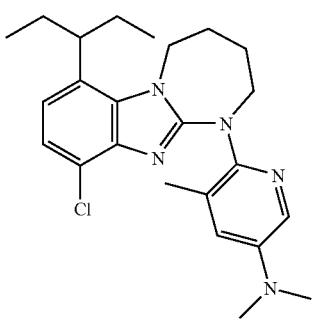 [SMILES: CCC(CC)c1ccc(Cl)c2nc3n(c12)CCCCN3c1ncc(N(C)C)cc1C]

To a solution of 6-[10-chloro-7-(1-ethylpropyl)-2,3,4,5-tetrahydro-1H-[1,3]diazepino[1,2-a]benzimidazol-1-yl]-5-methylpyridin-3-amine (35 mg, 0.088 mmol), formaldehyde (37% aqueous solution, 0.071 mL, 0.88 mmol) and acetic acid (0.020 mL, 0.352 mmol) in tetrahydrofuran (2.0 mL) was added sodium triacetoxyborohydride (111 mg, 0.528 mmol) portionwise at 0° C. The mixture was warmed to room temperature and stirred for 20 hr. Aqueous sodium bicarbonate was added and the mixture was extracted with ethyl acetate. Organic layer was washed with brine, dried over anhydrous sodium sulfate and concentrated in vacuo. The residue was purified by flash chromatography on silica gel eluting with a 40-70% ethyl acetate/n-hexane gradient mixture. The filtrate was concentrated in vacuo to give the title compound (16 mg, 0.038 mmol, 43%) as a colorless solid.

mp 188-190° C.

$^1$H NMR (CDCl$_3$) δ 0.85 (t, J=7.4 Hz, 6 H), 1.64-2.09 (m, 8 H), 1.89 (s, 3 H), 2.95 (s, 6 H), 2.97-3.10 (m, 1 H), 4.06-4.12 (m, 2 H), 4.31-4.38 (m, 2 H), 6.85 (d, J=8.2 Hz, 1 H), 6.90 (d, J=3.0 Hz, 1 H), 7.10 (d, J=8.5 Hz, 1 H), 7.82 (d, J=3.0 Hz, 1 H).

MS Calcd.: 425; Found: 426 (M+H).

Example 67

7-Bromo-1-(2,4-dichlorophenyl)-2,3,4,5-tetrahydro-1H-[1,3]diazepino[1,2-a]benzimidazole

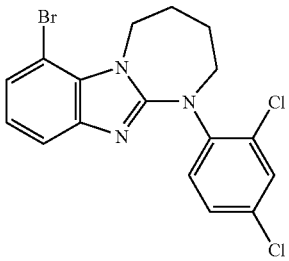 [SMILES: Clc1ccc(N2CCCCn3c2nc2cccc(Br)c23)c(Cl)c1]

To a solution of ethyl 4-{7-bromo-2-[(2,4-dichlorophenyl)amino]-1H-benzimidazol-1-yl}butanoate (Reference Example 78; 1.61 g, 3.42 mmol) in tetrahydrofuran (15 mL) was added lithium tetrahydroborate (372 mg, 17.1 mmol) at 0° C. The mixture was stirred at room temperature for 16 hr, and the reaction was quenched by methanol. The mixture was concentrated in vacuo, neutralized with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 5-30% ethyl acetate/n-hexane gradient mixture. The filtrate was concentrated in vacuo to give the crude product of 4-{7-bromo-2-[(2,4-dichlorophenyl)amino]-1H-benzimidazol-1-yl}butan-1-ol (945 mg).

MS Calcd.: 427; MS Found: 428 (M+H).

To a solution the above crude product (945 mg) in tetrahydrofuran (15 mL) and triethylamine (1.5 mL) was added methanesulfonyl chloride (0.51 mL, 6.57 mmol) at 0° C. The mixture was stirred at 0° C. for 12 hr, and diluted with aqueous sodium hydrogen carbonate and extracted with ethyl acetate. The combined organic layer was washed with brine, dried over anhydrous magnesium sulfate, filtered, and concentrated in vacuo. A mixture of the resulting mesylate, potassium carbonate (908 mg, 6.57 mmol) in N,N-dimethylformamide (15 mL) was stirred at 70° C. for 4 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 5-25% ethyl acetate/n-hexane gradient mixture. The filtrate was concentrated in vacuo to give the title compound as a colorless solid (570 mg, 1.39 mmol, 41%).

$^1$H NMR (CDCl$_3$) δ 1.98-2.08 (m, 4H), 3.77 (t, J=5.1 Hz, 2H), 4.72 (t, J=5.1 Hz, 2H), 6.97 (d, J=8.1 Hz, 1H), 7.25-7.44 (m, 5H).

MS Calcd.: 409; MS Found: 410 (M+H).

Example 68

1-[1-(2,4-Dichlorophenyl)-2,3,4,5-tetrahydro-1H-[1,3]diazepino[1,2-a]benzimidazol-7-yl]propan-1-ol

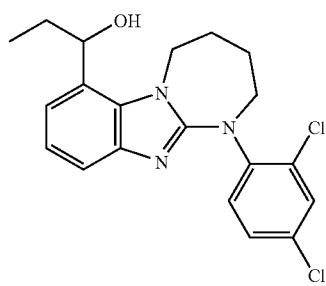 [SMILES: CCC(O)c1cccc2nc3n(c12)CCCCN3c1ccc(Cl)cc1Cl]

To a solution of 7-bromo-1-(2,4-dichlorophenyl)-2,3,4,5-tetrahydro-1H-[1,3]diazepino[1,2-a]benzimidazole (570 mg, 1.39 mmol) in tetrahydrofuran (10 mL) was added n-butyllithium (1.60 M solution in n-hexane, 0.97 mL, 1.55 mmol) at −78° C., and the mixture was stirred for 10 min. To the mixture was added propionaldehyde (0.30 mL, 4.16 mmol), and the mixture was stirred at −78° C. for 10 min, at 0° C. for 3 hr. The mixture was diluted with saturated aqueous ammonium chloride and extracted with ethyl acetate. The combined organic layer was washed with brine, dried over anhydrous magnesium sulfate, filtered, and concentrated in vacuo. The residue was purified by flash column chromatography on silica gel eluting with a 5-25% ethyl acetate/n-hexane gradient mixture. The filtrate was concentrated in vacuo to give the solid, which was recrystallized from ethyl acetate to give the title compound as a colorless crystal (101 mg, 0.259 mmol, 19%).

mp 241-243° C.

¹H NMR (CDCl₃) δ 1.06 (t, J=7.5 Hz, 3H), 1.97-2.09 (m, 7H), 3.76 (t, J=5.4 Hz, 2H), 4.55-4.62 (m, 2H), 4.98-5.06 (m, 1H), 7.06-7.15 (m, 2H), 7.29-7.47 (m, 4H).

MS Calcd.: 389; MS Found: 390 (M+H).

Example 69

1-[1-(2,4-Dichlorophenyl)-2,3,4,5-tetrahydro-1H-[1,3]diazepino[1,2-a]benzimidazol-7-yl]propan-1-one

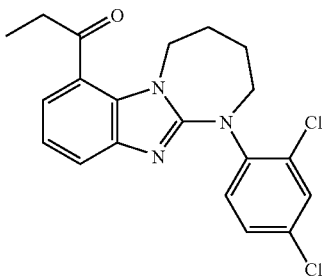 [SMILES: CCC(=O)c1cccc2nc3n(c12)CCCCN3c1ccc(Cl)cc1Cl]

A mixture of 1-[1-(2,4-dichlorophenyl)-2,3,4,5-tetrahydro-1H-[1,3]diazepino[1,2-a]benzimidazol-7-yl]propan-1-ol (160 mg, 0.409 mmol), tetra-n-propylammonium perruthenate (144 mg, 0.409 mmol), 4-methylmorpholine N-oxide (47.9 mg, 0.409 mmol) and dichloromethane (2.0 mL) was stirred at room temperature for 32 hr. The precipitate was removed by filtration, and the mother solution was diluted with aqueous sodium hydrogen carbonate and extracted with ethyl acetate. The combined organic layer was washed with brine, dried over anhydrous magnesium sulfate, filtered and concentrated in vacuo. The residue was purified by flash column chromatography on silica gel eluting with a 10-50% ethyl acetate/n-hexane gradient mixture. The filtrate was concentrated in vacuo to give the title compound as a colorless amorphous (11.0 mg, 0.0283 mmol, 7%).

¹H NMR (CDCl₃) δ 1.28 (t, J=7.5 Hz, 3H), 1.98-2.04 (m, 2H), 2.19-2.22 (m, 2H), 3.11 (q, J=7.5 Hz, 2H), 3.79-3.84 (m, 2H), 4.09 (t, J=5.1 Hz, 2H), 7.15 (t, J=7.8 Hz, 1H), 7.25-7.43 (m, 3H), 7.53 (dd, J=1.2 Hz, 7.8 Hz, 1H), 7.64 (dd, J=1.2 Hz, 7.8 Hz, 1H).

MS Calcd.: 387; MS Found: 388 (M+H).

Example 70

1-(2,4-Dichlorophenyl)-7-(diethylamino)-2,3,4,5-tetrahydro-1H-[1,3]diazepino[1,2-a]benzimidazol-4-ol

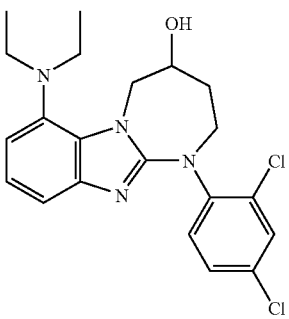 [SMILES: CCN(CC)c1cccc2nc3n(c12)CC(O)CCN3c1ccc(Cl)cc1Cl]

To a solution of 4-[2-[(2,4-dichlorophenyl)amino]-7-(diethylamino)-1H-benzimidazol-1-yl]butane-1,3-diol (Reference Example 84; 175 mg, 0.400 mmol) in pyridine (4 mL) was added methanesulfonyl chloride (0.0929 mL, 1.20 mmol) at 0° C. After the resultant mixture was stirred at 0° C. for 3 hr, the mixture was diluted with aqueous sodium hydrogen carbonate and extracted with ethyl acetate. The combined organic layer was washed with brine, dried over anhydrous sodium sulfate, filtered and concentrated in vacuo. The resulting mesylate was diluted with N,N-dimethylformamide (4 mL) and to the solution was added potassium carbonate (110 mg, 0.797 mmol) at room temperature. After the resultant mixture was stirred at 80° C. for 1 hr, the mixture was diluted with ethyl acetate, washed with water and brine, dried over anhydrous sodium sulfate, filtered and concentrated in vacuo. The residue was purified by flash column chromatography on silica gel eluting with a 40% ethyl acetate/n-hexane mixture to give the title compound as a solid (108 mg, 0.258 mmol, 65%). Analytically pure material was obtained by recrystallization from ethyl acetate/n-hexane.

mp 207-208° C.

¹H NMR (CDCl₃) δ 1.04 (t, J=7.2 Hz, 6H), 1.94-2.08 (m, 2H), 2.12-2.25 (m, 1H), 3.11 (q, J=7.1 Hz, 4H), 3.63-3.74 (m, 1H), 3.84-3.94 (m, 1H), 4.17-4.29 (m, 1H), 4.65 (dd, J=13.6, 7.8 Hz, 1H), 5.11 (dd, J=13.6, 1.9 Hz, 1H), 6.91 (dd, J=7.8, 1.1 Hz, 1H), 7.05 (t, J=7.8 Hz, 1H), 7.24-7.27 (m, 1H), 7.30 (dd, J=8.5, 2.4 Hz, 1H), 7.38 (d, J=8.5 Hz, 1H), 7.40 (d, J=2.4 Hz, 1H).

MS Calcd.: 418; MS Found: 419 (M+H).

Example 71

1-(2,4-Dichlorophenyl)-7-(diethylamino)-2,3-dihydro-1H-[1,3]diazepino[1,2-a]benzimidazol-4(5H)-one

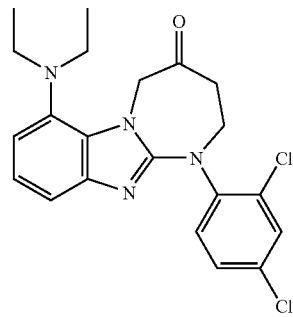 [SMILES: CCN(CC)c1cccc2nc3n(c12)CC(=O)CCN3c1ccc(Cl)cc1Cl]

A mixture of 1-(2,4-dichlorophenyl)-7-(diethylamino)-2,3,4,5-tetrahydro-1H-[1,3]diazepino[1,2-a]benzimidazol-4-ol (Example 70; 60.0 mg, 0.143 mmol), tetra-n-propylammonium perruthenate (5.0 mg, 0.014 mmol), 4-methylmorphorine N-oxide (41.9 mg, 0.358 mmol), molecular sieves 4A (60 mg) and acetonitrile (1.5 mL) was stirred at room temperature for 2 hr. The reaction mixture was diluted with water, filtered and extracted with ethyl acetate. The combined organic layer was washed with brine, dried over anhydrous sodium sulfate, filtered and concentrated in vacuo. The residue was purified by flash column chromatography on silica gel eluting with a 10-30% ethyl acetate/n-hexane gradient mixture and recrystallization from ethyl acetate/n-hexane to give the title compound as a solid (26.5 mg, 0.0635 mmol, 44%).

mp 169-170° C.

¹H NMR (CDCl₃) δ 0.96 (t, J=7.2 Hz, 6H), 2.95 (t, J=6.9 Hz, 2H), 2.99-3.12 (m, 4H), 3.94 (t, J=6.9 Hz, 2H), 5.56 (s, 2H), 7.04 (dd, J=7.8, 0.8 Hz, 1H), 7.14 (t, J=7.8 Hz, 1H), 7.32 (dd, J=8.8, 2.2 Hz, 1H), 7.35-7.41 (m, 3H).

MS Calcd.: 416; MS Found: 417 (M+H).

Example 72

Methyl [1-(2,4-dichlorophenyl)-5-(diethylamino)-2,3-dihydro-1H-imidazo[1,2-a]benzimidazol-2-yl]acetate

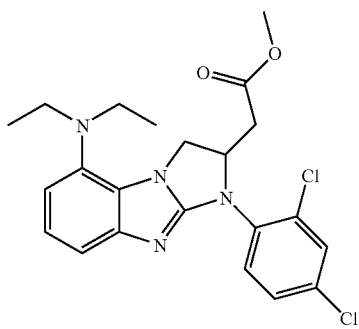 [SMILES: CCN(CC)c1cccc2nc3n(c12)CC(CC(=O)OC)N3c1ccc(Cl)cc1Cl]

To a solution of methyl 4-[2-[(2,4-dichlorophenyl)amino]-7-(diethylamino)-1H-benzimidazol-1-yl]-3-hydroxybutanoate (Reference Example 83; 200 mg, 0.430 mmol) in pyridine (4 mL) was added methanesulfonyl chloride (0.166 mL, 2.14 mmol) at 0° C. After the resultant mixture was stirred at room temperature for 16 hr, the mixture was diluted with aqueous sodium hydrogen carbonate and extracted with ethyl acetate. The combined organic layer was washed with brine, dried over anhydrous sodium sulfate, filtered and concentrated in vacuo. The resulting mesylate was diluted with N,N-dimethylformamide (9 mL) and to the solution was added potassium carbonate (119 mg, 0.862 mmol) at room temperature. After the resultant mixture was stirred at 80° C. for 2 hr, the mixture was diluted with ethyl acetate, washed with water and brine, dried over anhydrous sodium sulfate, filtered and concentrated in vacuo. The residue was purified by flash column chromatography on silica gel eluting with a 10-50% ethyl acetate/n-hexane gradient mixture to give the title compound as a solid (162 mg, 0.362 mmol, 84%). Analytically pure material was obtained by recrystallization from ethyl acetate/n-hexane.

mp 137-138° C.

$^1$H NMR (CDCl$_3$) δ 1.00 (t, J=7.2 Hz, 6H), 2.71 (d, J=6.8 Hz, 2H), 3.07 (q, J=7.2 Hz, 4H), 3.63 (s, 3H), 4.25 (dd, J=10.5, 5.1 Hz, 1H), 4.68 (dd, J=10.5, 8.3 Hz, 1H), 5.21-5.32 (m, 1H), 6.86 (dd, J=7.9, 0.9 Hz, 1H), 7.02 (t, J=7.9 Hz, 1H), 7.20 (dd, J=7.9, 0.9 Hz, 1H), 7.32 (dd, J=8.6, 2.4 Hz, 1H), 7.49 (d, J=2.3 Hz, 1H), 7.60 (d, J=8.6 Hz, 1H).

MS Calcd.: 446; MS Found: 447 (M+H).

Example 73

[1-(2,4-Dichlorophenyl)-5-(diethylamino)-2,3-dihydro-1H-imidazo [1,2-a]benzimidazol-2-yl]acetic acid

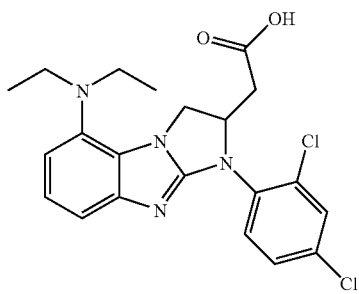 [SMILES: CCN(CC)c1cccc2nc3n(c12)CC(CC(=O)O)N3c1ccc(Cl)cc1Cl]

To a solution of methyl [1-(2,4-dichlorophenyl)-5-(diethylamino)-2,3-dihydro-1H-imidazo[1,2-a]benzimidazol-2-yl]acetate (Example 72; 50.0 mg, 0.112 mmol) in a mixture of tetrahydrofuran (1 mL) and methanol (0.5 mL) was added 1N sodium hydroxide solution (0.224 mL, 0.224 mmol) at room temperature. After the resultant mixture was stirred at room temperature for 1 hr, the mixture was neutralized with 1N hydrochloric acid and extracted with ethyl acetate. The combined organic layer was washed with brine, dried over anhydrous sodium sulfate, filtered and concentrated in vacuo. The residue was washed with ethyl acetate to give the title compound as a solid (31.7 mg, 0.0731 mmol, 65%). Analytically pure material was obtained by recrystallization from ethanol/diisopropyl ether.

mp 249-251° C.

$^1$H NMR (DMSO-d$_6$) δ 0.97 (t, J=7.1 Hz, 6H), 2.63 (dd, J=16.7, 4.9 Hz, 1H), 2.79 (dd, J=16.7, 8.0 Hz, 1H), 3.08 (q, J=7.1 Hz, 4H), 4.27 (dd, J=10.2, 6.1 Hz, 1H), 4.68 (dd, J=10.2, 9.1 Hz, 1H), 5.15-5.28 (m, 1H), 6.82 (dd, J=6.4, 2.3 Hz, 1H), 6.91-6.99 (m, 2H), 7.55 (dd, J=8.7, 2.5 Hz, 1H), 7.75 (d, J=8.7 Hz, 1H), 7.79 (d, J=2.5 Hz, 1H). hidden (1H)

MS Calcd.: 432; MS Found: 433 (M+H).

Example 74

2-[1-(2,4-Dichlorophenyl)-5-(diethylamino)-2,3-dihydro-1H-imidazo [1,2-a]benzimidazol-2-yl]ethanol

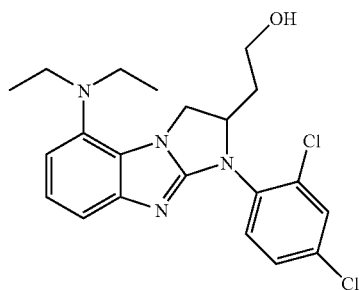 [SMILES: CCN(CC)c1cccc2nc3n(c12)CC(CCO)N3c1ccc(Cl)cc1Cl]

To a suspension of lithium aluminum hydride (20 mg, 0.54 mmol) in tetrahydrofuran (1.5 mL) was added a solution of methyl [1-(2,4-dichlorophenyl)-5-(diethylamino)-2,3-dihydro-1H-imidazo[1,2-a]benzimidazol-2-yl]acetate (Example 72, 60.0 mg, 0.134 mmol) in tetrahydrofuran (1.5 mL) at 0° C. and the resultant mixture was stirred at 0° C. for 10 min. After sodium sulfate decahydrate (600 mg) was added at 0° C., the resultant mixture was filtered and concentrated in vacuo. The residue was purified by flash column chromatography on silica gel eluting with a 30-60% ethyl acetate/n-hexane gradient mixture to give the title compound as a solid (43.1 mg, 0.103 mmol, 77%). Analytically pure material was obtained by recrystallization from ethyl acetate/n-hexane.

mp 222-223° C.

$^1$H NMR (CDCl$_3$) δ 1.00 (t, J=7.1 Hz, 6 H), 1.37 (t, J=4.7 Hz, 1 H), 1.89-2.00 (m, 2 H), 3.08 (q, J=7.1 Hz, 4 H), 3.69-3.82 (m, 2 H), 4.27 (dd, J=10.4, 5.9 Hz, 1 H), 4.60 (dd, J=10.4, 8.2 Hz, 1 H), 5.03-5.15 (m, 1 H), 6.84 (dd, J=8.0, 0.8 Hz, 1 H), 7.01 (t, J=8.0 Hz, 1 H), 7.19 (dd, J=8.0, 0.8 Hz, 1 H), 7.31 (dd, J=8.5, 2.5 Hz, 1H), 7.48 (d, J=2.5 Hz, 1 H), 7.59 (d, J=8.5 Hz, 1 H).

MS Calcd.: 418; MS Found: 419 (M+H).

Example 75

[1-(2,4-Dichlorophenyl)-5-(diethylamino)-2,3-dihydro-1H-imidazo [1,2-a]benzimidazol-2-yl]methyl acetate

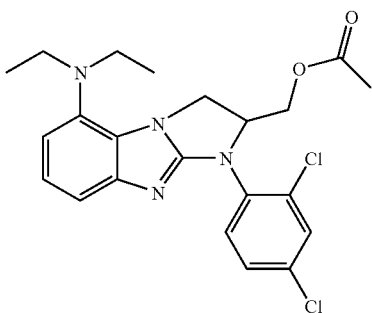 [SMILES: CCN(CC)c1cccc2nc3n(c12)CC(COC(C)=O)N3c1ccc(Cl)cc1Cl]

To a solution of 3-[2-[(2,4-dichlorophenyl)amino]-7-(diethylamino)-1H-benzimidazol-1-yl]-2-hydroxypropyl acetate (Reference Example 89; 32.5 mg, 0.0698 mmol) in pyridine (0.7 mL) was added methanesulfonyl chloride (0.0270 mL, 0.349 mmol) at 0° C. After the resultant mixture was stirred at room temperature for 1.5 hr, the mixture was quenched with aqueous sodium hydrogen carbonate, diluted with ethyl acetate, washed with water and brine, dried over anhydrous sodium sulfate, filtered, and concentrated in vacuo. The residue was diluted with N,N-dimethylformamide, and potassium carbonate (19.3 mg, 0.140 mmol) was added. After being stirred for 0.5 hr at 80° C., the reaction mixture was diluted with ethyl acetate, washed with water and brine, dried over anhydrous sodium sulfate, filtered, and concentrated in vacuo. The residue was purified by flash column chromatography on silica gel eluting with a 10-60% ethyl acetate/n-hexane gradient mixture to give the title compound as a colorless solid (30.5 mg, 0.0684 mmol, 98%).

$^1$H NMR (CDCl$_3$) δ 1.01 (t, J=7.3 Hz, 6H), 1.91 (s, 3H), 3.08 (q, J=7.3 Hz, 4H), 4.17 (dd, J=12.1, 4.7 Hz, 1H), 4.26-4.38 (m, 2H), 4.58 (dd, J=10.3, 8.9 Hz, 1H), 5.13-5.24 (m, 1H), 6.89 (d, J=7.7 Hz, 1H), 7.04 (t, J=7.7 Hz, 1H), 7.22 (d, J=7.7 Hz, 1H), 7.33 (dd, J=8.5, 2.2 Hz, 1H), 7.49 (d, J=2.2 Hz, 1H), 7.64 (d, J=8.5 Hz, 1H).

MS Calcd.: 446; MS Found: 447 (M+H).

Example 76

[1-(2,4-Dichlorophenyl)-5-(diethylamino)-2,3-dihydro-1H-imidazo [1,2-a]benzimidazol-2-yl]methanol

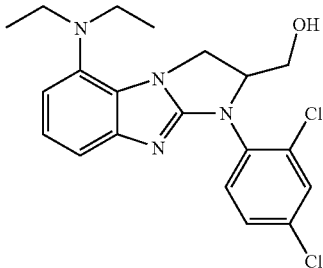 [SMILES: CCN(CC)c1cccc2nc3n(c12)CC(CO)N3c1ccc(Cl)cc1Cl]

To a solution of [1-(2,4-dichlorophenyl)-5-(diethylamino)-2,3-dihydro-1H-imidazo[1,2-a]benzimidazol-2-yl] methyl acetate (30.5 mg, 0.0682 mmol) in methanol (0.7 mL) was added potassium carbonate (9.4 mg, 0.0682 mmol) at room temperature. After 1 hr, the mixture was diluted with ethyl acetate, washed with water and brine, dried over anhydrous sodium sulfate, filtered and concentrated in vacuo. The residue was purified by flash column chromatography on silica gel eluting with a 20-70% ethyl acetate/n-hexane gradient mixture to give the title compound as a colorless solid (24.1 mg, 0.0593 mmol, 87%). Analytically pure material was obtained by recrystallization from ethyl acetate/n-hexane.

mp 187-190° C.

$^1$H NMR (CDCl$_3$) δ 1.03 (t, J=7.1 Hz, 6H), 2.18 (brs, 1H), 3.10 (q, J=7.1 Hz, 4H), 3.64-3.73 (m, 1H), 3.78 (dd, J=11.8, 3.9 Hz, 1H), 4.45-4.64 (m, 2H), 4.86-5.01 (m, 1H), 6.87 (d, J=8.0 Hz, 1H), 7.02 (t, J=8.0 Hz, 1H), 7.19 (d, J=8.0 Hz, 1H), 7.29 (dd, J=8.5, 2.5 Hz, 1H), 7.50 (d, J=2.5 Hz, 1H), 7.56 (d, J=8.5 Hz, 1H).

MS Calcd.: 404; MS Found: 405 (M+H).

Example 77

1-(2,4-Dichlorophenyl)-6-(diethylamino)-1,2,3,4-tetrahydropyrimido[1,2-a]benzimidazol-3-ol

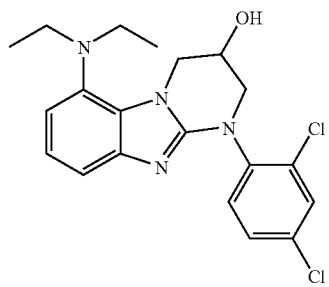 [SMILES: CCN(CC)c1cccc2nc3n(c12)CC(O)CN3c1ccc(Cl)cc1Cl]

To a solution of 3-[2-[(2,4-dichlorophenyl)amino]-7-(diethylamino)-1H-benzimidazol-1-yl]propane-1,2-diol (Reference Example 88; 46.2 mg, 0.109 mmol) in pyridine (1 mL) was added methanesulfonyl chloride (0.0127 mL, 0.164 mmol) at 0° C. After 5 hr, the mixture was warmed up to room temperature. After 1 hr, methanesulfonyl chloride (0.0042 mL, 0.0545 mmol) was added, and the mixture was stirred for additional 1 hr. The reaction mixture was quenched with aqueous sodium hydrogen carbonate and extracted with ethyl acetate. The organic layer was washed with brine, dried over anhydrous sodium sulfate, filtered and concentrated in vacuo. The residue was purified by flash column chromatography on NH-silica gel eluting with a 20-80% ethyl acetate/n-hexane gradient mixture, to give the title compound as a colorless solid (20.6 mg, 0.0512 mmol, 47%). Analytically pure material was obtained by recrystallization from methanol/ethyl acetate.

mp 239-242° C.

$^1$H NMR (CDCl$_3$) δ 1.01 (t, J=7.1 Hz, 6H), 2.86 (brs, 1 H), 2.96-3.15 (m, 4H), 3.55-3.69 (m, 1H), 3.82-3.95 (m, 1H), 4.36-4.54 (m, 2H), 4.84-4.98 (m, 1H), 6.90 (d, J=7.7 Hz, 1H), 7.03 (t, J=7.7 Hz, 1H), 7.22 (d, J=7.7 Hz, 1H), 7.28-7.39 (m, 1H), 7.44-7.57 (m, 2H).

MS Calcd.: 404; MS Found: 405 (M+H).

Example 78

5-[8-Chloro-5-(1-ethylpropyl)-2-methyl-2,3-dihydro-1H-imidazo[1,2-a]benzimidazol-1-yl]-N,N-4-trimethylpyridin-2-amine

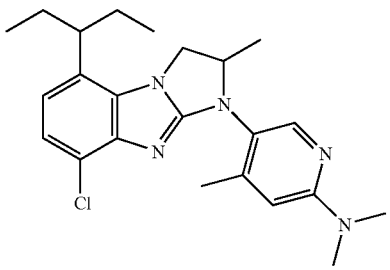 [SMILES: CCC(CC)c1ccc(Cl)c2nc3n(c12)CC(C)N3c1cnc(N(C)C)cc1C]

To a solution of 1-[4-chloro-2-{[6-(dimethylamino)-4-methylpyridin-3-yl]amino}-7-(1-ethylpropyl)-1H-benzimidazol-1-yl]propan-2-ol (Reference Example 94; 23 mg, 0.053 mmol) in pyridine (0.50 mL) was added methanesulfonyl chloride (0.012 mL, 0.160 mmol) dropwise at 0° C. The mixture was warmed to room temperature and stirred for 5 hr. Aqueous sodium bicarbonate was added and the mixture was extracted with ethyl acetate. Organic layer was washed with brine, dried over anhydrous sodium sulfate and concentrated in vacuo. The resulting crude mesylate was dissolved in 1-methyl-2-pyrrolidinone (1.0 mL) and potassium carbonate (22 mg, 0.159 mmol) was added. The mixture was stirred at 50° C. for 4 hr. Water was added and the mixture was extracted with ethyl acetate. Organic layer was washed with water and brine, dried over sodium sulfate and concentrated in vacuo. The residue was purified by flash chromatography on silica gel eluting with a 50-100% ethyl acetate/n-hexane gradient mixture. The filtrate was concentrated in vacuo to give the title compound (15 mg, 0.036 mmol, 69%) as a colorless solid.

mp 204-206° C.

$^1$H NMR (CDCl$_3$) δ 0.77-0.90 (m, 6 H), 1.39 (d, J=5.8 Hz, 3 H), 1.59-1.84 (m, 4 H), 2.25 (s, 3 H), 2.66-2.78 (m, 1 H), 3.09 (s, 6 H), 3.89-3.98 (m, 1 H), 4.55-4.67 (m, 2 H), 6.41 (s, 1 H), 6.74 (d, J=8.2 Hz, 1 H), 7.03 (d, J=8.2 Hz, 1 H), 8.06 (s, 1 H).

MS Calcd.: 411; Found: 412 (M+H).

Example 79

1-(2,4-Dimethoxypyrimidin-5-yl)-N,N-diethyl-1,2,3,4-tetrahydropyrimido[1,2-a]benzimidazol-6-amine

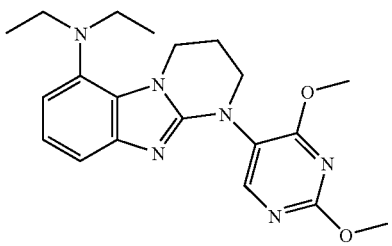 [SMILES: CCN(CC)c1cccc2nc3n(c12)CCCN3c1cnc(OC)nc1OC]

To a solution of 3-{7-(diethylamino)-2-[(2,4-dimethoxypyrimidin-5-yl)amino]-1H-benzimidazol-1-yl}propan-1-ol (Reference Example 97; 90 mg, 0.224 mmol) in pyridine (2.0 mL) was added methanesulfonyl chloride (0.035 mL, 0.449 mmol) at 0° C. The mixture was warmed to room temperature and stirred for 3 hr. Aqueous sodium bicarbonate was added and the mixture was extracted with ethyl acetate. Organic layer was washed with brine, dried over anhydrous sodium sulfate and concentrated in vacuo to give a solid, which was recrystallized from n-hexane/ethyl acetate to give the title compound (50 mg, 0.131 mmol, 58%) as a pale brown solid.

mp 170-171° C.

$^1$H NMR (CDCl$_3$) δ 1.01 (t, J=7.0 Hz, 6 H), 2.21-2.37 (m, 2 H), 2.95-3.15 (m, 4 H), 3.59-3.67 (m, 2 H), 3.99 (s, 3 H), 4.01 (s, 3 H), 4.62 (t, J=6.0 Hz, 2 H), 6.86 (d, J=8.0 Hz, 1 H), 7.01 (t, J=7.8 Hz, 1 H), 7.21 (d, J=7.7 Hz, 1 H), 8.37 (s, 1 H).

MS Calcd.: 382; Found: 383 (M+H).

Example 80

1-(6-Chloro-4-methylpyridazin-3-yl)-N,N-diethyl-1,2,3,4-tetrahydropyrimido[1,2-a]benzimidazol-6-amine

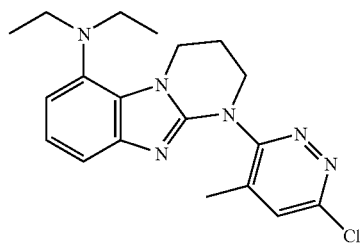 [SMILES: CCN(CC)c1cccc2nc3n(c12)CCCN3c1nnc(Cl)cc1C]

To a solution of 3-[(2,6-diaminophenyl)amino]propan-1-ol (Reference Example 115; 181 mg, 1.00 mmol) in tetrahydrofuran (3.0 mL) was added 6-chloro-3-isothiocyanato-4-methylpyridazine (Reference Example 98; 204 mg, 1.10 mmol) portionwise at room temperature. After stirring for 3 hr, the mixture was concentrated in vacuo. The residue was dissolved in tetrahydrofuran (3.0 mL). N-(3-dimethylaminopropyl)-N'-ethylcarbodiimide hydrochloride (211 mg, 1.10 mmol) and trimethylamine (0.166 mL, 1.20 mmol) was added and the mixture was stirred at 50° C. for 3 hr. Water was added to the mixture, which was extracted with ethyl acetate. Organic layer was washed with brine, dried over sodium sulfate and concentrated in vacuo. The residue was dissolved in ethyl acetate and passed through a pad of silica gel. The filtrate was concentrated in vacuo. Obtained orange amorphous was dissolved in tetrahydrofuran (10 mL). The solution was cooled to 0° C. followed by addition of acetaldehyde (90%, 0.620 mL, 10.0 mmol), acetic acid (0.229 mL, 4.00 mmol) and sodium triacetoxyborohydride (1.34 g, 10.0 mmol). The mixture was warmed to room temperature and, stirred for 16 hr. Aqueous sodium bicarbonate was added and the mixture was extracted with ethyl acetate. Organic layer was washed with brine, dried over anhydrous sodium sulfate and concentrated in vacuo. The residue was passed through a pad of silica gel eluting with a methanol/ethyl acetate mixture. The filtrate was concentrated in vacuo to give a yellow amorphous which was dissolved in pyridine (1.0 mL). The mixture was cooled to 0° C. followed by addition of methanesulfonyl chloride (0.026 mL, 0.340 mmol). The mixture was warmed to room temperature and stirred for 5 hr. Aqueous sodium bicarbonate was added and the mixture was extracted with ethyl acetate. Organic layer was washed with brine, dried over sodium sulfate and concentrated in vacuo. The residue was dissolved in 1-methyl-2-pyrrolidinone (1.0 mL) followed by addition of potassium carbonate (70 mg, 0.510 mmol). The mixture was warmed to 50° C. and stirred for 5 hr. Water was added to the mixture, which was extracted with ethyl acetate. Organic layer was washed with water and brine, dried over anhydrous sodium sulfate and concentrated in vacuo. The residue was purified by flash chromatography on silica gel eluting with a 10-50% ethyl acetate/n-hexane gradient mixture. The filtrate was concentrated in vacuo to give the title compound (16 mg, 0.043 mmol, 4.3%) as a yellow solid.

mp 193-195° C.

$^1$H NMR (CDCl$_3$) δ 1.03 (t, J=7.1 Hz, 6 H), 2.37 (d, J=0.8 Hz, 3 H), 2.38-2.46 (m, 2 H), 2.99-3.15 (m, 4 H), 4.06-4.15 (m, 2 H), 4.56-4.67 (m, 2 H), 6.93 (dd, J=7.7, 1.1 Hz, 1 H), 7.05 (t, J=7.8 Hz, 1 H), 7.21 (dd, J=7.7, 1.1 Hz, 1 H), 7.39 (q, J=0.8 Hz, 1 H).

MS Calcd.: 370; Found: 371 (M+H).

Example 81

Methyl 1-(2,4-dichlorophenyl)-1,2,3,4-tetrahydropyrimido[1,2-a]benzimidazole-6-carboxylate

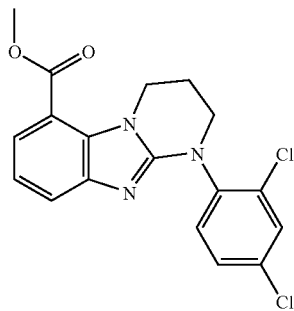 [SMILES: COC(=O)c1cccc2nc3n(c12)CCCN3c1ccc(Cl)cc1Cl]

To a solution of methyl 2-[(2,4-dichlorophenyl)amino]-1-(3-hydroxypropyl)-1H-benzimidazole-7-carboxylate (Reference Example 103; 72.0 g, 0.183 mol) in tetrahydrofuran (800 mL) and triethylamine (127 mL) was added methanesulfonyl chloride (42.5 mL, 0.731 mol) at 0° C. The mixture was stirred at 0° C. for 2 hr, and diluted with aqueous sodium hydrogen carbonate and extracted with ethyl acetate. The combined organic layer was washed with brine, dried over anhydrous magnesium sulfate, filtered, and concentrated in vacuo. The mixture of the residue, potassium carbonate (75.9 g, 0.549 mol) in N,N-dimethylformamide (800 mL) was stirred at 70° C. for 3 h. The mixture was diluted with water, and the precipitate was collected by filtration, washed with water, washed with diisopropyl ether to give the solid, which was recrystallized from ethanol/ethyl acetate to give the title compound as a colorless crystal (50.2 g, 0.133 mol, 73% in 2 steps).

$^1$H NMR (CDCl$_3$) δ 2.30-2.34 (m, 2H), 3.69-3.73 (m, 2H), 3.95 (s, 3H), 4.43 (t, J=6.3 Hz, 2H), 7.08 (t, J=8.1 Hz, 1H), 7.30-7.34 (m, 1H), 7.44 (d, J=8.7 Hz, 1H), 7.51-7.58 (m, 3H

MS Calcd.: 375; MS Found: 376 (M+H).

Example 82

1-(2,4-Dichlorophenyl)-1,2,3,4-tetrahydropyrimido[1,2-a]benzimidazole-6-carbaldehyde

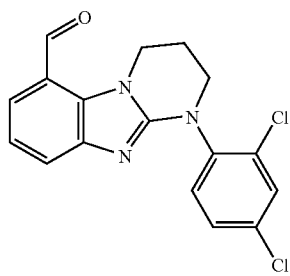 [SMILES: O=Cc1cccc2nc3n(c12)CCCN3c1ccc(Cl)cc1Cl]

To a suspension of methyl 1-(2,4-dichlorophenyl)-1,2,3,4-tetrahydropyrimido[1,2-a]benzimidazole-6-carboxylate (15.0 g, 39.9 mmol) was added lithium aluminum hydride (3.03 g, 79.8 mmol) at 0° C., and the mixture was stirred at 0° C. for 30 min. The mixture was poured into crashed ice, neutralized with aqueous saturated ammonium chloride, and extracted with ethyl acetate. The combined organic layer was washed with brine, dried over anhydrous magnesium sulfate, filtered and concentrated in vacuo to give the crude product of [1-(2,4-dichlorophenyl)-1,2,3,4-tetrahydropyrimido[1,2-a]benzimidazol-6-yl]methanol (13.7 g). To a solution of the above crude product in triethylamine (43.6 mL), dimethylsulfoxide (200 mL), and dichloromethane (40 mL) was added sulfur trioxide-pyridine complex (43.8 g, 275 mmol), and the mixture was stirred at room temperature for 12 hr. The mixture was diluted with water, and extracted with ethyl acetate. The combined organic layer was washed with brine, dried over anhydrous magnesium sulfate, filtered and concentrated in vacuo. The residue was purified by flash column chromatography on silica gel eluting with a 15-60% ethyl acetate/n-hexane gradient mixture. The filtrate was concentrated in vacuo to give the solid, which was washed with diisopropyl ether to give the title compound as a pale yellow powder (11.6 g, 33.5 mmol, 84% in 2 steps).

$^1$H NMR (CDCl$_3$) δ 2.35-2.39 (m, 2H), 3.68-3.75 (m, 2H), 4.72 (t, J=6.3 Hz, 2H), 7.20 (t, J=7.8 Hz, 1H), 7.33 (dd, J=2.4 Hz, 8.7 Hz, 1H), 7.42-7.48 (m, 2H), 7.52 (d, J=2.4 Hz, 1H), 7.64 (dd, J=1.2 Hz, 7.8 Hz, 1H), 10.22 (s, 1H).

MS Calcd.: 345; MS Found: 346 (M+H).

Example 83

1-(2,4-Dichlorophenyl)-1,2,3,4-tetrahydropyrimido[1,2-a]benzimidazole-6-carboxamide

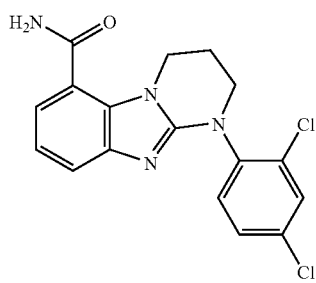 [SMILES: NC(=O)c1cccc2nc3n(c12)CCCN3c1ccc(Cl)cc1Cl]

A mixture of methyl 1-(2,4-dichlorophenyl)-1,2,3,4-tetrahydropyrimido[1,2-a]benzimidazole-6-carboxylate (Example 81; 350 mg, 0.930 mmol), formamide (3.0 mL), and sodium methoxide (28% solution in methanol, 1.0 mL), and N,N-dimethylformamide (3.0 mL) was stirred at 120° C. for 20 hr. The mixture was diluted with aqueous saturated ammonium chloride, and the precipitate was collected by filtration, washed with water, washed with diisopropyl ether to give the title compound as a colorless powder (280 mg, 0.775 mmol, 83%).

mp 198-200° C.

$^1$H NMR (DMSO-$d_6$) δ 2.26 (t, J=5.1 Hz, 2H), 3.68 (t, J=5.1 Hz, 2H), 4.19 (t, J=5.1 Hz, 2H), 6.97 (t, J=7.5 Hz, 1H), 7.04 (dd, J=1.5 Hz, 7.5 Hz, 1H), 7.20 (dd, J=1.5 Hz, 7.5 Hz, 1H), 7.48 (s, 1H), 7.49-7.62 (m, 2H), 7.78 (d, J=2.4 Hz, 1H), 7.96 (s, 1H).

MS Calcd.: 360; MS Found: 361 (M+H).

Example 84

1-(2,4-Dichlorophenyl)-1,2,3,4-tetrahydropyrimido[1,2-a]benzimidazole-6-carbonitrile

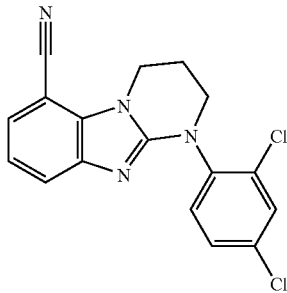 [SMILES: N#Cc1cccc2nc3n(c12)CCCN3c1ccc(Cl)cc1Cl]

To a suspension of 1-(2,4-dichlorophenyl)-1,2,3,4-tetrahydropyrimido[1,2-a]benzimidazole-6-carboxamide (280 mg, 0.775 mmol) in N,N-dimethylformamide (3.0 mL) was added thionyl chloride (0.17 mL, 2.33 mmol), and the mixture was stirred at 50° C. for 40 min. The mixture was poured into saturated aqueous sodium hydrogen carbonate, and extracted with ethyl acetate. The combined organic layer was washed with brine, dried over anhydrous magnesium sulfate, filtered and concentrated in vacuo to give the solid, which was recrystallized from ethyl acetate/diisopropyl ether to give the title compound as a colorless crystal (261 mg, 0.760 mmol, 98%).

mp 170-171° C.

$^1$H NMR (CDCl$_3$) δ 2.39-2.51 (m, 2H), 3.69-3.81 (m, 2H), 4.53-4.65 (m, 2H), 7.10 (t, J=7.8 Hz, 1H), 7.25-7.36 (m, 2H), 7.43 (d, J=8.7 Hz, 1H), 7.53 (d, J=1.8 Hz, 1H), 7.57 (dd, J=1.8 Hz, 8.7 Hz, 1H).

MS Calcd.: 342; MS Found: 343 (M+H).

Example 85

1-(2,4-Dichlorophenyl)-1,2,3,4-tetrahydropyrimido[1,2-a]benzimidazole-6-carboxylic acid

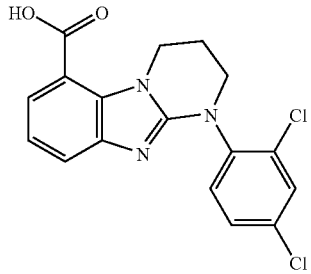

A mixture of methyl 1-(2,4-dichlorophenyl)-1,2,3,4-tetrahydropyrimido[1,2-a]benzimidazole-6-carboxylate (Example 81; 10.0 g, 26.6 mmol), methanol (100 mL), 8.0 M aqueous sodium hydroxide (150 mL) was stirred at 90° C. for 2 hr. The mixture was acidified with 6.0 M hydrochloric acid, and the precipitate was collected by filtration, washed with water, washed with ethyl acetate to give the title compound as a colorless powder (8.47 g, 23.4 mmol, 88%).

$^1$H NMR (DMSO-$d_6$) δ 2.20-2.45 (m, 2H), 3.74-3.90 (m, 2H), 4.22-4.49 (m, 2H), 7.35 (t, J=7.5 Hz, 1H), 7.49-7.53 (m, 1H), 7.67-7.74 (m, 2H), 7.85 (d, J=8.1 Hz, 1H), 8.00 (d, J=2.4 Hz, 1H), 13.80 (s, 1H).

MS Calcd.: 361; MS Found: 362 (M+H).

Example 86

1-(2,4-Dichlorophenyl)-N,N-dimethyl-1,2,3,4-tetrahydropyrimido[1,2-a]benzimidazole-6-carboxamide

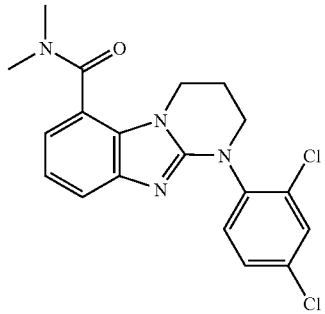 [SMILES: CN(C)C(=O)c1cccc2nc3n(c12)CCCN3c1ccc(Cl)cc1Cl]

To a suspension of 1-(2,4-dichlorophenyl)-1,2,3,4-tetrahydropyrimido[1,2-a]benzimidazole-6-carboxylic acid (430 mg, 1.18 mmol) in N,N-dimethylformamide (8.0 mL) were added 1-hydroxy-1H-benzotriazole (235 mg, 1.53 mmol), 1-ethyl-3-(3-dimethylaminopropyl)carbodiimide hydrochloride (249 mg, 1.30 mmol), and methylamine (2.0 M solution in tetrahydrofuran, 1.20 mL, 2.40 mmol). The mixture was stirred at room temperature for 15 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 40-85% ethyl acetate/n-hexane gradient mixture. The filtrate was concentrated in vacuo to give the solid, which was recrystallized from ethanol/ethyl acetate to give the title compound as a colorless crystal (305 mg, 0.783 mmol, 66%).

mp 212-213° C.

$^1$H NMR (CDCl$_3$) δ 2.34 (t, J=5.1 Hz, 2H), 3.02 (s, 3H), 3.20 (s, 3H), 3.62-3.74 (m, 2H), 3.95-4.20 (m, 2H), 6.88 (dd, J=0.9 Hz, 7.5 Hz, 1H), 7.06 (t, J=7.5 Hz, 1H), 7.32 (dd, J=2.1 Hz, 8.4 Hz, 1H), 7.40-7.46 (m, 2H), 7.51 (d, J=2.1 Hz, 1H).

MS Calcd.: 388; MS Found: 389 (M+H).

Example 87

1-[1-(2,4-Dichlorophenyl)-1,2,3,4-tetrahydropyrimido[1,2-a]benzimidazol-6-yl]-N,N-dimethyl-methanamine

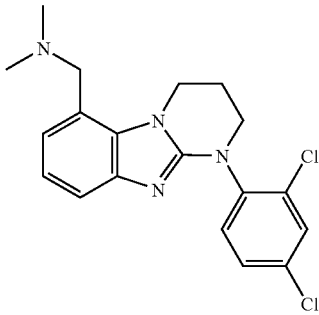 [SMILES: CN(C)Cc1cccc2nc3n(c12)CCCN3c1ccc(Cl)cc1Cl]

To a solution of 1-(2,4-dichlorophenyl)-N,N-dimethyl-1,2,3,4-tetrahydropyrimido[1,2-a]benzimidazole-6-carboxamide (200 mg, 0.513 mmol) was added boron-tetrahydrofuran complex (1.0 M solution in tetrahydrofuran, 2.6 mL, 2.6 mmol), and the mixture was stirred at 70° C. for 13 hr. To the mixture was added aqueous saturated ammonium chloride, and the mixture was stirred at 70° C. for 20 min. The mixture was extracted with ethyl acetate. The combined organic layer was washed with brine, dried over anhydrous magnesium sulfate, filtered and concentrated in vacuo. The residue was purified by flash column chromatography on silica gel eluting with a 50-100% ethyl acetate/n-hexane gradient mixture. The filtrate was concentrated in vacuo to give the solid, which was washed with diisopropyl ether to give the title compound as a colorless powder (54.8 mg, 0.146 mmol, 28%).

mp 158-159° C.

$^1$H NMR (CDCl$_3$) δ 2.23 (s, 6H), 2.32-2.41 (m, 2H), 3.58 (s, 2H), 3.63-3.75 (m, 2H), 4.71 (t, J=6.0 Hz, 2H), 6.77 (d, J=7.5 Hz, 1H), 6.96 (t, J=7.5 Hz, 1H), 7.28-7.44 (m, 2H), 7.46-7.50 (m, 2H).

MS Calcd.: 374; MS Found: 375 (M+H).

Example 88

1-(2,4-Dichlorophenyl)-N,N-diethyl-1,2,3,4-tetrahydropyrimido[1,2-a]benzimidazole-6-carboxamide

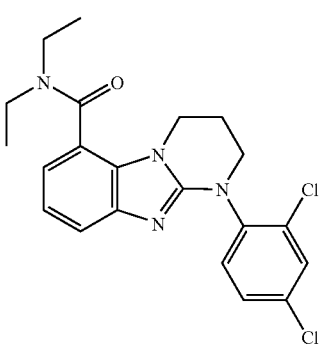 [SMILES: CCN(CC)C(=O)c1cccc2nc3n(c12)CCCN3c1ccc(Cl)cc1Cl]

A mixture of 1-(2,4-dichlorophenyl)-1,2,3,4-tetrahydropyrimido[1,2-a]benzimidazole-6-carboxylic acid (350 mg, 0.966 mmol), 1-hydroxy-1H-benzotriazole (193 mg, 1.26 mmol), 1-ethyl-3-(3-dimethylaminopropyl)carbodiimide hydrochloride (203 mg, 1.06 mmol), and ethylamine (141 mg, 1.93 mmol), and N,N-dimethylformamide (7.0 mL) was stirred at room temperature for 3 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 20-60% ethyl acetate/n-hexane gradient mixture. The filtrate was concentrated in vacuo to give the solid, which was recrystallized from ethanol/ethyl acetate to give the title compound as a colorless crystal (276 mg, 0.661 mmol, 68%).

mp 183-184° C.

$^1$H NMR (CDCl$_3$) δ 1.12 (t, J=6.9 Hz, 3H), 1.31 (t, J=7.2 Hz, 3H), 2.27-2.39 (m, 2H), 3.33 (q, J=7.2 Hz, 2H), 3.50-3.80 (m, 2H), 3.62-3.76 (m, 2H), 3.80-4.00 (m, 1H), 4.25-4.50 (m, 1H), 6.87 (dd, J=0.9 Hz, 7.5 Hz, 1H), 7.05 (t, J=7.5 Hz, 1H), 7.31 (dd, J=2.4 Hz, 8.4 Hz, 1H), 7.39-7.46 (m, 2H), 7.51 (d, J=2.4 Hz, 1H).

MS Calcd.: 416; MS Found: 417 (M+H).

Example 89

N-{[1-(2,4-Dichlorophenyl)-1,2,3,4-tetrahydropyrimido [1,2, a]benzimidazol-6-yl]methyl}-N-ethyl-ethanamine

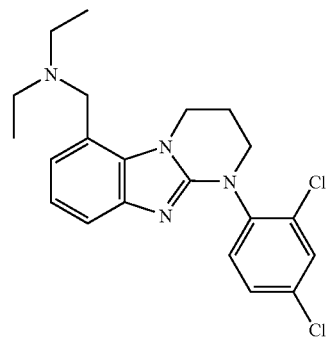 [SMILES: CCN(CC)Cc1cccc2nc3n(c12)CCCN3c1ccc(Cl)cc1Cl]

To a solution of 1-(2,4-dichlorophenyl)-N,N-diethyl-1,2,3,4-tetrahydropyrimido[1,2-a]benzimidazole-6-carboxamide (180 mg, 0.431 mmol) was added boron-tetrahydrofuran complex (1.0 M solution in tetrahydrofuran, 2.2 mL, 2.2 mmol), and the mixture was stirred at 80° C. for 3 hr. The mixture was diluted with aqueous saturated ammonium chloride, and extracted with ethyl acetate. The combined organic layer was washed with brine, dried over anhydrous magnesium sulfate, filtered and concentrated in vacuo. The residue was purified by flash column chromatography on silica gel eluting with a 10-50% ethyl acetate/n-hexane gradient mixture. The filtrate was concentrated in vacuo to give the solid, which was recrystallized from ethyl acetate/diisopropyl ether to give the title compound as a colorless crystal (72.2 mg, 0.179 mmol, 42%).

mp 112-114° C.

$^1$H NMR (CDCl$_3$) δ 1.01 (t, J=7.2 Hz, 6H), 2.30-2.40 (m, 2H), 2.55 (q, J=7.2 Hz, 4H), 3.66-3.77 (m, 2H), 3.78 (s, 2H), 4.79 (t, J=6.0 Hz, 2H), 6.82 (dd, J=0.9 Hz, 7.5 Hz, 1H), 6.96 (t, J=7.5 Hz, 1H), 7.28-7.36 (m, 2H), 7.45-7.50 (m, 2H).

MS Calcd.: 402; MS Found: 403 (M+H).

Example 90

1-{[1-(2,4-Dichlorophenyl)-1,2,3,4-tetrahydropyrimido[1,2-a]benzimidazol-6-yl]carbonyl}azetidin-3-ol

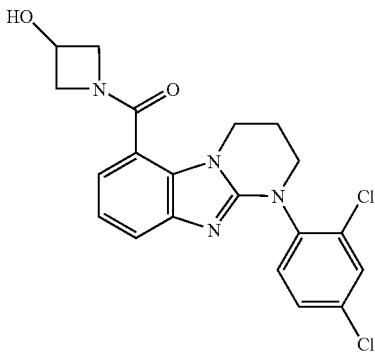 [SMILES: O=C(c1cccc2nc3n(c12)CCCN3c1ccc(Cl)cc1Cl)N1CC(O)C1]

To a suspension of 1-(2,4-dichlorophenyl)-1,2,3,4-tetrahydropyrimido[1,2-a]benzimidazole-6-carboxylic acid (430 mg, 1.18 mmol) in N,N-dimethylformamide (8.0 mL) were added 1-hydroxy-1H-benzotriazole (235 mg, 1.53 mmol), 1-ethyl-3-(3-dimethylaminopropyl)carbodiimide hydrochloride (249 mg, 1.30 mmol), 3-hydroxyazetidine hydrochloride (258 mg, 2.36 mmol), and triethylamine (0.50 mL). The mixture was stirred at room temperature for 15 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 75-100% ethyl acetate/n-hexane gradient mixture. The filtrate was concentrated in vacuo to give the solid, which was washed with ethyl acetate to give the title compound as a colorless powder (235 mg, 0.563 mmol, 48%).

mp 257-258° C.

$^1$H NMR (CDCl$_3$) δ 2.26-2.38 (m, 2H), 3.05-3.18 (m, 1H), 3.63-3.75 (m, 2H), 3.91-4.00 (m, 1H), 4.03-4.10 (m, 1H), 4.21-4.32 (m, 3H), 4.39-4.48 (m, 1H), 4.61-4.70 (m, 1H), 6.94 (dd, J=0.9 Hz, 7.5 Hz, 1H), 7.03 (t, J=7.5 Hz, 1H), 7.31 (dd, J=2.4 Hz, 8.7 Hz, 1H), 7.39-7.44 (m, 2H), 7.50 (d, J=2.4 Hz, 1H).

MS Calcd.: 416; MS Found: 417 (M+H).

Example 91

1-{[1-(2,4-Dichlorophenyl)-1,2,3,4-tetrahydropyrimido[1,2-a]benzimidazol-6-yl]methyl}azetidin-3-ol

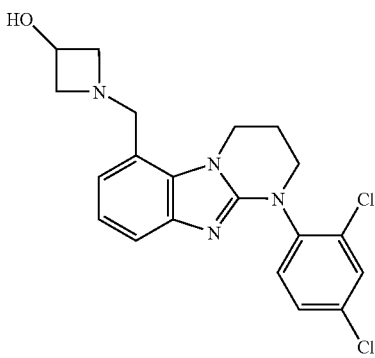 [SMILES: OC1CN(Cc2cccc3nc4n(c23)CCCN4c2ccc(Cl)cc2Cl)C1]

To a suspension of 1-{[1-(2,4-dichlorophenyl)-1,2,3,4-tetrahydropyrimido[1,2-a]benzimidazol-6-yl]carbonyl}azetidin-3-ol (150 mg, 0.359 mmol) was added boron-tetrahydrofuran complex (1.0 M solution in tetrahydrofuran, 1.8 mL, 1.8 mmol), and the mixture was stirred at 70° C. for 13 hr. To the mixture was added aqueous saturated ammonium chloride, and the mixture was stirred at 70° C. for 20 min. The mixture was extracted with ethyl acetate. The combined organic layer was washed with brine, dried over anhydrous magnesium sulfate, filtered and concentrated in vacuo to give the solid, which was washed with ethanol to give the title compound as a colorless powder (91.5 mg, 0.227 mmol, 63%).

mp 240-241° C.

$^1$H NMR (DMSO-d$_6$) δ 2.26-2.38 (m, 2H), 3.36-3.48 (m, 2H), 3.56-3.69 (m, 4H), 4.21 (s, 2H), 4.25-4.37 (m, 2H), 4.46-4.56 (m, 1H), 5.50-5.53 (m, 1H), 6.95 (dd, J=1.2 Hz, 7.5 Hz, 1H), 7.04 (t, J=7.5 Hz, 1H), 7.22 (dd, J=1.2 Hz, 7.5 Hz, 1H), 7.52 (dd, J=2.4 Hz, 8.4 Hz, 1H), 7.62 (d, J=8.4 Hz, 1H), 7.78 (d, J=2.4 Hz, 1H).

MS Calcd.: 402; MS Found: 403 (M+H).

Example 92

1-[1-(2,4-Dichlorophenyl)-1,2,3,4-tetrahydropyrimido[1,2-a]benzimidazol-6-yl]propan-1-ol

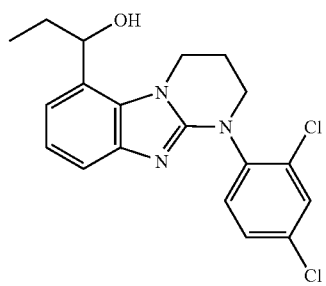 [SMILES: CCC(O)c1cccc2nc3n(c12)CCCN3c1ccc(Cl)cc1Cl]

To a solution of 1-(2,4-dichlorophenyl)-1,2,3,4-tetrahydropyrimido[1,2-a]benzimidazole-6-carbaldehyde (3.00 g, 8.67 mmol) in tetrahydrofuran (25 mL) was added dropwise ethylmagnesium bromide (3.0 M solution in diethyl ether, 3.4 mL, 10.4 mmol) at 0° C., and the mixture was stirred at 0° C. for 1 hr. The reaction was quenched by methanol, and the mixture was neutralized with aqueous saturated ammonium chloride, and extracted with ethyl acetate. The combined organic layer was washed with brine, dried over anhydrous magnesium sulfate, filtered and concentrated in vacuo. The residue was purified by flash column chromatography on silica gel eluting with a 40-100% ethyl acetate/n-hexane gradient mixture. The filtrate was concentrated in vacuo to give the solid, which was recrystallized from ethanol/ethyl acetate to give the title compound as a colorless crystal (2.95 g, 7.84 mmol, 90%).

mp 186-188° C.

$^1$H NMR (CDCl$_3$) δ 1.06 (t, J=7.5 Hz, 3H), 1.65 (s, 1H), 1.94-2.05 (m, 2H), 2.31-2.44 (m, 2H), 3.63-3.75 (m, 2H), 4.41-4.55 (m, 1H), 4.57-4.69 (m, 1H), 5.00-5.10 (m, 1H), 7.03-7.09 (m, 2H), 7.28-7.42 (m, 2H), 7.43 (d, J=8.7 Hz, 1H), 7.50 (d, J=2.4 Hz, 1H).

MS Calcd.: 375; MS Found: 376 (M+H).

Example 93

1-(2,4-Dichlorophenyl)-6-(1-methoxypropyl)-1,2,3,4-tetrahydropyrimido[1,2-a]benzimidazole

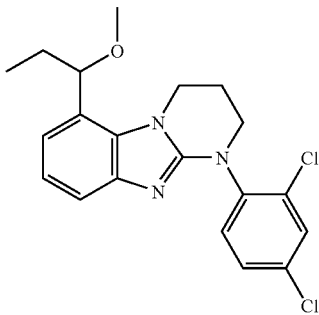 [SMILES: CCC(OC)c1cccc2nc3n(c12)CCCN3c1ccc(Cl)cc1Cl]

To a solution of 1-[1-(2,4-dichlorophenyl)-1,2,3,4-tetrahydropyrimido[1,2-a]benzimidazol-6-yl]propan-1-ol (350 mg, 0.930 mmol) in N,N-dimethylformamide (3.0 mL) was added sodium hydride (60% in oil, 44.8 mg, 1.12 mmol), and the mixture was stirred at room temperature for 5 min. To the mixture was added methyl iodide (657 mg, 4.65 mmol), and the mixture was stirred at room temperature for 1 hr. The mixture was diluted with water, and extracted with ethyl acetate. The combined organic layer was washed with brine, dried over anhydrous magnesium sulfate, filtered and concentrated in vacuo. The residue was purified by flash column chromatography on silica gel eluting with a 10-50% ethyl acetate/n-hexane gradient mixture. The filtrate was concentrated in vacuo to give the solid, which was recrystallized from ethyl acetate/diisopropyl ether to give the title compound as a colorless crystal (76.5 mg, 0.196 mmol, 21%).

mp 151-153° C.

$^1$H NMR (CDCl$_3$) δ 0.95-1.02 (m, 3H), 1.79-2.03 (m, 2H), 2.31-2.43 (m, 2H), 3.25 (s, 3H), 3.63-3.75 (m, 2H), 4.34-4.43 (m, 1H), 4.54 (t, J=7.5 Hz, 1H), 4.55-4.65 (m, 1H), 6.93-7.00 (m, 1H), 7.04 (d, J=7.5 Hz, 1H), 7.28-7.45 (m, 2H), 7.45-7.51 (m, 2H).

MS Calcd.: 389; MS Found: 390 (M+H).

Example 94

1-(2,4-Dichlorophenyl)-6-[1-(2-methoxyethoxy)propyl]-1,2,3,4-tetrahydropyrimido[1,2-a]benzimidazole

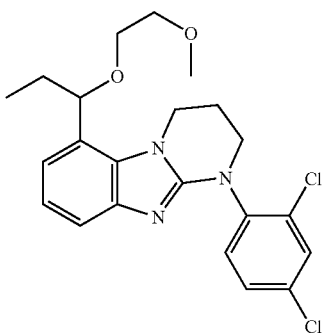 [SMILES: CCC(OCCOC)c1cccc2nc3n(c12)CCCN3c1ccc(Cl)cc1Cl]

To a solution of 1-[1-(2,4-dichlorophenyl)-1,2,3,4-tetrahydropyrimido[1,2-a]benzimidazol-6-yl]propan-1-ol (300 mg, 0.797 mmol) in N,N-dimethylformamide (3.0 mL) was added sodium hydride (60% in oil, 35.0 mg, 0.877 mmol), and the mixture was stirred at room temperature for 10 min. To the mixture was added 2-bromoethyl methyl ether (166 mg, 1.19 mmol), and the mixture was stirred at room temperature for 3 hr. The mixture was diluted with water, and extracted with ethyl acetate. The combined organic layer was washed with brine, dried over anhydrous magnesium sulfate, filtered and concentrated in vacuo. The residue was purified by flash column chromatography on silica gel eluting with a 10-50% ethyl acetate/n-hexane gradient mixture. The filtrate was concentrated in vacuo to give the title compound as a colorless amorphous (218 mg, 0.502 mmol, 63%).

$^1$H NMR (CDCl$_3$) δ 0.95-1.02 (m, 3H), 1.80-1.92 (m, 1H), 2.00-2.11 (m, 1H), 2.29-2.41 (m, 2H), 3.31 (s, 3H), 3.32-3.56 (m, 4H), 3.62-3.76 (m, 2H), 4.32-4.42 (m, 1H), 4.67 (t, J=6.9 Hz, 1H), 4.72-4.79 (m, 1H), 6.95 (dd, J=1.2 Hz, 7.8 Hz, 1H), 7.02 (d, J=7.8 Hz, 1H), 7.29-7.37 (m, 2H), 7.44-7.51 (m, 2H).

MS Calcd.: 433; MS Found: 434 (M+H).

Example 95

Cyclopropyl[1-(2,4-dichlorophenyl)-1,2,3,4-tetrahydropyrimido[1,2-a]benzimidazol-6-yl]methanol

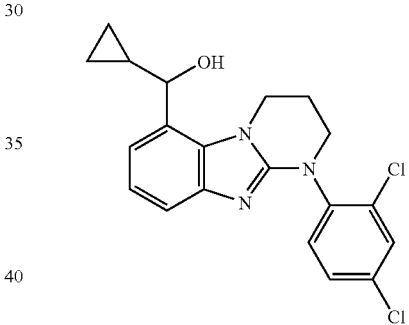

To a solution of 1-(2,4-dichlorophenyl)-1,2,3,4-tetrahydropyrimido[1,2-a]benzimidazole-6-carbaldehyde (3.00 g, 8.67 mmol) in tetrahydrofuran (25 mL) was added dropwise cyclopropylmagnesium bromide (1.0 M solution in tetrahydrofuran, 11.6 mL, 11.6 mmol) at 0° C., and the mixture was stirred at 0° C. for 1 h. The reaction was quenched by methanol, and the mixture was neutralized with aqueous saturated ammonium chloride, and extracted with ethyl acetate. The combined organic layer was washed with brine, dried over anhydrous magnesium sulfate, filtered and concentrated in vacuo. The residue was purified by flash column chromatography on silica gel eluting with a 20-60% ethyl acetate/n-hexane gradient mixture. The filtrate was concentrated in vacuo to give the solid, which was recrystallized from ethanol to give the title compound as a colorless crystal (1.71 g, 4.40 mmol, 76%).

mp 208-209° C.

$^1$H NMR (CDCl$_3$) δ 0.31-0.39 (m, 1H), 0.47-0.55, (m, 1H), 0.62-0.70 (m, 1H), 0.70-0.78 (m, 1H), 1.46-1.55 (m, 1H), 2.07-2.10 (m, 1H), 2.31-2.40 (m, 2H), 3.62-3.74 (m, 2H), 4.44-4.51 (m, 1H), 4.53-4.61 (m, 1H), 4.70-4.80 (m, 1H), 7.05 (t, J=7.5 Hz, 1H), 7.19-7.45 (m, 4H), 7.50 (d, J=2.4 Hz, 1H).

MS Calcd.: 387; MS Found: 388 (M+H).

Example 96

10-Chloro-1-(2,4-dichlorophenyl)-7-nitro-2,3,4,5-tetrahydro-1H-[1,3]diazepino[1,2-a]benzimidazole

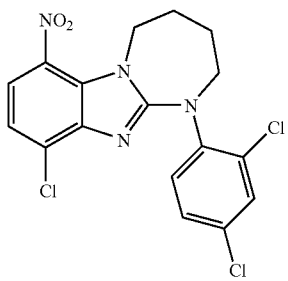 [SMILES: O=[N+]([O-])c1ccc(Cl)c2nc3n(c12)CCCCN3c1ccc(Cl)cc1Cl]

A mixture of 10-chloro-7-nitro-2,3,4,5-tetrahydro-1H-[1,3]diazepino[1,2-a]benzimidazole (Reference Example 106; 1.74 g, 6.50 mmol), 2,4-dichloro-1-iodobenzene (8.87 g, 32.5 mmol), copper(I) iodide (1.24 g, 6.50 mmol), 2,2'-bipyridyl (2.02 g, 13.0 mmol) and cesium carbonate (4.24 g, 13.0 mmol) in N,N-dimethylformamide (100 mL) was stirred at 150° C. for 12 hr. The mixture was diluted with ethyl acetate, washed with water, dried over anhydrous sodium sulfate and concentrated in vacuo. The residue was purified by flash chromatography on silica gel eluting with a 10-25% ethyl acetate/n-hexane gradient mixture. The filtrate was concentrated in vacuo to give the title compound (1.20 g, 2.91 mmol, 45%) as a light yellow amorphous.

$^1$H-NMR (CDCl$_3$, 300 MHz) δ: 2.15-2.36 (4H, m), 3.70-3.86 (2H, m), 4.22-4.40 (2H, m), 7.14 (1H, d, J=9.0 Hz), 7.34 (1H, dd, J=2.4, 8.4 Hz), 7.47 (1H, d, J=8.4 Hz), 7.53 (1H, d, J=2.4 Hz), 7.61 (1H, d, J=9.0 Hz).

MS Calcd.: 410; Found: 411 (M+H)

Example 97

10-Chloro-1-(2,4-dichlorophenyl)-2,3,4,5-tetrahydro-1H-[1,3]diazepino[1,2-a]benzimidazol-7-amine

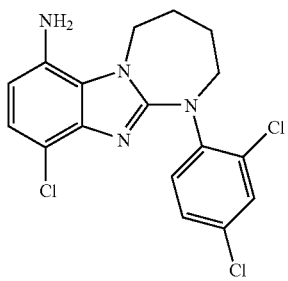

A mixture of 10-chloro-1-(2,4-dichlorophenyl)-7-nitro-2,3,4,5-tetrahydro-1H-[1,3]diazepino[1,2-a]benzimidazole (53 mg, 0.129 mmol) and 10% palladium on carbon (6 mg) in acetic acid (5.0 mL) was stirred under hydrogen atmosphere at room temperature for 6 hr. The catalyst was removed by filtration and the filtrate was concentrated in vacuo. The residue was purified by flash chromatography on silica gel eluting with a 50-100% ethyl acetate/n-hexane gradient mixture. The filtrate was concentrated in vacuo to give the title compound (32 mg, 0.084 mmol, 65%) as an oil.

$^1$H-NMR (CDCl$_3$, 300 MHz) δ: 2.00-2.20 (4H, m), 3.42-3.53 (2H, m), 3.60 (2H, brs), 4.72 (2H, t, J=5.1 Hz), 6.22 (1H, d, J=9.0 Hz), 6.84 (1H, d, J=9.0 Hz), 7.29 (1H, dd, J=2.4, 8.4 Hz), 7.47 (1H, d, J=2.4 Hz), 7.52 (1H, d, J=8.4 Hz).

MS Calcd.: 380; Found: 381 (M+H)

Example 98

10-Chloro-1-(2,4-dichlorophenyl)-diethyl-2,3,4,5-tetrahydro-1H-[1,3]diazepino[1,2-a]benzimidazol-7-amine

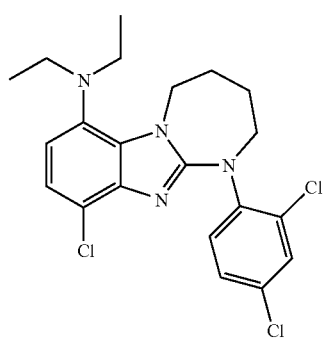 [SMILES: CCN(CC)c1ccc(Cl)c2nc3n(c12)CCCCN3c1ccc(Cl)cc1Cl]

To a solution of 10-chloro-1-(2,4-dichlorophenyl)-2,3,4,5-tetrahydro-1H-[1,3]diazepino[1,2-a]benzimidazol-7-amine (29 mg, 0.075 mmol) in methanol (5.0 mL) and acetic acid (1.0 mL) was added acetaldehyde (0.05 mL, 0.84 mmol) at 0° C. The resultant mixture was stirred at 0° C. for 30 min. To the reaction mixture was added sodium triacetoxyborohydride (173 mg, 0.84 mmol) at 0° C. After stirring at room temperature for 5 h, the mixture was con concentrated in vacuo, diluted with water, and extracted with ethyl acetate. The organic layer was dried over anhydrous magnesium sulfate, filtered and concentrated in vacuo. The residue was purified by column chromatography on a silica gel eluting with a 10-50% ethyl acetate/n-hexane gradient mixture. The filtrate was concentrated in vacuo to give the title compound (8 mg, 0.018 mmol, 24%) as a white amorphous.

$^1$H NMR (CDCl$_3$) δ 1.00 (6H, t, J=7.2 Hz), 1.98-2.08 (m, 4H), 3.02 (4H, q, J=7.2 Hz), 3.77 (t, J=5.1 Hz, 2H), 4.72 (t, J=5.1 Hz, 2H), 6.78 (1H, d, J=8.4 Hz), 7.01 (1H, d, J=8.4 Hz), 7.31 (1H, dd, J=2.4, 8.7 Hz), 7.49 (1H, d, J=2.4 Hz), 7.51 (1H, d, J=8.7 Hz).

MS Calcd.: 436; MS Found: 437 (M+H).

Example 99

9-Chloro-1-(2,4-dichlorophenyl)-6-nitro-1,2,3,4-tetrahydropyrimido[1,2-a]benzimidazole

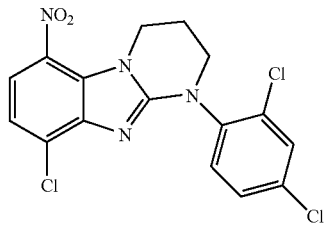 [SMILES: O=[N+]([O-])c1ccc(Cl)c2nc3n(c12)CCCN3c1ccc(Cl)cc1Cl]

A mixture of 9-chloro-6-nitro-1,2,3,4-tetrahydropyrimido[1,2-a]benzimidazole (Reference Example 108; 10.0 g, 39.6 mmol), 2,4-dichloro-1-iodobenzene (54.0 g, 197.9 mmol), copper(I) iodide (7.57 g, 39.6 mmol), 2,2'-bipyridyl (12.3 g, 79.2 mmol) and cesium carbonate (25.8 g, 79.2 mmol) in N,N-dimethylformamide (600 mL) was stirred at 150° C. for 12 hr. The mixture was diluted with ethyl acetate, washed with water, dried over anhydrous sodium sulfate and concentrated in vacuo. The residue was purified by flash chromatography on silica gel eluting with a 10-25% ethyl acetate/n-hexane gradient mixture. The filtrate was concentrated in vacuo to give the title compound (750 mg, 1.88 mmol, 5%) as a light yellow amorphous.

$^1$H-NMR (CDCl$_3$, 300 MHz) δ: 2.30-2.42 (2H, m), 3.70-3.85 (2H, m), 4.36 (2H, t, J=6.0 Hz), 7.14 (1H, d, J=9.0 Hz), 7.34 (1H, dd, J=2.4, 8.4 Hz), 7.47 (1H, d, J=8.4 Hz), 7.53 (1H, d, J=2.4 Hz), 7.61 (1H, d, J=9.0 Hz).

MS Calcd.: 396; Found: 397 (M+H)

Example 100

9-Chloro-1-(2,4-dichlorophenyl)-1,2,3,4-tetrahydropyrimido[1,2-a]benzimidazol-6-amine

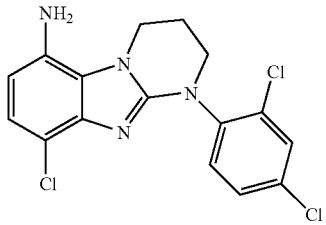

A mixture of 9-chloro-1-(2,4-dichlorophenyl)-6-nitro-1,2,3,4-tetrahydropyrimido[1,2-a]benzimidazole (123 mg, 0.308 mmol) and, 10% palladium on carbon (12 mg) in acetic acid (5.0 mL) was stirred under hydrogen atmosphere at room temperature for 8 hr. The catalyst was removed by filtration and the filtrate was concentrated in vacuo. The residue was purified by flash chromatography on silica gel eluting with a 50-100% ethyl acetate/n-hexane gradient mixture. The filtrate was concentrated in vacuo to give the title compound (51 mg, 0.139 mmol, 45%) as an oil.

$^1$H-NMR (CDCl$_3$, 300 MHz) δ: 2.33-2.42 (2H, m), 3.56 (2H, brs), 3.62-3.75 (2H, m), 4.58 (2H, t, J=6.0 Hz), 6.32 (1H, d, J=9.0 Hz), 6.86 (1H, d, J=9.0 Hz), 7.29 (1H, dd, J=2.4, 8.4 Hz), 7.47 (1H, d, J=2.4 Hz), 7.52 (1H, d, J=8.4 Hz).

MS Calcd.: 366; Found: 367 (M+H).

Example 101

9-Chloro-1-(2,4-dichlorophenyl)-N,N-diethyl-1,2,3,4-tetrahydropyrimido[1,2-a]benzimidazol-6-amine

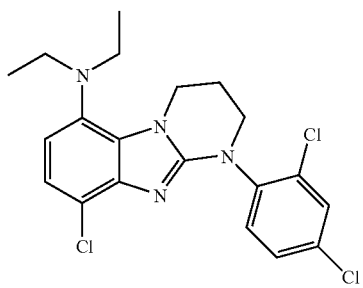 [SMILES: CCN(CC)c1ccc(Cl)c2nc3n(c12)CCCN3c1ccc(Cl)cc1Cl]

To a solution of 9-chloro-1-(2,4-dichlorophenyl)-1,2,3,4-tetrahydropyrimido[1,2-a]benzimidazol-6-amine (45 mg, 0.122 mmol) in methanol (5.0 mL) and acetic acid (1.0 mL) was added acetaldehyde (0.10 mL, 1.64 mmol) at 0° C. The resultant mixture was stirred at 0° C. for 30 min. To the reaction mixture was added sodium triacetoxyborohydride (346 mg, 1.64 mmol) at 0° C. After stirring at room temperature for 1 hr, the mixture was concentrated in vacuo, diluted with water, and extracted with ethyl acetate. The organic layer was dried over anhydrous magnesium sulfate, filtered and concentrated in vacuo. The residue was purified by column chromatography on a silica gel eluting with a 10-50% ethyl acetate/n-hexane gradient mixture. The filtrate was concentrated in vacuo to give the title compound (50 mg, 0.120 mmol, 98%) as a white amorphous.

$^1$H NMR (CDCl$_3$) δ 1.00 (6H, t, J=7.2 Hz), 2.28-2.35 (2H, m), 3.02 (4H, q, J=7.2 Hz), 3.69 (2H, brs), 4.61 (2H, t, J=6.0 Hz), 6.78 (1H, d, J=8.4 Hz), 7.01 (1H, d, J=8.4 Hz), 7.30 (1H, dd, J=2.4, 8.7 Hz), 7.49 (1H, d, J=2.4 Hz), 7.52 (1H, d, J=8.7 Hz).

MS Calcd.: 422; MS Found: 423 (M+H).

Example 102

1-(2,4-Dichlorophenyl)-N,N-diethyl-1,2,3,4,5,6-hexahydro[1,3]diazocino[1,2-a]benzimidazol-8-amine

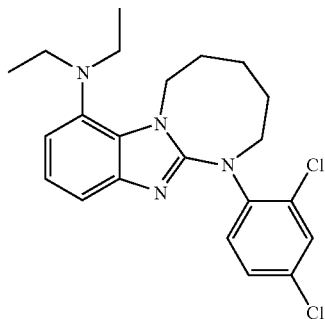 [SMILES: CCN(CC)c1cccc2nc3n(c12)CCCCCN3c1ccc(Cl)cc1Cl]

To a solution of 5-[2-[(2,4-dichlorophenyl)amino]-7-(diethylamino)-1H-benzimidazol-1-yl]pentan-1-ol (Reference Example 113; 100 mg, 0.230 mmol) in pyridine (2 mL) was added methanesulfonyl chloride (0.0890 mL, 1.15 mmol) at 0° C. After the resultant mixture was stirred at 0° C. for 2 hr, the mixture was diluted with aqueous sodium hydrogen carbonate and extracted with ethyl acetate. The combined organic layer was washed with brine, dried over anhydrous sodium sulfate, filtered and concentrated in vacuo. The residue was diluted with N,N-dimethylformamide (5 mL) and to the solution was added potassium carbonate (63.5 mg, 0.460 mmol) at room temperature. After the resultant mixture was stirred at 80° C. for 2 hr, the mixture was diluted with ethyl acetate, washed with water and brine, dried over anhydrous sodium sulfate, filtered and concentrated in vacuo. The residue was purified by flash column chromatography on silica gel eluting with a 0-30% ethyl acetate/n-hexane gradient mixture to give the title compound as a solid (72.6 mg, 0.174 mmol, 76%). Analytically pure material was obtained by recrystallization from n-hexane.

mp 120-121° C.

$^1$H NMR (CDCl$_3$) δ 1.02 (t, J=7.1 Hz, 6 H), 1.54-1.65 (m, 2 H), 1.68-1.79 (m, 2 H), 1.89-1.99 (m, 2 H), 3.05 (q, J=7.2 Hz, 4 H), 3.60 (t, J=5.8 Hz, 2 H), 4.85-4.92 (m, 2 H), 7.07 (dd, J=7.7, 1.4 Hz, 1 H), 7.13 (t, J=7.7 Hz, 1 H), 7.25-7.29 (m, 2 H), 7.43 (dd, J=7.7, 1.4 Hz, 1 H), 7.50 (d, J=8.7 Hz, 1 H).

MS Calcd.: 416; MS Found: 417 (M+H).

Example 103

Methyl 9-chloro-1-(2,4-dichlorophenyl)-1,2,3,4-tetrahydropyrimido[1,2-a]benzimidazole-6-carboxylate

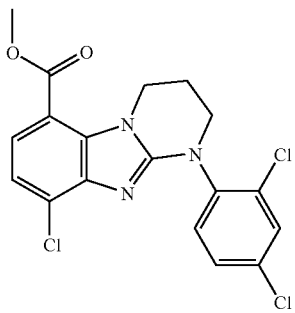

Methanesulfonyl chloride (11.3 mL, 143 mmol) was added to a stirred solution of methyl 4-chloro-2-[(2,4-dichlorophenyl)amino]-1-(3-hydroxypropyl)-1H-benzimidazole-7-carboxylate (Reference example 117, 15.3 g, 35.7 mmol), pyridine (50 mL) and triethylamine (25 mL) in tetrahydrofuran (100 mL) at 0° C. The mixture was stirred at 0° C. for 13 hr, and diluted with aqueous sodium hydrogen carbonate and extracted with ethyl acetate. The combined organic layer was washed with brine, dried over anhydrous magnesium sulfate, filtered, and concentrated in vacuo. A mixture of the resulting mesylate and potassium carbonate (14.7 g, 106 mmol) in N,N-dimethylformamide (60 mL) was stirred at 70° C. for 4 hr. The mixture was diluted with aqueous sodium hydrogen carbonate, and extracted with ethyl acetate. The combined organic layer was washed with brine, dried over anhydrous magnesium sulfate, filtered, and concentrated in vacuo. The residue was washed with diisopropyl ether to give the title compound as a colorless powder (12.8 g, 31.2 mmol, 87% in 2 steps).

$^1$H NMR (CDCl$_3$) δ 2.27-2.35 (m, 2H), 3.69-3.77 (m, 2H), 3.94 (s, 3H), 4.42 (t, J=6.0 Hz, 2H), 7.09 (d, J=8.4 Hz, 1H), 7.32 (dd, J=2.4 Hz, 8.4 Hz, 1H), 7.43-7.50 (m, 3H).

MS Calcd.: 409; MS Found: 410 (M+H).

Example 104

[9-Chloro-1-(2,4-dichlorophenyl)-1,2,3,4-tetrahydropyrimido[1,2-a]benzimidazol-6-yl]methanol

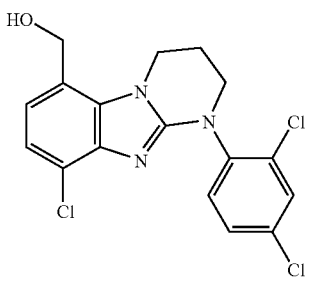 [SMILES: OCc1ccc(Cl)c2nc3n(c12)CCCN3c1ccc(Cl)cc1Cl]

Lithium borohydride (2.12 g, 97.4 mmol) was added to a stirred solution of methyl 9-chloro-1-(2,4-dichlorophenyl)-1,2,3,4-tetrahydropyrimido[1,2-a]benzimidazole-6-carboxylate (10.0 g, 24.3 mmol) in tetrahydrofuran (80 mL) at room temperature, and the mixture was stirred at room temperature for 16 hr. The reaction was quenched by aqueous saturated ammonium chloride at 0° C., and the mixture was extracted with ethyl acetate. The combined organic layer was washed with brine, dried over anhydrous magnesium sulfate, filtered, and concentrated in vacuo to give the solid, which was washed with ethyl acetate/diisopropyl ether to give the title compound as a colorless powder (8.31 g, 21.7 mmol, 89%).

$^1$H NMR (DMSO-d$_6$) δ 2.25-2.33 (m, 2H), 3.63-3.71 (m, 2H), 4.49-4.60 (m, 2H), 4.74 (d, J=5.1 Hz, 2H), 5.38 (t, J=5.1 Hz, 1H), 6.85 (d, J=8.1 Hz, 1H), 6.96 (d, J=8.1 Hz, 1H), 7.54 (dd, J=2.4 Hz, 8.4 Hz, 1H), 7.63 (d, J=8.4 Hz, 1H), 7.81 (d, J=2.4 Hz, 1H).

MS Calcd.: 381; MS Found: 382 (M+H).

Example 105

9-Chloro-1-(2,4-dichlorophenyl)-1,2,3,4-tetrahydropyrimido[1,2-a]benzimidazole-6-carbaldehyde

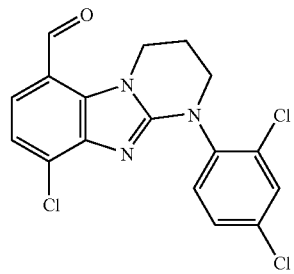

Sulfur trioxide-pyridine complex (24.1 g, 152 mmol) was added to a stirred solution of [9-chloro-1-(2,4-dichlorophenyl)-1,2,3,4-tetrahydropyrimido[1,2-a]benzimidazol-6-yl]methanol (8.30 g, 21.7 mmol), triethylamine (24 mL), and dimethyl sulfoxide (150 mL) in dichloromethane (100 mL) at room temperature, and the mixture was stirred at room temperature for 3 hr. The mixture was concentrated in vacuo, diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 15-50% ethyl acetate/n-hexane gradient mixture. The filtrate was concentrated in vacuo to give the solid, which was washed with ethyl acetate/diisopropyl ether to give the title compound as a pale yellow powder (6.82 g, 17.9 mmol, 82%).

$^1$H NMR (CDCl$_3$) δ 2.31-2.41 (m, 2H), 3.67-3.80 (m, 2H), 4.69 (t, J=6.0 Hz, 2H), 7.22 (d, J=8.4 Hz, 1H), 7.25-7.37 (m, 2H), 7.47-7.51 (m, 2H), 9.98 (s, 1H).

MS Calcd.: 379; MS Found: 380 (M+H).

Example 106

2-[9-Chloro-1-(2,4-dichlorophenyl)-1,2,3,4-tetrahydropyrimido[1,2-a]benzimidazol-6-yl]propan-2-ol

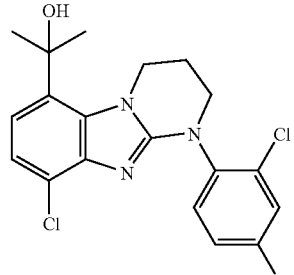

Methylmagnesium bromide (3.0 M solution in diethyl ether, 2.0 mL, 6.0 mmol) was added to a stirred solution of methyl 9-chloro-1-(2,4-dichlorophenyl)-1,2,3,4-tetrahydropyrimido[1,2-a]benzimidazole-6-carboxylate (500 mg, 1.21 mmol) in tetrahydrofuran (4.0 mL), and the mixture was stirred at 60° C. for 2 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was purified by flash column chromatography on silica gel eluting with a 15-50% ethyl acetate/n-hexane gradient mixture. The filtrate was concentrated in vacuo to give the solid, which was recrystallized from ethanol to give the title compound as a colorless crystal (290 mg, 0.706 mmol, 58%).

mp 216-218° C.

$^1$H NMR (DMSO-$d_6$) δ 1.61 (s, 6H), 2.21-2.30 (m, 2H), 3.61-3.67 (m, 2H), 4.75-4.91 (m, 2H), 5.51 (s, 1H), 6.86 (d, J=8.4 Hz, 1H), 6.95 (d, J=8.4 Hz, 1H), 7.55 (dd, J=2.4 Hz, 8.7 Hz, 1H), 7.64 (d, J=8.7 Hz, 1H), 7.81 (d, J=2.4 Hz, 1H).

MS Calcd.: 409; MS Found: 410 (M+H).

Example 107

3-[9-Chloro-1-(2,4-dichlorophenyl)-1,2,3,4-tetrahydropyrimido[1,2-a]benzimidazol-6-yl]pentan-3-ol

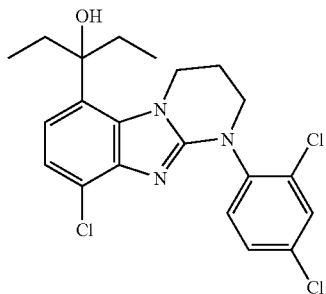 [SMILES: CCC(O)(CC)c1ccc(Cl)c2nc3n(c12)CCCN3c1ccc(Cl)cc1Cl]

Ethylmagnesium bromide (3.0 M solution in diethyl ether, 2.9 mL, 8.7 mmol) was added to a stirred solution of methyl 9-chloro-1-(2,4-dichlorophenyl)-1,2,3,4-tetrahydropyrimido[1,2-a]benzimidazole-6-carboxylate (720 mg, 1.75 mmol) in tetrahydrofuran (7.0 mL), and the mixture was stirred at 60° C. for 2 hr. The reaction was quenched by water, and the mixture was extracted with ethyl acetate. The combined organic layer was washed with brine, dried over anhydrous magnesium sulfate, filtered, and concentrated in vacuo. The residue was purified by flash column chromatography on silica gel eluting with a 10-50% ethyl acetate/n-hexane gradient mixture. The filtrate was concentrated in vacuo to give the solid, which was recrystallized from ethanol to give the title compound as a colorless crystal (378 mg, 0.861 mmol, 49%).

mp 199-201° C.

$^1$H NMR (DMSO-$d_6$) δ 0.79 (t, J=6.9 Hz, 6H), 1.82-1.96 (m, 4H), 2.23 (t, J=5.4 Hz, 2H), 3.64 (t, J=5.4 Hz, 2H), 4.60-4.90 (m, 2H), 5.18 (s, 1H), 6.73 (d, J=8.4 Hz, 1H), 6.95 (d, J=8.4 Hz, 1H), 7.54 (dd, J=2.4 Hz, 8.4 Hz, 1H), 7.63 (d, J=8.4 Hz, 1H), 7.80 (d, J=2.4 Hz, 1H).

MS Calcd.: 437; MS Found: 438 (M+H).

Example 108

[9-Chloro-1-(2,4-dichlorophenyl)-1,2,3,4-tetrahydropyrimido[1,2-a]benzimidazol-6-yl](dicyclopropyl)methanol

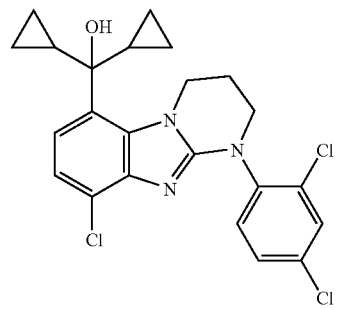 [SMILES: OC(c1ccc(Cl)c2nc3n(c12)CCCN3c1ccc(Cl)cc1Cl)(C1CC1)C1CC1]

Cyclopropylmagnesium bromide (1.0 M solution in tetrahydrofuran, 4.8 mL, 4.8 mmol) was added to a stirred solution of methyl 9-chloro-1-(2,4-dichlorophenyl)-1,2,3,4-tetrahydropyrimido[1,2-a]benzimidazole-6-carboxylate (400 mg, 0.974 mmol) in tetrahydrofuran (5.0 mL), and the mixture was stirred at 60° C. for 3 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was purified by flash column chromatography on silica gel eluting with a 10-50% ethyl acetate/n-hexane gradient mixture. The filtrate was concentrated in vacuo to give the solid, which was recrystallized from ethyl acetate/diisopropyl ether to give the title compound as a colorless crystal (320 mg, 0.691 mmol, 71%).

mp 184-186° C.

$^1$H NMR (CDCl$_3$) δ 0.22-0.29 (m, 2H), 0.51-0.65, (m, 6H), 1.37-1.47 (m, 2H), 1.74 (s, 1H), 2.24-2.35 (m, 2H), 3.63-3.75 (m, 2H), 4.82 (t, J=6.0 Hz, 2H) 7.00 (d, J=8.1 Hz, 1H), 7.14 (d, J=8.1 Hz, 1H), 7.30 (dd, J=2.1 Hz, 8.4 Hz, 1H), 7.47-7.50 (m, 2H).

MS Calcd.: 461; MS Found: 462 (M+H).

Anal. Calcd for $C_{23}H_{22}N_3OCl_3$: C, 59.69; H, 4.79; N, 9.08; Cl, 22.98. Found: C, 59.87; H, 4.77; N, 9.05; Cl, 23.03.

Example 109

9-Chloro-1-(2,4-dichlorophenyl)-6-(1-methoxy-1-methylethyl)-1,2,3,4-tetrahydropyrimido[1,2-a]benzimidazole

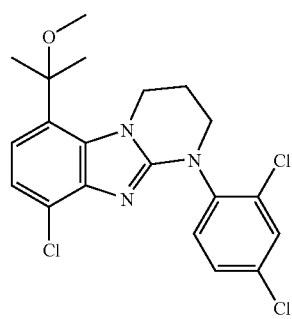 [SMILES: COC(C)(C)c1ccc(Cl)c2nc3n(c12)CCCN3c1ccc(Cl)cc1Cl]

Sodium hydride (60% in oil, 17.5 mg, 0.438 mmol) was added to a stirred solution of 2-[9-chloro-1-(2,4-dichlorophenyl)-1,2,3,4-tetrahydropyrimido[1,2-a]benzimidazol-6-yl]propan-2-ol (150 mg, 0.365 mmol) in N,N-dimethylformamide (1.5 mL) at room temperature. After stirring 5 min, methyl iodide (77.7 mg, 0.548 mmol) was added to the mixture, and the mixture was stirred at room temperature for 4 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 10-40% ethyl acetate/n-hexane gradient mixture. The filtrate was concentrated in vacuo to give the solid, which was recrystallized from ethyl acetate/diisopropyl ether to give the title compound as a colorless crystal (133 mg, 0.313 mmol, 86%).

mp 203-204° C.

$^1$H NMR (CDCl$_3$) δ 1.69 (s, 6H), 2.27-2.37 (m, 2H), 3.04 (s, 3H), 3.64-3.76 (m, 2H), 4.74 (t, J=5.7 Hz, 2H), 6.82 (d, J=8.4 Hz, 1H), 7.02 (d, J=8.4 Hz, 1H), 7.32 (dd, J=2.1 Hz, 8.4 Hz, 1H), 7.49-7.52 (m, 2H).

MS Calcd.: 423; MS Found: 424 (M+H).

Anal. Calcd for C$_{20}$H$_{20}$N$_3$OCl$_3$: C, 56.55; H, 4.75; N, 9.89; Cl, 25.04. Found: C, 56.60; H, 4.71; N, 9.90; Cl, 25.24.

Example 110

9-Chloro-1-(2,4-dichlorophenyl)-6-(1-ethyl-1-methoxypropyl)-1,2,3,4-tetrahydropyrimido[1,2-a]benzimidazole

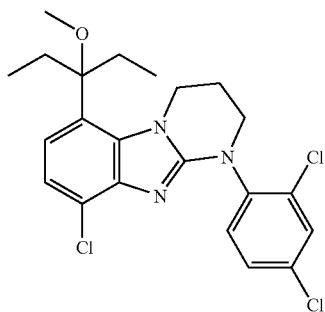 [SMILES: CCC(CC)(OC)c1ccc(Cl)c2nc3n(c12)CCCN3c1ccc(Cl)cc1Cl]

Sodium hydride (60% in oil, 21.8 mg, 0.546 mmol) was added to a stirred solution of 3-[9-chloro-1-(2,4-dichlorophenyl)-1,2,3,4-tetrahydropyrimido[1,2-a]benzimidazol-6-yl]pentan-3-ol (200 mg, 0.456 mmol) in N,N-dimethylformamide (2.0 mL) at room temperature. After stirring 5 min, methyl iodide (97.0 mg, 0.684 mmol) was added to the mixture, and the mixture was stirred at room temperature for 5 hr. The mixture was diluted with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 10-50% ethyl acetate/n-hexane gradient mixture. The filtrate was concentrated in vacuo to give the solid, which was recrystallized from ethyl acetate/diisopropyl ether to give the title compound as a colorless crystal (174 mg, 0.384 mmol, 84%).

mp 124-125° C.

$^1$H NMR (CDCl$_3$) δ 0.81 (t, J=7.2 Hz, 6H), 1.93-2.08 (m, 4H), 2.27-2.36 (m, 2H), 2.99 (s, 3H), 3.67-3.74 (m, 2H), 4.76 (t, J=6.0 Hz, 2H), 6.76 (d, J=8.4 Hz, 1H), 7.02 (d, J=8.4 Hz, 1H), 7.31 (dd, J=2.4 Hz, 8.7 Hz, 1H), 7.50 (d, J=2.4 Hz, 1H), 7.51 (d, J=8.7 Hz, 1H).

MS Calcd.: 451; MS Found: 452 (M+H).

Example 111

9-Chloro-1-(2,4-dichlorophenyl)-6-[dicyclopropyl(methoxy)methyl]-1,2,3,4-tetrahydropyrimido[1,2-a]benzimidazole

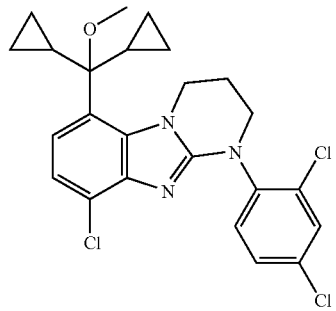 [SMILES: COC(c1ccc(Cl)c2nc3n(c12)CCCN3c1ccc(Cl)cc1Cl)(C1CC1)C1CC1]

Sodium hydride (60% in oil, 17.5 mg, 0.438 mmol) was added to a stirred solution of [9-chloro-1-(2,4-dichlorophenyl)-1,2,3,4-tetrahydropyrimido[1,2-a]benzimidazol-6-yl](dicyclopropyl)methanol (100 mg, 0.216 mmol) in N,N-dimethylformamide (1.0 mL) at room temperature. After stirring min, methyl iodide (61.3 mg, 0.422 mmol) was added to the mixture, and the mixture was stirred at room temperature for 6 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 10-40% ethyl acetate/n-hexane gradient mixture. The filtrate was concentrated in vacuo to give the solid, which was recrystallized from ethyl acetate/n-hexane to give the title compound as a colorless crystal (59.4 mg, 0.125 mmol, 58%).

mp 99-100° C.

$^1$H NMR (CDCl$_3$) δ 0.32-0.39 (m, 2H), 0.51-0.68 (m, 6H), 1.17-1.26 (m, 2H), 2.22-2.30 (m, 2H), 3.24 (s, 3H), 3.63-3.75 (m, 2H), 4.77 (t, J=6.0 Hz, 2H) 7.02 (d, J=8.4 Hz, 1H), 7.16 (d, J=8.4 Hz, 1H), 7.32 (dd, J=2.4 Hz, 8.4 Hz, 1H), 7.49-7.52 (m, 2H).

MS Calcd.: 475; MS Found: 476 (M+H).

Example 112

1-[9-Chloro-1-(2,4-dichlorophenyl)-1,2,3,4-tetrahydropyrimido[1,2-a]benzimidazol-6-yl]propan-1-ol

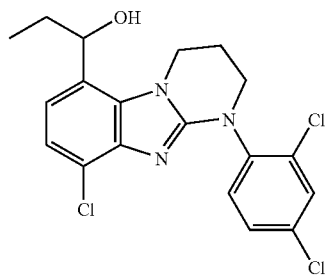 [SMILES: CCC(O)c1ccc(Cl)c2nc3n(c12)CCCN3c1ccc(Cl)cc1Cl]

Ethylmagnesium bromide (3.0 M solution in diethyl ether, 1.1 mL, 3.3 mmol) was added to a stirred solution of 9-chloro-1-(2,4-dichlorophenyl)-1,2,3,4-tetrahydropyrimido[1,2-a]benzimidazole-6-carbaldehyde (1.00 g, 2.63 mmol) in tetrahydrofuran (13 mL) at 0° C., and the mixture was stirred at 0° C. for 1 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was recrystallized from ethanol to give the title compound as a colorless crystal (992 mg, 2.42 mmol, 92%).

mp 244-245° C.

$^1$H NMR (DMSO-$d_6$) δ 0.94 (t, J=7.5 Hz, 3H), 1.72-1.85 (m, 2H), 2.23-2.35 (m, 2H), 3.60-3.71 (m, 2H), 4.43-4.55 (m, 2H), 4.91-5.03 (m, 1H), 5.30 (d, J=4.5 Hz, 1H), 6.96 (d, J=8.4 Hz, 1H), 6.99 (d, J=8.4 Hz, 1H), 7.54 (dd, J=2.4 Hz, 8.7 Hz, 1H), 7.63 (d, J=8.7 Hz, 1H), 7.80 (d, J=2.4 Hz, 1H).

MS Calcd.: 409; MS Found: 410 (M+H).

Anal. Calcd for $C_{19}H_{18}N_3OCl_3$: C, 55.56; H, 4.42; N, 10.23; Cl, 25.90. Found: C, 55.41; H, 4.32; N, 10.21; Cl, 25.89.

Example 113

[9-Chloro-1-(2,4-dichlorophenyl)-1,2,3,4-tetrahydropyrimido[1,2-a]benzimidazol-6-yl](cyclopropyl)methanol

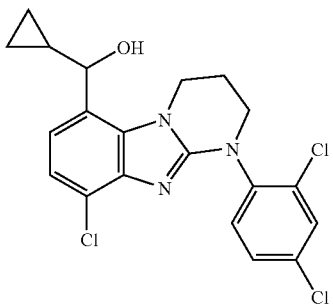 [SMILES: OC(c1ccc(Cl)c2nc3n(c12)CCCN3c1ccc(Cl)cc1Cl)C1CC1]

Cyclopropylmagnesium bromide (1.0 M solution in tetrahydrofuran, 2.9 mL, 2.9 mmol) was added to a stirred solution of 9-chloro-1-(2,4-dichlorophenyl)-1,2,3,4-tetrahydropyrimido[1,2-a]benzimidazole-6-carbaldehyde (1.00 g, 2.63 mmol) in tetrahydrofuran (13 mL) at 0° C., and the mixture was stirred at 0° C. for 1 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was recrystallized from ethanol to give the title compound as a colorless crystal (863 mg, 2.04 mmol, 78%).

mp 223-224° C.

$^1$H NMR (DMSO-$d_6$) δ 0.22-0.27 (m, 1H), 0.43-0.50 (m, 2H), 0.54-0.63 (m, 1H), 1.29-1.38 (m, 1H), 2.25-2.31 (m, 2H), 3.62-3.69 (m, 2H), 4.50-4.70 (m, 3H), 5.34 (t, J=5.1 Hz, 1H) 6.98 (d, J=8.4 Hz, 1H), 7.08 (d, J=8.4 Hz, 1H), 7.54 (dd, J=2.4 Hz, 8.7 Hz, 1H), 7.62 (d, J=8.7 Hz, 1H), 7.80 (d, J=2.4 Hz, 1H).

MS Calcd.: 421; MS Found: 422 (M+H).

Example 114

1-[9-Chloro-1-(2,4-dichlorophenyl)-1,2,3,4-tetrahydropyrimido[1,2-a]benzimidazol-6-yl]butan-1-ol

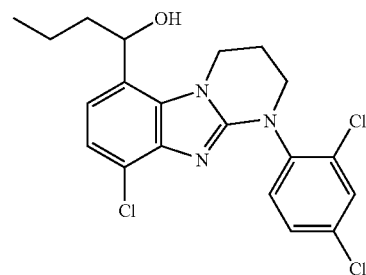 [SMILES: CCCC(O)c1ccc(Cl)c2nc3n(c12)CCCN3c1ccc(Cl)cc1Cl]

n-Propylmagnesium bromide (2.0 M solution in tetrahydrofuran, 0.72 mL, 1.44 mmol) was added to a stirred solution of 9-chloro-1-(2,4-dichlorophenyl)-1,2,3,4-tetrahydropyrimido[1,2-a]benzimidazole-6-carbaldehyde (500 mg, 1.31 mmol) in tetrahydrofuran (3.0 mL) at 0° C., and the mixture was stirred at room temperature for 2 hr. The reaction was quenched by water, and the mixture was extracted with ethyl acetate. The combined organic layer was washed with brine, dried over anhydrous magnesium sulfate, filtered, and concentrated in vacuo. The residue was recrystallized from ethanol to give the title compound as a colorless crystal (435 mg, 1.02 mmol, 78%).

mp 220-221° C.

$^1$H NMR (DMSO-$d_6$) δ 0.92 (t, J=7.2 Hz, 3H), 1.28-1.57 (m, 2H), 1.70-1.79 (m, 2H), 2.24-2.36 (m, 2H), 3.61-3.71 (m, 2H), 4.42-4.59 (m, 2H), 5.06 (q, J=6.0 Hz, 1H), 5.28 (d, J=6.0 Hz, 1H), 6.96 (d, J=8.4 Hz, 1H), 6.99 (d, J=8.4 Hz, 1H), 7.54 (dd, J=2.4 Hz, 8.7 Hz, 1H), 7.63 (d, J=8.7 Hz, 1H), 7.80 (d, J=2.4 Hz, 1H).

MS Calcd.: 423; MS Found: 424 (M+H).

Anal. Calcd for $C_{20}H_{20}N_3OCl_3$: C, 56.55; H, 4.75; N, 9.89; Cl, 25.04. Found: C, 56.38; H, 4.72; N, 9.90; Cl, 24.68.

Example 115

9-Chloro-1-(2,4-dichlorophenyl)-6-(1-methoxypropyl)-1,2,3,4-tetrahydropyrimido[1,2-a]benzimidazole

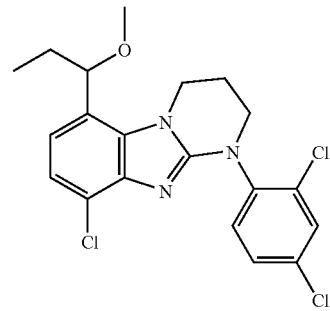 [SMILES: CCC(OC)c1ccc(Cl)c2nc3n(c12)CCCN3c1ccc(Cl)cc1Cl]

A mixture of 1-[9-chloro-1-(2,4-dichlorophenyl)-1,2,3,4-tetrahydropyrimido[1,2-a]benzimidazol-6-yl]propan-1-ol (460 mg, 1.12 mmol), potassium carbonate (201 mg, 1.46 mmol) and methyl iodide (207 mg, 1.46 mmol) in N,N-dimethylformamide (4.5 mL) was stirred at room temperature for 9 hr. The mixture was diluted with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 5-40% ethyl acetate/n-hexane gradient mixture. The filtrate was concentrated in vacuo to give the solid, which was recrystallized from ethyl acetate/diisopropyl ether to give the title compound as a colorless crystal (363 mg, 0.855 mmol, 76%).

mp 136-137° C.

$^1$H NMR (CDCl$_3$) δ 0.97 (t, J=7.5 Hz, 3H), 1.75-1.90 (m, 1H), 1.91-2.06 (m, 1H), 2.32-2.40 (m, 2H), 3.24 (s, 3H), 3.65-3.78 (m, 2H), 4.30-4.43 (m, 1H), 4.50-4.63 (m, 1H), 4.52 (t, J=6.9 Hz, 1H), 6.88 (d, J=8.1 Hz, 1H), 7.06 (d, J=8.1 Hz, 1H), 7.31 (dd, J=2.1 Hz, 8.4 Hz, 1H), 7.49 (d, J=2.1 Hz, 1H), 7.52 (d, J=8.4 Hz, 1H).

MS Calcd.: 423; MS Found: 424 (M+H).

Anal. Calcd for C$_{20}$H$_{20}$N$_3$OCl$_3$: C, 56.55; H, 4.75; N, 9.89; Cl, 25.04. Found: C, 56.58; H, 4.64; N, 9.96; Cl, 25.16.

Example 116

9-Chloro-1-(2,4-dichlorophenyl)-6-(1-ethoxypropyl)-1,2,3,4-tetrahydropyrimido[1,2-a]benzimidazole

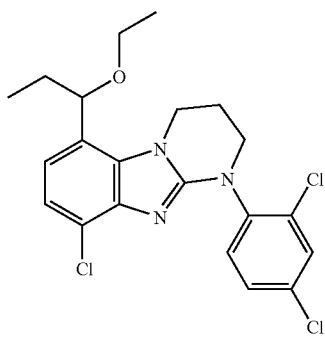 [SMILES: CCOC(CC)c1ccc(Cl)c2nc3n(c12)CCCN3c1ccc(Cl)cc1Cl]

Sodium hydride (60% in oil, 10.7 mg, 0.269 mmol) was added to a stirred solution of 1-[9-chloro-1-(2,4-dichlorophenyl)-1,2,3,4-tetrahydropyrimido[1,2-a]benzimidazol-6-yl]propan-1-ol (92.0 mg, 0.223 mmol) in N,N-dimethylformamide (1.0 mL) at room temperature. After stirring 5 min, methyl iodide (70.0 mg, 0.494 mmol) was added to the mixture, and the mixture was stirred at room temperature for 5 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 5-50% ethyl acetate/n-hexane gradient mixture. The filtrate was concentrated in vacuo to give the solid, which was recrystallized from ethyl acetate/n-hexane to give the title compound as a colorless crystal (76.0 mg, 0.173 mmol, 78%).

mp 108-110° C.

$^1$H NMR (CDCl$_3$) δ 0.97 (t, J=7.5 Hz, 3H), 1.18 (t, J=6.9 Hz, 3H), 1.75-1.99 (m, 2H), 2.32-2.40 (m, 2H), 3.29-3.47 (m, 2H), 3.64-3.76 (m, 2H), 4.31-4.40 (m, 1H), 4.58 (t, J=6.9 Hz, 1H), 4.64-4.73 (m, 1H), 6.89 (d, J=7.8 Hz, 1H), 7.04 (d, J=7.8 Hz, 1H), 7.31 (dd, J=2.1 Hz, 8.4 Hz, 1H), 7.49 (d, J=2.1 Hz, 1H), 7.52 (d, J=8.4 Hz, 1H).

MS Calcd.: 437; MS Found: 438 (M+H).

Example 117

9-Chloro-6-[cyclopropyl(methoxy)methyl]-1-(2,4-dichlorophenyl)-1,2,3,4-tetrahydropyrimido[1,2-a]benzimidazole

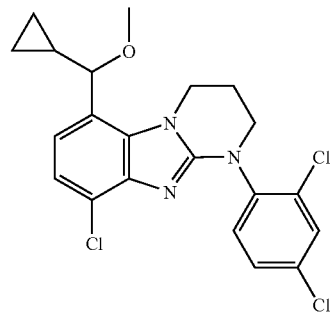 [SMILES: COC(c1ccc(Cl)c2nc3n(c12)CCCN3c1ccc(Cl)cc1Cl)C1CC1]

Sodium hydride (60% in oil, 79.6 mg, 1.99 mmol) was added to a stirred solution of [9-chloro-1-(2,4-dichlorophenyl)-1,2,3,4-tetrahydropyrimido[1,2-a]benzimidazol-6-yl](cyclopropyl)methanol (700 mg, 1.66 mmol) in N,N-dimethylformamide (5.5 mL) at room temperature. After stirring (5 min, methyl iodide (353 mg, 2.49 mmol) was added to the mixture, and the mixture was stirred at room temperature for 3 hr. The mixture was diluted with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 5-40% ethyl acetate/n-hexane gradient mixture. The filtrate was concentrated in vacuo to give the solid, which was recrystallized from ethyl acetate/n-hexane to give the title compound as a colorless crystal (569 mg, 1.30 mmol, 78%).

mp 138-139° C.

$^1$H NMR (CDCl$_3$) δ 0.23-0.28 (m, 1H), 0.38-0.45 (m, 1H), 0.53-0.58 (m, 1H), 0.65-0.77 (m, 1H), 1.35-1.42 (m, 1H), 2.31-2.40 (m, 2H), 3.30 (s, 3H), 3.62-3.80 (m, 2H), 4.11 (d, J=7.8 Hz, 1H) 4.42-4.51 (m, 1H), 4.60-4.70 (m, 1H), 6.88 (d, J=8.1 Hz, 1H), 7.04 (d, J=8.1 Hz, 1H), 7.31 (dd, J=2.4 Hz, 8.4 Hz, 1H), 7.48 (d, J=2.4 Hz, 1H), 7.51 (d, J=8.4 Hz, 1H).

MS Calcd.: 435; MS Found: 436 (M+H).

Anal. Calcd for C$_{21}$H$_{20}$N$_3$OCl$_3$: C, 57.75; H, 4.62; N, 9.62; Cl, 24.35. Found: C, 57.74; H, 4.52; N, 9.63; Cl, 24.37.

Example 118

9-Chloro-1-(2,4-dichlorophenyl)-6-(1-methoxybutyl)-1,2,3,4-tetrahydropyrimido[1,2-a]benzimidazole

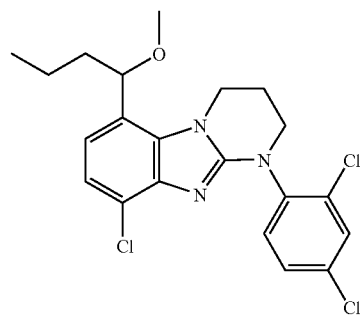 [SMILES: CCCC(OC)c1ccc(Cl)c2nc3n(c12)CCCN3c1ccc(Cl)cc1Cl]

Sodium hydride (60% in oil, 50.8 mg, 1.27 mmol) was added to a stirred solution of 1-[9-chloro-1-(2,4-dichlorophenyl)-1,2,3,4-tetrahydropyrimido[1,2-a]benzimidazol-6-yl]butan-1-ol (250 mg, 1.06 mmol) in N,N-dimethylformamide (3.0 mL) at room temperature. After stirring 5 min, methyl iodide (226 mg, 1.59 mmol) was added to the mixture, and the mixture was stirred at room temperature for 3 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 5-50% ethyl acetate/n-hexane gradient mixture. The filtrate was concentrated in vacuo to give the solid, which was recrystallized from ethyl acetate/diisopropyl ether to give the title compound as a colorless crystal (166 mg, 0.378 mmol, 36%).

mp 139-140° C.

$^1$H NMR (CDCl$_3$) δ 0.95 (t, J=7.5 Hz, 3H), 1.30-1.40 (m, 1H), 1.40-1.57 (m, 1H), 1.67-1.81 (m, 1H), 1.86-2.00 (m, 1H), 2.37 (t, J=5.4 Hz, 2H), 3.23 (s, 3H), 3.65-3.78 (m, 2H), 4.32-4.43 (m, 1H), 4.52-4.64 (m, 2H), 6.88 (d, J=8.1 Hz, 1H), 7.05 (d, J=8.1 Hz, 1H), 7.31 (dd, J=2.4 Hz, 8.4 Hz, 1H), 7.49 (d, J=2.4 Hz, 1H), 7.53 (d, J=8.4 Hz, 1H).

MS Calcd.: 437; MS Found: 438 (M+H).

Anal. Calcd for C$_{21}$H$_{22}$N$_3$OCl$_3$: C, 57.48; H, 5.05; N, 9.58; Cl, 24.24. Found: C, 57.56; H, 5.06; N, 9.61; Cl, 24.28.

Example 119

9-Chloro-1-(2,4-dichlorophenyl)-6-[1-(1H-imidazol-1-yl)propyl]-1,2,3,4-tetrahydropyrimido[1,2-a]benzimidazole

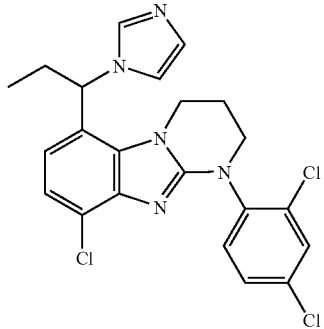 [SMILES: CCC(c1ccc(Cl)c2nc3n(c12)CCCN3c1ccc(Cl)cc1Cl)n1ccnc1]

A mixture of 1-[9-chloro-1-(2,4-dichlorophenyl)-1,2,3,4-tetrahydropyrimido[1,2-a]benzimidazol-6-yl]propan-1-ol (150 mg, 0.326 mmol) and N,N'-carbonyldiimidazole (119 mg, 0.734 mmol) in dichloromethane (2.0 mL) was stirred at 50° C. for 22 hr. The mixture was concentrated in vacuo, diluted with 1N hydrochloric acid and extracted with ethyl acetate. The combined organic layer was washed with brine, dried over anhydrous magnesium sulfate, filtered, and concentrated in vacuo. The residue was purified by flash column chromatography on silica gel eluting with a 50-100% ethyl acetate/n-hexane gradient mixture. The filtrate was concentrated in vacuo to give the solid, which was recrystallized from ethyl acetate/n-hexane to give the title compound as a colorless crystal (141 mg, 0.306 mmol, 94%).

mp 197-199° C.

$^1$H NMR (CDCl$_3$) δ 1.04 (t, J=7.5 Hz, 3H), 2.25-2.39 (m, 4H), 3.62-3.74 (m, 2H), 3.99-4.09 (m, 1H), 4.30-4.40 (m, 1H), 5.65 (t, J=7.5 Hz, 1H), 6.90 (d, J=1.2 Hz, 1H), 6.94 (d, J=8.1 Hz, 1H), 7.06 (d, J=1.2 Hz, 1H), 7.13 (d, J=8.1 Hz, 1H), 7.31 (dd, J=2.4 Hz, 8.7 Hz, 1H), 7.46-7.52 (m, 3H).

MS Calcd.: 459; MS Found: 460 (M+H).

Anal. Calcd for C$_{22}$H$_{20}$N$_5$OCl$_3$: C, 57.34; H, 4.37; N, 15.20; Cl, 23.08. Found: C, 57.10; H, 4.34; N, 15.25; Cl, 22.93.

Example 120

1-[9-Chloro-1-(2,4-dichlorophenyl)-1,2,3,4-tetrahydropyrimido[1,2-a]benzimidazol-6-yl]propan-1-one

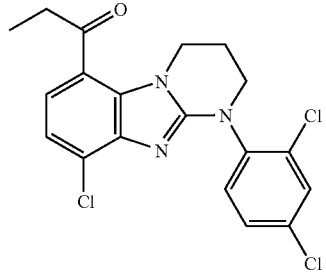 [SMILES: CCC(=O)c1ccc(Cl)c2nc3n(c12)CCCN3c1ccc(Cl)cc1Cl]

Dess-Martin reagent (1.27 g, 3.00 mmol) was added to a stirred suspension of 1-[9-chloro-1-(2,4-dichlorophenyl)-1,2,3,4-tetrahydropyrimido[1,2-a]benzimidazol-6-yl]propan-1-ol (1.12 g, 2.73 mmol) in acetonitrile (23 mL) at 0° C., and the mixture was stirred at room temperature for 1 hr. The mixture was diluted with saturated aqueous sodium hydrogen carbonate, concentrated in vacuo, and extracted with ethyl acetate/tetrahydrofuran. The combined organic layer was washed with brine, dried over anhydrous magnesium sulfate, filtered, and concentrated in vacuo. The residue was purified by flash column chromatography on silica gel eluting with a 15-50% ethyl acetate/n-hexane gradient mixture. The filtrate was concentrated in vacuo to give the solid, which was washed with diisopropyl ether to give the title compound as a colorless powder (980 mg, 2.40 mmol, 88%).

mp 156-157° C.

$^1$H NMR (CDCl$_3$) δ 1.26 (t, J=7.5 Hz, 3H), 2.24-2.33 (m, 2H), 3.05 (q, J=7.5 Hz, 2H), 3.67-3.77 (m, 2H), 4.16 (t, J=6.0 Hz, 2H), 7.11 (d, J=8.1 Hz, 1H), 7.26 (d, J=8.1 Hz, 1H), 7.29-7.33 (m, 1H), 7.47-7.50 (m, 2H).

MS Calcd.: 407; MS Found: 408 (M+H).

Example 121

(1E)-1-[9-Chloro-1-(2,4-dichlorophenyl)-1,2,3,4-tetrahydropyrimido[1,2-a]benzimidazol-6-yl]propan-1-one O-methyloxime Example 122

(1Z)-1-[9-Chloro-1-(2,4-dichlorophenyl)-1,2,3,4-tetrahydropyrimido[1,2-a]benzimidazol-6-yl]propan-1-one O-methyloxime (Example 121)

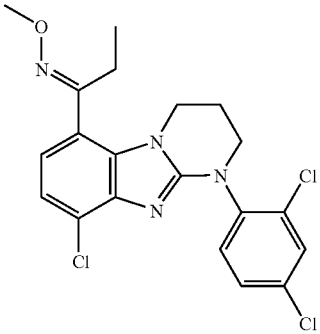

(Example 122)

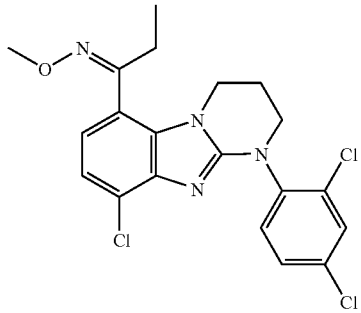

A mixture of 1-[9-chloro-1-(2,4-dichlorophenyl)-1,2,3,4-tetrahydropyrimido[1,2-a]benzimidazol-6-yl]propan-1-one (630 mg, 1.54 mmol), O-methylhydroxylamine hydrochloride (386 mg, 4.62 mmol) and pyridine (3.9 mL) in ethanol (16 mL) was stirred at 80° C. for 26 hr. The mixture was concentrated in vacuo, diluted with saturated aqueous sodium hydrogen carbonate, and extracted with ethyl acetate. The combined organic layer was washed with brine, dried over anhydrous magnesium sulfate, filtered, and concentrated in vacuo. The residue was purified by flash column chromatography on silica gel eluting with a 20-40% ethyl acetate/n-hexane gradient mixture. The filtrate was concentrated in vacuo to give the solid, which was recrystallized from ethanol/ethyl acetate to give the title compounds as a colorless crystal respectively (E (Example 121): 266 mg, 0.608 mmol, 39%, Z (Example 122): 159 mg, 0.363 mmol, 24%).

E Isomer (Example 121):

mp 144-145° C.

$^1$H NMR (CDCl$_3$) δ 1.10 (t, J=7.5 Hz, 3H), 2.28-2.36 (m, 2H), 2.79 (q, J=7.5 Hz, 2H), 3.66-3.78 (m, 2H), 3.99 (s, 3H), 4.11 (t, J=6.0 Hz, 2H), 6.83 (d, J=8.1 Hz, 1H), 7.10 (d, J=8.1 Hz, 1H), 7.30 (dd, =2.4 Hz, 8.4 Hz, 1H), 7.48-7.52 (m, 2H).

MS Calcd.: 436; MS Found: 437 (M+H).

Anal. Calcd for C$_{20}$H$_{19}$N$_4$OCl$_3$: C, 54.87; H, 4.37; N, 12.80; Cl, 24.30. Found: C, 54.60; H, 4.42; N, 12.69; Cl, 24.41.

Z Isomer (Example 122):

mp 180-181° C.

$^1$H NMR (CDCl$_3$) δ 1.15 (t, J=7.2 Hz, 3H), 2.28-2.40 (m, 2H), 2.58-2.67 (m, 2H), 3.66-3.74 (m, 2H), 3.83 (s, 3H), 3.90-3.99 (m, 1H), 4.10-4.19 (m, 1H), 6.65 (d, J=8.4 Hz, 1H), 7.10 (d, J=8.4 Hz, 1H), 7.31 (dd, J=2.4 Hz, 8.4 Hz, 1H), 7.49 (d, J=2.4 Hz, 1H), 7.53 (d, J=8.4 Hz, 1H).

MS Calcd.: 436; MS Found: 437 (M+H).

Anal. Calcd for C$_{20}$H$_{19}$N$_4$OCl$_3$: C, 54.87; H, 4.37; N, 12.80; Cl, 24.30. Found: C, 54.65; H, 4.52; N, 12.59; Cl, 24.51.

Example 123

(1E)-1-[9-Chloro-1-(2,4-dichlorophenyl)-1,2,3,4-tetrahydropyrimido[1,2-a]benzimidazol-6-yl]propan-1-one O-ethyloxime Example 124

(1Z)-1-[9-Chloro-1-(2,4-dichlorophenyl)-1,2,3,4-tetrahydropyrimido[1,2-a]benzimidazol-6-yl]propan-1-one O-ethyloxime (Example 123)

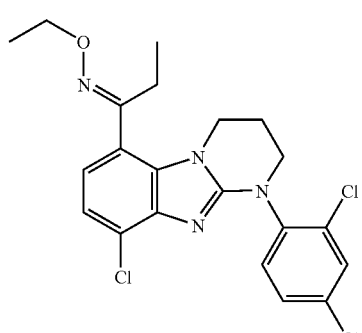

(Example 124)

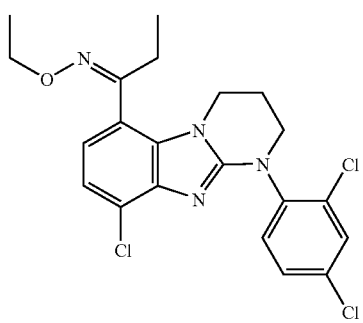

A mixture of 1-[9-chloro-1-(2,4-dichlorophenyl)-1,2,3,4-tetrahydropyrimido[1,2-a]benzimidazol-6-yl]propan-1-one (250 mg, 0.612 mmol), O-ethylhydroxylamine hydrochloride (179 mg, 1.84 mmol) and pyridine (1.5 mL) in ethanol (6.0 mL) was stirred at 80° C. for 26 hr. The mixture was concentrated in vacuo, diluted with saturated aqueous sodium hydrogen carbonate, and extracted with ethyl acetate. The combined organic layer was washed with brine, dried over anhydrous magnesium sulfate, filtered, and concentrated in vacuo. The residue was purified by flash column chromatography on silica gel eluting with a 20-40% ethyl acetate/n-hexane gradient mixture. The filtrate was concentrated in vacuo to give the solid, which was recrystallized from ethyl acetate/diisopropyl ether to give the title compounds as a colorless crystal respectively (E (Example 123): 111 mg, 0.246 mmol, 40%, Z (Example 124): 31.0 mg, 0.0686 mmol, 11%).

E Isomer (Example 123):

mp 140-141° C.

$^1$H NMR (CDCl$_3$) δ 1.10 (t, J=7.5 Hz, 3H), 1.34 (t, J=6.9 Hz, 3H), 2.28-2.36 (m, 2H), 2.79 (q, J=7.5 Hz, 2H), 3.66-3.74 (m, 2H), 4.11 (t, J=6.0 Hz, 2H), 4.22 (q, J=6.9 Hz, 2H), 6.83

(d, J=8.1 Hz, 1H), 7.09 (d, J=8.1 Hz, 1H), 7.30 (dd, J=2.1 Hz, 8.4 Hz, 1H), 7.48-7.52 (m, 2H).

MS Calcd.: 450; MS Found: 451 (M+H).

Anal. Calcd for $C_{21}H_{21}N_4OCl_3$: C, 55.83; H, 4.69; N, 12.40; Cl, 23.54. Found: C, 55.76; H, 4.68; N, 12.33; Cl, 23.67.

Z Isomer (Example 124):

mp 150-151° C.

$^1$H NMR (CDCl$_3$) δ 1.11-1.21 (m, 6H), 2.27-2.35 (m, 2H), 2.58-2.67 (m, 2H), 3.65-3.74 (m, 2H), 3.88-3.96 (m, 1H), 4.08 (q, J=7.2 Hz, 2H), 4.17-4.25 (m, 1H), 6.64 (d, J=7.8 Hz, 1H), 7.10 (d, J=7.8 Hz, 1H), 7.31 (dd, J=2.4 Hz, 8.4 Hz, 1H), 7.48-7.55 (m, 2H).

MS Calcd.: 450; MS Found: 451 (M+H).

Anal. Calcd for $C_{21}H_{21}N_4OCl_3$: C, 55.83; H, 4.69; N, 12.40; Cl, 23.54. Found: C, 55.70; H, 4.67; N, 12.35; Cl, 23.65.

Example 125

Methyl 9-chloro-1-[4-chloro-2-(trifluoromethyl) phenyl]-1,2,3,4-tetrahydropyrimido[1,2-a]benzimidazole-6-carboxylate

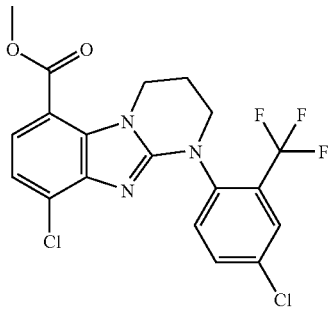 [SMILES: COC(=O)c1ccc(Cl)c2nc3n(c12)CCCN3c1ccc(Cl)cc1C(F)(F)F]

A mixture of methyl 3-amino-4-chloro-2-[(3-hydroxypropyl)amino]benzoate (12.5 g, 48.3 mmol) and 4-chloro-1-isothiocyanato-2-(trifluoromethyl)benzene (14.9 g, 62.8 mmol) in tetrahydrofuran (150 mL) was stirred at room temperature for 2 days. The mixture was concentrated in vacuo. The residue was purified by flash column chromatography on silica gel eluting with ethyl acetate. The filtrate was concentrated in vacuo to give methyl 4-chloro-3-({[4-chloro-2-(trifluoromethyl)phenyl]carbamothioyl}amino)-2-[(3-hydroxypropyl)amino]benzoate as a brown oil (22.0 g)

MS Calcd.: 495; MS Found: 496 (M+H).

A mixture of the resulting thiourea (22.0 g), 1-ethyl-3-(3-dimethylaminopropyl)carbodiimide hydrochloride (8.49 g, 44.3 mmol), and triethylamine (6.2 mL) in tetrahydrofuran (150 mL) was stirred at 50° C. for 15 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with n-hexane to give methyl 4-chloro-2-{[4-chloro-2-(trifluoromethyl)phenyl]amino}-(3-hydroxypropyl)-1H-benzimidazole-7-carboxylate as a brown powder (20.2 g).

MS Calcd.: 461; MS Found: 462 (M+H).

Methanesulfonyl chloride (13.8 mL, 175 mmol) was added dropwise to a stirred solution of the residue (20.2 g) and triethylamine (30.6 mL) in tetrahydrofuran (150 mL) at 0° C. The mixture was stirred at 0° C. for 3 hr, and diluted with aqueous sodium hydrogen carbonate and extracted with ethyl acetate. The combined organic layer was washed with brine, dried over anhydrous magnesium sulfate, filtered, and concentrated in vacuo. A mixture of the resulting mesylate, potassium carbonate (18.1 g, 131 mmol) in dimethylformamide (150 mL) was stirred at 80° C. for 4 hr. The mixture was diluted with aqueous sodium hydrogen carbonate, and extracted with ethyl acetate. The combined organic layer was washed with brine, dried over anhydrous magnesium sulfate, filtered, and concentrated in vacuo. The residue was washed with ethyl acetate/diisopropyl ether to give the title compound as a colorless powder (16.3 g, 36.7 mmol, 76% in 4 steps).

$^1$H NMR (DMSO-d$_6$) δ 2.10-2.38 (m, 2H), 3.51-3.59 (m, 1H), 3.74-3.82 (m, 1H), 3.90 (s, 3H), 4.18-4.28 (m, 1H), 4.31-4.40 (m, 1H), 7.13 (d, J=8.4 Hz, 1H), 7.33 (d, J=8.4 Hz, 1H), 7.80 (d, J=8.1 Hz, 1H), 7.91-7.96 (m, 2H).

MS Calcd.: 443; MS Found: 444 (M+H).

Example 126

{9-Chloro-1-[4-chloro-2-(trifluoromethyl)phenyl]-1,2,3,4-tetrahydropyrimido[1,2-a]benzimidazol-6-yl}methanol

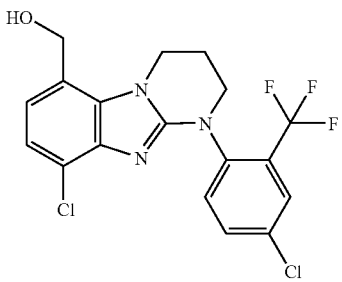 [SMILES: OCc1ccc(Cl)c2nc3n(c12)CCCN3c1ccc(Cl)cc1C(F)(F)F]

Lithium borohydride (2.14 g, 98.1 mmol) was added to a stirred solution of methyl 9-chloro-1-[4-chloro-2-(trifluoromethyl)phenyl]-1,2,3,4-tetrahydropyrimido[1,2-a]benzimidazole-6-carboxylate (10.9 g, 24.5 mmol) in tetrahydrofuran (80 mL) at room temperature, and the mixture was stirred at room temperature for 12 hr and at 50° C. for 4 hr. The reaction was quenched by methanol, and the mixture was diluted with aqueous saturated ammonium chloride at 0° C. and extracted with ethyl acetate. The combined organic layer was washed with brine, dried over anhydrous magnesium sulfate, filtered, and concentrated in vacuo. The residue was washed with ethyl acetate/diisopropyl ether to give the title compound as a colorless powder (8.81 g, 21.2 mmol, 87%).

$^1$H NMR (DMSO-d$_6$) δ 2.19-2.39 (m, 2H), 3.46-3.54 (m, 1H), 3.70-3.77 (m, 1H), 4.38-4.46 (m, 1H), 4.65-4.79 (m, 3H), 5.36 (t, J=5.4 Hz, 1H), 6.85 (d, J=8.1 Hz, 1H), 6.96 (d, J=8.1 Hz, 1H), 7.76 (d, J=8.1 Hz, 1H), 7.89-7.95 (m, 2H).

MS Calcd.: 415; MS Found: 416 (M+H).

Example 127

9-Chloro-1-[4-chloro-2-(trifluoromethyl)phenyl]-1,2,3,4-tetrahydropyrimido[1,2-a]benzimidazole-6-carbaldehyde

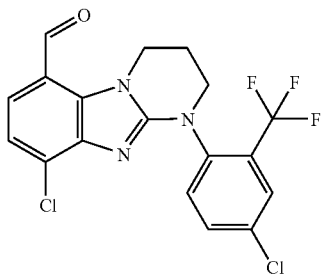 [SMILES: O=Cc1ccc(Cl)c2nc3n(c12)CCCN3c1ccc(Cl)cc1C(F)(F)F]

Sulfur trioxide-pyridine complex (23.4 g, 147 mmol) was added to a stirred solution of {9-chloro-1-[4-chloro-2-(trifluoromethyl)phenyl]-1,2,3,4-tetrahydropyrimido[1,2-a]benzimidazol-6-yl}methanol (8.72 g, 20.9 mmol), triethylamine (23.3 mL), and dimethyl sulfoxide (140 mL) in dichloromethane (30 mL) at room temperature, and the mixture was stirred at room temperature for 3 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with diisopropyl ether to give the title compound as a colorless powder (6.90 g, 16.7 mmol, 80%).

$^1$H NMR (CDCl$_3$) δ 2.23-2.50 (m, 2H), 3.60-3.75 (m, 2H), 4.50-4.63 (m, 1H), 4.70-4.83 (m, 1H), 7.21 (d, J=8.1 Hz, 1H), 7.36 (d, J=8.1 Hz, 1H), 7.46 (d, J=8.7 Hz, 1H), 7.61 (dd, J=2.1 Hz, 8.7 Hz, 1H), 7.75 (d, J=2.1 Hz, 1H), 9.98 (s, 1H).

MS Calcd.: 413; MS Found: 414 (M+H).

Example 128

3-{9-Chloro-1-[4-chloro-2-(trifluoromethyl)phenyl]-1,2,3,4-tetrahydropyrimido[1,2-a]benzimidazol-6-yl}pentan-3-ol

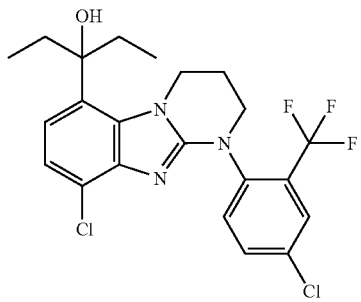 [SMILES: CCC(O)(CC)c1ccc(Cl)c2nc3n(c12)CCCN3c1ccc(Cl)cc1C(F)(F)F]

Ethylmagnesium bromide (3.0 M solution in diethyl ether, 2.6 mL, 7.8 mmol) was added to a stirred solution of methyl 9-chloro-1-[4-chloro-2-(trifluoromethyl)phenyl]-1,2,3,4-tetrahydropyrimido[1,2-a]benzimidazole-6-carboxylate (700 mg, 1.57 mmol) in tetrahydrofuran (5.0 mL), and the mixture was stirred at 60° C. for 7 hr. The reaction was quenched by water, and the mixture was extracted with ethyl acetate. The combined organic layer was washed with brine, dried over anhydrous magnesium sulfate, filtered, and concentrated in vacuo. The residue was purified by flash column chromatography on silica gel eluting with a 10-50% ethyl acetate/n-hexane gradient mixture. The filtrate was concentrated in vacuo to give the solid, which was recrystallized from ethanol/diisopropyl ether to give the title compound as a colorless crystal (412 mg, 0.872 mmol, 56%).

mp 178-180° C.

$^1$H NMR (DMSO-d$_6$) δ 0.75 (t, J=6.9 Hz, 3H), 0.83 (t, J=7.2 Hz, 3H), 1.82-1.96 (m, 4H), 2.17-2.34 (m, 2H), 3.45-3.58 (m, 1H), 3.65-3.78 (m, 1H), 4.40-4.52 (m, 1H), 5.11-5.20 (m, 1H), 5.19 (s, 1H), 6.74 (d, J=8.4 Hz, 1H), 6.95 (d, J=8.4 Hz, 1H), 7.78 (d, J=8.1 Hz, 1H), 7.90-7.93 (m, 2H).

MS Calcd.: 471; MS Found: 472 (M+H).

Example 129

4-{9-Chloro-1-[4-chloro-2-(trifluoromethyl)phenyl]-1,2,3,4-tetrahydropyrimido[1,2-a]benzimidazol-6-yl}heptan-4-ol

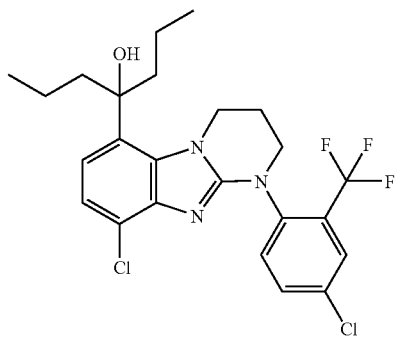 [SMILES: CCCC(O)(CCC)c1ccc(Cl)c2nc3n(c12)CCCN3c1ccc(Cl)cc1C(F)(F)F]

n-Propylmagnesium bromide (2.0 M solution in tetrahydrofuran, 3.9 mL, 7.8 mmol) was added to a stirred solution of methyl 9-chloro-1-[4-chloro-2-(trifluoromethyl)phenyl]-1,2,3,4-tetrahydropyrimido[1,2-a]benzimidazole-6-carboxylate (700 mg, 1.58 mmol) in tetrahydrofuran (5.0 mL), and the mixture was stirred at 60° C. for 6 hr. The reaction was quenched by water, and the mixture was extracted with ethyl acetate. The combined organic layer was washed with brine, dried over anhydrous magnesium sulfate, filtered, and concentrated in vacuo. The residue was purified by preparative HPLC to give a mixture contained an intermediate of the title compound as the trifluoroacetic acid salt. The mixture was washed with aqueous sodium hydrogen carbonate and extracted with ethyl acetate. The extract was washed with brine, dried over anhydrous magnesium sulfate, filtered and concentrated in vacuo to give the solid, which was recrystallized from ethanol/ethyl acetate to give the title compound as a colorless crystal (129 mg, 0.258 mmol, 16%).

mp 200-202° C.

$^1$H NMR (DMSO-d$_6$) δ 0.81-0.90 (m, 6H), 1.03-1.30 (m, 4H), 1.77-1.87 (m, 4H), 2.05-2.14 (m, 2H), 3.45-3.56 (m, 1H), 3.66-3.77 (m, 1H), 4.40-4.53 (m, 1H), 5.11-5.23 (m, 1H), 5.21 (s, 1H), 6.73 (d, J=8.4 Hz, 1H), 6.94 (d, J=8.4 Hz, 1H), 7.78 (d, J=8.1 Hz, 1H), 7.89-7.93 (m, 2H).

MS Calcd.: 499; MS Found: 500 (M+H).

Anal. Calcd for $C_{24}H_{26}N_3OCl_2F_3$: C, 57.61; H, 5.24; N, 8.40; Cl, 14.17; F, 11.39. Found: C, 57.48; H, 5.20; N, 8.36; Cl, 14.15; F, 11.18.

Example 130

9-Chloro-1-[4-chloro-2-(trifluoromethyl)phenyl]-6-(1-ethyl-1-methoxypropyl)-1,2,3,4-tetrahydropyrimido[1,2-a]benzimidazole

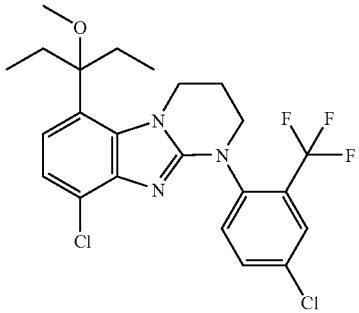 [SMILES: CCC(CC)(OC)c1ccc(Cl)c2nc3n(c12)CCCN3c1ccc(Cl)cc1C(F)(F)F]

Sodium hydride (60% in oil, 25.4 mg, 0.635 mmol) was added to a stirred solution of 3-{9-chloro-1-[4-chloro-2-(trifluoromethyl)phenyl]-1,2,3,4-tetrahydropyrimido[1,2-a]benzimidazol-6-yl}pentan-3-ol (250 mg, 0.529 mmol) in N,N-dimethylformamide (5.0 mL) at room temperature. After stirring 5 min, methyl iodide (113 mg, 0.794 mmol) was added to the mixture, and the mixture was stirred at room temperature for 3 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 5-40% ethyl acetate/n-hexane gradient mixture. The filtrate was concentrated in vacuo to give the solid, which was recrystallized from ethyl acetate/diisopropyl ether to give the title compound as a colorless crystal (175 mg, 0.360 mmol, 68%).

mp 172-173° C.

$^1$H NMR (CDCl$_3$) δ 0.81 (t, J=7.2 Hz, 6H), 1.95-2.03 (m, 4H), 2.20-2.41 (m, 2H), 2.98 (s, 3H), 3.60-3.70 (m, 2H), 4.58-4.90 (m, 2H), 6.76 (d, J=8.4 Hz, 1H), 7.01 (d, J=8.4 Hz, 1H), 7.51 (d, J=8.7 Hz, 1H), 7.61 (dd, J=2.4 Hz, 8.7 Hz, 1H), 7.74 (d, J=2.4 Hz, 1H).

MS Calcd.: 485; MS Found: 486 (M+H).

Anal. Calcd for C$_{23}$H$_{24}$N$_3$OCl$_2$F$_3$: C, 56.80; H, 4.97; N, 8.64; Cl, 14.58; F, 11.72. Found: C, 56.71; H, 4.98; N, 8.57; Cl, 14.57; F, 11.34.

Example 131

1-{9-Chloro-1-[4-chloro-2-(trifluoromethyl)phenyl]-1,2,3,4-tetrahydropyrimido[1,2-a]benzimidazol-6-yl}propan-1-ol

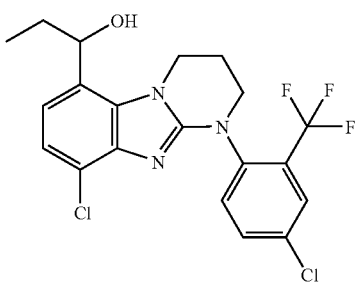 [SMILES: CCC(O)c1ccc(Cl)c2nc3n(c12)CCCN3c1ccc(Cl)cc1C(F)(F)F]

Ethylmagnesium bromide (3.0 M solution in diethyl ether, 0.35 mL, 1.05 mmol) was added to a stirred solution of 9-chloro-1-[4-chloro-2-(trifluoromethyl)phenyl]-1,2,3,4-tetrahydropyrimido[1,2-a]benzimidazole-6-carbaldehyde (400 mg, 0.966 mmol) in tetrahydrofuran (3.0 mL) at 0° C., and the mixture was stirred at room temperature for 1 hr. The reaction was quenched by water, and the mixture was extracted with ethyl acetate. The combined organic layer was washed with brine, dried over anhydrous magnesium sulfate, filtered, and concentrated in vacuo. The residue was recrystallized from ethanol to give the title compound as a colorless crystal (411 mg, 0.925 mmol, 96%).

mp 220-222° C.

$^1$H NMR (DMSO-d$_6$) δ 0.94 (t, J=7.5 Hz, 3H), 1.73-1.81 (m, 2H), 2.19-2.40 (m, 2H), 3.44-3.56 (m, 1H), 3.68-3.80 (m, 1H), 4.30-4.43 (m, 1H), 4.56-4.68 (m, 1H), 4.93-5.05 (m, 1H), 5.23-5.34 (m, 1H), 6.96-7.01 (m, 2H), 7.76 (d, J=8.4 Hz, 1H), 7.89-7.94 (m, 2H).

MS Calcd.: 443; MS Found: 444 (M+H).

Example 132

{9-Chloro-1-[4-chloro-2-(trifluoromethyl)phenyl]-1,2,3,4-tetrahydropyrimido[1,2-a]benzimidazol-6-yl}(cyclopropyl)methanol

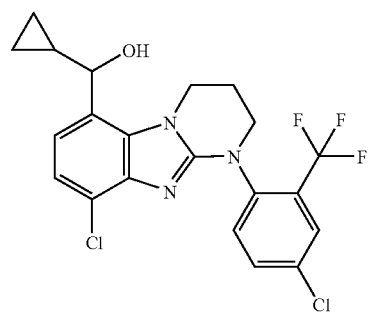 [SMILES: OC(c1ccc(Cl)c2nc3n(c12)CCCN3c1ccc(Cl)cc1C(F)(F)F)C1CC1]

Cyclopropylmagnesium bromide (1.0 M solution in tetrahydrofuran, 2.9 mL, 2.9 mmol) was added to a stirred solution of 9-chloro-1-[4-chloro-2-(trifluoromethyl)phenyl]-1,2,3,4-tetrahydropyrimido[1,2-a]benzimidazole-6-carbaldehyde (1.00 g, 2.41 mmol) in tetrahydrofuran (10 mL) at 0° C., and the mixture was stirred at room temperature for 1 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was recrystallized from ethyl acetate to give the title compound as a colorless crystal (567 mg, 1.24 mmol, 51%).

mp 224-225° C.

$^1$H NMR (DMSO-d$_6$) δ 0.20-0.28 (m, 1H), 0.44-0.68 (m, 3H), 1.31-1.45 (m, 1H), 2.20-2.40 (m, 2H), 3.44-3.56 (m, 1H), 3.68-3.80 (m, 1H), 4.30-4.44 (m, 1H), 4.45-4.58 (m, 1H), 4.63-4.80 (m, 1H), 5.34 (dd, J=4.4 Hz, 18.9 Hz, 1H), 6.95-7.16 (m, 2H), 7.75 (d, J=8.4 Hz, 1H), 7.89-7.95 (m, 2H).

MS Calcd.: 455; MS Found: 456 (M+H).

Example 133

9-Chloro-1-[4-chloro-2-(trifluoromethyl)phenyl]-6-(1-methoxypropyl)-1,2,3,4-tetrahydropyrimido[1,2-a]benzimidazole

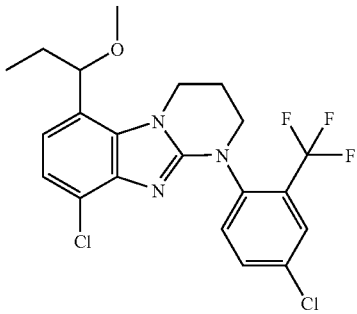 [SMILES: CCC(OC)c1ccc(Cl)c2nc3n(c12)CCCN3c1ccc(Cl)cc1C(F)(F)F]

Sodium hydride (60% in oil, 40.0 mg, 1.00 mmol) was added to a stirred solution of 1-{9-chloro-1-[4-chloro-2-(trifluoromethyl)phenyl]-1,2,3,4-tetrahydropyrimido[1,2-a]benzimidazol-6-yl}propan-1-ol (370 mg, 0.833 mmol) in N,N-dimethylformamide (3.0 mL) at room temperature. After stirring 5 min, methyl iodide (177 mg, 1.25 mmol) was added to the mixture, and the mixture was stirred at, room temperature for 4 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 10-40% ethyl acetate/n-hexane gradient mixture. The filtrate was concentrated in vacuo to give the solid, which was recrystallized from ethyl acetate/diisopropyl ether to give the title compound as a colorless crystal (299 mg, 0.652 mmol, 78%).

mp 202-203° C.

$^1$H NMR (CDCl$_3$) δ 0.97 (t, J=7.2 Hz, 3H), 1.75-2.02 (m, 2H), 2.22-2.50 (m, 2H), 3.24 (s, 3H), 3.58-3.70 (m, 2H), 4.23-4.70 (m, 2H), 4.52 (t, J=6.9 Hz, 1H), 6.89 (d, J=8.4 Hz, 1H), 7.05 (d, J=8.4 Hz, 1H), 7.50 (d, J=8.7 Hz, 1H), 7.60 (dd, J=2.1 Hz, 8.7 Hz, 1H), 7.74 (d, J=2.1 Hz, 1H).

MS Calcd.: 457; MS Found: 458 (M+H).

Anal. Calcd for C$_{21}$H$_{20}$N$_3$OCl$_2$F$_3$: C, 55.03; H, 4.40; N, 9.17; Cl, 15.47; F, 12.44. Found: C, 54.92; H, 4.39; N, 9.12; Cl, 15.60; F, 12.12.

Example 134

9-Chloro-1-[4-chloro-2-(trifluoromethyl)phenyl]-6-[cyclopropyl(methoxy)methyl]-1,2,3,4-tetrahydropyrimido[1,2-a]benzimidazole

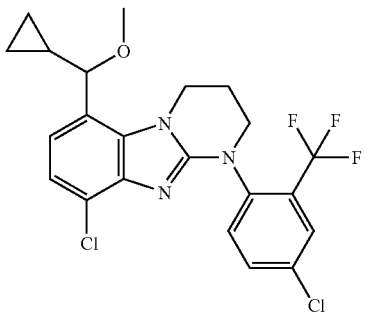 [SMILES: COC(c1ccc(Cl)c2nc3n(c12)CCCN3c1ccc(Cl)cc1C(F)(F)F)C1CC1]

Sodium hydride (60% in oil, 52.4 mg, 1.31 mmol) was added to a stirred solution of {9-chloro-1-[4-chloro-2-(trifluoromethyl)phenyl]-1,2,3,4-tetrahydropyrimido[1,2-a]benzimidazol-6-yl}(cyclopropyl)methanol (500 mg, 1.09 mmol) in N,N-dimethylformamide (4.0 mL) at room temperature. After stirring 5 min, methyl iodide (232 mg, 1.64 mmol) was added to the mixture, and the mixture was stirred at room temperature for 3 hr. The mixture was diluted with water, and extracted with ethyl acetate. The combined organic layer was washed with brine, dried over anhydrous magnesium sulfate, filtered, and concentrated in vacuo. The residue was recrystallized from ethyl acetate/n-hexane to give the title compound as a colorless crystal (396 mg, 0.842 mmol, 77%).

mp 208-209° C.

$^1$H NMR (CDCl$_3$) δ 0.22-0.29 (m, 1H), 0.38-0.45 (m, 1H), 0.53-0.62 (m, 1H), 0.68-0.80 (m, 1H), 1.34-1.42 (m, 1H), 2.20-2.48 (m, 2H), 3.30 (s, 3H), 3.58-3.72 (m, 2H), 4.11 (d, J=7.2 Hz, 1H), 4.30-4.80 (m, 2H), 6.88 (d, J=8.1 Hz, 1H), 7.03 (d, J=8.1 Hz, 1H), 7.49 (d, J=8.4 Hz, 1H), 7.59 (dd, J=2.7 Hz, 8.4 Hz, 1H), 7.74 (d, J=2.7 Hz, 1H).

MS Calcd.: 469; MS Found: 470 (M+H).

Anal. Calcd for C$_{22}$H$_{20}$N$_3$OCl$_2$F$_3$: C, 56.18; H, 4.29; N, 8.93; Cl, 15.08; F, 12.12. Found: C, 56.14; H, 4.27; N, 8.84; Cl, 15.11; F, 11.97.

Example 135

Methyl 9-chloro-1-(2,4-dichloro-6-methylphenyl)-1,2,3,4-tetrahydropyrimido[1,2-a]benzimidazole-6-carboxylate

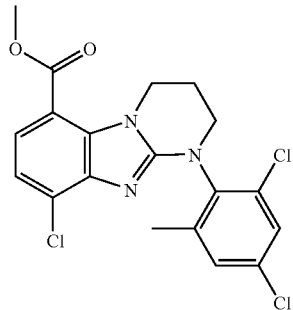 [SMILES: COC(=O)c1ccc(Cl)c2nc3n(c12)CCCN3c1c(C)cc(Cl)cc1Cl]

A mixture of methyl 4-chloro-3-{[(2,4-dichloro-6-methylphenyl)carbamothioyl]amino}-2-[(3-hydroxypropyl)amino]benzoate (Reference example 118, 2.17 g, 4.55 mmol), 1-ethyl-3-(3-dimethylaminopropyl)carbodiimide hydrochloride (872 mg, 4.55 mmol) and triethylamine (0.70 mL) in tetrahydrofuran (20 mL) was stirred at 50° C. for 12 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 10-60% ethyl acetate/n-hexane gradient mixture. The filtrate was concentrated in vacuo to give methyl 4-chloro-2-[(2,4-dichloro-6-methylphenyl)amino]-1-(3-hydroxypropyl)-1H-benzimidazole-7-carboxylate as a brown wax (1.67 g).

MS Calcd.: 441; MS Found: 442 (M+H).

Methanesulfonyl chloride (1.2 mL, 14.9 mmol) was added dropwise to a stirred solution of the residue (1.66 g) and triethylamine (2.6 mL) in tetrahydrofuran (20 mL) at 0° C. The mixture was stirred at room temperature for 18 hr, and diluted with aqueous sodium hydrogen carbonate and extracted with ethyl acetate. The combined organic layer was washed with brine, dried over anhydrous magnesium sulfate, filtered, and concentrated in vacuo. A mixture of the resulting mesylate and potassium carbonate (1.56 g, 11.3 mmol) in N,N-dimethylformamide (30 mL) was stirred at 80° C. for 5 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 10-50% ethyl acetate/n-hexane gradient mixture. The filtrate was concentrated in vacuo to give the solid, which was washed with diisopropyl ether to give the title compound as a colorless powder (1.35 g, 3.18 mmol, 70% in 3 steps).

$^1$H NMR (CDCl$_3$) δ 2.25 (s, 3H), 2.26-2.43 (s, 2H), 3.49-3.57 (m, 1H), 3.72-3.78 (m, 1H), 3.94 (s, 3H), 4.39-4.44 (m, 2H), 7.07 (d, J=8.7 Hz, 1H), 7.20-7.21 (m, 1H), 7.34-7.35 (m, 1H), 7.43 (d, J=8.7 Hz, 1H).

MS Calcd.: 423; MS Found: 424 (M+H).

Example 136

[9-Chloro-1-(2,4-dichloro-6-methylphenyl)-1,2,3,4-tetrahydropyrimido[1,2-a]benzimidazol-6-yl]methanol

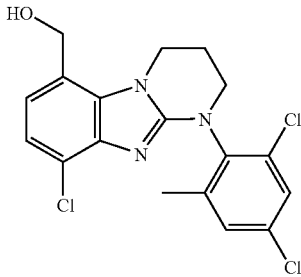 [SMILES: Cc1cc(Cl)cc(Cl)c1N1CCCn2c1nc1c(Cl)ccc(CO)c12]

Lithium borohydride (205 mg, 9.42 mmol) was added to a stirred solution of methyl 9-chloro-1-(2,4-dichloro-6-methylphenyl)-1,2,3,4-tetrahydropyrimido[1,2-a]benzimidazole-6-carboxylate (800 mg, 1.88 mmol) in tetrahydrofuran (4.0 mL) at room temperature, and the mixture was stirred at 50° C. for 13 hr. The reaction was quenched by aqueous saturated ammonium chloride at 0° C. and the mixture was extracted with ethyl acetate. The combined organic layer was washed with brine, dried over anhydrous magnesium sulfate, filtered, and concentrated in vacuo. The residue was washed with ethyl acetate/diisopropyl ether to give the title compound as a colorless powder (620 mg, 1.56 mmol, 83%).

$^1$H NMR (DMSO-d$_6$) δ 2.23 (s, 3H), 2.27-2.33 (m, 2H), 3.56-3.64 (m, 2H), 4.51-4.60 (m, 2H), 4.73 (d, J=5.4 Hz, 2H), 5.36 (t, J=5.4 Hz, 1H), 6.83 (d, J=8.1 Hz, 1H), 6.94 (d, J=8.1 Hz, 1H), 7.49 (d, J=2.4 Hz, 1H), 7.63 (d, J=2.4 Hz, 1H).

MS Calcd.: 395; MS Found: 396 (M+H).

Example 137

9-Chloro-1-(2,4-dichloro-6-methylphenyl)-1,2,3,4-tetrahydropyrimido[1,2-a]benzimidazole-6-carbaldehyde

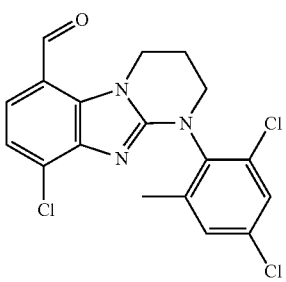 [SMILES: Cc1cc(Cl)cc(Cl)c1N1CCCn2c1nc1c(Cl)ccc(C=O)c12]

Sulfur trioxide-pyridine complex (1.71 g, 10.7 mmol) was added to a stirred solution of [9-chloro-1-(2,4-dichloro-6-methylphenyl)-1,2,3,4-tetrahydropyrimido[1,2-a]benzimidazol-6-yl]methanol (610 mg, 1.54 mmol), triethylamine (1.72 mL) in dimethyl sulfoxide (20 mL) at room temperature, and the mixture was stirred at room temperature for 7 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 10-50% ethyl acetate/n-hexane gradient mixture. The filtrate was concentrated in vacuo to give the title compound as a colorless solid (185 mg, 0.469 mmol, 30%).

$^1$H NMR (CDCl$_3$) δ 2.26 (s, 3H), 2.26-2.50 (m, 2H), 3.51-3.58 (m, 1H), 3.72-3.78 (m, 1H), 4.66-4.72 (m, 2H), 7.18-7.23 (m, 2H), 7.32-7.36 (m, 2H), 9.98 (s, 1H).

MS Calcd.: 393; MS Found: 394 (M+H).

Example 138

[9-Chloro-1-(2,4-dichloro-6-methylphenyl)-1,2,3,4-tetrahydropyrimido[1,2-a]benzimidazol-6-yl](dicyclopropyl)methanol

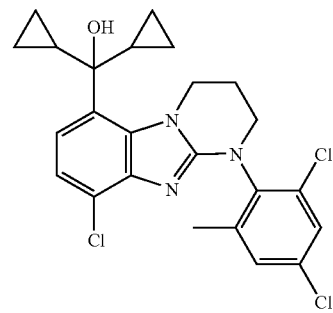 [SMILES: Cc1cc(Cl)cc(Cl)c1N1CCCn2c1nc1c(Cl)ccc(C(O)(C3CC3)C3CC3)c12]

Cyclopropylmagnesium bromide (1.0 M solution in tetrahydrofuran, 2.4 mL, 2.4 mmol) was added to a stirred solution of methyl 9-chloro-1-(2,4-dichloro-6-methylphenyl)-1,2,3,4-tetrahydropyrimido[1,2-a]benzimidazole-6-carboxylate (200 mg, 0.471 mmol) in tetrahydrofuran (3.0 mL), and the mixture was stirred at 60° C. for 8 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was purified by flash column chromatography on silica gel eluting with a 8-50% ethyl acetate/n-hexane gradient mixture. The filtrate was concentrated in vacuo to give the solid, which was recrystallized from ethyl acetate/diisopropyl ether to give the title compound as a colorless crystal (179 mg, 0.375 mmol, 80%).

mp 210-212° C.

$^1$H NMR (CDCl$_3$) δ 0.20-0.30 (m, 2H), 0.51-0.65 (m, 6H), 1.36-1.48 (m, 2H), 1.73 (s, 1H), 2.18-2.40 (m, 2H), 2.26 (s, 3H), 3.43-3.51 (m, 1H), 3.67-3.76 (m, 1H), 4.83 (t, J=5.7 Hz, 2H) 6.98 (d, J=8.1 Hz, 1H), 7.12 (d, J=8.1 Hz, 1H), 7.19-7.21 (m, 1H), 7.34 (d, J=2.4 Hz, 1H).

MS Calcd.: 475; MS Found: 476 (M+H).

Anal. Calcd for $C_{24}H_{24}N_3OCl_3$: C, 60.45; H, 5.07; N, 8.81; Cl, 22.31. Found: C, 60.54; H, 5.15; N, 8.69; Cl, 22.11.

Example 139

4-[9-Chloro-1-(2,4-dichloro-6-methylphenyl)-1,2,3,4-tetrahydropyrimido[1,2-a]benzimidazol-6-yl]heptan-4-ol

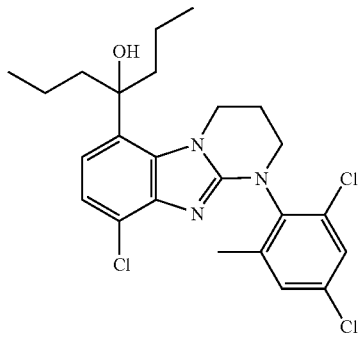 [SMILES: CCCC(O)(CCC)c1ccc(Cl)c2nc3n(c12)CCCN3c1c(C)cc(Cl)cc1Cl]

n-Propylmagnesium bromide (2.0 M solution in tetrahydrofuran, 1.2 mL, 2.4 mmol) was added to a stirred solution of methyl 9-chloro-1-(2,4-dichloro-6-methylphenyl)-1,2,3,4-tetrahydropyrimido[1,2-a]benzimidazole-6-carboxylate (200 mg, 0.471 mmol) in tetrahydrofuran (3.0 mL), and the mixture was stirred at 60° C. for 8 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was purified by flash column chromatography on silica gel eluting with a 2-50% ethyl acetate/n-hexane gradient mixture. The filtrate was concentrated in vacuo to give the solid, which was recrystallized from ethyl acetate/diisopropyl ether to give the title compound as a colorless crystal (113 mg, 0.235 mmol, 50%).

mp 176-178° C.

$^1$H NMR (CDCl$_3$) δ 0.88-0.97 (m, 6H), 1.22-1.31 (m, 2H), 1.37-1.50 (m, 2H), 1.65-2.04 (m, 5H), 2.20-2.42 (m, 2H), 2.26 (s, 3H), 3.42-3.52 (m, 1H), 3.68-3.77 (m, 1H), 4.74 (t, J=6.0 Hz, 2H), 6.68 (d, J=8.4 Hz, 1H), 6.98 (d, J=8.4 Hz, 1H), 7.20-7.21 (m, 1H), 7.33-7.34 (m, 1H).

MS Calcd.: 479; MS Found: 480 (M+H).

Example 140

1-[9-Chloro-1-(2,4-dichloro-6-methylphenyl)-1,2,3,4-tetrahydropyrimido[1,2-a]benzimidazol-6-yl]butan-1-ol

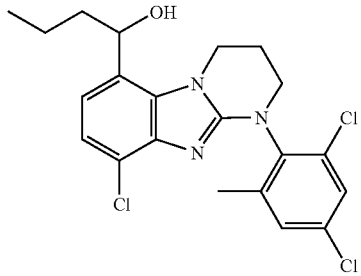 [SMILES: CCCC(O)c1ccc(Cl)c2nc3n(c12)CCCN3c1c(C)cc(Cl)cc1Cl]

n-Propylmagnesium bromide (2.0 M solution in tetrahydrofuran, 0.25 mL, 0.50 mmol) was added to a stirred solution of 9-chloro-1-(2,4-dichloro-6-methylphenyl)-1,2,3,4-tetrahydropyrimido[1,2-a]benzimidazole-6-carbaldehyde (179 mg, 0.453 mmol) in tetrahydrofuran (2.0 mL) at 0° C., and the mixture was stirred at room temperature for 12 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was purified by flash column chromatography on silica gel eluting with a 2-50% ethyl acetate/n-hexane gradient mixture. The filtrate was concentrated in vacuo to give the title compound as a colorless amorphous (rotamer 1; 72.3 mg, 0.165 mmol, 36%, rotamer 2; 68.7 mg, 0.157 mmol, 35%).

Rotamer 1;
Amorphous.
$^1$H NMR (CDCl$_3$) δ 0.97 (t, J=7.2 Hz, 3H), 1.37-1.57 (m, 2H), 1.78-1.90 (m, 2H), 2.22 (s, 3H), 2.23-2.48 (m, 3H), 3.45-3.53 (m, 1H), 3.68-3.75 (m, 1H), 4.06-4.14 (m, 1H), 4.38-4.58 (m, 1H), 5.06 (t, J=5.1 Hz, 1H), 6.92 (d, J=8.4 Hz, 1H), 6.98 (d, J=8.4 Hz, 1H), 7.17-7.19 (m, 1H), 7.34 (d, J=1.5 Hz, 1H).

MS Calcd.: 437; MS Found: 438 (M+H).

Rotamer 2;
Amorphous.
$^1$H NMR (CDCl$_3$) δ 0.99 (t, J=7.2 Hz, 3H), 1.32-1.63 (m, 2H), 1.80-1.97 (m, 2H), 2.16 (s, 1H), 2.28 (s, 3H), 2.29-2.48 (m, 2H), 3.46-3.52 (m, 1H), 3.70-3.78 (m, 1H), 4.45-4.58 (m, 2H), 5.03-5.13 (m, 1H), 6.90 (d, J=8.1 Hz, 1H), 7.00 (d, J=8.1 Hz, 1H), 7.19-7.21 (m, 1H), 7.31-7.33 (m, 1H).

MS Calcd.: 437; MS Found: 438 (M+H).

Example 141

9-Chloro-1-(2,4-dichloro-6-methylphenyl)-6-(1-methoxybutyl)-1,2,3,4-tetrahydropyrimido[1,2-a]benzimidazole

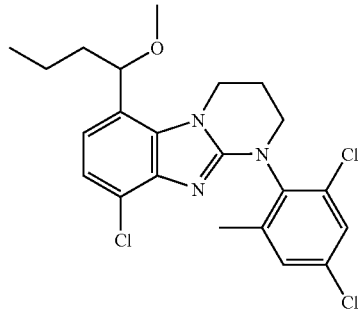

Sodium hydride (60% in oil, 7.6 mg, 0.190 mmol) was added to a stirred solution of 1-[9-chloro-1-(2,4-dichloro-6-methylphenyl)-1,2,3,4-tetrahydropyrimido[1,2-a]benzimidazol-6-yl]butan-1-ol (69.5 mg, 0.158 mmol) in N,N-dimethylformamide (1.0 mL) at room temperature. After stirring 5 min, methyl iodide (33.6 mg, 0.237 mmol) was added to the mixture, and the mixture was stirred at room temperature for 3 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 5-50% ethyl acetate/n-hexane gradient mixture. The filtrate was concentrated in vacuo to give the solid, which was recrystallized from ethyl acetate/diisopropyl ether to give the title compound as a colorless crystal (43.4 mg, 0.0958 mmol, 61%).

mp 151-152° C.

$^1$H NMR (CDCl$_3$) δ 0.95 (t, J=7.2 Hz, 3H), 1.35-1.60 (m, 2H), 1.70-1.79 (m, 1H), 1.86-1.95 (m, 1H), 2.04 (s, 3H), 2.04-2.45 (m, 2H), 3.24 (s, 3H), 3.23-3.51 (m, 1H), 3.75-3.82 (m, 1H), 4.34-4.43 (m, 1H), 4.56-4.63 (m, 2H), 6.85 (d, J=8.1 Hz, 1H), 7.03 (d, J=8.1 Hz, 1H), 7.20-7.21 (m, 1H), 7.34 (d, J=2.4 Hz, 1H).

MS Calcd.: 451; MS Found: 452 (M+H).

Example 142

[9-Chloro-1-(2,4-dichlorophenyl)-1,2,3,4-tetrahydropyrimido[1,2-a]benzimidazol-6-yl]acetonitrile

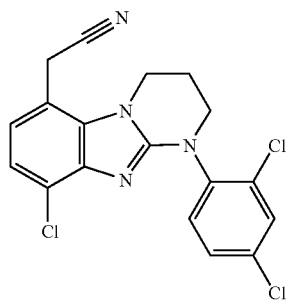 [SMILES: N#CCc1ccc(Cl)c2nc3n(c12)CCCN3c1ccc(Cl)cc1Cl]

Thionyl chloride (0.53 mL, 7.22 mmol) was added to a stirred solution of [9-chloro-1-(2,4-dichlorophenyl)-1,2,3,4-tetrahydropyrimido[1,2-a]benzimidazol-6-yl]methanol (1.38 g, 3.61 mmol) and pyridine (0.10 mL) in tetrahydrofuran (30 mL) at 0° C., and the mixture was stirred at room temperature for 90 min. The mixture was diluted with saturated aqueous sodium hydrogen carbonate, and extracted with ethyl acetate. The combined organic layer was washed with brine, dried over anhydrous magnesium sulfate, filtered, and concentrated in vacuo. A solution of sodium cyanide (354 mg, 7.22 mmol) in water (1.5 mL) was added to the resulting benzyl chloride in dimethylsulfoxide (12 mL), and the mixture was stirred at room temperature for 14 hr. The mixture was diluted with saturated aqueous sodium hydrogen carbonate, and the precipitate was collected by filtration, washed with diisopropyl ether to give the title compound as a colorless powder (1.36 g, 3.47 mmol, 96% in 2 steps).

$^1$H NMR (CDCl$_3$) δ 2.39-2.49 (m, 2H), 3.68-3.78 (m, 2H), 4.00 (s, 2H), 4.54 (t, J=6.0 Hz, 2H), 6.82 (d, J=8.1 Hz, 1H), 7.06 (d, J=8.1 Hz, 1H), 7.22 (dd, J=2.1 Hz, 8.7 Hz, 1H), 7.47-7.50 (m, 2H).
MS Calcd.: 390; MS Found: 391 (M+H).

Example 143

2-[9-Chloro-1-(2,4-dichlorophenyl)-1,2,3,4-tetrahydropyrimido[1,2-a]benzimidazol-6-yl]butanenitrile

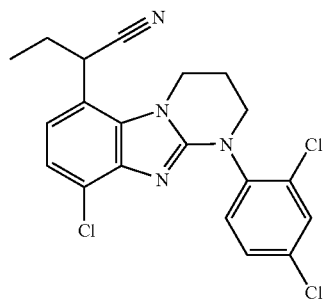 [SMILES: CCC(C#N)c1ccc(Cl)c2nc3n(c12)CCCN3c1ccc(Cl)cc1Cl]

Potassium t-butoxide (315 mg, 2.81 mmol) was added to a stirred solution of [9-chloro-1-(2,4-dichlorophenyl)-1,2,3,4-tetrahydropyrimido[1,2-a]benzimidazol-6-yl]acetonitrile (500 mg, 1.28 mmol) and ethyl iodide (499 mg, 3.20 mmol) in tetrahydrofuran (13 mL) at 0° C., and the mixture was stirred at 0° C. for 1 hr. The mixture was diluted with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 20-50% ethyl acetate/n-hexane gradient mixture. The filtrate was concentrated in vacuo to give the solid, which was recrystallized from ethanol/ethyl acetate to give the title compound as a colorless crystal (202 mg, 0.481 mmol, 38%).
mp 220-221° C.
$^1$H NMR (CDCl$_3$) δ 1.18 (t, J=7.5 Hz, 3H), 2.00-2.10 (m, 2H), 2.39-2.46 (m, 2H), 3.68-3.76 (m, 2H), 4.27-4.37 (m, 2H), 4.44-4.50 (m, 1H), 7.01 (d, J=8.4 Hz, 1H), 7.12 (d, J=8.4 Hz, 1H), 7.31 (dd, J=2.4 Hz, 8.7 Hz, 1H), 7.48-7.51 (m, 2H).
MS Calcd.: 418; MS Found: 419 (M+H).

Example 144

2-[9-Chloro-1-(2,4-dichlorophenyl)-1,2,3,4-tetrahydropyrimido[1,2-a]benzimidazol-6-yl]-2-methylpropanenitrile

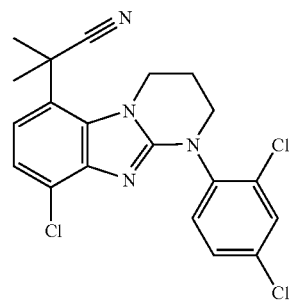 [SMILES: CC(C)(C#N)c1ccc(Cl)c2nc3n(c12)CCCN3c1ccc(Cl)cc1Cl]

Potassium t-butoxide (315 mg, 2.81 mmol) was added to a stirred solution of [9-chloro-1-(2,4-dichlorophenyl)-1,2,3,4-tetrahydropyrimido[1,2-a]benzimidazol-6-yl]acetonitrile (500 mg, 1.28 mmol) and methyl iodide (454 mg, 3.20 mmol) in tetrahydrofuran (13 mL) at 0° C., and the mixture was stirred at 0° C. for 1 hr. The mixture was diluted with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 25-60% ethyl acetate/n-hexane gradient mixture. The filtrate was concentrated in vacuo to give mono-methylated compound (295 mg). Potassium t-butoxide (178 mg, 1.58 mmol) was added to a stirred solution of the mono-methylated compound (293 mg, 0.722 mmol) and methyl iodide (255 mg, 1.81 mmol) in tetrahydrofuran (2.5 mL) at 0° C., and the mixture was stirred at room temperature for 11 hr. The mixture was diluted with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 15-50% ethyl acetate/n-hexane gradient mixture. The filtrate was concentrated in vacuo to give the solid, which was washed diisopropyl ether/n-hexane to give the title compound as a colorless amorphous (255 mg, 0.608 mmol, 47%).
Amorphous.
$^1$H NMR (CDCl$_3$) δ 1.91 (s, 6H), 2.39-2.47 (m, 2H), 3.68-3.77 (m, 2H), 4.78 (t, J=6.0 Hz, 2H), 6.86 (d, J=8.4 Hz, 1H), 7.06 (d, J=8.4 Hz, 1H), 7.32 (dd, J=2.1 Hz, 8.7 Hz, 1H), 7.47-7.51 (m, 2H).
MS Calcd.: 418; MS Found: 419 (M+H).

Example 145

2-[9-Chloro-1-(2,4-dichlorophenyl)-1,2,3,4-tetrahydropyrimido[1,2-a]benzimidazol-6-yl]butanal

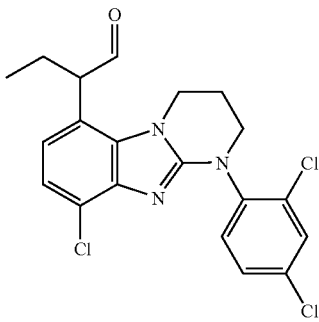 [SMILES: CCC(C=O)c1ccc(Cl)c2nc3n(c12)CCCN3c1ccc(Cl)cc1Cl]

Diisobutylaluminium hydride (1.5 M solution in toluene, 0.28 mL, 0.42 mmol) was added to a stirred solution of 2-[9-chloro-1-(2,4-dichlorophenyl)-1,2,3,4-tetrahydropyrimido[1,2-a]benzimidazol-6-yl]butanenitrile (122 mg, 0.291 mmol) in toluene (2.9 mL) at 0° C., and the mixture was stirred at 0° C. for 1 hr. The reaction was quenched by aqueous saturated ammonium chloride, and the mixture was diluted with 1N hydrochloric acid. The mixture was stirred at room temperature for 30 min, and neutralized with saturated aqueous sodium hydrogen carbonate, and extracted with ethyl acetate. The combined organic layer was washed with brine, dried over anhydrous magnesium sulfate, filtered, and concentrated in vacuo. The residue was purified by flash column chromatography on silica gel eluting with a 20-50% ethyl acetate/n-hexane gradient mixture. The filtrate was concentrated in vacuo to give the title compound as a colorless solid (92.7 mg, 0.219 mmol, 75%).

$^1$H NMR (CDCl$_3$) δ 1.01 (t, J=7.5 Hz, 3H), 1.89-2.00 (m, 1H), 2.12-2.23 (m, 1H), 2.36-2.42 (m, 2H), 3.66-3.74 (m, 2H), 4.01-4.08 (m, 1H), 4.31-4.37 (m, 1H), 4.55-4.61 (m, 1H), 6.74 (d, J=8.1 Hz, 1H), 7.11 (d, J=8.1 Hz, 1H), 7.30 (dd, J=2.4 Hz, 8.4 Hz, 1H), 7.47-7.52 (m, 2H), 9.60 (d, J=3.3 Hz, 1H).

MS Calcd.: 421; MS Found: 422 (M+H).

Example 146

2-[9-Chloro-1-(2,4-dichlorophenyl)-1,2,3,4-tetrahydropyrimido[1,2-a]benzimidazol-6-yl]-2-methylpropanal

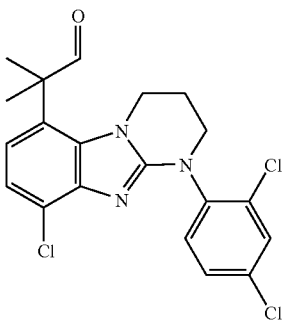 [SMILES: CC(C)(C=O)c1ccc(Cl)c2nc3n(c12)CCCN3c1ccc(Cl)cc1Cl]

Diisobutylaluminium hydride (1.5 M solution in toluene, 0.39 mL, 0.585 mmol) was added to a stirred solution of 2-[9-chloro-1-(2,4-dichlorophenyl)-1,2,3,4-tetrahydropyrimido[1,2-a]benzimidazol-6-yl]-2-methylpropanenitrile (169 mg, 0.403 mmol) in toluene (4.0 mL) at 0° C., and the mixture was stirred at 0° C. for 1 hr. The reaction was quenched by aqueous saturated ammonium chloride, and the mixture was diluted with 1N hydrochloric acid. The mixture was stirred at room temperature for 30 min, and neutralized with saturated aqueous sodium hydrogen carbonate, and extracted with ethyl-acetate. The combined organic layer was washed with brine, dried over anhydrous magnesium sulfate, filtered, and concentrated in vacuo. The residue was purified by flash column chromatography on silica gel eluting with a 20-50% ethyl acetate/n-hexane gradient mixture. The filtrate was concentrated in vacuo to give the title compound as a colorless solid (150 mg, 0.355 mmol, 88%).

$^1$H NMR (CDCl$_3$) δ 1.58 (s, 6H), 2.26-2.34 (m, 2H), 3.62-3.70 (m, 2H), 4.02-4.09 (m, 2H), 6.94 (d, J=8.7 Hz, 1H), 7.12 (d, J=8.7 Hz, 1H), 7.31 (dd, J=2.4 Hz, 8.7 Hz, 1H), 7.46-7.49 (m, 2H), 9.82 (s, 1H).

MS Calcd.: 421; MS Found: 422 (M+H).

Example 147

2-[9-Chloro-1-(2,4-dichlorophenyl)-1,2,3,4-tetrahydropyrimido[1,2-a]benzimidazol-6-yl]butan-1-ol

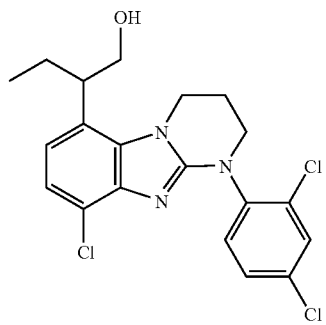 [SMILES: CCC(CO)c1ccc(Cl)c2nc3n(c12)CCCN3c1ccc(Cl)cc1Cl]

Sodium borohydride (13.5 mg, 0.357 mmol) was added to a stirred solution of 2-[9-chloro-1-(2,4-dichlorophenyl)-1,2,3,4-tetrahydropyrimido[1,2-a]benzimidazol-6-yl]butanal (151 mg, 0.357 mmol) in tetrahydrofuran (3.0 mL) at 0° C., and the mixture was stirred at 0° C. for 2 hr. The reaction was quenched by aqueous saturated ammonium chloride at 0° C. and the mixture was extracted with ethyl acetate. The combined organic layer was washed with brine, dried over anhydrous magnesium sulfate, filtered, and concentrated in vacuo. The residue was recrystallized from ethanol/ethyl acetate to give the title compound as a colorless crystal (143 mg, 0.337 mmol, 94%).

mp 162-164° C.

$^1$H NMR (CDCl$_3$) δ 0.90 (t, J=7.5 Hz, 3H), 1.42-1.47 (m, 1H), 1.64-1.84 (m, 2H), 2.32-2.40 (m, 2H), 3.46-3.57 (m, 1H), 3.60-3.80 (m, 3H), 3.80-3.93 (m, 1H), 4.25-4.38 (m, 1H), 4.59-4.69 (m, 1H), 6.80 (d, J=8.4 Hz, 1H), 7.10 (d, J=8.4 Hz, 1H), 7.29 (dd, J=2.4 Hz, 9.0 Hz, 1H), 7.48 (d, J=2.4 Hz, 1H), 7.52 (d, J=9.0 Hz, 1H).

MS Calcd.: 423; MS Found: 424 (M+H).

Example 148

2-[9-Chloro-1-(2,4-dichlorophenyl)-1,2,3,4-tetrahydropyrimido[1,2-a]benzimidazol-6-yl]-2-methylpropan-1-ol

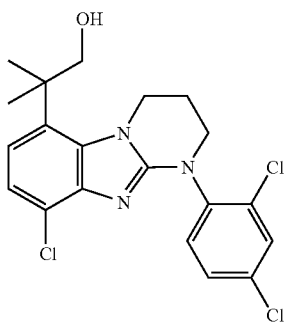 [SMILES: CC(C)(CO)c1ccc(Cl)c2nc3n(c12)CCCN3c1ccc(Cl)cc1Cl]

Sodium borohydride (11.4 mg, 0.300 mmol) was added to a stirred solution of 2-[9-chloro-1-(2,4-dichlorophenyl)-1,2,3,4-tetrahydropyrimido[1,2-a]benzimidazol-6-yl]-2-methylpropanal (127 mg, 0.300 mmol) in tetrahydrofuran (3.0 mL) at 0° C., and the mixture was stirred at 0° C. for 1 hr. The reaction was quenched by aqueous saturated ammonium chloride at 0° C. and the mixture was extracted with ethyl acetate. The combined organic layer was washed with brine, dried over anhydrous magnesium sulfate, filtered, and concentrated in vacuo. The residue was recrystallized from ethanol/ethyl acetate to give the title compound as a colorless crystal (108 mg, 0.254 mmol, 85%).

mp 176-177° C.
$^1$H NMR (CDCl$_3$) δ 1.53 (s, 6H), 1.62 (t, J=6.3 Hz, 1H), 2.35-2.43 (m, 2H), 3.67-3.75 (m, 2H), 3.85 (d, J=6.3 Hz, 2H), 4.50 (t, J=5.7 Hz, 2H), 6.93 (d, J=8.4 Hz, 1H), 7.04 (d, J=8.4 Hz, 1H), 7.32 (dd, J=2.1 Hz, 8.4 Hz, 1H), 7.47-7.50 (m, 2H).
MS Calcd.: 423; MS Found: 424 (M+H).
Anal. Calcd for C$_{20}$H$_{20}$N$_3$OCl$_3$: C, 56.55; H, 4.75; N, 9.89; Cl, 25.04. Found: C, 56.56; H, 4.86; N, 9.74; Cl, 24.99.

Example 149

9-Chloro-1-(2,4-dichlorophenyl)-6-[1-(methoxymethyl)propyl]-1,2,3,4-tetrahydropyrimido[1,2-a]benzimidazole

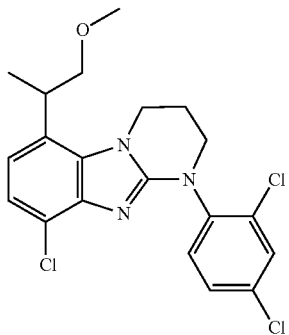 [SMILES: COCC(C)c1ccc(Cl)c2nc3n(c12)CCCN3c1ccc(Cl)cc1Cl]

Sodium hydride (60% in oil, 15.2 mg, 0.381 mmol) was added to a stirred solution of 2-[9-chloro-1-(2,4-dichlorophenyl)-1,2,3,4-tetrahydropyrimido[1,2-a]benzimidazol-6-yl]butan-1-ol (108 mg, 0.254 mmol) in N,N-dimethylformamide (2.0 mL) at room temperature. After stirring 5 min, methyl iodide (71.7 mg, 0.508 mmol) was added to the mixture, and the mixture was stirred at room temperature for 5 hr. The mixture was diluted with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 10-50% ethyl acetate/n-hexane gradient mixture. The filtrate was concentrated in vacuo to give the solid, which was recrystallized from ethyl acetate/diisopropyl ether to give the title compound as a colorless crystal (56.1 mg, 0.128 mmol, 50%).

mp 130-131° C.
$^1$H NMR (CDCl$_3$) δ 0.87 (t, J=7.5 Hz, 3H), 1.62-1.95 (m, 2H), 2.31-2.39 (m, 2H), 3.30 (s, 3H), 3.45-3.60 (m, 3H), 3.60-3.78 (m, 2H), 4.29-4.38 (m, 1H), 4.55-4.64 (m, 1H), 6.78 (d, J=8.4 Hz, 1H), 7.06 (d, J=8.4 Hz, 1H), 7.29 (dd, J=2.4 Hz, 8.4 Hz, 1H), 7.48 (d, J=2.4 Hz, 1H), 7.54 (d, J=8.4 Hz, 1H).
MS Calcd.: 437; MS Found: 438 (M+H).
Anal. Calcd for C$_{21}$H$_{22}$N$_3$OCl$_3$: C, 57.48; H, 5.05; N, 9.58; Cl, 24.24. Found: C, 57.41; H, 5.04; N, 9.48; Cl, 24.03.

Example 150

9-Chloro-1-(2,4-dichlorophenyl)-6-(2-methoxy-1,1-dimethylethyl)-1,2,3,4-tetrahydropyrimido[1,2-a]benzimidazole

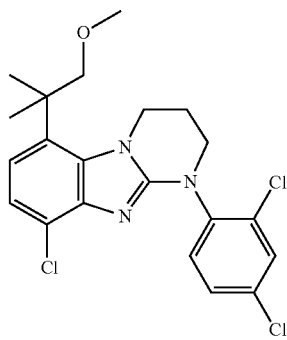 [SMILES: COCC(C)(C)c1ccc(Cl)c2nc3n(c12)CCCN3c1ccc(Cl)cc1Cl]

Sodium hydride (60% in oil, 10.2 mg, 0.255 mmol) was added to a stirred solution of 2-[9-chloro-1-(2,4-dichlorophenyl)-1,2,3,4-tetrahydropyrimido[1,2-a]benzimidazol-6-yl]-2-methylpropan-1-ol (90.3 mg, 0.213 mmol) in N,N-dimethylformamide (2.0 mL) at room temperature. After stirring 5 min, methyl iodide (45.1 mg, 0.320 mmol) was added to the mixture, and the mixture was stirred at room temperature for 50 min. The mixture was diluted with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 10-40% ethyl acetate/n-hexane gradient mixture. The filtrate was concentrated in vacuo to give the solid, which was recrystallized from ethyl acetate/diisopropyl ether to give the title compound as a colorless crystal (71.5 mg, 0.163 mmol, 77%).

mp 188-190° C.
$^1$H NMR (CDCl$_3$) δ 1.51 (s, 6H), 2.35-2.43 (m, 2H), 3.40 (s, 3H), 3.57 (s, 2H), 3.65-3.76 (m, 2H), 4.50 (t, J=5.7 Hz, 2H), 6.92 (d, J=8.4 Hz, 1H), 7.02 (d, J=8.7 Hz, 1H), 7.31 (dd, J=2.4 Hz, 8.4 Hz, 1H), 7.48-7.51 (m, 2H).
MS Calcd.: 437; MS Found: 438 (M+H).
Anal. Calcd for C$_{21}$H$_{22}$N$_3$OCl$_3$: C, 57.48; H, 5.05; N, 9.58; Cl, 24.24. Found: C, 57.22; H, 5.05; N, 9.39; Cl, 24.21.

Example 151

Methyl 9-chloro-1-[6-(dimethylamino)-4-methylpyridin-3-yl]-1,2,3,4-tetrahydropyrimido[1,2-a]benzimidazole-6-carboxylate

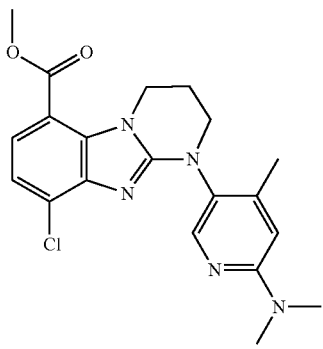 [SMILES: COC(=O)c1ccc(Cl)c2nc3n(c12)CCCN3c1cnc(N(C)C)cc1C]

Methanesulfonyl chloride (1.7 mL, 21.0 mmol) was added to a stirred solution of methyl 4-chloro-2-{[6-(dimethylamino)-4-methylpyridin-3-yl]amino}-1-(3-hydroxypropyl)-1H-benzimidazole-7-carboxylate (Reference example 119, 2.20 g, 5.26 mmol) and triethylamine (3.7 mL) in tetrahydrofuran (26 mL) at 0° C. The mixture was stirred at room temperature for 13 hr, and concentrated in vacuo. A mixture of the resulting mesylate, potassium carbonate (2.18 g, 15.8 mmol) in N,N-dimethylformamide (30 mL) was stirred at 80° C. for 4 hr. The mixture was diluted with aqueous sodium hydrogen carbonate, and extracted with ethyl acetate. The combined organic layer was washed with brine, dried over anhydrous magnesium sulfate, filtered, and concentrated in vacuo. The residue was washed with diisopropyl ether to give the title compound as a colorless powder (1.22 g, 3.05 mmol, 58% in 2 steps).

$^1$H NMR (DMSO-$d_6$) δ 2.12 (s, 3H), 2.13-2.30 (m, 2H), 3.05 (s, 6H), 3.55-3.75 (m, 2H), 3.89 (s, 3H), 4.18-4.29 (m, 2H), 6.59 (s, 1H), 7.08 (d, J=8.7 Hz, 1H), 7.27 (d, J=8.7 Hz, 1H), 8.02 (s, 1H).

MS Calcd.: 399; MS Found: 400 (M+H).

Example 152

{9-Chloro-1-[6-(dimethylamino)-4-methylpyridin-3-yl]-1,2,3,4-tetrahydropyrimido[1,2-a]benzimidazol-6-yl}methanol

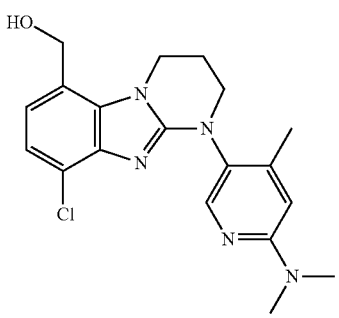 [SMILES: Cc1cc(N(C)C)ncc1N1CCCn2c1nc1c(Cl)ccc(CO)c12]

Lithium borohydride (265 mg, 12.2 mmol) was added to a stirred solution of methyl 9-chloro-1-[6-(dimethylamino)-4-methylpyridin-3-yl]-1,2,3,4-tetrahydropyrimido[1,2-a]benzimidazole-6-carboxylate (1.22 g, 3.05 mmol) in tetrahydrofuran (20 ml) at room temperature, and the mixture was stirred at 40° C. for 24 hr. The reaction was quenched by aqueous saturated ammonium chloride at 0° C., concentrated in vacuo and the precipitate was collected by filtration, washed with water, diisopropyl ether to give the title compound as a colorless powder (1.13 g, 3.04 mmol, 99%).

$^1$H NMR (DMSO-$d_6$) δ 2.12 (s, 3H), 2.20-2.33 (m, 2H), 3.04 (s, 6H), 3.47-3.70 (m, 2H), 4.40-4.61 (m, 2H), 4.70-4.74 (brs, 2H), 5.32 (t, J=5.1 Hz, 1H), 6.59 (s, 1H), 6.79 (d, J=8.1 Hz, 1H), 6.92 (d, J=8.1 Hz, 1H), 8.00 (s, 1H).

MS Calcd.: 371; MS Found: 372 (M+H).

Example 153

9-Chloro-1-[6-(dimethylamino)-4-methylpyridin-3-yl]-1,2,3,4-tetrahydropyrimido[1,2-a]benzimidazole-6-carbaldehyde

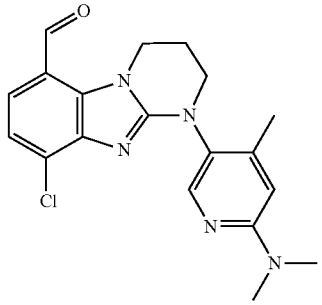 [SMILES: Cc1cc(N(C)C)ncc1N1CCCn2c1nc1c(Cl)ccc(C=O)c12]

Sulfur trioxide-pyridine complex (3.15 g, 19.8 mmol) was added to a stirred solution of [9-chloro-1-(2,4-dichloro-6-methylphenyl)-1,2,3,4-tetrahydropyrimido[1,2-a]benzimidazol-6-yl]methanol (1.13 g, 3.04 mmol) and triethylamine (3.4 mL) in dimethyl sulfoxide (10 mL) at room temperature, and the mixture was stirred at room temperature for 2 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with diisopropyl ether to give the title compound as a pale yellow powder (1.08 g, 2.92 mmol, 96%).

$^1$H NMR (CDCl$_3$) δ 2.18 (s, 3H), 2.30-2.39 (m, 2H), 3.10 (s, 6H), 3.55-3.65 (m, 1H), 3.72-3.82 (m, 1H), 4.57-4.75 (m, 2H), 6.41 (s, 1H), 7.18 (d, J=8.4 Hz, 1H), 7.32 (d, J=8.4 Hz, 1H), 8.08 (s, 1H), 9.98 (s, 1H).

MS Calcd.: 369; MS Found: 370 (M+H).

Example 154

1-{9-Chloro-1-[6-(dimethylamino)-4-methylpyridin-3-yl]-1,2,3,4-tetrahydropyrimido[1,2-a]benzimidazol-6-yl}propan-1-ol

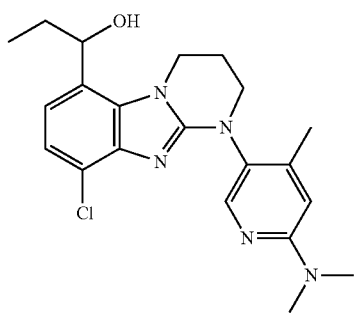 [SMILES: CCC(O)c1ccc(Cl)c2nc3n(c12)CCCN3c1cnc(N(C)C)cc1C]

Ethylmagnesium bromide (3.0 M solution in diethyl ether, 1.17 mL, 1.76 mmol) was added to a stirred solution of 9-chloro-1-[6-(dimethylamino)-4-methylpyridin-3-yl]-1,2,3,4-tetrahydropyrimido[1,2-a]benzimidazole-6-carbaldehyde (1.08 g, 2.92 mmol) in tetrahydrofuran (29 mL) at 0° C., and the mixture was stirred at room temperature for 3 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was washed with ethyl acetate/diisopropyl ether to give the title compound as a colorless powder (920 mg, 2.30 mmol, 79%).

$^1$H NMR (DMSO-d$_6$) δ 0.93 (t, J=7.2 Hz, 3H), 1.78-1.82 (m, 2H), 2.12 (s, 3H), 2.07-2.21 (m, 2H), 3.04 (s, 6H), 3.50-3.73 (m, 2H), 4.37-4.60 (m, 2H), 4.92-5.03 (m, 1H), 5.20-5.32 (m, 1H), 6.59 (s, 1H), 6.90-6.97 (m, 2H), 7.99 (s, 1H).

MS Calcd.: 399; MS Found: 400 (M+H).

Example 155

1-{9-Chloro-1-[6-(dimethylamino)-4-methylpyridin-3-yl]-1,2,3,4-tetrahydropyrimido[1,2-a]benzimidazol-6-yl}propyl acetate

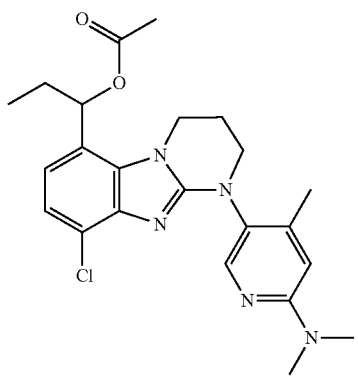 [SMILES: CCC(OC(C)=O)c1ccc(Cl)c2nc3n(c12)CCCN3c1cnc(N(C)C)cc1C]

Acetic anhydride (142 μL, 1.50 mmol) was added to a stirred solution of 1-{9-chloro-1-[6-(dimethylamino)-4-methylpyridin-3-yl]-1,2,3,4-tetrahydropyrimido[1,2-a]benzimidazol-6-yl}propan-1-ol (200 mg, 0.500 mmol) in pyridine (1.6 mL) at room temperature, and the mixture was stirred at room temperature for 19 hr. The mixture was concentrated in vacuo, diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 10-50% ethyl acetate/n-hexane gradient mixture. The filtrate was concentrated in vacuo to give the solid, which was recrystallized from ethyl acetate/diisopropyl ether to give the title compound as a colorless crystal (168 mg, 0.380 mmol, 76%).

mp 159-160° C.

$^1$H NMR (CDCl$_3$) δ 0.90-0.97 (m, 3H), 1.83-2.05 (m, 2H), 2.08 (s, 3H), 2.19 (s, 3H), 2.31-2.41 (m, 2H), 3.09 (s, 6H), 3.53-3.63 (m, 2H), 3.72-3.82 (m, 1H), 4.25-4.36 (m, 1H), 4.61-4.79 (m, 1H), 6.30 (t, J=6.6 Hz, 1H) 6.41 (s, 1H), 6.94 (d, J=8.4 Hz, 1H), 7.05 (d, J=8.4 Hz, 1H), 8.08 (s, 1H).

MS Calcd.: 441; MS Found: 442 (M+H).

Example 156

5-[9-Chloro-6-(1-ethoxypropyl)-3,4-dihydropyrimido[1,2-a]benzimidazol-1(2H)-yl]-N,N,4-trimethylpyridin-2-amine

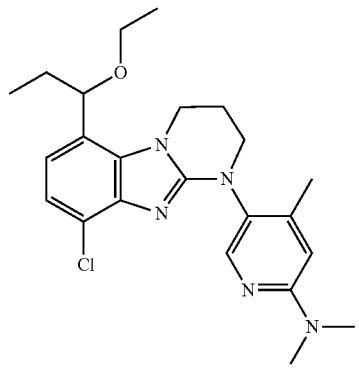 [SMILES: CCOC(CC)c1ccc(Cl)c2nc3n(c12)CCCN3c1cnc(N(C)C)cc1C]

Sodium hydride (60% in oil, 27.1 mg, 0.678 mmol) was added to a stirred solution of 1-{9-chloro-1-[6-(dimethylamino)-4-methylpyridin-3-yl]-1,2,3,4-tetrahydropyrimido[1,2-a]benzimidazol-6-yl}propan-1-ol (226 mg, 0.565 mmol) in N,N-dimethylformamide (5.0 mL) at room temperature. After stirring 5 min, ethyl iodide (132 mg, 0.848 mmol) was added to the mixture, and the mixture was stirred at room temperature for 6 hr. The mixture was diluted with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 50-100% ethyl acetate/n-hexane gradient mixture. The filtrate was concentrated in vacuo to give the solid, which was recrystallized from ethyl acetate to give the title compound as a colorless crystal (121 mg, 0.283 mmol, 50%).

mp 179-180° C.

$^1$H NMR (CDCl$_3$) δ 0.98 (t, J=7.5 Hz, 3H), 1.18 (t, J=7.2 Hz, 3H), 1.75-2.00 (m, 2H), 2.20 (s, 3H), 2.26-2.38 (m, 2H), 3.09 (s, 6H), 3.28-3.50 (m, 2H), 3.50-3.83 (m, 2H), 4.26-4.43 (m, 1H), 4.58 (t, J=6.6 Hz, 1H), 4.55-4.76 (m, 1H), 6.41 (s, 1H), 6.85 (d, J=8.4 Hz, 1H), 7.01 (d, J=8.4 Hz, 1H), 8.09 (s, 1H).

MS Calcd.: 427; MS Found: 428 (M+H).

Anal. Calcd for C$_{23}$H$_{30}$N$_5$OCl: C, 64.55; H, 7.07; N, 16.36; Cl, 8.28. Found: C, 64.52; H, 7.14; N, 16.39; Cl, 8.35.

Example 157

Methyl 9-chloro-1-(6-methoxy-4-methylpyridin-3-yl)-1,2,3,4-tetrahydropyrimido[1,2-a]benzimidazole-6-carboxylate

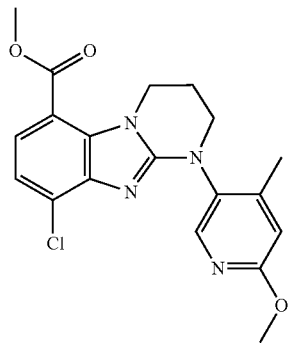 [SMILES: COC(=O)c1ccc(Cl)c2nc3n(c12)CCCN3c1cnc(OC)cc1C]

Methanesulfonyl chloride (7.8 mL, 35.5 mmol) was added to a stirred solution of methyl 4-chloro-1-(3-hydroxypropyl)-2-[(6-methoxy-4-methylpyridin-3-yl)amino]-1H-benzimidazole-7-carboxylate (Reference example 120, 3.60 g, 8.89 mmol) and triethylamine (6.2 mL) in tetrahydrofuran (44 mL) at 0° C. The mixture was stirred at room temperature for 13 hr, and concentrated in vacuo. A mixture of the resulting mesylate and potassium carbonate (3.67 g, 26.7 mmol) in N,N-dimethylformamide (40 mL) was stirred at 80° C. for 4 hr. The mixture was diluted with aqueous sodium hydrogen carbonate, and extracted with ethyl acetate. The combined organic layer was washed with brine, dried over anhydrous magnesium sulfate, filtered, and concentrated in vacuo. The residue was washed with ethyl acetate/diisopropyl ether to give the title compound as a colorless powder (1.29 g, 3.33 mmol, 37% in 2 steps).

¹H NMR (DMSO-d₆) δ 2.17 (s, 3H), 2.15-2.30 (m, 2H), 3.60-3.80 (m, 2H), 3.86 (s, 3H), 3.88 (s, 3H), 4.20-4.36 (m, 2H), 6.82 (s, 1H), 7.09 (d, J=8.1 Hz, 1H), 7.29 (d, J=8.1 Hz, 1H), 8.14 (s, 1H).

MS Calcd.: 386; MS Found: 387 (M+H).

Example 158

[9-Chloro-1-(6-methoxy-4-methylpyridin-3-yl)-1,2,3,4-tetrahydropyrimido[1,2-a]benzimidazol-6-yl]methanol

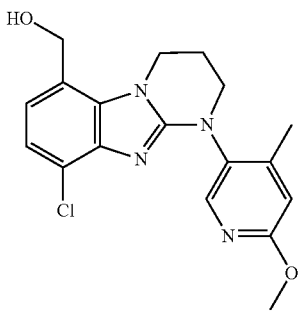 [SMILES: COc1cc(C)c(N2CCCn3c2nc2c(Cl)ccc(CO)c23)cn1]

Lithium borohydride (290 mg, 13.3 mmol) was added to a stirred solution of methyl 9-chloro-1-(6-methoxy-4-methylpyridin-3-yl)-1,2,3,4-tetrahydropyrimido[1,2-a]benzimidazole-6-carboxylate (1.29 g, 3.33 mmol) in tetrahydrofuran (25 mL) at room temperature, and the mixture was stirred at 40° C. for 24 hr. The reaction was quenched by aqueous saturated ammonium chloride at 0° C. and the mixture was extracted with ethyl acetate. The combined organic layer was washed with brine, dried over anhydrous magnesium sulfate, filtered, and concentrated in vacuo.

The residue was washed with diisopropyl ether to give the title compound as a colorless powder (1.19 g, 3.32 mmol, 99%).

¹H NMR (DMSO-d₆) δ 2.17 (s, 3H), 2.24-2.34 (m, 2H), 3.57-3.80 (m, 2H), 3.86 (m, 3H), 4.35-4.65 (m, 2H), 4.73 (d, J=4.5 Hz, 2H), 5.34 (t, J=4.5 Hz, 1H), 6.80-6.83 (m, 2H), 6.94 (d, J=7.8 Hz, 1H), 8.13 (s, 1H).

MS Calcd.: 358; MS Found: 359 (M+H).

Example 159

9-Chloro-1-(6-methoxy-4-methylpyridin-3-yl)-1,2,3,4-tetrahydropyrimido[1,2-a]benzimidazole-6-carbaldehyde

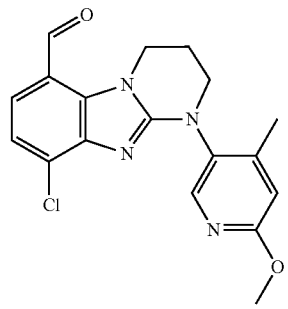 [SMILES: COc1cc(C)c(N2CCCn3c2nc2c(Cl)ccc(C=O)c23)cn1]

Sulfur trioxide-pyridine complex (3.42 g, 21.5 mmol) was added to a stirred solution of [9-chloro-1-(6-methoxy-4-methylpyridin-3-yl)-1,2,3,4-tetrahydropyrimido[1,2-a]benzimidazol-6-yl]methanol (1.19 g, 3.31 mmol), triethylamine (3.7 mL) in dimethyl sulfoxide (10 mL) at room temperature, and the mixture was stirred at room temperature for 5 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo to give the title compound as a pale yellow solid (220 mg, 0.617 mmol, 19%).

¹H NMR (CDCl₃) δ 2.21 (s, 3H), 2.33-2.41 (m, 2H), 3.58-3.83 (m, 2H), 3.94 (s, 3H), 4.63-4.80 (m, 2H), 6.68 (s, 1H), 7.20 (d, J=8.1 Hz, 1H), 7.34 (d, J=8.1 Hz, 1H), 8.10 (s, 1H), 9.98 (s, 1H).

MS Calcd.: 356; MS Found: 357 (M+H).

Example 160

1-[9-Chloro-1-(6-methoxy-4-methylpyridin-3-yl)-1,2,3,4-tetrahydropyrimido[1,2-a]benzimidazol-6-yl]propan-1-ol

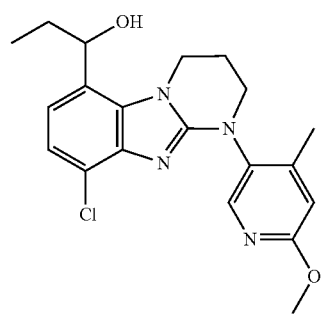 [SMILES: CCC(O)c1ccc(Cl)c2nc3n(c12)CCCN3c1cnc(OC)cc1C]

Ethylmagnesium bromide (3.0 M solution in diethyl ether, 0.23 mL, 0.69 mmol) was added to a stirred solution of 9-chloro-1-(6-methoxy-4-methylpyridin-3-yl)-1,2,3,4-tetrahydropyrimido[1,2-a]benzimidazole-6-carbaldehyde (207 mg, 0.580 mmol) in tetrahydrofuran (5.0 mL) at 0° C., and the mixture was stirred at room temperature for 3 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was washed with diisopropyl ether to give the title compound as a colorless powder (141 mg, 0.364 mmol, 63%).

$^1$H NMR (DMSO-$d_6$) δ 0.89-0.96 (m, 3H), 1.72-1.82 (m, 2H), 2.17 (s, 3H), 2.21-2.35 (m, 2H), 3.57-3.80 (m, 2H), 3.86 (s, 3H), 4.37-4.60 (m, 2H), 4.90-5.01 (m, 1H), 5.27 (s, 1H), 6.82 (s, 1H), 6.92-6.98 (m, 2H), 8.12 (s, 1H).

MS Calcd.: 386; MS Found: 387 (M+H).

Example 161

1-[9-Chloro-1-(6-methoxy-4-methylpyridin-3-yl)-1,2,3,4-tetrahydropyrimido[1,2-a]benzimidazol-6-yl]propyl acetate

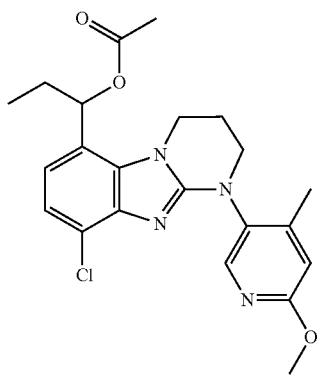 [SMILES: CCC(OC(C)=O)c1ccc(Cl)c2nc3n(c12)CCCN3c1cnc(OC)cc1C]

Acetic anhydride (103 μL, 1.09 mmol) was added to a stirred solution of 1-[9-chloro-1-(6-methoxy-4-methylpyridin-3-yl)-1,2,3,4-tetrahydropyrimido[1,2-a]benzimidazol-6-yl]propan-1-ol (140 mg, 0.362 mmol) in pyridine (1.2 mL) at room temperature, and the mixture was stirred at room temperature for 19 hr. The mixture was concentrated in vacuo, diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 10-50% ethyl acetate/n-hexane gradient mixture. The filtrate was concentrated in vacuo to give the title compound as a colorless amorphous (89.9 mg, 0.210 mmol, 58%). Amorphous.

$^1$H NMR (CDCl$_3$) δ 0.88-1.03 (m, 3H), 1.90-2.10 (m, 2H), 2.08 (s, 3H), 2.23 (s, 3H), 2.38-2.41 (m, 2H), 3.58-3.82 (m, 2H), 3.92 (s, 3H), 4.23-4.41 (m, 1H), 4.65-4.85 (m, 1H), 6.30 (t, J=7.2 Hz, 1H), 6.66 (s, 1H), 6.96 (d, J=8.4 Hz, 1H), 7.07 (d, J=8.4 Hz, 1H), 8.08 (s, 1H).

MS Calcd.: 428; MS Found: 429 (M+H).

Example 162

Methyl 9-chloro-1-[6-(dimethylamino)-2-methylpyridin-3-yl]-1,2,3,4-tetrahydropyrimido[1,2-a]benzimidazole-6-carboxylate

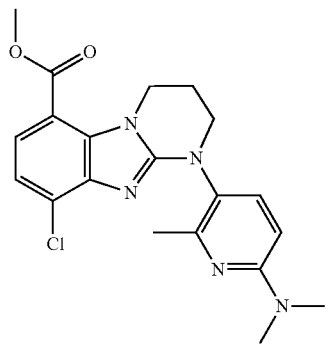 [SMILES: COC(=O)c1ccc(Cl)c2nc3n(c12)CCCN3c1ccc(N(C)C)nc1C]

Methanesulfonyl chloride (0.29 mL, 3.66 mmol) was added to a stirred solution of methyl 4-chloro-2-{[6-(dimethylamino)-2-methylpyridin-3-yl]amino}-1-(3-hydroxypropyl)-1H-benzimidazole-7-carboxylate (Reference example 121, 510 mg, 1.22 mmol) and triethylamine (0.68 mL) in tetrahydrofuran (12 mL) at 0° C. The mixture was stirred at 0° C. for 90 min, and concentrated in vacuo. A mixture of the resulting mesylate, potassium carbonate (506 mg, 3.66 mmol) in N,N-dimethylformamide (12 mL) was stirred at 80° C. for 17 hr. The mixture was diluted with aqueous sodium hydrogen carbonate, and extracted with ethyl acetate. The combined organic layer was washed with brine, dried over anhydrous magnesium sulfate, filtered, and concentrated in vacuo. The residue was purified by flash column chromatography on silica gel eluting with a 5-40% ethyl acetate/n-hexane gradient mixture. The filtrate was concentrated in vacuo to give the title compound as a colorless solid (341 mg, 0.853 mmol, 70% in 2 steps).

$^1$H NMR (CDCl$_3$) δ 2.22-2.30 (m, 2H), 2.34 (s, 3H), 3.10 (s, 6H), 3.63 (t, J=5.4 Hz, 2H), 3.93 (s, 3H), 4.33-4.41 (s, 2H), 6.40 (d, J=8.4 Hz, 1H), 7.06 (d, J=8.4 Hz, 1H), 7.36-7.41 (m, 2H).

MS Calcd.: 399; MS Found: 400 (M+H).

Example 163

{9-Chloro-1-[6-(dimethylamino)-2-methylpyridin-3-yl]-1,2,3,4-tetrahydropyrimido[1,2-a]benzimidazol-6-yl}methanol

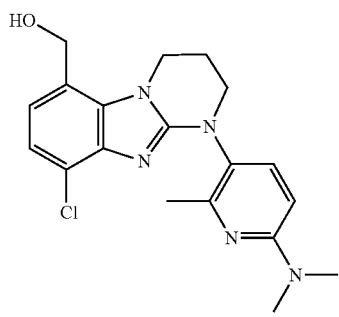 [SMILES: Cc1nc(N(C)C)ccc1N1CCCn2c1nc1c(Cl)ccc(CO)c12]

Lithium borohydride (74.3 mg, 3.41 mmol) was added to a stirred solution of methyl 9-chloro-1-[6-(dimethylamino)-2-methylpyridin-3-yl]-1,2,3,4-tetrahydropyrimido[1,2-a]benzimidazole-6-carboxylate (341 mg, 0.853 mmol) in tetrahydrofuran (5.0 mL) at room temperature, and the mixture was stirred at 40° C. for 20 hr. The reaction was quenched by aqueous saturated ammonium chloride at 0° C., concentrated in vacuo and the precipitate was collected by filtration, washed with water, diisopropyl ether to give the title compound as a colorless powder (317 mg, 0.853 mmol, 100%).

$^1$H NMR (DMSO-$d_6$) δ 2.21-2.29 (m, 2H), 2.22 (s, 3H), 3.04 (s, 6H), 3.50-3.66 (m, 2H); 4.41-4.60 (m, 2H), 4.70-4.75 (m, 2H), 5.30-5.36 (m, 1H), 6.53 (d, J=8.7 Hz, 1H), 6.79 (d, J=8.1 Hz, 1H), 6.91 (d, J=8.1 Hz, 1H), 7.44 (d, J=8.7 Hz, 1H).

MS Calcd.: 371; MS Found: 372 (M+H).

Example 164

9-Chloro-1-[6-(dimethylamino)-2-methylpyridin-3-yl]-1,2,3,4-tetrahydropyrimido[1,2-a]benzimidazole-6-carbaldehyde

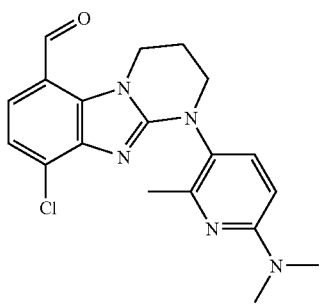 [SMILES: Cc1nc(N(C)C)ccc1N1CCCn2c1nc1c(Cl)ccc(C=O)c12]

Dess-Martin reagent (410 mg, 0.967 mmol) was added to a stirred solution of {9-chloro-1-[6-(dimethylamino)-2-methylpyridin-3-yl]-1,2,3,4-tetrahydropyrimido[1,2- a]benzimidazol-6-yl}lmethanol (327 mg, 0.879 mmol) in dimethyl sulfoxide (1.0 mL) and acetonitrile (6.0 mL) at 0 ° C., and the mixture was stirred at 0 ° C. for 4 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 20-60% ethyl acetate/n-hexane gradient mixture. The filtrate was concentrated in vacuo to give the title compound as a pale yellow solid (243 mg, 0.657 mmol, 75%).

$^1$H NMR (CDCl$_3$) δ 2.27-2.35 (m, 2H), 2.33 (s, 3H), 3.10 (s, 6H), 3.60-3.66 (m, 2H), 4.58-4.71 (m, 2H), 6.40 (d, J=8.7 Hz, 1H), 7.18 (d, J=8.4 Hz, 1H), 7.31 (d, J=8.4 Hz, 1H), 7.36 (d, J=8.7 Hz, 1H), 9.98 (s, 1H).

MS Calcd.: 369; MS Found: 370 (M+H).

Example 165

1-{9-Chloro-1-[6-(dimethylamino)-2-methylpyridin-3-yl]-1,2,3,4-tetrahydropyrimido[1,2-a]benzimidazol-6-yl}propan-1-ol

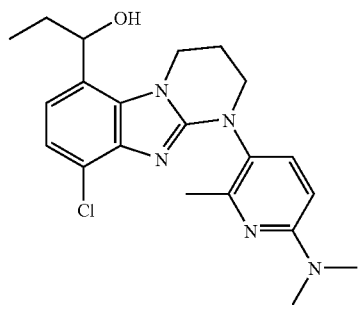 [SMILES: CCC(O)c1ccc(Cl)c2nc3n(c12)CCCN3c1ccc(N(C)C)nc1C]

Ethylmagnesium bromide (3.0 M solution in diethyl ether, 0.24 mL, 0.72 mmol) was added to a stirred solution of 9-chloro-1-[6-(dimethylamino)-2-methylpyridin-3-yl]-1,2,3,4-tetrahydropyrimido[1,2-a]benzimidazole-6-carbaldehyde (240 mg, 0.649 mmol) in tetrahydrofuran (3.5 mL) at 0° C., and the mixture was stirred at 0° C. for 40 min. The reaction wars quenched by aqueous saturated ammonium chloride, and the mixture was extracted with tetrahydrofuran/ethyl acetate. The combined organic layer was washed with brine, dried over anhydrous magnesium sulfate, filtered, and concentrated in vacuo. The residue was washed with diisopropyl ether to give the title compound as a colorless powder (207 mg, 0.518 mmol, 80%).

$^1$H NMR (DMSO-$d_6$) δ 0.93 (t, J=7.2 Hz, 3H), 1.70-1.82 (m, 2H), 2.20-2.35 (m, 2H), 2.22 (s, 3H), 3.05 (s, 6H), 3.43-3.70 (m, 2H), 4.35-4.57 (m, 2H), 4.91-5.03 (m, 1H), 5.21-5.29 (m, 1H), 6.53 (d, J=9.0 Hz, 1H), 6.91 (d, J=8.4 Hz, 1H), 6.95 (d, J=8.4 Hz, 1H), 7.43 (d, J=8.7 Hz, 1H).

MS Calcd.: 399; MS Found: 400 (M+H).

Example 166

1-{9-Chloro-1-[6-(dimethylamino)-2-methylpyridin-3-yl]-1,2,3,4-tetrahydropyrimido[1,2-a]benzimidazol-6-yl}propyl acetate

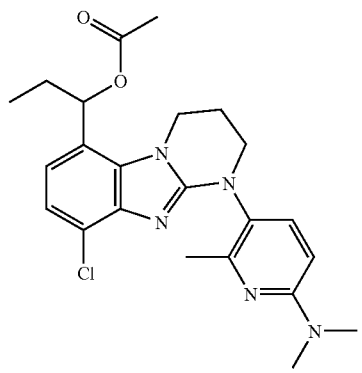 [SMILES: CCC(OC(C)=O)c1ccc(Cl)c2nc3n(c12)CCCN3c1ccc(N(C)C)nc1C]

Acetic anhydride (0.30 mL, 3.15 mmol) was added to a stirred solution of 1-{9-chloro-1-[6-(dimethylamino)-2-methylpyridin-3-yl]-1,2,3,4-tetrahydropyrimido[1,2-a]benzimidazol-6-yl}propan-1-ol (103 mg, 0.258 mmol) in pyridine (2.0 mL) at room temperature, and the mixture was stirred at room temperature for 6 hr. The mixture was concentrated in vacuo, diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 20-90% ethyl acetate/n-hexane gradient mixture. The filtrate was concentrated in vacuo to give the solid, which was recrystallized from ethyl acetate to give the title compound as a colorless crystal (86.9 mg, 0.197 mmol, 76%)

mp 165-166° C.

$^1$H NMR (CDCl$_3$) δ 0.94 (t, J=7.2 Hz, 3H), 1.85-2.05 (m, 2H), 2.08 (s, 3H), 2.30-2.42 (m, 2H), 2.35 (s, 3H), 3.09 (s, 6H), 3.51-3.67 (m, 2H), 4.22-4.40 (m, 1H), 4.55-4.80 (m, 1H), 6.30 (t, J=7.2 Hz, 1H), 6.39 (d, J=8.7 Hz, 1H), 6.93 (d, J=8.4 Hz, 1H), 7.05 (d, J=8.4 Hz, 1H), 7.38 (d, J=8.7 Hz, 1H).

MS Calcd.: 441; MS Found: 442 (M+H).

Anal. Calcd for $C_{23}H_{28}N_5O_2Cl$: C, 62.51; H, 6.39; N, 15.85; Cl, 8.02. Found: C, 62.53; H, 6.39; N, 15.89; Cl, 8.10.

Example 167

5-{9-Chloro-6-[1-(2,2,2-trifluoroethoxy)propyl]-3,4-dihydropyrimido[1,2-a]benzimidazol-1(2H)-yl}-N,N,6-trimethylpyridin-2-amine

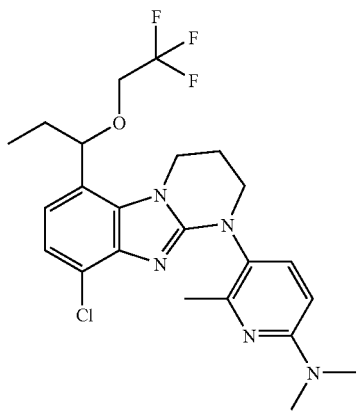 [SMILES: CCC(OCC(F)(F)F)c1ccc(Cl)c2nc3n(c12)CCCN3c1ccc(N(C)C)nc1C]

A mixture of 1-{9-chloro-1-[6-(dimethylamino)-2-methylpyridin-3-yl]-1,2,3,4-tetrahydropyrimido[1,2-a]benzimidazol-6-yl}propan-1-ol (71.1 mg, 0.178 mmol), 1,1'-(azodicarbonyl)dipiperidine (89.7 mg, 0.355 mmol) and n-butylphosphine (71.8 mg, 0.355 mmol) in tetrahydrofuran (2.0 mL) was stirred at room temperature for 15 min. 2,2,2-Trifluoroethanol (178 mg, 1.78 mmol) was added to the mixture, and the mixture was stirred at 60° C. for 7 hr. The mixture was concentrated in vacuo, and the residue was purified by flash column chromatography on silica gel eluting with a 35-80% ethyl acetate/n-hexane gradient mixture. The filtrate was concentrated in vacuo to give the solid, which was recrystallized from ethyl acetate/diisopropyl ether to give the title compound as a colorless crystal (30.8 mg, 0.0639 mmol, 36%)

mp 144-146° C.

$^1$H NMR (CDCl$_3$) δ 1.03 (t, J=7.5 Hz, 3H), 1.80-1.91 (m, 1H), 1.97-2.10 (m, 1H), 2.25-2.35 (m, 2H), 2.35 (s, 3H), 3.10 (s, 6H), 3.57-3.80 (m, 4H), 4.20-4.35 (m, 1H), 4.48-4.63 (m, 1H), 4.53-5.02 (m, 1H), 6.40 (d, J=8.7 Hz, 1H), 6.81 (d, J=8.4 Hz, 1H), 7.03 (d, J=8.4 Hz, 1H), 7.39 (d, J=8.7 Hz, 1H).

MS Calcd.: 481; MS Found: 482 (M+H).

Example 168

Methyl 9-chloro-1-(3,5-dichloropyridin-2-yl)-1,2,3,4-tetrahydropyrimido[1,2-a]benzimidazole-6-carboxylate

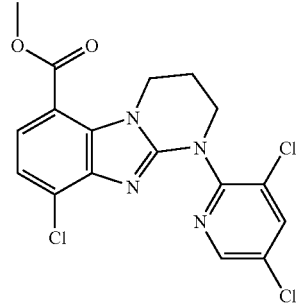 [SMILES: COC(=O)c1ccc(Cl)c2nc3n(c12)CCCN3c1ncc(Cl)cc1Cl]

Methanesulfonyl chloride (1.8 mL, 23.1 mmol) was added to a stirred solution of methyl 4-chloro-2-[(3,5-dichloropyridin-2-yl)amino]-1-(3-hydroxypropyl)-1H-benzimidazole-7-carboxylate (Reference example 123, 3.32 g, 7.73 mmol) and triethylamine (4.3 mL) in tetrahydrofuran (100 mL) at 0° C. The mixture was stirred at room temperature for 5 hr. The mixture was diluted with aqueous sodium hydrogen carbonate, and the precipitate was collected by filtration. A mixture of the resulting mesylate and potassium carbonate (4.27 g, 30.9 mmol) in N,N-dimethylformamide (40 mL) was stirred at 80° C. for 2 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 20-50% ethyl acetate/n-hexane gradient mixture. The filtrate was concentrated in vacuo to give the solid, which was washed with diisopropyl ether to give the title compound as a colorless powder (2.37 g, 5.76 mmol, 75% in 2 steps).

$^1$H NMR (CDCl$_3$) δ 2.30-2.38 (m, 2H), 3.87-3.95 (m, 2H), 3.94 (s, 3H), 4.47 (t, J=6.0 Hz, 2H), 7.12 (d, J=8.1 Hz, 1H), 7.49 (d, J=8.1 Hz, 1H), 7.83 (d, J=2.1 Hz, 1H), 8.36 (d, J=2.1 Hz, 1H).

MS Calcd.: 410; MS Found: 411 (M+H).

Example 169

9-Chloro-1-(3,5-dichloropyridin-2-yl)-1,2,3,4-tetrahydropyrimido[1,2-a]benzimidazole-6-carbaldehyde

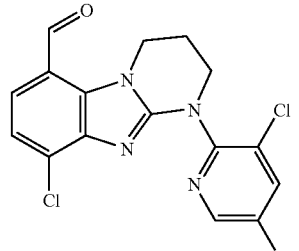

Lithium borohydride (211 mg, 9.72 mmol) was added to a stirred solution of methyl 9-chloro-1-(3,5-dichloropyridin-2-yl)-1,2,3,4-tetrahydropyrimido[1,2-a]benzimidazole-6-carboxylate (1.00 g, 2.43 mmol) in tetrahydrofuran (10 mL) at room temperature, and the mixture was stirred at room temperature for 2 hr. The reaction was quenched by aqueous saturated ammonium chloride at 0° C. and the mixture was extracted with ethyl acetate. The combined organic layer was washed with brine, dried over anhydrous magnesium sulfate, filtered, and concentrated in vacuo. The residue was washed with diisopropyl ether to give a mixture of [9-chloro-1-(3,5-dichloropyridin-2-yl)-1,2,3,4-tetrahydropyrimido[1,2-a]benzimidazol-6-yl]methanol and dechlorinated product as a colorless powder (930 mg).

Sulfur trioxide-pyridine complex (2.51 g, 15.8 mmol) was added to a stirred solution of the residue (930 mg) and triethylamine (2.7 mL) in dimethyl sulfoxide (12 mL) at room temperature, and the mixture was stirred at room temperature for 5 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 20-50% ethyl acetate/n-hexane gradient mixture. The filtrate was concentrated in vacuo to give the title compound as a pale yellow wax (161 mg, 0.423 mmol, 17% in 2 steps).

$^1$H NMR (CDCl$_3$) δ 2.36-2.43 (m, 2H), 3.88-3.94 (m, 2H), 4.68-4.74 (m, 2H), 7.24 (d, J=8.1 Hz, 1H), 7.39 (d, J=8.1 Hz, 1H), 7.83 (d, J=2.4 Hz, 1H), 8.36 (d, J=2.4 Hz, 1H), 9.98 (s, 1H).

MS Calcd.: 380; MS Found: 381 (M+H).

Example 170

1-[9-Chloro-1-(3,5-dichloropyridin-2-yl)-1,2,3,4-tetrahydropyrimido[1,2-a]benzimidazol-6-yl]propan-1-ol

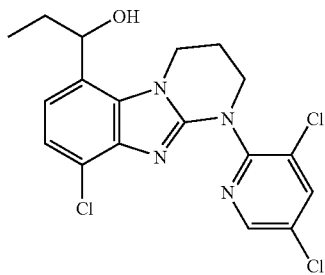

Ethylmagnesium bromide (3.0 M solution in diethyl ether, 51 μL, 0.153 mmol) was added to a stirred solution of 9-chloro-1-(3,5-dichloropyridin-2-yl)-1,2,3,4-tetrahydropyrimido[1,2-a]benzimidazole-6-carbaldehyde (53.7 mg, 0.141 mmol) in tetrahydrofuran (1.0 mL) at 0° C., and the mixture was stirred at 0° C. for 50 min. The reaction was quenched by aqueous saturated ammonium chloride, and the mixture was extracted with ethyl acetate. The combined organic layer was washed with brine, dried over anhydrous magnesium sulfate, filtered, and concentrated in vacuo to give the title compound as a colorless solid (57.8 mg, 0.141 mmol, 100%).

$^1$H NMR (CDCl$_3$) δ 0.99 (t, J=7.5 Hz, 3H), 1.78-1.87 (m, 2H), 2.25-2.34 (m, 2H), 2.80-3.20 (brs, 1H), 3.77-3.89 (m, 2H), 4.29-4.37 (m, 2H), 4.91 (t, J=6.9 Hz, 1H), 6.96 (d, J=8.1 Hz, 1H), 7.05 (d, J=8.1 Hz, 1H), 7.81 (d, J=2.1 Hz, 1H), 8.36 (d, J=2.1 Hz, 1H).

MS Calcd.: 410; MS Found: 411 (M+H).

Example 171

1-[9-Chloro-1-(3,5-dichloropyridin-2-yl)-1,2,3,4-tetrahydropyrimido[1,2-a]benzimidazol-6-yl]propyl acetate

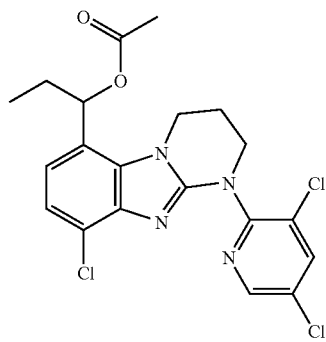 [SMILES: CCC(OC(C)=O)c1ccc(Cl)c2nc3n(c12)CCCN3c1ncc(Cl)cc1Cl]

Acetic anhydride (0.20 mL, 2.10 mmol) was added to a stirred solution of 1-[9-chloro-1-(3,5-dichloropyridin-2-yl)-1,2,3,4-tetrahydropyrimido[1,2-a]benzimidazol-6-yl]propan-1-ol (94.1 mg, 0.229 mmol) in pyridine (1.5 mL) at room temperature, and the mixture was stirred at room temperature for 13 hr. The mixture was concentrated in vacuo, diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 10-50% ethyl acetate/n-hexane gradient mixture. The filtrate was concentrated in vacuo to give the solid, which was recrystallized from ethyl acetate/diisopropyl ether to give the title compound as a colorless crystal (77.6 mg, 0.171 mmol, 75%)

mp 157-159° C.

$^1$H NMR (CDCl$_3$) δ 0.94 (t, J=7.5 Hz, 3H), 1.88-2.09 (m, 2H), 2.08 (s, 3H), 2.39-2.47 (m, 2H), 3.84-3.94 (m, 2H), 4.31-4.39 (m, 1H), 4.70-4.78 (m, 1H), 6.31 (t, J=7.2 Hz, 1H), 7.02 (d, J=8.7 Hz, 1H), 7.11 (d, J=8.7 Hz, 1H), 7.81 (d, J=2.4 Hz, 1H), 8.33 (d, J=2.4 Hz, 1H).

MS Calcd.: 452; MS Found: 453 (M+H).

Anal. Calcd for $C_{20}H_{19}N_4O_2Cl_3$: C, 52.94; H, 4.22; N, 12.35; Cl, 23.44. Found: C, 52.95; H, 4.29; N, 12.40; Cl, 23.62.

Example 172

1-[9-Chloro-1-(3,5-dichloropyridin-2-yl)-1,2,3,4-tetrahydropyrimido[1,2-a]benzimidazol-6-yl]propyl cyclopropanecarboxylate

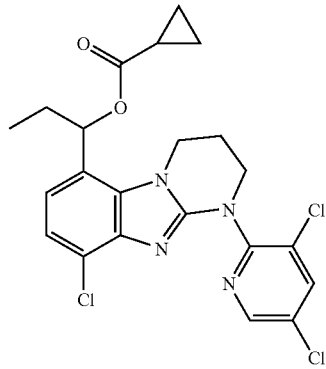 [SMILES: CCC(OC(=O)C1CC1)c1ccc(Cl)c2nc3n(c12)CCCN3c1ncc(Cl)cc1Cl]

A mixture of 1-[9-chloro-1-(3,5-dichloropyridin-2-yl)-1,2,3,4-tetrahydropyrimido[1,2-a]benzimidazol-6-yl]propan-1-ol (112 mg, 0.272 mmol), cyclopropanecarboxylic acid (35.1 mg, 0.408 mmol), 4-dimethylaminopyridine (49.8 mg, 0.408 mmol), triethylamine (76 μL) and 1-ethyl-3-(3-dimethylaminopropyl)carbodiimide hydrochloride, (104 mg, 0.544 mmol) in tetrahydrofuran (2.0 mL) was stirred at room temperature for 13 hr. The mixture was diluted with water and extracted with ethyl acetate. The combined organic layer was washed with brine, dried over anhydrous magnesium sulfate, filtered and concentrated in vacuo. The residue was purified by flash column chromatography on silica gel eluting with a 10-50% ethyl acetate/n-hexane gradient mixture. The filtrate was concentrated in vacuo to give the solid, which was recrystallized from ethyl acetate/diisopropyl ether to give the title compound as a colorless crystal (93.5 mg, 0.195 mmol, 72%).

mp 154-155° C.

$^1$H NMR (CDCl$_3$) δ 0.81-1.03 (m, 7H), 1.59-1.69 (m, 1H), 1.88-2.07 (m, 2H), 2.38-2.46 (m, 2H), 3.85-3.91 (m, 2H), 4.32-4.38 (m, 1H), 4.69-4.77 (m, 1H), 6.31 (t, J=6.9 Hz, 1H), 7.03 (d, J=8.4 Hz, 1H), 7.12 (d, J=8.4 Hz, 1H), 7.81 (d, J=2.1 Hz, 1H), 8.33 (d, J=2.1 Hz, 1H).

MS Calcd.: 478; MS Found: 479 (M+H).

Anal. Calcd for C$_{22}$H$_{21}$N$_4$O$_2$Cl$_3$: C, 55.07; H, 4.41; N, 11.68; Cl, 22.17. Found: C, 55.07; H, 4.33; N, 11.63; Cl, 22.26.

Example 173

Methyl 9-chloro-1-(4,6-dimethoxy-2-methylpyrimidin-5-yl)-1,2,3,4-tetrahydropyrimido[1,2-a]benzimidazole-6-carboxylate

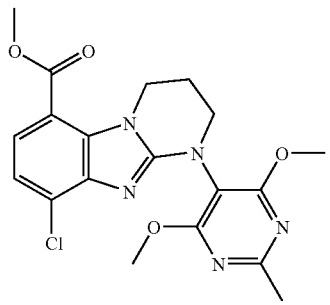 [SMILES: COC(=O)c1ccc(Cl)c2nc3n(c12)CCCN3c1c(OC)nc(C)nc1OC]

Methanesulfonyl chloride (0.11 mL, 1.43 mmol) was added to a stirred solution of methyl 4-chloro-2-[(4,6-dimethoxy-2-methylpyrimidin-5-yl)amino]-1-(3-hydroxypropyl)-1H-benzimidazole-7-carboxylate (Reference example 124, 208 mg, 0.477 mmol) and triethylamine (0.27 mL) in tetrahydrofuran (4.0 mL) at 0° C. The mixture was stirred at 0° C. for 2 hr, and concentrated in vacuo. A mixture of the resulting mesylate and potassium carbonate (264 mg, 1.91 mmol) in N,N-dimethylformamide (5.0 mL) was stirred at 80° C. for 2 hr. The mixture was diluted with water, and extracted with ethyl acetate. The combined organic layer was washed with brine, dried over anhydrous magnesium sulfate, filtered, and concentrated in vacuo. The residue was washed with diisopropyl ether to give the title compound as a colorless powder (160 mg, 0.383 mmol, 80% in 2 steps).

$^1$H NMR (CDCl$_3$) δ 2.20-2.28 (m, 2H), 2.55 (s, 3H), 3.57 (t, J=6.0 Hz, 2H), 3.93 (s, 9H), 4.35 (t, J=6.0 Hz, 2H), 7.05 (d, J=8.7 Hz, 1H), 7.39 (d, J=8.7 Hz, 1H).

MS Calcd.: 417; MS Found: 418 (M+H).

Example 174

[9-Chloro-1-(4,6-dimethoxy-2-methylpyrimidin-5-yl)-1,2,3,4-tetrahydropyrimido[1,2-a]benzimidazol-6-yl](dicyclopropyl)methanol

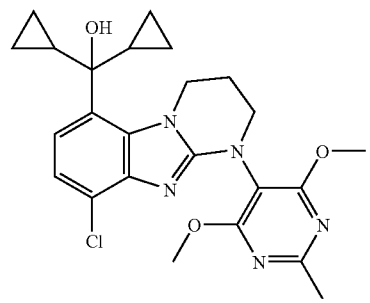 [SMILES: COc1nc(C)nc(OC)c1N1CCCn2c1nc1c(Cl)ccc(C(O)(C3CC3)C3CC3)c12]

Cyclopropylmagnesium bromide (1.0 M solution in tetrahydrofuran, 1.9 mL, 1.9 mmol) was added to a stirred solution of methyl 9-chloro-1-(4,6-dimethoxy-2-methylpyrimidin-5-yl)-1,2,3,4-tetrahydropyrimido[1,2-a]benzimidazole-6-carboxylate (159 mg, 0.381 mmol) in tetrahydrofuran (3.8 mL), and the mixture was stirred at 50° C. for 11 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was purified by flash column chromatography on silica gel eluting with a 15-50% ethyl acetate/n-hexane gradient mixture. The filtrate was concentrated in vacuo to give the solid, which was recrystallized from ethanol/ethyl acetate to give the title compound as a colorless crystal (98.6 mg, 0.210 mmol, 55%).

mp 204-205° C.

$^1$H NMR (CDCl$_3$) δ 0.20-0.30 (m, 2H), 0.50-0.63 (m, 6H), 1.38-1.49 (m, 2H), 1.70 (s, 1H), 2.18-2.26 (m, 2H), 2.55 (s, 3H), 3.54 (t, J=5.7 Hz, 2H), 3.92 (s, 6H), 4.77 (t, J=5.7 Hz, 2H), 6.96 (d, J=8.4 Hz, 1H), 7.10 (d, J=8.4 Hz, 1H).

MS Calcd.: 469; MS Found: 470 (M+H).

Anal. Calcd for C$_{24}$H$_{28}$N$_5$O$_3$Cl: C, 61.34; H, 6.01; N, 14.90; Cl, 7.54. Found: C, 61.26; H, 6.10; N, 14.80; Cl, 7.54.

Example 175

Methyl 9-chloro-1-(3,5-dimethylpyrazin-2-yl)-1,2,3,4-tetrahydropyrimido[1,2-a]benzimidazole-6-carboxylate

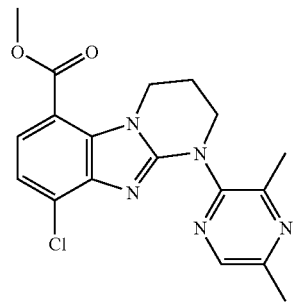 [SMILES: COC(=O)c1ccc(Cl)c2nc3n(c12)CCCN3c1ncc(C)nc1C]

A mixture of methyl 3-amino-4-chloro-2-[(3-hydroxypropyl)amino]benzoate (500 mg, 1.94 mmol) and 2-isothiocyanato-3,5-dimethylpyrazine (866 mg, 5.24 mmol) in tetrahydrofuran (4.0 mL) was stirred at 60° C. for 6 hr. The mixture was concentrated in vacuo, and the residue was purified by flash column chromatography on silica gel eluting with a 50-100% ethyl acetate/n-hexane gradient mixture. The filtrate was concentrated in vacuo to give methyl 4-chloro-3-{[(3,5-dimethylpyrazin-2-yl)carbamothioyl]amino}-2-[(3-hydroxypropyl)amino]benzoate as a yellow solid (430 mg).

MS Calcd.: 423; MS Found: 424 (M+H).

A mixture of the resulting thiourea (435 mg), 1-ethyl-3-(3-dimethylaminopropyl)carbodiimide hydrochloride (214 mg, 1.12 mmol), and triethylamine (0.16 mL) in tetrahydrofuran (3.0 ml) was stirred at 60° C. for 2 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was washed with ethyl acetate/diisopropyl ether to give methyl 4-chloro-2-[(3,5-dimethylpyrazin-2-yl)amino]-1-(3-hydroxypropyl)-1H-benzimidazole-7-carboxylate (294 mg).

MS Calcd.: 389; MS Found: 390 (M+H).

Methanesulfonyl chloride (0.12 mL, 1.51 mmol) was added to a stirred solution of the residue (294 mg) and triethylamine (0.32 mL) in tetrahydrofuran (4.0 mL) at 0° C. The mixture was stirred at 0° C. for 3 hr, and concentrated in vacuo. A mixture of the resulting mesylate and potassium carbonate (521 mg, 3.77 mmol) in N,N-dimethylformamide (4.0 mL) was stirred at 80° C. for 4 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 50-100% ethyl acetate/n-hexane gradient mixture. The filtrate was concentrated in vacuo to give the title compound as a colorless solid (148 mg, 0.398 mmol, 21% in 4 steps).

$^1$H NMR (DMSO-d$_6$) δ 2.22-2.31 (m, 2H), 2.41 (s, 3H), 2.51 (s, 3H), 3.80-4.00 (m, 2H), 3.90 (s, 3H), 4.32 (t, J=6.0 Hz, 2H), 7.16 (d, J=8.4 Hz, 1H), 7.37 (d, J=8.4 Hz, 1H), 8.30 (s, 1H).

MS Calcd.: 371; MS Found: 372 (M+H).

Example 176

[9-Chloro-1-(3,5-dimethylpyrazin-2-yl)-1,2,3,4-tetrahydropyrimido[1,2-a]benzimidazol-6-yl](dicyclopropyl)methanol

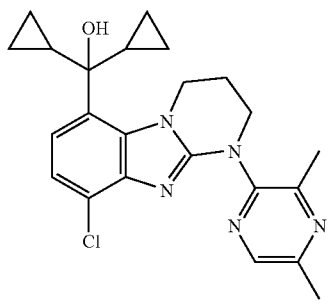 [SMILES: Cc1cnc(N2CCCn3c2nc2c(Cl)ccc(C(O)(C4CC4)C4CC4)c23)c(C)n1]

Cyclopropylmagnesium bromide (1.0 M solution in tetrahydrofuran, 1.59 mL, 1.59 mmol) was added to a stirred solution of methyl 9-chloro-1-(3,5-dimethylpyrazin-2-yl)-1,2,3,4-tetrahydropyrimido[1,2-a]benzimidazole-6-carboxylate (148 mg, 0.398 mmol) in tetrahydrofuran (2.0 mL), and the mixture was stirred at 60° C. for 3 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was purified by flash column chromatography on silica gel eluting with a 70-100% ethyl acetate/n-hexane gradient mixture. The filtrate was concentrated in vacuo to give the solid, which was recrystallized from ethyl acetate to give the title compound as a colorless crystal (59.7 mg, 0.141 mmol, 35%).

mp 152-153° C.

$^1$H NMR (CDCl$_3$) δ 0.24-0.30 (m, 2H), 0.51-0.68 (m, 6H), 1.39-1.49 (m, 2H), 1.77 (s, 1H), 2.25-2.35 (m, 2H), 2.46 (s, 3H), 2.56 (s, 3H), 3.87-3.99 (m, 2H), 4.84 (t, J=6.0 Hz, 2H), 7.03 (d, J=8.7 Hz, 1H), 7.18 (d, J=8.7 Hz, 1H), 8.11 (s, 1H).

MS Calcd.: 423; MS Found: 424 (M+H).

Anal. Calcd for $C_{23}H_{26}N_5OCl$: C, 65.16; H, 6.18; N, 16.52; Cl, 8.36. Found: C, 65.31; H, 6.12; N, 16.41; Cl, 8.56.

Example 177

Methyl 9-chloro-1-(4,6-diethyl-2-methylpyrimidin-5-yl)-1,2,3,4-tetrahydropyrimido[1,2-a]benzimidazole-6-carboxylate

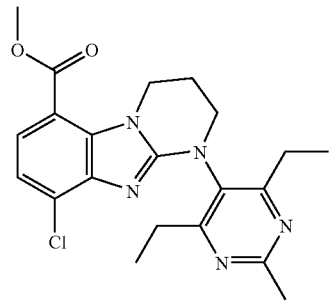 [SMILES: CCc1nc(C)nc(CC)c1N1CCCn2c1nc1c(Cl)ccc(C(=O)OC)c12]

Methanesulfonyl chloride (1.10 mL, 13.4 mmol) was added to a stirred solution of methyl 4-chloro-2-[(4,6-diethyl-2-methylpyrimidin-5-yl)amino]-1-(3-hydroxypropyl)-1H-benzimidazole-7-carboxylate (Reference example 125, 2.90 g, 6.71 mmol) and triethylamine (2.8 mL) in tetrahydrofuran (35 mL) at 0° C. The mixture was stirred at 0° C. for 90 min, and concentrated in vacuo. A mixture of the resulting mesylate and potassium carbonate (2.78 g, 20.1 mmol) in N,N-dimethylformamide (30 mL) was stirred at 70° C. for 4 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 70-100% ethyl acetate/n-hexane gradient mixture. The filtrate was concentrated in vacuo to give the title compound as a colorless solid (2.21 g, 5.34 mmol, 80% in 2 steps).

$^1$H NMR (CDCl$_3$) δ 1.27 (t, J=7.2 Hz, 6H), 2.29-2.37 (m, 2H), 2.58-2.72 (m, 4H), 2.74 (s, 3H), 3.60 (t, J=5.1 Hz, 2H), 3.95 (s, 3H), 4.46 (t, J=6.3 Hz, 2H), 7.08 (d, J=8.4 Hz, 1H), 7.44 (d, J=8.4 Hz, 1H).

MS Calcd.: 413; MS Found: 414 (M+H).

Example 178

9-Chloro-1-(4,6-diethyl-2-methylpyrimidin-5-yl)-1,2,3,4-tetrahydropyrimido[1,2-a]benzimidazole-6-carbaldehyde

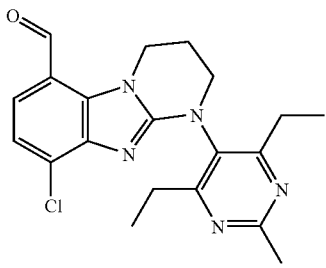 [SMILES: CCc1nc(C)nc(CC)c1N1CCCn2c1nc1c(Cl)ccc(C=O)c12]

Lithium borohydride (466 mg, 21.4 mmol) was added to a stirred solution of methyl 9-chloro-1-[6-(dimethylamino)-2-methylpyridin-3-yl]-1,2,3,4-tetrahydropyrimido[1,2-a]benzimidazole-6-carboxylate (2.21 g, 5.34 mmol) in tetrahydrofuran (26 mL) at room temperature, and the mixture was stirred at 40° C. for 15 hr. The reaction was quenched by aqueous saturated ammonium chloride at 0° C., and the mixture was extracted with ethyl acetate. The combined organic layer was washed with brine, dried over anhydrous magnesium sulfate, filtered and concentrated in vacuo to give [9-chloro-1-(4,6-diethyl-2-methylpyrimidin-5-yl)-1,2,3,4-tetrahydropyrimido[1,2-a]benzimidazol-6-yl]methanol as a pale yellow solid (2.06 g).

MS Calcd.: 385; MS Found: 386 (M+H).

Dess-Martin reagent (3.40 g, 8.01 mmol) was added to a stirred solution of the residue (2.06 g, 5.34 mmol) in dimethyl sulfoxide (1.0 mL) and acetonitrile (25 mL) at 0 ° C., and the mixture was stirred at 0 ° C. for 90 min. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 60-100% ethyl acetate/n-hexane gradient mixture. The filtrate was concentrated in vacuo to give the title compound as a pale yellow solid (1.35 g, 3.52 mmol, 66%).

$^1$H NMR (CDCl$_3$) δ 1.22-1.30 (m, 6H), 2.32-2.42 (m, 2H), 2.56-2.72 (m, 4H), 2.74 (s, 3H), 3.61 (t, J=5.7 Hz, 2H), 4.73 (t, J=6.3 Hz, 2H), 7.21 (d, J=8.4 Hz, 1H), 7.35 (d, J=8.4 Hz, 1H), 9.97 (s, 1H).

MS Calcd.: 383; MS Found: 384 (M+H).

Example 179

1-[9-Chloro-1-(4,6-diethyl-2-methylpyrimidin-5-yl)-1,2,3,4-tetrahydropyrimido[1,2-a]benzimidazol-6-yl]-2,2,2-trifluoroethanol

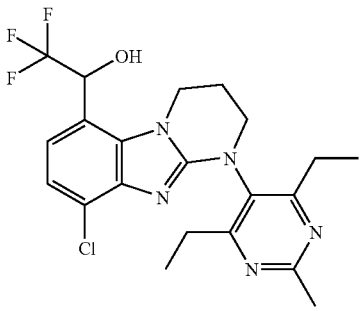 [SMILES: CCc1nc(C)nc(CC)c1N1CCCn2c1nc1c(Cl)ccc(C(O)C(F)(F)F)c12]

Tetrabutylammonium fluoride (1.0 M solution in tetrahydrofuran, 0.31 mL, 0.31 mmol) was added dropwise to a stirred solution of 9-chloro-1-(4,6-diethyl-2-methylpyrimidin-5-yl)-1,2,3,4-tetrahydropyrimido[1,2-a]benzimidazole-6-carbaldehyde (601 mg, 1.57 mmol) and trimethyl(trifluoromethyl)silane (670 mg, 4.71 mmol) in tetrahydrofuran (10 mL) at 0° C., and the mixture was stirred at 0° C. for 90 min. 1N hydrochloric acid (4.0 mL) was added to the mixture at 0° C., and the mixture was stirred at 0° C. for 10 min. The mixture was neutralized with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 70-100% ethyl acetate/n-hexane gradient mixture. The filtrate was concentrated in vacuo to give the title compound as a colorless solid (684 mg, 1.51 mmol, 96%).

$^1$H NMR (CDCl$_3$) δ 1.23-1.33 (m, 6H), 2.32-2.44 (m, 2H), 2.49-2.79 (m, 5H), 2.73 (s, 3H), 3.51-3.64 (m, 2H), 4.38 (t, J=5.7 Hz, 2H), 5.46-5.53 (m, 1H), 7.05-7.09 (m, 2H).

MS Calcd.: 453; MS Found: 454 (M+H).

Example 180

9-Chloro-1-(4,6-diethyl-2-methylpyrimidin-5-yl)-6-[1-(difluoromethoxy)-2,2,2-trifluoroethyl]-1,2,3,4-tetrahydropyrimido[1,2-a]benzimidazole

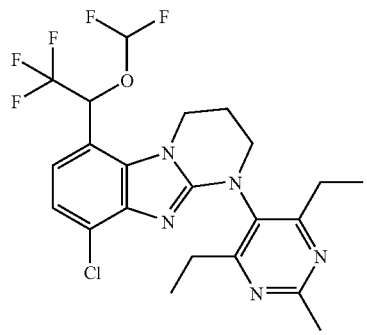 [SMILES: CCc1nc(C)nc(CC)c1N1CCCn2c1nc1c(Cl)ccc(C(OC(F)F)C(F)(F)F)c12]

A mixture of 1-[9-chloro-1-(4,6-diethyl-2-methylpyrimidin-5-yl)-1,2,3,4-tetrahydropyrimido[1,2-a]benzimidazol-6-yl]-2,2,2-trifluoroethanol (522 mg, 1.15 mmol), benzyltriethylammonium chloride (26.2 mg, 0.115 mmol), and 8N sodium hydroxide (4.0 mL) in tetrahydrofuran (4.0 mL) was stirred at room temperature under chloro(difluoro)methane atmosphere for 2 hr. The mixture was diluted with aqueous saturated ammonium chloride, and extracted with ethyl acetate. The combined organic layer was washed with brine, dried over anhydrous magnesium sulfate, filtered and concentrated in vacuo. The residue was recrystallized from ethyl acetate/diisopropyl ether to give the title compound as a colorless crystal (203 mg, 0.403 mmol, 35%).

mp 194-195° C.

$^1$H NMR (CDCl$_3$) δ 1.25-1.31 (m, 6H), 2.41-2.49 (m, 2H), 2.57-2.73 (m, 4H), 2.74 (s, 3H), 3.55-3.67 (m, 2H), 4.33-4.44 (m, 2H), 5.99 (q, J=6.0 Hz, 1H), 6.43 (t, J=72.3 Hz, 1H), 7.12-7.14 (m, 2H).

MS Calcd.: 503; MS Found: 504 (M+H).

Anal. Calcd for $C_{22}H_{23}N_5OClF_5$: C, 52.44; H, 4.60; N, 13.90; Cl, 7.04; F, 18.85. Found: C, 52.46; H, 4.53; N, 13.80; Cl, 7.18; F, 18.80.

Example 181

Methyl 9-chloro-1-(2-methoxy-4,6-dimethylpyrimidin-5-yl)-1,2,3,4-tetrahydropyrimido[1,2-a]benzimidazole-6-carboxylate

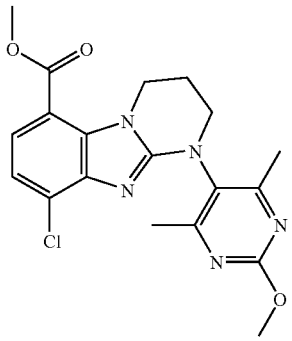 [SMILES: COC(=O)c1ccc(Cl)c2nc3n(c12)CCCN3c1c(C)nc(OC)nc1C]

Methanesulfonyl chloride (4.57 mL, 57.8 mmol) was added to a stirred solution of methyl 4-chloro-1-(3-hydroxypropyl)-2-[(2-methoxy-4,6-dimethylpyrimidin-5-yl)amino]-1H-benzimidazole-7-carboxylate (Reference example 127, 11.9 g, 28.9 mmol) and triethylamine (12.1 mL) in tetrahydrofuran (400 mL) at 0° C. The mixture was stirred at 0° C. for 50 min, and concentrated in vacuo. A mixture of the resulting mesylate and potassium carbonate (12.0 g, 86.8 mmol) in N,N-dimethylformamide (200 mL) was stirred at 80° C. for 2 hr. The mixture was diluted with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 50-100% ethyl acetate/n-hexane gradient mixture. The filtrate was concentrated in vacuo to give the title compound as a pale yellow solid (8.88 g, 22.1 mmol, 76% in 2 steps).

H NMR (CDCl₃) δ 2.27-2.37 (m, 2H), 2.37 (s, 6H), 3.59 (t, J=5.7 Hz, 2H), 3.95 (s, 3H), 4.01 (s, 3H), 4.44 (t, J=6.3 Hz, 2H), 7.09 (d, J=8.4 Hz, 1H), 7.45 (d, J=8.4 Hz, 1H).

MS Calcd.: 401; MS Found: 402 (M+H).

Example 182

[9-Chloro-1-(2-methoxy-4,6-dimethylpyrimidin-5-yl)-1,2,3,4-tetrahydropyrimido[1,2-a]benzimidazol-6-yl]methanol

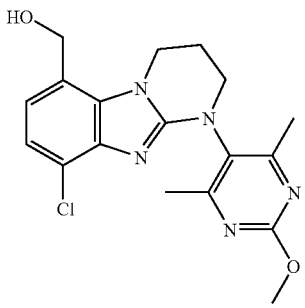 [SMILES: COc1nc(C)c(N2CCCn3c2nc2c(Cl)ccc(CO)c23)c(C)n1]

Lithium borohydride (1.93 g, 88.4 mmol) was added to a stirred solution of methyl 9-chloro-1-(2-methoxy-4,6-dimethylpyrimidin-5-yl)-1,2,3,4-tetrahydropyrimido[1,2-a]benzimidazole-6-carboxylate (8.87 g, 22.1 mmol) in tetrahydrofuran (100 mL) at room temperature, and the mixture was stirred at 40° C. for 14 hr. The reaction was quenched by methanol, and the mixture was diluted with aqueous saturated ammonium chloride at 0° C. The mixture was extracted with tetrahydrofuran/ethyl acetate. The combined organic layer was washed with brine, dried over anhydrous magnesium sulfate, filtered and concentrated in vacuo. The residue was washed with ethyl acetate/diisopropyl ether to give the title compound as a colorless powder (8.08 g, 21.6 mmol, 98%).

H NMR (DMSO-d₆) δ 2.20-2.40 (m, 2H), 2.29 (s, 6H), 3.57-3.65 (m, 2H), 3.92 (s, 3H), 4.56 (t, J=6.0 Hz, 2H), 4.74 (d, J=5.1 Hz, 2H), 5.35 (t, J=5.1 Hz, 1H), 6.83 (d, J=8.1 Hz, 1H), 6.95 (d, J=8.1 Hz, 1H).

MS Calcd.: 373; MS Found: 374 (M+H).

Example 183

9-Chloro-1-(2-methoxy-4,6-dimethylpyrimidin-5-yl)-1,2,3,4-tetrahydropyrimido[1,2-a]benzimidazole-6-carbaldehyde

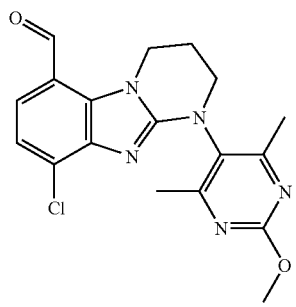 [SMILES: COc1nc(C)c(N2CCCn3c2nc2c(Cl)ccc(C=O)c23)c(C)n1]

Dess-Martin reagent (10.1 g, 23.8 mmol) was added to a stirred solution of [9-chloro-1-(2-methoxy-4,6-dimethylpyrimidin-5-yl)-1,2,3,4-tetrahydropyrimido[1,2-a]benzimidazol-6-yl]methanol (8.08 g, 21.6 mmol) in dimethyl sulfoxide (5.0 mL) and acetonitrile (100 mL) at 0 ° C., and the mixture was stirred at 0 ° C. for 50 min. Additional Dess-Matrin reagent (4.00 g, 9.43 mmol) was added to the stirred mixture, and the mixture was stirred at 0 ° C. for 60 min. The mixture was diluted with saturated aqueous sodium hydrogen carbonate, filtrated and extracted with ethyl acetate. The combined organic layer was washed with brine, dried over anhydrous magnesium sulfate, filtered and concentrated in vacuo to give the title compound as a yellow solid (6.35 g, 17.1 mmol, 79%).

¹H NMR (CDCl₃) δ 2.35-2.42 (m, 2H), 2.37 (s, 6H), 3.60 (t, J=5.7 Hz, 2H), 4.01 (s, 3H), 4.72 (t, J=5.7 Hz, 2H), 7.22 (d, J=8.4 Hz, 1H), 7.35 (d, J=8.4 Hz, 1H), 9.97 (s, 1H).

MS Calcd.: 371; MS Found: 372 (M+H).

Example 184

1-[9-Chloro-1-(2-methoxy-4,6-dimethylpyrimidin-5-yl)-1,2,3,4-tetrahydropyrimido[1,2-a]benzimidazol-6-yl]-2,2,2-trifluoroethanol

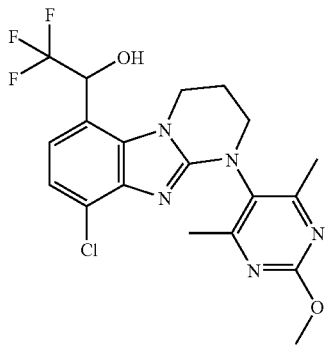 [SMILES: COc1nc(C)c(N2CCCn3c2nc2c(Cl)ccc(C(O)C(F)(F)F)c23)c(C)n1]

Tetrabutylammonium fluoride (1.0 M solution in tetrahydrofuran, 1.1 mL, 1.1 mmol) was added dropwise to a stirred solution of 9-chloro-1-(2-methoxy-4,6-dimethylpyrimidin-5-yl)-1,2,3,4-tetrahydropyrimido[1,2-a]benzimidazole-6-carbaldehyde (4.12 g, 11.1 mmol) and trimethyl(trifluoromethyl)silane (3.16 g, 22.2 mmol) in tetrahydrofuran (45 mL) at 0° C., and the mixture was stirred at 0° C. for 20 min. 1N hydrochloric acid (35 mL) was added to the mixture at 0° C., and the mixture was stirred at 0° C. for 30 min. The mixture was neutralized with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 75-100% ethyl acetate/n-hexane gradient mixture. The filtrate was concentrated in vacuo to give the solid, which was washed with ethyl acetate/diisopropyl ether to give the title compound as a colorless powder (3.96, 8.96 mmol, 81%).

$^1$H NMR (CDCl$_3$) δ 2.32 (s, 3H), 2.35-2.48 (m, 2H), 2.41 (s, 3H), 3.46 (d, J=5.1 Hz, 1H), 3.54-3.62 (m, 2H), 4.01 (s, 3H), 4.37-4.46 (m, 2H), 5.50-5.58 (m, 1H), 7.08-7.12 (m, 2H).

MS Calcd.: 441; MS Found: 442 (M+H).

Example 185

9-Chloro-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole

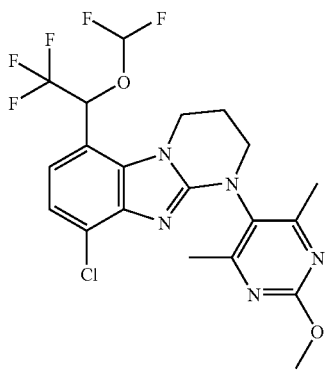

A mixture of 1-[9-chloro-1-(2-methoxy-4,6-dimethylpyrimidin-5-yl)-1,2,3,4-tetrahydropyrimido[1,2-a]benzimidazol-6-yl]-2,2,2-trifluoroethanol (370 mg, 0.837 mmol), benzyltriethylammonium chloride (25.0 mg, 0.110 mmol), and 8N sodium hydroxide (3.0 mL) in tetrahydrofuran (3.5 mL) was stirred at room temperature under chloro(difluoro)methane atmosphere for 3 hr. The mixture was diluted with aqueous saturated ammonium chloride, and extracted with ethyl acetate. The combined organic layer was washed with brine, dried over anhydrous magnesium sulfate, filtered and concentrated in vacuo. The residue was purified by flash column chromatography on silica gel eluting with a 50-100% ethyl acetate/n-hexane gradient mixture. The filtrate was concentrated in vacuo to give the solid, which was recrystallized from ethyl acetate/diisopropyl ether to give the title compound as a colorless crystal (125 mg, 0.255 mmol, 30%).

mp 169-170° C.

$^1$H NMR (CDCl$_3$) δ 2.38 (s, 6H), 2.41-2.49 (m, 2H), 3.54-3.67 (m, 2H), 4.01 (s, 3H), 4.33-4.41 (m, 2H), 5.99 (q, J=5.7 Hz, 1H), 6.42 (t, J=72.0 Hz, 1H), 7.12-7.17 (m, 2H).

MS Calcd.: 491; MS Found: 492 (M+H).

Anal. Calcd for C$_{20}$H$_{19}$N$_5$O$_2$ClF$_5$: C, 48.84; H, 3.89; N, 14.24; Cl, 7.21; F, 19.31. Found: C, 48.70; H, 3.98; N, 14.18; Cl, 7.23; F, 19.31.

Example 186

(−)-9-Chloro-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole

Example 187

(+)-9-Chloro-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole

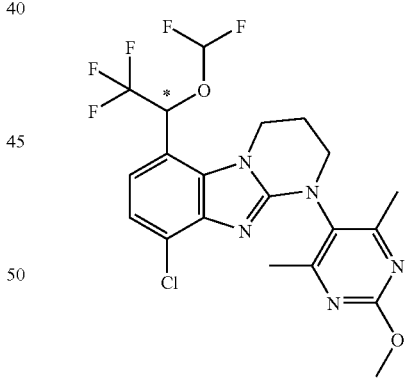

Racemic Example 185 (2454 mg) was resolved by preparative HPLC, using CHIRALCEL OJ (5 cm i.d.×50 cm, Daicel Chemical Industries, Ltd.) with the flow rate of 80 mL/min at 40° C. and hexane/ethanol (90/10) as the mobile phase, and obtaining the stereoisomer having a shorter retention time 1182 mg in an enantiomer excess greater than 99.9% and the stereoisomer having a longer retention time 1212 mg in an enantiomer excess of 99.7%. The obtained compounds were recrystallized from ethyl acetate/diisopropyl ether to give the optically active title compounds as a colorless crystal respectively (shorter retention time (Example 186): 958 mg, longer retention time (Example 187): 1.01 g).

Shorter Retention Time (Example 186):
>99.9% ee

[α]$_D^{20}$=−40.5 (c=0.4000, MeOH)

mp 215-217° C.

$^1$H NMR (CDCl$_3$) δ 2.37 (s, 6H), 2.39-2.50 (m, 2H), 3.53-3.67 (m, 2H), 4.01 (s, 3H), 4.33-4.42 (m, 2H), 5.99 (q, J=6.0 Hz, 1H), 6.42 (t, J=72.3 Hz, 1H), 7.12-7.17 (m, 2H).

MS Calcd.: 491; MS Found: 492 (M+H).

Anal. Calcd for C$_{20}$H$_{19}$N$_5$O$_2$ClF$_5$: C, 48.84; H, 3.89; N, 14.24; Cl, 7.21; F, 19.31. Found: C, 48.63; H, 3.92; N, 14.03; Cl, 7.22; F, 19.34.

longer Retention Time (Example 187):
99.4% ee

[α]$_D^{20}$=+39.6 (c=0.4195, MeOH)

mp 216-218° C.

$^1$H NMR (CDCl$_3$) δ 2.38 (s, 6H), 2.39-2.51 (m, 2H), 3.53-3.67 (m, 2H), 4.01 (s, 3H), 4.32-4.42 (m, 2H), 5.99 (q, J=5.7 Hz, 1H), 6.42 (t, J=72.3 Hz, 1H), 7.11-7.18 (m, 2H).

MS Calcd.: 491; MS Found: 492 (M+H).

Anal. Calcd for O$_{20}$H$_{19}$N$_5$O$_2$ClF$_5$: C, 48.84; H, 3.89; N, 14.24; Cl, 7.21; F, 19.31. Found: C, 48.84; H, 4.00; N, 14.17; Cl, 7.20; F, 19.24.

Example 188

[9-Chloro-1-(2-methoxy-4,6-dimethylpyrimidin-5-yl)-1,2,3,4-tetrahydropyrimido[1,2-a]benzimidazol-6-yl](dicyclopropyl)methanol

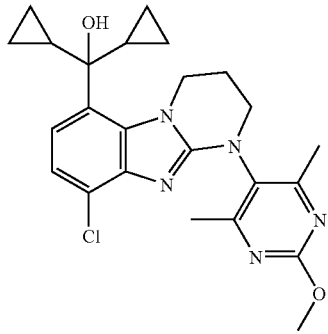 [SMILES: COc1nc(C)c(N2CCCn3c2nc2c(Cl)ccc(C(O)(C4CC4)C4CC4)c23)c(C)n1]

Cyclopropylmagnesium bromide (1.0 M solution in tetrahydrofuran, 1.84 mL, 1.84 mmol) was added to a stirred solution of methyl 9-chloro-1-(2-methoxy-4,6-dimethylpyrimidin-5-yl)-1,2,3,4-tetrahydropyrimido[1,2-a]benzimidazole-6-carboxylate (185 mg, 0.460 mmol) in tetrahydrofuran (2.3 mL), and the mixture was stirred at 60° C. for 3 hr. The reaction was quenched by aqueous saturated ammonium chloride, and the mixture was extracted with ethyl acetate. The combined organic layer was washed with brine, dried over anhydrous magnesium sulfate, filtered, and concentrated in vacuo. The residue was purified by flash column chromatography on silica gel eluting with a 70-100% ethyl acetate/n-hexane gradient mixture. The filtrate was concentrated in vacuo to give the solid, which was recrystallized from ethyl acetate to give the title compound as a colorless crystal (78.7 mg, 0.173 mmol, 38%).

mp 220-221° C.

$^1$H NMR (CDCl$_3$) δ 0.22-0.31 (m, 2H), 0.51-0.68 (m, 6H), 1.38-1.50 (m, 2H), 1.59 (s, 1H), 2.24-2.40 (m, 2H), 2.36 (s, 6H), 3.55 (t, J=6.0 Hz, 2H), 4.00 (s, 3H), 4.84 (t, J=6.0 Hz, 2H), 7.00 (d, J=8.4 Hz, 1H), 7.14 (d, J=8.4 Hz, 1H).

MS Calcd.: 453; MS Found: 454 (M+H).

Example 189

9-Chloro-6-[cyclopropyl(2,2,2-trifluoroethoxy)methyl]-1-(2-methoxy-4,6-dimethylpyrimidin-5-yl)-1,2,3,4-tetrahydropyrimido[1,2-a]benzimidazole

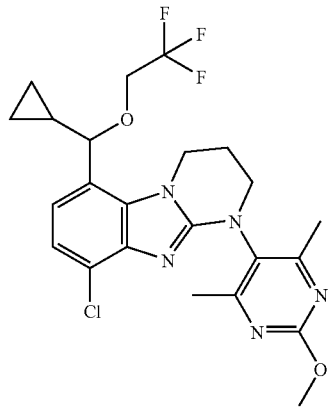 [SMILES: COc1nc(C)c(N2CCCn3c2nc2c(Cl)ccc(C(OCC(F)(F)F)C4CC4)c23)c(C)n1]

Cyclopropylmagnesium bromide (1.0 M solution in tetrahydrofuran, 0.33 mL, 0.33 mmol) was added to a stirred solution of 9-chloro-1-(2-methoxy-4,6-dimethylpyrimidin-5-yl)-1,2,3,4-tetrahydropyrimido[1,2-a]benzimidazole-6-carbaldehyde (111 mg, 0.299 mmol) in tetrahydrofuran (1.5 mL) at 0° C., and the mixture was stirred at 0° C. for 2 hr. The reaction was quenched by water, and the mixture was extracted with ethyl acetate. The combined organic layer was washed with brine, dried over anhydrous magnesium sulfate, filtered, and concentrated in vacuo to give [9-chloro-1-(2-methoxy-4,6-dimethylpyrimidin-5-yl)-1,2,3,4-tetrahydropyrimido[1,2-a]benzimidazol-6-yl](cyclopropyl)methanol (155 mg).

MS Calcd.: 413; MS Found: 414 (M+H).

A mixture of the residue (150 mg), 1,1'-(azodicarbonyl)dipiperidine (183 mg, 0.725 mmol) and h-butylphosphine (147 mg, 0.725 mmol) in tetrahydrofuran (4.0 mL) was stirred at room temperature for 15 min. 2,2,2-Trifluoroethanol (362 mg, 3.62 mmol) was added to the mixture, and the mixture was stirred at 50° C. for 13 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 50-100% ethyl acetate/n-hexane gradient mixture. The filtrate was concentrated in vacuo to give the solid, which was recrystallized from ethyl acetate/diisopropyl ether to give the title compound as a colorless crystal (105 mg, 0.212 mmol, 59%).

mp 225-227° C.

$^1$H NMR (CDCl$_3$) δ 0.29-0.36 (m, 1H), 0.48-0.55 (m, 1H), 0.63-0.70 (m, 1H), 0.75-0.82 (m, 1H), 1.40-1.51 (m, 1H), 2.33-2.42 (m, 2H), 2.37 (s, 6H), 3.52-3.63 (m, 2H), 3.63-3.82 (m, 2H), 4.08 (s, 3H), 4.31 (d, J=8.1 Hz, 1H), 4.42-4.54 (m, 1H), 4.62-4.74 (m, 1H), 6.85 (d, J=8.1 Hz, 1H), 7.05 (d, J=8.1 Hz, 1H).

MS Calcd.: 495; MS Found: 496 (M+H).

Example 190

N-{1-[9-Chloro-1-(2-methoxy-4,6-dimethylpyrimidin-5-yl)-1,2,3,4-tetrahydropyrimido[1,2-a]benzimidazol-6-yl]-2,2,2-trifluoroethyl}-2,2-difluoroacetamide

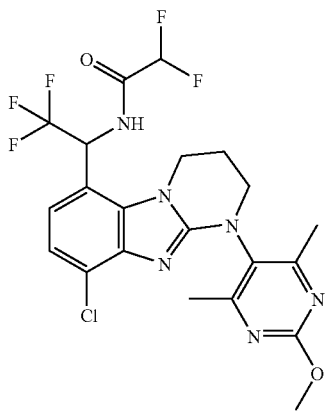 [SMILES: COc1nc(C)c(N2CCCn3c2nc2c(Cl)ccc(C(NC(=O)C(F)F)C(F)(F)F)c23)c(C)n1]

Thionyl chloride (65 μL, 0.892 mmol) was added to a stirred solution of 1-[9-chloro-1-(2-methoxy-4,6-dimethylpyrimidin-5-yl)-1,2,3,4-tetrahydropyrimido[1,2-a]benzimidazol-6-yl]-2,2,2-trifluoroethanol (197 mg, 0.446 mmol) and pyridine (0.10 mL) in tetrahydrofuran (4.0 mL) at 0° C., and the mixture was stirred at 0° C. for 40 min. The mixture was diluted with saturated aqueous sodium hydrogen carbonate, and extracted with ethyl acetate. The combined organic layer was washed with brine, dried over anhydrous magnesium sulfate, filtered, and concentrated in vacuo. A mixture of the resulting benzyl chloride (208 mg) and sodium azide (58.8 mg, 0.904 mmol) in dimethyl sulfoxide (2.0 mL) was stirred at 100° C. for 7 hr. The mixture was diluted with water and extracted with ethyl acetate. The combined organic layer was washed with brine, dried over anhydrous magnesium sulfate, filtered, and concentrated in vacuo. A mixture of the resulting azide, triphenylphosphine (81.6 mg, 0.311 mmol) and water (0.3 mL) in tetrahydrofuran (3.0 mL) was stirred at 50° C. for 14 hr. The mixture was acidified by 1N hydrochloric acid and extracted with ethyl acetate. The aqueous layer was neutralized with saturated aqueous sodium hydrogen carbonate and extracted with ethyl acetate. The combined organic layer was washed with brine, dried over anhydrous magnesium sulfate, filtered, and concentrated in vacuo. A mixture of the resulting benzylamine (66.4 mg), difluoroacetic acid (21.8 mg, 0.227 mmol), 1-ethyl-3-(3-dimethylaminopropyl)carbodiimide hydrochloride (31.8 mg, 0.166 mmol), 1-hydroxybenzotriazole (25.4 mg, 0.166 mmol) and triethylamine (0.15 mL) in N,N-dimethylformamide (1.0 mL) was stirred at room temperature for 16 hr. The mixture was diluted with saturated aqueous sodium hydrogen carbonate and extracted with ethyl acetate. The combined organic layer was washed with brine, dried over anhydrous magnesium sulfate, filtered, and concentrated in vacuo. The residue was purified by flash column chromatography on silica gel eluting with a 70-100% ethyl acetate/n-hexane gradient mixture. The filtrate was concentrated in vacuo to give the solid, which was recrystallized from ethyl acetate/diisopropyl ether to give the title compound as a colorless crystal (23.9 mg, 0.0461 mmol, 10% in 4 steps).

mp 155-156° C.

$^1$H NMR (CDCl$_3$) δ 2.35 (s, 3H), 2.38 (s, 3H), 2.39-2.55 (m, 2H), 3.55-3.69 (m, 2H), 4.01 (s, 3H), 4.38-4.46 (m, 1H), 4.56-4.63 (m, 1H), 6.00 (t, J=53.9 Hz, 1H), 6.35-6.46 (m, 1H), 6.94 (d, J=8.4 Hz, 1H), 7.04 (d, J=9.6 Hz, 1H), 7.17 (d, J=8.4 Hz, 1H).

MS Calcd.: 518; MS Found: 519 (M+H).

Example 191

1-[9-Chloro-1-(2-methoxy-4,6-dimethylpyrimidin-5-yl)-1,2,3,4-tetrahydropyrimido[1,2-a]benzimidazol-6-yl]propan-1-ol

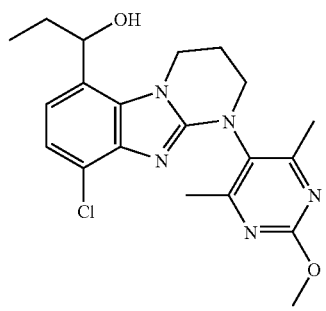 [SMILES: CCC(O)c1ccc(Cl)c2nc3n(c12)CCCN3c1c(C)nc(OC)nc1C]

Ethylmagnesium bromide (3.0 M solution in diethyl ether, 0.25 mL, 0.75 mmol) was added to a stirred solution of 9-chloro-1-(2-methoxy-4,6-dimethylpyrimidin-5-yl)-1,2,3,4-tetrahydropyrimido[1,2-a]benzimidazole-6-carbaldehyde (256 mg, 0.689 mmol) in tetrahydrofuran (3.5 mL) at 0° C., and the mixture was stirred at 0° C. for 30 min. The reaction was quenched by water, and the mixture was extracted with ethyl acetate. The combined organic layer was washed with brine, dried over anhydrous magnesium sulfate, filtered, and concentrated in vacuo. The residue was washed with ethyl acetate/diisopropyl ether to give the title compound as a colorless powder (224 mg, 0.557 mmol, 81%).

H NMR (DMSO-d$_6$) δ 0.95 (t, J=7.2 Hz, 3H), 1.70-1.88 (m, 2H), 2.28 (s, 6H), 2.20-2.38 (m, 2H), 3.54-3.66 (m, 2H), 3.92 (s, 3H), 4.45-4.57 (m, 2H), 4.93-5.01 (m, 1H), 5.28 (d, J=4.5 Hz, 1H), 6.92-6.97 (m, 2H).

MS Calcd.: 401; MS Found: 402 (M+H).

Example 192

1-[9-Chloro-1-(2-methoxy-4,6-dimethylpyrimidin-5-yl)-1,2,3,4-tetrahydropyrimido[1,2-a]benzimidazol-6-yl]propan-1-one

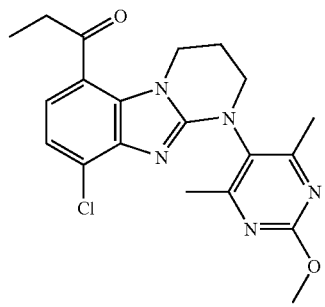 [SMILES: CCC(=O)c1ccc(Cl)c2nc3n(c12)CCCN3c1c(C)nc(OC)nc1C]

Dess-Martin reagent (207 mg, 0.487 mmol) was added to a stirred solution of 1-[9-chloro-1-(2-methoxy-4,6-dimethylpyrimidin-5-yl)-1,2,3,4-tetrahydropyrimido [1,2-a]benzimidazol-6-yl]propan-1-ol (178 mg, 0.443 mmol) in dimethyl sulfoxide (1.0 mL) and acetonitrile (3.0 mL) at 0 ° C., and the mixture was stirred at 0 ° C. for 30 min. The mixture was diluted with saturated aqueous sodium hydrogen carbonate, and extracted with ethyl acetate. The combined organic layer was washed with brine, dried over anhydrous magnesium sulfate, filtered and concentrated in vacuo to give the title compound as a yellow solid (172 mg, 0.430 mmol, 97%).

$^1$H NMR (CDCl$_3$) δ 1.27 (t, J=7.2 Hz, 3H), 2.25-2.34 (m, 2H), 2.36 (s, 6H), 3.06 (q, J=7.2 Hz, 2H), 3.59 (t, J=6.0 Hz, 2H), 4.01 (s, 3H), 4.19 (t, J=6.0 Hz, 2H), 7.11 (d, J=8.4 Hz, 1H), 7.29 (d, J=8.4 Hz, 1H).

MS Calcd.: 399; MS Found: 400 (M+H).

Example 193

(1E)-1-[9-Chloro-1-(2-methoxy-4,6-dimethylpyrimidin-5-yl)-1,2,3,4-tetrahydropyrimido[1,2-a]benzimidazol-6-yl]propan-1-one O-(difluoromethyl)oxime

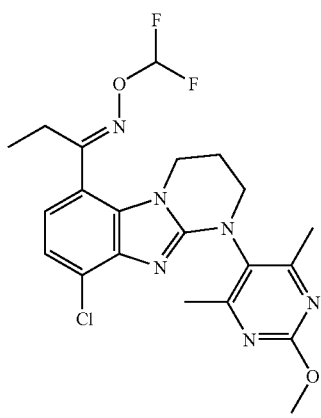 [SMILES: CC/C(=N\OC(F)F)c1ccc(Cl)c2nc3n(c12)CCCN3c1c(C)nc(OC)nc1C]

A mixture of 1-[9-chloro-1-(2-methoxy-4,6-dimethylpyrimidin-5-yl)-1,2,3,4-tetrahydropyrimido[1,2-a]benzimidazol-6-yl]propan-1-one (172 mg, 0.430 mmol), hydroxylamine hydrochloride (89.6 mg, 1.29 mmol) and pyridine (1.0 mL) in ethanol (2.0 mL) was stirred at 80° C. for 14 hr. The mixture was concentrated in vacuo, diluted with saturated aqueous sodium hydrogen carbonate, and extracted with ethyl acetate. The combined organic layer was washed with brine, dried over anhydrous magnesium sulfate, filtered, and concentrated in vacuo to give the solid, which was washed with diisopropyl ether. A mixture of the resulting oxime (103 mg), benzyltriethylammonium chloride (2.8 mg, 0.0123 mmol), and 8N sodium hydroxide (1.0 mL) in tetrahydrofuran (4.0 mL) was stirred at room temperature under chloro(difluoro)methane atmosphere for 4 hr. The mixture was diluted with aqueous saturated ammonium chloride, and extracted with ethyl acetate. The combined organic layer was washed with brine, dried over anhydrous magnesium sulfate, filtered and concentrated in vacuo. The residue was purified by flash column chromatography on silica gel eluting with a 70-100% ethyl acetate/n-hexane gradient mixture. The filtrate was concentrated in vacuo to give the solid, which was recrystallized from ethyl acetate/diisopropyl ether to give the title compound as a colorless crystal (30.2 mg, 0.0650 mmol, 15% in 2 steps).

mp 199-200° C.

$^1$H NMR (CDCl$_3$) δ 1.20 (t, J=7.5 Hz, 3H), 2.28-2.36 (m, 2H), 2.37 (s, 6H), 2.90 (q, J=7.5 Hz, 2H), 3.58 (t, J=5.7 Hz, 2H), 4.01 (s, 3H), 4.11 (t, J=5.7 Hz, 2H), 6.72 (t, J=72.8 Hz, 1H), 6.87 (d, J=8.1 Hz, 1H), 7.13 (d, J=8.1 Hz, 1H).

MS Calcd.: 464; MS Found: 465 (M+H).

Example 194

(1E)-1-[9-Chloro-1-(2,4,6-trichlorophenyl)-1,2,3,4-tetrahydropyrimido[1,2-a]benzimidazol-6-yl]propan-1-one O-(difluoromethyl)oxime

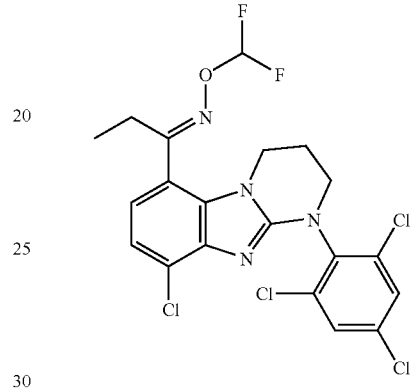

Dess-Martin reagent (82.5 mg, 0.195 mmol) was added to a stirred solution of 1-[9-chloro-1-(2,4,6-trichlorophenyl)-1,2,3,4-tetrahydropyrimido[1,2-a]benzimidazol-6-yl]propan-1-ol (78.8 mg, 0.177 mmol) in dimethyl sulfoxide (0.3 mL) and acetonitrile (1.0 mL) at 0 ° C., and the mixture was stirred at 0 ° C. for 3 hr. The mixture was diluted with saturated aqueous sodium hydrogen carbonate, and extracted with ethyl acetate. The combined organic layer was washed with brine, dried over anhydrous magnesium sulfate, filtered and concentrated in vacuo to give the solid, which was washed with diisopropyl ether. A mixture of the resulting ketone (78.1 mg), hydroxylamine hydrochloride (36.7 mg, 0.528 mmol) and pyridine (0.5 mL) in ethanol (1.0 mL) was stirred at 80 ° C. for 14 hr. The mixture was concentrated in vacuo, diluted with saturated aqueous sodium hydrogen carbonate, and extracted with ethyl acetate. The combined organic layer was washed with brine, dried over anhydrous magnesium sulfate, filtered, and concentrated in vacuo. A mixture of the resulting oxime (72.5 mg) and 8N sodium hydroxide (0.5 mL) in tetrahydrofuran (1.0 mL) was stirred at 50 ° C. under chloro(difluoro)methane atmosphere for 4 hr. The mixture was diluted with aqueous saturated ammonium chloride, and extracted with ethyl acetate. The combined organic layer was washed with brine, dried over anhydrous magnesium sulfate, filtered and concentrated in vacuo. The residue was purified by flash column chromatography on silica gel eluting with a 5-30% ethyl acetate/n-hexane gradient mixture. The filtrate was concentrated in vacuo to give the title compound as a colorless amorphous (4.8 mg, 0.0094 mmol, 5% in 3 steps).

Amorphous.

$^1$H NMR (CDCl$_3$) δ 1.18 (t, J=7.8 Hz, 3H), 2.31-2.40 (m, 2H), 2.89 (q, J=7.8 Hz, 2H), 3.67 (t, J=6.0 Hz, 2H), 4.09 (t, J=6.0 Hz, 2H), 6.72 (t, J=72.9 Hz, 1H), 6.86 (d, J=8.1 Hz, 1H), 7.12 (d, J=8.1 Hz, 1H), 7.45 (s, 2H).

MS Calcd.: 506; MS Found: 507 (M+H).

Example 195

1-[9-Chloro-1-(2,4-dichlorophenyl)-1,2,3,4-tetrahydropyrimido[1,2-a]benzimidazol-6-yl]pyrrolidin-2-one

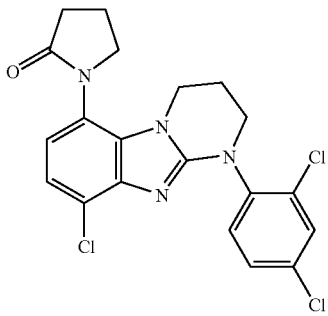 [SMILES: O=C1CCCN1c1ccc(Cl)c2nc3n(c12)CCCN3c1ccc(Cl)cc1Cl]

4-Chlorobutanoyl chloride (88.2 mg, 0.626 mmol) was added to a stirred solution of 9-chloro-1-(2,4-dichlorophenyl)-1,2,3,4-tetrahydropyrimido[1,2-a]benzimidazol-6-amine (Example 100, 230 mg, 0.626 mmol) and triethylamine (0.18 mL) in tetrahydrofuran (6.0 ml) at 0° C., and the mixture was stirred at 0° C. for 2 hr. Methanol (1.0 mL) and potassium t-butoxide (351 mg, 3.13 mmol) were added to the mixture, and the mixture was stirred at 60° C. for 16 hr. The mixture was concentrated in vacuo, diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 80-100% ethyl acetate/n-hexane gradient mixture. The filtrate was concentrated in vacuo to give the solid, which was recrystallized from ethyl acetate/diisopropyl ether to give the title compound as a colorless crystal (85.8 mg, 0.197 mmol, 31%).

mp 215-216° C.

$^1$H NMR (CDCl$_3$) δ 2.23-2.39 (m, 4H), 2.57-2.69 (m, 2H), 3.60-3.81 (m, 3H), 3.87-3.99 (m, 1H), 4.05-4.19 (m, 1H), 4.28-4.41 (m, 1H), 6.72 (d, J=8.4 Hz, 1H), 7.08 (d, J=8.4 Hz, 1H), 7.31 (dd, J=2.4 Hz, 8.7 Hz, 1H), 7.47-7.51 (m, 2H).

MS Calcd.: 434; MS Found: 435 (M+H).

Example 196

9-Chloro-1-(2,4-dichlorophenyl)-6-pyrrolidin-1-yl-1,2,3,4-tetrahydropyrimido[1,2-a]benzimidazole

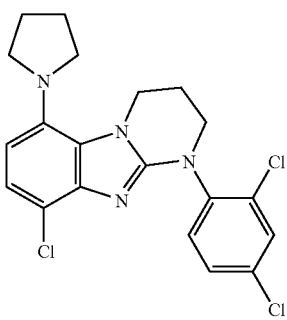 [SMILES: Clc1ccc(N2CCCn3c2nc2c(Cl)ccc(N4CCCC4)c23)c(Cl)c1]

Borane-tetrahydrofuran complex (1.0 M solution in tetrahydrofuran, 0.36 mL, 0.36 mmol) was added to a stirred solution of 1-[9-chloro-1-(2,4-dichlorophenyl)-1,2,3,4-tetrahydropyrimido[1,2-a]benzimidazol-6-yl]pyrrolidin-2-one (52.6 mg, 0.121 mmol) in tetrahydrofuran (1.5 mL) at room temperature, and the mixture was stirred at 70° C. for 13 hr.

The reaction was quenched by aqueous saturated ammonium chloride at 0° C., and the mixture was extracted with ethyl acetate. The combined organic layer was washed with brine, dried over anhydrous magnesium sulfate, filtered and concentrated in vacuo. The residue was purified by preparative HPLC to give a mixture contained an intermediate of the title compound as the trifluoroacetic acid salt. The mixture was washed with aqueous sodium hydrogen carbonate and extracted with ethyl acetate. The extract was washed with brine, dried over anhydrous magnesium sulfate, filtered and concentrated in vacuo to give the title compound as a colorless amorphous (14.5 mg, 0.0343 mmol, 28%).

Amorphous.

$^1$H NMR (CDCl$_3$) δ 1.92-1.99 (m, 4H), 2.25-2.35 (m, 2H), 3.04-3.19 (m, 4E), 3.65-3.76 (m, 2H), 4.59 (t, J=6.0 Hz, 2H), 6.76 (d, J=8.4 Hz, 1H), 6.98 (d, J=8.4 Hz, 1H), 7.29 (dd, J=2.7 Hz, 8.7 Hz, 1H), 7.48 (d, J=2.7 Hz, 1H), 7.52 (d, J=8.7 Hz, 1H).

MS Calcd.: 420; MS Found: 421 (M+H).

Example 197

9-Chloro-1-(2,4-dichlorophenyl)-6-(3,5-diethyl-1H-pyrazol-1-yl)-1,2,3,4-tetrahydropyrimido[1,2-a]benzimidazole

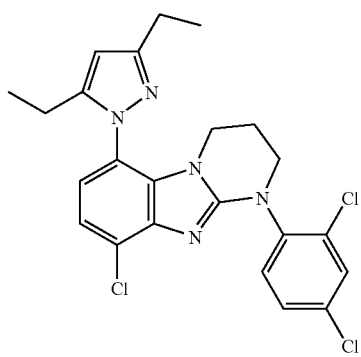 [SMILES: CCc1cc(CC)n(-c2ccc(Cl)c3nc4n(c23)CCCN4c2ccc(Cl)cc2Cl)n1]

Sodium nitrite (44.3 mg, 0.643 mmol) was added to a stirred solution of 9-chloro-1-(2,4-dichlorophenyl)-1,2,3,4-tetrahydropyrimido[1,2-a]benzimidazol-6-amine (225 mg, 0.612 mmol) in conc. hydrochloric acid (3.0 mL) at 0° C., and the mixture was stirred at 0° C. for 50 min. Tin chloride (232 mg, 1.22 mmol) in conc. hydrochloric acid (1.0 mL) was added to a stirred mixture at 0° C., and the mixture was stirred at room temperature for 5 hr. The mixture was neutralized with 1N sodium hydroxide and extracted with ethyl acetate. The combined organic layer was washed with brine, dried over anhydrous magnesium sulfate, filtered and concentrated in vacuo to give brown oil (175 mg). A mixture of the resulting hydrazine (175 mg), heptane-3,5-dione (70 4 mg, 0.549 mmol) and sodium acetate (75.0 mg, 0.914 mmol) in ethanol (3.0 mL) was stirred at 80° C. for 13 hr. The mixture was concentrated in vacuo, and the residue was purified by flash column chromatography on silica gel eluting with a 10-70% ethyl acetate/n-hexane gradient mixture. The filtrate was concentrated in vacuo to give the solid, which was recrystallized from ethyl acetate/diisopropyl ether to give the title compounds as a pale yellow crystal (36.8 mg, 0.0775 mmol, 17%).

mp 185-187° C.

$^1$H NMR (CDCl$_3$) δ 1.17 (t, J=7.8 Hz, 3H), 1.28 (t, J=7.8 Hz, 3H), 2.11-2.23 (m, 2H), 2.40-2.52 (m, 2H), 2.70 (q, J=7.8 Hz, 2H), 3.08-3.25 (m, 1H), 3.57-3.69 (m, 3H), 6.06 (s, 1H), 6.85 (d, J=8.7 Hz, 1H), 7.11 (d, J=8.7 Hz, 1H), 7.31 (dd, J=2.4 Hz, 8.4 Hz, 1H), 7.46-7.49 (m, 2H).

MS Calcd.: 473; MS Found: 474 (M+H).

Example 198

1-[1-(2,4-Dichlorophenyl)-1,2,3,4-tetrahydropyrimido[1,2-a]benzimidazol-6-yl]propan-1-one

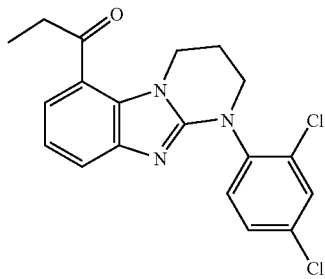 [SMILES: CCC(=O)c1cccc2nc3n(c12)CCCN3c1ccc(Cl)cc1Cl]

Ethylmagnesium bromide (3.0 M solution in diethyl ether, 14.6 mL, 43.7 mmol) was added to a stirred solution of 1-(2,4-dichlorophenyl)-1,2,3,4-tetrahydropyrimido[1,2-a]benzimidazole-6-carbonitrile (5.00 g, 14.6 mmol) in tetrahydrofuran (50 mL) at 0° C., and the mixture was stirred at 50° C. for 2 hr. The reaction was quenched by methanol, and the mixture was diluted with aqueous saturated ammonium chloride and extracted with ethyl acetate. The combined organic layer was washed with brine, dried over anhydrous magnesium sulfate, filtered, and concentrated in vacuo. A mixture of the resulting imine, acetic acid (10 mL) and 1N hydrochloric acid (20 mL) was stirred at 50° C. for 2 hr. The mixture was concentrated in vacuo, diluted with saturated aqueous sodium hydrogen carbonate and extracted with ethyl acetate. The combined organic layer was washed with brine, dried over anhydrous magnesium sulfate, filtered and concentrated in vacuo. The residue was recrystallized from ethyl acetate/diisopropyl ether to give the title compounds as a colorless crystal (3.04 g, 8.12 mmol, 56%).

mp 195-196° C.

$^1$H NMR (CDCl$_3$) δ 1.27 (t, J=7.5 Hz, 3H), 2.23-2.36 (m, 2H), 3.08 (q, J=7.5 Hz, 2H), 3.63-3.75 (m, 2H), 4.18 (t, J=6.0 Hz, 2H), 7.09 (t, J=7.8 Hz, 1H), 7.25-7.38 (m, 2H), 7.43 (d, J=8.4 Hz, 1H), 7.51 (d, J=2.1 Hz, 1H), 7.55 (dd, J=2.1 Hz, 7.8 Hz, 1H).

MS Calcd.: 373; MS Found: 374 (M+H).

Example 199

Cyclopropyl[1-(2,4-dichlorophenyl)-1,2,3,4-tetrahydropyrimido[1,2-a]benzimidazol-6-yl]methanone

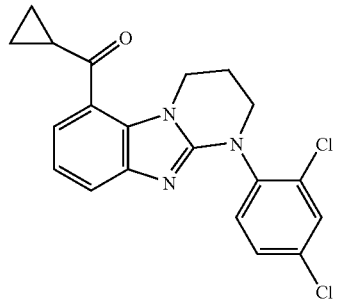 [SMILES: O=C(c1cccc2nc3n(c12)CCCN3c1ccc(Cl)cc1Cl)C1CC1]

Dess-Martin reagent (925 mg, 2.18 mmol) was added to a stirred solution of cyclopropyl[1-(2,4-dichlorophenyl)-1,2,3,4-tetrahydropyrimido[1,2-a]benzimidazol-6-yl]methanol (770 mg, 1.98 mmol) in dichloromethane (8.0 mL) at 0 ° C., and the mixture was stirred at 0 ° C. for 90 min. The mixture was diluted with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 5-50% ethyl acetate/n-hexane gradient mixture. The filtrate was concentrated in vacuo to give the solid, which was recrystallized from ethyl acetate/diisopropyl ether to give the title compound as a colorless crystal (226 mg, 0.585 mmol, 30%).

mp 189-190° C.

$^1$H NMR (CDCl$_3$) δ 1.08-1.50 (m, 2H), 1.26-1.32 (m, 2H), 2.27-2.32 (m, 2H), 2.66-2.72 (m, 1H), 3.60-3.75 (m, 2H), 4.13 (t, J=6.3 Hz, 2H), 7.13 (t, J=7.8 Hz, 1H), 7.32 (dd, J=2.4 Hz, 8.1 Hz, 1H), 7.44 (d, J=8.1 Hz, 1H), 7.51 (t, J=2.4 Hz, 1H), 7.53-7.58 (m, 2H).

MS Calcd.: 385; MS Found: 386 (M+H).

Anal. Calcd for C$_{20}$H$_{17}$N$_3$OCl$_2$: C, 62.19; H, 4.44; N, 10.88; Cl, 18.36. Found: C, 62.33; H, 4.44; N, 10.89; Cl, 18.16.

Example 200

6-[Cyclopropyl(methoxy)methyl]-1-(2,4-dichlorophenyl)-1,2,3,4-tetrahydropyrimido[1,2-a]benzimidazole

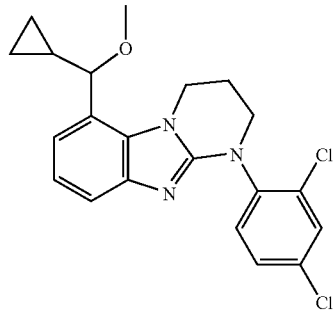 [SMILES: COC(c1cccc2nc3n(c12)CCCN3c1ccc(Cl)cc1Cl)C1CC1]

Sodium hydride (60% in oil, 45.3 mg, 1.13 mmol) was added to a stirred solution of cyclopropyl[1-(2,4-dichlorophenyl)-1,2,3,4-tetrahydropyrimido[1,2-a]benzimidazol-6-yl]methanol (400 mg, 1.03 mmol) in N,N-dimethylformamide (3.0 mL) at 0° C. After stirring 5 min, methyl iodide (219 mg, 1.55 mmol) was added to the mixture, and the mixture was stirred at room temperature for 5 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 0-30% ethyl acetate/n-hexane gradient mixture. The filtrate was concentrated in vacuo to give the solid, which was recrystallized from ethyl acetate/n-hexane to give the title compound as a colorless crystal (265 mg, 0.659 mmol, 64%).

mp 118-119° C.

$^1$H NMR (CDCl$_3$) δ 0.25-0.32 (m, 1H), 0.40-0.49 (m, 1H), 0.54-0.59 (m, 1H), 0.71-0.76 (m, 1H), 1.38-1.46 (m, 1H), 2.37 (t, J=5.4 Hz, 2H), 3.31 (s, 3H), 3.60-3.80 (m, 2H), 4.10 (d, J=7.8 Hz, 1H), 4.45-4.52 (m, 1H), 4.66-4.71 (m, 1H), 6.93-7.00 (m, 1H), 7.03 (t, J=7.5 Hz, 1H), 7.31 (dd, J=2.1 Hz, 8.4 Hz, 1H), 7.37 (dd, J=1.8 Hz, 7.5 Hz, 1H), 7.46 (d, J=8.4 Hz, 1H), 7.50 (d, J=2.1 Hz, 1H).

MS Calcd.: 401; MS Found: 402 (M+H).

Anal. Calcd for C$_{21}$H$_{21}$N$_3$OCl$_2$: C, 62.69; H, 5.26; N, 10.44; Cl, 17.62. Found: C, 62.83; H, 5.30; N, 10.48; Cl, 17.43.

Example 201

1-[1-(2,4-Dichlorophenyl)-1,2,3,4-tetrahydropyrimido[1,2-a]benzimidazol-6-yl]-2,2,2-trifluoroethanol

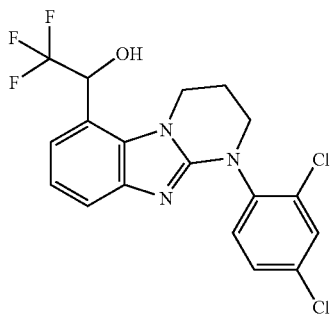 [SMILES: OC(c1cccc2nc3n(c12)CCCN3c1ccc(Cl)cc1Cl)C(F)(F)F]

Tetra-n-butylammonium fluoride (1.0 M solution in tetrahydrofuran, 1.3 mL, 1.3 mmol) was added dropwise to a stirred solution of 1-(2,4-dichlorophenyl)-1,2,3,4-tetrahydropyrimido[1,2-a]benzimidazole-6-carbaldehyde (1.50 g, 4.33 mmol) and trimethyl(trifluoromethyl)silane (1.83 g, 12.9 mmol) in tetrahydrofuran (11 mL) at 0° C., and the mixture was stirred at room temperature for 10 hr. The mixture was diluted with 1N hydrochloric acid and extracted with ethyl acetate. The combined organic layer was washed with brine, dried over anhydrous magnesium sulfate, filtered and concentrated in vacuo. The residue was purified by flash column chromatography on silica gel eluting with a 10-50% ethyl acetate/n-hexane gradient mixture. The filtrate was concentrated in vacuo to give the title compound as a colorless solid (1.19 g, 2.86 mmol, 66%).

$^1$H NMR (CDCl$_3$) δ 2.26-2.38 (m, 2H), 3.58-3.69 (m, 2H), 4.19-4.37 (m, 2H), 4.67 (s, 1H), 5.35-5.41 (m, 1H), 7.07 (t, J=7.8 Hz, 1H), 7.16 (d, J=7.8 Hz, 1H), 7.24-7.42 (m, 4H).

MS Calcd.: 415; MS Found: 416 (M+H).

Example 202

1-(2,4-Dichlorophenyl)-6-(2,2,2-trifluoro-1-methoxyethyl)-1,2,3,4-tetrahydropyrimido[1,2-a]benzimidazole

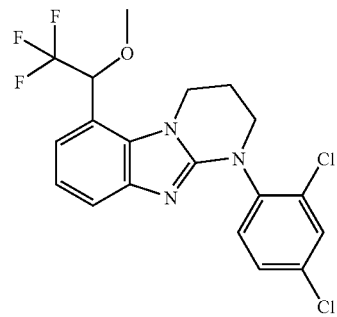 [SMILES: COC(c1cccc2nc3n(c12)CCCN3c1ccc(Cl)cc1Cl)C(F)(F)F]

A mixture of 1-[1-(2,4-dichlorophenyl)-1,2,3,4-tetrahydropyrimido[1,2-a]benzimidazol-6-yl]-2,2,2-trifluoroethanol (475 mg, 1.14 mmol), potassium carbonate (174 mg, 1.26 mmol) and methyl iodide (242 mg, 1.71 mmol) in N,N-dimethylformamide (3.0 mL) was stirred at room temperature for 3 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 10-30% ethyl acetate/n-hexane gradient mixture. The filtrate was concentrated in vacuo to give the solid, which was recrystallized from ethyl acetate/n-hexane to give the title compound as a colorless crystal (49.2 mg, 0.114 mmol, 10%).

mp 164-165° C.

$^1$H NMR (CDCl$_3$) δ 2.37-2.43 (m, 2H), 3.46 (s, 3H), 3.65-3.77 (m, 2H), 4.34-4.46 (m, 2H), 5.08-5.14 (m, 1H), 7.08-7.16 (m, 3H), 7.32 (dd, J=2.1 Hz, 8.7 Hz, 1H), 7.45 (dd, J=1.8 Hz, 7.2 Hz, 1H), 7.52 (d, J=2.1 Hz, 1H).

MS Calcd.: 429; MS Found: 430 (M+H).

Example 203

1-[1-(2,4-Dichlorophenyl)-1,2,3,4-tetrahydropyrimido[1,2-a]benzimidazol-6-yl]-N,N-dimethylpropan-1-amine

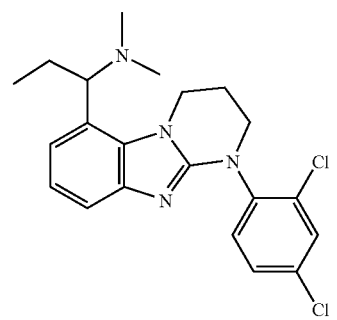 [SMILES: CCC(c1cccc2nc3n(c12)CCCN3c1ccc(Cl)cc1Cl)N(C)C]

Ethylmagnesium bromide (3.0 M solution in diethyl ether, 3.19 mL, 9.57 mmol) was added to a stirred solution of 1-(2,4-dichlorophenyl)-1,2,3,4-tetrahydropyrimido[1,2-a]benzimidazole-6-carbonitrile (1.64 g, 4.78 mmol) in tetrahydrofuran (15 mL) at 0° C., and the mixture was stirred at 50° C. for 2 hr. The reaction was quenched by water, and the mixture was extracted with ethyl acetate. The combined organic layer was washed with brine, dried over anhydrous magnesium sulfate, filtered, and concentrated in vacuo. Sodium borohydride (361 mg, 9.54 mmol) was added to a stirred solution of the resulting imine, and the mixture was stirred at room temperature for 2 hr. The reaction was quenched by aqueous saturated ammonium chloride and the mixture was extracted with ethyl acetate. The combined organic layer was washed with brine, dried over anhydrous magnesium sulfate, filtered, and concentrated in vacuo. Formaldehyde (36-38% solution in water, 678 mg) was added to a solution of the resulting benzylamine (510 mg) in acetonitrile (4.0 mL). After 5 min sodium cyanoborohydride (510 mg, 8.14 mmol) was added to the mixture, and the mixture was stirred at room temperature for 3 hr. The mixture was diluted with saturated aqueous sodium hydrogen carbonate and extracted with ethyl acetate. The combined organic layer was washed with brine, dried over anhydrous magnesium sulfate, filtered and concentrated in vacuo. The residue was purified by flash column chromatography on silica gel eluting with a 5-50% ethyl acetate/n-hexane gradient mixture. The filtrate was concentrated in vacuo to give the solid, which was recrystallized from ethyl acetate/diisopropyl ether to give the title compound as a colorless crystal (100 mg, 0.248 mmol, 18% in 3 steps).

mp 144-145° C.

$^1$H NMR (CDCl$_3$) δ 0.79 (t, J=7.5 Hz, 3H), 1.80-2.06 (m, 2H), 2.26 (s, 6H), 2.30-2.44 (m, 2H), 3.60-3.78 (m, 3H), 4.45-4.70 (m, 2H), 6.90-7.06 (m, 2H), 7.28-7.46 (m, 2H), 7.45-7.51 (m, 2H).

MS Calcd.: 402; MS Found: 403 (M+H).

Anal. Calcd for C$_{21}$H$_{24}$N$_4$Cl$_2$: C, 62.53; H, 6.00; N, 13.89; Cl, 17.58. Found: C, 62.75; H, 6.02; N, 13.59; Cl, 17.28.

Example 204

Ethyl (2E)-3-[1-(2,4-dichlorophenyl)-1,2,3,4-tetrahydropyrimido[1,2-a]benzimidazol-6-yl]prop-2-enoate

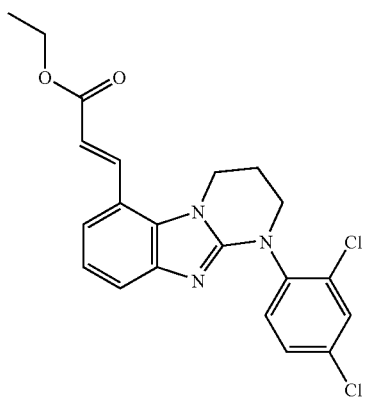 [SMILES: CCOC(=O)/C=C/c1cccc2nc3n(c12)CCCN3c1ccc(Cl)cc1Cl]

Sodium hydride (60% in oil, 230 mg, 5.76 mmol) was added to a stirred solution of ethyl (diethoxyphosphoryl)acetate (1.94 g, 8.67 mmol) in tetrahydrofuran (14 mL) at 0° C. After stirring 10 min, 1-(2,4-dichlorophenyl)-1,2,3,4-tetrahydropyrimido[1,2-a]benzimidazole-6-carbaldehyde (1.00 g, 2.88 mmol) in tetrahydrofuran (1.0 mL) was added to the mixture, and the mixture was stirred at room temperature for 12 hr. The mixture was diluted with water, and extracted with ethyl acetate. The combined organic layer was washed with brine, dried over anhydrous magnesium sulfate, filtered, and concentrated in vacuo. The residue was purified by flash column chromatography on silica gel eluting with a 10-50% ethyl acetate/n-hexane gradient mixture. The filtrate was concentrated in vacuo to give the solid, which was washed with diisopropyl ether to give the title compound as a colorless powder (908 mg, 2.18 mmol, 76%).

$^1$H NMR (CDCl$_3$) δ 1.36 (t, J=7.2 Hz, 3H), 2.40 (t, J=5.7 Hz, 2H), 3.60-3.75 (m, 2H), 4.28 (q, J=7.2 Hz, 2H), 4.49 (q, J=5.7 Hz, 2H), 6.42 (d, J=15.6 Hz, 1H), 7.07 (t, J=7.8 Hz, 1H), 7.21-7.25 (m, 1H), 7.32 (dd, J=2.4 Hz, 8.7 Hz, 1H), 7.41-7.46 (m, 2H), 7.51 (d, J=2.4 Hz, 1H), 8.35 (d, J=15.6 Hz, 1H).

MS Calcd.: 415; MS Found: 416 (M+H).

Example 205

3-[1-(2,4-Dichlorophenyl)-1,2,3,4-tetrahydropyrimido[1,2-a]benzimidazol-6-yl]pentanamide

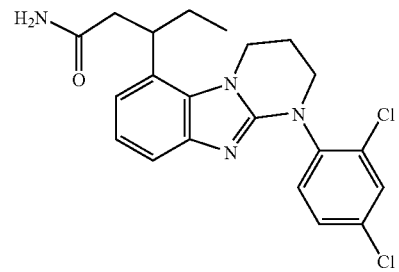 [SMILES: CCC(CC(N)=O)c1cccc2nc3n(c12)CCCN3c1ccc(Cl)cc1Cl]

Ethylmagnesium bromide (3.0 M solution in diethyl ether, 3.19 mL, 9.57 mmol) was added to a stirred mixture of ethyl (2E)-3-[1-(2,4-dichlorophenyl)-1,2,3,4-tetrahydropyrimido[1,2-a]benzimidazol-6-yl]prop-2-enoate (650 mg, 1.56 mmol) and copper bromide (223 mg, 1.56 mmol) in tetrahydrofuran (15 mL) at 0° C., and the mixture was stirred at 0° C. for 1 hr. The mixture was diluted with aqueous saturated ammonium chloride and the precipitate was removed by filtration. The mother solution was extracted with ethyl acetate. The combined organic layer was washed with brine, dried over anhydrous magnesium sulfate, filtered, and concentrated in vacuo. The residue was purified by flash column chromatography on silica gel eluting with a 10-50% ethyl acetate/n-hexane gradient mixture. The filtrate was concentrated in vacuo to give colorless amorphous (540 mg). A mixture of the resulting ester (201 mg) and 8N sodium hydroxide (1.0 mL) in methanol (1.0 mL) was stirred at 0° C. for 1 hr. The mixture was neutralized with 1N hydrochloric acid and extracted with ethyl acetate. The combined organic layer was washed with brine, dried over anhydrous magnesium sulfate, filtered, and concentrated in vacuo. The residue was purified by flash column chromatography on silica gel eluting with a 40-100% ethyl acetate/n-hexane gradient mixture. The filtrate was concentrated in vacuo to give the solid (145 mg). A mixture of the resulting carboxylic acid (145 mg), 1-ethyl-3-(3-dimethylaminopropyl)carbodiimide hydrochloride (73.1 mg, 0.382 mmol) and 1-hydroxybenzotriazole (76.6 mg, 0.451 mmol) in N,N-dimethylformamide (1.0 mL) was stirred at room temperature for 17 hr. The mixture was diluted with saturated aqueous sodium hydrogen carbonate and extracted with ethyl acetate. The combined organic layer was washed with brine, dried over anhydrous magnesium sulfate, filtered, and concentrated in vacuo. The residue was purified by flash column chromatography on silica gel eluting with a 50-100% ethyl acetate/n-hexane gradient mixture. The filtrate was concentrated in vacuo to give the solid, which was recrystallized from ethanol/ethyl acetate to give the title compound as a colorless crystal (59.9 mg, 0.144 mmol, 9% in 3 steps).

mp 132-133° C.

$^1$H NMR (CDCl$_3$) δ 0.87 (t, J=7.2 Hz, 3H), 1.74-1.88 (m, 2H), 2.31-2.44 (m, 2H), 2.50-2.62 (m, 2H), 3.61-3.70 (m, 2H), 3.78-3.95 (m, 1H), 4.37-4.40 (m, 1H), 4.71-4.79 (m, 1H), 5.04 (s, 1H), 5.15 (s, 1H), 6.87 (dd, J=1.2 Hz, 7.8 Hz, 1H), 7.08 (t, J=7.8 Hz, 1H), 7.25-7.35 (m, 2H), 7.43-7.50 (m, 2H).

MS Calcd.: 416; MS Found: 417 (M+H).

Example 206

1-(2,4-Dichlorophenyl)-1,2,3,4-tetrahydropyrimido[1,2-a]benzimidazol-6-amine

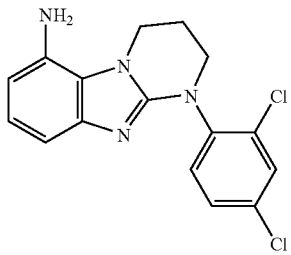 [SMILES: Nc1cccc2nc3n(c12)CCCN3c1ccc(Cl)cc1Cl]

A mixture of 1-(2,4-dichlorophenyl)-1,2,3,4-tetrahydropyrimido[1,2-a]benzimidazole-6-carboxylic acid (9.40 g, 25.9 mmol), diphenylphosphinic acid (7.85 g, 28.5 mmol) and triethylamine (4.0 mL) in t-butanol (250 mL) was stirred at 90° C. for 12 hr and concentrated in vacuo. A mixture of the residue and trifluoroacetic acid (100 mL) in dichloromethane (50 mL) was stirred at room temperature for 20 hr and concentrated in vacuo. The residue was diluted with saturated aqueous sodium hydrogen carbonate and extracted with ethyl acetate. The combined organic layer was washed with brine, dried over anhydrous magnesium sulfate, filtered, and concentrated in vacuo. The residue was purified by flash column chromatography on silica gel eluting with a 10-60% ethyl acetate/n-hexane gradient mixture. The filtrate was concentrated in vacuo to give the title compound as a yellow amorphous (440 mg, 1.32 mmol, 5%).

$^1$H NMR (CDCl$_3$) δ 2.30-2.45 (m, 2H), 3.59 (s, 2H), 3.61-3.78 (m, 2H), 4.59 (t, J=6.0 Hz, 2H), 6.38 (dd, J=1.2 Hz, 7.5 Hz, 1H), 6.87 (t, J=7.5 Hz, 1H), 6.96 (dd, J=1.2 Hz, 7.5 Hz, 1H), 7.29 (dd, J=2.7 Hz, 8.4 Hz, 1H), 7.44 (d, J=8.4 Hz, 1H), 7.49 (d, J=2.7 Hz, 1H).

MS Calcd.: 332; MS Found: 333 (M+H).

Example 207

1-(2,4-Dichlorophenyl)-N-(1-methylpropyl)-1,2,3,4-tetrahydropyrimido[1,2-a]benzimidazol-6-amine

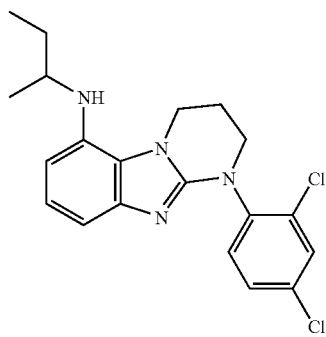 [SMILES: CCC(C)Nc1cccc2nc3n(c12)CCCN3c1ccc(Cl)cc1Cl]

Sodium triacetoxyborohydride (171 mg, 0.807 mmol) was added to a stirred solution of 1-(2,4-dichlorophenyl)-1,2,3,4-tetrahydropyrimido[1,2-a]benzimidazol-6-amine (183 mg, 0.549 mmol) and butan-2-one (1.0 mL) in methanol (1.0 ml) at 0° C., and the mixture was stirred at room temperature for 8 hr. The mixture was diluted with saturated aqueous sodium hydrogen carbonate and extracted with ethyl acetate. The combined organic layer was washed with brine, dried over anhydrous magnesium sulfate, filtered, and concentrated in vacuo. The residue was purified by flash column chromatography on silica gel eluting with a 5-50% ethyl acetate/n-hexane gradient mixture. The filtrate was concentrated in vacuo to give the solid, which was recrystallized from ethyl acetate/n-hexane to give the title compound as a colorless crystal (86.4 mg, 0.222 mmol, 40%).

mp 180-181° C.

$^1$H NMR (CDCl$_3$) δ 0.99 (t, J=7.5 Hz, 3H), 1.21 (t, J=6.3 Hz, 3H), 1.38-1.56 (m, 1H), 1.63-1.72 (m, 1H), 2.32-2.39 (m, 2H), 3.31 (s, 1H), 3.34-3.44 (m, 1H), 3.60-3.70 (m, 2H), 4.61 (t, J=6.0 Hz, 2H), 6.38-6.42 (m, 1H), 6.89-6.96 (m, 2H), 7.27-7.31 (m, 1H), 7.44 (d, J=8.7 Hz, 1H), 7.48 (d, J=2.1 Hz, 1H).

MS Calcd.: 388; MS Found: 389 (M+H).

Anal. Calcd for C$_{20}$H$_{22}$N$_4$Cl$_2$: C, 61.70; H, 5.70; N, 14.39; Cl, 18.21. Found: C, 61.90; H, 5.71; N, 14.46; Cl, 18.14.

Example 208

Methyl 1-(4-carbamoyl-2-methylphenyl)-9-chloro-1,2,3,4-tetrahydropyrimido[1,2-a]benzimidazole-6-carboxylate

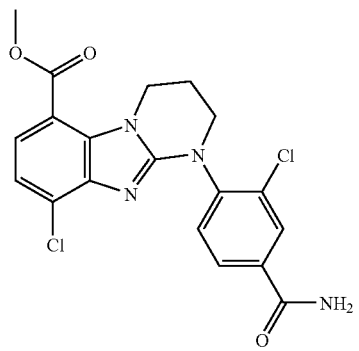 [SMILES: COC(=O)c1ccc(Cl)c2nc3n(c12)CCCN3c1ccc(C(N)=O)cc1Cl]

Tsunoda reagent (904 mg, 3.74 mmol) was added to a stirred suspension of methyl 2-[(4-carbamoyl-2-methylphenyl)amino]-4-chloro-1-(3-hydroxypropyl)-1H-benzimidazole-7-carboxylate (1.30 g, 3.12 mmol) in dichlorobenzene (30 mL) at room temperature, and the mixture was stirred at 110° C. for 23 hr. The mixture was concentrated in vacuo, crystallized from ethyl acetate/diisopropyl ether and washed with diisopropyl ether to give the title compound as a pale yellow powder (761 mg, 1.91 mmol, 61%).

$^1$H NMR (DMSO-$d_6$) δ 2.20-2.40 (m, 2H), 2.24 (s, 3H), 3.60-3.80 (m, 2H), 3.90 (s, 3H), 4.21-4.33 (m, 2H), 7.10 (d, J=8.4 Hz, 1H), 7.30 (d, J=8.4 Hz, 1H), 7.36 (s, 1H), 7.44 (d, J=8.4 Hz, 1H), 7.74-7.79 (m, 1H), 7.83-7.85 (m, 1H), 7.98 (s, 1H).

MS Calcd.: 398; MS Found: 399 (M+H).

Example 209

9-Chloro-1-(2-chloro-4,6-dimethylpyrimidin-5-yl)-6-[1-(difluoromethoxy)-2,2,2-trifluoroethyl]-1,2,3,4-tetrahydropyrimido[1,2-a]benzimidazole

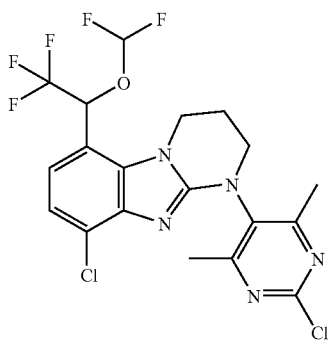 [SMILES: Cc1nc(Cl)nc(C)c1N1CCCn2c1nc1c(Cl)ccc(C(OC(F)F)C(F)(F)F)c12]

A mixture of 9-chloro-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole (Example 185, 2.10 g, 4.27 mmol) and phosphoryl chloride (11 mL) was stirred at 100° C. for 5 hr. The mixture was concentrated in vacuo, diluted with water, neutralized with saturated aqueous sodium hydrogen carbonate and extracted with ethyl acetate. The combined organic layer was washed with brine, dried over anhydrous magnesium sulfate, filtered and concentrated in vacuo. The residue was purified by flash column chromatography on silica gel eluting with a 50-100% ethyl acetate/n-hexane gradient mixture. The filtrate was concentrated in vacuo to give the solid, which was washed with diisopropyl ether/n-hexane to give the title compound as a colorless powder (889 mg, 1.79 mmol, 42%).

$^1$H NMR (CDCl$_3$) δ 2.45 (s, 6H), 2.45-2.55 (m, 2H), 3.57-3.70 (m, 2H), 4.36-4.45 (m, 2H), 5.98 (q, J=6.0 Hz, 1H), 6.43 (t, J=72.0 Hz, 1H), 7.15-7.19 (m, 2H).

MS Calcd.: 495; MS Found: 496 (M+H).

Example 210

9-Chloro-6-[1-(difluoromethoxy)-2,2,2-trifluoroethyl]-1-(2-ethoxy-4,6-dimethylpyrimidin-5-yl)-1,2,3,4-tetrahydropyrimido[1,2-a]benzimidazole

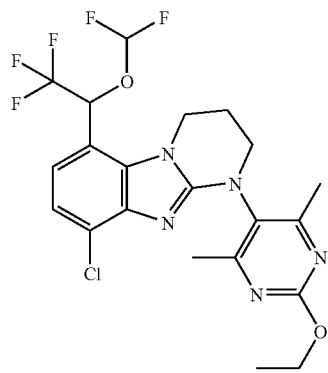

A mixture of 9-chloro-1-(2-chloro-4,6-dimethylpyrimidin-5-yl)-6-[1-(difluoromethoxy)-2,2,2-trifluoroethyl]-1,2,3,4-tetrahydropyrimido[1,2-a]benzimidazole (142 mg, 0.286 mmol) and sodium ethoxide (20% solution in ethanol, 292 mg, 0.858 mmol) in ethanol (1.0 mL) was stirred at 50° C. for 5 hr. The mixture was concentrated in vacuo, diluted with water and extracted with ethyl acetate. The combined organic layer was washed with brine, dried over anhydrous magnesium sulfate, filtered and concentrated in vacuo. The residue was purified by flash column chromatography on silica gel eluting with a 50-100% ethyl acetate/n-hexane gradient mixture. The filtrate was concentrated in vacuo to give the solid, which was purified by preparative HPLC to give a mixture contained an intermediate of the title compound as the trifluoroacetic acid salt. The mixture was washed with aqueous sodium hydrogen carbonate and extracted with ethyl acetate. The extract was washed with brine, dried over magnesium sulfate, filtered and concentrated in vacuo to give the solid, which was recrystallized from ethyl acetate/n-hexane to give the title compound as a colorless crystal (65.3 mg, 0.286 mmol, 45%).

mp 218-220° C.

$^1$H NMR (CDCl$_3$) δ 1.44 (t, J=7.2 Hz, 3H), 2.37 (s, 6H), 2.40-2.49 (m, 2H), 3.54-3.66 (m, 2H), 4.31-4.46 (m, 4H), 5.99 (q, J=6.0 Hz, 1H), 6.42 (t, J=72.3 Hz, 1H), 7.12-7.18 (m, 2H).

MS Calcd.: 505; MS Found: 506 (M+H).

Anal. Calcd for C$_{21}$H$_{21}$N$_5$O$_2$ClF$_5$: C, 49.86; H, 4.18; N, 13.84; Cl, 7.01; F, 18.78. Found: C, 49.79; H, 4.16; N, 13.75; Cl, 7.08; F, 18.75.

Example 211

9-Chloro-6-[1-(difluoromethoxy)-2,2,2-trifluoroethyl]-1-[4,6-dimethyl-2-(1-methylethoxy)pyrimidin-5-yl]-1,2,3,4-tetrahydropyrimido[1,2-a]benzimidazole

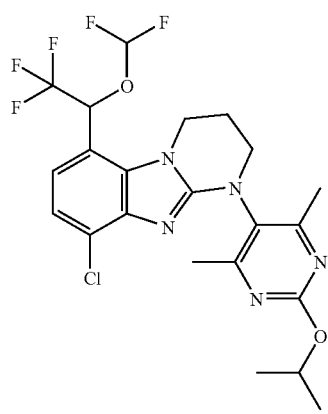 [SMILES: Cc1nc(OC(C)C)nc(C)c1N1CCCn2c1nc1c(Cl)ccc(C(OC(F)F)C(F)(F)F)c12]

A mixture of 9-chloro-1-(2-chloro-4,6-dimethylpyrimidin-5-yl)-6-[1-(difluoromethoxy)-2,2,2-trifluoroethyl]-1,2,3,4-tetrahydropyrimido[1,2-a]benzimidazole (161 mg, 0.324 mmol) and lithium isopropoxide (64.3 mg, 0.973 mmol) in 2-propanol (2.2 mL) was stirred at 70° C. for 17 hr. The mixture was concentrated in vacuo, diluted with water and extracted with ethyl acetate. The combined organic layer was washed with brine, dried over anhydrous magnesium sulfate, filtered and concentrated in vacuo. The residue was purified by flash column chromatography on silica gel eluting with a 30-70% ethyl acetate/n-hexane gradient mixture. The filtrate was concentrated in vacuo to give the solid, which was purified by preparative HPLC to give a mixture contained an intermediate of the title compound as the trifluoroacetic acid salt. The mixture was washed with aqueous sodium hydrogen carbonate and extracted with ethyl acetate. The extract was washed with brine, dried over magnesium sulfate, filtered and concentrated in vacuo to give the solid, which was recrystallized from ethyl acetate/n-hexane to give the title compound as a colorless crystal (71.0 mg, 0.137 mmol, 42%).

mp 227-230° C.

$^1$H NMR (CDCl$_3$) δ 1.40 (d, J=6.0 Hz, 6H), 2.36 (s, 6H), 2.38-2.52 (m, 2H), 3.50-3.69 (m, 2H), 4.31-4.42 (m, 2H), 5.30 (spt, J=6.0 Hz, 1H), 5.99 (q, J=6.0 Hz, 1H), 6.42 (t, J=72.3 Hz, 1H), 7.13-7.17 (m, 2H).

MS Calcd.: 519; MS Found: 520 (M+H).

Example 212

9-Chloro-6-[1-(difluoromethoxy)-2,2,2-trifluoroethyl]-1-(2,4,6-trimethylpyrimidin-5-yl)-1,2,3,4-tetrahydropyrimido[1,2-a]benzimidazole

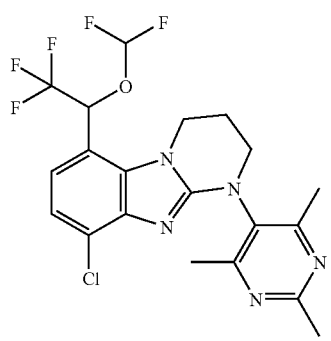 [SMILES: Cc1nc(C)c(N2CCCn3c2nc2c(Cl)ccc(C(OC(F)F)C(F)(F)F)c23)c(C)n1]

Methylmagnesium bromide (1.0 M solution in tetrahydrofuran, 0.49 mL, 0.490 mmol) was added dropwise to a stirred suspension of 9-chloro-1-(2-chloro-4,6-dimethylpyrimidin-5-yl)-6-[1-(difluoromethoxy)-2,2,2-trifluoroethyl]-1,2,3,4-tetrahydropyrimido[1,2-a]benzimidazole (163 mg, 0.328 mmol) and [1,3-bis(diphenylphosphino)propane]dichloronickel (17.8 mg, 0.0328 mmol) in tetrahydrofuran (1.3 mL) at 0° C., and the mixture was stirred at room temperature for 7 hr. The mixture was diluted with water and extracted with ethyl acetate. The combined organic layer was washed with brine, dried over anhydrous magnesium sulfate, filtered and concentrated in vacuo. The residue was purified by flash column chromatography on silica gel eluting with a 30-100% ethyl acetate/n-hexane gradient mixture. The filtrate was concentrated in vacuo to give the solid, which was purified by preparative HPLC to give a mixture contained an intermediate of the title compound as the trifluoroacetic acid salt. The mixture was washed with aqueous sodium hydrogen carbonate and extracted with ethyl acetate. The extract was washed with brine, dried over magnesium sulfate, filtered and concentrated in vacuo to give the solid, which was recrystallized from ethyl acetate/n-hexane to give the title compound as a colorless crystal (49.8 mg, 0.105 mmol, 32%)

mp 168-170° C.

$^1$H NMR (CDCl$_3$) δ 2.40-2.53 (m, 2H), 2.42 (s, 6H), 2.71 (s, 3H), 3.56-3.69 (m, 2H), 4.34-4.45 (m, 2H), 5.99 (q, J=6.0 Hz, 1H), 6.43 (t, J=72.3 Hz, 1H), 7.12-7.18 (m, 2H).

MS Calcd.: 475; MS Found: 476 (M+H).

Anal. Calcd for C$_{20}$H$_{19}$N$_5$OClF$_5$: C, 50.48; H, 4.02; N, 14.72; Cl, 7.45; F, 19.96. Found: C, 50.09; H, 4.01; N, 14.42; Cl, 7.42; F, 19.80.

Example 213

9-Chloro-6-[1-(difluoromethoxy)-2,2,2-trifluoroethyl]-1-(2-ethyl-4,6-dimethylpyrimidin-5-yl)-1,2,3,4-tetrahydropyrimido[1,2-a]benzimidazole

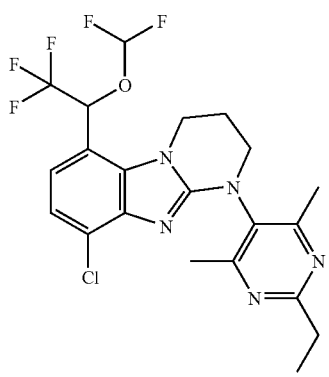 [SMILES: CCc1nc(C)c(N2CCCn3c2nc2c(Cl)ccc(C(OC(F)F)C(F)(F)F)c23)c(C)n1]

Ethylmagnesium chloride (2.0 M solution in tetrahydrofuran, 0.37 mL, 0.740 mmol) was added dropwise to a stirred suspension of 9-chloro-1-(2-chloro-4,6-dimethylpyrimidin-5-yl)-6-[1-(difluoromethoxy)-2,2,2-trifluoroethyl]-1,2,3,4-tetrahydropyrimido[1,2-a]benzimidazole (183 mg, 0.369 mmol) and [1,3-bis(diphenylphosphino)propane]dichloronickel (20.0 mg, 0.0369 mmol) in tetrahydrofuran (1.5 mL) at 0° C., and the mixture was stirred at room temperature for 14 hr. The mixture was diluted with aqueous ammonium chloride and extracted with ethyl acetate. The combined organic layer was washed with brine, dried over anhydrous magnesium sulfate, filtered and concentrated in vacuo. The residue was purified by flash column chromatography on silica gel eluting with a 70-100% ethyl acetate/n-hexane gradient mixture. The filtrate was concentrated in vacuo to give the solid, which was purified by preparative HPLC to give a mixture containing an intermediate of the title compound as the trifluoroacetic acid salt. The mixture was washed with aqueous sodium hydrogen carbonate and extracted with ethyl acetate. The extract was washed with brine, dried over magnesium sulfate, filtered and concentrated in vacuo to give the solid, which was washed with ethyl acetate/n-hexane to give the title compound as a colorless amorphous (16.5 mg, 0.0337 mmol, 9%).

$^1$H NMR (CDCl$_3$) δ 1.39 (t, J=7.5 Hz, 3H), 2.40-2.51 (m, 2H), 2.42 (s, 6H), 2.94 (q, J=7.5 Hz, 2H), 3.56-3.68 (m, 2H), 4.34-4.43 (m, 2H), 5.99 (q, J=6.0 Hz, 1H), 6.43 (t, J=72.3 Hz, 1H), 7.13-7.18 (m, 2H).

MS Calcd.: 489; MS Found: 490 (M+H).

Example 214

9-Chloro-6-[1-(difluoromethoxy)-2,2,2-trifluoroethyl]-1-[4,6-dimethyl-2-(1-methylethyl)pyrimidin-5-yl]-1,2,3,4-tetrahydropyrimido[1,2-a]benzimidazole

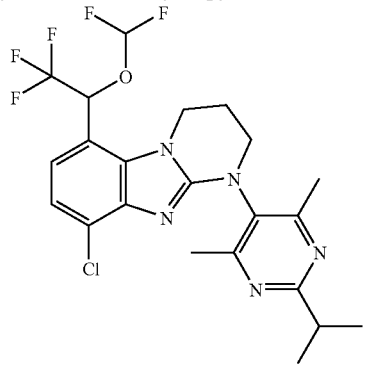 [SMILES: Cc1nc(C(C)C)nc(C)c1N1CCCn2c1nc1c(Cl)ccc(C(OC(F)F)C(F)(F)F)c12]

i-Propylmagnesium chloride (1.0 M solution in tetrahydrofuran, 0.76 mL, 0.760 mmol) was added dropwise to a stirred suspension of 9-chloro-1-(2-chloro-4,6-dimethylpyrimidin-5-yl)-6-[1-(difluoromethoxy)-2,2,2-trifluoroethyl]-1,2,3,4-tetrahydropyrimido[1,2-a]benzimidazole (189 mg, 0.381 mmol) and [1,3-bis(diphenylphosphino)propane]dichloronickel (20.7 mg, 0.0381 mmol) in tetrahydrofuran (1.5 mL) at 0° C., and the mixture was stirred at room temperature for 14 hr. The mixture was diluted with aqueous ammonium chloride and extracted with ethyl acetate. The combined organic layer was washed with brine, dried over anhydrous magnesium sulfate, filtered and concentrated in vacuo. The residue was purified by flash column chromatography on silica gel eluting with a 50-100% ethyl acetate/n-hexane gradient mixture. The filtrate was concentrated in vacuo to give the solid, which was purified by preparative HPLC to give a mixture containing an intermediate of the title compound as the trifluoroacetic acid salt. The mixture was washed with aqueous sodium hydrogen carbonate and extracted with ethyl acetate. The extract was washed with brine, dried over magnesium sulfate, filtered and concentrated in vacuo to give the solid, which was recrystallized from ethyl acetate/n-hexane to give the title compound as a colorless crystal (19.1 mg, 0.0379 mmol, 10%).

mp 204-206° C.

$^1$H NMR (CDCl$_3$) δ 1.36 (d, J=6.9 Hz, 6H), 2.40-2.50 (m, 2H), 2.42 (s, 6H), 3.12-3.21 (m, 1H), 3.56-3.68 (m, 2H), 4.34-4.43 (m, 2H), 6.00 (q, J=6.3 Hz, 1H), 6.43 (t, J=72.0 Hz, 1H), 7.13-7.18 (m, 2H).

MS Calcd.: 503; MS Found: 504 (M+H).

Example 215

5-{9-Chloro-6-[1-(difluoromethoxy)-2,2,2-trifluoroethyl]-3,4-dihydropyrimido[1,2-a]benzimidazol-1(2H)-yl}-4,6-dimethylpyrimidin-2-ol

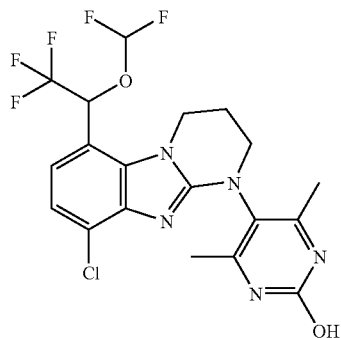 [SMILES: Cc1nc(O)nc(C)c1N1CCCn2c1nc1c(Cl)ccc(C(OC(F)F)C(F)(F)F)c12]

Iodo(trimethyl)silane (0.52 mL, 3.63 mmol) was added to a stirred mixture of 9-chloro-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole (595 mg, 1.21 mmol) and sodium iodide (544 mg, 363 mmol) in acetonitrile (8.0 mL) at room temperature, and the mixture was stirred at room temperature for 8 hr. The mixture was diluted with saturated aqueous sodium hydrogen carbonate and extracted with ethyl acetate. The combined organic layer was washed with brine, dried over anhydrous magnesium sulfate, filtered and concentrated in vacuo. The residue was recrystallized from ethanol/ethyl acetate to give the title compound as a colorless crystal (366 mg, 0.766 mmol, 63%).

mp 208-210° C.

$^1$H NMR (CDCl$_3$) δ 2.36 (s, 6H), 2.40-2.50 (m, 2H), 3.57-3.69 (m, 2H), 4.30-4.42 (m, 2H), 5.98 (q, J=5.7 Hz, 1H), 6.43 (t, J=72.0 Hz, 1H), 7.14-7.19 (m, 2H), 13.62 (s, 1H).

MS Calcd.: 477; MS Found: 478 (M+H).

Example 216

9-Chloro-1-[2-(difluoromethoxy)-4,6-dimethylpyrimidin-5-yl]-6-[1-(difluoromethoxy)-2,2,2-trifluoroethyl]-1,2,3,4-tetrahydropyrimido[1,2-a]benzimidazole

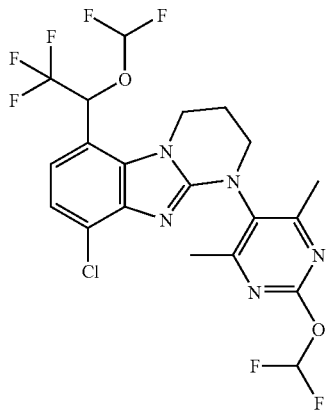 [SMILES: Cc1nc(OC(F)F)nc(C)c1N1CCCn2c1nc1c(Cl)ccc(C(OC(F)F)C(F)(F)F)c12]

A mixture of 5-{9-chloro-6-[1-(difluoromethoxy)-2,2,2-trifluoroethyl]-3,4-dihydropyrimido[1,2-a]benzimidazol-1(2H)-yl}-4,6-dimethylpyrimidin-2-ol (290 mg, 0.607 mmol), benzyltriethylammonium chloride (6.9 mg, 0.0303 mmol), and 8N sodium hydroxide (2.4 mL) in tetrahydrofuran (2.4 mL) was stirred at room temperature under chloro(difluoro)methane atmosphere for 60 min. The mixture was diluted with aqueous saturated ammonium chloride, and extracted with ethyl acetate. The combined organic layer was washed with brine, dried over anhydrous magnesium sulfate, filtered and concentrated in vacuo. The residue was purified by flash column chromatography on silica gel eluting with a 20-50% ethyl acetate/n-hexane gradient mixture. The filtrate was concentrated in vacuo to give the solid, which was purified by preparative HPLC to give a mixture containing an intermediate of the title compound as the trifluoroacetic acid salt. The mixture was washed with aqueous sodium hydrogen carbonate and extracted with ethyl acetate. The extract was washed with brine, dried over magnesium sulfate, filtered and concentrated in vacuo to give the solid, which was recrystallized from ethyl acetate/n-hexane to give the title compound as a colorless crystal (84.0 mg, 0.159 mmol, 26%).

mp 165-166° C.

$^1$H NMR (CDCl$_3$) δ 2.40-2.53 (m, 2H), 2.43 (s, 6H), 3.56-3.68 (m, 2H), 4.35-4.44 (m, 2H), 5.98 (q, J=6.0 Hz, 1H), 6.43 (t, J=72.0 Hz, 1H), 7.14-7.18 (m, 2H), 7.46 (t, J=72.0 Hz, 1H).

MS Calcd.: 527; MS Found: 528 (M+H).

Anal. Calcd for $C_{20}H_{17}N_5O_2ClF_7$: C, 45.51; H, 3.25; N, 13.27; Cl, 6.72; F, 25.20. Found: C, 45.19; H, 3.25; N, 13.08; Cl, 6.76; F, 25.21.

Example 217

1-[9-Chloro-1-(2-cyclopropyl-4,6-dimethylpyrimidin-5-yl)-1,2,3,4-tetrahydropyrimido[1,2-a]benzimidazol-6-yl]-2,2,2-trifluoroethanol

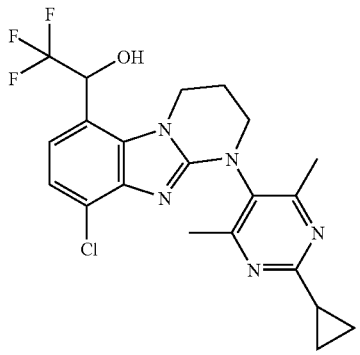 [SMILES: Cc1nc(C2CC2)nc(C)c1N1CCCn2c1nc1c(Cl)ccc(C(O)C(F)(F)F)c12]

Tetrabutylammonium fluoride (1.0 M solution in tetrahydrofuran, 0.10 mL, 0.10 mmol) was added dropwise to a stirred solution of 9-chloro-1-(2-cyclopropyl-4,6-dimethylpyrimidin-5-yl)-1,2,3,4-tetrahydropyrimido[1,2-a]benzimidazole-6-carbaldehyde (294 mg, 0.770 mmol) and trimethyl(trifluoromethyl)silane (219 mg, 1.54 mmol) in tetrahydrofuran (3.0 mL) at 0° C., and the mixture was stirred at 0° C. for 40 min. 1N hydrochloric acid (3.0 mL) was added to the mixture at 0° C., and the mixture was stirred at 0° C. for 30 min. The mixture was neutralized with saturated aqueous sodium hydrogen carbonate, and extracted with ethyl acetate. The combined organic layer was washed with brine, dried over anhydrous magnesium sulfate, filtered and concentrated in vacuo. The residue was purified by flash column chromatography on silica gel eluting with a 70-100% ethyl acetate/n-hexane gradient mixture. The filtrate was concentrated in vacuo to give the title compound as a colorless solid (308 mg, 0.682 mmol, 89%).

$^1$H NMR (CDCl$_3$) δ 1.00-1.07 (m, 2H), 1.11-1.18 (m, 2H), 2.04-2.23 (m, 1H), 2.30 (s, 3H), 2.32-2.45 (m, 2H), 2.38 (s, 3H), 3.48 (d, J=5.7 Hz, 1H), 3.51-3.61 (m, 2H), 4.40 (t, J=6.0 Hz, 2H), 5.48-5.56 (m, 1H), 7.07-7.13 (m, 2H).

MS Calcd.: 451; MS Found: 452 (M+H).

Example 218

9-Chloro-1-(2-cyclopropyl-4,6-dimethylpyrimidin-5-yl)-6-[1-(difluoromethoxy)-2,2,2-trifluoroethyl]-1,2,3,4-tetrahydropyrimido[1,2-a]benzimidazole

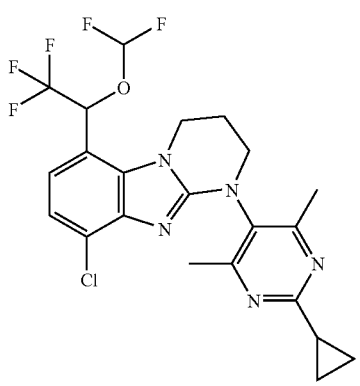 [SMILES: Cc1nc(C2CC2)nc(C)c1N1CCCn2c1nc1c(Cl)ccc(C(OC(F)F)C(F)(F)F)c12]

A mixture of 1-[9-chloro-1-(2-cyclopropyl-4,6-dimethylpyrimidin-5-yl)-1,2,3,4-tetrahydropyrimido[1,2-a]benzimidazol-6-yl]-2,2,2-trifluoroethanol (305 mg, 0.675 mmol), benzyltriethylammonium chloride (7.7 mg, 0.0338 mmol), and 8N sodium hydroxide (2.7 mL) in tetrahydrofuran (2.7 mL) was stirred at room temperature under chloro(difluoro)methane atmosphere for 60 min. The mixture was diluted with aqueous saturated ammonium chloride, and extracted with ethyl acetate. The combined organic layer was washed with brine, dried over anhydrous magnesium sulfate, filtered and concentrated in vacuo. The residue was purified by flash column chromatography on silica gel eluting with a 60-100% ethyl acetate/n-hexane gradient mixture. The filtrate was concentrated in vacuo to give the solid, which was purified by preparative HPLC to give a mixture containing an intermediate of the title compound as the trifluoroacetic acid salt. The mixture was washed with aqueous sodium hydrogen carbonate and extracted with ethyl acetate. The extract was washed with brine, dried over magnesium sulfate, filtered and concentrated in vacuo to give the solid, which was recrystallized from ethyl acetate/n-hexane to give the title compound as a colorless crystal (98.2 mg, 0.196 mmol, 29%).

mp 191-193° C.

$^1$H NMR (CDCl$_3$) δ 1.01-1.08 (m, 2H), 1.12-1.19 (m, 2H), 2.15-2.24 (m, 1H), 2.37 (s, 6H), 2.40-2.49 (m, 2H), 3.53-3.65 (m, 2H), 4.32-4.41 (m, 2H), 5.99 (q, J=5.7 Hz, 1H), 6.42 (t, J=72.3 Hz, 1H), 7.12-7.17 (m, 2H).

MS Calcd.: 501; MS Found: 502 (M+H).

Anal. Calcd for $C_{22}H_{21}N_5OClF_5$: C, 52.65; H, 4.22; N, 13.95; Cl, 7.06; F, 18.93. Found: C, 52.56; H, 4.20; N, 13.85; Cl, 7.10; F, 19.01.

Example 219

[9-Chloro-1-(2-methoxy-4,6-dimethylpyrimidin-5-yl)-1,2,3,4-tetrahydropyrimido[1,2-a]benzimidazol-6-yl]acetonitrile

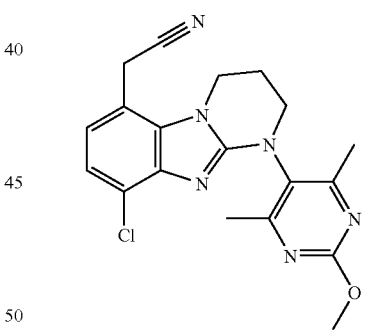

Thionyl chloride (0.56 mL, 7.65 mmol) was added to a stirred solution of [9-chloro-1-(2-methoxy-4,6-dimethylpyrimidin-5-yl)-1,2,3,4-tetrahydropyrimido[1,2-a]benzimidazol-6-yl]methanol (1.43 g, 3.83 mmol) and pyridine (0.10 mL) in tetrahydrofuran (20 mL) at 0° C., and the mixture was stirred at 0° C. for 30 min. The mixture was diluted with saturated aqueous sodium hydrogen carbonate and extracted with ethyl acetate. The combined organic layer was washed with brine, dried over anhydrous magnesium sulfate, filtered, and concentrated in vacuo. A solution of sodium cyanide (375 mg, 7.65 mmol) in water (1.0 mL) was added to the resulting benzyl chloride in dimethylsulfoxide (20 mL), and the mixture was stirred at room temperature for 14 hr. The mixture was diluted with saturated aqueous sodium hydrogen carbonate, and the precipitate was collected by filtration, washed with diisopropyl ether to give the title compound as a colorless powder (1.42 g, 3.71 mmol, 97% in 2 steps).

$^1$H NMR (DMSO-d$_6$) δ 2.23-2.37 (m, 2H), 2.28 (s, 6H), 3.56-3.68 (m, 2H), 3.92 (s, 3H), 4.47 (s, 2H), 4.53 (t, J=6.0 Hz, 2H), 6.89 (d, J=8.1 Hz, 1H), 7.05 (d, J=8.1 Hz, 1H).

MS Calcd.: 382; MS Found: 383 (M+H).

Example 220

2-[9-Chloro-1-(2-methoxy-4,6-dimethylpyrimidin-5-yl)-1,2,3,4-tetrahydropyrimido[1,2-a]benzimidazol-6-yl]butanenitrile

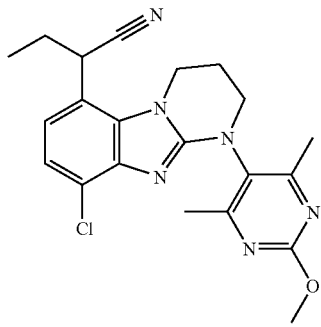 [SMILES: CCC(C#N)c1ccc(Cl)c2nc3n(c12)CCCN3c1c(C)nc(OC)nc1C]

Potassium t-butoxide (908 mg, 8.09 mmol) was added to a stirred solution of [9-chloro-1-(2-methoxy-4,6-dimethylpyrimidin-5-yl)-1,2,3,4-tetrahydropyrimido[1,2-a]benzimidazol-6-yl]acetonitrile (1.41 g, 3.68 mmol) and ethyl iodide (1.43 g, 9.20 mmol) in tetrahydrofuran (18 mL) at 0° C., and the mixture was stirred at 0° C. for 50 min. The mixture was diluted with aqueous saturated ammonium chloride, and extracted with ethyl acetate. The combined organic layer was washed with brine, dried over anhydrous magnesium sulfate, filtered, and concentrated in vacuo. The residue was purified by flash column chromatography on silica gel eluting with a 70-100% ethyl acetate/n-hexane gradient mixture. The filtrate was concentrated in vacuo to give the title compound as a colorless solid (1.20 g, 2.92 mmol, 79%).

$^1$H NMR (CDCl$_3$) δ 1.20 (t, J=7.5 Hz, 3H), 2.04-2.18 (m, 2H), 2.36 (s, 6H), 2.37-2.50 (m, 2H), 3.60 (t, J=5.7 Hz, 2H), 4.01 (s, 3H), 4.25-4.40 (m, 2H), 4.46-4.55 (m, 1H), 7.00 (d, J=8.1 Hz, 1H), 7.11 (d, J=8.1 Hz, 1H).

MS Calcd.: 410; MS Found: 411 (M+H).

Example 221

2-[9-Chloro-1-(2-methoxy-4,6-dimethylpyrimidin-5-yl)-1,2,3,4-tetrahydropyrimido[1,2-a]benzimidazol-6-yl]butanal

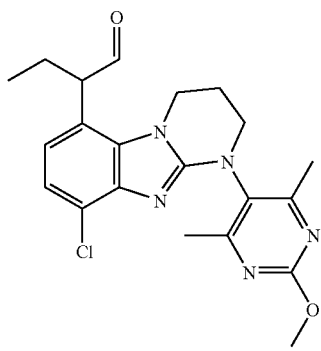 [SMILES: CCC(C=O)c1ccc(Cl)c2nc3n(c12)CCCN3c1c(C)nc(OC)nc1C]

Diisobutylaluminium hydride (1.5 M solution in toluene, 2.6 mL, 3.90 mmol) was added to a stirred solution of 2-2-[9-chloro-1-(2-methoxy-4,6-dimethylpyrimidin-5-yl)-1,2,3,4-tetrahydropyrimido[1,2-a]benzimidazol-6-yl]butanenitrile (1.08 g, 2.63 mmol) in toluene (18 mL) at 0° C., and the mixture was stirred at 0° C. for 20 min. The reaction was quenched by water, and the mixture was diluted with 1N hydrochloric acid. The mixture was stirred at 0° C. for 15 min, neutralized with saturated aqueous sodium hydrogen carbonate, and extracted with ethyl acetate. The combined organic layer was washed with brine, dried over anhydrous magnesium sulfate, filtered, and concentrated in vacuo. The residue was purified by flash column chromatography on silica gel eluting with a 75-100% ethyl acetate/n-hexane gradient mixture. The filtrate was concentrated in vacuo to give the title compound as a colorless solid (607 mg, 1.47 mmol, 56%).

MS Calcd.: 413; MS Found: 414 (M+H).

Example 222

9-Chloro-6-[1-(difluoromethyl)propyl]-1-(2-methoxy-4,6-dimethylpyrimidin-5-yl)-1,2,3,4-tetrahydropyrimido[1,2-a]benzimidazole

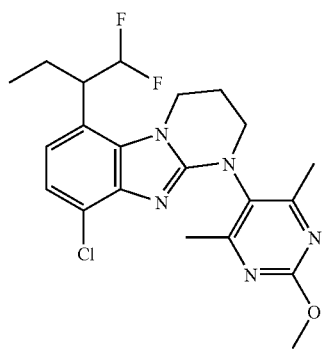 [SMILES: CCC(c1ccc(Cl)c2nc3n(c12)CCCN3c1c(C)nc(OC)nc1C)C(F)F]

To a solution of 2-[9-chloro-1-(2-methoxy-4,6-dimethylpyrimidin-5-yl)-1,2,3,4-tetrahydropyrimido[1,2-a]benzimidazol-6-yl]butanal (570 mg, 1.38 mmol) in acetonitrile (7.0 mL) was added bis-2-(methoxyethyl)aminosulfur trifluoride (0.73 mL, 5.52 mmol) at 0° C., and the mixture was stirred at 0° C. for 80 min. The mixture was quenched with aqueous saturated sodium hydrogen carbonate and extracted with ethyl acetate. The combined organic layer was washed with brine, dried over anhydrous magnesium sulfate, filtered and concentrated in vacuo. The residue was purified by flash column chromatography on silica gel eluting with a 75-100% ethyl acetate/n-hexane gradient mixture. The filtrate was concentrated in vacuo to give the solid, which was recrystallized from ethyl acetate/n-hexane to give the title compound as a colorless crystal (95.1 mg, 0.218 mmol, 16%).

mp 181-183° C.

$^1$H NMR (CDCl$_3$) δ 0.93 (t, J=7.2 Hz, 3H), 1.82-1.93 (m, 1H), 2.00-2.11 (m, 1H), 2.37 (s, 6H), 2.37-2.46 (m, 2H), 3.48-3.70 (m, 3H), 4.00 (s, 3H), 4.28-4.36 (m, 1H), 4.49-4.57 (m, 1H), 5.88 (dt, J=5.7 Hz, 56.7 Hz, 1H), 6.82 (d, J=8.1 Hz, 1H), 7.10 (d, J=8.1 Hz, 1H).

MS Calcd.: 435; MS Found: 436 (M+H).

Example 223

5-Chloro-2-[8-chloro-5-(1-ethylpropyl)-2,3-dihydro-1H-imidazo[1,2-a]benzimidazol-1-yl]benzamide

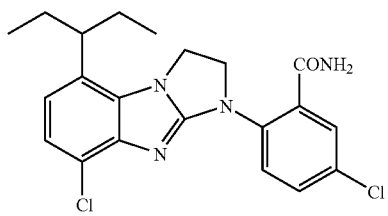 [SMILES: CCC(CC)c1ccc(Cl)c2nc3n(c12)CCN3c1ccc(Cl)cc1C(N)=O]

To a solution of 5-chloro-2-[8-chloro-5-(1-ethylpropyl)-2,3-dihydro-1H-imidazo[1,2-a]benzimidazol-1-yl]benzonitrile (55.0 mg, 0.138 mmol) in tert-butyl alcohol (1.5 mL) was added potassium hydroxide (30.9 mg, 0.551 mmol). The reaction mixture was stirred at 80° C. for 15 min. After cooling, the reaction mixture was diluted with water and extracted with ethyl acetate (×3). The combined organic layer was washed with brine (×1), dried over anhydrous magnesium sulfate, filtered and concentrated in vacuo. The residue was purified by silica gel column chromatography eluting with a 10-60% ethyl acetate/n-hexane gradient mixture. The resulting solid was recrystallized from methanol to give the title compound as a colorless powder (24.6 mg, 0.0872 mmol, 43%).

mp >300° C.

$^1$H NMR (CDCl$_3$) δ: 0.67-0.78 (m, 6H), 1.28-1.62 (m, 4H), 1.99-2.17 (m, 1H), 3.49-3.65 (m, 1H), 4.06-4.21 (m, 1H), 4.25-4.41 (m, 1H), 4.46-4.60 (m, 1H), 4.65 (s, 2H), 6.53 (d, J=8.3 Hz, 1H), 6.65 (d, J=8.3 Hz, 1H), 7.26 (d, J=8.7 Hz, 1H), 7.39 (dd, J=2.2, 8.7 Hz, 1H), 7.82 (d, J=2.2 Hz, 1H).

MS Calcd.: 416, MS Found: 417 (M+H).

Anal. Calcd for C$_{20}$H$_{20}$N$_4$OCl$_2$ (0.5 molH$_2$O): C, 59.16; H, 5.44; N, 13.14; C, 5.63; Cl, 16.63. Found: C, 59.11; H, 5.21; N, 13.12.

Example 224

8-Chloro-5-(1-ethylpropyl)-2,3-dihydro-1H-imidazo[1,2-a]benzimidazole

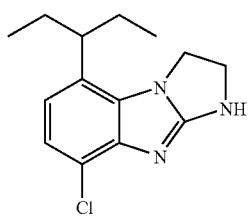 [SMILES: CCC(CC)c1ccc(Cl)c2nc3n(c12)CCN3]

To a solution of 2-[2,4-Dichloro-7-(1-ethylpropyl)-1H-benzimidazol-1-yl]ethanol (1.41 g, 4.681 mmol) in tetrahydrofuran (18 mL) were added triphenylphosphine (1.84 g, 7.022 mmol), diethylazodicarboxylate (ca. 2.2 mol/L in toluene, 3.19 mL, 7.022 mmol) and phthalimide (1.03 g, 7.022 mmol). The reaction mixture was stirred at room temperature for 2 hrs. The mixture was concentrated in vacuo. The residue was purified by silica gel column chromatography eluting with a 0-30% ethyl acetate/n-hexane gradient mixture to give the mixture containing the title compound. To a solution of the crude material in tetrahydrofuran (12 mL) and ethanol (1 mL) was added hydrazine monohydrate (2 mL). The reaction mixture was stirred at room temperature for 7 hrs. The precipitate was removed by filtration. The filtrate was concentrated in vacuo, and the residue was recrystallized with ethyl acetate/tetrahydrofuran to give the title compound as a colorless solid (725.5 mg, 2.751 mmol, 59%).

$^1$H NMR (DMSO-d$_6$) δ: 0.85 (t, J=7.3 Hz, 6H), 1.63-1.87 (m, 4H), 2.12 (brs, 1H), 3.07-3.23 (m, 1H), 4.01, (t, J=6.1 Hz, 2H), 4.57 (t, J=6.1 Hz, 2H), 7.04 (d, J=8.3 Hz, 1H), 7.24 (d, J=8.3 Hz, 1H).

MS Calcd.: 300, MS Found: 301 (M+H).

Example 225

8-Chloro-1-[3-chloro-5-(trifluoromethyl)pyridin-2-yl]-5-(1-ethylpropyl)-2,3-dihydro-1H-imidazo[1,2-a]benzimidazole

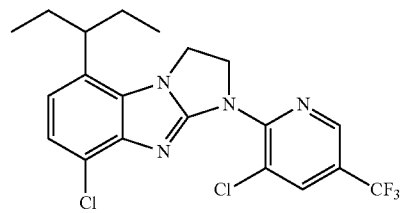 [SMILES: CCC(CC)c1ccc(Cl)c2nc3n(c12)CCN3c1ncc(C(F)(F)F)cc1Cl]

A mixture of 8-chloro-5-(1-ethylpropyl)-2,3-dihydro-1H-imidazo[1,2-a]benzimidazole (28.6 mg, 0.108 mmol), 2-bromo-3-chloro-5-(trifluoromethyl)pyridine (56.3 mg, 0.217 mmol), copper(I) iodide (20.6 mg, 0.108 mmol), 2,2'-bipyridyl (33.9 mg, 0.217 mmol) and cesium carbonate (70.7 mg, 0.217 mmol) in 1-methyl-2-pyrrolidinone (1.0 mL) was stirred at 150° C. for 4 hrs. After cooling, the mixture was diluted with ethyl acetate, the precipitate was filtered through a pad of celite. The filtrate was extracted with ethyl acetate (×3). The combined organic layer was washed with 1N hydrochloric acid (×1) and brine (×1), dried over anhydrous magnesium sulfate and concentrated in vacuo. The residue was purified by silica gel column chromatography eluting with a 0-15%, ethyl acetate/n-hexane gradient mixture to give the title compound as a yellow amorphous (14.2 mg, 0.0320 mmol, 30%).

$^1$H NMR (CDCl$_3$) δ 0.83 (t, J=7.4 Hz, 6H), 1.61-1.90 (m, 4H), 2.64-2.83 (m, 1H), 4.43-4.60 (m, 2H), 4.68-4.81 (m, 2H), 6.86 (d, J=8.3 Hz, 1H), 7.14 (d, J=8.3 Hz, 1H), 8.03 (d, J=2.3 Hz, 1H), 8.60 (d, J=2.3 Hz, 1H).

MS Calcd.: 442; Found: 443 (M+H).

Example 226

8-Chloro-5-(1-ethylpropyl)-1-(3-methyl-5-nitropyridin-2-yl)-2,3-dihydro-1H-imidazo[1,2-a]benzimidazole

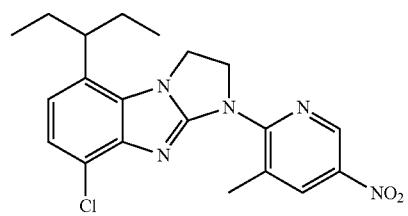 [SMILES: CCC(CC)c1ccc(Cl)c2nc3n(c12)CCN3c1ncc([N+](=O)[O-])cc1C]

A mixture of 8-chloro-5-(1-ethylpropyl)-2,3-dihydro-1H-imidazo[1,2-a]benzimidazole (30.6 mg, 0.116 mmol), 2-bromo-3-methyl-5-nitropyridine (50.4 mg, 0.232 mmol), copper(I) iodide (22.1 mg, 0.116 mmol), 2,2'-bipyridyl (36.2 mg, 0.232 mmol) and cesium carbonate (75.6 mg, 0.232 mmol) in 1-methyl-2-pyrrolidinone (1.0 mL) was stirred at 150° C. for 5 hrs. After cooling, the mixture was diluted with ethyl acetate, the precipitate was filtered through a pad of celite. The filtrate was extracted with ethyl acetate (×3). The combined organic layer was washed with 1N hydrochloric acid (×1) and brine (×1), dried over anhydrous magnesium sulfate and concentrated in vacuo. The residue was purified by silica gel column chromatography eluting with a 0-30% ethyl acetate/n-hexane gradient mixture to give the title compound as a yellow amorphous (13.5 mg, 0.0338 mmol, 29%).

$^1$H NMR (CDCl$_3$) δ 0.85 (t, J=7.2 Hz, 6H), 1.63-1.91 (m, 4H), 2.69-2.83 (m, 1H), 2.74 (s, 3H), 4.56 (brs, 2H), 4.83 (brs, 2H), 6.89 (d, J=8.3 Hz, 1H), 7.16 (d, J=8.3 Hz, 1H), 8.39 (d, J=2.3 Hz, 1H), 9.05 (d, J=2.3 Hz, 1H).

MS Calcd.: 399; Found: 400 (M+H).

Example 227

N-{3-Chloro-4-[8-chloro-5-(1-ethylpropyl)-2,3-dihydro-1H-imidazo[1,2-a]benzimidazol-1-yl]phenyl}acetamide

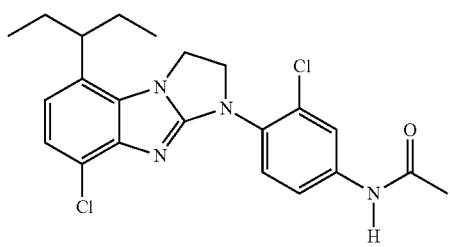 [SMILES: CCC(CC)c1ccc(Cl)c2nc3n(c12)CCN3c1ccc(NC(C)=O)cc1Cl]

A mixture of 1-(4-bromo-2-chlorophenyl)-8-chloro-5-(1-ethylpropyl)-2,3-dihydro-1H-imidazo[1,2-a]benzimidazole (56.5 mg, 0.125 mmol), xantphos (10.8 mg, 0.0188 mmol), tris(dibenzylideneacetone)dipalladium (5.7 mg, 0.00625 mmol), cesium carbonate (61.1 mg, 0.188 mmol), acetamide (14.8 mg, 0.250 mmol) and tetrahydrofuran (0.5 mL) was stirred at 70° C. for 5 hrs. After cooling, the mixture was diluted with ethyl acetate and the precipitate was removed by filtration and the filtrate was concentrated in vacuo to give the title compound as an amorphous (3.8 mg, 0.0088 mmol, 7%).

$^1$H NMR (CDCl$_3$) δ: 0.87 (t, J=7.4 Hz, 6H), 1.66-1.88 (m, 4H), 2.01 (s, 3H), 2.65-2.83 (m, 1H), 4.33-4.57 (m, 4H), 6.83 (d, J=8.5 Hz, 1H), 7.10 (d, J=8.5 Hz, 1H), 7.20 (d, J=8.5 Hz, 1H), 7.45 (dd, J=2.4, 8.7 Hz, 1H), 7.74 (d, J=2.4 Hz, 1H), 10.70 (brs, 1H).

MS Calcd.: 430, MS Found: 431 (M+H).

Example 228

8-Chloro-1-[(6-chloropyridin-3-yl)carbonyl]-5-(1-ethylpropyl)-2,3-dihydro-1H-imidazo[1,2-a]benzimidazole

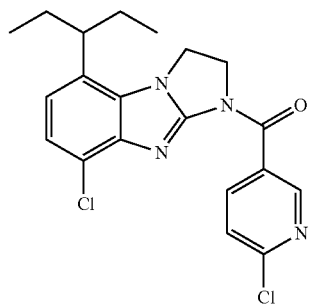 [SMILES: CCC(CC)c1ccc(Cl)c2nc3n(c12)CCN3C(=O)c1ccc(Cl)nc1]

To a suspension of 8-chloro-5-(1-ethylpropyl)-2,3-dihydro-1H-imidazo[1,2-a]benzimidazole (31.2 mg, 0.118 mmol) in tetrahydrofuran (0.5 mL) were added triethylamine (19.8 μL, 0.142 mmol) and 6-chloronicotinoyl chloride (25.0 mg, 0.142 mmol). The reaction mixture was stirred at room temperature for 4 hrs. The mixture was diluted with water and extracted with ethyl acetate (×3). The combined organic layer was washed with brine (×1), dried over anhydrous magnesium sulfate and concentrated in vacuo. The residue was purified by silica gel column chromatography eluting with a 0-30% ethyl acetate/n-hexane gradient mixture. The resulting solid was recrystallized from n-hexane to give the title compound as a colorless powder (27.1 mg, 0.0672 mmol, 57%).

mp 205-207° C.

$^1$H NMR (CDCl$_3$) δ 0.80 (t, J=7.4 Hz, 6H), 1.60-1.85 (m, 4H), 2.64-2.82 (m, 1H), 4.51 (t, J=7.8 Hz, 2H), 4.78 (t, J=7.8 Hz, 2H), 6.90 (d, J=8.3 Hz, 1H), 7.16 (d, J=8.3 Hz, 1H), 7.46 (t, J=8.3 Hz, 1H), 8.26 (dd, J=2.7, 8.1 Hz, 1H), 8.90 (d, J=2.7 Hz, 1H).

MS Calcd.: 402; Found: 403 (M+H).

Anal. Calcd for O$_{20}$H$_{20}$N$_4$OCl$_2$: C, 58.26; H, 5.13; N, 13.59; Cl, 17.20. Found: C, 58.49; H, 4.90; N, 13.46.

Example 229

8-Chloro-5-(1-ethylpropyl)-1-[(2,4,6-trimethylphenyl)carbonyl]-2,3-dihydro-1H-imidazo[1,2-a]benzimidazole

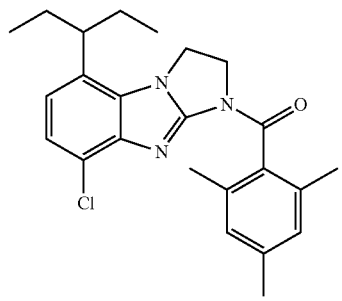 [SMILES: CCC(CC)c1ccc(Cl)c2nc3n(c12)CCN3C(=O)c1c(C)cc(C)cc1C]

To a solution of 8-chloro-5-(1-ethylpropyl)-2,3-dihydro-1H-imidazo[1,2-a]benzimidazole (32.9 mg, 0.125 mmol) in N,N-dimethylformamide (0.5 mL) was added sodium hydride (19.8 μL, 0.142 mmol) at 0° C. After 15 min, to the mixture was added 2,4,6-trimethylacetophenone (27.2 mg, 0.149 mmol). The reaction mixture was stirred at room temperature for 18 hrs. The mixture was diluted with water and extracted with ethyl acetate (×3). The combined organic layer was washed and brine (×1), dried over anhydrous magnesium sulfate and concentrated in vacuo. The residue was purified by silica gel column chromatography eluting with a 0-30% ethyl acetate/n-hexane gradient mixture. The resulting solid was recrystallized from n-hexane to give the title compound as a pale pink powder (24.0 mg, 0.0585 mmol, 47%).

mp 234-236° C.

$^1$H NMR (CDCl$_3$) δ 0.80 (t, J=7.4 Hz, 6H), 1.63-1.82 (m, 4H), 2.23 (s, 4H), 2.31 (s, 1H), 2.35 (s, 4H), 2.63-2.77 (m, 1H), 4.13 (t, J=7.8 Hz, 2/3H), 4.38 (t, J=8.0 Hz, 4/3H), 4.46 (t, J=8.0 Hz, 4/3H), 4.77 (t, J=7.8 Hz, 2/3H), 6.83 (d, J=8.3 Hz, 2/3H), 6.91-6.95 (m, 7/3H), 7.07 (d, J=8.3 Hz, 2/3H), 7.23 (t, J=8.3 Hz, 1/3H).

MS Calcd.: 409; Found: 410 (M+H).

Anal. Calcd for C$_{24}$H$_{28}$N$_3$OCl: C, 70.31; H, 6.88; N, 10.25; Cl, 8.65. Found: C, 69.96; H, 6.88; N, 9.98.

Example 230

10-Chloro-1-(1,6-dimethyl-1H-benzimidazol-4-yl)-7-(1-ethylpropyl)-2,3,4,5-tetrahydro-1H-[1,3]diazepino[1,2-a]benzimidazole

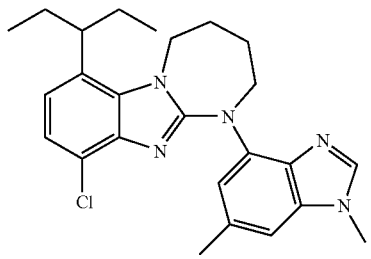 [SMILES: CCC(CC)c1ccc(Cl)c2nc3n(c12)CCCCN3c1cc(C)cc2c1ncn2C]

A mixture of 10-chloro-7-(1-ethylpropyl)-2,3,4,5-tetrahydro-1H-[1,3]diazepino[1,2-a]benzimidazole (100.0 mg, 0.343 mmol), 4-bromo-1,6-dimethyl-1H-benzimidazole (154.9 mg), xantphos (20.0 mg, 0.0343 mmol), sodium tert-butoxide (40.0 mg, 0.412 mmol), tris(dibenzylideneacetone)dipalladium (31.0 mg, 0.0343 mmol) and toluene (2.0 mL) was stirred at 100° C. for 3 days. After cooling, the mixture was diluted with ethyl acetate and the precipitate was removed by filtration and the filtrate was concentrated in vacuo. The residue was purified by silica gel column chromatography eluting with a 0-80% ethyl acetate/n-hexane gradient mixture to give the mixture containing the title compound. The residue was purified by preparative HPLC to give the title compound as the trifluoroacetic acid salt. The salt was neutralized with aqueous sodium hydrogen carbonate and extracted with ethyl acetate. The extract was washed with brine, dried over anhydrous magnesium sulfate, filtered and concentrated in vacuo to give the title compound. The resulting solid was recrystallized from ethyl acetate/n-hexane to give the title compound as a colorless solid (51.0 mg, 0.117 mmol, 34%).

mp 259-260° C.

$^1$H NMR (CDCl$_3$) δ: 0.86 (t, J=7.4 Hz, 6H), 1.62-1.90 (m, 4H), 1.94-2.10 (m, 4H), 2.44 (s, 3H), 2.97-3.19 (m, 1H), 3.72 (s, 3H), 4.29 (d, J=4.9 Hz, 2H), 4.45 (d, J=4.9 Hz, 2H), 6.87 (s, 1H), 6.89 (d, J=8.3 Hz, 1H), 6.98 (s, 1H), 7.13 (d, J=8.3 Hz, 1H), 7.63 (s, 1H).

MS Calcd.: 435, MS Found: 436 (M+H).

Anal. Calcd for O$_{25}$H$_{30}$N$_5$OCl: C, 68.87; H, 6.94; N, 16.06; Cl, 8.13. Found: C, 68.65; H, 6.93; N, 16.01.

Example 231

1-(2,4-Dichlorophenyl)-N,N-diethyl-3,3-difluoro-1,2,3,4-tetrahydropyrimido[1,2-a]benzimidazol-6-amine

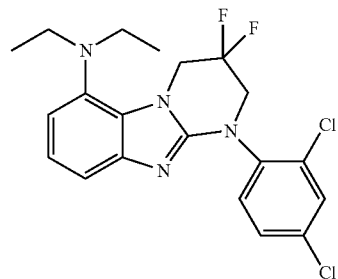 [SMILES: CCN(CC)c1cccc2nc3n(c12)CC(F)(F)CN3c1ccc(Cl)cc1Cl]

To a solution of 3-{2-[(2,4-dichlorophenyl)amino]-7-(diethylamino)-1H-benzimidazol-1-yl}-2,2-difluoropropan-1-ol (Reference example 154, 48.9 mg, 0.110 mmol) in pyridine (1.5 mL) was added methanesulfonyl chloride (25.6 μL, 0.330 mmol) at 0° C. The mixture was stirred at 0° C. for 2 hrs. The starting material wasn't consumed completely. To the mixture was added methanesulfonyl chloride (25.6 μL, 0.330 mmol) at 0° C. and the mixture was stirred at room temperature for 14 hrs. The mixture was quenched with aqueous sodium hydrogen carbonate and extracted with ethyl acetate. The combined organic layer was washed with brine, dried over anhydrous magnesium sulfate, filtered and concentrated in vacuo. The resulting mesylate was dissolved into N,N-dimethylformamide (1.5 mL) and to the solution was added potassium carbonate (30.4 mg, 0.220 mmol) at room temperature. The mixture was stirred at 40° C. for 1 hr. After cooling, the mixture was diluted with water and extracted with ethyl acetate. The combined organic layer was washed with water and brine, dried over anhydrous magnesium sulfate, filtered and concentrated in vacuo. The residue was purified by silica gel column chromatography eluting with a 0-40% ethyl acetate/n-hexane gradient mixture. The resulting solid was recrystallized from hexane to give the title compound as a solid (24.0 mg, 0.0564 mmol, 51%).

mp 125-127° C.

$^1$H NMR (CDCl$_3$) δ 1.02 (t, J=7.2 Hz, 6H), 3.07 (q, J=7.2 Hz, 4H), 4.00 (t, J=11.4 Hz, 2H), 4.89 (t, J=11.4 Hz, 2H), 6.95 (d, J=7.2 Hz, 1H), 7.08 (t, J=7.8 Hz, 1H), 7.23-7.28 (m, 1H), 7.31-7.38 (m, 1H), 7.42-7.49 (m, 1H), 7.53 (d, J=2.7 Hz, 1H).

MS Calcd.: 424; MS Found: 425 (M+H).

Anal. Calcd for C$_{20}$H$_{20}$N$_4$Cl$_2$F$_2$: C, 56.48; H, 4.74; N, 13.17; Cl, 16.67; F, 8.93. Found: C, 56.31; H, 4.74; N, 13.15.

Example 232

2-[(2,4-Dichlorophenyl)amino]-5,5-difluoro-4,5-dihydroimidazo[1,5,4-ef][1,5]benzodiazepin-6(7H)-one

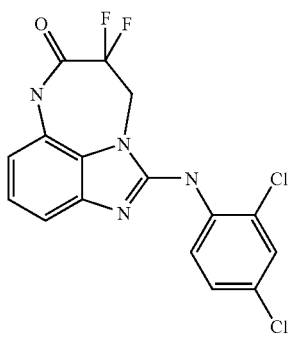 [SMILES: O=C1Nc2cccc3nc(Nc4ccc(Cl)cc4Cl)n(c23)CC1(F)F]

To a mixture of ethyl 3-[(2-amino-6-{[(2,4-dichlorophenyl)carbamothioyl]amino}phenyl)amino]-2,2-difluoropropanoate (1.60 g, 3.453 mmol) in tetrahydrofuran (25 mL) was added 1-ethyl-3-(3-dimethylaminopropyl)-carbodiimide hydrochloride (1.99 g, 10.360 mmol). The mixture was stirred at 50° C. for 2 hrs. After cooling, the mixture was diluted with water, extracted with ethyl acetate. The combined organic layer was washed with brine, dried over anhydrous magnesium sulfate, filtered and concentrated in vacuo. The residue was purified by silica gel column chromatography eluting with a 0-50% ethyl acetate/n-hexane gradient mixture to give the title compound as an amorphous (100.0 mg, 0.261 mmol, 8%).

$^1$H NMR (DMSO-d$_6$) δ 4.94 (brs, 2H), 6.83 (brs, 2H), 7.05 (brs, 1H), 7.42 (brs, 1H), 7.66 (d, J=9.5 Hz, 1H), 7.89 (brs, 1H), 8.85 (brs, 1H), 11.20 (brs, 1H).

MS Calcd.: 382; MS Found: 383 (M+H).

Example 233

4-[9-Chloro-1-(2,4-dichlorophenyl)-1,2,3,4-tetrahydropyrimido[1,2-a]benzimidazol-6-yl]heptan-4-ol

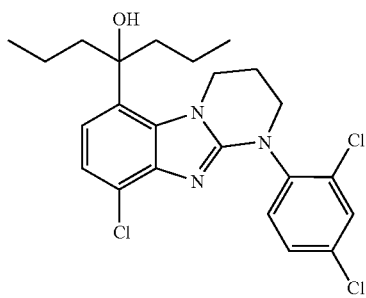 [SMILES: CCCC(O)(CCC)c1ccc(Cl)c2nc3n(c12)CCCN3c1ccc(Cl)cc1Cl]

To a solution of methyl 9-chloro-1-(2,4-dichlorophenyl)-1,2,3,4-tetrahydropyrimido[1,2-a]benzimidazole-6-carboxylate (200.0 mg, 0.487 mmol) in tetrahydrofuran (3.0 mL) was added n-propylmagnesium bromide (1.0 M solution in tetrahydrofuran, 2.44 mL, 2.435 mmol). The reaction mixture was stirred at 60° C. for 14 hrs. After cooling, the mixture was quenched with aqueous saturated ammonium chloride and extracted with ethyl acetate (×3). The combined organic layer was washed with brine, dried over anhydrous magnesium sulfate, filtered and concentrated in vacuo. The residue was purified by silica gel column chromatography eluting with a 0-50% ethyl acetate/n-hexane gradient mixture. The resulting solid was recrystallized from hexane to give the title compound as a solid (60.0 mg, 0.129 mmol, 26%).

mp 133-135° C.

$^1$H NMR (CDCl$_3$) δ 0.82-1.00 (m, 6H), 1.15-1.50 (m, 4H), 1.80-2.07 (m, 5H), 2.31 (quin, J=5.8 Hz, 2H), 3.70 (brs, 2H), 4.71-4.78 (m, 2H), 6.72 (d, J=8.7 Hz, 1H), 7.01 (d, J=8.7 Hz, 1H), 7.32 (dd, J=2.5, 8.5 Hz, 1H), 7.49-7.53 (m, 2H).

MS Calcd.: 465; MS Found: 466 (M+H).

Anal. Calcd for C$_{23}$H$_{26}$N$_3$Cl$_3$: C, 59.17; H, 5.61; N, 9.00; Cl, 22.78. Found: C, 59.18; H, 5.65; N, 8.97.

Example 234

1-[9-Chloro-1-(2,4-dichlorophenyl)-1,2,3,4-tetrahydropyrimido[1,2-a]benzimidazol-6-yl]-2-methylpropan-1-ol

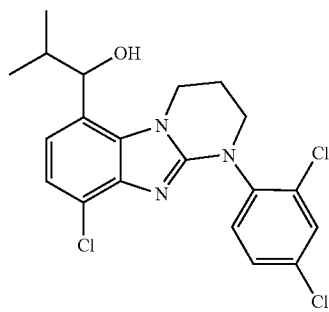 [SMILES: CC(C)C(O)c1ccc(Cl)c2nc3n(c12)CCCN3c1ccc(Cl)cc1Cl]

To a solution of 9-chloro-1-(2,4-dichlorophenyl)-1,2,3,4-tetrahydropyrimido[1,2-a]benzimidazole-6-carbaldehyde (150.0 mg, 0.394 mmol) in tetrahydrofuran (3.0 mL) was added i-propylmagnesium chloride (1.0 M solution in tetrahydrofuran, 0.59 mL, 0.591 mmol). The reaction mixture was stirred at 0° C. for 2 hrs. To the mixture was added i-propylmagnesium chloride (1.0 M solution in tetrahydrofuran, 0.59 mL, 0.591 mmol). The mixture was stirred at 0° C. for 1 hr. After cooling, the mixture was quenched with aqueous saturated ammonium chloride and extracted with ethyl acetate (×3). The combined organic layer was washed with brine, dried over anhydrous magnesium sulfate, filtered and concentrated in vacuo. The residue was purified by silica gel column chromatography eluting with a 10-60% ethyl acetate/n-hexane gradient mixture to give the title compound as a solid (78.8 mg, 0.186 mmol, 47%).

$^1$H NMR (CDCl$_3$) δ 0.85 (d, J=6.4 Hz, 3H), 1.15 (d, J=6.4 Hz, 3H), 2.02 (brs, 1H), 2.08-2.22 (m, 1H), 2.37 (quin, J=5.8 Hz, 2H), 3.71 (brs, 2H), δ 4.38-4.62 (m, 2H), 4.73 (d, J=8.3 Hz, 1H), 6.95 (d, J=8.3 Hz, 1H), 7.07 (d, J=8.3 Hz, 1H), 7.32 (dd, J=2.6, 8.7 Hz, 1H), 7.50 (d, J=2.6 Hz, 1H), 7.52 (d, J=8.3 Hz, 1H).

MS Calcd.: 423; MS Found: 424 (M+H).

Example 235

9-Chloro-1-(2,4-dichlorophenyl)-6-(1-methoxy-2-methylpropyl)-1,2,3,4-tetrahydropyrimido[1,2-a]benzimidazole

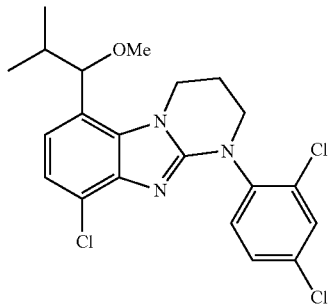 [SMILES: COC(c1ccc(Cl)c2nc3n(c12)CCCN3c1ccc(Cl)cc1Cl)C(C)C]

To a solution of 1-[9-chloro-1-(2,4-dichlorophenyl)-1,2,3,4-tetrahydropyrimido[1,2-a]benzimidazol-6-yl]-2-methylpropan-1-ol (73.6 mg, 0.173 mmol) in N,N-dimethylformamide (1.0 mL) was added sodium hydride (10.3 mg, 0.260 mmol) at 0° C. After 30 min, to the mixture was added methyl iodide (53.9 µL, 0.865 mmol) at 0° C. The reaction mixture was stirred at room temperature for 12 hrs. The mixture was quenched with water and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-50% ethyl acetate/n-hexane gradient mixture. The resulting solid was recrystallized from n-hexane to give the title compound as a colorless powder (43.7 mg, 0.0996 mmol, 58%).

mp 162-164° C.

$^1$H NMR (CDCl$_3$) δ 0.78 (d, J=6.8 Hz, 3H), 1.11 (d, J=6.8 Hz, 3H), 1.93-2.15 (m, 1H), 2.29-2.45 (m, 2H), 3.22 (s, 3H), 3.71 (brs, 2H), 4.15 (d, J=8.0 Hz, 1H), 4.25-4.38 (m, 1H), 4.59-4.72 (m, 1H), 6.85 (d, J=8.3 Hz, 1H), 7.06 (d, J=8.3 Hz, 1H), 7.32 (dd, J=2.5, 8.5 Hz, 1H), 7.50 (d, J=2.5 Hz, 1H), 7.54 (d, J=8.7 Hz, 1H).

MS Calcd.: 437; MS Found: 438 (M+H).

Anal. Calcd for C$_{23}$H$_{22}$N$_3$OCl$_3$: C, 59.69; H, 4.79; N, 9.08; Cl, 22.98. Found: C, 59.62; H, 4.89; N, 8.85.

Example 236

9-Chloro-6-[1-(cyclopropylmethoxy)propyl]-1-(2,4-dichlorophenyl)-1,2,3,4-tetrahydropyrimido[1,2-a]benzimidazole

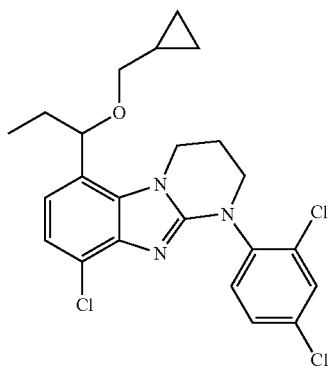 [SMILES: CCC(OCC1CC1)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-ol (120.0 mg, 0.292 mmol) in N,N-dimethylformamide (1.5 mL) was added sodium hydride (23.4 mg, 0.584 mmol) at 0° C. After 20 min, to the mixture was added cyclopropylmethyl bromide (0.14 mL, 1.46 mmol). The reaction mixture was stirred at room temperature for 1 day. The mixture was quenched with water and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-30% ethyl acetate/n-hexane gradient mixture. The resulting solid was recrystallized from n-hexane to give the title compound as a colorless powder (123.0 mg, 0.265 mmol, 91%).

mp 159-160° C.

$^1$H NMR (CDCl$_3$) δ 0.04-0.16 (m, 2H), 0.46-0.53 (m, 2H), 0.99 (t, J=7.4 Hz, 4H), 1.71-2.11 (m, 2H), 2.25-2.46 (m, 2H), 2.29-3.31 (m, 2H), 3.71 (brs, 2H), 4.28-4.43 (m, 1H), 4.59 (d, J=6.4 Hz, 1H), 4.72-4.83 (m, 1H), 6.88 (d, J=8.3 Hz, 1H), 7.04 (d, J=8.3 Hz, 1H), 7.29-7.34 (m, 1H), 7.50 (d, J=2.3 Hz, 1H), 7.53 (d, J=8.7 Hz, 1H).

MS Calcd.: 463; MS Found: 464 (M+H).

Anal. Calcd for C$_{23}$H$_{24}$N$_3$OCl$_3$: C, 59.43; H, 5.2; N, 9.04; Cl, 22.88. Found: C, 59.83; H, 5.15; N, 9.27.

Example 237

9-Chloro-1-(2,4-dichlorophenyl)-6-[1-(1-methylethoxy)propyl]-1,2,3,4-tetrahydropyrimido[1,2-a]benzimidazole

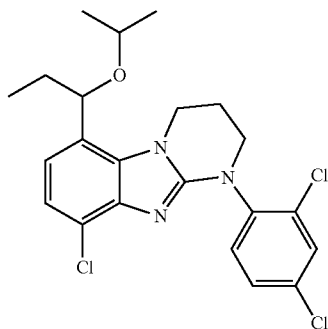 [SMILES: CCC(OC(C)C)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-ol (151.3 mg, 0.368 mmol) in 2-propanol (10.0 mL) was added sulfuric acid (0.45 mL) at 0° C. The reaction mixture was stirred at 100° C. for 16 hrs. The mixture was poured into aqueous saturated sodium hydrogen carbonate and concentrated. The residue was extracted with ethyl acetate (×3). The combined organic layer was washed with brine (×1), dried over anhydrous magnesium sulfate, filtered and concentrated in vacuo. The residue was purified by silica gel column chromatography eluting with a 0-30% ethyl acetate/n-hexane gradient mixture to give the title compound as a colorless amorphous (84.7 mg, 0.187 mmol, 51%).

$^1$H NMR (CDCl$_3$) δ 0.98 (t, J=7.4 Hz, 3H), 1.08 (d, J=6.4 Hz, 3H), 1.16 (d, J=6.1 Hz, 3H), 1.66-2.00 (m, 2H), 2.24-2.44 (m, 2H), 3.46-3.61 (m, 1H), 3.71 (brs, 2H), 4.18-4.35 (m, 1H), 4.58-4.67 (m, 1H), 4.75-4.92 (m, 1H), 6.91 (d, J=8.0 Hz, 1H), 7.04 (d, J=8.3 Hz, 1H), 7.32 (dd, J=2.5, 8.5 Hz, 1H), 7.50 (d, J=2.3 Hz, 1H), 7.53 (d, J=8.7 Hz, 1H).

MS Calcd.: 451; MS Found: 452 (M+H).

Anal. Calcd for C$_{22}$H$_{24}$N$_3$OCl$_3$: C, 58.36; H, 5.34; N, 9.28; Cl, 23.49. Found: C, 58.36; H, 5.39; N, 9.07.

Example 238

1-[9-Chloro-1-(2,4-dichlorophenyl)-1,2,3,4-tetrahydropyrimido[1,2-a]benzimidazol-6-yl]propyl acetate

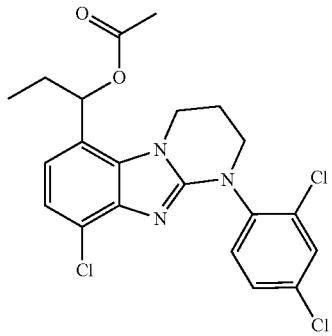 [SMILES: CCC(OC(C)=O)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-ol (139.8 mg, 0.340 mmol) in pyridine (0.8 mL) was added acetic anhydride (0.5 mL) at 0° C. The reaction mixture was stirred at room temperature for 16 hrs. The mixture was concentrated. The residue was neutralized with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified by silica gel column chromatography eluting with a 0-40% ethyl acetate/n-hexane gradient mixture. The residue was recrystallized from diisopropyl ether/n-hexane to give the title compound as a colorless powder (123.2 mg, 0.272 mmol, 80%). mp 174-176° C.

$^1$H NMR(CDCl$_3$) δ 0.94 (t, J=7.4 Hz, 3H), 1.85-2.07 (m, 2H), 2.08 (s, 3H), 2.32-2.47 (m, 2H), 3.72 (brs, 2H), 4.26-4.42 (m, 1H), 4.64-4.82 (m, 1H), 6.30 (t, J=7.2 Hz, 1H), 6.99 (d, J=8.3 Hz, 1H), 7.10 (d, J=8.3 Hz, 1H), 7.32 (dd, J=2.5, 8.5 Hz, 1H), 7.50 (d, J=2.3 Hz, 1H), 7.52 (d, J=8.7 Hz, 1H).

MS Calcd.: 451; MS Found: 452 (M+H).

Anal. Calcd for C$_{21}$H$_{20}$N$_3$O$_2$Cl$_3$: C, 55.71; H, 4.45; N, 9.28; Cl, 23.49. Found: C, 55.42; H, 4.47; N, 9.23.

Example 239

(−)-1-[9-Chloro-1-(2,4-dichlorophenyl)-1,2,3,4-tetrahydropyrimido[1,2-a]benzimidazol-6-yl]propyl acetate

Example 240

(+)-1-[9-Chloro-1-(2,4-dichlorophenyl)-1,2,3,4-tetrahydropyrimido[1,2-a]benzimidazol-6-yl]propyl acetate

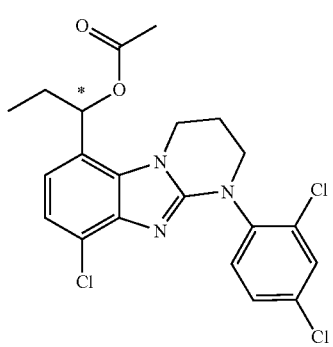 [SMILES: CCC(OC(C)=O)c1ccc(Cl)c2nc3n(c12)CCCN3c1ccc(Cl)cc1Cl]

Racemic Example 238 (388 mg) was resolved by preparative HPLC, using CHIRALPAK AD (5 cm i.d.×50 cm, Daicel Chemical Industries, Ltd.) with the flow rate of 60 mL/min at 30° C. and hexane/ethanol (30/70) as the mobile phase, and obtaining the stereoisomer having a shorter retention time 186 mg in an enantiomer excess greater than 99.9% and the stereoisomer having a longer retention time 178 mg in an enantiomer excess greater than 99.9%. The obtained compounds were washed with diisopropyl ether/hexane to give the optically active title compounds as a colorless amorphous respectively (shorter retention time (Example 239): 120 mg, longer retention time (Example 240): 111 mg).

Shorter Retention Time (Example 239):

$[α]_D^{20}$=−16.0 (c=0.4335, MeOH)

$^1$H NMR (CDCl$_3$) δ 0.94 (t, J=7.2 Hz, 3H), 1.83-2.07 (m, 2H), 2.08 (s, 3H), 2.35-2.47 (m, 2H), 3.71 (brs, 2H), 4.27-4.43 (m, 1H), 4.67-4.81 (m, 1H), 6.30 (t, J=7.2 Hz, 1H), 7.00 (d, J=8.3 Hz, 1H), 7.10 (d, J=8.3 Hz, 1H), 7.32 (dd, J=2.3, 8.7 Hz, 1H), 7.50 (d, J=2.3 Hz, 1H), 7.52 (d, J=8.7 Hz, 1H).

MS Calcd.: 451; MS Found: 452 (M+H).

Longer Retention Time (Example 240):

$[α]_D^{20}$=+16.8 (c=0.4350, MeOH)

$^1$H NMR (CDCl$_3$) δ 0.94 (t, J=7.4 Hz, 3H), 1.85-2.07 (m, 2H), 2.08 (s, 3H), 2.32-2.50 (m, 2H), 3.72 (brs, 2H), 4.28-4.42 (m, 1H), 4.67-4.82 (m, 1H), 6.30 (t, J=7.0 Hz, 1H), 7.00 (d, J=8.3 Hz, 1H), 7.10 (d, J=8.3 Hz, 1H), 7.32 (dd, J=2.5, 8.5 Hz, 1H), 7.47-7.55 (m, 2H).

MS Calcd.: 451; MS Found: 452 (M+H).

Example 241

1-[9-Chloro-1-(2,4-dichlorophenyl)-1,2,3,4-tetrahydropyrimido[1,2-a]benzimidazol-6-yl]propyl propanoate

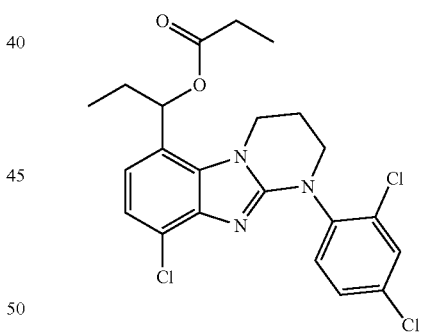

To a solution of 1-[9-chloro-1-(2,4-dichlorophenyl)-1,2,3,4-tetrahydropyrimido[1,2-a]benzimidazol-6-yl]propan-1-ol (140.0 mg, 0.341 mmol) in pyridine (0.5 mL) was added propionic anhydride (0.3 mL) at 0° C. The reaction mixture was stirred at room temperature for 13 hrs. The mixture was quenched with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified by silica gel column chromatography eluting with a 0-30% ethyl acetate/n-hexane gradient mixture. The residue was recrystallized from methanol/n-hexane to give the title compound as a colorless powder (130.2 mg, 0.279 mmol, 82%).

mp 133-135° C.

¹H NMR (CDCl₃) δ 0.95 (t, J=7.4 Hz, 3H), 1.13 (t, J=7.6 Hz, 3H), 1.83-2.13 (m, 2H), 2.26-2.48 (m, 4H), 3.72 (brs, 2H), 4.24-4.43 (m, 1H), 4.69-4.83 (m, 1H), 6.31 (t, J=7.0 Hz, 1H), 6.98 (d, J=8.3 Hz, 1H), 7.09 (d, J=8.3 Hz, 1H), 7.32 (dd, J=2.3, 8.7 Hz, 1H), 7.50 (d, J=2.3 Hz, 1H), 7.53 (d, J=8.7 Hz, 1H).

MS Calcd.: 465; MS Found: 466 (M+H).

Anal. Calcd for C₂₂H₂₂N₃O₂Cl₃: C, 56.61; H, 4.75; N, 9.00; Cl, 22.79. Found: C, 56.36; H, 4.73; N, 9.05.

Example 242

2-{1-[9-Chloro-1-(2,4-dichlorophenyl)-1,2,3,4-tetrahydropyrimido[1,2-a]benzimidazol-6-yl]propoxy}ethanol

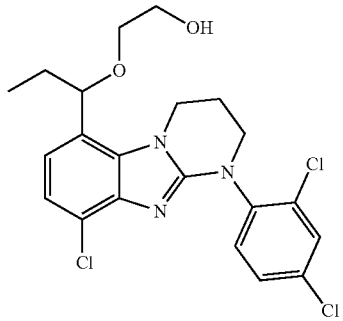 [SMILES: CCC(OCCO)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-ol (150.0 mg, 0.365 mmol) in N,N-dimethylformamide (1.5 mL) was added sodium hydride (23.4 mg, 0.584 mmol) at 0° C.

After 30 min, to the mixture was added (2-bromomethoxy)-tert-butyldimethylsilane (0.39 mL, 1.83 mmol). The reaction mixture was stirred at room temperature for 3 hrs. The mixture was quenched with aqueous saturated ammonium chloride and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-50% ethyl acetate/n-hexane gradient mixture. To a solution of silyl ether (76.3 mg, 0.134 mmol) in tetrahydrofuran (1.0 mL) was added tetrabutylammonium fluoride (1.0 M solution in tetrahydrofuran, 0.27 mL, 0.268 mmol) at 0° C. The reaction mixture was stirred at room temperature for 2 hrs. The starting material wasn't consumed completely. To the mixture was added tetrabutylammonium fluoride (1.0 M solution in tetrahydrofuran, 0.13 mL, 0.134 mmol) at 0° C. The reaction mixture was stirred at room temperature for 2 hrs. The mixture was quenched with aqueous saturated ammonium chloride and extracted with ethyl acetate (×3). The combined organic layer was washed with brine (×1), dried over anhydrous magnesium sulfate, filtered and concentrated in vacuo. The residue was purified by silica gel column chromatography eluting with a 0-50% ethyl acetate/n-hexane gradient mixture to give the title compound as an amorphous (35.6 mg, 0.0783 mmol, 21% (2 steps)).

¹H NMR (CDCl₃) δ 1.00 (t, J=7.4 Hz, 3H), 1.79-1.91 (m, 2H), 1.94-2.07 (m, 1H), 2.28-2.47 (m, 2H), 3.34-3.57 (m, 2H), 3.67-3.78 (m, 4H), 4.30-4.44 (m, 1H), 4.57-4.66 (m, 1H), 4.71 (d, J=6.8 Hz, 1H), 6.91 (d, J=8.0 Hz, 1H), 7.07 (d, J=8.3 Hz, 1H), 7.32 (dd, J=2.3, 8.3 Hz, 1H), 7.49-7.55 (m, 2H).

MS Calcd.: 453; MS Found: 454 (M+H).

Example 243

1-[9-Chloro-1-(2,4-dichlorophenyl)-1,2,3,4-tetrahydropyrimido[1,2-a]benzimidazol-6-yl]ethyl acetate

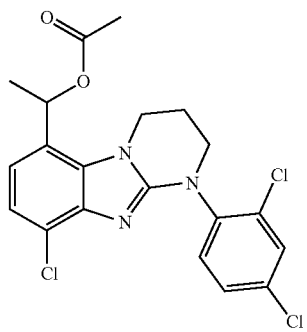 [SMILES: CC(=O)OC(C)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]ethanol (50.0 mg, 0.126 mmol) in pyridine (0.5 mL) was added acetic anhydride (0.3 mL) at 0° C. The reaction mixture was stirred at room temperature for 3 hrs. The mixture was concentrated. The residue was neutralized with aqueous saturated sodium hydrogen carbonate and extracted with ethyl acetate (×3). The combined organic layer was washed with brine (×1), dried over anhydrous magnesium sulfate, filtered and concentrated in vacuo. The residue was recrystallized from ethyl acetate/n-hexane to give the title compound as a colorless powder (38.8 mg, 0.0884 mmol, 70%).

mp 204-206° C.

¹H NMR (CDCl₃) δ 1.65 (d, J=6.4 Hz, 3H), 2.09 (s, 3H), 2.34-2.46 (m, 2H), 3.71 (brs, 2H), 4.30-4.45 (m, 1H), 4.55-4.69 (m, 1H), 6.52 (q, J=6.4 Hz, 1H), 7.00-7.15 (m, 2H), 7.32 (dd, J=2.3, 8.7 Hz, 1H), 7.48-7.54 (m, 2H).

MS Calcd.: 437; MS Found: 438 (M+H).

Anal. Calcd for C₂₀H₁₈N₃O₂Cl₃: C, 52.59; H, 4.41; N, 9.2; Cl, 23.29. Found: C, 52.88; H, 4.07; N, 9.09.

Example 244

[9-Chloro-1-(2,4-dichlorophenyl)-1,2,3,4-tetrahydropyrimido[1,2-a]benzimidazol-6-yl](cyclopropyl)methyl acetate

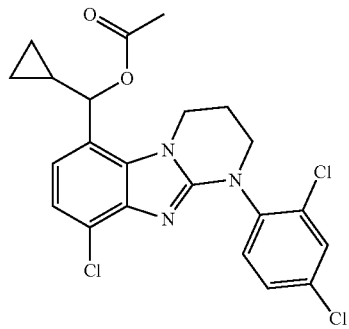 [SMILES: CC(=O)OC(c1ccc(Cl)c2nc3n(c12)CCCN3c1ccc(Cl)cc1Cl)C1CC1]

To a solution of [9-chloro-1-(2,4-dichlorophenyl)-1,2,3,4-tetrahydropyrimido[1,2-a]benzimidazol-6-yl](cyclopropyl)methanol (120.0 mg, 0.284 mmol) in pyridine (0.5 mL) was added acetic anhydride (0.3 mL) at 0° C. The reaction mixture was stirred at room temperature for 7 hrs. The mixture was concentrated. The residue was neutralized with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified, by silica gel column chromatography eluting with a 0-40% ethyl acetate/n-hexane gradient mixture. The residue was recrystallized from diisopropyl ether/n-hexane to give the title compound as a colorless powder (94.5 mg, 0.203 mmol, 72%).

mp 208-210° C.

$^1$H NMR (CDCl$_3$) δ 0.30-0.49 (m, 2H), 0.51-0.74 (m, 2H), 1.39-1.52 (m, 1H), 2.10 (s, 3H), 2.33-2.47 (m, 2H), 3.71 (brs, 2H), 4.31-4.47 (m, 1H), 4.57-4.68 (m, 1H), 6.01 (d, J=7.9 Hz, 1H), 7.05 (d, J=8.3 Hz, 1H), 7.10 (d, J=8.3 Hz, 1H), 7.32 (dd, J=2.3, 8.7 Hz, 1H), 7.50 (d, J=2.3 Hz, 1H), 7.52 (d, J=8.7 Hz, 1H).

MS Calcd.: 463; MS Found: 464 (M+H).

Anal. Calcd for C$_{22}$H$_{20}$N$_3$O$_2$Cl$_3$: C, 56.85; H, 4.34; N, 9.04; Cl, 22.88. Found: C, 56.81; H, 4.46; N, 8.85.

Example 245

Methyl 1-(4-bromo-2-chlorophenyl)-9-chloro-1,2,3,4-tetrahydropyrimido[1,2-a]benzimidazole-6-carboxylate

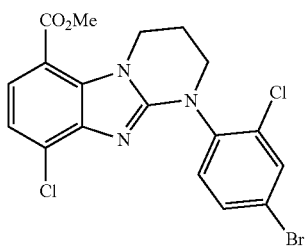 [SMILES: COC(=O)c1ccc(Cl)c2nc3n(c12)CCCN3c1ccc(Br)cc1Cl]

To a solution of methyl 2-[(4-bromo-2-chlorophenyl)amino]-4-chloro-1-(3-hydroxypropyl)-1H-benzimidazole-7-carboxylate (9.08 g, 19.20 mmol) in tetrahydrofuran (90.0 mL) were added triethylamine (13.4 mL, 96.00 mmol) and methanesulfonyl chloride (5.94 mL, 76.80 mmol) at 0° C. The reaction mixture was stirred at room temperature for 3.5 hrs. The mixture was quenched with aqueous sodium hydrogen carbonate and extracted with ethyl acetate (×3). The combined organic layer was washed with brine (×1), dried over anhydrous magnesium sulfate, filtered and concentrated in vacuo. The resulting mesylate was dissolved into N,N-dimethylformamide (50.0 mL) and to the solution was added potassium carbonate (5.31 g, 38.40 mmol). The mixture was stirred at 60° C. for 17 hrs. After cooling, the mixture was diluted with water. The generated precipitate was collected by filtration and washed with diisopropyl ether/ethyl acetate to give the title compound as a colorless solid (7.60 g, 16.70 mmol, 87%).

$^1$H NMR (CDCl$_3$) δ 2.18-2.40 (m, 2H), 3.74 (brs, 2H), 3.94 (s, 3H), 4.42 (t, J=6.2 Hz, 2H), 7.11 (d, J=8.3 Hz, 1H), 7.41-7.48 (m, 3H), 7.66 (d, J=2.3 Hz, 1H).

MS Calcd.: 453; MS Found: 454 (M+H).

Example 246

[1-(4-Bromo-2-chlorophenyl)-9-chloro-1,2,3,4-tetrahydropyrimido[1,2-a]benzimidazol-6-yl]methanol

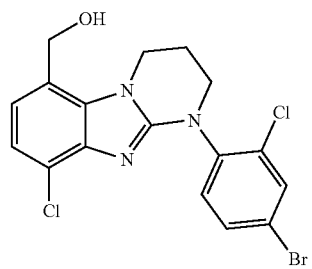 [SMILES: OCc1ccc(Cl)c2nc3n(c12)CCCN3c1ccc(Br)cc1Cl]

To a solution of methyl 1-(4-bromo-2-chlorophenyl)-9-chloro-1,2,3,4-tetrahydropyrimido[1,2-a]benzimidazole-6-carboxylate (2.00 g, 4.39 mmol) in tetrahydrofuran (15.0 mL) was added lithium tetrahydroborate (382.8 mg, 17.58 mmol) at 0° C. The reaction mixture was stirred at 40° C. for 15 hrs. The starting material wasn't consumed completely. The reaction mixture was stirred at 50° C. for 4.5 hrs. After cooling, the reaction mixture was quenched with water at 0° C. The solvent was concentrated and the precipitate was collected by filtration and washed with water to give the title compound as a colorless solid (1.70 g, 3.97 mmol, 90%).

$^1$H NMR (DMSO-d$_6$) δ 2.19-2.38 (m, 2H), 3.63-3.72 (m, 2H), 4.55 (brs, 2H), 4.74 (d, J=5.3 Hz, 2H), 5.36 (t, J=5.3 Hz, 1H), 6.85 (d, J=8.0 Hz, 1H), 6.97 (d, J=8.0 Hz, 1H), 7.57 (d, J=8.7 Hz, 1H), 7.68 (dd, J=2.3, 8.7 Hz, 1H), 7.92 (d, J=2.3 Hz, 1H).

MS Calcd.: 425; MS Found: 426 (M+H).

Example 247

1-(4-Bromo-2-chlorophenyl)-9-chloro-1,2,3,4-tetrahydropyrimido[1,2-a]benzimidazole-6-carbaldehyde

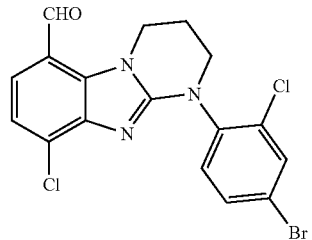 [SMILES: O=Cc1ccc(Cl)c2nc3n(c12)CCCN3c1ccc(Br)cc1Cl]

To a solution of [1-(4-bromo-2-chlorophenyl)-9-chloro-1,2,3,4-tetrahydropyrimido[1,2-a]benzimidazol-6-yl]methanol (1.24 g, 2.924 mmol) in dimethylsulfoxide (25.0 mL) was added Dess-Martin reagent (1.36 g, 3.216 mmol). The reaction mixture was stirred at room temperature for 2 hrs. The mixture was quenched with aqueous saturated sodium hydrogen carbonate and aqueous saturated sodium thiosulfate and extracted with ethyl acetate (×3). The combined organic layer was washed with water (×2) and brine (×1), dried over anhydrous magnesium sulfate, filtered and concentrated in vacuo. The resulting solid was washed with ethyl acetate/diisopropyl ether to give the title compound as a pale yellow solid (1.20 g, 2.82 mmol, 97%).

$^1$H NMR (CDCl$_3$) δ 2.37 (q, J=6.0 Hz, 2H), 3.74 (brs, 2H), 4.70 (d, J=6.3 Hz, 2H), 7.23 (d, J=8.3 Hz, 1H), 7.37 (d, J=8.3 Hz, 1H), 7.43 (d, J=8.7 Hz, 1H), 7.49 (dd, J=2.3, 8.3 Hz, 1H), 7.67 (d, J=2.3 Hz, 1H), 10.00 (s, 1H).

MS Calcd.: 423; MS Found: 424 (M+H).

Example 248

1-[1-(4-Bromo-2-chlorophenyl)-9-chloro-1,2,3,4-tetrahydropyrimido[1,2-a]benzimidazol-6-yl]propan-1-ol

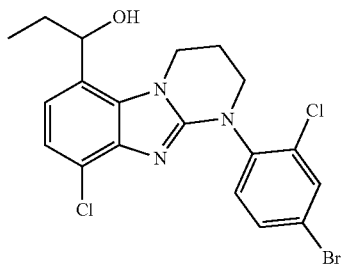 [SMILES: CCC(O)c1ccc(Cl)c2nc3n(c12)CCCN3c1ccc(Br)cc1Cl]

To a solution of 1-(4-bromo-2-chlorophenyl)-9-chloro-1,2,3,4-tetrahydropyrimido[1,2-a]benzimidazole-6-carbaldehyde (1.00 g, 2.352 mmol) in tetrahydrofuran (12.0 mL) was added ethylmagnesium bromide (3.0 M solution in diethyl ether, 1.18 mL, 3.528 mmol) at 0° C. The reaction mixture was stirred at room temperature for 5 hrs. The mixture was quenched with aqueous saturated ammonium chloride and extracted with ethyl acetate (×3). The combined organic layer was washed with brine, dried over anhydrous magnesium sulfate, filtered and concentrated in vacuo. The resulting solid was washed with diisopropyl ether/ethyl acetate to give the title compound as a colorless solid (925.8 mg, 2.034 mmol, 87%).

$^1$H NMR (CDCl$_3$) δ 1.04 (t, J=7.4 Hz, 3H), 1.88-2.01 (m, 2H), 2.28-2.46 (m, 2H), 3.71 (brs, 2H), 4.39-4.51 (m, 1H), 4.51-4.64 (m, 1H), 4.99-5.05 (m, 1H), 6.97 (d, J=8.3 Hz, 1H), 7.06 (d, J=8.3 Hz, 1H), 7.47 (d, J=1.1 Hz, 2H), 7.65 (d, J=1.3 Hz, 1H), 1H hidden.

MS Calcd.: 453; MS Found: 454 (M+H).

Example 249

1-{3-Chloro-4-[9-chloro-6-(1-hydroxypropyl)-3,4-dihydropyrimido[1,2-a]benzimidazol-1(2H)-yl]phenyl}ethanone

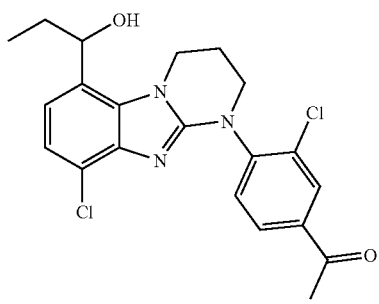 [SMILES: CCC(O)c1ccc(Cl)c2nc3n(c12)CCCN3c1ccc(C(C)=O)cc1Cl]

To a solution of 1-[9-chloro-1-(2,4-dichlorophenyl)-1,2,3,4-tetrahydropyrimido[1,2-a]benzimidazol-6-yl]propan-1-ol (700.0 mg, 1.538 mmol) in tetrahydrofuran (12.0 mL) was added n-butyllithium (1.60 M solution in n-hexane, 2.57 mL, 4.12 mmol) at −78° C., and the mixture was stirred for 30 min. To the mixture was added N,N-dimethylacetamide (0.77 mL, 8.24 mmol) at −78° C. The mixture was stirred at room temperature for 3 hrs. The mixture was quenched with aqueous saturated ammonium chloride and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-100% ethyl acetate/n-hexane gradient mixture to give the title compound as a pale yellow amorphous (130.2 mg, 0.311 mmol, 20%).

$^1$H NMR (CDCl$_3$) δ 1.04 (t, J=7.4 Hz, 3H), 1.83-2.03 (m, 2H), 2.18 (brs, 1H), 2.26-2.46 (m, 2H), 2.62 (s, 3H), 3.79 (brs, 2H), 4.41-4.54 (m, 1H), 4.54-4.68 (m, 1H), 4.91-5.15 (m, 1H), 7.00 (d, J=8.0 Hz, 1H), 7.09 (d, J=8.3 Hz, 1H), 7.72 (d, J=8.3 Hz, 1H), 7.90 (dd, J=1.7, 8.1 Hz, 1H), 8.08 (d, J=1.7 Hz, 1H).

MS Calcd.: 417; MS Found: 418 (M+H).

Example 250

1-[1-(4-Acetyl-2-chlorophenyl)-9-chloro-1,2,3,4-tetrahydropyrimido[1,2-a]benzimidazol-6-yl]propyl acetate

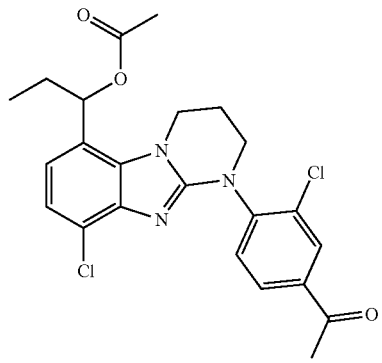 [SMILES: CCC(OC(C)=O)c1ccc(Cl)c2nc3n(c12)CCCN3c1ccc(C(C)=O)cc1Cl]

To a solution of 1-{3-Chloro-4-[9-chloro-6-(1-hydroxypropyl)-3,4-dihydropyrimido[1,2-a]benzimidazol-1(2H)-yl]phenyl}ethanone (120.0 mg, 0.287 mmol) in pyridine (0.2 mL)/tetrahydrofuran (0.5 mL) was added acetic anhydride (0.5 mL) at 0° C. The reaction mixture was stirred at room temperature for 7 hrs. The mixture was concentrated. The residue was neutralized with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified by silica gel column chromatography eluting with a 10-40% ethyl acetate/n-hexane gradient mixture. The residue was recrystallized from ethanol/n-hexane to give the title compound as a colorless powder (92.5 mg, 0.201 mmol, 70%).

mp 183-186° C.

$^1$H NMR (CDCl$_3$) δ 0.95 (t, J=7.4 Hz, 3H), 1.86-2.08 (m, 2H), 2.09 (s, 3H), 2.35-2.49 (m, 2H), 2.61 (s, 3H), 3.70-3.86 (m, 2H), 4.29-4.44 (m, 1H), 4.64-4.87 (m, 1H), 6.31 (t, J=7.2 Hz, 1H), 7.02 (d, J=8.7 Hz, 1H), 7.12 (d, J=8.3 Hz, 1H), 7.73 (d, J=8.3 Hz, 1H), 7.90 (dd, J=2.3, 8.3 Hz, 1H), 8.07 (d, J=2.3 Hz, 1H).

MS Calcd.: 459; MS Found: 460 (M+H).

Anal. Calcd for $C_{23}H_{23}N_3O_3Cl_2$: C, 60.01; H, 5.04; N, 9.13; Cl, 15.4. Found: C, 59.53; H, 5.03; N, 8.9.

Example 251

1-{9-Chloro-1-[2-chloro-4-(1-hydroxy-1-methylethyl)phenyl]-1,2,3,4-tetrahydropyrimido[1,2-a]benzimidazol-6-yl}propan-1-ol

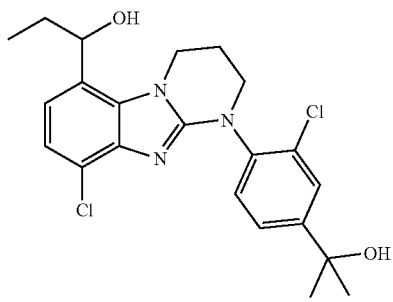 [SMILES: CCC(O)c1ccc(Cl)c2nc3n(c12)CCCN3c1ccc(C(C)(C)O)cc1Cl]

To a solution of 1-[9-chloro-1-(2,4-dichlorophenyl)-1,2,3,4-tetrahydropyrimido[1,2-a]benzimidazol-6-yl]propan-1-ol (300.0 mg, 0.659 mmol) in tetrahydrofuran (6.0 mL) was added n-butyllithium (1.60 M solution in n-hexane, 1.03 mL, 1.65 mmol) at −78° C., and the mixture was stirred for 30 min. To the mixture was added acetone (0.24 mL, 3.30 mmol) at −78° C. The mixture was stirred at room temperature for 4.5 hrs. The mixture was quenched with aqueous saturated ammonium chloride and extracted with ethyl acetate (×3). The combined organic layer was washed with brine (×1), dried over anhydrous magnesium sulfate, filtered and concentrated in vacuo. The residue was purified by silica gel column chromatography eluting with a 10-70% ethyl acetate/n-hexane gradient mixture to give the title compound as a colorless amorphous (80.0 mg, 0.185 mmol, 28%).

$^1$H NMR (CDCl$_3$) δ 1.05 (t, J=7.4 Hz, 3H), 1.61 (s, 6H), 1.87 (s, 1H), 1.92-2.03 (m, 2H), 2.21-2.53 (m, 2H), 3.48 (d, J=4.5 Hz, 2H), 3.73 (brs, 1H), 4.36-4.55 (m, 1H), 4.54-4.69 (m, 1H), 4.97-5.13 (m, 1H), 6.97 (d, J=8.3 Hz, 1H), 7.06 (d, J=8.3 Hz, 1H), 7.43 (dd, J=2.3, 8.3 Hz, 1H), 7.54 (d, J=8.3 Hz, 1H), 7.63 (d, J=2.3 Hz, 1H).

MS Calcd.: 433; MS Found: 434 (M+H).

Example 252

1-{9-Chloro-1-[2-chloro-4-(1-hydroxy-1-methylethyl)phenyl]-1,2,3,4-tetrahydropyrimido[1,2-a]benzimidazol-6-yl}propyl acetate

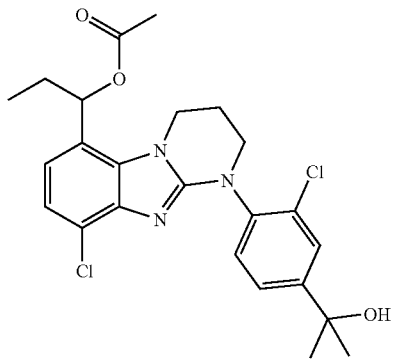 [SMILES: CCC(OC(C)=O)c1ccc(Cl)c2nc3n(c12)CCCN3c1ccc(C(C)(C)O)cc1Cl]

To a solution of 1-{9-chloro-1-[2-chloro-4-(1-hydroxy-1-methylethyl)phenyl]-1,2,3,4-tetrahydropyrimido[1,2-a]benzimidazol-6-yl}propan-1-ol (78.3 mg, 0.180 mmol) in pyridine (0.5 mL) was added acetic anhydride (0.2 mL) at 0° C. The reaction mixture was stirred at room temperature for 4 hrs. The mixture was concentrated. The residue was neutralized with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified by silica gel column chromatography eluting with a 0-40% ethyl acetate/n-hexane gradient mixture. The residue was recrystallized from ethanol/n-hexane to give the title compound as a colorless powder (47.4 mg, 0.0995 mmol, 55%).

mp 184-186° C.

$^1$H NMR (CDCl$_3$) δ 0.95 (t, J=7.4 Hz, 3H), 1.61 (s, 6H), 1.80 (s, 1H), 1.87-2.12 (m, 2H), 2.09 (s, 3H), 2.41 (t, J=5.7 Hz, 2H), 3.74 (brs, 2H), 4.26-4.43 (m, 1H), 4.65-4.82 (m, 1H), 6.32 (t, J=7.2 Hz, 1H), 6.98 (d, J=8.3 Hz, 1H), 7.09 (d, J=8.3 Hz, 1H), 7.42 (dd, J=2.3, 8.3 Hz, 1H), 7.55 (d, J=8.3 Hz, 1H), 7.62 (d, J=2.3 Hz, 1H).

MS Calcd.: 475; MS Found: 476 (M+H).

Anal. Calcd for C$_{24}$H$_{27}$N$_3$O$_3$Cl$_2$: C, 60.51; H, 5.71; N, 8.82; Cl, 14.88. Found: C, 60.35; H, 5.84; N, 8.63.

Example 253

1-[9-Chloro-1-(2-chlorophenyl)-1,2,3,4-tetrahydropyrimido[1,2-a]benzimidazol-6-yl]propyl acetate

Example 254

1-{9-Chloro-1-[2-chloro-4-(methylsulfonyl)phenyl]-1,2,3,4-tetrahydropyrimido[1,2-a]benzimidazol-6-yl}propyl acetate

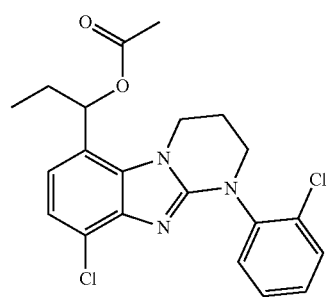

Example 253

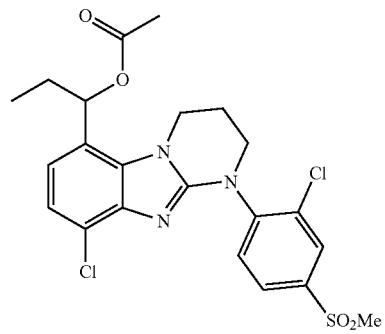

Example 254

To a solution of 1-[1-(4-bromo-2-chlorophenyl)-9-chloro-1,2,3,4-tetrahydropyrimido[1,2-a]benzimidazol-6-yl]propan-1-ol (500.0 mg, 1.098 mmol) in tetrahydrofuran (10.0 mL) was added n-butyllithium (1.60 M solution in n-hexane, 1.51 mL, 2.42 mmol) at −78° C., and the mixture was stirred for 30 min. To the mixture was added dimethyl disulfide (0.49 mL, 5.49 mmol) at −78° C. The mixture was stirred at room temperature for 3 hrs. The mixture was quenched with aqueous saturated ammonium chloride and extracted with ethyl acetate (×3). The combined organic layer was washed with brine, dried over anhydrous magnesium sulfate, filtered and concentrated in vacuo. The crude compound was subjected to next step without further purification. To a solution of crude material (73.2 mg) in pyridine (5.0 mL) was added acetic anhydride (1.5 mL) at 0° C. The reaction mixture was stirred at room temperature for 2 hrs. The mixture was neutralized with aqueous saturated sodium hydrogen carbonate. The residue was extracted with ethyl acetate (×3). The combined organic layer was washed with brine (×1), dried over anhydrous magnesium sulfate, filtered and concentrated in vacuo. The crude compound was subjected to next step without further purification. To a solution of crude material in acetonitrile (1.3 mL) was added m-chloroperbenzoic acid (211.8 mg, 1.227 mmol) at 0° C. The reaction mixture was stirred at 0° C. for 1 hr. The reaction mixture was quenched with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified by silica gel column chromatography eluting with a 0-100% ethyl acetate/gradient mixture to give Example 253 and Example 254. Example 253 was recrystallized from diisopropyl ether/n-hexane to give the title compound as a colorless powder (114.4 mg, 0.237 mmol, 25% (3 steps)) and Example 254 was recrystallized from ethyl acetate/diisopropyl ether to give the title compound as a colorless powder (117.6 mg, 0.237 mmol, 22% (3 steps)).

Example 253 mp 165-167° C.

$^1$H NMR (CDCl$_3$) δ: 0.95 (t, J=7.4 Hz, 3H), 1.85-2.07 (m, 2H), 2.09 (s, 3H), 2.34-2.47 (m, 2H), 3.74 (brs, 2H), 4.27-4.42 (m, 1H), 4.64-4.83 (m, 1H), 6.32 (t, J=7.2 Hz, 1H), 6.98 (d, J=8.3 Hz, 1H), 7.09 (d, J=8.3 Hz, 1H), 7.26 (dt, J=1.5, 7.5 Hz, 1H), 7.34 (dt, J=1.7, 7.6 Hz, 1H), 7.49 (dd, J=1.5, 7.9 Hz, 1H), 7.57 (dd, J=1.7, 7.7 Hz, 1H).

MS Calcd.: 417, MS Found: 418 (M+H).

Anal. Calcd for C$_{21}$H$_{21}$N$_3$O$_2$Cl$_2$: C, 60.3; H, 5.06; N, 10.05; Cl, 16.95.

Found: C, 60.16; H, 5.17; N, 9.81.

Example 254 mp 209-211° C.

$^1$H NMR (CDCl$_3$) δ: 0.96 (t, J=7.4 Hz, 3H), 1.86-2.14 (m, 2H), 2.09 (s, 3H), 2.33-2.52 (m, 2H), 3.12 (s, 3H), 3.71-3.90 (m, 2H), 4.29-4.46 (m, 1H), 4.67-4.87 (m, 1H), 6.30 (t, J=7.0 Hz, 1H), 7.04 (d, J=8.3 Hz, 1H), 7.14 (d, J=8.3 Hz, 1H), 7.88 (d, J=1.5 Hz, 2H), 8.06 (s, 1H).

MS Calcd.: 495, MS Found: 496 (M+H).

Anal. Calcd for C$_{22}$H$_{23}$N$_3$O$_4$SCl$_2$: C, 53.23; H, 4.67; N, 8.46; S, 6.46; Cl, 14.28. Found: C, 53.15; H, 4.65; N, 8.33.

Example 255

1-[1-(4-Carbamoyl-2-chlorophenyl)-9-chloro-1,2,3,4-tetrahydropyrimido[1,2-a]benzimidazol-6-yl]propyl acetate

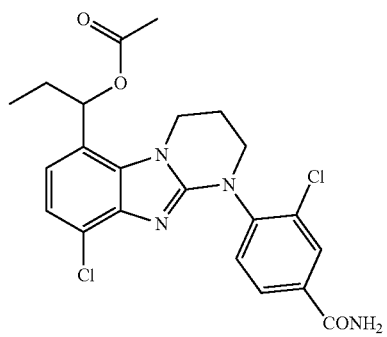 [SMILES: CCC(OC(C)=O)c1ccc(Cl)c2nc3n(c12)CCCN3c1ccc(C(N)=O)cc1Cl]

To a solution of 1-[1-(4-bromo-2-chlorophenyl)-9-chloro-1,2,3,4-tetrahydropyrimido[1,2-a]benzimidazol-6-yl]propan-1-ol (300.0 mg, 0.659 mmol) in tetrahydrofuran (4.0 mL) was added n-butyllithium (1.60 M solution in n-hexane, 0.91 mL, 1.450 mmol) at −78° C., and the mixture was stirred for 30 min. Carbon dioxide gas was bubbled through the mixture for 30 min. The mixture was quenched with aqueous saturated ammonium chloride and added 1N sodium hydroxide solution and extracted with ethyl acetate (×2). The aqueous layer was acidified with 1N hydrochloric acid and extracted with ethyl acetate (×3). The combined organic layer was washed with brine, dried over anhydrous magnesium sulfate, filtered and concentrated in vacuo. The crude compound was subjected to next step without further purification. To a solution of crude material (73.2 mg) in tetrahydrofuran (2.0 mL)/pyridine (0.2 mL) was added acetic anhydride (0.1 mL) at 0° C. The reaction mixture was stirred at room temperature for 14 hrs. The mixture was neutralized with aqueous saturated sodium hydrogen carbonate and concentrated. The residue was extracted with ethyl acetate (×3). The combined organic layer was washed with brine (×1), dried over anhydrous magnesium sulfate, filtered and concentrated in vacuo. The crude compound was subjected to next step without further purification. To a solution of crude material (58.9 mg) in N,N-dimethylformamide (1.3 mL) were added 1-hydroxy-1H-benzotriazole ammonium salt (25.2 mg, 0.166 mmol) and 1-ethyl-3-(3-dimethylaminopropyl)carbodiimide hydrochloride (26.8 mg, 0.140 mmol). The reaction mixture was stirred at room temperature for 16 hrs. The reaction mixture was quenched with aqueous saturated sodium hydrogen carbonate and extracted with ethyl acetate (×3). The combined organic layer was washed with water (×2), aqueous saturated sodium hydrogen carbonate (×1) and brine (×1), dried over anhydrous magnesium sulfate, filtered and concentrated in vacuo. The residue was purified by silica gel column chromatography eluting with a 0-100% ethyl acetate/n-hexane gradient mixture to give the title compound as a mixture. The residue was purified preparative HPLC to, give the title compound as the trifluoroacetic acid salt. The salt was neutralized with aqueous saturated sodium hydrogen carbonate and extracted with ethyl acetate. The extract was washed with brine, dried over

Example 256

Methyl 9-chloro-1-(2-chloro-4-methoxyphenyl)-1,2,3,4-tetrahydropyrimido[1,2-a]benzimidazole-6-carboxylate

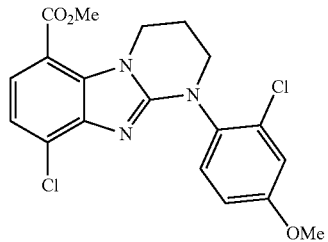 [SMILES: COC(=O)c1ccc(Cl)c2nc3n(c12)CCCN3c1ccc(OC)cc1Cl]

To a solution of methyl 1-(4-bromo-2-chlorophenyl)-9-chloro-1,2,3,4-tetrahydropyrimido[1,2-a]benzimidazole-6-carboxylate (200.0 mg, 0.439 mmol) in N,N-dimethylformamide (2.0 mL) were added copper(I) iodide (125.5 mg, 0.659 mmol) and sodium methoxide (28% wt methanol solution, 1.0 mL). The reaction mixture was stirred at 100° C. for 10 hrs. After cooling, the mixture was filtered through on the pad of celite. The filtrate was diluted with water and extracted with ethyl acetate (×1). The aqueous layer was acidified with 1N hydrochloric acid and extracted with ethyl acetate (×3). The combined organic layer was washed with brine (×1), dried over anhydrous magnesium sulfate, filtered and concentrated in vacuo. The crude product was subject to next step without further purification. The resulting carboxylic acid was dissolved into N,N-dimethylformamide (3.0 mL) and to the mixture were added potassium carbonate (130.9 mg, 0.947 mmol) and methyl iodide (88.5 μL, 1.422 mmol) at 0° C. The reaction mixture was stirred at room temperature for 16.5 hrs. The mixture was quenched with aqueous saturated ammonium chloride and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-35% ethyl acetate/n-hexane gradient mixture to give the title compound as a colorless amorphous (121.8 mg, 0.300 mmol, 68% (2 steps)).

$^1$H NMR (CDCl$_3$) δ 2.31 (brs, 2H), 3.73 (brs, 2H), 3.83 (s, 3H), 3.94 (s, 3H), 4.40 (t, J=6.1 Hz, 2H), 6.84-6.94 (m, 1H), 7.03 (d, J=3.0 Hz, 1H), 7.08 (d, J=8.3 Hz, 1H), 7.41-7.43 (m, 1H), 7.44-7.45 (m, 1H).

MS Calcd.: 405; MS Found: 406 (M+H).

Example 257

[9-Chloro-1-(2-chloro-4-methoxyphenyl)-1,2,3,4-tetrahydropyrimido[1,2-a]benzimidazol-6-yl]methanol

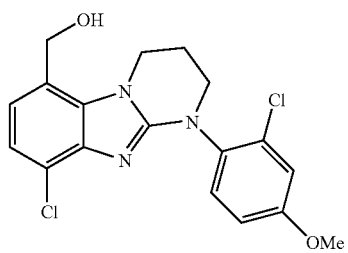 [SMILES: COc1ccc(N2CCCn3c2nc2c(Cl)ccc(CO)c23)c(Cl)c1]

To a solution of methyl 9-chloro-1-(2-chloro-4-methoxyphenyl)-1,2,3,4-tetrahydropyrimido[1,2-a]benzimidazole-6-carboxylate (694.5 mg, 1.50 mmol) in tetrahydrofuran (4.0 mL) was added lithium tetrahydroborate (35.7 mg, 1.641 mmol) at 0° C. The reaction mixture was stirred at room temperature for 17 hrs. The starting material wasn't consumed completely. To the reaction mixture was added lithium tetrahydroborate (35.7 mg, 1.641 mmol) at 0° C. The reaction mixture was stirred at room temperature for 7 hrs. The solvent was removed by concentration. The precipitate was collected by filtration and washed with water to give the title compound as a colorless solid (144.0 mg, 0.381 mmol, 93%).

$^1$H NMR (DMSO-d$_6$) δ 2.11-2.37 (m, 2H), 3.62 (brs, 2H), 3.83 (s, 3H), 4.52 (brs, 2H), 4.74 (d, J=4.9 Hz, 2H), 5.35 (t, J=5.3 Hz, 1H), 6.83 (d, J=7.9 Hz, 1H), 6.94 (t, J=7.9 Hz, 1H), 7.03 (dd, J=2.6, 8.7 Hz, 1H), 7.20 (d, J=2.6 Hz, 1H), 7.48 (d, J=8.7 Hz, 1H).

MS Calcd.: 377; MS Found: 378 (M+H).

Example 258

9-Chloro-1-(2-chloro-4-methoxyphenyl)-1,2,3,4-tetrahydropyrimido[1,2-a]benzimidazole-6-carbaldehyde

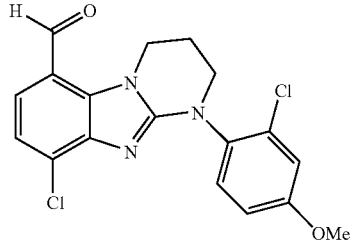 [SMILES: COc1ccc(N2CCCn3c2nc2c(Cl)ccc(C=O)c23)c(Cl)c1]

To a solution of [9-chloro-1-(2-chloro-4-methoxyphenyl)-1,2,3,4-tetrahydropyrimido[1,2-a]benzimidazol-6-yl]methanol (143.5 mg, 0.379 mmol) in dimethylsulfoxide (2.0 mL) was added Dess-Martin reagent (177.0 mg, 0.417 mmol). The reaction mixture was stirred at room temperature for 2 hrs. The mixture was, quenched with aqueous saturated sodium hydrogen carbonate and aqueous saturated sodium thiosulfate. The generated precipitate was collected by filtration and washed with water to give the title compound as a colorless solid (129.6 mg, 0.344 mmol, 91%).

$^1$H NMR (CDCl$_3$) δ 2.35 (brs, 2H), 3.69 (brs, 2H), 3.84 (s, 3H), 4.68 (t, J=6.3 Hz, 2H), 6.89 (dd, J=2.7, 8.7 Hz, 1H), 7.04 (d, J=2.7 Hz, 1H), 7.21 (d, J=8.3 Hz, 1H), 7.35 (d, J=8.3 Hz, 1H), 7.42 (d, J=8.7 Hz, 1H), 10.00 (s, 1H).

MS Calcd.: 375; MS Found: 376 (M+H).

---

Page 353 content:

magnesium sulfate, filtered and concentrated in vacuo to give the title compound as an amorphous (16.5 mg, 0.0358 mmol, 5.4% (3 steps)).

$^1$H NMR (CDCl$_3$) δ: 0.97 (t, J=7.4 Hz, 3H), 1.84-2.08 (m, 2H), 2.09 (s, 3H), 2.33-2.50 (m, 2H), 3.73 (brs, 2H), 4.30-4.45 (m, 1H), 4.69-4.88 (m, 1H), 5.38 (brs, 1H), 6.30 (d, J=7.0 Hz, 1H), 7.03 (d, J=8.3 Hz, 1H), 7.12 (d, J=8.3 Hz, 1H), 7.43 (d, J=8.3 Hz, 1H), 7.91 (brs, 1H), 7.96 (dd, J=2.3, 8.3 Hz, 1H), 8.17 (d, J=2.3 Hz, 1H).

MS Calcd.: 460, MS Found: 461 (M+H).

Example 259

1-[9-Chloro-1-(2-chloro-4-methoxyphenyl)-1,2,3,4-tetrahydropyrimido[1,2-a]benzimidazol-6-yl]propan-1-ol

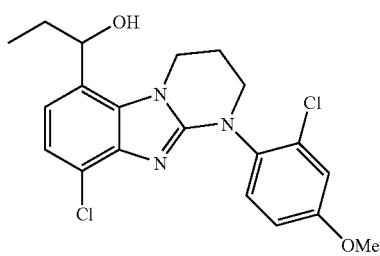 [SMILES: CCC(O)c1ccc(Cl)c2nc3n(c12)CCCN3c1ccc(OC)cc1Cl]

To a solution of 9-chloro-1-(2-chloro-4-methoxyphenyl)-1,2,3,4-tetrahydropyrimido[1,2-a]benzimidazole-6-carbaldehyde (128.4 mg, 0.341 mmol) in tetrahydrofuran (4.0 mL) was added ethylmagnesium bromide (3.0 M solution in diethyl ether, 0.17 mL, 0.512 mmol) at 0° C. The reaction mixture was stirred at room temperature for 1 hr. The mixture was quenched with aqueous saturated ammonium chloride and extracted with ethyl acetate (×3). The combined organic layer was washed with brine, dried over anhydrous magnesium sulfate, filtered and concentrated in vacuo. The residue was purified by silica gel column chromatography eluting with a 0-50% ethyl acetate/n-hexane gradient mixture to give the title compound as a colorless amorphous (122.5 mg, 0.301 mmol, 88%).

$^1$H NMR (CDCl$_3$) δ 1.04 (t, J=7.5 Hz, 3H), 1.90-2.02 (m, 2H), 2.36 (brs, 2H), 3.49 (d, J=4.9 Hz, 1H), 3.70 (brs, 2H), 3.83 (s, 3H), 4.37-4.51 (m, 1H), 4.57 (brs, 1H), 4.92-5.10 (m, 1H), 6.88 (dd, J=3.0, 8.7 Hz, 1H), 6.95 (d, J=8.3 Hz, 1H), 7.02 (d, J=3.0 Hz, 1H), 7.05 (d, J=8.3 Hz, 1H), 7.45 (d, J=8.7 Hz, 1H).

MS Calcd.: 405; MS Found: 406 (M+H).

Example 260

1-[9-Chloro-1-(2-chloro-4-methoxyphenyl)-1,2,3,4-tetrahydropyrimido[1,2-a]benzimidazol-6-yl]propyl acetate

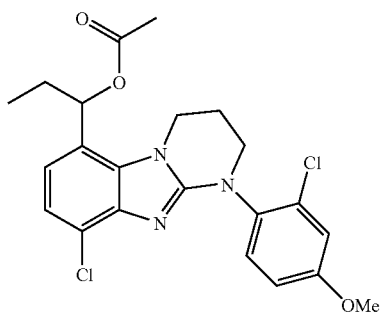 [SMILES: CCC(OC(C)=O)c1ccc(Cl)c2nc3n(c12)CCCN3c1ccc(OC)cc1Cl]

To a solution of 1-[9-chloro-1-(2-chloro-4-methoxyphenyl)-1,2,3,4-tetrahydropyrimido[1,2-a]benzimidazol-6-yl]propan-1-ol (122.0 mg, 0.300 mmol) in pyridine (0.5 mL) was added acetic anhydride (0.5 mL) at 0° C. The reaction mixture was stirred at room temperature for 5 hrs. The mixture was concentrated. The residue was neutralized with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified by silica gel column chromatography eluting with a 0-40% ethyl acetate/n-hexane gradient mixture. The residue was recrystallized from methanol/n-hexane to give the title compound as a colorless powder (94.7 mg, 0.211 mmol, 70%).

mp 178-180° C.

$^1$H NMR (CDCl$_3$) δ 0.94 (t, J=7.5 Hz, 3H), 1.87-2.07 (m, 2H), 2.09 (s, 3H), 2.39 (brs, 2H), 3.69 (brs, 2H), 3.82 (s, 3H), 4.23-4.44 (m, 1H), 4.70 (brs, 1H), 6.31 (d, J=7.2 Hz, 1H), 6.87 (dd, J=2.6, 8.7 Hz, 1H), 6.96 (d, J=8.3 Hz, 1H), 7.02 (d, J=2.6 Hz, 1H), 7.07 (d, J=8.3 Hz, 1H), 7.45 (d, J=8.7 Hz, 1H).

MS Calcd.: 447; MS Found: 448 (M+H).

Anal. Calcd for C$_{22}$H$_{23}$N$_3$O$_3$Cl$_2$: C, 58.94; H, 5.17; N, 9.37; Cl, 15.82. Found: C, 58.55; H, 5.11; N, 9.14.

Example 261

Methyl 9-chloro-1-(6-methoxy-2-methylpyridin-3-yl)-1,2,3,4-tetrahydropyrimido[1,2-a]benzimidazole-6-carboxylate

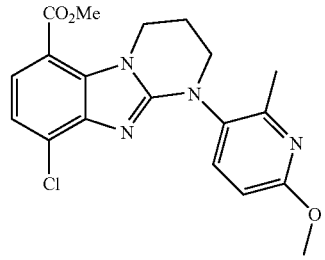 [SMILES: COC(=O)c1ccc(Cl)c2nc3n(c12)CCCN3c1ccc(OC)nc1C]

To a solution of methyl 4-chloro-1-(3-hydroxypropyl)-2-[(6-methoxy-2-methylpyridin-3-yl)amino]-1H-benzimidazole-7-carboxylate (Reference example 156, 6.40 g, 15.81 mmol) in tetrahydrofuran (42.0 mL) were added triethylamine (4.42 mL, 31.62 mmol) and methanesulfonyl chloride (1.84 mL, 23.71 mmol) at 0° C. The reaction mixture was stirred at room temperature for 1.5 hrs. The mixture was quenched with aqueous sodium hydrogen carbonate and extracted with ethyl acetate (×3). The combined organic layer was washed with brine (×1), dried over anhydrous magnesium sulfate, filtered and concentrated in vacuo. The resulting mesylate was dissolved into N,N-dimethylformamide (67.0 mL) and to the solution was added potassium carbonate (4.27 g, 31.62 mmol). The mixture was stirred at 70° C. for 4 hrs. After cooling, the mixture was diluted with water. The generated precipitate was collected by filtration and washed with diisopropyl ether to give the title compound as a colorless solid (5.50 g, 14.22 mmol, 90%).

$^1$H NMR (CDCl$_3$) δ 2.25-2.37 (m, 2H), 2.40 (s, 3H), 3.53-3.78 (m, 2H), 3.94 (s, H), 3.95 (s, 3H), 4.26-4.57 (m, 2H), 6.65 (d, J=8.7 Hz, 1H), 7.09 (d, J=8.3 Hz, 1H), 7.44 (d, J=8.7 Hz, 1H), 7.53 (d, J=8.7 Hz, 1H).

MS Calcd.: 386; MS Found: 387 (M+H).

Example 262

[9-Chloro-1-(6-methoxy-2-methylpyridin-3-yl)-1,2,3,4-tetrahydropyrimido[1,2-a]benzimidazol-6-yl]methanol

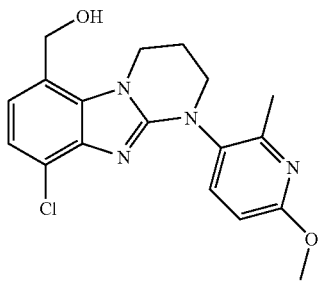 [SMILES: COc1ccc(N2CCCn3c2nc2c(Cl)ccc(CO)c23)c(C)n1]

To a solution of methyl 9-chloro-1-(6-methoxy-2-methylpyridin-3-yl)-1,2,3,4-tetrahydropyrimido[1,2-a]benzimidazole-6-carboxylate (1.50 g, 3.88 mmol) in tetrahydrofuran (15.0 mL) was added lithium tetrahydroborate (337.8 mg, 15.51 mmol) at 0° C. The reaction mixture was stirred at 50° C. for 6.5 hrs. After cooling, the reaction mixture was quenched with aqueous saturated ammonium chloride at 0° C. The solvent was concentrated and the precipitate was collected by filtration and washed with water to give the title compound as a colorless solid (1.38 g, 3.83 mmol, 99%).

$^1$H NMR (DMSO-$d_6$) δ 2.25-2.30 (m, 2H), 2.32 (s, 3H), 3.62 (brs, 2H), 3.88 (s, 3H), 4.33-4.65 (m, 2H), 4.74 (d, J=5.3 Hz, 2H), 5.27-5.38 (m, 1H), 6.75 (d, J=9.1 Hz, 1H), 6.82 (d, J=8.0 Hz, 1H), 6.94 (d, J=8.0 Hz, 1H), 7.69 (d, J=9.1 Hz, 1H).

MS Calcd.: 358; MS Found: 359 (M+H).

Example 263

9-Chloro-1-(6-methoxy-2-methylpyridin-3-yl)-1,2,3,4-tetrahydropyrimido[1,2-a]benzimidazole-6-carbaldehyde

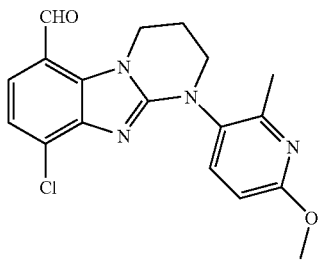 [SMILES: COc1ccc(N2CCCn3c2nc2c(Cl)ccc(C=O)c23)c(C)n1]

To a solution of [9-chloro-1-(6-methoxy-2-methylpyridin-3-yl)-1,2,3,4-tetrahydropyrimido[1,2-a]benzimidazol-6-yl]methanol (4.00 g, 11.15 mmol) in dimethylsulfoxide (70.0 mL) was added Dess-Martin reagent (5.20 g, 12.26 mmol). The mixture was stirred at room temperature for 3 hrs. The mixture was quenched with aqueous saturated sodium hydrogen carbonate and aqueous saturated sodium thiosulfate and extracted with ethyl acetate (×3). The combined organic layer was washed with water (×2) and brine (×1), dried over anhydrous magnesium sulfate, filtered and concentrated in vacuo. The resulting solid was washed with ethyl acetate/diisopropyl ether to give the title compound as a pale yellow solid (3.69 g, 10.34 mmol, 93%).

$^1$H NMR (CDCl$_3$) δ 2.29-2.39 (m, 2H), 2.39 (s, 3H), 3.67 (t, J=5.7 Hz, 2H), 3.95 (s, 3H), 4.70 (brs, 2H), 6.65 (d, J=8.3 Hz, 1H), 7.22 (d, J=8.3 Hz, 1H), 7.35 (d, J=8.3 Hz, 1H), 7.52 (d, J=8.3 Hz, 1H), 9.99 (s, 1H).

MS Calcd.: 356; MS Found: 357 (M+H).

Example 264

1-[9-Chloro-1-(6-methoxy-2-methylpyridin-3-yl)-1,2,3,4-tetrahydropyrimido[1,2-a]benzimidazol-6-yl]propan-1-ol

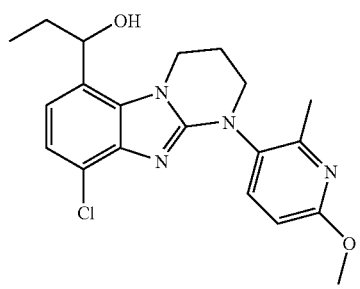 [SMILES: CCC(O)c1ccc(Cl)c2nc3n(c12)CCCN3c1ccc(OC)nc1C]

To a solution of 9-chloro-1-(6-methoxy-2-methylpyridin-3-yl)-1,2,3,4-tetrahydropyrimido[1,2-a]benzimidazole-6-carbaldehyde (673.0 mg, 1.886 mmol) in tetrahydrofuran (10.0 mL) was added ethylmagnesium bromide (3.0 M solution in diethyl ether, 0.94 mL, 2.829 mmol) at 0° C. The reaction mixture was stirred at room temperature for 2 hrs. The mixture was quenched with aqueous saturated ammonium chloride and extracted with ethyl acetate (×3). The combined organic layer was washed with brine, dried over anhydrous magnesium sulfate, filtered and concentrated in vacuo. The resulting solid was washed with diisopropyl ether to give the title compound as a colorless solid (702.4 mg, 1.816 mmol, 97%).

$^1$H NMR (CDCl$_3$) δ 1.05 (t, J=7.4 Hz, 3H), 1.88-2.04 (m, 3H), 2.31-2.39 (m, 2H), 2.40 (s, 3H), 3.64 (t, J=5.5 Hz, 2H), 3.95 (s, 3H), 4.48 (brs, 1H), 4.61 (brs, 1H), 4.93-5.12 (m, 1H), 6.64 (d, J=8.7 Hz, 1H), 6.95 (d, J=8.3 Hz, 1H), 7.05 (d, J=8.33 Hz, 1H), 7.54 (d, J=8.7 Hz, 1H).

MS Calcd.: 386; MS Found: 387 (M+H).

Example 265

1-[9-Chloro-1-(6-methoxy-2-methylpyridin-3-yl)-1,2,3,4-tetrahydropyrimido[1,2-a]benzimidazol-6-yl]propyl acetate

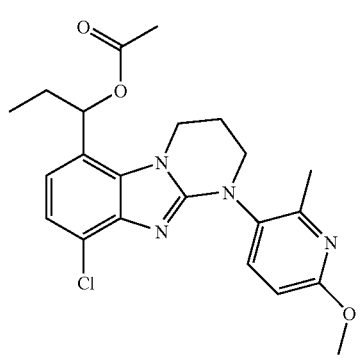 [SMILES: CCC(OC(C)=O)c1ccc(Cl)c2nc3n(c12)CCCN3c1ccc(OC)nc1C]

To a solution of 1-[9-chloro-1-(6-methoxy-2-methylpyridin-3-yl)-1,2,3,4-tetrahydropyrimido[1,2-a]benzimidazol-6-yl]propan-1-ol (200.0 mg, 0.517 mmol) in pyridine (1.0 mL) was added acetic anhydride (0.5 mL) at 0° C. The reaction mixture was stirred at room temperature for 5.5 hrs. The mixture was concentrated. The residue was neutralized with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified by silica gel column chromatography eluting with a 0-50% ethyl acetate/n-hexane gradient mixture. The residue was recrystallized from ethanol/n-hexane to give the title compound as a colorless powder (148.4 mg, 0.346 mmol, 67%).

mp 157-159° C.

$^1$H NMR (CDCl$_3$) δ 0.94 (t, J=7.2 Hz, 3H), 1.84-2.08 (m, 2H), 2.08 (s, 3H), 2.34-2.45 (m, 5H), 3.63 (t, J=5.3 Hz, 2H), 3.94 (s, 3H), 4.34 (brs, 1H), 4.74 (brs, 1H), 6.31 (t, J=7.2 Hz, 1H), 6.63 (d, J=8.3 Hz, 1H), 6.97 (d, J=8.3 Hz, 1H), 7.08 (d, J=8.3 Hz, 1H), 7.53 (d, J=8.3 Hz, 1H).

MS Calcd.: 428; MS Found: 429 (M+H).

Anal. Calcd for C$_{22}$H$_{25}$N$_4$O$_3$Cl: C, 61.61; H, 5.87; N, 13.06; Cl, 8.27. Found: C, 61.6; H, 5.87; N, 13.01.

Example 266

(−)-1-[9-Chloro-1-(6-methoxy-2-methylpyridin-3-yl)-1,2,3,4-tetrahydropyrimido[1,2-a]benzimidazol-6-yl]propyl acetate Example 267

(+)-1-[9-Chloro-1-(6-methoxy-2-methylpyridin-3-yl)-1,2,3,4-tetrahydropyrimido[1,2-a]benzimidazol-6-yl]propyl acetate

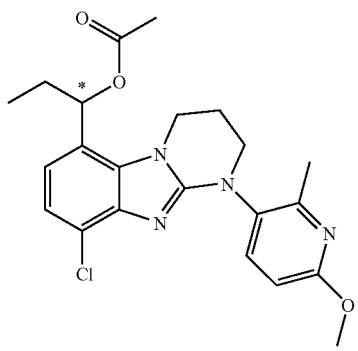 [SMILES: CCC(OC(C)=O)c1ccc(Cl)c2nc3n(c12)CCCN3c1ccc(OC)nc1C]

Racemic Example 265 (460 mg) was resolved by preparative HPLC, using CHIRALPAK AD (5 cm i.d.×50 cm, Daicel Chemical Industries, Ltd.) with the flow rate of 60 mL/min at 30° C. and hexane/ethanol (30/70) as the mobile phase, and obtaining the stereoisomer having a shorter retention time 235 mg in an enantiomer excess greater than 99.9% and the stereoisomer having a longer retention time 227 mg in an enantiomer excess greater than 99.9%. The obtained compounds were recrystallized from ethanol/hexane to give the optically active title compounds as a colorless crystal respectively (shorter retention time (Example 266): 190 mg, longer retention time (Example 267): 194 mg).

Shorter Retention Time (Example 266):

[α]$_D^{20}$=−20.9 (c=0.4680, MeOH)

mp 110-114° C.

$^1$H NMR (CDCl$_3$) δ 0.94 (t, J=7.2 Hz, 3H), 1.82-2.07 (m, 2H), 2.08 (s, 3H), 2.30-2.49 (m, 5H), 3.51-3.78 (m, 2H), 3.94 (s, 3H), 4.34 (brs, 1H), 4.71 (brs, 1H), 6.30 (t, J=7.0 Hz, 1H), 6.63 (d, J=8.7 Hz, 1H), 6.97 (d, J=8.3 Hz, 1H), 7.08 (d, J=8.3 Hz, 1H), 7.53 (d, J=8.7 Hz, 1H).

MS Calcd.: 428; MS Found: 429 (M+H).

Anal. Calcd for C$_{22}$H$_{25}$N$_4$O$_3$Cl: C, 61.61; H, 5.87; N, 13.06; Cl, 8.27. Found: C, 61.33; H, 6.02; N, 12.91.

Longer Retention Time (Example 267):

[α]$_D^{20}$=+20.5 (c=0.4745, MeOH)

mp 110-113° C.

$^1$H NMR (CDCl$_3$) δ 0.94 (t, J=7.2 Hz, 3H), 1.83-2.07 (m, 2H), 2.08 (s, 3H), 2.30-2.47 (m, 5H), 3.63 (t, J=5.1 Hz, 2H), 3.94 (s, 3H), 4.34 (brs, 1H), 4.74 (brs, 1H), 6.31 (t, J=7.2 Hz, 1H), 6.64 (d, J=8.7 Hz, 1H), 6.97 (d, J=8.3 Hz, 1H), 7.08 (d, J=8.3 Hz, 1H), 7.53 (d, J=8.7 Hz, 1H).

MS Calcd.: 428; MS Found: 429 (M+H).

Anal. Calcd for C$_{22}$H$_{25}$N$_4$O$_3$Cl: C, 61.61; H, 5.87; N, 13.06; Cl, 8.27. Found: C, 61.54; H, 6.0; N, 12.78.

Example 268

1-[9-Chloro-1-(6-methoxy-2-methylpyridin-3-yl)-1,2,3,4-tetrahydropyrimido[1,2-a]benzimidazol-6-yl]propyl cyclopropanecarboxylate

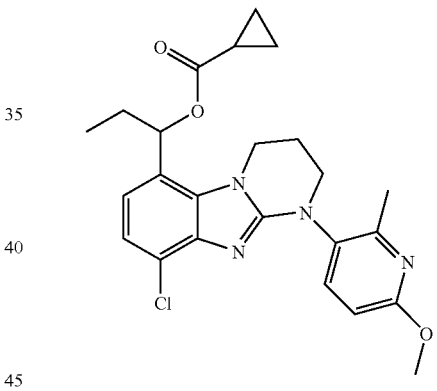

To a solution of 1-[9-chloro-1-(6-methoxy-2-methylpyridin-3-yl)-1,2,3,4-tetrahydropyrimido[1,2-a]benzimidazol-6-yl]propan-1-ol (122.3 mg, 0.316 mmol) in tetrahydrofuran (0.5 mL) were added 1-ethyl-3-(3-dimethylaminopropyl)carbodiimide hydrochloride (121.2 mg, 0.632 mmol), triethylamine (88 µL, 0.632 mmol), cyclopropanecarboxylic acid (37.8 µL, 0.474 mmol) and 4-dimethylaminopyridine (57.9 mg, 0.474 mmol). The reaction mixture was stirred at room temperature for 3.5 hrs. The mixture was quenched with aqueous saturated ammonium chloride and extracted with ethyl acetate (×3). The combined organic layer was washed with brine (×1), dried over anhydrous magnesium sulfate, filtered and concentrated in vacuo. The residue was purified by silica gel column chromatography eluting with a 0-40% ethyl acetate/n-hexane gradient mixture. The residue was recrystallized from diisopropyl ether/n-hexane to give the title compound as a colorless powder (105.2 mg, 0.231 mmol, 73%).

mp 149-151° C.

$^1$H NMR (CDCl$_3$) δ 0.78-1.10 (m, 7H), 1.60-1.73 (m, 1H), 1.85-2.12 (m, 2H), 2.33-2.39 (m, 2H), 2.40 (s, 3H), 3.62 (t,

J=5.3 Hz, 2H), 3.94 (s, 3H), 4.32 (brs, 1H), 4.72 (brs, 1H), 6.31 (t, J=7.0 Hz, 1H), 6.63 (d, J=8.3 Hz, 1H), 6.98 (d, J=8.3 Hz, 1H), 7.09 (d, J=8.3 Hz, 1H), 7.53 (d, J=8.3 Hz, 1H).

MS Calcd.: 454; MS Found: 455 (M+H).

Anal. Calcd for $C_{24}H_{27}N_4O_3Cl$: C, 63.36; H, 5.98; N, 12.31; Cl, 7.79. Found: C, 63; H, 6.04; N, 12.21.

Example 269

9-Chloro-6-(1-ethoxypropyl)-1-(6-methoxy-2-methylpyridin-3-yl)-1,2,3,4-tetrahydropyrimido[1,2-a]benzimidazole

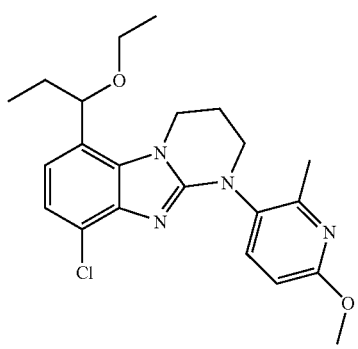 [SMILES: CCOC(CC)c1ccc(Cl)c2nc3n(c12)CCCN3c1ccc(OC)nc1C]

To a solution of 1-[9-chloro-1-(6-methoxy-2-methylpyridin-3-yl)-1,2,3,4-tetrahydropyrimido[1,2-a]benzimidazol-6-yl]propan-1-ol (138.3 mg, 0.357 mmol) in N,N-dimethylformamide (2.3 mL) was added sodium hydride (21.4 mg, 0.536 mmol) at 0° C. After 30 min, to the mixture was added ethyl iodide (143 μL, 1.785 mmol) at 0° C. The reaction mixture was stirred at room temperature for 17.5 hrs. The mixture was quenched with aqueous saturated ammonium chloride and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-40% ethyl acetate/n-hexane gradient mixture. The resulting solid was recrystallized from ethyl acetate/n-hexane to give the title compound as a colorless powder (112.1 mg, 0.270 mmol, 58%).

mp 174-176° C.

$^1$H NMR (CDCl$_3$) δ 0.98 (t, J=7.4 Hz, 3H), 1.18 (t, J=7.0 Hz, 3H), 1.71-2.09 (m, 2H), 2.28-2.39 (m, 2H), 2.41 (s, 3H), 3.27-3.51 (m, 2H), 3.55-3.72 (m, 2H), 3.95 (s, 3H), 4.35 (brs, 1H), 4.53-4.64 (m, 1H), 4.68 (s, 1H), 6.64 (d, J=8.7 Hz, 1H), 6.87 (d, J=8.3 Hz, 1H), 7.04 (d, J=8.3 Hz, 1H), 7.55 (d, J=8.7 Hz, 1H).

MS Calcd.: 414; MS Found: 415 (M+H).

Anal. Calcd for $C_{22}H_{27}N_4O_2Cl$: C, 63.68; H, 6.56; N, 13.5; Cl, 8.54. Found: C, 63.28; H, 6.54; N, 13.35.

Example 270

9-Chloro-6-[1-(ethenyloxy)propyl]-1-(6-methoxy-2-methylpyridin-3-yl)-1,2,3,4-tetrahydropyrimido[1,2-a]benzimidazole

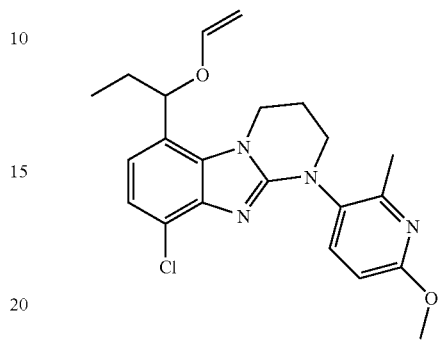

To a suspension of sodium carbonate (16.4 mg, 0.155 mmol) in dichlorobenzene (0.5 mL) were added di-μ-chloro-bis[(η-cycloocta-1,5-diene)iridium(I)] (8.7 mg, 0.0129 mmol), 1-[9-chloro-1-(6-methoxy-2-methylpyridin-3-yl)-1,2,3,4-tetrahydropyrimido[1,2-a]benzimidazol-6-yl]propan-1-ol (100.0 mg, 0.155 mmol) and vinyl acetate (47.7 μL, 0.517 mmol). The reaction mixture was stirred at 100° C. for 3.5 hrs. The mixture was concentrated. The residue was purified by silica gel column chromatography eluting with a 0-40% ethyl acetate/n-hexane gradient mixture to give the title compound as a colorless amorphous (66.4 mg, 0.161 mmol, 62%).

$^1$H NMR (CDCl$_3$) δ 1.02 (t, J=7.4 Hz, 3H), 1.82-2.17 (m, 2H), 2.31-2.40 (m, 2H), 2.41 (s, 3H), 3.57-3.70 (m, 2H), 3.95 (s, 3H), 4.01 (dd, J=1.7, 6.6 Hz, 1H), 4.30 (dd, J=1.7, 14.2 Hz, 1H), 4.35-4.59 (m, 2H), 5.02-5.11 (m, 1H), 6.33 (dd, J=6.6, 14.2 Hz, 1H), 6.65 (dd, J=0.8, 8.7 Hz, 1H), 6.87 (d, J=8.3 Hz, 1H), 7.05 (d, J=8.3 Hz, 1H), 7.54 (d, J=8.7 Hz, 1H).

MS Calcd.: 412; MS Found: 413 (M+H).

Example 271

9-Chloro-6-[1-(cyclopropyloxy)propyl]-1-(6-methoxy-2-methylpyridin-3-yl)-1,2,3,4-tetrahydropyrimido[1,2-a]benzimidazole

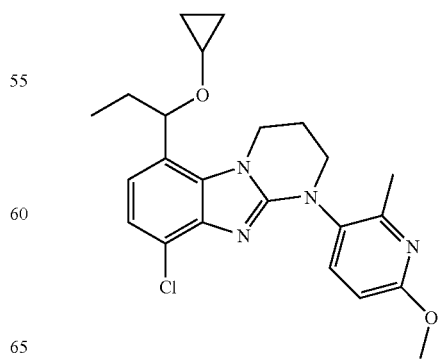

To a solution of 9-chloro-6-[1-(ethenyloxy)propyl]-1-(6-methoxy-2-methylpyridin-3-yl)-1,2,3,4-tetrahydropyrimido[1,2-a]benzimidazole (65.0 mg, 0.157 mmol) in dichloromethane (1.5 mL) were added diethyl zinc (1.0 M solution in n-hexane, 0.787 mL, 0.787 mmol) and diiodomethane (0.13 mL, 1.57 mmol) at 0° C. The reaction mixture was stirred at 0° C. for 5 hrs. The mixture was quenched with aqueous saturated ammonium chloride and extracted with ethyl acetate (×3). The combined organic layer was washed with water (×2) and brine (×1), dried over anhydrous magnesium sulfate, filtered and concentrated in vacuo, the residue was purified by silica gel column chromatography eluting with a 0-40% ethyl acetate/n-hexane gradient mixture to give the mixture contained title compound. To the solution of residue in ethyl acetate/MeOH (1.0 mL/0.5 mL) was added 4N hydrochloric acid/ethyl acetate (25 μL). The reaction mixture was stirred at room temperature for 3 hrs. After the mixture was concentrated. The residue was purified by silica gel column chromatography eluting with a 0-40% ethyl acetate/n-hexane gradient mixture to give the title compound as a colorless amorphous (7.0 mg, 0.0184 mmol, 10%).

$^1$H NMR (CDCl$_3$) δ 0.32-0.58 (m, 3H), 0.63-0.74 (m, 1H), 0.93 (t, J=7.4 Hz, 3H), 1.71-1.83 (m, 1H), 1.84-1.96 (m, 1H), 2.32-2.45 (m, 5H), 3.16-3.26 (m, 1H), 3.59-3.73 (m, 2H), 3.95 (s, 3H), 4.40 (brs, 1H), 4.60 (brs, 1H), 4.67-4.78 (m, 1H), 6.64 (d, J=8.7 Hz, 1H), 6.96 (d, J=8.3 Hz, 1H), 7.07 (d, J=8.0 Hz, 1H), 7.55 (d, J=8.3 Hz, 1H).

MS Calcd.: 426; MS Found: 427 (M+H).

Example 272

9-Chloro-1-(6-methoxy-2-methylpyridin-3-yl)-6-[1-(2,2,2-trifluoroethoxy)propyl]-1,2,3,4-tetrahydropyrimido[1,2-a]benzimidazole

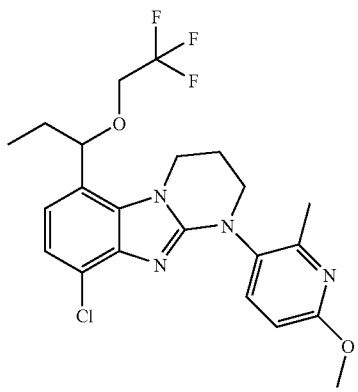 [SMILES: CCC(OCC(F)(F)F)c1ccc(Cl)c2nc3n(c12)CCCN3c1ccc(OC)nc1C]

To a solution of 1-[9-chloro-1-(6-methoxy-2-methylpyridin-3-yl)-1,2,3,4-tetrahydropyrimido[1,2-a]benzimidazol-6-yl]propan-1-ol (120.0 mg, 0.310 mmol) in tetrahydrofuran (3.0 mL) was added 1,1'-(azodicarbonyl)dipiperidine (156.4 mg, 0.620 mmol) and tributylphosphine (154.5 μL, 0.620 mmol). After 10 min, to the mixture was added 2,2,2-trifluoroethanol (225.9 μL, 3.100 mmol). The reaction mixture was stirred at 60° C. for 5 hrs. The mixture was concentrated. To the residue was added diethyl ether and the precipitate was removed by filtration. The residue was purified by silica gel column chromatography eluting with a 0-40% ethyl acetate/n-hexane gradient mixture. The resulting solid was recrystallized from diisopropyl ether/n-hexane to give the title compound as a colorless powder (56.5 mg, 0.120 mmol, 39%).

mp 124-126° C.

$^1$H NMR (CDCl$_3$) δ 1.03 (t, J=7.4 Hz, 3H), 1.79-1.97 (m, 1H), 1.96-2.14 (m, 1H), 2.31-2.38 (m, 2H), 2.40 (s, 3H), 3.48-3.81 (m, 4H), 3.87-3.97 (m, 3H), 4.32 (brs, 1H), 4.60 (brs, 1H), 4.72-4.84 (m, 1H), 6.63 (d, J=8.7 Hz, 1H), 6.84 (d, J=8.3 Hz, 1H), 7.06 (d, J=8.3 Hz, 1H), 7.53 (d, J=8.7 Hz, 1H).

MS Calcd.: 468; MS Found: 469 (M+H).

Anal. Calcd for C$_{22}$H$_{24}$N$_4$O$_2$ClF$_3$: C, 56.35; H, 5.16; N, 11.95; Cl, 7.56; F, 12.16. Found: C, 56.26; H, 5.34; N, 11.8.

Example 273

9-Chloro-6-[1-(2,2-difluoroethoxy)propyl]-1-(6-methoxy-2-methylpyridin-3-yl)-1,2,3,4-tetrahydropyrimido[1,2-a]benzimidazole

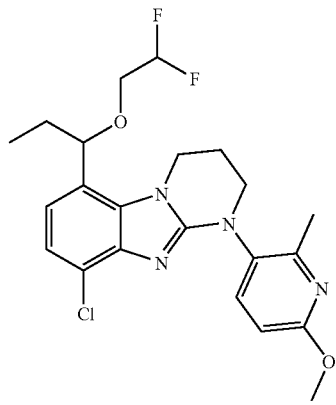 [SMILES: CCC(OCC(F)F)c1ccc(Cl)c2nc3n(c12)CCCN3c1ccc(OC)nc1C]

To a solution of 1-[9-chloro-1-(6-methoxy-2-methylpyridin-3-yl)-1,2,3,4-tetrahydropyrimido[1,2-a]benzimidazol-6-yl]propan-1-ol (111.0 mg, 0.287 mmol) in tetrahydrofuran (2.8 mL) was added 1,1'-(azodicarbonyl)dipiperidine (144.8 mg, 0.574 mmol) and tributylphosphine (143.0 μL, 0.574 mmol). After 10 min, to the mixture was added 2,2-difluoroethanol (209.1 μL, 2.870 mmol). The reaction mixture was stirred at 60° C. for 4 hrs. To the mixture was added 1,1'-(azodicarbonyl)dipiperidine (144.8 mg, 0.574 mmol) and tributylphosphine (143.0 μL, 0.574 mmol). After 30 min, to the mixture was added 2,2-difluoroethanol (209.1 μL, 2.870 mmol). The reaction mixture was stirred at 60° C. for 1.5 hrs. The mixture was concentrated. To the residue was added diethyl ether and the precipitate was removed by filtration. The residue was purified by silica gel column chromatography eluting with a 0-40% ethyl acetate/n-hexane gradient mixture to give the mixture contained the title compound. The residue was purified by preparative HPLC to give the title compound as the trifluoroacetic acid salt. The salt was neutralized with aqueous sodium hydrogen carbonate and extracted with ethyl acetate. The extract was washed with brine, dried over anhydrous magnesium sulfate, filtered and concentrated in vacuo to give the title compound. The resulting solid was recrystallized from ethyl acetate/n-hexane to give the title compound as a colorless solid (50.0 mg, 0.111 mmol, 39%).

mp 130-132° C.

$^1$H NMR (CDCl$_3$) δ 1.01 (t, J=7.4 Hz, 3H), 1.80-1.95 (m, 1H), 1.95-2.12 (m, 1H), 2.29-2.39 (m, 2H), 2.41 (s, 3H), 3.43-3.67 (m, 4H), 3.95 (s, 3H), 4.34 (s, 1H), 4.63 (brs, 1H), 4.68-4.76 (m, 1H), 5.84 (dt, J=3.8, 55.3 Hz, 1H), 6.64 (dd, J=0.8, 8.7 Hz, 1H), 6.85 (d, J=8.3 Hz, 1H), 7.05 (d, J=8.3 Hz, 1H), 7.54 (d, J=8.7 Hz, 1H).

MS Calcd: 450; MS Found: 451 (M+H).

Anal. Calcd for O$_{22}$H$_{25}$N$_4$O$_2$ClF$_2$ (0.25 mmolH$_2$O): C, 58.02; H, 5.63; N, 12.30. Found: C, 58.47; H, 5.42; N, 12.39.

Example 274

[9-Chloro-1-(6-methoxy-2-methylpyridin-3-yl)-1,2,3,4-tetrahydropyrimido[1,2-a]benzimidazol-6-yl](cyclopropyl)methanol

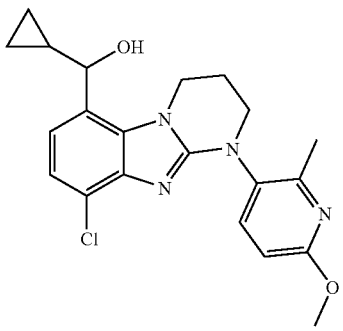 [SMILES: COc1ccc(N2CCCn3c2nc2c(Cl)ccc(C(O)C4CC4)c23)c(C)n1]

To a solution of 9-chloro-1-(6-methoxy-2-methylpyridin-3-yl)-1,2,3,4-tetrahydropyrimido[1,2-a]benzimidazole-6-carbaldehyde (213.6 mg, 0.599 mmol) in tetrahydrofuran (3.0 mL) was added cyclopropylmagnesium bromide (1.0 M solution in tetrahydrofuran, 898 µL, 0.898 mmol) at 0° C. The reaction mixture was stirred at room temperature for 1 hr. The starting material wasn't consumed completely. To the mixture was added cyclopropylmagnesium bromide (1.0 M solution in tetrahydrofuran, 449 µL, 0.449 mmol) at 0° C. The reaction mixture was stirred at room temperature for 1 hr. The mixture was quenched with aqueous saturated ammonium chloride and extracted with ethyl acetate (×3). The combined organic layer was washed with brine, dried over anhydrous magnesium sulfate, filtered and concentrated in vacuo. The resulting solid was washed with diisopropyl ether to give the title compound as a colorless solid (231.2 mg, 0.580 mmol, 97%).

$^1$H NMR (CDCl$_3$) δ 0.28-0.41 (m, 1H), 0.45-0.56 (m, 1H), 0.61-0.72 (m, 1H), 0.71-0.84 (m, 1H), 1.42-1.52 (m, 1H), 1.99 (d, J=4.9 Hz, 1H), 2.28-2.38 (m, 2H), 2.39 (s, 3H), 3.54-3.70 (m, 2H), 3.94 (s, 3H), 4.44 (brs, 1H), 4.51-4.65 (m, 1H), 4.75 (brs, 1H), 6.64 (d, J=8.7 Hz, 1H), 7.06 (d, J=8.3 Hz, 1H), 7.13 (d, J=8.3 Hz, 1H), 7.54 (d, J=8.7 Hz, 1H).

MS Calcd.: 398; MS Found: 399 (M+H).

Example 275

[9-Chloro-1-(6-methoxy-2-methylpyridin-3-yl)-1,2,3,4-tetrahydropyrimido[1,2-a]benzimidazol-6-yl](cyclopropyl)methanone

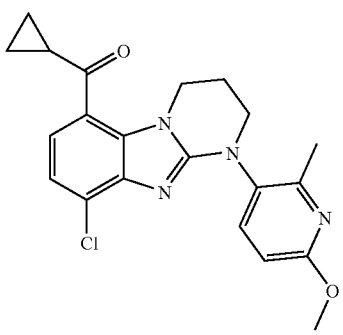 [SMILES: COc1ccc(N2CCCn3c2nc2c(Cl)ccc(C(=O)C4CC4)c23)c(C)n1]

To a solution of [9-chloro-1-(6-methoxy-2-methylpyridin-3-yl)-1,2,3,4-tetrahydropyrimido[1,2-a]benzimidazol-6-yl](cyclopropyl)methanol (145.7 mg, 0.365 mmol) in dimethyl sulfoxide (3.0 mL) was added Dess-Martin reagent (170.4 mg, 0.402 mmol). The reaction mixture was stirred at room temperature for 2 hrs. The mixture was quenched with aqueous saturated sodium hydrogen carbonate and aqueous saturated sodium thiosulfate and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-50% ethyl acetate/n-hexane gradient mixture to give the title compound as a colorless amorphous (137.0 mg, 0.345 mmol, 95%).

$^1$H NMR (CDCl$_3$) δ 1.06-1.18 (m, 2H), 1.26-1.30 (m, 2H), 2.21-2.32 (m, 2H), 2.39 (s, 3H), 2.55-2.72 (m, 1H), 3.59-3.69 (m, 2H), 3.95 (s, 3H), 4.11 (t, J=6.3 Hz, 2H), 6.60-6.68 (m, 1H), 7.14 (d, J=8.3 Hz, 1H), 7.45 (d, J=8.3 Hz, 1H), 7.52 (d, J=8.3 Hz, 1H).

MS Calcd.: 396; MS Found: 397 (M+H).

Example 276

[9-Chloro-1-(6-methoxy-2-methylpyridin-3-yl)-1,2,3,4-tetrahydropyrimido[1,2-a]benzimidazol-6-yl](dicyclopropyl)methanol

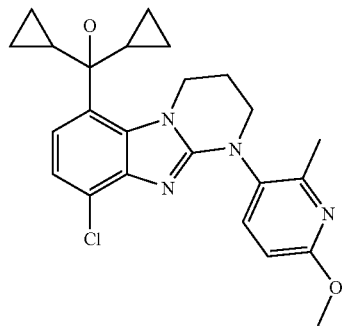 [SMILES: COc1ccc(N2CCCn3c2nc2c(Cl)ccc(C(O)(C4CC4)C4CC4)c23)c(C)n1]

To a solution of methyl [9-chloro-1-(6-methoxy-2-methylpyridin-3-yl)-1,2,3,4-tetrahydropyrimido[1,2-a]benzimidazol-6-yl](cyclopropyl)methanone (145.7 mg, 0.365 mmol) in tetrahydrofuran (2.0 mL) was added c-propylmagnesium bromide (1.0 M solution in tetrahydrofuran, 3.42 mL, 3.420 mmol). The reaction mixture was stirred at room temperature for 2 hrs. After cooling, the mixture was quenched with aqueous saturated ammonium chloride and extracted with ethyl acetate (×3). The combined organic layer was washed with brine, dried over anhydrous magnesium sulfate, filtered and concentrated in vacuo. The residue was purified by silica gel column chromatography eluting with a 0-55% ethyl acetate/n-hexane gradient mixture. The resulting solid was recrystallized from hexane to give the title compound as a solid (105.5 mg, 0.240 mmol, 70%).

mp 208-210° C.

$^1$H NMR (CDCl$_3$) δ 0.20-0.33 (m, 2H), 0.48-0.68 (m, 6H), 1.34-1.51 (m, 2H), 1.72 (s, 1H), 2.19-2.35 (m, 2H), 2.38 (s, 3H), 3.62 (t, J=5.9 Hz, 2H), 3.95 (s, 3H), 4.83 (brs, 2H), 6.64 (d, J=8.7 Hz, 1H), 7.00 (d, J=8.7 Hz, 1H), 7.13 (d, J=8.7 Hz, 1H), 7.54 (d, J=8.7 Hz, 1H).

MS Calcd.: 438; MS Found: 439 (M+H).

Anal. Calcd for $O_{24}H_{27}N_4O_2Cl$: C, 65.67; H, 6.2; N, 12.76; Cl, 8.08. Found: C, 65.66; H, 6.35; N, 12.81.

Example 277

9-Chloro-6-[cyclopropyl(2,2,2-trifluoroethoxy)methyl]-1-(6-methoxy-2-methylpyridin-3-yl)-1,2,3,4-tetrahydropyrimido[1,2-a]benzimidazole

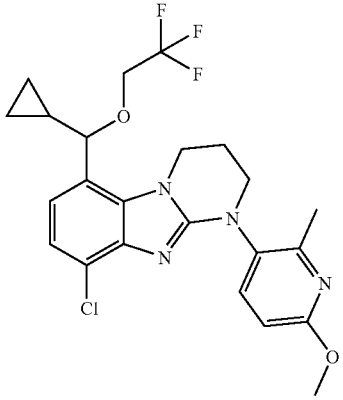 [SMILES: COc1ccc(N2CCCn3c2nc2c(Cl)ccc(C(OCC(F)(F)F)C4CC4)c23)c(C)n1]

To a solution of [9-chloro-1-(6-methoxy-2-methylpyridin-3-yl)-1,2,3,4-tetrahydropyrimido[1,2-a]benzimidazol-6-yl](cyclopropyl)methanol (111.5 mg, 0.280 mmol) in tetrahydrofuran (2.8 mL) was added 1,1'-(azodicarbonyl)dipiperidine (141.1 mg, 0.559 mmol) and tributylphosphine (139.3 µL, 0.559 mmol). After 10 min, to the mixture was added 2,2,2-trifluoroethanol (204.0 µL, 2.800 mmol). The reaction mixture was stirred at 60° C. for 2 hrs. The mixture was concentrated. To the residue was added diethyl ether and the precipitate was removed by filtration. The residue was purified by silica gel column chromatography eluting with a 0-50% ethyl acetate/n-hexane gradient mixture. The resulting solid was recrystallized from ethyl acetate/n-hexane to give the title compound as a colorless powder (92.4 mg, 0.192 mmol, 69%).

mp 158-160° C.

$^1$H NMR (CDCl$_3$) δ 0.26-0.40 (m, 1H), 0.42-0.57 (m, 1H), 0.57-0.70 (m, 1H), 0.70-0.82 (m, 1H), 1.35-1.49 (m, 1H), 2.27-2.39 (m, 2H), 2.40 (s, 3H), 3.62-3.83 (m, 4H), 3.95 (s, 3H), 4.37 (d, J=7.6 Hz, 1H), 4.46 (brs, 1H), 4.61 (brs, 1H), 6.65 (d, J=8.3 Hz, 1H), 6.85 (d, J=8.3 Hz, 1H), 7.05 (d, J=8.3 Hz, 1H), 7.54 (d, J=8.3 Hz, 1H).

MS Calcd.: 480; MS Found: 481 (M+H).

Anal. Calcd for C$_{23}$H$_{24}$N$_4$O$_2$ClF$_3$: C, 57.44; H, 5.03; N, 11.65; Found: C, 57.31; H, 5.09; N, 11.35.

Example 278

9-Chloro-6-[cyclopropyl(2,2-difluoroethoxy)methyl]-1-(6-methoxy-2-methylpyridin-3-yl)-1,2,3,4-tetrahydropyrimido[1,2-a]benzimidazole

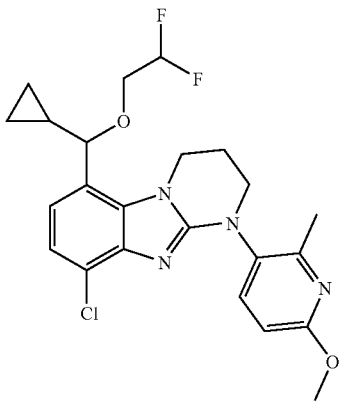 [SMILES: COc1ccc(N2CCCn3c2nc2c(Cl)ccc(C(OCC(F)F)C4CC4)c23)c(C)n1]

To a solution of [9-chloro-1-(6-methoxy-2-methylpyridin-3-yl)-1,2,3,4-tetrahydropyrimido[1,2-a]benzimidazol-6-yl](cyclopropyl)methanol (112.9 mg, 0.283 mmol) in tetrahydrofuran (2.8 mL) was added 1,1'-(azodicarbonyl)dipiperidine (142.8 mg, 0.566 mmol) and tributylphosphine (141.0 µL, 0.566 mmol). After 10 min, to the mixture was added 2,2-difluoroethanol (179.2 µL, 2.830 mmol). The reaction mixture was stirred at 60° C. for 4 hrs. The mixture was concentrated. To the residue was added diethyl ether and the precipitate was removed by filtration. The residue was purified by silica gel column chromatography eluting with a 0-50% ethyl acetate/n-hexane gradient mixture to give the mixture. The resulting solid was recrystallized from ethyl acetate/n-hexane to give the title compound as a colorless powder (62.0 mg, 0.134 mmol, 47%).

mp 124-126° C.

$^1$H NMR (CDCl$_3$) δ 0.21-0.38 (m, 1H), 0.40-0.51 (m, 1H), 0.55-0.68 (m, 1H), 0.72-0.83 (m, 1H), 1.34-1.49 (m, 1H), 2.30-2.39 (m, 2H), 2.40 (s, 3H), 3.56-3.68 (m, 4H), 3.95 (s, 3H), 4.29 (d, J=8.3 Hz, 1H), 4.47 (brs, 1H), 4.65 (brs, 1H), 5.83 (dt, J=4.2, 55.7 Hz, 1H), 6.64 (d, J=8.7 Hz, 1H), 6.86 (d, J=8.3 Hz, 1H), 7.04 (d, J=8.3 Hz, 1H), 7.54 (d, J=8.7 Hz, 1H).

MS Calcd.: 462; MS Found: 463 (M+H).

Anal. Calcd for C$_{23}$H$_{25}$N$_4$O$_2$ClF$_2$: C, 59.67; H, 5.44; N, 12.10; Cl, 7.66; F, 8.21. Found: C, 59.7; H, 5.42; N, 12.17.

Example 279

1-[9-Chloro-1-(6-methoxy-2-methylpyridin-3-yl)-1,2,3,4-tetrahydropyrimido[1,2-a]benzimidazol-6-yl]-2,2,2-trifluoroethanol

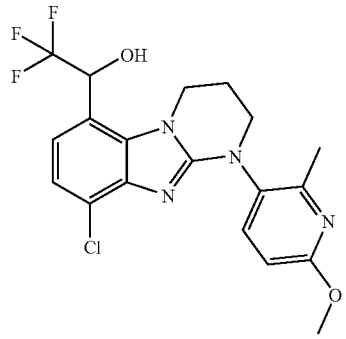 [SMILES: COc1ccc(N2CCCn3c2nc2c(Cl)ccc(C(O)C(F)(F)F)c23)c(C)n1]

To a solution of 9-chloro-1-(6-methoxy-2-methylpyridin-3-yl)-1,2,3,4-tetrahydropyrimido[1,2-a]benzimidazole-6-carbaldehyde (2.20 g, 6.17 mmol) in tetrahydrofuran (28.0 mL) was added trimethyl(trifluoromethyl)silane (2.73 mL, 18.50 mmol) and tetrabutylammonium fluoride (1.0 M solution in tetrahydrofuran, 0.617 mL, 0.617 mmol) at 0° C. After 30 min, to the mixture was added 1N hydrochloric acid (9.0 mL) and the reaction mixture was stirred at 0° C. for 1 hr. The mixture was quenched with aqueous saturated sodium hydrogen carbonate and extracted with ethyl acetate (×3). The combined organic layer was washed with brine (×1), dried over anhydrous magnesium sulfate, filtered and concentrated in vacuo. The resulting solid was washed with diisopropyl ether to give the title compound as a colorless solid (2.49 g, 5.82 mmol, 94%).

$^1$H NMR (DMSO-d$_6$) δ 2.19-2.39 (m, 5H), 3.47-3.78 (m, 2H), 3.88 (s, 3H), 4.22-4.61 (m, 2H), 5.73 (brs, 1H), 6.69-6.82 (m, 1H), 7.03 (brs, 1H), 7.05-7.17 (m, 2H), 7.71 (d, J=8.3 Hz, 1H).

Example 280

9-Chloro-1-(6-methoxy-2-methylpyridin-3-yl)-6-(2,2,2-trifluoro-1-methoxyethyl)-1,2,3,4-tetrahydropyrimido[1,2-a]benzimidazole

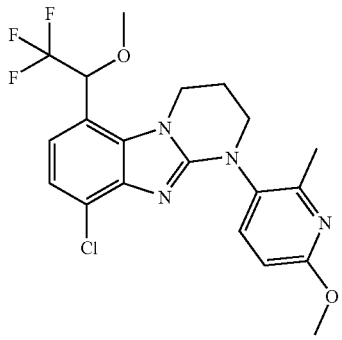 [SMILES: COc1ccc(N2CCCn3c2nc2c(Cl)ccc(C(OC)C(F)(F)F)c23)c(C)n1]

To a solution of 1-[9-chloro-1-(6-methoxy-2-methylpyridin-3-yl)-1,2,3,4-tetrahydropyrimido[1,2-a]benzimidazol-6-yl]-2,2,2-trifluoroethanol (100.7 mg, 0.236 mmol) in N,N-dimethylformamide (1.5 mL) was added sodium hydride (14.2 mg, 0.354 mmol) at 0° C. After 30 min, to the mixture was added methyl iodide (73.5 µL, 1.180 mmol) at 0° C. The reaction mixture was stirred at room temperature for 2.5 hrs. The mixture was quenched with aqueous saturated ammonium chloride and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-40% ethyl acetate/n-hexane gradient mixture. The resulting solid was recrystallized from ethyl acetate/n-hexane to give the title compound as a colorless powder (85.5 mg, 0.194 mmol, 82%).

mp 144-146° C.

$^1$H NMR (CDCl$_3$) δ 2.31-2.40 (m, 2H), 2.41 (s, 3H), 3.45 (s, 3H), 3.57-3.73 (m, 2H), 3.95 (s, 3H), 4.23-4.55 (m, 2H), 5.09 (q, J=6.7 Hz, 1H), 6.64 (d, J=8.3 Hz, 1H), 7.06 (d, J=8.3 Hz, 1H), 7.13 (d, J=8.3 Hz, 1H), 7.53 (d, J=8.3 Hz, 1H).

MS Calcd.: 440; MS Found: 441 (M+H).

Anal. Calcd for C$_{20}$H$_{20}$N$_4$O$_2$ClF$_3$: C, 54.49; H, 4.57; N, 12.71; Found: C, 54.47; H, 4.5; N, 12.53.

Example 281

9-Chloro-6-(1-ethoxy-2,2,2-trifluoroethyl)-1-(6-methoxy-2-methylpyridin-3-yl)-1,2,3,4-tetrahydropyrimido[1,2-a]benzimidazole

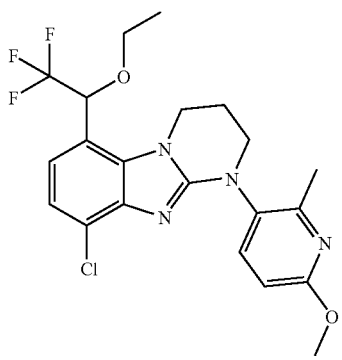 [SMILES: CCOC(c1ccc(Cl)c2nc3n(c12)CCCN3c1ccc(OC)nc1C)C(F)(F)F]

To a solution of 1-[9-chloro-1-(6-methoxy-2-methylpyridin-3-yl)-1,2,3,4-tetrahydropyrimido[1,2-a]benzimidazol-6-yl]-2,2,2-trifluoroethanol (100.5 mg, 0.235 mmol) in N,N-dimethylformamide (1.5 mL) was added sodium hydride (14.1 mg, 0.353 mmol) at 0° C. After 30 min, to the mixture was added ethyl iodide (94 µL, 1.175 mmol) at 0° C. The reaction mixture was stirred at room temperature for 3.5 hrs. The mixture was quenched with aqueous saturated ammonium chloride and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-40% ethyl acetate/n-hexane gradient mixture. The resulting solid was recrystallized from ethyl acetate/n-hexane to give the title compound as a colorless powder (80.7 mg, 0.177 mmol, 76%).

mp 168-170° C.

$^1$H NMR (CDCl$_3$) δ 1.25-1.31 (m, 3H), 2.30-2.40 (m, 2H), 2.41 (s, 3H), 3.52-3.71 (m, 4H), 3.95 (s, 3H), 4.35 (brs, 1H), 4.49 (brs, 1H), 5.17 (q, J=6.8 Hz, 1H), 6.65 (d, J=8.7 Hz, 1H), 7.07 (d, J=8.7 Hz, 1H), 7.12 (d, J=8.7 Hz, 1H), 7.54 (d, J=8.7 Hz, 1H).

MS Calcd.: 454; MS Found: 455 (M+H).

Anal. Calcd for C$_{21}$H$_{22}$N$_4$O$_2$ClF$_3$: C, 55.45; H, 4.87; N, 12.32; Found: C, 55.39; H, 4.86; N, 12.45.

Example 282

9-Chloro-6-[1-(difluoromethoxy)-2,2,2-trifluoroethyl]-1-(6-methoxy-2-methylpyridin-3-yl)-1,2,3,4-tetrahydropyrimido[1,2-a]benzimidazole

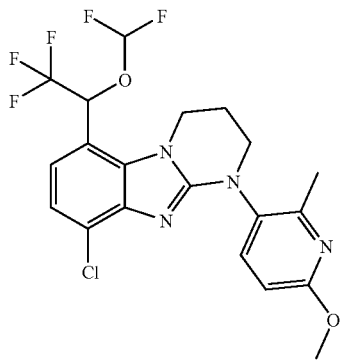 [SMILES: COc1ccc(N2CCCn3c2nc2c(Cl)ccc(C(OC(F)F)C(F)(F)F)c23)c(C)n1]

To a solution of 1-[9-chloro-1-(6-methoxy-2-methylpyridin-3-yl)-1,2,3,4-tetrahydropyrimido[1,2-a]benzimidazol-6-yl]-2,2,2-trifluoroethanol (127.0 mg, 0.235 mmol) in tetrahydrofuran (0.9 mL) was added 8N sodium hydroxide (0.36 mL). The mixture was stirred at 50° C. for 4 hrs under chloro(difluoro)methane atmosphere. The mixture was diluted with water and extracted with ethyl acetate (×3). The combined organic layer was washed with brine (×1), dried over anhydrous magnesium sulfate, filtered and concentrated in vacuo. The residue was purified by silica gel column chromatography eluting with a 0-40% ethyl acetate/n-hexane gradient mixture. The resulting solid was recrystallized from ethyl acetate/n-hexane to give the title compound as a colorless powder (47.9 mg, 0.100 mmol, 34%).

mp 175-177° C.

$^1$H NMR (CDCl$_3$) δ 2.41 (s, 5H), 3.66 (d, J=4.9 Hz, 2H), 3.95 (s, 3H), 4.36 (brs, 2H), 6.01 (q, J=6.1 Hz, 1H), 6.13-6.65 (m, 1H), 6.64 (d, J=8.7 Hz, 1H), 7.04-7.25 (m, 2H), 7.53 (d, J=8.7 Hz, 1H).

MS Calcd.: 476; MS Found: 477 (M+H).
Anal. Calcd for $C_{20}H_{18}N_4O_2ClF_5$: C, 50.38; H, 3.8; N, 11.75; Cl, 7.44; F, 19.92. Found: C, 50.55; H, 3.79; N, 11.72.

Example 283

(+)-9-Chloro-6-[1-(difluoromethoxy)-2,2,2-trifluoroethyl]-1-(6-methoxy-2-methylpyridin-3-yl)-1,2,3,4-tetrahydropyrimido[1,2-a]benzimidazole Example 284

(−)-9-Chloro-6-[1-(difluoromethoxy)-2,2,2-trifluoroethyl]-1-(6-methoxy-2-methylpyridin-3-yl)-1,2,3,4-tetrahydropyrimido[1,2-a]benzimidazole

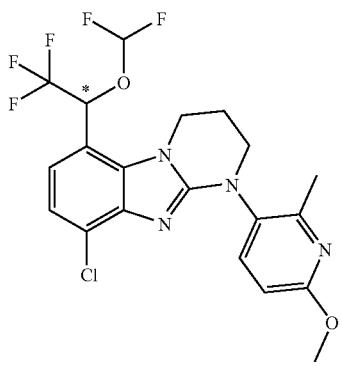 [SMILES: COc1ccc(N2CCCn3c2nc2c(Cl)ccc(C(OC(F)F)C(F)(F)F)c23)c(C)n1]

Racemic Example 282 (2595 mg) was resolved by preparative HPLC, using CHIRALPAK AD (5 cm i.d.×50 cm, Daicel Chemical Industries, Ltd.) with the flow rate of 80 mL/min at 30° C. and hexane/2-propanol (70/30) as the mobile phase, and obtaining the stereoisomer having a shorter retention time 1229 mg in an enantiomer excess of 99.7% and the stereoisomer having a longer retention time 1233 mg in an enantiomer excess of 99.2%. The obtained compounds were recrystallized from ethyl acetate/diisopropyl ether to give the optically active title compounds as a colorless crystal respectively (shorter retention time (Example 283): 1.00 g, longer retention time (Example 284): 1.03 g).
Shorter Retention Time (Example 283):
  $[\alpha]_D^{20}$=+43.3 (c=0.4770, MeOH)
  mp 167-169° C.
  $^1$H NMR (CDCl$_3$) δ 2.40-2.50 (m, 2H), 2.41 (s; 3H), 3.58-3.70 (m, 2H), 3.94 (s, 3H), 4.36 (brs, 2H), 6.00 (q, J=6.0 Hz, 1H), 6.41 (t, J=72.6 Hz, 1H), 6.64 (d, J=8.4 Hz, 1H), 7.10-7.16 (m, 2H), 7.53 (d, J=8.4 Hz, 1H).
  MS Calcd.: 476; MS Found: 477 (M+H).
  Anal. Calcd for $C_{20}H_{18}N_4O_2ClF_5$: C, 50.38; H, 3.8; N, 11.75; Cl, 7.44; F, 19.92. Found: C, 50.44; H, 3.71; N, 11.76; Cl, 7.49; F, 19.98.
Longer Retention Time (Example 284):
  $[\alpha]_D^{20}$=−43.9 (c=0.4700, MeOH)
  mp 166-168° C.
  $^1$H NMR (CDCl$_3$) δ 2.40-2.50 (m, 2H), 2.41 (s, 3H), 3.58-3.70 (m, 2H), 3.94 (s, 3H), 4.36 (brs, 2H), 6.00 (q, J=5.7 Hz, 1H), 6.40 (t, J=72.3 Hz, 1H), 6.64 (d, J=8.4 Hz, 1H), 7.10-7.16 (m, 2H), 7.53 (d, J=8.4 Hz, 1H).
  MS Calcd.: 476; MS Found: 477 (M+H).
  Anal. Calcd for $C_{20}H_{18}N_4O_2ClF_5$: C, 50.38; H, 3.8; N, 11.75; Cl, 7.44; F, 19.92. Found: C, 50.49; H, 3.71; N, 11.78; Cl, 7.46; F, 19.92.

Example 285

5-{9-Chloro-6-[1-(difluoromethoxy)-2,2,2-trifluoroethyl]-3,4-dihydropyrimido[1,2-a]benzimidazol-1(2H)-yl}-6-methylpyridin-2-ol

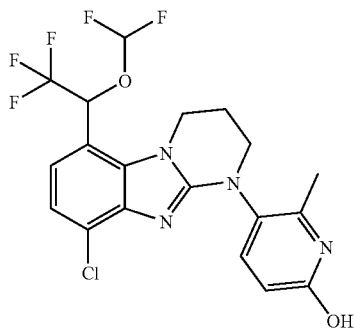 [SMILES: Cc1nc(O)ccc1N1CCCn2c1nc1c(Cl)ccc(C(OC(F)F)C(F)(F)F)c12]

To a solution of 9-chloro-6-[1-(difluoromethoxy)-2,2,2-trifluoroethyl]-1-(6-methoxy-2-methylpyridin-3-yl)-1,2,3,4-tetrahydropyrimido[1,2-a]benzimidazole (152.2 mg, 0.319 mmol) in acetonitrile (3.0 mL) were added sodium iodide (143.5 mg, 0.958 mmol) and trimethylsilyl chloride (121.6 μL, 0.958 mmol). The mixture was stirred at room temperature for 1 day. To the mixture were added sodium iodide (71.8 mg, 0.479 mmol) and trimethylsilyl chloride (60.8 μL, 0.479 mmol). The mixture was stirred at room temperature for 3 hrs. The mixture was quenched with aqueous saturated ammonium chloride and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 10% methanol/ethyl acetate gradient mixture to give the title compound as a colorless amorphous (119.8 mg, 0.259 mmol, 81%).
  $^1$H NMR (CDCl$_3$) δ 2.33 (s, 3H), 2.38-2.52 (m, 2H), 3.51-3.85 (m, 2H), 4.36 (brs, 2H), 6.00 (q, J=6.2 Hz, 1H), 6.42 (t, J=72.7 Hz, 1H), 6.48 (d, J=9.5 Hz, 1H), 7.17 (s, 2H), 7.44 (d, J=9.47 Hz, 1H).
  MS Calcd.: 462; MS Found: 463 (M+H).

Example 286

9-Chloro-6-[1-(difluoromethoxy)-2,2-difluoroethenyl]-1-(6-ethoxy-2-methylpyridin-3-yl)-1,2,3,4-tetrahydropyrimido[1,2-a]benzimidazole Example 287

9-Chloro-6-[1-(difluoromethoxy)-2,2,2-trifluoroethyl]-1-(6-ethoxy-2-methylpyridin-3-yl)-1,2,3,4-tetrahydropyrimido[1,2-a]benzimidazole Example 286

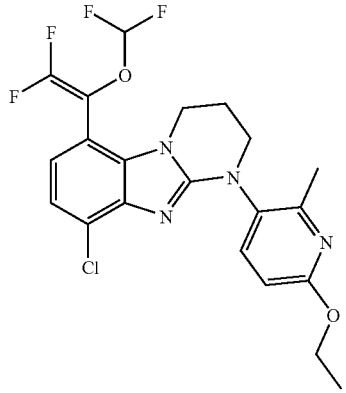

Example 287

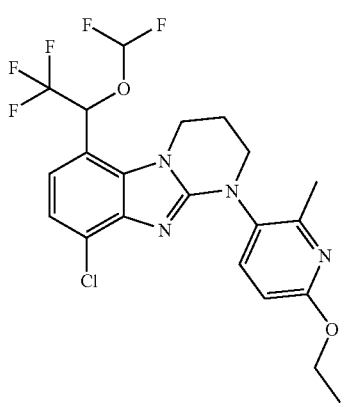

To a solution of 5-{9-chloro-6-[1-(difluoromethoxy)-2,2,2-trifluoroethyl]-3,4-dihydropyrimido[1,2-a]benzimidazol-1(2H)-yl}-6-methylpyridin-2-ol (117.0 mg, 0.253 mmol) in N,N-dimethylformamide (2.0 mL) was added sodium hydride (15.2 mg, 0.379 mmol) at 0° C. After 30 min, to the mixture was added ethyl iodide (101 μL, 1.265 mmol) at 0° C. The reaction mixture was stirred at room temperature for 4 hrs. The mixture was quenched with aqueous saturated ammonium chloride and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-30% ethyl acetate/n-hexane gradient mixture to give Example 286 as a colorless amorphous (18.0 mg, 0.0382 mmol, 15%) and Example 287 as a colorless solid. The resulting solid was recrystallized from ethanol/n-hexane to give the title compound as a colorless powder (43.8 mg, 0.0892 mmol, 35%).

Example 286

$^1$H NMR (CDCl$_3$) δ 1.41 (t, J=7.0 Hz, 3H), 2.29-2.39 (m, 2H), 2.39 (s, 3H), 3.66 (t, J=5.3 Hz, 2H), 4.15-4.51 (m, 4H), 6.22 (t, J=73.8 Hz, 1H), 6.62 (d, J=8.7 Hz, 1H), 6.86 (d, J=8.0 Hz, 1H), 7.10 (d, J=8.0 Hz, 1H), 7.52 (d, J=8.7 Hz, 1H).

MS Calcd.: 470; MS Found: 471 (M+H).

Example 287 mp 159-162° C.

$^1$H NMR (CDCl$_3$) δ 1.41 (t, J=6.97 Hz, 3H), 2.40 (s, 3H), 2.41-2.50 (m, 2H), 3.55-3.73 (m, 2H), 4.27-4.48 (m, 4H), 6.01 (q, J=6.2 Hz, 1H), 6.50 (t, J=72.7 Hz, 1H), 6.62 (d, J=8.7 Hz, 1H), 7.15 (s, 2H), 7.53 (d, J=8.7 Hz, 1H).

MS Calcd.: 490; MS Found: 491 (M+H).

Anal. Calcd for $C_{21}H_{20}N_4O_2ClF_5$: C, 51.38; H, 4.11; N, 11.41; Found: C, 51.38; H, 4.13; N, 11.26.

Example 288

9-Chloro-6-[1-(difluoromethoxy)-2,2,2-trifluoroethyl]-1-[2-methyl-6-(1-methylethoxy)pyridin-3-yl]-1,2,3,4-tetrahydropyrimido[1,2-a]benzimidazole

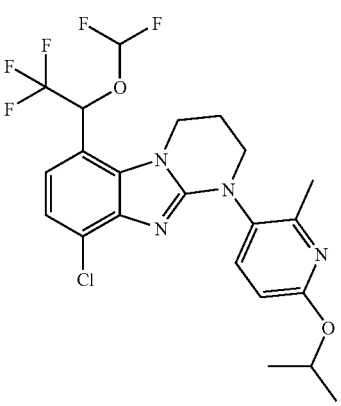 [SMILES: Cc1nc(OC(C)C)ccc1N1CCCn2c1nc1c(Cl)ccc(C(OC(F)F)C(F)(F)F)c12]

To a solution of 5-{9-chloro-6-[1-(difluoromethoxy)-2,2,2-trifluoroethyl]-3,4-dihydropyrimido[1,2-a]benzimidazol-1(2H)-yl}-6-methylpyridin-2-ol (30.0 mg, 0.0648 mmol) in toluene (1.0 mL) was added silver carbonate (35.7 mg, 0.130 mmol) and 2-iodopropane (32.3 μL, 0.324 mmol). The reaction mixture was stirred at room temperature for 5 hrs. The starting material wasn't consumed completely. The mixture was stirred at 50° C. for 5 hrs. After cooling the mixture was filtered through on the pad of celite. The filtrate was concentrated. The residue was purified by silica gel column chromatography eluting with a 0-30% ethyl acetate/n-hexane gradient mixture to give the title compound as a colorless amorphous (29.3 mg, 0.0633 mmol, 98%).

$^1$H NMR (CDCl$_3$) δ 1.36 (d, J=6.2 Hz, 6H), 2.39 (s, 3H), 2.39-2.48 (m, 2H), 3.52-3.76 (m, 2H), 4.21-4.47 (m, 2H), 5.31 (spt, J=6.2 Hz, 1H), 6.01 (q, J=6.0 Hz, 1H), 6.48 (t, J=72.3 Hz, 1H), 6.57 (d, J=8.7 Hz, 1H), 7.15 (s, 2H), 7.51 (d, J=8.7 Hz, 1H).

MS Calcd.: 504; MS Found: 505 (M+H).

Example 289

9-Chloro-6-[1-(difluoromethoxy)-2,2,2-trifluoroethyl]-1-(2-methyl-6-propoxypyridin-3-yl)-1,2,3,4-tetrahydropyrimido[1,2-a]benzimidazole

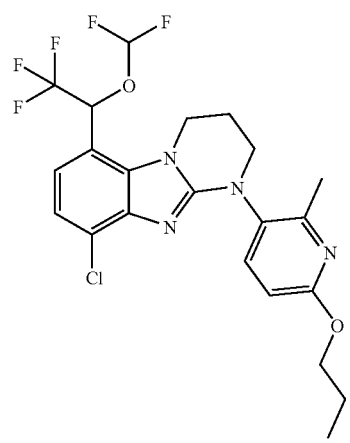 [SMILES: CCCOc1ccc(N2CCCn3c2nc2c(Cl)ccc(C(OC(F)F)C(F)(F)F)c23)c(C)n1]

To a solution of 5-{9-chloro-6-[1-(difluoromethoxy)-2,2,2-trifluoroethyl]-3,4-dihydropyrimido[1,2-a]benzimidazol-1(2H)-yl}-6-methylpyridin-2-ol (65.3 mg, 0.141 mmol) in toluene (1.5 mL) was added silver carbonate (77.8 mg, 0.282 mmol) and 1-iodopropane (68.8 μL, 0.705 mmol). The reaction mixture was stirred at 50° C. for 13 hrs. After cooling the mixture was filtered through on the pad of celite. The filtrate was concentrated. The residue was purified by silica gel column chromatography eluting with a 0-40% ethyl acetate/n-hexane gradient mixture. The resulting solid was recrystallized from ethyl acetate/n-hexane to give the title compound as a colorless powder (52.5 mg, 0.104 mmol, 74%).

mp 156-158° C.

$^1$H NMR (CDCl$_3$) δ 1.04 (t, J=7.4 Hz, 3H), 1.67-1.93 (m, 2H), 2.32-2.50 (m, 5H), 3.57-3.76 (m, 2H), 4.26 (t, J=6.8 Hz, 2H), 4.34 (brs, 2H), 5.93-6.07 (m, 1H), 6.13-6.70 (m, 1H), 6.63 (d, J=8.7 Hz, 1H), 7.14 (s, 2H), 7.53 (d, J=8.7 Hz, 1H).

MS Calcd.: 504; MS Found: 505 (M+H).

Anal. Calcd for O$_{22}$H$_{22}$N$_4$O$_2$ClF$_5$ (0.5 mol H$_2$O): C, 51.42; H, 4.51; N, 10.90; Found: C, 51.35; H, 4.39; N, 10.92.

Example 290

9-Chloro-1-[6-(difluoromethoxy)-2-methylpyridin-3-yl]-6-[1-(difluoromethoxy)-2,2,2-trifluoroethyl]-1,2,3,4-tetrahydropyrimido[1,2-a]benzimidazole

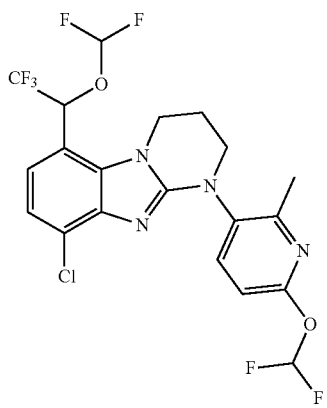 [SMILES: Cc1nc(OC(F)F)ccc1N1CCCn2c1nc1c(Cl)ccc(C(OC(F)F)C(F)(F)F)c12]

To a solution of 5-{9-chloro-6-[1-(difluoromethoxy)-2,2,2-trifluoroethyl]-3,4-dihydropyrimido[1,2-a]benzimidazol-1(2H)-yl}-6-methylpyridin-2-ol (90.0 mg, 0.194 mmol) in acetonitrile (2.0 mL) was added sodium carbonate (41.1 mg, 0.389 mmol) and 2,2-difluoro-2-fluorosulfonyl-aceticacid (40.2 μL, 0.389 mmol) 0° C. The reaction mixture was stirred at room temperature for 1.5 hrs. The mixture was concentrated. The precipitate was removed by filtration. The filtrate was concentrated and the residue was purified by silica gel column chromatography eluting with a 0-35% ethyl acetate/n-hexane gradient mixture. The resulting solid was recrystallized from ethyl acetate/n-hexane to give the title compound as a colorless powder (77.3 mg, 0.151 mmol, 78%).

mp 145-148° C.

$^1$H NMR (CDCl$_3$) δ 2.39-2.58 (m, 5H), 3.59-3.78 (m, 2H), 4.37 (brs, 2H), 6.01 (q, J=6.1 Hz, 1H), 6.42 (t, J=72.3 Hz, 1H), 6.82 (d, J=8.3 Hz, 1H), 7.17 (s, 2H), 7.50-7.78 (m, 2H).

MS Calcd.: 512; MS Found: 513 (M+H).

Anal. Calcd for C$_{20}$H$_{16}$N$_4$O$_2$ClF$_7$: C, 46.84; H, 3.14; N, 10.93; Found: C, 46.82; H, 3.26; N, 10.87.

Example 291

5-{9-Chloro-6-[1-(difluoromethoxy)-2,2,2-trifluoroethyl]-3,4-dihydropyrimido[1,2-a]benzimidazol-1(2H)-yl}-6-methylpyridin-2-yl trifluoromethanesulfonate

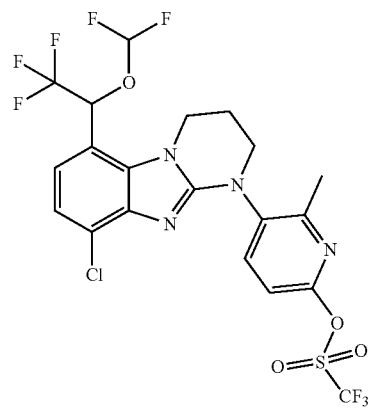 [SMILES: Cc1nc(OS(=O)(=O)C(F)(F)F)ccc1N1CCCn2c1nc1c(Cl)ccc(C(OC(F)F)C(F)(F)F)c12]

To a solution of 5-{9-chloro-6-[1-(difluoromethoxy)-2,2,2-trifluoroethyl]-3,4-dihydropyrimido[1,2-a]benzimidazol-1(2H)-yl}-6-methylpyridin-2-ol (203.0 mg, 0.439 mmol) in pyridine (2.0 mL) was added trifluoromethanesulfonic anhydride (110.7 μL, 0.658 mmol) at 0° C. The reaction mixture was stirred at room temperature for 4.5 hrs. The mixture was quenched with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified by silica gel column chromatography eluting with a 0-30% ethyl acetate/n-hexane gradient mixture to give a title compound as a colorless amorphous (243.7 mg, 0.410 mmol, 93%).

$^1$H NMR (CDCl$_3$) δ 2.38-2.56 (m, 5H), 3.62-3.82 (m, 2H), 4.31-4.50 (m, 2H), 6.01 (q, J=6.0 Hz, 1H), 6.43 (t, J=72.3 Hz, 1 H), 7.10 (d, J=8.7 Hz, 1H), 7.20 (s, 2H), 7.89 (d, J=8.7 Hz, 1H).

MS Calcd.: 594; MS Found: 595 (M+H).

Example 292

5-{9-Chloro-6-[1-(difluoromethoxy)-2,2,2-trifluoroethyl]-3,4-dihydropyrimido[1,2-a]benzimidazol-1(2H)-yl}-6-methylpyridine-2-carbonitrile

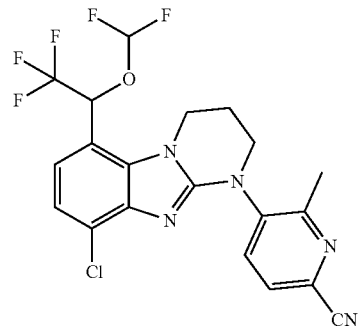 [SMILES: Cc1nc(C#N)ccc1N1CCCn2c1nc1c(Cl)ccc(C(OC(F)F)C(F)(F)F)c12]

Under nitrogen atmosphere, to a solution of 5-{9-chloro-6-[1-(difluoromethoxy)-2,2,2-trifluoroethyl]-3,4-dihydropyrimido[1,2-a]benzimidazol-1(2H)-yl}-6-methylpyridin-2-yl trifluoromethanesulfonate (209.5 mg, 0.352 mmol), zinc cyanide (62.0 mg, 0.528 mmol), tetrakis(triphenylphosphine)palladium(0) (40.7 mg, 0.0352 mmol) and N,N-dimethylformamide (1.5 mL) was stirred at 100° C. for 2 hrs. The reaction mixture was diluted with water and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-50% ethyl acetate/n-hexane gradient mixture. The resulting solid was recrystallized from ethyl acetate/n-hexane to give a title compound as a colorless powder (136.1 mg, 0.288 mmol, 82%).

mp 177-180° C.

$^1$H NMR (CDCl$_3$) δ 2.50 (quin, J=5.9 Hz, 2H), 2.58 (s, 3H), 3.65-3.85 (m, 2H), 4.33-4.51 (m, 2H), 6.02 (q, J=6.0 Hz, 1H), 6.44 (t, J=72.3 Hz, 1H), 7.21 (s, 2H), 7.64 (d, J=7.9 Hz, 1H), 7.83 (d, J=7.9 Hz, 1H).

MS Calcd.: 471; MS Found: 472 (M+H).

Anal. Calcd for C$_{20}$H$_{15}$N$_5$OClF$_5$: C, 50.91; H, 3.2; N, 14.84; Found: C, 50.95; H, 3.31; N, 14.77.

Example 293

5-{9-Chloro-6-[1-(difluoromethoxy)-2,2,2-trifluoroethyl]-3,4-dihydropyrimido[1,2-a]benzimidazol-1(2H)-yl}-6-methylpyridine-2-carboxamide

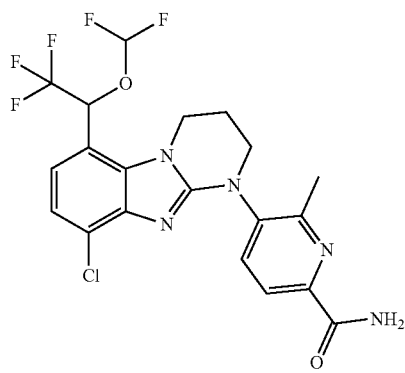 [SMILES: Cc1nc(C(N)=O)ccc1N1CCCn2c1nc1c(Cl)ccc(C(OC(F)F)C(F)(F)F)c12]

To a solution of 5-{9-chloro-6-[1-(difluoromethoxy)-2,2,2-trifluoroethyl]-3,4-dihydropyrimido[1,2-a]benzimidazol-1(2H)-yl}-6-methylpyridine-2-carbonitrile (47.2 mg, 0.100 mmol) in tert-butyl alcohol (2 mL) potassium hydroxide (22.4 mg, 0.400 mmol). The reaction mixture was stirred at 80° C. for 5 min. After cooling, the reaction mixture was diluted with water and extracted with ethyl acetate (×3). The combined organic layer was washed with brine (×1), dried over anhydrous magnesium sulfate, filtered and concentrated in vacuo. The residue was purified by silica gel column, chromatography eluting with a 30-80% ethyl acetate/n-hexane gradient mixture to give a title compound as a colorless amorphous (16.6 mg, 0.0399 mmol, 34%).

$^1$H NMR (CDCl$_3$) δ 2.30-2.79 (m, 5H), 3.77 (brs, 2H), 4.41 (brs, 2H), 5.65 (brs, 1H), 6.03 (brs, 1H), 6.44 (m, J=71.9 Hz, 1H), 7.19 (brs, 2H), 7.83 (brs, 2H), 8.13 (brs, 1H).

MS Calcd.: 489; MS Found: 490 (M+H).

Example 294

9-Chloro-6-[1-(difluoromethoxy)-2,2,2-trifluoroethyl]-1-(2-methyl-6-pyrrolidin-1-ylpyridin-3-yl)-1,2,3,4-tetrahydropyrimido[1,2-a]benzimidazole

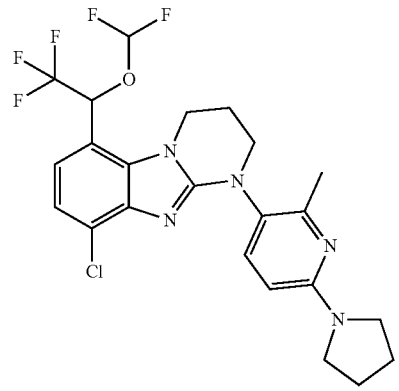 [SMILES: Cc1nc(N2CCCC2)ccc1N1CCCn2c1nc1c(Cl)ccc(C(OC(F)F)C(F)(F)F)c12]

To a solution of 5-{9-chloro-6-[1-(difluoromethoxy)-2,2,2-trifluoroethyl]-3,4-dihydropyrimido[1,2-a]benzimidazol-1(2H)-yl}-6-methylpyridin-2-yl trifluoromethanesulfonate (123.7 mg, 0.208 mmol) in N,N-dimethylformamide (2.5 mL) was added pyrrolidine (86.8 μL, 1.04 mmol). The reaction mixture was stirred at 80° C. for 2.5 hrs. The reaction mixture was diluted with water and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-60% ethyl acetate/n-hexane gradient mixture. The resulting solid was recrystallized from ethyl acetate/n-hexane to give a title compound as a colorless powder (94.6 mg, 0.183 mmol, 88%).

mp 233-236° C.

$^1$H NMR (CDCl$_3$) δ 1.92-2.06 (m, 4H), 2.36 (s, 3H), 2.37-2.46 (m, 2H), 3.42-3.53 (m, 4H), 3.63 (brs, 2H), 4.33 (brs, 2H), 6.01 (q, J=6.1 Hz, 1H), 6.34 (t, J=72.3 Hz, 1H), 6.26 (d, J=8.7 Hz, 1H), 7.05-7.18 (m, 2H), 7.37 (d, J=8.7 Hz, 1H).

MS Calcd.: 515; MS Found: 516 (M+H).

Anal. Calcd for C$_{23}$H$_{23}$N$_5$OClF$_5$: C, 53.55; H, 4.49; N, 13.57; Found: C, 53.32; H, 4.5; N, 13.37.

Example 295

9-Chloro-6-[1-(difluoromethoxy)-2,2,2-trifluoroethyl]-1-(2-methyl-6-piperidin-1-ylpyridin-3-yl)-1,2,3,4-tetrahydropyrimido[1,2-a]benzimidazole

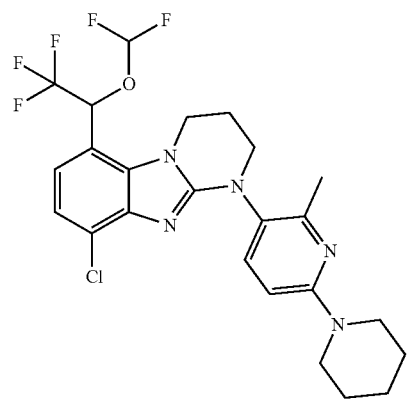 [SMILES: Cc1nc(N2CCCCC2)ccc1N1CCCn2c1nc1c(Cl)ccc(C(OC(F)F)C(F)(F)F)c12]

To a solution of 5-{9-chloro-6-[1-(difluoromethoxy)-2,2,2-trifluoroethyl]-3,4-dihydropyrimido[1,2-a]benzimidazol-1(2H)-yl}-6-methylpyridin-2-yl trifluoromethanesulfonate (102.1 mg, 0.172 mmol) in N,N-dimethylformamide (1.5 mL) was added piperidine (85.0 μL, 0.858 mmol). The reaction mixture was stirred, at 80° C. for 7 hrs. The reaction mixture was diluted with water and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-40% ethyl acetate/n-hexane gradient mixture. The resulting solid was recrystallized from ethyl acetate/n-hexane to give a title compound as a colorless powder (78.7 mg, 0.288 mmol, 86%).

mp 164-167° C.

$^1$H NMR (CDCl$_2$) δ 1.66 (s, 6H), 2.35 (s, 3H), 2.37-2.46 (m, 2H), 3.56 (brs, 4H), 3.59-3.70 (m, 2H), 4.25-4.38 (m, 2H), 6.01 (q, J=6.2 Hz, 1H), 6.45 (t, J=72.3 Hz, 1H), 6.53 (d, J=8.7 Hz, 1H), 7.10-7.15 (m, 2H), 7.39 (d, J=8.7 Hz, 1H).

MS Calcd.: 529; MS Found: 530 (M+H).

Anal. Calcd for $C_{24}H_{25}N_5OClF_5$: C, 54.39; H, 4.76; N, 13.22; Found: C, 54.34; H, 4.83; N, 13.01.

Example 296

9-Chloro-6-[1-(difluoromethoxy)-2,2,2-trifluoroethyl]-1-(2-methyl-6-morpholin-4-ylpyridin-3-yl)-1,2,3,4-tetrahydropyrimido[1,2-a]benzimidazole

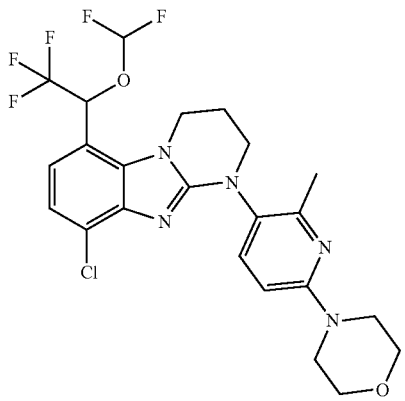 [SMILES: Cc1nc(N2CCOCC2)ccc1N1CCCn2c1nc1c(Cl)ccc(C(OC(F)F)C(F)(F)F)c12]

To a solution of 5-{9-chloro-6-[1-(difluoromethoxy)-2,2,2-trifluoroethyl]-3,4-dihydropyrimido[1,2-a]benzimidazol-1(2H)-yl}-6-methylpyridin-2-yl trifluoromethanesulfonate (100.4 mg, 0.169 mmol) in N,N-dimethylformamide (1.5 mL) was added morpholine (73.6 μL, 0.844 mmol). The reaction mixture was stirred, at 80° C. for 1.5 hrs. The starting material wasn't consumed completely. To the mixture was added morpholine (73.6 μL, 0.844 mmol). The reaction mixture was stirred at 80° C. for 3.5 hrs. The reaction mixture was diluted with water and extracted with ethyl acetate (×3). The combined organic layer was washed with water (×2) and brine (×1), dried over anhydrous magnesium sulfate, filtered and concentrated in vacuo. The residue was purified by silica gel column chromatography eluting with a 0-60% ethyl acetate/n-hexane gradient mixture. The resulting solid was recrystallized from ethyl acetate/n-hexane to give a title compound as a colorless powder (74.6 mg, 0.140 mmol, 83%).

mp 191-193° C.

$^1$H NMR (CDCl$_3$) δ 2.37 (s, 3H), 2.39-2.45 (m, 2H), 3.50-3.58 (m, 4H), 3.59-3.70 (m, 2H), 3.78-3.90 (m, 4H), 4.34 (brs, 2H), 6.01 (q, J=6.1 Hz, 1H), 6.46 (t, J=72.3 Hz, 1H), 6.53 (d, J=8.7 Hz, 1H), 7.11-7.16 (m, 2H), 7.46 (d, J=8.7 Hz, 1H).

MS Calcd.: 531; MS Found: 532 (M+H).

Anal. Calcd for $C_{23}H_{23}N_5O_2ClF_5$: C, 51.94; H, 4.36; N, 13.17. Found: C, 51.79; H, 4.44; N, 12.88.

Example 297

9-Chloro-6-[1-(difluoromethoxy)-2,2,2-trifluoroethyl]-1-[2-methyl-6-(4-methylpiperazin-1-yl)pyridin-3-yl]-1,2,3,4-tetrahydropyrimido[1,2-a]benzimidazole

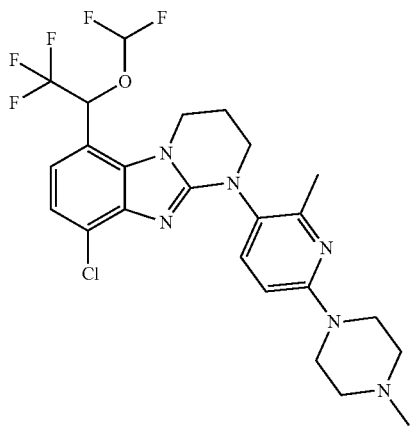 [SMILES: Cc1nc(N2CCN(C)CC2)ccc1N1CCCn2c1nc1c(Cl)ccc(C(OC(F)F)C(F)(F)F)c12]

To a solution of 5-{9-chloro-6-[1-(difluoromethoxy)-2,2,2-trifluoroethyl]-3,4-dihydropyrimido[1,2-a]benzimidazol-1(2H)-yl}-6-methylpyridin-2-yl trifluoromethanesulfonate (113.7 mg, 0.191 mmol) in N,N-dimethylformamide (1.5 mL) was added 1-methylpiperadine (106.0 μL, 0.956 mmol). The reaction mixture was stirred at 80° C. for 18 hrs. The reaction mixture was diluted with water and extracted with ethyl acetate (×3). The combined organic layer was washed with water (×2) and brine (×1), dried over anhydrous magnesium sulfate, filtered and concentrated in vacuo. The residue was purified by basic silica gel column chromatography eluting with a 20-60% ethyl acetate/n-hexane gradient mixture. The resulting solid was recrystallized from ethyl acetate/n-hexane to give a title compound as a colorless powder (76.8 mg, 0.141 mmol, 74%).

mp 193-195° C.

$^1$H NMR (CDCl$_5$) δ 2.36 (s, 6H), 2.37-2.46 (m, 2H) 2.53 (t, J=5.1 Hz, 4H), 3.53-3.74 (m, 6H), 4.21-4.45 (m, 2H), 6.01 (q, J=5.8 Hz, 1H), 6.40 (d, J=72.3 Hz, 1H), 6.54 (d, J=9.0 Hz, 1H), 7.11 (d, J=9.0 Hz, 1H), 7.15 (d, J=9.0 Hz, 1H), 7.43 (d, J=9.0 Hz, 1H).

MS Calcd.: 544; MS Found: 545 (M+H).

Anal: Calcd for $C_{24}H_{26}N_6OClF_5$: C, 52.19; H, 4.81; N, 15.42; Cl, 6.51; F, 17.43. Found: C, 52.83; H, 4.83; N, 15.14.

Example 298

5-{9-Chloro-6-[1-(difluoromethoxy)-2,2,2-trifluoroethyl]-3,4-dihydropyrimido[1,2-a]benzimidazol-1(2H)-yl}-N,N,6-trimethylpyridin-2-amine

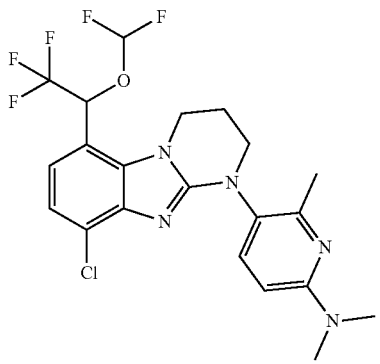 [SMILES: Cc1nc(N(C)C)ccc1N1CCCn2c1nc1c(Cl)ccc(C(OC(F)F)C(F)(F)F)c12]

A mixture of 5-{9-chloro-6-[1-(difluoromethoxy)-2,2,2-trifluoroethyl]-3,4-dihydropyrimido[1,2-a]benzimidazol-1(2H)-yl}-6-methylpyridin-2-yl trifluoromethanesulfonate (122.3 mg, 0.206 mmol) and dimethylamine (2.0 M tetrahydrofuran solution, 1.0 mL) was stirred at 70° C. for 24 hrs. The reaction mixture was concentrated in vacuo. The residue was purified by silica gel column chromatography eluting with a 0-40% ethyl acetate/n-hexane gradient mixture. The resulting solid was recrystallized from ethyl acetate/n-hexane to give a title compound as a colorless powder (67.3 mg, 0.137 mmol, 67%).

mp 233-235° C.

$^1$H NMR (CDCl$_3$) δ 2.36 (s, 3H), 2.37-2.46 (m, 2H), 3.11 (s, 6H), 3.54-3.72 (m, 2H), 4.24-4.38 (m, 2H), 6.01 (q, J=6.0 Hz, 1H), 6.12-6.71 (m, 1H), 6.41 (d, J=8.3 Hz, 1H), 7.10 (d, J=9.0 Hz, 1H), 7.14 (d, J=8.3 Hz, 1H), 7.39 (d, J=9.0 Hz, 1H).

MS Calcd.: 489; MS Found: 490 (M+H).

Anal. Calcd for C$_{21}$H$_{21}$N$_5$OClF$_5$: C, 51.49; H, 4.32; N, 14.3; Cl, 7.24; F, 19.39. Found: C, 51.22; H, 4.29; N, 14.06.

Example 299

5-{9-Chloro-6-[1-(difluoromethoxy)-2,2,2-trifluoroethyl]-3,4-dihydropyrimido[1,2-a]benzimidazol-1(2H)-yl}-N-cyclopropyl-6-methylpyridin-2-amine

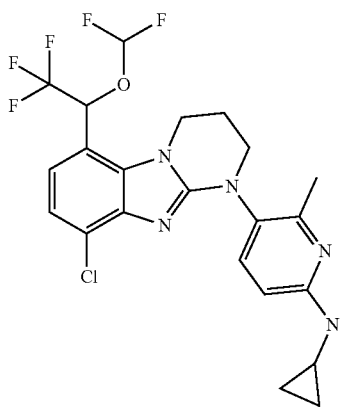 [SMILES: Cc1nc(NC2CC2)ccc1N1CCCn2c1nc1c(Cl)ccc(C(OC(F)F)C(F)(F)F)c12]

A mixture of 5-{9-chloro-6-[1-(difluoromethoxy)-2,2,2-trifluoroethyl]-3,4-dihydropyrimido[1,2-a]benzimidazol-1(2H)-yl}-6-methylpyridin-2-yl trifluoromethanesulfonate (130.4 mg, 0.219 mmol) and cyclopropylamine (2.0 mL) was stirred at 60° C. for 25.5 hrs. The reaction mixture was concentrated in vacuo. The residue was purified by silica gel column chromatography eluting with a 10-60% ethyl acetate/n-hexane gradient mixture. The resulting solid was recrystallized from ethyl acetate/n-hexane to give a title compound as a colorless powder (45.6 mg, 0.909 mmol, 42%).

mp 168-170° C.

$^1$H NMR (CDCl$_3$) δ 0.58 (brs, 2 H), 0.72-0.84 (m, 2H), 2.32 (s, 3H), 2.41 (d, J=5.7 Hz, 2H), 2.48-2.61 (m, 1H), 3.64 (d, J=3.0 Hz, 2H), 4.34 (brs, 2H), 5.16 (s, 1H), 6.01 (q, J=5.9 Hz, 1H), 6.41 (t, J=72.7 Hz, 1H), 6.69 (d, J=8.7 Hz, 1 H), 7.06-7.19 (m, 2H), 7.48 (d, J=8.3 Hz, 1H).

MS Calcd.: 501; MS Found: 502 (M+H).

Example 300

[9-Chloro-1-(6-methoxy-2-methylpyridin-3-yl)-1,2,3,4-tetrahydropyrimido[1,2-a]benzimidazol-6-yl]acetonitrile

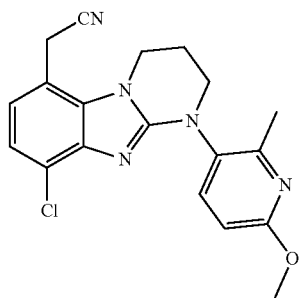 [SMILES: COc1ccc(N2CCCn3c2nc2c(Cl)ccc(CC#N)c23)c(C)n1]

To a solution of [9-chloro-1-(6-methoxy-2-methylpyridin-3-yl)-1,2,3,4-tetrahydropyrimido[1,2-a]benzimidazol-6-yl]acetonitrile (211.0 mg, 0.588 mmol) in tetrahydrofuran (6.0 mL) were added pyridine (4 drops) and thionyl chloride (86 µL, 1.176 mmol) at 0° C. The reaction mixture was stirred at room temperature for 4 hrs. The starting material wasn't consumed completely. To the mixture were added pyridine (2 drops) and thionyl chloride (43 µL, 0.558 mmol). The reaction mixture was stirred at room temperature for 1 day. The mixture was quenched with aqueous saturated ammonium chloride and extracted with ethyl acetate (×3). The combined organic layer was washed with water (×2) and brine (×1), dried over anhydrous magnesium sulfate, filtered and concentrated in vacuo. The crude product was subject to next step without, further purification. To a solution of crude product in dimethylsulfoxide (3.0 mL) was added sodium cyanide (57.6 mg, 1.176 mmol) in water (200 µL). The reaction mixture was stirred at room temperature for 30 min. The mixture was quenched with aqueous saturated ammonium chloride and water. The generated precipitate was collected by filtration. The resulting solid was washed with diisopropyl ether to give the title compound as a pale brown powder (178.8 mg, 0.486 mmol, 83% (2 steps)).

$^1$H NMR (CDCl$_3$) δ 2.31-2.50 (m, 5H), 3.66 (t, J=5.3 Hz, 2H), 3.95 (s, 3H), 4.00 (s, 2H), 4.54 (brs, 2H), 6.64 (d, J=8.3 Hz, 1H), 6.80 (d, J=8.3 Hz, 1H), 7.06 (d, J=8.3 Hz, 1H), 7.52 (d, J=8.3 Hz, 1H).

MS Calcd.: 367; MS Found: 368 (M+H).

Example 301

2-[9-Chloro-1-(6-methoxy-2-methylpyridin-3-yl)-1,2,3,4-tetrahydropyrimido[1,2-a]benzimidazol-6-yl]butanenitrile

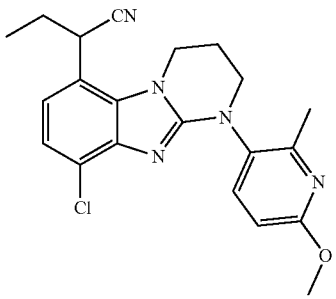 [SMILES: CCC(C#N)c1ccc(Cl)c2nc3n(c12)CCCN3c1ccc(OC)nc1C]

To a solution of [9-chloro-1-(6-methoxy-2-methylpyridin-3-yl)-1,2,3,4-tetrahydropyrimido[1,2-a]benzimidazol-6-yl]acetonitrile (176.0 mg, 0.478 mmol) in tetrahydrofuran (4.5 mL) was added ethyl iodide (57.3 µL, 0.717 mmol) and potassium tert-butoxide (75.8 mg, 0.574 mmol) at 0° C. The reaction mixture was stirred at 0° C. for 1 hr under nitrogen atmosphere. The mixture was quenched with aqueous saturated ammonium chloride and extracted with ethyl acetate (×3). The combined organic layer was washed with brine (×1), dried over anhydrous magnesium sulfate, filtered and concentrated in vacuo. The residue was purified by silica gel column chromatography eluting with a 0-60% ethyl acetate/n-hexane gradient mixture to give the title compound as a colorless powder (154.3 mg, 0.390 mmol, 82%).

$^1$H NMR (CDCl$_3$) δ 1.18 (t, J=7.4 Hz, 3H), 1.93-2.14 (m, 2H), 2.34-2.50 (m, 5H), 3.65 (t, J=5.5 Hz, 2H), 3.95 (s, 3H), 4.23-4.39 (m, 2H), 4.47 (brs, 1H), 6.64 (d, J=8.3 Hz, 1H), 7.00 (d, J=8.3 Hz, 1H), 7.11 (d, J=8.3 Hz, 1H), 7.52 (d, J=8.3 Hz, 1H).

MS Calcd.: 395; MS Found: 396 (M+H).

Example 302

2-[9-Chloro-1-(6-methoxy-2-methylpyridin-3-yl)-1,2,3,4-tetrahydropyrimido[1,2-a]benzimidazol-6-yl]butanal

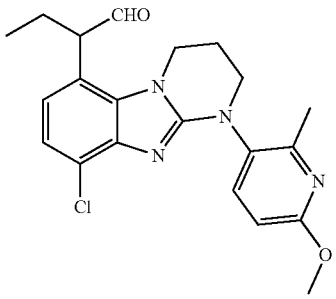 [SMILES: CCC(C=O)c1ccc(Cl)c2nc3n(c12)CCCN3c1ccc(OC)nc1C]

To a solution of 2-[9-chloro-1-(6-methoxy-2-methylpyridin-3-yl)-1,2,3,4-tetrahydropyrimido[1,2-a]benzimidazol-6-yl]butanenitrile (83.4 mg, 0.211 mmol) in toluene (2.0 mL) was added diisobutylaluminum hydride (0.28 mL, 0.421 mmol) at 0° C. The reaction mixture was stirred at 0° C. for 2 hrs under nitrogen atmosphere. The mixture was quenched with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified by silica gel column chromatography eluting with a 0-60% ethyl acetate/n-hexane gradient mixture to give the title compound as a colorless amorphous (24.2 mg, 0.0607 mmol, 29%).

$^1$H NMR (CDCl$_3$) δ 1.01 (t, J=7.4 Hz, 3H), 1.84-2.01 (m, 1H), 2.10-2.29 (m, 1H), 2.32-2.44 (m, 5H), 3.55-3.73 (m, 3H), 3.94 (s, 3H), 4.23-4.40 (m, 1H), 4.58 (brs, 1H), 6.62 (d, J=8.7 Hz, 1H), 6.72 (d, J=8.3 Hz, 1H), 7.09 (d, J=8.3 Hz, 1H), 7.51 (d, J=8.7 Hz, 1 H), 9.60 (d, J=3.0 Hz, 1H).

MS Calcd.: 398; MS Found: 399 (M+H).

Example 303

9-Chloro-6-[1-(difluoromethyl)propyl]-1-(6-methoxy-2-methylpyridin-3-yl)-1,2,3,4-tetrahydropyrimido[1,2-a]benzimidazole

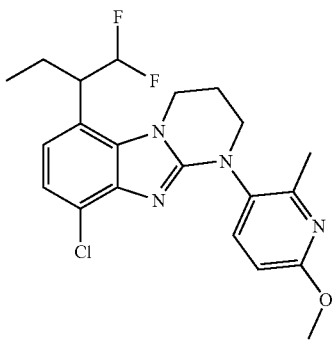 [SMILES: CCC(c1ccc(Cl)c2nc3n(c12)CCCN3c1ccc(OC)nc1C)C(F)F]

To a solution of 2-[9-chloro-1-(6-methoxy-2-methylpyridin-3-yl)-1,2,3,4-tetrahydropyrimido[1,2-a]benzimidazol-6-yl]butanal (24.0 mg, 0.0602 mmol) in acetonitrile (0.5 mL) was added bis-2-(methoxyethyl)aminosulfur trifluoride (44.3 µL, 0.241 mmol) at 0° C. The reaction mixture was stirred at 0° C. for 1 hr. The mixture was quenched with aqueous saturated sodium hydrogen carbonate and extracted with ethyl acetate (×3). The combined organic layer was washed with brine (×1), dried over anhydrous magnesium sulfate, filtered and concentrated in vacuo. The residue was purified by silica gel column chromatography eluting with a 0-40% ethyl acetate/n-hexane gradient mixture to give the title compound as a colorless amorphous (8.5 mg, 0.0202 mmol, 34%).

$^1$H NMR (CDCl$_3$) δ 0.82-0.95 (m, 3H), 1.76-1.95 (m, 1H), 1.95-2.14 (m, 1H), 2.30-2.48 (m, 5H), 3.53-3.77 (m, 3H), 3.95 (s, 3H), 4.31 (brs, 1H), 4.50 (brs, 1H), 5.88 (dt, J=5.7, 56.9 Hz, 1H), 6.64 (d, J=8.3 Hz, 1H), 6.81 (d, J=8.3 Hz, 1H), 7.10 (d, J=8.7 Hz, 1H), 7.54 (d, J=8.7 Hz, 1H)

MS Calcd.: 420; MS Found: 421 (M+H).

Example 304

9-Chloro-1-(2,4-dichlorophenyl)-6-(1-fluoropropyl)-1,2,3,4-tetrahydropyrimido[1,2-a]benzimidazole

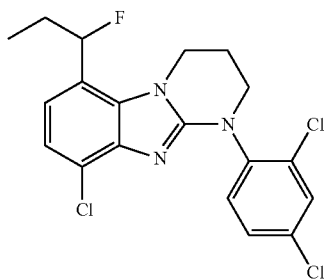 [SMILES: CCC(F)c1ccc(Cl)c2nc3n(c12)CCCN3c1ccc(Cl)cc1Cl]

To a stirred suspension of 1-[9-chloro-1-(2,4-dichlorophenyl)-1,2,3,4-tetrahydropyrimido[1,2-a]benzimidazol-6-yl]propan-1-ol (82.1 mg, 0.200 mmol) in acetonitrile (1.0 mL) was added bis(2-methoxyethyl)aminosulfur trifluoride at room temperature. After 15 h, the reaction mixture was diluted with ethyl acetate, washed with aqueous sodium hydrogen carbonate and brine, dried over sodium sulfate, filtered, and concentrated in vacuo. The residue was purified by flash column chromatography on silica gel eluting with a 0-30% ethyl acetate/n-hexane gradient mixture to give the title compound as a colorless solid (63.8 mg, 0.155 mmol, 77%). Analytically pure material was obtained by recrystallization from ethyl acetate/hexane.

mp 172-174° C.

$^1$H NMR (CDCl$_3$) δ 1.11 (t, J=7.4 Hz, 3H), 1.90-2.33 (m, 2H), 2.32-2.48 (m, 2H), 3.59-3.89 (m, 2H), 4.32-4.45 (m, 1H), 4.46-4.58 (m, 1H), 5.80 (ddd, J=48.1, 8.3, 5.5 Hz, 1H), 6.96 (dd, J=8.2, 1.6 Hz, 1H), 7.09 (d, J=8.2 Hz, 1H), 7.32 (dd, J=8.5, 2.2 Hz, 1H), 7.47-7.55 (m, 2H)

MS Calcd.: 411; MS Found: 412 (M+H).

Example 305

9-Chloro-1-(2,4-dichlorophenyl)-6-[1-(ethenyloxy)propyl]-1,2,3,4-tetrahydropyrimido[1,2-a]benzimidazole

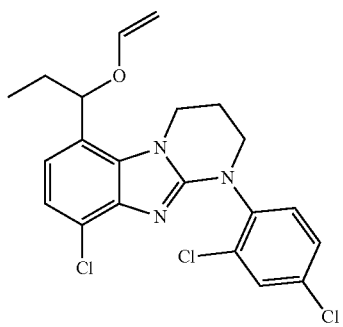 [SMILES: C=COC(CC)c1ccc(Cl)c2nc3n(c12)CCCN3c1ccc(Cl)cc1Cl]

A suspension of 1-[9-chloro-1-(2,4-dichlorophenyl)-1,2,3,4-tetrahydropyrimido[1,2-a]benzimidazol-6-yl]propan-1-ol (329 mg, 0.800 mmol), vinyl acetate (148 μL, 1.60 mmol), di-μ-chlorobis[(η-cycloocta-1,5-diene)iridium (I)] (26.9 mg, 0.0400 mmol) and sodium carbonate (50.9 mg, 0.480 mmol) in o-dichlorobenzene (1.6 mL) was stirred for 3 h at 100° C. After vinyl acetate (148 μL, 1.60 mmol) was added, the reaction mixture was purified by flash column chromatography on silica gel eluting with a 20% ethyl acetate/n-hexane to give the title compound as a pale yellow amorphous (279 mg, 0.638 mmol, 80%).

$^1$H NMR (CDCl$_3$) δ 1.02 (t, J=7.4 Hz, 3H), 1.80-2.02 (m, 2H), 2.33-2.45 (m, 2H), 3.62-3.80 (m, 2H), 4.01 (dd, J=6.6, 1.6 Hz, 1H), 4.30 (dd, J=14.0, 1.6 Hz, 1H), 4.36-4.58 (m, 2H), 5.03-5.12 (m, 1H), 6.33 (dd, J=14.0, 6.6 Hz, 1H), 6.89 (d, J=8.2 Hz, 1H), 7.06 (d, J=8.2 Hz, 1H), 7.31 (dd, J=8.7, 2.3 Hz, 1H), 7.47-7.56 (m, 2H).

Example 306

9-Chloro-6-[1-(cyclopropyloxy)propyl]-1-(2,4-dichlorophenyl)-1,2,3,4-tetrahydropyrimido[1,2-a]benzimidazole

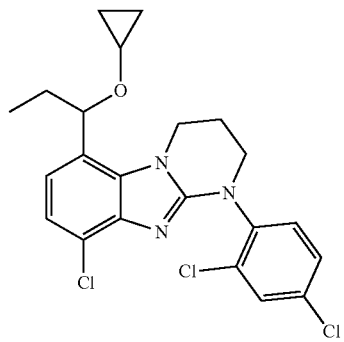 [SMILES: CCC(OC1CC1)c1ccc(Cl)c2nc3n(c12)CCCN3c1ccc(Cl)cc1Cl]

To a stirred solution of 9-chloro-1-(2,4-dichlorophenyl)-6-[1-(ethenyloxy)propyl]-1,2,3,4-tetrahydropyrimido[1,2-a]benzimidazole (246 mg, 0.563 mmol) in dichloromethane (5.6 mL) was added a solution of diethyl zinc in hexane (1.0 M, 2.82 mL, 2.82 mmol) and diiodomethane (454 μL, 5.63 mmol) at 0° C. After 1.5 h, the reaction mixture was diluted with ethyl acetate, quenched with aqueous ammonium chloride, washed with water and brine, dried over sodium sulfate, filtered, and concentrated in vacuo. The residue was purified by flash column chromatography on silica gel eluting with a 0-40% ethyl acetate/n-hexane gradient mixture to give the title compound as a pale yellow solid (233 mg, 0.517 mmol, 92%). Analytically pure material was obtained by recrystallization from ethyl acetate/hexane.

mp 147-149° C.

$^1$H NMR (CDCl$_3$) δ 0.30-0.58 (m, 3H), 0.63-0.74 (m, 1H), 0.94 (t, J=7.4 Hz, 3H), 1.69-1.99 (m, 2H), 2.31-2.49 (m, 2H), 3.16-3.25 (m, 1H), 3.61-3.83 (m, 2H), 4.31-4.46 (m, 1H), 4.53-4.66 (m, 1H), 4.68-4.79 (m, 1H), 6.99 (d, J=8.2 Hz, 1H), 7.09 (d, J=8.2 Hz, 1H), 7.32 (dd, J=8.5, 2.2 Hz, 1H), 7.50 (d, 2.2 Hz, 1H), 7.54 (d, J=8.5 Hz, 1H).

MS Calcd.: 449; MS Found: 450 (M+H).

Example 307

1-[9-Chloro-1-(2,4-dichlorophenyl)-1,2,3,4-tetrahydropyrimido[1,2-a]benzimidazol-6-yl]-2,2,2-trifluoroethanol

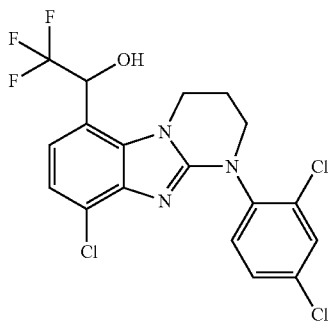 [SMILES: OC(c1ccc(Cl)c2nc3n(c12)CCCN3c1ccc(Cl)cc1Cl)C(F)(F)F]

To a stirred solution of 9-chloro-1-(2,4-dichlorophenyl)-1,2,3,4-tetrahydropyrimido[1,2-a]benzimidazole-6-carbaldehyde (500 mg, 1.31 mmol) and trimethyl(trifluoromethyl)silane (582 μL, 3.94 mmol) in tetrahydrofuran (6.5 mL) was added a solution of tetrabutylammonium fluoride in tetrahydrofuran (1.0 M, 131 μL, 0.131 mmol) at 0° C. After 15 min, hydrochloric acid (1.0 M, 2.0 mL) was added. After 30 min, the reaction mixture was diluted with ethyl acetate, washed with aqueous sodium hydrogen carbonate and brine, dried over sodium sulfate, filtered, and concentrated in vacuo. The resulting solid was washed with diisopropyl ether to give the title compound as a colorless solid (590 mg, 1.30 mmol, 99%)

$^1$H NMR (CDCl$_3$) δ 2.16-2.49 (m, 2H), 3.49-3.67 (m, 1H), 3.77-3.98 (m, 1H), 4.16-4.29 (m, 2H), 4.64 (brs, 1H), 5.43 (q, J=6.2 Hz, 1H), 7.11 (d, J=8.3 Hz, 1H), 7.20 (d, J=8.3 Hz, 1H), 7.30-7.40 (m, 1H), 7.45-7.60 (m, 2H).

MS Calcd.: 449; MS Found: 450 (M+H).

Example 308

9-Chloro-6-[1-(cyclopropyloxy)-2,2,2-trifluoroethyl]-1-(2,4-dichlorophenyl)-1,2,3,4-tetrahydropyrimido[1,2-a]benzimidazole

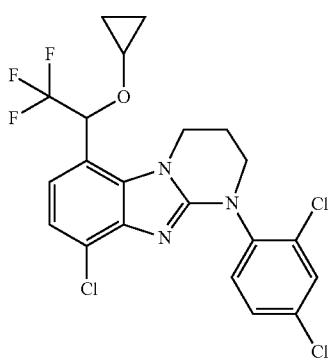 [SMILES: FC(F)(F)C(OC1CC1)c1ccc(Cl)c2nc3n(c12)CCCN3c1ccc(Cl)cc1Cl]

A suspension of 1-[9-chloro-1-(2,4-dichlorophenyl)-1,2,3,4-tetrahydropyrimido[1,2-a]benzimidazol-6-yl]-2,2,2-trifluoroethanol (135 mg, 0.300 mmol), vinyl acetate (277 μL, 3.00 mmol), di-μ-chlorobis[(η-cycloocta-1,5-diene)iridium (I)] (50.4 mg, 0.0750 mmol) and sodium carbonate (19.1, mg, 0.180 mmol) in o-dichlorobenzene (3.0 mL) was stirred for 27 h at 100° C. The reaction mixture was purified by flash column chromatography on silica gel eluting with a 25% ethyl acetate/n-hexane. The obtained compound was dissolved in dichloromethane (1.6 mL). A solution of diethyl zinc in hexane (1.0 M, 818 μL, 0.818 mmol) and diiodomethane (132 μL, 1.64 mmol) was added at 0° C. After being stirred for 4 h at room temperature, the reaction mixture was diluted with ethyl acetate, quenched with aqueous ammonium chloride, washed with water and brine, dried over sodium sulfate, filtered, and concentrated in vacuo. The residue was purified by flash column chromatography on NH silica gel eluting with a 0-12% ethyl acetate/n-hexane gradient mixture to give the title compound as a colorless solid (62.9 mg, 0.110 mmol, 37%). Analytically pure material was obtained by recrystallization from ethyl acetate/hexane.

mp 197-200° C.

$^1$H NMR (CDCl$_3$) δ 0.42-0.75 (m, 3H), 0.77-0.91 (m, 1H), 2.31-2.52 (m, 2H), 3.44-3.54 (m, 1H), 3.62-3.84 (m, 2H), 4.28-4.52 (m, 2H), 5.28 (q, J=6.8 Hz, 1H), 7.14 (s, 2H), 7.33 (dd, J=8.5, 2.5 Hz, 1H), 7.47-7.57 (m, 2H).

MS Calcd.: 489; MS Found: 490 (M+H).

Example 309

9-Chloro-1-(2,4-dichlorophenyl)-6-(2,2,2-trifluoro-1-methoxyethyl)-1,2,3,4-tetrahydropyrimido[1,2-a]benzimidazole

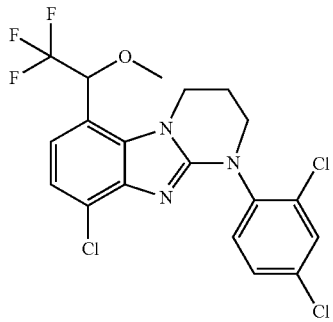 [SMILES: COC(c1ccc(Cl)c2nc3n(c12)CCCN3c1ccc(Cl)cc1Cl)C(F)(F)F]

To a stirred solution of 1-[9-chloro-1-(2,4-dichlorophenyl)-1,2,3,4-tetrahydropyrimido[1,2-a]benzimidazol-6-yl]-2,2,2-trifluoroethanol (67.6 mg, 0.150 mmol) in tetrahydrofuran (1.0 mL) was added sodium hydride (60% in oil, 7.2 mg, 0.18 mmol) at 0° C. After 15 min, iodomethane (46.7 μL, 0.75 mmol) was added. After being stirred for 1.5 h at room temperature, the reaction mixture was diluted with ethyl acetate, washed with aqueous sodium hydrogen carbonate and brine, dried over sodium sulfate, filtered, and concentrated in vacuo. The residue was purified by flash column chromatography on silica gel eluting with a 0-50% ethyl acetate/n-hexane gradient mixture to give the title compound as a colorless solid (67.2 mg, 0.145 mmol, 96%).

mp 161-163° C.

$^1$H NMR (CDCl$_3$) δ 2.31-2.48 (m, 2H), 3.46 (s, 3H), 3.63-3.83 (m, 2H), 4.28-4.50 (m, 2H), 5.10 (q, J=6.7 Hz, 1H), 7.03-7.11 (m, J=8.2 Hz, 1H), 7.12-7.18 (m, J=8.2 Hz, 1H), 7.33 (dd, J=8.5, 2.5 Hz, 1H), 7.46-7.58 (m, 2H).

MS Calcd.: 463; MS Found: 464 (M+H).

Analytically pure material was obtained by recrystallization from ethyl acetate/hexane.

Example 310

9-Chloro-1-(2,4-dichlorophenyl)-6-(1-ethoxy-2,2,2-trifluoroethyl)-1,2,3,4-tetrahydropyrimido[1,2-a]benzimidazole

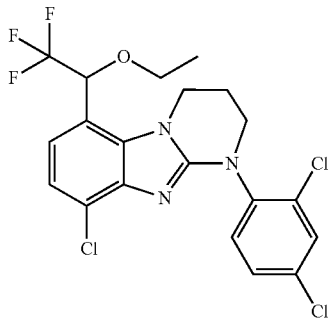 [SMILES: CCOC(c1ccc(Cl)c2nc3n(c12)CCCN3c1ccc(Cl)cc1Cl)C(F)(F)F]

To a stirred solution of 1-[9-chloro-1-(2,4-dichlorophenyl)-1,2,3,4-tetrahydropyrimido[1,2-a]benzimidazol-6-yl]-2,2,2-trifluoroethanol (67.6 mg, 0.150 mmol) in tetrahydrofuran (1.0 mL) was added sodium hydride (60% in oil, 7.2 mg, 0.18 mmol) at 0° C. After 15 min iodoethane (60.0 µL, 0.75 mmol) was added. After being stirred for 8 h at 40° C., the reaction mixture was diluted with ethyl acetate, washed with aqueous sodium, hydrogen carbonate and brine, dried over sodium sulfate, filtered, and concentrated in vacuo. The residue was purified by flash column chromatography on silica gel eluting with a 0-300 ethyl acetate/n-hexane gradient mixture to give the title compound as a colorless solid (58.2 mg, 0.122 mmol, 81%). Analytically pure material was obtained by recrystallization from ethyl acetate/hexane.

mp 129-131° C.

$^1$H NMR (CDCl$_3$) δ 1.29 (t, J=7.0 Hz, 3H), 2.33-2.50 (m, 2H), 3.51-3.80 (m, 4H), 4.27-4.40 (m, 1H), 4.44-4.57 (m, 1H), 5.18 (q, J=6.5 Hz, 1H), 7.05-7.18 (m, 2H), 7.33 (dd, J=8.8, 2.2 Hz, 1H), 7.46-7.55 (m, 2H).

MS Calcd.: 477; MS Found: 478 (M+H).

Example 311

1-[9-Chloro-1-(2,4-dichlorophenyl)-1,2,3,4-tetrahydropyrimido[1,2-a]benzimidazol-6-yl]-2,2,2-trifluoroethyl acetate

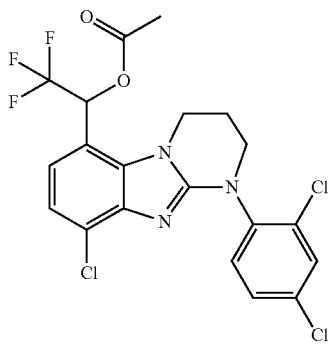 [SMILES: CC(=O)OC(c1ccc(Cl)c2nc3n(c12)CCCN3c1ccc(Cl)cc1Cl)C(F)(F)F]

To a stirred solution of 1-[9-chloro-1-(2,4-dichlorophenyl)-1,2,3,4-tetrahydropyrimido[1,2-a]benzimidazol-6-yl]-2,2,2-trifluoroethanol (84.1 mg, 0.187 mmol) and triethylamine (33.8 µL, 0.242 mmol) in tetrahydrofuran (1.0 mL) was added acetyl chloride (15.9 µL, 0.224 mmol) at 0° C. After 1 h, triethylamine (18.2 µL, 0.131 mmol) and acetyl chloride (8.0 µL, 0.112, mmol) was added. After 1 h, the reaction mixture was quenched with water, concentrated in vacuo, and purified by flash column chromatography on silica gel eluting with a 0-30% ethyl acetate/n-hexane gradient mixture to give the title compound as a colorless solid (93.2 mg, 0.187 mmol, 100%). Analytically pure material was obtained by recrystallization from ethyl acetate/hexane.

mp 197-199° C.

$^1$H NMR (CDCl$_3$) δ 2.22 (s, 3H), 2.37-2.53 (m, 2H), 3.60-3.83 (m, 2H), 4.32-4.44 (m, 1H), 4.53-4.69 (m, 1H), 6.84 (q, J=6.6 Hz, 1H), 7.15 (s, 2H), 7.33, (dd, J=8.7, 2.3 Hz, 1H), 7.49-7.53 (m, 2H).

MS Calcd.: 491; MS Found: 492 (M+H).

Example 312

9-Chloro-1-(2,4-dichlorophenyl)-6-[1-(difluoromethoxy)-2,2,2-trifluoroethyl]-1,2,3,4-tetrahydropyrimido[1,2-a]benzimidazole

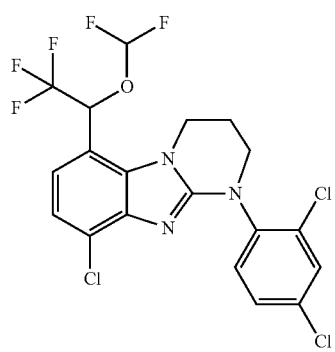

A solution of 1-[9-chloro-1-(2,4-dichlorophenyl)-1,2,3,4-tetrahydropyrimido[1,2-a]benzimidazol-6-yl]-2,2,2-trifluoroethanol (75.1 mg, 0.167 mmol) in tetrahydrofuran (0.5 mL) and aqueous sodium hydroxide (8 M, 0.2 mL) was stirred for 3 h at 50° C. under chloro(difluoro)methane atmosphere. The reaction mixture was diluted with ethyl acetate, washed with brine, dried over sodium sulfate, filtered, and concentrated in vacuo. The residue was purified by flash column chromatography on silica gel eluting with a 0-30% ethyl acetate/n-hexane gradient mixture to give the title compound as a colorless solid (38.7 mg, 0.0734 mmol, 44%). Analytically pure material was obtained by recrystallization from ethyl acetate/hexane.

mp 200-202° C.

$^1$H NMR (CDCl$_3$) δ 2.38-2.55 (m, 2H), 3.62-3.85 (m, 2H), 4.27-4.43 (m, 2H), 6.02 (q, J=5.9 Hz, 1H), 6.42 (t, J=72.2 Hz, 1H), 7.17 (s, 2H), 7.34 (dd, J=8.5, 2.2 Hz, 1H), 7.48-7.56 (m, 2H).

MS Calcd.: 499; MS Found: 500 (M+H).

Example 313

(−)-9-Chloro-1-(2,4-dichlorophenyl)-6-[1-(difluoromethoxy)-2,2,2-trifluoroethyl]-1,2,3,4-tetrahydropyrimido[1,2-a]benzimidazole

Example 314

(+)-9-Chloro-1-(2,4-dichlorophenyl)-6-[1-(difluoromethoxy)-2,2,2-trifluoroethyl]-1,2,3,4-tetrahydropyrimido[1,2-a]benzimidazole

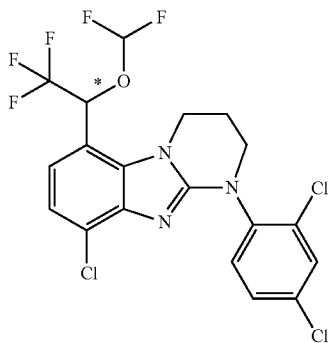 [SMILES: FC(F)OC(c1ccc(Cl)c2nc3n(c12)CCCN3c1ccc(Cl)cc1Cl)C(F)(F)F]

Racemic Example 312 (2570 mg) was resolved by preparative HPLC, using CHIRALCEL OD (5 cm i.d.×50 cm, Daicel Chemical Industries, Ltd.) with the flow rate of 60 mL/min at 30° C. and hexane/ethanol (50/50) as the mobile phase, and obtaining the stereoisomer having a shorter retention time 1262 mg in an enantiomer excess of 99.2% and the stereoisomer having a longer retention time 1253 mg in an enantiomer excess of 99.8%. The obtained compounds (shorter retention time: 237 mg, longer retention time: 209 mg) were recrystallized from ethyl acetate/hexane to give the optically active title compounds as a colorless crystal respectively (shorter retention time (Example 313): 175 mg, longer retention time (Example 314): 171 mg).

Shorter Retention Time (Example 313):

[α]$_D^{20}$=−41.2 (c=0.5030, MeOH)

mp 150-152° C.

$^1$H NMR (CDCl$_3$) δ 2.38-2.56 (m, 2H), 3.65-3.86 (m, 2H), 4.29-4.43 (m, 2H), 6.02 (q, J=6.0 Hz, 1H), 6.41 (t, J=72.3 Hz, 1H), 7.16 (s, 2H), 7.33 (dd, J=8.7, 2.3 Hz, 1H), 7.48-7.55 (m, 2H).

MS Calcd.: 499; MS Found: 500 (M+H).

Anal. Calcd for C$_{19}$H$_{13}$N$_3$Cl$_3$F$_5$O: C, 45.58; H, 2.62; N, 8.39. Found: C, 45.50; H, 2.62; N, 8.22.

Longer Retention Time (Example 314):

[α]$_D^{20}$=+41.7 (c=0.5090, MeOH)

mp 150-152° C.

$^1$H NMR (CDCl$_3$) δ 2.38-2.54 (m, 2H), 3.64-3.85 (m, 2H), 4.26-4.43 (m, 2H), 6.02 (q, J=6.2 Hz, 1H), 6.41 (t, J=72.3 Hz, 1H), 7.16 (s, 2H), 7.33 (dd, J=8.7, 2.3 Hz, 1H), 7.48-7.55 (m, 2H).

MS Calcd.: 499; MS Found: 500 (M+H).

Anal. Calcd for C$_{19}$H$_{13}$N$_3$Cl$_3$F$_5$O: C, 45.58; H, 2.62; N, 8.39. Found: C, 45.54; H, 2.71; N, 8.23.

Example 315

3-[9-Chloro-1-(2,4-dichlorophenyl)-1,2,3,4-tetrahydropyrimido[1,2-a]benzimidazol-6-yl]pentanamide

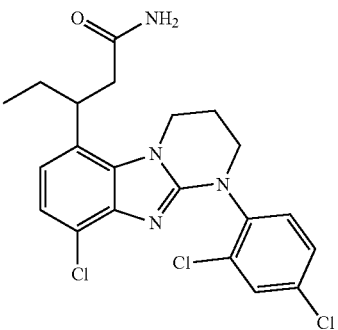 [SMILES: CCC(CC(N)=O)c1ccc(Cl)c2nc3n(c12)CCCN3c1ccc(Cl)cc1Cl]

A solution of ethyl 3-[9-chloro-1-(2,4-dichlorophenyl)-1,2,3,4-tetrahydropyrimido[1,2-a]benzimidazol-6-yl]pentanoate (173 mg, 0.360 mmol) and aqueous sodium hydroxide (8 M, 0.09 mL) in tetrahydrofuran (1.8 mL) was stirred for 24 h at reflux. The reaction mixture was concentrated in vacuo. To the residue was added tetrahydrofuran (3.0 mL) and ethyl chloroformate (74.3 μL, 0.780 mmol) at 0° C. After being stirred for 1.5 h at room temperature, the reaction mixture was cooled down to 0° C. And then aqueous ammonia solution (28%, 150 μL) was added. After 2 h, the reaction mixture was diluted with ethyl acetate, washed with brine, dried over sodium sulfate, filtered, and concentrated in vacuo. The residue was purified by flash column chromatography on NH silica gel eluting with ethyl acetate to give the title compound as a colorless solid (60.1 mg, 0.133 mmol, 37%).

$^1$H NMR (CDCl$_3$) δ 0.86 (t, J=7.3 Hz, 3 H), 1.68-1.90 (m, 2H), 2.30-2.44 (m, 2H), 2.46-2.66 (m, 2H), 3.59-3.77 (m, 2H), 3.77-3.90 (m, 1H), 4.27-4.39 (m, 1H), 4.72-4.86 (m, 1H), 5.12 (brs, H), 5.27 (brs, 1H), 6.76 (d, J=8.5 Hz, 1H), 7.06 (d, J=8.5 Hz, 1H), 7.29 (dd, J=8.6, 2.3 Hz, 1H), 7.44-7.55 (m, 2H)

MS Calcd.: 450; MS Found: 451 (M+H).

Example 316

3-[9-Chloro-1-(2,4-dichlorophenyl)-1,2,3,4-tetrahydropyrimido[1,2-a]benzimidazol-6-yl]pentanenitrile

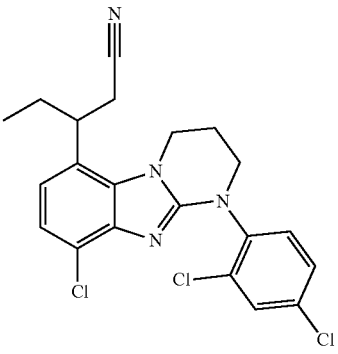 [SMILES: CCC(CC#N)c1ccc(Cl)c2nc3n(c12)CCCN3c1ccc(Cl)cc1Cl]

To a stirred solution of 3-[9-chloro-1-(2,4-dichlorophenyl)-1,2,3,4-tetrahydropyrimido[1,2-a]benzimidazol-6-yl]pentanamide (60.1 mg, 0.133 mmol) and triethylamine (112 µL, 0.800 mmol) in tetrahydrofuran (1.5 mL) was added trifluoroacetic anhydride (55.6 µL, 0.400 mmol) at 0° C. After 0.5 h, the reaction mixture was diluted with ethyl acetate, washed with brine, dried over sodium sulfate, filtered, and concentrated in vacuo. The residue was purified by flash column chromatography on silica gel eluting with a 0-70% ethyl acetate/n-hexane gradient mixture give the title compound as a colorless amorphous (45.1 mg, 0.104 mmol, 78%).

$^{1}$H NMR (CDCl$_{3}$) δ 0.91 (t, J=7.3 Hz, 3H), 1.80-2.01 (m, 2H), 2.31-2.51 (m, 2H), 2.57-2.83 (m, 2H), 3.52-3.86 (m, 3H), 4.29-4.53 (m, 2H), 6.77 (d, J=8.5 Hz, 1H), 7.10 (d, J=8.5 Hz, 1H), 7.32 (dd, J=8.5, 2.5 Hz, 1H), 7.44-7.60 (m, 2H).

MS Calcd.: 432; MS Found: 433 (M+H).

Example 317

3-[9-chloro-1-(2,4-dichlorophenyl)-1,2,3,4-tetrahydropyrimido[1,2-a]benzimidazol-6-yl]-1,1,1-trifluoropentan-2-ol

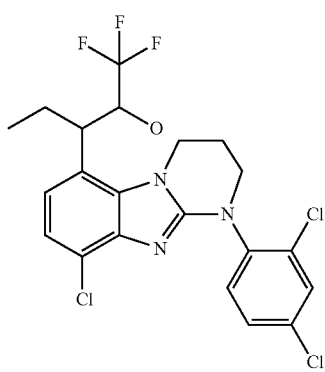 [SMILES: CCC(c1ccc(Cl)c2nc3n(c12)CCCN3c1ccc(Cl)cc1Cl)C(O)C(F)(F)F]

To a stirred solution of 2-[9-chloro-1-(2,4-dichlorophenyl)-1,2,3,4-tetrahydropyrimido[1,2-a]benzimidazol-6-yl]butanal (51.8 mg, 0.123 mmol) and trimethyl(trifluoromethyl)silane (54.3 µL, 0.368 mmol) in tetrahydrofuran (0.6 mL) was added a solution of tetrabutylammonium fluoride in tetrahydrofuran (1.0 M, 12.3 µL, 0.0123 mmol) at 0° C. After 30 min, hydrochloric acid (1.0 M, 0.25 mL) was added. After 1 h, the reaction mixture was diluted with ethyl acetate, washed with aqueous sodium hydrogen carbonate and brine, dried over sodium sulfate, filtered, and concentrated in vacuo. The residue was purified by flash column chromatography on silica gel eluting with a 0-50% ethyl acetate/n-hexane gradient mixture to give the title compound as a colorless oil (49.0 mg, 0.0995 mmol, 81%).

MS Calcd.: 491; MS Found: 492 (M+H).

Example 318

3-[9-Chloro-1-(2,4-dichlorophenyl)-1,2,3,4-tetrahydropyrimido[1,2-a]benzimidazol-6-yl]-1,1,1-trifluoropentan-2-one

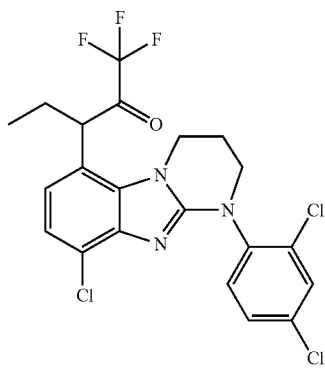 [SMILES: CCC(C(=O)C(F)(F)F)c1ccc(Cl)c2nc3n(c12)CCCN3c1ccc(Cl)cc1Cl]

To a stirred solution of 3-[9-chloro-1-(2,4-dichlorophenyl)-1,2,3,4-tetrahydropyrimido[1,2-a]benzimidazol-6-yl]-1,1,1-trifluoropentan-2-ol (47.4 mg, 0.0961 mmol) in acetonitrile (0.6 mL) was added Dess-Martin reagent (48.9 mg, 0.115 mmol) at room temperature. After 1 h, the reaction mixture was concentrated in vacuo and purified by flash column chromatography on NH silica gel eluting with a 0-10% methanol/ethyl acetate gradient mixture to give the title compound as a colorless amorphous (33.3 mg, 0.0678 mmol, 71%).

$^{1}$H NMR (CDCl$_{3}$) δ 0.96 (t, J=7.3 Hz, 3H), 1.82-2.03 (m, 1H), 2.12-2.32 (m, 1H), 2.37-2.57 (m, 2H), 3.59-3.88 (m, 2H), 4.32-4.52 (m, 2H), 4.60 (t, J=7.3 Hz, 1H), 6.62 (d, J=8.2 Hz, 1H), 7.07 (d, J=8.3 Hz, 1H), 7.33 (dd, J=8.7, 2.3 Hz, 1H), 7.44-7.60 (m, 2H).

MS Calcd.: 489; MS Found: 490 (M+H).

Example 319

2-[9-Chloro-1-(2,4-dichlorophenyl)-1,2,3,4-tetrahydropyrimido[1,2-a]benzimidazol-6-yl]-1,1,1,3,3,3-hexafluoropropan-2-ol

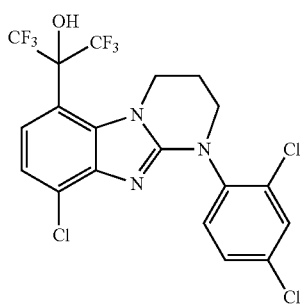 [SMILES: OC(c1ccc(Cl)c2nc3n(c12)CCCN3c1ccc(Cl)cc1Cl)(C(F)(F)F)C(F)(F)F]

To a stirred solution of a solution of methyl 9-chloro-1-(2,4-dichlorophenyl)-1,2,3,4-tetrahydropyrimido[1,2-a]benzimidazole-6-carboxylate (103 mg, 0.818 mmol) and trimethyl(trifluoromethyl)silane (185 µL, 1.25 mmol) in tetrahydrofuran (1.25 mL) was added a solution of tetrabutylammonium fluoride in tetrahydrofuran (1.0 M, 50.0 μL, 0.0500 mmol) at room temperature. After being stirred for 6 h at 50° C., trimethyl(trifluoromethyl)silane (185 μL, 1.25 mmol) was added. After 15 h, the reaction mixture was diluted with ethyl acetate, quenched with aqueous ammonium chloride, washed with and brine: dried over sodium sulfate, filtered, and concentrated in vacuo. The residue was purified by flash column chromatography on NH silica gel eluting with a 0-15% methanol/ethyl acetate gradient mixture and on silica gel eluting with ethyl acetate/hexane to give the title compound as a colorless solid (45.2 mg, 0.0871 mmol, 35%). Analytically pure material was obtained by recrystallization from ethyl acetate/hexane.

mp 237-240° C.

$^1$H NMR (CDCl$_3$) δ 2.15-2.35 (m, 2H), 3.57-3.80 (m, 2H), 4.01 (s, 1H), 4.50 (t, J=6.1 Hz, 2H), 7.13 (s, 2H), 7.33 (dd, J=8.5, 2.5 Hz, 1H), 7.48 (d, J=8.5 Hz, 1H), 7.51 (d, J=2.5 Hz, 1H).

MS Calcd.: 517 MS Found: 518 (M+H).

Example 320

9-Chloro-N,N-dicyclopropyl-1-(2,4-dichlorophenyl)-1,2,3,4-tetrahydropyrimido[1,2-a]benzimidazol-6-amine

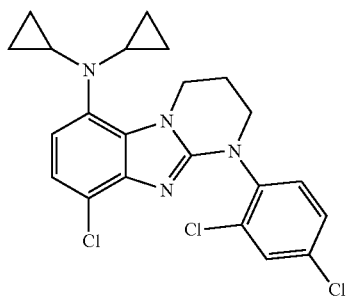 [SMILES: Clc1ccc(N2CCCn3c2nc2c(Cl)ccc(N(C4CC4)C4CC4)c23)c(Cl)c1]

A solution of 9-chloro-1-(2,4-dichlorophenyl)-1,2,3,4-tetrahydropyrimido[1,2-a]benzimidazol-6-amine (367 mg, 1.00 mmol), (1-ethoxycyclopropoxy)trimethylsilane (1.01 mL, 5.00 mmol), sodium cyanoborohydride (314 mg, 5.00 mmol), and acetic acid (572 μL, 10.0 mmol) in methanol (3.0 mL) was stirred at reflux for 40 h. The reaction mixture was diluted with ethyl acetate, quenched with aqueous sodium hydrogen carbonate, and filtrated. The organic layer was washed with brine, dried over sodium sulfate, filtered, and concentrated in vacuo. The residue was purified by flash column chromatography on silica gel eluting with a 20% ethyl acetate/hexane mixture to give the title compound as a colorless solid (83.5 mg, 0.186 mmol, 19%). Analytically pure material was obtained by recrystallization from ethyl acetate/hexane.

mp 211-213° C.

$^1$H NMR (DMSO-d$_6$) δ 0.19-0.42 (m, 4H), 0.46-0.70 (m, 4H), 2.09-2.31 (m, 2H), 2.59-2.77 (m, 2H), 3.53-3.67 (m, 2H), 4.12-4.31 (m, 2H), 6.94 (s, 2H), 7.52 (dd, J=8.5, 2.5 Hz, 1H), 7.63 (d, J=8.5 Hz, 1H), 7.78 (d, J=2.5 Hz, 1H).

MS Calcd.: 446; MS Found: 447 (M+H).

Example 321

9-Chloro-1-(4,6-dimethoxy-2-methylpyrimidin-5-yl)-1,2,3,4-tetrahydropyrimido[1,2-a]benzimidazole-6-carbaldehyde

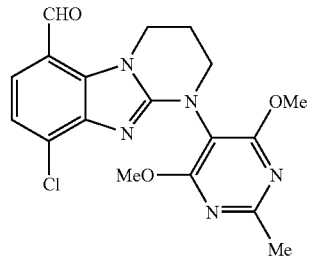 [SMILES: COc1nc(C)nc(OC)c1N1CCCn2c1nc1c(Cl)ccc(C=O)c12]

To a stirred solution of methyl 9-chloro-1-(4,6-dimethoxy-2-methylpyrimidin-5-yl)-1,2,3,4-tetrahydropyrimido[1,2-a]benzimidazole-6-carboxylate (627 mg, 1.50 mmol) in tetrahydrofuran (15 mL) was added lithium borohydride (131 mg, 6.00 mmol) at room temperature. After being stirred for 15 h at ° C., the reaction mixture was quenched with aqueous ammonium chloride, extracted with ethyl acetate, and concentrated in vacuo. The resulting solid was washed with ethyl acetate and dissolved in dimethyl sulfoxide (15 mL). To the solution was added Dess-Martin reagent (1.27 g, 3.00 mmol) at room temperature, and the mixture was stirred for 15 h. The reaction mixture was diluted with ethyl acetate, quenched with aqueous sodium hydrogen carbonate, washed with water and brine, dried over sodium sulfate, filtered, and concentrated in vacuo. The residue was purified by flash column chromatography on silica gel eluting with a 20-80% ethyl acetate/hexane gradient mixture to give the title compound as a pale yellow solid (439 mg, 75%).

$^1$H NMR (CDCl$_3$) δ 2.24-2.36 (m, 2H), 2.56 (s, 3H), 3.54-3.65 (m, 2H), 3.93 (s, 6H), 4.64 (t, J=6.2 Hz, 2H), 7.18 (d, J=8.2 Hz, 1H), 7.32 (d, J=8.2 Hz, 1H), 10.00 (s, 1H).

MS Calcd.: 387; MS Found: 388 (M+H).

Example 322

1-[9-Chloro-1-(4,6-dimethoxy-2-methylpyrimidin-5-yl)-1,2,3,4-tetrahydropyrimido[1,2-a]benzimidazol-6-yl]-2,2,2-trifluoroethanol

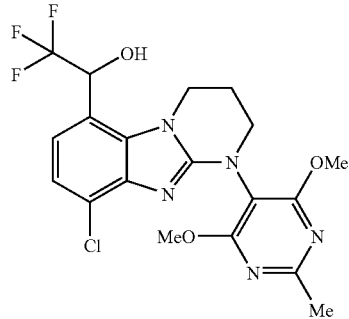 [SMILES: COc1nc(C)nc(OC)c1N1CCCn2c1nc1c(Cl)ccc(C(O)C(F)(F)F)c12]

To a stirred solution of 9-chloro-1-(4,6-dimethoxy-2-methylpyrimidin-5-yl)-1,2,3,4-tetrahydropyrimido[1,2-a]benzimidazole-6-carbaldehyde (433 mg, 1.12 mmol) and trimethyl(trifluoromethyl)silane (495 μL, 3.35 mmol) in tetrahydrofuran (6.0 mL) was added a solution of tetrabutylammonium fluoride in tetrahydrofuran (1.0 M, 112 μL, 0.112 mmol) at 0° C. After 30 min, hydrochloric acid (1.0 M, 2.5 mL) was added. After 1 h, the reaction mixture was diluted with ethyl acetate, washed with aqueous sodium hydrogen carbonate and brine, dried over sodium sulfate, filtered, and concentrated in vacuo. The resulting solid was washed with diisopropyl ether to give the title compound as a pale yellow solid (445 mg, 0.972 mmol, 87%).

MS Calcd.: 447; MS Found: 458 (M+H).

Example 323

9-Chloro-6-[1-(difluoromethoxy)-2,2,2-trifluoroethyl]-1-(4,6-dimethoxy-2-methylpyrimidin-5-yl)-1,2,3,4-tetrahydropyrimido[1,2-a]benzimidazole

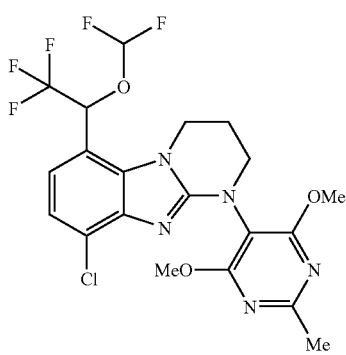 [SMILES: COc1nc(C)nc(OC)c1N1CCCn2c1nc1c(Cl)ccc(C(OC(F)F)C(F)(F)F)c12]

A solution of 1-[9-chloro-1-(4,6-dimethoxy-2-methylpyrimidin-5-yl)-1,2,3,4-tetrahydropyrimido[1,2-a]benzimidazol-6-yl]-2,2,2-trifluoroethanol (437 mg, 0.955 mmol) and benzyltriethylammonium chloride (21.7 mg, 0.0955 mmol) in tetrahydrofuran (5.0 mL) and aqueous sodium hydroxide (8 M, 5.0 mL) was stirred for 30 min at room temperature under chlorodifluoromethane atmosphere. The reaction mixture was diluted with ethyl acetate(washed with water and brine, dried over sodium sulfate filtered, and concentrated in vacuo. The residue was purified by flash column chromatography on silica gel eluting with a 0-50% ethyl acetate/n-hexane gradient mixture to give the title compound as a colorless solid (248 mg, 0.489 mmol, 51%). Analytically pure material was obtained by recrystallization from methanol/diisopropyl ether.

mp 190-192° C.

$^1$H NMR (CDCl$_3$) δ 2.29-2.45 (m, 2H), 2.56 (s, 3H), 3.49-3.68 (m, 2H), 3.95 (s, 6H), 4.22-4.38 (m, 2H), 6.01 (q, J=6.2 Hz, 1H), 6.39 (t, J=72.5 Hz, 1H), 7.06-7.16 (m, 2H).

MS Calcd.: 507; MS Found: 508 (M+H).

Example 324

4-[9-Chloro-6-(2,2,2-trifluoro-1-hydroxyethyl)-3,4-dihydropyrimido[1,2-a]benzimidazol-1(2H)-yl]-3-methylbenzonitrile

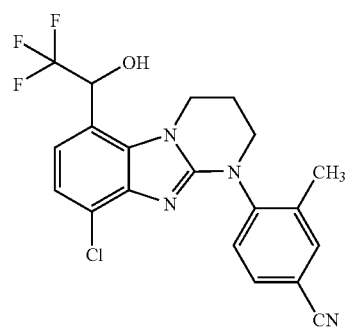 [SMILES: Cc1cc(C#N)ccc1N1CCCn2c1nc1c(Cl)ccc(C(O)C(F)(F)F)c12]

To a stirred solution of 4-(9-chloro-6-formyl-3,4-dihydropyrimido[1,2-a]benzimidazol-1(2H)-yl)-3-methylbenzonitrile (68.5 mg, 0.195 mmol) and trimethyl(trifluoromethyl)silane (86.5 μL, 0.585 mmol) in tetrahydrofuran (1.0 mL) was added a solution of tetrabutylammonium fluoride in tetrahydrofuran (1.0 M, 19.5 μL, 0.0195 mL) at 0° C. After 10 min, hydrochloric acid (1.0 M, 0.3 mL) was added. After 30 min, the reaction mixture was diluted with ethyl acetate, washed with aqueous sodium hydrogen carbonate and brine, dried over sodium sulfate, filtered, and concentrated in vacuo. The resulting solid was washed with diisopropyl ether to give the title compound as a pale yellow solid (67.4 mg, 0.160 mmol, 82%).

MS Calcd.: 420; MS Found: 421 (M+H).

Example 325

4-{9-chloro-6-[1-(difluoromethoxy)-2,2,2-trifluoroethyl]-3,4-dihydropyrimido[1,2-a]benzimidazol-1(2H)-yl}-3-methylbenzonitrile

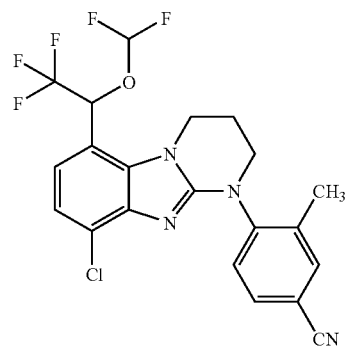 [SMILES: Cc1cc(C#N)ccc1N1CCCn2c1nc1c(Cl)ccc(C(OC(F)F)C(F)(F)F)c12]

A solution of 4-[9-chloro-6-(2,2,2-trifluoro-1-hydroxyethyl)-3,4-dihydropyrimido[1,2-a]benzimidazol-1(2H)-yl]-3-methylbenzonitrile (56.4 mg, 0.134 mmol) and benzyltriethylammonium chloride (3.1 mg, 0.0134 mmol) in tetrahydrofuran (0.6 mL) and aqueous sodium hydroxide (8 M, 0.6 mL) was stirred for 20 min at 50° C. under chloro(difluoro)methane atmosphere. The reaction mixture was diluted with ethyl acetate, washed with water and brine, dried over sodium sulfate, filtered, and concentrated in vacuo. The residue was purified by preparative TLC eluting with a 33% ethyl acetate/n-hexane mixture to give the title compound as a colorless solid (33.3 mg, 0.0706 mmol, 53%). Analytically pure material was obtained by recrystallization from methanol/diisopropyl ether.

mp 195-197° C.

$^1$H NMR (CDCl$_3$) δ 2.34 (s, 3H), 2.39-2.53 (m, 2H), 3.65-3.86 (m, 2H), 4.28-4.48 (m, 2H), 6.02 (q, J=5.8 Hz, 1H), 6.43 (t, J=72.3 Hz, 1H), 7.18 (s, 2H), 7.43 (d, J=8.0 Hz, 1H), 7.51-7.66 (m, 2H).

MS Calcd.: 470; MS Found: 471 (M+H).

Example 326

Methyl 10-chloro-1-(3,5-dichloropyridin-2-yl)-2,3,4,5-tetrahydro-1H-[1,3]diazepino[1,2-a]benzimidazole-7-carboxylate

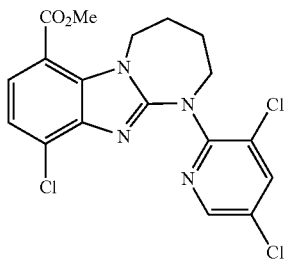 [SMILES: COC(=O)c1ccc(Cl)c2nc3n(c12)CCCCN3c1ncc(Cl)cc1Cl]

To a stirred solution of methyl 4-chloro-2-[(3,5-dichloropyridin-2-yl)amino]-1-(4-hydroxybutyl)-1H-benzimidazole-7-carboxylate (Reference example 165, 2.45 g, 5.52 mmol) and triethylamine (1.92 mL, 13.8 mmol) in tetrahydrofuran (30 mL) was added methanesulfonyl chloride (513 μL, 6.62 mol) at 0° C. After 15 min, the reaction mixture was diluted with ethyl acetate, washed with brine, dried over sodium sulfate, filtered, and concentrated in vacuo. The residue was dissolved in N,N-dimethylformamide (55 mL) and potassium carbonate (2.29 g, 16.6 mmol) was added. After being stirred for 1 h at 80° C., the reaction mixture was diluted with ethyl acetate, washed with water and brine, dried over sodium sulfate, filtered and concentrated in vacuo. The resulting solid was washed with diisopropyl ether to give the title compound as a colorless solid (2.24 g, 5.26 mmol, 95%).

$^1$H NMR (CDCl$_3$) δ 1.86-1.99 (m, 2H), 2.06-2.19 (m, 2H), 3.98 (s, 3H), 4.11-4.21 (m, 2H), 4.35-4.46 (m, 2H), 7.22 (d, J=8.3 Hz, 1H), 7.64 (d, J=2.2 Hz, 1H), 7.69 (d, J=8.3 Hz, 1H), 8.26 (d, J=2.2 Hz, 1H).

MS Calcd.: 424; MS Found: 425 (M+H).

Example 327

[10-Chloro-1-(3,5-dichloropyridin-2-yl)-2,3,4,5-tetrahydro-1H-[1,3]diazepino[1,2-a]benzimidazol-7-yl]methanol

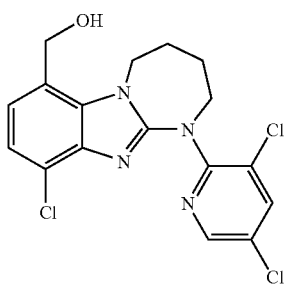 [SMILES: OCc1ccc(Cl)c2nc3n(c12)CCCCN3c1ncc(Cl)cc1Cl]

To a stirred solution of methyl 10-chloro-1-(3,5-dichloropyridin-2-yl)-2,3,4,5-tetrahydro-1H-[1,3]diazepino[1,2-a]benzimidazole-7-carboxylate (426 mg, 1.00 mmol) in tetrahydrofuran (10 mL) was added lithium borohydride (54.5 mg, 2.50 mmol) at 0° C. After being stirred for 30 h at room temperature, the reaction mixture was diluted with ethyl acetate, quenched with aqueous ammonium chloride, washed with water and brine, dried over sodium sulfate, filtrated, and concentrated in vacuo to get the title compound as colorless solid (376 mg, 0.946 mmol, 95%).

$^1$H NMR (CDCl$_3$) δ 1.84-1.97 (m, 3H), 1.98-2.09 (m, 2H), 4.06-4.17 (m, 2H), 4.53-4.64 (m, 2H), 4.91-4.98 (m, 2H), 6.98 (d, J=8.0 Hz, 1H), 7.14 (d, J=8.0 Hz, 1H), 7.62 (d, J=2.2 Hz, 1H), 8.23 (d, J=2.2 Hz, 1H).

MS Calcd.: 396; MS Found: 397 (M+H).

Example 328

1-[10-Chloro-1-(3,5-dichloropyridin-2-yl)-2,3,4,5-tetrahydro-1H-[1,3]diazepino[1,2-a]benzimidazol-7-yl]propan-1-ol

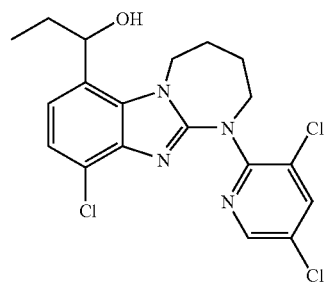 [SMILES: CCC(O)c1ccc(Cl)c2nc3n(c12)CCCCN3c1ncc(Cl)cc1Cl]

To a stirred suspension of [10-chloro-1-(3,5-dichloropyridin-2-yl)-2,3,4,5-tetrahydro-1H-[1,3]diazepino[1,2-a]benzimidazol-7-yl]methanol (376 mg, 0.946 mmol) in acetonitrile (10 mL) was added Dess-Martin reagent (481 mg, 1.14 mmol) at room temperature. After 2 h, the reaction mixture was diluted with ethyl acetate, washed with aqueous sodium hydrogen carbonate and brine, dried over sodium sulfate, filtered, and concentrated in vacuo. The residue was dissolved in tetrahydrofuran (10 mL) and a solution of ethyl magnesium bromide in diethyl ether (3.0 M, 568 μL, 1.70 mmol) was added at −78° C. After 30 min, the reaction mixture was quenched with aqueous ammonium chloride, diluted with ethyl acetate, washed with water and brine, dried over sodium sulfate, filtrated, and concentrated in vacuo. The residue was purified by flash column chromatography on silica gel eluting with a 0-40% ethyl acetate/n-hexane gradient mixture to give the title compound as a colorless solid (301 mg, 0.707 mmol, 75%).

$^1$H NMR (CDCl$_3$) δ 1.07 (t, J=7.4 Hz, 3H), 1.85-1.95 (m, 2H), 1.96-2.09 (m, 5H), 4.06-4.18 (m, 2H), 4.51-4.74 (m, 2H), 4.97-5.07 (m, 1H), 7.12 (d, J=8.3 Hz, 1H), 7.17 (d, J=8.3 Hz, 1H), 7.61 (d, J=2.3 Hz, 1H), 8.23 (d, J=2.3 Hz, 1H).

MS Calcd.: 424; MS Found: 425 (M+H).

Example 329

1-[10-Chloro-1-(3,5-dichloropyridin-2-yl)-2,3,4,5-tetrahydro-1H-[1,3]diazepino[1,2-a]benzimidazol-7-yl]propyl acetate

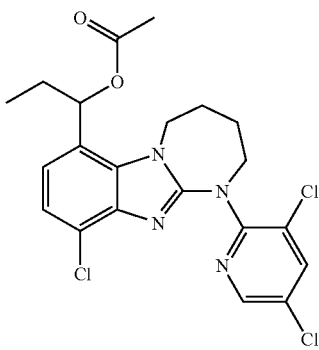 [SMILES: CCC(OC(C)=O)c1ccc(Cl)c2nc3n(c12)CCCCN3c1ncc(Cl)cc1Cl]

To a stirred solution of 1-[10-chloro-1-(3,5-dichloropyridin-2-yl)-2,3,4,5-tetrahydro-1H-[1,3]diazepino[1,2-a]benzimidazol-7-yl]propan-1-ol (200 mg, 0.470 mmol) in pyridine (1.0 mL) was added acetic anhydride (133 μL, 1.41 mmol) at room temperature. After 18 h, the reaction mixture was quenched with aqueous sodium hydrogen carbonate, diluted with ethyl acetate, washed with water, hydrochloric acid (1 M) and brine, dried over sodium sulfate, filtrated, and concentrated in vacuo. The residue was purified by flash column chromatography on silica gel eluting with a ethyl acetate/n-hexane gradient mixture to give the title compound as a colorless solid (207 mg, 0.443 mmol, 94%). Analytically pure material was obtained by recrystallization from ethyl acetate/hexane.

mp 158-160° C.
$^1$H NMR (CDCl$_3$) δ 0.96 (t, J=7.4 Hz, 3H), 1.84-2.09 (m, 6H), 2.13 (s, 4H), 4.03-4.22 (m, 2H), 4.43-4.55 (m, 1H), 4.54-4.66 (m, 1H), 6.25 (t, J=7.0 Hz, 1H), 7.14 (d, J=8.2 Hz, 1H), 7.19 (d, J=8.2 Hz, 1H), 7.62 (d, J=2.2 Hz, 1H), 8.24 (d, J=2.2 Hz, 1H).
MS Calcd.: 466; MS Found: 467 (M+H).

Example 330

Methyl 10-chloro-1-(2-chloro-4-methoxyphenyl)-2,3,4,5-tetrahydro-1H-[1,3]diazepino[1,2-a]benzimidazole-7-carboxylate

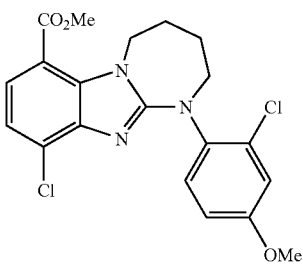 [SMILES: COC(=O)c1ccc(Cl)c2nc3n(c12)CCCCN3c1ccc(OC)cc1Cl]

To a stirred solution of methyl 4-chloro-2-[(2-chloro-4-methoxyphenyl)amino]-1-(4-hydroxybutyl)-1H-benzimidazole-7-carboxylate (Reference example 169, 1.31 g, 2.98 mmol) and triethylamine (1.04 mL, 7.45 mmol) in tetrahydrofuran (15 mL) was added methanesulfonyl chloride (277 μL, 3.58 mol) at 0° C. After 15 min, the reaction mixture was diluted with ethyl acetate, washed with brine, dried over sodium sulfate, filtered, and concentrated in vacuo. The residue was dissolved in N,N-dimethylformamide (30 mL) and potassium carbonate (1.24 g, 8.94 mmol) was added. After being stirred for 1 h at 80° C., the reaction mixture was diluted with ethyl acetate, washed with water and brine, dried over sodium sulfate, filtered and concentrated in vacuo. The resulting solid was washed with diisopropyl ether to give the title compound as a colorless solid (1.18 g, 2.81 mmol, 94%).

$^1$H NMR (CDCl$_3$) δ 1.96-2.08 (m, 2H), 2.10-2.22 (m, 2H), 3.76-3.82 (m, 2H), 3.83 (s, 3H), 3.97 (s, 3H), 4.20-4.31 (m, 2H), 6.91 (dd, J=8.8, 2.8 Hz, 1H), 6.99 (d, J=2.7 Hz, 1H), 7.13 (d, J=8.2 Hz, 1H), 7.46 (d, J=8.8 Hz, 1H), 7.57 (d, J=8.2 Hz, 1H).
MS Calcd.: 419; MS Found: 420 (M+H).

Example 331

[10-Chloro-1-(2-chloro-4-methoxyphenyl)-2,3,4,5-tetrahydro-1H-[1,3]diazepino[1,2-a]benzimidazol-7-yl]methanol

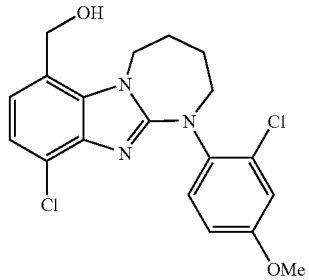 [SMILES: COc1ccc(N2CCCCn3c2nc2c(Cl)ccc(CO)c23)c(Cl)c1]

To a stirred solution of methyl 10-chloro-1-(2-chloro-4-methoxyphenyl)-2,3,4,5-tetrahydro-1H-[1,3]diazepino[1,2-a]benzimidazole-7-carboxylate (336 mg, 0.800 mmol) in tetrahydrofuran (6 mL) was added lithium borohydride (69.7 mg, 3.20 mmol) at 0° C. After being stirred for 20 h at 60° C., the reaction mixture was diluted with ethyl acetate, quenched with aqueous ammonium chloride, washed with water and brine, dried over sodium sulfate, filtrated, and concentrated in vacuo to give the title compound as a colorless solid (318 mg, 0.798 mmol, 99%).

$^1$H NMR (CDCl$_3$) δ 1.83-1.91 (m, 1H), 1.94-2.12 (m, 4H), 3.70-3.77 (m, 2H), 3.82 (s, 3H), 4.51-4.60 (m, 2H), 4.86-4.94 (m, 2H), 6.84-6.93 (m, 2H), 6.97 (d, J=2.7 Hz, 1H), 7.06 (d, J=8.0 Hz, 1H), 7.48 (d, J=8.8 Hz, 1H).
MS Calcd.: 391; MS Found: 392 (M+H).

Example 332

10-Chloro-1-(2-chloro-4-methoxyphenyl)-2,3,4,5-tetrahydro-1H-[1,3]diazepino[1,2-a]benzimidazole-7-carbaldehyde

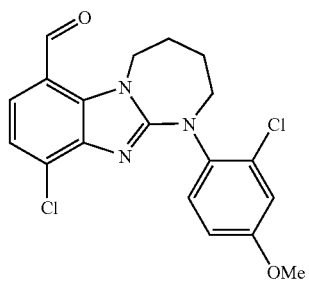 [SMILES: COc1ccc(N2CCCCn3c2nc2c(Cl)ccc(C=O)c23)c(Cl)c1]

To a stirred suspension of [10-chloro-1-(2-chloro-4-methoxyphenyl)-2,3,4,5-tetrahydro-1H-[1,3]diazepino[1,2-a]benzimidazol-7-yl]methanol (313 mg, 0.798 mmol) in acetonitrile (8 mL) was added Dess-Martin reagent (406 mg, 0.958 mmol) at room temperature. After 15 min, the reaction mixture was diluted with ethyl acetate, washed with aqueous sodium hydrogen carbonate and brine, dried over sodium sulfate, filtered, and concentrated in vacuo to give the title compound as a pale brown solid (267 mg, 0.684 mmol, 85%).

$^1$H NMR (CDCl$_3$) δ 1.98-2.08 (m, 2H), 2.14-2.26 (m, 2H), 3.75-3.83 (m, 2H), 3.83 (s, 3H), 4.47-4.59 (m, 2H), 6.91 (dd, J=8.8, 2.8 Hz, 1H), 6.99 (d, J=2.7 Hz, 1H), 7.27 (d, J=8.2 Hz, 1H), 7.40-7.49 (m, 2H), 9.98 (s, 1H).

MS Calcd.: 389; MS Found: 390 (M+H).

Example 333

1-[10-Chloro-1-(2-chloro-4-methoxyphenyl)-2,3,4,5-tetrahydro-1H-[1,3]diazepino[1,2-a]benzimidazol-7-yl]propan-1-ol

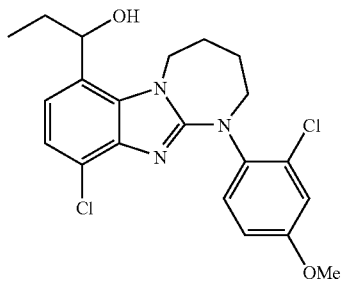 [SMILES: CCC(O)c1ccc(Cl)c2nc3n(c12)CCCCN3c1ccc(OC)cc1Cl]

To a stirred suspension of 10-chloro-1-(2-chloro-4-methoxyphenyl)-2,3,4,5-tetrahydro-1H-[1,3]diazepino[1,2-a]benzimidazole-7-carbaldehyde (267 mg, 0.684 mmol) in tetrahydrofuran (7 mL) and a solution of ethyl magnesium bromide in diethyl ether (3.0 M, 274 μL, 0.821 mmol) was added at 0° C. After 15 min, the reaction mixture was quenched with aqueous ammonium chloride, diluted with ethyl acetate, washed with water and brine, dried over sodium sulfate, filtrated, and concentrated in vacuo. The residue was purified by flash column chromatography on silica gel eluting with a 10-40% ethyl acetate/n-hexane gradient mixture to give the title compound as a colorless solid (137 mg, 0.325 mmol, 48%).

$^1$H NMR (CDCl$_3$) δ 1.03 (t, J=7.4 Hz, 3H), 1.77 (brs, 1H), 1.91-2.05 (m, 5H), 2.19-2.29 (m, 1H), 3.73 (d, J=5.5 Hz, 2H), 3.81 (s, 3H), 4.44-4.64 (m, 2H), 4.89-5.05 (m, 1H), 6.89 (dd, J=8.8, 3.0 Hz, 1H), 6.94-7.02 (m, 2H), 7.07 (d, J=8.2 Hz, 1H), 7.46 (d, J=8.8 Hz, 1H).

MS Calcd.: 419; MS Found: 420 (M+H).

Example 334

1-[10-Chloro-1-(2-chloro-4-methoxyphenyl)-2,3,4,5-tetrahydro-1H-[1,3]diazepino[1,2-a]benzimidazol-7-yl]propyl acetate

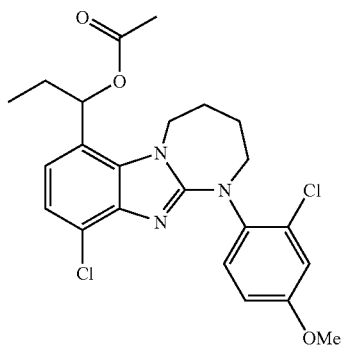 [SMILES: CCC(OC(C)=O)c1ccc(Cl)c2nc3n(c12)CCCCN3c1ccc(OC)cc1Cl]

To a stirred solution of 1-[10-chloro-1-(2-chloro-4-methoxyphenyl)-2,3,4,5-tetrahydro-1H-[1,3]diazepino[1,2-a]benzimidazol-7-yl]propan-1-ol (136 mg, 0.325 mmol) in pyridine (1.0 mL) was added acetic anhydride (92.2 μL, 0.975 mmol) at room temperature. After 24 h, the reaction mixture was quenched with aqueous sodium hydrogen carbonate, diluted with ethyl acetate, washed with water, hydrochloric acid (1 M) and brine, dried over sodium sulfate, filtrated, and concentrated in vacuo. The residue was purified by flash column chromatography on silica gel eluting with a 10-50% ethyl acetate/n-hexane gradient mixture to give the title compound as a colorless solid (125 mg, 0.270 mmol, 83%). Analytically pure material was obtained by recrystallization from ethyl acetate/hexane.

mp 177-179° C.

$^1$H NMR (CDCl$_3$) δ 0.94 (t, J=7.3 Hz, 3H), 1.88-2.14 (m, 6H), 2.11 (s, 3H), 3.68-3.80 (m, 2H), 3.82 (s, 3H), 4.35-4.60 (m, 2H), 6.18-6.26 (m, 1H), 6.90 (dd, J=8.8, 2.8 Hz, 1H), 6.98 (d, J=2.7 Hz, 1H), 7.03 (d, J=8.2 Hz, 1H), 7.11 (d, J=8.3 Hz, 1H), 7.47 (d, J=8.8 Hz, 1H).

MS Calcd.: 461; MS Found: 462 (M+H).

Example 335

1-(2,4-Dichlorophenyl)-N,N-diethyl-8-fluoro-1,2,3,4-tetrahydropyrimido[1,2-a]benzimidazol-6-amine

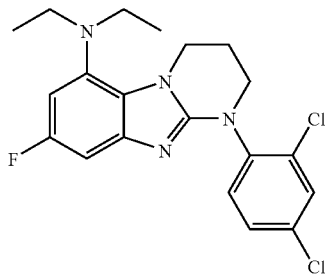 [SMILES: CCN(CC)c1cc(F)cc2nc3n(c12)CCCN3c1ccc(Cl)cc1Cl]

To a stirred solution of 3-{2-[(2,4-dichlorophenyl)amino]-7-(diethylamino)-5-fluoro- 1H-benzimidazol-1-yl}propan- 1-ol (Reference example 176, 170 mg, 0.400 mmol) in pyridine (2 mL) was added methanesulfonyl chloride (61.9 µL, 0.800 mol) at 0° C. After being stirred for 2.5 h, the reaction mixture was quenched with aqueous sodium hydrogen carbonate, diluted with ethyl acetate, washed with water and brine, dried over sodium sulfate, filtered, and concentrated in vacuo. The residue was purified by column chromatography on silica gel to give the title compound as a colorless solid (150 mg, 0.369 mmol, 92%).

mp 142-145° C.

$^1$H NMR (CDCl$_3$) δ 1.03 (t, J=7.1 Hz, 6H), 2.23-2.41 (m, 2H), 3.03 (q, J=7.0 Hz, 4H), 3.60-3.78 (m, 2H), 4.52-4.63 (m, 2H), 6.60 (dd, J=11.4, 2.3 Hz, 1H), 6.90 (dd, J=9.2, 2.3 Hz, 1H), 7.32 (dd, J=8.5, 2.5 Hz, 1H), 7.45 (d, J=8.5 Hz, 1H), 7.51 (d, J=2.5 Hz, 1H).

MS Calcd.: 406; MS Found: 407 (M+H).

Example 336

5-[9-Chloro-6-(1-ethylpropyl)-3,4-dihydropyrimido[1,2-a]benzimidazol-1(2H)-yl]-N,N,4-trimethylpyridin-2-amine

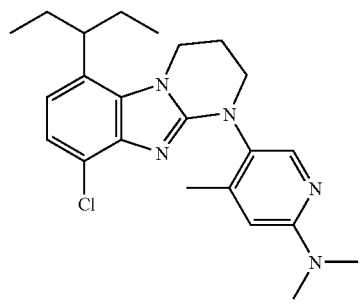 [SMILES: CCC(CC)c1ccc(Cl)c2nc3n(c12)CCCN3c1cnc(N(C)C)cc1C]

To a solution of 3-[4-chloro-2-{[6-(dimethylamino)-4-methylpyridin-3-yl]amino}-7-(1-ethylpropyl)-1H-benzimidazol-1-yl]propan-1-ol (100 mg, 0.233 mmol) in pyridine (2 mL) was added methanesulfonyl chloride (0.036 mL, 0.465 mmol) dropwise at 0° C. After stirring for 2 hr at room temperature, aqueous sodium bicarbonate was added and the mixture was extracted with ethyl acetate. Organic layer was washed with brine, dried over anhydrous sodium sulfate and concentrated in vacuo. The crude mesylate was dissolved in 1-methyl-2-pyrrolidinone (1.0 mL) and potassium carbonate (64 mg, 0.465 mmol) was added. The mixture was stirred at 50° C. for 4 hr. Water was added and the mixture was extracted with ethyl acetate. Organic layer was washed with water and brine, dried over anhydrous sodium sulfate and concentrated in vacuo. The residue was purified by flash chromatography on silica gel eluting with a 50-80% ethyl acetate/n-hexane gradient mixture followed by recrystallization from ethyl acetate/n-hexane to afford the title compound (50 mg, 0-12 mmol, 52%) as a colorless solid.

mp 228-230° C.

$^1$H NMR (CDCl$_3$) δ 0.69-1.00 (m, 6 H), 1.56-1.87 (m, 4 H), 2.21 (s, 3 H), 2.28-2.42 (m, 2 H), 3.09 (s, 6 H), 3.07-3.19 (m, 1 H), 3.51-3.83 (m, 2 H), 4.32-4.47 (m, 2 H), 6.42 (s, 1 H), 6.74 (d, J=8.3 Hz, 1 H), 7.03 (d, J=8.3 Hz, 1 H), 8.09 (s, 1 H).

MS Calcd.: 411; Found: 412 (M+H).

Example 337

1-(5-Bromo-3-methylpyridin-2-yl)-10-chloro-7-(1-ethylpropyl)-2,3,4,5-tetrahydro-1H-[1,3]diazepino[1,2-a]benzimidazole

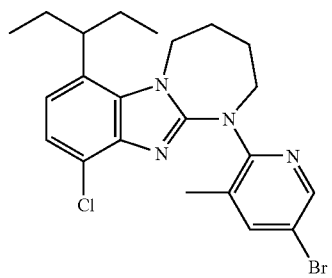 [SMILES: CCC(CC)c1ccc(Cl)c2nc3n(c12)CCCCN3c1ncc(Br)cc1C]

Example 338

1-(6-Bromo-5-methylpyridin-3-yl)-10-chloro-7-(1-ethylpropyl)-2,3,4,5-tetrahydro-1H-[1,3]diazepino[1,2-a]benzimidazole

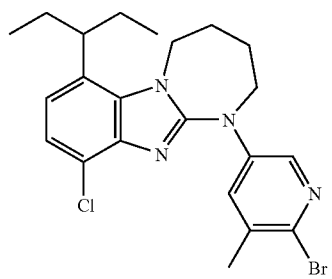 [SMILES: CCC(CC)c1ccc(Cl)c2nc3n(c12)CCCCN3c1cnc(Br)c(C)c1]

A mixture of 10-chloro-7-(1-ethylpropyl)-2,3,4,5-tetrahydro-1H-[1,3]diazepino[1,2-a]benzimidazole (Reference example 72, 1.0 g, 3.42 mmol), 2,5-dibromo-3-methylpyridine (1.72 g, 6.85 mmol), copper(I) iodide (650 mg, 3.42 mmol), 2,2'-bipyridyl (1.07 g, 6.85 mmol) and cesium carbonate (2.23 g, 6.85 mmol) in 1-methyl-2-pyrrolidinone (10 mL) was stirred at 150° C. for 12 hr. The mixture was diluted with ethyl acetate, filtered through a pad of celite, washed with water and brine, dried over anhydrous sodium sulfate and concentrated in vacuo. The residue was purified by flash chromatography on silica gel eluting with a 5-30% ethyl acetate/n-hexane gradient mixture. The filtrate was concentrated in vacuo to give 1-(5-bromo-3-methylpyridin-2-yl)-10-chloro-7-(1-ethylpropyl)-2,3,4,5-tetrahydro-1H-[1,3]diazepino[1,2-a]benzimidazole (870 mg, 55%) as a colorless solid and 1-(6-bromo-5-methylpyridin-3-yl)-10-chloro-7-(1-ethylpropyl)-2,3,4,5-tetrahydro-1H-[1,3]diazepino[1,2-a]benzimidazole (130 mg, 8%) as a colorless solid.

1-(5-Bromo-3-methylpyridin-2-yl)-10-chloro-7-(1-ethylpropyl)-2,3,4,5-tetrahydro-1H-[1,3]diazepino[1,2-a]benzimidazole (Example 337)

$^1$H NMR (CDCl$_3$) δ 0.86 (t, J=7.3 Hz, 6 H), 1.60-2.10 (m, 8 H), 1.74 (s, 3 H), 3.00-3.13 (m, 1 H), 4.12-4.20 (m, 2 H), 4.38-4.48 (m, 2 H), 6.93 (d, J=8.3 Hz, 1 H), 7.16 (d, J=8.3 Hz, 1 H), 7.52-7.56 (m, 1 H), 8.29 (d, J=3.0 Hz, 1 H).

MS Calcd.: 462; Found: 463 (M+H).

1-(6-Bromo-5-methylpyridin-3-yl)-10-chloro-7-(1-ethylpropyl)-2,3,4,5-tetrahydro-1H-[1,3]diazepino[1,2-a]benzimidazole (Example 338)

mp 137-140° C.

$^1$H NMR (CDCl$_3$) δ 0.86 (d, J=7.3 Hz, 6 H), 1.65-2.09 (m, 8 H), 2.33 (s, 3 H), 2.99-3.12 (m, 1 H), 3.75-3.84 (m, 2 H), 4.32-4.40 (m, 2 H), 7.00 (d, J=8.3 Hz, 1 H), 7.24 (d, J=8.3 Hz, 1 H), 7.56 (dd, J=3.0, 0.8 Hz, 1 H), 8.10 (d, J=3.0 Hz, 1 H).

MS Calcd.: 462; Found: 463 (M+H).

Example 339

6-[10-Chloro-7-(1-ethylpropyl)-2,3,4,5-tetrahydro-1H-[1,3]diazepino[1,2-a]benzimidazol-1-yl]-5-methylpyridine-3-carbonitrile

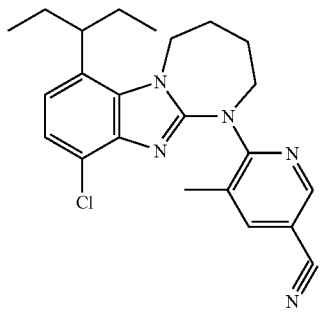 [SMILES: CCC(CC)c1ccc(Cl)c2nc3n(c12)CCCCN3c1ncc(C#N)cc1C]

A mixture of 1-(5-bromo-3-methylpyridin-2-yl)-10-chloro-7-(1-ethylpropyl)-2,3,4,5-tetrahydro-1H-[1,3]diazepino[1,2-a]benzimidazole (463 mg, 1.0 mmol), tetrakis(triphenylphosphine)palladium (116 mg, 0.10 mmol) and zinc cyanide (176 mg, 1.5 mmol) in 1-methyl-2-pyrrolidinone (2.0 mL) was stirred at 100° C. for 14 hr. The mixture was diluted with ethyl acetate, filtered through a pad of celite, washed with water and brine, dried over anhydrous sodium sulfate and concentrated in vacuo. The residue was purified by flash chromatography on silica gel eluting with a 10-30% ethyl acetate/n-hexane gradient mixture followed by recrystallization from ethyl acetate/isopropyl ether to afford the title compound (195 mg, 48%) as a colorless solid.

mp 213° C.

$^1$H NMR (CDCl$_3$) δ 0.87 (t, J=7.4 Hz, 6 H), 1.68 (s, 3 H), 1.70-2.09 (m, 8 H), 3.03-3.15 (m, 1 H), 4.19-4.30 (m, 2 H), 4.44-4.54 (m, 2 H), 6.99 (d, J=8.5 Hz, 1 H), 7.21 (d, J=8.2 Hz, 1 H), 7.56-7.62 (m, 1 H), 8.50 (d, J=2.2 Hz, 1 H).

MS Calcd.: 407; Found: 408 (M+H).

Example 340

6-[10-Chloro-7-(1-ethylpropyl)-2,3,4,5-tetrahydro-1H-[1,3]diazepino[1,2-a]benzimidazol-1-yl]-5-methylpyridine-3-carboxamide

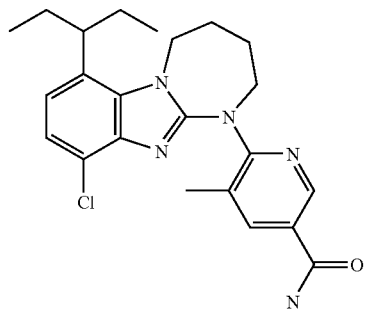 [SMILES: CCC(CC)c1ccc(Cl)c2nc3n(c12)CCCCN3c1ncc(C(N)=O)cc1C]

A mixture of 6-[10-chloro-7-(1-ethylpropyl)-2,3,4,5-tetrahydro-1H-[1,3]diazepino[1,2-a]benzimidazol-1-yl]-5-methylpyridine-3-carbonitrile (100 mg, 0.245 mmol) and potassium hydroxide (41 mg, 0.735 mmol) in tert-butanol (2 mL) was stirred at 80° C. for 2 hr. After cooling, water was added and the mixture was extracted with ethyl acetate. Organic layer was washed with brine, dried over anhydrous sodium sulfate and concentrated in vacuo. The residue was recrystallized from ethyl acetate/isopropyl ether to afford the title compound (70 mg, 67%) as a colorless solid.

mp 234-235° C.

$^1$H NMR (CDCl$_3$) δ 0.87 (d, J=7.3 Hz, 6 H), 1.69-2.10 (m, 8 H), 1.73 (s, 3 H), 3.00-3.18 (m, 1 H), 4.18-4.29 (m, 2 H), 4.42-4.51 (m, 2 H), 6.97 (d, J=8.3 Hz, 1 H), 7.18 (d, J=8.3 Hz, 1 H), 7.94-8.03 (m, 1 H), 8.73 (d, J=2.3 Hz, 1 H).

MS Calcd.: 425; Found: 426 (M+H).

Example 341

10-Chloro-7-(1-ethylpropyl)-1-[3-methyl-5-(methylsulfonyl)pyridin-2-yl]-2,3,4,5-tetrahydro-1H-[1,3]diazepino[1,2-a]benzimidazole

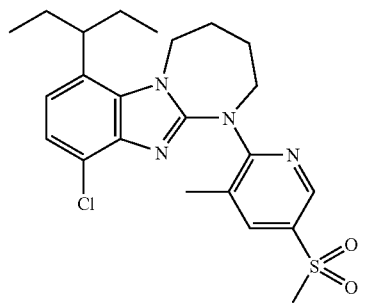 [SMILES: CCC(CC)c1ccc(Cl)c2nc3n(c12)CCCCN3c1ncc(S(C)(=O)=O)cc1C]

A mixture of 1-(5-bromo-3-methylpyridin-2-yl)-10-chloro-7-(1-ethylpropyl)-2,3,4,5-tetrahydro-1H-[1,3]diazepino[1,2-a]benzimidazole (463 mg, 0.216 mmol), 1.0 sodium methanesulfinate (66 mg, 0.648 mmol) and copper(I) iodide (123 mg, 0.648 mmol) in 1-methyl-2-pyrrolidinone (1.0 mL) was heated under microwave irradiation at 180° C.

for 1 hr. After cooling, the mixture was diluted with ethyl acetate, filtered through a pad of celite, washed with water and brine, dried over anhydrous sodium sulfate and concentrated in vacuo. The residue was purified by flash chromatography on silica gel eluting with a 10-50% ethyl acetate/n-hexane gradient mixture followed by recrystallization from ethyl acetate/n-hexane to afford the title compound (36 mg, 36%) as a colorless solid.

mp 137-139° C.

$^1$H NMR (CDCl$_3$) δ 0.87 (t, J=7.3 Hz, 6 H), 1.70-2.09 (m, 8 H), 1.72 (s, 3 H), 3.04-3.14 (m, 1 H), 3.10 (s, 3 H), 4.24-4.36 (m, 2 H), 4.47-4.55 (m, 2 H), 7.01 (d, J=8.3 Hz, 1 H), 7.22 (d, J=8.3 Hz, 1 H), 7.84 (dd, J=2.3, 0.8 Hz, 1 H), 8.73 (d, J=2.3 Hz, 1 H).

MS Calcd.: 460; Found: 461 (M+H).

Example 342

1-{6-[10-Chloro-7-(1-ethylpropyl)-2,3,4,5-tetrahydro-1H-[1,3]diazepino[1,2-a]benzimidazol-1-yl]-5-methylpyridin-3-yl}ethanone

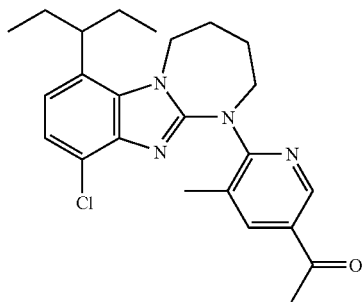 [SMILES: CCC(CC)c1ccc(Cl)c2nc3n(c12)CCCCN3c1ncc(C(C)=O)cc1C]

A mixture of 6-[10-chloro-7-(1-ethylpropyl)-2,3,4,5-tetrahydro-1H-[1,3]diazepino[1,2-a]benzimidazol-1-yl]-5-methylpyridine-3-carbonitrile (90 mg, 0.22 mmol) in tetrahydrofuran (2 mL) was added methyllithium (1.8 M solution in ether, 0.61 mL, 1.10 mmol) at −78° C. After stirring for 1 hr at −78° C., 1 N hydrochloric acid was added and the mixture was warmed to room temperature during 15 min. Aqueous sodium bicarbonate was added and the mixture was extracted with ethyl acetate. Organic layer was washed with brine, dried over anhydrous sodium sulfate and concentrated in vacuo. The residue was purified by flash chromatography on silica gel eluting with a 20-50% ethyl acetate/n-hexane gradient mixture followed by recrystallization from ethyl acetate/n-hexane to afford the title compound (70 mg, 67%) as a colorless solid.

mp 142° C.

$^1$H NMR (CDCl$_3$) δ 0.87 (t, J=7.3 Hz, 6 H), 1.66-2.09 (m, 8 H), 1.72 (s, 3 H), 2.59 (s, 3 H), 3.03-3.15 (m, 1 H), 4.23-4.34 (m, 2 H), 4.45-4.54 (m, 2 H), 6.98 (d, J=8.3 Hz, 1 H), 7.20 (d, J=8.3 Hz, 1 H), 7.95 (dd, J=2.3, 0.8 Hz, 1 H), 8.81 (d, J=2.3 Hz, 1 H).

MS Calcd.: 424; Found: 425 (M+H).

Example 343

10-Chloro-1-(3,5-dimethylisoxazol-4-yl)-7-(1-ethylpropyl)-2,3,4,5-tetrahydro-1H-[1,3]diazepino[1,2-a]benzimidazole

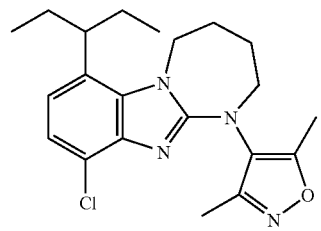 [SMILES: CCC(CC)c1ccc(Cl)c2nc3n(c12)CCCCN3c1c(C)noc1C]

To a solution of 4-{4-chloro-2-[(3,5-dimethylisoxazol-4-yl)amino]-7-(1-ethylpropyl)-1H-benzimidazol-1-yl}butan-1-ol (173 mg, 0.428 mmol) in pyridine (2 mL) was added methanesulfonyl chloride (0.10 mL, 1.28 mmol) dropwise at 0° C. The mixture was warmed to room temperature and stirred for 3 hr. Aqueous sodium bicarbonate was added and the mixture was extracted with ethyl acetate. Organic layer was washed with brine, dried over anhydrous sodium sulfate and concentrated in vacuo. The crude mesylate was dissolved in 1-methyl-2-pyrrolidinone (2 mL) and potassium carbonate (160 mg, 1.16 mmol) was added. The mixture was stirred at 80° C. for 3 hr. After cooling, the mixture was diluted with ethyl acetate, washed with water and brine, dried over anhydrous sodium sulfate and concentrated in vacuo. The residue was purified by flash chromatography on silica gel eluting with a 20-40% ethyl acetate/n-hexane gradient mixture followed by recrystallization from ethyl acetate/n-hexane to give the title compound (93 mg, 0.24 mmol, 56%) as a colorless solid.

mp 163-164° C.

$^1$H NMR (CDCl$_3$) δ 0.84 (t, J=7.3 Hz, 6 H), 1.62-1.88 (m, 4 H), 1.95-2.13 (m, 4 H), 2.31 (s, 3 H), 2.43 (s, 3 H), 2.92-3.05 (m, 1 H), 3.54-3.64 (m, 2 H), 4.22-4.32 (m, 2 H), 6.85 (d, J=8.3 Hz, 1 H), 7.12 (d, J=8.3 Hz, 1 H).

MS Calcd.: 386; Found: 387 (M+H).

Example 344

Methyl 1-(4-bromo-2-methylphenyl)-9-chloro-1,2,3,4-tetrahydropyrimido[1,2-a]benzimidazole-6-carboxylate

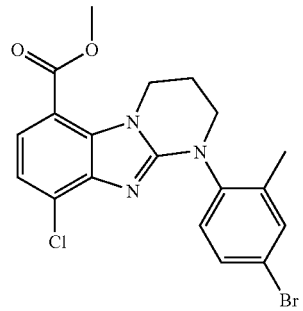 [SMILES: COC(=O)c1ccc(Cl)c2nc3n(c12)CCCN3c1ccc(Br)cc1C]

To a solution of methyl 3-amino-4-chloro-2-[(3-hydroxypropyl)amino]benzoate (20.0 g, 77.3 mmol) in tetrahydrofuran (150 mL) was added 4-bromo-2-methylphenylisothiocyanate (17.6 g, 77.3 mmol) at room temperature, and the mixture was stirred at 70° C. for 18 h. 4-Bromo-2-methylphenylisothiocyanate (17.6 g, 77.3 mmol) was added to the reaction mixture, and the mixture was stirred at 70° C. for 30 h. The reaction mixture was diluted with saturated aqueous sodium hydrogen carbonate at room temperature, and the mixture was extracted with ethyl acetate. The combined organic layer was washed with brine, dried over anhydrous magnesium sulfate, filtered and concentrated in vacuo. The residue was purified by flash column chromatography on silica gel eluting with a 20-30% ethyl acetate/n-hexane gradient mixture. The desired fractions were concentrated in vacuo.

To a suspension of the residue (10.1 g, 20.7 mol), triethylamine (4.32 mL, 31.0 mmol) and 1-ethyl-3-(3-dimethylaminopropyl)-carbodiimide hydrochloride (5.95 g, 31.0 mmol) in tetrahydrofuran (200 mL) was stirred at 5.0° C. for 1 h. The reaction mixture was diluted with brine, and the mixture was extracted with ethyl acetate. The combined organic layer was washed with brine, dried over anhydrous magnesium sulfate, filtered and concentrated in vacuo. The residual solid was collected by filtration and was washed with diisopropyl ether.

To a suspension of the residual solid (7.94 g, 17.5 mmol) and triethylamine (4.89 mL, 35.1 mmol) in tetrahydrofuran (100 mL) was added methanesulfonyl chloride (2.05 mL, 26.3 mmol) at 0° C., and the mixture was stirred at room temperature for 1 h. The reaction mixture was diluted with brine, and the mixture was extracted with ethyl acetate. The combined organic layer was washed with brine, dried over anhydrous magnesium sulfate, filtered and concentrated in vacuo. The mixture of the residue and potassium carbonate (4.85 g, 35.1 mmol) in N,N-dimethylformamide (100 mL) was stirred at 70° C. for 4 h. The reaction mixture was diluted with brine, and the mixture was extracted with ethyl acetate. The combined organic layer was washed with brine, dried over anhydrous magnesium sulfate, filtered and concentrated in vacuo. The residue was purified by flash column chromatography on silica gel eluting with a 20-50% ethyl acetate/n-hexane gradient mixture. The desired fractions were concentrated in vacuo. To give the title compound as a pale yellow powder (5.00 g, 11.5 mmol, 6.6% in 3 steps).

$^1$H NMR (CDCl$_3$) δ: 2.26 (s, 3H), 2.30-2.33 (m, 2H), 3.71 (m, 2H), 3.96 (s, 3H), 4.43 (m, 2H), 7.10 (d, J=8.4 Hz, 1H), 7.20 (d, J=8.4 Hz, 1H), 7.38-7.46 (m, 3H).

MS Calcd.: 435; Found: 436 (M+H).

Example 345

[9-Chloro-1-(4-bromo-2-methylphenyl)-1,2,3,4-tetrahydropyrimido[1,2-a]benzimidazol-6-yl]methanol

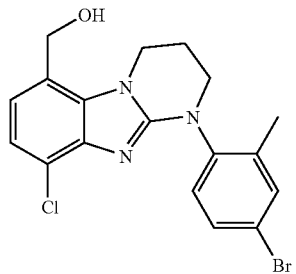 [SMILES: Cc1cc(Br)ccc1N1CCCn2c1nc1c(Cl)ccc(CO)c12]

Under nitrogen atmosphere, lithium borohydride (1.00 g, 46.0 mmol) was added to a suspension of methyl 1-(4-bromo-2-methylphenyl)-9-chloro-1,2,3,4-tetrahydropyrimido[1,2-a]benzimidazole-6-carboxylate (5.0 g, 11.5 mmol) in tetrahydrofuran (70 mL) at 0° C., and the mixture was stirred at 50° C. for 20 h. The reaction mixture was quenched by aqueous saturated ammonium chloride at 0° C., and the mixture extracted with ethyl acetate/tetrahydrofuran. The combined organic layer was washed with brine, dried over anhydrous magnesium sulfate, filtered and concentrated in vacuo to give the crude product of the title compound as a white powder (4.68 g, 11.5 mmol, quant.).

$^1$H NMR (DMSO-d$_6$) δ: 2.19 (s, 3H), 2.27 (br, 2H), 3.60 (br, 2H), 4.48 (br, 2H), 4.72 (d, J=3.9 Hz, 2H), 5.34 (t, J=5.4 Hz, 1H), 6.81 (d, J=8.4 Hz, 1H), 6.93 (d, J=8.1 Hz, 1H), 7.31 (d, J=8.4 Hz, 1H), 7.46 (dd, J=2.1 Hz, 8.4 Hz, 1H), 7.56 (d, J=1.8 Hz, 1H).

MS Calcd.: 407; Found: 408 (M+H).

Example 346

9-Chloro-1-(4-bromo-2-methylphenyl)-1,2,3,4-tetrahydropyrimido[1,2-a]benzimidazole-6-carbaldehyde

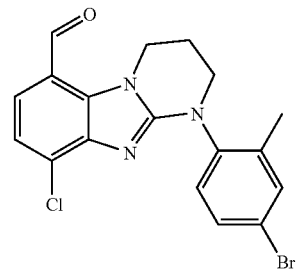 [SMILES: Cc1cc(Br)ccc1N1CCCn2c1nc1c(Cl)ccc(C=O)c12]

To a solution of [9-chloro-1-(4-bromo-2-methylphenyl)-1,2,3,4-tetrahydropyrimido[1,2-a]benzimidazol-6-yl]methanol (4.68 g, 11.5 mmol) in dimethylsulfoxide (80 mL) was added Dess-Martin reagent (5.37 g, 12.7 mmol), and the mixture was stirred at room temperature for 1 h. To the reaction mixture was added Dess-Martin reagent (0.49 g, 1.15 mmol), and the mixture was stirred at room temperature for 1 h. To the reaction mixture was added Dess-Martin reagent (1.46 g, 3.45 mmol), and the mixture was stirred at room temperature for 1 h. The reaction mixture diluted with ethyl acetate, and the mixture was quenched by saturated aqueous sodium hydrogen carbonate. The solid was removed by filtration. The filtrate was extracted with ethyl acetate. The combined organic layer was washed with brine, dried over anhydrous magnesium sulfate, filtered and concentrated in vacuo to give the title compound as a pale yellow powder (4.54 g, 11.2 mmol, 97%).

$^1$H NMR (CDCl$_3$) δ: 2.26 (s, 3H), 2.36 (m, 2H), 3.71 (br, 2H), 4.72 (br, 2H), 7.20 (d, J=7.5 Hz, 1H), 7.22 (d, J=7.5 Hz, 1H), 7.35-7.42 (m, 2H), 7.47 (s, 1H), 9.99 (s, 1H).

MS Calcd.: 405; Found: 406 (M+H).

Example 347

1-[1-(4-Bromo-2-methylphenyl)-9-chloro-1,2,3,4-tetrahydropyrimido[1,2-a]benzimidazol-6-yl]-2,2,2-trifluoroethanol

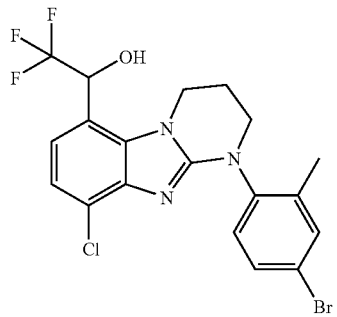 [SMILES: Cc1cc(Br)ccc1N1CCCn2c1nc1c(Cl)ccc(C(O)C(F)(F)F)c12]

To a suspension of 9-chloro-1-(4-bromo-2-methylphenyl)-1,2,3,4-tetrahydropyrimido[1,2-a]benzimidazole-6-carbaldehyde (4.54 g, 11.2 mmol), trifluoromethyltrimethylsilane (4.97 mL, 33.7 mmol) in tetrahydrofuran (150 mL) was added tetrabutylammonium fluoride (1M solution in tetrahydrofuran 1.12 mL, 1.12 mmol), and the mixture was stirred at 0° C. for 15 min. To the reaction mixture was added tetrabutylammonium fluoride (1M solution in tetrahydrofuran 1.12 mL, 1.12 mmol), and the mixture was stirred at 0° C. for 15 min. To the reaction mixture was added trimethyl(trifluoromethyl)silane (4.97 mL, 33.7 mmol), and the mixture was stirred at 0° C. for 30 min. 1N hydrochloric acid (20 mL 20 mmol) was added to the reaction mixture, and the mixture was stirred at room temperature for 10 min. The reaction mixture was extracted with ethyl acetate. The combined organic layer was washed with brine, dried over anhydrous magnesium sulfate, filtered and concentrated in vacuo. The residue was purified by flash column chromatography on silica gel eluting with a 20-60% ethyl acetate/n-hexane gradient mixture. The desired fractions were concentrated in vacuo to give the title compound as a colorless powder (3.24 g, 6.83 mmol, 61%).

$^1$H NMR (DMSO-$d_6$) δ: 2.18 (s, 3H), 2.29 (br, 2H), 3.57-3.71 (br, 2H), 4.37 (br, 2H), 5.71 (t, J=6.6 Hz, 1H), 6.99 (d, J=4.8 Hz, 1H), 7.06 (d, J=8.1 Hz, 1H), 7.11 (d, J=8.4 Hz, 1H), 7.31 (d, J=8.1 Hz, 1H), 7.47 (d, J=8.7 Hz, 1H), 7.56 (s, 1H).

MS Calcd.: 475; Found: 476 (M+H).

Example 348

1-[9-Chloro-1-(4-methoxy-2-methylphenyl)-1,2,3,4-tetrahydropyrimido[1,2-a]benzimidazo-6-yl]-2,2,2-trifluoroethanol

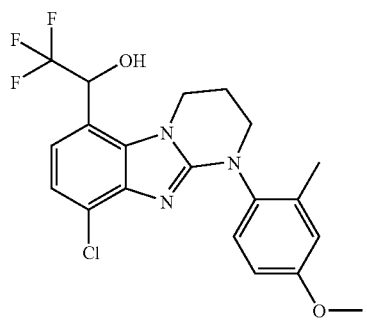 [SMILES: COc1ccc(N2CCCn3c2nc2c(Cl)ccc(C(O)C(F)(F)F)c23)c(C)c1]

Under nitrogen atmosphere, to a solution of 1-[1-(4-bromo-2-methylphenyl)-9-chloro-1,2,3,4-tetrahydropyrimido[1,2-a]benzimidazol-6-yl]-2,2,2-trifluoroethanol (0.40 g, 0.84 mmol) and sodium methoxide (28% solution in methanol, 6.0 mL) in N,N-dimethylformamide (6.0 mL) was added copper (I) iodide (0.241 mg, 1.26 mmol), and the mixture was stirred at 100° C. for 3 h. The reaction mixture was diluted with saturated aqueous ammonium chloride, and the mixture was extracted with ethyl acetate. The combined organic layer was washed with brine, dried over anhydrous magnesium sulfate, filtered and concentrated in vacuo to give the title compound as a colorless powder (0.34 g, 0.80 mmol, 94%).

$^1$H NMR (DMSO-$d_6$) δ: 2.15 (s, 3H), 2.28 (br, 2H), 3.52-3.60 (br, 2H), 3.77 (s, 3H), 4.37 (br, 2H), 5.71 (br, 1H), 6.82 (dd, J=2.7 Hz, 8.4 Hz, 1H), 6.89 (d, J=2.7 Hz, 1H), 7.00 (br, 1H), 7.03 (d, J=8.4 Hz, 1H), 7.08 (d, J=8.4 Hz, 1H), 7.23 (d, J=8.4 Hz, 1H).

MS Calcd.: 425; Found: 426 (M+H).

Example 349

9-Chloro-6-[1-(difluoromethoxy)-2,2,2-trifluoroethyl]-1-(4-methoxy-2-methylphenyl)-1,2,3,4-tetrahydropyrimido[1,2-a]benzimidazole

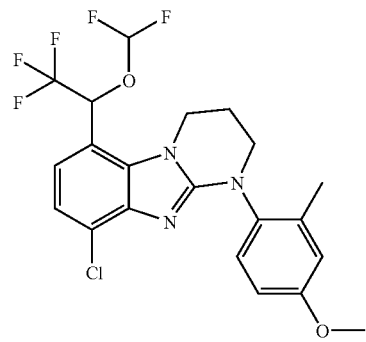 [SMILES: COc1ccc(N2CCCn3c2nc2c(Cl)ccc(C(OC(F)F)C(F)(F)F)c23)c(C)c1]

To a solution of 1-[9-chloro-1-(4-methoxy-2-methylphenyl)-1,2,3,4-tetrahydropyrimido[1,2-a]benzimidazo-6-yl]-2,2,2-trifluoroethanol (0.34 g, 0.80 mmol) and 8N aqueous sodium hydroxide solution (10 mL) in tetrahydrofuran (10 mL) was added benzyltriethylammonium chloride (18.1 mg, 0.08 mmol), and the mixture was stirred at room temperature for 2 h under chloro(difluoro)methane atmosphere. The reaction mixture was diluted with saturated aqueous ammonium chloride, and the mixture was adjusted to around pH 7.0 by addition to 6N aqueous hydrochloric acid solution. The mixture was extracted with ethyl acetate. The combined organic layer was washed with brine, dried over anhydrous magnesium sulfate, filtered and concentrated in vacuo. The residue was purified by flash column chromatography on silica gel eluting with a 10-20% ethyl acetate/n-hexane gradient mixture. The desired fractions were concentrated in vacuo. The residual oil was crystallized from ethyl acetate/diisopropyl ether to give the title compound as a colorless crystal (0.13 g, 0.26 mmol, 33%).

mp 178-182° C.

$^1$H NMR (CDCl$_3$) δ: 2.28 (s, 3H), 2.43 (m, 2H), 3.60-3.70 (m, 2H), 3.84 (s, 3H), 4.36 (m, 2H), 6.03 (m, 1H), 6.41 (br, 1H), 6.79-6.85 (m, 2H), 7.13 (m, 2H), 7.23 (d, J=8.4 Hz, 1H).

MS Calcd.: 475; Found: 476 (M+H).

Example 350

Methyl 9-chloro-1-(4-methoxy-2-methylphenyl)-1,2,3,4-tetrahydropyrimido[1,2-a]benzimidazole-6-carboxylate

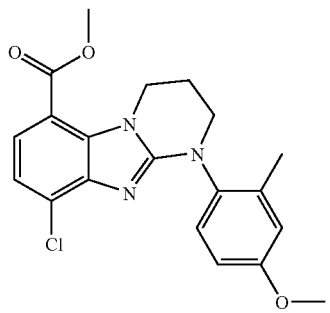 [SMILES: COC(=O)c1ccc(Cl)c2nc3n(c12)CCCN3c1ccc(OC)cc1C]

To a solution of methyl 3-amino-4-chloro-2-[(3-hydroxypropyl)amino]benzoate (2.00 g, 7.73 mmol) in tetrahydrofuran (6.0 mL) was added 4-methoxy-2-methylphenylisothiocyanate (1.39 g, 7.73 mmol), and the mixture was stirred at 70° C. for 19 h. To the reaction mixture was added 4-methoxy-2-methylphenylisothiocyanate (1.39 g, 7.73 mmol), and the mixture was stirred at 70° C. for 43 h. The reaction mixture was diluted with brine at 0° C. The mixture was extracted with ethyl acetate. The combined organic layer was washed with brine, dried over anhydrous magnesium sulfate, filtered and concentrated in vacuo. The residue was purified by flash column chromatography on silica gel eluting with a 40-50% ethyl acetate/n-hexane gradient mixture. The desired fractions were concentrated in vacuo.

A solution of the residue (0.75 g, 1.71 mmol), triethylamine (0.36 mL, 2.57 mmol) and 1-ethyl-3-(3-dimethylaminopropyl)-carbodiimide hydrochloride (0.49 g, 2.57 mmol) in tetrahydrofuran (7.5 mL) was stirred at 50° C. for 1 h. The reaction mixture was diluted with brine, and the mixture was extracted with ethyl acetate. The combined organic layer was washed with brine, dried over anhydrous magnesium sulfate, filtered and concentrated in vacuo. The residual oil was crystallized from ethyl acetate. The solid was collected by filtration.

To a solution of the residual solid (0.55 g, 1.36 mmol) and triethylamine (0.38 mL, 2.72 mmol) in tetrahydrofuran (5.5 mL) was added methanesulfonyl chloride (0.16 mL, 2.04 mmol) at 0° C., and the mixture was stirred at room temperature for 1 h. The reaction mixture was diluted with brine, and the mixture was extracted with ethyl acetate. The combined organic layer was washed with brine, dried over anhydrous magnesium sulfate, filtered and concentrated in vacuo. The mixture of the residue and potassium carbonate (0.38 g, 2.72 mmol) in N,N-dimethylformamide (5.5 mL) was stirred at 70° C. for 4 h. The reaction mixture was diluted with brine, and the mixture was extracted with ethyl acetate. The combined organic layer was washed with brine, dried over anhydrous magnesium sulfate, filtered and concentrated in vacuo. The residue was purified by flash column chromatography on silica gel eluting with a 40% ethyl acetate/n-hexane mixture. The desired fractions were concentrated in vacuo to give the title compound as a pale yellow powder (0.22 g, 0.57 mmol, 7.4% in 3 steps).

$^1$H NMR (CDCl$_3$) δ: 2.23-2.29 (m, 5H), 3.64-3.68 (m, 2H), 3.81 (s, 3H), 3.93 (s, 3H), 4.38-4.40 (m, 2H), 6.77-6.82 (m, 2H), 7.05 (d, J=8.1 Hz, 1H), 7.21 (d, J=8.7 Hz, 1H), 7.39 (d, J=8.4 Hz, 1H).

MS Calcd.: 385; Found: 386 (M+H).

Example 351

9-Chloro-1-(4-methoxy-2-methylphenyl)-1,2,3,4-tetrahydropyrimido[1,2-a]benzimidazole-6-carbaldehyde

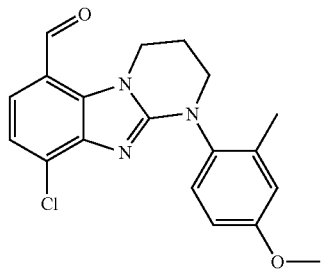 [SMILES: COc1ccc(N2CCCn3c2nc2c(Cl)ccc(C=O)c23)c(C)c1]

Under nitrogen atmosphere, lithium borohydride (49.7 mg, 2.28 mmol) was added to a suspension of methyl 9-chloro-1-(4-methoxy-2-methylphenyl)-1,2,3,4-tetrahydropyrimido[1,2-a]benzimidazole-6-carboxylate (0.22 g, 0.57 mmol) in tetrahydrofuran (3.0 mL) at 0° C., and the mixture was stirred at 50° C. for 5 h. The reaction mixture was quenched by aqueous saturated ammonium chloride at 0° C., and the mixture was extracted with ethyl acetate/tetrahydrofuran. The combined organic layer was washed with brine, dried over anhydrous magnesium sulfate, filtered and concentrated in vacuo.

To a solution of the residue in acetonitrile (3.0 mL) was added Dess-Martin reagent (0.27 g, 0.63 mmol), and the mixture was stirred at room temperature for 45 min. The reaction mixture was quenched by saturated aqueous sodium hydrogen carbonate. The solid was removed by filtration. The filtrate was extracted with ethyl acetate. The combined organic layer was washed with brine, dried over anhydrous magnesium sulfate, filtered and concentrated in vacuo to give the title compound as a pale yellow powder (0.20 g, 0.57 mmol, quant.).

$^1$H NMR (CDCl$_3$) δ: 2.23-2.37 (m, 5H), 3.65-3.72 (m, 2H), 3.81 (s, 3H), 4.62-4.71 (m, 2H), 6.77-6.84 (m, 2H), 7.17-7.25 (m, 2H), 7.33 (d, J=9.0 Hz, 1H), 10.0 (s, 1H).

MS Calcd.: 335; Found: 336 (M+H).

Example 352

[9-Chloro-1-(4-methoxy-2-methylphenyl)-1,2,3,4-tetrahydropyrimido[1,2-a]benzimidazol-6-yl](cyclopropyl)methanol

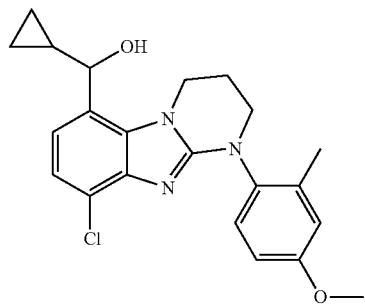 [SMILES: COc1ccc(N2CCCn3c2nc2c(Cl)ccc(C(O)C4CC4)c23)c(C)c1]

417

Under nitrogen atmosphere, to a solution of 9-chloro-1-(4-methoxy-2-methylphenyl)-1,2,3,4-tetrahydropyrimido[1,2-a]benzimidazole-6-carbaldehyde (0.10 g, 0.28 mmol) in tetrahydrofuran (0.84 mL) was added cyclopropyl magnesium bromide (1M solution in tetrahydrofuran, 0.84 mL, 0.84 mmol) at 0° C., and the mixture was stirred at 0° C. for 1 h. The reaction mixture was quenched by aqueous saturated ammonium chloride, and the mixture was extracted with ethyl acetate. The combined organic layer was washed with brine, dried over anhydrous magnesium sulfate, filtered and concentrated in vacuo. The residual solid was recrystallized from ethyl acetate/n-hexane to give the title compound as a pale yellow powder (82.4 mg, 0.21 mmol, 74%).

$^1$H NMR (CDCl$_3$) δ: 0.33 (m, 1H), 0.45 (m, 1H), 0.65 (m, 1H), 0.76 (m, 1H), 0.88 (m, 1H), 1.46 (m, 1H), 1.90 (m, 3H), 2.22 (s, 3H), 2.35 (m, 2H), 3.60 (m, 2H), 3.79 (s, 3H), 6.75-6.80 (m, 2H), 7.03 (m, 2H), 7.20-7.23 (m, 1H).

MS Calcd.: 397; Found: 398 (M+H).

Example 353

9-Chloro-6-[cyclopropyl(2,2,2-trifluoroethoxy)methyl]-1-(4-methoxy-2-methylphenyl)-1,2,3,4-tetrahydropyrimido[1,2-a]benzimidazole

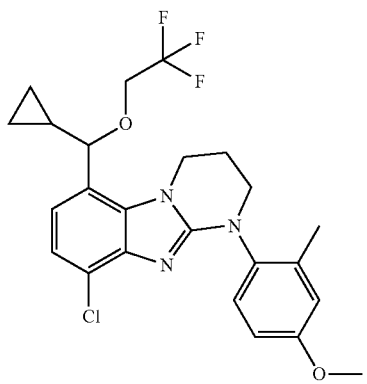 [SMILES: COc1ccc(N2CCCn3c2nc2c(Cl)ccc(C(OCC(F)(F)F)C4CC4)c23)c(C)c1]

To a solution of [9-chloro-1-(4-methoxy-2-methylphenyl)-1,2,3,4-tetrahydropyrimido[1,2-a]benzimidazol-6-yl](cyclopropyl)methanol (82 mg, 0.21 mmol) and tributyl phosphine (0.10 mL, 0.41 mmol) in tetrahydrofuran (0.84 mL) was added 1,1'-(azodicarbonyl) dipiperidine (104 mg, 0.41 mmol), and the mixture was stirred at room temperature for 10 min. To the reaction mixture was added 2,2,2,-trifluoroethanol (0.15 mL, 2.06 mmol), and the mixture was stirred at 60° C. for 1 h. The reaction mixture was cooled at room temperature and concentrated in vacuo. The residue was diluted with diethyl ether. The residual solid was removed by filtration. The filtrate was concentrated in vacuo. The residue was purified by flash column chromatography on silica gel eluting with a 40% ethyl acetate/n-hexane mixture. The desired fractions were concentrated in vacuo. The residual oil was crystallized from ethyl acetate/diisopropyl ether to give the title compound as a colorless crystal (35.8 mg, 0.075 mmol, 36%).

mp 157-158° C.

$^1$H NMR (CDCl$_3$) δ: 0.35 (m, 1H), 0.50 (m, 1H), 0.65 (m, 1H), 0.78 (m, 1H), 1.45 (m, 1H), 1.58 (m, 2H), 2.26 (s, 3H), 2.34 (m, 2H), 3.70 (m, 4H), 3.84 (s, 3H), 4.38 (m, 1H), 6.80-6.84 (m, 3H), 7.04 (d, J=9.0 Hz, 1H), 7.26 (m, 1H).

MS Calcd.: 479; Found: 480 (M+H).

418

Example 354

[9-Chloro-1-(4-methoxy-2-methylphenyl)-1,2,3,4-tetrahydropyrimido[1,2-a]benzimidazol-6-yl](dicyclopropyl)methanol

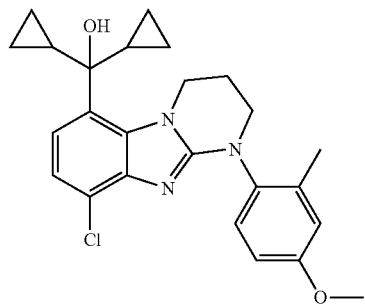 [SMILES: COc1ccc(N2CCCn3c2nc2c(Cl)ccc(C(O)(C4CC4)C4CC4)c23)c(C)c1]

Under nitrogen atmosphere, to a solution of methyl 9-chloro-1-(4-methoxy-2-methylphenyl)-1,2,3,4-tetrahydropyrimido[1,2-a]benzimidazole-6-carboxylate (0.10 g, 0.26 mmol) in tetrahydrofuran (1.3 mL) was added cyclopropyl magnesium bromide (1M solution in tetrahydrofuran, 1.3 mL, 1.30 mmol) at room temperature, and the mixture was stirred at 70° C. for 1 h. The reaction mixture was quenched by aqueous saturated ammonium chloride, and the mixture was extracted with ethyl acetate. The combined organic layer was washed with brine, dried over anhydrous magnesium sulfate, filtered and concentrated in vacuo. The residue was purified by flash column chromatography on silica gel eluting with a 30% ethyl acetate/n-hexane mixture. The desired fractions were concentrated in vacuo. The residual oil was crystallized from ethyl acetate/n-hexane to give the title compound as a colorless crystal (50.1 mg, 0.11 mmol, 44%).

mp 181-182° C.

$^1$H NMR (CDCl$_3$) δ: 0.26-0.29 (m, 2H), 0.57-0.63 (m, 6H), 1.44 (m, 2H), 1.72 (s, 1H), 2.23 (s, 3H), 2.26 (m, 2H), 3.67 (m, 2H), 3.83 (s, 3H), 4.83 (m, 2H), 6.78-6.83 (m, 2H), 6.99 (d, J=9.0 Hz, 1H), 7.12 (d, J=9.0 Hz, 1H), 7.25 (m, 1H).

MS Calcd.: 437; Found: 438 (M+H).

Example 355

1-(4-Bromo-2-methylphenyl)-9-chloro-6-[1-(difluoromethoxy)-2,2,2-trifluoroethyl]-1,2,3,4-tetrahydropyrimido[1,2-a]benzimidazole

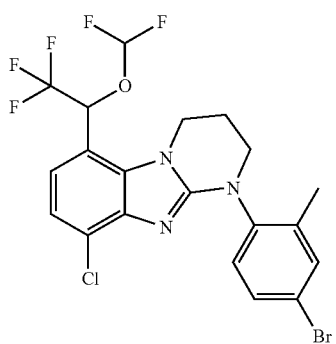 [SMILES: Cc1cc(Br)ccc1N1CCCn2c1nc1c(Cl)ccc(C(OC(F)F)C(F)(F)F)c12]

To a solution of 1-[1-(4-bromo-2-methylphenyl)-9-chloro-1,2,3,4-tetrahydropyrimido[1,2-a]benzimidazol-6-yl]-2,2,2-trifluoroethanol (2.84 g, 5.98 mmol) and 8N aqueous sodium hydroxide solution (85 mL) in tetrahydrofuran (85 mL) was added benzyltriethylammonium chloride (0.14 g, 0.60 mmol), and the mixture was stirred at room temperature for 2 h under chloro(difluoro)methane. The reaction mixture was diluted with saturated aqueous ammonium chloride, and the mixture was adjusted to around pH 7.0 by addition to 6N aqueous hydrochloric acid solution, and the mixture was extracted with ethyl acetate. The combined organic layer was washed with brine, dried over anhydrous magnesium sulfate, filtered and concentrated in vacuo. The residue was purified by flash column chromatography on silica gel eluting with a 10-20% ethyl acetate/n-hexane gradient mixture. The desired fractions were concentrated in vacuo to give the title compound as a colorless powder (1.07 g, 2.04 mmol, 34%).

$^1$H NMR (CDCl$_3$) δ: 2.28 (s, 3H), 2.44 (m, 2H), 3.71 (br, 2H), 4.36-4.38 (br, 2H), 6.03 (m, 1H), 6.42 (m, 1H), 7.16-7.22 (m, 3H), 7.39 (dd, J=2.1 Hz, 8.4 Hz, 1H), 7.47 (d, J=2.1 Hz, 1H).

MS Calcd.: 525; Found: 526 (M+H).

Example 356

9-Chloro-6-[1-(difluoromethoxy)-2,2,2-trifluoroethyl]-1-(4-ethoxy-2-methylphenyl)-1,2,3,4-tetrahydropyrimido[1,2-a]benzimidazole

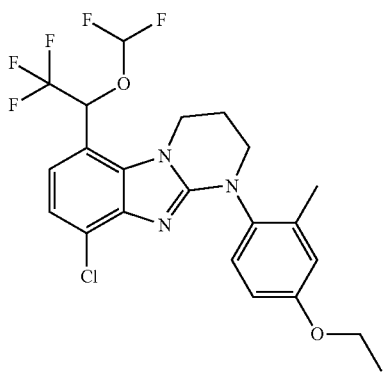 [SMILES: CCOc1ccc(N2CCCn3c2nc2c(Cl)ccc(C(OC(F)F)C(F)(F)F)c23)c(C)c1]

Under nitrogen atmosphere, to a suspension of 1-(4-bromo-2-methylphenyl)-9-chloro-6-[1-(difluoromethoxy)-2,2,2-trifluoroethyl]-1,2,3,4-tetrahydropyrimido[1,2-a]benzimidazole (0.20 g, 0.38 mmol), potassium hydroxide (64.2 mg, 1.14 mmol), water (2 mL) and di-tert-butyl[3,4,5,6-tetramethyl-2',4',6'-tri(propan-2-yl)biphenyl-2-yl]phosphane (73.3 mg, 0.15 mmol) in 1,2-dimethoxyethane (2 mL) was added tris(dibenzylideneacetone)dipalladium(0) (34.9 mg, 0.04 mmol), and the mixture was stirred at 100° C. for 1 h. The reaction mixture was diluted with brine at room temperature, and the mixture was extracted with ethyl acetate. The combined organic layer was washed with brine, and concentrated in vacuo. To a suspension of the residue in N,N-dimethylformamide (4 mL) was added potassium carbonate (35.5 mg, 0.26 mmol), and the mixture was stirred at room temperature for 5 min. To the reaction mixture was added iodoethane (0.02 mL, 0.26 mmol) at 0° C., and the mixture was stirred at room temperature for 87 h. The reaction mixture was diluted with brine, and the mixture was extracted with ethyl acetate. The combined organic layer was washed with brine, dried over anhydrous magnesium sulfate, filtered and concentrated in vacuo. The residue was purified by flash column chromatography on silica gel eluting with a 10-20% ethyl acetate/n-hexane gradient mixture. The desired fractions were concentrated in vacuo. The residual oil was crystallized from ethyl acetate/n-hexane to give the title compound as a colorless crystal (58.9 mg, 0.12 mmol, 32%).

mp 179-182° C.

$^1$H NMR (CDCl$_3$) δ: 1.45 (t, J=6.9 Hz, 3H) 2.27 (s, 3H), 2.43 (m, 2H), 3.69 (m, 2H), 4.07 (q, J=6.9 Hz, 2H), 4.36 (br, 2H), 6.07 (m, 1H), 6.42 (m, 1H), 6.79 (dd, J=2.7 Hz, 8.4 Hz, 1H), 6.84 (d, J=2.7 Hz, 1H), 7.14 (m, 2H), 7.22 (d, J=8.7 Hz, 1H).

MS Calcd.: 489; Found: 490 (M+H).

Example 357

9-Chloro-6-[1-(difluoromethoxy)-2,2,2-trifluoroethyl]-1-[2-methyl-4-(propan-2-yloxy)phenyl]-1,2,3,4-tetrahydropyrimido[1,2-a]benzimidazole

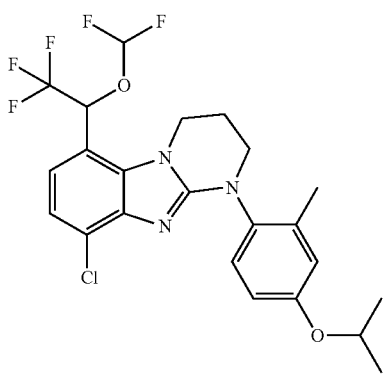 [SMILES: Cc1cc(OC(C)C)ccc1N1CCCn2c1nc1c(Cl)ccc(C(OC(F)F)C(F)(F)F)c12]

Under nitrogen atmosphere, to a suspension of 1-(4-bromo-2-methylphenyl)-9-chloro-6-[1-(difluoromethoxy)-2,2,2-trifluoroethyl]-1,2,3,4-tetrahydropyrimido[1,2-a]benzimidazole (0.20 g, 0.38 mmol), potassium hydroxide (64.2 mg, 1.14 mmol), water (2 mL) and di-tert-butyl[3,4,5,6-tetramethyl-2',4',6'-tri(propan-2-yl)biphenyl-2-yl]phosphane (73.3 mg, 0.15 mmol) in 1,2-dimethoxyethane (2 mL) was added tris(dibenzylideneacetone)dipalladium(0) (34.9 mg, 0.04 mmol), and the mixture was stirred at 100° C. for 1 h. The reaction mixture was diluted with brine at room temperature, and the mixture was extracted with ethyl acetate. The combined organic layer was washed with brine, and concentrated in vacuo. To a suspension of the residue in N,N-dimethylformamide (4 mL) was added potassium carbonate (35.5 mg, 0.26 mmol), and the mixture was stirred at 0° C. for 15 min. To the reaction mixture was added 2-iodopropane (0.04 mL, 0.42 mmol) at 0° C., and the mixture was stirred at room temperature for 17 h. The reaction mixture was warmed up at 60° C. and stirred at 60° C. for 25 h. The reaction mixture was diluted with brine, and the mixture was extracted with ethyl acetate. The combined organic layer was washed with brine, dried over anhydrous magnesium sulfate, filtered and concentrated in vacuo. The residue was purified by flash column chromatography on silica gel eluting with a 10-20% ethyl acetate/n-hexane gradient mixture. The desired fractions were concentrated in vacuo. The residual solid was recrystallized from ethyl acetate/n-hexane to give the title compound as a colorless crystal (43.8 mg, 0.09 mmol, 14%).

mp 198-204° C.

$^1$H NMR (CDCl$_3$) δ: 1.38 (d, J=6.0 Hz, 6H), 2.26 (s, 3H), 2.42 (m, 2H), 3.65-3.72 (m, 2H), 4.36 (m, 2H), 4.56 (m, 1H), 6.03 (m, 1H), 6.41 (m, 1H), 6.77 (dd, J=3.0 Hz, 9.0 Hz, 1H), 6.82 (d, J=3.0 Hz, 1H), 7.13 (m, 2H), 7.21 (d, J=9.0 Hz, 1H).

MS Calcd.: 503; Found: 504 (M+H).

Example 358

1-(2,4-Dichlorophenyl)-N,N-diethyl-4-methoxy-2,3, 4,5-tetrahydro-1H-[1,3]diazepino[1,2-a]benzimidazol-7-amine

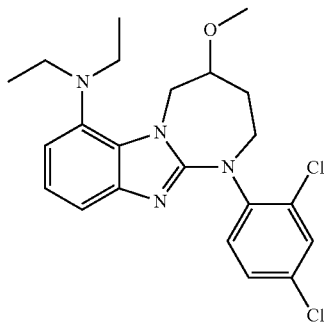 [SMILES: CCN(CC)c1cccc2nc3n(c12)CC(OC)CCN3c1ccc(Cl)cc1Cl]

To a suspension of sodium hydride (60%, 5.7 mg, 0.14 mmol) in tetrahydrofuran (1 mL) was added a solution of 1-(2,4-dichlorophenyl)-7-(diethylamino)-2,3,4,5-tetrahydro-1H-[1,3]diazepino[1,2-a]benzimidazol-4-ol (40.0 mg, 0.0954 mmol) in tetrahydrofuran (1 mL) at 0° C. After 30 min, methyl iodide (0.0178 mL, 0.286 mmol) was added to the reaction mixture at 0° C. and the resultant mixture was stirred at 40° C. for 2 hr. Ethyl acetate was added and the resultant mixture was washed with water and brine, dried over anhydrous sodium sulfate, filtered and concentrated in vacuo. The residue was purified by flash column chromatography on silica gel eluting with a 0-40% ethyl acetate/n-hexane gradient mixture to give the title compound as a colorless solid (39.5 mg, 0.0911 mmol, 95%).

mp 120-122° C. (diisopropyl ether/n-hexane).

$^1$H NMR (CDCl$_3$) δ: 1.04 (brs, 6 H), 1.97-2.25 (m, 2 H), 3.14 (q, J=6.8 Hz, 4 H), 3.52 (s, 3 H), 3.62-3.75 (m, 2 H), 3.84-3.95 (m, 1 H), 4.29 (dd, J=13.3, 9.1 Hz, 1 H), 5.52 (dd, J=13.3, 1.9 Hz, 1 H), 6.91 (dd, J=7.9, 0.8 Hz, 1 H), 7.06 (t, J=7.9 Hz, 1 H), 7.24-7.28 (m, 1 H), 7.31 (dd, J=8.7, 2.3 Hz, 1 H), 7.39 (d, J=8.7 Hz, 1 H), 7.42 (d, J=2.3 Hz, 1 H).

MS Calcd.: 432, MS Found: 433 (M+H).

Example 359

1-(2,4-Dichlorophenyl)-N,N-diethyl-4,4-difluoro-2, 3,4,5-tetrahydro-1H-[1,3]diazepino[1,2-a]benzimidazol-7-amine

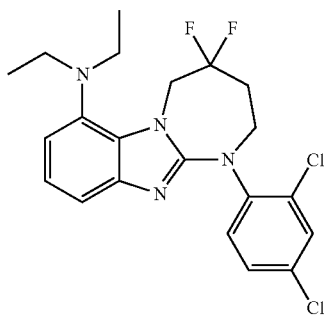 [SMILES: CCN(CC)c1cccc2nc3n(c12)CC(F)(F)CCN3c1ccc(Cl)cc1Cl]

Under nitrogen atmosphere, diethylaminosulfure trifluoride (0.0809 mL, 0.612 mmol) was added to a solution of 1-(2,4-dichlorophenyl)-7-(diethylamino)-2,3-dihydro-1H-[1,3]diazepino[1,2-a]benzimidazol-4(5H)-one (128 mg, 0.306 mmol) in toluene (1.5 mL) at 0° C. The resultant mixture was stirred at room temperature for 1 hr and purified by column chromatography on silica gel eluting with ethyl acetate and thin layer chromatography (20% ethyl acetate/n-hexane) to give the title compound as a yellow solid (5.0 mg, 0.011 mmol, 4%).

$^1$H NMR (CDCl$_3$) δ: 1.06 (t, J=7.0 Hz, 6 H), 2.36-2.52 (m, 2 H), 3.13 (q, J=7.0 Hz, 4 H), 3.84-3.91 (m, 2 H), 5.21 (t, J=11.3 Hz, 2 H), 6.96 (dd, J=8.0, 1.1 Hz, 1 H), 7.10 (t, J=8.0 Hz, 1 H), 7.27-7.30 (m, 1 H), 7.35 (dd, J=8.5, 2.2 Hz, 1 H), 7.39-7.46 (m, 2 H).

MS Calcd.: 438, MS Found: 439 (M+H).

Example 360

1-(2,4-Dichlorophenyl)-7-(diethylamino)-2,3,4,5-tetrahydro-1H-[1,3]diazepino[1,2-a]benzimidazol-4-yl methanesulfonate

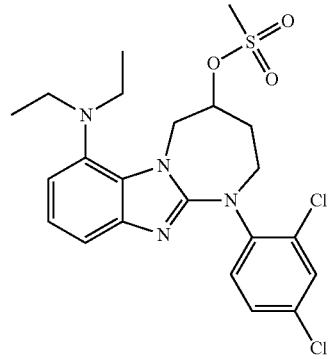 [SMILES: CCN(CC)c1cccc2nc3n(c12)CC(OS(C)(=O)=O)CCN3c1ccc(Cl)cc1Cl]

To a solution of 1-(2,4-dichlorophenyl)-6-(diethylamino)-1,2,3,4-tetrahydropyrimido[1,2-a]benzimidazol-3-ol (235 mg, 0.563 mmol) in pyridine (1 mL) was added methanesulfonyl chloride (0.436 mL, 5.63 mmol) at room temperature. The resultant mixture was stirred at room temperature for 30 min. Aqueous sodium bicarbonate was added and the mixture was extracted with ethyl acetate. The combined organic layer was washed with brine, dried over anhydrous sodium sulfate, filtered and concentrated in vacuo to afford the title compound as an orange amorphous solid (279 mg, 0.560 mmol, 99%).

$^1$H NMR (CDCl$_3$) δ: 0.95-1.11 (m, 6 H), 2.34-2.42 (m, 2 H), 3.08-3.20 (m, 4 H), 3.10 (s, 3 H), 3.71-3.82 (m, 1 H), 3.89-4.00 (m, 1 H), 4.83-4.94 (m, 1 H), 5.17-5.37 (m, 2 H), 6.92 (dd, J=7.8, 1.1 Hz, 1 H), 7.07 (t, J=7.8 Hz, 1 H), 7.26 (dd, J=7.8, 1.1 Hz, 1 H); 7.33 (dd, J=8.5, 2.2 Hz, 1 H), 7.40 (d, J=8.5 Hz, 1 H), 7.43 (d, J=2.2 Hz, 1 H).

MS Calcd.: 496, MS Found: 497 (M+H).

Example 361

4-Azido-1-(2,4-dichlorophenyl)-N,N-diethyl-2,3,4,5-tetrahydro-1H-[1,3]diazepino[1,2-a]benzimidazol-7-amine

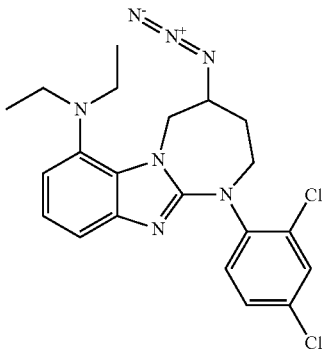 [SMILES: CCN(CC)c1cccc2nc3n(c12)CC(N=[N+]=[N-])CCN3c1ccc(Cl)cc1Cl]

Example 362

1-(2,4-Dichlorophenyl)-N,N-diethyl-2,3-dihydro-1H-[1,3]diazepino[1,2-a]benzimidazol-7-amine

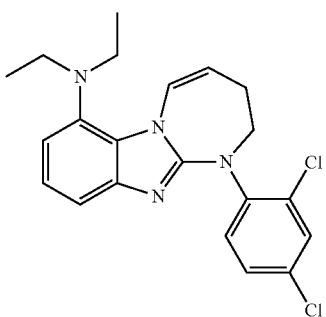 [SMILES: CCN(CC)c1cccc2nc3n(c12)C=CCCN3c1ccc(Cl)cc1Cl]

A mixture of 1-(2,4-dichlorophenyl)-7-(diethylamino)-2,3,4,5-tetrahydro-1H-[1,3]diazepino[1,2-a]benzimidazol-4-yl methanesulfonate (144 mg, 0.289 mmol) and sodium azide (56.4 mg, 0.868 mmol) in N,N-dimethylformamide (1.4 mL) was stirred at 100° C. for 3 hr. Ethyl acetate was added, and the resultant mixture was washed with water and brine, dried over anhydrous sodium sulfate, filtered and concentrated in vacuo. The residue was purified by flash column chromatography on silica gel eluting with a 10-30% ethyl acetate/n-hexane gradient mixture to give 4-azido-1-(2,4-dichlorophenyl)-N,N-diethyl-2,3,4,5-tetrahydro-1H-[1,3]diazepino[1,2-a]benzimidazol-7-amine as a colorless solid (96.6 mg, 0.217 mmol, 75%) and 1-(2,4-dichlorophenyl)-N,N-diethyl-2,3-dihydro-1H-[1,3]diazepino[1,2-a]benzimidazol-7-amine (21.4 mg, 00532 mmol, 18%).

4-Azido-1-(2,4-dichlorophenyl)-N,N-diethyl-2,3,4,5-tetrahydro-1H-[1,3]diazepino[1,2-a]benzimidazol-7-amine (Example 361)

$^1$H NMR (CDCl$_3$) δ: 0.95-1.16 (m, 6 H), 2.00-2.16 (m, 1 H), 2.19-2.31 (m, 1 H), 3.14 (q, J=7.1 Hz, 4 H), 3.66-3.78 (m, 1 H), 3.87-4.02 (m, 2 H), 4.29 (dd, J=13.3, 9.2 Hz, 1 H), 5.59 (d, J=13.3 Hz, 1 H), 6.92 (dd, J=7.8, 1.0 Hz, 1 H), 7.07 (t, J=7.8 Hz, 1 H), 7.26 (dd, J=7.8, 1.0 Hz, 1 H), 7.32 (dd, J=8.5, 2.2 Hz, 1 H), 7.38 (d, J=8.5 Hz, 1 H), 7.42 (d, J=2.2 Hz, 1 H).

MS Calcd.: 443, MS Found: 444 (M+H).

1-(2,4-Dichlorophenyl)-N,N-diethyl-2,3-dihydro-1H-[1,3]diazepino[1,2-a]benzimidazol-7-amine (Example 362)

mp 105-106° C. (hexane).

$^1$H NMR (CDCl$_3$) δ: 1.02 (t, J=7.2 Hz, 6 H), 2.52-2.60 (m, 2 H), 3.12 (q, J=7.2 Hz, 4 H), 3.92 (t, J=5.3 Hz, 2 H), 5.29 (dt, J=10.2, 4.4 Hz, 1 H), 6.81 (dd, J=7.8, 1.0 Hz, 1 H), 7.02 (t, J=7.8 Hz, 1 H), 7.15 (dd, J=7.8, 1.0 Hz, 1 H), 7.29 (dd, J=8.5, 2.2 Hz, 1 H), 7.33 (d, J=8.5 Hz, 1 H), 7.46 (d, J=2.2 Hz, 1 H), 8.21 (dt, J=10.2, 1.8 Hz, 1 H).

MS Calcd.: 400, MS Found: 401 (M+H).

Example 363

1-(2,4-Dichlorophenyl)-N$^7$,N$^7$-diethyl-2,3,4,5-tetrahydro-1H-[1,3]diazepino[1,2-a]benzimidazole-4,7-diamine

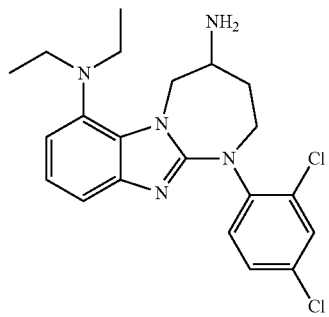 [SMILES: CCN(CC)c1cccc2nc3n(c12)CC(N)CCN3c1ccc(Cl)cc1Cl]

To a suspension of lithium aluminum hydride (31.8 mg, 0.858 mmol) in tetrahydrofuran (1 mL) was added a solution of 4-azido-1-(2,4-dichlorophenyl)-N,N-diethyl-2,3,4,5-tetrahydro-1H-[1,3]diazepino[1,2-a]benzimidazol-7-amine (95.0 mg, 0.214 mmol) in tetrahydrofuran (1 mL) at 0° C. After the resultant mixture was stirred at 0° C. for 2 hr, sodium sulfate decahydrate (320 mg) was added. The resultant mixture was filtered and concentrated in vacuo. The residue was recrystallized from ethyl acetate/diisopropyl ether to give the title compound as a colorless solid (67.2 mg, 0.161 mmol, 75%).

mp 149-151° C.

$^1$H NMR (CDCl$_3$) δ: 0.96-1.14 (m, 6 H), 1.36 (br. s., 2 H), 1.78-1.94 (m/1 H), 2.05-2.21 (m, 1 H), 3.02-3.23 (m, 4 H), 3.31-3.43 (m, 1 H), 3.65-3.77 (m, 1 H), 3.82-4.01 (m, 2 H), 5.46-5.54 (m, 1 H), 6.89 (dd, J=8.0, 1.1 Hz, 1 H), 7.04 (t, J=8.0 Hz, 1 H), 7.25 (dd, J=8.0, 1.1 Hz, 1 H), 7.30 (dd, J=8.5, 2.2 Hz, 1 H), 7.37 (d, J=8.5 Hz, 1 H), 7.41 (d, J=2.2 Hz, 1 H).

MS Calcd.: 417, MS Found: 418 (M+H).

Example 364

N-[1-(2,4-Dichlorophenyl)-7-(diethylamino)-2,3,4,5-tetrahydro-1H-[1,3]diazepino[1,2-a]benzimidazol-4-yl]acetamide

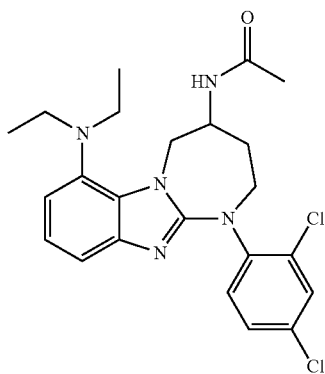 [SMILES: CCN(CC)c1cccc2nc3n(c12)CC(NC(C)=O)CCN3c1ccc(Cl)cc1Cl]

To a mixture of 1-(2,4-dichlorophenyl)-$N^7,N^7$-diethyl-2,3,4,5-tetrahydro-1H-[1,3]diazepino[1,2-a]benzimidazole-4,7-diamine (59.5 mg, 0.142 mmol) and triethylamine (0.0396 mL, 0.284 mmol) in tetrahydrofuran (1.4 mL) was added acetic anhydride (0.161 mL, 0.170 mmol) at 0° C. After the resultant mixture was stirred at 0° C. for 1 hr, aqueous sodium bicarbonate was added and the mixture was concentrated in vacuo. The residue was purified by flash column chromatography on silica gel eluting with a 50-100% ethyl acetate/n-hexane gradient mixture to give a solid, which was recrystallized from ethyl acetate to afford the title compound as a colorless solid (27.1 mg, 0.0589 mmol, 41%).

$^1$H NMR (CDCl$_3$) δ: 0.95-1.09 (m, 6 H), 1.94-2.08 (m, 4 H), 2.14-2.27 (m, 1 H), 3.09 (q, J=7.0 Hz, 4 H), 3.76 (t, J=5.4 Hz, 2 H), 4.47-4.59 (m, 1 H), 4.78-4.87 (m, 1 H), 4.92-5.03 (m, 1 H), 5.79 (d, J=8.5 Hz, 1 H), 6.94 (dd, J=7.8, 0.8 Hz, 1 H), 7.07 (t, J=7.8 Hz, 1 H), 7.28 (dd, J=7.8, 0.8 Hz, 1 H), 7.32 (dd, J=8.8, 2.2 Hz, 1 H), 7.36-7.42 (m, 2 H).

MS Calcd.: 459, MS Found: 460 (M+H).

Example 365

1-(2,4-Dichlorophenyl)-N,N-diethyl-9-fluoro-1,2,3,4-tetrahydropyrimido[1,2-a]benzimidazol-6-amine

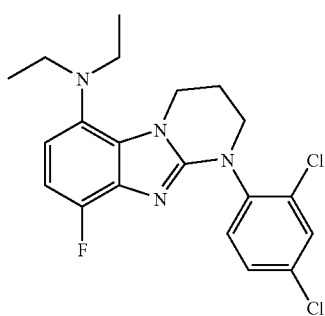 [SMILES: CCN(CC)c1ccc(F)c2nc3n(c12)CCCN3c1ccc(Cl)cc1Cl]

A mixture of $N^2$-(2,4-dichlorophenyl)-$N^7,N^7$-diethyl-4-fluoro-1H-benzimidazole-2,7-diamine (96.7 mg, 0.263 mmol), 1,3-dibromopropane (72.6 mg, 0.360 mmol) and potassium carbonate (113 mg, 0.819 mmol) in N,N-dimethylformamide (6 mL) was stirred at 80° C. for 3 hr. After ethyl acetate was added, the resultant mixture was washed with water and brine, dried over anhydrous sodium sulfate, filtered and concentrated in vacuo. The residue was purified by column chromatography on silica gel eluting with ethyl acetate and preparative HPLC eluting with a 10-100% acetonitrile/water gradient mixture to give the title compound as a pale pink solid (38.2 mg, 0.0938 mmol, 36%).

mp 170-172° C. (ethyl acetate/hexane).

$^1$H NMR (CDCl$_3$) δ: 0.99 (t, J=7.1 Hz, 6 H), 2.27-2.38 (m, 2 H), 3.01 (q, J=7.1 Hz, 4 H), 3.64-3.75 (m, 2 H), 4.58-4.65 (m, 2 H), 6.69-6.77 (m, 2 H), 7.30 (dd, J=8.5, 2.5 Hz, 1 H), 7.46-7.50 (m, 2 H).

MS Calcd.: 406, MS Found: 407 (M+H).

Example 366

Methyl 9-bromo-1-(2,4-dichlorophenyl)-1,2,3,4-tetrahydropyrimido[1,2-a]benzimidazole-6-carboxylate

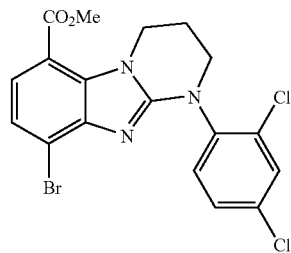 [SMILES: COC(=O)c1ccc(Br)c2nc3n(c12)CCCN3c1ccc(Cl)cc1Cl]

A mixture of above crude methyl 4-bromo-1-(3-chloropropyl)-2-[(2,4-dichlorophenyl)amino]-1H-benzimidazole-7-carboxylate and potassium carbonate (205 mg, 1.49 mmol) in N,N-dimethylformamide (10 mL) was stirred at 80° C. for 15 min. After ethyl acetate was added, the resultant mixture was washed with water and brine, dried over anhydrous sodium sulfate, filtered, and concentrated in vacuo. The residue was purified by flash column chromatography on silica gel eluting with a 10-40% ethyl acetate/n-hexane gradient mixture to give the title compound as a colorless solid (414 mg, 0.910 mmol, 92%).

$^1$H NMR (CDCl$_3$) δ: 2.24-2.38 (m, 2 H), 3.72 (brs, 2 H), 3.93 (s, 3 H), 4.39 (t, J=6.2 Hz, 2 H), 7.24-7.28 (m, 1 H), 7.31 (dd, J=8.3, 2.3 Hz, 1 H), 7.37 (d, J=8.2 Hz, 1 H), 7.47-7.52 (m, 2 H).

MS Calcd.: 453, MS Found: 454 (M+H).

Example 367

Methyl 1-(2,4-dichlorophenyl)-9-methoxy-1,2,3,4-tetrahydropyrimido[1,2-a]benzimidazole-6-carboxylate

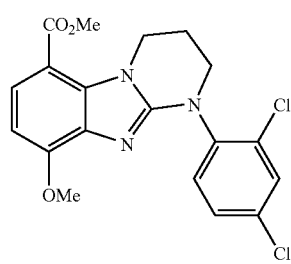 [SMILES: COC(=O)c1ccc(OC)c2nc3n(c12)CCCN3c1ccc(Cl)cc1Cl]

A mixture of methyl 9-bromo-1-(2,4-dichlorophenyl)-1,2,3,4-tetrahydropyrimido[1,2-a]benzimidazole-6-carboxylate (200 mg, 0.439 mmol), sodium methoxide (237 mg, 4.39 mmol), copper(I) iodide (100 mg, 0.525 mmol), Methanol (1.8 mL) and N,N-dimethylformamide (2.6 mL) was stirred at 100° C. for 4 hr. The reaction was quenched by aqueous saturated ammonium chloride, and the mixture was extracted with ethyl acetate. The combined organic layer was washed with brine, dried over anhydrous sodium sulfate, filtered, and concentrated in vacuo. The residue was purified by flash column chromatography on silica gel eluting with a 10-40% ethyl acetate/n-hexane gradient mixture to give the title compound as a colorless solid (54.4 mg, 0.134 mmol, 31%).

$^1$H NMR (CDCl$_3$) δ: 2.21-2.35 (m, 2 H), 3.65-3.79 (m, 2 H), 3.91 (s, 3 H), 3.92 (s, 3 H), 4.46 (t, J=6.3 Hz, 2 H), 6.59 (d, J=8.5 Hz, 1 H), 7.28 (dd, J=8.5, 2.5 Hz, 1 H), 7.44-7.51 (m, 2 H), 7.59 (d, J=8.5 Hz, 1 H).

MS Calcd.: 405, MS Found: 406 (M+H).

Example 368

[9-Bromo-1-(2,4-dichlorophenyl)-1,2,3,4-tetrahydropyrimido[1,2-a]benzimidazol-6-yl](dicyclopropyl)methanol

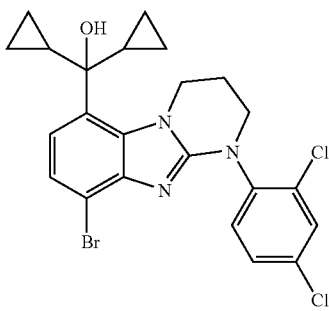 [SMILES: OC(c1ccc(Br)c2nc3n(c12)CCCN3c1ccc(Cl)cc1Cl)(C1CC1)C1CC1]

Cyclopropylmagnesium bromide (1.0 M solution in tetrahydrofuran, 0.880 mL, 0.880 mmol) was added to a stirred solution of methyl 9-bromo-1-(2,4-dichlorophenyl)-1,2,3,4-tetrahydropyrimido[1,2-a]benzimidazole-6-carboxylate (80.0 mg, 0.176 mmol) in tetrahydrofuran (0.88 mL), and the mixture was stirred at 60° C. for 90 min. The reaction was quenched by aqueous saturated ammonium chloride, and the mixture was extracted with ethyl acetate.

The combined organic layer was washed with brine, dried over anhydrous sodium sulfate, filtered, and concentrated in vacuo. The residue was purified by flash column chromatography on silica gel eluting with a 10-40% ethyl acetate/n-hexane gradient mixture to give the title compound as a colorless amorphous solid (78.3 mg, 0.154 mmol, 88%).

$^1$H NMR (CDCl$_3$) δ: 0.18-0.31 (m, 2 H), 0.48-0.66 (m, 6 H), 1.34-1.49 (m, 2 H), 1.72 (s, 1 H), 2.22-2.32 (m, 2 H), 3.62-3.76 (m, 2 H), 4.78-4.86 (m, 2 H), 7.07 (d, J=8.5 Hz, 1 H), 7.16 (d, J=8.5 Hz, 1 H), 7.30 (dd, J=8.5, 2.5 Hz, 1 H), 7.46-7.52 (m, 2 H).

MS Calcd.: 505 (MS Found: 506 (M+H).

Example 369

Dicyclopropyl[1-(2,4-dichlorophenyl)-9-methoxy-1,2,3,4-tetrahydropyrimido[1,2-a]benzimidazol-6-yl]methanol

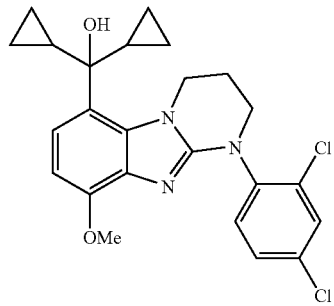 [SMILES: COc1ccc(C(O)(C2CC2)C2CC2)c2c1nc1n2CCCN1c1ccc(Cl)cc1Cl]

Cyclopropylmagnesium bromide (1.0 M solution in tetrahydrofuran, 0.640 mL, 0.640 mmol) was added to a stirred suspension of methyl 1-(2,4-dichlorophenyl)-9-methoxy-1,2,3,4-tetrahydropyrimido[1,2-a]benzimidazole-6-carboxylate (52.0 mg, 0.128 mmol) in tetrahydrofuran (0.64 mL), and the mixture was stirred at 60° C. for 30 min. The reaction was quenched by aqueous saturated ammonium chloride, and the mixture was extracted with ethyl acetate. The combined organic layer was washed with brine, dried over anhydrous sodium sulfate, filtered, and concentrated in vacuo. The residue was purified by flash column chromatography on silica gel eluting with a 10-40% ethyl acetate/n-hexane gradient mixture to give the title compound as a colorless solid (47.4 mg, 0.103 mmol, 80%).

mp 219-220° C.

$^1$H NMR (CDCl$_3$) δ: 0.18-0.28 (m, 2 H), 0.49-0.63 (m, 6 H), 1.38-1.49 (m, 2 H), 1.66 (s, 1 H), 2.22-2.32 (m, 2 H), 3.66 (brs, 2 H), 3.85 (s, 3 H), 4.80-4.87 (m, 2 H), 6.48 (d, J=8.5 Hz, 1 H), 7.16 (d, J=8.5 Hz, 1 H), 7.27 (dd, J=8.5, 2.5 Hz, 1 H), 7.44 (d, J=2.5 Hz, 1 H), 7.48 (d, J=8.5 Hz, 1 H).

MS Calcd.: 457, MS Found: 458 (M+H).

Example 370

9-Chloro-1-(2,4-dichlorophenyl)-1,2,3,4-tetrahydropyrimido[1,2-a]benzimidazole-6-carboxamide

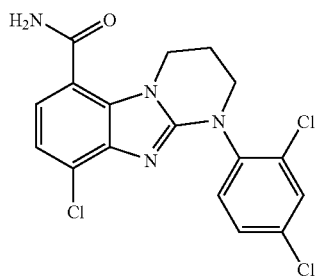 [SMILES: NC(=O)c1ccc(Cl)c2nc3n(c12)CCCN3c1ccc(Cl)cc1Cl]

A mixture of methyl 9-chloro-1-(2,4-dichlorophenyl)-1,2,3,4-tetrahydropyrimido[1,2-a]benzimidazole-6-carboxylate (2.00 g, 4.87 mmol), formamide (1.94 mL, 48.7 mmol) and sodium methoxide (28% solution in methanol, 4.8 mL) in N,N-dimethylformamide (12 mL) was stirred at 120° C. for 19 hr. The mixture was diluted with aqueous saturated ammonium chloride. The resultant precipitate was collected by filtration, washed with water and diisopropyl ether to give the title compound (1.73 g, 4.37 mmol, 90%) as a pale yellow solid.

MS Calcd.: 394, MS Found: 395 (M+H).

Example 371

9-Chloro-1-(2,4-dichlorophenyl)-1,2,3,4-tetrahydropyrimido[1,2-a]benzimidazole-6-carbonitrile

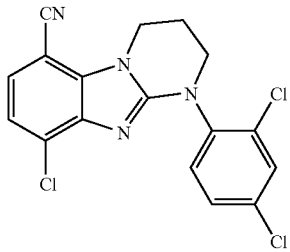 [SMILES: N#Cc1ccc(Cl)c2nc3n(c12)CCCN3c1ccc(Cl)cc1Cl]

To a solution of 9-chloro-1-(2,4-dichlorophenyl)-1,2,3,4-tetrahydropyrimido[1,2-a]benzimidazole-6-carboxamide (1.73 g, 4.37 mmol) in N,N-dimethylformamide (20 mL) was added thionyl chloride (1.05 mL, 14.4 mmol). The resultant mixture was stirred at 50° C. for 1.5 hr and poured into saturated aqueous sodium hydrogen carbonate at 0° C. The resultant precipitate was collected by filtration, washed with water and diisopropyl ether to give the title compound as a pale white solid (1.496 g, 3.96 mmol, 91%).

$^1$H NMR (CDCl$_3$) δ: 2.40-2.52 (m, 2 H), 3.76 (brs, 2 H), 4.51-4.63 (m, 2 H), 7.12 (d, J=8.2 Hz, 1 H), 7.19 (d, J=8.2 Hz, 1 H), 7.34 (dd, J=8.5, 2.2 Hz, 1 H), 7.47 (d, J=8.5 Hz, 1 H), 7.52 (d, J=2.2 Hz, 1 H).

MS Calcd.: 376, MS Found: 377 (M+H).

Example 372

1-[9-Chloro-1-(2,4-dichlorophenyl)-1,2,3,4-tetrahydropyrimido[1,2-a]benzimidazol-6-yl]propan-1-amine

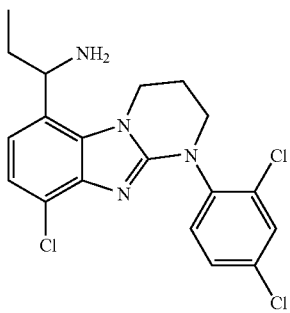 [SMILES: CCC(N)c1ccc(Cl)c2nc3n(c12)CCCN3c1ccc(Cl)cc1Cl]

To a solution of 9-chloro-1-(2,4-dichlorophenyl)-1,2,3,4-tetrahydropyrimido[1,2-a]benzimidazole-6-carbonitrile (1.496 g, 3.096 mmol) in tetrahydrofuran (40 mL) was added ethylmagnesium bromide (3.0 M solution in diethyl ether, 13.2 mL, 39.6 mmol) at 0° C. The reaction mixture was stirred at 50° C. for 4 hr, then the mixture was cooled to room temperature. A suspension of sodium tetrahydroborate (3.0 g, 79.3 mmol) in 2-propanol (40 mL) was added to the reaction mixture at room temperature. After the mixture was stirred at room temperature for 18 hr, water was added to the reaction mixture at 0° C. The mixture was extracted with ethyl acetate. The organic layer was washed with water and brine; dried over anhydrous magnesium sulfate, concentrated in vacuo to give title compound (1.68 g) as a pale yellow amorphous.

MS Calcd.: 408; Found: 409 (M+H).

Example 373

N-{1-[9-Chloro-1-(2,4-dichlorophenyl)-1,2,3,4-tetrahydropyrimido[1,2-a]benzimidazol-6-yl]propyl}methanesulfonamide

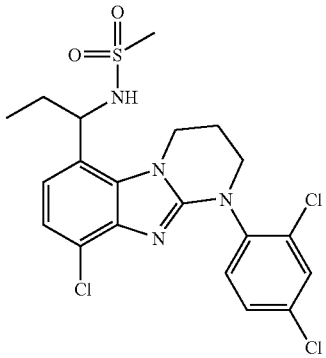 [SMILES: CCC(NS(C)(=O)=O)c1ccc(Cl)c2nc3n(c12)CCCN3c1ccc(Cl)cc1Cl]

To a mixture of crude 1-[9-chloro-1-(2,4-dichlorophenyl)-1,2,3,4-tetrahydropyrimido[1,2-a]benzimidazol-6-yl]propan-1-amine (100 mg) and triethylamine (0.0652 mL, 0.468 mmol) in tetrahydrofuran (5 mL) was added acetic anhydride (0.0530 mL, 0.561 mmol) at 0° C. The resultant mixture was stirred at room temperature for 30 min, diluted with ethyl acetate, washed with water, aqueous sodium bicarbonate and brine, dried over anhydrous sodium sulfate, filtered, and concentrated in vacuo. The residue was purified by flash column chromatography on silica gel eluting with a 10-50% ethyl acetate/n-hexane gradient mixture to give the title compound as a colorless solid (62.1 mg, 0.12 mmol).

mp 125-126° C. (ethyl acetate/hexane).

$^1$H NMR (CDCl$_3$) δ: 0.96 (t, J=7.4 Hz, 3 H), 1.84-1.99 (m, 2 H), 2.35-2.46 (m, 2 H), 2.49 (s, 3 H), 3.71 (brs, 2 H), 4.21-4.32 (m, 1 H), 4.62-4.74 (m, 2 H), 5.08-5.18 (m, 1 H), 6.89 (d, J=8.5 Hz, 1 H), 7.12 (d, J=8.5 Hz, 1 H), 7.31 (dd, J=8.5, 2.2 Hz, 1 H), 7.47-7.53 (m, 2 H).

MS Calcd.: 486, MS Found: 487 (M+H).

Example 374

1-{1-[9-Chloro-1-(2,4-dichlorophenyl)-1,2,3,4-tetrahydropyrimido[1,2-a]benzimidazol-6-yl]propyl}-3-ethylurea

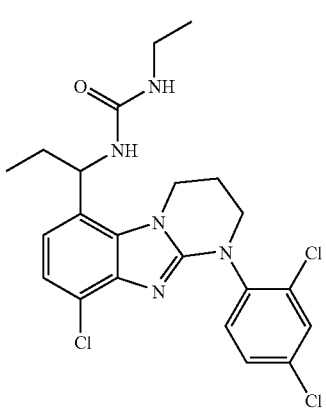 [SMILES: CCNC(=O)NC(CC)c1ccc(Cl)c2nc3n(c12)CCCN3c1ccc(Cl)cc1Cl]

To a solution of crude 1-[9-chloro-1-(2,4-dichlorophenyl)-1,2,3,4-tetrahydropyrimido[1,2-a]benzimidazol-6-yl]propan-1-amine (100 mg) in tetrahydrofuran (2.3 mL) was added ethyl isocyanate (0.0222 mL, 0.280 mmol) at 0° C. The resultant mixture, was stirred at room temperature for 30 min and concentrated in vacuo. The residue was washed with ethyl acetate to give the title compound as a colorless solid (44.1 mg, 0.0917 mmol).

mp 250-252° C. (ethyl acetate).

$^1$H NMR (DMSO-$d_6$) δ: 0.87 (t, J=7.3 Hz, 3 H), 0.95 (t, J=7.1 Hz, 3 H), 1.64-1.81 (m, 2 H), 2.22-2.42 (m, 2 H), 2.89-3.05 (m, 2 H), 3.59-3.75 (m, 2 H), 4.25-4.44 (m, 1 H), 4.65-4.85 (m, 1 H), 5.16-5.30 (m, 1 H), 5.73 (t, J=5.4 Hz, 1 H), 6.44 (d, J=8.5 Hz, 1 H), 6.85 (d, J=8.2 Hz, 1 H), 7.02 (d, J=8.2 Hz, 1 H), 7.54 (dd, J=8.5, 2.5 Hz, 1H), 7.63 (d, J=8.5 Hz, 1H), 7.80 (d, J=2.5 Hz, 1 H).

MS Calcd.: 479, MS Found: 480 (M+H).

Example 375

9-Chloro-1-(2,4-dichloro-6-methylphenyl)-1,2,3,4-tetrahydropyrimido[1,2-a]benzimidazole-6-carboxamide

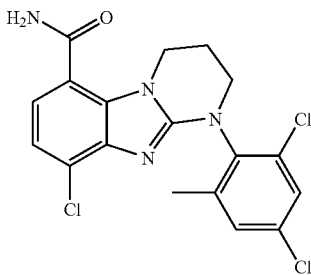

A mixture of methyl 9-chloro-1-(2,4-dichloro-6-methylphenyl)-1,2,3,4-tetrahydropyrimido[1,2-a]benzimidazole-6-carboxylate (1.00 g, 2.35 mmol), formamide (0.937 mL, 2.35 mmol) and sodium methoxide (28% solution in methanol, 2.4 mL) in N,N-dimethylformamide (6 mL) was stirred at 120° C. for 14 hr. The mixture was diluted with aqueous saturated ammonium chloride. The resultant precipitate was collected by filtration, washed with water and diisopropyl ether to give the title compound as a colorless solid.

$^1$H NMR (DMSO-$d_6$) δ: 2.20-2.34 (m, 5H), 3.57-3.68 (m, 2H), 4.14-4.26 (m, 2H), 6.98-7.08 (m, 2H), 7.48-7.59 (m, 2H), 7.64 (d, J=2.5 Hz, 1H), 8.02 (brs, 1H).

MS Calcd.: 408, MS Found: 409 (M+H).

Example 376

9-Chloro-1-(2,4-dichloro-6-methylphenyl)-1,2,3,4-tetrahydropyrimido[1,2-a]benzimidazole-6-carbonitrile

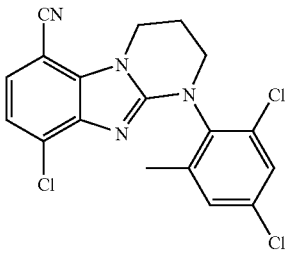 [SMILES: Cc1cc(Cl)cc(Cl)c1N1CCCn2c1nc1c(Cl)ccc(C#N)c12]

To a solution of 9-chloro-1-(2,4-dichloro-6-methylphenyl)-1,2,3,4-tetrahydropyrimido[1,2-a]benzimidazole-6-carboxamide (850 mg 2.07 mmol) in N,N-dimethylformamide (10 mL) was added thionyl chloride (0.448 mL, 6.21 mmol). The resultant mixture was stirred at 50° C. for 30 min and poured into saturated aqueous sodium hydrogen carbonate at 0° C. The resultant precipitate was collected by filtration, washed with water and diisopropyl ether to give the title compound as a colorless solid (532 mg, 1.39 mmol, 67%).

$^1$H NMR (CDCl$_3$) δ: 2.27 (s, 3 H), 2.33-2.59 (m, 2 H), 3.53-3.63 (m, 1 H), 3.75-3.86 (m, 1 H), 4.51-4.66 (m, 2 H), 7.10 (d, J=8.2 Hz, 1 H), 7.18 (d, J=8.2 Hz, 1 H), 7.22-7.25 (m, 1 H), 7.36-7.38 (m, 1 H).

MS Calcd.: 390, MS Found: 391 (M+H).

Example 377

N-{1-[9-Chloro-1-(2,4-dichloro-6-methylphenyl)-1,2,3,4-tetrahydropyrimido[1,2-a]benzimidazol-6-yl]propyl}acetamide Short Retention Time on LC-MS Example 378

N-{1-[9-Chloro-1-(2,4-dichloro-6-methylphenyl)-1,2,3,4-tetrahydropyrimido[1,2-a]benzimidazol-6-yl]propyl}acetamide Long Retention Time on LC-MS

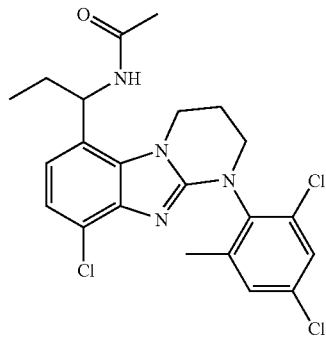 [SMILES: CCC(NC(C)=O)c1ccc(Cl)c2nc3n(c12)CCCN3c1c(C)cc(Cl)cc1Cl]

Ethylmagnesium bromide 0 M solution in diethyl ether, 4.50 mL, 13.5 mmol) was added to a stirred suspension of 9-chloro-1-(2,4-dichloro-6-methylphenyl)-1,2,3,4-tetrahydropyrimido[1,2-a]benzimidazole-6-carbonitrile (530 mg, 1.35 mmol) in tetrahydrofuran (14 mL) at room temperature. After the resultant mixture was refluxed for 3 hr, a suspension of sodium tetrahydroborate (1.02 g, 27.0 mmol) in 2-propanol (14 mL) was added at room temperature. The resultant mixture was stirred at 50° C. for 30 min, diluted with water, and extracted with ethyl acetate. The combined organic layer was washed with brine, dried over anhydrous sodium sulfate, filtered, and concentrated in vacuo to give crude 1-[9-chloro-1-(2,4-dichloro-6-methylphenyl)-1,2,3,4-tetrahydropyrimido[1,2-a]benzimidazol-6-yl]propan-1-amine (609 mg), which was used for the next step without further purification.

To a mixture of crude 1-[9-chloro-1-(2,4-dichloro-6-methylphenyl)-1,2,3,4-tetrahydropyrimido[1,2-a]benzimidazol-6-yl]propan-1-amine (120 mg) and triethylamine (0.0742 mL, 0.532 mmol) in tetrahydrofuran (2.7 mL) was added acetic anhydride (0.0302 mL, 0.319 mmol) at 0° C. The resultant mixture was stirred at room temperature for 10 min, diluted with aqueous sodium bicarbonate and concentrated in vacuo. The residue was purified by flash column chromatography on silica gel eluting with a 20-100% ethyl acetate/n- hexane gradient mixture and preparative HPLC eluting with a 10-40% acetonitrile/water gradient mixture to give the two title compounds as colorless solids.

(Short Retention Time on LC-MS, 27.5 mg, 0.0602 mmol, 11%)

$^1$H NMR (CDCl$_3$) δ: 0.93 (t, J=7.4 Hz, 3 H), 1.84-2.04 (m, 5 H), 2.25 (s, 3 H), 2.26-2.58 (m, 2 H), 3.48-3.59 (m, 1 H), 3.64-3.75 (m, 1 H), 4.28-4.39 (m, 1 H), 4.68-4.79 (m, 1 H), 5.50-5.61 (m, 1 H), 5.76 (d, J=9.1 Hz, 1 H), 6.80 (d, J=8.2 Hz, 1 H), 7.05 (d, J=8.2 Hz, 1 H), 7.18-7.22 (m, 1 H), 7.32-7.36 (m, 1 H).

MS Calcd.: 464, MS Found: 465 (M+H).

(Long Retention Time on LC-MS, 4.5 mg, 0.0097 mmol, 2%)
MS Calcd.: 464, MS Found: 465 (M+H).

Example 379

1-[9-Chloro-1-(2,4-dichloro-6-methylphenyl)-1,2,3,4-tetrahydropyrimido[1,2-a]benzimidazol-6-yl]propan-1-ol Short Retention Time on LC-MS Example 380

1-[9-Chloro-1-(2,4-dichloro-6-methylphenyl)-1,2,3,4-tetrahydropyrimido[1,2-a]benzimidazol-6-yl]propan-1-ol Long Retention Time on LC-MS

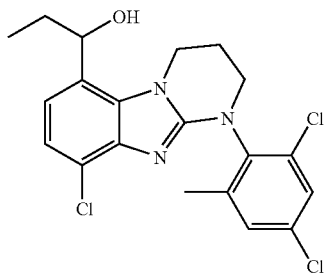 [SMILES: CCC(O)c1ccc(Cl)c2nc3n(c12)CCCN3c1c(C)cc(Cl)cc1Cl]

To a suspension of 9-chloro-1-(2,4-dichloro-6-methylphenyl)-1,2,3,4-tetrahydropyrimido[1,2-a]benzimidazole-6-carbaldehyde (150 mg, 0.380 mmol) in tetrahydrofuran (3.8 mL) was added dropwise ethylmagnesium bromide (3.0 M solution in diethyl ether, 0.152 mL, 0.456 mmol) at 0° C., and the mixture was stirred at room temperature for 30 min. The reaction mixture was diluted with aqueous saturated ammonium chloride, and extracted with ethyl acetate. The combined organic layer was washed with brine, dried over anhydrous sodium sulfate, filtered and concentrated in vacuo. The residue was purified by flash column chromatography on silica gel eluting with a 35% ethyl acetate/n-hexane mixture to give the two title compounds as colorless solids.

(Short retention time on LC-MS, 46.9 mg, 0.110 mmol, 29%)
mp 210-211° C. (ethyl acetate/hexane).

$^1$H NMR (CDCl$_3$) δ: 1.05 (t, J=7.3 Hz, 3 H), 1.82 (d, J=5.5 Hz, 1 H), 1.92-2.04 (m, 2 H), 2.22-2.52 (m, 5 H), 3.47-3.59 (m, 1 H), 3.67-3.79 (m, 1 H), 4.411-4.51 (m, 1 H), 4.61-4.71 (m, 1 H), 4.98-5.07 (m, 1 H), 6.93 (d, J=8.2 Hz, 1 H), 7.03 (d, J=8.2 Hz, 1 H), 7.16-7.22 (m, 1 H), 7.31-7.36 (m, 1 H).

MS Calcd.: 423, MS Found: 424 (M+H).

(Long retention time on LC-MS, 39.8 mg, 0.0936 mmol, 25%)

mp 214-216° C. (ethyl acetate/hexane).

$^1$H NMR (DMSO-d$_6$) δ: 0.95 (t, J=7.3 Hz, 3 H), 1.72-1.87 (m, 2 H), 2.23 (s, 3 H), 2.31 (brs, 2 H), 3.55-3.67 (m, 2 H), 4.46-4.60 (m, 2 H), 4.93-5.01 (m, 1 H), 5.30 (d, J=4.7 Hz, 1 H), 6.93-7.02 (m, 2 H), 7.51 (d, J=2.5 Hz, 1 H), 7.64 (d, J=2.5 Hz, 1 H)

MS Calcd.: 423, MS Found: 424 (M+H).

Example 381

1-[9-Chloro-1-(2,4-dichloro-6-methylphenyl)-1,2,3,4-tetrahydropyrimido[1,2-a]benzimidazol-6-yl]pent-4-en-1-ol Short Retention Time on LC-MS Example 382

1-[9-Chloro-1-(2,4-dichloro-6-methylphenyl)-1,2,3,4-tetrahydropyrimido[1,2-a]benzimidazol-6-yl]pent-4-en-1-ol Long Retention Time on LC-MS

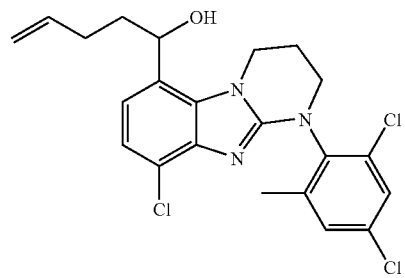 [SMILES: C=CCCC(O)c1ccc(Cl)c2nc3n(c12)CCCN3c1c(C)cc(Cl)cc1Cl]

To a suspension of 9-chloro-1-(2,4-dichloro-6-methylphenyl)-1,2,3,4-tetrahydropyrimido[1,2-a]benzimidazole-6-carbaldehyde (150 mg, 0.380 mmol) in tetrahydrofuran (3.8 mL) was added dropwise 3-butenylmagnesium bromide (ca. 0.8 M solution in diethyl ether, 0.900 mL) at 0° C., and the mixture was stirred at room temperature for 30 min. The reaction mixture was diluted with aqueous saturated ammonium chloride, and extracted with ethyl acetate. The combined organic layer was washed with brine, dried over anhydrous sodium sulfate, filtered and concentrated in vacuo. The residue was purified by flash column chromatography on silica gel eluting with a 10-50% ethyl acetate/n-hexane gradient mixture to give the two title compounds as colorless solids.

(Short retention time on LC-MS, 60.9 mg, 0.135 mmol, 36%)

$^1$H NMR (DMSO-d$_6$) δ: 1.81-1.93 (m, 2 H), 2.10-2.38 (m, 7 H), 3.58-3.64 (m, 2 H), 4.47-4.54 (m, 2 H), 4.95-5.13 (m, 3 H), 5.37 (d, J=4.9 Hz, 1 H), 5.82-5.99 (m, 1 H), 6.95-7.03 (m, 2 H), 7.50-7.53 (m, 1 H), 7.65 (d, J=2.4 Hz, 1 H)

MS Calcd.: 449, MS Found: 450 (M+H).

(Long retention time on LC-MS, 56.9 mg, 0.126 mmol, 33%)

$^1$H NMR (DMSO-d$_6$) δ: 1.81-1.92 (m, 2 H), 2.08-2.37 (m, 7 H), 3.55-3.68 (m, 2 H), 4.46-4.56 (m, 2 H), 4.94-5.12 (m, 3 H), 5.36 (d, J=4.7 Hz, 1 H), 5.81-5.98 (m, 1 H), 6.93-7.02 (m, 2 H), 7.51 (dd, J=2.4, 0.8 Hz, 1 H), 7.64 (dd, J=2.4, 0.8 Hz, 1 H).

MS Calcd.: 449, MS Found: 450 (M+H).

Example 383

1-[9-Chloro-1-(2,4-dichloro-6-methylphenyl)-1,2,3,4-tetrahydropyrimido[1,2-a]benzimidazol-6-yl]but-3-en-1-ol Short Retention Time on LC-MS

Example 384

1-[9-Chloro-1-(2,4-dichloro-6-methylphenyl)-1,2,3,4-tetrahydropyrimido[1,2-a]benzimidazol-6-yl]but-3-en-1-ol Long Retention Time on LC-MS

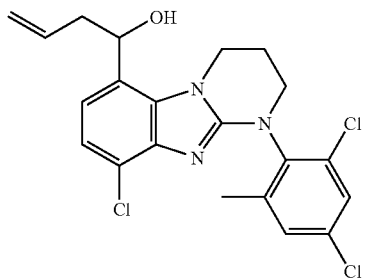 [SMILES: C=CCC(O)c1ccc(Cl)c2nc3n(c12)CCCN3c1c(C)cc(Cl)cc1Cl]

To a suspension of 9-chloro-1-(2,4-dichloro-6-methylphenyl)-1,2,3,4-tetrahydropyrimido[1,2-a]benzimidazole-6-carbaldehyde (200 mg, 0.507 mmol) in tetrahydrofuran (5 mL) was added dropwise allylmagnesium bromide (1 M solution in diethyl ether, 1.00 mL, 1.00 mmol) at 0° C., and the mixture was stirred at room temperature for 1 hr. The reaction mixture was diluted with aqueous saturated ammonium chloride, and extracted with ethyl acetate. The combined organic layer was washed with brine, dried over anhydrous sodium sulfate, filtered and concentrated in vacuo. The residue was purified by flash column chromatography on silica gel eluting with a 20-50% ethyl acetate/n-hexane gradient mixture to give the two title compounds as colorless solids.

(Short retention time on LC-MS, 89.2 mg, 0.204 mmol, 40%)

$^1$H NMR (CDCl$_3$) δ: 2.07 (d, J=4.9 Hz, 1 H), 2.24 (s, 3 H), 2.26-2.54 (m, 2 H), 2.68-2.75 (m, 2 H), 3.47-3.57 (m, 1 H), 3.67-3.77 (m, 1 H), 4.37-4.49 (m, 1 H), 4.61-4.71 (m, 1 H), 5.15-5.28 (m, 3 H), 5.81-5.98 (m, 1 H), 6.96 (d, J=8.2 Hz, 1 H), 7.04 (d, J=8.2 Hz, 1 H), 7.18-7.21 (m, 1 H), 7.32-7.34 (m, 1 H).

MS Calcd.: 435, MS Found: 436 (M+H).

(Long retention time on LC-MS, 87.0 mg, 0.199 mmol, 39%)

$^1$H NMR (DMSO-d$_6$) δ: 2.23 (s, 3 H), 2.26-2.38 (m, 2 H), 2.55-2.63 (m, 2 H), 3.53-3.73 (m, 2 H), 4.39-4.63 (m, 2 H), 5.00-5.23 (m, 3 H), 5.44 (d, J=4.7 Hz, 1 H), 5.80-5.97 (m, 1 H), 7.00 (s, 2 H), 7.52 (d, J=2.4 Hz, 1 H), 7.65 (d, J=2.4 Hz, 1 H).

MS Calcd.: 435, MS Found: 436 (M+H).

Example 385

N-{1-[9-Chloro-1-(2,4-dichlorophenyl)-1,2,3,4-tetrahydropyrimido[1,2-a]benzimidazol-6-yl]propyl}-N-methylmethanesulfonamide

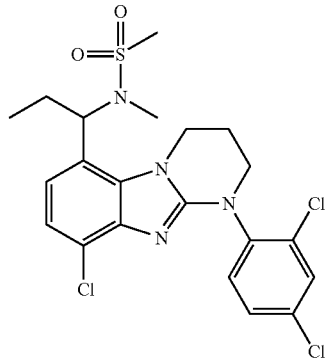 [SMILES: CCC(c1ccc(Cl)c2nc3n(c12)CCCN3c1ccc(Cl)cc1Cl)N(C)S(C)(=O)=O]

To a solution of N-{1-[9-chloro-1-(2,4-dichlorophenyl)-1,2,3,4-tetrahydropyrimido[1,2-a]benzimidazol-6-yl]propyl}methanesulfonamide (60.4 mg, 0.124 mmol) in N,N-dimethylformamide (1.2 mL) was added sodium hydride (60%, 6.0 mg, 0.15 mmol. After the resultant mixture was stirred at room temperature for 30 min, methyl iodide (0.010 mL, 0.16 mmol) was added. The resultant mixture wad stirred at room temperature for 30 min, diluted with aqueous sodium bicarbonate and extracted with ethyl acetate. The combined organic layer was washed with brine, dried over anhydrous sodium sulfate, filtered and concentrated in vacuo. The residue was purified by flash column chromatography on silica gel eluting with a 20-50% ethyl acetate/n-hexane gradient mixture to give the title compound as a colorless solid (55.6 mg, 0.111 mmol, 90%).

$^1$H NMR (DMSO-d$_6$) δ: 0.90 (t, J=7.2 Hz, 3 H), 1.91-2.18 (m, 2 H), 2.25-2.39 (m, 2 H), 2.72 (s, 3 H), 2.78 (s, 3 H), 3.63-3.71 (m, 2 H), 4.33-4.50 (m, 1 H), 4.54-4.72 (m, 1 H), 5.44 (t, J=7.9 Hz, 1 H), 6.97-7.12 (m, 2 H), 7.55 (dd, J=8.7, 2.5 Hz, 1 H), 7.66 (d, J=8.7 Hz, 1 H), 7.81 (d, J=2.5 Hz, 1 H).

MS Calcd.: 500, MS Found: 501 (M+H).

Example 386

1-[9-Chloro-1-(2,4-dichloro-6-methylphenyl)-1,2,3,4-tetrahydropyrimido[1,2-a]benzimidazol-6-yl]-2-cyclopropylethanol

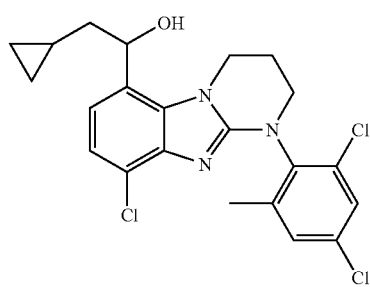 [SMILES: Cc1cc(Cl)cc(Cl)c1N1CCCn2c1nc1c(Cl)ccc(C(O)CC3CC3)c12]

Under nitrogen atmosphere, diethyl zinc (1 M solution in hexane, 0.860 mL, 0.860 mmol) was added to a solution of 1-[9-chloro-1-(2,4-dichloro-6-methylphenyl)-1,2,3,4-tetrahydropyrimido[1,2-a]benzimidazol-6-yl]but-3-en-1-ol (75.0 mg, 0.172 mmol) in dichloromethane (1.7 mL) at 0° C., and then diiodemethane (0.139 mL, 1.73 mmol) was added at 0° C. The resultant mixture was stirred at room temperature for 2 hr, diluted with aqueous saturated ammonium chloride, and extracted with ethyl acetate. The combined organic layer was washed with brine, dried over anhydrous sodium sulfate, filtered and concentrated in vacuo. The residue was purified by flash column chromatography on silica gel eluting with a 20-50% ethyl acetate/n-hexane gradient mixture to give a solid, which was recrystallized from ethyl acetate/hexane to afford the title compound as a colorless solid (17.5 mg, 00388 mmol, 23%).

$^1$H NMR (CDCl$_3$) δ: 0.05-0.27 (m, 2 H), 0.42-0.62 (m, 2 H), 0.73-0.87 (m, 1 H), 1.84 (t, J=6.9 Hz, 2 H), 2.21-2.54 (m, 5 H), 3.46-3.57 (m, 1 H), 3.69-3.80 (m, 1 H), 4.45-4.56 (m, 1 H), 4.60-4.71 (m, 1 H), 5.23 (t, J=6.7 Hz, 1 H), 6.95 (d, J=8.2 Hz, 1 H), 7.02 (d, J=8.2 Hz, 1 H), 7.20 (d, J=2.5 Hz, 1 H), 7.34 (d, J=2.5 Hz, 1 H), hidden (1H).

MS Calcd.: 449, MS Found: 450 (M+H).

Example 387

1-[9-Chloro-1-(2,4-dichloro-6-methylphenyl)-1,2,3,4-tetrahydropyrimido[1,2-a]benzimidazol-6-yl]-2-cyclopropylethanol

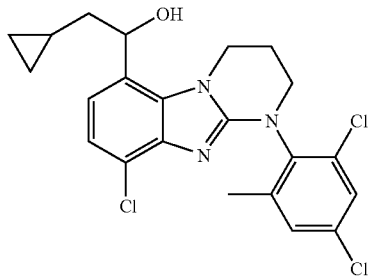 [SMILES: Cc1cc(Cl)cc(Cl)c1N1CCCn2c1nc1c(Cl)ccc(C(O)CC3CC3)c12]

Under nitrogen atmosphere, diethyl zinc (1 M solution in hexane, 0.800 mL, 0.800 mmol) was added to a solution of 1-[9-chloro-1-(2,4-dichloro-6-methylphenyl)-1,2,3,4-tetrahydropyrimido[1,2-a]benzimidazol-6-yl]but-3-en-1-ol (70.0 mg, 0.160 mmol) in dichloromethane (3.2 mL) at 0° C., and then diiodemethane (0.129 mL, 1.60 mmol) was added at 0° C. The resultant mixture was stirred at room temperature for 2 hr, diluted with aqueous saturated ammonium chloride, and extracted with ethyl acetate. The combined organic layer was washed with brine, dried over anhydrous sodium sulfate, filtered and concentrated in vacuo. The residue was purified by flash column chromatography on silica gel eluting with a 20-50% ethyl acetate/n-hexane gradient mixture to give a solid, which was recrystallized from ethyl acetate/hexane to afford the title compound as a colorless solid (24.6 mg, 00540 mmol, 34%).

$^1$H NMR (CDCl$_3$) δ: 0.04-0.28 (m, 2 H), 0.43-0.62 (m, 2 H), 0.73-0.91 (m, 1 H), 1.75-1.95 (m, 2 H), 2.14-2.51 (m, 6 H), 3.44-3.54 (m, 1 H), 3.70-3.83 (m, 1 H), 4.46-4.70 (m, 2 H), 5.24 (t, J=6.6 Hz, 1 H), 6.94 (d, J=8.2 Hz, 1 H), 7.02 (d, J=8.2 Hz, 1 H), 7.21 (d, J=2.5 Hz, 1 H), 7.33 (d, J=2.5 Hz, 1 H).

MS Calcd.: 449, MS Found: 450 (M+H).

Example 388

N-{1-[9-Chloro-1-(2,4-dichlorophenyl)-1,2,3,4-tetrahydropyrimido[1,2-a]benzimidazol-6-yl]propyl}-N-methylacetamide

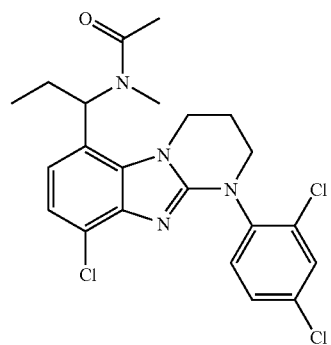 [SMILES: CCC(c1ccc(Cl)c2nc3n(c12)CCCN3c1ccc(Cl)cc1Cl)N(C)C(C)=O]

To a solution of N-{1-[9-chloro-1-(2,4-dichlorophenyl)-1,2,3,4-tetrahydropyrimido[1,2-a]benzimidazol-6-yl]propyl}acetamide (72.0 mg, 0.159 mmol) in N,N-dimethylformamide (1.6 mL) was added sodium hydride (60%, 7.6 mg, 0.19 mmol). After the resultant mixture was stirred at room temperature for 30 min, methyl iodide (0.0119 mL, 0.191 mmol) was added, and the resultant mixture wad stirred at 60° C. for 2 hr. After sodium hydride (60%, 7.6 mg, 0.19 mmol) and methyl iodide (0.0119 mL, 0.191 mmol) were added again, the resultant mixture was stirred at 60° C. for 2 hr, diluted with water and extracted with ethyl acetate. The combined organic layer was washed with brine, dried over anhydrous sodium sulfate, filtered and concentrated in vacuo. The residue was purified by flash column chromatography on silica gel eluting with a 20-90% ethyl acetate/n-hexane gradient mixture to give the title compound as a colorless amorphous solid (12.8 mg, 0.0275 mmol, 17%).

$^1$H NMR (CDCl$_3$) δ: 0.94 (t, J=7.3 Hz, 3 H), 1.85-2.07 (m, 2 H), 2.11 (s, 3 H), 2.27-2.40 (m, 2 H), 2.74 (s, 3 H), 3.66 (br. s., 2 H), 4.34-4.54 (m, 2 H), 6.14-6.22 (m, H), 6.93 (d, J=8.2 Hz, 1 H), 7.08 (d, J=8.2 Hz, 1 H), 7.29 (dd, J=8.5, 2.5 Hz, 1 H), 7.45-7.51 (m, 2 H).

MS Calcd.: 464, MS Found: 465 (M+H).

Example 389

Methyl 9-chloro-1-(2,4,6-trichlorophenyl)-1,2,3,4-tetrahydropyrimido[1,2-a]benzimidazole-6-carboxylate

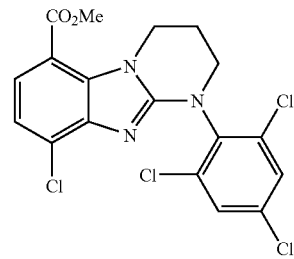 [SMILES: COC(=O)c1ccc(Cl)c2nc3n(c12)CCCN3c1c(Cl)cc(Cl)cc1Cl]

To a mixture of methyl 4-chloro-1-(3-hydroxypropyl)-2-[(2,4,6-trichlorophenyl)amino]-1H-benzimidazole-7-carboxylate (250 mg, 0.540 mmol) and triethylamine (0.376 mL, 2.70 mmol) in tetrahydrofuran (2.7 mL) was added methanesulfonyl chloride (0.171 mL, 2.16 mmol) at 0° C. The resultant mixture was stirred at room temperature for 1 hr and concentrated in vacuo. After N,N-dimethylformamide (5.4 mL) and potassium carbonate (746 mg, 5.40 mmol) were added to the residue, the resultant mixture was stirred at 80° C. for 1 hr, diluted with ethyl acetate, washed with water and brine, dried over anhydrous sodium sulfate, filtered and concentrated in vacuo. The residue was purified by flash column chromatography on silica gel eluting with a 10-50% ethyl acetate/n-hexane gradient mixture to give the title compound as a colorless solid (210 mg, 0.472 mmol, 87%).

$^1$H NMR (CDCl$_3$) δ: 2.28-2.39 (m, 2 H), 3.64-3.70 (m, 2 H), 3.93 (s, 3 H), 4.43 (t, J=6.0 Hz, 2 H), 7.07 (d, J=8.5 Hz, 1 H), 7.42-7.47 (m, 3 H).

MS Calcd.: 443, MS Found: 444 (M+H).

Example 390

9-Chloro-1-(2,4,6-trichlorophenyl)-1,2,3,4-tetrahydropyrimido[1,2-a]benzimidazole-6-carbaldehyde

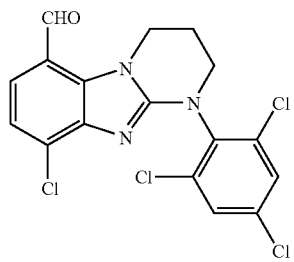 [SMILES: O=Cc1ccc(Cl)c2nc3n(c12)CCCN3c1c(Cl)cc(Cl)cc1Cl]

To a suspension of lithium aluminum hydride (53.7 mg, 1.42 mmol) in tetrahydrofuran (5 mL) was added a solution of methyl 9-chloro-1-(2,4,6-trichlorophenyl)-1,2,3,4-tetrahydropyrimido[1,2-a]benzimidazole-6-carboxylate (210 mg, 0.472 mmol) in tetrahydrofuran (5 mL) at 0° C., and the resultant mixture was stirred at 0° C. for 5 min. After sodium sulfate decahydrate (500 mg) was added at 0° C., the resultant mixture was filtered and concentrated in vacuo to give a crude solid. To a solution of the crude solid in acetonitrile (5 mL) and dimethylsulfoxide (1 mL) was added Dess-Martin reagent (240 mg, 0.566 mmol) at room temperature, and the resultant mixture was stirred at room temperature for 30 min, diluted with aqueous sodium bicarbonate and ethyl acetate, filtered and extracted with ethyl acetate. The combined organic layer was washed with brine, dried over anhydrous sodium sulfate, filtered and concentrated in vacuo. The residue was purified by flash column chromatography on silica gel eluting with a 10-50% ethyl acetate/n-hexane gradient mixture to give the title compound as a colorless solid (166 mg, 0.400 mmol, 85%).

$^1$H NMR (CDCl$_3$) δ: 2.33-2.45 (m, 2 H), 3.65-3.73 (m, 2 H), 4.71 (t, J=6.0 Hz, 2 H), 7.21 (d, J=8.2 Hz, 1 H), 7.35 (d, J=8.2 Hz, 1 H), 7.45 (s, 2 H), 9.97 (s, 1 H).

MS Calcd.: 413, MS Found: 414 (M+H).

Example 391

1-[9-Chloro-1-(2,4,6-trichlorophenyl)-1,2,3,4-tetrahydropyrimido[1,2-a]benzimidazol-6-yl]propan-1-ol

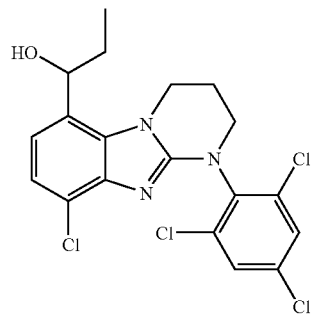 [SMILES: CCC(O)c1ccc(Cl)c2nc3n(c12)CCCN3c1c(Cl)cc(Cl)cc1Cl]

To a suspension of 9-chloro-1-(2,4,6-trichlorophenyl)-1,2,3,4-tetrahydropyrimido[1,2-a]benzimidazole-6-carbaldehyde (166 mg, 0.400 mmol) in tetrahydrofuran (5 mL) was added dropwise ethylmagnesium bromide (3 M solution in diethyl ether, 0.270 mL, 0.810 mmol) at 0° C., and the mixture was stirred at 0° C. for 15 min. The reaction mixture was diluted with aqueous saturated ammonium chloride, and extracted with ethyl acetate. The combined organic layer was washed with brine, dried over anhydrous sodium sulfate, filtered and concentrated in vacuo. The residue was purified by flash column chromatography on silica gel eluting with a 20-60% ethyl acetate/n-hexane gradient mixture to give the title compound as a colorless solid (170 mg, 0.381 mmol, 95%).

mp 213-214° C. (ethyl acetate/hexane).

$^1$H NMR (CDCl$_3$) δ: 1.05 (t, J=7.3 Hz, 3 H), 1.87 (d, J=5.5 Hz, 1 H), 1.91-2.03 (m, 2 H), 2.32-2.49 (m, 2 H), 3.58-3.74 (m, 2 H), 4.43-4.54 (m, 1 H), 4.59-4.68 (m, 1 H), 4.97-5.06 (m, 1 H), 6.94 (d, J=8.2 Hz, 1 H), 7.04 (d, J=8.2 Hz, 1 H), 7.40-7.44 (m, 2 H).

MS Calcd.: 443, MS Found: 444 (M+H).

Example 392

Methyl 9-chloro-1-(2,6-dichloro-4-methoxyphenyl)-1,2,3,4-tetrahydropyrimido[1,2-a]benzimidazole-6-carboxylate

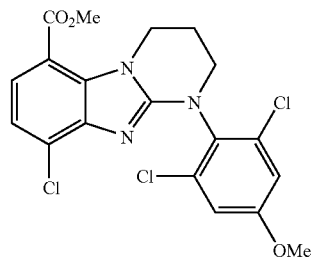 [SMILES: COC(=O)c1ccc(Cl)c2nc3n(c12)CCCN3c1c(Cl)cc(OC)cc1Cl]

To a mixture of methyl 4-chloro-2-[(2,6-dichloro-4-methoxyphenyl)amino]-1-(3-hydroxypropyl)-1H-benzimidazole-7-carboxylate (215 mg, 0.469 mmol) and triethylamine (0.327 mL, 2.35 mmol) in tetrahydrofuran (4.7 mL) was added methanesulfonyl chloride (0.148 mL, 1.87 mmol) at 0° C. The resultant mixture was stirred at room temperature for 30 min and concentrated in vacuo. After N,N-dimethylformamide (4.7 mL) and potassium carbonate (648 mg, 4.69 mmol) were added to the residue, the resultant mixture was stirred at 80° C. for 30 min, diluted with ethyl acetate, washed with water and brine, dried over anhydrous sodium sulfate, filtered and concentrated in vacuo. The residue was purified by flash column chromatography on silica gel eluting with a 20-50% ethyl acetate/n-hexane gradient mixture to give the title compound as a colorless solid (177 mg, 0.401 mmol, 86%).

$^1$H NMR (CDCl$_3$) δ: 2.27-2.37 (m, 2 H), 3.64-3.69 (m, 2 H), 3.81 (s, 3 H), 3.92 (s, 3 H), 4.40 (t, J=6.0 Hz, 2 H), 6.96 (s, 2 H), 7.05 (d, J=8.5 Hz, 1 H), 7.41 (d, J=8.5 Hz, 1 H).

MS Calcd.: 439, MS Found: 440 (M+H).

Example 393

9-Chloro-1-(2,6-dichloro-4-methoxyphenyl)-1,2,3,4-tetrahydropyrimido[1,2-a]benzimidazole-6-carbaldehyde

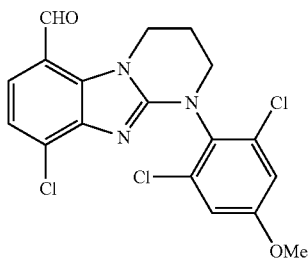 [SMILES: COc1cc(Cl)c(N2CCCn3c2nc2c(Cl)ccc(C=O)c23)c(Cl)c1]

To a suspension of lithium aluminum hydride (45.7 mg, 1.20 mmol) in tetrahydrofuran (4 mL) was added a solution of methyl 9-chloro-1-(2,6-dichloro-4-methoxyphenyl)-1,2,3,4-tetrahydropyrimido[1,2-a]benzimidazole-6-carboxylate (177 mg, 0.401 mmol) in tetrahydrofuran (4 mL) at 0° C., and the resultant mixture was stirred at 0° C. for 5 min. After sodium sulfate decahydrate (450 mg) was added at 0° C., the resultant mixture was filtered and concentrated in vacuo to give a crude solid. To a solution of the crude solid in acetonitrile (4 mL) and dimethylsulfoxide (0.8 mL) was added Dess-Martin reagent (204 mg, 0.481 mmol) at room temperature, and the resultant mixture was stirred at room temperature for 20 min, diluted with aqueous sodium bicarbonate and ethyl acetate, filtered and extracted with ethyl acetate. The combined organic layer was washed with brine, dried over anhydrous sodium sulfate, filtered and concentrated in vacuo. The residue was purified by flash column chromatography on silica gel eluting with a 20-50% ethyl acetate/n-hexane gradient mixture to give the title compound as a colorless solid (146 mg, 0.356 mmol, 89%).

$^1$H NMR (CDCl$_3$) δ: 2.32-2.43 (m, 2 H), 3.65-3.72 (m, 2 H), 3.83 (s, 3 H), 4.69 (t, J=6.0 Hz, 2 H), 6.98 (s, 2 H), 7.19 (d, J=8.2 Hz, 1 H), 7.34 (d, J=8.2 Hz, 1 H), 9.98 (s, 1 H).

MS Calcd.: 409, MS Found: 410 (M+H).

Example 394

1-[(9-Chloro-1-(2,6-dichloro-4-methoxyphenyl)-1,2,3,4-tetrahydropyrimido[1,2-a]benzimidazol-6-yl] propan-1-ol

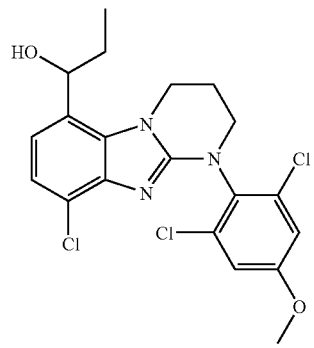 [SMILES: CCC(O)c1ccc(Cl)c2nc3n(c12)CCCN3c1c(Cl)cc(OC)cc1Cl]

To a solution of 9-chloro-1-(2,6-dichloro-4-methoxyphenyl)-1,2,3,4-tetrahydropyrimido[1,2-a]benzimidazole-6-carbaldehyde (146 mg, 0.356 mmol) in tetrahydrofuran (4 mL) was added dropwise ethylmagnesium bromide (3 M solution in diethyl ether, 0.237 mL, 0.711 mmol) at 0° C., and the mixture was stirred at 0° C. for 5 min. The reaction mixture was diluted with aqueous saturated ammonium chloride, and extracted with ethyl acetate. The combined organic layer was washed with brine, dried over anhydrous sodium sulfate, filtered and concentrated in vacuo. The residue was purified by flash column chromatography on silica gel eluting with a 20-50% ethyl acetate/n-hexane gradient mixture to give the title compound as a colorless solid (137 mg, 0.311 mmol, 87%).

mp 206-208° C. (ethyl acetate/hexane).

$^1$H NMR (CDCl$_3$) δ: 1.07 (t, J=7.4 Hz, 3 H), 1.90 (d, J=5.5 Hz, 1 H), 1.93-2.04 (m, 2 H), 2.32-2.47 (m, 2 H), 3.58-3.75 (m, 2 H), 3.83 (s, 3 H), 4.40-4.54 (m, 1 H), 4.57-4.71 (m, 1 H), 4.99-5.09 (m, 1 H), 6.92-7.00 (m, 3 H), 7.02-7.07 (m, 1 H).

MS Calcd.: 439, MS Found: 440 (M+H).

Example 395

Methyl 9-chloro-1-(2,6-dibromo-4-methoxyphenyl)-1,2,3,4-tetrahydropyrimido[1,2-a]benzimidazole-6-carboxylate

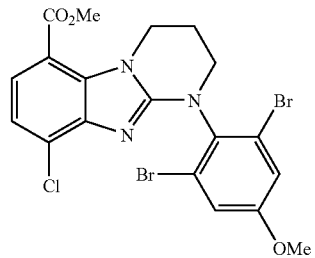 [SMILES: COC(=O)c1ccc(Cl)c2nc3n(c12)CCCN3c1c(Br)cc(OC)cc1Br]

A mixture of methyl 4-chloro-3-{[(2,6-dibromo-4-methoxyphenyl)carbamothioyl]amino}-2-[(3-hydroxypropyl)amino]benzoate (560 mg, 0.963 mmol), 1-ethyl-3-(3-dimethylaminopropyl)carbodiimide hydrochloride (203 mg, 1.06 mmol) and triethylamine (0.148 mL, 1.06 mmol) in tetrahydrofuran (10 mL) was stirred at 50° C. for 2 hr. The reaction mixture was diluted with ethyl acetate, washed with water and brine, dried over anhydrous sodium sulfate, filtered and concentrated in vacuo. To a mixture of residue and triethylamine (0.671 mL, 4.81 mmol) in tetrahydrofuran (10 mL) was added methanesulfonyl chloride (0.304 mL, 3.85 mmol) at 0° C. The resultant mixture was stirred at room temperature for 1 h and concentrated in vacuo. After N,N-dimethylformamide (10 mL) and potassium carbonate (1.33 g, 9.62 mmol) were added to the residue, the resultant mixture was stirred at 80° C. for 4 h, diluted with ethyl acetate, washed with water and brine, dried over anhydrous sodium sulfate, filtered and concentrated in vacuo. The residue was purified by flash column chromatography on silica gel eluting with a 30-60% ethyl acetate/n-hexane gradient mixture to give the title compound as a brown solid (466 mg, 0.881 mmol, 91%).

$^1$H NMR (CDCl$_3$) δ: 2.30-2.44 (m, 2 H), 3.66-3.74 (m, 2 H), 3.83 (s, 3 H), 3.94 (s, 3 H), 4.43 (t, J=6.0 Hz, 2 H), 7.08 (d, J=8.5 Hz, 1 H), 7.20 (s, 2 H), 7.43 (d, J=8.5 Hz, 1 H).

MS Calcd.: 527, MS Found: 528 (M+H).

Example 396

9-Chloro-1-(2,6-dibromo-4-methoxyphenyl)-1,2,3,4-tetrahydropyrimido[1,2-a]benzimidazole-6-carbaldehyde

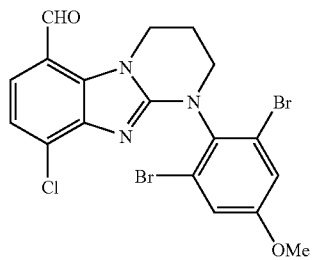 [SMILES: COc1cc(Br)c(N2CCCn3c2nc2c(Cl)ccc(C=O)c23)c(Br)c1]

To a suspension of lithium aluminum hydride (100 mg, 2.64 mmol) in tetrahydrofuran (8 mL) was added a solution of methyl 9-chloro-1-(2,6-dibromo-4-methoxyphenyl)-1,2,3,4-tetrahydropyrimido[1,2-a]benzimidazole-6-carboxylate (466 mg, 0.881 mmol) in tetrahydrofuran (8 mL) at −10° C., and the resultant mixture was stirred at −10° C. for 30 min. After sodium sulfate decahydrate (1.0 g) was added at 0° C., the resultant mixture was filtered and concentrated in vacuo.

To a solution of the residue in acetonitrile (9 mL) and dimethylsulfoxide (1.8 mL) was added Dess-Martin reagent (448 mg, 1.06 mmol) at room temperature, and the resultant mixture was stirred at room temperature for 30 min, diluted with aqueous sodium bicarbonate and ethyl acetate, filtered and extracted with ethyl acetate. The combined organic layer was washed with brine, dried over anhydrous sodium sulfate, filtered and concentrated in vacuo. The residue was purified by flash column chromatography on silica gel eluting with a 10-50% ethyl acetate/n-hexane gradient mixture to give the title compound as a colorless solid (194 mg, 0.388 mmol, 44%).

$^1$H NMR (CDCl$_3$) δ: 2.36-2.46 (2 H, m), 3.67-3.72 (2 H, m), 3.82 (3 H, s), 4.69 (2 H, t, J=6.2 Hz), 7.17-7.22 (3 H, m), 7.33 (1 H, d, J=8.2 Hz), 9.98 (1 H,$).

MS Calcd.: 497, MS Found: 498 (M+H).

Example 397

1-[9-Chloro-1-(2,6-dibromo-4-methoxyphenyl)-1,2,3,4-tetrahydropyrimido[1,2-a]benzimidazol-6-yl]propan-1-ol

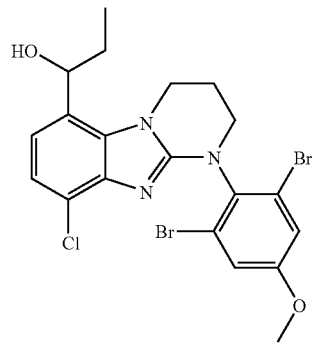 [SMILES: CCC(O)c1ccc(Cl)c2nc3n(c12)CCCN3c1c(Br)cc(OC)cc1Br]

To a solution of 9-chloro-1-(2,6-dibromo-4-methoxyphenyl)-1,2,3,4-tetrahydropyrimido[1,2-a]benzimidazole-6-carbaldehyde (80.0 mg, 0.160 mmol) in tetrahydrofuran (3.2 mL) was added dropwise ethylmagnesium bromide (3 M solution in diethyl ether, 0.107 mL, 0.321 mmol) at 0° C., and the mixture was stirred at 0° C. for 5 min. The reaction mixture was diluted with aqueous saturated ammonium chloride, and extracted with ethyl acetate. The combined organic layer was washed with brine, dried over anhydrous sodium sulfate, filtered and concentrated in vacuo. The residue was purified by flash column chromatography on silica gel eluting with a 10-50% ethyl acetate/n-hexane gradient mixture to give the title compound as a colorless solid (78.0 mg, 0.147 mmol, 92%).

mp 138-140° C.

$^1$H NMR (CDCl$_3$) δ: 1.08 (t, J=7.4 Hz, 3 H), 1.84 (d, J=5.5 Hz, 1 H), 1.95-2.05 (m, 2 H), 2.37-2.51 (m, 2 H), 3.63-3.76 (m, 2 H), 3.83 (s, 3 H), 4.42-4.53 (m, 1 H), 4.60-4.70 (m, 1 H), 5.01-5.10 (m, 1 H), 6.95 (d, J=8.2 Hz, 1 H), 7.05 (d, J=8.2 Hz, 1 H), 7.19 (s, 2 H).

MS Calcd.: 527, MS Found: 528 (M+H).

Example 398

1-[9-Chloro-1-(2,4-dichlorophenyl)-1,2,3,4-tetrahydropyrimido[1,2-a]benzimidazol-6-yl]prop-2-yn-1-ol

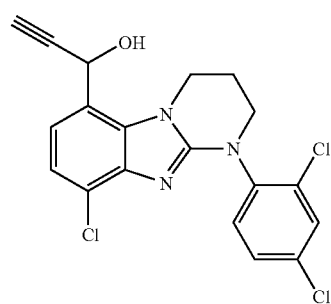 [SMILES: C#CC(O)c1ccc(Cl)c2nc3n(c12)CCCN3c1ccc(Cl)cc1Cl]

To a solution of 9-chloro-1-(2,4-dichlorophenyl)-1,2,3,4-tetrahydropyrimido[1,2-a]benzimidazole-6-carbaldehyde (100 mg, 0.263 mmol) in tetrahydrofuran (1.5 mL) was added dropwise ethynylmagnesium chloride (0.5 M solution in tetrahydrofuran, 1.05 mL, 0.525 mmol) at 0° C., and the mixture was stirred at 0° C. for 10 min. The reaction mixture was diluted with aqueous saturated ammonium chloride, and extracted with ethyl acetate. The combined organic layer was washed with brine, dried over anhydrous sodium sulfate, filtered and concentrated in vacuo. The residue was purified by flash column chromatography on silica gel eluting with a 20-50% ethyl acetate/n-hexane gradient mixture to give the title compound as a colorless solid (99.3 mg, 0.244 mmol, 93%).

$^1$H NMR (CDCl$_3$) δ: 2.30-2.47 (m, 2 H), 2.78 (d, J=2.2 Hz, 1 H), 2.89 (d, J=6.6 Hz, 1 H), 3.72 (brs, 2 H), 4.44-4.55 (m, 1 H), 4.67-4.79 (m, 1 H), 5.83 (dd, J=6.6, 2.2 Hz, 1 H), 7.07 (d, J=8.2 Hz, 1 H), 7.20 (d, J=8.2 Hz, 1 H), 7.32 (dd, J=8.4, 2.3 Hz, 1 H), 7.47-7.53 (m, 2 H).

MS Calcd.: 405, MS Found: 406 (M+H).

Example 399

4-[9-Chloro-6-(hydroxymethyl)-3,4-dihydropyrimido[1,2-a]benzimidazol-1(2H)-yl]-3-methylbenzamide

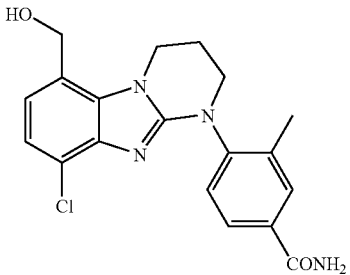 [SMILES: Cc1cc(C(N)=O)ccc1N1CCCn2c1nc1c(Cl)ccc(CO)c12]

To a suspension of lithium aluminum hydride (142 mg, 3.74 mmol) in tetrahydrofuran (12 mL) was added a suspension of methyl 1-(4-carbamoyl-2-methylphenyl)-9-chloro-1,2,3,4-tetrahydropyrimido[1,2-a]benzimidazole-6-carboxylate (500 mg, 1.25 mmol) in tetrahydrofuran (24 mL) at 0° C., and the resultant mixture was stirred at 0° C. for 1 h. After sodium sulfate decahydrate (1.4 g) was added at 0° C., the resultant mixture was filtered and concentrated in vacuo to give the title compound as a yellow solid (433 mg, 1.17 mmol, 94%).

$^1$H NMR (DMSO-d$_6$) δ: 2.18-2.36 (5 H, m), 3.69 (2 H, brs), 4.55 (2 H, brs), 4.73 (2 H, d, J=5.2 Hz), 5.34 (1 H, t, J=5.2 Hz), 6.82 (1 H, d, J=8.2 Hz), 6.93 (1 H, d, J=8.2 Hz), 7.34 (1 H, brs), 7.40 (1 H, d, J=8.2 Hz), 7.75 (1 H, dd, J=8.2, 1.9 Hz), 7.82 (1 H, s), 7.96 (1 H, brs).

MS Calcd.: 370, MS Found: 371 (M+H).

Example 400

4-(9-Chloro-6-formyl-3,4-dihydropyrimido[1,2-a]benzimidazol-1(2H)-yl)-3-methylbenzamide

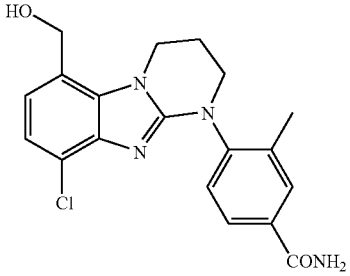

To a solution of 4-[9-chloro-6-(hydroxymethyl)-3,4-dihydropyrimido[1,2-a]benzimidazol-1(2H)-yl]-3-methylbenzamide (390 mg, 1.05 mmol) in acetonitrile (11 mL) and dimethylsulfoxide (2.2 mL) was added Dess-Martin reagent (534 mg, 1.26 mmol) at room temperature, and the resultant mixture was stirred at room temperature for 3 h and diluted with aqueous sodium bicarbonate and aqueous sodium thiosulfate. The resultant mixture was extracted with ethyl acetate. The combined organic layer was washed with brine, dried over anhydrous sodium sulfate, filtered and concentrated in vacuo. The residue was purified by flash column chromatography on silica gel eluting with ethyl acetate to give the title compound as a yellow solid (302 mg, 0.818 mmol, 78%).

$^1$H NMR (CDCl$_3$) δ: 2.25-2.43 (5 H, m), 3.73 (2 H, brs), 4.71 (2 H, brs), 5.52 (1 H, brs), 6.72 (1 H, brs), 7.23 (1 H, d, J=8.2 Hz), 7.32 (1 H, d, J=8.2 Hz), 7.37 (1 H, d, J=8.2 Hz), 7.70-7.75 (1 H, m), 7.80-7.82 (1 H, m), 9.99 (1 H, s).

MS Calcd.: 368, MS Found: 369 (M+H).

Example 401

4-(9-Chloro-6-formyl-3,4-dihydropyrimido[1,2-a]benzimidazol-1(2H)-yl)-3-methylbenzonitrile

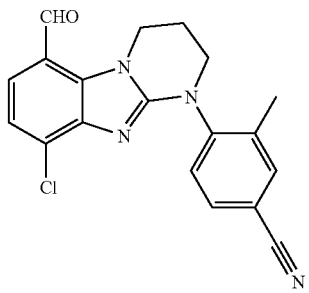 [SMILES: Cc1cc(C#N)ccc1N1CCCn2c1nc1c(Cl)ccc(C=O)c12]

To a mixture of 4-(9-chloro-6-formyl-3,4-dihydropyrimido[1,2-a]benzimidazol-1(2H)-yl)-3-methylbenzamide (100 mg, 0.271 mmol) and triethylamine (0.189 mL, 1.36 mmol) in N,N-dimethylformamide (2.7 mL) was added thionyl chloride (0.0293 mL, 0.406 mmol) at room temperature, and the mixture was stirred at 40° C. for 30 min. After triethylamine (0.189 mL, 1.36 mmol) and thionyl chloride (0.0293 mL, 0.406 mmol) were added to the reaction mixture, the mixture was stirred at 40° C. for 10 min and diluted with aqueous sodium bicarbonate. The resultant mixture was extracted with ethyl acetate. The combined organic layer was washed with brine, dried over anhydrous sodium sulfate, filtered and concentrated in vacuo. The residue was purified by flash column chromatography on silica gel eluting with a 30-70% ethyl acetate/n-hexane gradient mixture to give the title compound as a yellow solid (66.2 mg, 0.189 mmol, 70%).

$^1$H NMR (CDCl$_3$) δ: 2.30 (3 H, s), 2.33-2.42 (2 H, m), 3.71-3.79 (2 H, m), 4.71 (2 H, brs), 7.23 (1 H, d, J=8.3 Hz), 7.38 (1 H, d, J=8.3 Hz), 7.42 (1 H, d, J=8.2 Hz), 7.54-7.58 (1 H, m), 7.60-7.62 (1 H, m), 9.98 (1 H, s).

MS Calcd.: 350, MS Found: 351 (M+H).

Example 402

4-{9-Chloro-6-[cyclopropyl(2,2,2-trifluoroethoxy)methyl]-3,4-dihydropyrimido[1,2-a]benzimidazol-1(2H)-yl}-3-methylbenzonitrile

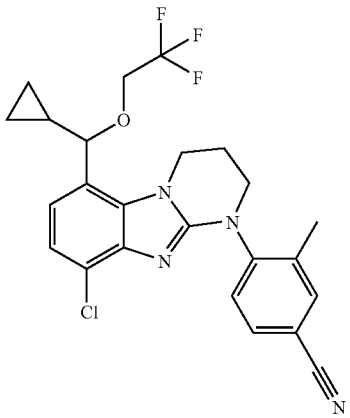 [SMILES: Cc1cc(C#N)ccc1N1CCCn2c1nc1c(Cl)ccc(C(OCC(F)(F)F)C3CC3)c12]

To a solution of 4-(9-chloro-6-formyl-3,4-dihydropyrimido[1,2-a]benzimidazol-1(2H)-yl)-3-methylbenzonitrile (80.1 mg, 0.228 mmol) in tetrahydrofuran (1 mL) was added dropwise cyclopropylmagnesium bromide (1 M solution in tetrahydrofuran, 2.28 mL, 2.28 mmol) at −78° C., and the mixture was stirred at 0° C. for 30 min. The reaction mixture was diluted with aqueous saturated ammonium chloride, and extracted with ethyl acetate. The combined organic layer was washed with brine, dried over anhydrous sodium sulfate, filtered and concentrated in vacuo. The residue was purified by flash column chromatography on silica gel eluting with a 50-90% ethyl acetate/n-hexane gradient mixture to give a crude solid.

To a solution of the solid in tetrahydrofuran (2.3 mL) was added 1,1'-(azodicarbonyl)dipiperidine (115 mg, 0.456 mmol) and tributylphosphine (0.114 mL, 0.456 mmol). After 10 min, to the mixture was added 2,2,2-trifluoroethanol (0.166 mL, 2.28 mmol). The reaction mixture was stirred at 60° C. for 10 min. To the mixture was added diethyl ether and the precipitate was removed by filtration. The filtrate was concentrated in vacuo. The residue was purified by silica gel column chromatography eluting with a 5-30% ethyl acetate/n-hexane gradient mixture to give the title compound as a colorless solid (76.5 mg, 0.161 mmol, 71%).

mp 207-209° C.

$^1$H NMR (CDCl$_3$) δ: 0.26-0.37 (1 H, m), 0.45-0.57 (1 H, m), 0.59-0.71 (1 H, m), 0.73-0.84 (1 H, m), 1.37-1.50 (1 H, m), 2.30 (3 H, s), 2.33-2.43 (2 H, m), 3.63-3.86 (4 H, m), 4.35 (1 H, d, J=8.0 Hz), 4.44-4.74 (2 H, m), 6.89 (1 H, d, J=8.3 Hz), 7.07 (1 H, d, J=8.3 Hz), 7.43 (1 H, d, J=8.0 Hz), 7.53-7.58 (1 H, m), 7.58-7.61 (1 H, m).

MS Calcd.: 474, MS Found: 475 (M+H).

Example 403

9-Chloro-1-(2,4-dichlorophenyl)-6-[1-(difluoromethyl)propyl]-1,2,3,4-tetrahydropyrimido[1,2-a]benzimidazole

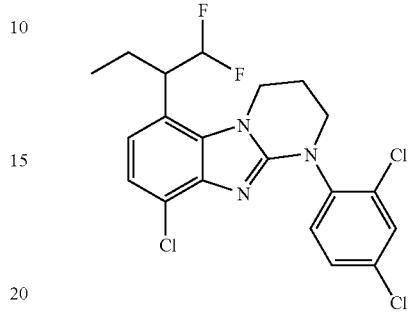

To a solution of 2-[9-chloro-1-(2,4-dichlorophenyl)-1,2,3,4-tetrahydropyrimido[1,2-a]benzimidazol-6-yl]butanal (65.0 mg, 0.154 mmol) in acetonitrile (1.5 mL) was added bis-2-(methoxyethyl)aminosulfur trifluoride (0.114 mL, 0.618 mmol) at 0° C., and the mixture was stirred at room temperature for 1 h. The mixture was quenched with aqueous saturated sodium hydrogen carbonate and extracted with ethyl acetate. The combined organic layer was washed with brine, dried over anhydrous sodium sulfate, filtered and concentrated in vacuo. The residue was purified by flash column chromatography on silica gel eluting with a 15% ethyl acetate/n-hexane mixture to give the title compound as a colorless solid (24.5 mg, 0.0551 mmol, 36%).

$^1$H NMR (CDCl$_3$) δ: 0.91 (3 H, t, J=7.4 Hz), 1.77-2.15 (2 H, m), 2.36-2.48 (2 H, m), 3.58-3.83 (3 H, m), 4.26-4.37 (1 H, m), 4.46-4.56 (1 H, m), 5.88 (1 H, td, J=56.6, 5.5 Hz), 6.83 (1 H, d, J=8.3 Hz), 7.11 (1 H, d, J=8.3 Hz), 7.32 (1 H, dd, J=8.5, 2.2 Hz), 7.50 (1 H, d, J=2.2 Hz), 7.53 (1 H, d, J=8.5 Hz).

MS Calcd.: 443, MS Found: 444 (M+H).

Example 404

3-[9-Chloro-1-(2,4-dichlorophenyl)-1,2,3,4-tetrahydropyrimido[1,2-a]benzimidazol-6-yl]pentan-2-ol

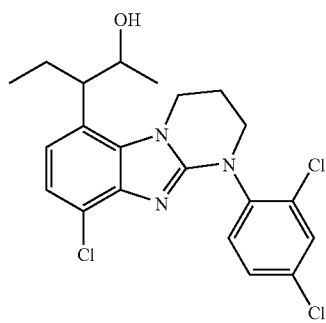 [SMILES: CCC(c1ccc(Cl)c2nc3n(c12)CCCN3c1ccc(Cl)cc1Cl)C(C)O]

To a solution of 2-[9-chloro-1-(2,4-dichlorophenyl)-1,2,3,4-tetrahydropyrimido[1,2-a]benzimidazol-6-yl]butanal (333 mg, 0.790 mmol) in tetrahydrofuran (8 mL) was added drop-

Example 405

3-[9-Chloro-1-(2,4-dichlorophenyl)-1,2,3,4-tetrahydropyrimido[1,2-a]benzimidazol-6-yl]pentan-2-one

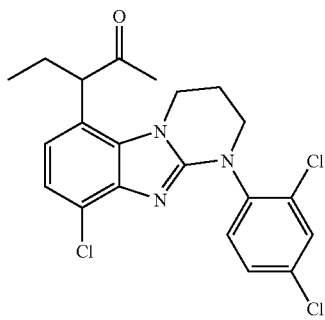 [SMILES: CCC(C(C)=O)c1ccc(Cl)c2nc3n(c12)CCCN3c1ccc(Cl)cc1Cl]

To a solution of 3-[9-chloro-1-(2,4-dichlorophenyl)-1,2,3,4-tetrahydropyrimido[1,2-a]benzimidazol-6-yl]pentan-2-ol (234 mg, 0.533 mmol) in acetonitrile (5 mL) was added Dess-Martin reagent (271 mg, 0.639 mmol) at 0° C., and the resultant mixture was stirred at room temperature for 1 h and diluted with aqueous sodium bicarbonate and aqueous sodium thiosulfate. The resultant mixture was extracted with ethyl acetate. The combined organic layer was washed with brine, dried over anhydrous sodium sulfate, filtered and concentrated in vacuo. The residue was purified by flash column chromatography on silica gel eluting with a 20-50% ethyl acetate/n-hexane gradient mixture to give the title compound as a colorless amorphous solid (205 mg, 0.470 mmol, 88%).

wise methylmagnesium bromide (3 M solution in diethyl ether, 0.395 mL, 1.19 mmol) at −78° C., and the mixture was stirred at −78° C. for 1 h. The reaction mixture was diluted with aqueous saturated ammonium chloride, and extracted with ethyl acetate. The combined organic layer was washed with brine, dried over anhydrous sodium sulfate, filtered and concentrated in vacuo. The residue was purified by flash column chromatography on silica gel eluting with a 20-50% ethyl acetate/n-hexane gradient mixture to give the title compound as a colorless amorphous solid (192 mg, 0.437 mmol, 55%).

¹H NMR (CDCl₃) δ: 0.84 (3 H, t, J=7.4 Hz), 1.09 (3 H, d, J=6.3 Hz), 1.66-1.83 (2 H, m), 1.91-2.02 (1 H, m), 2.31-2.44 (2 H, m), 3.30-3.41 (1 H, m), 3.69 (2 H, brs), 3.95-4.06 (1 H, m), 4.25-4.36 (1 H, m), 4.58-4.72 (1 H, m), 6.74 (1 H, d, J=8.2 Hz), 7.06 (1 H, d, J=8.2 Hz), 7.30 (1 H, dd, J=8.5, 2.2 Hz), 7.48 (1 H, d, J=2.2 Hz), 7.52 (1 H, d, J=8.5 Hz).

MS Calcd.: 437, MS Found: 438 (M+H).

¹H NMR (CDCl₃) δ: 0.96 (3 H, t, J=7.4 Hz), 1.84-1.96 (1 H, m), 2.07 (3 H, s), 2.12-2.24 (1 H, m), 2.36-2.49 (2 H, m), 3.72 (2 H, brs), 4.05-4.18 (1 H, m), 4.31-4.43 (1 H, m), 4.56-4.69 (1 H, m), 6.76 (1 H, d, J=8.3 Hz), 7.08 (1 H, d, J=8.3 Hz), 7.31 (1 H, dd, J=8.4, 2.3 Hz), 7.49-7.53 (2 H, m).

MS Calcd.: 435, MS Found: 436 (M+H).

Example 406

9-Chloro-1-(2,4,6-trichlorophenyl)-1,2,3,4-tetrahydropyrimido[1,2-a]benzimidazole-6-carboxamide

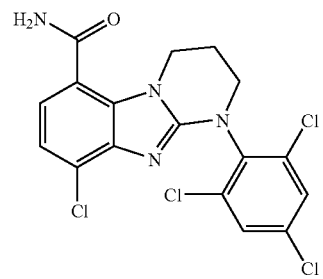 [SMILES: NC(=O)c1ccc(Cl)c2nc3n(c12)CCCN3c1c(Cl)cc(Cl)cc1Cl]

A mixture of methyl 9-chloro-1-(2,4,6-trichlorophenyl)-1,2,3,4-tetrahydropyrimido[1,2-a]benzimidazole-6-carboxylate (500 mg, 1.12 mmol), formamide (0.446 mL, 1.20 mmol) and sodium methoxide (28% solution in methanol, 1.1 mL) in N,N-dimethylformamide (5 mL) was stirred at 60° C. for 5 min. The mixture was diluted with aqueous saturated ammonium chloride. The resultant precipitate was collected by filtration, washed with water and diisopropyl ether to give the title compound as a colorless solid (432 mg, 1.00 mmol, 89%).

¹H NMR (DMSO-d₆) δ: 2.21-2.35 (2 H, m), 3.62-3.71 (2 H, m), 4.21 (2 H, t, J=6.0 Hz), 7.01-7.09 (2 H, m), 7.57 (1 H, s), 7.90 (2 H, s), 8.04 (1 H, s).

MS Calcd.: 428, MS Found: 429 (M+H).

Example 407

9-Chloro-1-(2,4,6-trichlorophenyl)-1,2,3,4-tetrahydropyrimido[1,2-a]benzimidazole-6-carbonitrile

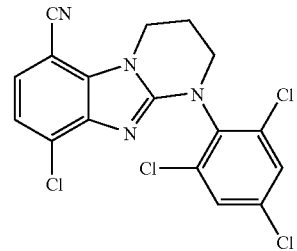 [SMILES: N#Cc1ccc(Cl)c2nc3n(c12)CCCN3c1c(Cl)cc(Cl)cc1Cl]

To a mixture of 9-chloro-1-(2,4,6-trichlorophenyl)-1,2,3,4-tetrahydropyrimido[1,2-a]benzimidazole-6-carboxamide (430 mg, 1.00 mmol) and triethylamine (1.39 mL, 9.97 mmol) in N,N-dimethylformamide (5 mL) was added thionyl chloride (0.216 mL, 3.00 mmol) at 0° C., and the mixture was stirred at 0° C. for 10 min. After the mixture was diluted with aqueous sodium bicarbonate, the resultant mixture was extracted with ethyl acetate. The combined organic layer was washed with brine, dried over anhydrous sodium sulfate, filtered and concentrated in vacuo. The residue was purified by flash column chromatography on silica gel eluting with a 20-50% ethyl acetate/n-hexane gradient mixture to give the title compound as a yellow solid (317 mg, 0.773 mmol, 77%).

¹H NMR (CDCl₃) δ: 2.42-2.52 (2 H, m), 3.69-3.75 (2 H, m), 4.58 (2 H, t, J=6.0 Hz), 7.11 (1 H, d, J=8.2 Hz), 7.19 (1 H, d, J=8.2 Hz), 7.46 (2 H, s).

MS Calcd.: 410, MS Found: 411 (M+H).

Example 408

1-[9-Chloro-1-(2,4,6-trichlorophenyl)-1,2,3,4-tetrahydropyrimido[1,2-a]benzimidazol-6-yl]propan-1-amine

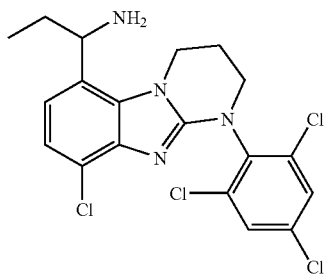 [SMILES: CCC(N)c1ccc(Cl)c2nc3n(c12)CCCN3c1c(Cl)cc(Cl)cc1Cl]

Ethylmagnesium bromide (3 M solution in diethyl ether, 2.58 mL, 7.74 mmol) was added to a stirred solution of 9-chloro-1-(2,4,6-trichlorophenyl)-1,2,3,4-tetrahydropyrimido[1,2-a]benzimidazole-6-carbonitrile (317 mg, 0.773 mmol) in tetrahydrofuran (7 mL) at 0° C. The resultant mixture was stirred at 60° C. for 1 hr. Ethylmagnesium bromide (3 M solution in diethyl ether, 2.58 mL, 7.74 mmol) was added to the reaction mixture at room temperature. The resultant mixture was stirred at 60° C. for 30 min. A suspension of sodium tetrahydroborate (585 mg, 15.5 mmol) in 2-propanol (7 mL) was added at room temperature. The resultant mixture was stirred at room temperature for 1 h, diluted with water, and extracted with ethyl acetate. The combined organic layer was washed with brine, dried over anhydrous sodium sulfate, filtered, and concentrated in vacuo to give the title compound as a crude amorphous solid (392 mg).

MS Calcd.: 442, MS Found: 443 (M+H).

Example 409

N-{1-[9-Chloro-1-(2,4,6-trichlorophenyl)-1,2,3,4-tetrahydropyrimido[1,2-a]benzimidazol-6-yl]propyl}-2,2-difluoroacetamide

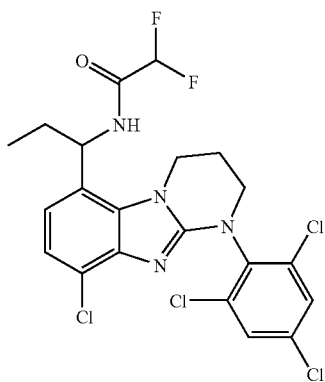 [SMILES: CCC(NC(=O)C(F)F)c1ccc(Cl)c2nc3n(c12)CCCN3c1c(Cl)cc(Cl)cc1Cl]

A mixture of crude 1-[9-chloro-1-(2,4,6-trichlorophenyl)-1,2,3,4-tetrahydropyrimido[1,2-a]benzimidazol-6-yl]propan-1-amine (100 mg), difluoroacetic acid (0.0186 mL, 0.296 mmol), 1-ethyl-3-(3-dimethylaminopropyl)carbodiimide hydrochloride (75.5 mg, 0.394 mmol), 1-hydroxybenzotriazole (53.2 mg, 0.394 mmol) and triethylamine (0.0824 mL, 0.591 mmol) in N,N-dimethylformamide (2 mL) was stirred at room temperature for 3 h, and diluted with ethyl acetate. The resultant mixture was washed with water and brine, dried over anhydrous sodium sulfate, filtered and concentrated in vacuo. The residue was purified by flash column chromatography on silica gel eluting with a 0-30% ethyl acetate/n-hexane gradient mixture and NH silica gel eluting with a 30% ethyl acetate/n-hexane mixture to give the title compound as a colorless solid (42.4 mg, 0.0812 mmol).

mp 211-213° C.

¹H NMR (CDCl₃) δ: 0.98 (3 H, t, J=7.4 Hz), 1.95-2.10 (2 H, m), 2.38-2.49 (2 H, m), 3.59-3.76 (2 H, m), 4.32-4.43 (1 H, m), 4.62-4.74 (1 H, m), 5.55-5.65 (1 H, m), 5.89 (1 H, t, J=54.2 Hz), 6.51-6.58 (1 H, m), 6.85 (1 H, d, J=8.2 Hz), 7.11 (1 H, d, J=8.2 Hz), 7.45 (2 H, s).

MS Calcd.: 520, MS Found: 521 (M+H).

Example 410

Methyl {1-[9-chloro-1-(2,4,6-trichlorophenyl)-1,2,3,4-tetrahydropyrimido[1,2-a]benzimidazol-6-yl]propyl}carbamate

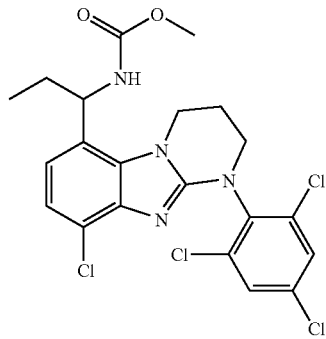 [SMILES: CCC(NC(=O)OC)c1ccc(Cl)c2nc3n(c12)CCCN3c1c(Cl)cc(Cl)cc1Cl]

Methyl chloroformate was added to a mixture of crude 1-[9-chloro-1-(2,4,6-trichlorophenyl)-1,2,3,4-tetrahydropyrimido[1,2-a]benzimidazol-6-yl]propan-1-amine (192 mg) and triethylamine (0.158 mL, 1.13 mmol) in tetrahydrofuran (3.5 mL) at 0° C. The resultant mixture was stirred at 0° C. for 30 min, diluted with aqueous sodium bicarbonate, and concentrated in vacuo. The residue was purified by flash column chromatography on silica gel eluting with a 1-30% ethyl acetate/n-hexane gradient mixture and NH silica gel eluting with a 25% ethyl acetate/n-hexane mixture to give the title compound as a colorless solid (78.2 mg, 0.156 mmol).

mp 231-233° C.

¹H NMR (CDCl₃) δ: 0.96 (3 H, t, J=7.3 Hz), 1.82-2.01 (2 H, m), 2.38-2.49 (2 H, m), 3.58-3.75 (5 H, m), 4.32-4.41 (1 H, m), 4.70-4.84 (1 H, m), 4.99-5.09 (1 H, m), 5.23-5.34 (1 H, m), 6.81 (1 H, d, J=8.2 Hz), 7.08 (1H, d, J=8.2 Hz), 7.44 (2 H, s).

MS Calcd.: 500, MS Found: 501 (M+H).

Example 411

1-[9-Chloro-1-(2,4,6-trichlorophenyl)-1,2,3,4-tetrahydropyrimido[1,2-a]benzimidazol-6-yl]-2,2,2-trifluoroethanol

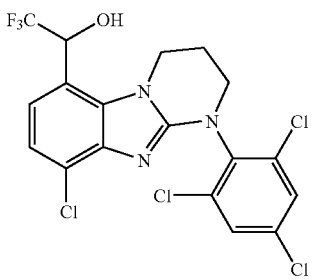

To a solution of 9-chloro-1-(2,4,6-trichlorophenyl)-1,2,3,4-tetrahydropyrimido[1,2-a]benzimidazole-6-carbaldehyde (640 mg, 1.54 mmol) in tetrahydrofuran (8 mL) was added trimethyl(trifluoromethyl)silane (0.683 mL, 4.62 mmol) and tetrabutylammonium fluoride (1.0 M solution in tetrahydrofuran, 0.308 mL, 0.308 mmol) at 0° C. After the mixture was stirred at 0° C. for 30 min and at room temperature for 1 h, to the mixture was added 1N hydrochloric acid (2 mL) at 0° C., and the reaction mixture was stirred at room temperature for 30 min. The mixture was quenched with aqueous saturated sodium hydrogen carbonate and extracted with ethyl acetate. The combined organic layer was washed with brine, dried over anhydrous sodium sulfate, filtered and concentrated in vacuo. The residue was purified by flash column chromatography on silica gel eluting with a 20-70% ethyl acetate/n-hexane gradient mixture to give the title compound as a colorless solid (329 mg, 0.678 mmol, 44%).

$^1$H NMR (DMSO-$d_6$) δ: 2.28-2.40 (2 H, m), 3.65 (2 H, t, J=5.5 Hz), 4.33-4.57 (2 H, m), 5.65-5.79 (1 H m), 7.02-7.07 (1 H, m), 7.08-7.19 (2 H, m), 7.89 (2 H, s).

MS Calcd.: 483, MS Found: 484 (M+H).

Example 412

9-Chloro-6-(1-chloro-2,2,2-trifluoroethyl)-1-(2,4,6-trichlorophenyl)-1,2,3,4-tetrahydropyrimido[1,2-a]benzimidazole

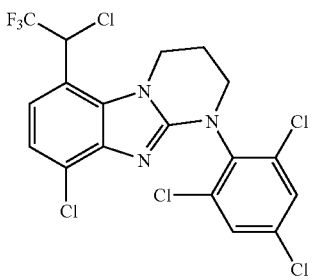

A mixture of 1-[9-chloro-1-(2,4,6-trichlorophenyl)-1,2,3,4-tetrahydropyrimido[1,2-a]benzimidazol-6-yl]-2,2,2-trifluoroethanol (325 mg, 0.670 mmol), thionyl chloride (0.0978 mL, 1.34 mmol) and catalytic amount of dimethylformamide in tetrahydrofuran (6.7 mL) was stirred at room temperature for 2 h. The mixture was quenched with aqueous saturated sodium hydrogen carbonate and extracted with ethyl acetate. The combined organic layer was washed with brine, dried over anhydrous sodium sulfate, filtered and concentrated in vacuo. The residue was purified by flash column chromatography on silica gel eluting with a 10-30% ethyl acetate/n-hexane gradient mixture to give the title compound as a colorless solid (297 mg, 0.590 mmol, 88%).

$^1$H NMR (CDCl$_3$) δ: 2.43-2.56 (2 H, m), 3.67-3.74 (2 H, m), 4.34-4.53 (2 H, m), 5.77-5.86 (1 H, m), 7.16 (1 H, d, J=8.5 Hz), 7.27 (1 H, d, J=8.5 Hz), 7.46 (2 H, s).

MS Calcd.: 501, MS Found: 502 (M+H).

Example 413

6-(1-Azido-2,2,2-trifluoroethyl)-9-chloro-1-(2,4,6-trichlorophenyl)-1,2,3,4-tetrahydropyrimido[1,2-a]benzimidazole

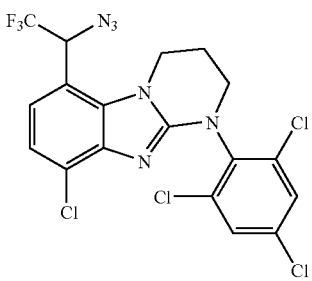 [SMILES: FC(F)(F)C(Cl)c1ccc(Cl)c2nc3n(c12)CCCN3c1c(Cl)cc(Cl)cc1Cl]

A mixture of 9-chloro-6-(1-chloro-2,2,2-trifluoroethyl)-1-(2,4,6-trichlorophenyl)-1,2,3,4-tetrahydropyrimido[1,2-a]benzimidazole (290 mg, 0.576 mmol) and sodium azide (74.9 mg, 1.15 mmol) in dimethylsulfoxide (2.8 mL) was stirred at 100° C. for 2 h. After the mixture was diluted with ethyl acetate, the resultant mixture was washed with water and brine, dried over anhydrous sodium sulfate, filtered and concentrated in vacuo. The residue was purified by flash column chromatography on silica gel eluting with a 0-30% ethyl acetate/n-hexane gradient mixture to give the title compound as a colorless amorphous solid (286 mg, 0.560 mmol, 97%).

$^1$H NMR (CDCl$_3$) δ: 2.42-2.53 (2 H, m), 3.67-3.75 (2 H, m), 4.34-4.52 (2 H, m), 5.36-5.46 (1 H, m), 7.09 (1 H, d, J=8.5 Hz), 7.16 (1 H, d, J=8.5 Hz), 7.46 (2 H, s).

MS Calcd.: 508, MS Found: 509 (M+H).

Example 414

1-[9-Chloro-1-(2,4,6-trichlorophenyl)-1,2,3,4-tetrahydropyrimido[1,2-a]benzimidazol-6-yl]-2,2,2-trifluoroethanamine

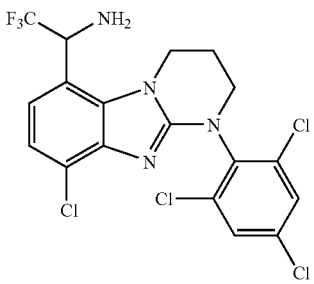 [SMILES: NC(c1ccc(Cl)c2nc3n(c12)CCCN3c1c(Cl)cc(Cl)cc1Cl)C(F)(F)F]

A mixture of 6-(1-azido-2,2,2-trifluoroethyl)-9-chloro-1-(2,4,6-trichlorophenyl)-1,2,3,4-tetrahydropyrimido[1,2-a]benzimidazole (286 mg, 0.560 mmol), triphenylphosphine (220 mg, 0.839 mmol) and water (0.560 mL) in tetrahydrofuran (5.6 mL) was stirred at 60° C. for 1 day. After the mixture was diluted with ethyl acetate, the resultant mixture was extracted with 1N hydrochloric acid. The extract was washed with diethyl ether and neutralized with aqueous saturated sodium hydrogen carbonate. The resultant mixture was extracted with ethyl acetate. The extract was washed with brine, dried over anhydrous sodium sulfate, filtered and concentrated in vacuo to give the title compound as a colorless solid (257 mg, 0.532 mmol, 95%).

$^1$H NMR (CDCl$_3$) δ: 1.87 (2 H, d, J=6.6 Hz), 2.38-2.50 (2 H, m), 3.65-3.71 (2 H, m), 4.38-4.48 (1 H, m), 4.55-4.66 (1 H, m), 4.92-5.10 (1 H, m), 7.07-7.15 (2 H, m), 7.45 (2 H, s).

MS Calcd.: 482, MS Found: 483 (M+H).

Example 415

N-{1-[9-Chloro-1-(2,4,6-trichlorophenyl)-1,2,3,4-tetrahydropyrimido[1,2-a]benzimidazol-6-yl]-2,2,2-trifluoroethyl}acetamide

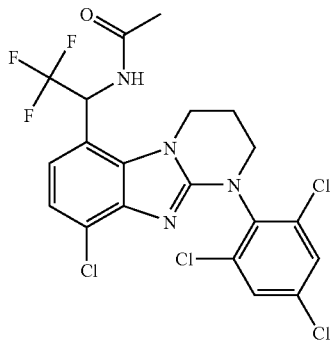 [SMILES: CC(=O)NC(c1ccc(Cl)c2nc3n(c12)CCCN3c1c(Cl)cc(Cl)cc1Cl)C(F)(F)F]

To a mixture of 1-[9-chloro-1-(2,4,6-trichlorophenyl)-1,2,3,4-tetrahydropyrimido[1,2-a]benzimidazol-6-yl]-2,2,2-trifluoroethanamine (80.0 mg, 0.165 mmol) and triethylamine (0.0460 mL, 0.330 mmol) in tetrahydrofuran (2 mL) was added acetyl chloride (0.0141 mL, 0.198 mmol) at 0° C. The resultant mixture was stirred at room temperature for 30 min and diluted with aqueous sodium bicarbonate. The resultant mixture was extracted with ethyl acetate. The extract was washed with brine, dried over anhydrous sodium sulfate, filtered and concentrated in vacuo. The residue was purified by flash column chromatography on silica gel eluting with a 10-50% ethyl acetate/n-hexane gradient mixture to give the title compound as a colorless solid (82.2 mg, 0.156 mmol, 95%).

$^1$H NMR (DMSO-d$_6$) δ: 1.96 (3 H, s), 2.32-2.45 (2 H, m), 3.63-3.70 (2 H, m), 4.35-4.47 (1 H, m), 4.48-4.60 (1 H, m), 6.36-6.50 (1 H, m), 7.17 (2 H, s), 7.8 (2 H, s), 9.34 (1 H, d, J=8.8 Hz).

MS Calcd.: 524, MS Found: 525 (M+H).

Example 416

N-{1-[9-Chloro-1-(2,4,6-trichlorophenyl)-1,2,3,4-tetrahydropyrimido[1,2-a]benzimidazol-6-yl]-2,2,2-trifluoroethyl}methanesulfonamide

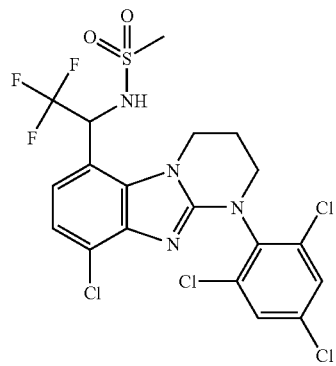 [SMILES: CS(=O)(=O)NC(c1ccc(Cl)c2nc3n(c12)CCCN3c1c(Cl)cc(Cl)cc1Cl)C(F)(F)F]

To a mixture of 1-[9-chloro-1-(2,4,6-trichlorophenyl)-1,2,3,4-tetrahydropyrimido[1,2-a]benzimidazol-6-yl]-2,2,2-trifluoroethanamine (80.0 mg, 0.165 mmol) and triethylamine (0.0460 mL, 0.330 mmol) in tetrahydrofuran (2 mL) was added methanesulfonyl chloride (0.0153 mL, 0.198 mmol) at 0° C. The resultant mixture was stirred at room temperature for 30 min and diluted with aqueous sodium bicarbonate. The resultant mixture was extracted with ethyl acetate. The extract was washed with brine, dried over anhydrous sodium sulfate, filtered and concentrated in vacuo. The residue was purified by flash column chromatography on silica gel eluting with a 20-50% ethyl acetate/n-hexane gradient mixture to give the title compound as a colorless solid (83.7 mg, 0.149 mmol, 90%).

mp 290-291° C.

$^1$H NMR (DMSO-d$_6$) δ: 2.32-2.44 (2 H, m), 2.88 (3 H, s), 3.62-3.73 (2 H, m), 4.29-4.50 (2 H, m), 5.71-5.83 (1 H, m), 7.17 (1 H, d, J=8.2 Hz), 7.23 (1 H, d, J=8.2 Hz), 7.89 (2 H, s), 9.13 (1 H, s).

MS Calcd.: 560, MS Found: 561 (M+H).

Example 417

N-{1-[9-Chloro-1-(2,4,6-trichlorophenyl)-1,2,3,4-tetrahydropyrimido[1,2-a]benzimidazol-6-yl]-2,2,2-trifluoroethyl}-2,2,2-trifluoroethanesulfonamide

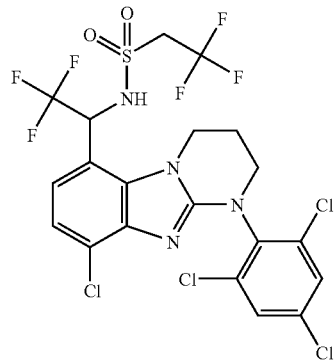 [SMILES: O=S(=O)(CC(F)(F)F)NC(c1ccc(Cl)c2nc3n(c12)CCCN3c1c(Cl)cc(Cl)cc1Cl)C(F)(F)F]

457

To a mixture of 1-[9-chloro-1-(2,4,6-trichlorophenyl)-1,2,3,4-tetrahydropyrimido[1,2-a]benzimidazol-6-yl]-2,2,2-trifluoroethanamine (80.0 mg, 0.165 mmol) and triethylamine (0.0460 mL, 0.330 mmol) in tetrahydrofuran (2 mL) was added 2,2,2-trifluoroethanesulfonyl chloride (0.0219 mL, 0.198 mmol) at 0° C. The resultant mixture was stirred at room temperature for 30 min and diluted with aqueous sodium bicarbonate. The resultant mixture was extracted with ethyl acetate. The extract was washed with brine, dried over anhydrous sodium sulfate, filtered and concentrated in vacuo. The residue was purified by flash column chromatography on silica gel eluting with a 0-30% ethyl acetate/n-hexane gradient mixture to give the title compound as a colorless solid (100 mg, 0.159 mmol, 96%).

mp 237-239° C.

$^1$H NMR (DMSO-$d_6$) δ: 2.31-2.44 (2 H, m), 3.63-3.71 (2 H, m), 4.25-4.68 (4 H, m), 5.75-5.89 (1 H, m), 7.16 (1 H, d, J=8.5 Hz), 7.24 (1 H, d, J=8.5 Hz), 7.87-7.90 (2 H, m), 9.94 (1 H, s).

MS Calcd.: 628, MS Found: 629 (M+H).

Example 418

Methyl 9-bromo-1-(4-methoxy-2-methylphenyl)-1,2,3,4-tetrahydropyrimido[1,2-a]benzimidazole-6-carboxylate

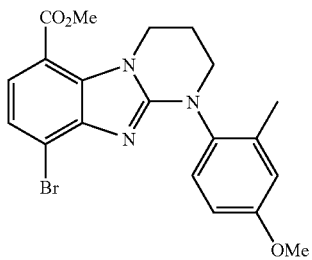 [SMILES: COC(=O)c1ccc(Br)c2nc3n(c12)CCCN3c1ccc(OC)cc1C]

A mixture of methyl 4-bromo-2-chloro-1-(3-chloropropyl)-1H-benzimidazole-7-carboxylate (429 mg, 1.17 mmol), 4-methoxy-2-methylaniline (0.301 mL, 2.34 mmol) and p-toluenesulfonic acid monohydrate (0.0223, 0.117 mmol) in o-xylene (2.4 mL) was stirred at 120° C. for 3 days, and diluted with aqueous sodium bicarbonate. The resultant mixture was extracted with ethyl acetate. The extract was washed with brine, dried over anhydrous sodium sulfate, filtered and concentrated in vacuo. The residue was purified by flash column chromatography on NH silica gel eluting with a 10-40% ethyl acetate/n-hexane gradient mixture to give the title compound as a brown solid (301 mg, 0.700 mmol, 60%).

$^1$H NMR (CDCl$_3$) δ: 2.20-2.32 (5 H, m), 3.57-3.76 (2 H, m), 3.82 (3 H, s), 3.93 (3 H, s), 4.32-4.44 (2 H, m), 6.75-6.84 (2 H, m), 7.19-7.24 (2 H, m), 7.32 (1 H, d, J=8.2 Hz).

MS Calcd.: 429, MS Found: 430 (M+H).

458

Example 419

9-Bromo-1-(4-methoxy-2-methylphenyl)-1,2,3,4-tetrahydropyrimido[1,2-a]benzimidazole-6-carbaldehyde

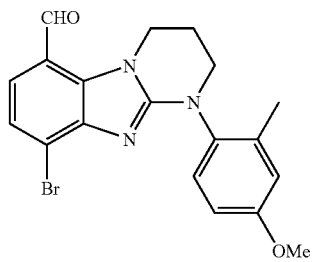 [SMILES: COc1ccc(N2CCCn3c2nc2c(Br)ccc(C=O)c23)c(C)c1]

To a suspension of lithium aluminum hydride (106 mg, 2.79 mmol) in tetrahydrofuran (3.5 mL) was added a solution of methyl 9-bromo-1-(4-methoxy-2-methylphenyl)-1,2,3,4-tetrahydropyrimido[1,2-a]benzimidazole-6-carboxylate (301 mg, 0.700 mmol) in tetrahydrofuran (3.5 mL) at 0° C., and the resultant mixture was stirred at 0° C. for 10 min. After sodium sulfate decahydrate (1 g) was added at 0° C., the resultant mixture was filtered and concentrated in vacuo. To a solution of the residue in acetonitrile (7 mL) and dimethylsulfoxide (1.4 mL) was added Dess-Martin reagent (356 mg, 0.839 mmol) at room temperature. The resultant mixture was stirred at room temperature for 30 min and diluted with aqueous sodium bicarbonate and aqueous sodium thiosulfate. The resultant mixture was extracted with ethyl acetate. The combined organic layer was washed with brine, dried over anhydrous sodium sulfate, filtered and concentrated in vacuo. The residue was purified by flash column chromatography on silica gel eluting with a 10-50% ethyl acetate/n-hexane gradient mixture to give the title compound as a yellow solid (249 mg, 0.622 mmol, 89%).

$^1$H NMR (CDCl$_3$) δ: 2.23 (3 H, s), 2.28-2.38 (2 H, m), 3.57-3.80 (2 H, m), 3.82 (3 H, s), 4.52-4.80 (2 H, m), 6.75-6.85 (2 H, m), 7.19-7.27 (2 H, m), 7.36 (1 H, m, J=8.2 Hz), 9.99 (1 H, s).

MS Calcd.: 399, MS Found: 400 (M+H).

Example 420

1-[9-Bromo-1-(4-methoxy-2-methylphenyl)-1,2,3,4-tetrahydropyrimido[1,2-a]benzimidazol-6-yl]-2,2,2-trifluoroethanol

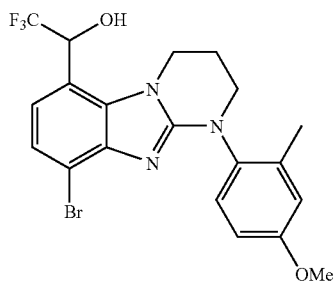 [SMILES: COc1ccc(N2CCCn3c2nc2c(Br)ccc(C(O)C(F)(F)F)c23)c(C)c1]

To a solution of 9-bromo-1-(4-methoxy-2-methylphenyl)-1,2,3,4-tetrahydropyrimido[1,2-a]benzimidazole-6-carbaldehyde (249 mg, 0.622 mmol) in tetrahydrofuran (3 mL) was added trimethyl(trifluoromethyl)silane (0.276 mL, 1.87 mmol) and tetrabutylammonium fluoride (1.0 M solution in tetrahydrofuran, 0.124 mL, 0.124 mmol) at 0° C. After the mixture was stirred at 0° C. for 15 min, to the reaction mixture was added trimethyl(trifluoromethyl)silane (0.276 mL, 1.87 mmol) (and tetrabutylammonium fluoride (1.0 M solution in tetrahydrofuran, 0.124 mL, 0.124 mmol) at 0° C. After the mixture was stirred at 0° C. for 15 min, to the mixture was added 1N hydrochloric acid (3 mL) at 0° C., and the reaction mixture was stirred at 0° C. for 10 min. The mixture was quenched with aqueous saturated sodium hydrogen carbonate and extracted with ethyl acetate. The combined organic layer was washed with brine, dried over anhydrous sodium sulfate, filtered and concentrated in vacuo. The residue was purified by flash column chromatography on silica gel eluting with a 20-80% ethyl acetate/n-hexane gradient mixture to give the title compound as a yellow solid (241 mg, 0.512 mmol, 82%).

$^1$H NMR (DMSO-$d_6$) δ: 2.16 (3 H, s), 2.23-2.35 (2 H, m), 3.42-3.75 (2 H, m), 3.78 (3 H, s), 4.20-4.55 (2 H, m), 5.64-5.79 (1 H, m), 6.83 (1 H, dd, J=8.7, 3.0 Hz), 6.90 (1 H, d, J=3.0 Hz), 6.94-7.07 (2 H, m), 7.20 (1 H, d, J=8.5 Hz), 7.25 (1 H, d, J=8.7 Hz).

MS Calcd.: 469, MS Found: 470 (M+H).

Example 421

9-Bromo-6-[1-(difluoromethoxy)-2,2,2-trifluoroethyl]-1-(4-methoxy-2-methylphenyl)-1,2,3,4-tetrahydropyrimido[1,2-a]benzimidazole

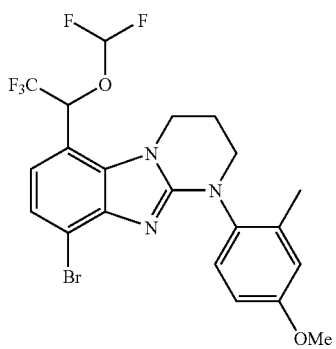 [SMILES: COc1ccc(N2CCCn3c2nc2c(Br)ccc(C(OC(F)F)C(F)(F)F)c23)c(C)c1]

Under chloro(difluoro)methane atmosphere, a mixture of 1-[9-bromo-1-(4-methoxy-2-methylphenyl)-1,2,3,4-tetrahydropyrimido[1,2-a]benzimidazol-6-yl]-2,2,2-trifluoroethanol (235 mg, 0.500 mmol), benzyltriethylammonium chloride (11.4 mg, 0.0501 mmol) and 8N sodium hydroxide (2.5 mL) in tetrahydrofuran (2.5 mL) was stirred at room temperature for 15 min. The mixture was diluted with aqueous saturated ammonium chloride and extracted with ethyl acetate. The combined organic layer was washed with brine, dried over anhydrous sodium sulfate, filtered and concentrated in vacuo. The residue was purified by flash column chromatography on silica gel eluting with a 10-50% ethyl acetate/n-hexane gradient mixture and flash column chromatography on silica gel eluting with a 20% ethyl acetate/n-hexane mixture to give the title compound as a colorless solid (84.0 mg, 0.159 mmol, 26%).

$^1$H NMR (CDCl$_3$) δ 2.26 (3 H, s), 2.35-2.45 (2 H, m), 3.55-3.78 (2 H, m), 3.82 (3 H, s), 4.23-4.43 (2 H, m), 5.96-6.05 (1 H, m), 6.39 (1 H, t, J=72.0 Hz), 6.76-6.81 (1 H, m), 6.83 (1 H, d, J=3.0 Hz), 7.04 (1 H, d, J=8.5 Hz), 7.22 (1 H, d, J=8.5 Hz), 7.29 (1 H, d, J=8.5 Hz).

MS Calcd.: 519; MS Found: 520 (M+H).

Example 422

2,2,2-Trifluoro-1-[9-methoxy-1-(4-methoxy-2-methylphenyl)-1,2,3,4-tetrahydropyrimido[1,2-a]benzimidazol-6-yl]ethanol

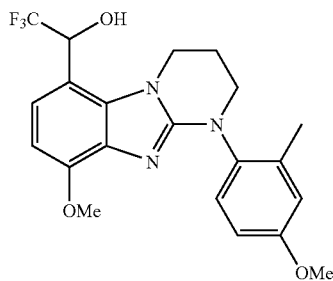 [SMILES: COc1ccc(N2CCCn3c2nc2c(OC)ccc(C(O)C(F)(F)F)c23)c(C)c1]

A mixture of 1-[9-bromo-1-(4-methoxy-2-methylphenyl)-1,2,3,4-tetrahydropyrimido[1,2-a]benzimidazol-6-yl]-2,2,2-trifluoroethanol (200 mg, 0.425 mmol), sodium methoxide (28% methanol solution, 3 mL), copper(I) iodide (121 mg, 0.635 mmol) in N,N-dimethylformamide (3 mL) was stirred at 100° C. for 1 hr. The reaction was quenched by aqueous saturated ammonium chloride, and the mixture was extracted with ethyl acetate. The combined organic layer was washed with brine, dried over anhydrous sodium sulfate, filtered, and concentrated in vacuo. The residue was purified by flash column chromatography on silica gel eluting with a 40-80% ethyl acetate/n-hexane gradient mixture to give the title compound as a colorless oil (96.6 mg, 0.229 mmol, 54%).

$^1$H NMR (CDCl$_3$) δ: 2.11-2.28 (5 H, m), 3.40-3.70 (2 H, m), 3.69-3.83 (6 H, m), 4.02-4.34 (2 H, m), 5.28-5.39 (1 H, m), 6.55 (1 H, d, J=8.5 Hz), 6.66-6.77 (2 H, m), 7.01-7.23 (2 H, m), hidden (1H).

MS Calcd.: 421, MS Found: 422 (M+H).

Example 423

6-[1-(Difluoromethoxy)-2,2,2-trifluoroethyl]-9-methoxy-1-(4-methoxy-2-methylphenyl)-1,2,3,4-tetrahydropyrimido[1,2-a]benzimidazole

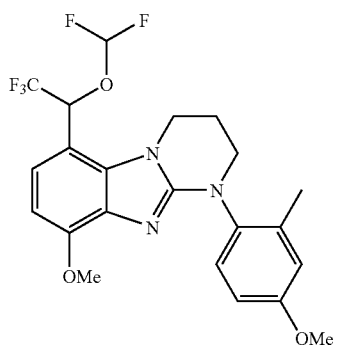 [SMILES: COc1ccc(N2CCCn3c2nc2c(OC)ccc(C(OC(F)F)C(F)(F)F)c23)c(C)c1]

Under chloro(difluoro)methane atmosphere, a mixture of 2,2,2-trifluoro-1-[9-methoxy-1-(4-methoxy-2-methylphenyl)-1,2,3,4-tetrahydropyrimido[1,2-a]benzimidazol-6-yl]ethanol (96.6 mg, 0.229 mmol), benzyltriethylammonium chloride (5.22 mg, 0.0229 mmol) and 8N sodium hydroxide (1.2 mL) in tetrahydrofuran (1.2 mL) was stirred 0° C. for 2 h. The mixture was diluted with aqueous saturated ammonium chloride and extracted with ethyl acetate. The combined organic layer was washed with brine, dried over anhydrous sodium sulfate, filtered and concentrated in vacuo. The residue was purified by flash column chromatography on silica gel eluting with a 10-50% ethyl acetate/n-hexane gradient mixture, flash column chromatography on NH silica gel eluting with a 20-50% ethyl acetate/n-hexane gradient mixture, and recrystallization from ethyl acetate/hexane to give the title compound as a colorless solid (30.8 mg, 0.0653 mmol, 29%).

$^1$H NMR (CDCl$_3$) δ 2.25 (3 H, s), 2.31-2.46 (2 H, m), 3.50-3.74 (2 H, m), 3.79 (3 H, s), 3.88 (3 H, s), 4.22-4.45 (2 H, m), 5.91-6.00 (1 H, m), 6.35 (1 H, t, J=73.3 Hz), 6.64 (1 H, d, J=8.5 Hz), 6.72-6.81 (2 H, m), 7.14 (1 H, d, J=8.5 Hz), 7.21 (1 H, d, J=8.5 Hz).

MS Calcd.: 471; MS Found: 472 (M+H).

Example 424

9-Cyclopropyl-6-[1-(difluoromethoxy)-2,2,2-trifluoroethyl]-1-(4-methoxy-2-methylphenyl)-1,2,3,4-tetrahydropyrimido[1,2-a]benzimidazole

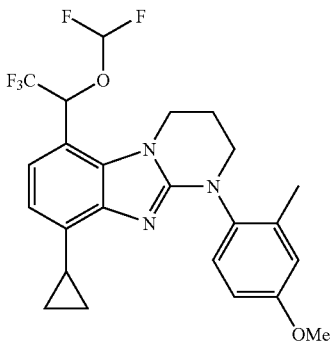 [SMILES: COc1ccc(N2CCCn3c2nc2c(C4CC4)ccc(C(OC(F)F)C(F)(F)F)c23)c(C)c1]

A mixture of 1-[9-bromo-1-(4-methoxy-2-methylphenyl)-1,2,3,4-tetrahydropyrimido[1,2-a]benzimidazol-6-yl]-2,2,2-trifluoroethanol (200 mg, 0.425 mmol), cyclopropylboronic acid (54.8 mg, 0.638 mmol), palladium(II) diacetate (9.5 mg, 0.043 mmol), tricyclohexylphosphine (12 mg, 0.043 mmol) and potassium t-butoxide (167 mg, 1.49 mmol) in toluene (2 mL) was stirred at 100° C. for 20 min. The reaction was diluted with water and ethyl acetate, and the mixture was filtered and extracted with ethyl acetate. The combined organic layer was washed with brine, dried over anhydrous sodium sulfate, filtered, and concentrated in vacuo. The residue was purified by flash column chromatography on NH silica gel eluting with a 30-90% ethyl acetate/n-hexane gradient mixture and flash column chromatography on silica gel eluting with a 30-70% ethyl acetate/n-hexane gradient mixture to give the title compound as a crude solid. Under chloro(difluoro)methane atmosphere, a mixture of the crude solid, benzyltriethylammonium chloride (1.7 mg, 0.0075 mmol) and 8N sodium hydroxide (0.35 mL) in tetrahydrofuran (0.35 mL) was stirred 0° C. for 5 h. The mixture was diluted with aqueous saturated ammonium chloride and extracted with ethyl acetate. The combined organic layer was washed with brine, dried over anhydrous sodium sulfate, filtered and concentrated in vacuo. The residue was purified by flash column chromatography on silica gel eluting with a 15% ethyl acetate/n-hexane mixture to give the title compound as a colorless solid (6.6 mg, 0.014 mmol, 3%).

$^1$H NMR (CDCl$_3$) δ 0.74-0.99 (4 H, m), 2.27 (3 H, s), 2.33-2.52 (3 H, m), 3.52-3.78 (2 H, m), 3.82 (3 H, s), 4.22-4.43 (2 H, m), 5.92-6.01 (1 H, m), 6.34 (1 H, t, J=73.4 Hz), 6.54 (1 H, d, J=8.0 Hz), 6.79 (1 H, dd, J=8.5, 3.0 Hz), 6.83 (1 H, d, J=3.0 Hz), 7.09 (1 H, d, J=8.5 Hz), 7.21-7.26 (1 H, m).

MS Calcd.: 481; MS Found: 482 (M+H).

Example 425

Methyl 8-chloro-1-(2,4-dichloro-6-methylphenyl)-2,3-dihydro-1H-imidazo[1,2-a]benzimidazole-5-carboxylate

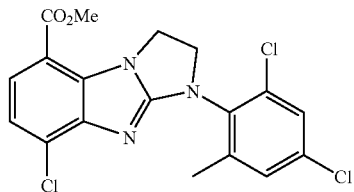 [SMILES: COC(=O)c1ccc(Cl)c2nc3n(c12)CCN3c1c(C)cc(Cl)cc1Cl]

To a solution of methyl 4-chloro-2-[(2,4-dichloro-6-methylphenyl)amino]-1-(2-hydroxyethyl)-1H-benzimidazole-7-carboxylate (156 mg, 0.364 mmol) and triethylamine (0.203 mL, 1.46 mmol) in tetrahydrofuran (7.2 mL) was added methanesulfonyl chloride (0.056 mL, 0.72 mmol) at 0° C. The reaction mixture was stirred at 0° C. for 0.5 hr and at room temperature for 14 hr. Then the mixture was warmed to 45° C. and stirred at 45° C. for 10 hr. Water was added to the mixture and the mixture was extracted with ethyl acetate. Organic layer was washed with water and brine, dried over anhydrous magnesium sulfate and concentrated in vacuo. The residue was purified by flash chromatography on silica gel eluting with a 25-70% ethyl acetate/n-hexane gradient mixture to give the title compound (99 mg, 0.24 mmol, 66%) as colorless crystals.

$^1$H NMR (CDCl$_3$) δ 2.34 (d, J=0.6 Hz, 3 H), 3.93 (s, 3 H), 4.11-4.19 (m, 1 H), 4.40-4.48 (m, 1 H), 4.75-4.85 (m, 2 H), 7.09 (d, J=8.6 Hz, 1 H), 7.20-7.21 (m, 1 H), 7.33-7.34 (m, 1 H), 7.57 (d, J=8.6 Hz, 1 H).

MS Calcd.: 409; Found: 410 (M+H).

Example 426

[8-Chloro-1-(2,4-dichloro-6-methylphenyl)-2,3-dihydro-1H-imidazo[1,2-a]benzimidazol-5-yl](dicyclopropyl)methanol

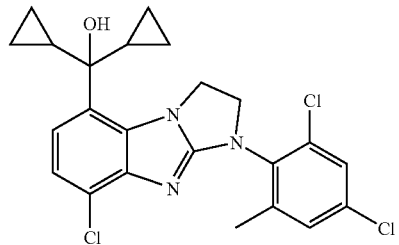 [SMILES: Cc1cc(Cl)cc(Cl)c1N1CCn2c1nc1c(Cl)ccc(C(O)(C3CC3)C3CC3)c12]

To a solution of methyl 8-chloro-1-(2,4-dichloro-6-methylphenyl)-2,3-dihydro-1H-imidazo[1,2-a]benzimidazole-5-carboxylate (90 mg, 0.219 mmol) in tetrahydrofuran (2.2 mL) was added a solution of cyclopropyl magnesium bromide in tetrahydrofuran (1.0 M, 1.3 mL, 1.3 mmol) at room temperature. The mixture was stirred at 60° C. for 1.5 hr. Water was added to the reaction mixture at room temperature and the mixture was extracted with ethyl acetate. Organic layer was washed with brine, dried over magnesium sulfate and concentrated in vacuo. The residue was purified by flash chromatography on silica gel eluting with a 25-60% ethyl acetate/n-hexane gradient mixture and recrystallization from ethyl acetate to give the title compound (29.9 mg, 0.065 mmol, 30%) as colorless crystals.

mp 193-196° C.

$^1$H NMR (CDCl$_3$) δ 0.26-0.38 (m, 2 H); 0.44-0.65 (m, 6 H), 1.27-1.42 (m, 2 H), 1.66 (s, 1 H), 2.34 (s, 3 H), 4.02-4.10 (m, 1 H), 4.33-4.41 (m, 1 H), 4.61-4.73 (m, 2 H), 7.02 (d, J=8.4 Hz, 1 H), 7.09 (d, J=8.4 Hz, 1 H), 7.18-7.19 (m, 1 H), 7.31-7.32 (m, 1 H).

MS Calcd.: 461; Found: 462 (M+H).

Example 427

Methyl 1-(2,4-dichloro-6-methylphenyl)-2,3-dihydro-1H-imidazo[1,2-a]benzimidazole-5-carboxylate

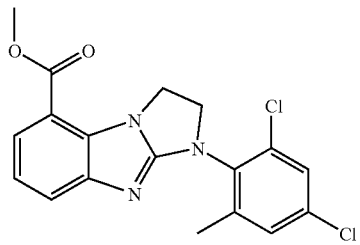 [SMILES: COC(=O)c1cccc2nc3n(c12)CCN3c1c(C)cc(Cl)cc1Cl]

To a solution of methyl 3-{[(2,4-dichloro-6-methylphenyl)carbamothioyl]amino}-2-[(2-hydroxyethyl)amino]benzoate (300 mg, 0.70 mmol) in tetrahydrofuran (7.0 mL) was added 1-ethyl-3-(3 dimethylaminopropyl)carbodiimide hydrochloride (148 mg, 0.77 mmol) and triethylamine (0.108 mL, 0.77 mmol) at room temperature. The mixture was stirred at 50° C. for 14 hr. Water was added to the reaction mixture at room temperature and the mixture was extracted with ethyl acetate. The organic layer was washed with, water and brine, dried over anhydrous magnesium sulfate and concentrated in vacuo to give methyl 2-[(2,4-dichloro-6-methylphenyl)amino]-1-(2-hydroxyethyl)-1H-benzimidazole-7-carboxylate (210 mg, 0.53 mmol, 76%) as a pale yellow solid. To a solution of methyl 2-[(2,4-dichloro-6-methylphenyl)amino]-1-(2-hydroxyethyl)-1H-benzimidazole-7-carboxylate (200 mg, 0.507 mmol) and triethylamine (0.28 mL, 3.8 mmol) was added methanesulfonyl chloride (0.079 mL, 1.02 mmol) at 0° C. The reaction mixture was stirred at 0° C. for 0.5 hr and at room temperature for 14 hr. Then the mixture was warmed to 45° C. and stirred at 45° C. for 8 hr. Water was added to the mixture and the mixture was extracted with ethyl acetate. The organic layer was washed with water and brine, dried over anhydrous magnesium sulfate and concentrated in vacuo. The residue was purified by flash chromatography on silica gel eluting with a 25-70% ethyl acetate/n-hexane gradient mixture to give the title compound (170 mg, 0.45 mmol, 89%) as colorless crystals.

$^1$H NMR (CDCl$_3$) δ 2.36 (d, J=0.6 Hz, 3 H), 3.94 (s, 3 H), 4.14-4.22 (m, 1 H), 4.39-4.48 (m, 1 H), 4.73-4.90 (m, 2 H), 7.07 (d, J=7.8 Hz, 1 H), 7.22-7.23 (m, 1 H), 7.34-7.35 (m, 1 H), 7.54 (dd, J=8.6, 1.2 Hz, 1 H), 7.65 (dd, J=7.8, 1.2 Hz, 1 H).

Example 428

Dicyclopropyl[1-(2,4-dichloro-6-methylphenyl)-2,3-dihydro-1H-imidazo[1,2-a]benzimidazol-5-yl]methanol

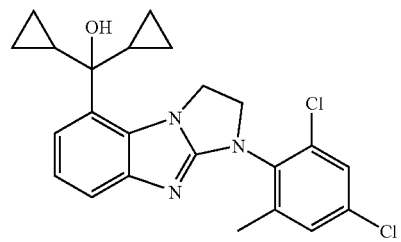 [SMILES: Cc1cc(Cl)cc(Cl)c1N1CCn2c1nc1cccc(C(O)(C3CC3)C3CC3)c12]

To a solution of methyl 1-(2,4-dichloro-6-methylphenyl)-2,3-dihydro-1H-imidazo[1,2-a]benzimidazole-5-carboxylate (90 mg, 0.239 mmol) in tetrahydrofuran (2.4 mL) was added a solution of cyclopropyl magnesium bromide in tetrahydrofuran (1.0 M, 1.4 mL, 1.4 mmol) at room temperature. The mixture was stirred at 60° C. for 1.5 hr. Water was added to the reaction mixture at room temperature and the mixture was extracted with ethyl acetate. Organic layer was washed with brine, dried over anhydrous magnesium sulfate and concentrated in vacuo. The residue was purified by flash chromatography on silica gel eluting with a 25-60% ethyl acetate/n-hexane gradient mixture and recrystallization from ethyl acetate/diisopropyl ether to give the title compound (40.2 mg, 0.094 mmol, 39%) as colorless crystals.

mp 243-246° C.

$^1$H NMR (CDCl$_3$) δ 0.25-0.39 (m, 2 H), 0.44-0.67 (m, 6 H), 1.29-1.45 (m, 2 H), 1.68 (s, 1 H), 2.35 (s, 3 H), 4.05-4.13 (m, 1 H), 4.33-4.41 (m, 1 H), 4.61-4.78 (m, 2 H), 7.00 (t, J=7.8 Hz, 1 H), 7.17-7.21 (m, 2 H), 7.32-7.34 (m, 2 H).

MS Calcd.: 427; Found: 428 (M+H).

Example 429

Methyl 8-chloro-1-(2,4-dichlorophenyl)-2,3-dihydro-1H-imidazo[1,2-a]benzimidazole-5-carboxylate

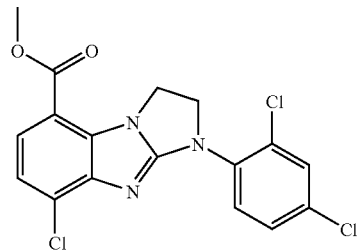 [SMILES: COC(=O)c1ccc(Cl)c2nc3n(c12)CCN3c1ccc(Cl)cc1Cl]

To a solution of methyl 4-chloro-3-{[(2,4-dichlorophenyl)carbamothioyl]amino}-2-[(2-hydroxyethyl)amino]benzoate (686.9 mg, 1.53 mmol) in tetrahydrofuran (15.3 mL) were added 1-ethyl-3-(3-dimethylaminopropyl)carbodiimide hydrochloride (323 mg, 1.68 mmol) and triethylamine (0.234 mL, 1.68 mmol) at room temperature. The mixture was stirred at 50° C. for 14 hr. Water was added to the reaction mixture at room temperature and the mixture was extracted with ethyl acetate. The organic layer was washed with brine, dried over anhydrous magnesium sulfate and concentrated in vacuo to give methyl 8-chloro-2-[(2,4-dichlorophenyl) amino]-1-(2-hydroxyethyl)-1H-benzimidazole-7-carboxylate (567.2 mg, 1.37 mmol, 89%) as a pale yellow solid. To a solution of methyl 8-chloro-2-[(2,4-dichlorophenyl)amino]-1-(2-hydroxyethyl)-1H-benzimidazole-7-carboxylate (553 mg, 1.33 mmol) and triethylamine (0.93 mL, 6.67 mmol) in tetrahydrofuran (13 mL) was added methanesulfonyl chloride (0.21 mL, 2.71 mmol) at 0° C. The reaction mixture was stirred at 0° C. for 1 hr and at room temperature for 0.5 hr. Then the mixture was warmed to 50° C. and stirred at 50° C. for 14 hr. Water was added to the mixture and the mixture was extracted with ethyl acetate. Organic layer was washed with water and brine, dried over anhydrous magnesium sulfate and concentrated in vacuo. The precipitated pale yellow crystals were collected by filtration, washed with ethyl acetate and diisopropyl ether to give the title compound (111.7 mg, 0.28 mmol, 21%) as colorless crystals.

$^1$H NMR (CDCl$_3$) δ 3.94 (s, 3 H), 4.45 (t, J=7.9 Hz, 2 H), 4.79 (t, J=7.9 Hz, 2 H), 7.14 (d, J=8.7 Hz, 1 H), 7.33 (dd, J=8.7, 2.4 Hz, 1 H), 7.47 (d, J=2.4 Hz, 1 H), 7.62 (d, J=8.7 Hz, 1 H), 7.74 (d, J=8.7 Hz, 1 H).

MS Calcd.: 395; Found: 396 (M+H).

Example 430

[8-Chloro-1-(2,4-dichlorophenyl)-2,3-dihydro-1H-imidazo[1,2-a]benzimidazol-5-yl](dicyclopropyl) methanol

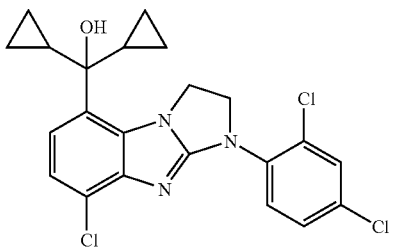 [SMILES: OC(c1ccc(Cl)c2nc3n(c12)CCN3c1ccc(Cl)cc1Cl)(C1CC1)C1CC1]

To a solution of methyl 8-chloro-1-(2,4-dichlorophenyl)-2,3-dihydro-1H-imidazo[1,2-a]benzimidazole-5-carboxylate (100 mg, 0.25 mmol) in tetrahydrofuran (2.5 mL) was added a solution of cyclopropyl magnesium bromide in tetrahydrofuran (1.0 M, 1.5 mL, 1.5 mmol) at 0° C. The mixture was stirred at 60° C. for 1.5 hr. Water was added to the reaction mixture at room temperature and the mixture was extracted with ethyl acetate. Organic layer was washed with brine, dried over anhydrous magnesium sulfate and concentrated in vacuo. The residue was passed through the silica gel pad eluting with ethyl acetate and recrystallized from ethyl acetate to give the title compound (64.4 mg, 0.144 mmol, 57%) as colorless crystals.

mp 238-239° C.

$^1$H NMR (CDCl$_3$) δ 0.25-0.37 (m, 2 H), 0.43-0.68 (m, 6 H), 1.29-1.39 (m, 2 H), 1.69 (s, 1 H), 4.37 (t, J=7.8 Hz, 2 H), 4.66 (t, J=7.8 Hz, 2 H), 7.07 (d, J=8.6 Hz, 1 H), 7.14 (d, J=8.6 Hz, 1 H), 7.31 (dd, J=8.4, 2.4 Hz, 1 H), 7.45 (d, J=2.4 Hz, 1 H), 7.80 (d, J=8.4 Hz, 1 H).

MS Calcd.: 447; Found: 448 (M+H).

Example 431

1-[9-Chloro-1-(2,4-dichlorophenyl)-1,2,3,4-tetrahydropyrimido[1,2-a]benzimidazol-6-yl]propyl cyclopropanecarboxylate

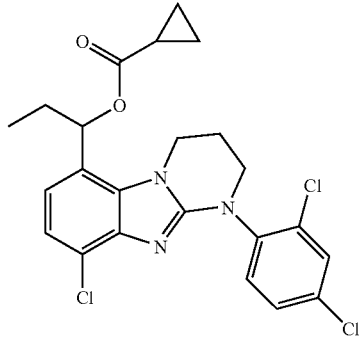 [SMILES: CCC(OC(=O)C1CC1)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-ol (100 mg, 0.243 mmol), cyclopropanecarboxylic acid (0.0272 mL, 0.342 mmol), triethylamine (0.0733 mL, 0.526 mmol) and 4-dimethylaminopyridine (41.0 mg, 0.336 mmol) in tetrahydrofuran (5.0 mL) was added 1-ethyl-3-(3-dimethylaminopropyl)carbodiimide hydrochloride 08.0 mg, 0.511 mmol) at room temperature. The mixture was stirred at room temperature for 15 hr. Cyclopropanecarboxylic acid (0.0147 mL, 0.185 mmol) and 1-ethyl-3-(3-dimethylaminopropyl)carbodiimide hydrochloride (53.2 mg, 0.278 mmol) were added to the reaction mixture at room temperature. The mixture was stirred at room temperature for 8 hr. Water was added to the reaction mixture and the mixture was extracted with ethyl acetate. The organic layer was washed with water and brine, dried over anhydrous magnesium sulfate and concentrated in vacuo. The residue was purified by flash chromatography on silica gel eluting with a 25-80% ethyl acetate/n-hexane gradient mixture and recrystallization from 2-propanol/n-hexane to give the title compound (61.6 mg, 0.13 mmol, 53%) as colorless crystals.

mp 159-161° C.

$^1$H NMR (CDCl$_3$) δ 0.80-1.02 (m, 7 H), 1.60-1.70 (m, 1 H), 1.85-2.09 (m, 2 H), 2.32-2.46 (m, 2 H), 3.63-3.76 (m, 2 H), 4.28-4.39 (m, 1 H), 4.67-4.76 (m, 1 H), 6.30 (t, J=6.9 Hz, 1 H), 6.99 (d, J=8.4 Hz, 1 H), 7.09 (d, J=8.4 Hz, 1 H), 7.30 (dd, J=8.4, 2.4 Hz, 1 H), 7.48 (d, J=2.4 Hz, 1 H), 7.51 (d, J=8.4 Hz, 1H).

MS Calcd.: 477; Found: 478 (M+H).

Example 432

1-[9-Chloro-1-(2,4-dichlorophenyl)-1,2,3,4-tetrahydropyrimido[1,2-a]benzimidazol-6-yl]propyl methoxyacetate

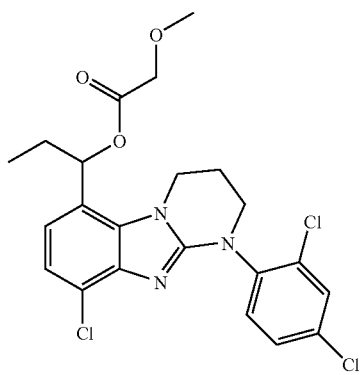 [SMILES: CCC(OC(=O)COC)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-ol (150 mg, 0.365 mmol), methoxyacetic acid (0.0453 mL, 0.59 mmol), triethylamine (0.25 mL, 1.79 mmol) and 4-dimethylaminopyridine (48.0 mg, 0.39 mmol) in tetrahydrofuran (5.0 ml) was added 1-ethyl-3-(3-dimethylaminopropyl)carbodiimide hydrochloride (170 mg, 0.887 mmol) at room temperature. The mixture was stirred at room temperature for 24 hr. Water was added to the reaction mixture and the mixture was extracted with ethyl acetate. The organic layer was washed with water and brine, dried over anhydrous magnesium sulfate and concentrated in vacuo. The residue was purified by flash chromatography on silica gel eluting with a 25-80% ethyl acetate/n-hexane gradient mixture and recrystallization from 2-propanol/diisopropyl ether to give the title compound (98.4 mg, 0.204 mmol, 56%) as colorless crystals.

mp 156-158° C.

$^1$H NMR (CDCl$_3$) δ 0.95 (t, J=7.5 HZ, 3 H), 1.90-2.12 (m, 2 H), 2.34-2.48 (m, 2 H), 3.42 (s, 3 H), 3.63-3.78 (m, 2 H), 3.99 (d, J=16.4 Hz, 1 H), 4.09 (d, J=16.4 Hz, 1 H), 4.50-4.61 (m, 1 H), 4.73-4.83 (m, 1 H), 6.40 (t, J=7.1 Hz, 1 H), 6.97 (d, J=8.3 Hz, 1 H), 7.09 (d, J=8.3 Hz, 1 H), 7.31 (dd, J=8.4, 2.1 Hz, 1H), 7.49 (d, J=2.1 Hz, 1 H), 7.51 (d, J=8.4 Hz, 1H).

MS Calcd.: 481; Found: 482 (M+H).

Example 433

1-[9-Chloro-1-(2,4-dichlorophenyl)-1,2,3,4-tetrahydropyrimido[1,2-a]benzimidazol-6-yl]propyl (methylsulfonyl)acetate

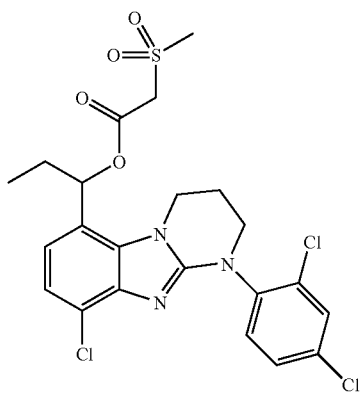 [SMILES: CCC(OC(=O)CS(C)(=O)=O)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-ol (150 mg, 0.365 mmol), (methylsulfonyl)acetic acid (81.6 mg, 0.59 mmol), triethylamine (0.11 mL, 0.789 mmol) and 4-dimethylaminopyridine (48.0 mg, 0.39 mmol) in tetrahydrofuran (5.0 mL) was added 1-ethyl-3-(3-dimethylaminopropyl)carbodiimide hydrochloride (136 mg, 0.709 mmol) at room temperature. The mixture was stirred at room temperature for 3 days. (Methylsulfonyl)acetic acid (82.0 mg, 0.59 mmol), 1-ethyl-3-(3-dimethylaminopropyl)carbodiimide hydrochloride (140 mg, 0.73 mmol), triethylamine (0.11 mL, 0.789 mmol) and N,N-dimethylformamide (10 mL) were added to the reaction mixture at room temperature. The mixture was stirred at room temperature for 24 hr. Water was added to the reaction mixture and the mixture was extracted with ethyl acetate. The organic layer was washed with water and brine, dried over anhydrous magnesium sulfate and concentrated in vacuo. The residue was purified by flash chromatography on NH-silica gel eluting with a 40-70% ethyl acetate/n-hexane gradient mixture and recrystallization from 2-propanol/diisopropyl ether to give the title compound (68.9 mg, 0.13 mmol, 36%) as colorless crystals.

mp 187-189° C.

$^1$H NMR (CDCl$_3$) δ 0.99 (t, J=7.4 HZ, 3 H), 1.94-2.21 (m, 2 H), 2.36-2.49 (m, 2 H), 3.04 (s, 3 H), 3.63-3.78 (m, 2 H), 4.00 (t, J=1.1 Hz, 1 H), 4.27-4.39 (m, 1 H), 4.61-4.74 (m, 1H), 6.36 (t, J=7.2 Hz, 1 H), 7.04 (d, J=8.3 Hz, 1 H), 7.10 (d, J=8.3 Hz, 1 H), 7.31 (dd, J=8.7, 2.4 Hz, 1 H), 7.50 (d, J=2.4 Hz, 1H), 7.51 (d, J=8.7 Hz, 1 H).

MS Calcd.: 529; Found: 530 (M+H).

Example 434

[8-Chloro-1-(2,4-dichloro-6-methylphenyl)-2,3-dihydro-1H-imidazo[1,2-a]benzimidazol-5-yl]methanol

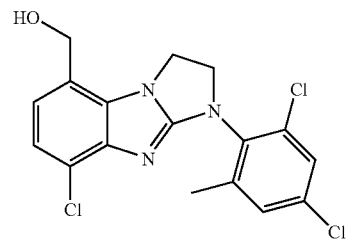 [SMILES: Cc1cc(Cl)cc(Cl)c1N1CCn2c1nc1c(Cl)ccc(CO)c12]

To a solution of methyl 8-chloro-1-(2,4-dichloro-6-methylphenyl)-2,3-dihydro-1H-imidazo[1,2-a]benzimidazole-5-carboxylate (200 mg, 0.487 mmol) in tetrahydrofuran (10 mL) was added lithium tetrahydroborate (53 mg, 2.43 mmol) at 0° C. The reaction mixture was stirred at room temperature for 2 days. Aqueous ammonium chloride was added to the reaction mixture at 0° C. and the mixture was concentrated in vacuo. The precipitated solid was collected by filtration, washed with water, 2-propanol and diisopropyl ether to give the title compound (165.9 mg, 0.43 mmol, 89%) as a colorless solid.

$^1$H NMR (DMSO-d$_6$) δ 2.31 (s, 3 H), 4.26-4.39 (m, 2 H), 4.52-4.65 (m, 2 H), 4.68 (d, J=5.4 Hz, 1 H), 5.30 (t, J=5.4 Hz, 1 H), 6.88 (d, J=8.7 Hz, 1 H), 6.97 (d, J=8.7 Hz, 1 H), 7.53 (dd, J=2.7, 0.6 Hz, 1 H), 7.66 (d, J=2.7 Hz, 1 H).

MS Calcd.: 381; Found: 382 (M+H).

Example 435

8-Chloro-1-(2,4-dichloro-6-methylphenyl)-2,3-dihydro imidazo[1,2-a]benzimidazole-5-carbaldehyde

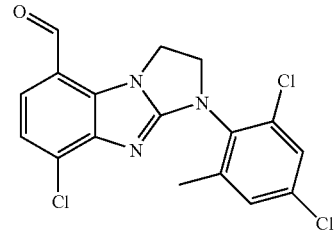 [SMILES: Cc1cc(Cl)cc(Cl)c1N1CCn2c1nc1c(Cl)ccc(C=O)c12]

To a solution of [8-chloro-1-(2,4-dichloro-6-methylphenyl)-2,3-dihydro-1H-imidazo[1,2-a]benzimidazol-5-yl]methanol (163 mg, 0.426 mmol) and triethylamine (0.48 mL, 3.44 mmol) in dimethylsulfoxide (5.0 mL) was added sulfur trioxide-pyridine complex (0.44 g, 2.76 mmol) at room temperature. The mixture was stirred at room temperature for 24 hr. Aqueous sodium hydrogen carbonate was added dropwise to the reaction mixture at room temperature. The precipitated solid was collected by filtration. The solid was washed with water, 2-propanol and diisopropyl ether to give the title compound (140.8 mg, 0.37 mmol, 87%) as a pale yellow solid.

$^1$H NMR (CDCl$_3$) δ 2.34 (s, 3 H), 4.13-4.22 (m, 1 H), 4.42-4.50 (m, 1 H), 4.86-4.93 (m, 2 H), 7.19-7.23 (m, 2 H), 7.33-7.36 (m, 2 H), 9.91 (s, 1 H).

MS Calcd.: 379; Found: 380 (M+H).

Example 436

1-[8-Chloro-1-(2,4-dichloro-6-methylphenyl)-2,3-dihydro-1H-imidazo[1,2-a]benzimidazol-5-yl]propan-1-ol

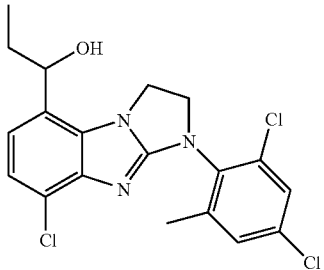 [SMILES: CCC(O)c1ccc(Cl)c2nc3n(c12)CCN3c1c(C)cc(Cl)cc1Cl]

To a solution of 8-chloro-1-(2,4-dichloro-6-methylphenyl)-2,3-dihydro-1H-imidazo[1,2-a]benzimidazole-5-carbaldehyde (140 mg, 0.368 mmol) in tetrahydrofuran (30 mL) was added ethylmagnesium bromide (3.0 M solution in diethyl ether, 0.50 mL, 15.0 mmol) at 0° C. The mixture was stirred at 0° C. for 2 hr. Water was added to the reaction mixture at 0° C. and the mixture was extracted with ethyl acetate. The organic layer was washed with brine, dried over anhydrous magnesium sulfate, and concentrated in vacuo to give the title compound (150 mg).

1H NMR (CDCl$_3$) δ 1.01 (t, J=7.5 Hz, 3 H), 1.82-1.98 (m, 3 H), 2.34-2.35 (m, 3 H), 4.08-4.22 (m, 1 H), 4.40-4.67 (m, 3 H), 4.76-4.85 (m, 1 H), 6.85 (d, J=8.3 Hz, 1 H), 7.04 (d, J=8.3 Hz, 1 H), 7.29-7.20 (m, 1 H), 7.32-7.33 (m, 1 H).

MS Calcd.: 409; Found: 410 (M+H).

Example 437

1-[8-Chloro-1-(2,4-dichloro-6-methylphenyl)-2,3-dihydro-1H-imidazo[1,2-a]benzimidazol-5-yl]propyl acetate

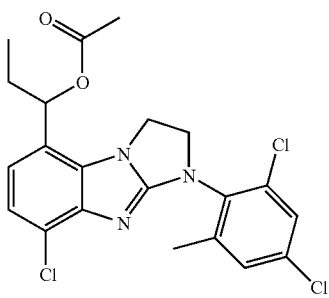 [SMILES: CCC(OC(C)=O)c1ccc(Cl)c2nc3n(c12)CCN3c1c(C)cc(Cl)cc1Cl]

To a solution of 1-[8-chloro-1-(2,4-dichloro-6-methylphenyl)-2,3-dihydro-1H-imidazo[1,2-a]benzimidazol-5-yl]propan-1-ol (150 mg, 0.365 mmol) and pyridine (0.15 mL, 1.85 mmol) in tetrahydrofuran (10 mL) was added acetic anhydride (0.113 mL, 1.20 mmol) at room temperature. The mixture was stirred at room temperature for 5 hr. Then the mixture was warmed to 45° C. and stirred at 45° C. for 16 hr. Acetic anhydride (0.113 mL, 1.2 mmol) and pyridine (0.30 mL, 3.71 mmol) were added to the reaction mixture at room temperature. The mixture was stirred at 45° C. for 20 hr. The reaction mixture was concentrated in vacuo. The residue was purified by flash chromatography on silica gel eluting with a 20-50% ethyl acetate/n-hexane gradient mixture and recrystallization from 2-propanol/n-hexane to give the title compound (116.5 mg, 0.257 mmol, 60%) as colorless crystals.

mp 190-192° C.

$^1$H NMR (CDCl$_3$) δ 0.94 (dt, J=7.5 1.8 HZ, 3 H), 1.86-2.10 (m, 5 H), 2.34-2.35 (m, 3 H), 4.16-4.22 (m, 1 H), 4.43-4.53 (m, 2 H), 4.69-4.73 (m, 1 H), 5.94 (dt, J=7.2, 3.0 Hz, 1 H), 6.96 (d, J=8.1 Hz, 1 H), 7.08 (d, J=8.1 Hz, 1 H), 7.20-7.21 (m, 1 H), 7.32-7.33 (m, 1 H).

MS Calcd.: 451; Found: 452 (M+H).

Example 438

(−)-1-[9-Chloro-1-(2,4-dichlorophenyl)-1,2,3,4-tetrahydropyrimido[1,2-a]benzimidazol-6-yl]propan-1-ol

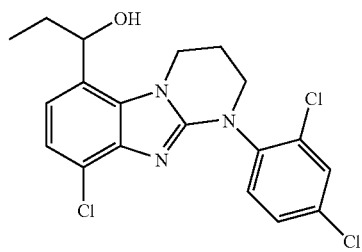 [SMILES: CCC(O)c1ccc(Cl)c2nc3n(c12)CCCN3c1ccc(Cl)cc1Cl]

To a solution of (−)-1-[9-chloro-1-(2,4-dichlorophenyl)-1,2,3,4-tetrahydropyrimido[1,2-a]benzimidazol-6-yl]propyl acetate (79.6 mg, 0476 mmol) in methanol (1.5 mL) was added potassium carbonate (36.4 mg, 0.264 mmol). The reaction mixture was stirred at room temperature for 1 hr. After the mixture was concentrated, the residue was diluted with water and extracted with ethyl acetate (×3). The combined organic layer was washed with brine (×1), dried over anhydrous magnesium sulfate, filtered and concentrated in vacuo. The residue was purified by silica gel column chromatography eluting with a 0-50% ethyl acetate/n-hexane gradient mixture. The resulting solid was recrystallized from ethyl acetate/n-hexane to give the title compound as a colorless powder (51.1 mg, 0.124 mmol, 71%).

mp 221-223° C.

[α]$_D^{20}$=−5.9 (c=0.4745, MeOH)

$^1$H NMR (CDCl$_3$) δ 1.05 (t, J=7.4 Hz, 3H), 1.87 (d, J=5.7 Hz, 1H), 1.97 (q, J=7.2 Hz, 2H), 2.29-2.44 (m, 2H), 3.72 (brs, 2H), 4.42-4.55 (m, 1H), 4.56-4.70 (m, 1H), 5.04 (q, J=6.4 Hz, 1H), 6.97 (d, J=8.3 Hz, 1H), 7.08 (d, J=8.3 Hz, 1H), 7.32 (dd, J=2.3, 8.3 Hz, 1H), 7.50 (d, J=2.3 Hz, 1H), 7.52 (d, J=8.3 Hz, 1H).

MS Calcd.: 409; MS Found: 410 (M+H).

Example 439

(+)-1-[9-Chloro-1-(2,4-dichlorophenyl)-1,2,3,4-tetrahydropyrimido[1,2-a]benzimidazol-6-yl]propan-1-ol

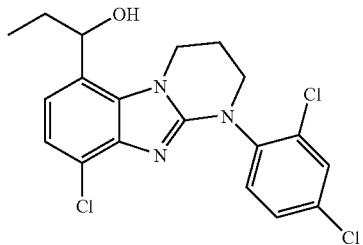 [SMILES: CCC(O)c1ccc(Cl)c2nc3n(c12)CCCN3c1ccc(Cl)cc1Cl]

To a solution of (+)-1-[9-chloro-1-(2,4-dichlorophenyl)-1,2,3,4-tetrahydropyrimido[1,2-a]benzimidazol-6-yl]propyl acetate (80.6 mg, 0.178 mmol) in methanol (1.5 mL) was added potassium carbonate (36.9 mg, 0.267 mmol). The reaction mixture was stirred at room temperature for 1.5 hrs. After the mixture was concentrated, the residue was diluted with water and extracted with ethyl acetate (×3). The combined organic layer was washed with brine (×1), dried over anhydrous magnesium sulfate, filtered and concentrated in vacuo. The residue was purified by silica gel column chromatography eluting with a 0-50% ethyl acetate/n-hexane gradient mixture. The resulting solid was recrystallized from ethyl acetate/n-hexane to give the title compound as a colorless powder (51.6 mg, 0.126 mmol, 71%).

mp 233-235° C.

$[\alpha]_D^{20}$=+6.1 (c=0.4705, MeOH)

$^1$H NMR (CDCl$_3$) δ 1.03 (t, J=7.6 Hz, 3H), 1.84 (d, J=5.3 Hz, 1H), 1.99 (quip, J=7.3 Hz, 2H), 2.32-2.44 (m, 2H), 3.72 (brs, 2H), 4.42-4.56 (m, 1H), 4.57-4.71 (m, 1H), 5.05 (q, J=6.7 Hz, 1H), 6.97 (d, J=8.3 Hz, 1H), 7.08 (d, J=8.3 Hz, 1H), 7.32 (dd, J=2.3, 8.3 Hz, 1H), 7.50 (d, J=2.3 Hz, 1H), 7.52 (d, J=8.3 Hz, 1H).

MS Calcd.: 409; MS Found: 410 (M+H).

Example 440

N-{1-[9-Chloro-1-(2,4-dichlorophenyl)-1,2,3,4-tetrahydropyrimido[1,2-a]benzimidazol-6-yl]propyl}acetamide

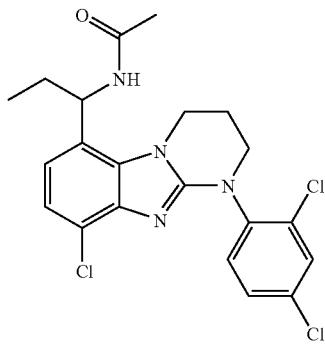

To a mixture of crude 1-[9-chloro-1-(2,4-dichlorophenyl)-1,2,3,4-tetrahydropyrimido[1,2-a]benzimidazol-6-yl]propan-1-amine (200 mg) and triethylamine (0.130 mL, 0.933 mmol) in tetrahydrofuran (5 mL) was added acetic anhydride (0.0530 mL, 0.561 mmol) at 0° C. The resultant mixture was stirred at room temperature for 30 min, diluted with ethyl acetate, washed with water, aqueous sodium bicarbonate and brine, dried over anhydrous sodium sulfate, filtered, and concentrated in vacuo. The residue was purified by flash column chromatography on silica gel eluting with a 10-90% ethyl acetate/n-hexane gradient mixture to give the title compound as a colorless solid (111 mg, 0.246 mmol).

mp 237-239° C. (ethyl acetate/hexane).

$^1$H NMR (CDCl$_3$) δ: 0.93 (t, J=7.4 Hz, 3H), 1.83-2.03 (m, 5H), 2.35-2.45 (m, 2H), 3.70 (brs, 2H); 4.30-4.42 (m, 1H), 4.73-4.83 (m, 1H), 5.52-5.62 (m, 1H), 5.82 (d, J=8.5 Hz, 1H), 6.83 (d, J=8.2 Hz, 1H), 7.08 (d, J=8.2 Hz, 1H), 7.31 (dd, J=8.7, 2.3 Hz, 1H), 7.46-7.52 (m, 2H)

MS Calcd.: 450, MS Found: 451 (M+H).

Example 441

N-{1-[9-Chloro-1-(2,4-dichlorophenyl)-1,2,3,4-tetrahydropyrimido[1,2-a]benzimidazol-6-yl]propyl}cyclopropanecarboxamide

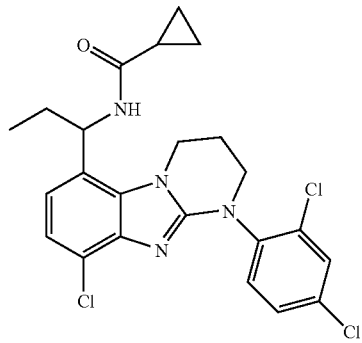

To a solution of 1-[9-chloro-1-(2,4-dichlorophenyl)-1,2,3,4-tetrahydropyrimido[1,2-a]benzimidazol-6-yl]propan-1-amine (100 mg, 0.24 mmol) and triethylamine (0.17 mL, 1.22 mmol) in tetrahydrofuran (5.0 mL) was added cyclopropanecarbonyl chloride (0.0664 mL, 0.73 mmol) at 0° C. The mixture was stirred at room temperature for 1 hr. Water was added to the reaction mixture at room temperature and the mixture was extracted with ethyl acetate. The organic layer was washed with brine, dried over anhydrous magnesium sulfate, and concentrated in vacuo. The residue was purified by flash chromatography on silica gel eluting with a 50-100% ethyl acetate/n-hexane gradient mixture and recrystallization from ethyl acetate/n-hexane to give the title compound (55.4 mg, 0.116 mmol, 48%) as colorless crystals.

mp 251-253° C.

$^1$H NMR (CDCl$_3$) δ 0.67-0.83 (m, 2H), 0.88-1.04 (m, 5H), 1.28-1.38 (m, 1H), 1.84-2.06 (m, 2H), 2.31-2.44 (m, 2H), 3.61-3.76 (m, 2H), 4.27-4.39 (m, 1H), 4.70-4.82 (m, 1H), 5.52-5.63 (m, 1H), 5.88-5.97 (m, 1H), 6.86 (d, J=8.3 Hz, 1H), 7.10 (d, J=8.3 Hz, 1H), 7.30 (dd, J=8.4, 2.4 Hz, 1H), 7.48-7.51 (m, 2H).

MS Calcd.: 476; Found: 477 (M+H).

Example 442

1-[9-Chloro-1-(2,4-dichlorophenyl)-1,2,3,4-tetrahydropyrimido[1,2-a]benzimidazol-6-yl]propyl{[tert-butyl(dimethyl)silyl]oxy}acetate

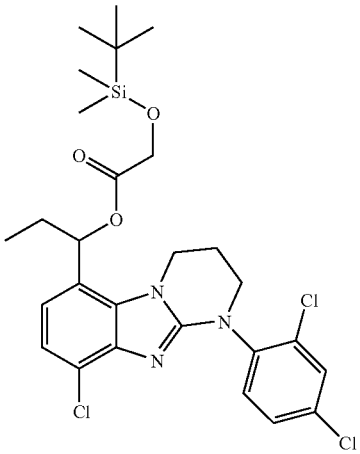 [SMILES: CCC(OC(=O)CO[Si](C)(C)C(C)(C)C)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-ol (200 mg, 0.487 mmol), {[tert-butyl(dimethyl)silyl]oxy}acetic acid (0.30 g, 1.58 mmol), triethylamine (0.33 mL, 2.37 mmol) and 4-dimethylaminopyridine (64.0 mg, 0.524 mmol) in tetrahydrofuran (10.0 mL) was added 1-ethyl-3-(3-dimethylaminopropyl)carbodiimide hydrochloride (454 mg, 2.36 mmol) at room temperature. The mixture was stirred at room temperature for 4 days. Water was added to the reaction mixture and the mixture was extracted with ethyl acetate. The organic layer was washed with water and brine, dried over anhydrous magnesium sulfate and concentrated in vacuo. The residue was purified by flash chromatography on silica gel eluting with a 20-80% ethyl acetate/n-hexane gradient mixture to give the title compound (137.1 mg, 0.235 mmol, 48%) as a colorless amorphous.

$^1$H NMR (CDCl$_3$) δ 0.09 (s, 6 H), 0.91 (s, 9 H), 0.94 (t, J=7.2 Hz, 3 H), 1.88-2.11 (m, 2 H), 2.35-2.46 (m, 2 H), 3.63-3.78 (m, 2 H), 4.21 (d, J=16.7 Hz, 1 H), 4.29 (d, J=16.7 Hz, 1 H), 4.29-4.39 (m, 1 H), 4.69-4.80 (m, 1 H), 6.38 (t, J=6.9 Hz, 1 H), 6.96 (d, J=8.4 Hz, 1 H), 7.08 (d, J=8.4 Hz, 1H), 7.31 (dd, J=8.7, 2.4 Hz, 1 H), 7.49 (d, J=2.4 Hz, 1 H), 7.51 (d, J=8.7 Hz, 1 H).

MS Calcd.: 581; Found: 582 (M+H).

Example 443

1-[9-Chloro-1-(2,4-dichlorophenyl)-1,2,3,4-tetrahydropyrimido[1,2-a]benzimidazol-6-yl]propyl hydroxyacetate

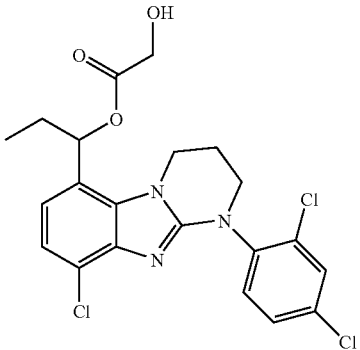 [SMILES: CCC(OC(=O)CO)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propyl{[tert-butyl(dimethyl)silyl]oxy}acetate (137.1 mg, 0.235 mmol) in tetrahydrofuran (5.0 mL) was added 1N hydrogen chloride (1.0 mL, 1.0 mmol) at room temperature. The mixture was stirred at room temperature for 1 hr. Aqueous sodium hydrogen carbonate (4.0 mL) was added to the reaction mixture at room temperature and the mixture was extracted with ethyl acetate. The organic layer was washed with brine, dried over anhydrous magnesium sulfate, and concentrated in vacuo. The residue was purified by flash chromatography on silica gel eluting with a 50-100% ethyl acetate/n-hexane gradient mixture and recrystallization from ethyl acetate/n-hexane to give the title compound (88.0 mg, 0.188 mmol, 80%) as colorless crystals.

mp 191-193° C.

$^1$H NMR (CDCl$_3$) δ 0.96 (t, J=7.5 HZ, 3 H), 1.94-2.11 (m, 2 H), 2.25-2.28 (m, 1 H), 2.38-2.48 (m, 2 H), 3.64-3.79 (m, 2 H), 4.13 (dd, J=17.1, 5.0 Hz, 1 H), 4.24 (dd, J=17.1, 6.2 Hz, 1 H), 4.28-4.39 (m, 1 H), 4.68-4.80 (m, 1 H), 6.41 (t, J=7.1 Hz, 1 H), 6.95 (d, J=8.4 Hz, 1 H), 7.09 (d, J=8.4 Hz, 1 H), 7.31 (dd, J=8.4, 2.1 Hz, 1 H), 7.49 (d, J=2.1 Hz, 1 H), 7.52 (d, J=8.4 Hz, 1 H).

MS Calcd.: 467; Found: 468 (M+H).

Example 444

1-[9-Chloro-1-(2,4-dichlorophenyl)-1,2,3,4-tetrahydropyrimido[1,2-a]benzimidazol-6-yl]propyl 3-hydroxy-3-methylbutanoate

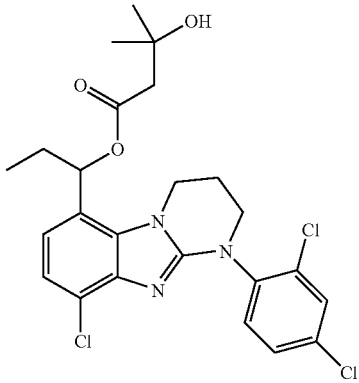 [SMILES: CCC(OC(=O)CC(C)(C)O)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-ol (200 mg; 0.487 mmol), 3-hydroxy-3-methylbutanoic acid (74.4 g, 0.63 mmol), triethylamine (0.11 mL, 0.79 mmol) and 4-dimethylaminopyridine (64.0 mg, 0.524 mmol) in tetrahydrofuran (10.0 mL) was added 1-ethyl-3-(3-dimethylaminopropyl)carbodiimide hydrochloride (144.9 mg, 0.76 mmol) at room temperature. The mixture was stirred at room temperature for 2 days. Water was added to the reaction mixture and the mixture was extracted with ethyl acetate. The organic layer was washed with water and brine, dried over anhydrous magnesium sulfate and concentrated in vacuo. The residue was purified by flash chromatography on silica gel eluting with a 25-60% ethyl acetate/n-hexane gradient mixture to give the title compound (103.3 mg, 0.20 mmol, 41%) as a colorless amorphous.

$^1$H NMR (CDCl$_3$) δ 0.96 (t, J=7.4 Hz, 3 H), 1.22 (s, 3 H), 1.28 (s, 3 H), 1.87-2.11 (m, 2 H), 2.37-2.48 (m, 2 H), 2.50 (d, J=15.3 Hz, 1 H), 2.56 (d, J=15.3 Hz, 1 H), 3.32 (s, 1 H), 3.65-3.79 (m, 2 H), 4.27-4.41 (m, 1 H), 4.65-4.79 (m, 1 H), 6.96 (d, J=8.6 Hz, 1 H), 7.08 (d, J=8.6 Hz, 1H), 7.31 (dd, J=8.4, 2.4 Hz, 1 H), 7.49 (d, J=2.4 Hz, 1 H), 7.53 (d, J=8.4 Hz, 1 H).

MS Calcd.: 509; Found: 510 (M+H).

Example 445

1-[9-Chloro-1-(2,4-dichlorophenyl)-1,2,3,4-tetrahydropyrimido[1,2-a]benzimidazol-6-yl]propyl 2-methyl-2-(methylsulfonyl)propanoate

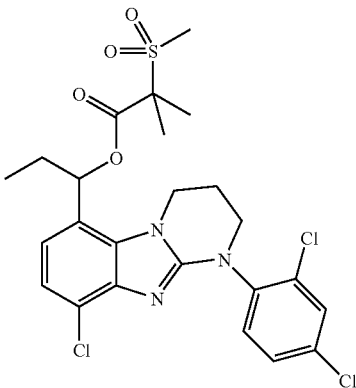 [SMILES: CCC(OC(=O)C(C)(C)S(C)(=O)=O)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-ol (100 mg, 0.243 mmol), 2-methyl-2-(methylsulfonyl)propanoic acid (65.6 mg, 0.395 mmol) and triphenylphosphine (104 mg, 0.397 mmol) in tetrahydrofuran (5.0 mL) was added a solution of diethylazodicarboxylate in toluene (2.2 M, 0.18 mL, 0.396 mmol) at 0° C. After stirring at room temperature for 20 hr, the mixture was concentrated in vacuo. The residue was purified by flash chromatography on silica gel eluting with a 25-60% ethyl acetate/n-hexane gradient mixture to give the title compound (83.0 mg, 0.149 mmol, 61%) as a colorless amorphous.

$^1$H NMR (CDCl$_3$) δ 0.99 (t, J=7.5 Hz, 3 H), 1.63 (s, 3 H), 1.67 (s, 3 H), 1.94-2.21 (m, 2 H), 2.36-2.48 (m, 2 H), 2.91 (s, 3 H), 3.63-3.79 (m, 2 H), 4.26-4.41 (m, 1 H), 4.62-4.76 (m, 1 H), 6.34 (t, J=7.4 Hz, 1 H), 6.96 (d, J=8.4 Hz, 1 H), 7.10 (d, J=8.4 Hz, 1 H), 7.31 (dd, J=8.4, 2.4 Hz, 1H), 7.50 (d, J=2.4 Hz, 1 H), 7.51 (d, J=8.4 Hz, 1 H).

MS Calcd.: 557; Found: 558 (M+H).

Example 446

Methyl {1-[9-chloro-1-(2,4-dichlorophenyl)-1,2,3,4-tetrahydropyrimido[1,2-a]benzimidazol-6-yl]propyl}carbamate

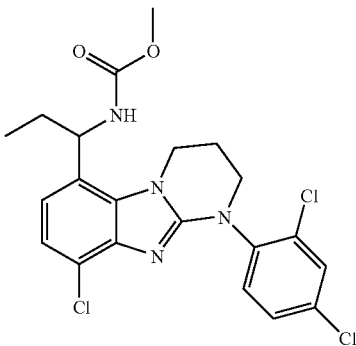 [SMILES: CCC(NC(=O)OC)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-amine (100 mg, 0.24 mmol) and triethylamine (0.10 mL, 0.72 mmol) in tetrahydrofuran (5.0 mL) was added methyl chloroformate (0.0377 mL, 0.488 mmol) at 0° C. The mixture was stirred at 0° C. for 1 hr. Water was added to the reaction mixture at room temperature and the mixture was extracted with ethyl acetate. The organic layer was washed with brine, dried over anhydrous magnesium sulfate, and concentrated in vacuo. The residue was purified by flash chromatography on silica gel eluting with a 35-65% ethyl acetate/n-hexane gradient mixture and recrystallization from ethyl acetate/n-hexane to give the title compound (31.5 mg, 0.067 mmol, 28%) as colorless crystals.

mp 201-203° C.

$^1$H NMR (CDCl$_3$) δ 0.94 (t, J=7.5 Hz, 3 H), 1.79-2.00 (m, 2 H), 2.33-2.46 (m, 2 H), 3.59-3.79 (m, 5 H), 4.27-4.40 (m, 1 H), 4.70-4.83 (m, 1 H), 4.98-5.08 (m, 1H), 5.21-5.34 (m, 1 H), 6.81 (d, J=8.1 Hz, 1 H), 7.08 (d, J=8.1 Hz, 1 H), 7.30 (dd, J=8.7, 2.4 Hz, 1 H), 7.48 (d, J=2.4 Hz, 1 H), 7.51 (d, J=8.7 Hz, 1 H).

MS Calcd.: 466; Found: 467 (M+H).

Example 447

N-{1-[9-Chloro-1-(2,4-dichlorophenyl)-1,2,3,4-tetrahydropyrimido[1,2-a]benzimidazol-6-yl]propyl}-3,3,3-trifluoropropanamide

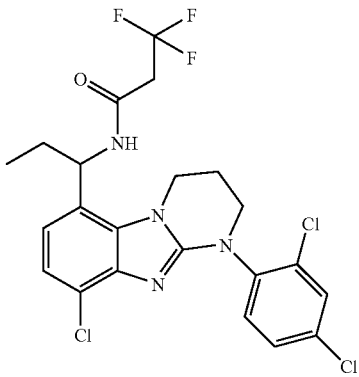 [SMILES: CCC(NC(=O)CC(F)(F)F)c1ccc(Cl)c2nc3n(c12)CCCN3c1ccc(Cl)cc1Cl]

A mixture of 1-[9-chloro-1-(2,4-dichlorophenyl)-1,2,3,4-tetrahydropyrimido[1,2-a]benzimidazol-6-yl]propan-1-amine (150 mg, <0.366 mmol), 2,2,2-trifluoropropionic acid (70.3 mg, 0.55 mmol), 1-ethyl-3-(3-dimethylaminopropyl)carbodiimide hydrochloride (158 mg, 0.824 mmol), 1-hydroxybenzotriazole monohydrate (126 mg, 0.823 mmol) and triethylamine (0.15 mL, 1.07 mmol) in N,N-dimethylformamide (5.0 mL) was stirred at room temperature for 20 hr. Water was added to the reaction mixture at room temperature and the mixture was extracted with ethyl acetate. The organic layer was washed with water and brine, dried over anhydrous magnesium sulfate, and concentrated in vacuo. The residue was purified by flash chromatography on silica gel eluting with a 30-50% ethyl acetate/n-hexane gradient mixture and recrystallization from ethyl acetate to give the title compound (59.1 mg, 0.114 mmol, 31%) as colorless crystals.

mp 285-290° C.

$^1$H NMR (CDCl$_3$) δ 0.94 (t, J=7.2 Hz, 3 H), 1.85-2.04 (m, 2 H), 2.32-2.45 (m, 2 H), 3.05 (q, J=10.5 Hz, 2 H), 3.64-3.78 (m, 2 H), 4.26-4.40 (m, 1 H), 4.63-4.77 (m, 1 H), 5.52-5.63 (m, 1 H), 5.92-6.03 (m, 1 H), 6.81 (d, J=8.3 Hz, 1 H), 7.09 (d, J=8.3 Hz, 1 H), 7.31 (dd, J=8.7, 2.4 Hz, 1 H), 7.49 (d, J=2.4 Hz, 1 H), 7.50 (d, J=8.7 Hz, 1 H).

MS Calcd.: 518; Found: 519 (M+H).

Example 448

Ethyl (2E)-3-[9-chloro-1-(2,4-dichlorophenyl)-1,2,3,4-tetrahydropyrimido[1,2-a]benzimidazol-6-yl]prop-2-enoate

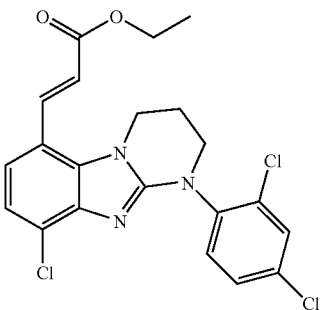 [SMILES: CCOC(=O)/C=C/c1ccc(Cl)c2nc3n(c12)CCCN3c1ccc(Cl)cc1Cl]

To a solution of ethyl diethylphosphonoacetate (0.78 mL, 3.93 mmol) in tetrahydrofuran (10 mL) was added sodium hydride (60% dispersion in mineral oil, 0.157 g, 3.93 mmol) at 0° C. The mixture was stirred at 0° C. for 1 hr. To the reaction mixture was added 9-chloro-1-(2,4-dichlorophenyl)-1,2,3,4-tetrahydropyrimido[1,2-a]benzimidazole-6-carbaldehyde (500 mg, 1.31 mmol) at 0° C. The mixture was stirred at room temperature for 4 hr and at 40° C. for 18 hr. Water was added to the reaction mixture at room temperature and the mixture was extracted with ethyl acetate. The organic layer was washed with water and brine, dried over anhydrous magnesium sulfate, and concentrated in vacuo. The residue was purified by flash chromatography on silica gel eluting with a 20-50% ethyl acetate/n-hexane gradient mixture to give the title compound (489 mg, 1.08 mmol, 83%) as a colorless solid.

$^1$H NMR (CDCl$_3$) δ 1.35 (t, J=7.1 Hz, 3 H), 2.33-2.45 (m, 2 H), 3.68-3.80 (m, 2 H), 4.28 (q, J=7.1 Hz, 2 H), 4.47 (t, J=6.3 Hz, 2 H), 6.31 (d, J=15.5 Hz, 1 H), 7.07 (d, J=8.4 Hz, 1 H), 7.13 (d, J=8.4 Hz, 1 H); 7.31 (dd, J=8.4, 2.4 Hz, 1 H), 7.49 (d, J=2.4 Hz, 1 H), 7.50 (d, J=8.4 Hz, 1 H), 8.27 (d, J=15.5 Hz, 1 H).

MS Calcd.: 449; Found: 450 (M+H).

Example 449

Ethyl 3-[9-chloro-1-(2,4-dichlorophenyl)-1,2,3,4-tetrahydropyrimido[1,2-a]benzimidazol-6-yl]pentanoate

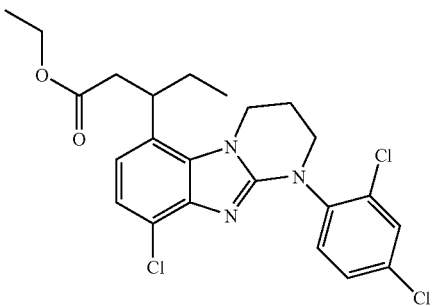 [SMILES: CCOC(=O)CC(CC)c1ccc(Cl)c2nc3n(c12)CCCN3c1ccc(Cl)cc1Cl]

To a mixture of ethyl (2E)-3-[9-chloro-1-(2,4-dichlorophenyl)-1,2,3,4-tetrahydropyrimido[1,2-a]benzimidazol-6-yl]prop-2-enoate (489 mg, 1.08 mmol) and copper (I) iodide (155 mg, 1.08 mmol) was added ethylmagnesium bromide (3.0 M in diethyl ether, 1.44 mL, 4.32 mmol) at 0° C. The mixture was stirred at 0° C. for 1 hr. Aqueous ammonium chloride was added to the reaction mixture at 0° C. and the mixture was extracted with ethyl acetate. The organic layer was washed with brine, dried over anhydrous magnesium sulfate, and concentrated in vacuo. The residue was purified by flash chromatography on silica gel eluting with a 20-50% ethyl acetate/n-hexane gradient mixture to give the title compound (308 mg, 0.641 mmol, 59%) as a colorless amorphous.

$^1$H NMR (CDCl$_3$) δ 0.86 (t, J=7.4 Hz, 3 H), 1.11 (t, J=7.2 Hz, 3 H), 1.66-1.82 (m, 2 H), 2.33-2.46 (m, 2H), 2.70 (d, J=7.8 Hz, 2 H), 3.63-3.85 (m, 3 H), 3.95-4.08 (m, 2 H), 4.33-4.44 (m, 1 H), 4.68-4.80 (m, 1 H), 6.76 (d, J=8.4 Hz, 1 H), 7.06 (d, J=8.4 Hz, 1 H), 7.30 (dd, J=8.7, 2.4 Hz, 1 H), 7.48 (d, J=2.4 Hz, 1 H), 7.53 (d, J=8.7 Hz, 1 H).

MS Calcd.: 479; Found: 480 (M+H).

Example 450

3-[9-Chloro-1-(2,4-dichlorophenyl)-1,2,3,4-tetrahydropyrimido[1,2-a]benzimidazol-6-yl]pentan-1-ol

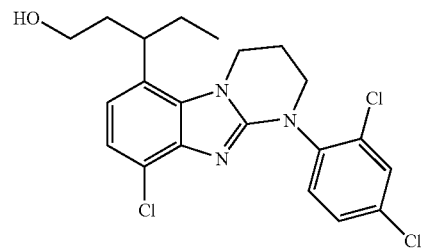 [SMILES: CCC(CCO)c1ccc(Cl)c2nc3n(c12)CCCN3c1ccc(Cl)cc1Cl]

To a solution of ethyl 3-[9-chloro-1-(2,4-dichlorophenyl)-1,2,3,4-tetrahydropyrimido[1,2-a]benzimidazol-6-yl]pentanoate (100 mg, 0.208 mmol) in tetrahydrofuran (10 mL) was added lithium tetrahydroborate (23 mg, 1.06 mmol) at 0° C. The mixture was stirred at room temperature for 18 hr. Then the mixture was warmed to 40° C. and stirred at 40° C. for 5 hr. Aqueous ammonium chloride was added to the reaction mixture at 0° C. and the mixture was extracted with ethyl acetate. The organic layer was washed with brine, dried over anhydrous magnesium sulfate, and concentrated in vacuo. The residue was purified by flash chromatography on silica gel eluting with a 50-100% ethyl acetate/n-hexane gradient mixture and recrystallization from ethyl acetate/n-hexane to give the title compound (41.7 mg, 0.095 mmol, 46%) as colorless crystals.

mp 183-185° C.

$^1$H NMR (CDCl$_3$) δ 0.85 (t, J=7.5 Hz, 3 H), 1.13-1.19 (m, 1 H), 1.63-2.10 (m, 4 H), 2.30-2.40 (m, 2 H), 3.38-3.74 (m, 5 H), 4.38-4.41 (m, 1 H), 4.60-4.71 (m, 1 H), 6.77 (d, J=8.1 Hz, 1 H), 7.07 (d, J=8.1 Hz, 1 H), 7.30 (dd, J=8.6, 2.4 Hz, 1 H), 7.48 (d, J=2.4 Hz, 1 H), 7.55 (d, J=8.6 Hz, 1 H).

MS Calcd.: 437; Found: 438 (M+H).

Example 451

3-[9-Chloro-1-(2,4-dichlorophenyl)-1,2,3,4-tetrahydropyrimido[1,2-a]benzimidazol-6-yl]-N-methoxy-N-methylpentanamide

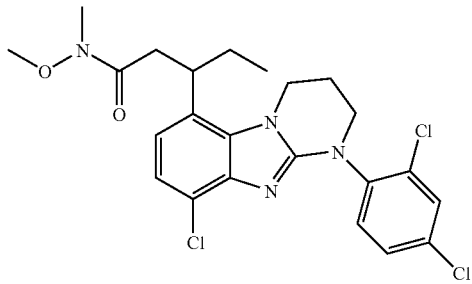 [SMILES: CCC(CC(=O)N(C)OC)c1ccc(Cl)c2nc3n(c12)CCCN3c1ccc(Cl)cc1Cl]

To a solution of ethyl 3-[9-chloro-1-(2,4-dichlorophenyl)-1,2,3,4-tetrahydropyrimido[1,2-a]benzimidazol-6-yl]pentanoate (200 mg, 0.416 mmol) in tetrahydrofuran (10 mL) and methanol (5.0 mL) was added 1N sodium hydroxide (2.0 mL, 2.0 mmol) at room temperature. The mixture was stirred at room temperature for 3 days. To the reaction mixture was added 1N hydrogen chloride (2.0 mL, 2.0 mmol) at room temperature and the mixture was concentrated in vacuo. To the residue was added N,N-dimethylformamide (10 mL) and to the mixture were added N,O-dimethylhydroxylamine hydrochloride (81 mg, 0.83 mmol), 1-ethyl-3-(3-dimethylaminopropyl)carbodiimide hydrochloride (159 mg, 0.83 mmol), 1-hydroxybenzotriazole monohydrate (127 mg, 0.83 mmol) and triethylamine (0.29 mL, 2.08 mmol). The mixture was stirred at room temperature for 24 hr. Water was added to the reaction mixture at room temperature and the mixture was extracted with ethyl acetate. The organic layer was washed with water and brine, dried over anhydrous magnesium sulfate, and concentrated in vacuo. The residue was purified by flash chromatography on silica gel eluting with a 25-75% ethyl acetate/n-hexane gradient mixture to give the title compound (148.6 mg, 0.30 mmol, 72%) as a pale yellow amorphous.

$^1$H NMR (CDCl$_3$) δ 0.85 (t, J=7.4 Hz, 3 H), 1.68-1.84 (m, 2 H), 2.31-2.47 (m, 2 H), 2.64-2.78 (m, 1 H), 2.86-3.04 (m, 1 H), 3.09 (s, 3 H), 3.58 (s, 3 H), 3.62-3.77 (m, 2 H), 3.84-3.98 (m, 1 H), 4.31-4.43 (m, 1 H), 4.84-4.96 (m, 1 H), 6.80 (d, J=8.4 Hz, 1 H), 7.05 (d, J=8.4 Hz, 1 H), 7.29 (dd, J=8.4, 2.4 Hz, 1 H), 7.48 (d, J=2.4 Hz, 1 H), 7.53 (d, J=8.4 Hz, 1 H).

MS Calcd.: 494; Found: 495 (M+H).

Example 452

4-[9-Chloro-1-(2,4-dichlorophenyl)-1,2,3,4-tetrahydropyrimido[1,2-a]benzimidazol-6-yl]hexan-2-one

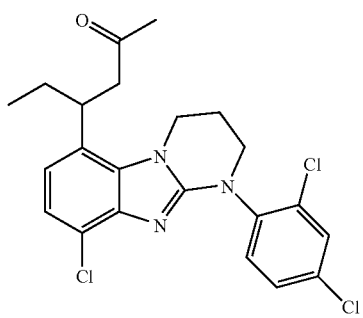 [SMILES: CCC(CC(C)=O)c1ccc(Cl)c2nc3n(c12)CCCN3c1ccc(Cl)cc1Cl]

To a solution of 3-[9-chloro-1-(2,4-dichlorophenyl)-1,2,3,4-tetrahydropyrimido[1,2-a]benzimidazol-6-yl]-N-methoxy-N-methylpentanamide (148.6 mg, 0.30 mmol) in tetrahydrofuran (10 mL) was added methylmagnesium bromide (3.0 M in diethyl ether, 0.3 mL, 0.9 mmol) at 0° C. The reaction mixture was stirred at 0° C. for 2 hr and at room temperature for 1 hr. Methylmagnesium bromide (3.0 M in diethyl ether, 0.3 mL, 0.9 mmol) was added to the reaction mixture at room temperature. After the mixture was stirred at room temperature for 2 hr, aqueous ammonium chloride was added to the reaction mixture. The mixture was extracted with ethyl acetate. The organic layer was washed with brine, dried over anhydrous magnesium sulfate, and concentrated in vacuo. The residue was purified by flash chromatography on silica gel eluting with a 20-60% ethyl acetate/n-hexane gradient mixture to give the title compound (96.0 mg, 0.213 mmol, 71%) as colorless crystals.

mp 195-197° C.

$^1$H NMR (CDCl$_3$) δ 0.83 (t, J=7.5 Hz, 3 H), 1.61-1.78 (m, 2 H), 2.03 (s, 3 H), 2.33-2.46 (m, 2 H), 2.77 (dd, J=17.1, 5.7 Hz, 1 H), 2.95 (dd, J=17.1, 8.0 Hz, 1 H), 3.63-3.76 (m, 2 H), 3.78-3.89 (m, 1 H), 4.31-4.43 (m, 1H), 4.72-4.84 (m, 1 H), 6.74 (d, J=8.4 Hz, 1 H), 7.05 (d, J=8.4 Hz, 1 H), 7.29 (dd, J=8.7, 2.4 Hz, 1 H), 7.48 (d, J=2.4 Hz, 1 H), 7.53 (d, J=8.7 Hz, 1 H).

MS Calcd.: 449; Found: 450 (M+H).

Example 453

9-Chloro-1-(2,4-dichlorophenyl)-6-(1-ethyl-3-methoxypropyl)-1,2,3,4-tetrahydropyrimido[1,2-a]benzimidazole

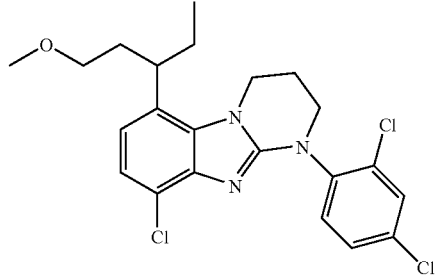 [SMILES: CCC(CCOC)c1ccc(Cl)c2nc3n(c12)CCCN3c1ccc(Cl)cc1Cl]

To a solution of 3-[9-chloro-1-(2,4-dichlorophenyl)-1,2,3,4-tetrahydropyrimido[1,2-a]benzimidazol-6-yl]pentan-1-ol (148 mg, 0.34 mmol) in N,N-dimethylformamide (5.0 mL) was added sodium hydride (60% dispersion in mineral oil, 27 mg, 0.675 mmol) at 0° C. After the mixture was stirred at 0° C. for 0.5 hr, iodomethane (0.064 mL, 1.03 mmol) was added to the reaction mixture at 0° C. The mixture was stirred at room temperature for 4 hr. Water was added to the reaction mixture at room temperature and the mixture was extracted with ethyl acetate. The organic layer was washed with water and brine, dried over anhydrous magnesium sulfate, and concentrated in vacuo. The residue was purified by flash chromatography on silica gel eluting with a 10-50% ethyl acetate/n-hexane gradient mixture and recrystallization from 2-propanol/n-hexane to give the title compound (81.1 mg, 0.179 mmol, 53%) as colorless crystals.

mp 144-146° C.

$^1$H NMR (CDCl$_3$) δ 0.83 (t, J=7.5 Hz, 3 H), 1.65-1.86 (m, 3 H), 1.97-2.11 (m, 1 H), 2.30-2.42 (m, 2 H), 3.00-3.10 (m, 1 H), 3.22 (s, 3 H), 3.29-3.37 (m, 1 H), 3.39-3.52 (m, 1 H), 3.63-3.76 (m, 2 H), 4.22-4.34 (m, 1H), 4.60-4.72 (m, 1 H), 6.76 (d, J=8.3 Hz, 1 H), 7.06 (d, J=8.3 Hz, 1 H), 7.30 (dd, J=8.4, 2.4 Hz, 1 H), 7.48 (d, J=2.4 Hz, 1 H), 7.54 (d, J=8.4 Hz, 1 H).

MS Calcd.: 451; Found: 452 (M+H).

Example 454

9-Chloro-1-(2,4-dichlorophenyl)-6-[1-(2,2,2-trifluoroethoxy)propyl]-1,2,3,4-tetrahydropyrimido[1,2-a]benzimidazole

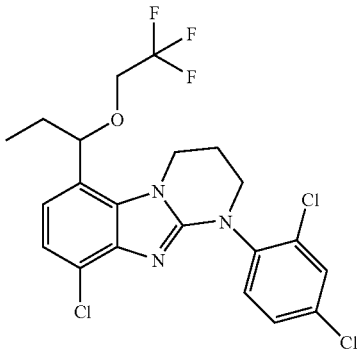 [SMILES: CCC(OCC(F)(F)F)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-ol (100 mg, 0.243 mmol) and 1,1'-(azodicarbonyl)dipiperidine (123 mg, 0.49 mmol) in tetrahydrofuran (5.0 mL) was added tri(n-butyl)phosphine (0.122 mL, 0.49 mmol) at room temperature. After the mixture was stirred at room temperature for 10 min under nitrogen atmosphere, 2,2,2-trifluoroethanol (0.177 mL, 2.32 mmol) was added to the reaction mixture. The mixture was stirred at 60° C. for 8 hr under nitrogen atmosphere. The mixture was concentrated in vacuo and diethyl ether was added to the residue. The solid was removed by filtration and the filtrate was concentrated in vacuo. The residue was purified by flash chromatography on silica gel eluting with a 10-40% ethyl acetate/n-hexane gradient mixture and recrystallization from 2-propanol/n-hexane to give the title compound (41.8 mg, 0.085 mmol, 35%) as colorless crystals.

mp 146-148° C.

$^1$H NMR (CDCl$_3$) δ 1.03 (t, J=7.2 Hz, 3 H), 1.81-2.12 (m, 2 H), 2.31-2.43 (m, 2 H), 3.54-3.82 (m, 4 H), 4.26-4.39 (m, 1 H), 4.52-4.64 (m, 1 H), 4.77-4.81 (m, 1 H), 6.86 (d, J=8.1 Hz, 1 H), 7.07 (d, J=8.1 Hz, 1 H), 7.32 (dd, J=8.6, 2.2 Hz, 1 H), 7.50 (d, J=2.2 Hz, 1 H), 7.51 (d, J=8.6 Hz, 1 H).

MS Calcd.: 491; Found: 492 (M+H).

Example 455

9-Chloro-6-[cyclopropyl(2,2,2-trifluoroethoxy)methyl]-1-(2,4-dichlorophenyl)-1,2,3,4-tetrahydropyrimido[1,2-a]benzimidazole

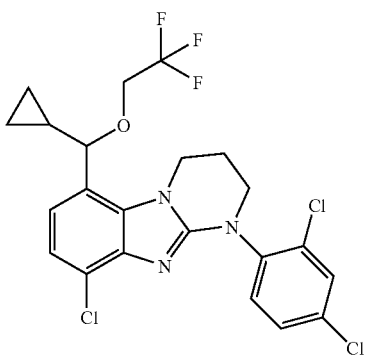 [SMILES: FC(F)(F)COC(c1ccc(Cl)c2nc3n(c12)CCCN3c1ccc(Cl)cc1Cl)C1CC1]

To a solution of [9-chloro-1-(2,4-dichlorophenyl)-1,2,3,4-tetrahydropyrimido[1,2-a]benzimidazol-6-yl](cyclopropyl)methanol (150 mg, 0.355 mmol), 1,1'-(azodicarbonyl)dipiperidine (179 mg, 0.709 mmol) in tetrahydrofuran (7.5 mL) was added tri(n-butyl)phosphine (0.177 mL, 0.709 mmol) at room temperature. After the mixture was stirred at room temperature for 10 min under nitrogen atmosphere, 2,2,2-trifluoroethanol (0.259 mL, 3.55 mmol) was added to the reaction mixture. The mixture was stirred at 65° C. for 15 hr under nitrogen atmosphere. The mixture was concentrated in vacuo and diethyl ether was added to the residue. The solid was removed by filtration and the filtrate was concentrated in vacuo. The residue was purified by flash chromatography on silica gel eluting with a 10-30% ethyl acetate/n-hexane gradient mixture and recrystallization from 2-propanol/n-hexane to give the title compound (102.9 mg, 0.204 mmol, 57%) as colorless crystals.

mp 143-145° C.

$^1$H NMR (CDCl$_3$) δ 0.26-0.39 (m, 1 H), 0.46-0.55 (m, 1 H), 0.59-0.70 (m, 1 H), 0.72-0.82 (m, 1 H), 1.38-1.49 (m, 1 H), 2.31-2.42 (m, 2 H), 3.62-3.82 (m, 4 H), 4.32-4.49 (m, 2 H), 4.55-4.68 (m, 1 H), 6.86 (d, J=8.1 Hz, 1 H), 7.06 (d, J=8.1 Hz, 1 H), 7.32 (dd, J=8.4, 2.4 Hz, 1 H), 7.50 (d, J=2.4 Hz, 1 H), 7.51 (d, J=8.4 Hz, 1 H).

MS Calcd.: 503; Found: 504 (M+H).

Example 456

N-{1-[9-Chloro-1-(2,4-dichlorophenyl)-1,2,3,4-tetrahydropyrimido[1,2-a]benzimidazol-6-yl]propyl}-2,2,2-trifluoroacetamide

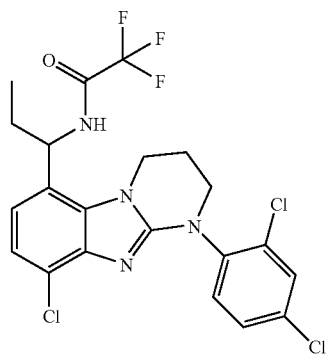 [SMILES: CCC(NC(=O)C(F)(F)F)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-amine (600 mg, <1.46 mmol) and triethylamine (0.41 mL, 2.94 mmol) in acetonitrile (10 mL) was added ethyl trifluoroacetate (0.35 mL, 2.94 mmol) at room temperature. The mixture was stirred at room temperature for 3 hr.

Ethyl trifluoroacetate (0.35 mL, 2.94 mmol) and triethylamine (0.5 mL, 3.59 mmol) were added to the reaction mixture at room temperature. The mixture was stirred at room temperature for 18 hr and at 60° C. for 20 hr. The reaction mixture was concentrated in vacuo. Water was added to the residue and the mixture was extracted with ethyl acetate. The organic layer was washed with brine, dried over anhydrous magnesium sulfate, and concentrated in vacuo. The residue was purified by flash chromatography on silica gel eluting with a 30-70% ethyl acetate/n-hexane gradient mixture to give the title compound (611.7 mg, 1.21 mmol, 83%) as a pale yellow solid.

$^1$H NMR (CDCl$_3$) δ 0.97 (t, J=7.4 Hz, 3 H), 1.95-2.15 (m, 2 H), 2.36-2.49 (m, 2 H), 3.63-3.78 (m, 2 H), 4.30-4.42 (m, 1 H), 4.59-4.70 (m, 1 H), 5.51-5.63 (m, 1 H), 6.45-6.59 (m, 1 H), 6.84 (d, J=8.4 Hz, 1 H), 7.13 (d, J=8.4 Hz, 1 H), 7.31 (dd, J=8.4, 2.4 Hz, 1 H), 7.495 (d, J=2.4 Hz, 1 H), 7.503 (d, J=8.4 Hz, 1 H).

MS Calcd.: 504; Found: 505 (M+H).

Example 457

N-{1-[9-Chloro-1-(2,4-dichlorophenyl)-1,2,3,4-tetrahydropyrimido[1,2-a]benzimidazol-6-yl]propyl}-N-ethyl-2,2,2-trifluoroacetamide

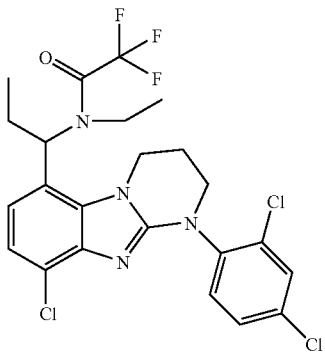 [SMILES: CCC(c1ccc(Cl)c2nc3n(c12)CCCN3c1ccc(Cl)cc1Cl)N(CC)C(=O)C(F)(F)F]

To a solution of N-{1-[9-chloro-1-(2,4-dichlorophenyl)-1,2,3,4-tetrahydropyrimido[1,2-a]benzimidazol-6-yl]propyl}-2,2,2-trifluoroacetamide (400 mg, 0.79 mmol) in N,N-dimethylformamide (5.0 mL) was added sodium hydride (60% dispersion in mineral oil, 38 mg, 0.95 mmol) at 0° C. The mixture was stirred at 0° C. for 0.5 hr. Iodoethane (0.095 mL, 1.19 mmol) was added to the reaction mixture at 0° C. The mixture was stirred at 60° C. for 16 hr. Water was added to the reaction mixture at room temperature and the mixture was extracted with ethyl acetate. The organic layer was washed with water and brine, dried over anhydrous magnesium sulfate, and concentrated in vacuo. The residue was purified by flash chromatography on silica gel eluting with a 10-40% ethyl acetate/n-hexane gradient mixture to give the title compound (131 mg, 0.245 mmol, 31%) as a pale yellow amorphous.

$^1$H NMR (CDCl$_3$) δ 0.82 (t, J=6.9 Hz, 3 H); 0.97 (t, J=7.5 Hz, 3 H), 1.93-2.23 (m, 2 H), 2.26-2.41 (m, 2H), 3.10-3.44 (m, 2 H), 3.62-3.75 (m, 2 H), 3.99-4.12 (m, 1 H), 4.36-4.48 (m, 1 H), 5.94-6.05 (m, 1 H), 7.03 (d, J=8.6 Hz, 1 H), 7.14 (d, J=8.6 Hz, 1 H), 7.31 (dd, J=8.4, 2.5 Hz, 1 H), 7.490 (d, J=8.4 Hz, 1 H), 7.492 (d, J=2.5 Hz, 1 H).

MS Calcd.: 532; Found: 5.33 (M+H).

Example 458

1-[9-Chloro-1-(2,4-dichlorophenyl)-1,2,3,4-tetrahydropyrimido[1,2-a]benzimidazol-6-yl]-N-ethylpropan-1-amine

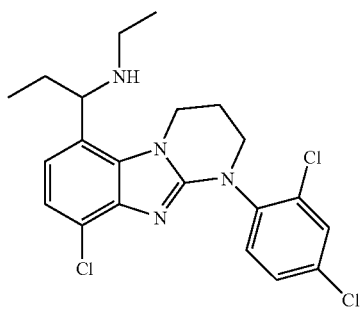 [SMILES: CCNC(CC)c1ccc(Cl)c2nc3n(c12)CCCN3c1ccc(Cl)cc1Cl]

To a solution of N-{1-[9-chloro-1-(2,4-dichlorophenyl)-1,2,3,4-tetrahydropyrimido[1,2-a]benzimidazol-6-yl]propyl}-N-ethyl-2,2,2-trifluoroacetamide (131 mg, 0.245 mmol) in ethanol (5.0 mL) was added sodium tetrahydroborate (28 mg, 0.74 mmol) at room temperature. The mixture was stirred at room temperature for 18 hr. Water was added to the reaction mixture at room temperature and the mixture was extracted with ethyl acetate. The organic layer was washed with brine, dried over anhydrous magnesium sulfate, and concentrated in vacuo. The residue was purified by flash chromatography on NH-silica gel eluting with a 30-80% ethyl acetate/n-hexane gradient mixture to give the title compound (35.4 mg, 0.081 mmol, 33%) as a colorless solid.

mp 124-127° C.

$^1$H NMR (CDCl$_3$) δ 0.89 (t, J=7.5 Hz, 3 H), 1.07 (t, J=7.0 Hz, 3 H), 1.71-1.90 (m, 2 H), 2.30-2.42 (m, 2 H), 2.54 (q, J=7.0 Hz, 2 H), 3.65-3.76 (m, 2 H), 4.13-4.25 (m, 1 H), 4.35-4.47 (m, 1 H), 4.59-4.79 (m, 1 H), 6.96 (d, J=8.1 Hz, 1 H), 7.07 (d, J=8.1 Hz, 1 H), 7.30 (dd, J=8.4, 2.7 Hz, 1 H), 7.49 (d, J=2.7 Hz, 1 H), 7.54 (d, J=8.4 Hz, 1 H).

MS Calcd.: 436; Found: 437 (M+H).

Example 459

1-[9-Chloro-1-(2,4-dichlorophenyl)-1,2,3,4-tetrahydropyrimido[1,2-a]benzimidazol-6-yl]-N-(2,2,2-trifluoroethyl)propan-1-amine

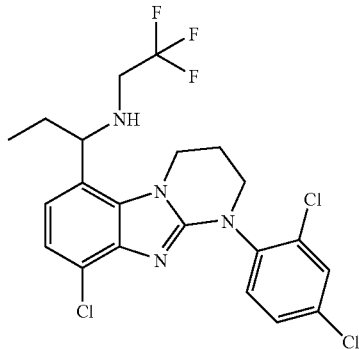

To a solution of 1-[9-chloro-1-(2,4-dichlorophenyl)-1,2,3,4-tetrahydropyrimido[1,2-a]benzimidazol-6-yl]propan-1-amine (200 mg, 0.488 mmol) and ethyldiisopropylamine (0.166 mL, 0.976 mmol) in N,N-dimethylformamide (10 mL) was added 2,2,2-trifluoroethyl trifluoromethanesulfonate (0.0774 mL, 0.54 mmol) at room temperature. The mixture was stirred at room temperature for 20 hr. To the reaction mixture was added 2,2,2-trifluoroethyl trifluoromethanesulfonate (0.030 mL, 0.208 mmol) at room temperature and the mixture was stirred at room temperature for 24 hr. Water was added to the reaction mixture and the mixture was extracted with ethyl acetate. The organic layer was washed with water and brine, dried over anhydrous magnesium sulfate, and concentrated in vacuo. The residue was purified by flash chromatography on NH-silica gel eluting with a 25-45% ethyl acetate/n-hexane gradient mixture to give the title compound (76.4 mg, 0.155 mmol, 32%) as a colorless solid.

mp 133-135° C.

$^1$H NMR (CDCl$_3$) δ 0.94 (t, J=7.4 Hz, 3 H), 1.68-1.89 (m, 3 H), 2.30-2.43 (m, 2 H), 2.99-3.16 (m, 2 H), 3.64-3.79 (m, 2 H), 4.27-4.43 (m, 2 H), 4.54-4.75 (m, 1 H), 6.94 (d, J=8.3 Hz, 1 H), 7.07 (d, J=8.3 Hz, 1 H), 7.31 (dd, J=8.4, 2.4 Hz, 1 H), 7.49 (d, J=2.4 Hz, 1 H), 7.52 (d, J=8.4 Hz, 1 H).

MS Calcd.: 490; Found: 491 (M+H).

Example 460

9-Chloro-1-(2,4-dichlorophenyl)-6-[(ethylsulfanyl)methyl]-1,2,3,4-tetrahydropyrimido[1,2-a]benzimidazole

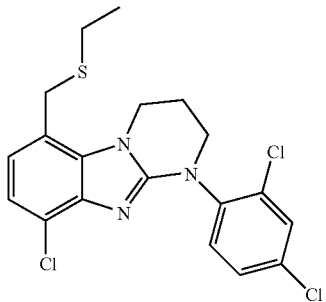 [SMILES: CCSCc1ccc(Cl)c2nc3n(c12)CCCN3c1ccc(Cl)cc1Cl]

To a solution of [9-chloro-1-(2,4-dichlorophenyl)-1,2,3,4-tetrahydropyrimido[1,2-a]benzimidazol-6-yl]methanol (300 mg, 0.784 mmol) and N,N-dimethylformamide (1 drop) in tetrahydrofuran (10 mL) was added thionyl chloride (0.086 mL, 1.18 mmol) at room temperature. The mixture was stirred at room temperature for 2 h. The mixture was concentrated in vacuo. To a solution of the residue in tetrahydrofuran (10 mL) and 2-propanol (10 mL) were added triethylamine (0.5 mL, 3.58 mmol) and sodium ethanethiolate (79.1 mg, 0.94 mmol) at room temperature. The mixture was stirred at 60° C. for 3 days. Sodium ethanethiolate (79.1 mg, 0.94 mmol) was added to the reaction mixture at room temperature and the mixture was stirred at 60° C. for 4 days. Water was added to the reaction mixture at room temperature and the mixture was extracted with ethyl acetate. The organic layer was washed with brine, dried over anhydrous magnesium sulfate, and concentrated in vacuo. The residue was purified by flash chromatography on NH-silica gel eluting with a 10-40% ethyl acetate/n-hexane gradient mixture to give the title compound (216 mg, 0.506 mmol, 65%) as a colorless amorphous.

$^1$H NMR (CDCl$_3$) δ 1.27 (t, J=7.4 Hz, 3 H), 2.35-2.43 (m, 2 H), 2.49 (q, J=7.4 Hz, 2 H), 3.65-3.75 (m, 2 H), 3.96 (s, 2 H), 4.64 (t, J=6.2 Hz, 2 H), 6.68 (d, J=8.1 Hz, 1H), 6.98 (d, J=8.1 Hz, 1 H), 7.31 (dd, J=8.6, 2.5 Hz, 1 H), 7.49 (d, J=2.5 Hz, 1 H), 7.52 (d, J=8.6 Hz, 1H).

MS Calcd.: 425; Found: 426 (M+H).

Example 461

9-Chloro-1-(2,4-dichlorophenyl)-6-[(ethylsulfonyl)methyl]-1,2,3,4-tetrahydropyrimido[1,2-a]benzimidazole

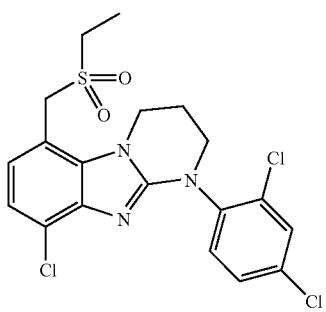 [SMILES: CCS(=O)(=O)Cc1ccc(Cl)c2nc3n(c12)CCCN3c1ccc(Cl)cc1Cl]

To a solution of 9-Chloro-1-(2,4-dichlorophenyl)-6-[(ethylsulfanyl)methyl]-1,2,3,4-tetrahydropyrimido[1,2-a]benzimidazole (216 mg, 0.506 mmol) in acetonitrile (10 mL) was added 3-chloroperbenzoic acid (70%, 0.274 g, 1.11 mmol) at 0° C. The mixture was stirred at 0° C. for 1 hr. Aqueous sodium thiosulfate was added to the reaction mixture at 0° C. and the mixture was stirred at room temperature. The mixture was extracted with ethyl acetate. The organic layer was washed with aqueous sodium hydrogen carbonate and brine. The organic layer was concentrated in vacuo and the precipitated solid was collected by filtration. The solid was washed with water, 2-propanol and diisopropyl ether to give the title compound (190 mg, 0.414 mmol, 82%) as a colorless solid.

mp 300-302° C.

$^1$H NMR (CDCl$_3$) δ 1.40 (t, J=7.4 Hz, 3 H), 2.35-2.46 (m, 2 H), 2.98 (q, J=7.4 Hz, 2 H), 3.63-3.79 (m, 2 H), 4.54 (s, 2 H), 4.58 (t, J=6.2 Hz, 2 H), 6.74 (d, J=8.1 Hz, 1 H), 7.08 (d, J=8.1 Hz, 1 H), 7.31 (dd, J=8.6, 2.3 Hz, 1 H), 7.4905 (d, J=2.3 Hz, 1 H), 7.4910 (d, J=8.6 Hz, 1 H).

MS Calcd.: 457; Found: 458 (M+H).

Example 462

9-Chloro-1-(2,4-dichlorophenyl)-6-[(ethylsulfonyl)methyl]-1,2,3,4-tetrahydropyrimido[1,2-a]benzimidazole

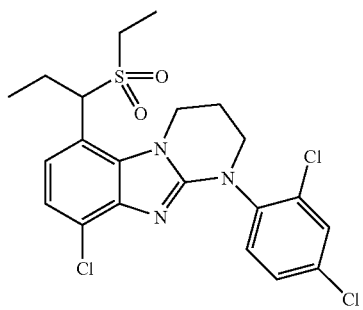 [SMILES: CCC(c1ccc(Cl)c2nc3n(c12)CCCN3c1ccc(Cl)cc1Cl)S(=O)(=O)CC]

To a solution of 9-chloro-1-(2,4-dichlorophenyl)-6-[(ethylsulfonyl)methyl]-1,2,3,4-tetrahydropyrimido[1,2-a]benzimidazole (120 mg, 0.262 mmol) and iodoethane (0.042 mL, 0.525 mmol) in N,N-dimethylformamide (5.0 mL) was added potassium tert-butoxide (32.3 mg, 0.29 mmol) at 0° C. The mixture was stirred at 0° C. for 5 hr and at room temperature for 0.5 hr. Water was added to the reaction mixture at room temperature and the mixture was extracted with ethyl acetate. The organic layer was washed with water and brine, dried over anhydrous magnesium sulfate, and concentrated in vacuo. The residue was purified by flash chromatography on NH-silica gel eluting with a 30-80% ethyl acetate/n-hexane gradient mixture to give the title compound (94.1 mg, 0.19 mmol, 74%) as colorless crystals.

mp 278-280° C.

$^1$H NMR (CDCl$_3$) δ 1.01 (t, J=7.2 Hz, 3 H), 1.30 (t, J=7.7 Hz, 3 H), 2.20-2.60 (m, 4 H), 2.78-2.88 (m, 2 H), 3.64-3.80 (m, 2 H), 4.18-4.29 (m, 1 H), 4.63-4.81 (m, 2 H), 7.04 (d, J=8.3 Hz, 1 H), 7.15 (d; J=8.3 Hz, 1 H), 7.32 (dd, J=8.7, 2.3 Hz, 1 H), 7.50 (d, J=2.3 Hz, 1 H), 7.51 (d, J=8.7 Hz, 1 H).

MS Calcd.: 485; Found: 486 (M+H).

Example 463

N-{1-[9-Chloro-1-(2,4-dichlorophenyl)-1,2,3,4-tetrahydropyrimido[1,2-a]benzimidazol-6-yl]propyl}-2,2-difluoroacetamide

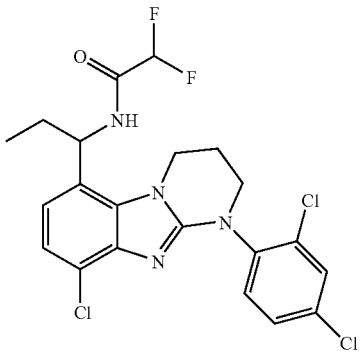 [SMILES: CCC(NC(=O)C(F)F)c1ccc(Cl)c2nc3n(c12)CCCN3c1ccc(Cl)cc1Cl]

A mixture of 1-[9-chloro-1-(2,4-dichlorophenyl)-1,2,3,4-tetrahydropyrimido[1,2-a]benzimidazol-6-yl]propan-1-amine (150 mg, <0.366 mmol), difluoroacetic acid (0.0346 mL, 0.55 mmol), 1-ethyl-3-(3-dimethylaminopropyl)carbodiimide hydrochloride (158 mg, 0.824 mmol), 1-hydroxybenzotriazole monohydrate (126 mg, 0.823 mmol) and triethylamine (0.15 mL, 1.07 mmol) in N,N-dimethylformamide (5.0 mL) was stirred at room temperature for 5 days. Water was added to the reaction mixture at room temperature and the mixture was extracted with ethyl acetate. The organic layer was washed with water and brine, dried over anhydrous magnesium sulfate, and concentrated in vacuo. The residue was purified by flash chromatography on silica gel eluting with a 25-75% ethyl acetate/n-hexane gradient mixture and recrystallization from ethyl acetate/diisopropyl ether to give the title compound (56.3 mg, 0.115 mmol, 32%) as colorless crystals.

mp 248-250° C.

$^1$H NMR (CDCl$_3$) δ 0.96 (t, J=7.5 Hz, 3 H), 1.92-2.09 (m, 2 H), 2.33-2.46 (m, 2 H), 3.64-3.78 (m, 2 H), 4.30-4.42 (m, 1 H), 4.63-4.75 (m, 1 H), 5.55-5.63 (m, 1 H), 5.88 (t, J=54.3 Hz, 1 H), 6.50-6.60 (m, 1 H), 6.84 (d, J=8.3 Hz, 1 H), 7.12 (d, J=8.3 Hz, 1 H), 7.31 (dd, J=8.5, 2.2 Hz, 1 H), 7.49 (d, J=2.2 Hz, 1 H), 7.51 (d, J=8.5 Hz, 1 H).

MS Calcd.: 486; Found: 487 (M+H).

Example 464

9-Chloro-6-[cyclopropyl(2,2-difluoroethoxy)methyl]-1-(2,4-dichlorophenyl)-1,2,3,4-tetrahydropyrimido[1,2-a]benzimidazole

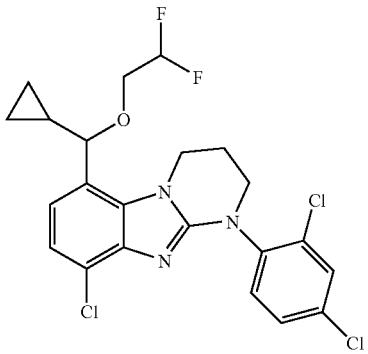

To a solution of [9-chloro-1-(2,4-dichlorophenyl)-1,2,3,4-tetrahydropyrimido[1,2-a]benzimidazol-6-yl](cyclopropyl)methanol (183 mg, 0.433 mmol), 1,1'-(azodicarbonyl)dipiperidine (219 mg, 0.868 mmol) in tetrahydrofuran (5.0 mL) was added tri(n-butyl)phosphine (0.217 mL, 0.869 mmol) at room temperature. After the mixture was stirred at room temperature for 10 min under nitrogen atmosphere, 2,2-difluoroethanol (0.272 mL, 4.30 mmol) was added to the reaction mixture. The mixture was stirred at 50° C. for 14 hr under nitrogen atmosphere. The mixture was concentrated in vacuo and diethyl ether was added to the residue. The solid was removed by filtration and the filtrate was concentrated in vacuo. The residue was purified by flash chromatography on silica gel eluting with a 10-40% ethyl acetate/n-hexane gradient mixture and recrystallization from 2-propanol/n-hexane to give the title compound (102 mg, 0.21 mmol, 48%) as colorless crystals.

$^1$H NMR (CDCl$_3$) δ 0.23-0.33 (m, 1 H), 0.43-0.53 (m, 1 H), 0.56-0.65 (m, 1 H), 0.69-0.80 (m, 1 H), 1.35-1.49 (m, 1 H), 2.30-2.43 (m, 2 H), 3.61 (td, J=14.4, 3.9 Hz, 2 H), 3.63-3.77 (m, 2 H), 4.30 (d, J=7.8 Hz, 1 H), 4.41-4.51 (m, 1 H), 4.59-4.69 (m, 1 H), 5.85 (tt, J=55.3, 4.1 Hz, 1 H), 6.87 (d, J=8.3 Hz, 1 H), 7.05 (d, J=8.3 Hz, 1 H), 7.32 (d, J=8.6, 2.6 Hz, 1 H), 7.50-7.53 (m, 2 H).

MS Calcd.: 485; Found: 486 (M+H).

Example 465

[9-Chloro-1-(2-chloro-4-methoxyphenyl)-1,2,3,4-tetrahydropyrimido[1,2-a]benzimidazol-6-yl](dicyclopropyl)methanol

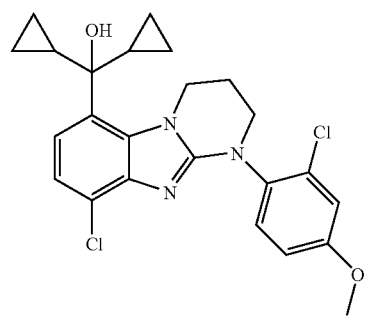 [SMILES: COc1ccc(N2CCCn3c2nc2c(Cl)ccc(C(O)(C4CC4)C4CC4)c23)c(Cl)c1]

To a solution of methyl 9-chloro-1-(2-chloro-4-methoxyphenyl)-1,2,3,4-tetrahydropyrimido[1,2-a]benzimidazole-6-carboxylate (100 mg, 0.246 mmol) in tetrahydrofuran (2.5 mL) was added a solution of cyclopropyl magnesium bromide in tetrahydrofuran (1.0 M, 1.5 mL, 1.5 mmol) at 0° C. The mixture was stirred at room temperature for 0.5 hr and at 50° C. for 1 hr. Aqueous ammonium chloride was added to the reaction mixture at room temperature and the mixture was extracted with ethyl acetate. The organic layer was washed with brine, dried over anhydrous magnesium sulfate and concentrated in vacuo. The residue was purified by flash chromatography on silica gel eluting with a 30-70% ethyl acetate/n-hexane gradient mixture and recrystallization from ethyl acetate/n-hexane to give the title compound (58.6 mg, 0.128 mmol, 52%) as colorless crystals.

$^1$H NMR (CDCl$_3$) δ 0.20-0.31 (m, 2 H), 0.51-0.66 (m, 6 H), 1.38-1.46 (m, 2 H), 1.72 (s, 1 H), 2.21-2.32 (m, 2 H), 3.57-3.78 (m, 2 H), 3.83 (s, 3 H), 4.82 (t, J=5.7 Hz, 2 H), 6.88 (dd, J=8.7, 2.8 Hz, 1 H), 6.98 (d, J=8.1 Hz, 1 H), 7.02 (d, J=8.1 Hz, 1 H), 7.12 (d, J=8.1 Hz, 1 H), 7.42 (d, J=8.7 Hz, 1 H).

MS Calcd.: 457; Found: 458 (M+H).

Example 466

9-Chloro-1-(2-chloro-4-methoxyphenyl)-6-[1-(2,2,2-trifluoroethoxy)propyl]-1,2,3,4-tetrahydropyrimido[1,2-a]benzimidazole

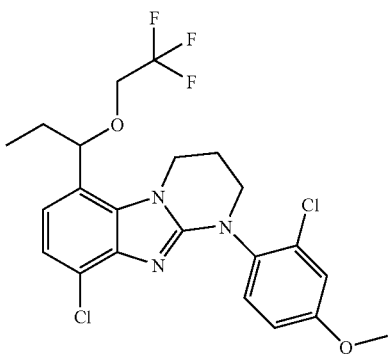 [SMILES: CCC(OCC(F)(F)F)c1ccc(Cl)c2nc3n(c12)CCCN3c1ccc(OC)cc1Cl]

To a solution of 1-[9-chloro-1-(2-chloro-4-methoxyphenyl)-1,2,3,4-tetrahydropyrimido[1,2-a]benzimidazol-6-yl]propan-1-ol (110 mg, 0.27 mmol), 1,1'-(azodicarbonyl)dipiperidine (137 mg, 0.54 mmol) in tetrahydrofuran (5.0 mL) was added tri(n-butyl)phosphine (0.136 mL, 0.54 mmol) at room temperature. After the mixture was stirred at room temperature for 10 min under nitrogen atmosphere, 2,2,2-trifluoroethanol (0.197 mL, 2.70 mmol) was added to the reaction mixture. The mixture was stirred at 60° C. for 6 hr under nitrogen atmosphere. The mixture was concentrated in vacuo and diethyl ether was added to the residue. The solid was removed by filtration and the filtrate was concentrated in vacuo. The residue was purified by flash chromatography on silica gel eluting with a 10-30% ethyl acetate/n-hexane gradient mixture and recrystallization from ethyl acetate/n-hexane to give the title compound (43.3 mg, 0.089 mmol, 33%) as colorless crystals.

$^1$H NMR (CDCl$_3$) δ 1.03 (t, J=7.4 Hz, 3 H), 1.79-1.94 (m, 1 H), 1.97-2.10 (m, 1 H), 2.29-2.45 (m, 2 H), 3.53-3.80 (m, 4 H), 3.83 (s, 3 H), 4.25-4.39 (m, 1 H), 4.50-4.63 (m, 1 H), 4.75-4.84 (m, 1 H), 6.83 (d, J=8.4 Hz, 1H), 6.88 (dd, J=8.8, 2.8 Hz, 1 H), 7.02 (d, J=2.8 Hz, 1 H), 7.0% (d, J=8.4 Hz, 1 H), 7.43 (d, J=8.8 Hz, 1 H).

MS Calcd.: 487; Found: 488 (M+H).

Example 467

[9-Chloro-1-(2-chloro-4-methoxyphenyl)-1,2,3,4-tetrahydropyrimido[1,2-a]benzimidazol-6-yl](cyclopropyl)methanol

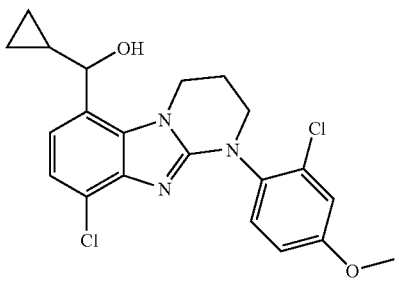 [SMILES: COc1ccc(N2CCCn3c2nc2c(Cl)ccc(C(O)C4CC4)c23)c(Cl)c1]

To a solution of 9-chloro-1-(2-chloro-4-methoxyphenyl)-1,2,3,4-tetrahydropyrimido[1,2-a]benzimidazole-6-carbaldehyde (274 mg, 0.728 mmol) in tetrahydrofuran (10 mL) was added cyclopropylmagnesium bromide in tetrahydrofuran (1.0 M, 2.2 mL, 2.2 mmol) at 0° C. The mixture was stirred at 0° C. for 0.5 hr. Aqueous ammonium chloride was added to the reaction mixture at 0° C. and the mixture was extracted with ethyl acetate. The organic layer was washed with brine, dried over anhydrous magnesium sulfate and concentrated in vacuo. The residue was purified by flash chromatography on silica gel eluting with a 50-80% ethyl acetate/n-hexane gradient mixture to give the title compound (261.7 mg, 0.57 mmol, 77%) as colorless crystals.

$^1$H NMR (CDCl$_3$) δ 0.30-3.40 (m, 1 H), 0.43-0.55 (m, 1 H), 0.62-0.81 (m, 2 H), 1.42-1.51 (m, 1 H), 1.98 (d, J=5.4 Hz, 1 H), 2.25-2.45 (m, 2 H), 3.56-3.78 (m, 2 H), 3.82 (s, 3 H), 4.36-4.49 (m, 1 H), 4.57-4.61 (m, 1 H), 4.66-4.79 (m, 1 H), 6.87 (dd, J=8.8, 2.9 Hz, 1 H), 7.01 (d, J=2.9 Hz, 1 H), 7.04 (d, J=8.1 Hz, 1 H), 7.11 (d, J=8.1 Hz, 1 H), 7.43 (d, J=8.8 Hz, 1H).

MS Calcd.: 417; Found: 418 (M+H).

Example 468

9-Chloro-1-(2-chloro-4-methoxyphenyl)-6-[cyclopropyl(2,2,2-trifluoroethoxy)methyl]-1,2,3,4-tetrahydropyrimido[1,2-a]benzimidazole

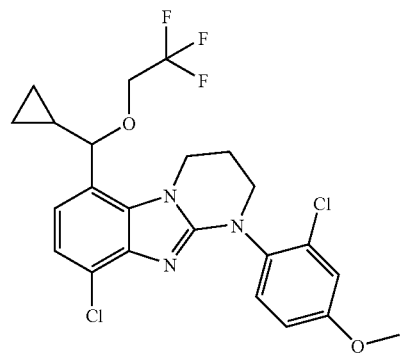 [SMILES: COc1ccc(N2CCCn3c2nc2c(Cl)ccc(C(OCC(F)(F)F)C4CC4)c23)c(Cl)c1]

To a solution of [9-chloro-1-(2-chloro-4-methoxyphenyl)-1,2,3,4-tetrahydropyrimido[1,2-a]benzimidazol-6-yl](cyclopropyl)methanol (120 mg, 0.26 mmol), 1,1'-(azodicarbonyl)dipiperidine (131 mg, 0.52 mmol) in tetrahydrofuran (5.0 mL) was added tri(n-butyl)phosphine (0.130 mL, 0.52 mmol) at room temperature. After the mixture was stirred at room temperature for 10 min under nitrogen atmosphere, 2,2,2-trifluoroethanol (0.189 mL, 2.58 mmol) was added to the reaction mixture. The mixture was stirred at 60° C. for 5 hr under nitrogen atmosphere. The mixture was concentrated in vacuo and diethyl ether was added to the residue. The solid was removed by filtration and the filtrate was concentrated in vacuo. The residue was purified by flash chromatography on silica gel eluting with a 10-25% ethyl acetate/n-hexane gradient mixture and recrystallization from ethyl acetate/n-hexane to give the title compound (77.4 mg, 0.155 mmol, 60%) as colorless crystals.

$^1$H NMR (CDCl$_3$) δ 0.26-0.38 (m, 1 H), 0.43-0.53 (m, 1 H), 0.56-0.67 (m, 1 H), 0.70-0.82 (m, 1 H), 1.36-1.49 (m, 1 H), 2.27-2.42 (m, 2 H), 3.59-3.81 (m, 4 H), 3.83 (s, 3 H), 4.34-4.49 (m, 2 H), 4.56-4.66 (m, 1 H), 6.83 (d, J=8.1 Hz, 1 H), 6.88 (dd, J=8.8, 2.9 Hz, 1 H), 7.02 (d, J=2.9 Hz, 1 H), 7.03 (d, J=8.1 Hz, 1 H), 7.43 (d, J=8.8 Hz, 1 H).

MS Calcd.: 499; Found: 500 (M+H).

Example 469

1-[9-Chloro-1-(2-chloro-4-methoxyphenyl)-1,2,3,4-tetrahydropyrimido[1,2-a]benzimidazol-6-yl]-2,2,2-trifluoroethanol

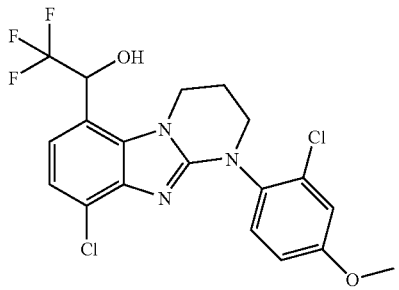 [SMILES: COc1ccc(N2CCCn3c2nc2c(Cl)ccc(C(O)C(F)(F)F)c23)c(Cl)c1]

To a solution of 9-chloro-1-(2-chloro-4-methoxyphenyl)-1,2,3,4-tetrahydropyrimido[1,2-a]benzimidazole-6-carbaldehyde (200 mg, 0.53 mmol) and trimethyl(trifluoromethyl)silane (0.24 mL, 1.62 mmol) in tetrahydrofuran (10 mL) was added tetra(n-butyl)ammonium fluoride in tetrahydrofuran (1.0 M, 0.053 mL, 0.053 mmol) at 0° C. After the mixture was stirred at 0° C. for 0.5 hr, 1N hydrogen chloride (2.0 mL) was added to the reaction mixture. The reaction mixture was stirred at 0° C. for 1 hr. Aqueous sodium hydrogen carbonate was added to the reaction mixture at 0° C. and the mixture was extracted with ethyl acetate. The organic layer was washed with brine, dried over anhydrous magnesium sulfate and concentrated in vacuo. The residue was purified by flash chromatography on silica gel eluting with a 30-70% ethyl acetate/n-hexane gradient mixture to give the title compound (212 mg, 0.475 mmol, 90%) as pale yellow crystals.

$^1$H NMR (CDCl$_3$) δ 2.23-2.37 (m, 2 H), 3.54-3.68 (m, 2 H), 3.83 (s, 3 H), 4.26-4.55 (m, 2 H), 5.65-5.78 (m, 1 H), 6.94-7.13 (m, 4 H), 7.19 (d, J=2.7 Hz, 1 H), 7.49 (d, J=9.0 Hz, 1 H).

MS Calcd.: 445; Found: 446 (M+H).

Example 470

1-[9-Chloro-1-(2-chloro-4-methoxyphenyl)-1,2,3,4-tetrahydropyrimido[1,2-a]benzimidazol-6-yl]-2,2,2-trifluoroethanol

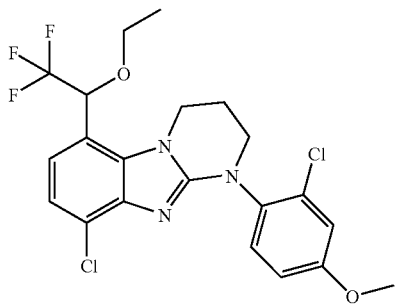 [SMILES: CCOC(c1ccc(Cl)c2nc3n(c12)CCCN3c1ccc(OC)cc1Cl)C(F)(F)F]

To a solution of 1-[9-chloro-1-(2-chloro-4-methoxyphenyl)-1,2,3,4-tetrahydropyrimido[1,2-a]benzimidazol-6-yl]-2,2,2-trifluoroethanol (100 mg, 0.224 mmol) in N,N-dimethylformamide (4.0 mL) was added sodium hydride (60% dispersion in mineral oil, 14 mg, 0.35 mmol) at 0° C. After the mixture was stirred at 0° C. for 0.5 hr, iodoethane (0.090 mL, 1.12 mmol) was added to the reaction mixture at 0° C. The mixture was stirred at room temperature for 15 hr. Water was added to, the reaction mixture at room temperature and the mixture was extracted with ethyl acetate. The organic layer was washed with water and brine, dried over anhydrous magnesium sulfate, and concentrated in vacuo. The residue was purified by flash chromatography on silica gel eluting with a 10-50% ethyl acetate/n-hexane gradient mixture and recrystallization from ethyl acetate/n-hexane to give the title compound (73.1 mg, 0.154 mmol, 69%) as colorless crystals.

$^1$H NMR (CDCl$_3$) δ 1.27 (t, J=7.1 Hz, 3 H), 2.31-2.46 (m, 2 H), 3.51-3.80 (m, 4 H), 3.83 (s, 3 H), 4.26-4.38 (m, 1 H), 4.41-4.54 (m, 1 H), 5.18 (q, J=6.5 Hz, 1 H), 6.88 (dd, J=9.0, 2.8 Hz, 1 H), 7.03 (d, J=2.8 Hz, 1 H), 7.06 (d, J=8.4 Hz, 1 H), 7.11 (d, J=8.4 Hz, 1 H), 7.43 (d, J=9.0 Hz, 1 H).

MS Calcd.: 473; Found: 474 (M+H).

Example 471

9-Chloro-1-(2-chloro-4-methoxyphenyl)-6-(2,2,2-trifluoro-1-methoxyethyl)-1,2,3,4-tetrahydropyrimido[1,2-a]benzimidazole

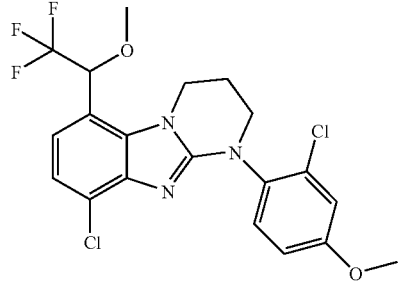 [SMILES: COc1ccc(N2CCCn3c2nc2c(Cl)ccc(C(OC)C(F)(F)F)c23)c(Cl)c1]

To a solution of 1-[9-chloro-1-(2-chloro-4-methoxyphenyl)-1,2,3,4-tetrahydropyrimido[1,2-a]benzimidazol-6-yl]-2,2,2-trifluoroethanol (100 mg, 0.224 mmol) in N,N-dimethylformamide (2.0 mL) was added sodium hydride (60% dispersion in mineral oil, 14 mg, 0.35 mmol) at 0° C. After the mixture was stirred at 0° C. for 0.5 hr, iodomethane (0.0697 mL, 1.12 mmol) was added to the reaction mixture at 0° C. The mixture was stirred at room temperature for 8 hr. Water was added to the reaction mixture at room temperature and the mixture was extracted with ethyl acetate. The organic layer was washed with water and brine, dried over anhydrous magnesium sulfate, and concentrated in vacuo. The residue was purified by flash chromatography on silica gel eluting with a 10-50% ethyl acetate/n-hexane gradient mixture and recrystallization from ethyl acetate/n-hexane to give the title compound (79.1 mg, 0.172 mmol, 77%) as colorless crystals.

$^1$H NMR (CDCl$_3$) δ 2.31-2.46 (m, 2 H), 3.44 (s, 3 H), 3.57-3.81 (m, 2 H), 3.83 (s, 3 H), 4.27-4.47 (m, 2 H), 5.10 (q, J=6.6 Hz, 1 H), 6.88 (dd, J=9.0, 3.0 Hz, 1 H), 7.03 (d, J=3.0 Hz, 1 H), 7.05 (d, J=8.1 Hz, 1 H), 7.12 (d, J=8.1 Hz, 1 H), 7.43 (d, J=9.0 Hz, 1 H).

MS Calcd.: 459; Found: 460 (M+H).

Example 472

9-Chloro-1-(2-chloro-4-methoxyphenyl)-6-[cyclopropyl(2,2-difluoroethoxy)methyl]-1,2,3,4-tetrahydropyrimido[1,2-a]benzimidazole

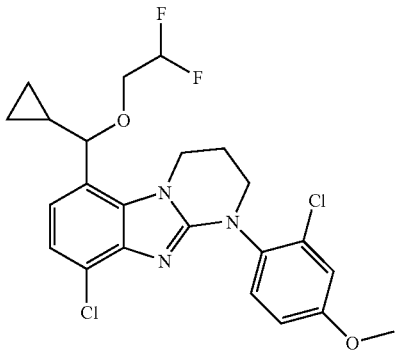 [SMILES: COc1ccc(N2CCCn3c2nc2c(Cl)ccc(C(OCC(F)F)C4CC4)c23)c(Cl)c1]

To a solution of [9-chloro-1-(2-chloro-4-methoxyphenyl)-1,2,3,4-tetrahydropyrimido[1,2-a]benzimidazol-6-yl](cyclopropyl)methanol (120 mg, 0.26 mmol), 1,1'-(azodicarbonyl)dipiperidine (131 mg, 0.52 mmol) in tetrahydrofuran (5.0 mL) was added tri(n-butyl)phosphine (0.130 mL, 0.52 mmol) at room temperature. After the mixture was stirred at room temperature for 10 min under nitrogen atmosphere, 2,2-difluoroethanol (0.165 mL, 2.61 mmol) was added to the reaction mixture. The mixture was stirred at 50° C. for 16 hr under nitrogen atmosphere. The mixture was concentrated in vacuo and diethyl ether was added to the residue. The solid was removed by filtration and the filtrate was concentrated in vacuo. The residue was purified by flash chromatography on silica gel eluting with a 10-50% ethyl acetate/n-hexane gradient mixture and recrystallization from ethyl acetate/n-hexane to give the title compound (72.8 mg, 0.155 mmol, 58%) as colorless crystals.

$^1$H NMR (CDCl$_3$) δ 0.24-0.36 (m, 1 H), 0.42-0.53 (m, 1 H), 0.57-0.66 (m, 1 H), 0.70-0.82 (m, 1 H), 1.38-1.48 (m, 1 H), 2.28-2.43 (m, 2 H), 3.48-3.79 (m, 4 H), 3.83 (s, 3 H), 4.25-4.33 (m, 1 H), 4.39-4.50 (m, 1 H), 4.57-4.68 (m, 1 H), 5.85 (tt, J=55.4, 4.1 Hz, 1 H), 6.85 (d, J=8.3 Hz, 1 H), 6.89 (dd, J=8.9, 2.9 Hz, 1 H), 7.026 (d, J=2.9 Hz, 1 H), 7.029 (d, J=8.3 Hz, 1 H), 7.43 (d, J=8.9 Hz, 1 H).

MS Calcd.: 481; Found: 482 (M+H).

Example 473

9-Chloro-1-(2-chloro-4-methoxyphenyl)-6-[1-(ethenyloxy)propyl]-1,2,3,4-tetrahydropyrimido[1,2-a]benzimidazole

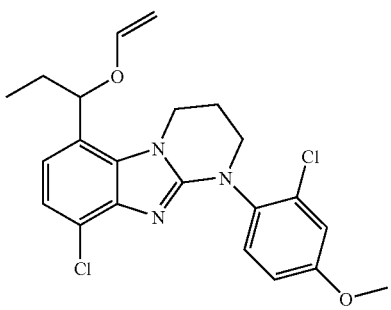 [SMILES: C=COC(CC)c1ccc(Cl)c2nc3n(c12)CCCN3c1ccc(OC)cc1Cl]

A mixture of 1-[9-chloro-1-(2-chloro-4-methoxyphenyl)-1,2,3,4-tetrahydropyrimido[1,2-a]benzimidazol-6-yl]propan-1-ol (200 mg, 0.492 mmol), vinyl acetate (182 μL, 1.97 mmol), di-μ-chlorobis[(η-cycloocta-1,5-diene)iridium (I)] (16.5 mg, 0.0246 mmol) and sodium carbonate (31.3 mg, 0.295 mmol) in o-dichlorobenzene (0.98 mL) was stirred at 100° C. for 2 hr. Vinyl acetate (100 μL, 1.08 mmol) was added to the reaction mixture and the mixture was stirred at 100° C. for 1.5 hr. The reaction mixture was purified by flash column chromatography on silica gel eluting with a 10-50% ethyl acetate/n-hexane to give the title compound (175.2 mg, 0.405 mmol, 82%) as a white yellow amorphous.

$^1$H NMR (CDCl$_3$) δ 1.01 (t, J=7.5 Hz, 3 H), 1.85-2.11 (m, 2 H), 2.31-2.43 (m, 2 H), 3.55-3.80 (m, 2 H), 3.83 (s, 3 H), 4.00 (dd, J=6.6, 1.7 Hz, 1 H), 4.29 (dd, J=14.1, 1.7 Hz, 1 H), 4.34-4.55 (m, 2 H), 5.06-5.10 (m, 1 H), 6.33 (dd, J=14.1, 6.1 Hz, 1 H), 6.86 (d, J=8.3 Hz, 1 H), 6.87 (dd, J=8.7, 2.7 Hz, 1 H), 7.02 (d, J=2.7 Hz, 1 H), 7.03 (d, J=8.3 Hz, 1 H), 7.44 (d, J=8.7 Hz, 1 H).

Example 474

9-Chloro-1-(2-chloro-4-methoxyphenyl)-6-[1-(cyclopropyloxy)propyl]-1,2,3,4-tetrahydropyrimido[1,2-a]benzimidazole

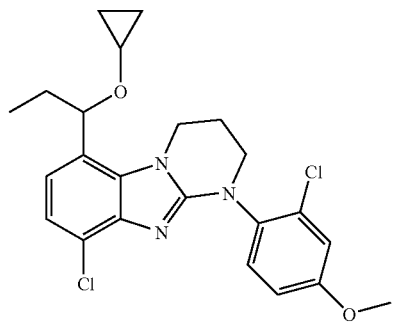 [SMILES: CCC(OC1CC1)c1ccc(Cl)c2nc3n(c12)CCCN3c1ccc(OC)cc1Cl]

To a solution of 9-chloro-1-(2-chloro-4-methoxyphenyl)-6-[1-(ethenyloxy)propyl]-1,2,3,4-tetrahydropyrimido[1,2-a]benzimidazole (170 mg, 0.39 mmol) in dichloromethane (4.0 mL) was added a solution of diethyl zinc id hexane (1.0 M, 2.0 mL, 2.0 mmol) and diiodomethane (0.31 mL, 3.84 mmol) at 0° C. After stirring at 0° C. for 1.5 hr, aqueous ammonium chloride was added to the reaction mixture at 0° C. The mixture was extracted with ethyl acetate. The organic layer was washed with water and brine, dried over anhydrous magnesium sulfate and concentrated in vacuo. The residue was purified by flash column chromatography on silica gel eluting with a 10-50% ethyl acetate/n-hexane gradient mixture to give the title compound (87.7 mg, 0.196 mmol, 50%) as a pale yellow solid.

$^1$H NMR (CDCl$_3$) δ 0.31-0.57 (m, 3 H), 0.62-0.71 (m, 1 H), 0.93 (t, J=7.4 Hz, 3 H), 1.71-1.97 (m, 2 H), 2.27-2.46 (m, 2 H), 3.15-3.24 (m, 1 H), 3.83 (s, 3 H), 3.54-3.87 (m, 2 H), 4.30-4.43 (m, 1 H), 4.50-4.63 (m, 1 H), 4.69-4.77 (m, 1 H), 6.88 (dd, J=8.7, 3.0 Hz, 1 H), 6.96 (d, J=8.1 Hz, 1 H), 7.03 (d, J=3.0 Hz, 1 H), 7.06 (d, J=8.1 Hz, 1 H), 7.45 (d, J=8.7 Hz, 1 H).

MS Calcd.: 445; MS Found: 446 (M+H).

Example 475

6-(1-Azido-2,2,2-trifluoroethyl)-9-chloro-1-(2,4-dichlorophenyl)-1,2,3,4-tetrahydropyrimido[1,2-a]benzimidazole

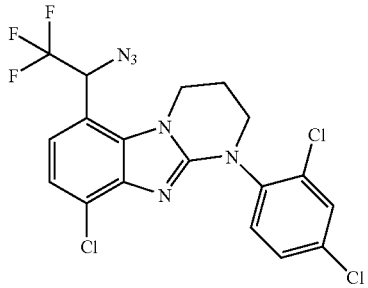 [SMILES: [N-]=[N+]=NC(c1ccc(Cl)c2nc3n(c12)CCCN3c1ccc(Cl)cc1Cl)C(F)(F)F]

To a solution of 1-[9-chloro-1-(2,4-dichlorophenyl)-1,2,3,4-tetrahydropyrimido[1,2-a]benzimidazol-6-yl]-2,2,2-trifluoroethanol (200 mg, 0.44 mmol) in tetrahydrofuran (4.0 mL) were added thionyl chloride (0.065 mL, 0.891 mmol) and 1 drop of N,N-dimethylformamide at room temperature. After stirring at room temperature for 2 hr, aqueous sodium hydrogen carbonate was added to the reaction mixture at room temperature, and the mixture was extracted with ethyl acetate. The organic layer was washed with brine, dried over anhydrous magnesium sulfate, and concentrated in vacuo to give 1-[9-chloro-1-(2,4-dichlorophenyl)-1,2,3,4-tetrahydropyrimido[1,2-a]benzimidazol-6-yl]-2,2,2-trifluoroethanol (200 mg, 0.43 mmol, 93%) as pale yellow solid. A mixture of 1-[9-chloro-1-(2,4-dichlorophenyl)-1,2,3,4-tetrahydropyrimido[1,2-a]benzimidazol-6-yl]-2,2,2-trifluoroethanol (68.6 mg, 0.146 mmol) and sodium azide (19 mg, 0.292 mmol) in dimethylsulfoxide (5.0 mL) was stirred at 110° C. for 20 hr. Water was added to the reaction mixture at room temperature and the mixture was extracted with ethyl acetate. The organic layer was washed with water and brine, dried over anhydrous magnesium sulfate, and concentrated in vacuo. The residue was purified by flash column chromatography on silica gel eluting with a 10-50% ethyl acetate/n-hexane gradient mixture to give the title compound (68.2 mg, 0.143 mmol, 98%) as a white solid.

$^1$H NMR (CDCl$_3$) δ 2.39-2.53 (m, 2 H), 3.66-3.83 (m, 2 H), 4.32-4.48 (m, 2 H), 5.38-5.46 (m, 1 H), 7.09-7.11 (m, 1 H), 7.17 (d, J=8.7 Hz, 1 H), 7.33 (dd, J=8.6, 2.4 Hz, 1 H), 7.50 (d, J=8.6 Hz, 1 H), 7.51 (d, J=2.4 Hz, 1 H).

MS Calcd.: 474; MS Found: 475 (M+H).

Example 476

N-{1-[9-chloro-1-(2,4-dichlorophenyl)-1,2,3,4-tetrahydropyrimido[1,2-a]benzimidazol-6-yl]-2,2,2-trifluoroethyl}acetamide

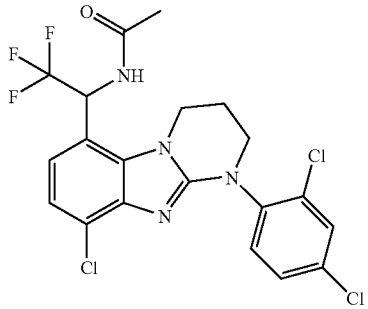 [SMILES: CC(=O)NC(c1ccc(Cl)c2nc3n(c12)CCCN3c1ccc(Cl)cc1Cl)C(F)(F)F]

A solution of 6-(1-Azido-2,2,2-trifluoroethyl)-9-chloro-1-(2,4-dichlorophenyl)-1,2,3,4-tetrahydropyrimido[1,2-a]benzimidazole (68.2 mg, 0.143 mmol) and triphenylphosphine (56.3 mg, 0.215 mmol) in tetrahydrofuran (5.0 mL) and water (0.10 mL) was stirred at 60° C. for 20 hr. The reaction mixture was concentrated in vacuo and the residue was purified by flash column chromatography on silica gel eluting with a 30-100% ethyl acetate/n-hexane gradient mixture to give 1-[9-Chloro-1-(2,4-dichlorophenyl)-1,2,3,4-tetrahydropyrimido[1,2-a]benzimidazol-6-yl]-2,2,2-trifluoroethanamine as a white solid (67.2 mg). To a solution of 1-[9-Chloro-1-(2,4-dichlorophenyl)-1,2,3,4-tetrahydropyrimido[1,2-a]benzimidazol-6-yl]-2,2,2-trifluoroethanamine (67.9 mg) and pyridine (0.12 mL, 1.48 mmol) in tetrahydrofuran (5.0 mL) was added acetyl chloride (0.051 mL, 0.717 mmol) at 0° C. The mixture was stirred at 0° C. for 1 hr. Aqueous sodium hydrogen carbonate was added to the reaction mixture at room temperature and the mixture was extracted with ethyl acetate. The organic layer was washed with brine, dried over anhydrous magnesium sulfate, and concentrated in vacuo. The residue was purified by flash column chromatography on silica gel eluting with a 25-80% ethyl acetate/n-hexane gradient mixture to give the title compound (33.1 mg, 0.067 mmol, 47%) as white crystals.

$^1$H NMR (CDCl$_3$) δ 2.09 (s, 3 H), 2.39-2.49 (m, 2 H), 3.64-3.79 (m, 2 H), 4.31-4.44 (m, 1 H), 4.62-4.72 (m, 1 H), 6.13-6.25 (m, 1 H), 6.40-6.52 (m, 1 H), 6.91 (d, J=8.1 Hz, 1 H), 7.13 (d, J=8.3 Hz, 1 H), 7.31 (dd, J=8.6, 2.3 Hz, 1 H), 7.49 (d, J=8.6 Hz, 1 H), 7.50 (d, J=2.3 Hz, 1 H).

MS Calcd.: 490; MS Found: 491 (M+H).

Example 477

9-Chloro-6-[1-(difluoromethoxy)-2,2,2-trifluoroethyl]-1-[2-methyl-4-(methylsulfonyl)phenyl]-1,2,3,4-tetrahydropyrimido[1,2-a]benzimidazole

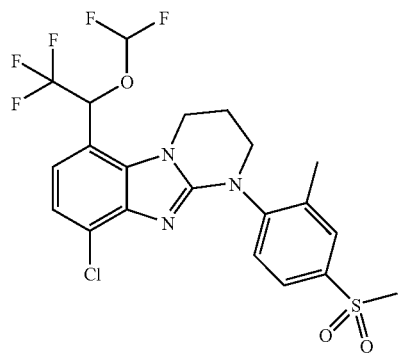 [SMILES: Cc1cc(S(C)(=O)=O)ccc1N1CCCn2c1nc1c(Cl)ccc(C(OC(F)F)C(F)(F)F)c12]

A mixture of 1-(4-bromo-2-methylphenyl)-9-chloro-6-[1-(difluoromethoxy)-2,2,2-trifluoroethyl]-1,2,3,4-tetrahydropyrimido[1,2-a]benzimidazole (200 mg, 0.381 mmol), sodium methanesulfinate (311 mg, 3.04 mmol), L-proline (44.0 mg, 0.382 mmol), sodium hydroxide (30.6 mg, 0.765 mmol) and copper (I) iodide (72.6 mg, 0.381 mmol) in dimethylsulfoxide (2.0 mL) was attired at 110° C. for 4 days. Aqueous ammonium chloride was added to the reaction mixture at room temperature and the mixture was extracted with ethyl acetate. The organic layer was washed with brine, dried over anhydrous magnesium sulfate, and concentrated in vacuo. The residue was purified by flash column chromatography on silica gel eluting with a 50-100% ethyl acetate/n-hexane gradient mixture to give the title compound (21.2 mg, 0.040 mmol, 11%) as white amorphous.

$^1$H NMR (CDCl$_3$) δ 2.38 (s, 3 H), 2.42-2.53 (m, 2H), 3.11 (s, 3 H), 3.71-3.85 (m, 2 H), 4.34-4.43 (m, 2 H), 6.00-6.05 (m, 1 H), 6.43 (t, J=72.0 Hz, 1 H), 7.18 (s, 2 H), 7.52 (d, J=8.4 Hz, 1 H), 7.83 (dd, J=8.4, 2.4 Hz, 1 H), 7.89 (d, J=2.4 Hz, 1 H).

MS Calcd.: 523; MS Found: 524 (M+H).

Example 478

1-[9-Chloro-1-(2,4-dichlorophenyl)-1,2,3,4-tetrahydropyrimido[1,2-a]benzimidazol-6-yl](cyclopropyl)methyl cyclopropanecarboxylate

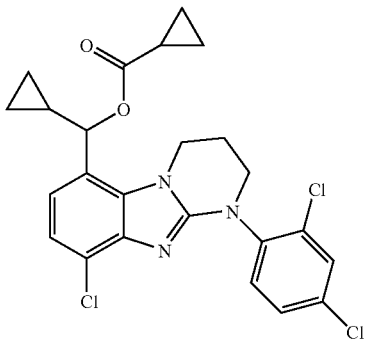 [SMILES: O=C(OC(c1ccc(Cl)c2nc3n(c12)CCCN3c1ccc(Cl)cc1Cl)C1CC1)C1CC1]

To a solution of 1-[9-chloro-1-(2,4-dichlorophenyl)-1,2,3,4-tetrahydropyrimido[1,2-a]benzimidazol-6-yl](cyclopropyl)methanol (200 mg, 0.473 mmol), cyclopropanecarboxylic acid (61 mg, 0.710 mmol), triethylamine (0.132 mL, 0.946 mmol) and 4-dimethylaminopyridine (87 mg, 0.710 mmol) in tetrahydrofuran (10 mL) was added 1-ethyl-3-(3-dimethylaminopropyl)carbodiimide hydrochloride (181 mg, 0.946 mmol) at room temperature. The mixture was stirred at room temperature for 15 hr. Saturated aqueous ammonium chloride was added to the reaction mixture and the mixture was extracted with ethyl acetate. The organic layer was washed with brine, dried over anhydrous magnesium sulfate and concentrated in vacuo. The residue was purified by flash chromatography on silica gel eluting with a 10-50% ethyl acetate/n-hexane gradient mixture and recrystallization from ethanol to give the title compound (155 mg, 0.316 mmol, 67%) as colorless crystals.

mp 168-170° C.

$^1$H NMR (CDCl$_3$) δ 0.30-0.50 (m, 2H), 0.55-0.70 (m, 2H), 0.80-1.05 (m, 4H), 1.40-1.55 (m, 1H), 1.60-1.70 (m, 1H), 2.30-2.45 (m, 2H), 3.65-3.80 (m, 2H), 4.30-4.45 (m, 1H), 4.55-4.65 (m, 1H), 6.02 (d, J=7.5 Hz, 1H), 7.06 (d, J=8.4 Hz, 1H), 7.10 (d, J=8.4 Hz, 1H), 7.31 (dd, J=8.7, 2.4 Hz, 1H), 7.71 (d, J=2.4 Hz, 1H), 7.51 (d, J=8.7 Hz, 1H).

MS Calcd.: 489; Found: 4.90 (M+H).

Example 479

1-[9-Chloro-1-(2,4-dichlorophenyl)-1,2,3,4-tetrahydropyrimido[1,2-a]benzimidazol-6-yl](cyclopropyl)ethyl methoxyacetate

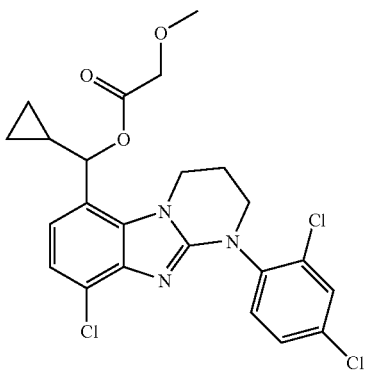 [SMILES: COCC(=O)OC(c1ccc(Cl)c2nc3n(c12)CCCN3c1ccc(Cl)cc1Cl)C1CC1]

To a solution of 1-[9-chloro-1-(2,4-dichlorophenyl)-1,2,3,4-tetrahydropyrimido[1,2-a]benzimidazol-6-yl](cyclopropyl)methanol (180 mg, 0.426 mmol), methoxyacetic acid (0.049 mL, 0.639 mmol), triethylamine (0.118 mL, 0.852 mmol) and 4-dimethylaminopyridine (78 mg, 0.639 mmol) in tetrahydrofuran (8.0 mL) was added 1-ethyl-3-(3-dimethylaminopropyl)carbodiimide hydrochloride (163 mg, 0.852 mmol) at room temperature. The mixture was stirred at room temperature for 24 hr. Saturated aqueous ammonium chloride was added to the reaction mixture and the mixture was extracted with ethyl acetate. The organic layer was washed with brine, dried over anhydrous magnesium sulfate and concentrated in vacuo. The residue was purified by flash chromatography on silica gel eluting with a 20-70% ethyl acetate/n-hexane gradient mixture and recrystallization from ethanol to give the title compound (31 mg, 0.0627 mmol, 15%) as colorless crystals.

mp 159-161° C.

$^1$H NMR (CDCl$_3$) δ 0.35-0.41 (m, 1H), 0.45-0.50 (m, 1H), 0.55-0.75 (m, 2H), 1.45-1.60 (m, 1H), 2.30-2.45 (m, 2H), 3.42 (s, 3H), 3.25-3.75 (m, 2H), 4.01 (d, J=16.5 Hz, 1H), 4.11 (d, J=16.5 Hz, 1H), 4.35-4.45 (m, 1H), 4.55-4.70 (m, 1H), 6.05 (d, J=7.8 Hz, 1H), 7.04 (d, J=8.4 Hz, 1H), 7.09 (d, J=8.4 Hz, 1H), 7.31 (dd, J=8.4, 2.4 Hz, 1H), 7.49 (d, J=2.4 Hz, 1H), 7.51 (d, J=8.4 Hz, 1H).

MS Calcd.: 493; Found: 4.94 (M+H).

Example 480

1-[9-Chloro-1-(2,4-dichlorophenyl)-1,2,3,4-tetrahydropyrimido[1,2-a]benzimidazol-6-yl]propyl 2-methylpropanoate

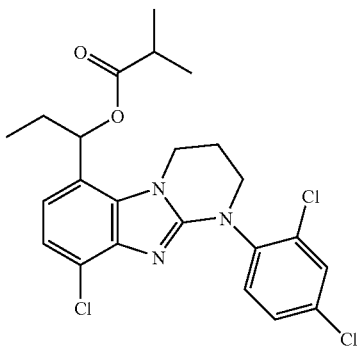 [SMILES: CCC(OC(=O)C(C)C)c1ccc(Cl)c2nc3n(c12)CCCN3c1ccc(Cl)cc1Cl]

To a solution of 1-[9-chloro-1-(2,4-dichlorophenyl)-1,2,3,4-tetrahydropyrimido[1,2-a]benzimidazol-6-yl]propan-1-ol (150 mg, 0.365 mmol) in pyridine (2 mL) was added isobutyric anhydride (289 mg, 1.83 mmol) and the mixture was stirred at room temperature for 18 hr. Aqueous sodium bicarbonate was added to the reaction mixture and the mixture was extracted with ethyl acetate. The extract was washed with brine, dried over anhydrous magnesium sulfate and concentrated in vacuo. The residue was purified by flash chromatography on silica gel eluting with a 10-60% ethyl acetate/n-hexane gradient mixture and recrystallization from ethyl acetate/n-hexane to give the title compound (113 mg, 0.235 mmol, 64%) as colorless amorphous.

$^1$H NMR (CDCl$_3$) δ 0.95 (t, J=7.5 Hz, 3H), 1.10-1.24 (m, 6H), 1.80-2.10 (m, 2H), 2.35-2.45 (m, 2H), 2.50-2.65 (m, 1H), 3.71 (bs, 3H), 4.30-4.40 (m, 1H), 4.70-4.80 (m, 1H), 6.28 (t, J=6.6 Hz, 1H), 6.82 (d, J=8.4 Hz, 1H), 7.08 (d, J=8.4 Hz, 1H), 7.30 (ddd, J=8.4, 2.4, 1.2 Hz, 1H), 7.48 (dd, J=2.4, 1.2 Hz, 1H), 7.52 (d, J=8.4 Hz, 1H).

MS Calcd.: 479; Found: 480 (M+H).

Example 481

1-[9-Chloro-1-(2,4-dichlorophenyl)-1,2,3,4-tetrahydropyrimido[1,2-a]benzimidazol-6-yl]propyl 2,2-dimethylpropanoate

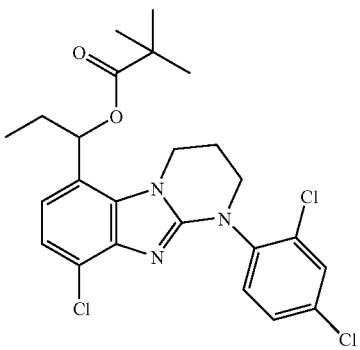 [SMILES: CCC(OC(=O)C(C)(C)C)c1ccc(Cl)c2nc3n(c12)CCCN3c1ccc(Cl)cc1Cl]

To a mixture of 1-[9-chloro-1-(2,4-dichlorophenyl)-1,2,3,4-tetrahydropyrimido[1,2-a]benzimidazol-6-yl]propan-1-ol (150 mg, 0.365 mmol) and 4-dimethylaminopyridine (22 mg, 0.182 mmol) in pyridine (2 mL) was added pivalic anhydride (341 mg, 1.83 mmol) and the mixture was stirred at room temperature for 18 hr. Aqueous sodium bicarbonate was added to the reaction mixture and the mixture was extracted with ethyl acetate. The extract was washed with brine, dried over anhydrous magnesium sulfate and concentrated in vacuo. The residue was purified by flash chromatography on silica gel eluting with a 10-50% ethyl acetate/n-hexane gradient mixture and recrystallization from isopropyl ether/n-hexane to give the title compound (113 mg, 0.235 mmol, 64%) as colorless amorphous.

$^1$H NMR (CDCl$_3$) δ 0.97 (t, J=7.5 Hz, 3H), 1.21 (s, 9H), 1.85-2.05 (m, 2H), 2.35-2.45 (m, 2H), 3.70 (bs, 3H), 4.30-4.40 (m, 1H), 4.70-4.80 (m, 1H), 6.26 (t, J=6.6 Hz, 1H), 6.95 (d, J=8.4 Hz, 1H), 7.07 (d, J=8.1 Hz, 1H), 7.30 (dd, J=8.4, 2.4, 1H), 7.48 (dd, J=2.4 Hz, 1H), 7.52 (d, J=8.4 Hz, 1H).

MS Calcd.: 493; Found: 494 (M+H).

Example 482

1-[9-Chloro-1-(2-chloro-4-methoxyphenyl)-1,2,3,4-tetrahydropyrimido[1,2-a]benzimidazol-6-yl]propyl cyclopropanecarboxylate

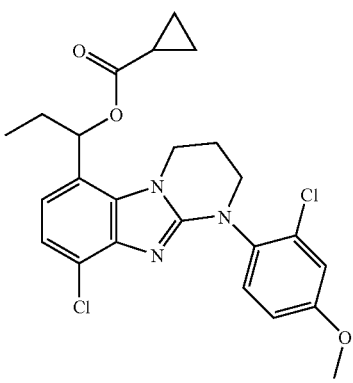 [SMILES: CCC(OC(=O)C1CC1)c1ccc(Cl)c2nc3n(c12)CCCN3c1ccc(OC)cc1Cl]

To a solution of 1-[9-chloro-1-(2,4-dichlorophenyl)-1,2,3,4-tetrahydropyrimido[1,2-a]benzimidazol-6-yl]propan-1-ol (50 mg, 0.123 mmol), cyclopropanecarboxylic acid (16 mg, 0.185 mmol), triethylamine (0.018 mL, 0.246 mmol) and 4-dimethylaminopyridine (23 mg, 0.185 mmol) in tetrahydrofuran (2 mL) was added 1-ethyl-3-(3-dimethylaminopropyl)carbodiimide hydrochloride (47 mg, 0.185 mmol) at room temperature. The mixture was stirred at room temperature for 18 hr. Saturated aqueous ammonium chloride was added to the reaction mixture and the mixture was extracted with ethyl acetate. The organic layer was washed with brine, dried over anhydrous magnesium sulfate and concentrated in vacuo. The residue was purified by flash chromatography on silica gel eluting with a 20-70% ethyl acetate/n-hexane gradient mixture and recrystallization from 2-propanol/n-hexane to give the title compound (25 mg, 0.0527 mmol, 43%) as colorless crystals.

mp 130-132° C.

$^1$H NMR (CDCl$_3$) δ 0.80-1.05 (m, 7H), 1.85-2.10 (m, 2H), 2.30-2.50 (m, 2H), 3.55-3.75 (m, 2H), 3.81 (s, 3H), 4.20-4.40 (m, 2H), 4.60-4.80 (m, 2H), 6.31 (t, J=7.2 Hz, 1H), 6.85 (dd, J=8.7, 2.0 Hz, 1H), 6.96 (d, J=8.4 Hz, 1H), 6.99 (d, J=2.0 Hz, 1H), 7.07 (d, J=8.4 Hz, 1H), 7.42 (d, J=8.7 Hz, 1H).

MS Calcd.: 473; Found: 474 (M+H).

Example 483

9-Chloro-6-[cyclopropyl(ethoxy)methyl]-1-(2,4-dichlorophenyl)-1,2,3,4-tetrahydropyrimido[1,2-a]benzimidazole

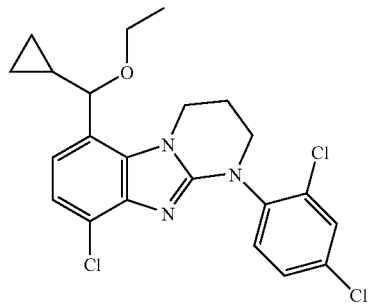 [SMILES: CCOC(c1ccc(Cl)c2nc3n(c12)CCCN3c1ccc(Cl)cc1Cl)C1CC1]

To a solution of 1-[9-chloro-1-(2,4-dichlorophenyl)-1,2,3,4-tetrahydropyrimido[1,2-a]benzimidazol-6-yl](cyclopropyl)methanol (150 mg, 0.355 mmol) in N,N-dimethylformamide (2 mL) was added sodium hydride (60% dispersion in mineral oil, 17 mg, 0.426 mmol) at 0° C. After the mixture was stirred at 0° C. for 0.5 hr, iodoethane (0.131 mL, 0.533 mmol) was added to the reaction mixture at 0° C. The mixture was stirred at room temperature for 2 hr. Saturated aqueous ammonium chloride was added to the reaction mixture at room temperature and the mixture was extracted with ethyl acetate. The organic layer was washed with brine, dried over anhydrous magnesium sulfate, and concentrated in vacuo. The residue was purified by flash chromatography on silica gel eluting with a 10-50% ethyl acetate/n-hexane gradient mixture and recrystallization from isopropyl ether/n-hexane to give the title compound (73.1 mg, 0.154 mmol, 69%) as colorless crystals.

mp 138-140° C.

$^1$H NMR (CDCl$_3$) δ 0.20-0.30 (m, 1H), 0.35-0.45 (m, 1H), 0.50-0.60 (m, 1H), 0.70-0.80 (m, 1H), 1.20 (t, J=7.2 Hz, 3H), 1.30-1.45 (m, 1H), 2.30-2.40 (m, 2H), 3.45 (q, 4H), 3.65-3.75 (m, 2H), 4.17 (d, J=7.8 Hz, 1H), 4.40-4.55 (m, 1H), 4.70-4.80 (m, 1H), 6.86 (d, J=8.4 Hz, 1H), 7.03 (d, J=8.4 Hz, 1H), 7.31 (dd, J=8.4, 2.4 Hz, 1H), 7.49 (d, J=2.4 Hz, 1H), 7.53 (d, J=8.4 Hz, 1H).

MS Calcd.: 449; Found: 450 (M+H).

Example 484

1-(2,4-Dichlorophenyl)-N,N-diethyl-4,5-dihydro-1H,3H-[1,4]oxazepino[4,3-a]benzimidazol-7-amine

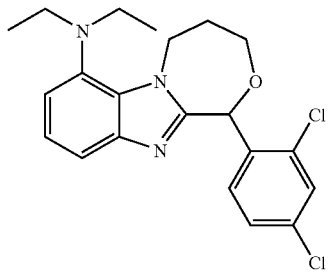 [SMILES: CCN(CC)c1cccc2nc3n(c12)CCCOC3c1ccc(Cl)cc1Cl]

To a stirred solution of 3-{2-[(2,4-dichlorophenyl)(hydroxy)methyl]-7-(diethylamino)-1H-benzimidazol-1-yl}propan-1-ol (Reference example 207, 1.37 g, 3.24 mmol) in pyridine (16 mL) was added methanesulfonyl chloride (502 μL, 6.49 mol) at 0° C. After 1 h, the reaction mixture was diluted with ethyl acetate, washed with brine, dried over sodium sulfate, filtered, and concentrated in vacuo. The residue was dissolved in dimethylformamide (32 mL) and potassium carbonate (897 mg, 6.49 mmol) was added. After being stirred for 12 h at 80° C., the reaction mixture was diluted with ethyl acetate, washed with water and brine, dried over sodium sulfate, filtered and concentrated in vacuo. The residue was purified by column chromatography on silica gel eluting with a 0-20% ethyl acetate/n-hexane gradient mixture to give the title compound as a colorless solid (341 mg, 0.844 mmol, 26%).

$^1$H NMR (CDCl$_3$) δ 1.03 (q, J=7.3 Hz, 6H), 1.94-2.20 (m, 2H), 2.94-3.25 (m, 4H), 3.92-4.14 (m, 1H), 4.30-4.51 (m, 2H), 6.00 (s, 1H), 6.12-6.27 (m, 1H), 7.06 (dd, J=7.7, 1.1 Hz, 1H), 7.12 (t, J=7.8 Hz, 1H), 7.36 (dd, J=8.5, 2.2 Hz, 1H), 7.42 (d, J=2.2 Hz, 1H), 7.48 (dd, J=7.7, 1.1 Hz, 1H), 7.65 (d, J=8.5 Hz, 1H).

MS Calcd.: 403; MS Found: 404 (M+H).

Example 485

1-(2,4-Dichlorophenyl)-N,N-diethyl-4,5-dihydro-1H,3H-[1,4]oxazepino[4,3-a]benzimidazol-7-amine (shorter retention time)

Example 486

1-(2,4-Dichlorophenyl)-N,N-diethyl-4,5-dihydro-1H,3H-[1,4]oxazepino[4,3-a]benzimidazol-7-amine (longer retention time)

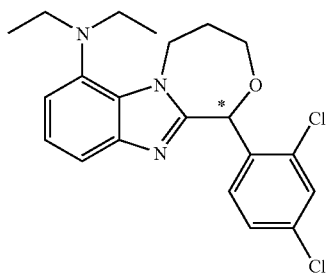 [SMILES: CCN(CC)c1cccc2nc3n(c12)CCCOC3c1ccc(Cl)cc1Cl]

Racemic Example 484 was resolved by preparative HPLC (high pressure liquid chromatography), using CHIRALPAK AD (5 cm i.d.×50 cm, Daicel Chemical Industries, Ltd.) with the flow rate of 80 mL/min at 30° C. and hexane/ethanol (95/5) as the mobile phase, and obtaining the stereoisomer having a shorter retention time 62 mg in an enantiomer excess greater than 99.9% and the stereoisomer having a longer retention time 61 mg in an enantiomer excess greater than 99.9%.

Shorter Retention Time (Example 485):
>99.9% ee $^1$H NMR (CDCl$_3$) δ 1.03 (q, J=7.1 Hz, 6H), 1.96-2.22 (m, 2H), 2.98-3.20 (m, 4H), 3.99-4.12 (m, 1H), 4.33-4.50 (m, 2H), 6.00 (s, 1H), 6.13-6.24 (m, 1H), 7.02-7.17 (m, 2H), 7.36 (dd, J=8.5, 2.2 Hz, 1H), 7.43 (d, J=2.2 Hz, 1H), 7.48 (dd, J=7.8, 1.2 Hz, 1H), 7.65 (d, J=8.5 Hz, 1H).

MS Calcd.: 403; MS Found: 404 (M+H).

Longer Retention Time (Example 486):
>99.9% ee $^1$H NMR (CDCl$_3$) δ 1.03 (q, J=7.1 Hz, 6H), 1.98-2.23 (m, 2H), 2.98-3.23 (m, 4H), 4.00-4.12 (m, 1H), 4.30-4.52 (m, 2H), 6.00 (s, 1H), 6.13-6.26 (m, 1H), 7.02-7.18 (m, 2H), 7.36 (dd, J=8.5, 2.2 Hz, 1H), 7.43 (d, J=2.2 Hz, 1H), 7.48 (dd, J=7.7, 1.1 Hz, 1H), 7.65 (d, J=8.5 Hz, 1H).

MS Calcd.: 403; MS Found: 404 (M+H).

Example 487

1-(2,4-Dichlorophenyl)-7-(diethylamino)-1,2,4,5-tetrahydro-3H-[1,4]diazepino[1,2-a]benzimidazol-3-one

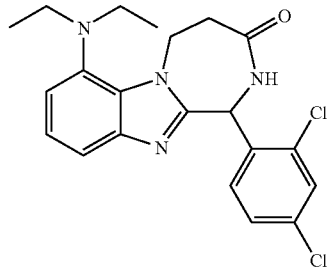 [SMILES: CCN(CC)c1cccc2nc3n(c12)CCC(=O)NC3c1ccc(Cl)cc1Cl]

To a stirred solution of methyl 3-{2-[(2,4-dichlorophenyl)(hydroxy)methyl]-7-(diethylamino)-1H-benzimidazol-1-yl}propanoate (1.00 g, 2.15 mmol) and diphenylphosphoryl azide (1.39 mL, 6.46 mmol) in toluene (11 mL) was added 1,8-diazabicyclo[5.4.0]undec-7-ene (966 μL, 6.46 mol) at room temperature. After 12 h, the reaction mixture was diluted with ethyl acetate, washed with brine, dried over sodium sulfate, filtered, and concentrated in vacuo. The residue was purified by column chromatography on silica gel eluting with a 0-35% ethyl acetate/n-hexane gradient mixture. A solution of the obtained compound was stirred in the presence of 1.9% palladium on fibroin (200 mg) under hydrogen atmosphere at room temperature for 17 h. The catalyst was removed and the filtrate was concentrated in vacuo. The residue was dissolved in tetrahydrofuran (10 mL) and aqueous sodium hydroxide (8 M, 0.5 mL) was added at room temperature. After 15 h, the reaction mixture was concentrated in vacuo. The residue was dissolved in N,N-dimethylformamide (10 mL) and 1-ethyl-3-(3-dimethylaminopropyl)-carbodiimide hydrochloride (973 mg, 5.08 mmol) was added at room temperature. After 6 h, 1-ethyl-3-(3-dimethylaminopropyl)-carbodiimide hydrochloride (155 mg, 1.02 mmol) was added. After 2 h, the reaction mixture was diluted with ethyl acetate, washed with water and brine, dried over sodium sulfate, filtered, and concentrated in vacuo. The residue was purified by column chromatography on silica gel eluting with a 0-35% ethyl acetate/n-hexane gradient mixture to afford the desired product as pale yellow solid (334 mg, 0.801 mmol, 39%).

$^1$H NMR (CDCl$_3$) δ 0.88-1.14 (m, 6H), 2.86-3.26 (m, 6H), 4.76-4.93 (m; 1H), 5.30-5.48 (m, 1H), 6.40 (d, J=4.4 Hz, 1H), 6.47 (d, J=4.4 Hz, 1H), 7.13 (d, J=7.7 Hz, 1H), 7.17-7.25 (m, 2H), 7.31 (dd, J=8.3, 2.2 Hz, 1H), 7.42-7.57 (m, 2H).

MS Calcd.: 416; MS Found: 417 (M+H).

Example 488

1-(2,4-Dichlorophenyl)-7-(diethylamino)-2-methyl-1,2,4,5-tetrahydro-3H-[1,4]diazepino[1,2-a]benzimidazol-3-one

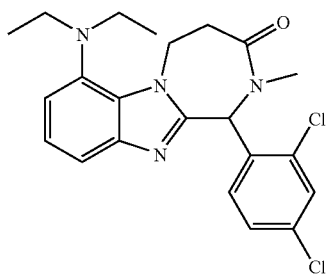 [SMILES: CCN(CC)c1cccc2nc3n(c12)CCC(=O)N(C)C3c1ccc(Cl)cc1Cl]

To a stirred solution of 1-(2,4-dichlorophenyl)-7-(diethylamino)-1,2,4,5-tetrahydro-3H-[1,4]diazepino[1,2-a]benzimidazol-3-one (83.5 mg, 0.200 mmol) in dimethylformamide (1 mL) was added sodium hydride (60%, 20.0 mg, 0.500 mmol) at room temperature. After 15 min, methyl iodide (62.3 μL, 1.00 mmol) was added. After 1 h, the reaction mixture was diluted with ethyl acetate, washed with water and brine, dried over anhydrous sodium sulfate, filtered and concentrated in vacuo. The residue was purified by flash column chromatography on silica gel eluting with a 0-50% ethyl acetate/n-hexane gradient mixture and by preparative NH TLC eluting with a 33% ethyl acetate/n-hexane mixture to give the title compound as a colorless solid (5.0 mg, 0.0115 mmol, 5.7%).

$^1$H NMR (CDCl$_3$) δ 0.88-1.06 (m, 6H), 2.67-2.82 (m, 1H), 2.94-3.18 (m, 5H), 3.28 (s, 3H), 4.54-4.67 (m, 1H), 4.96-5.10 (m, 1H), 6.20 (s, 1H), 6.96 (d, J=8.5 Hz, 1H), 7.12 (d, J=7.7 Hz, 1H), 7.21-7.28 (m, 2H), 7.48 (d, J=1.9 Hz, 1H), 7.54 (d, J=8.0 Hz, 1H).

MS Calcd.: 430, MS Found: 431 (M+H).

Example 489

1-(2,4-Dichlorophenyl)-7-(diethylamino)-4,5-dihydro-1H,3H-[1,4]oxazepino[4,3-a]benzimidazol-3-one

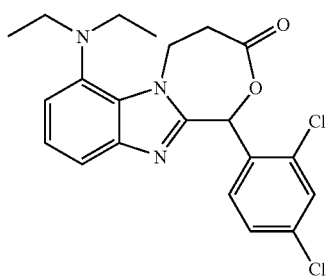 [SMILES: CCN(CC)c1cccc2nc3n(c12)CCC(=O)OC3c1ccc(Cl)cc1Cl]

To a stirred solution of methyl 3-{2-[(2,4-dichlorophenyl)(hydroxy)methyl]-7-(diethylamino)-1H-benzimidazol-1-yl}propanoate (92.9 mg, 0.200 mmol) in tetrahydrofuran (1 mL) was added aqueous sodium hydroxide (8 M, 0.05 mL) at room temperature. After 2 h, the reaction mixture was concentrated in vacuo. The residue was dissolved in N,N-dimethylformamide (2 mL) and 1-ethyl-3-(3-dimethylaminopropyl)-carbodiimide hydrochloride (76.7 mg, 0.400 mmol) was added at room temperature. After 6 h, the reaction mixture was diluted with ethyl acetate, washed with water and brine, dried over sodium sulfate, filtered, and concentrated in vacuo. The residue was purified by column chromatography on silica gel eluting with a 0-30% ethyl acetate/n-hexane gradient mixture to afford the desired product as colorless amorphous (44.6 mg, 0.107 mmol, 53%).

$^1$H NMR (CDCl$_3$) δ 0.95-1.10 (m, 6H), 2.95-3.28 (m, 5H), 3.60-3.80 (m, 1H), 4.93-5.23 (m, 2H), 7.07 (s, 1H), 7.13 (dd, J=7.7, 1.4 Hz, 1H), 7.18 (d, J=7.7 Hz, 1H), 7.41 (dd, J=8.5, 2.2 Hz, 1H), 7.46-7.52 (m, 2H), 7.71 (d, J=8.5 Hz, 1H).

MS Calcd.: 417; MS Found: 418 (M+H).

Example 490

1-(2,4-Dichlorophenyl)-N,N-diethyl-1-methyl-4,5-dihydro-1H,3H-[1,4]oxazepino[4,3-a]benzimidazol-7-amine

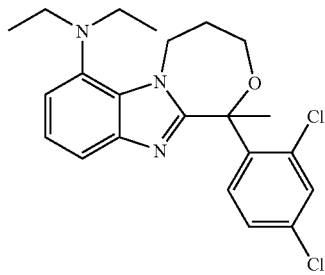 [SMILES: CCN(CC)c1cccc2nc3n(c12)CCCOC3(C)c1ccc(Cl)cc1Cl]

To a stirred solution of 3-{2-[1-(2,4-dichlorophenyl)-1-hydroxyethyl]-7-(diethylamino)-1H-benzimidazol-1-yl}propan-1-ol (Reference example 209, 210 mg, 0.500 mmol) and triphenylphosphine (157 mg, 0.600 mmol) in tetrahydrofuran (10 mL) was added a solution of diethyl azodicarboxylate in toluene (40%, 342 μL, 0.750 mmol) at room temperature. The mixture was stirred at 40° C. for 12 h, concentrated in vacuo, and purified by column chromatography on NH silica gel eluting with a 5-20% ethyl acetate/n-hexane gradient mixture to give a colorless amorphous (97.6 mg, 0.233 mmol, 47%).

$^1$H NMR (CDCl$_3$) δ 0.92-1.05 (m, 6H), 1.77-1.87 (m, 1H), 1.93-2.07 (m, 1H), 2.25 (s, 3H), 2.93-3.19 (m, 4H), 3.62-3.76 (m, 1H), 3.77-3.89 (m, 1H), 3.99-4.10 (m, 1H), 5.96-6.11 (m, 1H), 6.61 (d, J=8.5 Hz, 1H), 7.06-7.11 (m, 2H), 7.22 (t, J=7.8 Hz, 1H), 7.45 (d, J=2.2 Hz, 1H), 7.61 (dd, J=8.0, 1.1 Hz, 1H).

MS Calcd.: 417; MS Found: 418 (M+H).

Example 491

1-(2,4-Dichlorophenyl)-N,N-diethyl-1-methyl-3,4-dihydro-1H-[1,4]oxazino[4,3-a]benzimidazol-6-amine

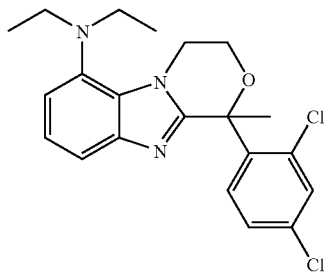 [SMILES: CCN(CC)c1cccc2nc3n(c12)CCOC3(C)c1ccc(Cl)cc1Cl]

To a stirred solution of 1-(2,4-dichlorophenyl)-1-[7-(diethylamino)-1-(2-hydroxyethyl)-1H-benzimidazol-2-yl]ethanol (Reference example 210, 63.8 mg, 0.151 mmol) and triphenylphosphine (59.4 mg, 0.227 mmol) in tetrahydrofuran (4 mL) was added a solution of diethyl azodicarboxylate in toluene (40%, 103 μL, 0.227 mmol) at room temperature. After 2.5 h, the reaction mixture was concentrated in vacuo, and purified by column chromatography on silica gel eluting with a 0-20% ethyl acetate/n-hexane gradient mixture to give a colorless amorphous (53.3 mg, 0.132 mmol, 87%).

$^1$H NMR (CDCl$_3$) δ 1.01 (t, J=7.0 Hz, 6H), 2.20 (s, 3H), 2.96-3.22 (m, 4H), 3.87-4.00 (m, 1H), 4.15-4.25 (m, 1H), 4.53-4.69 (m, 2H), 7.06-7.17 (m, 2H), 7.18-7.32 (m, 2H), 7.42 (d, J=1.9 Hz, 1H), 7.57 (d, J=7.7 Hz, 1H).

MS Calcd.: 403; MS Found: 404 (M+H).

Example 492

4-(2,4-Dichlorophenyl)-N,N-diethyl-1,2-dihydropyrido[1,2-a]benzimidazol-9-amine

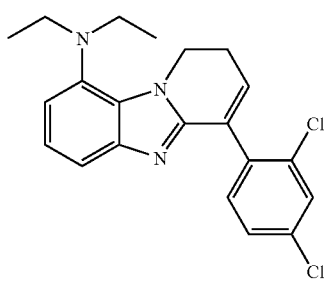 [SMILES: CCN(CC)c1cccc2nc3n(c12)CCC=C3c1ccc(Cl)cc1Cl]

A solution of [1-(3-bromopropyl)-7-(diethylamino)-1H-benzimidazol-2-yl](2,4-dichlorophenyl)methanone (Reference example 211, 360 mg, 0.745 mmol) and triphenylphosphine (586 mg, 2.23 mmol) in acetonitrile (5 mL) was stirred for 60 h at 80° C. The reaction mixture was concentrated in vacuo. Toluene (5 mL), tetrahydrofuran (1 mL), and potassium tert-butoxide (85%, 83.6 mg, 0.745 mmol) was added at room temperature. After 1 h, the reaction mixture was diluted with ethyl acetate, washed with brine, dried over sodium sulfate, filtrated, and concentrated in vacuo. The residue was purified by column chromatography on silica gel eluting with a 5-25% ethyl acetate/n-hexane gradient mixture to afford the desired product as pale yellow solid (65.5 mg, 0.170 mmol, 23%).

$^1$H NMR (CDCl$_3$) δ 1.03 (t, J=7.0 Hz, 6H), 2.72-2.87 (m, 2H), 2.94-3.24 (m, 4H), 4.81 (t, J=7.3 Hz, 2H), 6.37 (t, J=4.7 Hz, 1H), 7.04 (d, J=7.8 Hz, 1H), 7.13 (t, J=7.8 Hz, 1H), 7.27-7.33 (m, 1H), 7.38 (d, J=8.3 Hz, 1H), 7.43-7.56 (m, 2H).

MS Calcd.: 385; MS Found: 386 (M+H).

Example 493

4-(2,4-Dichlorophenyl)-N,N-diethyl-1,2,3,4-tetrahydropyrido[1,2-a]benzimidazol-9-amine

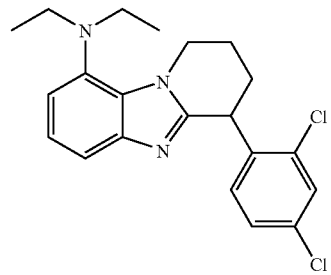 [SMILES: CCN(CC)c1cccc2nc3n(c12)CCCC3c1ccc(Cl)cc1Cl]

A solution of 4-(2,4-dichlorophenyl)-N,N-diethyl-1,2-dihydropyrido[1,2-a]benzimidazol-9-amine (53.0 mg, 0.137 mmol) was stirred in the presence of 1.9% palladium on fibroin (10 mg) under hydrogen atmosphere at room temperature for 7 days. The catalyst was removed and the filtrate was concentrated in vacuo. The residue was purified by column chromatography on silica gel eluting with a 0-30% ethyl acetate/n-hexane gradient mixture to afford the desired product as pale yellow oil (24.8 mg, 0.0640 mmol, 47%).

$^1$H NMR (CDCl$_3$) δ 1.03 (t, J=6.9 Hz, 6H), 1.92-2.20 (m, 3H), 2.28-2.41 (m, 1H), 2.96-3.21 (m, 4H), 4.45-4.55 (m, 1H), 4.70-4.90 (m, 2H), 6.90 (d, J=8.2 Hz, 1H), 7.05 (dd, J=7.7, 1.0 Hz, 1H), 7.09-7.21 (m, 2H), 7.41 (d, J=1.9 Hz, 1H), 7.46 (dd, J=7.7, 1.0 Hz, 1H).

MS Calcd.: 387; MS Found: 388 (M+H).

Example 494

1-(2,4-Dichlorophenyl)-N,N-diethyl-9-fluoro-4,5-dihydro-1H,3H-[1,4]oxazepino[4,3-a]benzimidazol-7-amine

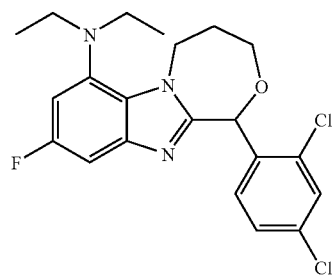 [SMILES: CCN(CC)c1cc(F)cc2nc3n(c12)CCCOC3c1ccc(Cl)cc1Cl]

To a stirred solution of 3-{2-[(2,4-dichlorophenyl)(hydroxy)methyl]-7-(diethylamino)-5-fluoro-1H-benzimidazol-1-yl}propan-1-ol (Reference example 212, 44.0 mg, 0.100 mmol) and triphenylphosphine (26.2 mg, 0.100 mmol) in tetrahydrofuran (2 mL) was added a solution of diethyl azodicarboxylate in toluene (40%, 68.3 μL, 0.150 mmol) at room temperature. After 90 h, the reaction mixture was concentrated in vacuo, and purified by column chromatography on NH silica gel eluting with a 0-20% ethyl acetate/n-hexane gradient mixture to give colorless oil (10.1 mg, 0.0238 mmol, 24%).

$^1$H NMR (CDCl$_3$) δ 0.97-1.12 (m, 6H), 1.98-2.18 (m, 2H), 2.98-3.15 (m, 4H), 3.99-4.12 (m, 1H), 4.29-4.51 (m, 2H), 5.97 (s, 1H), 6.05 (dd, J=13.3, 4.8 Hz, 1H), 6.82 (dd, J=11.1, 2.3 Hz, 1H), 7.14 (dd, J=8.9, 2.3 Hz, 1H), 7.36 (dd, J=8.4, 2.2 Hz, 1H), 7.43 (d, J=2.2 Hz, 1H), 7.64 (d, J=8.5 Hz, 1H).

MS Calcd.: 421; MS Found: 422 (M+H).

Example 495

Methyl 10-chloro-1-(2,4-dichlorophenyl)-4,5-dihydro-1H,3H-[1,4]oxazepino[4,3-a]benzimidazole-7-carboxylate

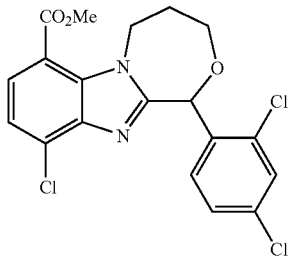 [SMILES: COC(=O)c1ccc(Cl)c2nc3n(c12)CCCOC3c1ccc(Cl)cc1Cl]

A solution of methyl 4-chloro-2-[(2,4-dichlorophenyl)(hydroxy)methyl]-1-(3-hydroxypropyl)-1H-benzimidazole-7-carboxylate (Reference example 215, 703 mg, 1.58 mmol) and cyanomethylenetributylphosphorane (763 mg, 3.16 mmol) in toluene (32 mL) was stirred for 12 h at 110° C. The reaction mixture was concentrated in vacuo and purified by column chromatography on NH silica gel eluting with a 0-20% ethyl acetate/n-hexane gradient mixture to afford the desired product as pale yellow oil (212 mg, 0.499 mmol, 32%).

$^1$H NMR (CDCl$_3$) δ 2.16 (brs, 2H), 3.99 (s, 3H), 4.01-4.17 (m, 1H), 4.31-4.52 (m, 2H), 5.15-5.28 (m, 1H), 6.14 (s, 1H), 7.25 (d, J=8.3 Hz, 1H), 7.33 (dd, J=8.5, 1.9 Hz, 1H), 7.44 (d, J=1.9 Hz, 1H), 7.54 (d, J=8.5 Hz, 1H), 7.76 (d, J=8.2 Hz, 1H).

MS Calcd.: 424; MS Found: 425 (M+H).

Example 496

[10-Chloro-1-(2,4-dichlorophenyl)-4,5-dihydro-1H,3H-[1,4]oxazepino[4,3-a]benzimidazol-7-yl]methanol

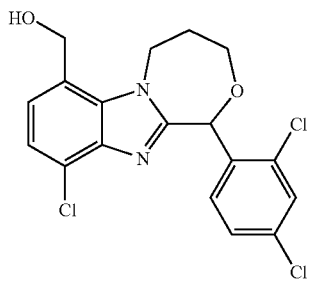 [SMILES: OCc1ccc(Cl)c2nc3n(c12)CCCOC3c1ccc(Cl)cc1Cl]

To a suspension of lithium aluminum hydride (35.7 mg, 0.940 mmol) in tetrahydrofuran (2 mL) was added a solution of methyl 10-chloro-1-(2,4-dichlorophenyl)-4,5-dihydro-1H,3H-[1,4]oxazepino[4,3-a]benzimidazole-7-carboxylate (200 mg, 0.470 mmol) in tetrahydrofuran (2 mL) at 0° C. After 5 min, sodium sulfate decahydrate was added. After 30 min, the resultant mixture was filtrated and concentrated in vacuo to give the title compound as a colorless solid (187 mg, 0.470 mmol, 100%).

$^1$H NMR (CDCl$_3$) δ 1.93 (t, J=5.8 Hz, 1H), 2.09-2.27 (m, 2H), 3.99-4.10 (m, 1H), 4.28-4.39 (m, 1H), 4.60-4.70 (m, 1H), 4.91-5.04 (m, 2H), 5.07-5.19 (m, 1H), 6.18 (s, 1H), 7.04 (d, J=8.0 Hz, 1H), 7.16 (d, J=8.0 Hz, 1H), 7.32 (dd, J=8.2, 1.9 Hz, 1H), 7.44 (d, J=1.9 Hz, 1H), 7.50 (d, J=8.2 Hz, 1H).

MS Calcd.: 396; MS Found: 397 (M+H).

Example 497

10-Chloro-1-(2,4-dichlorophenyl)-4,5-dihydro-1H,3H-[1,4]oxazepino[4,3-a]benzimidazole-7-carbaldehyde

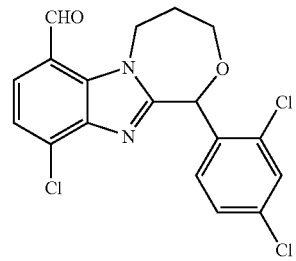 [SMILES: O=Cc1ccc(Cl)c2nc3n(c12)CCCOC3c1ccc(Cl)cc1Cl]

To a stirred solution of [10-chloro-1-(2,4-dichlorophenyl)-4,5-dihydro-1H,3H-[1,4]oxazepino[4,3-a]benzimidazol-7-yl]methanol (113 mg, 0.284 mmol) in acetonitrile (2.8 mL) was added Dess-Martin reagent (145 mg, 0.341 mmol) at room temperature. After 5 h, the reaction mixture was diluted with ethyl acetate, quenched with aqueous sodium hydrogen carbonate, washed with water and brine, dried over sodium sulfate, filtered, and concentrated in vacuo. The residue was purified by flash column chromatography on silica gel eluting with a 10-50% ethyl acetate/n-hexane gradient mixture to give the title compound as a colorless amorphous (88.1 mg, 0.223 mmol, 78%).

$^1$H NMR (CDCl$_3$) δ 2.11-2.25 (m, 2H), 4.02-4.12 (m, 1H), 4.35-4.45 (m, 1H), 4.57-4.70 (m, 1H), 5.81-5.93 (m, 1H), 6.11 (s, 1H), 7.35 (dd, J=8.3, 2.2 Hz, 1H), 7.40 (d, J=8.0 Hz, 1H), 7.44 (d, J=2.2 Hz, 1H), 7.58 (d, J=8.2 Hz, 1H), 7.66 (d, J=8.0 Hz, 1H), 9.98 (s, 1H).

Example 498

[10-Chloro-1-(2,4-dichlorophenyl)-4,5-dihydro-1H,3H-[1,4]oxazepino[4,3-a]benzimidazol-7-yl](cyclopropyl)methanol

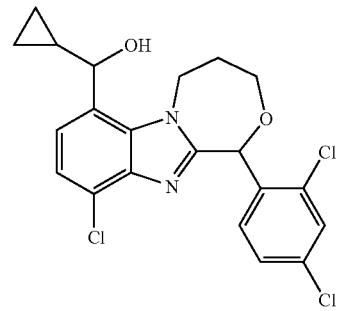 [SMILES: OC(c1ccc(Cl)c2nc3n(c12)CCCOC3c1ccc(Cl)cc1Cl)C1CC1]

To a stirred solution of 10-chloro-1-(2,4-dichlorophenyl)-4,5-dihydro-1H,3H-[1,4]oxazepino[4,3-a]benzimidazole-7-carbaldehyde (88.1 mg, 0.223 mmol) in tetrahydrofuran (2 mL) was added a solution of cyclopropyl magnesium bromide in tetrahydrofuran (1.0 M, 357 µL, 0.357 mmol) at 0° C. After 0.5 h, the reaction mixture was quenched with aqueous ammonium chloride, diluted with ethyl acetate, washed with water and brine, dried over sodium sulfate, filtrated, and concentrated in vacuo. The residue was purified by flash column chromatography on silica gel eluting with a 10-50% ethyl acetate/n-hexane gradient mixture to give the title compound as a colorless solid (81.4 mg, 0.186 mmol, 83%).

MS Calcd.: 436; MS Found: 437 (M+H).

Example 499

[10-Chloro-1-(2,4-dichlorophenyl)-4,5-dihydro-1H,3H-[1,4]oxazepino[4,3-a]benzimidazol-7-yl](cyclopropyl)methanone

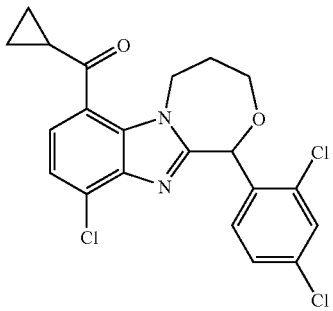 [SMILES: O=C(c1ccc(Cl)c2nc3n(c12)CCCOC3c1ccc(Cl)cc1Cl)C1CC1]

To a stirred solution of [10-chloro-1-(2,4-dichlorophenyl)-4,5-dihydro-1H,3H-[1,4]oxazepino[4,3-a]benzimidazol-7-yl](cyclopropyl)methanol (81.4 mg, 0.186 mmol) in acetonitrile (2.5 mL) was added Dess-Martin reagent (94.7 mg, 0.223 mmol) at room temperature. After 5 h, the reaction mixture was diluted with ethyl acetate, quenched with aqueous sodium hydrogen carbonate, washed with water and brine, dried over sodium sulfate, filtered, and concentrated in vacuo. The residue was purified by flash column chromatography on silica gel eluting with a 10-40% ethyl acetate/n-hexane gradient mixture to give the title compound as a colorless solid (67.1 mg, 0.154 mmol, 83%).

$^1$H NMR (CDCl$_3$) δ 1.12-1.22 (m, 2H), 1.31-1.40 (m, 2H), 2.06-2.30 (m, 2H), 2.58-2.71 (m, 1H), 3.97-4.11 (m, 1H), 4.21-4.40 (m, 2H), 4.69-4.82 (m, 1H), 6.14 (s, 1H), 7.27-7.35 (m, 2H), 7.44 (d, J=1.9 Hz, 1H), 7.52 (d, J=8.5 Hz, 1H), 7.72 (d, J=8.0 Hz, 1H).

MS Calcd.: 434; MS Found: 435 (M+H).

Example 500

[10-Chloro-1-(2,4-dichlorophenyl)-4,5-dihydro-1H,3H-[1,4]oxazepino[4,3-a]benzimidazol-7-yl](dicyclopropyl)methanol

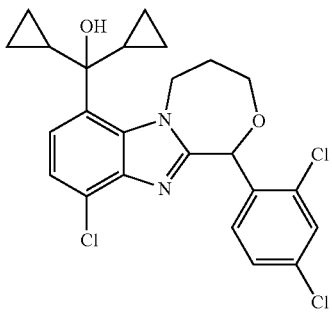 [SMILES: OC(c1ccc(Cl)c2nc3n(c12)CCCOC3c1ccc(Cl)cc1Cl)(C1CC1)C1CC1]

To a stirred solution of [10-chloro-1-(2,4-dichlorophenyl)-4,5-dihydro-1H,3H-[1,4]oxazepino[4,3-a]benzimidazol-7-yl](cyclopropyl)methanone (67.1 mg, 0.154 mmol) in tetrahydrofuran (1 mL) was added a solution of cyclopropyl magnesium bromide in tetrahydrofuran (1.0 M, 4.62 mL, 4.62 mmol) at 0° C. After 15 min, the reaction mixture was poured into a mixture of ethyl acetate and aqueous ammonium chloride. The organic phase was washed with brine, dried over sodium sulfate, filtrated, and concentrated in vacuo. The residue was purified by flash column chromatography on NH silica gel eluting with a 0-25% ethyl acetate/n-hexane gradient mixture to give the title compound as a colorless solid (48.2 mg, 0.101 mmol, 65%).

$^1$H NMR (CDCl$_3$) δ 0.16-0.41 (m, 2H), 0.44-0.74 (m, 6H), 1.37-1.52 (m, 2H), 1.83 (s, 1H), 1.92-2.18 (m, 2H), 3.97-4.10 (m, 1H), 4.28-4.41 (m, 1H), 4.52-4.68 (m, 1H), 5.90-6.07 (m, 1H), 6.14 (s, 1H), 7.15 (d, J=8.2 Hz, 1H), 7.34 (dd, J=8.4, 2.1 Hz, 1H), 7.38-7.46 (m, 2H), 7.58 (d, J=8.4 Hz, 1H).

MS Calcd.: 476; MS Found: 477 (M+H).

Example 501

1-(2,4-Dichlorophenyl)-N,N-diethyl-3,4-dihydro-1H-[1,4]oxazino[4,3-a]benzimidazol-6-amine

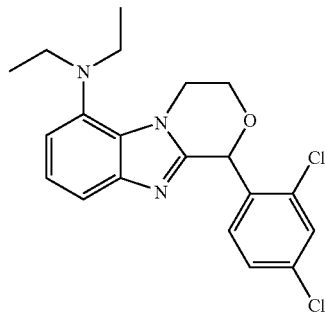 [SMILES: CCN(CC)c1cccc2nc3n(c12)CCOC3c1ccc(Cl)cc1Cl]

To a stirred solution of 2-{2-[(2,4-dichlorophenyl)(hydroxy)methyl]-7-(diethylamino)-1H-benzimidazol-1-yl}ethanol (Reference example 219, 200 mg, 0.490 mmol) and triphenylphosphine (193 mg, 0.736 mmol) in tetrahydrofuran (5 mL) was added a solution of diethyl azodicarboxylate in toluene (40%, 0.335 mL, 0.736 mmol) at room temperature. The mixture was stirred at room temperature for 12 h, concentrated in vacuo, and purified by column chromatography on silica gel eluting with a 5-15% ethyl acetate/n-hexane gradient mixture to give a colorless solid (112 mg, 0.287 mmol, 59%).

mp 130-131° C. (n-hexane).

$^1$H NMR (CDCl$_3$) δ 1.03 (t, J=7.1 Hz, 6 H), 3.11 (q, J=7.1 Hz, 4 H), 4.08-4.20 (m, 1 H), 4.29-4.38 (m, 1 H), 4.53-4.65 (m, 1 H), 4.82-4.92 (m, 1 H), 6.34 (s, 1 H), 7.07 (dd, J=7.7, 0.8 Hz, 1 H), 7.18 (t, J=7.7 Hz, 1 H), 7.22-7.23 (m, 2 H), 7.45-7.50 (m, 2 H).

MS Calcd.: 389; MS Found: 390 (M+H).

Example 502

9-Chloro-1-(2,4-dichlorophenyl)-N,N-diethyl-3,4-dihydro-1H-[1,4]oxazino[4,3-a]benzimidazol-6-amine

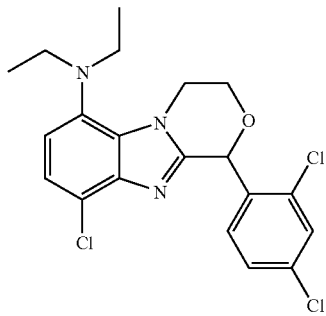 [SMILES: CCN(CC)c1ccc(Cl)c2nc3n(c12)CCOC3c1ccc(Cl)cc1Cl]

Example 503

7-Chloro-1-(2,4-dichlorophenyl)-N,N-diethyl-3,4-dihydro-1H-[1,4]oxazino[4,3-a]benzimidazol-6-amine

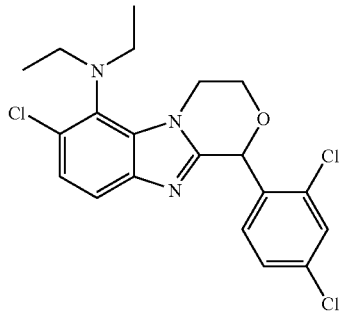 [SMILES: CCN(CC)c1c(Cl)ccc2nc3n(c12)CCOC3c1ccc(Cl)cc1Cl]

To a solution of 1-(2,4-dichlorophenyl)-N,N-diethyl-3,4-dihydro-1H-[1,4]oxazino[4,3-a]benzimidazol-6-amine (500 mg, 1.28 mmol) in acetonitrile (13 mL) was added N-chlorosuccinimide (171 mg, 1.28 mmol) at room temperature. After the resultant mixture was stirred at 60° C. for 5 h, the mixture was diluted with aqueous sodium hydrogen carbonate and water, and extracted with ethyl acetate. The combined organic layer was washed with brine, dried over sodium sulfate, filtered and concentrated in vacuo. The residue was purified by column chromatography on silica gel eluting with a 25-75% ethyl acetate/n-hexane gradient mixture and preparative HPLC eluting with a 10-100% acetonitrile/water to give 9-chloro-1-(2,4-dichlorophenyl)-N,N-diethyl-3,4-dihydro-1H-[1,4]oxazino[4,3-a]benzimidazol-6-amine as a colorless amorphous solid (Example 502, long retention time on HPLC, 128 mg, 0.302 mmol, 24%), and 7-chloro-1-(2,4-dichlorophenyl)-N,N-diethyl-3,4-dihydro-1H-[1,4]oxazino[4,3-a]benzimidazol-6-amine as a colorless amorphous solid (Example 503, short retention time on HPLC, 160 mg, 0.378 mmol, 30%)

9-Chloro-1-(2,4-dichlorophenyl)-N,N-diethyl-3,4-dihydro-1H-[1,4]oxazino[4,3-a]benzimidazol-6-amine (Example 502)

$^1$H NMR (CDCl$_3$) δ 1.03 (t, J=7.0 Hz, 6 H), 3.10 (q, J=7.0 Hz, 4 H), 4.04-4.14 (m, 1 H), 4.18-4.29 (m, 1 H), 4.59-4.70 (m, 1 H), 4.72-4.84 (m, 1 H), 6.43 (s, 1 H), 7.01 (d, J=8.2 Hz, 1 H), 7.08 (d, J=8.5 Hz, 1 H), 7.18-7.25 (m, 2 H), 7.48 (d, J=1.9 Hz, 1 H).

MS Calcd.: 423; MS Found: 424 (M+H).

7-Chloro-1-(2,4-dichlorophenyl)-N,N-diethyl-3,4-dihydro-1H-[1,4]oxazino[4,3-a]benzimidazol-6-amine (Example 503)

$^1$H NMR (CDCl$_3$) δ 0.97-1.08 (m, 6 H), 3.17-3.49 (m, 4 H), 4.11-4.22 (m, 1 H), 4.33-4.42 (m, 1 H), 4.49-4.60 (m, 1H), 4.83-4.91 (m, 1 H), 6.30 (s, 1 H), 7.17 (d, J=8.5 Hz, 1 H), 7.23-7.26 (m, 2 H), 7.45-7.48 (m, 2 H).

MS Calcd.: 423; MS Found: 424 (M+H).

Example 504 tert-Butyl 1-(2,4-dichlorophenyl)-6-(diethylamino)-3,4-dihydropyrazino[1,2-a]benzimidazole-2(1H)-carboxylate

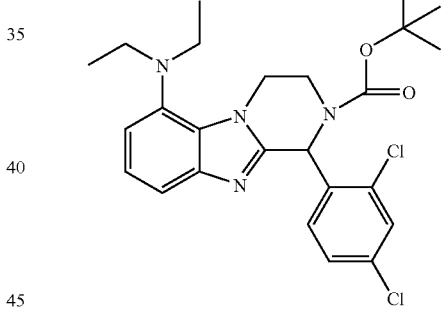

To a stirred solution of tert-butyl (2-{2-[(2,4-dichlorophenyl)(hydroxy)methyl]-7-(diethylamino)-1H-benzimidazol-1-yl}ethyl)carbamate (Reference example 223, 100 mg, 0.197 mmol) and triphenylphosphine (77.5 mg, 0.295 mmol) in tetrahydrofuran (2 mL) was added a solution of diethyl azodicarboxylate in toluene (40%, 0.135 mL, 0.296 mmol) at room temperature. The mixture was stirred at room temperature for 30 min, concentrated in vacuo, and purified by column chromatography on silica gel eluting with a 15-30% ethyl acetate/n-hexane gradient mixture to give a yellow oil (54.8 mg, 0.119 mmol, 60%).

$^1$H NMR (CDCl$_3$) δ 1.01 (t, J=7.0 Hz, 6 H), 1.42 (s, 9 H), 3.09 (q, J=7.0 Hz, 4 H), 3.45-3.57 (m, 1 H), 4.30-4.46 (m, 2 H), 4.99-5.08 (m, 1 H), 6.78 (s, 1 H), 6.90 (d, J=8.5 Hz, 1 H), 7.03 (dd, J=8.0, 1.0 Hz, 1 H), 7.10-7.20 (m, 2 H), 7.44 (d, J=2.2 Hz, 1 H), 7.47 (dd, J=8.0, 1.0 Hz, 1 H)

MS Calcd.: 488; MS Found: 489 (M+H).

Example 505

1-(2,4-Dichlorophenyl)-N,N-diethyl-1,2,3,4-tetrahydropyrazino[1,2-a]benzimidazol-6-amine

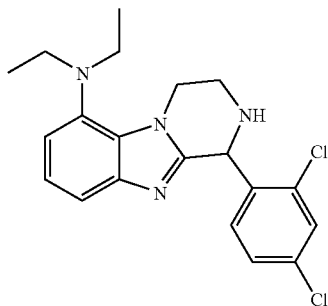 [SMILES: CCN(CC)c1cccc2nc3n(c12)CCNC3c1ccc(Cl)cc1Cl]

A mixture of tert-butyl 1-(2,4-dichlorophenyl)-6-(diethylamino)-3,4-dihydropyrazino[1,2-a]benzimidazole-2(1H)-carboxylate (244 mg, 0.499 mmol) and hydrochloric acid (4M, ethyl acetate solution, 5 mL) was stirred at room temperature for 1 h. The mixture was diluted with aqueous sodium hydrogen carbonate and extracted with ethyl acetate. The combined organic layer was washed with brine, dried over sodium sulfate, filtered and concentrated in vacuo. The residue was purified by column chromatography on silica gel eluting with a 40% ethyl acetate/n-hexane mixture to give a colorless amorphous solid (172 mg, 0.443 mmol, 89%).

$^1$H NMR (CDCl$_3$) δ 1.03 (t, J=7.0 Hz, 6 H), 2.28 (br. s., 1 H), 3.11 (q, J=7.0 Hz, 4 H), 3.24-3.44 (m, 2 H), 4.51-4.62 (m, 1 H), 4.72-4.81 (m, 1 H), 5.81 (s, 1 H), 7.03-7.08 (m, 2 H), 7.14-7.21 (m, 2 H), 7.44 (d, J=1.9 Hz, 1H), 7.47 (dd, J=8.0, 1.1 Hz, 1 H).

MS Calcd.: 388; MS Found: 389 (M+H).

Example 506

1-(2,4-Dichlorophenyl)-N,N-diethyl-2-methyl-1,2,3,4-tetrahydropyrazino[1,2-a]benzimidazol-6-amine

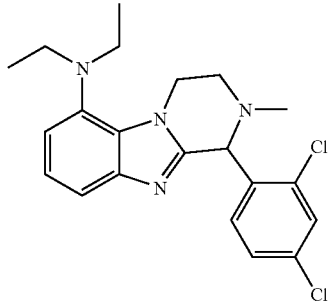 [SMILES: CCN(CC)c1cccc2nc3n(c12)CCN(C)C3c1ccc(Cl)cc1Cl]

To a solution of 1-(2,4-dichlorophenyl)-N,N-diethyl-1,2,3,4-tetrahydropyrazino[1,2-a]benzimidazol-6-amine (120 mg, 0.308 mmol) in methanol (3 mL) and acetic acid (0.15 mL) was added formaldehyde (37% in water, 75.0 mg, 0.924 mmol) at 0° C. The resultant mixture was stirred at 0° C. for 30 min. To the reaction mixture was added sodium acetoxyborohydride (196 mg, 0.925 mmol) at 0° C. After the resultant mixture was stirred at room temperature for 12 h, the mixture was diluted with aqueous sodium hydrogen carbonate and 1N aqueous sodium hydroxide, and extracted with ethyl acetate. The combined organic layer was washed with brine, dried over sodium sulfate, filtered and concentrated in vacuo. The residue was purified by column chromatography on silica gel eluting with a 10-30% ethyl acetate/n-hexane gradient mixture to give a colorless solid (90.9 mg, 0.225 mmol, 73%).

mp 186-187° C. (n-hexane).

$^1$H NMR (CDCl$_3$) δ 1.02 (t, J=7.2 Hz, 6 H), 2.35 (s, 3H), 2.90-3.02 (m, 1 H), 3.10 (q, J=7.2 Hz, 4 H), 3.25-3.34 (m, 1 H), 4.42-4.54 (m, 1 H), 4.94-5.02 (m, 1 H), 5.06 (s, 1 H), 7.03 (dd, J=7.8, 1.1 Hz, 1 H), 7.14 (t, J=7.8 Hz, 1 H), 7.21 (dd, J=8.2, 1.9 Hz, 1H), 7.26 (d, J=8.2 Hz, 1H), 7.43-7.48 (m, 2H).

MS Calcd.: 402; MS Found: 403 (M+H).

Example 507

1-(2,4-Dichlorophenyl)-N,N-diethyl-3,4-dihydropyrazino[1,2-a]benzimidazol-6-amine

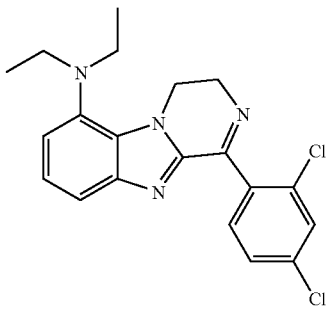 [SMILES: CCN(CC)c1cccc2nc3n(c12)CCN=C3c1ccc(Cl)cc1Cl]

A mixture of tert-butyl (2-{2-[(2,4-dichlorophenyl)carbonyl]-7-(diethylamino)-1H-benzimidazol-1-yl}ethyl)carbamate (Reference example 224, 395 mg, 0.781 mmol) and hydrochloric acid (10%, methanol solution, 2 mL) in methanol (2 mL) was stirred at room temperature for 14 h and at 50° C. for 2 h. The mixture was diluted with aqueous sodium hydrogen carbonate and extracted with ethyl acetate. The combined organic layer was washed with brine, dried over sodium sulfate, filtered and concentrated in vacuo. The residue was purified by column chromatography on silica gel eluting with a 10-30% ethyl acetate/n-hexane gradient mixture to give a yellow amorphous solid (258 mg, 0.666 mmol, 85%).

$^1$H NMR (CDCl$_3$) δ 1.03 (t, J=7.0 Hz, 6 H), 3.14 (q, J=7.0 Hz, 4 H), 4.26 (t, J=6.6 Hz, 2 H), 4.82 (t, J=6.6 Hz, 2H), 7.11 (dd, J=7.8, 1.1 Hz, 1 H), 7.22 (t, J=7.8 Hz, 1 H), 7.37 (dd, J=8.1, 2.1 Hz, 1 H), 7.48-7.52 (m, 2 H), 7.59 (dd, J=7.8, 1.1 Hz, 1H).

MS Calcd.: 386; MS Found: 387 (M+H).

Example 508 tert-Butyl 1-(2,4-dichlorophenyl)-7-(diethylamino)-4,5-dihydro-1H-[1,4]diazepino[1,2-a]benzimidazole-2(3H)-carboxylate

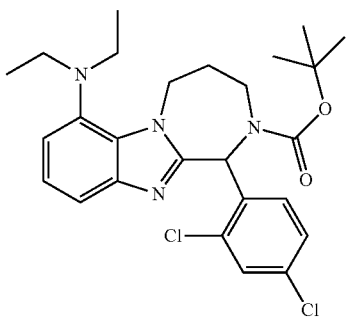 [SMILES: CCN(CC)c1cccc2nc3n(c12)CCCN(C(=O)OC(C)(C)C)C3c1ccc(Cl)cc1Cl]

To a stirred solution of tert-butyl (3-{2-[(2,4-dichlorophenyl)(hydroxy)methyl]-7-(diethylamino)-1H-benzimidazol-1-yl}propyl)carbamate (Reference example 228, 500 mg, 0.959 mmol) and triphenylphosphine (377 mg, 1.44 mmol) in tetrahydrofuran (30 mL) was added a solution of diethyl azodicarboxylate in toluene (40%, 0.655 mL, 1.44 mmol) at 0° C. The mixture was stirred at 0° C. for 2 h, concentrated in vacuo, and purified by column chromatography on silica gel eluting with a 10-20% ethyl acetate/n-hexane gradient mixture to give a colorless amorphous solid (138 mg, 0.274 mmol, 29%).

$^1$H NMR (CDCl$_3$) δ 0.95-1.13 (m, 6 H), 1.35 (s, 6 H), 1.49 (s, 3 H), 1.75-1.92 (m, 1 H), 2.07-2.30 (m, 1 H), 2.65-2.90 (m, 1 H), 3.01-3.26 (m, 4 H), 4.04-4.37 (m, 1 H), 4.49-4.67 (m, 1 H), 5.37-5.51 (m, 1 H), 6.79 (s, 0.7H), 6.93 (s, 0.3 H), 6.99-7.09 (m, 2 H), 7.15 (t, J=7.8 Hz, 1H), 7.20-7.25 (m, 1 H), 7.46 (d, J=1.9 Hz, 1 H), 7.49 (dd, J=7.8, 1.2 Hz, 1 H).

MS Calcd.: 502; MS Found: 503 (M+H).

Example 509

1-(2,4-Dichlorophenyl)-N,N-diethyl-2,3,4,5-tetrahydro-1H-[1,4]diazepino[1,2-a]benzimidazol-7-amine

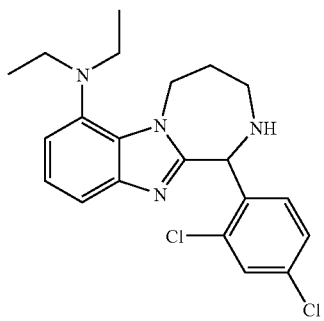 [SMILES: CCN(CC)c1cccc2nc3n(c12)CCCNC3c1ccc(Cl)cc1Cl]

A mixture of tert-butyl 1-(2,4-dichlorophenyl)-7-(diethylamino)-4,5-dihydro-1H-[1,4]diazepino[1,2-a]benzimidazole-2(3H)-carboxylate (434 mg; 0.862 mmol) and hydrochloric acid (4M, ethyl acetate solution, 9 mL) was stirred at room temperature for 30 min. The mixture was diluted with aqueous sodium hydrogen carbonate and extracted with ethyl acetate. The combined organic layer was washed with brine, dried over sodium sulfate, filtered and concentrated in vacuo. The residue was purified by column chromatography on silica gel eluting with a 20-60% ethyl acetate/n-hexane gradient mixture to give a colorless solid (326 mg, 0.808 mmol, 94%).

mp 186-188° C. (ethyl acetate/n-hexane).

$^1$H NMR (CDCl$_3$) δ 1.02 (t, J=7.1 Hz, 6 H), 1.70-1.87 (m, 2 H), 2.00-2.12 (m, 1 H), 3.00-3.28 (m, 5 H), 3.44-3.54 (m, 1 H), 4.38 (dd, J=14.3, 11.0 Hz, 1 H), 5.50 (s, 1 H), 6.05-6.15 (m, 1 H), 7.03 (dd, J=7.7, 1.1 Hz, 1 H), 7.09 (d, J=7.7 Hz, 1 H), 7.33 (dd, J=8.5, 2.2 Hz, 1 H), 7.41 (d, J=2.2 Hz, 1 H), 7.44 (dd, J=7.7, 1.1 Hz, 1 H), 7.51 (d, J=8.5 Hz, 1 H)

MS Calcd.: 402; MS Found: 403 (M+H).

Example 510

1-(2,4-Dichlorophenyl)-N,N-diethyl-2-methyl-2,3,4,5-tetrahydro-1H-[1,4]diazepino[1,2-a]benzimidazol-7-amine

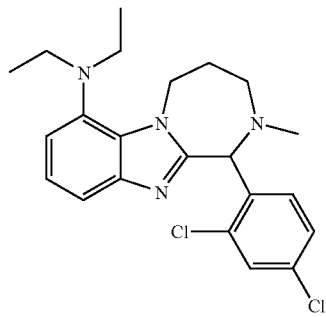 [SMILES: CCN(CC)c1cccc2nc3n(c12)CCCN(C)C3c1ccc(Cl)cc1Cl]

To a solution of 1-(2,4-dichlorophenyl)-N,N-diethyl-2,3,4,5-tetrahydro-1H-[1,4]diazepino[1,2-a]benzimidazol-7-amine (100 mg, 0.248 mmol) in methanol (2.5 mL) and acetic acid (0.125 mL) was added formaldehyde (37% in water, 60 mg, 0.74 mmol) at 0° C. The resultant mixture was stirred at 0° C. for 30 min. To the reaction mixture was added sodium acetoxyborohydride (158 mg, 0.745 mmol) at 0° C. After the resultant mixture was stirred at 0° C. for 2 h, the mixture was diluted with aqueous sodium hydrogen carbonate and 1N aqueous sodium hydroxide, and extracted with ethyl acetate. The combined organic layer was washed with brine, dried over sodium sulfate, filtered and concentrated in vacuo. The residue was purified by column chromatography on silica gel eluting with a 10-40% ethyl acetate/n-hexane gradient mixture to give a colorless solid (101 mg, 0.242 mmol, 98%).

mp 132-133° C. (n-hexane).

$^1$H NMR (CDCl$_3$) δ 0.98-1.09 (m, 6 H), 1.86-2.00 (m, 2 H), 2.32 (s, 3 H), 3.02-3.31 (m, 6 H), 4.68-4.82 (m, 1 H), 5.54-5.68 (m, 2 H), 7.05 (dd, J=7.8, 1.2 Hz, 1 H), 7.13 (t, J=7.8 Hz, 1 H), 7.29 (dd, J=8.4, 2.2 Hz, 1 H), 7.41 (d, J=2.2 Hz, 1 H), 7.48 (dd, J=7.8, 1.2 Hz, 1 H), 7.70 (d, J=8.4 Hz, 1 H).

MS Calcd.: 416; MS Found: 417 (M+H).

Example 511

1-(2,4-Dichlorophenyl)-N,N-diethyl-4,5-dihydro-3H-[1,4]diazepino[1,2-a]benzimidazol-7-amine

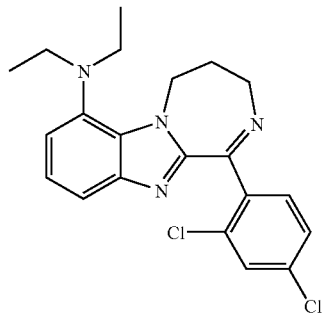 [SMILES: CCN(CC)c1cccc2nc3n(c12)CCCN=C3c1ccc(Cl)cc1Cl]

A mixture of 1-(2,4-dichlorophenyl)-N,N-diethyl-2,3,4,5-tetrahydro-1H-[1,4]diazepino[1,2-a]benzimidazol-7-amine (50.0 mg, 0.124 mmol) and manganese(IV) oxide (108 mg, 1.24 mmol) in tetrahydrofuran (0.6 mL) was stirred at 0° C. for 2 d, filtered and concentrated in vacuo. The residue was purified by column chromatography on silica gel eluting with a 20-30% ethyl acetate/n-hexane gradient mixture to give a yellow solid (31.8 mg, 0.0792 mmol, 64%).

mp 93-94° C. (n-hexane).

$^1$H NMR (CDCl$_3$) δ 1.05 (t, J=7.0 Hz, 6 H), 2.49-2.61 (m, 2H), 3.04-3.23 (m, 4 H), 3.82 (t, J=6.6 Hz, 2 H), 4.94 (t, J=7.1 Hz, 2 H), 7.11 (dd, J=8.0, 1.1 Hz, 1 H), 7.22 (t, J=8.0 Hz, 1 H), 7.34-7.40 (m, 2 H), 7.56 (dd, J=8.0, 1.1 Hz, 1 H), 7.62-7.67 (m, 1 H).

MS Calcd.: 400; MS Found: 401 (M+H).

Example 512

Methyl 9-chloro-1-[6-methoxy-2-(trifluoromethyl)pyridin-3-yl]-1,2,3,4-tetrahydropyrimido[1,2-a]benzimidazole-6-carboxylate

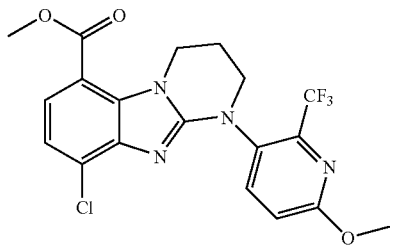

To a solution of methyl 4-chloro-1-(3-hydroxypropyl)-2-{[6-methoxy-2-(trifluoromethyl)pyridin-3-yl]amino}-1H-benzimidazole-7-carboxylate (1.50 g, 3.27 mmol) and triethylamine (0.91 mL, 6.53 mmol) in tetrahydrofuran (30 mL) was added methanesulfonyl chloride (0.38 mL, 4.90 mmol) at 0° C. The mixture was stirred at 0° C. for 0.5 hr. Aqueous sodium hydrogen carbonate was added to the reaction mixture at 0° C., and the mixture was extracted with ethyl acetate. The organic layer was washed with water and brine, dried over anhydrous magnesium sulfate, and concentrated in vacuo. A mixture of the residue and potassium carbonate (1.81 g, 13.1 mmol) in N,N-dimethylformamide (30 mL) was stirred at 80° C. for 13 hr. Water was added to the reaction mixture at room temperature and the mixture was extracted with ethyl acetate. The organic layer was washed with water and brine, dried over anhydrous magnesium sulfate, and concentrated in vacuo. The residue was purified by flash chromatography on silica gel eluting with a 30-100% ethyl acetate/n-hexane gradient mixture to give the title compound (1.33 g, 2.95 mmol, 90%) as a white solid.

$^1$H NMR (CDCl$_3$) δ 2.14-2.42 (m, 2 H), 3.58-3.78 (m, 2H), 3.94 (s, 3 H), 4.01 (s, 3 H), 4.34-4.47 (m, 2 H), 7.00 (d, J=8.7 Hz, 1 H), 7.09 (d, J=8.3 Hz, 1 H), 7.45 (d, J=8.3 Hz, 1 H), 7.74 (d, J=8.7 Hz, 1 H).

MS Calcd.: 440; Found: 441 (M+H).

Example 513

{9-Chloro-1-[6-methoxy-2-(trifluoromethyl)pyridin-3-yl]-1,2,3,4-tetrahydropyrimido[1,2-a]benzimidazol-6-yl}methanol

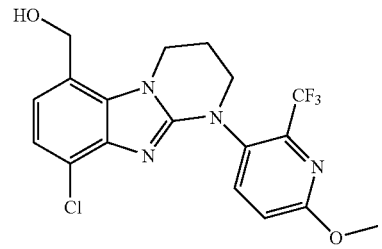 [SMILES: COc1ccc(N2CCCn3c2nc2c(Cl)ccc(CO)c23)c(C(F)(F)F)n1]

To a solution of calcium chloride (670 mg, 6.04 mmol) in ethanol (15 mL) was added sodium tetrahydroborate (457 mg, 12.08 mmol) at 0° C. The mixture was stirred at 0° C. for 1 hr. A solution of methyl 9-chloro-1-[6-methoxy-2-(trifluoromethyl)pyridin-3-yl]-1,2,3,4-tetrahydropyrimido[1,2-a]benzimidazole-6-carboxylate (1.33 g, 3.02 mmol) in tetrahydrofuran (15 mL) was added dropwise to the mixture at 0° C. The mixture was stirred at 0° C. for 12 hr. 1N HCl (ca. 9.0 mL) was added to the reaction mixture at 0° C., and the aqueous ammonium chloride was added to the mixture. The solvent was removed in vacuo. The precipitated solid was collected by filtration, washed with water and diisopropyl ether to give the title compound (1.33 g, 3.02 mmol, quant) as a white solid.

$^1$H NMR (DMSO-d$_6$) δ 2.17-2.38 (m, 2 H), 3.45-3.57 (m, 1 H), 3.68-3.83 (m, 1 H), 3.96 (s, 3 H), 4.33-4.48 (m, 1 H), 4.60-4.83 (m, 3 H), 5.37 (t, J=5.3 Hz, 1 H), 6.85 (d, J=8.1 Hz, 1 H), 6.96 (d, J=8.1 Hz, 1 H), 7.30 (d, J=8.9 Hz, 1 H), 8.08 (d, J=8.9 Hz, 1 H).

MS Calcd.: 412; Found: 413 (M+H).

Example 514

9-Chloro-1-[6-methoxy-2-(trifluoromethyl)Pyridin-3-yl]-1,2,3,4-tetrahydropyrimido[1,2-a]benzimidazole-6-carbaldehyde

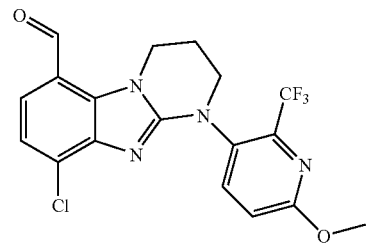 [SMILES: COc1ccc(N2CCCn3c2nc2c(Cl)ccc(C=O)c23)c(C(F)(F)F)n1]

A mixture of {9-chloro-1-[6-methoxy-2-(trifluoromethyl)pyridin-3-yl]-1,2,3,4-tetrahydropyrimido[1,2-a]benzimidazol-6-yl}methanol (500 mg, 1.21 mmol), 2,2,6,6-tetramethylpiperidine 1-oxyl (18.9 mg, 0.12 mmol) and sodium nitrate (33.4 mg, 0.484 mmol) in acetic acid (10 mL) was stirred at room temperature and ambient pressure for 64 hr. Water was added to the reaction mixture and the mixture was extracted with ethyl acetate. The organic layer was washed with aqueous sodium hydrogen carbonate and brine, dried over anhydrous magnesium sulfate, and concentrated in vacuo. The residue was purified by flash chromatography on silica gel eluting with a 20-80% ethyl acetate/n-hexane gradient mixture to give the title compound (336.3 mg, 0.82 mmol, 68%) as a pale yellow solid.

$^1$H NMR (CDCl$_3$) δ 2.21-2.47 (m, 2 H), 3.61-3.78 (m, 2 H), 4.01 (s, 3 H), 4.52-4.83 (m, 2 H), 7.01 (d, J=8.6 Hz, 1 H), 7.22 (d, J=8.3 Hz, 1 H), 7.37 (d, J=8.3 Hz, 1 H), 7.73 (dd, J=8.6, 0.8 Hz, 1 . H), 9.98 (s, 1 H).

MS Calcd.: 410; Found: 411 (M+H).

Example 515

1-{9-Chloro-1-[6-methoxy-2-(trifluoromethyl)pyridin-3-yl]-1,2,3,4-tetrahydropyrimido[1,2-a]benzimidazol-6-yl}-2,2,2-trifluoroethanol

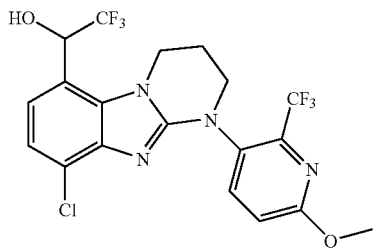 [SMILES: COc1ccc(N2CCCn3c2nc2c(Cl)ccc(C(O)C(F)(F)F)c23)c(C(F)(F)F)n1]

To a solution of 9-chloro-1-[6-methoxy-2-(trifluoromethyl)pyridin-3-yl]-1,2,3,4-tetrahydropyrimido[1,2-a]benzimidazole-6-carbaldehyde (336 mg, 0.82 mmol) and (trifluoromethyl)trimethylsilane (0.36 mL, 2.44 mmol) in tetrahydrofuran (10 mL) was added tetrabutylammonium fluoride MOM solution in tetrahydrofuran 0.082 mL, 0.082 mmol) at 0° C. The mixture was stirred at 0° C. for 0.5 hr. 1N HCl (2.0 mL) was added to the reaction mixture at 0° C. and the mixture was stirred at 0° C. for 0.5 hr. The mixture was basified with aqueous sodium hydrogen carbonate and the mixture was extracted with ethyl acetate. The organic layer was washed with water and brine, dried over anhydrous magnesium sulfate, and concentrated in vacuo. The residue was purified by flash chromatography on silica gel eluting with a 50-100% ethyl acetate/n-hexane gradient mixture to give the title compound (372.5 mg, 0.775 mmol, 94%) as a pale yellow solid.

$^1$H NMR (DMSO-d$_6$) δ 2.16-2.40 (m, 2 H), 3.45-3.57 (m, 1 H), 3.68-3.82 (m, 1 H), 3.96 (s, 3 H), 4.21-4.60 (m, 2H), 5.66-5.81 (m, 1 H), 6.99-7.16 (m, 3 H), 7.30 (d, J=8.7 Hz, 1 H), 8.10 (t, J=9.2 Hz, 1 H).

MS Calcd.: 410; Found: 411 (M+H).

Example 516

9-Chloro-6-[1-(difluoromethoxy)-2,2,2-trifluoroethyl]-1-[6-methoxy-2-(trifluoromethyl)pyridin-3-yl]-1,2,3,4-tetrahydropyrimido[1,2-a]benzimidazole

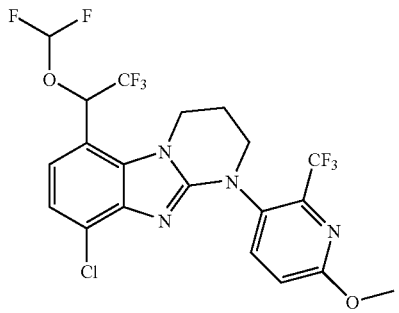 [SMILES: COc1ccc(N2CCCn3c2nc2c(Cl)ccc(C(OC(F)F)C(F)(F)F)c23)c(C(F)(F)F)n1]

A mixture of 1- {9-chloro-1-[6-methoxy-2-(trifluoromethyl)pyridin-3-yl]-1,2,3,4-tetrahydropyrimido[1,2-a]benzimidazol-6-yl} -2,2,2-trifluoroethanol (300 mg, 0.62 mmol) and benzyltriethylammonium chloride (7.0 mg, 0.031 mmol) in tetrahydrofuran (3.0 mL) and 8N aqueous sodium hydroxide solution (3.0 mL) was stirred at room temperature for 2 hr under chloro(difluoro)methane atmosphere. Water was added to the reaction mixture at room temperature and the mixture was extracted with ethyl acetate. The organic layer was washed with brine, dried over anhydrous magnesium sulfate, and concentrated in vacuo. The residue was purified by flash chromatography on silica gel eluting with a 10-50% ethyl acetate/n-hexane gradient mixture to give a white solid. Recrystallization from ethyl acetate/n-hexane gave the title compound (113 mg, 0.213 mmol, 34%) as colorless crystals.

$^1$H NMR (CDCl$_3$) δ 2.29-2.59 (m, 2 H), 3.58 0 3.78 (m, 2 H), 4.01 (s, 3 H), 4.23-4.45 (m, 2 H), 6.00 (q, J=5.8 Hz, 1 H), 6.41 (t, J=72.3 Hz, 1 H), 7.01 (dd, J=9.0, 0.6 Hz, 1 H), 7.16 (s, 2 H), 7.76 (d, J=9.0 Hz, 1 H).

MS Calcd.: 530; Found: 531 (M+H).

Example 517

2,2,2-Trifluoro-1-[1-(2-methoxy-4,6-dimethylpyrimidin-5-yl)-1,2,3,4-tetrahydropyrimido[1,2-a]benzimidazol-6-yl]ethanol

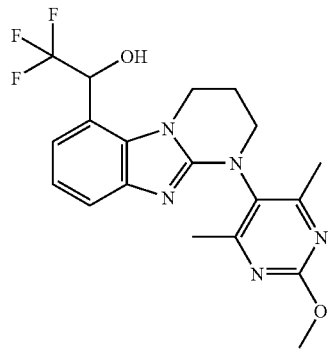 [SMILES: COc1nc(C)c(N2CCCn3c2nc2cccc(C(O)C(F)(F)F)c23)c(C)n1]

To a solution of 1-[9-chloro-1-(2-methoxy-4,6-dimethylpyrimidin-5-yl)-1,2,3,4-tetrahydropyrimido[1,2-a]benzimidazol-6-yl]-2,2,2-trifluoroethanol (563 mg, 1.27 mmol) in acetic acid (8.5 mL) was added 10% palladium on carbon (50% wet, 56.3 mg), and the mixture was purged with hydrogen and stirred under balloon pressure hydrogen at room temperature for 2 days. The catalyst was removed by filtration, and the filtrate was concentrated in vacuo. The residue was diluted with saturated aqueous sodium hydrogen carbonate and extracted with ethyl acetate. The combined organic layer was washed with brine, dried over anhydrous magnesium sulfate, filtered and concentrated in vacuo to give a solid, which was recrystallized from methanol to give the title compound as colorless crystals (362 mg, 0.889 mmol, 70%).

mp 296-299° C.

$^1$H NMR (DMSO-d$_6$) δ 2.26 (s, 3 H), 2.27 (s, 3 H), 2.27-2.38 (m, 2 H), 3.61 (t, J=5.4 Hz, 2 H), 3.91 (s, 3 H), 4.35-4.49 (m, 2 H), 5.65-5.74 (m, 1 H), 6.93-7.02 (m, 2 H), 7.12-7.16 (m, 2 H).

MS Calcd.: 407; MS Found: 408 (M+H).

Example 518

6-[1-(Difluoromethoxy)-2,2,2-trifluoroethyl]-1-(2-methoxy-4,6-dimethylpyrimidin-5-yl)-1,2,3,4-tetrahydropyrimido[1,2-a]benzimidazole

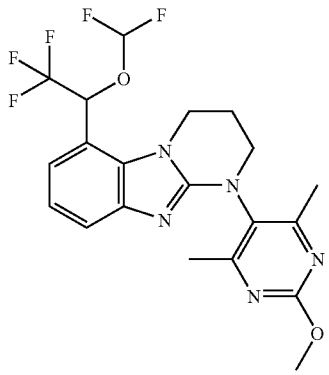 [SMILES: COc1nc(C)c(N2CCCn3c2nc2cccc(C(OC(F)F)C(F)(F)F)c23)c(C)n1]

To a solution of 9-chloro-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole (783 mg, 1.59 mmol) in acetic acid (8.0 mL) was added 10% palladium on carbon (50% wet, 78.3 mg), and the mixture was purged with hydrogen and stirred under balloon pressure hydrogen at room temperature for 2 days. The catalyst was removed by filtration, and the filtrate was concentrated in vacuo. The residue was diluted with saturated aqueous sodium hydrogen carbonate and extracted with ethyl acetate. The combined organic layer was washed with brine, dried over anhydrous magnesium sulfate, filtered and concentrated in vacuo. The residue was purified by flash column chromatography on silica gel eluting with a 75-100% ethyl acetate/n-hexane gradient mixture. The filtrate was concentrated in vacuo to give a solid, which was washed with ethyl acetate/diisopropyl ether to give the title compound as a colorless powder (507 mg, 1.11 mmol, 70%)

$^1$H NMR (CDCl$_3$) δ 2.38 (s, 6 H), 2.40-2.56 (m, 2 H), 3.55-3.66 (m, 2 H), 3.99 (s, 3 H), 4.35-4.44 (m, 2 H), 6.00 (q, J=6.3 Hz, 1 H), 6.42 (t, J=72.0 Hz, 1 H), 7.14 (t, J=7.8 Hz, 1 H), 7.21-7.24 (m, 1 H), 7.46 (dd, J=1.5 Hz, 7.8 Hz, 1 H).

MS Calcd.: 457; MS Found: 458 (M+H).

Example 519

9-Bromo-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole

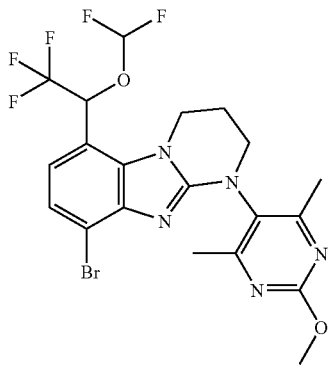 [SMILES: COc1nc(C)c(N2CCCn3c2nc2c(Br)ccc(C(OC(F)F)C(F)(F)F)c23)c(C)n1]

N-Bromosuccinimide (190 mg, 1.07 mmol) was added to a stirred solution of 6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole (469 mg, 1.02 mmol) in acetonitrile (5.0 mL) at room temperature, and the mixture was stirred at room temperature for 5 hr. The mixture was diluted with saturated aqueous sodium hydrogen carbonate and extracted with ethyl acetate. The combined organic layer was washed with brine, dried over anhydrous magnesium sulfate, filtered and concentrated in vacuo. The residue was purified by flash column chromatography on silica gel eluting with a 70-100% ethyl acetate/n-hexane gradient mixture. The filtrate was concentrated in vacuo to give a solid, which was recrystallized from ethyl acetate/n-hexane to give the title compound as colorless crystals (330 mg, 0.615 mmol, 60%).

mp 211-213° C.

$^1$H NMR (CDCl$_3$) δ 2.38 (s, 6 H), 2.40-2.56 (m, 2 H), 3.54-3.67 (m, 2 H), 4.02 (s, 3 H), 4.32-4.41 (m, 2 H), 5.98 (q, J=6.0 Hz, 1 H), 6.42 (t, J=72.3 Hz, 1 H), 7.07 (d, J=8.7 Hz, 1 H), 7.32 (d, J=8.7 Hz, 1 H).

MS Calcd.: 535; MS Found: 536 (M+H).

Example 520

6-[1-(Difluoromethoxy)-2,2,2-trifluoroethyl]-1-(2-methoxy-4,6-dimethylpyrimidin-5-yl)-1,2,3,4-tetrahydropyrimido[1,2-a]benzimidazole-9-carbonitrile

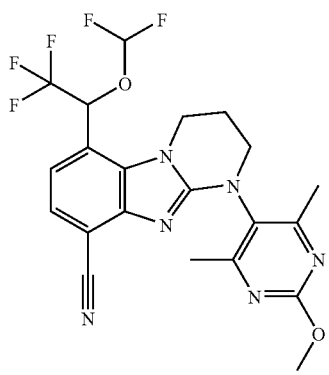 [SMILES: COc1nc(C)c(N2CCCn3c2nc2c(C#N)ccc(C(OC(F)F)C(F)(F)F)c23)c(C)n1]

A mixture of 9-bromo-6-[1-(difluoromethoxy)-2,2,2-trifluoroethyl]-1-(2-methoxy-4,6-dimethylpyrimidin-5-yl)-1,2,3,4-tetrahydropyrimido[1,2-a]benzimidazole (254 mg, 0.474 mmol), zinc cyanide (557 mg, 4.74 mmol), 2-(di-tert-butylphosphino)biphenyl (14.1 mg, 0.0474 mmol), and tris(dibenzylideneacetone)dipalladium (43.4 mg, 0.0474 mmol) in N,N-dimethylformamide (2.4 ml) was stirred at 120° C. under nitrogen for 7 hr. The mixture was diluted with saturated aqueous sodium hydrogen carbonate and extracted with ethyl acetate. The combined organic layer was washed with brine, dried over anhydrous magnesium sulfate, filtered and concentrated in vacuo. The residue was purified by flash column chromatography on silica gel eluting with a 75-100% ethyl acetate/n-hexane gradient mixture. The filtrate was concentrated in vacuo to give a solid, which was recrystallized from ethyl acetate/n-hexane to give the title compound as colorless crystals (118 mg, 0.245 mmol, 52%).

mp 250-252° C.

$^1$H NMR (CDCl$_3$) δ 2.37 (s, 6 H), 2.43-2.53 (m, 2 H), 3.58-3.71 (m, 2 H), 4.03 (s, 3 H), 4.35-4.44 (m, 2 H), 6.03 (q, J=6.0 Hz, 1 H), 6.47 (t, J=71.7 Hz, 1 H), 7.21 (d, J=8.1 Hz, 1 H), 7.39 (d, J=8.1 Hz, 1 H).

MS Calcd.: 482; MS Found: 483 (M+H).

Example 521

Methyl 9-methoxy-1-(2-methoxy-4,6-dimethylpyrimidin-5-yl)-1,2,3,4-tetrahydropyrimido[1,2-a]benzimidazole-6-carboxylate

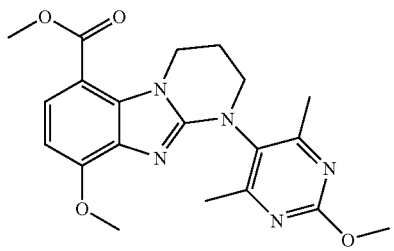

A mixture of methyl 1-(3-chloropropyl)-4-methoxy-2-[(2-methoxy-4,6-dimethylpyrimidin-5-yl)amino]-1H-benzimidazole-7-carboxylate (878.9 mg, 2.03 mmol) and potassium carbonate (0.84 g, 6.08 mmol) in N,N-dimethylformamide (9.0 mL) was stirred at 70° C. for 16 hr. Water was added to the reaction mixture at room temperature and the mixture was extracted with ethyl acetate. The organic layer was washed with water (×3) and brine, dried over anhydrous magnesium sulfate, and concentrated in vacuo. The Precipitated pale yellow solid was collected by filtration, washed with diisopropyl ether to give the title compound (720.7 mg, 1.81 mmol, 89%) as a pale yellow solid.

$^1$H NMR (CDCl$_3$) δ 2.22-2.32 (m, 2 H), 2.35 (s, 6 H), 3.56 (t, J=5.6 Hz, 2 H), 3.92 (s, 3 H), 3.95 (s, 3 H), 3.98 (s, 3 H), 4.48 (t, J=6.2 Hz, 2 H), 6.61 (d, J=8.7 Hz, 1H), 7.59 (d, J=8.7 Hz, 1 H).

MS Calcd.: 397; MS Found: 398 (M+H).

Example 522

[9-Methoxy-1-(2-methoxy-4,6-dimethylpyrimidin-5-yl)-1,2,3,4-tetrahydropyrimido[1,2-a]benzimidazol-6-yl]methanol

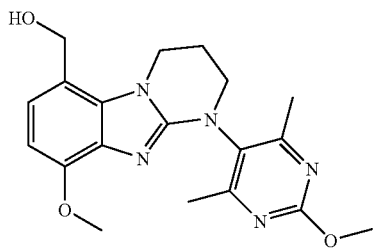 [SMILES: COc1nc(C)c(N2CCCn3c2nc2c(OC)ccc(CO)c23)c(C)n1]

To a suspension of lithium aluminum hydride (0.14 g, 3.69 mmol) in tetrahydrofuran (10 mL) was added dropwise a solution of methyl 9-methoxy-1-(2-methoxy-4,6-dimethylpyrimidin-5-yl)-1,2,3,4-tetrahydropyrimido[1,2-a]benzimidazole-6-carboxylate (720 mg, 1.81 mmol) in tetrahydrofuran (30 mL) at 0° C. After stirring at 0° C. for 1 hr, water (0.14 mL), 15% aqueous sodium hydroxide (0.14 mL) and water (0.42 mL) were successively added dropwise to the reaction mixture at 0° C. The mixture was stirred at room temperature for 4 hr and anhydrous magnesium sulfate was added to the mixture. The solid was removed by filtration. The filtrate was concentrated in vacuo and the residue was purified by flash column chromatography on silica gel eluting with a 5-25% methanol/ethyl acetate gradient mixture to give the title compound as a colorless solid (478 mg, 1.29 mmol, 71%).

$^1$H NMR (DMSO-d$_6$) δ 2.20-2.36 (m, 8 H), 3.54-3.62 (m, 2 H), 3.72 (s, 3 H), 3.91 (s, 3 H), 4.54 (t, J=5.6 Hz, 2H), 4.67 (d, J=5.0 Hz, 2 H), 5.15 (t, J=5.0 Hz, 1 H), 6.47 (d, J=8.1 Hz, 1 H), 6.75 (d, J=8.1 Hz, 1 H).

MS Calcd.: 369; MS Found: 370 (M+H).

Example 523

Methyl 9-chloro-1-(2-methoxy-4,6-dimethylpyrimidin-5-yl)-1,2,3,4-tetrahydropyrimido[1,2-a]benzimidazole-6-carboxylate

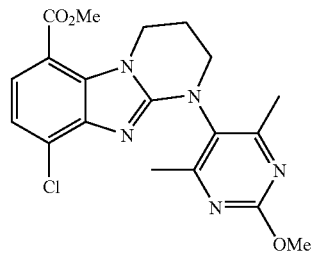 [SMILES: COC(=O)c1ccc(Cl)c2nc3n(c12)CCCN3c1c(C)nc(OC)nc1C]

A mixture of methyl 4-chloro-1-(3-chloropropyl)-2-[(2-methoxy-4,6-dimethylpyrimidin-5-yl)amino]1H-benzimidazole-7-carboxylate (560 mg, 1.28 mmol) and potassium carbonate (1.92 mmol) in N,N-dimethylformamide (5.6 mL) was stirred at 80° C. for 1 h, diluted with ethyl acetate, washed with water and brine, dried over anhydrous sodium sulfate, filtered and concentrated in vacuo. The residue was purified by flash column chromatography on silica gel eluting with a 50-100% ethyl acetate/n-hexane gradient mixture to give the title compound as a colorless solid (504 mg, 1.25 mmol, 98%).

MS Calcd.: 401; MS Found: 402 (M+H).

Example 524

9-Methoxy-1-(2-methoxy-4,6-dimethylpyrimidin-5-yl)-1,2,3,4-tetrahydropyrimido[1,2-a]benzimidazole-6-carbaldehyde

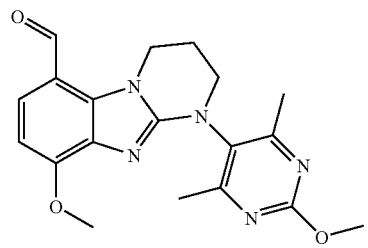 [SMILES: COc1nc(C)c(N2CCCn3c2nc2c(OC)ccc(C=O)c23)c(C)n1]

Dess-Martin reagent (1.31 g, 3.09 mmol) was added to a stirred solution of [9-methoxy-1-(2-methoxy-4,6-dimethylpyrimidin-5-yl)-1,2,3,4-tetrahydropyrimido[1,2-a]benzimidazol-6-yl]methanol (761 mg, 2.06 mmol) in dimethyl sulfoxide (0.50 mL) and acetonitrile (8.2 mL) at 0 °C., and the mixture was stirred at room temperature for 3 hr. The mixture was diluted with saturated aqueous sodium hydrogen carbonate and extracted with ethyl acetate. The combined organic layer was washed with brine, dried over anhydrous magnesium sulfate, filtered and concentrated in vacuo. The residue was purified by flash column chromatography on silica gel eluting with a 0-5% methanol/ethyl acetate gradient mixture. The eluate was concentrated in vacuo to give the title compound as a brown solid (467 mg).

MS Calcd.: 367; MS Found: 368 (M+H).

Example 525

2,2,2-Trifluoro-1-[9-methoxy-1-(2-methoxy-4,6-dimethylpyrimidin-5-yl)-1,2,3,4-tetrahydropyrimido[1,2-a]benzimidazol-6-yl]ethanol

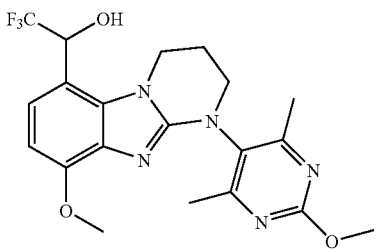 [SMILES: COc1nc(C)c(N2CCCn3c2nc2c(OC)ccc(C(O)C(F)(F)F)c23)c(C)n1]

Tetrabutylammonium fluoride (1.0 M solution in tetrahydrofuran, 0.13 mL, 0.13 mmol) was added to a stirred solution of the 9-methoxy-1-(2-methoxy-4,6-dimethylpyrimidin-5-yl)-1,2,3,4-tetrahydropyrimido[1,2-a]benzimidazole-6-carbaldehyde (467 mg) and trimethyl(trifluoromethyl)silane (361 mg, 2.54 mmol) in tetrahydrofuran (5.0 mL) at 0° C., and the mixture was stirred at 0° C. for 30 min, at room temperature for 70 min. 1N Hydrochloric acid (5.0 mL) was added to the mixture at room temperature, and the mixture was stirred for 15 min. The mixture was neutralized with saturated aqueous sodium hydrogen carbonate and extracted with ethyl acetate. The combined organic layer was washed with brine, dried over anhydrous magnesium sulfate, filtered and concentrated in vacuo. The residue was purified by flash column chromatography on silica gel eluting with a 0-7% methanol/ethyl acetate gradient mixture. The eluate was concentrated in vacuo to give the title compound as a colorless solid (224 mg, 0.512 mmol).

$^1$H NMR (CDCl$_3$) δ 2.35 (s, 6 H), 2.35-2.45 (m, 2 H), 2.85-3.00 (m, 1 H), 3.52-3.59 (m, 2 H), 3.90 (s, 3 H), 3.98 (s, 3 H), 4.37-4.57 (m, 2 H), 5.50-5.59 (m, 1 H), 6.64 (d, J=8.4 Hz, 1 H), 7.17 (d, J=8.4 Hz, 1 H).

MS Calcd.: 437; MS Found: 438 (M+H).

Example 526

6-[1-(Difluoromethoxy)-2,2,2-trifluoroethyl]-9-methoxy-1-(2-methoxy-4,6-dimethylpyrimidin-5-yl)-1,2,3,4-tetrahydropyrimido[1,2-a]benzimidazole

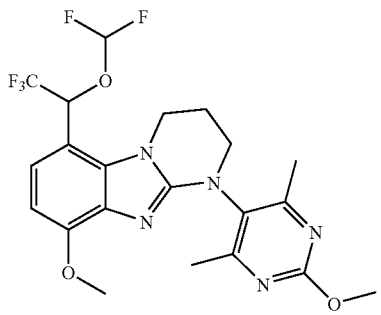 [SMILES: COc1nc(C)c(N2CCCn3c2nc2c(OC)ccc(C(OC(F)F)C(F)(F)F)c23)c(C)n1]

A mixture of 2,2,2-trifluoro-1-[9-methoxy-1-(2-methoxy-4,6-dimethylpyrimidin-5-yl)-1,2,3,4-tetrahydropyrimido[1,2-a]benzimidazol-6-yl]ethanol (184 mg, 0.421 mmol), benzyltriethylammonium chloride (4.8 mg, 0.0211 mmol), and 8N sodium hydroxide (1.7 mL) in tetrahydrofuran (1.7 mL) was stirred at room temperature under chloro(difluoro)methane atmosphere for 3 hr. The mixture was diluted with aqueous saturated ammonium chloride, and extracted with ethyl acetate. The combined organic layer was washed with brine, dried over anhydrous magnesium sulfate, filtered and concentrated in vacuo. The residue was purified by flash column chromatography on silica gel eluting with a 80-100% ethyl acetate/n-hexane gradient mixture. The eluate was concentrated in vacuo to give the solid, which was recrystallized from ethyl acetate/n-hexane to give the title compound as colorless crystals (74.4 mg, 0.153 mmol, 36%).

mp 201-203° C.

$^1$H NMR (CDCl$_3$) δ 2.36 (s, 6 H), 2.36-2.49 (m, 2 H), 3.50-3.65 (m, 2 H), 3.92 (s, 3 H), 3.98 (s, 3 H), 4.32-4.41 (m, 2 H), 5.95 (q, J=6.3 Hz, 1 H), 6.39 (t, J=72.9 Hz, 1H), 6.68 (d, J=9.0 Hz, 1 H), 7.18 (d, J=9.0 Hz, 1 H).

MS Calcd.: 487; MS Found: 488 (M+H).

Experimental Example 1

Measurement of CRF Binding Inhibitory Rate

A receptor binding experiment was carried out using a human CRF1 receptor expressing CHO cellular membrane fraction and ovine CRF, [$^{125}$I]-tyr$^0$($^{125}$I-CRF). 1000 nM of a test compound was incubated with 1 μg of human CRF receptor expressing CHO cellular membrane fraction and 50 pM of $^{125}$I-CRF in a binding assay buffer (50 mM Tris-HCl, 5 mM EDTA, 10 mM MgCl$_2$, 0.05% CHAPS, 0.1% BSA, 0.5 mM PMSF, 0.1 μg/mL pepstatin, 20 μg/mL leupeptin, pH 7.5). In addition, for measuring nonspecific binding (NSB), 0.1 μM unlabelled human Urocortin was incubated with 5 μg of human CRF receptor expressing CHO cellular membrane fraction and 50 pM of $^{125}$I-CRF in a binding assay buffer. After a binding reaction was carried out at room temperature for 1.5 hr, the membrane was entrapped on a glass filter (UniFilter plate GF-C/Perkin Elmer) by suction filtration using a cell harvester (Perkin Elmer), and washed with ice-cooled 50 mM Tris-HCl (pH 7.5). After drying the glass filter, a liquid scintillation cocktail (Microscinti 0, Perkin Elmer) was added, and the radioactivity of $^{125}$I-CRF remaining on a glass filter was measured using Topcount (Perkin Elmer).

(TB-SB)/(TB-NSB)×100 (SB: radioactivity when a compound is added, TB: maximum binding radioactivity, NSB: nonspecific binding radioactivity) were calculated to obtain binding inhibitory rates under the range of the presence from 0.05 nM to 10 μM of each compound. The $IC_{50}$ values were calculated by using GraphPad Prism software.

The compounds of Examples 1, 2, 3, 4, 5, 6, 8, 9, 10, 11, 12, 13, 15, 16, 18, 19, 20, 21, 22, 23, 24, 25, 26, 28, 29, 30, 31, 32, 33, 34, 35, 36, 37, 38, 39, 40, 41, 42, 43, 44, 45, 46, 48, 49, 50, 51, 53, 54, 55, 56, 59, 60, 61, 62, 63, 64, 65, 66, 68, 69, 70, 71, 74, 76, 77, 78, 79, 80, 93, 94, 98, 99, 101 and 102 have been tested in this assay and found to exhibit $IC_{50}$ values of less than 1 μM.

Also the compounds of Examples 106, 107, 108, 109, 110, 111, 112, 113, 114, 115, 116, 117, 118, 119, 120, 121, 122, 123, 124, 128, 129, 130, 131, 132, 133, 134, 138, 139, 140, 141, 143, 144, 147, 148, 149, 150, 155, 156, 161, 166, 167, 171, 172, 174, 175, 176, 180, 185, 186, 187, 188, 189, 193, 194, 196, 197, 200, 202, 205, 210, 211, 212, 213, 214, 216, 218, 222, 225, 230, 231, 233, 234, 235, 236, 237, 238, 239, 240, 241, 242, 243, 244, 250, 252, 253, 254, 255, 260, 265, 266, 267, 268, 269, 271, 272, 273, 276, 277, 278, 280, 282, 283, 284, 286, 287, 288, 289, 290, 292, 293, 298, 303, 304, 305, 306, 307, 308, 309, 310, 311, 312, 313, 314, 316, 317, 318, 320, 323, 325, 329, 330, 331, 334, 335, 336, 338, 339, 340, 341, 342, 343, 349, 353, 354, 356, 357, 358, 359, 361, 362, 363, 365, 368, 369, 373, 374, 377, 379, 380, 381, 382, 383, 384, 385, 386, 387, 388, 391, 394, 397, 402, 403, 404, 405, 409, 410, 412, 414, 415, 416, 426, 428, 431, 432, 433, 437, 438, 439, 440, 443, 444, 446, 447, 450, 452, 453, 454, 455, 458, 459, 462, 463, 464, 465, 466, 468, 470, 471, 472, 474, 476, 477, 478, 479, 480, 481, 482, 483, 484, 485, 486, 487, 492, 493, 494, 500, 501, 502, 506, 507, 509 and 511 have been tested in this assay and found to exhibit $IC_{50}$ values of less than 1 μM.

Binding inhibitory rates (% inhibition at the presence of 1 μM of a test compound) of exemplified compounds measured by the aforementioned method were for example, 91% (Example 25), 95% (Example 112), 89% (Example 185), 97% (Example 186), 66% (Example 187), 98% (Example 238), 90% (Example 239), 97% (Example 240), 89% (Example 265), 82% (Example 266), 96% (Example 267), 94% (Example 276), 94% (Example 282), 83% (Example 283), 95% (Example 284), 93% (Example 312), 99% (Example 313), 88% (Example 314), 95% (Example 365), 96% (Example 369), 98% (Example 426), 78% (Example 438), 84% (Example 439) and 98% (Example 450).

Preparation Example 1

| | | |
|---|---|---|
| (1) | Compound of Example 1 | 50 mg |
| (2) | Lactose | 34 mg |
| (3) | Corn starch | 10.6 mg |
| (4) | Corn starch (paste) | 5 mg |
| (5) | Magnesium stearate | 0.4 mg |
| (6) | Carboxymethylcellulose calcium | 20 mg |
| | Total | 120 mg |

According to a conventional method, the above (1) to (6) are mixed and compressed into a tablet with a tableting machine.

INDUSTRIAL APPLICABILITY

Compound (I') (including, compound (I)) shows high affinity for CRF receptors, etc. and has physiological activities such as CRF receptor affinity, acts as an antagonist of CRF1, especially a selective antagonist of CRF1 receptor, shows low toxicity, good pharmacokinetic profiles, and good physicochemical properties, and exhibits anxiolytic and antidepressive effects to an animal, especially to a mammal. Therefore Compound (I) is useful as a safe pharmaceutical and can be used as a pharmaceutical for preventing and/or treating diseases associated with the functions of a CRF receptor or a CRF.

This application is based on U.S. provisional application No. 61/006,554 filed in United States, the contents of which are incorporated in full herein by this reference.

The invention claimed is:

1. A compound represented by the following formula (I'''):

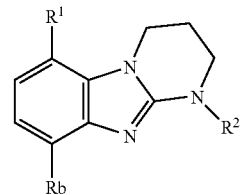

(I''')

wherein $R^1$ is
(1) mono- or di-$C_{1-6}$ alkylamino, or
(2) a $C_{1-9}$ alkyl optionally substituted by a substituent selected from the group consisting of halogen, hydroxy, $C_{3-6}$ cycloalkyl, an optionally substituted $C_{1-6}$ alkoxy, $C_{1-6}$ alkyl-carbonyloxy, $C_{3-6}$ cycloalkyl-carbonyloxy and an optionally substituted $C_{3-6}$ cycloalkyloxy;
$R^2$ is
an optionally substituted phenyl, an optionally substituted pyridyl or an optionally substituted pyrimidinyl; and
Rb is hydrogen, halogen, cyano, an optionally substituted $C_{1-9}$ alkyl, an optionally substituted $C_{1-6}$ alkoxy, or $C_{3-6}$ cycloalkyl, or a salt thereof.

2. The compound according to claim 1, wherein $R^1$ is a $C_{1-9}$ alkyl optionally substituted by a substituent selected from the group consisting of halogen, hydroxy, $C_{3-6}$ cycloalkyl, an optionally substituted $C_{1-6}$ alkoxy, $C_{1-6}$ alkyl-carbonyloxy, $C_{3-6}$ cycloalkyl-carbonyloxy and an optionally substituted $C_{3-6}$ cycloalkyloxy;
$R^2$ is
(1) phenyl optionally substituted by substituent(s) selected from the group consisting of halogen, an optionally halogenated $C_{1-6}$ alkoxy and an optionally halogenated $C_{1-9}$ alkyl,
(2) pyridyl optionally substituted by substituent(s) selected from the group consisting of halogen, an optionally halogenated $C_{1-9}$ alkyl, $C_{3-6}$ cycloalkyl and an optionally halogenated $C_{1-6}$ alkoxy, or
(3) pyrimidinyl optionally substituted by substituent(s) selected from the group consisting of $C_{1-9}$ alkyl, an optionally halogenated $C_{1-6}$ alkoxy and $C_{3-6}$ cycloalkyl; and Rb is hydrogen, halogen or $C_{1-6}$ alkoxy.

3. [9-Chloro-1-(6-methoxy-2-methylpyridin-3-yl)-1,2,3,4-tetrahydropyrimido[1,2-α]benzimidazol-6-yl](dicyclopropyl)methanol or a salt thereof.

4. A pharmaceutical composition, which comprises the compound according to claim 1 or a salt thereof, and a pharmaceutically acceptable carrier.

5. A pharmaceutical composition comprising [9-Chloro-1-(6-methoxy-2-methylpyridin-3-yl)-1,2,3,4-tetrahydropyrimido [1,2-α]benzimidazol-6-yl](dicyclopropyl)methanol or a salt thereof, and a pharmaceutically acceptable carrier.

* * * * *